United States Patent
Blum et al.

(10) Patent No.: US 10,590,135 B2
(45) Date of Patent: *Mar. 17, 2020

(54) SUBSTITUTED BRIDGED UREA ANALOGS AS SIRTUIN MODULATORS

(71) Applicant: GLAXOSMITHKLINE LLC, Wilmington, DE (US)

(72) Inventors: Charles A. Blum, Waltham, MA (US); Richard Dana Caldwell, Brookline, MA (US); Rebecca Casaubon, Garnet Valley, PA (US); Jeremy S. Disch, Natick, MA (US); Ryan Michael Fox, Collegeville, PA (US); Karsten Koppetsch, Woburn, MA (US); William Henry Miller, Collegeville, PA (US); Pui Yee Ng, Waltham, MA (US); Christopher Oalmann, Watertown, MA (US); Robert B. Perni, Marlborough, MA (US); Bruce G. Szczepankiewicz, Hopkinton, MA (US); Brian H. White, Malden, MA (US)

(73) Assignee: GLAXOSMITHKLINE LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/528,195

(22) PCT Filed: Nov. 19, 2015

(86) PCT No.: PCT/US2015/061501
§ 371 (c)(1),
(2) Date: May 19, 2017

(87) PCT Pub. No.: WO2016/081692
PCT Pub. Date: May 26, 2016

(65) Prior Publication Data
US 2017/0355697 A1 Dec. 14, 2017

Related U.S. Application Data

(63) Continuation of application No. 14/547,861, filed on Nov. 19, 2014, now Pat. No. 9,834,558, which is a continuation-in-part of application No. PCT/US2014/037767, filed on May 13, 2014.

(60) Provisional application No. 61/822,758, filed on May 13, 2013.

(51) Int. Cl.
| | |
|---|---|
| *A61K 31/506* | (2006.01) |
| *C07D 471/18* | (2006.01) |
| *A61K 31/4995* | (2006.01) |
| *A61K 31/551* | (2006.01) |
| *C07D 487/04* | (2006.01) |
| *C07D 513/18* | (2006.01) |
| *C07D 519/00* | (2006.01) |
| *A61K 45/06* | (2006.01) |
| *A61P 17/10* | (2006.01) |

(52) U.S. Cl.
CPC ........ *C07D 471/18* (2013.01); *A61K 31/4995* (2013.01); *A61K 31/506* (2013.01); *A61K 31/551* (2013.01); *A61K 45/06* (2013.01); *A61P 17/10* (2018.01); *C07D 487/04* (2013.01); *C07D 513/18* (2013.01); *C07D 519/00* (2013.01)

(58) Field of Classification Search
CPC .......................... C07D 471/04; C07D 471/18
See application file for complete search history.

(56) References Cited

U.S. PATENT DOCUMENTS

| | | | |
|---|---|---|---|
| 5,637,679 A | 6/1997 | Hassenruck et al. | |
| 8,501,991 B2 | 8/2013 | Lain et al. | |
| 9,326,986 B2 | 5/2016 | Vu et al. | |
| 9,765,075 B2 * | 9/2017 | Blum | C07D 471/18 |
| 9,834,558 B2 * | 12/2017 | Blum | C07D 471/18 |
| 2010/0016279 A1 | 1/2010 | Bradbury et al. | |
| 2011/0046110 A1 | 2/2011 | Vu et al. | |
| 2011/0263564 A1 | 10/2011 | Narayan et al. | |
| 2011/0306609 A1 | 12/2011 | Oalmann et al. | |
| 2012/0252780 A1 | 10/2012 | Ng et al. | |
| 2014/0288052 A1 | 9/2014 | Blum et al. | |
| 2015/0152108 A1 | 6/2015 | Blum et al. | |
| 2015/0175645 A1 | 6/2015 | Milburn et al. | |

FOREIGN PATENT DOCUMENTS

| | | |
|---|---|---|
| WO | WO 2006/094248 A1 | 9/2006 |
| WO | WO 2016/081692 A2 | 5/2016 |

OTHER PUBLICATIONS

Z. Wang et al., 19 Drug Discovery Today, 145-150 (2014).*
U.K. Marelli et al., 3 Frontiers in Oncology, 1-12 (2013).*
M.G. Haigis et al., 5 Annual Review of Pathology: Mechanisms of Disease, 253-295 (2010).*
K.T. Howitz et al., 425 Nature, 191-196 (2003).*
C.P. Hsu et al., Circulation, 2170-2182 (2010).*
G. Donmez et al., 5 EMBO Molecular Medicine, 344-352 (2013).*
M. Lagouge et al., 127 Cell, 1109-1122 (2006).*

(Continued)

*Primary Examiner* — Alexander R Pagano
(74) *Attorney, Agent, or Firm* — Nicole Ginanni; Duke M. Fitch

(57) ABSTRACT

The present invention relates to novel substituted bridged urea compounds, corresponding related analogs, pharmaceutical compositions and methods of use thereof. Sirtuin-modulating compounds of the present invention may be used for increasing the lifespan of a cell, and treating and/or preventing a wide variety of diseases and disorders, which include, but are not limited to, for example, diseases or disorders related to aging or stress, diabetes, obesity, neurodegenerative diseases, cardiovascular disease, blood clotting disorders, inflammation, cancer, and/or flushing as well as diseases or disorders that would benefit from increased mitochondrial activity. The present invention also related to compositions comprising a sirtuin-modulating compound in combination with another therapeutic agent.

11 Claims, No Drawings

Specification includes a Sequence Listing.

(56) References Cited

OTHER PUBLICATIONS

T. Liu et al., 69 Cancer Research, 1702-1705 (2009).*
T. Yoshizaki et al., 29 Molecular and Cellular Biology, 1363-1374 (2009).*
Szczepankiewicz et al., "Sirtuin Modulators: Targets for Metabolic Diseases and Beyond", *Current Topics in Medicinal Chemistry*, vol. 8, No. 17, pp. 1533-1544 (2008).

* cited by examiner

SEQUENCE LISTING

```
<160> NUMBER OF SEQ ID NOS: 2

<210> SEQ ID NO 1
<211> LENGTH: 27
<212> TYPE: PRT
<213> ORGANISM: Homo Sapien

<400> SEQUENCE: 1

Ala Glu Glu Lys Gly Gln Ser Thr Ser Ser His Ser Lys Ala Asn Ser
 1               5                  10                  15

Thr Glu Gly Lys Thr Met Arg Glu Glu Asn His
            20                  25

<210> SEQ ID NO 2
<211> LENGTH: 9
<212> TYPE: PRT
<213> ORGANISM: Homo Sapien

<400> SEQUENCE: 2

Ala Arg His Lys Lys Ala Trp Asn His
 1               5
```

SUBSTITUTED BRIDGED UREA ANALOGS AS SIRTUIN MODULATORS

CROSS REFERENCE TO RELATED APPLICATIONS

This application is a continuation-in-part of International Application No. PCT/US2014/037767, filed May 13, 2014, which claims the benefit of U.S. Provisional Application No. 61/822,758 filed May 13, 2013, which are incorporated herein by reference.

FIELD OF THE INVENTION

In general, the present invention relates to novel substituted bridged urea compounds of Formula (I) or pharmaceutically acceptable salts thereof, corresponding pharmaceutical compositions, processes for making and use of such compounds in sirtuin modulation and methods of for increasing the lifespan of a cell, treating and/or preventing a wide variety of diseases and disorders, which include, but are not limited to, for example, diseases or disorders related to aging or stress, diabetes, obesity, neurodegenerative diseases, cardiovascular disease, blood clotting disorders, inflammation, cancer, and/or flushing as well as diseases or disorders that would benefit from increased mitochondrial activity. The present invention also related to compositions comprising a sirtuin-modulating compound in combination with another therapeutic agent.

BACKGROUND

The Silent Information Regulator (SIR) family of genes represents a highly conserved group of genes present in the genomes of organisms ranging from archaebacteria to eukaryotes. The encoded SIR proteins are involved in diverse processes from regulation of gene silencing to DNA repair. A well-characterized gene in this family is *S. cerevisiae* SIR2, which is involved in silencing HM loci that contain information specifying yeast mating type, telomere position effects and cell aging. The yeast Sir2 protein belongs to a family of histone deacetylases. The proteins encoded by members of the SIR gene family show high sequence conservation in a 250 amino acid core domain. The Sir2 homolog, CobB, in *Salmonella typhimurium*, functions as an NAD (nicotinamide adenine dinucleotide)-dependent ADP-ribosyl transferase.

The Sir2 protein is a class III deacetylase which uses NAD as a cosubstrate. Unlike other deacetylases, many of which are involved in gene silencing, Sir2 is insensitive to class I and II histone deacetylase inhibitors like trichostatin A (TSA).

Deacetylation of acetyl-lysine by Sir2 is tightly coupled to NAD hydrolysis, producing nicotinamide and a novel acetyl-ADP ribose compound. The NAD-dependent deacetylase activity of Sir2 is essential for its functions, which can connect its biological role with cellular metabolism in yeast. Mammalian Sir2 homologs have NAD-dependent histone deacetylase activity.

Biochemical studies have shown that Sir2 can readily deacetylate the amino-terminal tails of histones H3 and H4, resulting in the formation of 2'/3'-O-acetyl-ADP-ribose (OAADPR) and nicotinamide. Strains with additional copies of SIR2 display increased rDNA silencing and a 30% longer life span. It has also been shown that additional copies of the *C. elegans* SIR2 homolog, sir-2.1, and the *D. melanogaster* dSir2 gene extend life span in those organisms. This implies that the SIR2-dependent regulatory pathway for aging arose early in evolution and has been well conserved. Today, Sir2 genes are believed to have evolved to enhance an organism's health and stress resistance to increase its chance of surviving adversity.

In humans, there are seven Sir2-like genes (SIRT1-SIRT7) that share the conserved catalytic domain of Sir2. SIRT1 is a nuclear protein with the highest degree of sequence similarity to Sir2. SIRT1 regulates multiple cellular targets by deacetylation including the tumor suppressor p53, the cellular signaling factor NF-κB, and the FOXO transcription factor.

SIRT3 is a homolog of SIRT1 that is conserved in prokaryotes and eukaryotes. The SIRT3 protein is targeted to the mitochondrial cristae by a unique domain located at the N-terminus. SIRT3 has $NAD^+$-dependent protein deacetylase activity and is ubiquitously expressed, particularly in metabolically active tissues. Upon transfer to the mitochondria, SIRT3 is believed to be cleaved into a smaller, active form by a mitochondrial matrix processing peptidase (MPP).

Caloric restriction has been known for over 70 years to improve the health and extend the lifespan of mammals. Yeast life span, like that of metazoans, is also extended by interventions that resemble caloric restriction, such as low glucose. The discovery that both yeast and flies lacking the SIR2 gene do not live longer when calorically restricted provides evidence that SIR2 genes mediate the beneficial health effects of a restricted calorie diet. Moreover, mutations that reduce the activity of the yeast glucose-responsive cAMP (adenosine 3',5'-monophosphate)-dependent (PKA) pathway extend life span in wild type cells but not in mutant sir2 strains, demonstrating that SIR2 is likely to be a key downstream component of the caloric restriction pathway.

In addition to therapeutic potential, structural and biophysical studies of SIRT1 activity and activation by small molecule sirtuin modualtors would be useful to advance understanding of the biological function of sirtuins, to further the understanding of the mechanism of action of sirtuin activation and to aid in the development of assays that identify novel sirtuin modulators.

SUMMARY

In general, the present invention relates to novel substituted bridged urea compounds of Formula (I) or pharmaceutically acceptable salts thereof, corresponding pharmaceutical compositions, processes for making and use of such compounds in sirtuin modulation and methods of for increasing the lifespan of a cell, treating and/or preventing a wide variety of diseases and disorders, which include, but are not limited to, for example, diseases or disorders related to aging or stress, diabetes, obesity, neurodegenerative diseases, cardiovascular disease, blood clotting disorders, inflammation, cancer, and/or flushing as well as diseases or disorders that would benefit from increased mitochondrial activity. The present invention also related to compositions comprising a sirtuin-modulating compound in combination with another therapeutic agent.

Provided herein are novel sirtuin-modulating compounds and methods of use thereof.

In one aspect, the invention provides sirtuin-modulating compounds of Structural Formulas (I), (IIa), (IIb), (IIIa), (IIIb) and (IV) as are described in detail below.

In other aspects, representative compounds of the present invention are compound structures as exemplified or set forth in Table 1 and/or Table 10 (i.e., additional representative compound examples), respectively, or their corresponding pharmaceutically acceptable salts thereof as defined in the present specification.

In another aspect, the invention provides methods for using sirtuin-modulating compounds, or compositions comprising sirtuin-modulating compounds.

In certain embodiments, sirtuin-modulating compounds that increase the level and/or activity of a sirtuin protein may be used for a variety of therapeutic applications including, for example, increasing the lifespan of a cell, and treating and/or preventing a wide variety of diseases and disorders including, for example, but not limited to diseases or disorders related to aging or stress, diabetes, obesity, neurodegenerative diseases, cardiovascular disease chemotherapeutic-induced neuropathy, neuropathy associated with an ischemic event, ocular diseases and/or disorders, cardiovascular disease, blood clotting disorders, inflammation, and/or flushing, etc.

Sirtuin-modulating compounds that increase the level and/or activity of a sirtuin protein may also be used for treating a disease or disorder in a subject that would benefit from increased mitochondrial activity, for enhancing muscle performance, for increasing muscle ATP levels, or for treating or preventing muscle tissue damage associated with hypoxia or ischemia. In other embodiments, sirtuin-modulating compounds that decrease the level and/or activity of a sirtuin protein may be used for a variety of therapeutic applications including, for example, increasing cellular sensitivity to stress, increasing apoptosis, treatment of cancer, stimulation of appetite, and/or stimulation of weight gain, etc. As described further below, the methods comprise administering to a subject in need thereof a pharmaceutically effective amount of a sirtuin-modulating compound.

Based on the foregoing, the present invention may be used in the treatment of other diseases or disorders related to aging or stress, diabetes and other metabolic dysfunctions and related conditions including but not limited to fatty liver, hepatic steatohepatitis and obesity. The present invention may also be used in the treatment of neurodegenerative diseases, cardiovascular disease, cancer, inflammatory disease which includes but is not limited to psoriasis, atopic dermatitis, acne, rosacea, inflammatory bowel disease, osteoporosis, sepsis, arthritis, COPD, systemic lupus erythematosus and ophthalmic inflammation, as well as other diseases or disorders that result from diminished SIRT1 expression or activity.

In certain aspects, the sirtuin-modulating compounds may be administered alone or in combination with other compounds, including other sirtuin-modulating compounds, or other therapeutic agents.

DETAILED DESCRIPTION

The present invention relates to novel substituted bridged urea compounds of Formula (I) or pharmaceutically acceptable salts thereof, corresponding pharmaceutical compositions, processes for making and use of such compounds in sirtuin modulation and methods of for increasing the lifespan of a cell, treating and/or preventing a wide variety of diseases and disorders, which include, but are not limited to, for example, diseases or disorders related to aging or stress, diabetes, obesity, neurodegenerative diseases, cardiovascular disease, blood clotting disorders, inflammation, cancer, and/or flushing as well as diseases or disorders that would benefit from increased mitochondrial activity.

The present invention also related to compositions comprising a sirtuin-modulating compound in combination with another therapeutic agent.

1. Definitions

As used herein, the following terms and phrases shall have the meanings set forth below. Unless defined otherwise, all technical and scientific terms used herein have the same meaning as commonly understood to one of ordinary skill in the art.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues.

The term "bioavailable", when referring to a compound, is art-recognized and refers to a form of a compound that allows for all or a portion of the amount of compound administered to be absorbed by, incorporated into, or otherwise physiologically available to a subject or patient to whom it is administered.

"Biologically active portion of a sirtuin" refers to a portion of a sirtuin protein having a biological activity, such as the ability to deacetylate ("catalytically active"). Catalytically active portions of a sirtuin may comprise the core domain of sirtuins. Catalytically active portions of SIRT1 having GenBank Accession No. NP_036370 that encompass the NAD$^+$ binding domain and the substrate binding domain, for example, may include without limitation, amino acids 240-664 or 240-505 of GenBank Accession No. NP_036370, which are encoded by the polynucleotide of GenBank Accession No. NM_012238. Therefore, this region is sometimes referred to as the core domain. Other catalytically active portions of SIRT1, also sometimes referred to as core domains, include about amino acids 261 to 447 of GenBank Accession No. NP_036370, which are encoded by nucleotides 834 to 1394 of GenBank Accession No. NM_012238; about amino acids 242 to 493 of GenBank Accession No. NP_036370, which are encoded by nucleotides 777 to 1532 of GenBank Accession No. NM_012238; or about amino acids 254 to 495 of GenBank Accession No. NP_036370, which are encoded by nucleotides 813 to 1538 of GenBank Accession No. NM_012238. Another "biologically active" portion of SIRT1 is amino acids 62-293 or 183-225 of GenBank Accession No. NP_036370, which comprise a domain N-terminal to the core domain that is important to the compound binding site.

The term "companion animals" refers to cats and dogs. As used herein, the term "dog(s)" denotes any member of the species Canis familiaris, of which there are a large number of different breeds. The term "cat(s)" refers to a feline animal including domestic cats and other members of the family Felidae, genus Felis.

"Diabetes" refers to high blood sugar or ketoacidosis, as well as chronic, general metabolic abnormalities arising from a prolonged high blood sugar status or a decrease in glucose tolerance. "Diabetes" encompasses both the type I and type II (Non Insulin Dependent Diabetes Mellitus or NIDDM) forms of the disease. The risk factors for diabetes include the following factors: waistline of more than 40 inches for men or 35 inches for women, blood pressure of 130/85 mmHg or higher, triglycerides above 150 mg/dl, fasting blood glucose greater than 100 mg/dl or high-density lipoprotein of less than 40 mg/dl in men or 50 mg/dl in women.

The term "$ED_{50}$" refers to the art-recognized measure of effective dose. In certain embodiments, $ED_{50}$ means the dose of a drug which produces 50% of its maximum response or effect, or alternatively, the dose which produces a pre-determined response in 50% of test subjects or preparations, such as isolated tissue or cells. The term "$LD_{50}$" refers to the art-recognized measure of lethal dose. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

The term "hyperinsulinemia" refers to a state in an individual in which the level of insulin in the blood is higher than normal.

The term "insulin resistance" refers to a state in which a normal amount of insulin produces a subnormal biologic response relative to the biological response in a subject that does not have insulin resistance.

An "insulin resistance disorder," as discussed herein, refers to any disease or condition that is caused by or contributed to by insulin resistance. Examples include: diabetes, obesity, metabolic syndrome, insulin-resistance syndromes, syndrome X, insulin resistance, high blood pressure, hypertension, high blood cholesterol, dyslipidemia, hyperlipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephrotic syndrome, hypertensive nephrosclerosis, some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol-related disorders, such as gallstones, cholecystitis and cholelithiasis, gout, obstructive sleep apnea and respiratory problems, osteoarthritis, and bone loss, e.g., osteoporosis in particular.

The term "livestock animals" refers to domesticated quadrupeds, which includes those being raised for meat and various byproducts, e.g., a bovine animal including cattle and other members of the genus Bos, a porcine animal including domestic swine and other members of the genus Sus, an ovine animal including sheep and other members of the genus Ovis, domestic goats and other members of the genus Capra; domesticated quadrupeds being raised for specialized tasks such as use as a beast of burden, e.g., an equine animal including domestic horses and other members of the family Equidae, genus Equus.

The term "mammal" is known in the art, and exemplary mammals include humans, primates, livestock animals (including bovines, porcines, etc.), companion animals (e.g., canines, felines, etc.) and rodents (e.g., mice and rats).

"Obese" individuals or individuals suffering from obesity are generally individuals having a body mass index (BMI) of at least 25 or greater. Obesity may or may not be associated with insulin resistance.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion.

A "patient", "subject", "individual" or "host" refers to either a human or a non-human animal.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prophylactic" or "therapeutic" treatment is art-recognized and refers to administration of a drug to a host. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "pyrogen-free", with reference to a composition, refers to a composition that does not contain a pyrogen in an amount that would lead to an adverse effect (e.g., irritation, fever, inflammation, diarrhea, respiratory distress, endotoxic shock, etc.) in a subject to which the composition has been administered. For example, the term is meant to encompass compositions that are free of, or substantially free of, an endotoxin such as, for example, a lipopolysaccharide (LPS).

"Replicative lifespan" of a cell refers to the number of daughter cells produced by an individual "mother cell." "Chronological aging" or "chronological lifespan," on the other hand, refers to the length of time a population of non-dividing cells remains viable when deprived of nutrients. "Increasing the lifespan of a cell" or "extending the lifespan of a cell," as applied to cells or organisms, refers to increasing the number of daughter cells produced by one cell; increasing the ability of cells or organisms to cope with stresses and combat damage, e.g., to DNA, proteins; and/or increasing the ability of cells or organisms to survive and exist in a living state for longer under a particular condition, e.g., stress (for example, heatshock, osmotic stress, high energy radiation, chemically-induced stress, DNA damage, inadequate salt level, inadequate nitrogen level, or inadequate nutrient level). Lifespan can be increased by at least about 10%, 20%, 30%, 40%, 50%, 60% or between 20% and 70%, 30% and 60%, 40% and 60% or more using methods described herein.

"Sirtuin-modulating compound" refers to a compound that increases the level of a sirtuin protein and/or increases at least one activity of a sirtuin protein. In an exemplary embodiment, a sirtuin-modulating compound may increase at least one biological activity of a sirtuin protein by at least about 10%, 25%, 50%, 75%, 100%, or more. Exemplary biological activities of sirtuin proteins include deacetylation, e.g., of histones and p53; extending lifespan; increasing genomic stability; silencing transcription; and controlling the segregation of oxidized proteins between mother and daughter cells.

proteins include deacetylation, e.g., of an acetylated peptide substrate.

"Sirtuin protein" refers to a member of the sirtuin deacetylase protein family, or preferably to the sir2 family, which include yeast Sir2 (GenBank Accession No. P53685), C. elegans Sir-2.1 (GenBank Accession No. NP_501912), and human SIRT1 (GenBank Accession No. NM_012238 and NP_036370 (or AF083106)) and SIRT2 (GenBank Accession No. NM_012237, NM_030593, NP_036369, NP_085096, and AF083107) proteins. Other family members include the four additional yeast Sir2-like genes termed "HST genes" (homologues of Sir two) HST1, HST2, HST3 and HST4, and the five other human homologues hSIRT3, hSIRT4, hSIRT5, hSIRT6 and hSIRT7 (Brachmann et al. (1995) Genes Dev. 9:2888 and Frye et al. (1999) BBRC 260:273).

"SIRT1 protein" refers to a member of the sir2 family of sirtuin deacetylases. In certain embodiments, a SIRT1 protein includes yeast Sir2 (GenBank Accession No. P53685), C. elegans Sir-2.1 (GenBank Accession No. NP_501912), human SIRT1 (GenBank Accession No. NM_012238 or NP_036370 (or AF083106)), mouse SIRT1 (GenBank Accession No. NM_019812 or NP_062786), and equivalents and fragments thereof. In another embodiment, a SIRT1 protein includes a polypeptide comprising a sequence consisting of, or consisting essentially of, the amino acid sequence set forth in GenBank Accession Nos. NP_036370, NP_501912, NP_085096, NP_036369, or P53685. SIRT1 proteins include polypeptides comprising all or a portion of the amino acid sequence set forth in GenBank Accession Nos. NP_036370, NP_501912, NP_085096, NP_036369, or P53685; the amino acid sequence set forth in GenBank Accession Nos. NP_036370, NP_501912, NP_085096, NP_036369, or P53685 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. NP_036370, NP_501912, NP_085096, NP_036369, or P53685, and functional fragments thereof. Polypeptides of the invention also include homologs (e.g., orthologs and paralogs), variants, or fragments, of GenBank Accession Nos. NP_036370, NP_501912, NP_085096, NP_036369, or P53685.

As used herein "SIRT2 protein", "SIRT3 protein", "SIRT4 protein", SIRT5 protein", "SIRT6 protein", and "SIRT7 protein" refer to other mammalian, e.g. human, sirtuin deacetylase proteins that are homologous to SIRT1 protein, particularly in the approximately 275 amino acid conserved catalytic domain. For example, "SIRT3 protein" refers to a member of the sirtuin deacetylase protein family that is homologous to SIRT1 protein. In certain embodiments, a SIRT3 protein includes human SIRT3 (GenBank Accession No. AAH01042, NP_036371, or NP_001017524) and mouse SIRT3 (GenBank Accession No. NP_071878) proteins, and equivalents and fragments thereof. In certain embodiments, a SIRT4 protein includes human SIRT4 (GenBank Accession No. NM_012240 or NP_036372). In certain embodiments, a SIRT5 protein includes human SIRT5 (GenBank Accession No. NM_012241 or NP_036373). In certain embodiments, a SIRT6 protein includes human SIRT6 (GenBank Accession No. NM_016539 or NP_057623). In another embodiment, a SIRT3 protein includes a polypeptide comprising a sequence consisting of, or consisting essentially of, the amino acid sequence set forth in GenBank Accession Nos. AAH01042, NP_036371, NP_001017524, or NP_071878. SIRT3 proteins include polypeptides comprising all or a portion of the amino acid sequence set forth in GenBank Accession AAH01042, NP_036371, NP_001017524, or NP_071878; the amino acid sequence set forth in GenBank Accession Nos. AAH01042, NP_036371, NP_001017524, or NP_071878 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. AAH01042, NP_036371, NP_001017524, or NP_071878, and functional fragments thereof. Polypeptides of the invention also include homologs (e.g., orthologs and paralogs), variants, or fragments, of GenBank Accession Nos. AAH01042, NP_036371, NP_001017524, or NP_071878. In certain embodiments, a SIRT3 protein includes a fragment of SIRT3 protein that is produced by cleavage with a mitochondrial matrix processing peptidase (MPP) and/or a mitochondrial intermediate peptidase (MIP).

The term "steroisomer" as used herein is art-recognized and refers to any of two or more isomers that have the same molecular constitution and differ only in the three-dimensional arrangement of their atomic groupings in space. When used herein to describe a compounds or genus of compounds, stereoisomer includes any portion of the compound or the compound in its entirety. For example, diastereomers and enantiomers are stereoisomers.

The terms "systemic administration" and "administered systemically," are art-recognized and refer to the administration of a subject composition, therapeutic or other material enterally or parenterally.

The term "tautomer" as used herein is art-recognized and refers to any one of the possible alternative structures that may exist as a result of tautomerism, which refers to a form of constitutional isomerism in which a structure may exist in two or more constitutional arrangements, particularly with respect to the position of hydrogens bonded to oxygen. When used herein to describe a compound or genus of compounds, it is further understood that a "tautomer" is readily interconvertible and exists in equilibrium. For example, keto and enol tautomers exist in proportions determined by the equilibrium position for any given condition, or set of conditions:

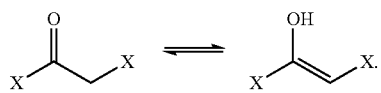

The term "therapeutic agent" is art-recognized and refers to any biologically, physiologically, or pharmacologically active substance that acts locally or systemically in a subject. The term also means any substance intended for use in the diagnosis, cure, mitigation, treatment or prevention of disease or in the enhancement of desirable physical or mental development and/or conditions in an animal or human.

The term "therapeutic effect" is art-recognized and refers to a beneficial local or systemic effect in animals, particularly mammals, and more particularly humans, caused by a pharmacologically active substance. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of skill in the art. For example, certain compositions described herein may be administered in a sufficient amount to produce a desired effect at a reasonable benefit/risk ratio applicable to such treatment.

"Treating" a condition or disease refers to curing as well as ameliorating at least one symptom of the condition or disease.

The term "vision impairment" refers to diminished vision, which is often only partially reversible or irreversible upon treatment (e.g., surgery). Particularly severe vision impairment is termed "blindness" or "vision loss", which refers to a complete loss of vision, vision worse than 20/200 that cannot be improved with corrective lenses, or a visual field of less than 20 degrees diameter (10 degrees radius).

2. Compounds

The present invention relates to novel substituted bridged urea compounds of Formula (I) or pharmaceutically acceptable salts thereof and corresponding pharmaceutical compositions.

In one aspect, the invention provides novel compounds for treating and/or preventing a wide variety of diseases and disorders including, for example, diseases or disorders related to aging or stress, diabetes, obesity, neurodegenerative diseases, ocular diseases and disorders, cardiovascular disease, blood clotting disorders, inflammation, cancer, and/or flushing, etc. Subject compounds, such as sirtuin-modulating compounds that increase the level and/or activity of a sirtuin protein, may also be used for treating a disease or disorder in a subject that would benefit from increased mitochondrial activity, for enhancing muscle performance, for increasing muscle ATP levels, or for treating or preventing muscle tissue damage associated with hypoxia or ischemia. Compounds disclosed herein may be suitable for use in pharmaceutical compositions and/or one or more methods disclosed herein.

In certain embodiments, compounds of the invention are represented by Structural Formula (I):

The invention includes pharmaceutical compositions of any of the compounds of Structural Formulas (I), (IIa), (IIb), (IIIa), (IIIb), and (IV) or as otherwise set forth above. The pharmaceutical composition of the compound of Structural Formulas I), (IIa), (IIb), (IIIa), (IIIb), and (IV) may comprise one or more pharmaceutically acceptable carriers or diluents.

In one embodiment, sirtuin-modulating compounds of the invention are represented by Structural Formula (I):

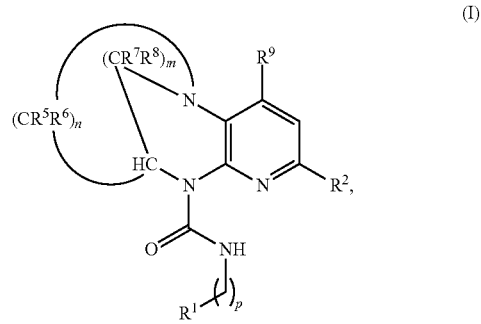

(I)

or a salt thereof wherein:

m is 1 or 2;

n is 2 or 3;

p is 0 to 4;

$R^1$ is selected from a carbocycle and heterocycle, wherein $R^1$ is optionally substituted with one or more substituents independently selected from halo, $C_1$-$C_4$ alkyl, fluoro-substituted $C_1$-$C_4$ alkyl, —C≡N, —Y, —X—C(=O)—Y, —X—O—Y, —X—OR$^4$, —X—C(=O)—NR$^3$R$^3$, —X—NH—C(=O)—Y—NR$^3$R$^3$, —X—NH—C(=O)—O—Y, —X—NR$^3$R$^3$, =O, —NH—S(=O)$_2$—R$_3$, —S(=O)$_2$—R$^3$, —S—R$^3$, —($C_3$-$C_7$) cycloalkyl, —C(=N)—NR$^3$R$^3$, —C(=N)—NH—X —NR$^3$R$^3$, —X—NH—C(=O)—Y, —C(=O)—NH—X, —NH—X, phenyl, —O-phenyl, 3- to 6-membered saturated or unsaturated heterocycle and —O-(5- to 6-membered saturated heterocycle), wherein any phenyl, 3- to 6-membered saturated or unsaturated heterocycle or —O-5- to 6-membered saturated heterocycle substituent of $R^1$ is optionally substituted at any substitutable carbon atom with one or more substituents selected from halo, —OR$^4$, —X—O—Y, —CF$_3$, —Y, —X—R$^3$R$^3$, —X—NH—C(=O)—Y—NR$^3$R$^3$, —X—NH—C(=O)—O—Y-(5- to 6-membered saturated heterocycle or carbocycle), —X—C(=N)—NR$^3$R$^3$ and —S—Y and optionally substituted at any substitutable nitrogen atom with —Y, —C(=O)—Y, —C(=O)—O—Y, —C(=O)—OR$^4$, —Y—C(=O)—Y—NR$^3$R$^3$, —Y—NH—C(=O)—O—Y, —Y—NH—C(=O)—OR$^4$, —Y—NH$_2$, —C(=O)—NH—Y or —C(=O)-3- to 5-membered saturated carbocycle;

$R^2$ is selected from a carbocycle and a heterocycle, wherein $R^2$ is optionally substituted with one or more substituents independently selected from halo, $C_1$-$C_4$ alkyl, fluoro-substituted $C_1$-$C_4$ alkyl, —C≡N, —Y, —X—OR$^4$, —X—O—Y, —SO$_2$—R$^3$, —X—NR$^3$R$^3$, —NH—S (=O)₂R³, —C(=O)—NR³R³, —C(=O)—Y, —C(=O)—O—Y, —SO₂—R_y, —SO₂—NH—R_y, —SO₂—NR³R³, 3- to 6-membered saturated carbocycle or heterocycle and phenyl, wherein any 3- to 6-membered saturated heterocycle substituent of R² is optionally substituted at any carbon atom with one or more substituents selected from halo, —CF₃, —Y, —X—O—Y, —NH—Y and —N(Y)₂, and is optionally substituted at any nitrogen atom with one or more substituents selected from —C(=O)—O—Y, —Y and —C(=O)—Y, and when R² is an N-linked 5- to 7-membered saturated or unsaturated heterocycle it is further substituted at any nitrogen atom with one or more substituents selected from —C(=O)—O—Y, —Y and —C(=O)—Y;

each R³ is independently selected from hydrogen, —C(=N)—NH₂, —C(=O)—Y, —Y, —Y—NH—C(=O)—O—Y, —Y—NH—C(=O)—OH, —Y—NH—C(=O)—CF₃, —C(=O)—Y-3- to 5-membered saturated heterocycle, —C(=O)—O—Y-(3- to 5-membered saturated heterocycle), —C(=O)—CF₃, —C(=O)—O—Y, —C(=O)—OH, —C(=O)—O—CF₃, —S(=O)₂—Y, —S(=O)₂—OH; two R³ are taken together with the nitrogen or carbon atom to which they are bound to form a 4- to 8-membered saturated heterocycle optionally comprising one additional heteroatom selected independently from N, S, S(=O), S(=O)₂, and O, wherein the heterocycle formed by two R³ is optionally substituted at any carbon atom with one or more of OH, halo, Y, NH₂, NH—Y, N(Y)₂, O—Y, and optionally substituted at any substitutable nitrogen atom with C(=O)—O—Y, Y or C(=O)—Y;

each R⁴ is independently selected from hydrogen, Y, —CF₃, —C(=O)—Y, —C(=O)—O—Y, —Y—C(=O)—Y or —Y—C(=O)—O—Y;

R⁵ and R⁶ are independently selected from hydrogen, —OH, —OCF₃, —O—Y, —O—C(=O)—Y, —O—C(=O)—O—Y, —O—C(=O)—NH—Y, —O—C(=O)—N(Y)₂, —O—C(=O)-5- to 6-membered saturated or unsaturated heterocycle or carbocycle, wherein only one of R⁵ and R⁶ is O—C(=O)-5- to 6-membered saturated or unsaturated heterocycle or carbocycle, and when R⁵ or R⁶ is O—C(=O)-5- to 6-membered saturated or unsaturated heterocycle or carbocycle it is further substituted with halo, —OH, Y, —O—Y, —OCF₃ or —O—C(=O)—Y; or R⁵ and R⁶ can be taken together to the carbon atom to which they are bound to form =O;

R⁷ and R⁸ are independently selected from hydrogen, halo, —OH, —O—Y and Y;

R⁹ is selected from hydrogen, halo, —OH, —OCF₃, —O—Y, Y, —O—C(=O)—Y, —NH—Y and —N(Y)₂;

each X is C₀-C₅ straight chain or branched alkyl, alkenyl or alkynyl; and each Y is C₁-C₅ straight chain or branched alkyl, alkenyl or alkynyl; wherein any Y or X is optionally substituted with one or more of —OH, —C₁-C₄ straight chain or branched alkyl, —C₁-C₄ alkene, —C₁-C₄ alkynyl, —O—(C₁-C₄ alkyl), —O—(C₁-C₄ alkene), —O—(C₁-C₄ alkynyl), —C(=O)—C₁-C₄ straight chain or branched alkyl, —C(=O)—C₁-C₄ alkene, —C(=O)—C₁-C₄ alkynyl, —C(=O)—O—C₁-C₄ straight chain or branched alkyl, —C(=O)—O—C₁-C₄ alkene, —C(=O)—O—C₁-C₄ alkynyl, halo, —NH₂, —NH(C₁-C₄ alkyl), —N(C₁-C₄ alkyl)₂, —(C₁-C₃ straight chain or branched alkyl)-NH—(=NH)—NH₂, —NH(alkoxy-substituted C₁-C₄ alkyl), —NH(hydroxy-substituted C₁-C₄ alkyl), —N(alkoxy-substituted C₁-C₄ alkyl)(hydroxy-substituted C₁-C₄ alkyl), —N(hydroxy-substituted C₁-C₄ alkyl)₂ or —N(alkoxy-substituted C₁-C₄ alkyl)₂.

In certain embodiments, compounds or salts of Structural Formula (I) are characterized by the structure represented by Structural Formula (IIa):

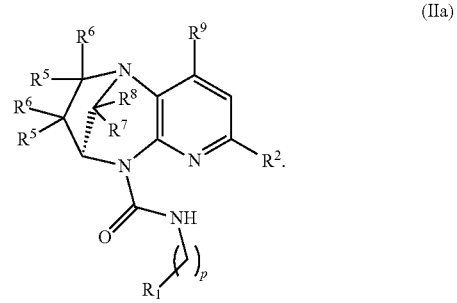

(IIa)

In certain embodiments, compounds or salts of Structural Formula (I) are characterized by the structure represented by Structural Formula (IIIa):

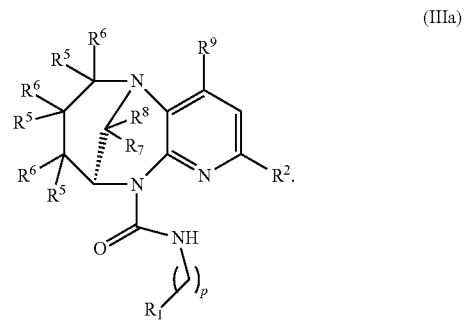

(IIIa)

In certain embodiments, compounds or salts of Structural Formula (I) are characterized by the structure represented by Structural Formulas (IIb) or (IIIb):

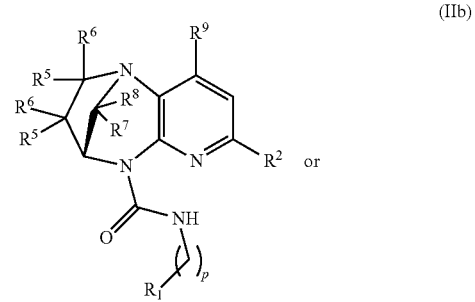

(IIb)

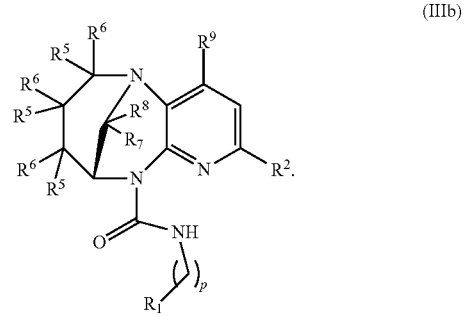

(IIIb)

In certain embodiments, compounds or salts of Structural Formula (I) are characterized by the structure represented by Structural Formula (IV):

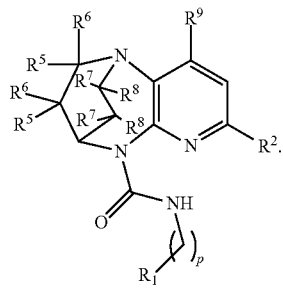

(IV)

In certain embodiments, compounds or salts of Structural Formula (I) are characterized by having a p=0 (i.e., no methylene between the C(O)—NH and $R_1$).

In certain embodiments, compounds or salts of Structural Formula (I) are characterized by having a p=1-4 (i.e., 1 to 4 methylenes between the C(O)—NH and $R_1$).

In certain embodiments, compounds or salts of Structural Formula (I) are characterized by having a —(CH$_2$)p-$R^1$ group selected from:

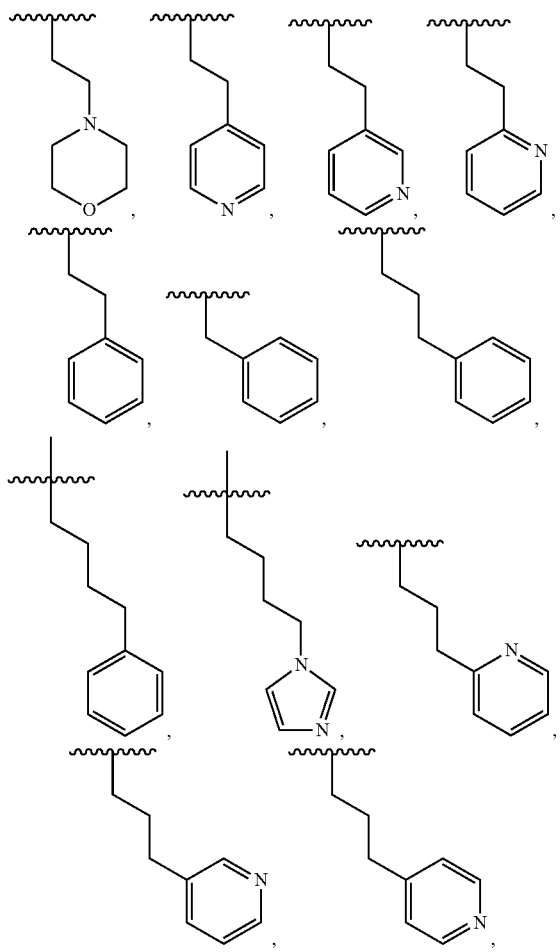

-continued

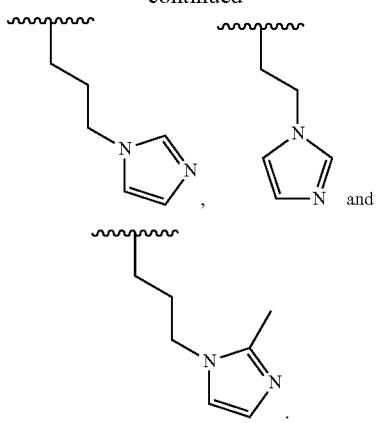

In certain embodiments, compounds or salts of Structural Formula (I) are characterized by an $R^1$ group that is phenyl, a saturated or unsaturated 5- to 6-membered heterocycle, or a fused bicyclic 8- to 11-membered saturated or unsaturated carbocycle or heterocycle.

In particular embodiments, compounds or salts of Structural Formula (I) are characterized by an $R^1$ that is a fused bicyclic 8- to 11-membered saturated or unsaturated heterocycle.

In certain embodiments, compounds or salts of Structural Formula (I) are characterized by an $R^1$ group that is selected from any one of:

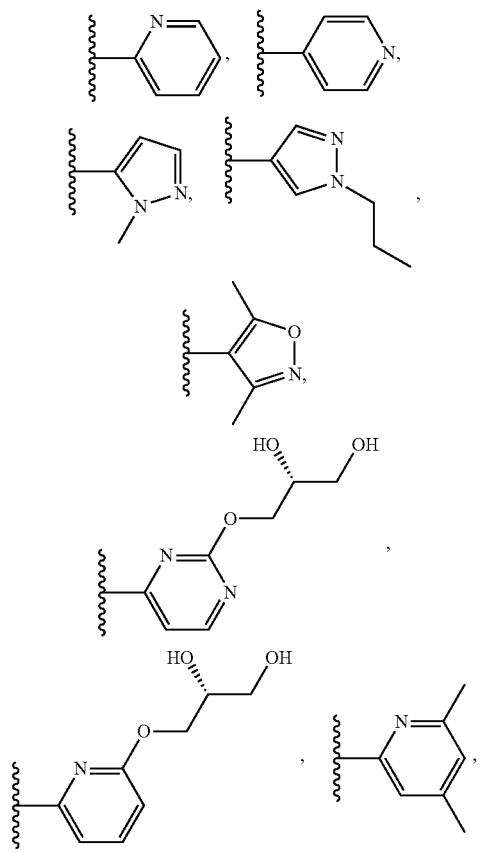

-continued
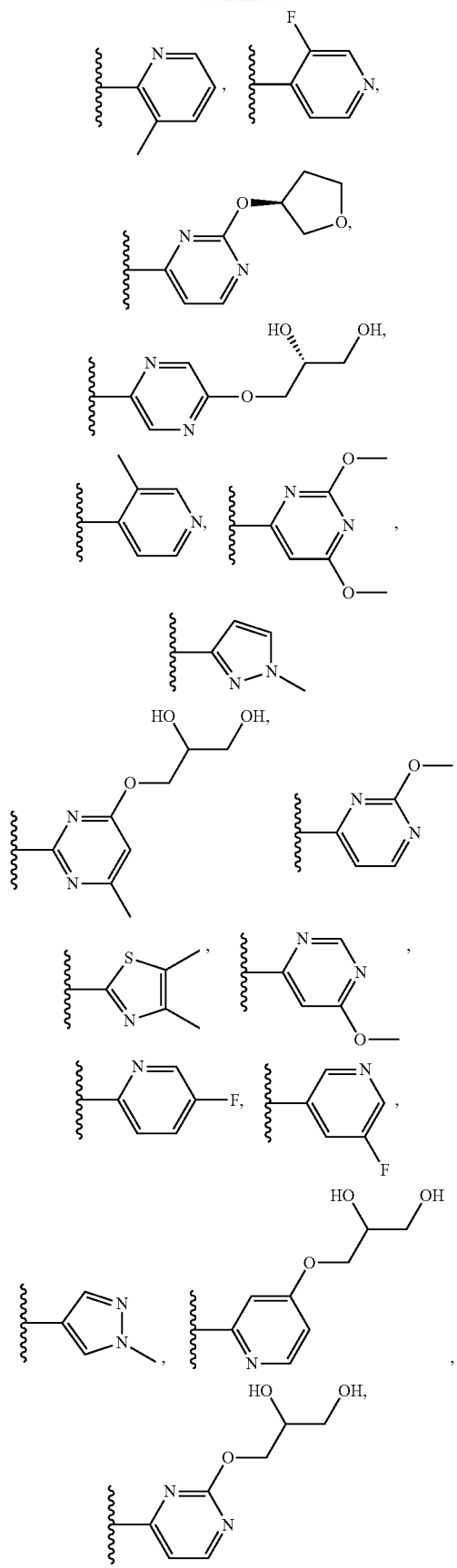
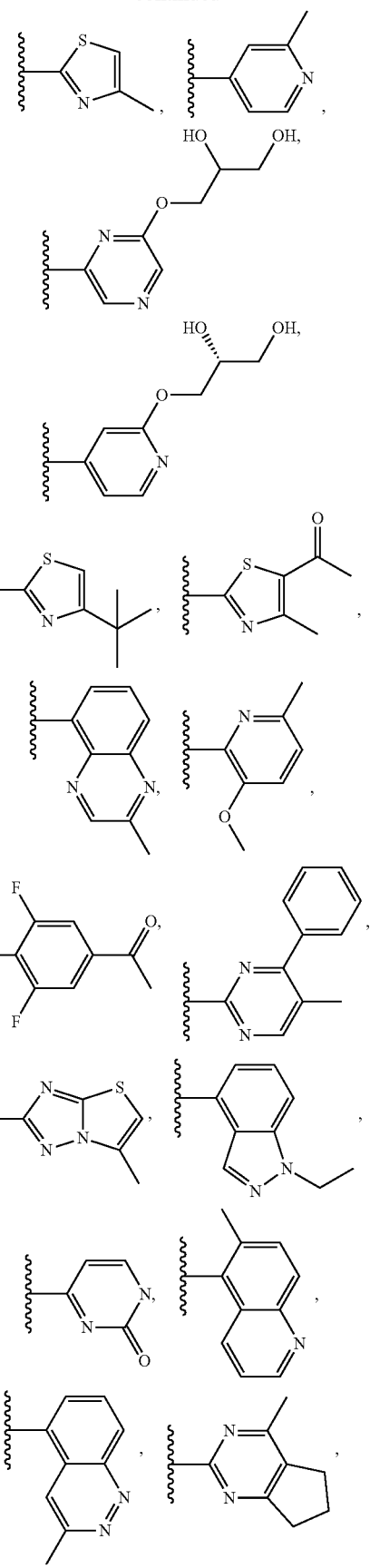

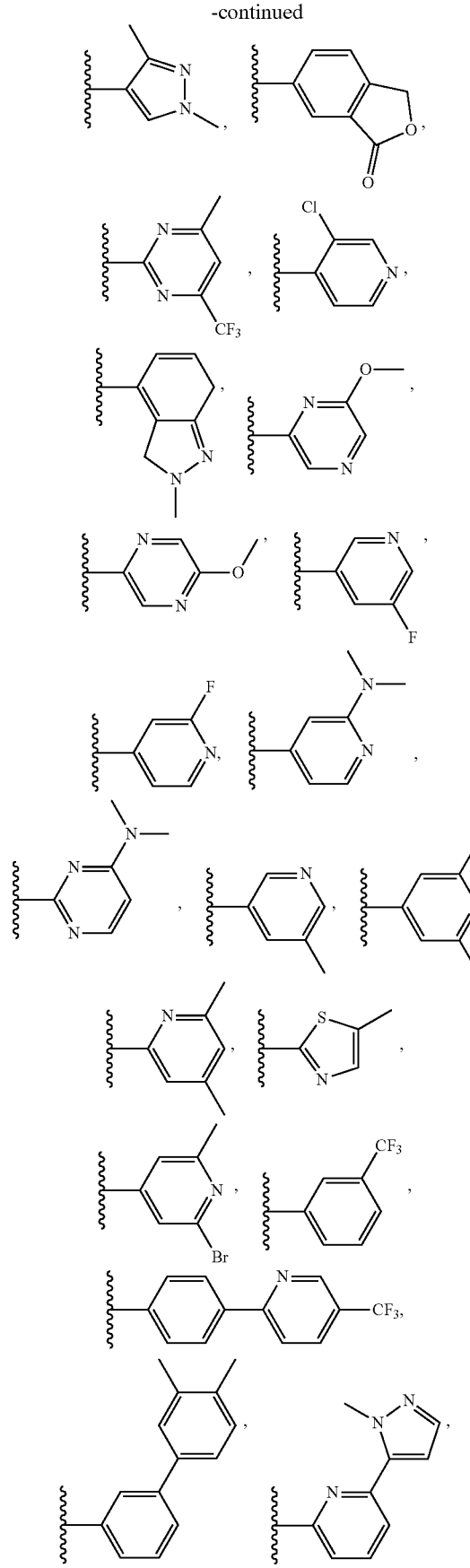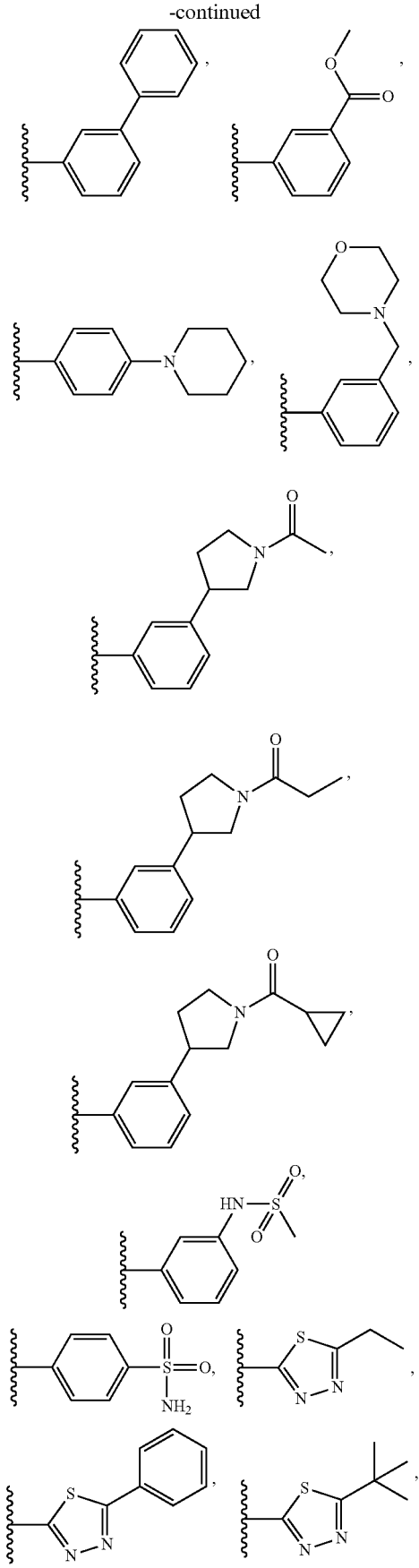

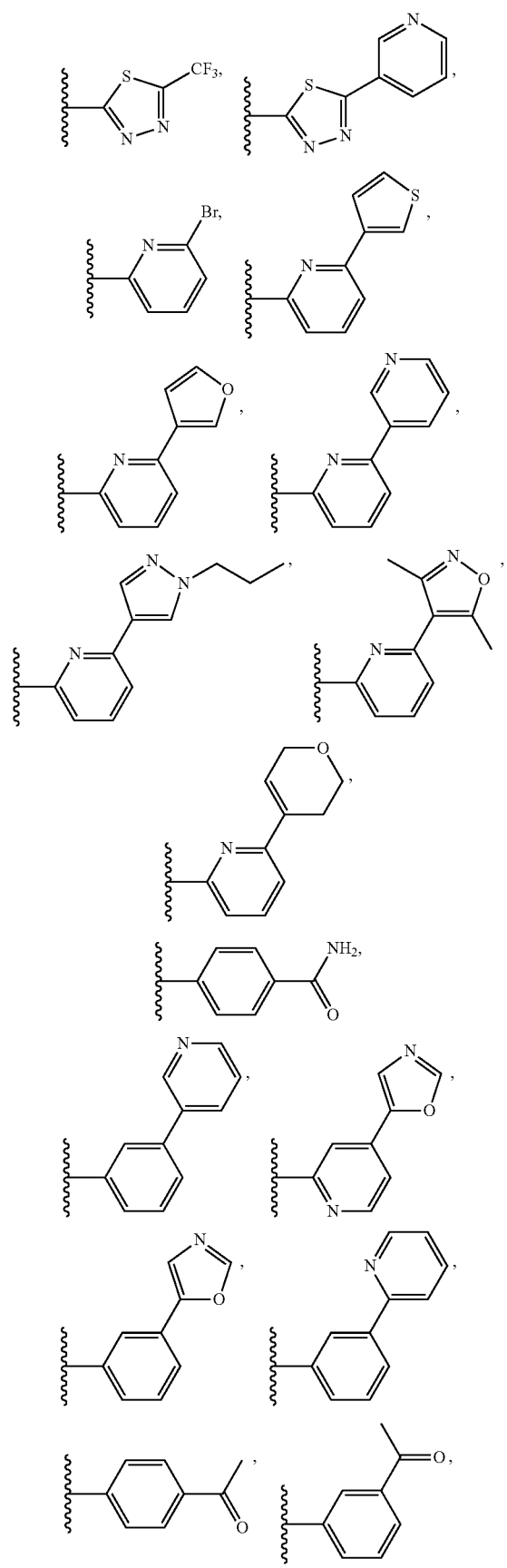

-continued
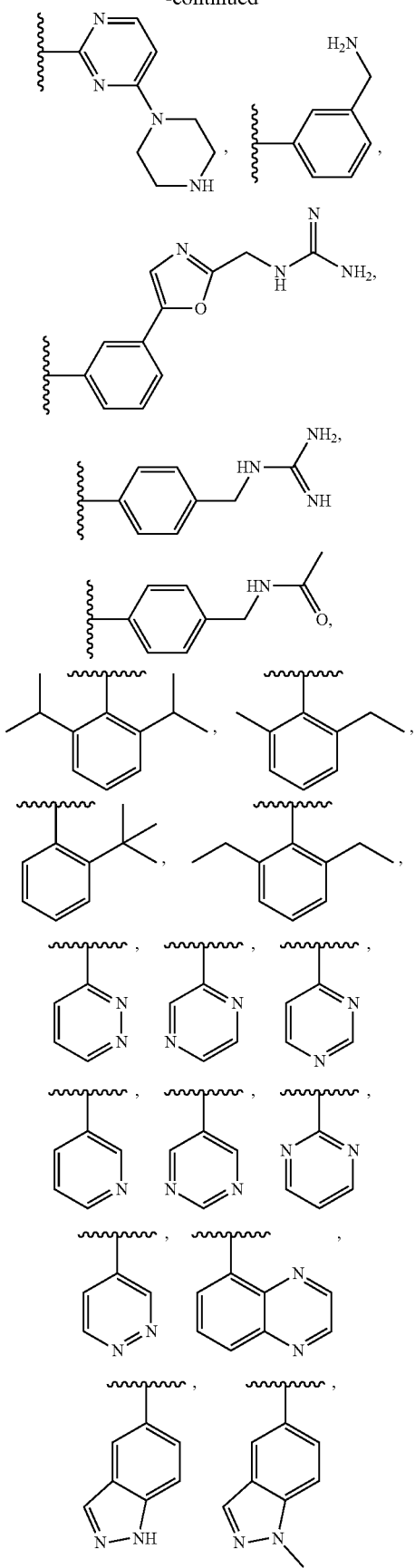
-continued
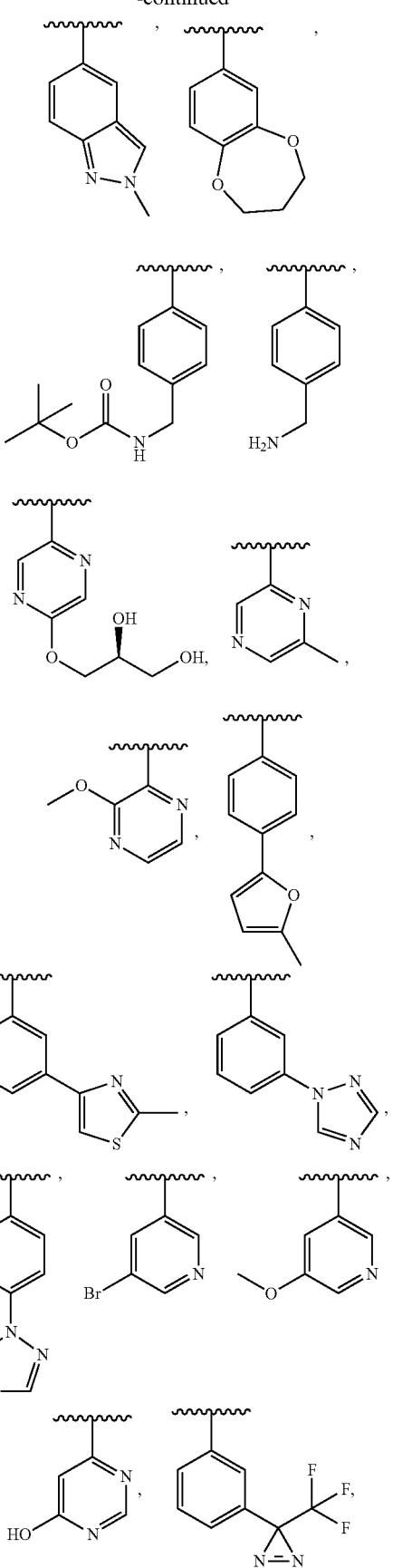

23
-continued
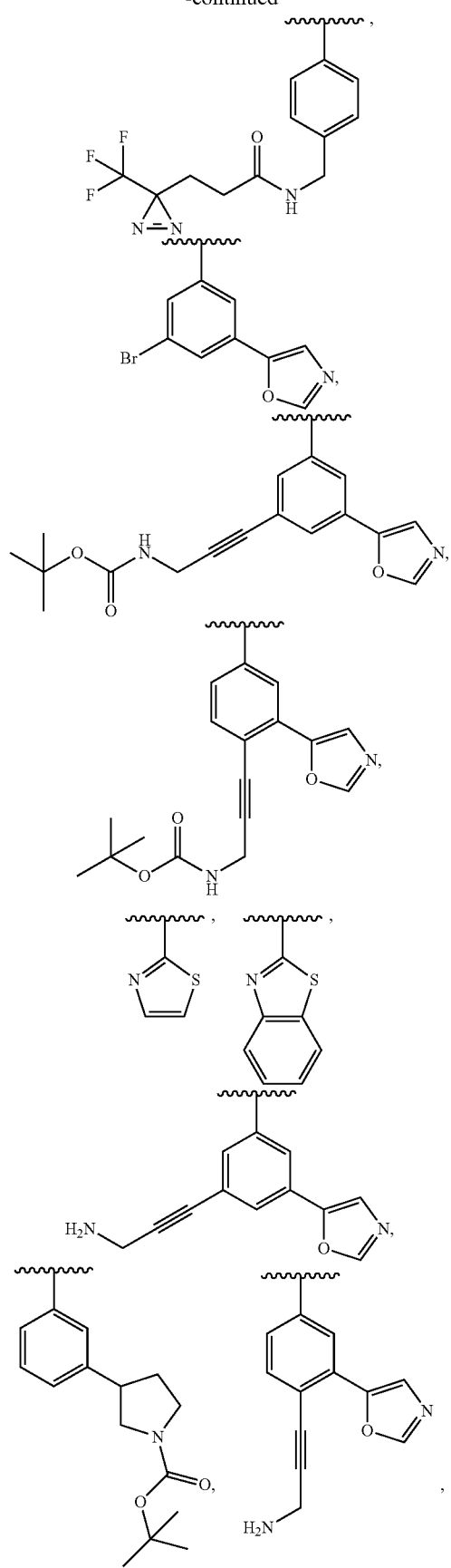
24
-continued
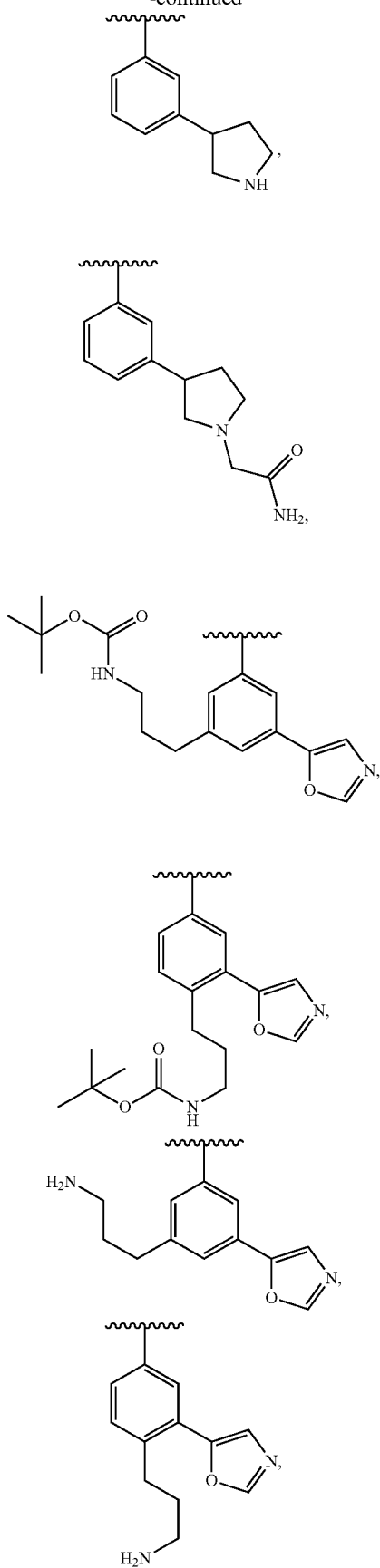

25
-continued
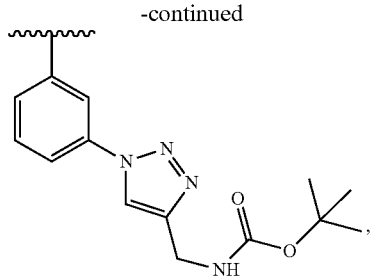
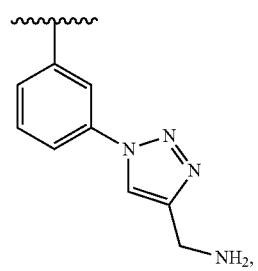
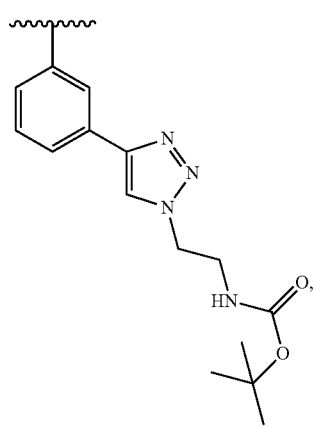
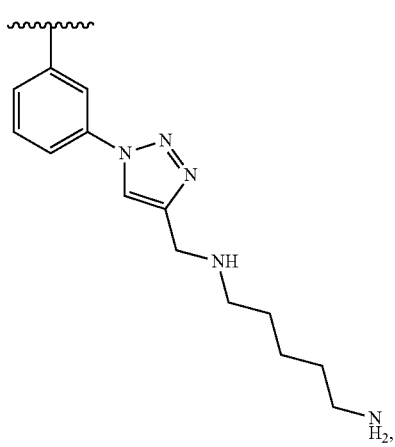
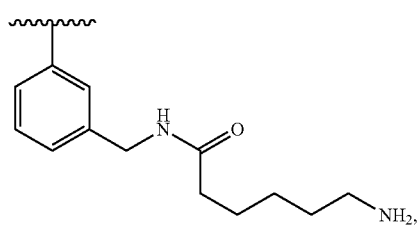
26
-continued
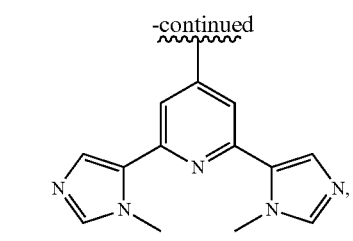
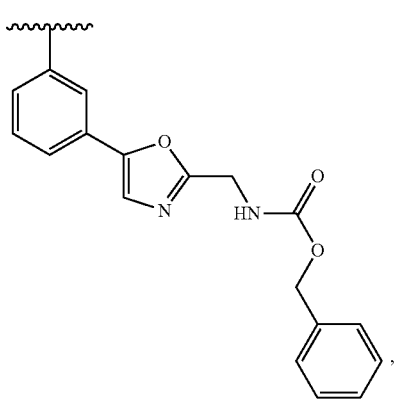
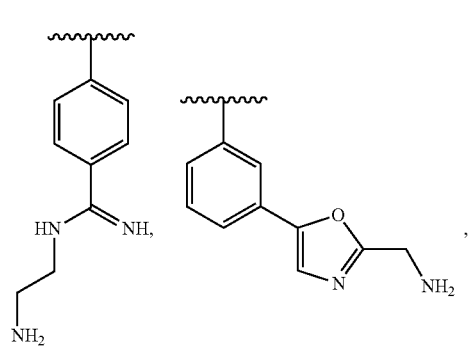
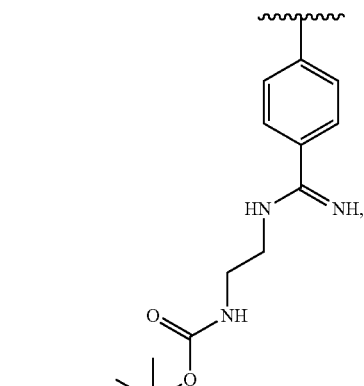
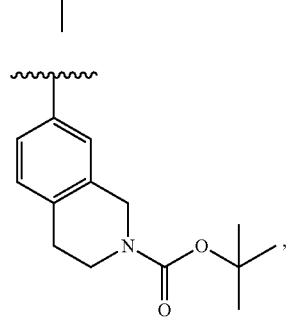

-continued

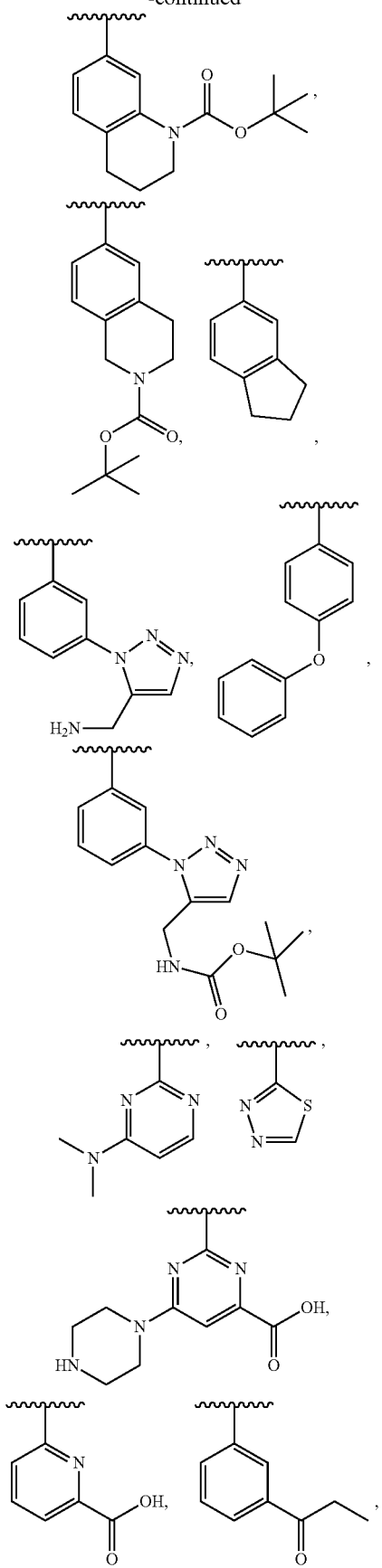

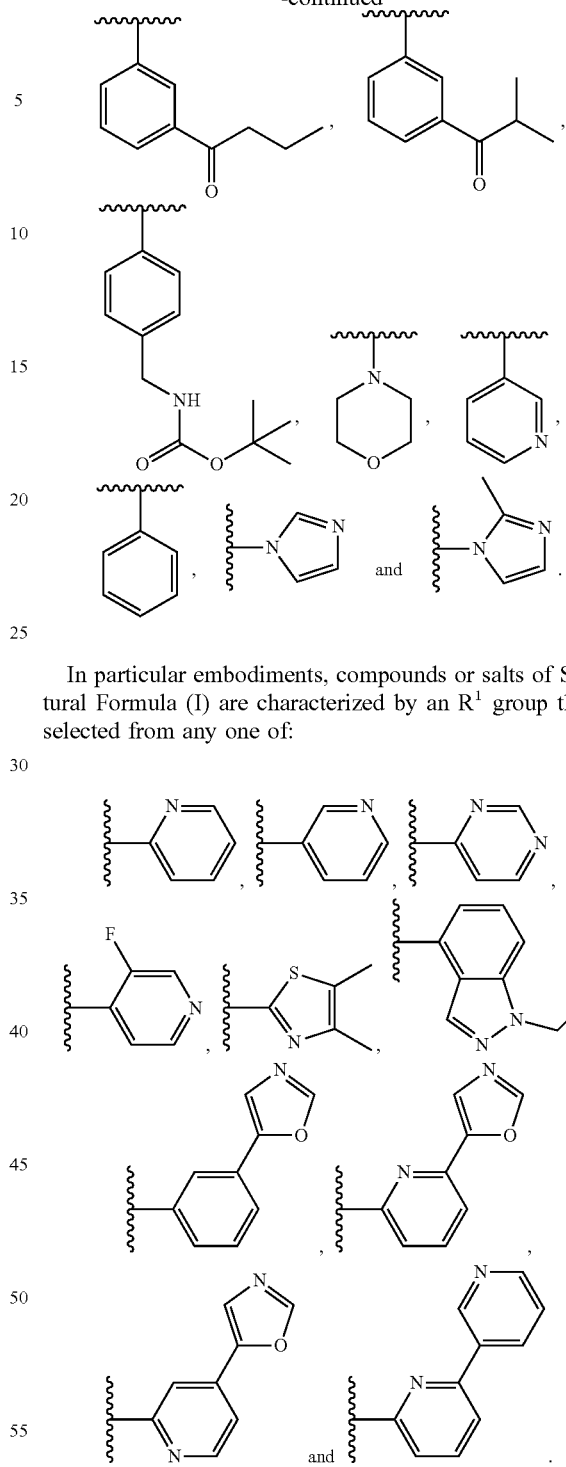

In particular embodiments, compounds or salts of Structural Formula (I) are characterized by an $R^1$ group that is selected from any one of:

In certain embodiments, compounds or salts of Structural Formula (I) are characterized by an $R^2$ group that is selected from a 5- to 7-membered saturated carbocycle or heterocycle, an N-linked heterocycle, and an 8- to 11-membered saturated or unsaturated heterocycle.

In particular embodiments, compounds or salts of Structural Formula (I) are characterized by an $R^2$ group that is an N-linked 5- to 7-membered saturated or unsaturated heterocycle.

In certain embodiments of the above, the compound is selected from any one of:

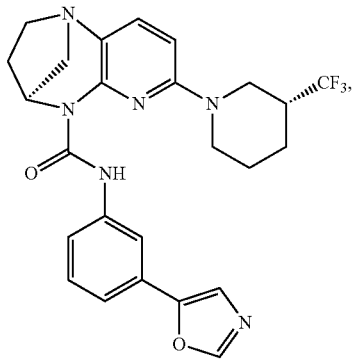

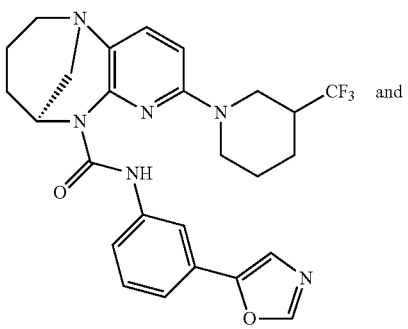

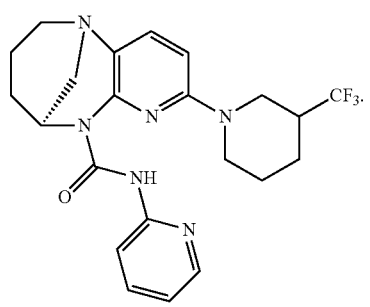

In certain embodiments, compounds or salts of Structural Formula (I) are characterized by an R² group that is a fused bicyclic 8- to 11-membered saturated or unsaturated heterocycle.

In certain embodiments of the above the compound is selected from any one of:

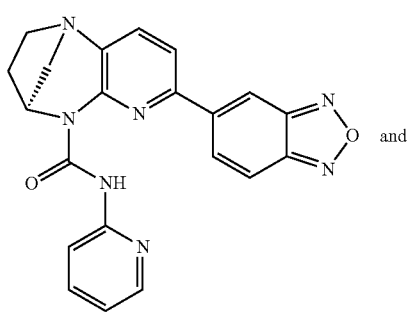

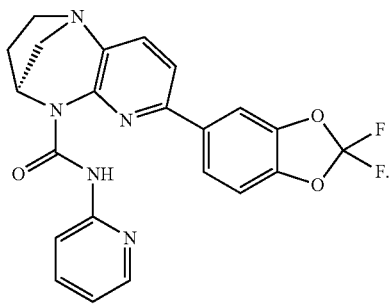

In certain embodiments, compounds or salts of Structural Formula (I) are characterized by an R² group that is selected from any one of:

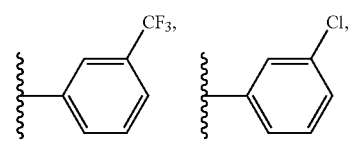

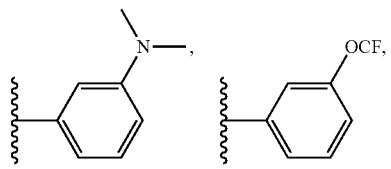

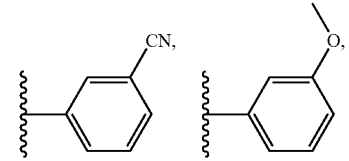

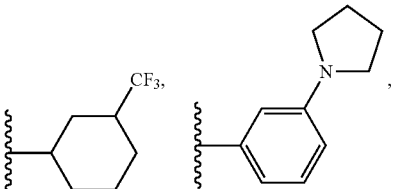

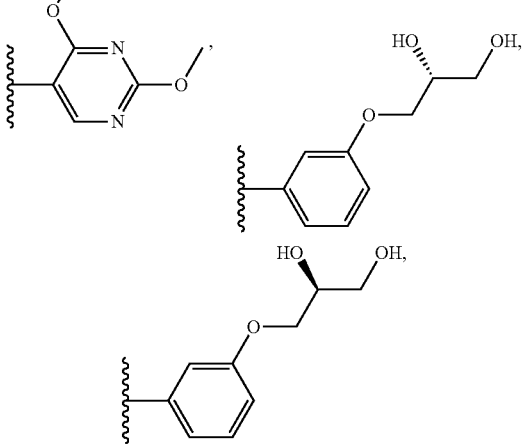

-continued
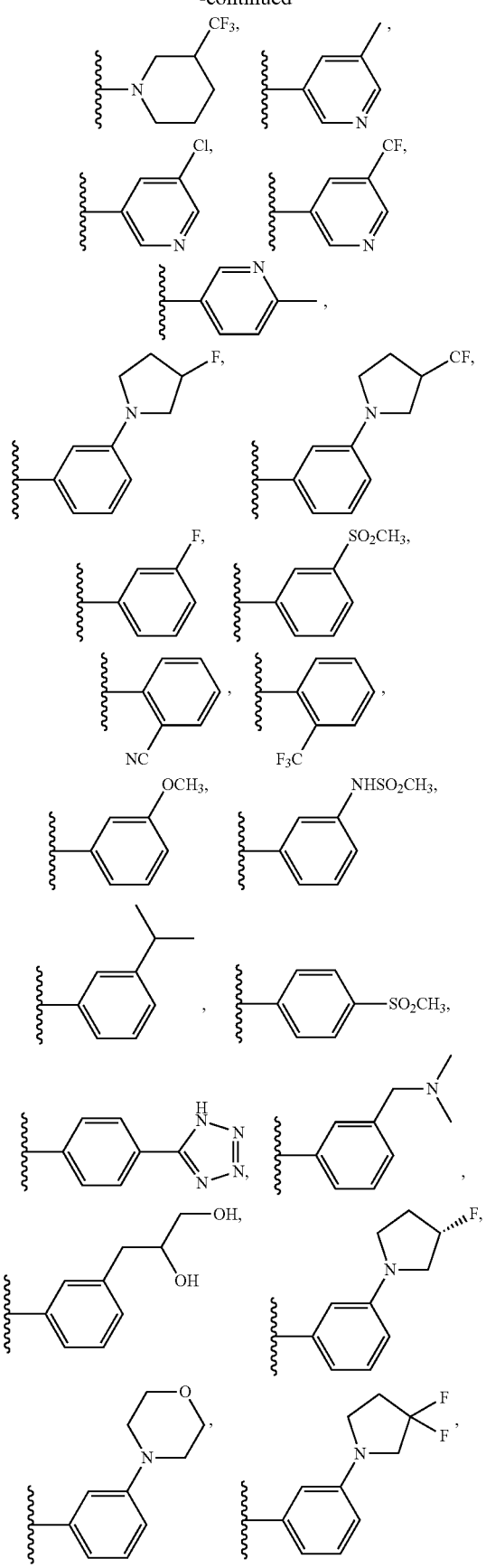
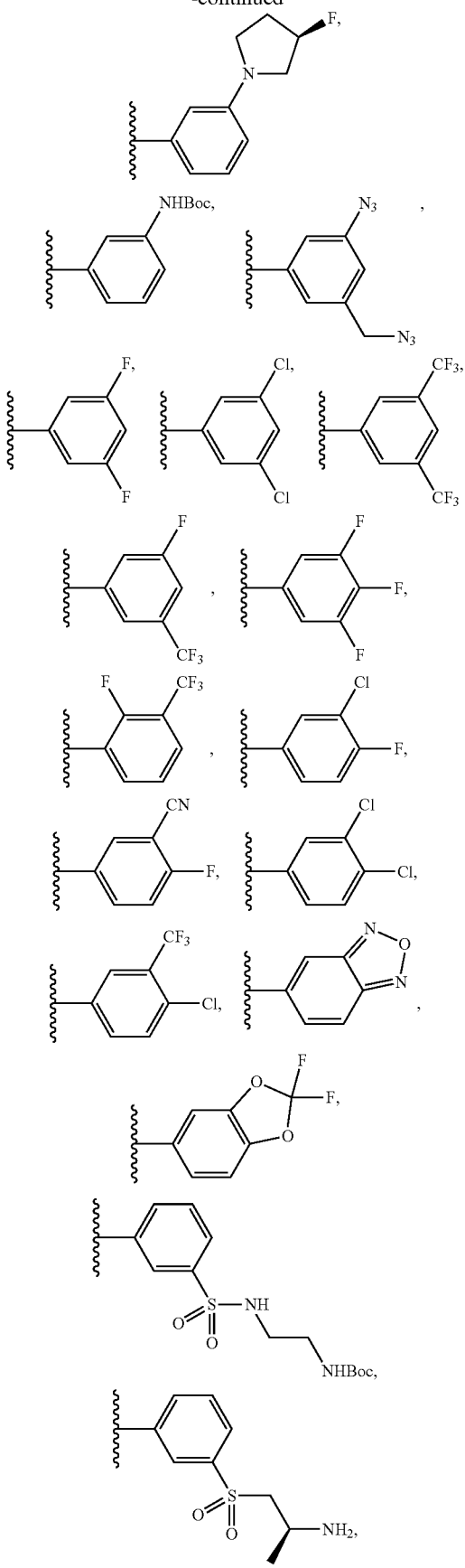

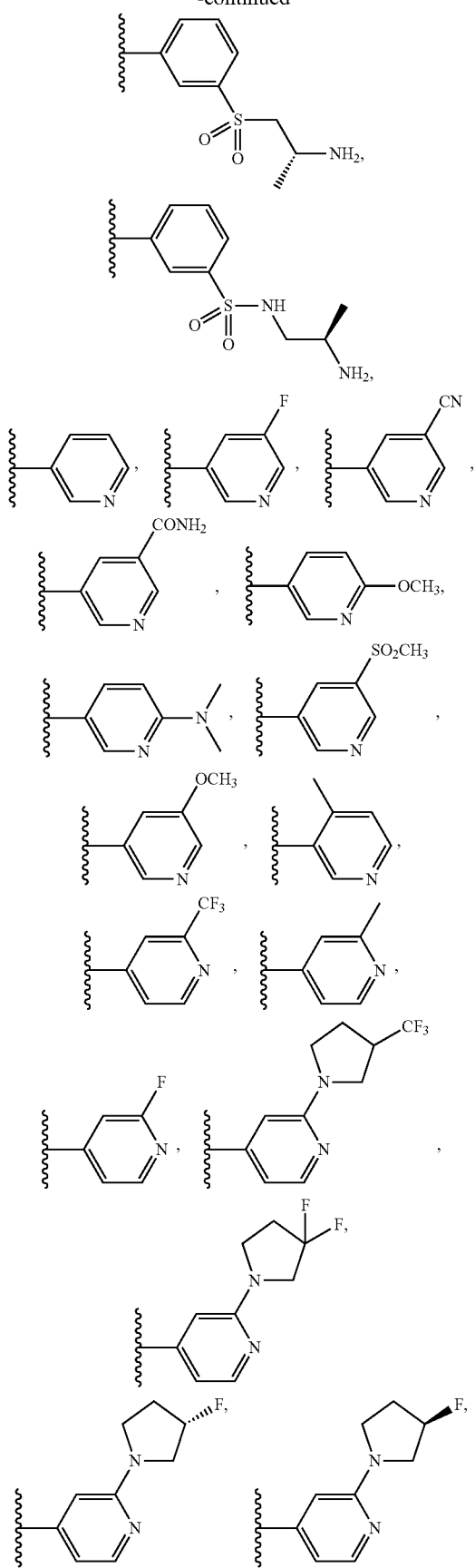
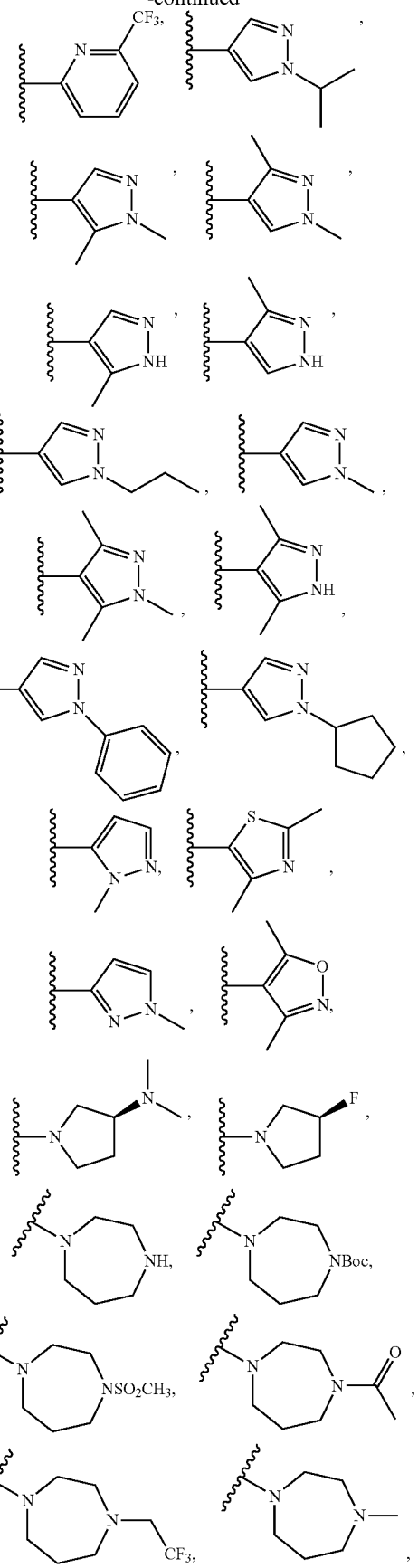

-continued
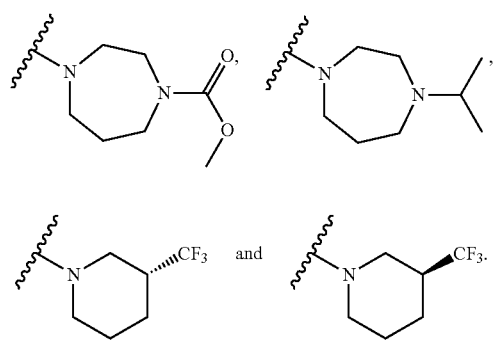
In particular embodiments, compounds or salts of Structural Formula (I) are characterized by an R² group that is selected from any one of:
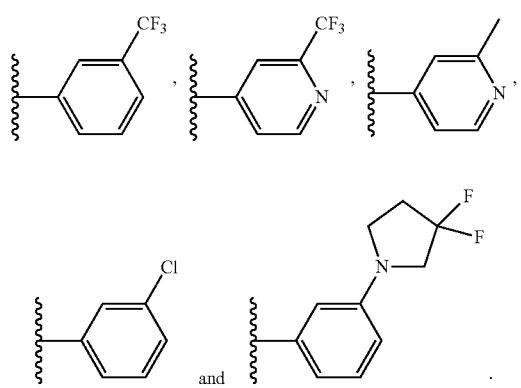
In certain embodiments, compounds or salts of Structural Formula (I) are selected from any one of:
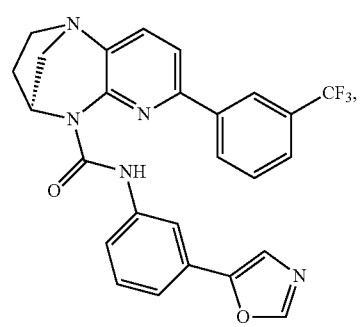
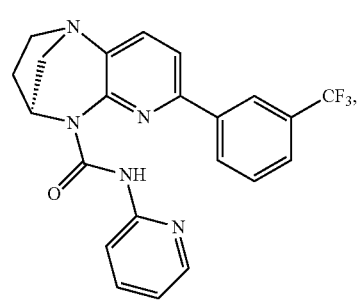
-continued
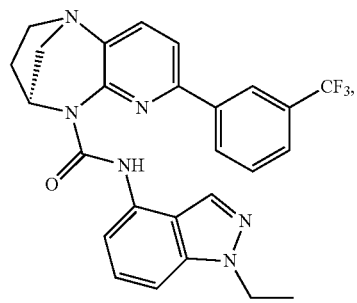
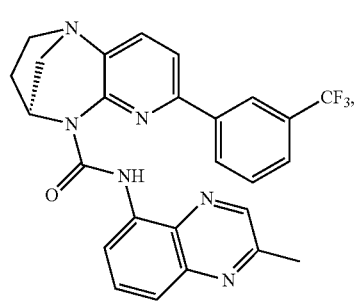
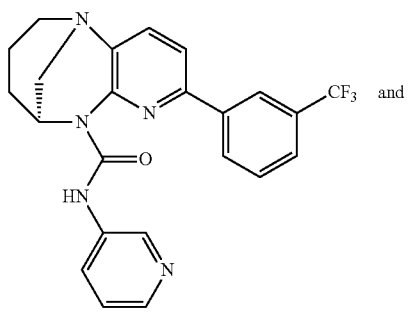
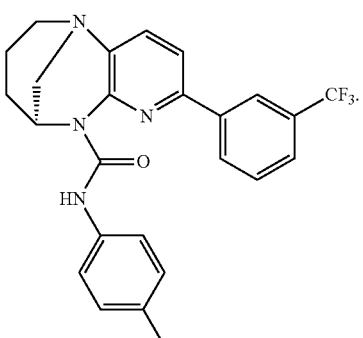
In certain embodiments, compounds or salts of Structural Formula (IIa) are selected from any one of:

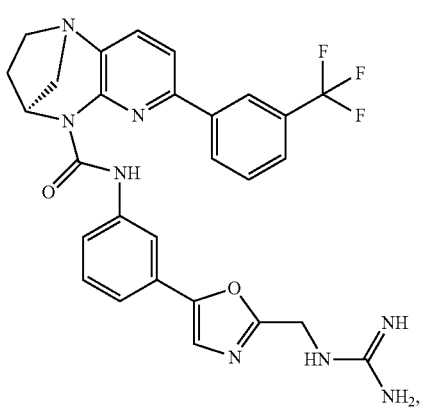
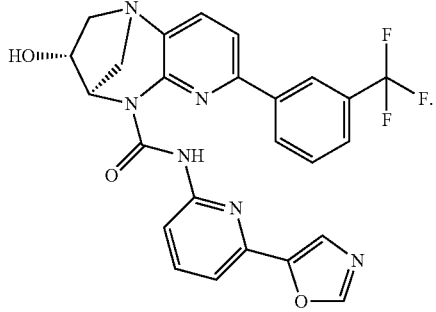
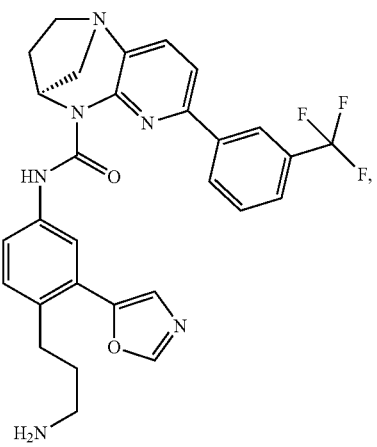
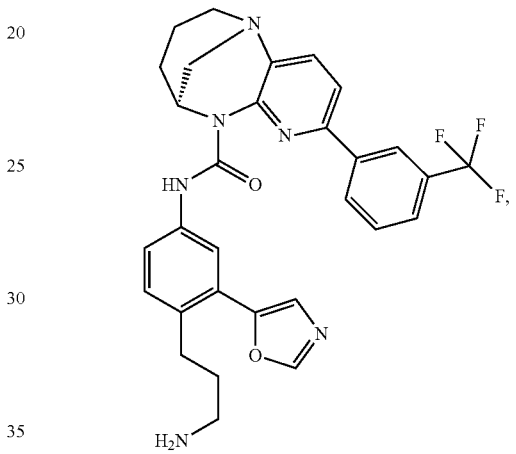
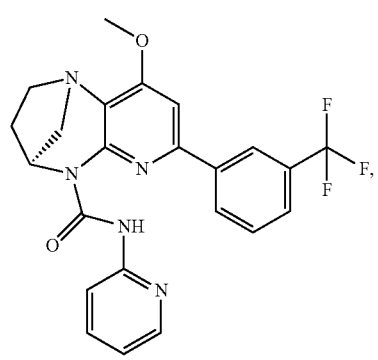
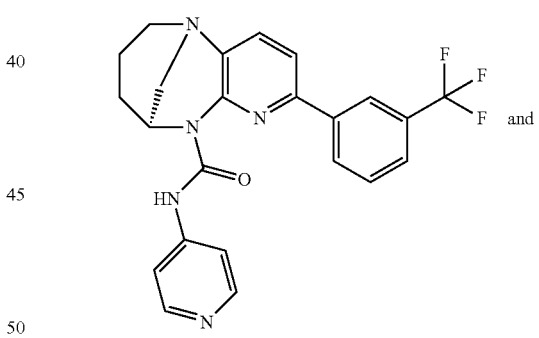
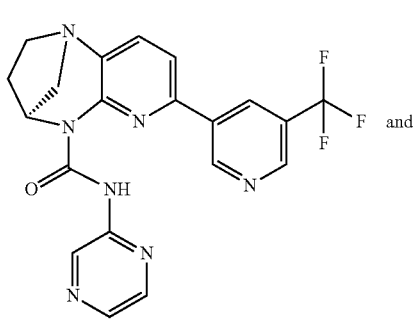
and
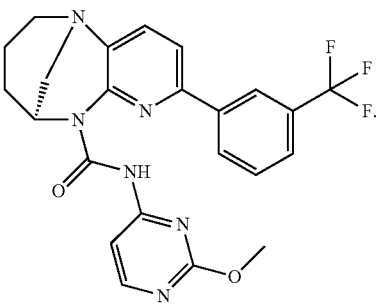
In certain embodiments, compounds or salts of Structural Formula (IIIa) are selected from any one of:
In certain embodiments, compounds or salts of Structural Formula (IIb) are selected from:

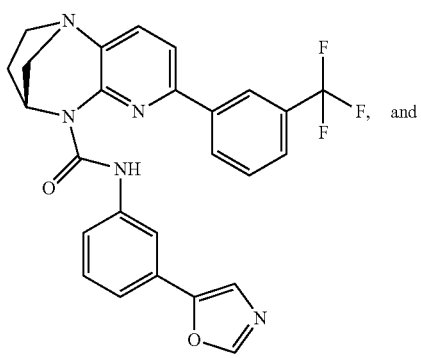

In certain embodiments, compounds or salts of Structural Formula (IIIb) are selected from:

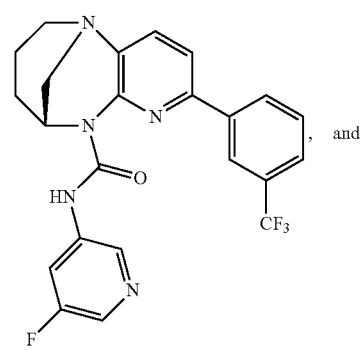

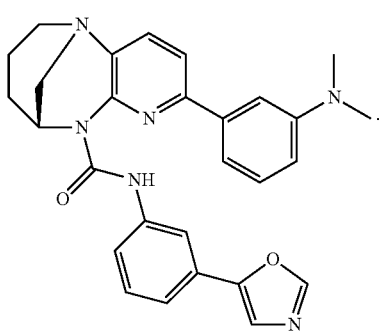

In certain embodiments, compounds or salts of Structural Formula (IV) are selected from any one of:

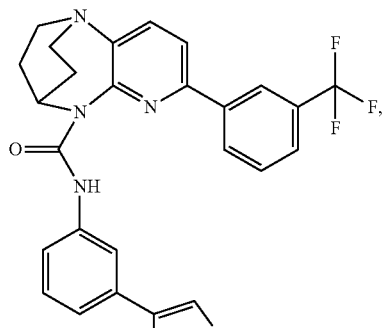

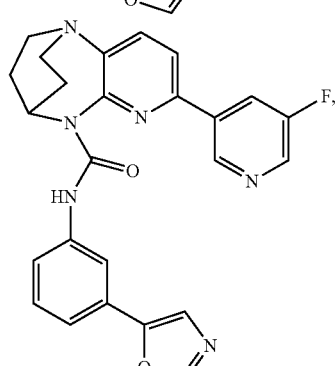

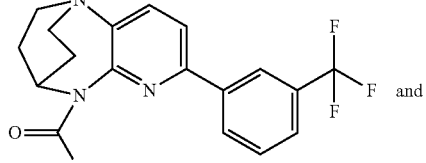

In other embodiments, representative compounds of the present invention are compound structures as exemplified or set forth in Table 1 and/or Table 10 (i.e., additional representative compound examples), respectively, or their corresponding pharmaceutically acceptable salts thereof as defined in the present specification.

Compounds of the invention, including novel compounds of the invention, can also be used in the pharmaceutical compositions and the methods described herein.

In any of the preceding embodiments, a $C_1$-$C_4$ alkoxy-substituted group may include one or more alkoxy substituents such as one, two or three methoxy groups or a methoxy group and an ethoxy group, for example. Exemplary $C_1$-$C_4$ alkoxy substituents include methoxy, ethoxy, isopropoxy, and tert-butoxy.

In any of the preceding embodiments, a hydroxy-substituted group may include one or more hydroxy substituents, such as two or three hydroxy groups.

In any of the preceding embodiments, a "halo-substituted" group includes from one halo substituent up to perhalo substitution. Exemplary halo-substituted $C_1$-$C_4$ alkyl includes $CFH_2$, $CClH_2$, $CBrH_2$, $CF_2H$, $CCl_2H$, $CBr_2H$, $CF_3$, $CCl_3$, $CBr_3$, $CH_2CH_2F$, $CH_2CH_2Cl$, $CH_2CH_2Br$, $CH_2CHF_2$, $CHFCH_3$, $CHClCH_3$, $CHBrCH_3$, $CF_2CHF_2$, $CF_2CHCl_2$, $CF_2CHBr_2$, $CH(CF_3)_2$, and $C(CF_3)_3$. Perhalo-substituted $C_1$-$C_4$ alkyl, for example, includes $CF_3$, $CCl_3$, $CBr_3$, $CF_2CF_3$, $CCl_2CF_3$ and $CBr_2CF_3$.

In any of the preceding embodiments, a "carbocycle" group may refer to a monocyclic carbocycle embodiment and/or a polycyclic carbocycle embodiment, such as a fused, bridged or bicyclic carbocycle embodiment. "Carbocycle" groups of the invention may further refer to an aromatic carbocycle embodiment and/or a non-aromatic carbocycle embodiment, or, in the case of polycyclic embodiments, a carbocycle having both one or more aromatic rings and/or one or more non-aromatic rings. Polycyclic carbocycle embodiments may be a bicyclic ring, a fused ring or a bridged bicycle. Non-limiting exemplary carbocycles include phenyl, cyclohexane, cyclopentane, or cyclohexene, amantadine, cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene, adamantane, decalin, naphthalene, 1,2,3,4-tetrahydronaphthalene, norbornane, decalin, spiropentane, memantine, biperiden, rimantadine, camphor, cholesterol, 4-phenylcyclcohexanol, bicyclo[4.2.0]octane, memantine and 4,5,6,7-tetrahydro-1H-indene and bicyclo[4.1.0]hept-3-ene.

In any of the preceding embodiments, a "heterocycle" group may refer to a monocyclic heterocycle embodiment and/or a polycyclic heterocycle embodiment, such as a fused, bridged or bicyclic heterocycle embodiment. "Heterocycle" groups of the invention may further refer to an aromatic heterocycle embodiment and/or a non-aromatic heterocycle embodiment, or, in the case of polycyclic embodiments, a heterocycle having both one or more aromatic rings and/or one or more non-aromatic rings. Polycyclic heterocycle embodiments may be a bicyclic ring, a fused ring or a bridged bicycle. Non-limiting exemplary heterocycles include pyridyl, pyrrolidine, piperidine, piperazine, pyrrolidine, morpholine, pyrimidine, benzofuran, indole, quinoline, lactones, lactams, benzodiazepine, indole, quinoline, purine, adenine, guanine, 4,5,6,7-tetrahydrobenzo[d]thiazole, hexamine and methenamine.

Certain compounds of the present invention may exist in particular geometric or stereoisomeric forms. The present invention contemplates all such compounds, including cis- and trans-isomers, (R)- and (S)-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

The compounds and salts thereof described herein can also be present as the corresponding hydrates (e.g., hemihydrate, monohydrate, dihydrate, trihydrate, tetrahydrate) or solvates. Suitable solvents for preparation of solvates and hydrates can generally be selected by a skilled artisan.

The compounds and salts thereof can be present in amorphous or crystalline (including co-crystalline and polymorph) forms.

Sirtuin-modulating compounds of the invention advantageously modulate the level and/or activity of a sirtuin protein, particularly the deacetylase activity of the sirtuin protein.

Separately or in addition to the above properties, certain sirtuin-modulating compounds of the invention do not substantially have one or more of the following activities: inhibition of PI3-kinase, inhibition of aldoreductase, inhibition of tyrosine kinase, transactivation of EGFR tyrosine kinase, coronary dilation, or spasmolytic activity, at concentrations of the compound that are effective for modulating the deacetylation activity of a sirtuin protein (e.g., such as a SIRT1 and/or a SIRT3 protein).

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_4$ straight chained or branched alkyl group is also referred to as a "lower alkyl" group.

The terms "alkenyl" ("alkene") and "alkynyl" ("alkyne") refer to unsaturated aliphatic groups analogous in length and possible substitution to the alkyl groups described above, but that contain at least one double or triple bond respectively.

The term "aromatic carbocycle" refers to an aromatic hydrocarbon ring system containing at least one aromatic ring. The ring may be fused or otherwise attached to other aromatic carbocyclic rings or non-aromatic carbocyclic rings. Examples of aromatic carbocycle groups include carbocyclic aromatic groups such as phenyl, naphthyl, and anthracyl.

"Azabicyclo" refers to a bicyclic molecule that contains a nitrogen atom in the ring skeleton. The two rings of the bicycle may be fused at two mutually bonded atoms, e.g., indole, across a sequence of atoms, e.g., azabicyclo[2.2.1]heptane, or joined at a single atom, e.g., spirocycle.

"Bicycle" or "bicyclic" refers to a two-ring system in which one, two or three or more atoms are shared between the two rings. Bicycle includes fused bicycles in which two adjacent atoms are shared by each of the two rings, e.g., decalin, indole. Bicycle also includes spiro bicycles in which two rings share a single atom, e.g., spiro[2.2]pentane, 1-oxa-6-azaspiro[3.4]octane. Bicycle further includes bridged bicycles in which at least three atoms are shared between two rings, e.g., norbornane.

"Bridged bicycle" compounds are bicyclic ring systems in which at least three atoms are shared by both rings of the system, i.e., they include at least one bridge of one or more atoms connecting two bridgehead atoms. Bridged azabicyclo refers to a bridged bicyclic molecule that contains a nitrogen atom in at least one of the rings.

The term "Boc" refers to a tert-butyloxycarbonyl group (a common amine protecting group).

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle"

includes 5-7 membered monocyclic and 8-12 membered bicyclic rings. Each ring of a bicyclic carbocycle may be selected from non-aromatic and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from non-aromaticaromatic rings. In an exemplary embodiment, an aromatic ring, e.g., phenyl, may be fused to a non-aromatic or aromatic ring, e.g., cyclohexane, cyclopentane, or cyclohexene. Any combination of non-aromtatic and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated (non-aromatic). Typically, a cycloalkyl group has from 3 to about 10 carbon atoms, more typically 3 to 8 carbon atoms unless otherwise defined. A "cycloalkenyl" group is a cyclic hydrocarbon containing one or more double bonds.

A "halogen" designates F, Cl, Br or I.

A "halogen-substitution" or "halo" substitution designates replacement of one or more hydrogens with F, Cl, Br or I.

The term "heteroaryl" or "aromatic heterocycle" includes substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" also includes ring systems having one or two rings wherein at least one of the rings is heteroaromatic, e.g., the other cyclic rings can be cycloalkyl, cycloalkenyl, cycloalkynyl, aromatic carbocycle, heteroaryl, and/or heterocyclyl. Heteroaryl groups include, for example, pyrrole, furan, thiophene, imidazole, oxazole, thiazole, pyrazole, pyridine, pyrazine, pyridazine, and pyrimidine.

The terms "heterocycle", and "heterocyclic", as used herein, refers to a non-aromatic or aromatic ring comprising one or more heteroatoms selected from, for example, N, O, B and S atoms, preferably N, O, or S. The term "heterocycle" includes both "aromatic heterocycles" and "non-aromatic heterocycles." Heterocycles include 4-7 membered monocyclic and 8-12 membered bicyclic rings. Heterocycle includes bicyclic molecules in which one, two or three or more atoms are shared between the two rings. Each ring of a bicyclic heterocycle may be selected from non-aromatic and aromatic rings. The term "fused heterocycle" refers to a bicyclic heterocycle in which each of the rings shares two adjacent atoms with the other ring. Each ring of a fused heterocycle may be selected from non-aromatic and aromatic rings. In an exemplary embodiment, an aromatic ring, e.g., pyridyl, may be fused to a non-aromatic or aromatic ring, e.g., cyclohexane, cyclopentane, pyrrolidine, 2,3-dihydrofuran or cyclohexene. "Heterocycle" groups include, for example, piperidine, piperazine, pyrrolidine, morpholine, pyrimidine, benzofuran, indole, quinoline, lactones, and lactams. Exemplary "fused heterocycles" include benzodiazepine, indole, quinoline, purine, and 4,5,6,7-tetrahydrobenzo[d]thiazole. "Heterocycles" may be substituted at any one or more positions capable of bearing a hydrogen atom.

"Monocyclic rings" include 5-7 membered aromatic carbocycle or heteroaryl, 3-7 membered cycloalkyl or cycloalkenyl, and 5-7 membered non-aromatic heterocyclyl. Exemplary monocyclic groups include substituted or unsubstituted heterocycles or carbocycles such as thiazolyl, oxazolyl, oxazinyl, thiazinyl, dithianyl, dioxanyl, isoxazolyl, isothiazolyl, triazolyl, furanyl, tetrahydrofuranyl, dihydrofuranyl, pyranyl, tetrazolyl, pyrazolyl, pyrazinyl, pyridazinyl, imidazolyl, pyridinyl, pyrrolyl, dihydropyrrolyl, pyrrolidinyl, piperidinyl, piperazinyl, pyrimidinyl, morpholinyl, tetrahydrothiophenyl, thiophenyl, cyclohexyl, cyclopentyl, cyclopropyl, cyclobutyl, cycloheptanyl, azetidinyl, oxetanyl, thiiranyl, oxiranyl, aziridinyl, and thiomorpholinyl.

As used herein, "substituted" means substituting a hydrogen atom in a structure with an atom or molecule other than hydrogen. A substitutable atom such as a "substitutable nitrogen" is an atom that bears a hydrogen atom in at least one resonance form. The hydrogen atom may be substituted for another atom or group such as a $CH_3$ or an OH group. For example, the nitrogen in a piperidine molecule is substitutable if the nitrogen is bound to a hydrogen atom. If, for example, the nitrogen of a piperidine is bound to an atom other than hydrogen, the nitrogen is not substitutable. An atom that is not capable of bearing a hydrogen atom in any resonance form is not substitutable.

Combinations of substituents and variables envisioned by this invention are only those that result in the formation of stable compounds. As used herein, the term "stable" refers to compounds that possess stability sufficient to allow manufacture and that maintain the integrity of the compound for a sufficient period of time to be useful for the purposes detailed herein.

The compounds disclosed herein also include partially and fully deuterated variants. In certain embodiments, deuterated variants may be used for kinetic studies. One of skill in the art can select the sites at which such deuterium atoms are present.

Also included in the present invention are salts, particularly pharmaceutically acceptable salts, of the compounds described herein. The compounds of the present invention that possess a sufficiently acidic, a sufficiently basic, or both functional groups, can react with any of a number of inorganic bases, and inorganic and organic acids, to form a salt. Alternatively, compounds that are inherently charged, such as those with quaternary nitrogen, can form a salt with an appropriate counterion (e.g., a halide such as bromide, chloride, or fluoride, particularly bromide).

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

According to another embodiment, the present invention provides methods of producing the above-defined compounds. The compounds may be synthesized using conventional techniques. Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis*, 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

In an exemplary embodiment, a therapeutic compound may traverse the cytoplasmic membrane of a cell. For example, a compound may have a cell-permeability of at least about 20%, 50%, 75%, 80%, 90% or 95%.

Compounds described herein may also have one or more of the following characteristics: the compound may be essentially non-toxic to a cell or subject; the compound may be an organic molecule or a small molecule of 2000 amu or less, 1000 amu or less; a compound may have a half-life under normal atmospheric conditions of at least about 30 days, 60 days, 120 days, 6 months or 1 year; the compound may have a half-life in solution of at least about 30 days, 60 days, 120 days, 6 months or 1 year; a compound may be more stable in solution than resveratrol by at least a factor of about 50%, 2 fold, 5 fold, 10 fold, 30 fold, 50 fold or 100 fold; a compound may promote deacetylation of the DNA repair factor Ku70; a compound may promote deacetylation of RelA/p65; a compound may increase general turnover rates and enhance the sensitivity of cells to TNF-induced apoptosis.

In certain embodiments, a sirtuin-modulating compound does not have any substantial ability to inhibit a histone deacetylase (HDAC) class I, and/or an HDAC class II at concentrations (e.g., in vivo) effective for modulating the deacetylase activity of the sirtuin. For instance, in preferred embodiments, the sirtuin-modulating compound is a sirtuin-modulating compound and is chosen to have an $EC_{50}$ for activating sirtuin deacetylase activity that is at least 5 fold less than the $EC_{50}$ for inhibition of an HDAC I and/or HDAC II, and even more preferably at least 10 fold, 100 fold or even 1000 fold less. Methods for assaying HDAC I and/or HDAC II activity are well known in the art and kits to perform such assays may be purchased commercially. See e.g., BioVision, Inc. (Mountain View, Calif.; world wide web at biovision.com) and Thomas Scientific (Swedesboro, N.J.; world wide web at tomassci.com).

In certain embodiments, a sirtuin-modulating compound does not have any substantial ability to modulate sirtuin homologs. In certain embodiments, an activator of a human sirtuin protein may not have any substantial ability to activate a sirtuin protein from lower eukaryotes, particularly yeast or human pathogens, at concentrations (e.g., in vivo) effective for activating the deacetylase activity of human sirtuin. For example, a sirtuin-modulating compound may be chosen to have an $EC_{50}$ for activating a human sirtuin, such as SIRT1 and/or SIRT3, deacetylase activity that is at least 5 fold less than the $EC_{50}$ for activating a yeast sirtuin, such as Sir2 (such as *Candida, S. cerevisiae*, etc.), and even more preferably at least 10 fold, 100 fold or even 1000 fold less. In another embodiment, an inhibitor of a sirtuin protein from lower eukaryotes, particularly yeast or human pathogens, does not have any substantial ability to inhibit a sirtuin protein from humans at concentrations (e.g., in vivo) effective for inhibiting the deacetylase activity of a sirtuin protein from a lower eukaryote. For example, a sirtuin-inhibiting compound may be chosen to have an $IC_{50}$ for inhibiting a human sirtuin, such as SIRT1 and/or SIRT3, deacetylase activity that is at least 5 fold less than the $IC_{50}$ for inhibiting a yeast sirtuin, such as Sir2 (such as *Candida, S. cerevisiae*, etc.), and even more preferably at least 10 fold, 100 fold or even 1000 fold less.

In certain embodiments, a sirtuin-modulating compound may have the ability to modulate one or more sirtuin protein homologs, such as, for example, one or more of human SIRT1, SIRT2, SIRT3, SIRT4, SIRT5, SIRT6, or SIRT7. In some embodiments, a sirtuin-modulating compound has the ability to modulate both a SIRT1 and a SIRT3 protein.

In other embodiments, a SIRT1 modulator does not have any substantial ability to modulate other sirtuin protein homologs, such as, for example, one or more of human SIRT2, SIRT3, SIRT4, SIRT5, SIRT6, or SIRT7, at concentrations (e.g., in vivo) effective for modulating the deacetylase activity of human SIRT1. For example, a sirtuin-modulating compound may be chosen to have an $ED_{50}$ for modulating human SIRT1 deacetylase activity that is at least 5 fold less than the $ED_{50}$ for modulating one or more of human SIRT2, SIRT3, SIRT4, SIRT5, SIRT6, or SIRT7, and even more preferably at least 10 fold, 100 fold or even 1000 fold less. In some embodiments, a SIRT1 modulator does not have any substantial ability to modulate a SIRT3 protein.

In other embodiments, a SIRT3 modulator does not have any substantial ability to modulate other sirtuin protein homologs, such as, for example, one or more of human SIRT1, SIRT2, SIRT4, SIRT5, SIRT6, or SIRT7, at concentrations (e.g., in vivo) effective for modulating the deacetylase activity of human SIRT3. For example, a sirtuin-modulating compound may be chosen to have an $ED_{50}$ for modulating human SIRT3 deacetylase activity that is at least 5 fold less than the $ED_{50}$ for modulating one or more of human SIRT1, SIRT2, SIRT4, SIRT5, SIRT6, or SIRT7, and even more preferably at least 10 fold, 100 fold or even 1000 fold less. In some embodiments, a SIRT3 modulator does not have any substantial ability to modulate a SIRT1 protein.

In certain embodiments, a sirtuin-modulating compound may have a binding affinity for a sirtuin protein of about $10^{-9}$M, $10^{-10}$M, $10^{-11}$M, $10^{-12}$M or less. A sirtuin-modulating compound may reduce (activator) or increase (inhibitor) the apparent Km of a sirtuin protein for its substrate or NAD$^+$ (or other cofactor) by a factor of at least about 2, 3, 4, 5, 10, 20, 30, 50 or 100. In certain embodiments, Km values are determined using the mass spectrometry assay described herein. Preferred activating compounds reduce the Km of a sirtuin for its substrate or cofactor to a greater extent than caused by resveratrol at a similar concentration or reduce the Km of a sirtuin for its substrate or cofactor similar to that caused by resveratrol at a lower concentration. A sirtuin-modulating compound may increase the Vmax of a sirtuin protein by a factor of at least about 2, 3, 4, 5, 10, 20, 30, 50 or 100. A sirtuin-modulating compound may have an ED$_{50}$ for modulating the deacetylase activity of a SIRT1 and/or SIRT3 protein of less than about 1 nM, less than about 10 nM, less than about 100 nM, less than about 1 µM, less than about 10 µM, less than about 100 µM, or from about 1-10 nM, from about 10-100 nM, from about 0.1-1 µM, from about 1-10 µM or from about 10-100 µM. A sirtuin-modulating compound may modulate the deacetylase activity of a SIRT1 and/or SIRT3 protein by a factor of at least about 5, 10, 20, 30, 50, or 100, as measured in a cellular assay or in a cell based assay. A sirtuin-modulating compound may cause at least about 10%, 30%, 50%, 80%, 2 fold, 5 fold, 10 fold, 50 fold or 100 fold greater induction of the deacetylase activity of a sirtuin protein relative to the same concentration of resveratrol. A sirtuin-modulating compound may have an ED$_{50}$ for modulating SIRT5 that is at least about 10 fold, 20 fold, 30 fold, 50 fold greater than that for modulating SIRT1 and/or SIRT3.

3. Exemplary Uses

In certain aspects, the invention provides methods for modulating the level and/or activity of a sirtuin protein and methods of use thereof.

In certain embodiments, the invention provides methods for using sirtuin-modulating compounds wherein the sirtuin-modulating compounds activate a sirtuin protein, e.g., increase the level and/or activity of a sirtuin protein. Sirtuin-modulating compounds that increase the level and/or activity of a sirtuin protein may be useful for a variety of therapeutic applications including, for example, increasing the lifespan of a cell, and treating and/or preventing a wide variety of diseases and disorders including, for example, diseases or disorders related to aging or stress, diabetes, obesity, neurodegenerative diseases, cardiovascular disease, blood clotting disorders, inflammation, cancer, and/or flushing, etc. The methods comprise administering to a subject in need thereof a pharmaceutically effective amount of a sirtuin-modulating compound, e.g., a sirtuin-modulating compound.

Based on the foregoing, the present invention may be used in the treatment of other diseases or disorders related to aging or stress, diabetes and other metabolic dysfunctions and related conditions including but not limited to fatty liver, hepatic steatohepatitis and obesity. The present invention may also be used in the treatment of neurodegenerative diseases, cardiovascular disease, cancer, inflammatory disease which includes but is not limited to psoriasis, atopic dermatitis, acne, rosacea, inflammatory bowel disease, osteoporosis, sepsis, arthritis, COPD, systemic lupus erythematosus and ophthalmic inflammation, as well as other diseases or disorders that result from diminished SIRT1 expression or activity.

Without wishing to be bound by theory, it is believed that activators of the instant invention may interact with a sirtuin at the same location within the sirtuin protein (e.g., active site or site affecting the Km or Vmax of the active site). It is believed that this is the reason why certain classes of sirtuin activators and inhibitors can have substantial structural similarity.

In certain embodiments, the sirtuin-modulating compounds described herein may be taken alone or in combination with other compounds. In certain embodiments, a mixture of two or more sirtuin-modulating compounds may be administered to a subject in need thereof.

In another embodiment, a sirtuin-modulating compound that increases the level and/or activity of a sirtuin protein may be administered with one or more of the following compounds: resveratrol, butein, fisetin, piceatannol, or quercetin. In an exemplary embodiment, a sirtuin-modulating compound that increases the level and/or activity of a sirtuin protein may be administered in combination with nicotinic acid or nicotinamide riboside.

In another embodiment, a sirtuin-modulating compound that decreases the level and/or activity of a sirtuin protein may be administered with one or more of the following compounds: nicotinamide (NAM), suramin; NF023 (a G-protein antagonist); NF279 (a purinergic receptor antagonist); Trolox (6-hydroxy-2,5,7,8,tetramethylchroman-2-carboxylic acid); (−)-epigallocatechin (hydroxy on sites 3,5,7, 3',4',5'); (−)-epigallocatechin gallate (Hydroxy sites 5,7,3', 4',5' and gallate ester on 3); cyanidin chloride (3,5,7,3',4'-pentahydroxyflavylium chloride); delphinidin chloride (3,5, 7,3',4',5'-hexahydroxyflavylium chloride); myricetin (cannabiscetin; 3,5,7,3',4',5'-hexahydroxyflavone); 3,7,3',4', 5'-pentahydroxyflavone; gossypetin (3,5,7,8,3',4'-hexahydroxyflavone), sirtinol; and splitomicin.

In yet another embodiment, one or more sirtuin-modulating compounds may be administered with one or more therapeutic agents for the treatment or prevention of various diseases, including, for example, cancer, diabetes, neurodegenerative diseases, cardiovascular disease, blood clotting, inflammation, flushing, obesity, aging, stress, etc. In various embodiments, combination therapies comprising a sirtuin-modulating compound may refer to (1) pharmaceutical compositions that comprise one or more sirtuin-modulating compounds in combination with one or more therapeutic agents (e.g., one or more therapeutic agents described herein); and (2) co-administration of one or more sirtuin-modulating compounds with one or more therapeutic agents wherein the sirtuin-modulating compound and therapeutic agent have not been formulated in the same compositions (but may be present within the same kit or package, such as a blister pack or other multi-chamber package; connected, separately sealed containers (e.g., foil pouches) that can be separated by the user; or a kit where the compound(s) and other therapeutic agent(s) are in separate vessels). When using separate formulations, the sirtuin-modulating compound may be administered simultaneous with, intermittent with, staggered with, prior to, subsequent to, or combinations thereof, the administration of another therapeutic agent.

In certain embodiments, methods for reducing, preventing or treating diseases or disorders using a compound described herein may also comprise increasing the protein level of a sirtuin, such as human SIRT1, SIRT2 and/or SIRT3, or homologs thereof. Increasing protein levels can be achieved by introducing into a cell one or more copies of a nucleic acid that encodes a sirtuin. For example, the level of a sirtuin can be increased in a mammalian cell by introducing into the mammalian cell a nucleic acid encoding the sirtuin, e.g., increasing the level of SIRT1 by introducing a nucleic acid encoding the amino acid sequence set forth in GenBank Accession No. NP_036370 and/or increasing the level of SIRT3 by introducing a nucleic acid encoding the amino acid sequence set forth in GenBank Accession No. AAH01042.

A nucleic acid that is introduced into a cell to increase the protein level of a sirtuin may encode a protein that is at least about 80%, 85%, 90%, 95%, 98%, or 99% identical to the sequence of a sirtuin, e.g., SIRT1 and/or SIRT3 protein. For example, the nucleic acid encoding the protein may be at least about 80%, 85%, 90%, 95%, 98%, or 99% identical to a nucleic acid encoding a SIRT1 (e.g. GenBank Accession No. NM_012238) and/or SIRT3 (e.g., GenBank Accession No. BC001042) protein. The nucleic acid may also be a nucleic acid that hybridizes, preferably under stringent hybridization conditions, to a nucleic acid encoding a wild-type sirtuin, e.g., SIRT1 and/or SIRT3 protein. Stringent hybridization conditions may include hybridization and a wash in 0.2×SSC at 65° C. When using a nucleic acid that encodes a protein that is different from a wild-type sirtuin protein, such as a protein that is a fragment of a wild-type sirtuin, the protein is preferably biologically active, e.g., is capable of deacetylation. It is only necessary to express in a cell a portion of the sirtuin that is biologically active. For example, a protein that differs from wild-type SIRT1 having GenBank Accession No. NP_036370, preferably contains the core structure thereof. The core structure sometimes refers to amino acids 62-293 of GenBank Accession No. NP_036370, which are encoded by nucleotides 237 to 932 of GenBank Accession No. NM_012238, which encompasses the NAD binding as well as the substrate binding domains. The core domain of SIRT1 may also refer to about amino acids 261 to 447 of GenBank Accession No. NP_036370, which are encoded by nucleotides 834 to 1394 of GenBank Accession No. NM_012238; to about amino acids 242 to 493 of GenBank Accession No. NP_036370, which are encoded by nucleotides 777 to 1532 of GenBank Accession No. NM_012238; or to about amino acids 254 to 495 of GenBank Accession No. NP_036370, which are encoded by nucleotides 813 to 1538 of GenBank Accession No. NM_012238. Whether a protein retains a biological function, e.g., deacetylation capabilities, can be determined according to methods known in the art.

In certain embodiments, methods for reducing, preventing or treating diseases or disorders using a sirtuin-modulating compound may also comprise decreasing the protein level of a sirtuin, such as human SIRT1, SIRT2 and/or SIRT3, or homologs thereof. Decreasing a sirtuin protein level can be achieved according to methods known in the art. For example, an siRNA, an antisense nucleic acid, or a ribozyme targeted to the sirtuin can be expressed in the cell. A dominant negative sirtuin mutant, e.g., a mutant that is not capable of deacetylating, may also be used. For example, mutant H363Y of SIRT1, described, e.g., in Luo et al. (2001) Cell 107:137 can be used. Alternatively, agents that inhibit transcription can be used.

Methods for modulating sirtuin protein levels also include methods for modulating the transcription of genes encoding sirtuins, methods for stabilizing/destabilizing the corresponding mRNAs, and other methods known in the art.

Aging/Stress

In one aspect, the invention provides a method extending the lifespan of a cell, extending the proliferative capacity of a cell, slowing aging of a cell, promoting the survival of a cell, delaying cellular senescence in a cell, mimicking the effects of calorie restriction, increasing the resistance of a cell to stress, or preventing apoptosis of a cell, by contacting the cell with a sirtuin-modulating compound of the invention that increases the level and/or activity of a sirtuin protein. In an exemplary embodiment, the methods comprise contacting the cell with a sirtuin-modulating compound.

The methods described herein may be used to increase the amount of time that cells, particularly primary cells (i.e., cells obtained from an organism, e.g., a human), may be kept alive in a cell culture. Embryonic stem (ES) cells and pluripotent cells, and cells differentiated therefrom, may also be treated with a sirtuin-modulating compound that increases the level and/or activity of a sirtuin protein to keep the cells, or progeny thereof, in culture for longer periods of time. Such cells can also be used for transplantation into a subject, e.g., after ex vivo modification.

In one aspect, cells that are intended to be preserved for long periods of time may be treated with a sirtuin-modulating compound that increases the level and/or activity of a sirtuin protein. The cells may be in suspension (e.g., blood cells, serum, biological growth media, etc.) or in tissues or organs. For example, blood collected from an individual for purposes of transfusion may be treated with a sirtuin-modulating compound that increases the level and/or activity of a sirtuin protein to preserve the blood cells for longer periods of time. Additionally, blood to be used for forensic purposes may also be preserved using a sirtuin-modulating compound that increases the level and/or activity of a sirtuin protein. Other cells that may be treated to extend their lifespan or protect against apoptosis include cells for consumption, e.g., cells from non-human mammals (such as meat) or plant cells (such as vegetables).

Sirtuin-modulating compounds that increase the level and/or activity of a sirtuin protein may also be applied during developmental and growth phases in mammals, plants, insects or microorganisms, in order to, e.g., alter, retard or accelerate the developmental and/or growth process.

In another aspect, sirtuin-modulating compounds that increase the level and/or activity of a sirtuin protein may be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated with the sirtuin-modulating compound prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically with a sirtuin-modulating compound or may have a subset of cells/tissue treated locally with a sirtuin-modulating compound that increases the level and/or activity of a sirtuin protein. In certain embodiments, the cells or tissue (or donor/recipient individuals) may additionally be treated with another therapeutic agent useful for prolonging graft survival, such as, for example, an immunosuppressive agent, a cytokine, an angiogenic factor, etc.

In yet other embodiments, cells may be treated with a sirtuin-modulating compound that increases the level and/or activity of a sirtuin protein in vivo, e.g., to increase their lifespan or prevent apoptosis. For example, skin can be protected from aging (e.g., developing wrinkles, loss of elasticity, etc.) by treating skin or epithelial cells with a sirtuin-modulating compound that increases the level and/or activity of a sirtuin protein. In an exemplary embodiment, skin is contacted with a pharmaceutical or cosmetic composition comprising a sirtuin-modulating compound that increases the level and/or activity of a sirtuin protein. Exemplary skin afflictions or skin conditions that may be treated in accordance with the methods described herein include disorders or diseases associated with or caused by inflammation, sun damage or natural aging. For example, the compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including pemphigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In another embodiment, sirtuin-modulating compounds that increase the level and/or activity of a sirtuin protein may be used for the treatment of wounds and/or burns to promote healing, including, for example, first-, second- or third-degree burns and/or thermal, chemical or electrical burns. The formulations may be administered topically, to the skin or mucosal tissue.

Topical formulations comprising one or more sirtuin-modulating compounds that increase the level and/or activity of a sirtuin protein may also be used as preventive, e.g., chemopreventive, compositions. When used in a chemopreventive method, susceptible skin is treated prior to any visible condition in a particular individual.

Sirtuin-modulating compounds may be delivered locally or systemically to a subject. In certain embodiments, a sirtuin-modulating compound is delivered locally to a tissue or organ of a subject by injection, topical formulation, etc.

In another embodiment, a sirtuin-modulating compound that increases the level and/or activity of a sirtuin protein may be used for treating or preventing a disease or condition induced or exacerbated by cellular senescence in a subject; methods for decreasing the rate of senescence of a subject, e.g., after onset of senescence; methods for extending the lifespan of a subject; methods for treating or preventing a disease or condition relating to lifespan; methods for treating or preventing a disease or condition relating to the proliferative capacity of cells; and methods for treating or preventing a disease or condition resulting from cell damage or death. In certain embodiments, the method does not act by decreasing the rate of occurrence of diseases that shorten the lifespan of a subject. In certain embodiments, a method does not act by reducing the lethality caused by a disease, such as cancer.

In yet another embodiment, a sirtuin-modulating compound that increases the level and/or activity of a sirtuin protein may be administered to a subject in order to generally increase the lifespan of its cells and to protect its cells against stress and/or against apoptosis. It is believed that treating a subject with a compound described herein is similar to subjecting the subject to hormesis, i.e., mild stress that is beneficial to organisms and may extend their lifespan.

Sirtuin-modulating compounds that increase the level and/or activity of a sirtuin protein may be administered to a subject to prevent aging and aging-related consequences or diseases, such as stroke, heart disease, heart failure, arthritis, high blood pressure, and Alzheimer's disease. Other conditions that can be treated include ocular disorders, e.g., associated with the aging of the eye, such as cataracts, glaucoma, and macular degeneration. Sirtuin-modulating compounds that increase the level and/or activity of a sirtuin protein can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amyotrophic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasia such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure or radiation exposure.

Sirtuin-modulating compounds that increase the level and/or activity of a sirtuin protein can also be administered to a subject suffering from an acute disease, e.g., damage to an organ or tissue, e.g., a subject suffering from stroke or myocardial infarction or a subject suffering from a spinal cord injury. Sirtuin-modulating compounds that increase the level and/or activity of a sirtuin protein may also be used to repair an alcoholic's liver.

Cardiovascular Disease

In another embodiment, the invention provides a method for treating and/or preventing a cardiovascular disease by administering to a subject in need thereof a sirtuin-modulating compound that increases the level and/or activity of a sirtuin protein.

Cardiovascular diseases that can be treated or prevented using the sirtuin-modulating compounds that increase the level and/or activity of a sirtuin protein include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable or preventable using compounds and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated or prevented include those related to platelet aggregation, the retinal arterioles, the glomerular arterioles, the vasa nervorum, cardiac arterioles, and associated capillary beds of the eye, the kidney, the heart, and the central and peripheral nervous systems. The sirtuin-modulating compounds that increase the level and/or activity of a sirtuin protein may also be used for increasing HDL levels in plasma of an individual.

Yet other disorders that may be treated with sirtuin-modulating compounds that increase the level and/or activity of a sirtuin protein include restenosis, e.g., following coronary intervention, and disorders relating to an abnormal level of high density and low density cholesterol.

In certain embodiments, a sirtuin-modulating compound that increases the level and/or activity of a sirtuin protein may be administered as part of a combination therapy with another cardiovascular agent. In certain embodiments, a sirtuin-modulating compound that increases the level and/or activity of a sirtuin protein may be administered as part of a combination therapy with an anti-arrhythmia agent. In another embodiment, a sirtuin-modulating compound that increases the level and/or activity of a sirtuin protein may be administered as part of a combination therapy with another cardiovascular agent.

Cell Death/Cancer

Sirtuin-modulating compounds that increase the level and/or activity of a sirtuin protein may be administered to subjects who have recently received or are likely to receive a dose of radiation or toxin. In certain embodiments, the dose of radiation or toxin is received as part of a work-related or medical procedure, e.g., administered as a prophylactic measure. In another embodiment, the radiation or toxin exposure is received unintentionally. In such a case, the compound is preferably administered as soon as possible after the exposure to inhibit apoptosis and the subsequent development of acute radiation syndrome.

Sirtuin-modulating compounds may also be used for treating and/or preventing cancer. In certain embodiments, sirtuin-modulating compounds that increase the level and/or activity of a sirtuin protein may be used for treating and/or preventing cancer. Calorie restriction has been linked to a reduction in the incidence of age-related disorders including cancer. Accordingly, an increase in the level and/or activity of a sirtuin protein may be useful for treating and/or preventing the incidence of age-related disorders, such as, for example, cancer. Exemplary cancers that may be treated using a sirtuin-modulating compound are those of the brain and kidney; hormone-dependent cancers including breast, prostate, testicular, and ovarian cancers; lymphomas, and leukemias. In cancers associated with solid tumors, a modulating compound may be administered directly into the tumor. Cancer of blood cells, e.g., leukemia, can be treated by administering a modulating compound into the blood stream or into the bone marrow. Benign cell growth, e.g., warts, can also be treated. Other diseases that can be treated include autoimmune diseases, e.g., systemic lupus erythematosus, scleroderma, and arthritis, in which autoimmune cells should be removed. Viral infections such as herpes, HIV, adenovirus, and HTLV-1 associated malignant and benign disorders can also be treated by administration of sirtuin-modulating compound. Alternatively, cells can be obtained from a subject, treated ex vivo to remove certain undesirable cells, e.g., cancer cells, and administered back to the same or a different subject.

Chemotherapeutic agents may be co-administered with modulating compounds described herein as having anti-cancer activity, e.g., compounds that induce apoptosis, compounds that reduce lifespan or compounds that render cells sensitive to stress.

Chemotherapeutic agents may be used by themselves with a sirtuin-modulating compound described herein as inducing cell death or reducing lifespan or increasing sensitivity to stress and/or in combination with other chemotherapeutics agents. In addition to conventional chemotherapeutics, the sirtuin-modulating compounds described herein may also be used with antisense RNA, RNAi or other polynucleotides to inhibit the expression of the cellular components that contribute to unwanted cellular proliferation.

Combination therapies comprising sirtuin-modulating compounds and a conventional chemotherapeutic agent may be advantageous over combination therapies known in the art because the combination allows the conventional chemotherapeutic agent to exert greater effect at lower dosage. In a preferred embodiment, the effective dose ($ED_{50}$) for a chemotherapeutic agent, or combination of conventional chemotherapeutic agents, when used in combination with a sirtuin-modulating compound is at least 2 fold less than the $ED_{50}$ for the chemotherapeutic agent alone, and even more preferably at 5 fold, 10 fold or even 25 fold less. Conversely, the therapeutic index (TI) for such chemotherapeutic agent or combination of such chemotherapeutic agent when used in combination with a sirtuin-modulating compound described herein can be at least 2 fold greater than the TI for conventional chemotherapeutic regimen alone, and even more preferably at 5 fold, 10 fold or even 25 fold greater.

Neuronal Diseases/Disorders

In certain aspects, sirtuin-modulating compounds that increase the level and/or activity of a sirtuin protein can be used to treat patients suffering from neurodegenerative diseases, and traumatic or mechanical injury to the central nervous system (CNS), spinal cord or peripheral nervous system (PNS). Neurodegenerative disease typically involves reductions in the mass and volume of the human brain, which may be due to the atrophy and/or death of brain cells, which are far more profound than those in a healthy person that are attributable to aging. Neurodegenerative diseases can evolve gradually, after a long period of normal brain function, due to progressive degeneration (e.g., nerve cell dysfunction and death) of specific brain regions. Alternatively, neurodegenerative diseases can have a quick onset, such as those associated with trauma or toxins. The actual onset of brain degeneration may precede clinical expression by many years. Examples of neurodegenerative diseases include, but are not limited to, Alzheimer's disease (AD), Parkinson's disease (PD), Huntington's disease (HD), amyotrophic lateral sclerosis (ALS; Lou Gehrig's disease), diffuse Lewy body disease, chorea-acanthocytosis, primary lateral sclerosis, ocular diseases (ocular neuritis), chemotherapy-induced neuropathies (e.g., from vincristine, paclitaxel, bortezomib), diabetes-induced neuropathies and Friedreich's ataxia. Sirtuin-modulating compounds that increase the level and/or activity of a sirtuin protein can be used to treat these disorders and others as described below.

AD is a CNS disorder that results in memory loss, unusual behavior, personality changes, and a decline in thinking abilities. These losses are related to the death of specific types of brain cells and the breakdown of connections and their supporting network (e.g. glial cells) between them. The earliest symptoms include loss of recent memory, faulty judgment, and changes in personality. PD is a CNS disorder that results in uncontrolled body movements, rigidity, tremor, and dyskinesia, and is associated with the death of brain cells in an area of the brain that produces dopamine. ALS (motor neuron disease) is a CNS disorder that attacks the motor neurons, components of the CNS that connect the brain to the skeletal muscles.

HD is another neurodegenerative disease that causes uncontrolled movements, loss of intellectual faculties, and emotional disturbance. Tay-Sachs disease and Sandhoff disease are glycolipid storage diseases where GM2 ganglioside and related glycolipids substrates for β-hexosaminidase accumulate in the nervous system and trigger acute neurodegeneration.

It is well-known that apoptosis plays a role in AIDS pathogenesis in the immune system. However, HIV-1 also induces neurological disease, which can be treated with sirtuin-modulating compounds of the invention.

Neuronal loss is also a salient feature of prion diseases, such as Creutzfeldt-Jakob disease in human, BSE in cattle (mad cow disease), Scrapie Disease in sheep and goats, and feline spongiform encephalopathy (FSE) in cats. Sirtuin-modulating compounds that increase the level and/or activity of a sirtuin protein may be useful for treating or preventing neuronal loss due to these prior diseases.

In another embodiment, a sirtuin-modulating compound that increases the level and/or activity of a sirtuin protein may be used to treat or prevent any disease or disorder involving axonopathy. Distal axonopathy is a type of peripheral neuropathy that results from some metabolic or toxic derangement of peripheral nervous system (PNS) neurons. It is the most common response of nerves to metabolic or toxic disturbances, and as such may be caused by metabolic diseases such as diabetes, renal failure, deficiency syndromes such as malnutrition and alcoholism, or the effects of toxins or drugs. Those with distal axonopathies usually present with symmetrical glove-stocking sensori-motor disturbances. Deep tendon reflexes and autonomic nervous system (ANS) functions are also lost or diminished in affected areas.

Diabetic neuropathies are neuropathic disorders that are associated with diabetes mellitus. Relatively common conditions which may be associated with diabetic neuropathy include third nerve palsy; mononeuropathy; mononeuritis multiplex; diabetic amyotrophy; a painful polyneuropathy; autonomic neuropathy; and thoracoabdominal neuropathy.

Peripheral neuropathy is the medical term for damage to nerves of the peripheral nervous system, which may be caused either by diseases of the nerve or from the side-effects of systemic illness. Major causes of peripheral neuropathy include seizures, nutritional deficiencies, and HIV, though diabetes is the most likely cause.

In an exemplary embodiment, a sirtuin-modulating compound that increases the level and/or activity of a sirtuin protein may be used to treat or prevent multiple sclerosis (MS), including relapsing MS and monosymptomatic MS, and other demyelinating conditions, such as, for example, chronic inflammatory demyelinating polyneuropathy (CIDP), or symptoms associated therewith.

In yet another embodiment, a sirtuin-modulating compound that increases the level and/or activity of a sirtuin protein may be used to treat trauma to the nerves, including, trauma due to disease, injury (including surgical intervention), or environmental trauma (e.g., neurotoxins, alcoholism, etc.).

Sirtuin-modulating compounds that increase the level and/or activity of a sirtuin protein may also be useful to prevent, treat, and alleviate symptoms of various PNS disorders. The term "peripheral neuropathy" encompasses a wide range of disorders in which the nerves outside of the brain and spinal cord—peripheral nerves—have been damaged. Peripheral neuropathy may also be referred to as peripheral neuritis, or if many nerves are involved, the terms polyneuropathy or polyneuritis may be used.

PNS diseases treatable with sirtuin-modulating compounds that increase the level and/or activity of a sirtuin protein include: diabetes, leprosy, Charcot-Marie-Tooth disease, Guillain-Barré syndrome and Brachial Plexus Neuropathies (diseases of the cervical and first thoracic roots, nerve trunks, cords, and peripheral nerve components of the brachial plexus.

In another embodiment, a sirtuin-modulating compound may be used to treat or prevent a polyglutamine disease. Exemplary polyglutamine diseases include Spinobulbar muscular atrophy (Kennedy disease), Huntington's Disease (HD), Dentatorubral-pallidoluysian atrophy (Haw River syndrome), Spinocerebellar ataxia type 1, Spinocerebellar ataxia type 2, Spinocerebellar ataxia type 3 (Machado-Joseph disease), Spinocerebellar ataxia type 6, Spinocerebellar ataxia type 7, and Spinocerebellar ataxia type 17.

In certain embodiments, the invention provides a method to treat a central nervous system cell to prevent damage in response to a decrease in blood flow to the cell. Typically the severity of damage that may be prevented will depend in large part on the degree of reduction in blood flow to the cell and the duration of the reduction. In certain embodiments, apoptotic or necrotic cell death may be prevented. In still a further embodiment, ischemic-mediated damage, such as cytotoxic edema or central nervous system tissue anoxemia, may be prevented. In each embodiment, the central nervous system cell may be a spinal cell or a brain cell.

Another aspect encompasses administrating a sirtuin-modulating compound to a subject to treat a central nervous system ischemic condition. A number of central nervous system ischemic conditions may be treated by the sirtuin-modulating compounds described herein. In certain embodiments, the ischemic condition is a stroke that results in any type of ischemic central nervous system damage, such as apoptotic or necrotic cell death, cytotoxic edema or central nervous system tissue anoxia. The stroke may impact any area of the brain or be caused by any etiology commonly known to result in the occurrence of a stroke. In one alternative of this embodiment, the stroke is a brain stem stroke. In another alternative of this embodiment, the stroke is a cerebellar stroke. In still another embodiment, the stroke is an embolic stroke. In yet another alternative, the stroke may be a hemorrhagic stroke. In a further embodiment, the stroke is a thrombotic stroke.

In yet another aspect, a sirtuin-modulating compound may be administered to reduce infarct size of the ischemic core following a central nervous system ischemic condition. Moreover, a sirtuin-modulating compound may also be beneficially administered to reduce the size of the ischemic penumbra or transitional zone following a central nervous system ischemic condition.

In certain embodiments, a combination drug regimen may include drugs or compounds for the treatment or prevention of neurodegenerative disorders or secondary conditions associated with these conditions. Thus, a combination drug regimen may include one or more sirtuin activators and one or more anti-neurodegeneration agents.

Blood Coagulation Disorders

In other aspects, sirtuin-modulating compounds that increase the level and/or activity of a sirtuin protein can be used to treat or prevent blood coagulation disorders (or hemostatic disorders). As used interchangeably herein, the terms "hemostasis", "blood coagulation," and "blood clotting" refer to the control of bleeding, including the physiological properties of vasoconstriction and coagulation. Blood coagulation assists in maintaining the integrity of mammalian circulation after injury, inflammation, disease, congenital defect, dysfunction or other disruption. Further, the formation of blood clots does not only limit bleeding in case of an injury (hemostasis), but may lead to serious organ damage and death in the context of atherosclerotic diseases by occlusion of an important artery or vein. Thrombosis is thus blood clot formation at the wrong time and place.

Accordingly, the present invention provides anticoagulation and antithrombotic treatments aiming at inhibiting the formation of blood clots in order to prevent or treat blood coagulation disorders, such as myocardial infarction, stroke, loss of a limb by peripheral artery disease or pulmonary embolism.

As used interchangeably herein, "modulating or modulation of hemostasis" and "regulating or regulation of hemostasis" includes the induction (e.g., stimulation or increase) of hemostasis, as well as the inhibition (e.g., reduction or decrease) of hemostasis.

In one aspect, the invention provides a method for reducing or inhibiting hemostasis in a subject by administering a sirtuin-modulating compound that increases the level and/or activity of a sirtuin protein. The compositions and methods disclosed herein are useful for the treatment or prevention of thrombotic disorders. As used herein, the term "thrombotic disorder" includes any disorder or condition characterized by excessive or unwanted coagulation or hemostatic activity, or a hypercoagulable state. Thrombotic disorders include diseases or disorders involving platelet adhesion and thrombus formation, and may manifest as an increased propensity to form thromboses, e.g., an increased number of thromboses, thrombosis at an early age, a familial tendency towards thrombosis, and thrombosis at unusual sites.

In another embodiment, a combination drug regimen may include drugs or compounds for the treatment or prevention of blood coagulation disorders or secondary conditions associated with these conditions. Thus, a combination drug regimen may include one or more sirtuin-modulating compounds that increase the level and/or activity of a sirtuin protein and one or more anti-coagulation or anti-thrombosis agents.

Weight Control

In another aspect, sirtuin-modulating compounds that increase the level and/or activity of a sirtuin protein may be used for treating or preventing weight gain or obesity in a subject. For example, sirtuin-modulating compounds that increase the level and/or activity of a sirtuin protein may be used, for example, to treat or prevent hereditary obesity, dietary obesity, hormone related obesity, obesity related to the administration of medication, to reduce the weight of a subject, or to reduce or prevent weight gain in a subject. A subject in need of such a treatment may be a subject who is obese, likely to become obese, overweight, or likely to become overweight. Subjects who are likely to become obese or overweight can be identified, for example, based on family history, genetics, diet, activity level, medication intake, or various combinations thereof.

In yet other embodiments, sirtuin-modulating compounds that increase the level and/or activity of a sirtuin protein may be administered to subjects suffering from a variety of other diseases and conditions that may be treated or prevented by promoting weight loss in the subject. Such diseases include, for example, high blood pressure, hypertension, high blood cholesterol, dyslipidemia, type 2 diabetes, insulin resistance, glucose intolerance, hyperinsulinemia, coronary heart disease, angina pectoris, congestive heart failure, stroke, gallstones, cholecystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), bladder control problems (such as stress incontinence); uric acid nephrolithiasis; psychological disorders (such as depression, eating disorders, distorted body image, and low self-esteem). Finally, patients with AIDS can develop lipodystrophy or insulin resistance in response to combination therapies for AIDS.

In another embodiment, sirtuin-modulating compounds that increase the level and/or activity of a sirtuin protein may be used for inhibiting adipogenesis or fat cell differentiation, whether in vitro or in vivo. Such methods may be used for treating or preventing obesity.

In other embodiments, sirtuin-modulating compounds that increase the level and/or activity of a sirtuin protein may be used for reducing appetite and/or increasing satiety, thereby causing weight loss or avoidance of weight gain. A subject in need of such a treatment may be a subject who is overweight, obese or a subject likely to become overweight or obese. The method may comprise administering daily or, every other day, or once a week, a dose, e.g., in the form of a pill, to a subject. The dose may be an "appetite reducing dose."

In an exemplary embodiment, sirtuin-modulating compounds that increase the level and/or activity of a sirtuin protein may be administered as a combination therapy for treating or preventing weight gain or obesity. For example, one or more sirtuin-modulating compounds that increase the level and/or activity of a sirtuin protein may be administered in combination with one or more anti-obesity agents.

In another embodiment, sirtuin-modulating compounds that increase the level and/or activity of a sirtuin protein may be administered to reduce drug-induced weight gain. For example, a sirtuin-modulating compound that increases the level and/or activity of a sirtuin protein may be administered as a combination therapy with medications that may stimulate appetite or cause weight gain, in particular, weight gain due to factors other than water retention.

Metabolic Disorders/Diabetes

In another aspect, sirtuin-modulating compounds that increase the level and/or activity of a sirtuin protein may be used for treating or preventing a metabolic disorder, such as insulin-resistance, a pre-diabetic state, type II diabetes, and/or complications thereof. Administration of a sirtuin-modulating compound that increases the level and/or activity of a sirtuin protein may increase insulin sensitivity and/or decrease insulin levels in a subject. A subject in need of such a treatment may be a subject who has insulin resistance or other precursor symptom of type II diabetes, who has type II diabetes, or who is likely to develop any of these conditions. For example, the subject may be a subject having insulin resistance, e.g., having high circulating levels of insulin and/or associated conditions, such as hyperlipidemia, dyslipogenesis, hypercholesterolemia, impaired glucose tolerance, high blood glucose sugar level, other manifestations of syndrome X, hypertension, atherosclerosis and lipodystrophy.

In an exemplary embodiment, sirtuin-modulating compounds that increase the level and/or activity of a sirtuin protein may be administered as a combination therapy for treating or preventing a metabolic disorder. For example, one or more sirtuin-modulating compounds that increase the level and/or activity of a sirtuin protein may be administered in combination with one or more anti-diabetic agents.

Inflammatory Diseases

In other aspects, sirtuin-modulating compounds that increase the level and/or activity of a sirtuin protein can be used to treat or prevent a disease or disorder associated with inflammation. Sirtuin-modulating compounds that increase the level and/or activity of a sirtuin protein may be administered prior to the onset of, at, or after the initiation of inflammation. When used prophylactically, the compounds are preferably provided in advance of any inflammatory response or symptom. Administration of the compounds may prevent or attenuate inflammatory responses or symptoms.

In another embodiment, sirtuin-modulating compounds that increase the level and/or activity of a sirtuin protein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, sirtuin-modulating compounds that increase the level and/or activity of a sirtuin protein may be used to treat autoimmune diseases, and/or inflammation associated with autoimmune diseases, such as arthritis, including rheumatoid arthritis, psoriatic arthritis, and ankylosing spondylitis, as well as organ-tissue autoimmune diseases (e.g., Raynaud's syndrome), ulcerative colitis, Crohn's disease, oral mucositis, scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), and Grave's disease.

In certain embodiments, one or more sirtuin-modulating compounds that increase the level and/or activity of a sirtuin protein may be taken alone or in combination with other compounds useful for treating or preventing inflammation.

Flushing

In another aspect, sirtuin-modulating compounds that increase the level and/or activity of a sirtuin protein may be used for reducing the incidence or severity of flushing and/or hot flashes which are symptoms of a disorder. For instance, the subject method includes the use of sirtuin-modulating compounds that increase the level and/or activity of a sirtuin protein, alone or in combination with other agents, for reducing incidence or severity of flushing and/or hot flashes in cancer patients. In other embodiments, the method provides for the use of sirtuin-modulating compounds that increase the level and/or activity of a sirtuin protein to reduce the incidence or severity of flushing and/or hot flashes in menopausal and post-menopausal woman.

In another aspect, sirtuin-modulating compounds that increase the level and/or activity of a sirtuin protein may be used as a therapy for reducing the incidence or severity of flushing and/or hot flashes which are side-effects of another drug therapy, e.g., drug-induced flushing. In certain embodiments, a method for treating and/or preventing drug-induced flushing comprises administering to a patient in need thereof a formulation comprising at least one flushing inducing compound and at least one sirtuin-modulating compound that increases the level and/or activity of a sirtuin protein. In other embodiments, a method for treating drug induced flushing comprises separately administering one or more compounds that induce flushing and one or more sirtuin-modulating compounds, e.g., wherein the sirtuin-modulating compound and flushing inducing agent have not been formulated in the same compositions. When using separate formulations, the sirtuin-modulating compound may be administered (1) at the same as administration of the flushing inducing agent, (2) intermittently with the flushing inducing agent, (3) staggered relative to administration of the flushing inducing agent, (4) prior to administration of the flushing inducing agent, (5) subsequent to administration of the flushing inducing agent, and (6) various combination thereof. Exemplary flushing inducing agents include, for example, niacin, raloxifene, antidepressants, anti-psychotics, chemotherapeutics, calcium channel blockers, and antibiotics.

In certain embodiments, sirtuin-modulating compounds that increase the level and/or activity of a sirtuin protein may be used to reduce flushing side effects of a vasodilator or an antilipemic agent (including anticholesteremic agents and lipotropic agents). In an exemplary embodiment, a sirtuin-modulating compound that increases the level and/or activity of a sirtuin protein may be used to reduce flushing associated with the administration of niacin.

In another embodiment, the invention provides a method for treating and/or preventing hyperlipidemia with reduced flushing side effects. In another representative embodiment, the method involves the use of sirtuin-modulating compounds that increase the level and/or activity of a sirtuin protein to reduce flushing side effects of raloxifene. In another representative embodiment, the method involves the use of sirtuin-modulating compounds that increase the level and/or activity of a sirtuin protein to reduce flushing side effects of antidepressants or anti-psychotic agent. For instance, sirtuin-modulating compounds that increase the level and/or activity of a sirtuin protein can be used in conjunction (administered separately or together) with a serotonin reuptake inhibitor, or a 5HT2 receptor antagonist.

In certain embodiments, sirtuin-modulating compounds that increase the level and/or activity of a sirtuin protein may be used as part of a treatment with a serotonin reuptake inhibitor (SRI) to reduce flushing. In still another representative embodiment, sirtuin-modulating compounds that increase the level and/or activity of a sirtuin protein may be used to reduce flushing side effects of chemotherapeutic agents, such as cyclophosphamide and tamoxifen.

In another embodiment, sirtuin-modulating compounds that increase the level and/or activity of a sirtuin protein may be used to reduce flushing side effects of calcium channel blockers, such as amlodipine.

In another embodiment, sirtuin-modulating compounds that increase the level and/or activity of a sirtuin protein may be used to reduce flushing side effects of antibiotics. For example, sirtuin-modulating compounds that increase the level and/or activity of a sirtuin protein can be used in combination with levofloxacin.

Ocular Disorders

One aspect of the present invention is a method for inhibiting, reducing or otherwise treating vision impairment by administering to a patient a therapeutic dosage of sirtuin modulator selected from a compound disclosed herein, or a pharmaceutically acceptable salt, prodrug or a metabolic derivative thereof.

In certain aspects of the invention, the vision impairment is caused by damage to the optic nerve or central nervous system. In particular embodiments, optic nerve damage is caused by high intraocular pressure, such as that created by glaucoma. In other particular embodiments, optic nerve damage is caused by swelling of the nerve, which is often associated with an infection or an immune (e.g., autoimmune) response such as in optic neuritis.

In certain aspects of the invention, the vision impairment is caused by retinal damage. In particular embodiments, retinal damage is caused by disturbances in blood flow to the eye (e.g., arteriosclerosis, vasculitis). In particular embodiments, retinal damage is caused by disruption of the macula (e.g., exudative or non-exudative macular degeneration).

Exemplary retinal diseases include Exudative Age Related Macular Degeneration, Nonexudative Age Related Macular Degeneration, Retinal Electronic Prosthesis and RPE Transplantation Age Related Macular Degeneration, Acute Multifocal Placoid Pigment Epitheliopathy, Acute Retinal Necrosis, Best Disease, Branch Retinal Artery Occlusion, Branch Retinal Vein Occlusion, Cancer Associated and Related Autoimmune Retinopathies, Central Retinal Artery Occlusion, Central Retinal Vein Occlusion, Central Serous Chorioretinopathy, Eales Disease, Epimacular Membrane, Lattice Degeneration, Macroaneurysm, Diabetic Macular Edema, Irvine-Gass Macular Edema, Macular Hole, Subretinal Neovascular Membranes, Diffuse Unilateral Subacute Neuroretinitis, Nonpseudophakic Cystoid Macular Edema, Presumed Ocular Histoplasmosis Syndrome, Exudative Retinal Detachment, Postoperative Retinal Detachment, Proliferative Retinal Detachment, Rhegmatogenous Retinal Detachment, Tractional Retinal Detachment, Retinitis Pigmentosa, CMV Retinitis, Retinoblastoma, Retinopathy of Prematurity, Birdshot Retinopathy, Background Diabetic Retinopathy, Proliferative Diabetic Retinopathy, Hemoglobinopathies Retinopathy, Purtscher Retinopathy, Valsalva Retinopathy, Juvenile Retinoschisis, Senile Retinoschisis, Terson Syndrome and White Dot Syndromes.

Other exemplary diseases include ocular bacterial infections (e.g. conjunctivitis, keratitis, tuberculosis, syphilis, gonorrhea), viral infections (e.g., Ocular Herpes Simplex Virus, Varicella Zoster Virus, Cytomegalovirus retinitis, Human Immunodeficiency Virus (HIV)) as well as progressive outer retinal necrosis secondary to HIV or other HIV-associated and other immunodeficiency-associated ocular diseases. In addition, ocular diseases include fungal infections (e.g., Candida choroiditis, histoplasmosis), protozoal infections (e.g., toxoplasmosis) and others such as ocular toxocariasis and sarcoidosis.

One aspect of the invention is a method for inhibiting, reducing or treating vision impairment in a subject undergoing treatment with a chemotherapeutic drug (e.g., a neurotoxic drug, or a drug that raises intraocular pressure, such as a steroid), by administering to the subject in need of such treatment a therapeutic dosage of a sirtuin modulator disclosed herein.

Another aspect of the invention is a method for inhibiting, reducing or treating vision impairment in a subject undergoing surgery, including ocular or other surgeries performed in the prone position such as spinal cord surgery, by administering to the subject in need of such treatment a therapeutic dosage of a sirtuin modulator disclosed herein. Ocular surgeries include cataract, iridotomy and lens replacements.

Another aspect of the invention is the treatment, including inhibition and prophylactic treatment, of age related ocular diseases include cataracts, dry eye, age-related macular degeneration (AMD), retinal damage and the like, by administering to the subject in need of such treatment a therapeutic dosage of a sirtuin modulator disclosed herein.

Another aspect of the invention is the prevention or treatment of damage to the eye caused by stress, chemical insult or radiation, by administering to the subject in need of such treatment a therapeutic dosage of a sirtuin modulator disclosed herein. Radiation or electromagnetic damage to the eye can include that caused by CRT's or exposure to sunlight or UV.

In certain embodiments, a combination drug regimen may include drugs or compounds for the treatment or prevention of ocular disorders or secondary conditions associated with these conditions. Thus, a combination drug regimen may include one or more sirtuin activators and one or more therapeutic agents for the treatment of an ocular disorder.

In certain embodiments, a sirtuin modulator can be administered in conjunction with a therapy for reducing intraocular pressure. In another embodiment, a sirtuin modulator can be administered in conjunction with a therapy for treating and/or preventing glaucoma. In yet another embodiment, a sirtuin modulator can be administered in conjunction with a therapy for treating and/or preventing optic neuritis. In certain embodiments, a sirtuin modulator can be administered in conjunction with a therapy for treating and/or preventing CMV Retinopathy. In another embodiment, a sirtuin modulator can be administered in conjunction with a therapy for treating and/or preventing multiple sclerosis.

Mitochondrial-Associated Diseases and Disorders

In certain embodiments, the invention provides methods for treating diseases or disorders that would benefit from increased mitochondrial activity. The methods involve administering to a subject in need thereof a therapeutically effective amount of a sirtuin-modulating compound. Increased mitochondrial activity refers to increasing activity of the mitochondria while maintaining the overall numbers of mitochondria (e.g., mitochondrial mass), increasing the numbers of mitochondria thereby increasing mitochondrial activity (e.g., by stimulating mitochondrial biogenesis), or combinations thereof. In certain embodiments, diseases and disorders that would benefit from increased mitochondrial activity include diseases or disorders associated with mitochondrial dysfunction.

In certain embodiments, methods for treating diseases or disorders that would benefit from increased mitochondrial activity may comprise identifying a subject suffering from a mitochondrial dysfunction. Methods for diagnosing a mitochondrial dysfunction may involve molecular genetics, pathologic and/or biochemical analyses. Diseases and disorders associated with mitochondrial dysfunction include diseases and disorders in which deficits in mitochondrial respiratory chain activity contribute to the development of pathophysiology of such diseases or disorders in a mammal. Diseases or disorders that would benefit from increased mitochondrial activity generally include for example, diseases in which free radical mediated oxidative injury leads to tissue degeneration, diseases in which cells inappropriately undergo apoptosis, and diseases in which cells fail to undergo apoptosis.

In certain embodiments, the invention provides methods for treating a disease or disorder that would benefit from increased mitochondrial activity that involves administering to a subject in need thereof one or more sirtuin-modulating compounds in combination with another therapeutic agent such as, for example, an agent useful for treating mitochondrial dysfunction or an agent useful for reducing a symptom associated with a disease or disorder involving mitochondrial dysfunction.

In exemplary embodiments, the invention provides methods for treating diseases or disorders that would benefit from increased mitochondrial activity by administering to a subject a therapeutically effective amount of a sirtuin-modulating compound. Exemplary diseases or disorders include, for example, neuromuscular disorders (e.g., Friedreich's Ataxia, muscular dystrophy, multiple sclerosis, etc.), disorders of neuronal instability (e.g., seizure disorders, migraine, etc.), developmental delay, neurodegenerative disorders (e.g., Alzheimer's Disease, Parkinson's Disease, amyotrophic lateral sclerosis, etc.), ischemia, renal tubular acidosis, age-related neurodegeneration and cognitive decline, chemotherapy fatigue, age-related or chemotherapy-induced menopause or irregularities of menstrual cycling or ovulation, mitochondrial myopathies, mitochondrial damage (e.g., calcium accumulation, excitotoxicity, nitric oxide exposure, hypoxia, etc.), and mitochondrial deregulation.

Muscular dystrophy refers to a family of diseases involving deterioration of neuromuscular structure and function, often resulting in atrophy of skeletal muscle and myocardial dysfunction, such as Duchenne muscular dystrophy. In certain embodiments, sirtuin-modulating compounds may be used for reducing the rate of decline in muscular functional capacities and for improving muscular functional status in patients with muscular dystrophy.

In certain embodiments, sirtuin-modulating compounds may be useful for treatment mitochondrial myopathies. Mitochondrial myopathies range from mild, slowly progressive weakness of the extraocular muscles to severe, fatal infantile myopathies and multisystem encephalomyopathies. Some syndromes have been defined, with some overlap between them. Established syndromes affecting muscle include progressive external ophthalmoplegia, the Kearns-Sayre syndrome (with ophthalmoplegia, pigmentary retinopathy, cardiac conduction defects, cerebellar ataxia, and sensorineural deafness), the MELAS syndrome (mitochondrial encephalomyopathy, lactic acidosis, and stroke-like episodes), the MERFF syndrome (myoclonic epilepsy and ragged red fibers), limb-girdle distribution weakness, and infantile myopathy (benign or severe and fatal).

In certain embodiments, sirtuin-modulating compounds may be useful for treating patients suffering from toxic damage to mitochondria, such as, toxic damage due to calcium accumulation, excitotoxicity, nitric oxide exposure, drug induced toxic damage, or hypoxia.

In certain embodiments, sirtuin-modulating compounds may be useful for treating diseases or disorders associated with mitochondrial deregulation.

In another embodiment, the present invention may be used in the treatment of other diseases or disorders related to aging or stress, diabetes and other metabolic dysfunctions and related conditions including but not limited to fatty liver, hepatic steatohepatitis and obesity. The present invention may also be used in the treatment of neurodegenerative diseases, cardiovascular disease, cancer, inflammatory disease which includes but is not limited to psoriasis, atopic dermatitis, acne, rosacea, inflammatory bowel disease, osteoporosis, sepsis, arthritis, COPD, systemic lupus erythematosus and ophthalmic inflammation, as well as other diseases or disorders that result from diminished SIRT1 expression or activity.

Muscle Performance

In other embodiments, the invention provides methods for enhancing muscle performance by administering a therapeutically effective amount of a sirtuin-modulating compound. For example, sirtuin-modulating compounds may be useful for improving physical endurance (e.g., ability to perform a physical task such as exercise, physical labor, sports activities, etc.), inhibiting or retarding physical fatigues, enhancing blood oxygen levels, enhancing energy in healthy individuals, enhance working capacity and endurance, reducing muscle fatigue, reducing stress, enhancing cardiac and cardiovascular function, improving sexual ability, increasing muscle ATP levels, and/or reducing lactic acid in blood. In certain embodiments, the methods involve administering an amount of a sirtuin-modulating compound that increase mitochondrial activity, increase mitochondrial biogenesis, and/or increase mitochondrial mass.

Sports performance refers to the ability of the athlete's muscles to perform when participating in sports activities. Enhanced sports performance, strength, speed and endurance are measured by an increase in muscular contraction strength, increase in amplitude of muscle contraction, shortening of muscle reaction time between stimulation and contraction. Athlete refers to an individual who participates in sports at any level and who seeks to achieve an improved level of strength, speed and endurance in their performance, such as, for example, body builders, bicyclists, long distance runners, short distance runners, etc. Enhanced sports performance in manifested by the ability to overcome muscle fatigue, ability to maintain activity for longer periods of time, and have a more effective workout.

In the arena of athlete muscle performance, it is desirable to create conditions that permit competition or training at higher levels of resistance for a prolonged period of time.

It is contemplated that the methods of the present invention will also be effective in the treatment of muscle related pathological conditions, including acute sarcopenia, for example, muscle atrophy and/or cachexia associated with burns, bed rest, limb immobilization, or major thoracic, abdominal, and/or orthopedic surgery.

In certain embodiments, the invention provides novel dietary compositions comprising sirtuin modulators, a method for their preparation, and a method of using the compositions for improvement of sports performance.

Accordingly, provided are therapeutic compositions, foods and beverages that have actions of improving physical endurance and/or inhibiting physical fatigues for those people involved in broadly-defined exercises including sports requiring endurance and labors requiring repeated muscle exertions. Such dietary compositions may additional comprise electrolytes, caffeine, vitamins, carbohydrates, etc.

Other Uses

Sirtuin-modulating compounds that increase the level and/or activity of a sirtuin protein may be used for treating or preventing viral infections (such as infections by influenza, herpes or papilloma virus) or as antifungal agents. In certain embodiments, sirtuin-modulating compounds that increase the level and/or activity of a sirtuin protein may be administered as part of a combination drug therapy with another therapeutic agent for the treatment of viral diseases. In another embodiment, sirtuin-modulating compounds that increase the level and/or activity of a sirtuin protein may be administered as part of a combination drug therapy with another anti-fungal agent.

Subjects that may be treated as described herein include eukaryotes, such as mammals, e.g., humans, ovines, bovines, equines, porcines, canines, felines, non-human primate, mice, and rats. Cells that may be treated include eukaryotic cells, e.g., from a subject described above, or plant cells, yeast cells and prokaryotic cells, e.g., bacterial cells. For example, modulating compounds may be administered to farm animals to improve their ability to withstand farming conditions longer.

Sirtuin-modulating compounds that increase the level and/or activity of a sirtuin protein may also be used to increase lifespan, stress resistance, and resistance to apoptosis in plants. In certain embodiments, a compound is applied to plants, e.g., on a periodic basis, or to fungi. In another embodiment, plants are genetically modified to produce a compound. In another embodiment, plants and fruits are treated with a compound prior to picking and shipping to increase resistance to damage during shipping. Plant seeds may also be contacted with compounds described herein, e.g., to preserve them.

In other embodiments, sirtuin-modulating compounds that increase the level and/or activity of a sirtuin protein may be used for modulating lifespan in yeast cells. Situations in which it may be desirable to extend the lifespan of yeast cells include any process in which yeast is used, e.g., the making of beer, yogurt, and bakery items, e.g., bread. Use of yeast having an extended lifespan can result in using less yeast or in having the yeast be active for longer periods of time. Yeast or other mammalian cells used for recombinantly producing proteins may also be treated as described herein.

Sirtuin-modulating compounds that increase the level and/or activity of a sirtuin protein may also be used to increase lifespan, stress resistance and resistance to apoptosis in insects. In this embodiment, compounds would be applied to useful insects, e.g., bees and other insects that are involved in pollination of plants. In a specific embodiment, a compound would be applied to bees involved in the production of honey. Generally, the methods described herein may be applied to any organism, e.g., eukaryote, which may have commercial importance. For example, they can be applied to fish (aquaculture) and birds (e.g., chicken and fowl).

Higher doses of sirtuin-modulating compounds that increase the level and/or activity of a sirtuin protein may also be used as a pesticide by interfering with the regulation of silenced genes and the regulation of apoptosis during development. In this embodiment, a compound may be applied to plants using a method known in the art that ensures the compound is bio-available to insect larvae, and not to plants.

At least in view of the link between reproduction and longevity, sirtuin-modulating compounds that increase the level and/or activity of a sirtuin protein can be applied to affect the reproduction of organisms such as insects, animals and microorganisms.

4. Assays

Yet other methods contemplated herein include screening methods for identifying compounds or agents that modulate sirtuins. An agent may be a nucleic acid, such as an aptamer. Assays may be conducted in a cell based or cell free format. For example, an assay may comprise incubating (or contacting) a sirtuin with a test agent under conditions in which a sirtuin can be modulated by an agent known to modulate the sirtuin, and monitoring or determining the level of modulation of the sirtuin in the presence of the test agent relative to the absence of the test agent. The level of modulation of a sirtuin can be determined by determining its ability to deacetylate a substrate. Exemplary substrates are acetylated peptides which can be obtained from BIOMOL (Plymouth Meeting, Pa.). Preferred substrates include peptides of p53, such as those comprising an acetylated K382. A particularly preferred substrate is the Fluor de Lys-SIRT1 (BIOMOL), i.e., the acetylated peptide Arg-His-Lys-Lys. Other substrates are peptides from human histones H3 and H4 or an acetylated amino acid. Substrates may be fluorogenic. The sirtuin may be SIRT1, Sir2, SIRT3, or a portion thereof. For example, recombinant SIRT1 can be obtained from BIOMOL. The reaction may be conducted for about 30 minutes and stopped, e.g., with nicotinamide. The HDAC fluorescent activity assay/drug discovery kit (AK-500, BIOMOL Research Laboratories) may be used to determine the level of acetylation. Similar assays are described in Bitterman et al. (2002) J. Biol. Chem. 277:45099. The level of modulation of the sirtuin in an assay may be compared to the level of modulation of the sirtuin in the presence of one or more (separately or simultaneously) compounds described herein, which may serve as positive or negative controls. Sirtuins for use in the assays may be full length sirtuin proteins or portions thereof. Since it has been shown herein that activating compounds appear to interact with the N-terminus of SIRT1, proteins for use in the assays include N-terminal portions of sirtuins, e.g., about amino acids 1-176 or 1-255 of SIRT1; about amino acids 1-174 or 1-252 of Sir2.

In certain embodiments, a screening assay comprises (i) contacting a sirtuin with a test agent and an acetylated substrate under conditions appropriate for the sirtuin to deacetylate the substrate in the absence of the test agent; and (ii) determining the level of acetylation of the substrate, wherein a lower level of acetylation of the substrate in the presence of the test agent relative to the absence of the test agent indicates that the test agent stimulates deacetylation by the sirtuin, whereas a higher level of acetylation of the substrate in the presence of the test agent relative to the absence of the test agent indicates that the test agent inhibits deacetylation by the sirtuin.

In another embodiment, the screening assay may detect the formation of a 2'/3'-O-acetyl-ADP-ribose product of sirtuin-mediated NAD-dependent deacetylation. This O-acetyl-ADP-ribose product is formed in equimolar quantities with the deacetylated peptide product of the sirtuin deacetylation reaction. Accordingly, the screening assay may include (i) contacting a sirtuin with a test agent and an acetylated substrate under conditions appropriate for the sirtuin to deacetylate the substrate in the absence of the test agent; and (ii) determining the amount of O-acetyl-ADP-ribose formation, wherein an increase in O-acetyl-ADP-ribose formation in the presence of the test agent relative to the absence of the test agent indicates that the test agent stimulates deacetylation by the sirtuin, while a decrease in O-acetyl-ADP-ribose formation in the presence of the test agent relative to the absence of the test agent indicates that the test agent inhibits deacetylation by the sirtuin.

Methods for identifying an agent that modulates, e.g., stimulates, sirtuins in vivo may comprise (i) contacting a cell with a test agent and a substrate that is capable of entering a cell in the presence of an inhibitor of class I and class II HDACs under conditions appropriate for the sirtuin to deacetylate the substrate in the absence of the test agent; and (ii) determining the level of acetylation of the substrate, wherein a lower level of acetylation of the substrate in the presence of the test agent relative to the absence of the test agent indicates that the test agent stimulates deacetylation by the sirtuin, whereas a higher level of acetylation of the substrate in the presence of the test agent relative to the absence of the test agent indicates that the test agent inhibits deacetylation by the sirtuin. A preferred substrate is an acetylated peptide, which is also preferably fluorogenic, as further described herein. The method may further comprise lysing the cells to determine the level of acetylation of the substrate. Substrates may be added to cells at a concentration ranging from about 1 µM to about 10 mM, preferably from about 10 µM to 1 mM, even more preferably from about 100 µM to 1 mM, such as about 200 µM. A preferred substrate is an acetylated lysine, e.g., e-acetyl lysine (Fluor de Lys, FdL) or Fluor de Lys-SIRT1. A preferred inhibitor of class I and class II HDACs is trichostatin A (TSA), which may be used at concentrations ranging from about 0.01 to 100 µM, preferably from about 0.1 to 10 µM, such as 1 µM. Incubation of cells with the test compound and the substrate may be conducted for about 10 minutes to 5 hours, preferably for about 1-3 hours. Since TSA inhibits all class I and class II HDACs, and that certain substrates, e.g., Fluor de Lys, is a poor substrate for SIRT2 and even less a substrate for SIRT3-7, such an assay may be used to identify modulators of SIRT1 in vivo.

5. Pharmaceutical Compositions

The compounds described herein may be formulated in a conventional manner using one or more physiologically or pharmaceutically acceptable carriers or excipients. For example, compounds and their pharmaceutically acceptable salts and solvates may be formulated for administration by, for example, injection (e.g. SubQ, IM, IP), inhalation or insufflation (either through the mouth or the nose) or oral, buccal, sublingual, transdermal, nasal, parenteral or rectal administration. In certain embodiments, a compound may be administered locally, at the site where the target cells are present, i.e., in a specific tissue, organ, or fluid (e.g., blood, cerebrospinal fluid, etc.).

The compounds can be formulated for a variety of modes of administration, including systemic and topical or localized administration. Techniques and formulations generally may be found in Remington's Pharmaceutical Sciences, Meade Publishing Co., Easton, Pa. For parenteral administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets, lozenges, or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation (e.g., pulmonary delivery), the compounds may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, compounds may also be formulated as a depot preparation. Such long acting formulations may be administered by implantation (for example subcutaneously or intramuscularly) or by intramuscular injection. Thus, for example, compounds may be formulated with suitable polymeric or hydrophobic materials (for example as an emulsion in an acceptable oil) or ion exchange resins, or as sparingly soluble derivatives, for example, as a sparingly soluble salt. Controlled release formula also includes patches.

In certain embodiments, the compounds described herein can be formulated for delivery to the central nervous system (CNS) (reviewed in Begley, Pharmacology & Therapeutics 104: 29-45 (2004)). Conventional approaches for drug delivery to the CNS include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

Liposomes are a further drug delivery system which is easily injectable. Accordingly, in the method of invention the active compounds can also be administered in the form of a liposome delivery system. Liposomes are well known by those skilled in the art. Liposomes can be formed from a variety of phospholipids, such as cholesterol, stearylamine of phosphatidylcholines. Liposomes usable for the method of invention encompass all types of liposomes including, but not limited to, small unilamellar vesicles, large unilamellar vesicles and multilamellar vesicles.

Another way to produce a formulation, particularly a solution, of a compound described herein, is through the use of cyclodextrin. By cyclodextrin is meant α-, β-, or γ-cyclodextrin. Cyclodextrins are described in detail in Pitha et al., U.S. Pat. No. 4,727,064, which is incorporated herein by reference. Cyclodextrins are cyclic oligomers of glucose; these compounds form inclusion complexes with any drug whose molecule can fit into the lipophile-seeking cavities of the cyclodextrin molecule.

Rapidly disintegrating or dissolving dosage forms are useful for the rapid absorption, particularly buccal and sublingual absorption, of pharmaceutically active agents. Fast melt dosage forms are beneficial to patients, such as aged and pediatric patients, who have difficulty in swallowing typical solid dosage forms, such as caplets and tablets. Additionally, fast melt dosage forms circumvent drawbacks associated with, for example, chewable dosage forms, wherein the length of time an active agent remains in a patient's mouth plays an important role in determining the amount of taste masking and the extent to which a patient may object to throat grittiness of the active agent.

Pharmaceutical compositions (including cosmetic preparations) may comprise from about 0.00001 to 100% such as from 0.001 to 10% or from 0.1% to 5% by weight of one or more compounds described herein. In other embodiments, the pharmaceutical composition comprises: (i) 0.05 to 1000 mg of the compounds of the invention, or a pharmaceutically acceptable salt thereof, and (ii) 0.1 to 2 grams of one or more pharmaceutically acceptable excipients.

In some embodiments, a compound described herein is incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Formulations may be colorless, odorless ointments, lotions, creams, microemulsions and gels.

The compounds may be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing.

The compounds may be incorporated into lotions, which generally are preparations to be applied to the skin surface without friction, and are typically liquid or semiliquid preparations in which solid particles, including the active agent, are present in a water or alcohol base. Lotions are usually suspensions of solids, and may comprise a liquid oily emulsion of the oil-in-water type.

The compounds may be incorporated into creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic or amphoteric surfactant.

The compounds may be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9).

The compounds may be incorporated into gel formulations, which generally are semisolid systems consisting of either suspensions made up of small inorganic particles (two-phase systems) or large organic molecules distributed substantially uniformly throughout a carrier liquid (single phase gels). Although gels commonly employ aqueous carrier liquid, alcohols and oils can be used as the carrier liquid as well.

Other active agents may also be included in formulations, e.g., other anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Conditions of the eye can be treated or prevented by, e.g., systemic, topical, intraocular injection of a compound, or by insertion of a sustained release device that releases a compound. A compound may be delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material. Alternatively, the compounds of the invention may be injected directly into the vitreous and aqueous humour. In a further alternative, the compounds may be administered systemically, such as by intravenous infusion or injection, for treatment of the eye.

The compounds described herein may be stored in oxygen free environment. For example, a composition can be prepared in an airtight capsule for oral administration, such as Capsugel from Pfizer, Inc.

Cells, e.g., treated ex vivo with a compound as described herein, can be administered according to methods for administering a graft to a subject, which may be accompanied, e.g., by administration of an immunosuppressant drug, e.g., cyclosporin A. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000.

Toxicity and therapeutic efficacy of compounds can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may lie within a range of circulating concentrations that include the $ED_{50}$ with little or no toxicity.

The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

6. Kits

Also provided herein are kits, e.g., kits for therapeutic purposes or kits for modulating the lifespan of cells or modulating apoptosis. A kit may comprise one or more compounds as described herein, e.g., in premeasured doses. A kit may optionally comprise devices for contacting cells with the compounds and instructions for use. Devices include syringes, stents and other devices for introducing a compound into a subject (e.g., the blood vessel of a subject) or applying it to the skin of a subject.

In yet another embodiment, the invention provides a composition of matter comprising a compound of this invention and another therapeutic agent (the same ones used in combination therapies and combination compositions) in separate dosage forms, but associated with one another. The term "associated with one another" as used herein means that the separate dosage forms are packaged together or otherwise attached to one another such that it is readily apparent that the separate dosage forms are intended to be sold and administered as part of the same regimen. The compound and the other agent are preferably packaged together in a blister pack or other multi-chamber package, or as connected, separately sealed containers (such as foil pouches or the like) that can be separated by the user (e.g., by tearing on score lines between the two containers).

In still another embodiment, the invention provides a kit comprising in separate vessels, a) a compound of this invention; and b) another therapeutic agent such as those described elsewhere in the specification.

The practice of the present methods will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXEMPLIFICATION

The invention now being generally described, it will be more readily understood by reference to the following examples which are included merely for purposes of illustration of certain aspects and embodiments of the present invention, and are not intended to limit the invention in any way.

Instrumentation Used

LCMS with PDA:
Waters Allaince2695-2996/Quattromicro
Agilent-1200/SQD
Preparative LC with UV Detector (Prep HPLC):
Waters-2545/2998 PDA and 2487 UV
Shimadzu -LC-20AP/20AV-UV
Gilson-333,334/115-UV
Chiral HPLC:
Waters Alliance-2695/2998 &2996
SFC Purification Systems:
Thar—SFC-80
Waters SFC—200
NMR (400 MHz):
Varian-400 MHz
$^1$H-NMR tabulation was generated with 2014 ACD labs software.

LCMS Methods Used

Acq. Method Conditions: RND-ABC-6-MIN
Column: XBridge BEH C18 (50 mm×4.6 mm, 2.5 µm)
Mobile Phase: A: 5 mM Ammonium Bicarbonate in water (PH-10 with Ammonia): ACN
Time (min)/% ACN: 0/5, 0.5/5, 1/15, 3.3/98, 5.2/98, 5.5/5, 6.0/5
Column temp: 35° C., Flow Rate 1.3 ml/min
MS Parameters:
Mass Range: 100-1000
Scan Time: 0.5 Sec
Inter-Scan delay: 0.1 sec
Run Time: 6.0 min
Acq. Method Conditions: RND-FA-4.5-MIN
Column: Acquity BEH C18 (50 mm×2.1 mm, 1.7 um)
Mobile Phase: A: 0.1% FA in water; B: 0.1% FA in ACN
Time (min)/% B: 0/3, 0.4/3, 3.2/98, 3.8/98, 4.2/3, 4.5/3
Column Temp: 35° C., Flow Rate: 0.6 mL/min
MS Parameters:
Mass Range: 100-1000
Scan Time: 0.5 Sec
Inter-Scan delay: 0.1 sec
Run Time: 4.5 min
Acq. Method Conditions: RND-FA-4.5-MIN
Column: Acquity BEH C18 (50 mm×2.1 mm, 1.7 um)
Mobile Phase: A: 0.1% FA in water; B: 0.1% FA in ACN
Time (min)/% B: 0/3, 0.4/3, 3.2/98, 3.8/98, 4.2/3, 4.5/3
Column Temp: 35° C., Flow Rate: 0.6 mL/min
MS Parameters:
Mass Range: 100-1000
Fragmentor: 100
Step Size: 0.1
Run Time: 4.5 min
Acq. Method Conditions: RND-ABC-6.5-MIN
Column: XBridge BEH C18 (50 mm×4.6 mm, 2.5 µm)
Mobile Phase: A: 5 mM Ammonium Bicarbonate in water (PH-10 with Ammonia): ACN
Time (min)/% ACN: 0/5, 0.5/5, 1/15, 3.3/98, 6.0/98, 6.1/5, 6.5/5
Column temp: 35° C., Flow Rate 1.3 ml/min
MS Parameters:
Mass Range: 100-1000
Fragmentor: 100
Step Size: 0.1
Run Time: 6.5 min
Acq. Method Conditions: RND-ABC-10-MIN
Column: XBridge BEH C18 (50 mm×4.6 mm, 2.5 µm)
Mobile Phase: A: 5 mM Ammonium Bicarbonate in water (PH-10 with Ammonia): ACN
Time (min)/% ACN: 0/5, 0.5/5, 1.5/15, 7/98, 9.0/98, 9.5/5, 10/5
Column temp: 35° C., Flow Rate 1.3 ml/min
MS Parameters:

Mass Range: 100-1000
Fragmentor: 100
Step Size: 0.1
Run Time: 10.0 min

Experimental Procedures for Chemical Intermediates

Synthesis of Bicyclic Pyridine Cores

Synthesis of (S)-Dimethyl 2-((6-chloro-3-nitropyridin-2-yl)amino)succinate

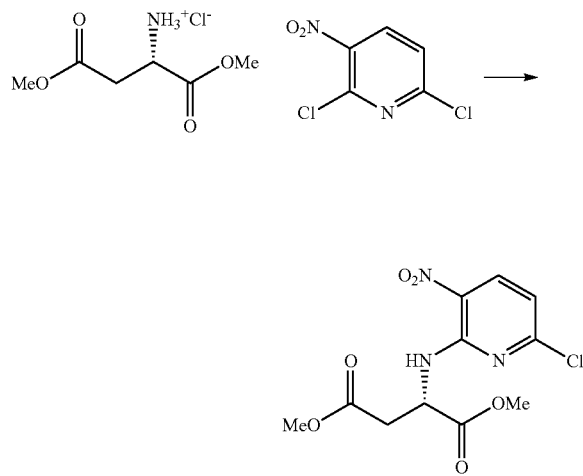

To a 2 L flask equipped with a thermometer, a reflux condenser, and a mechanical stirrer was added 2,6-dichloro-3-nitropyridine (100 g, 0.52 mol), (S)-aspartic acid dimethyl ester hydrochloride (205 g, 1.04 mol), NaHCO$_3$ (174 g, 2.07 mol) and tetrahydrofuran (1 L). The reaction was stirred at 40° C. for 16 h, and was monitored for the disappearance of 2,6-dichloropyridine by HPLC. After the reaction was complete, the solids were filtered away and washed with ethyl acetate (3×300 mL). The combined filtrate and washings were concentrated to dryness, and the residue was taken up in 1 L of ethyl acetate. The solution was stirred with charcoal (200 g) at ambient temperature for 2 h, and the charcoal was filtered away and washed with additional ethyl acetate (3×200 mL). The combined filtrate and washings were concentrated in vacuo to obtain crude (S)-dimethyl 2-((6-chloro-3-nitropyridin-2-yl)amino)succinate (180 g, >100%) as a yellow oil. This was used in the next step without further purification. LRMS (m/z): 318.0 [M+H]+; HRMS (m/z): [M+H]+ calcd for C$_{11}$H$_{13}$N$_3$O$_6$Cl, 318.0493; found, 318.0492; $^1$H-NMR (300 MHz, DMSO-d6): δ 9.00 (d, J=7.9 Hz, 1H, —NH), 8.50 (d, J=8.6 Hz, 1H), 6.92 (d, J=8.6 Hz, 1H), 5.23 (m, J=5.7, 7.9 Hz, 1H, —CHNH), 3.67 (s, 3H), 3.63 (s, 3H), 3.06 (m, J=5.8 Hz, 2H, —CHCH$_2$); $^{13}$C-NMR (APT) (75 MHz, DMSO-d6): δ 170.93 (C), 170.65 (C), 154.65 (C), 150.59 (C), 138.82 (CH), 127.28 (C), 112.81 (CH), 52.23 (CH$_3$), 51.74 (CH$_3$), 50.20 (CH), 35.31 (CH$_2$).

Synthesis of (S)-Methyl 2-(6-chloro-2-oxo-1,2,3,4-tetrahydropyrido[2,3-b]pyrazin-3-yl)acetate

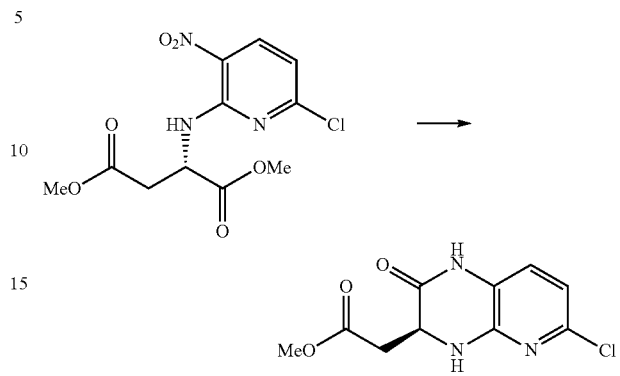

To a 5 L three necked flask equipped with a thermometer, a reflux condenser, and a mechanical stirrer was charged with crude (S)-dimethyl 2-((6-chloro-3-nitropyridin-2-yl)amino)succinate (180 g, 0.52 mol), iron powder (146 g, 2.59 mol), 2-propanol (2 L) and water (700 mL). The mixture was stirred at 40° C., and then acetic acid (15.5 g, 0.259 mmol) was added at a rate sufficient to keep the internal temperature below 70° C. The reaction was stirred at 70° C. for 30 min, HPLC indicated that the reaction was complete. The mixture was cooled to 40° C., then Na$_2$CO$_3$ (165 g, 1.55 mol) was added, and the mixture was stirred for 1 h. The solids were filtered, and the solids were washed with tetrahydrofuran (3×500 mL). The combined filtrate and washings were concentrated in vacuo, and then the residue was stirred in ethanol (1 L) for 12 hrs. The solid was filtered and washed with cold ethanol, and dried in vacuo to obtain (S)-methyl 2-(6-chloro-2-oxo-1,2,3,4-tetrahydropyrido[2,3-b]pyrazin-3-yl)acetate as an off-white solid (91 g, 68%). LRMS (m/z): 256.0 [M+H]+; HRMS (m/z): [M+H]+ calcd for Co$_{10}$H$_{11}$N$_3$O$_3$Cl, 256.0489; found, 256.0487; $^1$H-NMR (300 MHz, DMSO-d6): δ 10.55 (br s, 1H, —NHCO), 7.35 (br s, 1H, —NHCH), 6.92 (d, J=7.9 Hz, 1H), 6.57 (d, J=7.8 Hz, 1H), 4.43 (m, J=1.4, 5.1 Hz, 1H, —NHCH), 3.57 (s, 3H, —CO$_2$Me), 2.79 (m, J=5.1, 16.4 Hz, 2H, —CHCH$_2$); $^{13}$C-NMR (APT) (75 MHz, DMSO-d6): δ 170.32 (C), 164.96 (C), 146.13 (C), 140.32 (C), 122.41 (CH), 119.47 (C), 111.31 (CH), 51.81 (CH), 51.39 (CH$_3$), 37.01 (CH$_2$).

Synthesis of (S)-2-(6-Chloro-1,2,3,4-tetrahydropyrido[2,3-b]pyrazin-3-yl)ethanol

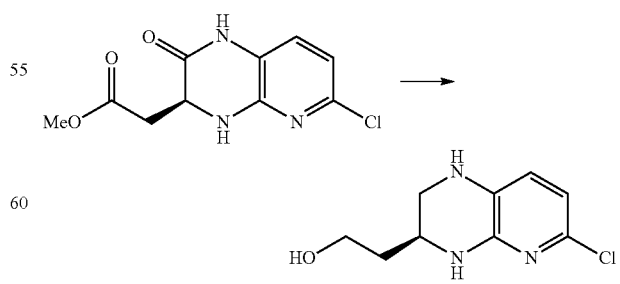

A 5 L 3-necked flask equipped with a mechanical stirrer, a reflux condenser, and a nitrogen inlet was charged with LiAlH$_4$ (60 g, 1.58 mol). The flask was cooled with an ice bath, and tetrahydrofuran (500 mL) was added. The stirred mixture was cooled to 0° C., then a solution of (S)-methyl 2-(6-chloro-2-oxo-1,2,3,4-tetrahydropyrido[2,3-b]pyrazin-3-yl)acetate (81 g, 0.32 mol) in tetrahydrofuran (2 L) was added, while keeping the internal temperature below 5° C. After the addition was complete, the reaction was heated at reflux for 16 h, while monitoring for the appearance of product by HPLC. The ester reduction occurred rapidly, while the lactam reduction required longer for complete reduction. The reaction was cooled to 5° C., and then water (60 mL) was added while keeping the internal temperature below 10° C. After addition was complete, the reaction was stirred for 15 min, then 15% (w/w) NaOH(aq) (60 mL) was added while keeping the internal temperature below 5° C. After addition was complete, the reaction was stirred for 15 min, then water (180 mL) was added and the mixture was stirred at ambient temperature for 1 h. The solids were filtered off and washed with tetrahydrofuran (3×150 mL). The filtrate and washings were concentrated in vacuo, then the solid residue was dried in vacuo to obtain (S)-2-(6-chloro-1,2,3,4-tetrahydropyrido[2,3-b]pyrazin-3-yl)ethanol as a brown solid (55 g, 81%). LRMS (m/z): 214.1 [M+H]+; HRMS (m/z): [M+H]+ calcd for $C_9H_{13}N_3OCl$, 214.0747; found, 214.0743; $^1$H-NMR (300 MHz, DMSO-d6): δ 6.60 (br s, 1H, —NHCH(CH$_2$)$_2$OH), 6.58 (d, J=7.8 Hz, 1H), 6.32 (d, J=7.8 Hz, 1H), 5.69 (m, 1H, —NHCH$_2$), 4.57 (t, J=5.0 Hz, 1H, —OH), 3.56 (m, J=5.8 Hz, 2H, —CH$_2$OH), 3.47 (m, 1H, —NHCH(CH$_2$)$_2$OH), 3.22 (m, J=2.7, 11.1 Hz, 1H, —NHCHH'), 2.84 (m, J=1.6, 6.7, 11.1 Hz, 1H, —NHCHH'), 1.65 (m, J=6.7 Hz, 1H, —CHH'CH$_2$OH), 1.54 (m, J=6.3 Hz, 1H, —CHH'CH$_2$OH); $^{13}$C-NMR (APT) (75 MHz, DMSO-d6): δ 146.75 (C), 134.44 (C), 128.20 (C), 118.97 (CH), 110.59 (CH), 57.97 (CH$_2$), 47.47 (CH), 43.99 (CH$_2$), 36.60 (CH$_2$).

Synthesis of (4S)-7-Chloro-2,3,4,5-tetrahydro-1,4-methanopyrido[2,3-b][1,4]diazepine

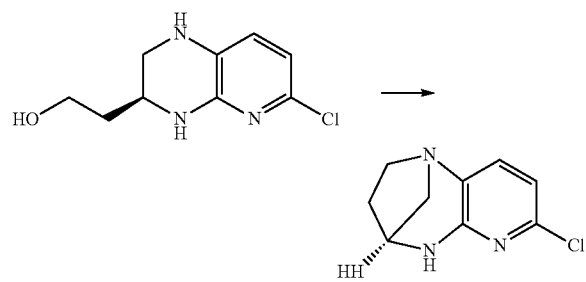

To a solution of (S)-2-(6-chloro-1,2,3,4-tetrahydropyrido[2,3-b]pyrazin-3-yl)ethanol (5; 50 g, 0.234 mol) in CH$_2$Cl$_2$ (500 mL) was added triethylamine (95 g, 0.936 mol). The mixture was stirred at ambient temperature until it was homogeneous, and then cooled to 0° C. To the reaction mixture was added dropwise POCl$_3$ (54 g, 0.351 mol) while maintaining the temperature between 0-5° C. Cooling was removed and the reaction was stirred at ambient temperature for 2 h, while monitoring for the disappearance of the starting alcohol by HPLC. After the reaction was complete, 1.2M NaHCO$_3$(aq.) (200 mL) was added. The layers were separated and the aqueous layer was extracted with CH$_2$Cl$_2$. The combined CH$_2$Cl$_2$ layers were extracted with 1M HCl (aq.) (4×300 mL), and the combined HCl layers were adjusted to pH 8 with solid NaHCO$_3$. The resulting mixture was extracted with CH$_2$Cl$_2$ (4×300 mL), and this set of CH$_2$Cl$_2$ layers were dried (Na$_2$SO$_4$), filtered, and treated with charcoal (50 g). The mixture was stirred at ambient temperature for 3 h, filtered, and the charcoal was washed with CH$_2$Cl$_2$ (200 mL). The combined filtrate and wash solution were concentrated to dryness, and the solid residue was dried in vacuo to obtain (4S)-7-chloro-2,3,4,5-tetrahydro-1,4-methanopyrido[2,3-b][1,4]diazepine as an off-white crystalline solid (30 g, 66%). LRMS (m/z): 196.1 [M+H]+; HRMS (m/z): [M+H]+ calcd for $C_9H_{11}N_3Cl$, 196.0642; found, 196.0637; $^1$H-NMR (300 MHz, DMSO-d6): δ 7.47 (br d, J=4.5 Hz, 1H, —NH), 7.09 (d, J=7.7 Hz, 1H), 6.39 (d, J=7.7 Hz, 1H), 3.89 (m, J=5.0 Hz, 1H, CHNH), 2.95-3.13 (m, 2H, —NCH$_2$CH$_2$CHNH), 2.77 (m, 2H, —NCHH'CHNH), 1.98 (m, J=5.0 Hz, 1H, —NHCHCHH'CH$_2$N), 1.86 (m, J=6.9 Hz, 1H, —NHCHCHH'CH$_2$N); $^{13}$C-NMR (APT) (75 MHz, DMSO-d6): δ 153.45 (C), 144.50 (C), 134.32 (CH), 133.19 (C), 109.73 (CH), 59.88 (CH$_2$), 53.07 (CH$_2$), 50.08 (CH), 38.38 (CH$_2$).

Synthesis of (R)-dimethyl 2-((6-chloro-3-nitropyridin-2-yl)amino)succinate

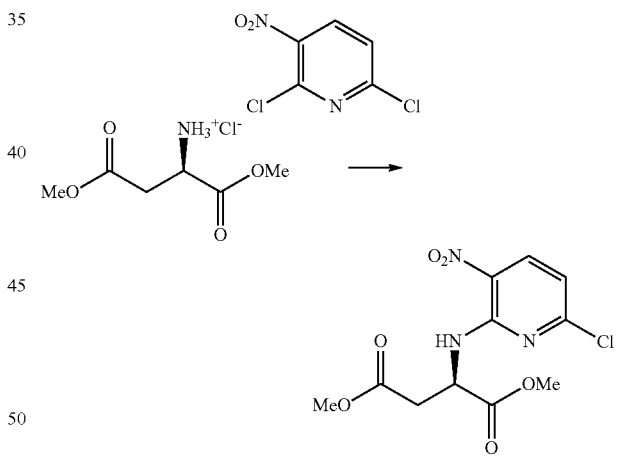

To a suspension of (R)-dimethyl 2-aminosuccinate hydrochloride (25 g, 127 mmol) in Tetrahydrofuran (THF) (130 mL) was added sodium bicarbonate (21.25 g, 253 mmol) and 2,6-dichloro-3-nitropyridine (12.21 g, 63.3 mmol) under nitrogen. The reaction mixture was stirred at 40° C. for 16 hr. The reaction mixture was filtered and washed with EtOAc (3×25 mL), the filtrate was concentrated to give the crude product which was then added to a silica gel column and was eluted with (9:1) Hex/EtOAc. Collected fractions were evaporated to obtain the desired product (16 g, 49.4 mmol, 39.0%), LCMS (m/z) 318.1 [M+H]+.

Synthesis of (R)-methyl 2-(6-chloro-2-oxo-1,2,3,4-tetrahydropyrido[2,3-b]pyrazin-3-yl)acetate

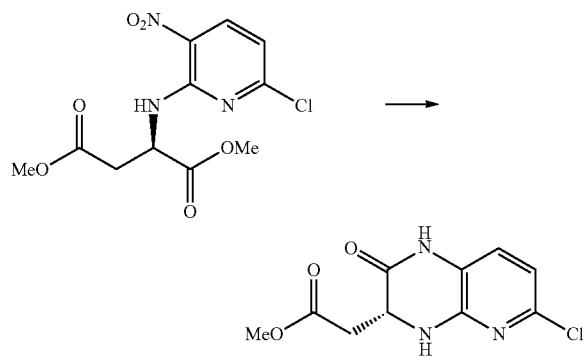

To a solution of (R)-dimethyl 2-((6-chloro-3-nitropyridin-2-yl)amino)succinate (16 g, 50.4 mmol) in isopropanol (200 mL) and Water (60 mL) was added iron (14.06 g, 252 mmol) heated to 40° C. To the above reaction mixture was added acetic acid (1.442 mL, 25.2 mmol) and heated to 70° C. for 1 hr. The reaction mixture was cooled to room temperature, filtered through celite and washed with EtOAc (3×20 mL), the filtrate was concentrated and dried. The reaction crude was recrystallized from ethanol to give the desired product (11.5 g, 43.4 mmol, 86%), LCMS (m/z) 256.1 [M+H]$^+$.

Synthesis of (R)-2-(6-chloro-1,2,3,4-tetrahydropyrido[2,3-b]pyrazin-3-yl)ethanol

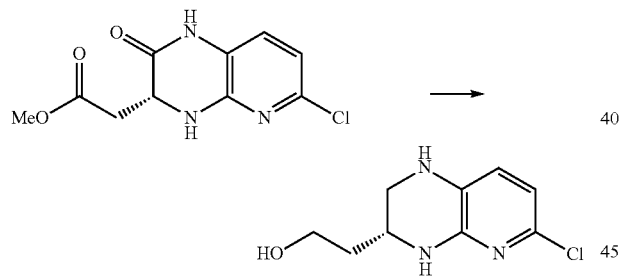

To a suspension of lithium aluminum hydride (8.54 g, 225 mmol) in Tetrahydrofuran (THF) (12 mL) was added a solution of (R)-methyl 2-(6-chloro-2-oxo-1,2,3,4-tetrahydropyrido[2,3-b]pyrazin-3-yl)acetate (11.5 g, 45.0 mmol) in Tetrahydrofuran (THF) (60 mL) dropwise at 0° C. under Nitrogen atmosphere. The reaction mixture was heated to 70° C. for 16 hr. The reaction mixture was cooled to 0° C., quenched with water (8 mL), keeping the internal temperature below 5° C. After addition was complete, the reaction was stirred for 15 min. Next, 10 mL of 15% (W/W) NaOH(aq.) was added, keeping the internal temp below 5° C., After addition was complete, the reaction was stirred for 15 min. To complete the workup, 12 mL of water was added then the mixture was stirred at room temperature for 1 h. The solids were filtered and washed with THF (3×20 mL) The filtrate and washings were concentrated in vacuo. The crude was added to a silica gel column and was eluted with (3:7) Hex/EtOAc. Collected fractions were evaporated to obtain the desired product (6 g, 27.0 mmol, 60.1%), LCMS (m/z) 214.1 [M+H]$^+$.

Synthesis of (4R)-7-chloro-2,3,4,5-tetrahydro-1,4-methanopyrido[2,3-b][1,4]diazepine

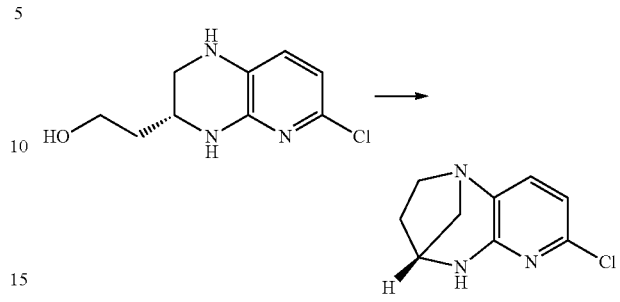

To a solution of (R)-2-(6-chloro-1,2,3,4-tetrahydropyrido[2,3-b]pyrazin-3-yl)ethanol (7 g, 32.8 mmol) in dichloromethane (DCM) (70 mL) was added triethylamine (18.27 mL, 131 mmol) under nitrogen. The mixture was stirred at room temperature until it was homogeneous, Then it was cooled to 0° C. Next POCl$_3$ (4.58 mL, 49.1 mmol) was added dropwise maintaining the temperature 0° C. to 5° C. The reaction mixture was stirred at 25° C. for 2 hr. After the reaction was completed 100 mL 1.2M NaHCO$_3$(aq.) was added. The layers were separated and the aqueous layer was extracted with DCM (2×200 mL). The combined organic layers were concentrated to dryness. The solid residue was dried in vacuo. The crude product 8 g was added to a silica gel column and was eluted with 70% EtOAc/Pet ether. Collected fractions was evaporated to obtain the desired product (5.2 g, 26.5 mmol, 81% yield), LCMS (m/z) 195.9 [M+H]$^+$.

Synthesis of (S)-dimethyl 2-((6-chloro-3-nitropyridin-2-yl)amino)pentanedioate

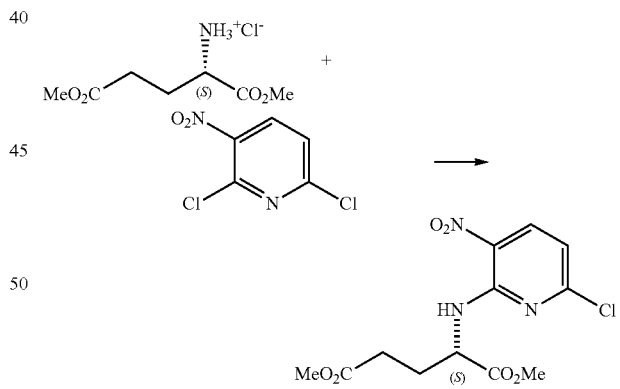

To a mixture of 40.0 g (207 mmol) of 2,6-dichloro-3-nitropyridine, 87.7 g (414 mmol) of L-glutamic acid dimethyl ester hydrochloride, and 69.6 g (829 mmol) of NaHCO$_3$ was added 600 mL of tetrahydrofuran. The mixture was stirred at 40° C. for 24 h, monitoring for the disappearance of 2,6-dichloro-3-nitropyridine by HPLC. After the reaction was complete, the solids were filtered away and washed with ethyl acetate (3×100 mL). The combined filtrate and washings were concentrated in vacuo, then the residue was purified via silica gel chromatography, eluting with 10/1 (v/v) hexanes/ethyl acetate, to give (60 g, 87%) of the product as a yellow solid, LCMS (m/z) 332.1 [M+H]$^+$.

Synthesis of (S)-methyl 3-(6-chloro-2-oxo-1,2,3,4-tetrahydropyrido[2,3-b]pyrazin-3-yl)propanoate

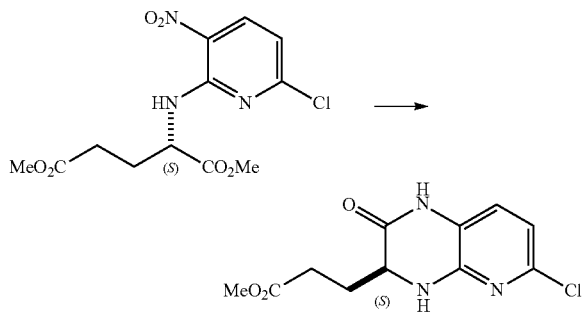

To a mixture of 20 g (60.2 mmol) of (S)-dimethyl 2-((6-chloro-3-nitropyridin-2-yl)amino)pentanedioate and 16.8 g (301 mmol) of iron powder was added 375 mL of 2-propanol, then 125 mL of water. To the stirred mixture was added 5.5 g (90.3 mmol) of acetic acid, then the reaction was stirred at reflux for 1 h. The reaction was monitored for the disappearance of starting material by HPLC. After the reaction was complete, the solids were filtered off and washed with 2-propanol (3×50 mL). The combined filtrate and washings were concentrated to dryness, and then the residue was dried in vacuo to give 15 g (81%) of the product as a dark yellow solid. This was used without further purification in the next step, LCMS (m/z) 270.1 [M+H]$^+$.

Synthesis of (S)-3-(6-chloro-1,2,3,4-tetrahydropyrido[2,3-b]pyrazin-3-yl)propan-1-ol

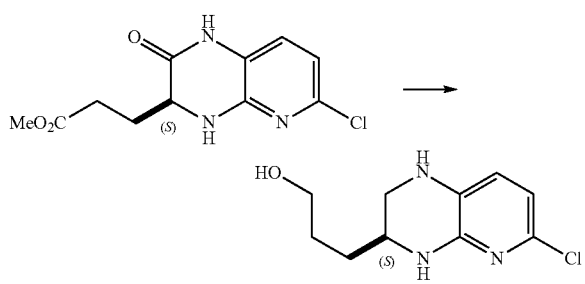

To a solution of 17.78 g (133.3 mmol) of AlCl$_3$ in 260 mL of tetrahydrofuran (THF) under N$_2$ was added 200 mL of 2M LiAlH$_4$ in THF, dropwise, at a rate to control gas evolution. This gave a solution of alane (AlH$_3$) in THF. In a separate flask, a solution of 26.0 g (96.4 mmol) of (S)-methyl 3-(6-chloro-2-oxo-1,2,3,4-tetrahydropyrido[2,3-b]pyrazin-3-yl)propanoate in 460 mL of THF was prepared under N$_2$, then cooled with a dry ice/acetone bath. To this was added the alane solution, dropwise with stirring, over 2 h. When the addition was complete, the cooling bath was removed, and the reaction was allowed to warm to ambient temperature. After 1.5 h, LCMS analysis showed that the reaction was complete. Next, a solution of 17.6 g NaOH in 65 mL of water was added slowly to control the evolution of H$_2$. The suspension was allowed to stir for 18 h, and then the solids were filtered away. The precipitate was washed with ethyl acetate, then the filtrate and washings were concentrated in vacuo. The product was purified via silica gel chromatography eluting with CH$_2$Cl$_2$, followed by a gradient of 0 to 10% methanol in CH$_2$Cl$_2$ to give 15.21 g (69%) of a yellow-orange solid, LCMS (m/z) 228.1 [M+H]$^+$.

Synthesis of (9S)-2-chloro-7,8,9,10-tetrahydro-6H-5,9-methanopyrido[2,3-b][1,4]diazocine

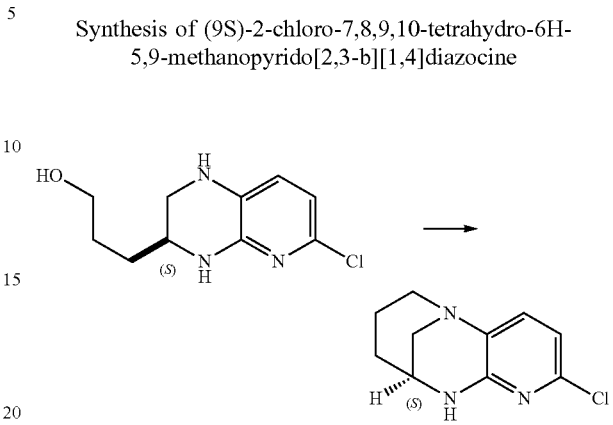

To 12 g (52.7 mmol) of (S)-3-(6-chloro-1,2,3,4-tetrahydropyrido[2,3-b]pyrazin-3-yl)propan-1-ol was added 160 mL of 48% (w/w) aq. HBr, then the reaction was stirred at 90° C. for 18 h. The reaction was monitored by HPLC for the disappearance of the starting alcohol. After the reaction was complete, it was cooled to ambient temperature, then 1.2 M aq. NaHCO$_3$ was added until pH=8. The mixture was extracted with ethyl acetate (3×100 mL), then the combined organic phases were washed with brine (1×100 mL), dried over Na$_2$SO$_4$ and filtered, and the filtrate was concentrated to dryness. The residue was purified via silica gel chromatography, eluting with 2/1 (v/v) hexanes/ethyl acetate to give 6.0 g (55%) of the product as a light yellow solid, LCMS (m/z) 210.1 [M+H]$^+$.

Synthesis of 4 Substituted Bicyclic Pyridine Core

Synthesis of 2,6-dichloro-4-methyl-3-nitropyridine

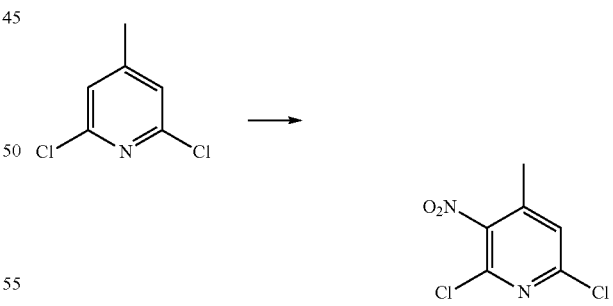

Nitric acid (1.5 mL, 33.6 mmol) was added to a solution of sulfuric acid (2.5 mL, 46.9 mmol) stirred under nitrogen at 0° C. Then 2,6-dichloro-4-methylpyridine (0.500 g, 3.09 mmol) was added at 0° C. Then the reaction mixture was stirred at 100° C. for 16 hr. The reaction was monitored by TLC. After completion, the reaction mixture was quenched with crushed ice and neutralized with NH$_4$OH solution and filtered the solid and dried under vacuum to give the desired product (0.300 g, 1.443 mmol, 46.8% yield) as a pale yellow solid, LCMS (m/z) 206.8 [M+H]$^+$.

Synthesis of (S)-dimethyl 2-((6-chloro-4-methyl-3-nitropyridin-2-yl)amino)succinate

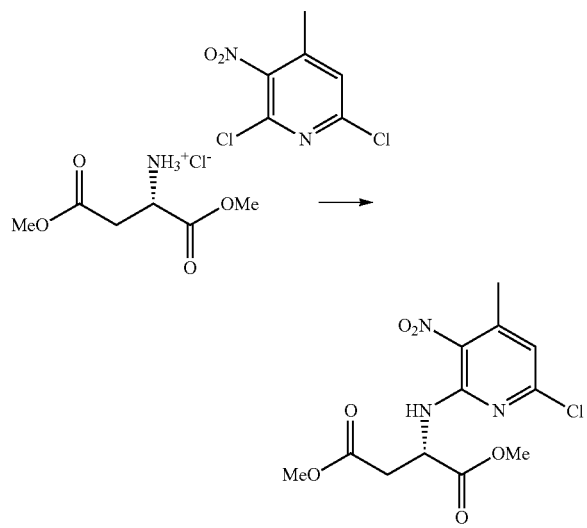

A suspension of 2,6-dichloro-4-methyl-3-nitropyridine (300 mg, 1.449 mmol) and sodium bicarbonate (243 mg, 2.90 mmol) in Tetrahydrofuran (THF) (20 mL)) was added (S)-dimethyl 2-aminosuccinate hydrochloride (430 mg, 2.174 mmol) at 0° C. under nitrogen. Then the reaction mixture was stirred at 65° C. for 24 hr. The reaction was monitored by TLC. The reaction mass filtered and washed with EtOAc (2×30 mL). The filtrate was concentrated under reduced pressure to give the crude material. The crude product was added to a neutral alumina column and was eluted with Hex/EtOAc (9:1). Collected fractions were concentrated under reduced pressure to afford the desired product (250 mg, 0.742 mmol, 51.2% yield) as yellow gummy liquid, LCMS (m/z) 339.1 (M+H)+.

Synthesis of (S)-methyl 2-(6-chloro-8-methyl-2-oxo-1,2,3,4-tetrahydropyrido[2,3-b]pyrazin-3-yl)acetate

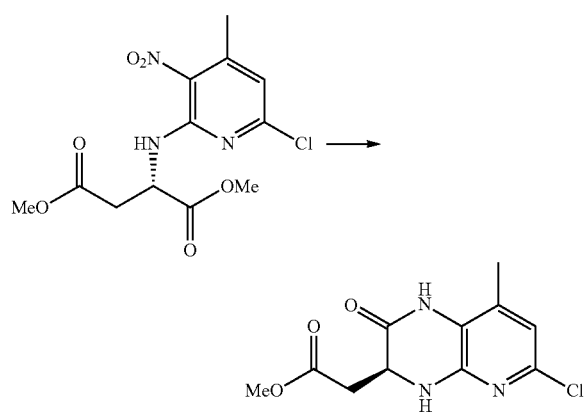

To a suspension of (S)-dimethyl 2-((6-chloro-4-methyl-3-nitropyridin-2-yl)amino)succinate (6.0 g, 18.09 mmol) and iron (5.05 g, 90 mmol) in isopropanol (80 mL) and Water (20 mL) stirred at 40° C. was added acetic acid (1.553 mL, 27.1 mmol). The reaction mixture was stirred at 80° C. for 1 hr. Reaction was monitored by TLC. The reaction mixture was cooled to room temperature, and quenched with saturated sodium bicarbonate solution and extracted with EtOAc. Organic layer washed with brine solution and dried out with sodium sulfate, filtered and evaporated to give the desired product (4.0 g, 14.32 mmol, 79% yield), LCMS (m/z) 269.9 [M+H]+.

Synthesis of (S)-2-(6-chloro-8-methyl-1,2,3,4-tetrahydropyrido[2,3-b]pyrazin-3-yl)ethanol

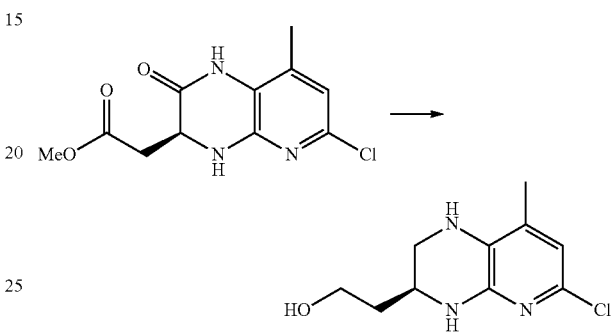

To a solution of aluminum chloride (0.173 g, 1.298 mmol), in Tetrahydrofuran (THF) (2.5 mL) stirred under nitrogen was added 2M solution of lithium aluminum hydride (2.220 mL, 4.44 mmol) in THF dropwise at a rate to control gas evolution. This gave a solution of alane (AlH3) in THF. In a separate flask, a solution of (S)-methyl 2-(6-chloro-8-methyl-2-oxo-1,2,3,4-tetrahydropyrido[2,3-b]pyrazin-3-yl)acetate (0.250 g, 0.927 mmol) in Tetrahydrofuran (THF) (5 mL) was prepared under nitrogen, to this was added the alane solution, dropwise at −78° C. over 15 minutes. When the addition was complete, the cooling bath was removed, and the reaction was allowed to warm to ambient temperature. The reaction was monitored by TLC. The reaction mixture was quenched with 10% NaOH solution at 0° C. and stirred 1 hr and extracted with EtOAc. EtOAc layer washed with water followed by brine solution and dried out with sodium sulfate, filtered and concentrated to give the desired product (150 mg, 0.407 mmol, 43.9% yield) as a pale yellow solid, LCMS (m/z) 228.2 [M+H]+.

Synthesis of (4S)-7-chloro-9-methyl-2,3,4,5-tetrahydro-1,4-methanopyrido[2,3-b][1,4]diazepine

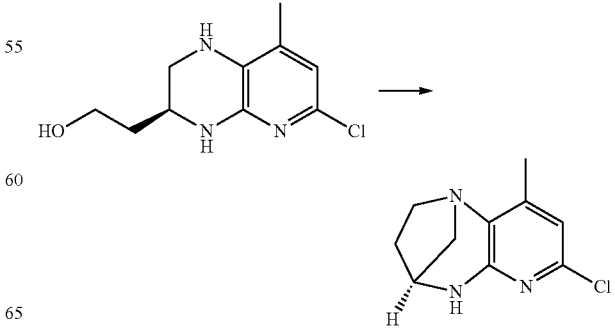

To (S)-2-(6-chloro-8-methyl-1,2,3,4-tetrahydropyrido[2,3-b]pyrazin-3-yl)ethanol (1.8 g, 7.91 mmol), was added HBr (4 mL, 35.4 mmol), the reaction mixture was stirred at 90° C. for 18 hr. The reaction was monitored by TLC. Following completion, the reaction mixture was quenched with saturated sodium bicarbonate solution and extracted with EtOAc. EtOAc layer washed with water followed by brine solution and dried out with sodium sulfate, filtered and concentrated to give crude product. The crude product was added to a neutral alumina and was eluted with 20% EtOAc/Hexane. Collected fractions were evaporated to afford the desired product (0.900 g, 4.27 mmol, 54.0% yield) as a pale yellow solid, LCMS (m/z) 210.2 [M+H]$^+$.

Chloride Coupling Reactions

Synthesis of (4S)-methyl 2,3,4,5-tetrahydro-1,4-methanopyrido[2,3-b][1,4]diazepine-7-carboxylate

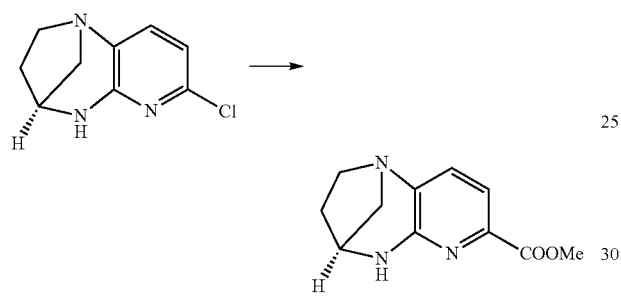

To a degassed solution of (4S)-7-chloro-2,3,4,5-tetrahydro-1,4-methanopyrido[2,3-b][1,4]diazepine (5 g, 25.55 mmol) in anhydrous MeOH (250 ml) were added TEA (17.77 mL, 127.77 mmol) and Pd(dppf)Cl$_2$ (934 mg, 1.2755 mmol) and the reaction mixture was stirred at 110° C. for 20 h under carbon monoxide atmosphere of 300 psi. The suspension was cooled to room temperature and the mixture was concentrated under reduced pressure to afford crude compound. The crude mixture was purified by flash column chromatography (100-200 silica-gel, was eluted with 2% Methanol in DCM) to afford (4S)-methyl-2,3,4,5-tetrahydro-1,4-methanopyrido[2,3-b][1,4]diazepine-7-carboxylate (3 g, 13.68 mmol, 53.5% yield) as a pale brown solid (TLC system: 5% Methanol in DCM, R$_f$ value: 0.2), LCMS (m/z) 220.3 [M+H]$^+$.

Synthesis of (4S)-7-(2-methylpyridin-4-yl)-2,3,4,5-tetrahydro-1,4-methanopyrido[2,3-b][1,4]diazepine

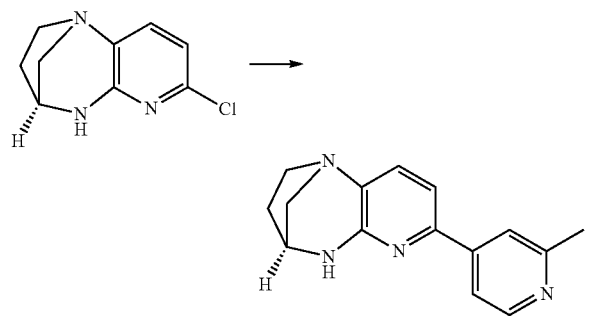

To a degassed solution of (4S)-7-chloro-2,3,4,5-tetrahydro-1,4-methanopyrido[2,3-b][1,4]diazepine (30 g, 153 mmol), (2-methylpyridin-4-yl)boronic acid (25.2 g, 184 mmol) and Potassium Phosphate Tri basic (65.1 g, 307 mmol) in 1-butanol (300 mL) and water (50.0 mL) were added tris(dibenzylideneacetone)dipalladium(0) (7.02 g, 7.67 mmol) and dicyclohexyl(2',4',6'-triisopropyl-[1,1'-biphenyl]-2-yl)phosphine (7.31 g, 15.33 mmol). The reaction mixture was heated at 100° C. for 3 h. The n-butanol solvent was evaporated under reduced pressure. The resulting residue was diluted with water (200 ml) and extracted with DCM (2×400 ml). The combined organic layer was washed with water, brine, dried over sodium sulfate and solvent was evaporated under reduced pressure to obtain the crude product. The crude product was triturated with diethyl ether and n-pentane (1:1) for 3 times (3×250 mL) afford (4S)-7-(2-methylpyridin-4-yl)-2,3,4,5-tetrahydro-1,4-methanopyrido[2,3-b][1,4]diazepine (25 g, 99.2 mmol, 62%) as an off white solid (TLC: 10% MeOH in EtOAc R$_f$: 0.2), LCMS (m/z) 252.9 [M+H]$^+$.

$^1$H NMR (400 MHz, DMSO-d6): δ 8.45 (dd, J=5.2, 0.8 Hz, 1H), 7.73 (dt, J=1.4, 0.7 Hz, 1H), 7.67-7.60 (m, 1H), 7.24-7.16 (m, 2H), 7.10 (d, J=7.7 Hz, 1H), 3.93 (td, J=5.0, 2.5 Hz, 1H), 3.19-2.98 (m, 2H), 2.92-2.71 (m, 2H), 2.50 (s, 3H), 2.11-1.96 (m, 1H), 1.94-1.81 (m, 1H).

Synthesis of (4S)-7-(6-methylpyridin-3-yl)-2,3,4,5-tetrahydro-1,4-methanopyrido[2,3-b][1,4]diazepine

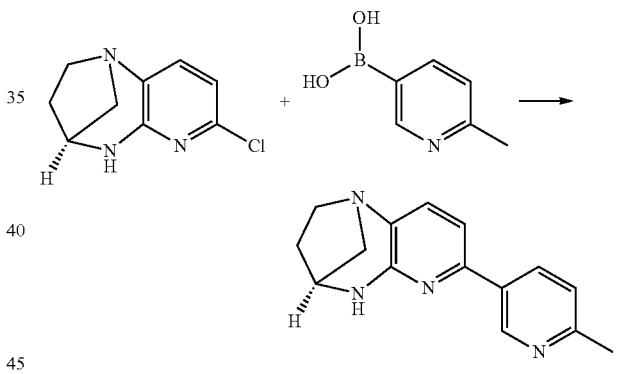

To a degassed solution of (4S)-7-chloro-2,3,4,5-tetrahydro-1,4-methanopyrido[2,3-b][1,4]diazepine (10 g, 51.1 mmol), (6-methylpyridin-3-yl)boronic acid (10.50 g, 77 mmol) and Potassium Phosphate Tri basic (21.70 g, 102 mmol) in 1,4-dioxane (100 mL) and water (20.0 mL) were added tris(dibenzylideneacetone)dipalladium(0) (4.68 g, 5.11 mmol) and x-phos (4.87 g, 10.22 mmol). The reaction mixture was heated at 100° C. for 8 h. The solvent was evaporated under reduced pressure; the obtained residue was diluted with water (200 ml) and extracted with DCM (2×100 ml). The combined organic layer was washed with water, brine, dried over sodium sulfate and solvent was evaporated under reduced pressure to obtain the crude product. The crude product was triturated with diethyl ether and n-pentane (1:1) for 3 times (3×100 mL) to afford (4S)-7-(6-methylpyridin-3-yl)-2,3,4,5-tetrahydro-1,4-methanopyrido[2,3-b][1,4]diazepine. (11.2 g, 44.4 mmol, 65%) as an off white solid (TLC: 10% MeOH in EtOAc R$_f$: 0.3). LCMS (m/z): 253.1 [M+H], Rt=2.86 min.

$^1$H NMR (400 MHz, CDCl$_3$): δ ppm 8.97 (d, J=2.19 Hz, 1H), 8.06 (dd, J=8.11, 2.41 Hz, 1H), 7.28-7.11 (m, 1H), 6.94

(d, J=7.89 Hz, 1H), 6.74 (d, J=7.67 Hz, 1H), 5.21 (s, 1H), 4.08-3.98 (m, 1H), 3.36-3.12 (m, 3H), 2.99-2.89 (m, 1H), 2.56 (s, 3H), 2.17-2.10 (m, 2H).

Synthesis of (4S)-7-(3-(trifluoromethyl)phenyl)-2,3,4,5-tetrahydro-1,4-methanopyrido[2,3-b][1,4]diazepine

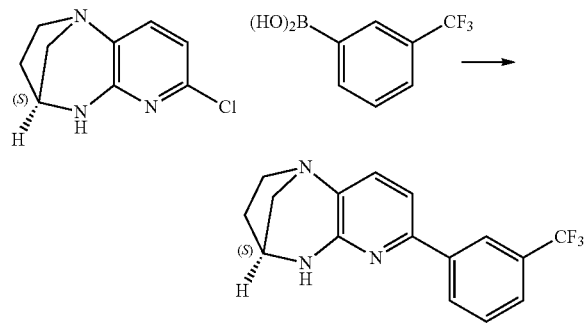

A suspension of (4S)-7-chloro-2,3,4,5-tetrahydro-1,4-methanopyrido[2,3-b][1,4]diazepine (20 g, 102 mmol), (3-(trifluoromethyl)phenyl)boronic acid (29.1 g, 153 mmol) and Cs₂CO₃ (100 g, 307 mmol) in 1,4-Dioxane (100 mL) and Water (10 mL) was stirred and degassed with argon at room temp for 15 mins. Next, palladium(II) acetate (0.574 g, 2.56 mmol) and 2-Dicyclohexylphosphino-2',4',6'-triisopropylbiphenyl 2-Dicyclohexylphosphino-2',4',6'-triisopropylbiphenyl (2.437 g, 5.11 mmol) were added to the reaction mixture. Then the reaction mixture was stirred at 110° C. for 2 hr. The reaction mass was filtered through celite and concentrated. The residue was diluted with EtOAc and washed with saturated NaHCO₃ followed by brine solution and dried out with sodium sulfate, filtered and evaporated. The crude product was added to a silica gel column and was eluted with Hex/EtOAc (1:1). Collected fractions were evaporated to afford (4S)-7-(3-(trifluoromethyl)phenyl)-2,3,4,5-tetrahydro-1,4-methanopyrido[2,3-b][1,4]diazepine (18 g, 58.3 mmol, 57.0% yield) as white solid, LCMS (m/z) 306.1 (M+H)⁺.

Synthesis of 2-(2-(trifluoromethyl)pyridin-4-yl)-7,8,9,10-tetrahydro-6H-5,9-methanopyrido[2,3-b][1,4]diazocine

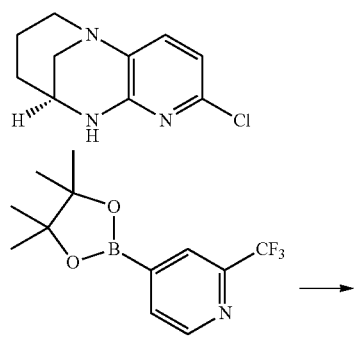

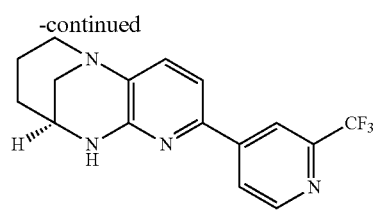

To a solution of 2-chloro-7,8,9,10-tetrahydro-6H-5,9-methanopyrido[2,3-b][1,4]diazocine (3 g, 14.31 mmol), 4-(4,4,5,5-tetramethyl-1,3,2-dioxaborolan-2-yl)-2-(trifluoromethyl)pyridine (3.91 g, 14.31 mmol) and cesium carbonate (4.66 g, 14.31 mmol) in 1,4-Dioxane (60 ml) and water (6 ml) at room temp and reaction mass degassed with argon for 20 min. Next, added solid palladium(II) acetate (3.21 g, 14.31 mmol) and x-phos (6.82 g, 14.31 mmol) in to the reaction mass in one charge. The reaction mixture was stirred at 105° C. for 3-4 hrs. The reaction mass was filtered through celite bed and concentrated. The crude material was taken and dissolved in ethyl acetate and washed with sodium bicarbonate solution and water. Organic phase was dried over sodium sulfate and concentrated to get. The residue was triturated with n-pentane (3×50 mL). The resulting solid was filtered through a Buchner funnel, rinsed with n-pentane, and collected as the desired product (4 g, 86%), LCMS (m/z) 321.3 (M+H)⁺.

Synthesis of (9S)-2-(5-(trifluoromethyl)pyridin-3-yl)-7,8,9,10-tetrahydro-6H-5,9-methanopyrido[2,3-b][1,4]diazocine

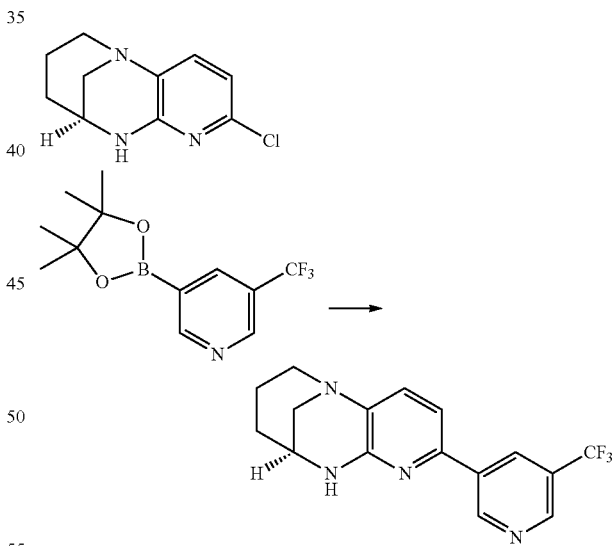

To a solution of (9S)-2-chloro-7,8,9,10-tetrahydro-6H-5,9-methanopyrido[2,3-b][1,4]diazocine (3 g, 14.31 mmol), (5-(trifluoromethyl)pyridin-3-yl)boronic acid (5.46 g, 28.6 mmol) and Cs2CO3 (13.99 g, 42.9 mmol) in Tetrahydrofuran (THF) (60 ml), water (4 ml) stirred under nitrogen at 25° C., purged with Argon gas for 20 minutes. Then palladium (II) acetate (0.080 g, 0.358 mmol) and X-Phos (227 mg) were added. The reaction mixture was stirred at 110° C. for 16 hr. Next, the reaction mixture was concentrated and the residue was taken up in DCM (100 mL). The solution was washed with water and brine, dried over Na₂SO₄, filtered and concentrated. The crude product was added to a silica gel column and was eluted with Hex/EtOAc (1:1) Collected fractions were evaporated to give as a off white solid (3.6 g, 11.1 mmol 76%), LCMS (m/z) 321.2 [M+H]+.

Synthesis of (9S)-2-(2-methylpyridin-4-yl)-7,8,9,10-tetrahydro-6H-5,9-methanopyrido[2,3-b][1,4]diazocine

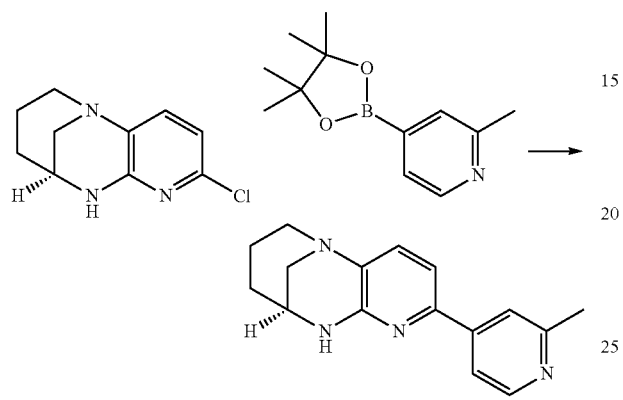

To a solution of (9S)-2-chloro-7,8,9,10-tetrahydro-6H-5,9-methanopyrido[2,3-b][1,4]diazocine (10 g, 47.7 mmol), (2-methylpyridin-4-yl)boronic acid (8.49 g, 62.0 mmol) and Potassium phosphate (30.4 g, 143 mmol) in 1-Butanol (300 ml), water (100 ml) stirred under nitrogen at 25° C., purged with Argon gas for 20 minutes was added X-Phos (2.274 g, 4.77 mmol), Pd2(dba)3 (2.184 g, 2.385 mmol). The reaction mixture was stirred at 120° C. for 16 hr. Before being concentrated and the residue was taken up in DCM (700 mL). The solution was washed with water and brine, dried over Na2SO4, filtered and concentrated to get brown semi-solid crude product. The crude product was purified by washing with hexane to get off white solid product (9 g, 32.4 mmol, 67.9% yield), LCMS (m/z): 267.3 (M+H)+.

Synthesis of (4S)-9-methyl-7-(6-methylpyridin-3-yl)-2,3,4,5-tetrahydro-1,4-methanopyrido[2,3-b][1,4]diazepine

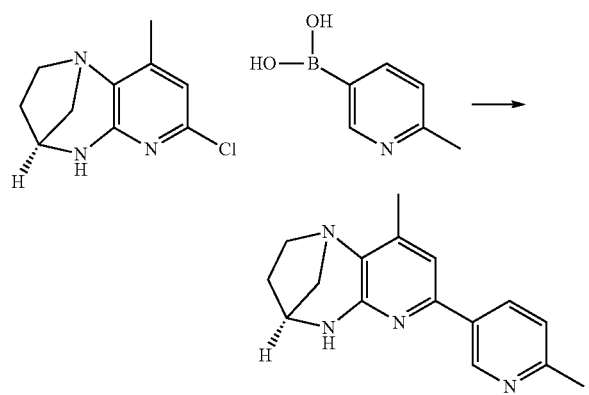

A suspension of (4S)-7-chloro-9-methyl-2,3,4,5-tetrahydro-1,4-methanopyrido[2,3-b][1,4]diazepine (0.900 g, 4.29 mmol), (6-methylpyridin-3-yl)boronic acid (0.882 g, 6.44 mmol) and tripotassium phosphate (2.73 g, 12.88 mmol) in 1,4-Dioxane (14.4 mL) & Water (3.6 mL) was stirred and degassed with argon at room temp for 15 mins. Then Pd2(dba)3 (0.393 g, 0.429 mmol) and X-Phos (0.409 g, 0.858 mmol) were added to the reaction mixture. The reaction mixture was stirred 16 hr at 90° C. The reaction was monitored by TLC (50% EtOAc/Hexanes). The reaction mixture was cooled to room temp and filtered through celite and washed with EtOAc. The filtrate was concentrated and dissolved with EtOAc. The EtOAc layer was washed with water followed by brine solution and dried over sodium sulfate, filtered and concentrated to give crude(4S)-9-methyl-7-(6-methylpyridin-3-yl)-2,3,4,5-tetrahydro-1,4-methanopyrido[2,3-b][1,4]diazepine (0.700 g, 2.60 mmol, 60.7% yield) as a off-white solid, LCMS (m/z) 267.0 [M+H]+.

Synthesis of (2R)-2-ethyl-4-((4S)-2,3,4,5-tetrahydro-1,4-methanopyrido[2,3-b][1,4]diazepin-7-yl)morpholine

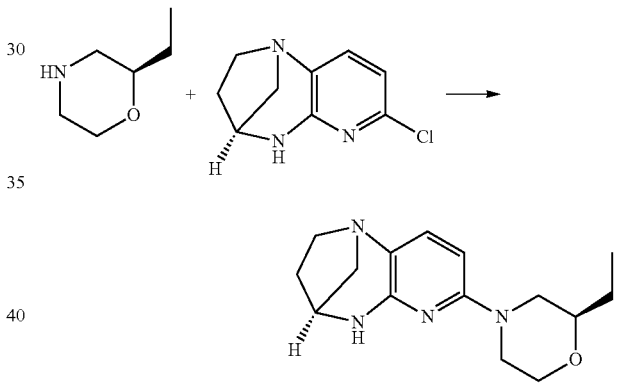

A suspension of (4S)-7-chloro-2,3,4,5-tetrahydro-1,4-methanopyrido[2,3-b][1,4]diazepine (900 mg, 4.60 mmol), (R)-2-ethylmorpholine (1060 mg, 9.20 mmol) and KOtBu (1032 mg, 9.20 mmol) in 1,2-Dimethoxyethane (DME) (20 mL) stirred under nitrogen and degassed at room temperature for 15 min, was added (1,3-Bis(2,6-di-isopropylphenyl)-4,5-dihydroimidazol-2-ylidene)chloro) (3-phenylallyl) palladium(2) (120 mg, 0.184 mmol). The reaction mixture was stirred at 90° C. for 12 hr. The reaction mass filtered through celite pad and the filtrate concentrated. Reaction mixture was diluted with water and extracted with EtOAc (2×20 mL). The organic layers were washed with water followed by brine solution and dried out with sodium sulfate. The organic layer was concentrated under reduced pressure. The Crude compound was purified by column chromatography (Neutral alumina) product was eluted with 20% ethyl acetate in hexane. Collected fractions evaporated under reduce pressure and dried under high vacuum to afford (2R)-2-ethyl-4-((4S)-2,3,4,5-tetrahydro-1,4-methanopyrido[2,3-b][1,4]diazepin-7-yl)morpholine (750 mg, 2.73 mmol, 59.4% yield) as a Pale yellow solid, LCMS (m/z) 275.3 [M+H]+.

Synthesis of (2S,6S)-2,6-dimethyl-4-((4S)-2,3,4,5-tetrahydro-1,4-methanopyrido[2,3-b][1,4]diazepin-7-yl)morpholine

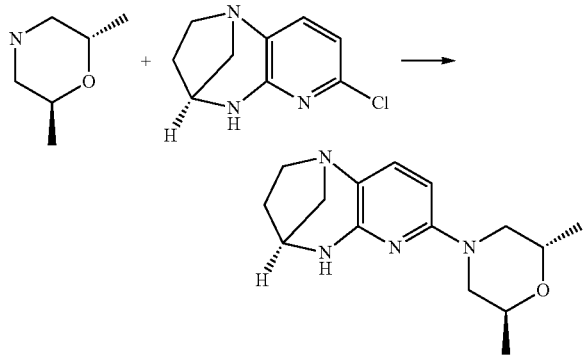

A suspension of (4S)-7-chloro-2,3,4,5-tetrahydro-1,4-methanopyrido[2,3-b][1,4]diazepine (0.800 g, 4.09 mmol), (2S,6S)-2,6-dimethylmorpholine (0.942 g, 8.18 mmol) and KOtBu (0.918 g, 8.18 mmol) in 1,2-Dimethoxyethane (DME) (30 mL) was stirred and degassed with argon at room temp for 15 mins. Then (1,3-Bis(2,6-di-isopropylphenyl)-4,5-dihydroimidazol-2-ylidene)chloro) (3-phenylallyl)palladium(II) (0.106 g, 0.164 mmol) added to the reaction mixture. Then the reaction mixture was stirred 16 hr at 90° C. The reaction was monitored by TLC. After completion, the reaction mass filtered through celite and the filtrate concentrated under reduced pressure. The resulting reaction mixture was diluted with EtOAc and washed with water followed by brine solution and dried out with sodium sulfate, filtered and evaporated to get crude. The crude product was added to a neutral alumina and was eluted with (1:2) EtOAc/Hexane. Collected fractions were evaporated to afford (2S,6S)-2,6-dimethyl-4-((4S)-2,3,4,5-tetrahydro-1,4-methanopyrido[2,3-b][1,4]diazepin-7-yl)morpholine (0.780 g, 2.79 mmol, 68% yield) as a off-white solid, LCMS (m/z) 275.3 [M+H]$^+$.

Synthesis of (2R,6R)-2,6-dimethyl-4-((4S)-2,3,4,5-tetrahydro-1,4-methanopyrido[2,3-b][1,4]diazepin-7-yl)morpholine

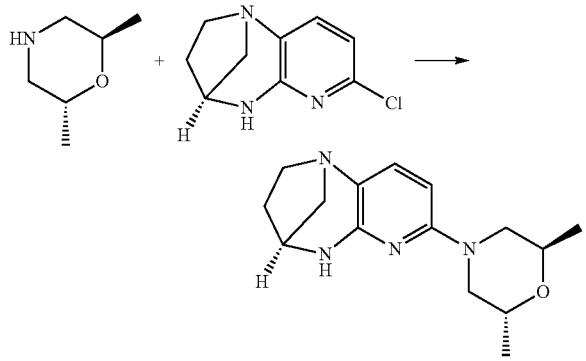

A suspension of (4S)-7-chloro-2,3,4,5-tetrahydro-1,4-methanopyrido[2,3-b][1,4]diazepine (0.800 g, 4.09 mmol), (2R,6R)-2,6-dimethylmorpholine (0.942 g, 8.18 mmol) and KOtBu (0.918 g, 8.18 mmol) in 1,2-Dimethoxyethane (DME) (30 mL) stirred and degassed with argon at room temperature for 15 mins. Then (1,3-Bis(2,6-di-isopropylphenyl)-4,5-dihydroimidazol-2-ylidene)chloro) (3-phenylallyl) palladium(2) (0.106 g, 0.164 mmol) added to the reaction mixture. Then the reaction mixture was stirred 16 hr at 90° C. The reaction was monitored by TLC (TLC: 100% EtOAc R$_f$ value: 0.2). The reaction mass filtered through celite and distill out the solvent completely. Reaction mixture was diluted with EtOAc and washed with water followed by brine solution and dried out with sodium sulfate, filtered and evaporated to get crude. The crude product was added to a neutral alumina and was eluted with (1:1) EtOAc/Hexane. Collected fractions were evaporated to afford (2R,6R)-2,6-dimethyl-4-((4S)-2,3,4,5-tetrahydro-1,4-methanopyrido[2,3-b][1,4]diazepin-7-yl)morpholine (0.800 g, 2.75 mmol, 67.3% yield) as an off-white solid, LCMS (m/z) 275.0 [M+H]$^+$.

Synthesis of (2S,6R)-2,6-dimethyl-4-((4S)-2,3,4,5-tetrahydro-1,4-methanopyrido[2,3-b][1,4]diazepin-7-yl)morpholine

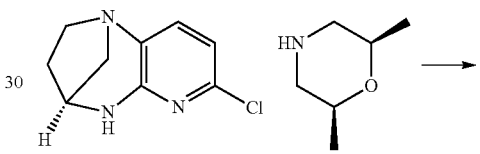

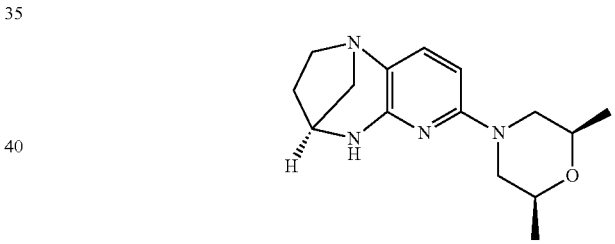

A suspension of (4S)-7-chloro-2,3,4,5-tetrahydro-1,4-methanopyrido[2,3-b][1,4]diazepine (1.00 g, 5.11 mmol), (2S,6R)-2,6-dimethylmorpholine (1.177 g, 10.22 mmol) and KOtBu (1.147 g, 10.22 mmol) in 1,2-Dimethoxyethane (DME) (20 mL) was stirred and degassed with argon at room temp for 15 mins. Then (1,3-Bis(2,6-di-isopropylphenyl)-4,5-dihydroimidazol-2-ylidene)chloro) (3-phenylallyl)palladium(II) (0.133 g, 0.204 mmol) was added to the reaction mixture. The reaction mixture was stirred 16 hr at 90° C. The reaction mass was filtered through celite and the solvent evaporated. The reaction mixture was diluted with EtOAc and washed with water followed by brine solution and dried over sodium sulfate, filtered and evaporated to give crude (2S,6R)-2,6-dimethyl-4-((4S)-2,3,4,5-tetrahydro-1,4-methanopyrido[2,3-b][1,4]diazepin-7-yl)morpholine (0.820 g, 2.86 mmol, 56.0% yield). The crude product was added to neutral alumina and was eluted with 20% EtOAc/Hexane to afford (2S,6R)-2,6-dimethyl-4-((4S)-2,3,4,5-tetrahydro-1,4-methanopyrido[2,3-b][1,4]diazepin-7-yl)morpholine (0.820 g, 2.86 mmol, 56.0% yield) as an off-white solid, LCMS (m/z) 275.2 [M+H]$^+$.

Synthesis of 2-cyclopropyl-4-((4S)-2,3,4,5-tetrahydro-1,4-methanopyrido[2,3-b][1,4] diazepine-7-morpholine

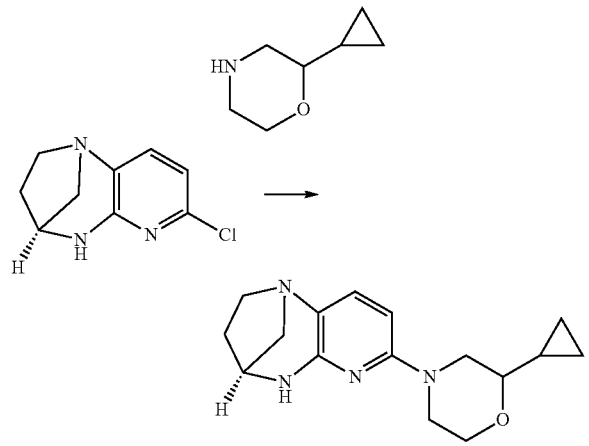

To a solution of (4S)-7-chloro-2,3,4,5-tetrahydro-1,4-methanopyrido[2,3-b][1,4]diazepine (1 g, 5.11 mmol) in 1,2-Dimethoxyethane (DME) (15 mL) with stirring at 0° C. was added 2-cyclopropylmorpholine (0.650 g, 5.11 mmol) and potassium tert-butoxide (0.574 g, 5.11 mmol). The solution was then degassed for 15 min and cinnamyl chloro [1,3-bis(diisopropylphenyl)-2-imidazolidinyliin]Pd(II) (3.32 g, 5.11 mmol) was added. The reaction was then stirred for 16 h at 90° C. The reaction mixture was quenched with 15 ml of water and extracted with 15 ml of ethyl acetate. The organic layer was dried over sodium sulfate and concentrated under reduced pressure to afford the crude compound. The crude product was added to a 100-200 silica gel column and was eluted with 2% DCM/MeOH 2-cyclopropyl-4-((4S)-2,3,4,5-tetrahydro-1,4-methanopyrido[2,3-b][1,4]diazepin-7-yl)morpholine (1 g, 3.49 mmol, 68.3% yield) to give the product as an off white solid, LCMS (m/z) 287.2 [M+H]$^+$.

Synthesis of 2,2-dimethyl-4-((4S)-2,3,4,5-tetrahydro-1,4-methanopyrido[2,3-b][1,4]diazepin-7-yl)morpholine

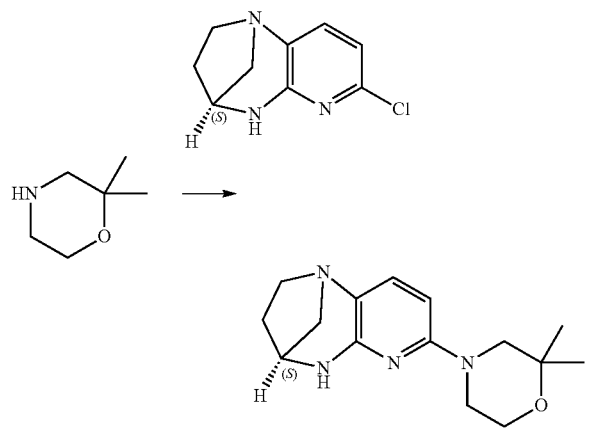

A suspension of (4S)-7-chloro-2,3,4,5-tetrahydro-1,4-methanopyrido[2,3-b][1,4]diazepine (1.0 g, 5.11 mmol), 2,2-dimethylmorpholine (1.177 g, 10.22 mmol) and KOtBu (1.147 g, 10.22 mmol) in 1,2-Dimethoxyethane (DME) (20 mL) was stirred and degassed with argon at room temp for 15 mins. Then (1,3-Bis(2,6-di-isopropylphenyl)-4,5-dihydroimidazol-2-ylidene)chloro) (3-phenylallyl)palladium(2) (0.133 g, 0.204 mmol) was added to the reaction mixture. The reaction mixture was stirred 16 hr at 90° C. The reaction mass was filtered through celite and the solvent evaporated. The reaction mixture was diluted with EtOAc and washed with water followed by brine solution. The solution was dried over sodium sulfate, filtered and evaporated to give the crude product. The crude product was added to a neutral alumina column and was eluted with DCM to afford 2,2-dimethyl-4-((4S)-2,3,4,5-tetrahydro-1,4-methanopyrido[2,3-b][1,4]diazepin-7-yl)morpholine (0.800 g, 2.67 mmol, 52.3% yield) as a white solid, LCMS (m/z) 275.0 [M+H]$^+$.

Synthesis of (9S)-2-((R)-2-(trifluoromethyl)pyrolidin-1-yl)pyrrolidin-1-yl)-7,8,9,10-tetrahydro-6H-5,9-methanopyrido[2,3-b][1,4]diazocine

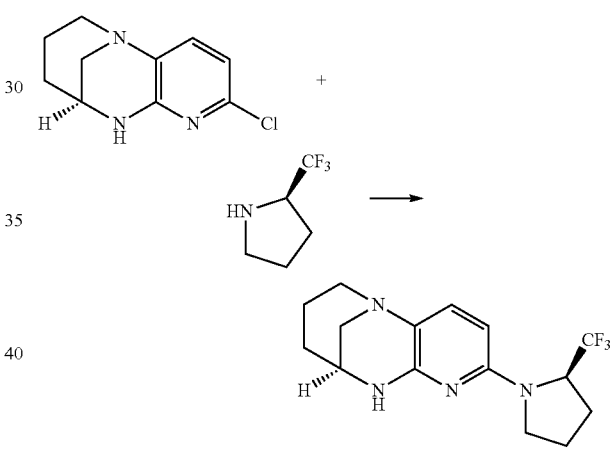

To a suspension of (9S)-2-chloro-7,8,9,10-tetrahydro-6H-5,9-methanopyrido[2,3-b][1,4]diazocine (0.5 g, 2.385 mmol), (R)-2-(trifluoromethyl)pyrrolidine (0.663 g, 4.77 mmol) and KO$^t$Bu (0.535 g, 4.77 mmol) in 1,2-Dimethoxyethane (DME) (10 mL) under nitrogen atmosphere at room temperature was added solid [1,3-Bis(2,6-di-isopropylphenyl)-4,5-dihydroimidazol-2-ylidene]chloro][3-phenylallyl]palladium(II) (1.549 g, 2.385 mmol) and stirred at 80° C. for 16 h. The reaction mass was cooled down to room temperature and filtered through celite and the solvent was evaporated under reduced pressure to obtain crude residue. The crude residue was diluted with EtOAc (100 mL) and washed with water (50 mL×2) followed by brine solution and dried over anhydrous sodium sulfate, filtered and evaporated to obtain the crude product. The crude product was purified by flash column chromatography (silica gel: 100-200 mesh, eluted with 1:1 Hex/EtOAc) to afford (9S)-2-((2R)-2-(trifluoromethyl)cyclopentyl)-6,7,8,9,10,10a-hexahydro-4aH-5,9-methanopyrido[2,3-b][1,4]diazocine (500 mg, 1.596 mmol, 64.6% yield) as a light green solid (TLC: R$_f$ 0.3, eluent: 80% EtOAc in Hexane), LCMS (m/z) 313.2 [M+H]$^+$.

Synthesis of (9S)-2-((S)-2-(trifluoromethyl)pyrrolidin-1-yl)-7,8,9,10-tetrahydro-6H-5,9-methanopyrido[2,3-b][1,4]diazocine

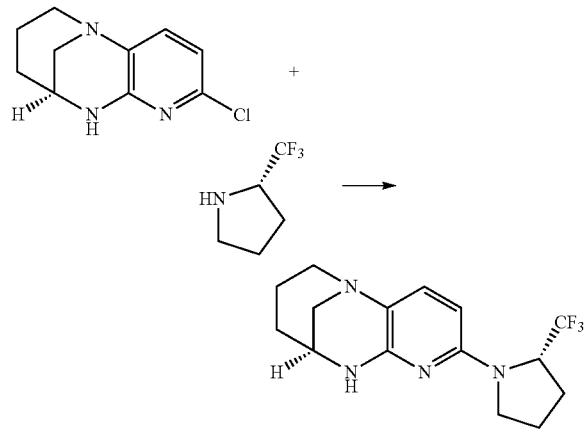

A suspension of (9S)-2-chloro-7,8,9,10-tetrahydro-6H-5,9-methanopyrido[2,3-b][1,4]diazocine (0.5 g, 2.385 mmol), (S)-2-(trifluoromethyl)pyrrolidine (0.663 g, 4.77 mmol) and KOtBu (0.535 g, 4.77 mmol) in 1,2-Dimethoxyethane (DME) (10 mL) was stirred and degassed with argon at room temp for 15 mins. Next, [1,3-Bis(2,6-di-isopropylphenyl)-4,5-dihydroimidazol-2-ylidene]chloro][3-phenylallyl]palladium(II) (1.549 g, 2.385 mmol) added to the reaction mixture. Then the reaction mixture was stirred 16 hr at 80° C. After completion, the reaction mass filtered through celite and concentrated to dryness. The resulting residue was diluted with EtOAc and washed with water followed by brine solution and dried out with sodium sulfate, filtered and evaporated. The crude product was added to a silica gel column, eluted with Hex/EtOAc (1:1). Collected fractions were evaporated to get (9S)-2-((S)-2-(trifluoromethyl)pyrrolidin-1-yl)-7,8,9,10-tetrahydro-6H-5,9-methanopyrido[2,3-b][1,4]diazocine (0.6 g, 1.868 mmol, 78% yield) as an off-white solid, LCMS (m/z) 313.3 [M+H]$^+$.

Synthesis of (9S)-2-(3-(trifluoromethyl)pyrrolidin-1-yl)-7,8,9,10-tetrahydro-6H-5,9-methanopyrido[2,3-b][1,4]diazocine

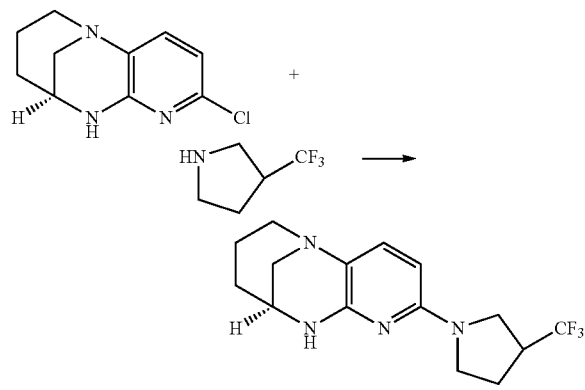

KOtBu (0.321 g, 2.86 mmol was added to a stirred solution of (9S)-2-chloro-7,8,9,10-tetrahydro-6H-5,9-methanopyrido[2,3-b][1,4]diazocine (0.3 g, 1.431 mmol), and 3-(trifluoromethyl)pyrrolidine (0.398 g, 2.86 mmol) in 1,2-Dimethoxyethane (DME) (10 mL). The reaction mixture was stirred and degassed with argon at room temp for 15 mins. and then (1,3-Bis(2,6-di-isopropylphenyl)-4,5-dihydroimidazol-2-ylidene)chloro) (3-phenylallyl)palladium(2) (0.037 g, 0.057 mmol) added to the reaction mixture. The reaction was stirred for 16 h at 80° C. The reaction was cooled to room temperature, filtered through celite and evaporated under reduced pressure. The reaction mixture was partitioned between water (20 mL) and EtOAc (50 mL). Organic layer was separated and was dried over anhydrous Na$_2$SO$_4$, filtered and filtrate was evaporated to give crude as brown solid (TLC eluent: 80% EtOAc: R$_f$-0.4; UV active). The crude was purified by column chromatography using (100-200 mesh) silica gel and was eluted with 50% EtOAc in Hexane to afford (85:15) mixture and further purified by SFC to afford pure (9S)-2-(3-(trifluoromethyl)pyrrolidin-1-yl)-7,8,9,10-tetrahydro-6H-5,9-methanopyrido[2,3-b][1,4]diazocine (0.151 g, 0.473 mmol, 33.1% yield) as a Off-white solid.

Analytical SFC Conditions: Peak-II Column/dimensions: Chiralpak AD-H (250×4.6) mm, 5 u
% CO2: 70.0%
% Co solvent: 30.0% (0.5% DEA In MeOH)
Total Flow: 3.0 g/min
Back Pressure: 100 bar
Temperature: 26.8° C.
UV: 212 nm
Preparative SFC Conditions
Column/dimensions: Chiralpak AD-H (250×30) mm
% CO2:75%
% Co solvent: 25.0% (MeOH)
Total Flow: 100.0 g/min
Back Pressure: 100 bar
UV: 212 nm
Stack time: 1.8 min
Load/inj: 5.5 mg
LCMS (m/z) 313.3 [M+H]$^+$.

$^1$H NMR (400 MHz, DMSO-d6): δ 6.87 (d, J=8.1 Hz, 1H), 6.49 (d, J=4.9 Hz, 1H), 5.58 (d, J=8.1 Hz, 1H), 3.60 (dd, J=10.8, 8.4 Hz, 1H), 3.47 (s, 1H), 3.39 (dd, J=10.6, 5.8 Hz, 2H), 3.30 (s, 2H), 3.14-2.98 (m, 2H), 2.90 (d, J=4.5 Hz, 1H), 2.50 (qd, J=3.2, 2.2, 1.6 Hz, 1H), 2.31-2.13 (m, 1H), 2.05 (d, J=7.1 Hz, 1H), 1.72 (dt, J=7.0, 3.0 Hz, 2H), 1.44 (s, 1H), 1.16 (d, J=14.4 Hz, 1H).

Synthesis of (9S)-2-(3-(trifluoromethyl)pyrrolidin-1-yl)-7,8,9,10-tetrahydro-6H-5,9-methanopyrido[2,3-b][1,4]diazocine

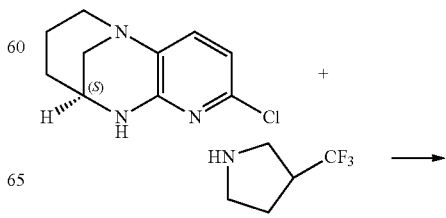

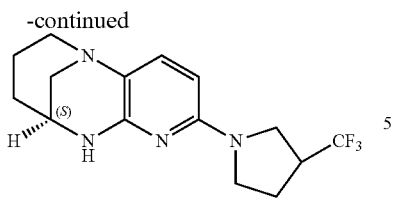

(1,3-Bis(2,6-di-isopropylphenyl)-4,5-dihydroimidazol-2-ylidene)chloro) (3-phenylallyl) palladium (0.062 g, 0.095 mmol) added to a degassed suspension of (9S)-2-chloro-7,8,9,10-tetrahydro-6H-5,9-methanopyrido[2,3-b][1,4]diazocine (0.5 g, 2.385 mmol), 3-(trifluoromethyl)pyrrolidine (0.663 g, 4.77 mmol) and KOtBu (0.535 g, 4.77 mmol) in 1,2-dimethoxyethane (20 mL) at RT. The reaction mixture was further degassed for 10 min and was stirred for 16 h at 80° C. The reaction mixture was cooled to RT and was filtered through a pad of celite. The filtrate was evaporated to obtain brown residue. The residue was partitioned between water (15 mL) and EtOAc (2×25 mL). The organic layer was washed with water followed by brine solution and dried over anhydrous sodium sulfate, filtered and filtrate was evaporated to get the crude (TLC eluent: 80% EtOAc/hexane, Rf value: 0.4, UV active). The crude was purified by column chromatography (100-200 mesh) using silica gel, and the product was eluted 50% ethyl acetate in pet ether to give (30:70) mixture of enantiomers which on further SFC purification afforded (9S)-2-(3-(trifluoromethyl)pyrrolidin-1-yl)-7,8,9,10-tetrahydro-6H-5,9-methanopyrido[2,3-b][1,4]diaz-ocine (0.125 g, 0.393 mmol, 16.46% yield) as a brown solid.

Analytical SFC Conditions: Peak I (major)
Chiralpak AD-H (250×4.6) mm, 5 u
% CO2: 70.0%
% Co solvent: 30.0% (0.5% DEA In MeOH)
Total Flow: 3.0 g/min
Back Pressure: 100 bar
Temperature: 26.8° C.
UV: 212 nm
Preparative SFC Conditions
Column/dimensions: Chiralpak AD-H (250×30) mm
% CO2: 75%
% Co solvent: 25.0% (MeOH)
Total Flow: 100.0 g/min
Back Pressure: 100 bar
UV: 212 nm
Stack time: 1.8 min
Load/inj: 5.5 mg
LCMS (m/z) 313.31 [M+H]+.

$^1$H NMR (400 MHz, CDCl$_3$): δ 7.03 (dd, J=8.2, 0.6 Hz, 1H), 5.67 (d, J=8.2 Hz, 1H), 4.91 (s, 1H), 3.71 (dd, J=10.8, 8.5 Hz, 1H), 3.62 (s, 1H), 3.52 (dd, J=10.8, 7.2 Hz, 2H), 3.43 (dt, J=9.6, 7.5 Hz, 1H), 3.24-3.08 (m, 3H), 2.99 (d, J=8.2 Hz, 1H), 2.83 (d, J=12.0 Hz, 1H), 2.27-2.08 (m, 2H), 1.91-1.75 (m, 2H), 1.65 (d, J=5.0 Hz, 2H), 1.26 (t, J=6.6 Hz, 1H).

Synthesis of (9S)-2-(3-(trifluoromethyl)piperidin-1-yl)-7,8,9,10-tetrahydro-6H-5,9-methanopyrido[2,3-b][1,4]diazocine

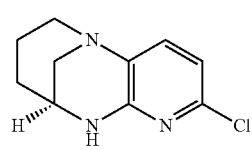 +

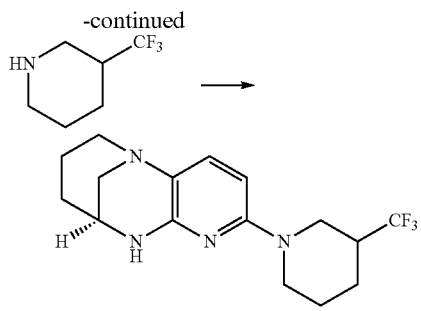

A suspension of (9S)-2-chloro-7,8,9,10-tetrahydro-6H-5,9-methanopyrido[2,3-b][1,4]diazocine (0.750 g, 3.58 mmol), 3-(trifluoromethyl)piperidine (1.096 g, 7.15 mmol) and KOtBu (1.204 g, 10.73 mmol) in 1,2-Dimethoxyethane (DME) (30 mL) stirred and degassed with argon at room temp for 15 mins. and then (1,3-Bis(2,6-di-isopropylphenyl)-4,5-dihydroimidazol-2-ylidene)chloro) (3-phenylallyl) palladium(2) (0.093 g, 0.143 mmol) added to the reaction mixture. Then the reaction mixture was stirred for 16 h at 80° C. The reaction mass filtered through celite and evaporated under reduced pressure completely. Reaction mixture was diluted with EtOAc (50 ml), washed with water followed by brine solution, dried with sodium sulfate, filtered and evaporated. The crude product was added to a silica gel column and was eluted with Hex/EtOAc (1:1). Collected fractions were evaporated and the resulting residue was purified via chiral SFC separation to get pure (9S)-2-(3-(trifluoromethyl)piperidin-1-yl)-7,8,9,10-tetrahydro-6H-5,9-methanopyrido[2,3-b][1,4]diazo cine (0.450 g, 1.371 mmol, 38.3% yield) as off white solid, (TLC: R$_f$ value: 0.4, 80% EtOAc/Hexane).

Analytical SFC Conditions: Peak-I
Column/dimensions: Chiralpak AD-H (250×4.6) mm, 5 u
% CO2: 60.0%
% Co solvent: 40.0% (0.5% DEA IN MeOH)
Total Flow: 4.0 g/min
Back Pressure: 100 bar
Temperature: 26.8° C.
UV: 215 nm
Preparative SFC Conditions
Column/dimensions: Chiralpak AD-H (250×30) mm
% CO2: 65.0%
% Co solvent: 35.0% (100% MeOH)
Total Flow: 100.0 g/min
Back Pressure: 100 bar
UV: 215 nm
Stack time: 2.2 min
Load/inj: 50.0 mg
LCMS (m/z) 327.3 [M+H]+.

$^1$H NMR (400 MHz, DMSO-d$_6$): δ 6.89 (dd, J=8.2, 0.7 Hz, 1H), 6.56 (d, J=4.6 Hz, 1H), 5.89 (d, J=8.3 Hz, 1H), 4.58-4.33 (m, 1H), 3.97 (d, J=12.8 Hz, 1H), 3.48 (s, 1H), 3.17-2.98 (m, 2H), 2.92 (d, J=4.4 Hz, 1H), 2.76-2.57 (m, 2H), 2.50 (p, J=1.9 Hz, 2H), 1.96 (d, J=10.6 Hz, 1H), 1.74 (dd, J=9.4, 3.3 Hz, 3H), 1.61-1.32 (m, 3H), 1.25-1.08 (m, 1H).

Synthesis of (9S)-2-(3-(trifluoromethyl)piperidin-1-yl)-7,8,9,10-tetrahydro-6H-5,9-methanopyrido[2,3-b][1,4]diazocine

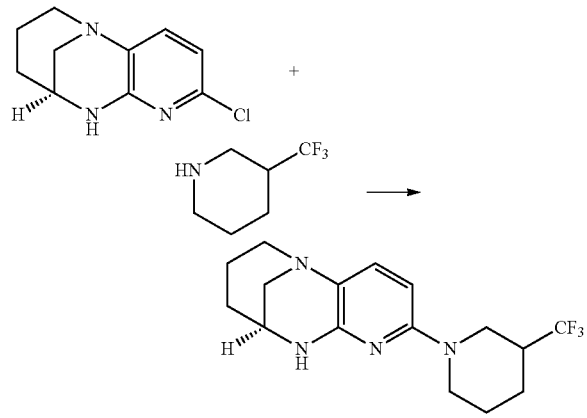

KOtBu (0.803 g, 7.15 mmol) was added to a stirred solution of (9S)-2-chloro-7,8,9,10-tetrahydro-6H-5,9-methanopyrido[2,3-b][1,4]diazocine (0.750 g, 3.58 mmol), and 3-(trifluoromethyl)piperidine (1.096 g, 7.15 mmol) in 1,2-Dimethoxyethane (DME) (20 mL). The reaction was stirred and degassed with argon at room temp for 15 mins. and then (1,3-Bis(2,6-di-isopropylphenyl)-4,5-dihydroimidazol-2-ylidene)chloro) (3-phenylallyl)palladium(2) (0.093 g, 0.143 mmol) added to the reaction mixture. The reaction mixture was stirred for 16 h at 80° C. The reaction was cooled to room temperature, filtered through celite and evaporated completely, and was partitioned between water (20 mL) and EtOAc (50 mL). Organic layer was separated and was dried over anhydrous $Na_2SO_4$, filtered and filtrate was evaporated to give crude as brown solid (TLC eluent: 80% EtOAc: Rf-0.4; UV active). The crude was purified by column chromatography using (100-200 mesh) silica gel and was eluted with 50% EtOAc in Hexane to afford (69:31) mixture and further purified by SFC to afford pure (9S)-2-(3-(trifluoromethyl)piperidin-1-yl)-7,8,9,10-tetrahydro-6H-5,9-methanopyrido[2,3-b][1,4]diazocine (450 mg, 1.310 mmol, 36.6% yield) as a pale yellow solid.
Analytical SFC Conditions: Peak-II
Column/dimensions: Chiralpak AD-H (250×4.6) mm, 5 u
% CO2: 60.0%
% Co solvent: 40.0% (0.5% DEA IN MeOH)
Total Flow: 4.0 g/min
Back Pressure: 100 bar
Temperature: 26.8° C.
UV: 215 nm
Preparative SFC Conditions
Column/dimensions: Chiralpak AD-H (250×30) mm
% CO2: 65.0%
% Co solvent: 35.0% (100% MeOH)
Total Flow: 100.0 g/min
Back Pressure: 100 bar
UV: 215 nm
Stack time: 2.2 min
Load/inj: 50.0 mg
LCMS (m/z) 327.2 [M+H]$^+$.
1H NMR (400 MHz, DMSO-d6): δ ppm 6.89 (d, J=8.11 Hz, 1H), 6.55 (br d, J=3.95 Hz, 1H), 5.89 (d, J=8.33 Hz, 1H), 4.49 (dt, J=12.44, 1.78 Hz, 1H), 3.96 (d, J=13.15 Hz, 1H), 3.48 (br s, 1H), 3.15-2.96 (m, 2H), 2.94-2.80 (m, 1H), 2.74-2.56 (m, 2H), 2.55-2.41 (m, 2H), 2.12-1.84 (m, 1H), 1.82-1.64 (m, 3H), 1.58-1.32 (m, 3H), 1.32-1.08 (m, 1H).

Synthesis of (4S)-7-(3-(trifluoromethyl)piperidin-1-yl)-2,3,4,5-tetrahydro-1,4-methano pyrido[2,3-b][1,4]diazepine

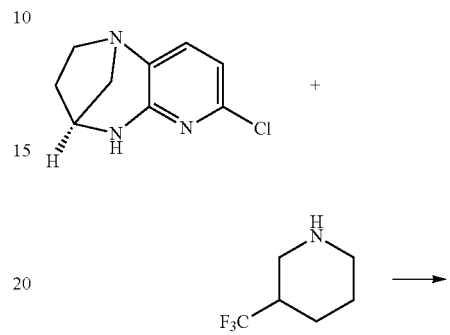

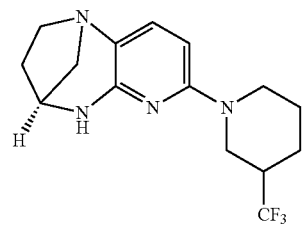

To a degassed solution of (4S)-7-chloro-2,3,4,5-tetrahydro-1,4-methanopyrido[2,3-b][1,4]diazepine (500 mg, 2.56 mmol), 3-(trifluoromethyl)piperidine (783 mg, 5.11 mmol S-isomer with unequal enatiomeric mixture)) in 1,2-dimethoxy ethane (15 mL) were added potassium tert-butoxide (574 mg, 5.11 mmol) and Umicorecatalyst (33.2 mg, 0.051 mmol) at 30° C. The reaction mixture was heated at 80° C. for 17 h. The reaction mixture was cooled RT and poured in cold water (70 mL), extracted with ethyl acetate (2×150 mL). The combined organic layer was dried over anhydrous $Na_2SO_4$, filtered and concentrated under reduced pressure to obtain the crude product. The crude mixture was purified by flash column chromatography (silica-gel: 100-200 mesh, eluent: 1 to 3% of methanol in ethyl acetate) to afford 400 mg of (4S)-7-(3-(trifluoromethyl)piperidin-1-yl)-2,3,4,5-tetrahydro-1,4-methanopy rido[2,3-b][1,4]diazepine. Chiral HPLC indicated 53:44 enantiomeric mixture, this unequal mixture of enantiomers were purified by chiral prep HPLC to obtained two separated peaks (Chiral Prep conditions: 4 g-40%-100 bar 10 0.5% DEA in Methanol, chiralpak, AD-H (4.6 mm*250 mm)) as fastest eluent peak: 210 mg (peak-I, 0.673 mmol, 15% yield) as a white solid (TLC: 10% MeOH in EtOAc R$_f$: 0.4) and slowest eluent peak: 310 mg (peak-II, 310 mg, 0.993 mmol, 22%) as a white solid (TLC: 10% MeOH in EtOAc, R$_f$: 0.4), LCMS (m/z) 313.2 [M+H]$^+$.
$^1$H NMR (400 MHz, DMSO-d$_6$): δ ppm 6.92 (d, J=8.33 Hz, 1H), 6.56 (d, J=4.38 Hz, 1H), 5.83 (d, J=8.11 Hz, 1H), 4.43 (d, J=12.28 Hz, 1H), 3.93 (d, J=12.28 Hz, 1H), 3.87-3.72 (m, 1H), 3.10-2.83 (m, 2H), 2.82-2.71 (m, 1H), 2.70-2.55 (m, 3H), 2.46-2.18 (m, 1H), 2.11-1.86 (m, 2H), 1.86-1.65 (m, 2H), 1.55-1.32 (m, 2H).

Synthesis of (4S)-7-(3-(trifluoromethyl)piperidin-1-yl)-2,3,4,5-tetrahydro-1,4-methano pyrido[2,3-b][1,4]diazepine

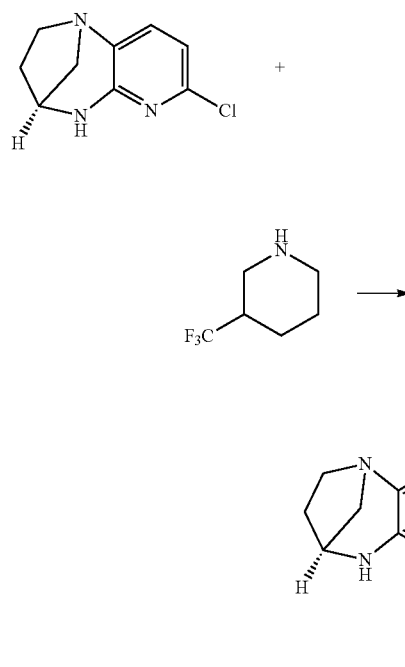

To a degassed solution of (4S)-7-chloro-2,3,4,5-tetrahydro-1,4-methanopyrido[2,3-b][1,4]diazepine (500 mg, 2.56 mmol), (R-isomer with unequal enatiomeric mixture) 3-(trifluoromethyl)piperidine (783 mg, 5.11 mmol) in 1,2-dimethoxy ethane (15 mL) were added potassium tert-butoxide (574 mg, 5.11 mmol) and Umicorecatalyst (33.2 mg, 0.051 mmol) at 30° C. The reaction mixture was heated at 80° C. for 17 h. The reaction mixture was cooled to room temperature and poured in cold water (70 mL), extracted with ethyl acetate (2×150 mL). The combined organic layer was dried over anhydrous $Na_2SO_4$, filtered and concentrated under reduced pressure to obtain the crude product. The crude mixture was purified by flash column chromatography (silica-gel: 100-200 mesh, eluent: 1 to 3% of methanol in ethyl acetate) to afford (4S)-7-(3-(trifluoromethyl)piperidin-1-yl)-2,3,4,5-tetrahydro-1,4-methanopy rido[2,3-b][1,4]diazepine. After column chromatography 500 mg of compound was isolated, Chiral HPLC indicated 36:63 enatiomeric mixture, this unequal mixture of enantiomers were purified by chiral prep HPLC to obtained two separated peaks (Chiral Prep conditions: 4 g-40%-100 bar 10 0.5% DEA in Methanol, chiralpak, AD-H (4.6*250) mm 5 u) as fastest eluent peak: 140 mg (peak-I) and slowest eluent peak: 310 mg (peak-II, 310 mg, 0.993 mmol, 22%) as a white solid (TLC: 10% MeOH in EtOAc, $R_f$: 0.4), LCMS (m/z) 313.2[M+H]$^+$.

$^1$H NMR (400 MHz, DMSO-$d_6$): δ ppm 6.92 (d, J=8.33 Hz, 1H), 6.56 (d, J=4.60 Hz, 1H), 5.83 (d, J=8.33 Hz, 1H), 4.41 (dt, J=12.50, 1.86 Hz, 1H), 3.93 (d, J=12.50 Hz, 1H), 3.81 (td, J=4.88, 2.74 Hz, 1H), 3.07-2.88 (m, 2H), 2.80-2.55 (m, 4H), 2.48-2.27 (m, 1H), 2.01-1.88 (m, 2H), 1.85-1.65 (m, 2H), 1.52-1.38 (m, 1H), 1.36-1.20 (m, 1H).

Basic Urea Intermediates

Synthesis of (4S)-7-chloro-N-(pyridin-2-yl)-3,4-dihydro-1,4-methanopyrido[2,3-b][1,4]diazepine-5(2H)-carboxamide

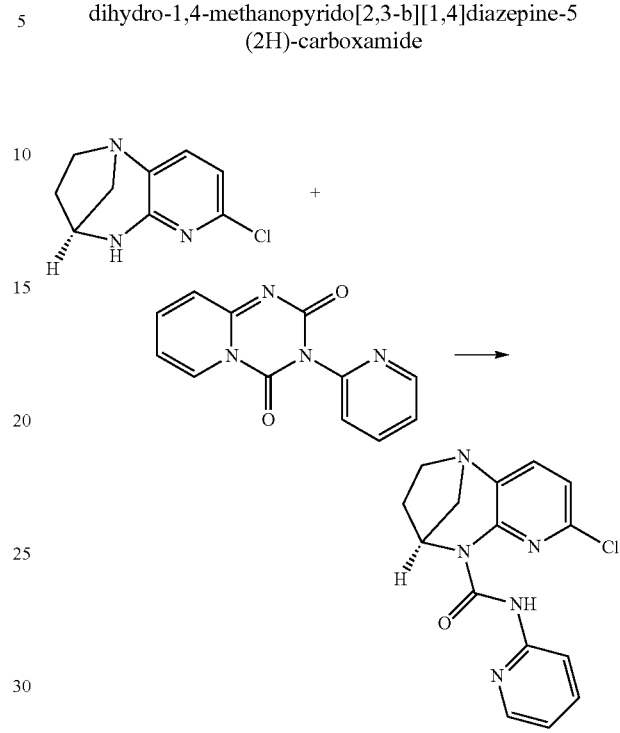

To a solution of (4S)-7-chloro-2,3,4,5-tetrahydro-1,4-methanopyrido[2,3-b][1,4]diazepine (1.2 g, 6.13 mmol) in Tetrahydrofuran (THF) (50 mL) stirred under nitrogen at 0° C. was added 3-(pyridin-2-yl)-2H-pyrido[1,2-a][1,3,5]triazine-2,4(3H)-dione (1.768 g, 7.36 mmol). The reaction mixture was stirred at 80° C. for 16 hr before being poured in to cold water (100 mL) and extracted with ethyl acetate (200 mL), The organic layer was successively washed with water (70 mL) and brine (70 mL), dried over anhydrous sodium sulfate under reduced pressure. The crude residue was purified by column chromatography using (100-200 mesh) gradient mixture of 30% to 70% as eluent. To give 1.3 g (66%) of the title compound as an off white mass, LCMS (m/z) 316.2 (M+H)$^+$.

Synthesis of (4R)-7-chloro-N-(pyrazin-2-yl)-3,4-dihydro-1,4-methanopyrido[2,3-b][1,4]diazepine-5(2H)-carboxamide

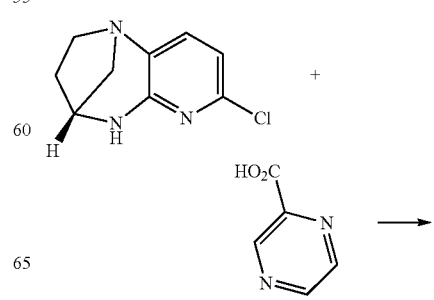

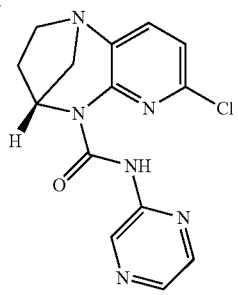

To a solution of pyrazine-2-carboxylic acid (800 mg, 6.45 mmol), DPPA (3548 mg, 12.89 mmol) and triethylamine (4.49 mL, 32.2 mmol) in Tetrahydrofuran (THF) (30 mL) stirred under nitrogen at 0° C. was added. The reaction was stirred and warmed to RT for 2 h. Next, (4R)-7-chloro-2,3,4,5-tetrahydro-1,4-methanopyrido[2,3-b][1,4]diazepine (1009 mg, 5.16 mmol). The reaction mixture was stirred at 90° C. for 16 hr. The reaction mixture was diluted with water (100 mL) and extracted with ethyl acetate (200 mL×2). The organic layer was dried over anhydrous $Na_2SO_4$, concentrated under reduced pressure to give semi pure compound. The crude product was added to a silica gel column and was eluted with Hex/EtOAc. Collected fractions to give the desired product (1.4 g, 3.71 mmol, 58%), LCMS (m/z) 317.2 $(M+H)^+$.

Synthesis of (4S)-7-chloro-N-(pyridin-3-yl)-3,4-dihydro-1,4-methanopyrido[2,3-b][1,4]diazepine-5 (2H)-carboxamide

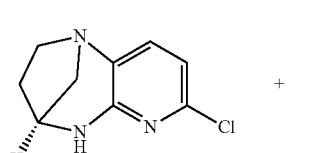

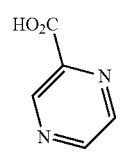

DIPEA (31.9 mL, 183 mmol) followed by DPPA (15.09 g, 54.8 mmol) were added to a stirred solution of nicotinic acid (4.5 g, 36.6 mmol) in Tetrahydrofuran (THF) (60 mL) at RT and stirred for 2 h. Then (4S)-7-chloro-2,3,4,5-tetrahydro-1,4-methanopyrido[2,3-b][1,4]diazepine (5.01 g, 25.6 mmol) was added to the reaction mixture and stirred to 80° C. for 16 h. Reaction mixture was cooled to room temperature, diluted with water (60 mL), extracted with ethyl acetate (2×50 mL), washed with brine (50 mL). Organic layer was separated, dried over sodium sulfate, filtered and concentrated to get crude compound. Crude compound was purified by column chromatography using silica gel (100-200 mesh), 1% methanol in DCM to give the desired product (4 g, 12.03 mmol, 32.9% yield), LCMS: (m/z) 316.2 $(M+H)^+$.

Synthesis of (4S)-7-chloro-N-(pyrazin-2-yl)-3,4-dihydro-1,4-methanopyrido[2,3-b][1,4]diazepine-5 (2H)-carboxamide

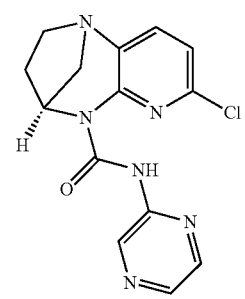

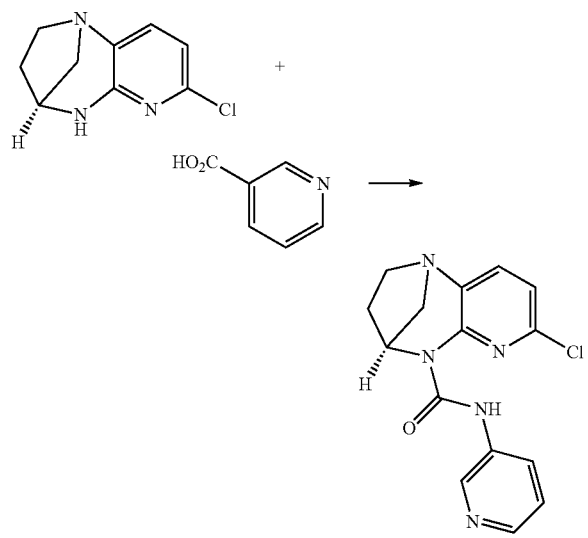

To a stirred solution of pyrazine-2-carboxylic acid (4.08 g, 32.9 mmol) in Tetrahydrofuran (THF) (100 ml) at 0 C was added diphenyl phosphorazidate (14.19 ml, 65.8 mmol) followed by TEA (22.94 ml, 165 mmol). The solution was warmed to room temperature and stirring continued for 3 h. Next, solid (4S)-7-chloro-2,3,4,5-tetrahydro-1,4-methanopyrido[2,3-b][1,4]diazepine (5.6 g, 28.6 mmol) was added and the mixture heated to reflux. The reaction was stirred for 2 h at reflux before being cooled to RT and stirring was continued overnight. The next day, the mixture was diluted with water and extracted with EtOAc (three times). The combined EtOAc Extracts were dried over $Na_2SO_4$ and concentrated to give the crude product. The dark residue purified by silica gel chromatography: 330 g column, 100 ml/min, 0-25% EtOAc/MeOH over 30 min. The fractions containing product were combined to give the desired product as yellow oil. To this oil was added $Et_2O$ (50 ml) and it was concentrated under reduced pressure. This caused the product to crystallize to a light yellow solid (6.9 g, 76% yield). $^1H$ NMR (400 MHz, $CDCl_3$) δ=12.61 (s, 1H), 9.47 (d, J=1.4 Hz, 1H), 8.68-7.99 (m, 2H), 7.50 (d, J=8.0 Hz, 1H), 6.96 (d, J=8.0 Hz, 1H), 5.65 (dd, J=6.0, 3.2 Hz, 1H), 3.30-3.15 (m, 1H), 3.11 (dt, J=12.1, 2.1 Hz, 1H), 3.00 (dd, J=12.1, 3.2 Hz, 1H), 2.39-2.22 (m, 1H), 2.11-1.97 (m, 2H); LCMS (m/z) 316.9 $(M+H)^+$.

Synthesis of (4S)-7-chloro-N-(pyridazin-4-yl)-3,4-dihydro-1,4-methanopyrido[2,3-b][1,4]diazepine-5(2H)-carboxamide

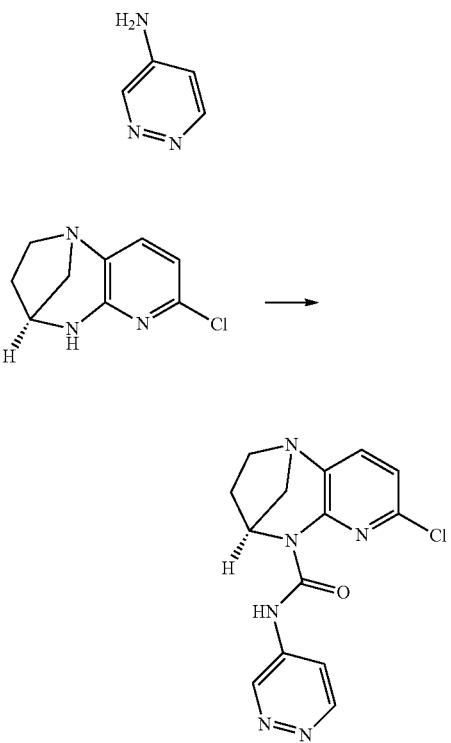

To a solution of pyridazine-4-carboxylic acid (0.5 g, 4.03 mmol) was added diphenyl phosphorazidate (1.308 mL, 6.04 mmol) and DIPEA (2.111 mL, 12.09 mmol) in THF (10 mL) which was stirred under nitrogen at 0° C. The reaction mixture was stirred at 30° C. for 2 h and (4S)-7-chloro-2,3,4,5-tetrahydro-1,4-methanopyrido[2,3-b][1,4]diazepine (0.473 g, 2.417 mmol) was added at 30° C. The reaction mixture was stirred at 90° C. for 6 h. The THF was evaporated under reduced pressure and the residue diluted with water and extracted into DCM. The organic layer was washed with water, brine and dried over sodium sulfate.

The solvent was evaporated under reduced pressure. The crude compound was purified by trituration with diethyl ether and n-pentane(1:1) to give the product (320 mg, 0.91 mmol, 23% yield) as an off-white solid. LCMS (m/z) 316.9 [M+H]$^+$.

Synthesis of (4S)—N-(3H-[1,2,3]triazolo[4,5-d]pyrimidin-7-yl)-7-chloro-3,4-dihydro-1,4-methanopyrido[2,3-b][1,4]diazepine-5(2H)-carboxamide

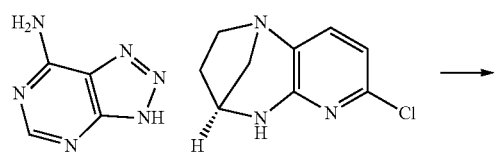

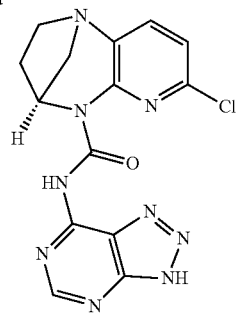

To a solution of (4S)-7-chloro-2,3,4,5-tetrahydro-1,4-methanopyrido[2,3-b][1,4]diazepine (500 mg, 2.56 mmol) in Tetrahydrofuran (THF) (10 mL) stirred under nitrogen at room temp was added triphosgene (758 mg, 2.56 mmol) and stirred for 30 min at RT, then triethylamine (0.356 mL, 2.56 mmol) and 3H-[1,2,3]triazolo[4,5-d]pyrimidin-7-amine (417 mg, 3.07 mmol) were added. The reaction mixture was stirred at 60° C. for 16 hr. The reaction was monitored by TLC (10% Methanol in DCM). The reaction mixture was quenched with 25 ml of water and extracted with 25 ml of ethyl acetate. The organic layer was dried over sodium sulfate and concentrated under reduced pressure to afford the crude compound. The crude product was added to a 100-200 silica gel column and was eluted with 3% DCM/MeOH to afford pure compound (4S)—N-(3H-[1,2,3]triazolo[4,5-d]pyrimidin-7-yl)-7-chloro-3,4-dihydro-1,4-methanopyrido[2,3-b][1,4]diazepine-5(2H)-carboxamide (200 mg, 0.527 mmol, 20.63% yield) as an off white solid, LCMS (m/z) 357.9 [M+H]$^+$.

Synthesis of Advanced Intermediates

Synthesis of 3-(pyridin-2-yl)-2H-pyrido[1,2-a][1,3,5]triazine-2,4(3H)-dione

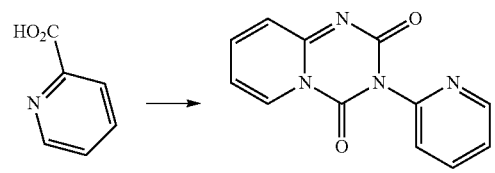 [SMILES: O=C(O)c1ccccn1 ; O=c1nc2ccccn2c(=O)n1-c1ccccn1]

To a solution of picolinic acid (1 g, 8.12 mmol) in Toluene (25 mL) stirred under nitrogen at room temp was added diphenyl phosphorazidate (2.235 g, 8.12 mmol) and TEA (1.132 mL, 8.12 mmol) and stirred for 30 min at room temperature. After that the reaction mixture was stirred at 80° C. for 2 hr. Next, the reaction mixture was cooled to room temperature and filtered, the solid was washed with toluene to afford compound 3-(pyridin-2-yl)-2H-pyrido[1,2-a][1,3,5]triazine-2,4(3H)-dione (600 mg, 2.352 mmol, 29.0% yield), LCMS (m/z) 241.2 [M+H]$^+$.

Synthesis of (R)-4-((2,2-dimethyl-1,3-dioxolan-4-yl)methoxy)pyridin-2-amine

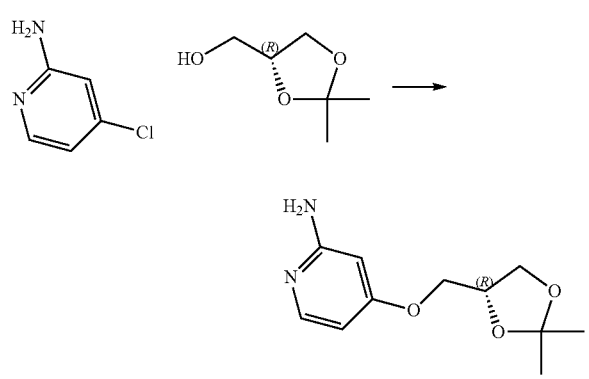

To a suspension of (R)-(2,2-dimethyl-1,3-dioxolan-4-yl)methanol (3.000 g, 22.70 mmol), 4-chloropyridin-2-amine (1.459 g, 11.35 mmol) and sodium (0.522 g, 22.70 mmol) in a sealed tube. The reaction mixture was stirred at 140° C. for 16 h. Next, the reaction mixture was cooled to room temperature, dissolved in MeOH and poured in to ice water and extracted with EtOAc. The organic phase was washed with brine solution and dried over sodium sulfate, filtered and evaporated to get crude compound. The crude compound was purified by column chromatography using silica gel and eluted with 2-3% MeOH/DCM to get pure compound (1.1 g, 21%), LCMS (m/z) 225.2 [M+H]$^+$.

Synthesis of (S)-4-((2,2-dimethyl-1,3-dioxolan-4-yl)methoxy)pyridin-2-amine

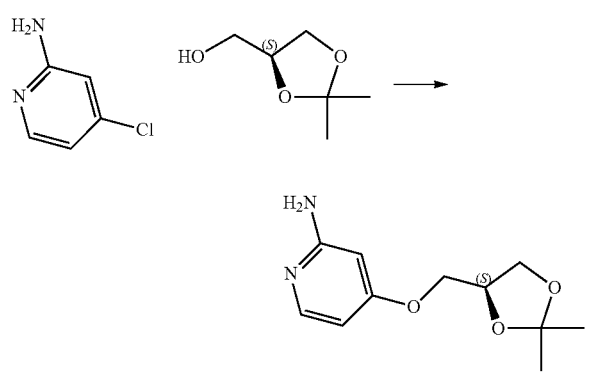

To a suspension of (S)-(2,2-dimethyl-1,3-dioxolan-4-yl)methanol (3.000 g, 22.70 mmol), 4-chloropyridin-2-amine (1.459 g, 11.35 mmol) and sodium (0.522 g, 22.70 mmol) in a sealed tube. The reaction mixture was stirred at 140° C. for 16 h before being cooled to room temperature, dissolved in MeOH and poured in to ice water and extracted with EtOAc. The organic phase was washed with brine solution and dried over sodium sulfate, filtered and evaporated. The crude material was purified by silica gel column chromatography eluting with 2-3% MeOH/DCM to give the desired product (1.2 g, 22%), LCMS (m/z) 225.2 [M+H]$^+$.

Synthesis of (R)-2-(tetrahydrofuran-3-yloxy)pyrimidin-4-amine

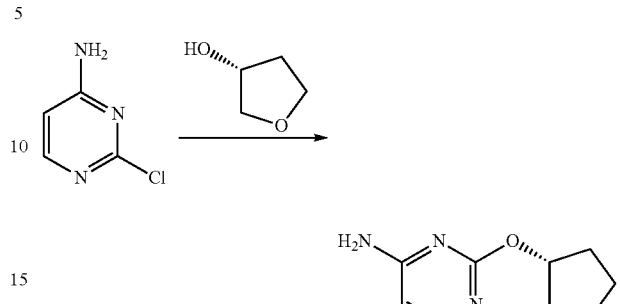

To a stirred solution of (R)-tetrahydrofuran-3-ol (2.72 g, 30.9 mmol) in THF (30 mL) was added NaH (0.926 g, 23.16 mmol) and stirred for 30 min at room temperature. To this 2-chloropyrimidin-4-amine (2.0 g, 15.44 mmol) was added in portions for about 15 min and heated at 70° C. for 16 h. The reaction mixture was allowed to room temperature and subsequently cooled to 0° C., quenched with ice cold water and extracted with ethyl acetate (3×50 ml). The combined organic layer was dried over anhydrous sodium sulfate, filtered and concentrated under reduced pressure to obtain the crude compound. The crude product was purified by flash column chromatography (silica-gel: 100-200 mesh) to afford (R)-2-(tetrahydrofuran-3-yloxy)pyrimidin-4-amine (1.6 g, 8.839 mmol, 51.5% yield) as an off white solid.

Synthesis of (R)-6-((2,2-dimethyl-1,3-dioxolan-4-yl)methoxy)pyrazin-2-amine

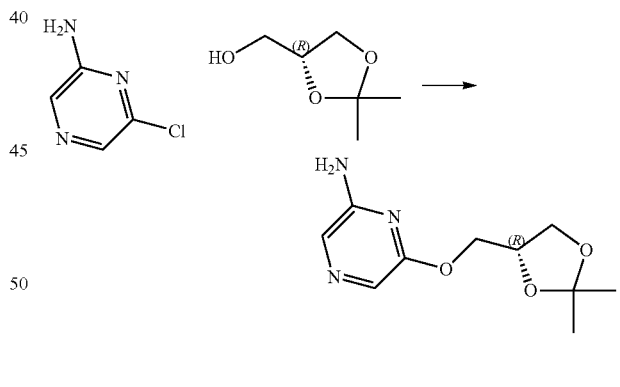

To a solution of 6-chloropyrazin-2-amine (5 g, 38.6 mmol), sodium hydride (2.316 g, 57.9 mmol) and (R)-(2,2-dimethyl-1,3-dioxolan-4-yl)methanol (5.61 g, 42.5 mmol) in Tetrahydrofuran (THF) (50 mL) stirred under nitrogen at 0° C. was added reaction mixture was stirred at 80° C. for 16 h. Reaction mixture was quenched with ice cold water and extracted into ethyl acetate. Organic layer dried over Na$_2$SO$_4$. Solvent evaporated under reduced pressure to afford the crude product. The crude product was added to a silica gel column and was eluted with DCM/MeOH. Fractions with product were combined and evaporated under reduced pressure to give the required product (2.8 g, 11.9 mmol, 31%), LCMS (m/z) 225.9 [M+H]$^+$.

Synthesis of (S)-6-((2,2-dimethyl-1,3-dioxolan-4-yl)methoxy)pyrazin-2-amine

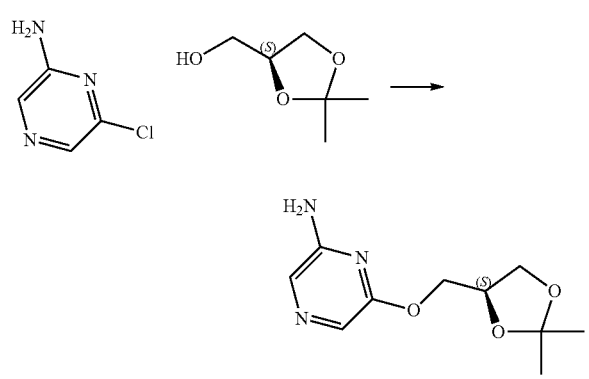

6-chloropyrazin-2-amine (0.980 g, 7.57 mmol), (S)-(2,2-dimethyl-1,3-dioxolan-4-yl)methanol (2 g, 15.13 mmol) and sodium (0.348 g, 15.13 mmol) were taken in a seal tube and heated at 130° C. for 16 hr and then the reaction mixture was quenched with methanol and ice cold water (100 mL) and extracted with ethyl acetate (5×50 mL). The combined organic layers were washed with water, saturated brine solution, dried over anhydrous sodium sulfate, filtered and concentrated to give the product (1 g, 4.26 mmol, 28.2% yield), LCMS (m/z) 265.1 [M+H]$^+$.

Synthesis of (S)-2-((2,2-dimethyl-1,3-dioxolan-4-yl)methoxy)pyrimidin-4-amine

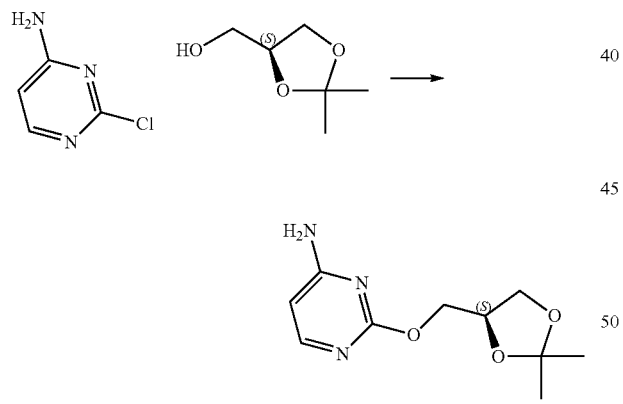

To suspension of (S)-(2,2-dimethyl-1,3-dioxolan-4-yl)methanol (10.20 g, 77 mmol), and NaH (4.63 g, 116 mmol) in tetrahydrofuran (THF) (50 mL) stirred under nitrogen at room temperature was added 2-chloropyrimidin-4-amine (5 g, 38.6 mmol) portion wise over 15 min. The reaction mixture was stirred at 70° C. for 16 hr. Next, the reaction mixture was quenched with solution of aq. NaHCO$_3$ and then extracted with EtOAc, dried Na$_2$SO$_4$ and evaporated. The crude product was added to a silica gel column and was eluted with 50% Hex/EtOAc. Collected fractions were evaporated to give the desired product (3 g, 11.84 mmol, 30.7% yield) as off white solid, LCMS (m/z) 226.2 [M+H]$^+$.

Synthesis of (R)-2-((2,2-dimethyl-1,3-dioxolan-4-yl)methoxy)pyrimidin-4-amine H$_2$N

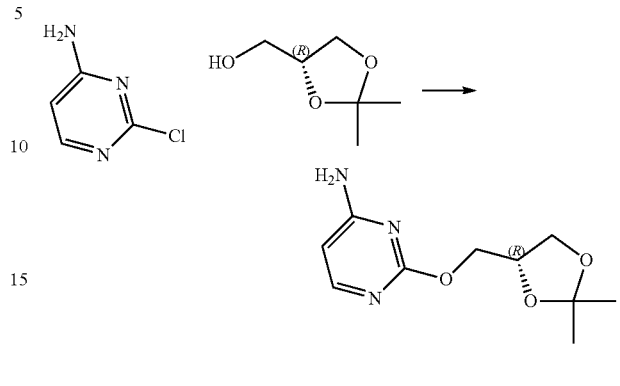

To a solution of sodium hydride (0.817 g, 34.1 mmol) in Tetrahydrofuran (THF) (30 mL) at room temperature was added a solution of (R)-(2,2-dimethyl-1,3-dioxolan-4-yl)methanol (3 g, 22.70 mmol) in THF (5 mL) over 1 min and stirred at room temperature for 15 min then add 2-chloropyrimidin-4-amine (2.059 g, 15.89 mmol) portion wise at room temperature. The reaction mixture was stirred at 65° C. for 16 h. The reaction mixture was poured in to water and extracted with EtOAc (3×100 mL). Then the combined organic layer was washed with water, brine solution, dried over sodium sulfate and evaporated to get 4.0 g of crude compound. The crude compound was purified by column chromatography using 100-200 silica gel mesh and eluted with 2-3% MeOH/DCM to get pure compound (2.5 g, 10.42 mmol, 46%), LCMS (m/z) 226.2 [M+H]$^+$.

Synthesis of (S)-2-((2,2-dimethyl-1,3-dioxolan-4-yl)methoxy)pyridin-4-amine

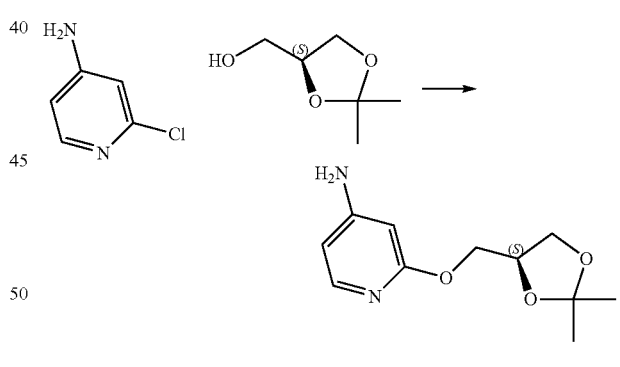

To a suspension of 2-chloropyridin-4-amine (1.459 g, 11.35 mmol), (S)-(2,2-dimethyl-1,3-dioxolan-4-yl)methanol (3.0 g, 22.70 mmol) was added sodium (0.522 g, 22.70 mmol). The reaction mixture was stirred at 140° C. for 16 hr and progress of the reaction was monitored by The reaction mixture was dissolved in MeOH, poured in to ice water and extracted with EtOAc (3×100 mL). Then the combined organic layer was washed with water, brine solution, dried over sodium sulfate and evaporated to get 4.0 g of crude compound. The crude compound was purified by column chromatography using 100-200 silica gel mesh and eluted with 2-3% MeOH/DCM to get (S)-2-((2,2-dimethyl-1,3-dioxolan-4-yl)methoxy)pyridin-4-amine (2.5 g, 10.73 mmol, 47.3% yield), LCMS (m/z) 225.3 [M+H]$^+$.

Synthesis of (R)-2-((2,2-dimethyl-1,3-dioxolan-4-yl)methoxy)pyridin-4-amine

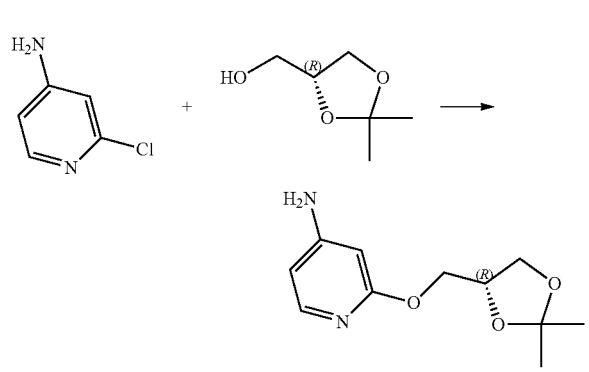

To a solution of 2-chloropyridin-4-amine (4 g, 31.1 mmol), (R)-(2,2-dimethyl-1,3-dioxolan-4-yl)methanol (2.056 g, 15.56 mmol) and sodium (0.715 g, 31.1 mmol) in sealed tube at room temperature. The reaction mixture was stirred at 140° C. for 48 hr. The reaction mixture was cooled to room temp and quenched with MeOH followed by water. Then reaction mass was extracted with the EtOAc. Then organic layer washed with water followed by brine solution and dried out with sodium sulfate and filtered and distill out completely. The crude product was added to a silica gel column and was eluted with Hex/EtOAc (1:1) collected fractions were evaporated to give the desired product (2.250 g, 9.93 mmol, 31.9% yield), LCMS (m/z) 225.0 [M+H]$^+$.

Synthesis of (S)-2-((tetrahydrofuran-3-yl)oxy)pyrimidin-4-amine

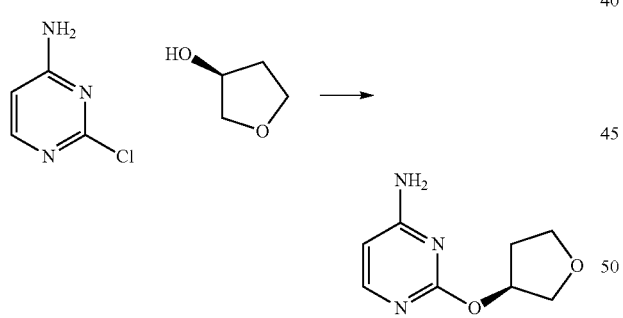

To a stirred solution of 2-chloropyrimidin-4-amine (2 g, 15.44 mmol) in Tetrahydrofuran (THF) (20 mL) was added NaH (0.741 g, 30.9 mmol) portion wise over a period of 5 min at room temperature. Then the reaction was stirred at 30° C. for about 10 min. To the above reaction added (S)-tetrahydrofuran-3-ol (1.088 g, 12.35 mmol) at 30° C. and stirred at 80° C. for 8 hrs. The reaction mixture was quenched with ice cold water at 0° C. and extracted with ethyl acetate. The organic layer was washed thoroughly with water and dried over Na$_2$SO$_4$. The solvent was evaporated under reduced pressure to afford the product. The crude product was triturated with pet ether, LCMS (m/z) 182.2 [M+H]$^+$.

Synthesis of phenyl (1-methyl-1H-pyrazol-4-yl)carbamate

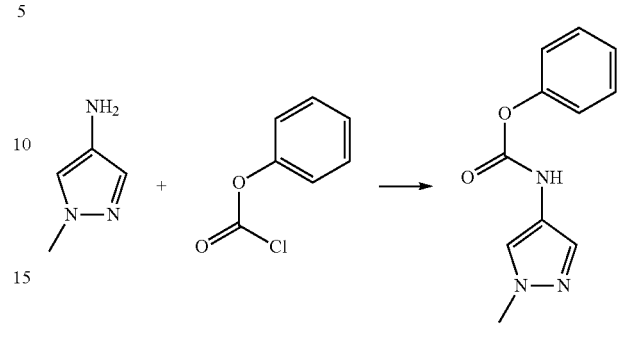

Phenyl carbonochloridate (2.90 g, 18.53 mmol) was added to a stirred solution of pyridine (3.12 mL, 38.6 mmol) in Dichloromethane (DCM) (50 mL) at 0° C. and stirred for 15 min and followed by addition of 1-methyl-1H-pyrazol-4-amine (1.5 g, 15.45 mmol) at same temperature. The reaction mixture was stirred at room temperature for 4 h. After consumption of starting material (monitored by TLC), ice cold water was added, separated organic layer was washed with water and brine. The organic layer was filtered through sodium sulfate and concentrated to get crude compound. The crude compound was purified by column chromatography by using 60-120 (silica gel) and eluted in 50% ethyl acetate in hexane to afford the desired product (1.6 g, 6.41 mmol, 42% yield) as light brown solid, LCMS (m/z) 218.1 (M+H)$^+$.

Synthesis of Phenyl pyridin-3-ylcarbamate

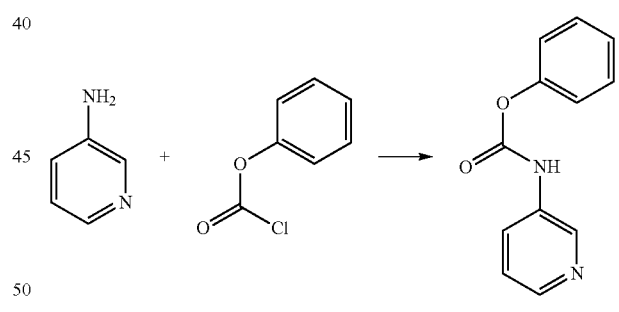

To a solution of phenyl carbonochloridate (2.163 g, 13.81 mmol), and pyridine (1.375 mL, 17.00 mmol) in Dichloromethane (DCM) (30 mL) stirred under nitrogen at room temp was added pyridin-3-amine (1.0 g, 10.63 mmol). The reaction mixture was stirred at RT for 30 min. The reaction mixture was quenched with saturated sodium bicarbonate solution.

Separated organic layer and the aqueous layer extracted with DCM (50 ml). Combined DCM layer washed with water and dried out with sodium sulfate, filtered and concentrated under high vacuum to get crude product. The Crude product was added to a silica gel column and was eluted with 20% EtOAc/Hexane. Collected fractions were evaporated to afford the desired product (1.3 g, 6.01 mmol, 57%) as a white solid, LCMS (m/z) 215.1 (M+H)$^+$.

111

Synthesis of phenyl pyrimidin-2-ylcarbamate

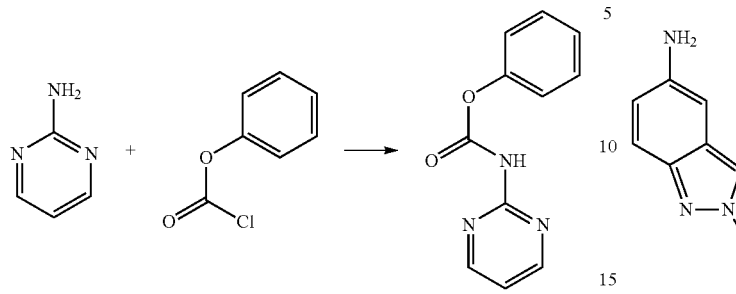

To a solution of phenyl carbonochloridate (2.140 g, 13.67 mmol), and pyridine (1.361 mL, 16.82 mmol) in dichloromethane (DCM) (10 mL) stirred under nitrogen at room temperature was added pyrimidin-2-amine (1.0 g, 10.51 mmol). The reaction mixture was stirred at room temperature for 30 min. The reaction mixture was quenched with saturated sodium bicarbonate solution. Separated organic layer and the aqueous layer extracted with DCM (50 ml). Combined DCM layer washed with water and dried out with sodium sulfate, filtered and concentrated under high vacuum to get crude product. This was added to a silica gel column and was eluted with 20% EtOAc/Hexane. Collected fractions were evaporated to afford the desired product (1.6 g, 6.49 mmol, 61.7%), LCMS (m/z) 216.3 (M+H)$^+$.

Synthesis of phenyl (5-fluoropyridin-2-yl)carbamate

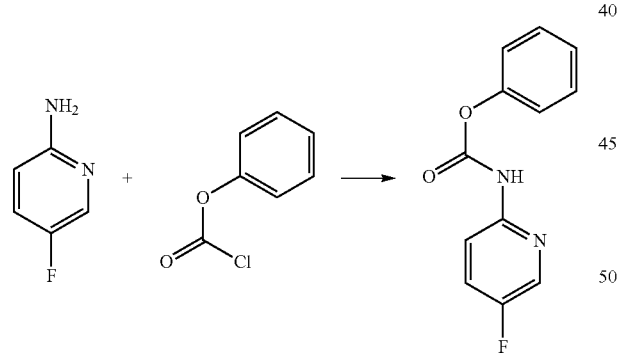

To a solution of phenyl carbonochloridate (1.397 g, 8.92 mmol), and Pyridine (0.721 mL, 8.92 mmol) in dichloromethane (DCM) (40 mL) stirred under nitrogen at room temp was added 5-fluoropyridin-2-amine (1.0 g, 8.92 mmol). The reaction mixture was stirred at RT for 30 min. The reaction mixture was quenched with saturated sodium bicarbonate solution. Separated organic layer and the aqueous layer extracted with DCM (20 ml). Combined organic layer washed with water followed by brine solution and dried out with sodium sulfate, filtered and concentrated under vacuum to give the desired product (1.4 g, 5.94 mmol, 67%), LCMS (m/z) 233.2 (M+H)$^+$.

112

Synthesis of phenyl (2-methyl-2H-indazol-5-yl)carbamate

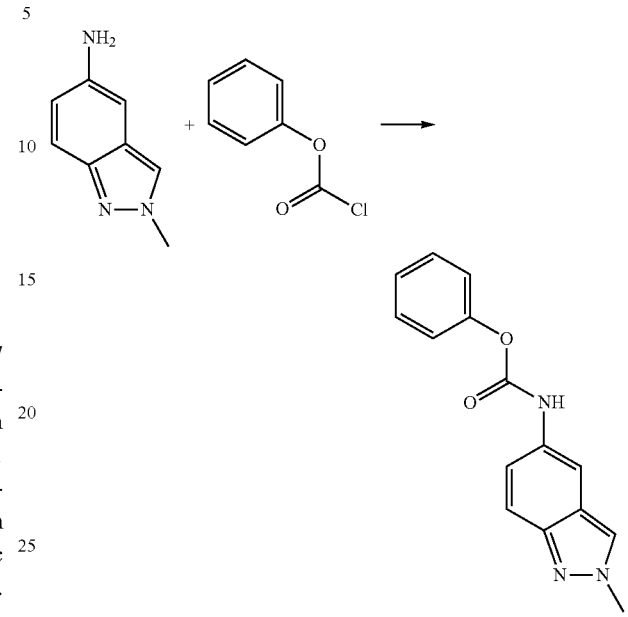

To a solution of phenyl carbonochloridate (1.064 g, 6.79 mmol), and pyridine (0.550 mL, 6.79 mmol) in Dichloromethane (DCM) (40 mL) stirred under nitrogen at room temp was added 2-methyl-2H-indazol-5-amine (1 g, 6.79 mmol). The reaction mixture was stirred at room temperature for 30 min. The reaction mixture was quenched with saturated sodium bicarbonate solution. Separated organic layer, aqueous layer extracted with DCM (20 ml).

Combined organic layer washed with water followed by brine solution and dried out with sodium sulfate and concentrated under vacuum to get phenyl (2-methyl-2H-indazol-5-yl)carbamate (1.3 g, 4.82 mmol, 70.9% yield), LCMS (m/z) 268.1 (M+H)$^+$.

Synthesis of Phenyl (5-ethylpyrazin-2-yl)carbamate

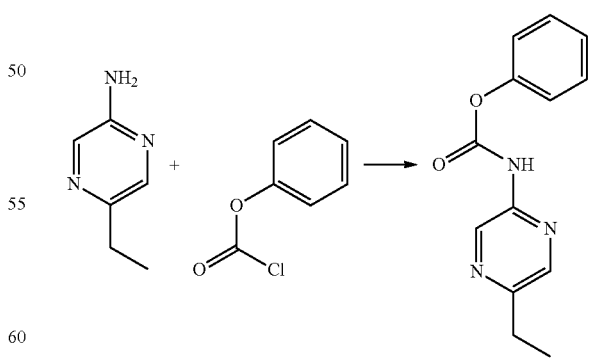

Pyridine (1.051 mL, 12.99 mmol) was added dropwise to a stirred solution of phenyl carbonochloridate (1.324 mL, 10.56 mmol) in dichloromethane (DCM) (20 ml) at room temperature and stirred for 30 minutes. Then 5-ethylpyrazin-2-amine (1 g, 8.12 mmol) dissolved in dichloromethane (DCM) (10 ml) was added dropwise at room temperature and stirred at 50° C. for 16 h. Allowed the reaction mixture to room temperature, diluted with DCM (3×50 mL), washed with water (2×30 mL) and brine (30 mL). Separated the organic layer and dried over sodium sulfate, filtered and concentrated. Residue was purified by column chromatography using silica gel (100-200 mesh) by 10% ethyl acetate in pet ether as eluent to get desired product as off white fluffy solid (1.6 g, 6.58 mmol, 81%), LCMS (m/z) 244.2 (M+H)+.

Synthesis of Phenyl (5-cyclopropylpyrazin-2-yl)carbamate

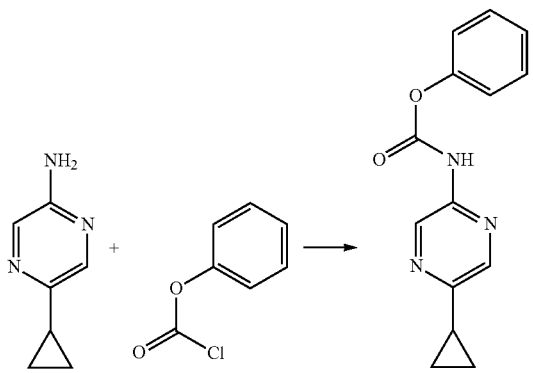 [SMILES: Nc1cnc(C2CC2)cn1 ; O=C(Cl)Oc1ccccc1 ; O=C(Nc1cnc(C2CC2)cn1)Oc1ccccc1]

Pyridine (0.598 mL, 7.40 mmol) was added dropwise to a stirred solution of phenyl carbonochloridate (0.928 mL, 7.40 mmol) in dichloromethane (DCM) (15 ml) at 0° C. and stirred at RT for 30 minutes. Then 5-cyclopropylpyrazin-2-amine (1 g, 7.40 mmol) dissolved in dichloromethane (DCM) (5 ml) was added dropwise at 0° C. and stirred at RT for 3 h. The reaction mixture was diluted with DCM (3×50 mL), washed with water (2×20 mL) and brine (20 mL). Separated the organic layer and dried over sodium sulfate, filtered and concentrated. Residue was purified by column chromatography using silica gel (100-200 mesh). 10% ethyl acetate in pet ether as eluent to give the desired product (1.4 g, 5.31 mmol, 72%) as off white fluffy solid, LCMS (m/z) 256.2 (M+H)+.

Synthesis of phenyl (6-ethoxypyrazin-2-yl)carbamate

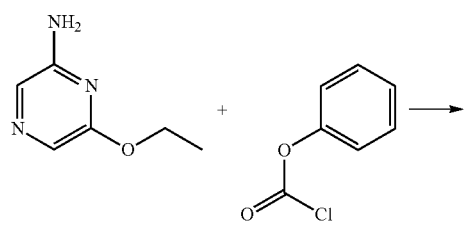

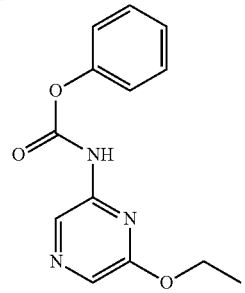

Pyridine (0.930 mL, 11.50 mmol) was added to a solution of phenyl carbonochloridate (1.463 g, 9.34 mmol) in DCM (15 mL) at room temperature and stirred for 20 min, then 6-ethoxypyrazin-2-amine (1.0 g, 7.19 mmol) in DCM (15 mL) was added and continued for another 40 min. The reaction mixture was diluted with DCM (2×20 mL), washed with water (20 mL×2) and brine (10 mL). Organic extracts were dried over Na2SO4 and solvent removed in vacuo to obtain the desired product (1.65 g, 5.22 mmol, 72.6% yield) as a yellow solid, LCMS (m/z) 260.2 (M+H)+.

Synthesis of phenyl pyridazin-3-ylcarbamate

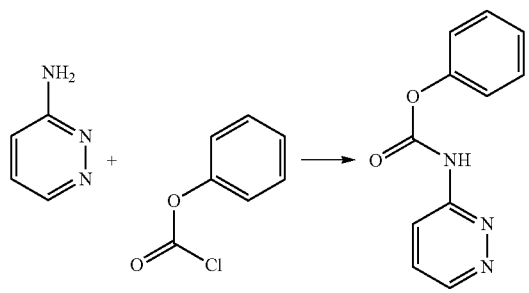 [SMILES: Nc1cccnn1 ; O=C(Cl)Oc1ccccc1 ; O=C(Nc1cccnn1)Oc1ccccc1]

To a solution of phenyl carbonochloridate (1.070 g, 6.83 mmol), pyridine (0.665 g, 8.41 mmol) in dichloromethane (10 ml) stirred under nitrogen at 25° C. was added a suspension of pyridazin-3-amine (0.5 g, 5.26 mmol) in dichloromethane (5 ml) during 5 min. The reaction mixture was stirred at 25° C. for 1 hr. Next, the organic phase was washed with water 3 mL, saturated brine 3 mL, dried over sodium sulfate and concentrated in vacuo to give the crude product as a white solid. The compound was washed with hexane, dried under reduced pressure, LCMS (m/z) 216.2 (M+H)+.

Synthesis of phenyl pyrimidin-4-ylcarbamate

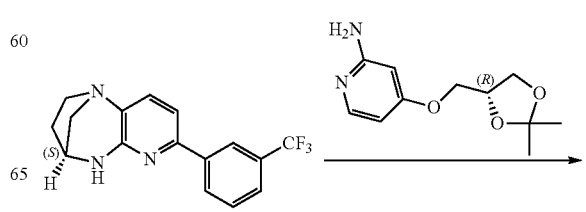

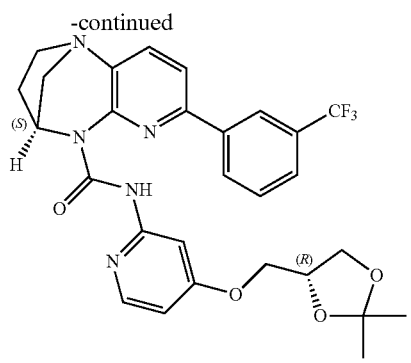

To a solution of phenyl carbonochloridate (1.070 g, 6.83 mmol), pyridine (0.665 g, 8.41 mmol) in DCM (15 ml) stirred under nitrogen at 25° C. was added a suspension of pyrimidin-4-amine (0.5 g, 5.26 mmol) in DCM (5 ml) dropwise during 5 min. The reaction mixture was stirred at 25° C. for 1 hr. The organic phase was washed with water 3 mL, brine 3 mL, dried over sodium sulfate and concentrated under vacuo to give the crude product as a off-white solid. The crude compound was washed with Hexane and then dried under reduced pressure to give the desired product (500 mg, 1.95 mmol, 37%), LCMS (m/z) 215.9 (M+H)+.

Synthesis Of Advanced Bicyclic Intermediates

Synthesis of (4S)—N-(4-(((R)-2,2-dimethyl-1,3-dioxolan-4-yl)methoxy)pyridin-2-yl)-7-(3-(trifluoromethyl)phenyl)-3,4-dihydro-1,4-methanopyrido[2,3-b][1,4]diazepine-5(2H)-carboxamide

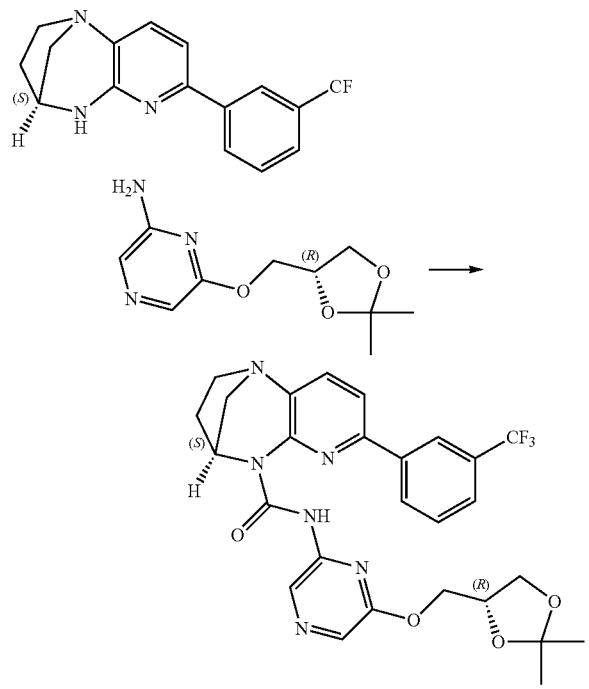

To a solution of (4R)-7-(3-(trifluoromethyl)phenyl)-2,3,4,5-tetrahydro-1,4-methanopyrido[2,3-b][1,4]diazepine (499.5 mg, 1.636 mmol), in Tetrahydrofuran (THF) (20 mL) stirred under nitrogen at room temp was added TEA (1.368 mL, 9.82 mmol), triphosgene (486 mg, 1.636 mmol). This was stirred at room temperature for 15 min and then a solution of (R)-4-((2,2-dimethyl-1,3-dioxolan-4-yl)methoxy)pyridin-2-amine (1101 mg, 4.91 mmol) in THF (5 mL) dropwise over 5 min. The reaction mixture was stirred at 65° C. for 16 h before being poured in to water and extracted with EtOAc (3×100 mL). Then the combined organic layer was washed with water, brine solution, dried over sodium sulfate and evaporated to give the crude product. The crude compound was purified by reverse phase chromatography (0.1% HCOOH&Water)/MeOH to give the desired product (450 mg, 49%), LCMS (m/z) 555.9 (M+H)+.

Synthesis of (4S)—N-(6-(((R)-2,2-dimethyl-1,3-dioxolan-4-yl)methoxy)pyrazin-2-yl)-7-(6-methylpyridin-3-yl)-3,4-dihydro-1,4-methanopyrido[2,3-b][1,4]diazepine-5(2H)-carboxamide

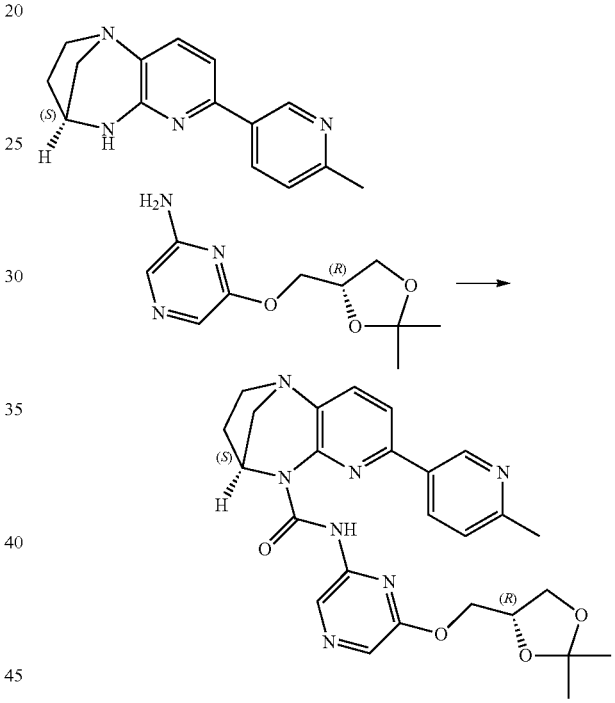

To a solution of (R)-6-((2,2-dimethyl-1,3-dioxolan-4-yl) methoxy)pyrazin-2-amine (803 mg, 3.57 mmol) in Tetrahydrofuran (THF) (20 mL) at 30° C. was added triphosgene (423 mg, 1.427 mmol) and stirred for 30 min at same temperature. Then added TEA (1.657 mL, 11.89 mmol) followed by (4S)-7-(6-methylpyridin-3-yl)-2,3,4,5-tetrahydro-1,4-methanopyrido[2,3-b][1,4]diazepine (600 mg, 2.378 mmol) at room temperature. The reaction mixture was stirred at 65° C. for 16 hr. Reaction was monitored by TLC and crude LCMS. THF evaporated under reduced pressure, residue diluted with water and extracted into DCM. Organic layer dried over Na2SO4, solvent evaporated under reduced pressure to afford crude product. The crude compound was purified by column chromatography using silica gel as an stationary phase (100-200 mesh) and 2-3% of MeOH/EtOAc as an eluent.

Pure fractions were collected and concentrated under reduced pressure to afford pure product 0.4 g as an off white solid (450 mg, 0.71 mmol, 30%), LCMS (m/z) 504.3 (M+H)+.

Synthesis of (4S)—N-(4-(((S)-2,2-dimethyl-1,3-dioxolan-4-yl)methoxy)pyridin-2-yl)-7-(3-(trifluoromethyl)phenyl)-3,4-dihydro-1,4-methanopyrido[2,3-b][1,4]diazepine-5(2H)-carboxamide

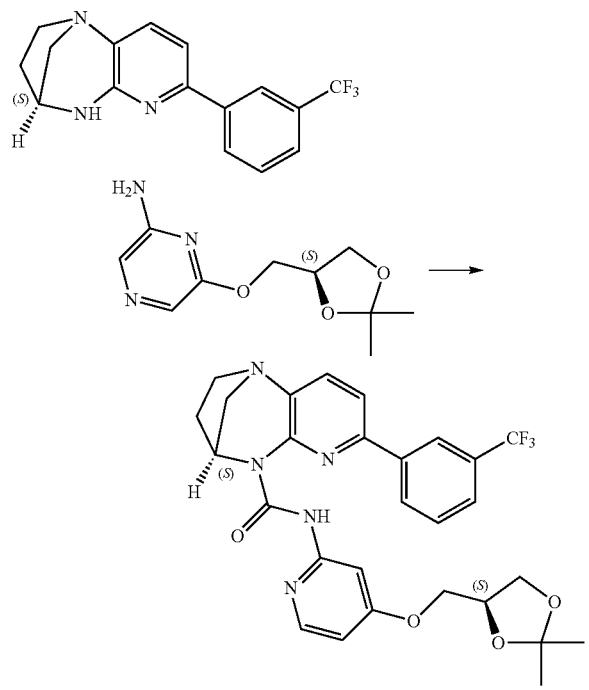

To a solution of (4R)-7-(3-(trifluoromethyl)phenyl)-2,3,4,5-tetrahydro-1,4-methanopyrido[2,3-b][1,4]diazepine (545 mg, 1.785 mmol) in Tetrahydrofuran (THF) (20 mL) stirred under nitrogen at room temp was added TEA (1.493 mL, 10.71 mmol), triphosgene (530 mg, 1.785 mmol). Then the reaction mixture was stirred for 15 min before a solution of (S)-4-((2,2-dimethyl-1,3-dioxolan-4-yl)methoxy)pyridin-2-amine (1201 mg, 5.36 mmol) in THF (5 mL) was added dropwise over 5 min. The reaction mixture was stirred at 65° C. for 16 h before being cooled to room temperature and poured in to water and extracted with EtOAc (3×100 mL). Then the combined organic layer was washed with water, brine solution, dried over sodium sulfate and evaporated to give the crude product. This was purified by reverse phase column chromatography (0.1% HCOOH&Water)/MeOH to give the desired product (500 mg, 49%), LCMS (m/z) 556.3 (M+H)$^+$.

Synthesis of (4S)—N-(6-(((R)-2,2-dimethyl-1,3-dioxolan-4-yl)methoxy)pyrazin-2-yl)-7-(3-(trifluoromethyl)phenyl)-3,4-dihydro-1,4-methanopyrido[2,3-b][1,4]diazepine-5(2H)-carboxamide

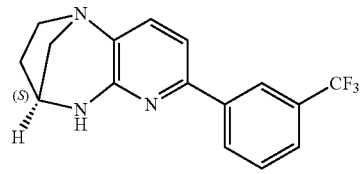

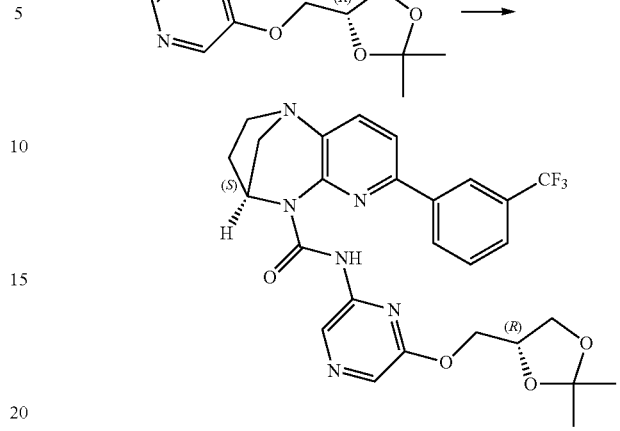

To a stirred solution of (4S)-7-(3-(trifluoromethyl)phenyl)-2,3,4,5-tetrahydro-1,4-methanopyrido[2,3-b][1,4]diazepine (850 mg, 2.78 mmol) in 40 mL of THF (sealed tube) was added triphosgene (324 mg, 1.093 mmol) at 25° C. and stirred for 30 min. To this reaction mixture was added (R)-6-((2,2-dimethyl-1,3-dioxolan-4-yl)methoxy)pyrazin-2-amine (938 mg, 4.16 mmol) was added and the reaction mixture was stirred at 65° C. for 16 h. The reaction mixture was allowed to cool to room temperature and the mixture was poured into cold water (70 mL) and extracted with ethyl acetate (3×50 mL). The combined organic layer was dried over anhydrous Na$_2$SO$_4$, filtered and concentrated under reduced pressure to obtain the crude product. The crude mixture was purified by flash column chromatography (silica-gel; 100-200 mesh, eluted with 1 to 2% methanol in dichloromethane) to afford (4S)—N-(6-(((R)-2,2-dimethyl-1,3-dioxolan-4-yl)methoxy)pyrazin-2-yl)-7-(3-(trifluoromethyl)phenyl)-3,4-dihydro-1,4-methanopyrido[2,3-b][1,4]diazepine-5(2H)-carboxamide (900 mg, 1.618 mmol 57% yield) as a white solid (TLC: eluent: 10% MeOH in DCM, R$_f$=0.3), LCMS (m/z) 557.3 (M+H)$^+$.

Synthesis of (4S)—N-(6-(((S)-2,2-dimethyl-1,3-dioxolan-4-yl)methoxy)pyrazin-2-yl)-7-(3-(trifluoromethyl)phenyl)-3,4-dihydro-1,4-methanopyrido[2,3-b][1,4]diazepine-5(2H)-carboxamide

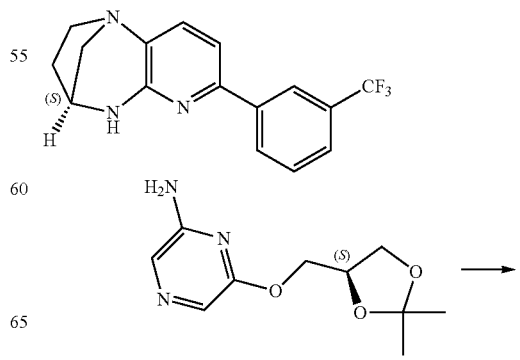

119

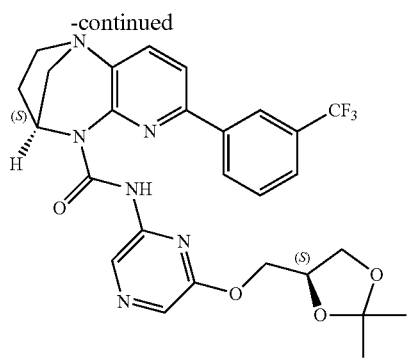

To a solution of (4S)-7-(3-(trifluoromethyl)phenyl)-2,3,4,5-tetrahydro-1,4-methanopyrido[2,3-b][1,4]diazepine (723 mg, 2.368 mmol) in tetrahydrofuran (THF) (25 mL) and add triphosgene (351 mg, 1.184 mmol) the reaction mixture was stirred at room temperature for 30 min before adding TEA (1.650 mL, 11.84 mmol) and (S)-6-((2,2-dimethyl-1,3-dioxolan-4-yl)methoxy)pyrazin-2-amine (800 mg, 3.55 mmol). The reaction mixture was stirred at 65° C. for 16 hr before cooling to room temperature and poured in to water and extracted with EtOAc (3×100 mL). Then the combined organic layer was washed with water, brine solution, dried over sodium sulfate and evaporated to give the crude compound which was purified by reverse phase column and eluted with 83% of (0.1% HCOOH&Water)/MeOH to get pure compound (300 mg, 0.534 mmol, 23%), LCMS (m/z) 557.4 (M+H)$^+$.

Synthesis of (4S)—N-(2-(((S)-2,2-dimethyl-1,3-dioxolan-4-yl)methoxy)pyrimidin-4-yl)-7-(3-(trifluoromethyl)phenyl)-3,4-dihydro-1,4-methanopyrido[2,3-b][1,4]diazepine-5(2H)-carboxamide

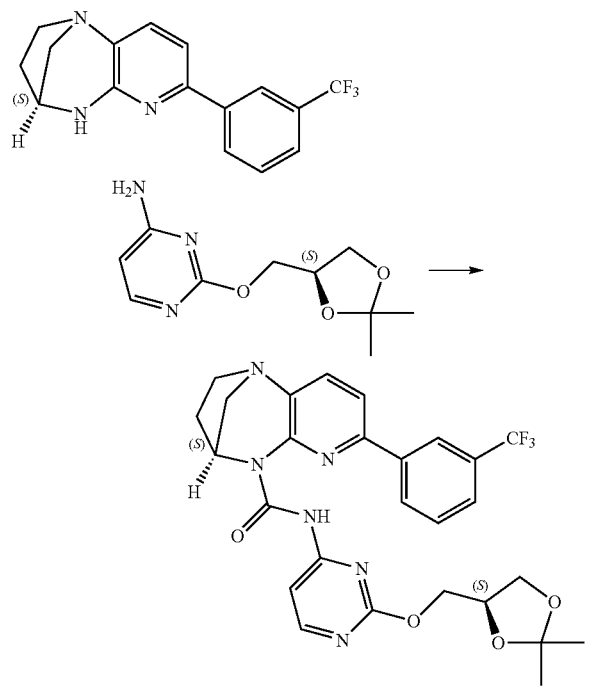

120

To a solution of (4S)-7-(3-(trifluoromethyl)phenyl)-2,3,4,5-tetrahydro-1,4-methanopyrido[2,3-b][1,4]diazepine (600 mg, 1.965 mmol) in Tetrahydrofuran (THF) (10 mL) was added triphosgene (583 mg, 1.965 mmol), TEA (1.644 mL, 11.79 mmol) stirred at rt for 15 min and add a solution of (S)-2-((2,2-dimethyl-1,3-dioxolan-4-yl)methoxy)pyrimidin-4-amine (1328 mg, 5.90 mmol) in THF (5 mL) over 1 min. The reaction mixture was stirred at 65° C. for 16 hr before being poured in to water and extracted with EtOAc (3×50 mL). Then the combined organic layer was washed with water, brine solution, dried over sodium sulfate and evaporated to give 600 mg. The crude compound was purified by reverse phase column and eluted with 90% (0.1% HCOOH&Water)/MeOH to give the desired compound (450 mg, 0.76 mmol, 39%), LCMS (m/z) 557.2 (M+H)$^+$.

Synthesis of (4S)—N-(2-(((S)-2,2-dimethyl-1,3-dioxolan-4-yl)methoxy)pyridin-4-yl)-7-(3-(trifluoromethyl)phenyl)-3,4-dihydro-1,4-methanopyrido[2,3-b][1,4]diazepine-5(2H)-carboxamide

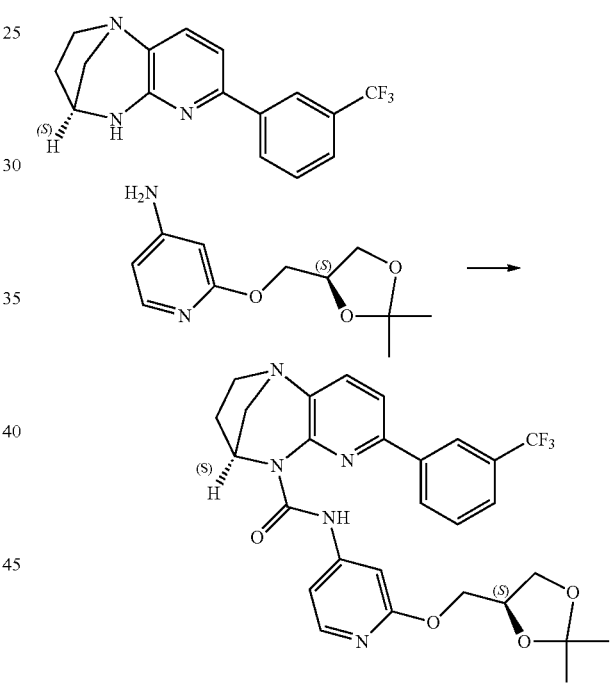

To a solution of (4S)-7-(3-(trifluoromethyl)phenyl)-2,3,4,5-tetrahydro-1,4-methanopyrido[2,3-b][1,4]diazepine (600 mg, 1.965 mmol) in Tetrahydrofuran (THF) (10 mL) was added TEA (1.644 mL, 11.79 mmol), triphosgene (583 mg, 1.965 mmol) stirred at for 15 min and added (S)-2-((2,2-dimethyl-1,3-dioxolan-4-yl)methoxy)pyridin-4-amine (1322 mg, 5.90 mmol) portion wise. The reaction mixture was stirred at 65° C. for 16 hr and progress of the reaction was monitored by TLC. The reaction mixture was poured in to ice water and extracted with EtOAc (3×100 mL). Then the combined organic layer was washed with water, brine solution, dried over sodium sulfate and evaporated to give the crude product. The crude compound was purified by reverse phase column and eluted with 93% (0.1% HCOOH&Water)/MeOH to give the desired product (450 mg, 0.807 mmol, 41.1% yield), LCMS (m/z) 556.4 (M+H)$^+$.

Synthesis of (4S)—N-(2-(((S)-2,2-dimethyl-1,3-dioxolan-4-yl)methoxy)pyridin-4-yl)-7-(3-(trifluoromethyl)phenyl)-3,4-dihydro-1,4-methanopyrido[2,3-b][1,4]diazepine-5(2H)-carboxamide

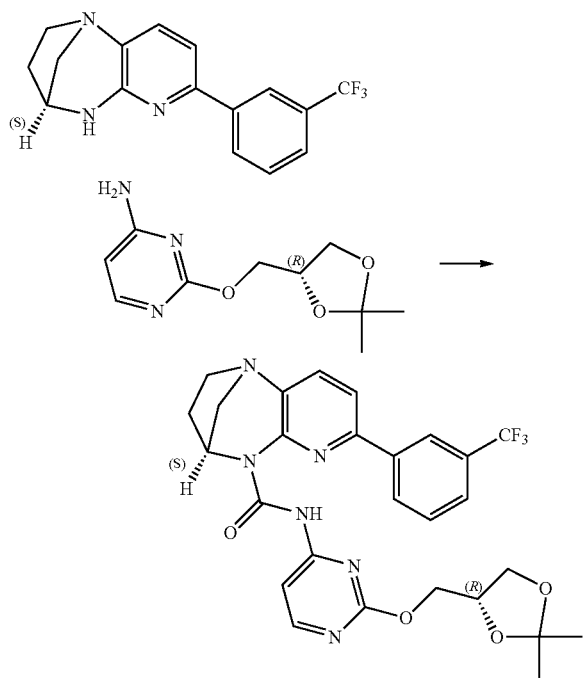

To a solution of (4R)-7-(3-(trifluoromethyl)phenyl)-2,3,4,5-tetrahydro-1,4-methanopyrido[2,3-b][1,4]diazepine (400 mg, 1.310 mmol) in Tetrahydrofuran (THF) (10 mL) and add TEA (1.096 mL, 7.86 mmol), triphosgene (389 mg, 1.310 mmol) stirred at room temp for 15 min was added a solution of (R)-2-((2,2-dimethyl-1,3-dioxolan-4-yl)methoxy)pyrimidin-4-amine (885 mg, 3.93 mmol) in THF (2.0 mL). The reaction mixture was stirred at 65° C. for 16 hr. The reaction mixture was poured in to water and extracted with EtOAc (3×100 mL). Then the combined organic layer was washed with water, brine solution, dried over sodium sulfate and evaporated to dryness. The crude compound was purified by reverse phase column and eluted with 90% (0.1% HCOOH&Water)/MeOH to get pure compound (350 mg, 0.602 mmol, 46%), LCMS (m/z) 557.0 (M+H)+.

Synthesis of (4S)—N-(2-(((R)-2,2-dimethyl-1,3-dioxolan-4-yl)methoxy)pyridin-4-yl)-7-(3-(trifluoromethyl)phenyl)-3,4-dihydro-1,4-methanopyrido[2,3-b][1,4]diazepine-5(2H)-carboxamide

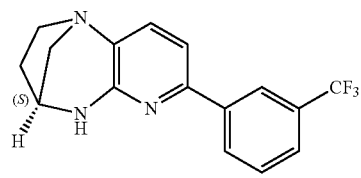

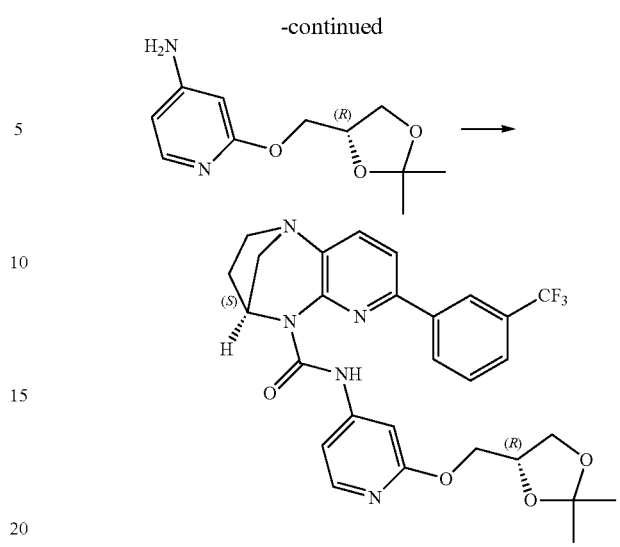

To a solution of (4S)-7-(3-(trifluoromethyl)phenyl)-2,3,4,5-tetrahydro-1,4-methanopyrido[2,3-b][1,4]diazepine (1 g, 3.28 mmol), in Tetrahydrofuran (THF) (15 mL) stirred under nitrogen at room temp was added a solution of TEA (2.74 mL) and triphosgene stirred under nitrogen at room temp for 30 minutes. To this (R)-2-((2,2-dimethyl-1,3-dioxolan-4-yl)methoxy)pyridin-4-amine (2.204 g, 9.83 mmol) in Tetrahydrofuran (THF) (8 mL) (2.204 g) was added. The reaction mixture was stirred at 60° C. for 16 hr. The reaction mixture was concentrated and the residue was taken up in DCM (100 mL). The solution was washed with water and brine, dried over Na2SO4, filtered and concentrated. The crude product was added to a silica gel column and was eluted with EtOAc/pet ether (60:20) collected fractions were evaporated to give the desired product (600 mg, 0.92 mmol, 28%) as an off white semi solid, LCMS (m/z) 556.3 (M+H)+.

Synthesis of (4S)-7-(2-methylpyridin-4-yl)-N-(2-(pyridin-3-yl)ethyl)-3,4-dihydro-1,4-methanopyrido[2,3-b][1,4]diazepine-5(2H)-carboxamide

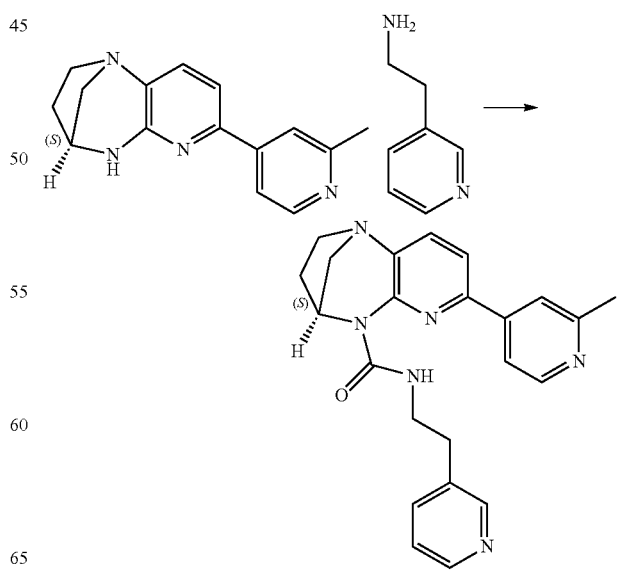

To a solution of (4S)-7-(2-methylpyridin-4-yl)-2,3,4,5-tetrahydro-1,4-methanopyrido[2,3-b][1,4]diazepine (400 mg, 1.585 mmol), triethylamine (1.105 mL, 7.93 mmol) and triphosgene (282 mg, 0.951 mmol) in Tetrahydrofuran (THF) (20 mL) stirred under nitrogen at room temp for 30 min was added a solution of 2-(pyridin-3-yl)ethanamine (387 mg, 3.17 mmol) in THF (5 mL) dropwise over 5 min. The reaction mixture was stirred at 65° C. for 16 hr and progress of the reaction was monitored by TLC. The reaction mixture was poured in to ice water and extracted with EtOAc (3×100 mL). Then the combined organic layer was washed with water, brine solution, dried over sodium sulfate and evaporated to give the crude compound. The crude compound was purified by reverse phase column and eluted with 25-30% (0.1% HCOOH&Water)/MeOH give the final product (250 mg, 0.599 mmol, 37.8% yield), LCMS (m/z) 401.1 (M+H)⁺.

Synthesis of tert-butyl 4-((4S)-5-(pyrazin-2-ylcarbamoyl)-2,3,4,5-tetrahydro-1,4-methanopyrido[2,3-b][1,4]diazepin-7-yl)piperazine-1-carboxylate

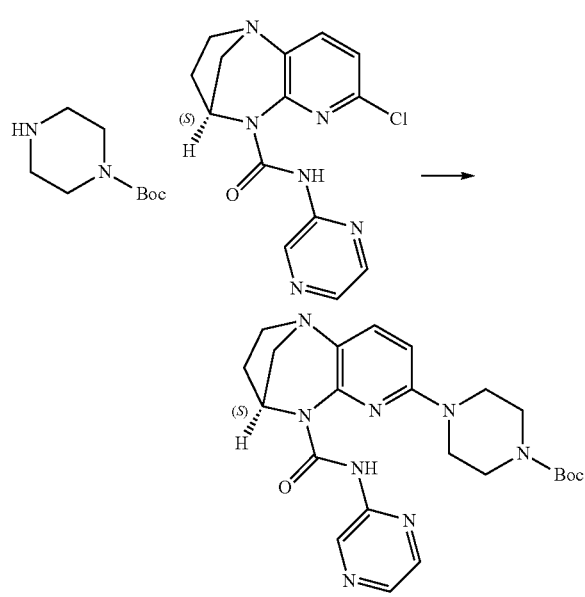

To a degassed solution of (4S)-7-chloro-N-(pyrazin-2-yl)-3,4-dihydro-1,4-methanopyrido[2,3-b][1,4]diazepine-5(2H)-carboxamide (600 mg, 1.894 mmol) and tert-butyl piperazine-1-carboxylate (706 mg, 3.79 mmol) in 1,4-Dioxane (10 mL) was added subsequentially at 20° C. Cs₂CO₃ (1852 mg, 5.68 mmol), xphos (361 mg, 0.758 mmol) and PdOAc₂ (85 mg, 0.379 mmol). The reaction mixture was stirred at 100° C. for 16 hr. The reaction mixture was poured in to cold water (20 mL) and extracted with ethyl acetate (50 mL). The organic layer was dried over anhydrous sodium sulfate and concentrated under reduced pressure to give the crude product. The crude product was added to a silica gel column and was eluted with 3% DCM/MeOH to give tert-butyl 4-((4S)-5-(pyrazin-2-ylcarbamoyl)-2,3,4,5-tetrahydro-1,4-methanopyrido[2,3-b][1,4]diazepin-7-yl)piperazine-1-carboxylate (359 mg, 0.616 mmol, 32.5% yield), LCMS (m/z) 467.3 (M+H)⁺.

Synthesis of tert-butyl 3-methyl-4-((4S)-5-(pyrazin-2-ylcarbamoyl)-2,3,4,5-tetrahydro-1,4-methanopyrido[2,3-b][1,4]diazepin-7-yl)piperazine-1-carboxylate

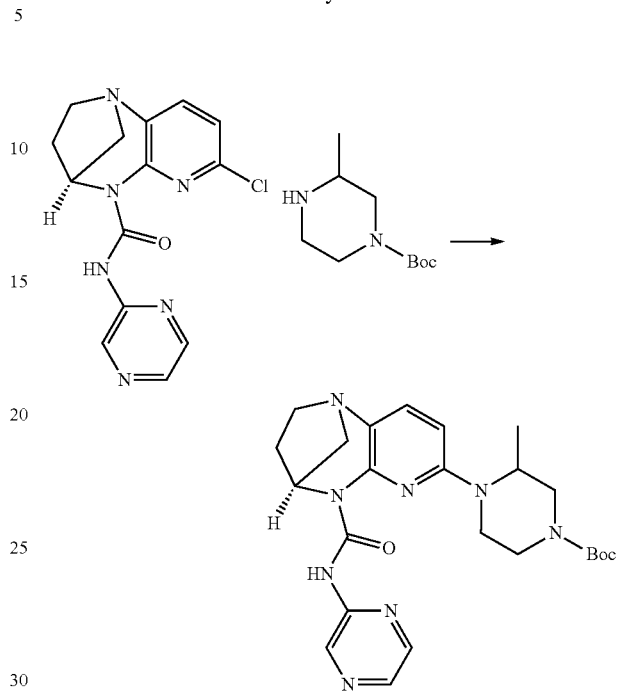

To a degassed solution of (4S)-7-chloro-N-(pyrazin-2-yl)-3,4-dihydro-1,4-methanopyrido[2,3-b][1,4]diazepine-5(2H)-carboxamide (800 mg, 2.53 mmol), tert-butyl 3-methylpiperazine-1-carboxylate (1012 mg, 5.05 mmol) in 1,4-Dioxane (10 mL) and was added sequentially at 20° C. Cs₂CO₃ (2469 mg, 7.58 mmol) and xphos (482 mg, 1.010 mmol), PdOAc₂ (113 mg, 0.505 mmol). The reaction mixture was stirred at 100° C. for 16 hr. The reaction was monitored by TLC. The reaction mixture was poured in to cold water (20 mL) and extracted with ethyl acetate (50 mL). The organic layer was dried over anhydrous sodium sulfate, concentrated under reduced pressure to give crude. The crude product was added to a silica gel column and was eluted with 2% DCM/MeOH. Collected fractions are evaporated to give the desired product (397.5 mg, 0.670 mmol, 26.5% yield), LCMS (m/z) 481.1 (M+H)⁺.

Synthesis of (4S)-7-(4-benzyl-3-methylpiperazin-1-yl)-N-(pyrazin-2-yl)-3,4-dihydro-1,4-methanopyrido[2,3-b][1,4]diazepine-5(2H)-carboxamide

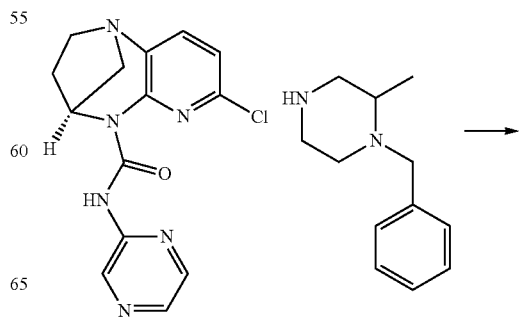

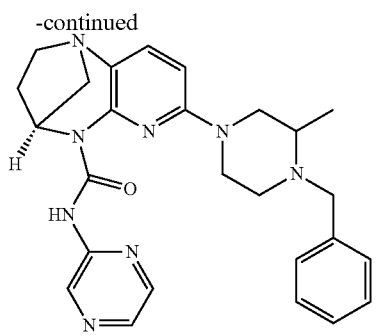

To a degassed solution of in (4S)-7-chloro-N-(pyrazin-2-yl)-3,4-dihydro-1,4-methanopyrido[2,3-b][1,4]diazepine-5(2H)-carboxamide (500 mg, 1.579 mmol), 1-benzyl-2-methylpiperazine (601 mg, 3.16 mmol) in 1,4-Dioxane (20 mL) was added sequentially at 20° C. $Cs_2CO_3$ (1543 mg, 4.74 mmol) and cinnamyl chloro[1,3-bis(diisopropylphenyl)-2-imidazolidinyliin]Pd(II) (51.3 mg, 0.079 mmol). The reaction mixture was stirred at 110° C. for 16 hrs. The reaction mixture was poured into cold water (50 mL) and extracted with ethyl acetate (200 mL). The organic layer was dried over anhydrous sodium sulfate and concentrated under reduced pressure to give the crude product. The crude product was added to a silica gel column and was eluted with 3% DCM/MeOH to give (4S)-7-(4-benzyl-3-methylpiperazin-1-yl)-N-(pyrazin-2-yl)-3,4-dihydro-1,4-methanopyrido[2,3-b][1,4]diazepine-5(2H)-carboxamide (501.5 mg, 0.885 mmol, 56.0% yield), LCMS (m/z) 471.3 $(M+H)^+$.

Synthesis of 4-bromo-2-(difluoromethyl)pyridine

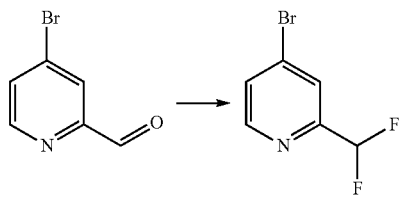 [SMILES: O=Cc1cc(Br)ccn1 ; FC(F)c1cc(Br)ccn1]

DAST (0.620 mL, 4.69 mmol) was added dropwise to a solution of 4-bromopicolinaldehyde (700 mg, 3.76 mmol) in Chloroform (21 mL) at 0° C. The reaction mixture was stirred at 20° C. for 12 h. The reaction mixture was poured in to saturated $NaHCO_3$ solution (20 mL), and was extracted with DCM (2×20 mL). The DCM layer was dried over anhydrous$Na_2SO_4$, filtered and filtrate was evaporated to afford 4-bromo-2-(difluoromethyl)pyridine (400 mg, 1.870 mmol, 49.7% yield) as light yellow solid, LCMS (m/z) 208.0 $[M+H]^+$.

Synthesis of (2-(difluoromethyl)pyridin-4-yl)boronic Acid

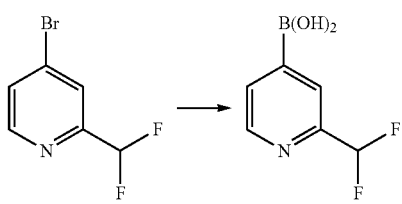 [SMILES: FC(F)c1cc(Br)ccn1 ; OB(O)c1ccnc(C(F)F)c1]

Potassium acetate (472 mg, 4.81 mmol) was added to a stirred solution of 4-bromo-2-(difluoromethyl)pyridine (400 mg, 1.923 mmol), and bis(pinacolato)diboron (610 mg, 2.404 mmol) in 1,4-Dioxane (10 mL) at 28° C. The reaction mixture was degassed for 15 min, was added $PdCl_2$(dppf) (4.22 mg, 5.77 µmol). The reaction mixture was further degassed for 15 min, and the reaction mixture was stirred for 48 hr at 80° C. The reaction mixture was cooled to 28° C., was evaporated and crude was partitioned between water (10 mL) and EtOAc (25 mL). EtOAc layer was separated and was dried over anhydrous $Na_2SO_4$, filtered, and filtrate was evaporated to afford (2-(difluoromethyl)pyridin-4-yl)boronic acid (330 mg, 1.107 mmol, 57.6% yield) as brown solid, LCMS (m/z) 174.1 $[M+H]^+$.

Synthesis of tert-butyl 4-benzyl-3-methylpiperazine-1-carboxylate

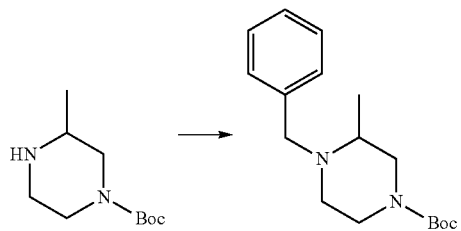 [SMILES: CC1CN(C(=O)OC(C)(C)C)CCN1 ; CC1CN(C(=O)OC(C)(C)C)CCN1Cc1ccccc1]

To a solution of tert-butyl 3-methylpiperazine-1-carboxylate (1 g, 4.99 mmol), in N,N-Dimethylformamide (DMF) (100 mL) was added $K_2CO_3$ (2.070 g, 14.98 mmol) at 0° C. After stirring 10 min at 0° C. benzyl bromide (0.891 mL, 7.49 mmol) was added dropwise and the reaction mixture was stirred at 35° C. for 16 hr and the reaction was monitored by TLC. The reaction mixture was poured in to aq $NaHCO_3$ (50 mL) and extracted with ethyl acetate (200 mL) and washed with water and then brine. The organic layer was dried over anhydrous sodium sulfate, concentrated under reduced pressure to give crude. The crude product was added to a silica gel column and was eluted with 10% Hex/EtOAc. Collected fractions are evaporated to give tert-butyl 4-benzyl-3-methylpiperazine-1-carboxylate (1 g, 3.17 mmol, 63.4% yield), LCMS (m/z) 174.1 $[M+H]^+$.

Synthesis of 1-benzyl-2-methylpiperazine

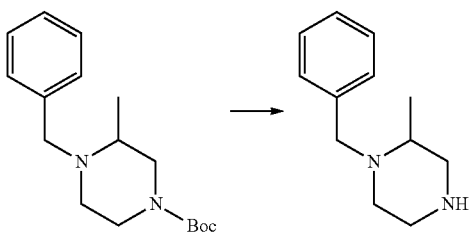 [SMILES: CC1CN(C(=O)OC(C)(C)C)CCN1Cc1ccccc1 ; CC1CNCCN1Cc1ccccc1]

To a solution of tert-butyl 4-benzyl-3-methylpiperazine-1-carboxylate (1.4 g, 4.82 mmol) in Dichloromethane (DCM) (25 mL) was added TFA (1.857 mL, 24.10 mmol) at 0° C. and the reaction mixture was stirred at 35° C. for 3 hr. The reaction was monitored by TLC. The solvent was evaporated under reduced pressure to give the crude product. The residue was triturated with Diethyl ether (2×50 mL).

127

The resulting solid was filtered and washed with Diethyl ether. This was dried under reduced pressure to give 1-benzyl-2-methylpiperazine Trifluoroacetic acid salt (800 mg, 2.63 mmol, 54.5% yield)

Synthesis of ((R)-2-methylmorpholino)(4S)-7-(2-methylpyridin-4-yl)-3,4-dihydro-1,4-methanopyrido[2,3-b][1,4]diazepin-5(2H)-yl)methanone

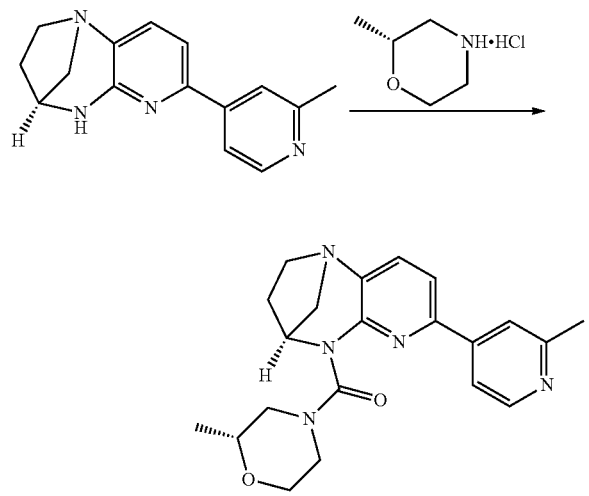

Triphosgene (0.529 g, 1.783 mmol) was added to a stirred solution of triethylamine (1.243 mL, 8.92 mmol) and (4S)-7-(2-methylpyridin-4-yl)-2,3,4,5-tetrahydro-1,4-methanopyrido [2,3-b][1,4]diazepine (0.45 g, 1.783 mmol) in tetrahydrofuran (50 mL) at room temperature and stirred for 1 h and followed by addition of (R)-2-methylmorpholine hydrochloride (0.368 g, 2.68 mmol) and heated to 70° C. for 15 h. Cooled to room temperature and diluted with ethyl acetate (100 mL) and water (100 mL). The separated organic layer was washed with water and brine. The organic layer was dried over sodium sulfate, filtered and concentrated under reduced pressure to get crude compound (TLC eluent: 10% MeOH in ethyl acetate; UV active; $R_f$-0.4). Crude compound was purified through column chromatography using neutral alumina and eluted in 50% ethyl acetate in hexane to afford (R)-2-methylmorpholino)((4S)-7-(2-methylpyridin-4-yl)-3,4-dihydro-1,4-methanopyrido[2,3-b][1,4]diazepin-5(2H)-yl)meth-anone (0.2 g, 0.514 mmol, 32.4% yield) as gummy compound, LCMS (m/z) 380.3 (M+H)$^+$.

Synthesis of ((S)-2-methylmorpholino)((4S)-7-(2-methylpyridin-4-yl)-3,4-dihydro-1,4-methanopyrido[2,3-b][1,4]diazepin-5(2H)-yl)methanone

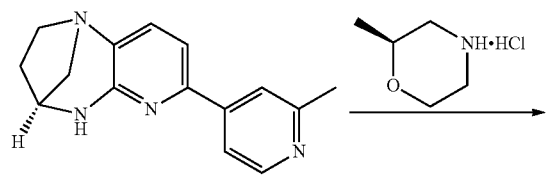

128

-continued

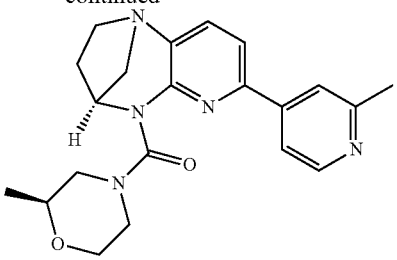

Triphosgene (0.470 g, 1.585 mmol) was added to a stirred solution of triethylamine (1.105 mL, 7.93 mmol) and (4S)-7-(2-methylpyridin-4-yl)-2,3,4,5-tetrahydro-1,4-methanopyrido [2,3-b][1,4]diazepine (0.4 g, 1.585 mmol) in tetrahydrofuran (50 mL) at room temperature and stirred for 1 h and followed by addition of (S)-2-methylmorpholine hydrochloride (0.327 g, 2.378 mmol) and heated to 70° C. for 15 h. Cooled to room temperature and diluted with ethyl acetate (100 mL) and water (100 mL). The separated organic layer was washed with water and brine. The organic layer was dried over sodium sulfate, filtered and concentrated under reduced pressure to get crude compound (TLC eluent: 10% MeOH in ethyl acetate; UV active; $R_f$-0.4). Crude compound was purified through column chromatography using neutral alumina and eluted in 50% ethyl acetate in hexane to afford (S)-2-methylmorpholino)((4S)-7-(2-methylpyridin-4-yl)-3,4-dihydro-1,4-methanopyrido[2,3-b][1,4]diazepin-5(2H)-yl)meth-anone (0.2 g, 0.514 mmol, 32.4% yield) as gummy compound, LCMS (m/z) 480.3 (M+H)$^+$.

EXAMPLES

Example 1. Preparation of (4S)—N-(pyridin-2-yl)-7-(3-(trifluoromethyl)phenyl)-3,4-dihydro-1,4-methanopyrido[2,3-b][1,4]diazepine-5-(2H)-carboxamide Step 1. Synthesis of (S)-dimethyl 2-((6-chloro-3-nitropyridin-2-yl)amino)succinate

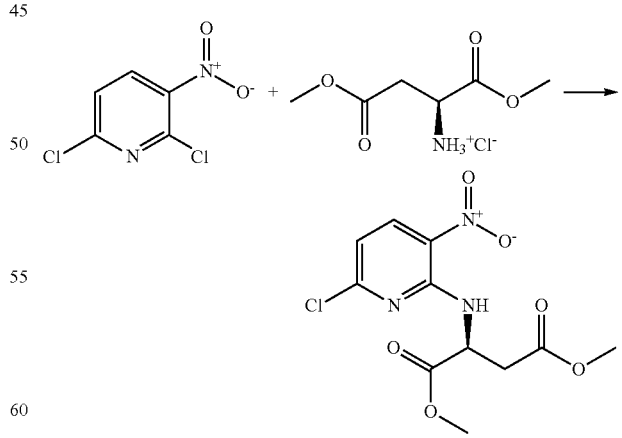

To a 2 L flask equipped with a thermometer, a reflux condenser, and a mechanical stirrer was added (100 g, 0.52 mol) of 2,6-dichloro-3-nitropyridine (205 g, 1.04 mol) of (S)-aspartic acid dimethyl ester hydrochloride (174 g, 2.07 mol) of NaHCO$_3$ and 1 L of tetrahydrofuran. The reaction was stirred at 40° C. for 16 h, and was monitored for the disappearance of 2,6-dichloropyridine by HPLC. After the reaction was complete, the solids were filtered away and washed with ethyl acetate (3×300 mL). The combined filtrate and washings were concentrated to dryness, and the residue was taken up in 1 L of ethyl acetate. The solution was stirred with 200 g of charcoal at ambient temperature for 2 h, and the charcoal was filtered away and washed with additional ethyl acetate (3×200 mL). The combined filtrate and washings were concentrated in vacuo to give the crude product (S)-dimethyl 2-((6-chloro-3-nitropyridin-2-yl) amino)succinate (180 g) as a yellow oil. This was used in the next step without further purification. MS (ESI) calcd for $C_{11}H_{12}ClN_3O_6$: 317.0; found: 318.0 (M+H)$^+$.

An analagous procedure could be used to prepare (R)-dimethyl 2-((6-chloro-3-nitropyridin-2-yl)amino)succinate by starting with (R)-aspartic acid dimethyl ester hydrochloride.

Step 2. Synthesis of (S)-methyl 2-(6-chloro-2-oxo-1,2,3,4-tetrahydropyrido[2,3-b]pyrazin-3-yl)acetate

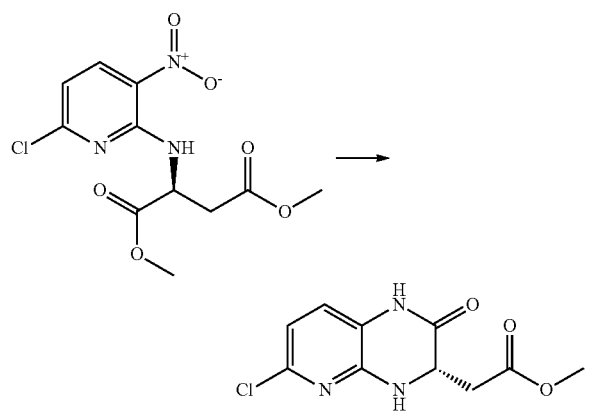

A 5 L three necked flask equipped with a thermometer, a reflux condenser, and a mechanical stirrer was charged with crude (S)-dimethyl 2-((6-chloro-3-nitropyridin-2-yl)amino) succinate (180 g, 0.52 mol) of iron powder (146 g, 2.59 mol), 2 L of 2-propanol, and 700 mL of water. The mixture was stirred at 40° C., acetic acid (15.5 g, 0.259 mmol) was added at a rate sufficient to keep the inner temperature below 70° C. The reaction was stirred at 70° C. for 30 min, HPLC indicated that the reaction was complete. The mixture was cooled to 40° C., then $Na_2CO_3$ (165 g, 1.55 mol) was added, and the mixture was stirred for 1 h. The solids were filtered away, then the solids were washed with tetrahydrofuran (3×500 mL). The combined filtrate and washings were concentrated in vacuo, then the residue was stirred in 1 L of ethanol for 12 hrs. The solid was filtered and washed with cold ethanol. This was dried in vacuo to give (S)-methyl 2-(6-chloro-2-oxo-1,2,3,4-tetrahydropyrido[2,3-b]pyrazin-3-yl)acetate (91 g, 68%) as an off-white solid. MS (ESI) calcd for $C_{10}H_{10}ClN_3O_3$: 255.0; found: 256.0 (M+H)$^+$.

An analogous procedure could be used to prepare (R)-methyl 2-(6-chloro-2-oxo-1,2,3,4-tetrahydropyrido[2,3-b] pyrazin-3-yl)acetate by starting with (R)-dimethyl 2-((6-chloro-3-nitropyridin-2-yl) amino)succinate.

Step 3. Synthesis of (S)-2-(6-chloro-1,2,3,4-tetrahydropyrido[2,3-b]pyrazin-3-yl)ethanol

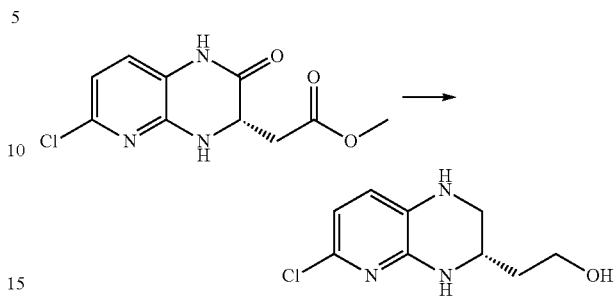

A 5 L 3-necked flask equipped with a mechanical stirrer, a reflux condenser, and a nitrogen inlet was charged with of $LiAlH_4$ (60 g, 1.58 mol). The flask was cooled with an ice bath, then 500 mL of tetrahydrofuran was added. The stirred mixture was cooled to 0° C., a solution of (S)-methyl 2-(6-chloro-2-oxo-1,2,3,4-tetrahydropyrido[2,3-b]pyrazin-3-yl)acetate (81 g, 0.32 mol) in 2 L of tetrahydrofuran was added, while keeping the internal temperature below 5° C. After the addition was complete, the reaction was heated at reflux for 16 h, monitoring by HPLC for the appearance of product. The ester reduction occurred rapidly, while the lactam reduction required longer for complete reduction. The reaction was cooled to 5° C., then 60 mL of water was added, keeping the internal temperature below 10° C. After addition was complete, the reaction was stirred for 15 min. Next, 60 mL of 15% (w/w) NaOH$_{(aq.)}$ was added, keeping the internal temperature below 5° C. After addition was complete, the reaction was stirred for 15 min. To complete the workup, 180 mL of water was added, then the mixture was stirred at ambient temperature for 1 h. The solids were filtered and washed with tetrahydrofuran (3×150 mL). The filtrate and washings were concentrated in vacuo, then the solid residue was dried in vacuo to give (S) 2-(6-chloro-1, 2,3,4-tetrahydropyrido[2,3-b]pyrazin-3-yl)ethanol (55 g, 81%) as a brown solid. MS (ESI) calcd for $C_9H_{12}ClN_3O$: 213.1; found: 214.1 (M+H)$^+$.

An analogous procedure could be used to prepare (R)-2-(6-chloro-1,2,3,4-tetrahydropyrido[2,3-b]pyrazin-3-yl)ethanol by starting with (R)-methyl 2-(6-chloro-2-oxo-1,2,3,4-tetrahydropyrido[2,3-b]pyrazin-3-yl)acetate.

Step 4. Synthesis of (4S)-7-chloro-2,3,4,5-tetrahydro-1,4-methanopyrido[2,3-b][1,4]diazepine

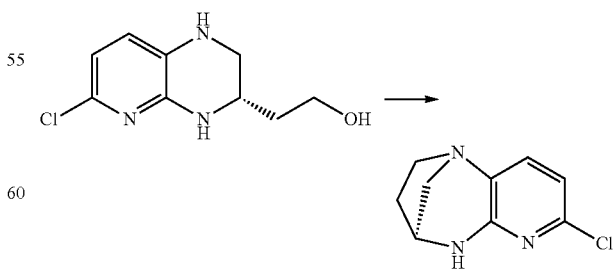

To a solution of (S)-2-(6-chloro-1,2,3,4-tetrahydropyrido [2,3-b]pyrazin-3-yl)ethanol (50 g, 0.234 mol) in 500 mL of $CH_2Cl_2$ was added triethylamine (95 g, 0.936 mol). The mixture was stirred at ambient temperature until it was homogeneous, then it was cooled to 0° C. Next, POCl₃ (54 g, 0.351 mol) was added, dropwise, maintaining the temperature at 0° C. 5. Cooling was removed, and the reaction was stirred at ambient temperature for 2 h and monitored by HPLC for the disappearance of the starting alcohol. After the reaction was complete, 200 mL of 1.2M NaHCO₃(aq.) was added. The layers were separated, and the aqueous layer was extracted with CH₂Cl₂. The combined CH₂Cl₂ layers were extracted with 1M HCl(aq.) (4×300 mL), and the combined HCl layers were adjusted to pH=8 with NaHCO₃(sat.). The resulting mixture was extracted with CH₂Cl₂(4×300 mL), and the combined CH₂Cl₂ layers were dried over Na₂SO₄, filtered, and treated with 50 g of charcoal. The mixture was stirred at ambient temperature for 3 h, filtered through charcoal, and the charcoal washed with an additional 200 mL of CH₂Cl₂. The combined filtrate and wash solution was concentrated to dryness. The solid residue was dried in vacuo to give (4S)-7-chloro-2,3,4,5-tetrahydro-1,4-methanopyrido[2,3-b][1,4]diazepine (30 g, 66%) as an off-white crystalline solid. MS (ESI) calcd for C₉H₁₀ClN₃: 195.1; found: 196.1 (M+H)⁺. An analogous procedure could be used to prepare (4R)-7-chloro-2,3,4,5-tetrahydro-1,4-methanopyrido[2,3-b][1,4]diazepine by starting with (R)-2-(6-chloro-1,2,3,4-tetrahydropyrido[2,3-b]pyrazin-3-yl)ethanol.

Step 5. Synthesis of (4S)-7-(3-(trifluoromethyl) phenyl)-2,3,4,5-tetrahydro-1,4-methanopyrido[2,3-b] [1,4]diazepine

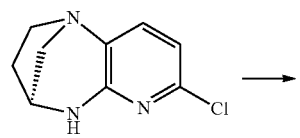

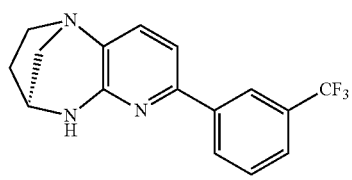

A mixture of (4S)-7-chloro-2,3,4,5-tetrahydro-1,4-methanopyrido[2,3-b][1,4]diazepine (1.88 g, 9.6 mmol), (3-trifluoromethylphenyl)boronic acid (2.4 g, 12.6 mmol), Pd(OAc)₂ (0.228 g, 1.02 mmol), 2-dicyclohexylphosphino-2',4',6'-triisopropylbiphenyl (0.972 g, 2.04 mmol), and Cs₂CO₃ (6.6 g, 20.4 mmol) was dissolved in dioxane/H₂O (50 mL, v/v=9:1). The reaction mixture was heated to 90° C. overnight. After cooling to room temp., it was diluted with EtOAc (120 mL) and washed with water. The aqueous layer was extracted with EtOAc, and the combined organic layers were washed with brine, dried over MgSO₄, filtered, and concentrated. Purification by silica gel chromatography (0 to 100% EtOAc in pentane gradient) afforded (4S)-7-(3-(trifluoromethyl)phenyl)-2,3,4,5-tetrahydro-1,4-methanopyrido [2,3-b][1,4]diazepine as a light yellow solid (2.26 g, 77%). MS (ESI) calcd for C₁₆H₁₄F₃N₃: 305.1; found: 306 [M+H].

An analogous coupling procedure using Pd(OAc)₂ could be used to prepare (4S)-7-(3-substituted phenyl)-2,3,4,5-tetrahydro-1,4-methanopyrido[2,3-b][1,4]diazepines by using the appropriate 3-substituted phenylboronic acids or esters. The analogous enantiomers could be made starting with (4R)-7-chloro-2,3,4,5-tetrahydro-1,4-methanopyrido [2,3-b][1,4]diazepine.

Step 6. Synthesis of (4S)—N-(pyridin-2-yl)-7-(3-(trifluoromethyl)phenyl)-3,4-dihydro-1,4-methanopyrido[2,3-b][1,4]diazepine-5(2H)-carboxamide

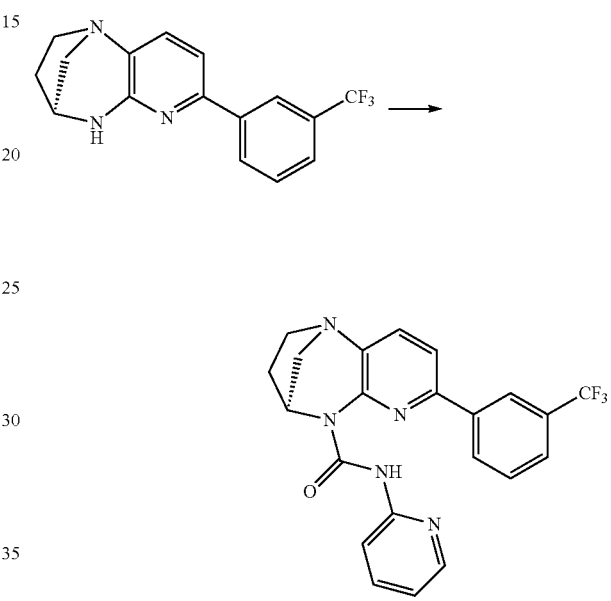

To a solution of (4S)-7-(3-(trifluoromethyl)phenyl)-2,3,4, 5-tetrahydro-1,4-methanopyrido[2,3-b][1,4]diazepine (0.100 g, 0.328 mmol) and Et₃N (160 μL, 1.15 mmol) in THF (4 mL) was added triphosgene (0.050 g, 0.164 mmol). After stirring for 30 min. at room temp., 2-pyridylamine (0.092 g, 0.983 mmol) was added. The reaction mixture was heated to 60° C. overnight, and the reaction mixture was concentrated and the residue taken up in CH₂Cl₂ (30 mL). The solution was washed with water and brine, dried over MgSO₄, filtered, and concentrated. Purification by silica gel chromatography (0 to 100% EtOAc in pentane gradient) afforded (4S)—N-(pyridin-2-yl)-7-(3-(trifluoromethyl)phenyl)-3,4-dihydro-1,4-methanopyrido[2,3-b][1,4]diazepine-5 (2H)-carboxamide (0.086 g, 62%). MS (ESI) calcd for C₂₂H₁₈F₃N₅O: 425.2; found: 426.2 [M+H].

An analogous procedure could be used to prepare a variety of (4S)-7-(3-trifluoromethlyphenyl)-N-(aryl)-3,4-dihydro-1,4-methanopyrido[2,3-b][1,4]diazepine-5(2H)-carboxamides by substituting the appropriate amine moiety for 2-pyridylamine. The analogous enantiomers could be made by starting with (4R)-7-(3-trifluoromethlyphenyl)-N-(aryl)-3,4-dihydro-1,4-methanopyrido[2,3-b][1,4]diazepine-5(2-H)-carboxamide. Analogously, (9S)-2-(3-(trifluoromethyl) phenyl)-N-(aryl)-8,9-dihydro-6H-5,9-methanopyrido[2,3-b] [1,4]diazocine-10(7H)-carboxamides could be prepared by this general procedure from (9S)-2-(3-(trifluoromethyl)phenyl)-7,8,9,10-tetrahydro-6H-5,9-methanopyrido[2,3-b][1,4] diazocine and the appropriate amine moiety.

Example 2. Preparation of (4S)—N-phenethyl-7-(3-(trifluoromethyl)phenyl)-3,4-dihydro-1,4-methanopyrido[2,3-b][1,4]diazepine-5(2H)-carboxamide

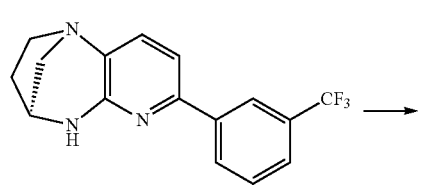

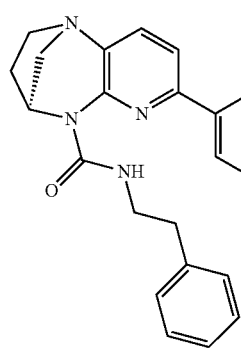

To a solution of (4S)-7-(3-(trifluoromethyl)phenyl)-2,3,4,5-tetrahydro-1,4-methanopyrido[2,3-b][1,4]diazepine (0.100 g, 0.326 mmol) in CH$_2$Cl$_2$ (10 mL) was added pyridine (0.0775 g, 0.980 mmol) and phenyl chloroformate (0.06117 g, 0.392 mmol) at 0° C. After 2 h, the mixture was quenched with sat. aqueous Na$_2$CO$_3$, extracted with CH$_2$Cl$_2$ (3×75 mL), washed with brine, dried with Na$_2$SO$_3$, and concentrated. The residue was purified by flash silica gel chromatography to give (4S)-phenyl 7-(3-(trifluoromethyl)phenyl)-3,4-dihydro-1,4-methanopyrido[2,3-b][1,4]diazepine-5 (2H)-carboxylate (0.120 g, yield 84%).

(4S)-phenyl 7-(3-(trifluoromethyl)phenyl)-3,4-dihydro-1,4-methanopyrido[2,3-b][1,4]diazepine-5(2H)-carboxylate, 2-phenylethanamine (0.057 g, 0.470 mmol), and DMAP (0.035 g, 0.282 mmol) in MeCN (3 mL) were stirred at 80° C. overnight. After cooling to room temperature, the mixture was concentrated and the residue purified by Prep-TLC eluting with CH$_2$Cl$_2$:MeOH (10:1) to give (4S)—N-phenethyl-7-(3-(trifluoromethyl)phenyl)-3,4-dihydro-1,4-methanopyrido[2,3-b][1,4]diazepine-5(2H)-carboxamide (0.020 g, yield 18%). MS (ESI) calcd for C$_{25}$H$_{23}$F$_3$N$_4$O: 452.18; found: 453 [M+H].

Example 3. Preparation of (4S)—N-(3-(3-aminoprop-1-yn-1-yl)-5-(oxazol-5-yl)phenyl)-7-(3-(trifluoromethyl)phenyl)-3,4-dihydro-1,4-methanopyrido[2,3-b][1,4]diazepine-5(2H)-carboxamide

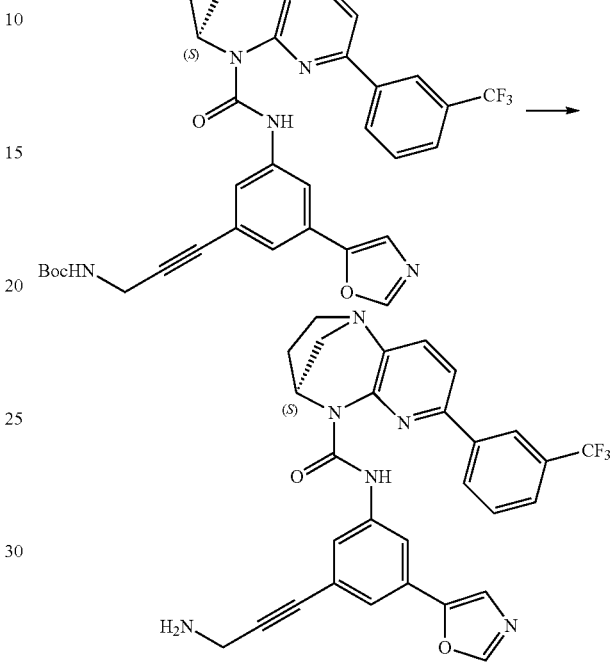

A suspension of (4S)—N-(3-(3-aminoprop-1-yn-1-yl)-5-(oxazol-5-yl)phenyl)-7-(3-(trifluoromethyl)phenyl)-3,4-dihydro-1,4-methanopyrido[2,3-b][1,4]diazepine-5 (2H)-carboxamide (A, 0.050 g, 0.08 mmol) in 4N HCl indioxane (10 mL) was stirred for 16 h at room temp. The mixture was concentrated under reduced pressure and triturated with CH$_3$CN. The residue was dissolved in CH$_3$CN:H$_2$O and lyophilized to give (4S)—N-(3-(3-aminoprop-1-yn-1-yl)-5-(oxazol-5-yl)phenyl)-7-(3-(trifluoromethyl)phenyl)-3,4-dihydro-1,4-methanopyrido[2,3-b][1,4]diazepine-5(2H)-carboxamide (0.030 g, yield 70%). MS (ESI) calcd for C$_{29}$H$_{23}$F$_3$N$_6$O$_2$: 544.18; found: 545 [M+H].

Example 4. Preparation of (4S)—N-methyl-N-(pyridin-2-yl)-7-(3-(trifluoromethyl)phenyl)-3,4-dihydro-1,4-methanopyrido[2,3-b][1,4]diazepine-5(2H)-carboxamide

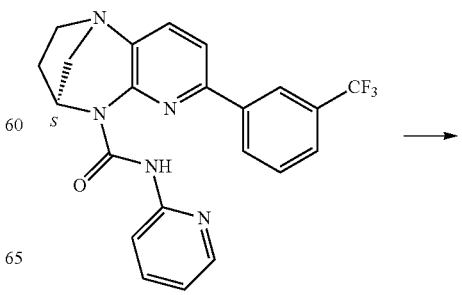

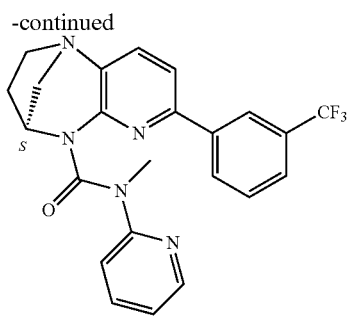

(4S)—N-(pyridin-2-yl)-7-(3-(trifluoromethyl)phenyl)-3,4-dihydro-1,4-methanopyrido[2,3-b][1,4]diazepine-5(2H)-carboxamide (0.267 g, 0.63 mmol) was dissolved in dimethylacetamide and one equivalent of NaH (0.025 g, 60% in oil) was added. The solution was stirred for 5 minutes before the addition of MeI (39 µL). The mixture was stirred overnight at room temperature then diluted with ethyl acetate and washed sequentially with brine (2×), water (2×), and brine. The solution was dried (Na₂SO₄) and concentrated under reduced pressure and loaded onto a silica gel cartridge (ethyl acetate: pentane eluent). Concentration of the pure fractions afforded pure (4S)—N-methyl-N-(pyridin-2-yl)-7-(3-(trifluoromethyl)phenyl)-3,4-dihydro-1,4-methanopyrido[2,3-b][1,4]diazepine-5 (2H)-carboxamide. MS (ESI) calcd for $C_{23}H_{20}F_3N_5O$: 439.16; found: 440.1 [M+H].

Example 5. Preparation of (4S)—N-(3-fluoropyridin-4-yl)-7-(3-(trifluoromethyl)phenyl)-3,4-dihydro-1,4-methanopyrido[2,3-b][1,4]diazepine-5(2H)-carboxamide

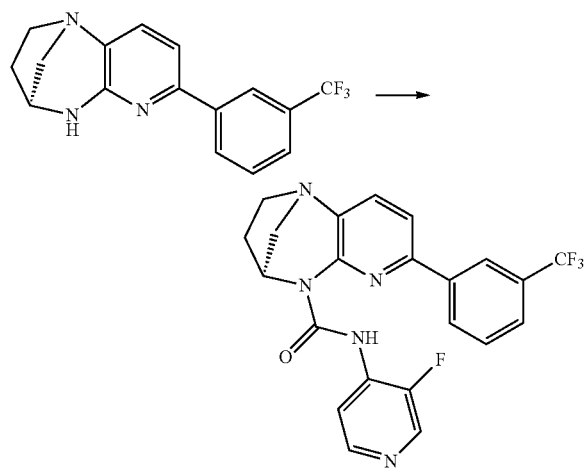

Phenyl chloroformate (1.46 g, 9.37 mmol) was added dropwise to a cooled solution of 3-fluoropyridin-4-amine (1 g, 8.92 mmol) and pyridine (0.95 mL, 11.16 mmol) in THF (10 mL). The reaction was stirred at room temp. overnight. Purification by prep-TLC afforded phenyl (3-fluoropyridin-4-yl)carbamate as a yellow solid.

A mixture of phenyl (3-fluoropyridin-4-yl)carbamate (72 mg, 0.31 mmol), (4S)-7-(3-(trifluoromethyl)phenyl)-2,3,4,5-tetrahydro-1,4-methanopyrido[2,3-b][1,4]diazepine (50 mg, 0.16 mmol) and DMAP (24 mg, 0.20 mmol) in 3 mL of acetonitrile was stirred at 60° C. overnight. The mixture was directly loaded onto prep-TLC and purified using ethyl acetate/pet.ether=1:3-1:8 as eluent to afford (4S)—N-(3-fluoropyridin-4-yl)-7-(3-(trifluoromethyl)phenyl)-3,4-dihydro-1,4-methanopyrido[2,3-b][1,4]diazepine-5 (2H)-carboxamide (18 mg, 25%) as a white solid. MS (ESI) calcd for $C_{22}H_{17}F_4N_5O$: 443.1; found: 444.1 [M+H].

This general urea formation procedure using phenyl carbamates could be used to prepare a variety of (4S)-7-(aryl)-N-(aryl)-3,4-dihydro-1,4-methanopyrido[2,3-b][1,4]diazepine-5(2H)-carboxamides by substituting the appropriate (4S)-7-(aryl)-2,3,4,5-tetrahydro-1,4-methanopyrido[2,3-b][1,4]diazepine for (4S)-7-(3-(trifluoromethyl)phenyl)-2,3,4,5-tetrahydro-1,4-methanopyrido[2,3-b][1,4]diazepine and by substituting the appropriate amine moiety for 3-fluoropyridin-4-amine. The enantiomer series could be made by starting with (4R)-7-(aryl)-2,3,4,5-tetrahydro-1,4-methanopyrido[2,3-b][1,4]diazepines.

Example 6. Preparation of (4S)-7-(3-chlorophenyl)-N-(pyridin-2-yl)-3,4-dihydro-1,4-methanopyrido[2,3-b][1,4]diazepine-5(2H)-carboxamide Step 1. Synthesis of (4S)-7-(3-chlorophenyl)-2,3,4,5-tetrahydro-1,4-methanopyrido[2,3-b][1,4]diazepine

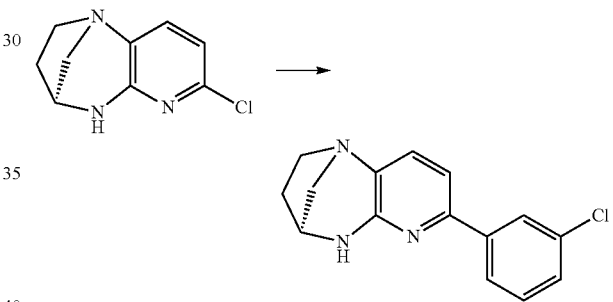

To dioxane/H₂O (10 mL/1 mL) was added (4S)-7-chloro-2,3,4,5-tetrahydro-1,4-methanopyrido[2,3-b][1,4]diazepine (500 mg, 2.56 mmol), (3-chlorophenyl)boronic acid (807 mg, 5.11 mmol), Pd(dppf)Cl₂ (212 mg, 0.26 mmol), and Cs₂CO₃ (2.08 g, 6.4 mmol).

The mixture was stirred at 90° C. overnight. The mixture was concentrated and purified by column chromatography (ethyl acetate/pet. ether=1/4) to afford (4S)-7-(3-chlorophenyl)-2,3,4,5-tetrahydro-1,4-methanopyrido[2,3-b][1,4]diazepine (506 mg, 81%). MS (ESI) calcd for C15H14ClN₃: 271.1, found: 272.1 [M+H].

An analogous procedure could be used to prepare (4S)-7-(3-fluorophenyl)-2,3,4,5-tetrahydro-1,4-methanopyrido[2,3-b][1,4]diazepine or (4S)-7-(3-methoxyphenyl)-2,3,4,5-tetrahydro-1,4-methanopyrido[2,3-b][1,4]diazepine by using the appropriate boronic acid or ester. The enantiomer series could be made by starting with the appropriate (4R)-7-(3-substituted phenyl)-2,3,4,5-tetrahydro-1,4-methanopyrido[2,3-b][1,4]diazepine. Also made via this method using the appropriate starting chloride were: (9S)-2-(3-(trifluoromethyl)phenyl)-7,8,9,10-tetrahydro-6H-5,9-methanopyrido[2,3-b][1,4]diazocine, (9R)-2-(3-(trifluoromethyl)phenyl)-7,8,9,10-tetrahydro-6H-5,9-methanopyrido[2,3-b][1,4]diazocine, 3-((9R)-7,8,9,10-tetrahydro-6H-5,9-methanopyrido[2,3-b][1,4]diazocin-2-yl)benzonitrile, 3-((9S)-7,8,9,10-tetrahydro-6H-5,9-methanopyrido[2,3-b][1,4]

diazocin-2-yl)benzonitrile, (9S)-2-(5-(methylsulfonyl)pyridin-3-yl)-7,8,9,10-tetrahydro-6H-5,9-methanopyrido[2,3-b][1,4]diazocine, (9S)-2-(5-(trifluoromethyl)pyridin-3-yl)-7,8,9,10-tetrahydro-6H-5,9-methanopyrido[2,3-b][1,4]diazocine, N,N-dimethyl-3-((9R)-7,8,9,10-tetrahydro-6H-5,9-methanopyrido[2,3-b][1,4]diazocin-2-yl)aniline, N,N-dimethyl-3-((9S)-7,8,9,10-tetrahydro-6H-5,9-methanopyrido[2,3-b][1,4]diazocin-2-yl)aniline, (9S)-2-(6-methylpyridin-3-yl)-7,8,9,10-tetrahydro-6H-5,9-methanopyrido[2,3-b][1,4]diazocine, (9S)-2-(pyridin-3-yl)-7,8,9,10-tetrahydro-6H-5,9-methanopyrido[2,3-b][1,4]diazocine, (9S)-2-(3-chlorophenyl)-7,8,9,10-tetrahydro-6H-5,9-methanopyrido[2,3-b][1,4]diazocine.

Step 2. Synthesis of (4S)-7-(3-chlorophenyl)-N-(pyridin-2-yl)-3,4-dihydro-1,4-methanopyrido[2,3-b][1,4]diazepine-5(2H)-carboxamide

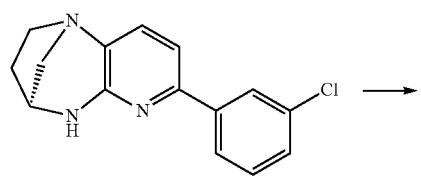

Phenyl chloroformate (6.99 mL, 55.79 mmol) was added dropwise to a cooled solution of 2-pyridylamine (5 g, 53.10 mmol) and pyridine (5.65 mL, 66.41 mmol) in THF (50 mL). The reaction was stirred at room temp. overnight. Brine was added slowly and the mixture was extracted with ethyl acetate. The layers were separated and organic layer was washed with sat. sodium bicarbonate and brine. The organic layer was then dried over anhydrous sodium sulfate and concentrated under reduced pressure. The residue was washed with pet. ether to afford phenyl pyridin-2-ylcarbamate (2.1 g, 18%).

A mixture of phenyl pyridin-2-ylcarbamate (66 mg, 0.30 mmol), (4S)-7-(3-chlorophenyl)-2,3,4,5-tetrahydro-1,4-methanopyrido[2,3-b][1,4]diazepine (40 mg, 0.15 mmol) and DMAP (23 mg, 0.18 mmol) in 3 mL of acetonitrile was stirred at 65° C. overnight. Reaction progress was monitored by TLC and LC-MS. The mixture was directly loaded on prep-TLC using ethyl acetate/petroleum ether=1:3-1:8 as eluent to give (4S)-7-(3-chlorophenyl)-N-(pyridin-2-yl)-3,4-dihydro-1,4-methanopyrido[2,3-b][1,4]diazepine-5(2H)-carboxamide (28 mg, 48%) as a white solid. MS (ESI) calcd for $C_{21}H_{18}ClN_5O$: 391.1; found: 392.1 [M+H].

This general urea formation procedure using phenyl carbamates could be used to prepare a variety of (4S)-7-(3-chloro, -fluoro, or -methoxyphenyl)-N-(aryl)-3,4-dihydro-1,4-methanopyrido[2,3-b][1,4]diazepine-5(2H)-carboxamides by using (4S)-7-(3-chloro, -fluoro or -methoxyphenyl)-2,3,4,5-tetrahydro-1,4-methanopyrido[2,3-b][1,4]diazepine and the appropriate amine moiety. The enantiomer series could be made by starting with the appropriate (4R)-7-(3-substituted phenyl)-2,3,4,5-tetrahydro-1,4-methanopyrido[2,3-b][1,4]diazepine. Analogously, (9S)-2-(5-fluoro- or chloropyridin-3-yl)-N-(aryl)-8,9-dihydro-6H-5,9-methanopyrido[2,3-b][1,4]diazocine-10(7H)-carboxamides could be prepared via this urea formation procedure; see the following example for preparation of the starting (9S)-2-(5-fluoro- or chloropyridin-3-yl)-7,8,9,10-tetrahydro-6H-5,9-methanopyrido[2,3-b][1,4]diazocines.

The analogous procedure used to prepare (4S)-7-(3-chlorophenyl)-N-(pyridin-2-yl)-3,4-dihydro-1,4-methanopyrido[2,3-b][1,4]diazepine-5(2H)-carboxamide (steps 1 and 2 above) can be used to make the following compounds starting with commercially available boronic esters:

Example 7. Preparation of (9S)-2-(5-chloropyridin-3-yl)-7,8,9,10-tetrahydro-6H-5,9-methanopyrido[2,3-b][1,4]diazocine Step 1. Synthesis of (S)-dimethyl 2-((6-chloro-3-nitropyridin-2-yl)amino)glutarate

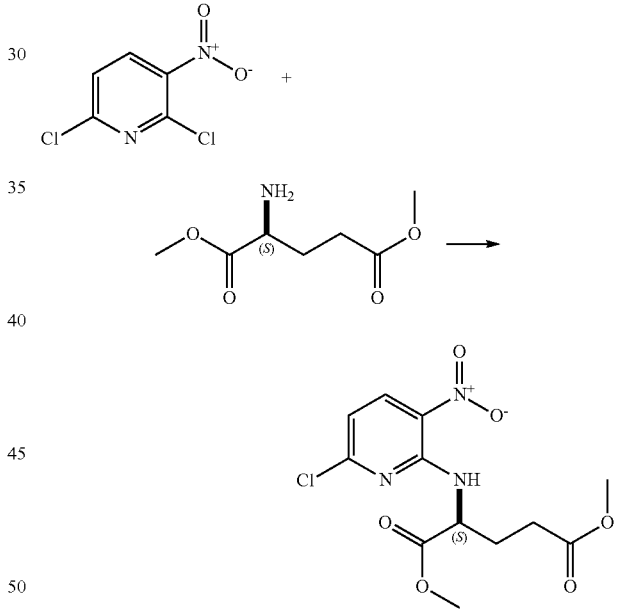

This moiety was made using the following protocol. To a mixture of 40.0 g (207 mmol) of 2,6-dichloro-3-nitropyridine, 87.7 g (414 mmol) of L-glutamic acid dimethyl ester hydrochloride, and 69.6 g (829 mmol) of $NaHCO_3$ was added 600 mL of tetrahydrofuran. The mixture was stirred at 40° C. for 24 h, monitoring for the disappearance of 2,6-dichloro-3-nitropyridine by HPLC. After the reaction was complete, the solids were filtered away and washed with ethyl acetate (3×100 mL). The combined filtrate and washings were concentrated in vacuo, then the residue was purified via silica gel chromatography, eluting with 10/1 (v/v) hexanes/ethyl acetate to give 60 g (87%) of the product as a yellow solid. MS (ESI) calcd for $C_{12}H_{14}ClN_3O_6$: 331.0; found: 332.1 (M+H)+.

Step 2. Synthesis of (S)-methyl 3-(6-chloro-2-oxo-1,2,3,4-tetrahydropyrido[2,3-b]pyrazin-3-yl)propanoate

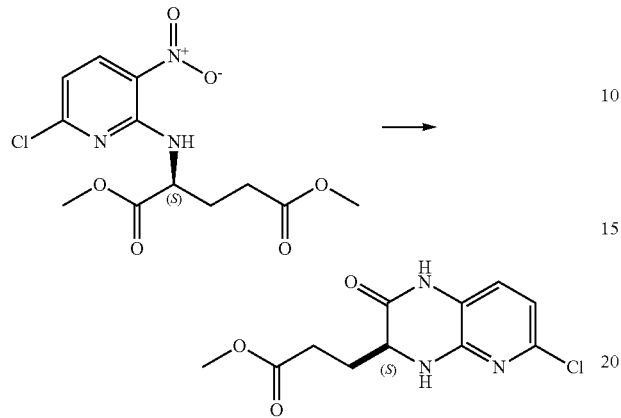

This moiety was made using the following protocol. To a mixture of 20 g (60.2 mmol) of (S)-dimethyl 2-((6-chloro-3-nitropyridin-2-yl)amino)pentanedioate, and 16.8 g (301 mmol) of iron powder was added 375 mL of 2-propanol, then 125 mL of water. To the stirred mixture was added 5.5 g (90.3 mmol) of acetic acid, then the reaction was stirred at reflux for 1 h. The reaction was monitored for the disappearance of starting material by HPLC. After the reaction was complete, the solids were filtered off and washed with 2-propanol (3×50 mL). The combined filtrate and washings were concentrated to dryness, then the residue was dried in vacuo to give 15 g (81%) of the product as a dark yellow solid. This was used without further purification in the next step. MS (ESI) calcd for $C_{11}H_{12}ClN_3O_3$: 269.0; found: 270.1.

Step 3. Synthesis of (S)-3-(6-chloro-1,2,3,4-tetrahydropyrido[2,3-b]pyrazin-3-yl)propan-1-ol

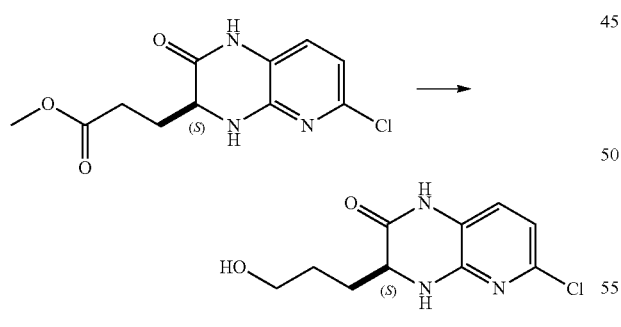

This moiety was made using the following protocol. To a solution of 17.78 g (133.3 mmol) of $AlCl_3$ in 260 mL of tetrahydrofuran (THF) under $N_2$ was added 200 mL of 2M $LiAlH_4$ in THF, dropwise, at a rate to control gas evolution. This gave a solution of alane ($AlH_3$) in THF. In a separate flask, a solution of 26.0 g (96.4 mmol) of (S)-methyl 3-(6-chloro-2-oxo-1,2,3,4-tetrahydropyrido[2,3-b]pyrazin-3-yl)propanoate in 460 mL of THF was prepared under $N_2$, then cooled with a dry ice/acetone bath. To this was added the alane solution, dropwise with stirring, over 2 h. When the addition was complete, the cooling bath was removed, and the reaction was allowed to warm to ambient temperature. After 1.5 h, LCMS analysis showed that the reaction was complete. Next, a solution of 17.6 g NaOH in 65 mL of water was added slowly to control the evolution of $H_2$. The suspension was allowed to stir for 18 h, then the solids were filtered away. The precipitate was washed with ethyl acetate, then the filtrate and washings were concentrated in vacuo. The product was purified via silica gel chromatography, (330 g prepacked column) eluting with $CH_2Cl_2$, followed by a gradient of 0 to 10% methanol in $CH_2Cl_2$ to give 15.21 g (69%) of a yellow-orange solid. MS (ESI) calcd for $C_{10}H_{14}ClN_3O$: 227.1; found: 228.1.

Step 4. Synthesis of (5R,9S)-2-chloro-7,8,9,10-tetrahydro-6H-5,9-methanopyrido[2,3-b][1,4]diazocine

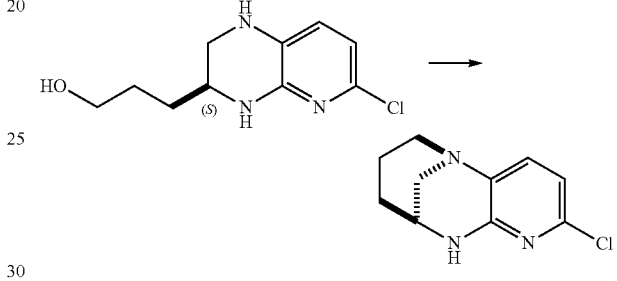

To 12 g (52.7 mmol) of (S)-3-(6-chloro-1,2,3,4-tetrahydropyrido[2,3-b]pyrazin-3-yl)propan-1-ol was added 160 mL of 48% (w/w) $HBr_{(aq.)}$, then the reaction was stirred at 90° C. for 18 h. The reaction was monitored by HPLC for the disappearance of the starting alcohol. After the reaction was complete, it was cooled to ambient temperature, then 1.2 M $NaHCO_{3(aq.)}$ was added until pH=8. The mixture was extracted with ethyl acetate (3×100 mL), then the organic phase was back extracted with brine (1×100 mL), dried over $Na_2SO_4$, filtered, and concentrated to dryness. The residue was purified via silica gel chromatography, eluting with 2/1 (v/v) hexanes/ethyl acetate to give 6.0 g (55%) of the product as a light yellow solid. MS (ESI) calcd for $Co_{10}H_{12}ClN_3$: 209.1; found: 210.1.

Step 5. Synthesis of (9S)-tert-butyl 2-chloro-8,9-dihydro-6H-5,9-methanopyrido[2,3-b][1,4]diazocine-10(7H)-carboxylate

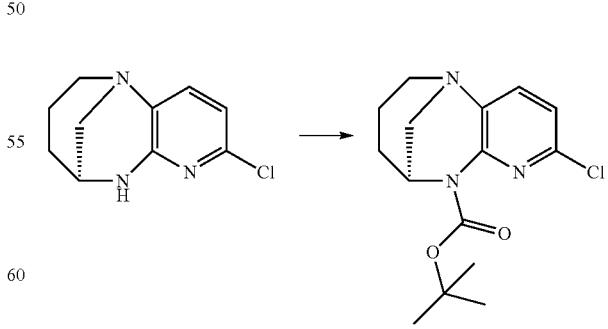

(9S)-2-chloro-7,8,9,10-tetrahydro-6H-5,9-methanopyrido[2,3-b][1,4]diazocine (1.3 g, 6.19 mmol, Note: the 5R stereochemistry is implied), $Boc_2O$ (2.02 g, 9.28 mmol, 1.5 equiv.) and DMAP (1.5 g, 12.38 mmol, 2.0 equiv.) in 5 mL THF were stirred at 60° C. for 2 h. Reaction progress was monitored by TLS and LC/MS. Water (30 mL) was added, and the mixture was extracted with DCM (3×15 mL). The organics were concentrated and the residue was purified via silica gel column chromatography to give (9S)-tert-butyl 2-chloro-8,9-dihydro-6H-5,9-methanopyrido[2,3-b][1,4]diazocine-10(7H)-carboxylate as a white solid (1.3 g, 92%). MS (ESI) calcd for $C_{15}H_{20}ClN_3O_2$: 309.1.

Step 6. Synthesis of (9S)-tert-butyl 2-(5-chloropyridin-3-yl)-8,9-dihydro-6H-5,9-methanopyrido[2,3-b][1,4]diazocine-10(7H)-carboxylate

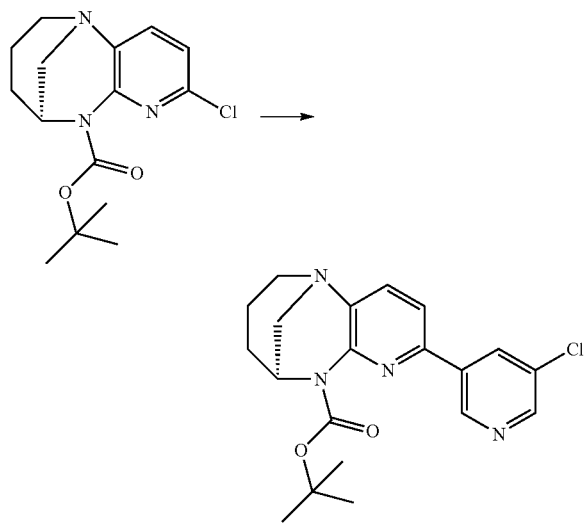

To a degassed mixture of dioxane/water (10 mL/1 mL) was added (9S)-tert-butyl 2-chloro-8,9-dihydro-6H-5,9-methanopyrido[2,3-b][1,4]diazocine-10(7H)-carboxylate (650 mg, 2.096 mmol), (5-chloropyridin-3-yl)boronic acid (658 mg, 4.19 mmol), Pd(dppf)Cl$_2$ (171 mg, 0.209 mmol), and Cs$_2$CO$_3$ (2.04 g, 6.29 mmol). The mixture was stirred at 110° C. for 12 h, then concentrated and purified via column chromatography (PE/EA=3/1) to give (9S)-tert-butyl 2-(5-chloropyridin-3-yl)-8,9-dihydro-6H-5,9-methanopyrido[2,3-b][1,4]diazocine-10(7H)-carboxylate (600 mg, 63%). MS (ESI) calcd for $C_{20}H_{23}ClN_4O_2$: 386.2.

(9S)-tert-butyl 2-(5-fluoropyridin-3-yl)-8,9-dihydro-6H-5,9-methanopyrido[2,3-b][1,4]diazocine-10(7H)-carboxylate was prepared via the same method, starting with (5-fluoropyridin-3-yl)boronic acid.

Step 7. Synthesis of (9S)-2-(5-chloropyridin-3-yl)-7,8,9,10-tetrahydro-6H-5,9-methanopyrido[2,3-b][1,4]diazocine

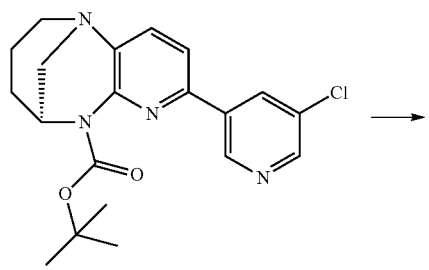

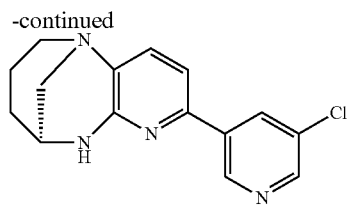

This moiety was made using the following protocol. (9S)-tert-butyl 2-(5-chloropyridin-3-yl)-8,9-dihydro-6H-5,9-methanopyrido[2,3-b][1,4]diazocine-10(7H)-carboxylate (600 mg, 1.55 mmol) was dissolved in HCl/MeOH (IM, 20 mL) and the reaction was stirred at room temp. for 1.5 h, then concentrated in vacuo. Water (20 mL) and K$_2$CO$_3$ (3 g) were added, and the mixture was stirred at room temp. for 2 h, then extracted with DCM (3×15 mL) to give (9S)-2-(5-chloropyridin-3-yl)-7,8,9,10-tetrahydro-6H-5,9-methanopyrido[2,3-b][1,4]diazocine (450 mg, quant.). MS (ESI) calcd for C15H$_{15}$ClN$_4$: 286.1. (9S)-2-(5-fluoropyridin-3-yl)-7,8,9,10-tetrahydro-6H-5,9-methanopyrido[2,3-b][1,4]diazocine was prepared via the same method.

These moieties were used to prepare urea compounds via the general urea coupling procedure described in the previous example.

Example 8. Preparation of (9S)-2-(5-methylpyridin-3-yl)-7,8,9,10-tetrahydro-6H-5,9-methanopyrido[2,3-b][1,4]diazocine

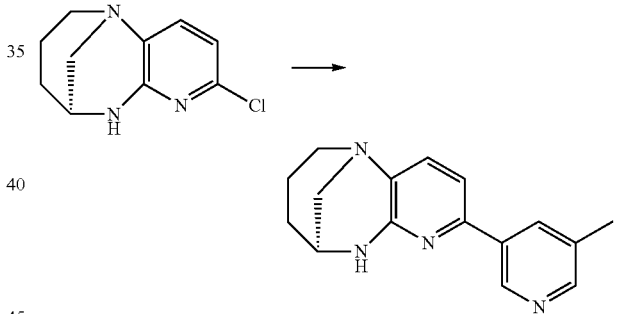

This moiety was made using the following protocol. To degassed 1, 4-dioxane/H$_2$O (20 ml, v/v=10/1) were added (9S)-2-chloro-7,8,9,10-tetrahydro-6H-5,9-methanopyrido[2,3-b][1,4]diazocine (600 mg, 2.87 mmol), 5-methylpyridin-3-ylboronic acid (1.18 g, 3.0 equiv.), PCy$_3$ (644 mg, 0.8 equiv.) and Pd$_2$(dba)$_3$ (330 mg, 0.2 equiv.). The mixture was heated to 110° C. in a sealed tube. After stirring 12 hr at 110° C., the black suspension was cooled to room temp and concentrated under reduced pressure. The concentrate was suspended in EtOAc (300 ml), washed with water (4×80 ml), brine (80 ml), dried over Na$_2$SO$_4$ and concentrated under reduced pressure. The concentrate was purified by column (DCM/MeOH=10/1) to afford the product as a light brown solid (756 mg, 99%). MS (ESI) calcd for $C_{16}H_{18}N_4$: 266.1; found: 267.2 [M+H].

These conditions were also used to prepare (9S)-2-(4-methylpyridin-3-yl)-7,8,9,10-tetrahydro-6H-5,9-methanopyrido[2,3-b][1,4]diazocine and 4-(3-((9S)-7,8,9,10-tetrahydro-6H-5,9-methanopyrido[2,3-b][1,4]diazocin-2-yl)phenyl)morpholine by starting with the appropriate boronic acid.

The resulting moieties were used to prepare urea compounds via the general urea coupling procedure described above.

Example 9. Preparation of (9S)—N-(pyridazin-3-yl)-2-(pyridin-3-yl)-8,9-dihydro-6H-5,9-methanopyrido[2,3-b][1,4]diazocine-10(7H)-carboxamide

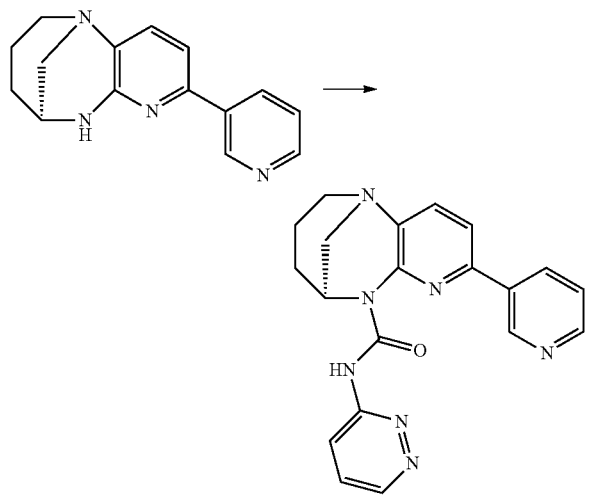

This moiety was prepared via the analogous carbamate protocol described for (4S)-7-(3-chlorophenyl)-N-(pyridin-2-yl)-3,4-dihydro-1,4-methanopyrido[2,3-b][1,4]diazepine-5(2H)-carboxamide, using the p-chlorophenyl carbamate instead of the phenyl carbamate. MS (ESI) calcd for $C_{20}H_{19}N_7$: 373.2; found: 374.3 [M+H].

Example 10. Preparation of (4S)-7-(3-chlorophenyl)-N-(6-(2,3-dihydroxypropoxy)pyrazin-2-yl)-3,4-dihydro-1,4-methanopyrido[2,3-b][1,4]diazepine-5(2H)-carboxamide

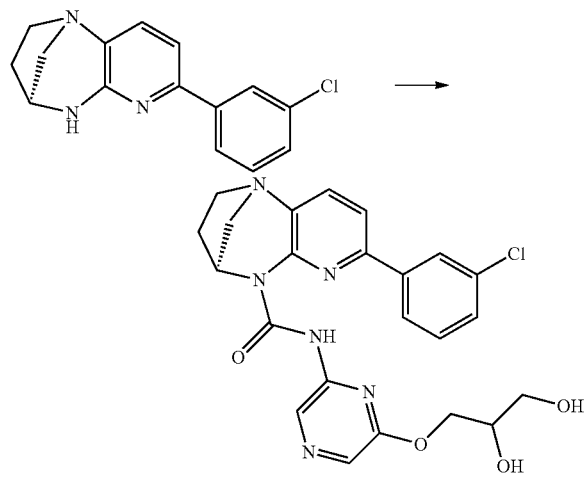

To the mixture of 6-((2,2-dimethyl-1,3-dioxolan-4-yl)methoxy)pyrazin-2-amine (83 mg, 0.37 mmol) and pyridine (29 mg, 1.37 mmol) in 3 mL of THF was added triphosgene (43 mg, 0.14 mmol). The above mixture was stirred at 60° C. for 2 hrs. Then (4S)-7-(3-chlorophenyl)-2,3,4,5-tetrahydro-1,4-methanopyrido[2,3-b][1,4]diazepine (50 mg, 0.18 mmol) was added to the reaction mixture and stirred overnight at 60° C. The crude product was purified by prep-TLC to afford the urea intermediate as a yellow solid. To a solution of this material in THF (3 mL) was added conc. HCl and the reaction was stirred at room temp. for 15 min. Sat. NaHCO₃ was added to adjust pH to 7-8. The reaction mixture was extracted with EtOAc and the organic layer washed with brine. Purification by prep-TLC afforded (4S)-7-(3-chlorophenyl)-N-(6-(2,3-dihydroxypropoxy)pyrazin-2-yl)-3,4-dihydro-1,4-methanopyrido[2,3-b][1,4]diazepine-5(2H)-carboxamide (8.9 mg, 40%) as a white solid. MS (ESI) calcd for $C_{23}H_{23}ClN_6O_4$: 482.2; found: 483.1 [M+H].

This general urea formation procedure using triphosgene could be used to prepare a variety of (4S)-7-(3-chloro or -fluorophenyl)-N-(aryl)-3,4-dihydro-1,4-methanopyrido[2,3-b][1,4]diazepine-5(2H)-carboxamides by also using (4S)-7-(3-fluorophenyl)-2,3,4,5-tetrahydro-1,4-methanopyrido[2,3-b][1,4]diazepine and the appropriate amine moiety.

Example 11. Preparation of (9S)-2-(3-cyanophenyl)-N-(pyridin-3-yl)-8,9-dihydro-6H-5,9-methanopyrido[2,3-b][1,4]diazocine-10(7H)-carboxamide

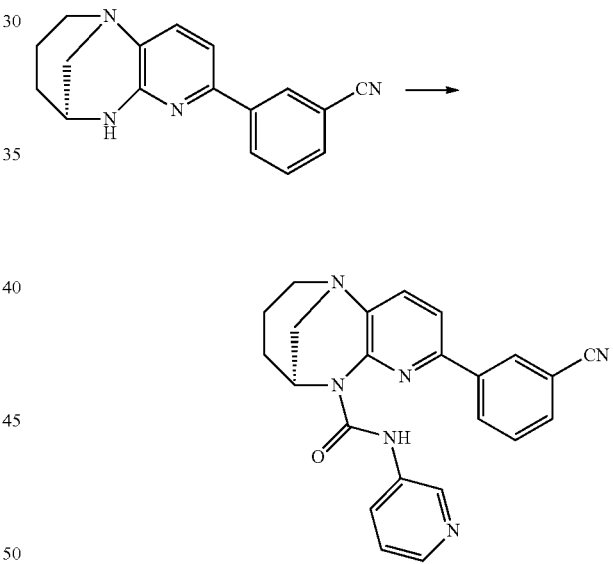

DIPEA (97 μL, 0.54 mmol) was added to a mixture of 3-((9S)-7,8,9,10-tetrahydro-6H-5,9-methanopyrido[2,3-b][1,4]diazocin-2-yl)benzonitrile (50 mg, 0.18 mmol) and triphosgene (27 mg, 0.10 mmol) in THF (12 mL) at room temperature. The mixture was heated at 60° C. for 30 minutes. 3-aminopyridine (102 mg, 1.09 mmol) was added and the reaction mixture was heated at reflux for 32 h. CH₃OH was added after cooling to room temperature. The mixture was concentrated and purified by prep HPLC. The TFA salt was suspended in CH₃CN, 1N HCl was added and the mixture lyophilized to give (9S)-2-(3-cyanophenyl)-N-(pyridin-3-yl)-8,9-dihydro-6H-5,9-methanopyrido[2,3-b][1,4]diazocine-10(7H)-carboxamide (48 mg, 61%) as the hydrochloride salt. MS (ESI) calcd for $C_{23}H_{20}N_6O$: 396.2; found: 397.1 [M+H].

145

Example 12. Preparation of (9S)—N-(pyridin-2-yl)-2-(5-(trifluoromethyl)pyridin-3-yl)-8,9-dihydro-6H-5,9-methanopyrido[2,3-b][1,4]diazocine-10(7H)-carboxamide

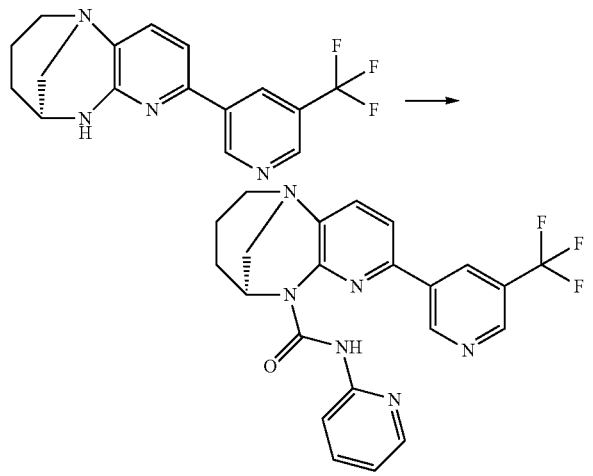

A mixture of 4-chlorophenyl pyridin-2-ylcarbamate (325 mg, 1.31 mmol), (9S)-2-(5-(trifluoromethyl)pyridin-3-yl)-7,8,9,10-tetrahydro-6H-5,9-methanopyrido[2,3-b][1,4]diazocine (70 mg, 0.22 mmol) and DMAP (160 mg, 1.31 mmol) in DMF (3 mL) was heated at 100° C. in a sealed tube for 24 h. The mixture was cooled to room temperature then portioned between EtOAc/H$_2$O (60 mL/30 mL). The organic layer was separated, washed with H$_2$O, brine, dried (Na$_2$SO$_4$) and concentrated. The crude product was purified by prep-TLC (eluting with CH$_2$Cl$_2$/EtOAc/CH$_3$OH, 120:40:2) to afford (9S)—N-(pyridin-2-yl)-2-(5-(trifluoromethyl)pyridin-3-yl)-8,9-dihydro-6H-5,9-methanopyrido[2,3-b][1,4]diazocine-10(7H)-carboxamide as a tan solid (80 mg, 83%). MS (ESI) calcd for C$_{22}$H$_{19}$F$_3$N$_6$O: 440.2; found: 441.2 [M+H].

Example 13. Preparation of (4S)—N-(2-methyl-2H-indazol-5-yl)-7-(2-methylpyridin-4-yl)-3,4-dihydro-1,4-methanopyrido[2,3-b][1,4]diazepine-5(2H)-carboxamide Step 1. Synthesis of (4S)-7-(2-methylpyridin-4-yl)-2,3,4,5-tetrahydro-1,4-methanopyrido[2,3-b][1,4]diazepine

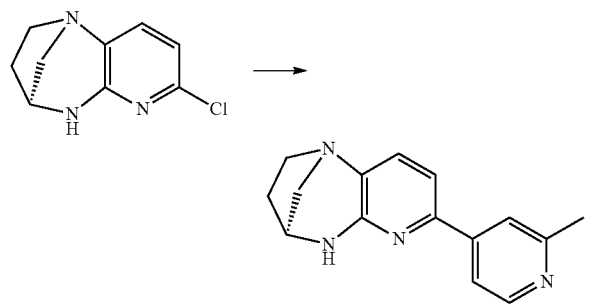

To a solution of (4S)-7-chloro-2,3,4,5-tetrahydro-1,4-methanopyrido[2,3-b][1,4]-diazepine (500 mg, 2.55 mmol) in degassed dioxane/H$_2$O (14 mL, v/v=10/1) was added 2-methylpyridin-4-boronic acid (1.048 g, 7.65 mmol), PCy$_3$ (286 mg, 1.02 mmol), K$_3$PO$_4$.3H$_2$O (1.698 g, 6.375 mmol) and Pd$_2$(dba)$_3$ (234 mg, 0.255 mmol). The resulting mixture was stirred at 110° C. overnight. The mixture was cooled to room temperature then concentrated. The residue was partitioned between EtOAc and water (50 mL each). The organic layer was washed with water and brine, dried over Na$_2$SO$_4$, and concentrated to dryness. The residue was purified by silica gel chromatography (CH$_2$Cl$_2$/THF=3/2) to give (4S)-7-(2-methylpyridin-4-yl)-2,3,4,5-tetrahydro-1,4-methanopyrido[2,3-b][1,4]diazepine (418 mg, 82%) as a light yellow solid. MS (ESI) calcd for C$_{15}$H$_{16}$N$_4$: 252.1; found: 253.2 [M+H].

The following intermediates were prepared using the above protocol substituting the appropriate boronic acid and 2-chloropyridine. 2-((9S)-7,8,9,10-tetrahydro-6H-5,9-methanopyrido[2,3-b][1,4]diazocin-2-yl)benzonitrile, 5-((9S)-7,8,9,10-tetrahydro-6H-5,9-methanopyrido[2,3-b][1,4]diazocin-2-yl)nicotinonitrile Step 2. Synthesis of (4S)—N-(2-methyl-2H-indazol-5-yl)-7-(2-methylpyridin-4-yl)-3,4-dihydro-1,4-methanopyrido[2,3-b][1,4]diazepine-5(2H)-carboxamide

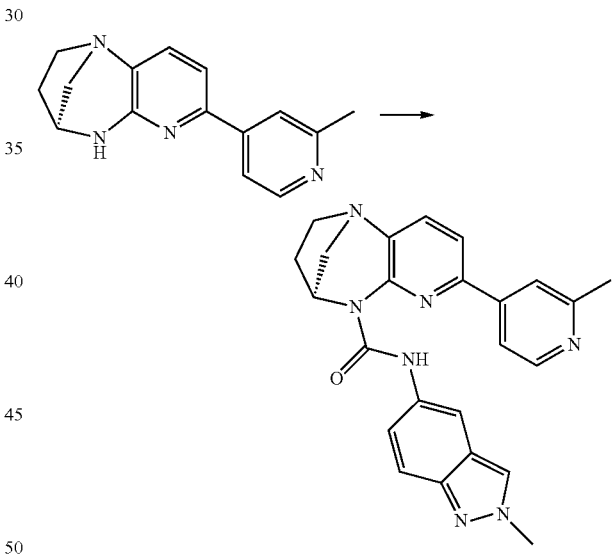

To a solution of phenyl chloroformate (0.2 mL, 1.6 mmol) and pyridine (0.16 mL, 1.95 mmol) in CH$_2$Cl$_2$ (18 mL) was added 2-methyl-2H-indazol-5-amine (180 mg, 1.22 mmol). The mixture was stirred at room temperature for 30 min., then quenched with sat. NaHCO$_3$ solution (10 mL). The aqueous phase was extracted with CH$_2$Cl$_2$ (10 mL). The combined organic phases were washed with brine (20 mL), dried over Na$_2$SO$_4$, and concentrated to dryness. The residue was washed with hexane (5 mL×3) to afford phenyl (2-methyl-2H-indazol-5-yl)carbamate (304 mg, 93%).

A mixture of (4S)-7-(2-methylpyridin-4-yl)-2,3,4,5-tetrahydro-1,4-methanopyrido[2,3-b][1,4]diazepine (90 mg, 0.36 mmol), phenyl (2-methyl-2H-indazol-5-yl)carbamate (285 mg, 1.07 mmol) and DMAP (130 mg, 1.07 mmol) in THF (3 mL) was heated to 80° C. in a sealed tube. After heating for 36 hrs at 80° C., the mixture was then cooled to room tem. and concentrated. The residue was suspended in EtOAc (60 mL) and filtered. The filtrate was washed with water (20 mL×3), then brine (20 mL), and dried over Na$_2$SO$_4$ and concentrated under reduced pressure. The concentrate was purified by prep-TLC (CH$_2$Cl$_2$/EtOAc/ MeOH=23/1/drops) to afford (4S)—N-(2-methyl-2H-indazol-5-yl)-7-(2-methylpyridin-4-yl)-3,4-dihydro-1,4-methanopyrido[2,3-b][1,4]diazepine-5(2H)-carboxamide (60 mg, 40%) as a brown solid. MS (ESI) calcd for C$_{24}$H$_{23}$N$_7$O: 425.2; found: 426.3 [M+H].

This general urea formation procedure using phenyl carbamates could be used to prepare a variety of (4S)—N-(aryl)-7-(2-methylpyridin-4-yl)-3,4-dihydro-1,4-methanopyrido[2,3-b][1,4]diazepine-5(2H)-carboxamides by using the appropriate amine moiety.

Example 14: Preparation of (4S)—N-(2,6-diethylphenyl)-7-(3-(trifluoromethyl)phenyl)-3,4-dihydro-1,4-methanopyrido[2,3-b][1,4]diazepine-5(2H)-carboxamide

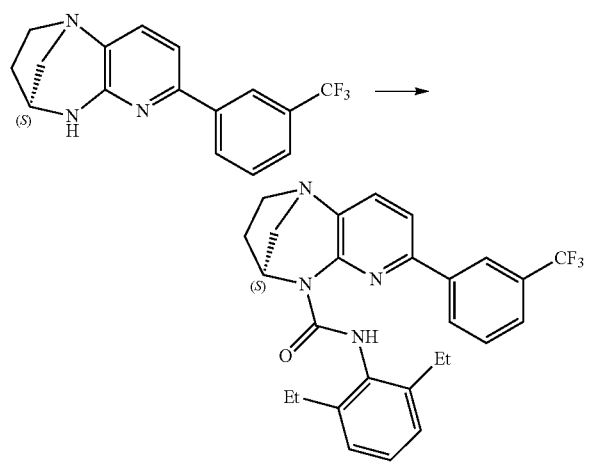

Under nitrogen atmosphere, to a mixture of 2,6-diethylaniline (39.1 mg, 0.262 mmol, 2.0 eq) and pyridine (0.5 ml, excessive) in dry THF (3 mL) was added triphosgene (54.4 mg, 0.183 mmol). The mixture was stirred at 60° C. for 2 hours and (4S)-7-(3-(trifluoromethyl)phenyl)-2,3,4,5-tetrahydro-1,4-methanopyrido[2,3-b][1,4]diazepine (40 mg, 0.131 mmol, 1.0 eq) was added to the reaction mixture and stirred for an additional 18 hours. Saturated sodium bicarbonate solution (5 ml) and dichloromethane (10 ml) were added to the reaction mixture; the organic layer was successively washed with water (10 mL) and brine, dried (Na$_2$SO$_4$) and concentrated in vacuuo. The crude product was purified by prep-TLC using 15:1 Ethyl Acetate in CH$_2$Cl$_2$ as eluent to afford (4S)—N-(2,6-diethylphenyl)-7-(3-(trifluoromethyl)phenyl)-3,4-dihydro-1,4-methanopyrido[2,3-b][1,4]diazepine-5(2H)-carboxamide a white solid. (5.1 mg, 8% Yield). MS (ESI) calcd for C$_{27}$H$_{27}$F$_3$N$_4$O: 480.21; found: 481 [M+H].

This general urea formation procedure using triphosgene could be used to prepare a variety of (4S)-7-(3-trifluoromethlyphenyl)-N-(aryl)-3,4-dihydro-1,4-methanopyrido[2,3-b][1,4]diazepine-5(2H)-carboxamides by substituting the appropriate amine moiety for 2,6-diethylaniline.

Example 15. Preparation of (4S)-7-(2-methylpyridin-4-yl)-N-(pyrazin-2-yl)-3,4-dihydro-1,4-methanopyrido[2,3-b][1,4]diazepine-5(2H)-carboxamide Step 1. Synthesis of (4S)-7-chloro-N-(pyrazin-2-yl)-3,4-dihydro-1,4-methanopyrido[2,3-b][1,4]diazepine-5(2H)-carboxamide

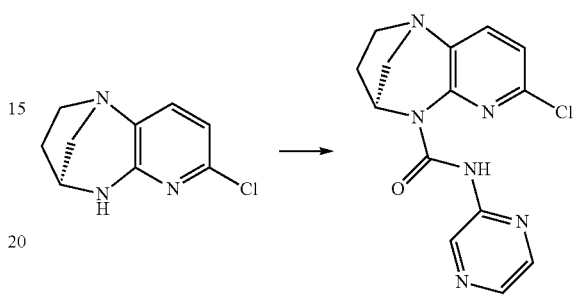

A mixture of (4S)-7-chloro-2,3,4,5-tetrahydro-1,4-methanopyrido[2,3-b][1,4]diazepine (400 mg, 2.04 mmol), phenyl pyrazin-2-ylcarbamate (1.32 g, 6.13 mmol) and DMAP (249 mg, 2.04 mmol) in DMF (8 mL) was heated to 82° C. in a sealed flask. After heating for 22 hrs, the mixture was then cooled to room temp. and diluted with EtOAc (100 mL). The mixture was washed with water (8 mL×9), then with brine, and dried over Na$_2$SO$_4$ and concentrated. The residue was purified by column chromatography (CH$_2$Cl$_2$/MeOH=50/1) to afford (4S)-7-chloro-N-(pyrazin-2-yl)-3,4-dihydro-1,4-methanopyrido[2,3-b][1,4]diazepine-5(2H)-carboxamide (600 mg, 93%) as a white solid. MS (ESI) calcd for C$_{14}$H$_{13}$ClN$_6$O: 316.1.

This general procedure could be used to prepare a variety of (4S)-7-chloro-N-(aryl)-3,4-dihydro-1,4-methanopyrido [2,3-b][1,4]diazepine-5(2H)-carboxamides by substituting the appropriate carbamate moiety for phenyl pyrazin-2-ylcarbamate.

Step 2. Synthesis of (4S)-7-(2-methylpyridin-4-yl)-N-(pyrazin-2-yl)-3,4-dihydro-1,4-methanopyrido[2,3-b][1,4]diazepine-5 (2H)-carboxamide

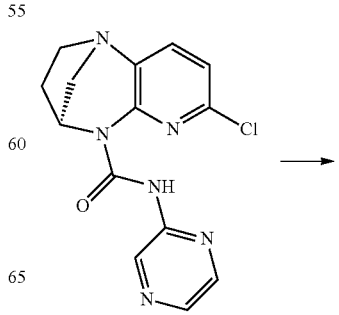

149

-continued

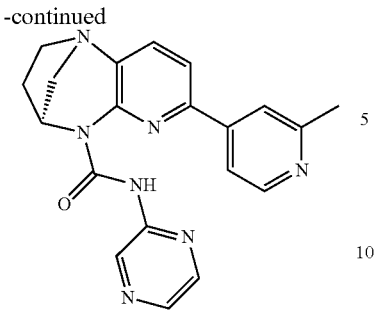

To a mixture of (4S)-7-chloro-N-(pyrazin-2-yl)-3,4-di-hydro-1,4-methanopyrido[2,3-b][1,4]diazepine-5(2H)-carboxamide (40 mg, 0.126 mmol), 2-methylpyridin-4-boronic acid (44 mg), and NaHCO$_3$ (32 mg) in toluene/EtOH/H$_2$O (1.9 mL, v/v/v=10/6/3) was added PdCl$_2$(PPh$_3$)$_2$(9 mg) under a nitrogen atmosphere. The reaction mixture was heated at reflux for 6 hrs. Another portion of 2-methylpyridin-4-boronic acid (44 mg), NaHCO$_3$(32 mg), and PdCl$_2$(PPh$_3$)$_2$(8 mg) was added and the mixture was degassed. After stirring at reflux overnight, the reaction mixture was cooled to room temp. and concentrated. The concentrate was suspended in EtOAc (30 mL) and water (5 mL). The aqueous suspension was extracted with EtOAc (8 mL). The combined EtOAc phases were washed with brine (10 mL), dried over MgSO$_4$, and concentrated. Purification by prep-TLC (CH$_2$Cl$_2$/MeOH=50/1) afforded (4S)-7-(2-methylpyridin-4-yl)-N-(pyrazin-2-yl)-3,4-dihydro-1,4-methanopyrido[2,3-b][1,4]diazepine-5(2H)-carboxamide (18 mg, 38%) as an off-white solid. MS (ESI) calcd for C$_{20}$H$_{19}$N$_7$O: 373.2; found: 374.3 [M+H].

This general procedure using PdCl$_2$(PPh$_3$)$_2$ could be used to prepare a variety of (4S)-7-(2-methylpyridin-4-yl)-N-(aryl)-3,4-dihydro-1,4-methanopyrido[2,3-b][1,4]diazepine-5(2H)-carboxamides and (4S)-7-(6-methylpyridin-3-yl)-N-(aryl)-3,4-dihydro-1,4-methanopyrido[2,3-b][1,4]diazepine-5(2H)-carboxamides by using the appropriate (4S)-7-chloro-N-(aryl)-3,4-dihydro-1,4-methanopyrido[2,3-b][1,4]diazepine-5(2H)-carboxamide and the appropriate boronic acid or ester.

Example 16. Preparation of (4S)-7-(3-((R)-3-fluoropyrrolidin-1-yl)phenyl)-N-(pyrazin-2-yl)-3,4-dihydro-1,4-methanopyrido[2,3-b][1,4]diazepine-5(2H)-carboxamide

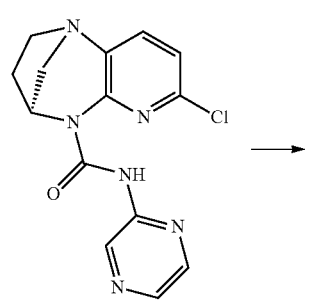

150

-continued

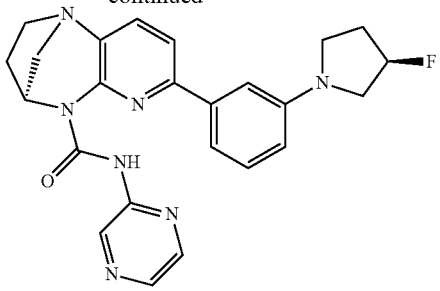

A mixture of (4S)-7-chloro-N-(pyrazin-2-yl)-3,4-dihydro-1,4-methanopyrido[2,3-b][1,4]diazepine-5(2H)-carboxamide (40 mg, 0.126 mmol), (R)-3-fluoro-1-(3-(4,4,5,5-tetramethyl-1,3,2-dioxaborolan-2-yl)phenyl)pyrrolidine (74 mg, 0.252 mmol), Pd(OAc)$_2$ (2 mg, 0.0126 mmol), 2-dicyclohexylphosphino-2',4',6'-triisopropylbiphenyl (12 mg, 0.0252 mmol), and Cs$_2$CO$_3$ (82 mg, 0.252 mmol) in dioxane/H$_2$O (1.5 mL, v/v=9/1) was heated at 110° C. in a sealed flask. After heating overnight, the mixture was cooled and filtered to remove insoluble materials. The filtrate was diluted with EtOAc (30 mL), washed with H$_2$O (5 mL×2), washed with brine (5 mL), dried over Na$_2$SO$_4$, and concentrated. Purification by prep-TLC (CH$_2$Cl$_2$/EtOAc=3/1) afforded (4S)-7-(3-((R)-3-fluoropyrrolidin-1-yl)phenyl)-N-(pyrazin-2-yl)-3,4-dihydro-1,4-methanopyrido[2,3-b][1,4]diazepine-5(2H)-carboxamide (18 mg, 32%) as a pale yellow solid. MS (ESI) calcd for C$_{24}$H$_{24}$FN$_7$O: 445.2; found: 446.3 [M+H].

This general procedure using Pd(OAc)$_2$ could be used to prepare a variety of (4S)-7-(3- and 2-substituted phenyl)-N-(aryl)-3,4-dihydro-1,4-methanopyrido[2,3-b][1,4]diazepine-5(2H)-carboxamides and (4S)-7-(2-(trifluoromethyl)pyridin-4-yl)-N-(aryl)-3,4-dihydro-1,4-methanopyrido[2,3-b][1,4]diazepine-5(2H)-carboxamides by using the appropriate (4S)-7-chloro-N-(aryl)-3,4-dihydro-1,4-methanopyrido[2,3-b][1,4]diazepine-5(2H)-carboxamide and the appropriate boronic acid or ester.

Example 17. Preparation of (4S)-7-(3-((S)-2,3-dihydroxypropoxy)phenyl)-N-(pyridin-2-yl)-3,4-dihydro-1,4-methanopyrido[2,3-b][1,4]diazepine-5(2H)-carboxamide Step 1. Synthesis of (4S)-7-chloro-N-(pyridin-2-yl)-3,4-dihydro-1,4-methanopyrido[2,3-b][1,4]diazepine-5(2H)-carboxamide

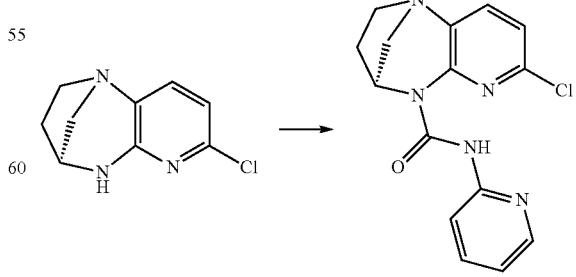

The mixture of (4S)-7-chloro-2,3,4,5-tetrahydro-1,4-methanopyrido[2,3-b][1,4]diazepine (300 mg, 1.53 mmol), phenyl pyridin-2-ylcarbamate (986 mg, 4.59 mmol) and DMAP (188 mg, 1.53 mmol) in DMF (6 mL) was degassed and heated to 80° C. in the sealed flask. After stirring overnight at 80° C., the reaction mixture was cooled to room temp. and partitioned into EtOAc/H₂O (150 mL/50 mL). The organic phase was washed with water (20 mL×6), brine (20 mL), dried over Na₂SO₄ and concentrated under reduced pressure. The concentrate was then purified by column (CH₂Cl₂/EtOAc=1/1) to afford (4S)-7-chloro-N-(pyridin-2-yl)-3,4-dihydro-1,4-methanopyrido[2,3-b][1,4]diazepine-5 (2H)-carboxamide (409 mg, 84%) as an off-white solid. MS (ESI) calcd for $C_{15}H_{14}ClN_5O$: 315.1; found: 316.1 [M+H].

Step 2. (4S)-7-(3-hydroxyphenyl)-N-(pyridin-2-yl)-3,4-dihydro-1,4-methanopyrido[2,3-b][1,4]diazepine-5(2H)-carboxamide

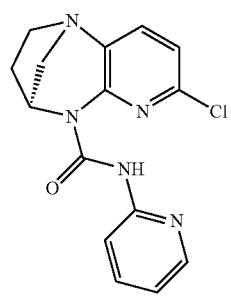

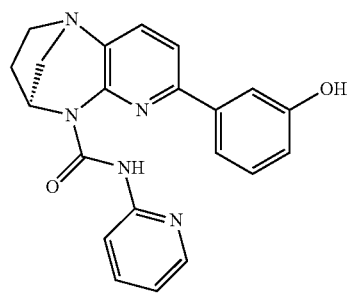

A mixture of (4S)-7-chloro-N-(pyridin-2-yl)-3,4-dihydro-1,4-methanopyrido[2,3-b][1,4]diazepine-5(2H)-carboxamide (80 mg, 0.284 mmol), (3-hydroxyphenyl)boronic acid (78 mg, 0.568 mmol), Pd(OAc)₂ (6 mg, 0.0384 mmol), 2-dicyclohexylphosphino-2',4',6'-triisopropylbiphenyl (27 mg, 0.0568 mmol) and Cs₂CO₃ (185 mg, 0.568 mmol) in dioxane/H₂O (3 mL, v/v=9/1) was degassed and heated at 110° C. overnight in sealed tube, then cooled to room temp. and concentrated under reduced pressure. The concentrate was suspended in EtOAc (20 mL), washed with water (5 mL×2), brine (5 mL), dried over Na₂SO₄, and concentrated. The residue was purified by column (CH₂Cl₂/EtOAc=1/1) to afford (4S)-7-(3-hydroxyphenyl)-N-(pyridin-2-yl)-3,4-dihydro-1,4-methanopyrido[2,3-b][1,4]diazepine-5(2H)-carboxamide (65 mg, 61%) as an off-white solid. MS (ESI) calcd for $C_{21}H_{19}N_5O_2$: 373.2; found: 374.2 [M+H].

Step 3. Synthesis of (4S)-7-(3-((S)-2,3-dihydroxypropoxy)phenyl)-N-(pyridin-2-yl)-3,4-dihydro-1,4-methanopyrido[2,3-b][1,4]diazepine-5(2H)-carboxamide

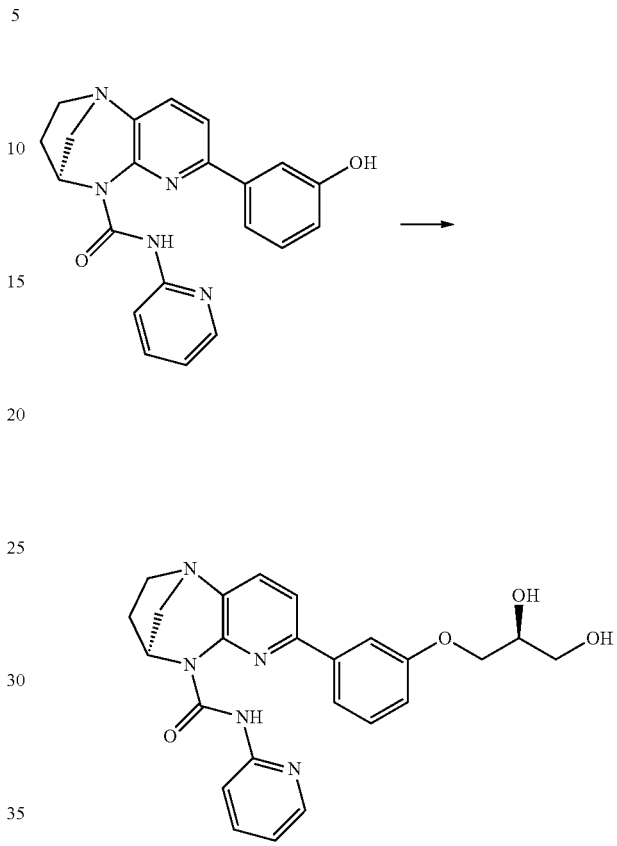

To a solution of (4S)-7-(3-hydroxyphenyl)-N-(pyridin-2-yl)-3,4-dihydro-1,4-methanopyrido[2,3-b][1,4]diazepine-5 (2H)-carboxamide (90 mg, 0.241 mmol) in DMF (3 mL) was added NaH (24 mg, 0.603 mmol). After stirring for 30 min at room temp., (S)-4-(chloromethyl)-2,2-dimethyl-1,3-dioxolane (217 mg, 1.45 mmol) was added and the mixture was heated to 85° C. for 32 hrs in a sealed flask. The mixture was cooled to room temp. and diluted with EtOAc and washed with water and brine. The organic phase was dried over Na₂SO₄ and concentrated. The concentrate was dissolved in CH₂Cl₂ (3 mL) and HCl solution in dioxane (6 mL) was added. The mixture thus obtained was stirred at room temp. for 4 hrs. The solvent was removed under reduced pressure and the concentrated was suspended in sat. NaHCO₃ (5 mL). The mixture was extracted with CH₂Cl₂ (5 mL×3) and the combined organic phases were dried over Na₂SO₄ and concentrated. Purification by prep-TLC afforded (4S)-7-(3-((S)-2,3-dihydroxypropoxy)phenyl)-N-(pyridin-2-yl)-3,4-dihydro-1,4-methanopyrido[2,3-b][1,4]diazepine-5(2H)-carboxamide (24 mg, 33%) as an off-white powder. MS (ESI) calcd for $C_{24}H_{25}N_5O_4$: 447.2; found: 448.3 [M+H].

This general procedure could be used to prepare a variety of (4S)-7-(3-((S)-2,3-dihydroxypropoxy)phenyl)-N-(aryl)-3,4-dihydro-1,4-methanopyrido[2,3-b][1,4]diazepine-5 (2H)-carboxamides by using the appropriate (4S)-7-(3-hydroxyphenyl)-N-(aryl)-3,4-dihydro-1,4-methanopyrido[2,3-b][1,4]diazepine-5(2H)-carboxamide.

Example 18. Preparation of (4S)-7-(1-propyl-1H-pyrazol-4-yl)-N-(pyridin-3-yl)-3,4-dihydro-1,4-methanopyrido[2,3-b][1,4]diazepine-5(2H)-carboxamide Step 1. Synthesis of (4S)-7-chloro-N-(pyradyl-3-yl)-3,4-dihydro-1,4-methanopyrido[2,3-b][1,4]diazepine-5(2H)-carboxamide

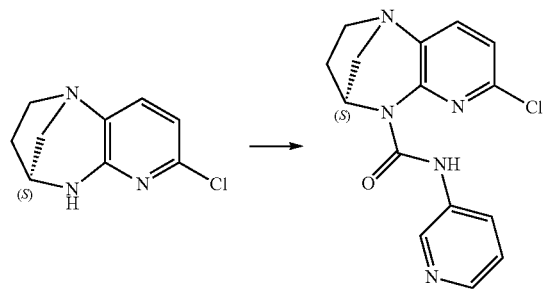

(4S)-7-chloro-2,3,4,5-tetrahydro-1,4-methanopyrido[2,3-b][1,4]diazepine (999 mg, 3.26 mmol, 1.0 eq) as combined with DIEA (1.7 mL, 9.78 mmol, 3.0 eq) into methylene chloride (30 mL) and cooled to 0° C. on an icebath. Triphosgene (482 mg, 1.63 mmol, 0.5 eq) was then added in several small portions to the stirring solution. The icebath was the removed and the reaction was allowed to warm to room temperature. The reaction was then left stirring overnight. Pyridine-3-amine (800 mg, 3.60 mmol, 1.1 eq) was then added slowly in small portions over several minutes. The mixture was then stirred at room temperature for 2 hours. The mixture was then treated with water (100 mL) diluted with EtOAc (100 mL). Phases were separated and the organic phase was dried over $Na_2SO_4$ and concentrated. The residue was purified by column chromatography using a gradient of 15-100% (EtOAc/Pentane) to afford (4S)-7-chloro-N-(pyradyl-3-yl)-3,4-dihydro-1,4-methanopyrido[2,3-b][1,4]diazepine-5(2H)-carboxamide (761 mg, yield 47%). MS (ESI) calcd for $C_{15}H_{14}ClN_5O$ 315.1; found: 315.7 [M+H].

Step 2. (4S)-7-(1-propyl-1H-pyrazol-4-yl)-N-(pyridin-3-yl)-3,4-dihydro-1,4-methanopyrido[2,3-b][1,4]diazepine-5(2H)-carboxamide

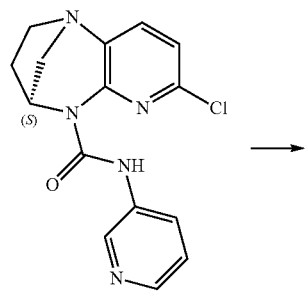

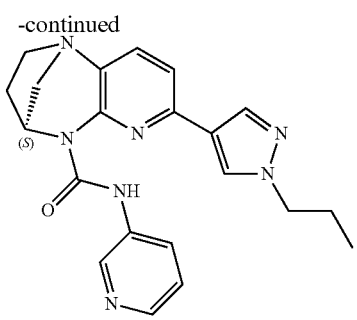

The title compound was prepared using the following protocol: A mixture of (4S)-7-chloro-N-(pyradyl-3-yl)-3,4-dihydro-1,4-methanopyrido[2,3-b][1,4]diazepine-5 (2H)-carboxamide (100 mg, 0.32 mmol, 1.0 eq), 1-ethyl-1H-pyrazole-4-boronic acid (151 mg, 0.64 mmol, 2.0 eq), Pd(dppf)Cl$_2$ (26.7 mg, 0.06 mmol, 0.2 eq) and Cs$_2$CO$_3$ (208 mg, 0.64 mmol, 2.0 eq) in dioxane/H$_2$O (5 mL) was stirred at 100° C. for 6 h. Water was added and the mixture was extracted with EtOAc. The organics were dried over anhydrous Na$_2$SO$_4$, concentrated and purified by pre-TLC to give (4S)-7-(1-propyl-1H-pyrazol-4-yl)-N-(pyridin-3-yl)-3,4-dihydro-1,4-methanopyrido[2,3-b][1,4]diazepine-5(2H)-carboxamide. (37.1 mg, yield 30%) MS (ESI) calcd for $C_{21}H_{23}N_7O$ 389.2; found: 390.3 [M+H].

This general procedure using Pd(dppf)Cl$_2$ could be used to prepare a variety of (4S)-7-(pyridin-3-yl)-N-(aryl)-3,4-dihydro-1,4-methanopyrido[2,3-b][1,4]diazepine-5(2H)-carboxamides by substituting the appropriate boronic acid or ester moiety for 2,2-difluorobenzo[d][1,3]dioxole-5-boronic acid.

Example 19: Preparation of (4S)-7-(2,2-difluorobenzo[d][1,3]dioxol-5-yl)-N-(pyridin-3-yl)-3,4-dihydro-1,4-methanopyrido[2,3-b][1,4]diazepine-5(2H)-carboxamide Step 1. Synthesis of 3-(Pyridin-2-yl)-2H-pyrido[1,2-a][1,3,5]triazine-2,4(3H)-dione

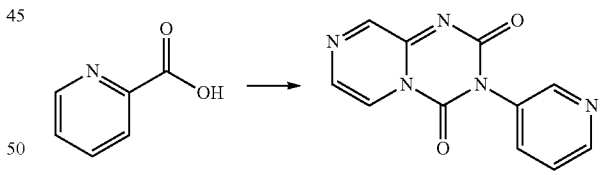

The title compound was prepared using the following protocol: 10.0 g of picolinic acid (81.2 mmol, 1 eq) was suspended in 250 mL of Toluene. 20.0 mL of diphenyl phosphoryl azide (92.6 mmol, 1.14 eq) was added. 13.4 mL of triethylamine (95.8 mmol, 1.18 eq) was added dropwise. The reaction mixture was stirred at room temperature for 30 minutes, then for 2 hrs at 80° C. The reaction mixture was allowed to cool to room temperature. Solids were filtered and washed with ethyl acetate and pentane. The solid was dried under high vacuum. Obtained 6.46 g (66% yield) of a brown solid. MS (ESI) calcd for $C_{15}H_{14}ClN_5O$: 240.06; found: 241.31 [M+H].

This general procedure could be used to prepare 3-(Pyridin-2-yl)-2H-pyrido[1,2-a][1,3,5]triazine-2,4(3H)-dione and 3-(pyrazin-2-yl)-2H-pyrazino[1,2-a][1,3,5]triazine-2,4

(3H)-dione by substituting the appropriate heteroaryl carboxylic acid bearing nitrogen heteroatom in the 2 position on the six membered aromatic ring.

Step 2. Synthesis of (4S)-7-chloro-N-(pyridin-2-yl)-3,4-dihydro-1,4-methanopyrido[2,3-b][1,4]diazepine-5(2H)-carboxamide (4S)-7-chloro-N-(pyridin-2-yl)-3,4-dihydro-1,4-methanopyrido[2,3-b][1,4]diazepine-5 (2H)-carboxamide

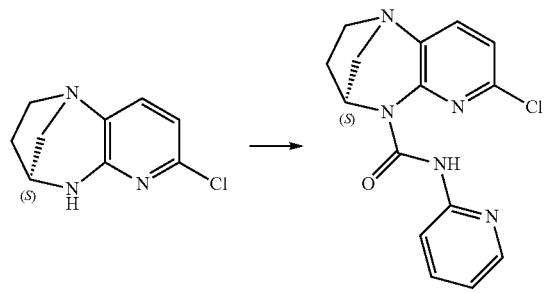

The title compound was prepared using the following protocol: (4S)-7-chloro-2,3,4,5-tetrahydro-1,4-methanopyrido[2,3-b][1,4]diazepine (2.0 g, 10.2 mmol, 1.0 eq) was dissolved in 2-methyl-tetrahydrofuran (40 mL) and treated with NaH (1.7 g, 30.6 mmol, 3.0 eq) at room temperature. The resulting mixture was then stirred at RT for 30 minutes. 3-(pyridin-2-yl)-2H-pyrido[1,2-a][1,3,5]triazine-2,4(3H)-dione (2.4 g, 10.2 mmol, 1.0 eq) was then added and the reaction was then fitted with a reflux condenser and heated to 80° C. overnight. The reaction was then cooled RT, placed on an icebath, and quenched with slow addition of NaHCO$_3$ (65 mL). Crude reaction was then extracted 3×'s EtOAc (75 mL each) and organics were dried over anhydrous MgSO$_4$ and concentrated. Reaction was purified via column chromatography using a gradient of 10-100% EtOAc/Pentane to give (4S)-7-chloro-N-(pyridin-2-yl)-3,4-dihydro-1,4-methanopyrido[2,3-b][1,4]diazepine-5(2H)-carboxamide (4S)-7-chloro-N-(pyridin-2-yl)-3,4-dihydro-1,4-methanopyrido[2,3-b][1,4]diazepine-5(2H)-carboxamide (2.5 g, 78%). MS (ESI) calcd for C$_{15}$H$_{14}$ClN$_5$O: 315.09; found: 316.10 [M+H].

Step 3. Synthesis of (4S)-7-(2,2-difluorobenzo[d][1,3]dioxol-5-yl)-N-(pyridin-2-yl)-3,4-dihydro-1,4-methanopyrido[2,3-b][1,4]diazepine-5(2H)-carboxamide

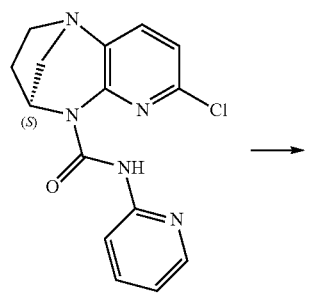

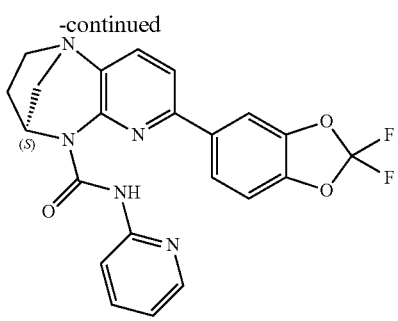

(4S)-7-chloro-N-(pyridin-2-yl)-3,4-dihydro-1,4-methanopyrido[2,3-b][1,4]diazepine-5(2H)-carboxamide (79 mg, 0.250 mmols, 1.0 eq) was combined with Pd$_2$(dba)$_3$ (2.3 mg, 0.006 mmols, 0.02 eq), K$_3$PO$_4$ (80 mg, 0.380 mmols, 2 eq), S-Phos (4.8 mg, 0.012 mmol, 0.05 eq) and the flask was purged with N$_2$ and sealed. N-butanol (1 mL) was then added via syringe and the reaction was heated to 100° C. for 3 hrs. Reaction was then cooled to room temperature filtered then purified directly via reverse phase chromatography using a gradient of 5-95% CH$_3$CN/H$_2$O (0.1% TFA) to give (4S)-7-(2,2-difluorobenzo[d][1,3]dioxol-5-yl)-N-(pyridin-3-yl)-3,4-dihydro-1,4-methanopyrido[2,3-b][1,4]diazepine-5(2H)-carboxamide (11 mg, 10%). C$_{15}$H$_{14}$ClN$_5$O: 437.13; found: 438.17 [M+H].

This general procedure using Pd(dppf)Cl$_2$ could be used to prepare a variety of (4S)-7-(pyridin-2-yl)-N-(aryl)-3,4-dihydro-1,4-methanopyrido[2,3-b][1,4]diazepine-5(2H)-carboxamides and (4S)—N-(pyrazin-2-yl)-3,4-dihydro-1,4-methanopyrido[2,3-b][1,4]diazepine-5(2H)-carboxamide by substituting the appropriate boronic acid or ester moiety for 2,2-difluorobenzo[d][1,3]dioxole-5-boronic acid.

Example 20. Preparation of (4S)—N-(5-fluoropyridin-2-yl)-7-(2-(3-(trifluoromethyl)pyrrolidin-1-yl)pyridin-4-yl)-3,4-dihydro-1,4-methanopyrido[2,3-b][1,4]diazepine-5(2H)-carboxamide Step 1. Synthesis of (4S)-7-chloro-N-(5-fluoropyridin-2-yl)-3,4-dihydro-1,4-methanopyrido[2,3-b][1,4]diazepine-5 (2H)-carboxamide

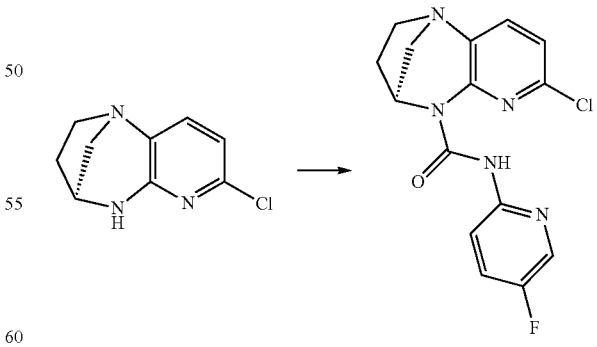

A mixture of (4S)-7-chloro-2,3,4,5-tetrahydro-1,4-methanopyrido[2,3-b][1,4]diazepine (280 mg, 1.43 mmol), 4-chlorophenyl (5-fluoropyridin-2-yl)carbamate (1.14 g, 4.29 mmol) and DMAP (174 mg, 1.43 mmol) in DMF (7 mL) was heated to 80° C. in a sealed flask. After stirring overnight at 80° C., the reaction mixture was cooled to room temp. and diluted with EtOAc (100 mL). The organic phase was washed with water (50 mL×1, 10 mL×6), then brine (50 mL), and dried over Na$_2$SO$_4$ and concentrated. The concentrate was then purified by column (CH$_2$Cl$_2$/EtOAc=1/1) to afford (4S)-7-chloro-N-(5-fluoropyridin-2-yl)-3,4-dihydro-1,4-methanopyrido[2,3-b][1,4]diazepine-5(2H)-carboxamide (360 mg, 75%) as an off-white solid. MS (ESI) calcd for C$_{15}$H$_{13}$ClFN$_5$O: 333.1.

Step 2. Synthesis of (4S)—N-(5-fluoropyridin-2-yl)-7-(2-(3-(trifluoromethyl)pyrrolidin-1-yl)pyridin-4-yl)-3,4-dihydro-1,4-methanopyrido[2,3-b][1,4]diazepine-5(2H)-carboxamide

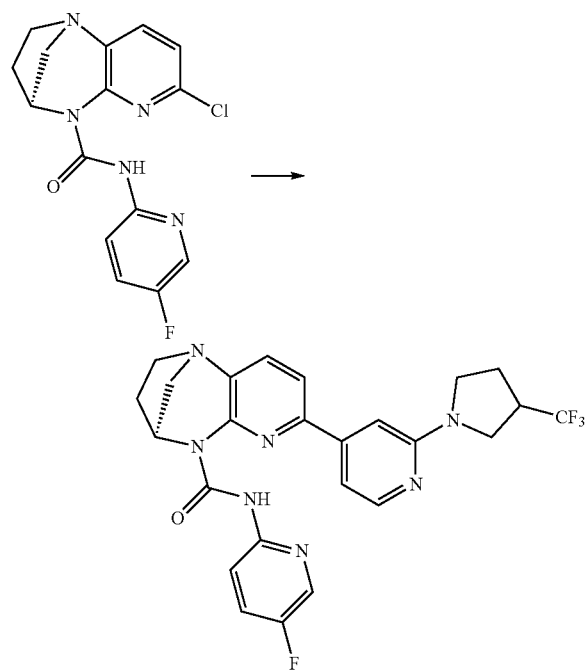

A mixture of (4S)-7-chloro-N-(5-fluoropyridin-2-yl)-3,4-dihydro-1,4-methanopyrido[2,3-b][1,4]diazepine-5(2H)-carboxamide (50 mg, 0.149 mmol), 4-(4,4,5,5-tetramethyl-1,3,2-dioxaborolan-2-yl)-2-(3-(trifluoromethyl)pyrrolidin-1-yl)pyridine (102 mg, 0.298 mmol), PCy$_3$ (8 mg, 0.0298 mmol), Pd$_2$(dba)$_3$ (14 mg, 0.0149 mmol), and K$_3$PO$_4$.3H$_2$O (79 mg, 0.373 mmol) in degassed dioxane/H$_2$O (2 mL, v/v=9/1) was heated to 120° C. in a sealed flask. After stirring overnight, the mixture was cooled to room temperature and diluted with EtOAc (60 mL). The diluted solution was washed with H$_2$O (20 mL×1, 10 mL×5) and brine (20 mL), dried over Na$_2$SO$_4$ and concentrated. Purification by prep-TLC (CH$_2$Cl$_2$/EtOAc/MeOH=3/1/2 drops) afforded (4S)—N-(5-fluoropyridin-2-yl)-7-(2-(3-(trifluoromethyl)pyrrolidin-1-yl)pyridin-4-yl)-3,4-dihydro-1,4-methanopyrido[2,3-b][1,4]diazepine-5(2H)-carboxamide (54 mg, 71%) as an off-white solid. MS (ESI) calcd for C$_{25}$H$_{23}$F$_4$N$_7$O: 513.2; found: 514.3 [M+H].

This general procedure using Pd$_2$(dba)$_3$ could be used to prepare a variety of (4S)-7-(2-(3-substituted-pyrrolidin-1-yl) pyridin-4-yl)-N-(aryl)-3,4-dihydro-1,4-methanopyrido[2,3-b][1,4]diazepine-5(2H)-carboxamides by using the appropriate (4S)-7-chloro-N-(aryl)-3,4-dihydro-1,4-methanopyrido[2,3-b][1,4]diazepine-5(2H)-carboxamide and the appropriate boronic acid or ester.

Example 21. Preparation of (4S)-7-(3-chlorophenyl)-9-methoxy-N-(pyrazin-2-yl)-3,4-dihydro-1,4-methanopyrido[2,3-b][1,4]diazepine-5(2H)-carboxamide Step 1. Synthesis of 2,6-dichloro-4-methoxypyridine

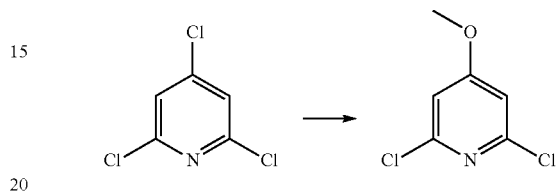

To a solution of 2,4,6-trichloropyridine (30 g, 165 mmol) in MeOH was slowly added sodium methoxide (10.7 g, 197 mmol). The mixture was stirred overnight and quenched with 300 ml of water. The suspension was filtered, washed with water and petroleum ether to obtain 2,6-dichloro-4-methoxypyridine as a white solid (18.0 g, 61% yield). MS (ESI) calcd for C$_6$H$_5$Cl$_2$NO: 176.97.

Step 2. Synthesis of 2,6-dichloro-4-methoxy-3-nitropyridine

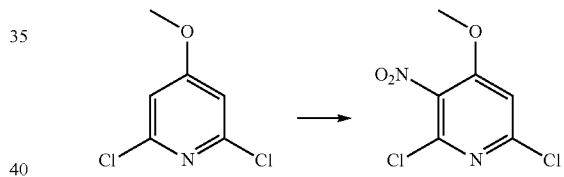

To a solution of 2,6-dichloro-4-methoxypyridine (18.1 g, 102 mmol) in sulfuric acid (110 mL) was added nitric acid (15.6 mL) dropwise at 0° C., and then the mixture was heated to 100° C. for 2 hours. The reaction mixture was poured into ice-water, the suspension was filtered and washed with water to obtain 2,6-dichloro-4-methoxy-3-nitropyridine as a white solid (19.9 g, 88% yield). MS (ESI) calcd for C$_6$H4Cl$_2$N$_2$O$_3$: 221.96.

Step 3. Synthesis of (S)-di-tert-butyl 2-((6-chloro-4-methoxy-3-nitropyridin-2-yl)amino)succinate

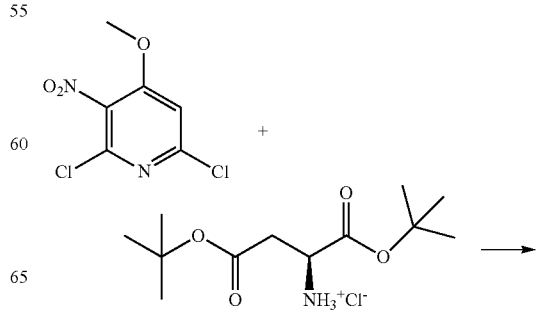

-continued

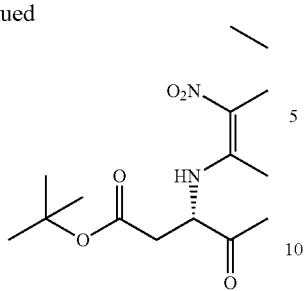

To a solution of 2,6-dichloro-4-methoxy-3-nitropyridine (14.5 g, 65 mmol) and (S)-1,4-di-tert-butoxy-1,4-dioxobutan-2-aminium chloride (22 g, 78 mmol) in DMF (150 mL) was added DIEA (32.3 mL), and the mixture was heated to 80° C. for 3 hours. DMF was removed under vacuum and the residue was dissolved in ethyl acetate, washed with brine, dried over anhydrous $Na_2SO_4$ and purified by flash chromatography (10% Ethyl Acetate in Petroleum Ether) to obtain (S)-di-tert-butyl 2-((6-chloro-4-methoxy-3-nitropyridin-2-yl)amino)succinate as a yellow oil (4.8 g, 16% yield). MS (ESI) calcd for $C_{18}H_{26}ClN_3O_7$: 431.15.

Step 4. Synthesis of (S)-tert-butyl 2-(6-chloro-8-methoxy-2-oxo-1,2,3,4-tetrahydropyrido[2,3-b]pyrazin-3-yl)acetate

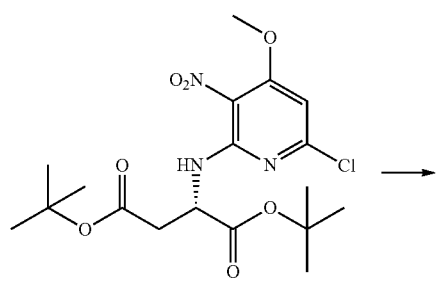

To a mixture of (S)-di-tert-butyl 2-((6-chloro-4-methoxy-3-nitropyridin-2-yl)amino)succinate (4.7 g, 10.9 mmol) in AcOH (60 ml) was added iron powder (6.107 g, 109 mmol) and the reaction mixture was stirred at 100° C. for 2 hours. The reaction was quenched with 1 N NaOH, and extracted with ethyl acetate. The organics were washed with brine and purified by flash chromatography (40% ethyl acetate in petroleum ether) to obtain (S)-tert-butyl 2-(6-chloro-8-methoxy-2-oxo-1,2,3,4-tetrahydropyrido[2,3-b]pyrazin-3-yl)acetate as a yellow oil (1.87 g, 52% yield). MS (ESI) calcd for $C_{14}H_{18}ClN_3O_4$: 327.10.

Step 5. Synthesis of (S)-2-(6-chloro-8-methoxy-1,2,3,4-tetrahydropyrido[2,3-b]pyrazin-3-yl)ethanol

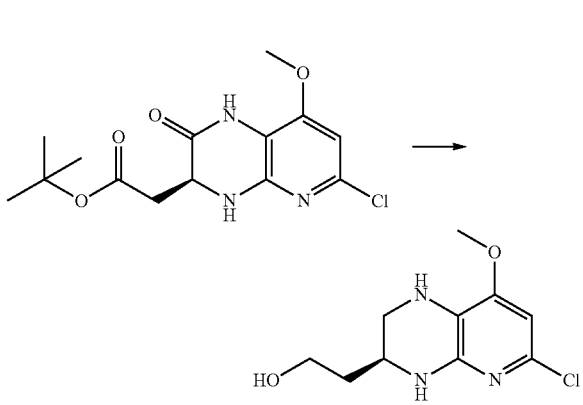

To a solution of (S)-tert-butyl 2-(6-chloro-8-methoxy-2-oxo-1,2,3,4-tetrahydropyrido[2,3-b]pyrazin-3-yl)acetate (1.7 g, 5.2 mmol) in THF (20 mL) was added $BH_3\text{-}Me_2S$ (5.2 mL, 10 M in $Me_2S$, 52 mL), and the reaction mixture was then heated at 50° C. overnight. Upon cooling to room temperature, the reaction was quenched with dropwise addition of water, then 1N aqueous HCl (10 mL) was added and the mixture was stirred at 50° C. for 2 hours. Saturated $NaHCO_3$ was added and the mixture was extracted with $CH_2Cl_2$, and concentrated to an oil. The oil was treated with TFA (15 mL) in $CH_2Cl_2$ (15 mL) for 2 hours and the DCM and TFA were removed under vacuum. The residue was dissolved in MeOH (20 mL) and $Cs_2CO_3$ (2 g) was added. The mixture was stirred for 1 hour, concentrated and purified by flash chromatography (30:1 $CH_2Cl_2$/MeOH) to obtain (S)-2-(6-chloro-8-methoxy-1,2,3,4-tetrahydropyrido[2,3-b]pyrazin-3-yl)ethanol as a yellow oil (997 mg, 79% yield). MS (ESI) calcd for $C_{10}H_{14}ClN_3O_2$: 243.08.

Step 6. Synthesis of (4S)-7-chloro-9-methoxy-2,3,4,5-tetrahydro-1,4-methanopyrido[2,3-b][1,4]diazepine

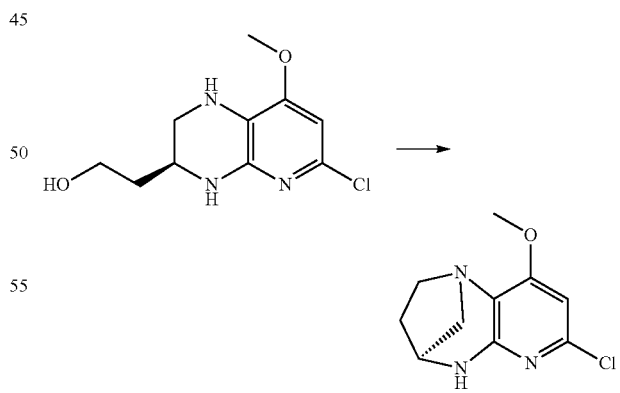

To a solution of $PPh_3$ (1.003 g, 3.83 mmol) in $CH_2Cl_2$ (50 mL) was added DDQ (869 mg, 3.83 mmol), then (S)-2-(6-chloro-8-methoxy-1,2,3,4-tetrahydropyrido[2,3-b]pyrazin-3-yl)ethanol (620 mg, 2.55 mmol) was added. The mixture was stirred for 30 min, concentrated and purified by flash chromatography (33 to 100% Ethyl acetate in Petroleum Ether) to obtain (4S)-7-chloro-9-methoxy-2,3,4,5-tetrahydro-1,4-methanopyrido[2,3-b][1,4]diazepine as a yellow solid (413 mg, 72% yield). MS (ESI) calcd for $C_{10}H_{12}ClN_3O$: 225.07.

Step 7. Synthesis of (4S)-7-(3-chlorophenyl)-9-methoxy-2,3,4,5-tetrahydro-1,4-methanopyrido[2,3-b][1,4]diazepine

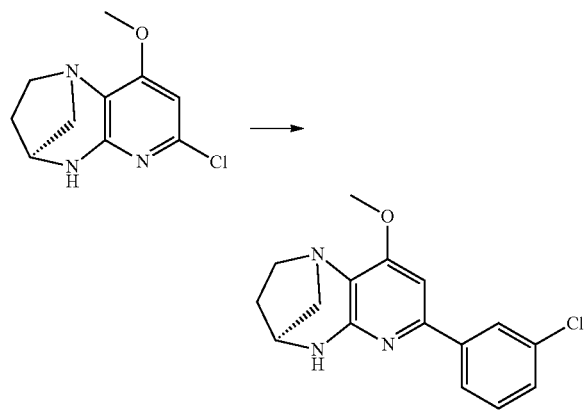

A mixture of (4S)-7-chloro-9-methoxy-2,3,4,5-tetrahydro-1,4-methanopyrido[2,3-b][1,4]diazepine (226 mg, 1.0 mmol, (3-chlorophenyl)boronic acid (187 mg, 1.2 mmol), $Cs_2CO_3$ (654 mg, 2.0 mmol) and $Pd(dppf)Cl_2 \cdot DCM$ (40 mg, 0.05 mmol) in 10:1 Dioxane/Water (6 mL) solution was microwave heated (130° C.×1 h). The reaction mixture was concentrated to dryness, suspended in $CH_2Cl_2$, washed with sat. $NaHCO_3$, water, brine, dried over $MgSO_4$ and concentrated. The reaction mixture was initially purified by silica gel chromatography (0 to 10% MeOH in $CH_2Cl_2$ gradient) and subsequently purified by Prep HPLC. The reaction was repeated a $2^{nd}$ time at the same scale, and the combined HPLC fractions were lyophilized to obtain (4S)-9-methoxy-7-(3-chlorophenyl)-2,3,4,5-tetrahydro-1,4-methanopyrido[2,3-b][1,4]diazepine (199 mg, 33% yield). MS (ESI) calcd for $C_{16}H_{16}ClN_3O$: 301.10; found: 302 [M+H].

This general procedure could be used to prepare (4S)-9-methoxy-7-(3-(trifluoromethyl)phenyl)-2,3,4,5-tetrahydro-1,4-methanopyrido[2,3-b][1,4]diazepine by substituting (3-(trifluoromethyl)phenyl)boronic acid for (3-chlorophenyl) boronic acid.

Step 8. Synthesis of (4S)-7-(3-chlorophenyl)-9-methoxy-N-(pyrazin-2-yl)-3,4-dihydro-1,4-methanopyrido[2,3-b][1,4]diazepine-5(2H)-carboxamide

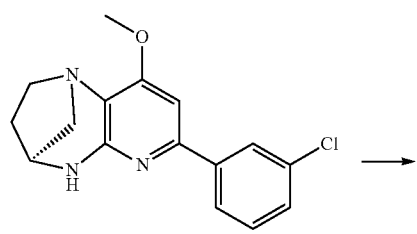

-continued

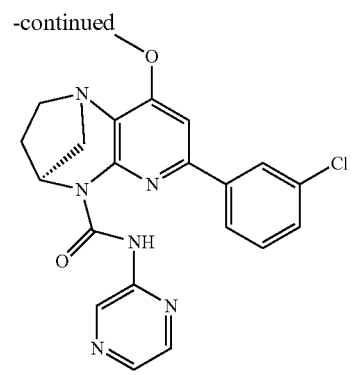

To a solution of (4S)-7-(3-chlorophenyl)-9-methoxy-2,3,4,5-tetrahydro-1,4-methanopyrido[2,3-b][1,4]diazepine (60 mg, 0.2 mmol) in THF (10 mL) was added 60% NaH suspension in mineral oil (24 mg, 1 mmol). The mixture was heated to reflux for 1 hour, 3-(pyrazin-2-yl)-2H-pyrazino[1,2-a][1,3,5]triazine-2,4(3H)-dione (73 mg, 0.3 mmol) was added and the mixture was heated at reflux for an additional 2 hours. The reaction mixture was cooled to room temperature, concentrated to dryness, diluted with sat. $NaHCO_3$, and extracted with $CH_2Cl_2$ (3×). The organics were washed with Brine, dried ($Na_2SO_4$), concentrated and purified by prep-HPLC and lyophilized to afford (4S)-7-(3-chlorophenyl)-9-methoxy-N-(pyrazin-2-yl)-3,4-dihydro-1,4-methanopyrido[2,3-b][1,4]diazepine-5(2H)-carboxamide (54 mg, 64% yield). MS (ESI) calcd for $C_{21}H_{19}ClN_6O_2$: 422.13; found: 423 [M+H].

Example 22. Preparation of (4S)-9-methoxy-N-(pyridin-2-yl)-7-(3-(trifluoromethyl)phenyl)-3,4-dihydro-1,4-methanopyrido[2,3-b][1,4]diazepine-5(2H)-carboxamide

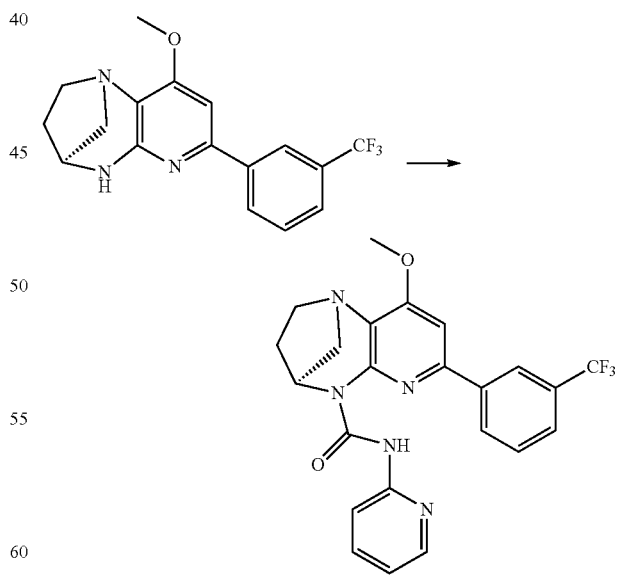

A mixture of the phenyl pyridin-2-ylcarbamate (191.6 mg, 0.8995 mmol), (4S)-9-methoxy-7-(3-(trifluoromethyl)phenyl)-2,3,4,5-tetrahydro-1,4-methanopyrido[2,3-b][1,4]diazepine (150 mg, 0.4477 mmol) and DMAP (65.55 mg, 0.5373 mmol) in 15 ml of acetonitrile were stirred at 60° C.

overnight. The mixture was directly loaded on prep-TLC and purified (using ethyl acetate as eluent) to afford (4S)-9-methoxy-N-(pyridin-2-yl)-7-(3-(trifluoromethyl)phenyl)-3,4-dihydro-1,4-methanopyrido[2,3-b][1,4]diazepine-5 (2H)-carboxamide as a white solid (150 mg, Yield: 74%). MS (ESI) calcd for $C_{23}H_{20}F_3N_5O_2$: 455.2; found: 456 [M+H].

This general procedure could be used to prepare (4S)-9-methoxy-N-(Aryl)-7-(3-(trifluoromethyl)phenyl)-3,4-dihydro-1,4-methanopyrido[2,3-b][1,4]diazepine-5 (2H)-carboxamides by substituting the appropriate carbamate moiety for phenyl pyridin-2-ylcarbamate.

Example 23. Preparation of (4S)-9-hydroxy-N-(pyridin-2-yl)-7-(3-(trifluoromethyl)phenyl)-3,4-dihydro-1,4-methanopyrido[2,3-b][1,4]diazepine-5 (2H)-carboxamide

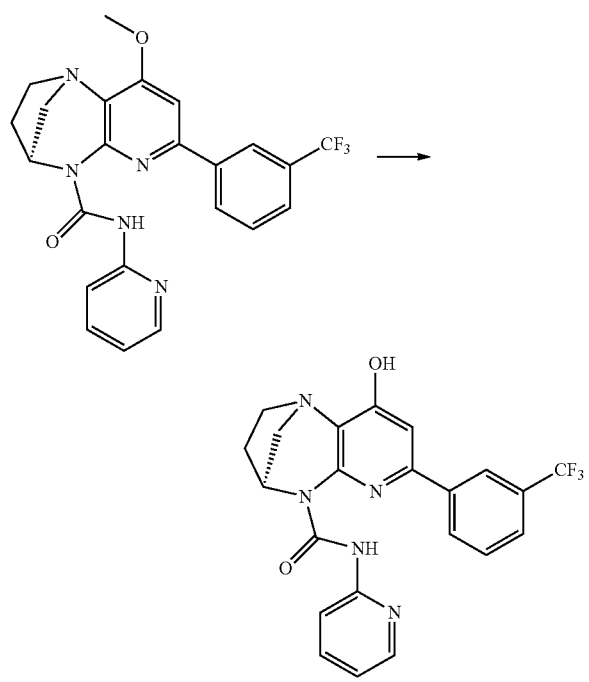

Under nitrogen atmosphere, to the mixture of (4S)-9-methoxy-N-(pyridin-2-yl)-7-(3-(trifluoromethyl)phenyl)-3,4-dihydro-1,4-methanopyrido[2,3-b][1,4]diazepine-5 (2H)-carboxamide (50 mg, 0.1098 mmol) in 3 ml of dry $CH_2Cl_2$ was added $BBr_3$ (0.5 mL, 0.5494 mmol) dropwise at 0° C. Then reaction mixture was stirred at 50° C. overnight. Sodium bicarbonate solution (5 mL) and dichloromethane (10 mL) were added to the reaction mixture and the organic layer was washed with water, brine, dried with anhydrous sodium sulfate and concentrated in vacuuo. The crude product was purified by prep-TLC using (1:20 MeOH in $CH_2Cl_2$) as eluent to afford (4S)-9-hydroxy-N-(pyridin-2-yl)-7-(3-(trifluoromethyl)phenyl)-3,4-dihydro-1,4-methanopyrido[2,3-b][1,4]diazepine-5 (2H)-carboxamide as a white solid (18 mg, 35% yield). MS (ESI) calcd for $C_{22}H_{18}F_3N_5O_2$: 441.1; found: 442 [M+H].

This general procedure could be used to prepare ((4S)-9-hydroxy-N-(Aryl)-7-(3 (trifluoromethyl)phenyl)-3,4-dihydro-1,4-methanopyrido[2,3-b][1,4]diazepine-5 (2H)-carboxamides by substituting the appropriate (4S)-9-methoxy-N-(Aryl)-7-(3-(trifluoromethyl)phenyl)-3,4-dihydro-1,4-methanopyrido[2,3-b][1,4]diazepine-5 (2H)-carboxamide for (4S)-9-methoxy-N-(pyridin-2-yl)-7-(3-(trifluoromethyl)phenyl)-3,4-dihydro-1,4-methanopyrido[2,3-b][1,4]diazepine-5(2H)-carboxamide.

Example 24. Preparation of (4S)—N-(4-((3-(3-methyl-3H-diazirin-3-yl)propanamido)methyl)phenyl)-7-(3-(trifluoromethyl)phenyl)-3,4-dihydro-1,4-methanopyrido[2,3-b][1,4]diazepine-5(2H)-carboxamide

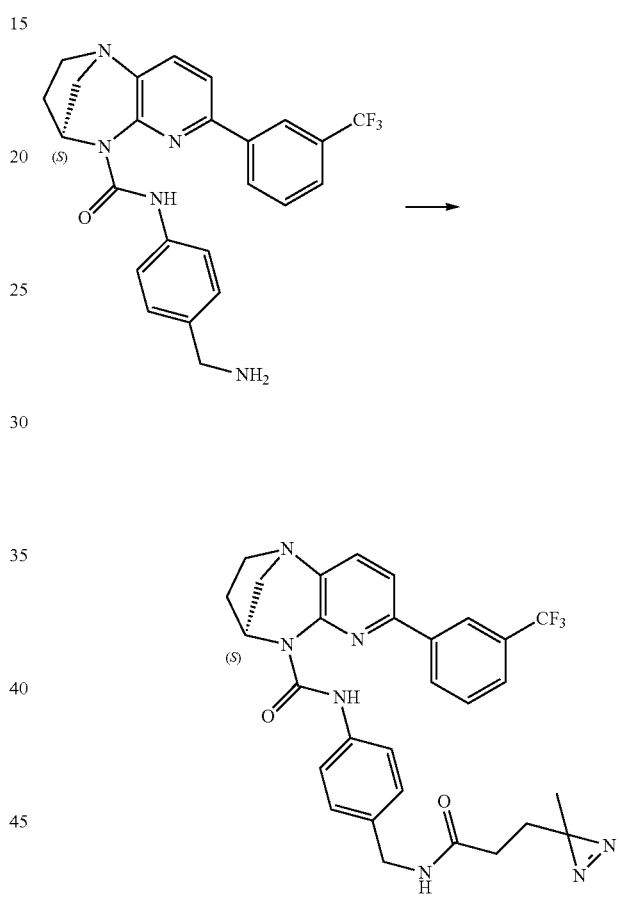

A solution of (4S)—N-(4-(aminomethyl)phenyl)-7-(3-(trifluoromethyl)phenyl)-3,4-dihydro-1,4-methanopyrido[2,3-b][1,4]diazepine-5(2H)-carboxamide hydrochloride (49 mg, 0.1 mmol), 2,5-dioxopyrrolidin-1-yl 3-(3-methyl-3H-diazirin-3-yl)propanoate (23 mg, 0.1 mmol), and triethylamine (70 µL, 0.5 mmol) in DMF (2 mL) was stirred at room temperature for 1 hour. Water (10 mL) and sat. $NaHCO_3$ (5 mL) was added, and the reaction mixture was extracted with $CH_2Cl_2$ (3×) and concentrated to dryness. The crude product was purified on silica gel chromatography (0 to 10% MeOH gradient in $CH_2Cl_2$), concentrated, chased with diethylether and pentane, and dried under vacuum to afford (4S)—N-(4-((3-(3-methyl-3H-diazirin-3-yl)propanamido)methyl)phenyl)-7-(3-(trifluoromethyl)phenyl)-3,4-dihydro-1,4-methanopyrido[2,3-b][1,4]diazepine-5(2H)-carboxamide as a white foam (39 mg, 68% yield). MS (ESI) calcd for $C_{29}H_{28}F_3N_7O_2$: 563.23; found: 564 [M+H].

Example 25: Preparation of (4S)—N-(3-(3-(trifluoromethyl)-3H-diazirin-3-yl)phenyl)-7-(3-(trifluoromethyl)phenyl)-3,4-dihydro-1,4-methanopyrido[2,3-b][1,4]diazepine-5(2H)-carboxamide

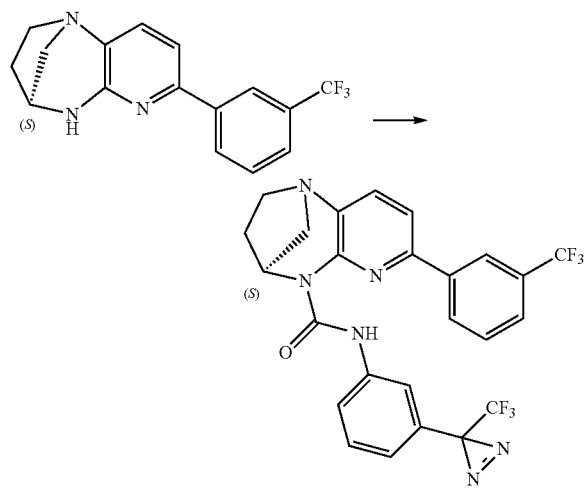

To a solution of (4S)-7-(3-(trifluoromethyl)phenyl)-2,3,4,5-tetrahydro-1,4-methanopyrido[2,3-b][1,4]diazepine (46 mg, 0.15 mmol) and triphosgene (36 mg, 120 mmol) in CH$_2$Cl$_2$ (2 mL) was added triethylamine (56 µL, 0.45 mmol). The reaction mixture was stirred at 40° C. for 2.5 hours and 3-(3-(trifluoromethyl)-3H-diazirin-3-yl)aniline (40 mg, 0.2 mmol) dissolved in CH$_2$Cl$_2$ (1 mL) was added. The reaction mixture was stirred at room temperature for 2 hours. The organic layer was washed with Sat. NaHCO$_3$, water, brine dried over Na$_2$SO$_4$ and conc. The residue was purified by flash chromatography (eluting first with a 0 to 100% CH$_2$Cl$_2$ gradient in pentane, then 0 to 10% MeOH in CH$_2$Cl$_2$) to afford (4S)—N-(3-(3-(trifluoromethyl)-3H-diazirin-3-yl)phenyl)-7-(3-(trifluoromethyl)phenyl)-3,4-dihydro-1,4-methanopyrido[2,3-b][1,4]diazepine-5(2H)-carboxamide (40 mg, 50% yield). MS (ESI) calcd for C$_{25}$H$_{18}$F$_6$N$_6$O: 532.14; found: 533 [M+H].

The above 3-(3-(Trifluoromethyl)-3H-diazirin-3-yl)aniline was prepared according to Biasotti B. et. al., Bioorganic and Medicinal Chemistry, 2003, 11, 2247-2254.

This general procedure was used to prepare a variety of (3-(3-(trifluoromethyl)-3H-diazirin-3-yl)phenyl)ureas by substituting (4S)-7-(3-(trifluoromethyl)phenyl)-2,3,4,5-tetrahydro-1,4-methanopyrido[2,3-b][1,4]diazepine with the appropriate amine.

Example 26. Preparation of (3R,4R)-7-chloro-3-((trimethylsilyl)oxy)-2,3,4,5-tetrahydro-1,4-methanopyrido[2,3-b][1,4]diazepine

Step 1. Synthesis of (S)-dimethyl 2-benzamidosuccinate

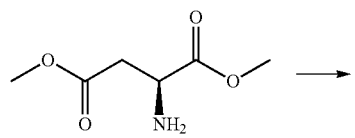

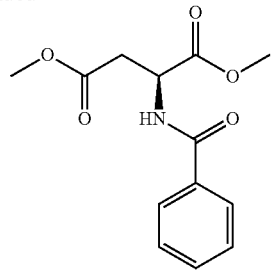

To a 5 L three-necked flask, equipped with a thermometer, a condenser, and a mechanical stirrer was added 161 g (1.00 mol) of L-aspartic acid dimethyl ester, 2500 mL of dichloromethane, and 198 g (1.96 mol) of triethylamine. The solution was cooled to −5° C., then 156 g (1.11 mol) of benzoyl chloride was added, dropwise, keeping the internal temperature at −5° C. The mixture was stirred at −5° C. for 1 h, then it was filtered. The precipitate was washed three times with additional dichloromethane, then the combined filtrate and washings were extracted with saturated aqueous K$_2$CO$_3$ solution. The dichloromethane layer was dried over Na$_2$SO$_4$ and then concentrated in vacuo to give 200 g (75%) of the product as a white solid. MS (ESI) calcd for C$_{13}$H$_{15}$NO$_5$: 265.1.

Step 2. Synthesis of (4S,5S)-dimethyl 2-phenyl-4,5-dihydrooxazole-4,5-dicarboxylate

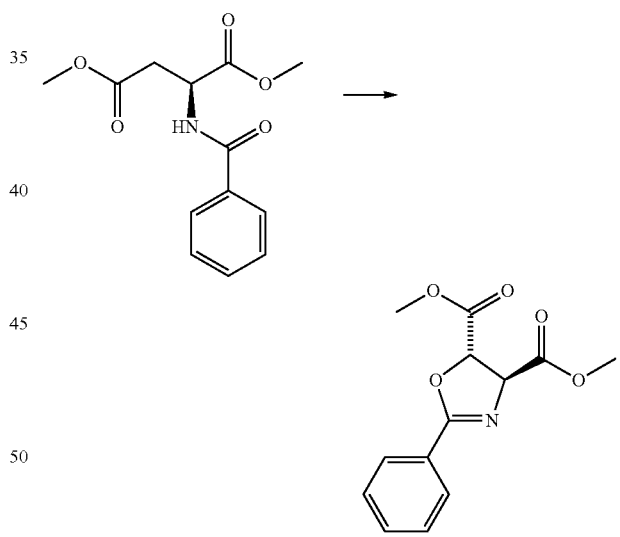

To a 10 L four necked flask, equipped with a thermometer, a mechanical stirrer, and a N$_2$ inlet was added 100 g (0.377 mol) of (S)-dimethyl 2-benzamidosuccinate, then 4 L of dry tetrahydrofuran. The mixture was stirred and cooled to 0° C. To the solution was added 770 mL (0.77 mol) of a 1.0 M solution of lithium bis(trimethylsilyl)amide in tetrahydrofuran, keeping the internal temperature at 0° C. during the addition. The reaction was stirred at 0° C. for 30 min, then it was cooled to −78° C. To this was added a solution of 195 g (0.77 mol) of iodine in 2 L of tetrahydrofuran, dropwise, at −78° C. The reaction was stirred at −78° C. for 1 h, then it was quenched by the addition of 2 L of saturated NH$_4$Cl$_{(aq.)}$, and 400 g (2.53 mol) of Na$_2$S$_2$O$_3$. The mixture was stirred at ambient temperature for 30 min, then 2 L of ethyl acetate was added, and the layers were separated. The aqueous phase was extracted with additional ethyl acetate (3×2 L). The combined ethyl acetate layers were dried over $Na_2SO_4$ and then concentrated in vacuo. The residue was purified via silica gel chromatography, eluting with 20:1 (v/v) heptanes: ethyl acetate to give 30 g (30%) of the product as a white solid. MS (ESI) calcd for $C_{13}H_{13}NO_5$: 263.1.

Step 3. Synthesis of
(2S,3S)-2-amino-3-hydroxysuccinic acid

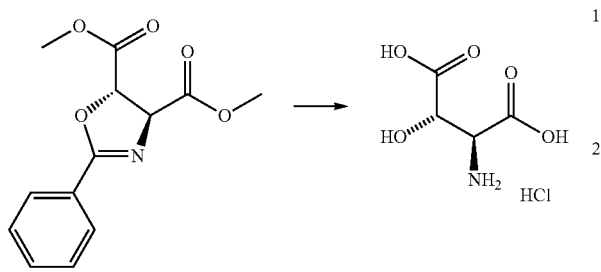

To a 500 mL flask equipped with a reflux condenser was added 13 g (50 mmol) of (4S,5S)-dimethyl 2-phenyl-4,5-dihydrooxazole-4,5-dicarboxylate, and 200 mL (2.4 mol) of 12M $HCl_{(aq.)}$. The reaction was stirred at 50° C. for 16 h, then the solvent was removed in vacuo. The residue was taken up in 1000 mL of water, and extracted with ethyl acetate until no benzoic acid was present in the aqueous layer by HPLC. The organic layers were discarded, and the aqueous layer was concentrated in vacuo to give 8.6 g (94%) of (2S,3S)-2-amino-3-hydroxysuccinic acid hydrochloride as a white crystalline solid. MS (ESI) calcd for $C_4H7NO_5$: 149.0.

Step 4. Synthesis of (2S,3S)-dimethyl
2-amino-3-hydroxysuccinate

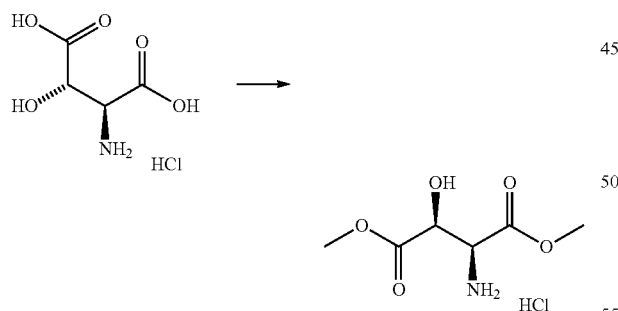

To a 500 mL three-necked flask equipped with a reflux condenser was added 170 mL of methanol. The methanol was cooled to −5° C., then 23.6 g (198 mmol) of $SOCl_2$, was added dropwise. After the addition was complete, 8.6 g (46 mmol) of (2S,3S)-2-amino-3-hydroxysuccinic acid HCl salt was added, and the solution was stirred at ambient temperature for 16 h. The solvent was removed in vacuo, to give crude (2S,3S)-dimethyl 2-amino-3-hydroxysuccinate HCl salt as a yellow oil, which was used without further purification in the next step. MS (ESI) calcd for $C_6H_{11}NO_5$: 177.1.

Step 5. Synthesis of (2S,3S)-dimethyl 2-((6-chloro-
3-nitropyridin-2-yl)amino)-3-hydroxysuccinate

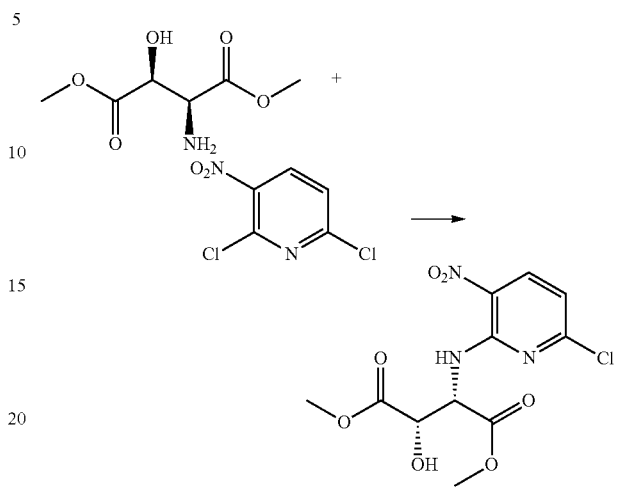

To a 500 mL round-bottomed flask equipped with a reflux condenser was added 18 g (84.3 mmol) of (2S,3S)-dimethyl 2-amino-3-hydroxysuccinate HCl, 29 g (150 mmol) of 2,6-dichloro-3-nitropyridine, 42.5 g $NaHCO_3$ (506 mmol), and 350 mL of THF. The reaction was stirred at 40° C. for 36 h. The solids were filtered away and washed with additional THF (30 mL×3). The filtrate and washings were combined and concentrated in vacuo. The residue was purified via silica gel chromatography, eluting with a gradient of 5:1 (v/v) to 1:1 (v/v) heptanes: ethyl acetate to give 22 g (63%) of (2S,3S)-dimethyl 2-((6-chloro-3-nitropyridin-2-yl) amino)-3-hydroxysuccinate as a yellow crystalline solid. MS (ESI) calcd for $C_{11}H_{12}ClN_3O_7$: 333.0.

This procedure could be used to prepare dimethyl 2-((6-chloro-3-nitropyridin-2-yl)amino)-3-hydroxysuccinate by substituting dimethyl 2-amino-3-hydroxysuccinate hydrochloride for (2S,3S)-dimethyl 2-amino-3-hydroxysuccinate hydrochloride.

Step 6. Synthesis of (S)-methyl 2-((S)-6-chloro-2-
oxo-1,2,3,4-tetrahydropyrido[2,3-b]pyrazin-3-yl)-2-
hydroxyacetate

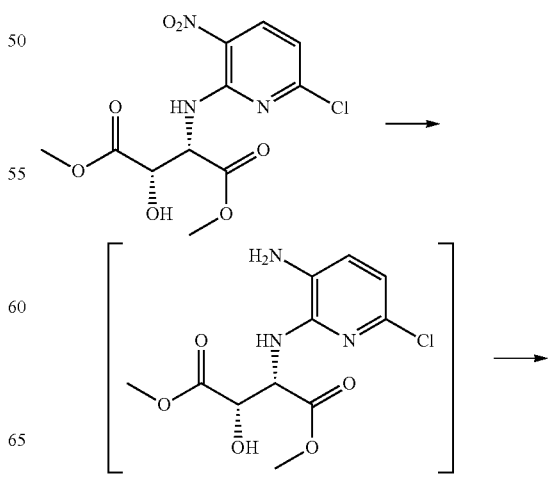

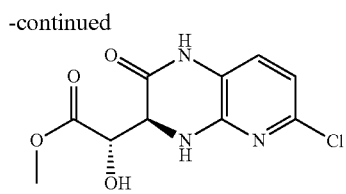

A slurry of 10 g Raney Ni in H₂O was decanted to remove the water, diluted with 2-propanol and decanted again to give a wet mixture weighing 10 g. To a 500 mL flask was added 10 g (30 mmol) of (2S,3S)-dimethyl 2-((6-chloro-3-nitropyridin-2-yl)amino)-3-hydroxysuccinate, 200 mL of 2-propanol, then 10 g of Raney Ni. The reaction was put under vacuum and back filled with hydrogen 3 times, then it was stirred under 1 atm. of H₂ for 3 h, or until no starting nitro compound remained by HPLC. The Raney Ni was filtered away, then the filtrate was put into a 500 mL round bottomed flask, and 5 mL (87 mmol) of glacial acetic acid was added. The flask was fitted with a reflux condenser, then the reaction was stirred at 80° C. for 16 h, until no intermediate diaminopyridine was present by HPLC. The solvents were removed in vacuo. The residue was purified via silica gel chromatography, eluting with 5/1 (v/v) heptanes/ethyl acetate to give 6 g (72%) of the product as a light yellow solid. MS (ESI) calcd for $Co_{10}H_{10}ClN_3O_4$: 271.0.

This procedure could be used to prepare methyl 2-(6-chloro-2-oxo-1,2,3,4-tetrahydropyrido[2,3-b]pyrazin-3-yl)-2-hydroxyacetate by substituting dimethyl 2-((6-chloro-3-nitropyridin-2-yl)amino)-3-hydroxysuccinate for (2S,3S)-dimethyl 2-((6-chloro-3-nitropyridin-2-yl)amino)-3-hydroxysuccinate.

Step 7. Synthesis of (S)-1-((R)-6-chloro-1,2,3,4-tetrahydropyrido[2,3-b]pyrazin-3-yl)ethane-1,2-diol

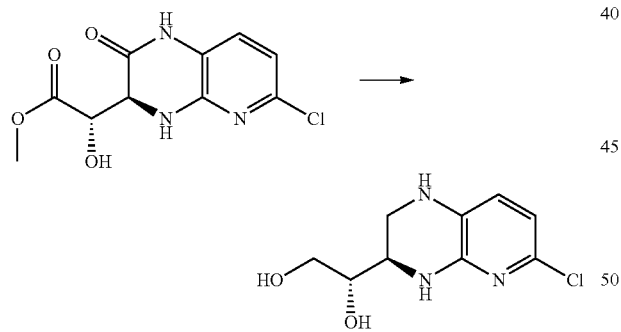

To a 100 mL 3-necked round bottomed flask equipped with a reflux condenser and a thermometer was added 20 mL of tetrahydrofuran, then 1.19 g (30 mmol) of LiAlH₄. The stirred mixture was cooled to −5° C., then a solution of 0.5 g (2 mmol) of (S)-methyl 2-((S)-6-chloro-2-oxo-1,2,3,4-tetrahydropyrido[2,3-b]pyrazin-3-yl)-2-hydroxyacetate in 20 mL of tetrahydrofuran was added dropwise. The reaction was stirred at 70° C. for 16 h, or until the reaction was complete by HPLC. (Lactam reduction was slower than ester reduction.) The reaction was cooled to −10° C., then 1.2 mL of water was added, dropwise, and the reaction was stirred for 10 min. Next, 1.2 mL of 15% (w/v) NaOH(aq.) was added dropwise, and the reaction was stirred for 20 min. To complete the quench of the excess LiAlH₄, another 3.6 mL of water was added dropwise, then the reaction was stirred for 20 min. The reaction was filtered, and the precipitate was washed with tetrahydrofuran (3×20 mL). The combined filtrate and washings were concentrated in vacuo to give about 1.5 g of a solid. This was diluted with 16 mL of ethyl acetate and filtered. The filtrate was concentrated in vacuo to give 310 mg (80%) of the product as a brown solid. MS (ESI) calcd for $C_9H_{12}ClN_3O_2$: 229.1.

This procedure could be used to prepare 1-(6-chloro-1,2,3,4-tetrahydropyrido[2,3-b]pyrazin-3-yl)ethane-1,2-diol by substituting methyl 2-((S)-6-chloro-2-oxo-1,2,3,4-tetrahydropyrido[2,3-b]pyrazin-3-yl)-2-hydroxyacetate for (S)-methyl 2-(6-chloro-2-oxo-1,2,3,4-tetrahydropyrido[2,3-b]pyrazin-3-yl)-2-hydroxyacetate.

Step 8. Synthesis of (1S,4R)-7-chloro-2,3,4,5-tetrahydro-1,4-methanopyrido[2,3-b][1,4]diazepin-3-ol

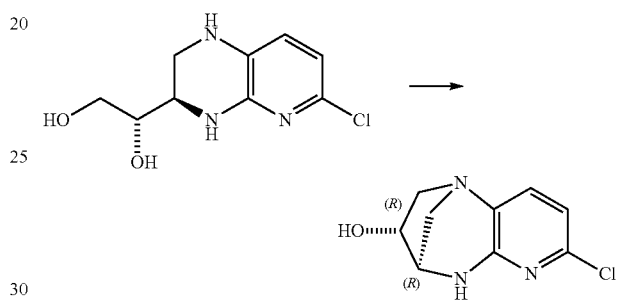

To a 10 mL round bottomed flask equipped with a reflux condenser was added 250 mg (1.1 mmol) of (S)-1-((R)-6-chloro-1,2,3,4-tetrahydropyrido[2,3-b]pyrazin-3-yl)ethane-1,2-diol, then 5 mL of 48% $HBr_{(aq.)}$. The reaction was heated at 105° C. for 16 h, or until HPLC showed that all of the starting material had been consumed. The reaction was cooled, then $K_2CO_{3(S)}$ was slowly added until pH=8. The solvent was removed in vacuo, then the residue was purified via silica gel chromatography, eluting with 20/1 (v/v) dichloromethane/methanol to give 110 mg (47%) of the product as a white crystalline solid. MS (ESI) calcd for $C_9H_{10}ClN_3O$: 211.1.

This procedure could be used to prepare 7-chloro-2,3,4,5-tetrahydro-1,4-methanopyrido[2,3-b][1,4]diazepin-3-ol by substituting 6-chloro-1,2,3,4-tetrahydropyrido[2,3-b]pyrazin-3-yl)ethane-1,2-diol for (S)-1-((R)-1-(6-chloro-1,2,3,4-tetrahydropyrido[2,3-b]pyrazin-3-yl)ethane-1,2-diol.

Step 9. Synthesis of (1S,4R)-7-chloro-3-((trimethylsilyl)oxy)-2,3,4,5-tetrahydro-1,4-methanopyrido[2,3-b][1,4]diazepine

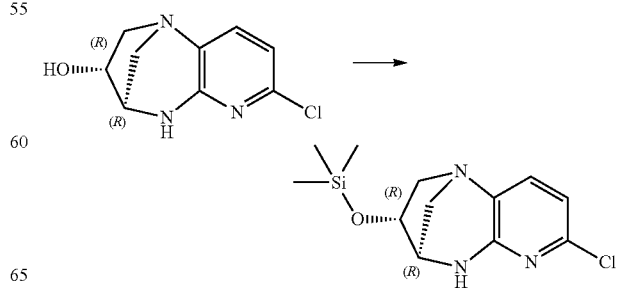

To a 10 mL round bottomed flask was added 1.68 g (7.9 mmol) of (1S,4R)-7-chloro-2,3,4,5-tetrahydro-1,4-methanopyrido[2,3-b][1,4]diazepin-3-ol, 5 mL of N,N-dimethylformamide, and 2.8 mL (24 mmol) of 2,6-dimethylpyridine. The mixture was stirred until it was homogeneous, then 1.5 mL (12 mmol) of chlorotrimethylsilane was added, dropwise, at ambient temperature. The reaction was stirred at ambient temperature for 3 h, then it was diluted with 100 mL of dichloromethane, and extracted with saturated NaHCO$_3$ (aq.) (1×50 mL), then brine (3×50 mL), and concentrated in vacuo to give 2.04 g (91%) of the product as a white crystalline solid. MS (ESI) calcd for C$_{12}$H$_{18}$ClN$_3$OSi: 283.1.

This procedure could be used to prepare 7-chloro-3-((trimethylsilyl)oxy)-2,3,4,5-tetrahydro-1,4-methanopyrido[2,3-b][1,4]diazepine by substituting 7-chloro-2,3,4,5-tetrahydro-1,4-methanopyrido[2,3-b][1,4]diazepin-3-ol for (1S,4R)-7-chloro-2,3,4,5-tetrahydro-1,4-methanopyrido[2,3-b][1,4]diazepin-3-ol.

Example 27. Preparation of (3R,4R)-7-(3-(trifluoromethyl)phenyl)-3-((trimethylsilyl)oxy)-2,3,4,5-tetrahydro-1,4-methanopyrido[2,3-b][1,4]diazepine

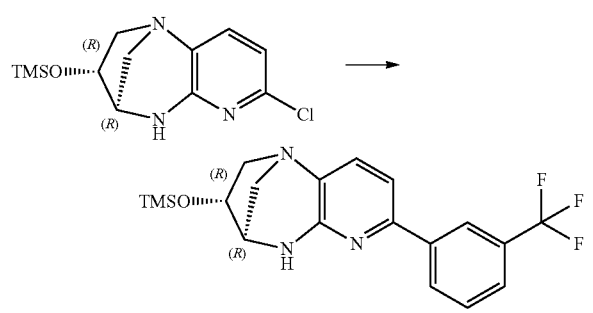

A mixture of (3R,4R)-7-chloro-3-((trimethylsilyl)oxy)-2,3,4,5-tetrahydro-1,4-methanopyrido[2,3-b][1,4]diazepine (283 mg, 1.0 mmol), (3-(trifluoromethyl)phenyl)boronic acid (285 mg, 1.5 mmol), XPhos (24 mg, 0.05 mmol), Pd(OAc)$_2$ (5.6 mg, 0.025 mmol), Cs$_2$CO$_3$ (977 mg, 3.0 mmol) in 10:1 dioxane:water (8.8 mL) was degassed and microwave heated at 100° C. for 25 min. The dioxane layer was concentrated and purified by flash chromatography (0 to 7% MeOH gradient in CH$_2$Cl$_2$) to obtain (3R,4R)-7-(3-(trifluoromethyl)phenyl)-3-((trimethylsilyl)oxy)-2,3,4,5-tetrahydro-1,4-methanopyrido[2,3-b][1,4]diazepine. The fractions were concentrated, dissolved in EtOAc, washed with sat. NaHCO$_3$, water, brine, dried (Na$_2$SO$_4$) and concentrated to obtain (3R,4R)-7-(3-(trifluoromethyl)phenyl)-3-((trimethylsilyl)oxy)-2,3,4,5-tetrahydro-1,4-methanopyrido[2,3-b][1,4]diazepine (338 mg, 85% yield). MS (ESI) calcd for C$_{19}$H$_{22}$F$_3$N$_3$OSi: 393.15; found: 394 [M+H].

This general coupling procedure using Sodium hydride could be used to prepare (3R,4R)-3-hydroxy-N-aryl-7-(3-(trifluoromethyl)phenyl)-3,4-dihydro-1,4-methanopyrido[2,3-b][1,4]diazepine-5(2H)-carboxamide by substituting the appropriate aryl isocyanate or aryl isocyante dimer for 3-(pyridin-2-yl)-2H-pyrido[1,2-a][1,3,5]triazine-2,4(3H)-dione. The non-stereospecific series could be made starting with the 7-(3-(trifluoromethyl)phenyl)-3-((trimethylsilyl)oxy)-2,3,4,5-tetrahydro-1,4-methanopyrido[2,3-b][1,4]diazepine.

Example 28. Preparation of (3R,4R)-3-hydroxy-N-(pyridin-2-yl)-7-(3-(trifluoromethyl)phenyl)-3,4-dihydro-1,4-methanopyrido[2,3-b][1,4]diazepine-5(2H)-carboxamide

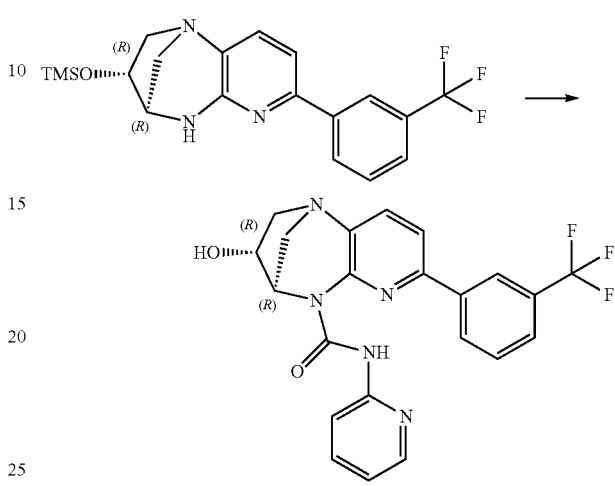

A solution of (3R,4R)-7-(3-(trifluoromethyl)phenyl)-3-((trimethylsilyl)oxy)-2,3,4,5-tetrahydro-1,4-methanopyrido[2,3-b][1,4]diazepine (215 mg, 0.55 mmol) and 60% NaH in mineral oil (66 mg, 1.65 mmol) in THF (30 mL) was heated to reflux for 20 min. 3-(pyridin-2-yl)-2H-pyrido[1,2-a][1,3,5]triazine-2,4(3H)-dione (197 mg, 0.82 mmol) was added and the reaction mixture was heated at reflux for 2 hours. The reaction mixture was cooled, concentrated to dryness, diluted with CH$_2$Cl$_2$. The organic layer was washed with sat. NaHCO$_3$, water, brine dried (Na$_2$SO$_4$) and concentrated to dryness. The residue was purified by Prep-HPLC, and the fractions were concentrated to dryness and triturated with a mixture of diethyl ether and pentane to obtain (3R,4R)-3-hydroxy-N-(pyridin-2-yl)-7-(3-(trifluoromethyl)phenyl)-3,4-dihydro-1,4-methanopyrido[2,3-b][1,4]diazepine-5 (2H)-carboxamide 2,2,2-trifluoroacetate as a white solid (132 mg, 44% yield). MS (ESI) calcd for C$_{22}$H$_{18}$F$_3$N$_5$O$_2$: 441.14; found: 442 [M+H].

Example 29. Preparation of (4R)-3-oxo-N-(pyridin-2-yl)-7-(3-(trifluoromethyl)phenyl)-3,4-dihydro-1,4-methanopyrido[2,3-b][1,4]diazepine-5(2H)-carboxamide

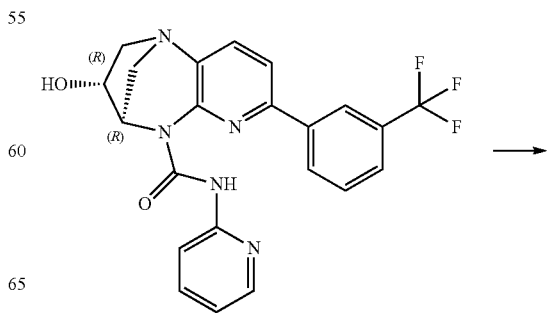

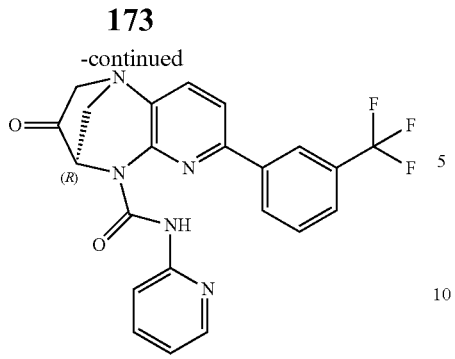

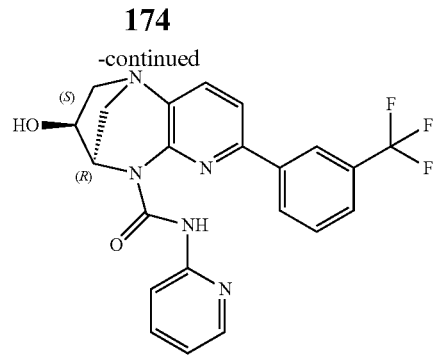

To a solution of (3R,4R)-3-hydroxy-N-(pyridin-2-yl)-7-(3-(trifluoromethyl)phenyl)-3,4-dihydro-1,4-methanopyrido[2,3-b][1,4]diazepine-5(2H)-carboxamide 2,2,2-trifluoroacetate (92 mg, 0.166 mmol) in CH$_2$Cl$_2$ (20 mL) was added Dess-Martin Periodane (105 mg, 0.25 mmol). The reaction mixture was stirred at room temperature for 1.5 hours. A second aliquot of Dess-Martin-Periodane (105 mg, 0.25 mmol) was charged and the reaction mixture was stirred at room temperature for 0.5 hours. A solution of Sat. NaHCO$_3$ (aq) was added and the reaction mixture was extracted with CH$_2$Cl$_2$. The organic layer was washed with brine, dried (Na$_2$SO$_4$), and concentrated to a white foam. The residue was purified by flash chromatography (0 to 100% Ethyl Acetate in Penate), and then purified by Prep-HPLC and lyophilized to obtain (4R)-3-oxo-N-(pyridin-2-yl)-7-(3-(trifluoromethyl)phenyl)-3,4-dihydro-1,4-methanopyrido[2,3-b][1,4]diazepine-5(2H)-carboxamide 2,2,2-trifluoroacetate (62 mg, 67% yield). MS (ESI) calcd for C$_{22}$H$_{16}$F$_3$N$_5$O$_2$: 439.13; found: 440 [M+H]. This general procedure was used to prepare (4R)—N-(3-(oxazol-5-yl)phenyl)-3-oxo-7-(3-(trifluoromethyl)phenyl)-3,4-dihydro-1,4-methanopyrido[2,3-b][1,4]diazepine-5 (2H)-carboxamide by substituting (3R,4R)-3-hydroxy-N-(pyridin-2-yl)-7-(3-(trifluoromethyl)phenyl)-3,4-dihydro-1,4-methanopyrido[2,3-b][1,4]diazepine-5 (2H)-carboxamide with (3R,4R)-3-hydroxy-N-(3-(oxazol-5-yl)phenyl)-7-(3-(trifluoromethyl)phenyl)-3,4-dihydro-1,4-methanopyrido[2,3-b][1,4]diazepine-5 (2H)-carboxamide Example 30. Preparation of (3S,4R)-3-hydroxy-N-(pyridin-2-yl)-7-(3-(trifluoromethyl)phenyl)-3,4-dihydro-1,4-methanopyrido[2,3-b][1,4]diazepine-5 (2H)-carboxamide

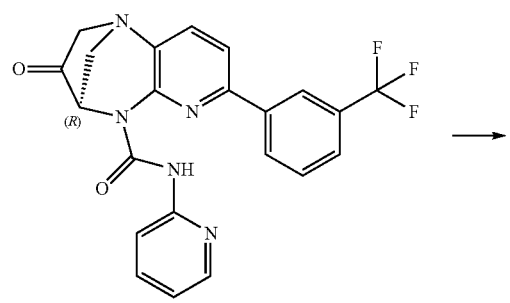

To a solution of (4R)-3-oxo-N-(pyridin-2-yl)-7-(3-(trifluoromethyl)phenyl)-3,4-dihydro-1,4-methanopyrido[2,3-b][1,4]diazepine-5(2H)-carboxamide 2,2,2-trifluoroacetate (50 mg, 0.09 mmol) in THF (10 mL) at −78 C, under nitrogen atmosphere, was dropwise added a solution of 1 M SuperHydride in THF (0.45 mL, 0.45 mmol). The reaction mixture was stirred at −78° C. for 30 min, quenched with the addition of EtOAc (5 mL), warmed to room temperature and concentrated. The residue was purified by flash chromatography (0 to 10% MeOH gradient in CH$_2$Cl) to afford (3S,4R)-3-hydroxy-N-(pyridin-2-yl)-7-(3-(trifluoromethyl)phenyl)-3,4-dihydro-1,4-methanopyrido[2,3-b][1,4]diazepine-5(2H)-carboxamide (22 mg, 55% yield). MS (ESI) calcd for C$_{22}$H$_{18}$F$_3$N$_5$O$_2$: 441.14; found: 442 [M+H].

Example 31. Preparation of (3S,4R)-5-(pyridin-2-ylcarbamoyl)-7-(3-(trifluoromethyl)phenyl)-2,3,4,5-tetrahydro-1,4-methanopyrido[2,3-b][1,4]diazepin-3-yl acetate

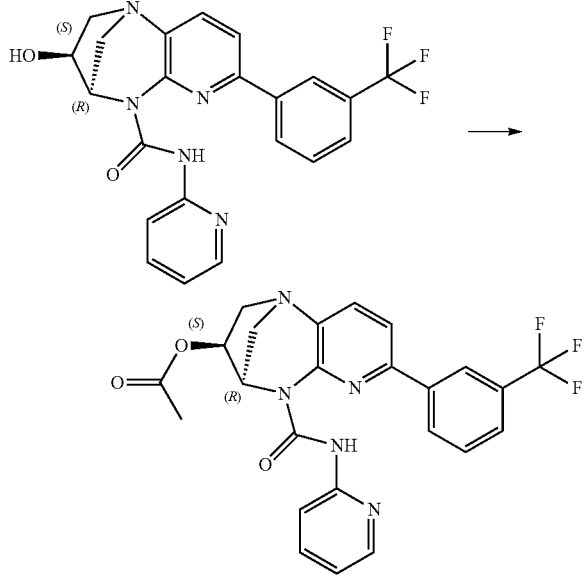

To a solution of (3S,4R)-3-hydroxy-N-(pyridin-2-yl)-7-(3-(trifluoromethyl)phenyl)-3,4-dihydro-1,4-methanopyrido[2,3-b][1,4]diazepine-5(2H)-carboxamide (15 mg, 0.034 mmol) in CH$_2$Cl$_2$ was added triethylamine (10 μL, 0.07 mmol) followed by DMAP (1 mg) and acetic anhydride (10 μL, 0.011 mmol). The reaction mixture was stirred at room temperature for 2 hours, concentrated to dryness and purified by Prep-HPLC. The fractions were lyophilized to obtain (3S,4R)-5-(pyridin-2-ylcarbamoyl)-7-(3-(trifluoromethyl)phenyl)-2,3,4,5-tetrahydro-1,4-methanopyrido[2,3-b][1,4]diazepin-3-yl acetate 2,2,2-trifluoroacetate (5.9 mg, 29% yield). MS (ESI) calcd for $C_{24}H_{20}F_3N_5O_3$: 483.15; found: 484 [M+H].

This general procedure was used to prepare (3R,4R)-5-(pyridin-2-ylcarbamoyl)-7-(3-(trifluoromethyl)phenyl)-2,3,4,5-tetrahydro-1,4-methanopyrido[2,3-b][1,4]diazepin-3-yl acetate by substituting (3S,4R)-3-hydroxy-N-(pyridin-2-yl)-7-(3-(trifluoromethyl)phenyl)-3,4-dihydro-1,4-methanopyrido[2,3-b][1,4]diazepine-5(2H)-carboxamide with (3R,4R)-3-hydroxy-N-(pyridin-2-yl)-7-(3-(trifluoromethyl)phenyl)-3,4-dihydro-1,4-methanopyrido[2,3-b][1,4]diazepine-5(2H)-carboxamide.

This general procedure was used to prepare (3R,4R)-5-(pyridin-2-ylcarbamoyl)-7-(3-(trifluoromethyl)phenyl)-2,3,4,5-tetrahydro-1,4-methanopyrido[2,3-b][1,4]diazepin-3-yl benzoate substituting (3S,4R)-3-hydroxy-N-(pyridin-2-yl)-7-(3-(trifluoromethyl)phenyl)-3,4-dihydro-1,4-methanopyrido[2,3-b][1,4]diazepine-5(2H)-carboxamide with (3R,4R)-3-hydroxy-N-(pyridin-2-yl)-7-(3-(trifluoromethyl)phenyl)-3,4-dihydro-1,4-methanopyrido[2,3-b][1,4]diazepine-5(2H)-carboxamide, and substituting acetic anhydride and benzoic anhydride.

Example 32. Preparation of (3R,4R)-3-hydroxy-N-(3-(oxazol-5-yl)phenyl)-7-(3-(trifluoromethyl)phenyl)-3,4-dihydro-1,4-methanopyrido[2,3-b][1,4]diazepine-5(2H)-carboxamide

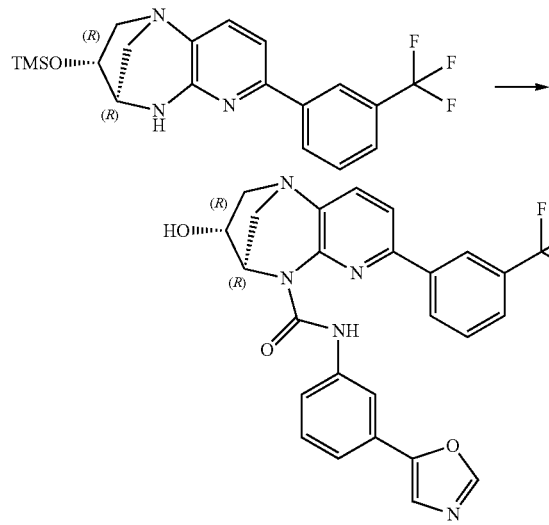

A solution of (3R,4R)-7-(3-(trifluoromethyl)phenyl)-3-((trimethylsilyl)oxy)-2,3,4,5-tetrahydro-1,4-methanopyrido[2,3-b][1,4]diazepine (284 mg, 0.722 mmol), phenyl (3-(oxazol-5-yl)phenyl)carbamate (404 mg, 1.44 mmol) and DMAP (44 mg, 0.36 mmol) in $CH_3CN$ (20 mL) was heated at 60° C. (overnight) and then 80° C. (2 h). Then to the reaction mixture was added an additional quantity of phenyl (3-(oxazol-5-yl)phenyl)carbamate (202 mg, 0.72 mmol) and DMAP (88 mg, 0.72 mmol). The reaction mixture was heated at 80° C. overnight and concentrated to dryness. The reaction mixture was initially purified by column chromatography (0 to 100% ethyl acetate in pentane gradient) and then purified by prep-HPLC and lyophilized to obtain (3R,4R)-3-hydroxy-N-(3-(oxazol-5-yl)phenyl)-7-(3-(trifluoromethyl)phenyl)-3,4-dihydro-1,4-methanopyrido[2,3-b][1,4]diazepine-5 (2H)-carboxamide as the trifluoroacetic acid salt (161 mg, 36%). MS (ESI) calcd for $C_{26}H_{20}F_3N_5O_3$: 507.15; found: 508 [M+H].

Example 33. Preparation of (3R,4R)-7-(3-chlorophenyl)-3-hydroxy-N-(pyridin-2-yl)-3,4-dihydro-1,4-methanopyrido[2,3-b][1,4]diazepine-5(2H)-carboxamide Step 1. Synthesis of (3R,4R)-3-((tert-butyldimethylsilyl)oxy)-7-chloro-2,3,4,5-tetrahydro-1,4-methanopyrido[2,3-b][1,4]diazepine

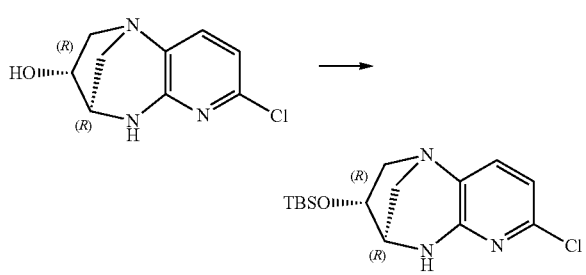

TBSOTf (111 mg, 0.42 mmol) was added slowly to a solution of (3R,4R)-7-chloro-2,3,4,5-tetrahydro-1,4-methanopyrido[2,3-b][1,4]diazepin-3-ol (90 mg, 0.28 mmol) in 2 mL of $CH_2Cl_2$ under $N_2$ at −20° C. The mixture was stirred for 1 h then washed with 1N HCl and water, dried over anhydrous $Na_2SO_4$ and evaporated to dryness. The residue was purified by Prep.TLC (DCM/EA=20:1) to give (3R,4R)-3-((tert-butyldimethylsilyl)oxy)-7-chloro-2,3,4,5-tetrahydro-1,4-methanopyrido[2,3-b][1,4]diazepine as a yellow solid (90 mg, 73% yield), MS (ESI) calcd for $C_{15}H_{24}ClN_3OSi$: 325.14;

Step 2. Synthesis of (3R,4R)-3-((tert-butyldimethylsilyl)oxy)-7-(3-chlorophenyl)-2,3,4,5-tetrahydro-1,4-methanopyrido[2,3-b][1,4]diazepine

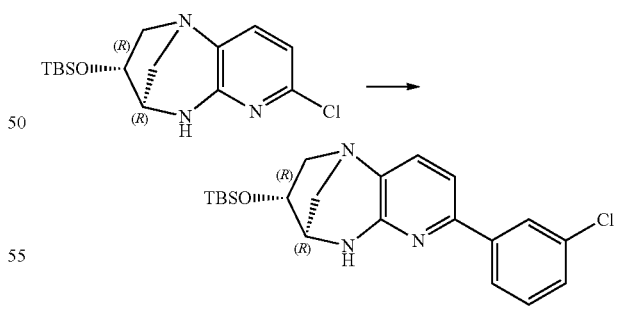

A mixture of (3R,4R)-3-((tert-butyldimethylsilyl)oxy)-7-chloro-2,3,4,5-tetrahydro-1,4-methanopyrido[2,3-b][1,4]diazepine (1.08 g, 3.32 mmol), (3-chlorophenyl)boronic acid (570 mg, 3.65 mmol), $CS_2CO_3$ (2.48 g, 7.63 mmol), Pd(dppf)$Cl_2$ (300 mg, 0.33 mmol) in dioxane/$H_2O$ (11 mL, 10:1) was heated at 130° C. for 2.5 h in a microwave reactor. The mixture was poured into water, and diluted with EtOAc. The organic phase washed with water and brine, dried over anhydrous $Na_2SO_4$, and evaporated to dryness. The residue was purified by prep. HPLC to give (3R,4R)-3-((tert-butyldimethylsilyl)oxy)-7-(3-chlorophenyl)-2,3,4,5-tetrahydro-1,4-methanopyrido[2,3-b][1,4]diazepine as a light yellow solid (850 mg, 63% yield), MS (ESI) calcd for $C_{21}H_{28}ClN_3OSi$: 401.17; This general procedure was used to prepare (3R,4R)-3-((tert-butyldimethylsilyl)oxy)-7-(5-(trifluoromethyl)pyridin-3-yl)-2,3,4,5-tetrahydro-1,4-methanopyrido[2,3-b][1,4]diazepine.

Step 3. Synthesis of (3R,4R)-3-((tert-butyldimethylsilyl)oxy)-7-(3-chlorophenyl)-N-(pyridin-2-yl)-3,4-dihydro-1,4-methanopyrido[2,3-b][1,4]diazepine-5(2H)-carboxamide

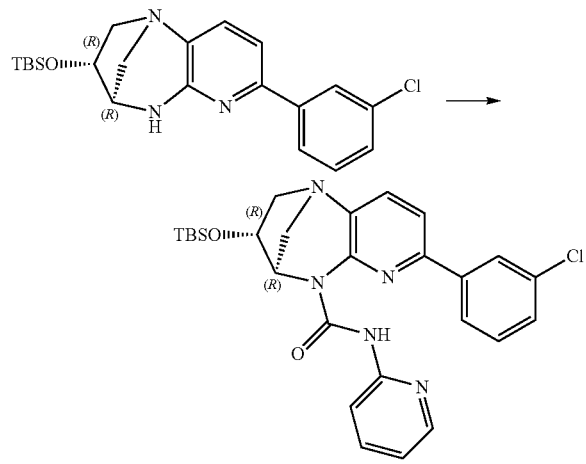

A mixture of phenyl pyridine-2-ylcarbamate (86 mg, 0.20 mmol), (3R,4R)-3-((tert-butyldimethylsilyl)oxy)-7-(3-chlorophenyl)-2,3,4,5-tetrahydro-1,4-methanopyrido[2,3-b][1,4]diazepine (80 mg, 0.20 mmol) and DMAP (24 mg, 0.20 mmol) in 5 ml of MeCN was stirred at 65° C. overnight. The crude reaction mixture was purified by prep. TLC eluting with DCM:EA=20:1 to give (3R,4R)-3-((tert-butyldimethylsilyl)oxy)-7-(3-chlorophenyl)-N-(pyridin-2-yl)-3,4-dihydro-1,4-methanopyrido[2,3-b][1,4]diazepine-5(2H)-carboxamide (110 mg). MS (ESI) calcd for $C_{27}H_{32}ClN_5O_2Si$: 521.2;

Step 4. Synthesis of (3R,4R)-7-(3-chlorophenyl)-3-hydroxy-N-(pyridin-2-yl)-3,4-dihydro-1,4-methanopyrido[2,3-b][1,4]diazepine-5(2H)-carboxamide

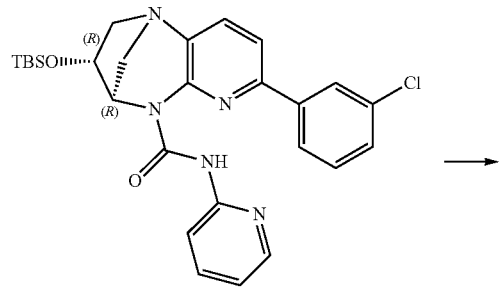

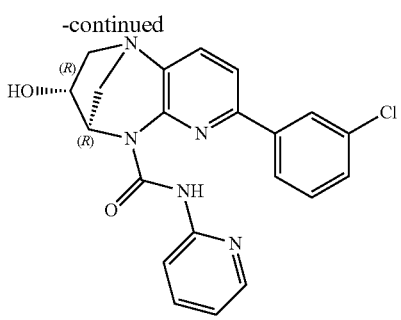

A solution of (3R,4R)-3-((tert-butyldimethylsilyl)oxy)-7-(3-chlorophenyl)-N-(pyridin-2-yl)-3,4-dihydro-1,4-methanopyrido[2,3-b][1,4]diazepine-5(2H)-carboxamide (110 mg, 0.21 mmol) in 10 mL of THF and conc. HCl (1 mL) was stirred at room temperature for 48 h. The mixture was concentrated under reduced pressure. The pH was adjusted to 8 using sat. aq NaHCO₃. The mixture was extracted with EtOAc, washed with brine, dried (Na₂SO₄) and concentrated. The residue was triturated in EtOAc to give (3R,4R)-7-(3-chlorophenyl)-3-hydroxy-N-(pyridin-2-yl)-3,4-dihydro-1,4-methanopyrido[2,3-b][1,4]diazepine-5(2H)-carboxamide (34 mg, 39% yield) as a white solid MS (ESI) calcd for $C_{21}H_{18}ClN_5O_2$: 407.1; found: 408 [M+H].

Example 34. Preparation of (3R,4R)—N-(4,5-dimethylthiazol-2-yl)-3-hydroxy-7-(3-(trifluoromethyl)phenyl)-3,4-dihydro-1,4-methanopyrido[2,3-b][1,4]diazepine-5(2H)-carboxamide Step 1. Synthesis of (3R,4R)-7-(3-(trifluoromethyl)phenyl)-2,3,4,5-tetrahydro-1,4-methanopyrido[2,3-b][1,4]diazepin-3-ol

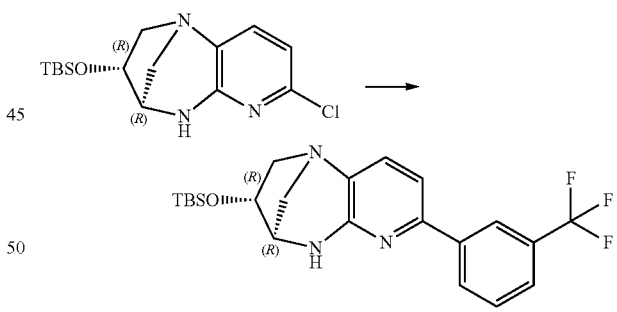

A mixture of (3R,4R)-7-chloro-3-((trimethylsilyl)oxy)-2,3,4,5-tetrahydro-1,4-methanopyrido[2,3-b][1,4]diazepine (1 g, 3.53 mmol), ((3-trifluoromethyl)phenyl)boronic acid (1.34 g, 7.06 mmol), CS₂CO₃ (3.44 g, 10.6 mmol), Pd(dppf)Cl₂ (300 mg, 0.35 mmol) in dioxane/H₂O (30 mL, 10:1) was reacted under microwave at 130° C. for 2.5 h. Then reaction mixture was poured into water, extracted with EtOAc, washed with water then brine, dried (Na₂SO₄), concentrated. The residue was purified through silica gel chromatography (PE/EA=4:1) to give (3R,4R)-7-(3-(trifluoromethyl)phenyl)-2,3,4,5-tetrahydro-1,4-methanopyrido[2,3-b][1,4]diazepin-3-ol (600 mg, 39% yield). MS (ESI) calcd for $C_{16}H_{14}F_3N_3O$: 321.1;

Step 2. Synthesis of (3R,4R)-3-((tert-butyldimethyl-silyl)oxy)-7-(3-(trifluoromethyl)phenyl)-2,3,4,5-tetrahydro-1,4-methanopyrido[2,3-b][1,4]diazepine

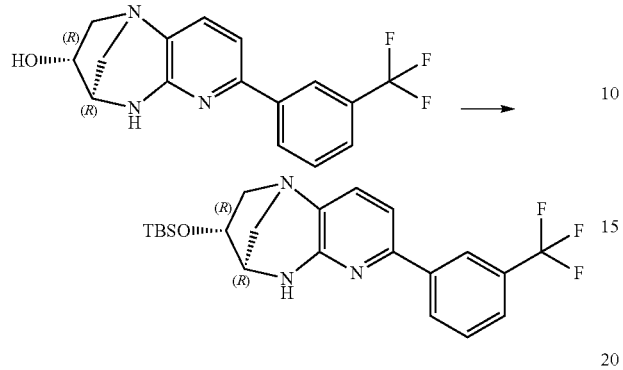

A mixture of TBSCl (338 mg, 2.24 mmol), (3R,4R)-7-chloro-2,3,4,5-tetrahydro-1,4-methanopyrido[2,3-b][1,4]diazepin-3-ol (600 mg, 1.87 mmol), triethyl amine (415 mg, 4.11 mmol) and DMAP (22 mg, 0.20 mmol) was stirred for 48 h. Additional TBSCl and TEA were required to consume the starting material. The crude residue was purified by column chromatography to give (3R,4R)-3-((tert-butyldimethylsilyl)oxy)-7-chloro-2,3,4,5-tetrahydro-1,4-methanopyrido[2,3-b][1,4]diazepine (90 mg, 73% yield). MS (ESI) calcd for $C_{22}H_{28}F_3N_3OSi$: 435.20;

Step 3. Synthesis of (3R,4R)-3-((tert-butyldimethyl-silyl)oxy)-N-(4,5-dimethylthiazol-2-yl)-7-(3-(trifluoromethyl)phenyl)-3,4-dihydro-1,4-methanopyrido[2,3-b][1,4]diazepine-5(2H)-carboxamide

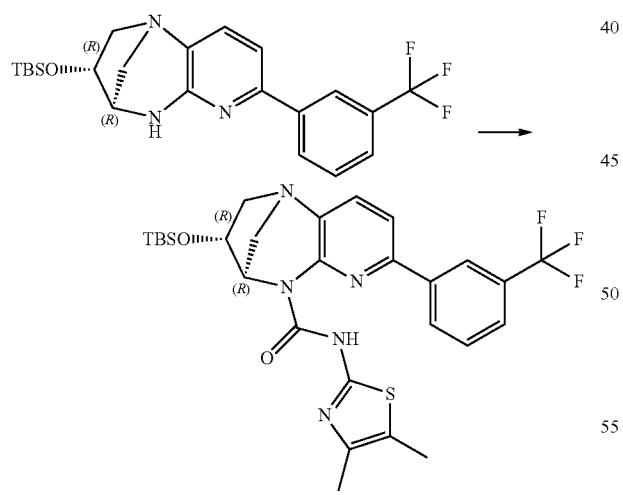

A mixture of phenyl (4,5-dimethylthiazol-2-yl)carbamate (25 mg, 0.10 mmol), (3R,4R)-3-((tert-butyldimethylsilyl)oxy)-7-(3-chlorophenyl)-2,3,4,5-tetrahydro-1,4-methanopyrido[2,3-b][1,4]diazepine (30 mg, 0.05 mmol) and DMAP (6 mg, 0.05 mmol) in 5 ml of MeCN was stirred at 65° C. overnight. The crude reaction mixture was purified by prep. TLC to give (3R,4R)-3-((tert-butyldimethylsilyl)oxy)-N-(4,5-dimethylthiazol-2-yl)-7-(3-(trifluoromethyl)phenyl)-3,4-dihydro-1,4-methanopyrido[2,3-b][1,4]diazepine-5 (2H)-carboxamide (30 mg, quant.). MS (ESI) calcd for $C_{28}H_{34}F_3N_5O_2SSi$: 589.22;

Step 4. Synthesis of (3R,4R)—N-(4,5-dimethylthiazol-2-yl)-3-hydroxy-7-(3-(trifluoromethyl)phenyl)-3,4-dihydro-1,4-methanopyrido[2,3-b][1,4]diazepine-5 (2H)-carboxamide

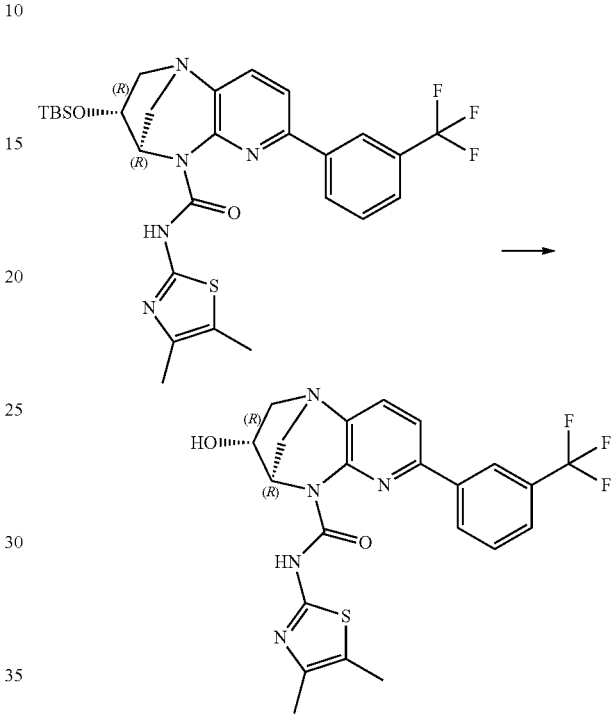

To a solution of (3R,4R)-3-((tert-butyldimethylsilyl)oxy)-N-(4,5-dimethylthiazol-2-yl)-7-(3-(trifluoromethyl)phenyl)-3,4-dihydro-1,4-methanopyrido[2,3-b][1,4]diazepine-5 (2H)-carboxamide (30 mg, 0.051 mmol) in THF (2 mL) was added TBAF/THF (0.1 mL, 0.1 mmol). The mixture was stirred at room temperature overnight, poured into water and extracted with EtOAc. The organic layer was washed with water then brine, dried over anhydrous $Na_2SO_4$, filtered and evaporated to dryness. The residue was purified by prep. TLC (EtOAc) to give (3R,4R)—N-(4,5-dimethylthiazol-2-yl)-3-hydroxy-7-(3-(trifluoromethyl)phenyl)-3,4-dihydro-1,4-methanopyrido[2,3-b][1,4]diazepine-5 (2H)-carboxamide as a white solid (12 mg, 50% yield). MS (ESI) calcd for $C_{22}H_{20}F_3N_5O_2S$: 475.13; found: 476 [M+H].

Example 35: Preparation of (4S)—N-(4-(oxazol-5-yl)pyridin-2-yl)-7-(3-(trifluoromethyl)phenyl)-3,4-dihydro-1,4-methanopyrido[2,3-b][1,4]diazepine-5 (2H)-carboxamide

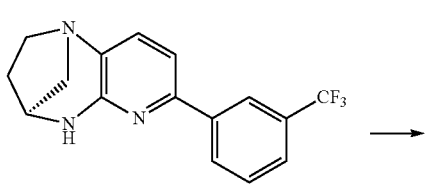

-continued

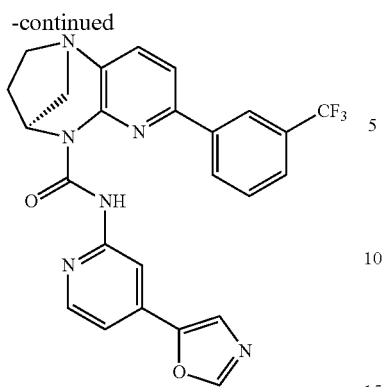

To a solution of 4-(oxazol-5-yl)pyridin-2-amine (500 mg, 3.10 mmol) in pyridine (780 µL, 9.65 mmol) and dichloromethane (10 mL), cooled to 0° C., was added phenyl chloroformate (466 µL, 3.72 mmol) over 1.5 h. The reaction was stirred at 0° C. for 2 h. Water (15 mL) was added slowly, and additional dichloromethane was added. The organic layer was separated, washed with saturated sodium carbonate (20 mL) and brine (20 mL), dried with sodium sulfate, and all solvent removed in vacuo. The residue was suspended in 5:1 petroleum ether:ethyl acetate for 30 min, then the suspension filtered to give phenyl (4-(oxazol-5-yl)pyridin-2-yl)carbamate (547 mg, 1.94 mmol, 63% yield).

A solution of (4S)-7-(3-(trifluoromethyl)phenyl)-2,3,4,5-tetrahydro-1,4-methanopyrido[2,3-b][1,4]diazepine (110 mg, 0.361 mmol), phenyl (4-(oxazol-5-yl)pyridin-2-yl)carbamate (203 mg, 0.722 mmol) and 4-(dimethylamino)pyridine (53.0 mg, 0.434 mmol) in acetonitrile (5 mL) was stirred at 60° C. overnight. The mixture was purified by preparative HPLC to give (4S)—N-(4-(oxazol-5-yl)pyridin-2-yl)-7-(3-(trifluoromethyl)phenyl)-3,4-dihydro-1,4-methanopyrido[2,3-b][1,4]diazepine-5 (2H)-carboxamide (24.3 mg, 0.0493 mmol, 14% yield). MS (ESI) calcd for $C_{25}H_{19}F_3N_6O_2$: 492.2; found: 493.2 [M+H].

Example 36: Synthesis of (4S)—N-(3,5-bis(oxazol-5-yl)phenyl)-7-(3-(trifluoromethyl)phenyl)-3,4-dihydro-1,4-methanopyrido[2,3-b][1,4]diazepine-5 (2H)-carboxamide Step 1. Synthesis of phenyl (3,5-bis(oxazol-5-yl)phenyl)carbamate

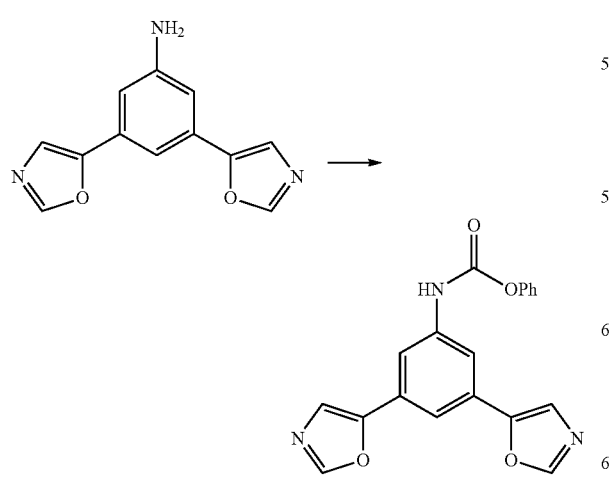

A mixture of 3,5-bis(oxazol-5-yl)aniline (100 mg, 0.44 mmol), phenyl chloroformate (76 mg, 0.48 mmol) and pyridine (0.20 mL) in dichloromethane (15 mL) was stirred at room temperature for 2 h. The solvent was removed in vacuo, and the remaining material purified by preparative TLC (1:1 petroleum ether:ethyl acetate) to give phenyl (3,5-bis(oxazol-5-yl)phenyl)carbamate (140 mg, 0.40 mmol, 92% yield). MS (ESI) calcd for $C_{19}H_{13}N_3O_4$: 347.1.

Step 2. Synthesis of (4S)—N-(3,5-bis(oxazol-5-yl)phenyl)-7-(3-(trifluoromethyl)phenyl)-3,4-dihydro-1,4-methanopyrido[2,3-b][1,4]diazepine-5(2H)-carboxamide

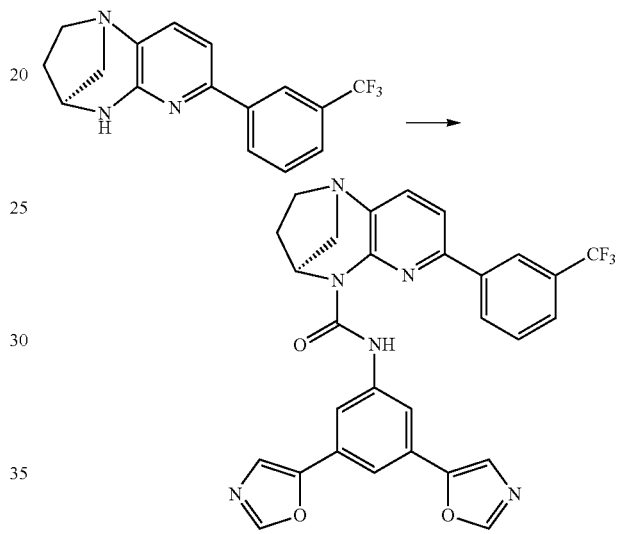

A mixture of (4S)-7-(3-(trifluoromethyl)phenyl)-2,3,4,5-tetrahydro-1,4-methanopyrido[2,3-b][1,4]diazepine (70 mg, 0.23 mmol), phenyl (3,5-bis(oxazol-5-yl)phenyl)carbamate (140 mg, 0.40 mmol) and DMAP (56 mg, 0.46 mmol) in acetonitrile (2 mL) was refluxed overnight. The solvent was removed in vacuo, and the remaining residue purified by preparative TLC (10:1 dichloromethane:methanol) to give (4S)—N-(3,5-bis(oxazol-5-yl)phenyl)-7-(3-(trifluoromethyl)phenyl)-3,4-dihydro-1,4-methanopyrido[2,3-b][1,4]diazepine-5(2H)-carboxamide (13.7 mg, 0.0245 mmol, 11% yield). MS (ESI) calcd for $C_{29}H_{21}F_3N_6O_3$: 558.2; found: 559.0.

Example 37. Preparation of tert-butyl ((1-(3-((4S)-7-(3-(trifluoromethyl)phenyl)-2,3,4,5-tetrahydro-1,4-methanopyrido[2,3-b][1,4]diazepine-5-carboxamido)phenyl)-1H-1,2,3-triazol-4-yl)methyl)carbamate

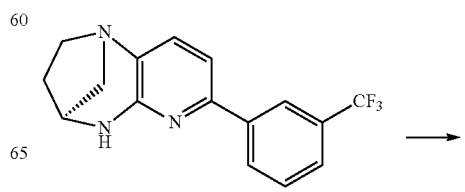

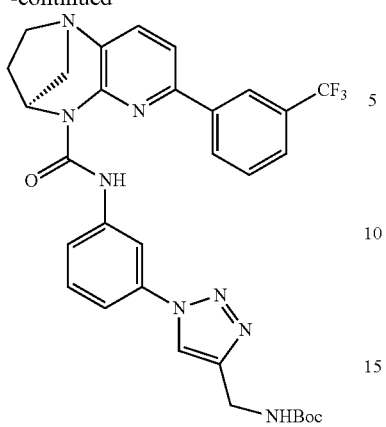

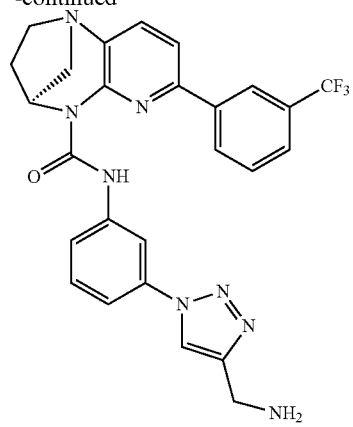

To a solution of triphosgene (214 mg, 0.721 mmol) in acetonitrile (5 mL) was added a solution of tert-butyl ((1-(3-aminophenyl)-1H-1,2,3-triazol-4-yl)methyl)carbamate (417 mg, 1.44 mmol) in acetonitrile (5 mL) and triethylamine (2 mL). The resulting suspension was stirred at room temperature for 10 min, then (4S)-7-(3-(trifluoromethyl)phenyl)-2,3,4,5-tetrahydro-1,4-methanopyrido[2,3-b][1,4]diazepine (Compound #; 302 mg, 0.989 mmol) and 4-(dimethylamino)pyridine (122 mg, 1.00 mmol) were added as solids. The reaction was stirred at 80° C. for 15 min. The reaction was cooled to room temperature, methanol (2 mL) was added, and the reaction was poured into saturated sodium bicarbonate (50 mL), and extracted with dichloromethane (3×50 mL). The combined organic layers were dried with magnesium sulfate, the solvent removed in vacuo, and the remaining material purified by flash chromatography (0% to 8% methanol in dichloromethane) to give tert-butyl ((1-(3-((4S)-7-(3-(trifluoromethyl)phenyl)-2,3,4,5-tetrahydro-1,4-methanopyrido[2,3-b][1,4]diazepine-5-carboxamido)phenyl)-1H-1,2,3-triazol-4-yl)methyl)carbamate (579 mg, 0.933 mmol, 94% yield). MS (ESI) calcd for $C_{31}H_{31}F_3N_8O_3$: 620.3; found: 621.0 [M+H].

Example 38. Preparation of (4S)—N-(3-(4-(aminomethyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide

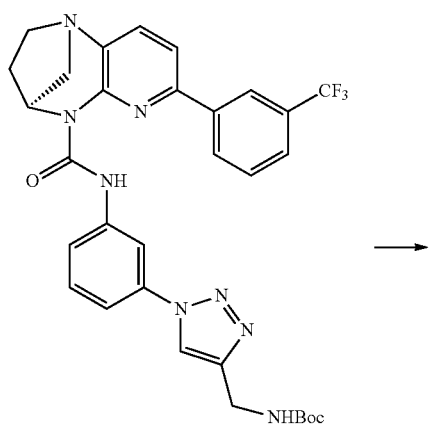

tert-butyl ((1-(3-((4S)-7-(3-(trifluoromethyl)phenyl)-2,3,4,5-tetrahydro-1,4-methanopyrido[2,3-b][1,4]diazepine-5-carboxamido)phenyl)-1H-1,2,3-triazol-4-yl)methyl)carbamate (160 mg, 0.258 mmol) was dissolved in trifluoroacetic acid (1.6 mL). The reaction was stirred at 50° C. for 10 min, then all solvent was removed in vacuo to give (4S)—N-(3-(4-(aminomethyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide trifluoroacetic acid salt (164 mg, 0.258 mmol, 100% yield). MS (ESI) calcd for $C_{26}H_{23}F_3N_8O$: 520.2; found: 521.0 [M+H].

Example 39: Synthesis of (4S)—N-(6-(1-methyl-1H-pyrazol-5-yl)pyridin-2-yl)-7-(3-(trifluoromethyl)phenyl)-3,4-dihydro-1,4-methanopyrido[2,3-b][1,4]diazepine-5(2H)-carboxamide Step 1: Preparation of (4S)—N-(6-bromopyridin-2-yl)-7-(3-(trifluoromethyl)phenyl)-3,4-dihydro-1,4-methanopyrido[2,3-b][1,4]diazepine-5(2H)-carboxamide

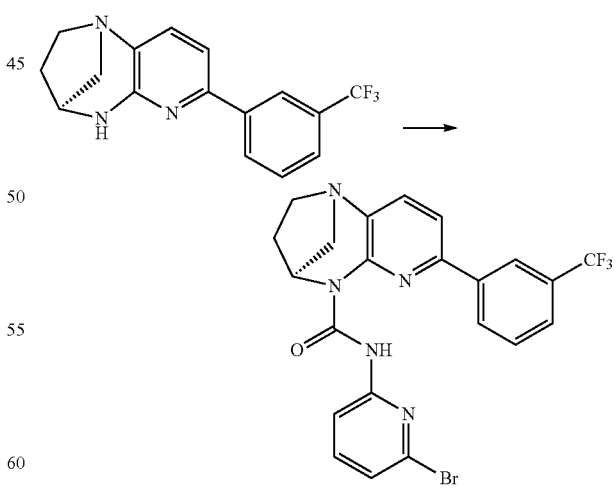

To a solution of triphosgene (1.81 g, 6.10 mmol) in acetonitrile (25 mL) was added a solution of 6-bromopyridin-2-amine (2.26 g, 13.1 mmol) in acetonitrile (25 mL). Triethylamine (8.00 mL, 57.4 mmol) was added, and the reaction stirred at 80° C. for 30 min. (4S)-7-(3-(trifluoromethyl)phenyl)-2,3,4,5-tetrahydro-1,4-methanopyrido[2,3-b][1,4]diazepine (1.04 g, 3.41 mmol) and 4-(dimethylamino)pyridine (410 mg, 3.36 mmol) were added as solids, and the reaction stirred at 80° C. for 1 h. The reaction was cooled to room temperature, poured into water (30 mL), and extracted with dichloromethane (2×50 mL). The combined organic layers were dried with magnesium sulfate, and all solvents removed in vacuo. The remaining residue was purified by flash chromatography (30% to 100% ethyl acetate in pentane) to give (4S)—N-(6-bromopyridin-2-yl)-7-(3-(trifluoromethyl)phenyl)-3,4-dihydro-1,4-methanopyrido[2,3-b][1,4]diazepine-5 (2H)-carboxamide (1.12 g, 2.22 mmol, 65% yield). MS (ESI) calcd for $C_{22}H_{17}BrF_3N_5O$: 503.1; found: 503.8 [M+H].

Step 2: Preparation of (4S)—N-(6-(1-methyl-1H-pyrazol-5-yl)pyridin-2-yl)-7-(3-(trifluoromethyl)phenyl)-3,4-dihydro-1,4-methanopyrido[2,3-b][1,4]diazepine-5 (2H)-carboxamide

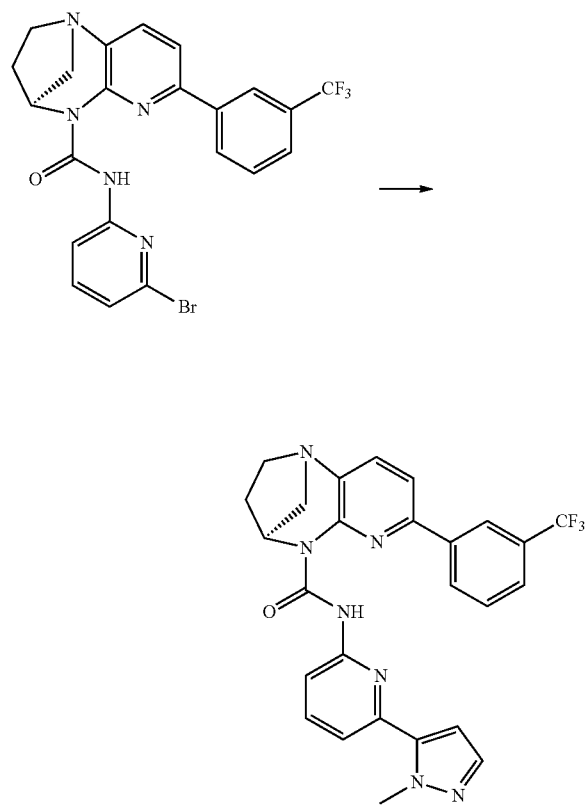

A microwave vial was charged with (4S)—N-(6-bromopyridin-2-yl)-7-(3-(trifluoromethyl)phenyl)-3,4-dihydro-1,4-methanopyrido[2,3-b][1,4]diazepine-5 (2H)-carboxamide (46.0 mg, 0.0912 mmol), tetrakis(triphenylphosphine)palladium (4.8 mg, 0.0042 mmol), cesium fluoride (180 mg, 1.18 mmol), 1-methyl-5-(4,4,5,5-tetramethyl-1,3,2-dioxaborolan-2-yl)-1H-pyrazole (60.0 mg, 0.288 mmol), DME (1.5 mL), and water (150 L). The microwave vial was sealed, and heated in the microwave at 100° C. for 3 h. The organic layer was separated, and the aqueous layer extracted with 10:1 ethyl acetate:methanol (2×2 mL). The combined organic layers were dried with magnesium sulfate, the solvent removed in vacuo, and the remaining residue dissolved in DMSO (4 mL), filtered, and the filtrate purified by preparative HPLC to give (4S)—N-(6-(1-methyl-1H-pyrazol-5-yl)pyridin-2-yl)-7-(3-(trifluoromethyl)phenyl)-3,4-dihydro-1,4-methanopyrido[2,3-b][1,4]diazepine-5(2H)-carboxamide trifluoroacetic acid salt (28.4 mg, 0.0460 mmol, 50% yield). MS (ESI) calcd for $C_{26}H_{22}F_3N_7O$: 505.2; found: 506.0 [M+H].

Example 40: Synthesis of (4S)—N-(3-(piperazin-1-ylmethyl)phenyl)-7-(3-(trifluoromethyl)phenyl)-3,4-dihydro-1,4-methanopyrido[2,3-b][1,4]diazepine-5 (2H)-carboxamide

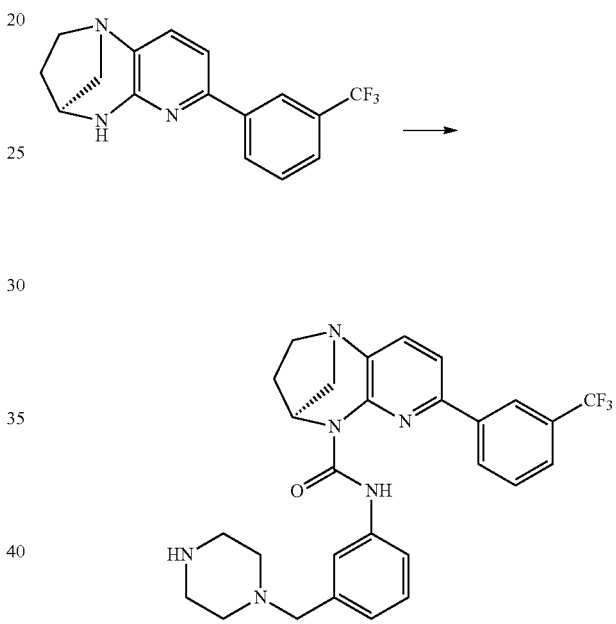

A vial was charged with triphosgene (75.0 mg, 0.253 mmol), and this was dissolved in acetonitrile (2.5 mL). A solution of (4S)-7-(3-(trifluoromethyl)phenyl)-2,3,4,5-tetrahydro-1,4-methanopyrido[2,3-b][1,4]diazepine (150 mg, 0.491 mmol) in acetonitrile (2.5 mL) was added, followed by triethylamine (0.50 mL, 3.59 mmol). The reaction was stirred at room temperature for 4 h, and tert-butyl 4-(3-aminobenzyl)piperazine-1-carboxylate (480 mg, 1.65 mmol) was added as a solid, followed by DMAP (360 mg, 2.95 mmol). The reaction was stirred at 80° C. for 16 h, and all solvents were removed in vacuo. The remaining material was dissolved in trifluoroacetic acid (5.0 mL), and the solution stirred at 50° C. for 20 min. Excess trifluoroacetic acid was removed in vacuo, the remaining material dissolved in DMSO, and the resulting solution purified by preparative HPLC to give (4S)—N-(3-(piperazin-1-ylmethyl)phenyl)-7-(3-(trifluoromethyl)phenyl)-3,4-dihydro-1,4-methanopyrido[2,3-b][1,4]diazepine-5(2H)-carboxamide trifluoroacetate (89.1 mg, 0.140 mmol, 29% yield). MS (ESI) calcd for $C_{28}H_{29}F_3N_6O$: 522.2.

187

Example 41: Synthesis of (4S)—N-(4-(piperazin-1-yl)pyrimidin-2-yl)-7-(3-(trifluoromethyl)phenyl)-3,4-dihydro-1,4-methanopyrido[2,3-b][1,4]diazepine-5(2H)-carboxamide Step 1. Synthesis of tert-butyl 4-(2-((4S)-7-(3-(trifluoromethyl)phenyl)-2,3,4,5-tetrahydro-1,4-methanopyrido[2,3-b][1,4]diazepine-5-carboxamido)pyrimidin-4-yl)piperazine-1-carboxylate

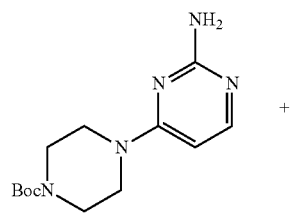

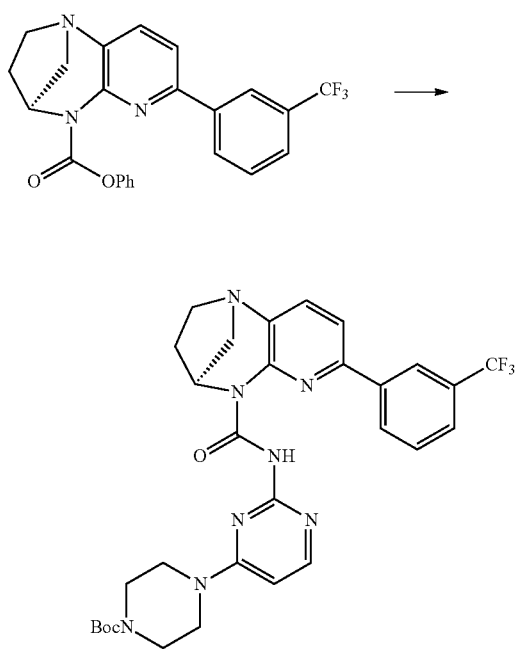

To a solution of tert-butyl 4-(2-aminopyrimidin-4-yl)piperazine-1-carboxylate (200 mg, 0.716 mmol) in THF (20 mL) at 0° C. was added sodium bis(trimethylsilyl)amide solution (1.0 M in THF, 1.50 mL, 1.50 mmol). The reaction was warmed to room temperature and stirred for 30 min, and a solution of (4S)-phenyl 7-(3-(trifluoromethyl)phenyl)-3,4-dihydro-1,4-methanopyrido[2,3-b][1,4]diazepine-5(2H)-carboxylate (327 mg, 1.07 mmol) in THF (5 mL) was added. The reaction was stirred at room temperature for 1.5 h, then the solvent removed in vacuo and the remaining residue purified by prep TLC (3:1 petroleum ether:ethyl acetate) to give tert-butyl 4-(2-((4S)-7-(3-(trifluoromethyl)phenyl)-2,3,4,5-tetrahydro-1,4-methanopyrido[2,3-b][1,4]diazepine-5-carboxamido)pyrimidin-4-yl)piperazine-1-carboxylate (160 mg, 0.262 mmol, 37% yield). MS (ESI) calcd for $C_{30}H_{33}F_3N_8O_3$: 610.3.

188

Step 2. Synthesis of (4S)—N-(4-(piperazin-1-yl)pyrimidin-2-yl)-7-(3-(trifluoromethyl)phenyl)-3,4-dihydro-1,4-methanopyrido[2,3-b][1,4]diazepine-5(2H)-carboxamide

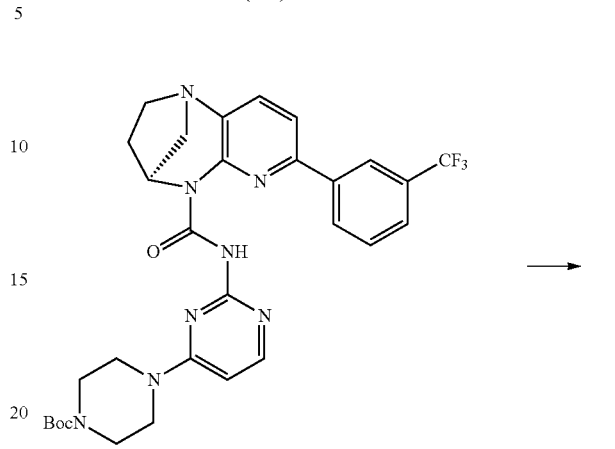

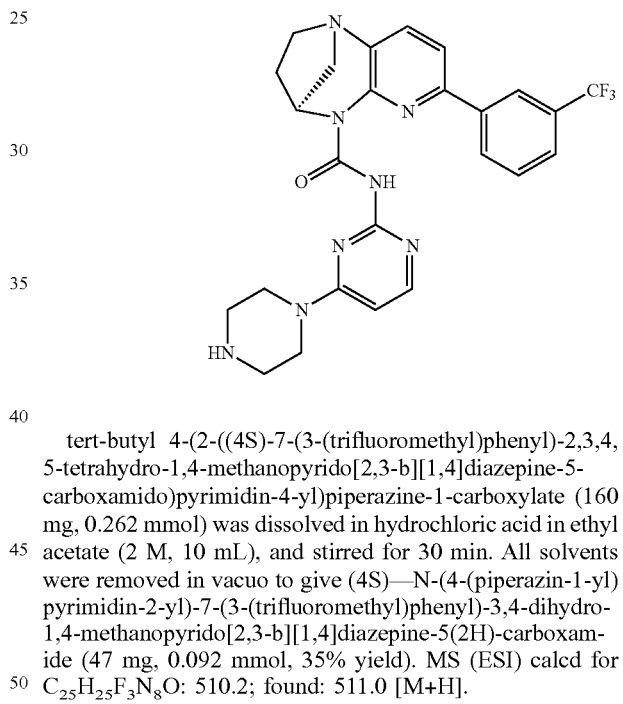

tert-butyl 4-(2-((4S)-7-(3-(trifluoromethyl)phenyl)-2,3,4,5-tetrahydro-1,4-methanopyrido[2,3-b][1,4]diazepine-5-carboxamido)pyrimidin-4-yl)piperazine-1-carboxylate (160 mg, 0.262 mmol) was dissolved in hydrochloric acid in ethyl acetate (2 M, 10 mL), and stirred for 30 min. All solvents were removed in vacuo to give (4S)—N-(4-(piperazin-1-yl)pyrimidin-2-yl)-7-(3-(trifluoromethyl)phenyl)-3,4-dihydro-1,4-methanopyrido[2,3-b][1,4]diazepine-5(2H)-carboxamide (47 mg, 0.092 mmol, 35% yield). MS (ESI) calcd for $C_{25}H_{25}F_3N_8O$: 510.2; found: 511.0 [M+H].

Example 42: Synthesis of tert-butyl (2-(4-(3-((9S)-2-(3-(trifluoromethyl)phenyl)-7,8,9,10-tetrahydro-6H-5,9-methanopyrido[2,3-b][1,4]diazocine-10-carboxamido)phenyl)-1H-1,2,3-triazol-1-yl)ethyl)carbamate

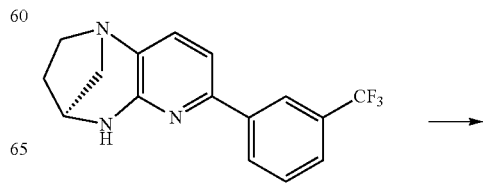

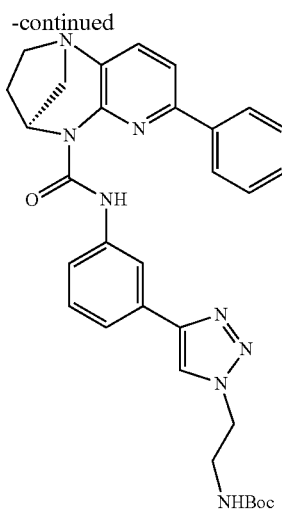

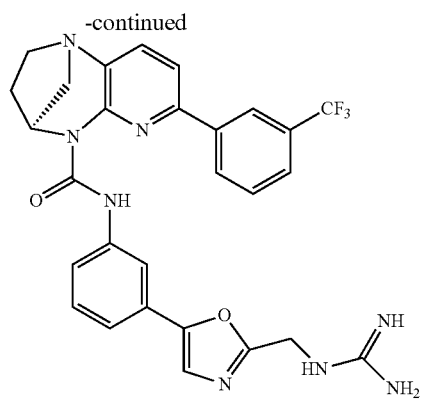

A vial was charged with triphosgene (180 mg, 0.607 mmol), and this was dissolved in dichloromethane (3 mL). A solution of (9S)-2-(3-(trifluoromethyl)phenyl)-7,8,9,10-tetrahydro-6H-5,9-methanopyrido[2,3-b][1,4]diazocine (320 mg, 1.00 mmol) was added, and N,N-diisopropylethylamine (1.00 mL, 5.74 mmol) was added. The reaction was stirred at room temperature for 25 min, and then a solution of tert-butyl (2-(4-(3-aminophenyl)-1H-1,2,3-triazol-1-yl)ethyl)carbamate (415 mg, 1.37 mmol) in dichloromethane (5 mL) was added. The reaction was stirred at 40° C. for 16 h, then heated in a microwave at 120° C. for 1 h. After cooling, the solvent was removed in vacuo, and the remaining residue purified by flash chromatography (0% to 8% methanol in dichloromethane) to give tert-butyl (2-(4-(3-((9S)-2-(3-(trifluoromethyl)phenyl)-7,8,9,10-tetrahydro-6H-5,9-methanopyrido[2,3-b][1,4]diazocine-10-carboxamido)phenyl)-1H-1,2,3-triazol-1-yl)ethyl)carbamate (99.0 mg, 0.153 mmol, 15% yield). MS (ESI) calcd for $C_{33}H_{35}F_3N_8O_3$: 648.3.

Example 43: Preparation of (4S)—N-(3-(2-(guanidinomethyl)oxazol-5-yl)phenyl)-7-(3-(trifluoromethyl)phenyl)-3,4-dihydro-1,4-methanopyrido[2,3-b][1,4]diazepine-5(2H)-carboxamide

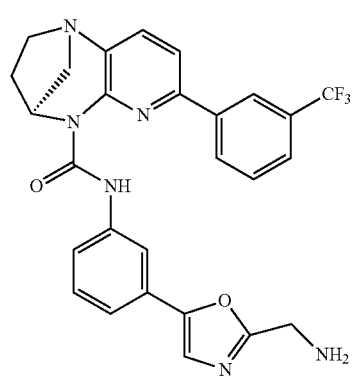

A solution of 1H-pyrazole-1-carboximidamide hydrochloride (15 mg, 0.10 mmol) and DIEA (17 μL, 0.10 mmol) in DMF (1 mL) was stirred at room temperature for 10 min, the (4S)—N-(3-(2-(aminomethyl)oxazol-5-yl)phenyl)-7-(3-(trifluoromethyl)phenyl)-3,4-dihydro-1,4-methanopyrido[2,3-b][1,4]diazepine-5(2H)-carboxamide (52 mg, 0.10 mmol) was added. The reaction mixture was stirred at room temperature overnight and then purified by prep-HPLC and lyophilized to obtain (4S)—N-(3-(2-(guanidinomethyl)oxazol-5-yl)phenyl)-7-(3-(trifluoromethyl)phenyl)-3,4-dihydro-1,4-methanopyrido[2,3-b][1,4]diazepine-5 (2H)-carboxamide trifluoroacetic acid salt (25.5 mg, 38% yield). MS (ESI) calcd for $C_{28}H_{25}F_3N_8O_2$: 562.21; found: 563 [M+H].

This general procedure was used to prepare other guanidines by substituting (4S)—N-(3-(2-(aminomethyl)oxazol-5-yl)phenyl)-7-(3-(trifluoromethyl)phenyl)-3,4-dihydro-1,4-methanopyrido[2,3-b][1,4]diazepine-5(2H)-carboxamide with the appropriate amine.

Example 44: Synthesis of (4S)—N-(pyrimidin-4-yl)-7-(3-(trifluoromethyl)piperidin-1-yl)-3,4-dihydro-1,4-methanopyrido[2,3-b][1,4]diazepine-5 (2H)-carboxamide Step 1. Synthesis of (9S)-2-(3-(trifluoromethyl)piperidin-1-yl)-7,8,9,10-tetrahydro-6H-5,9-methanopyrido[2,3-b][1,4]diazocine

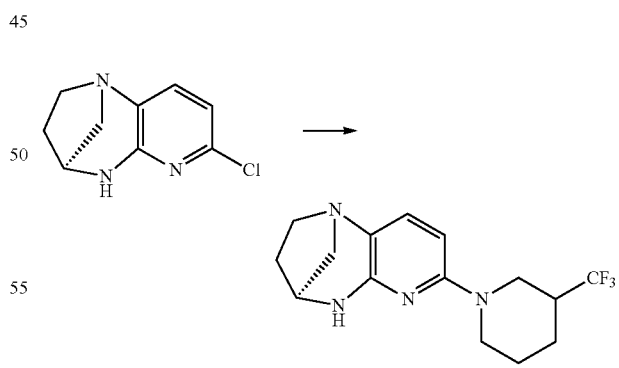

A 20 mL microwave vial was charged with a magnetic stir bar, (9S)-2-chloro-7,8,9,10-tetrahydro-6H-5,9-methanopyrido[2,3-b][1,4]diazocine (629 mg, 3.00 mmol), [1,3-Bis(2,6-di-isopropylphenyl)-4,5-dihydroimidazol-2-ylidene]chloro]allylpalladium(II) (62.1 mg, 0.120 mmol), 3-trifluoromethylpiperidine (919 mg, 6.00 mmol) and potassium tert-butoxide (673 mg, 6.00 mmol). DME (7.0 mL) was added, the microwave vial capped, and heated to 90° C.

for 2 h. After cooling to room temperature, methanol (5 mL) and silica gel (5 g) were added, and all solvents were removed in vacuo. The remaining silica gel slurry was loaded atop a 40 g silica gel column, and flash chromatography (50% to 100% ethyl acetate in pentane) gave (9S)-2-(3-(trifluoromethyl)piperidin-1-yl)-7,8,9,10-tetrahydro-6H-5,9-methanopyrido[2,3-b][1,4]diazocine 2 as a 1:1 mixture of diastereomers (713 mg, 2.18 mmol, 73% yield). MS (ESI) calcd for $C_{16}H_{21}F_3N_4$: 326.2.

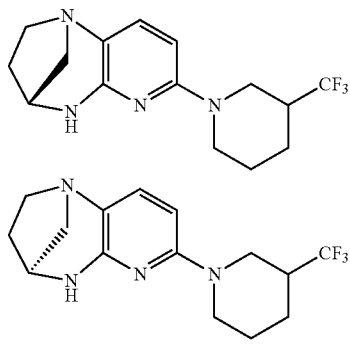

Step 2. Synthesis of (4S)—N-(pyrimidin-4-yl)-7-(3-(trifluoromethyl)piperidin-1-yl)-3,4-dihydro-1,4-methanopyrido[2,3-b][1,4]diazepine-5(2H)-carboxamide

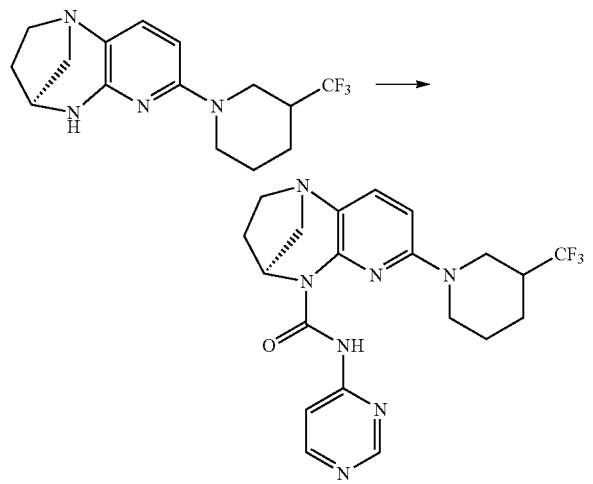

To a solution of (4S)-7-(3-(trifluoromethyl)piperidin-1-yl)-2,3,4,5-tetrahydro-1,4-methanopyrido[2,3-b][1,4]diazepine (40.0 mg, 0.128 mmol) in acetonitrile (2 mL) and pyridine (1 mL) was added triphosgene (26.0 mg, 0.0876 mmol) as a solid. The resulting red solution was stirred at 50° C. for 1 h. 4-aminopyrimidine (95.0 mg, 1.00 mmol) was then added as a solid, and the reaction stirred at 70° C. for 6 h. After 6 h, most of the acetonitrile was removed under a nitrogen stream, and methanol (1 mL) and DMSO (2 mL) was added to the reaction. The resulting solution was purified by prep HPLC, and the isolated material lyophilized from acetonitrile/aqueous 1N HCl to give (4S)—N-(pyrimidin-4-yl)-7-(3-(trifluoromethyl)piperidin-1-yl)-3,4-dihydro-1,4-methanopyrido[2,3-b][1,4]diazepine-5(2H)-carboxamide hydrochloride (34.9 mg, 0.0743 mmol, 58% yield). MS (ESI) calcd for $C_{20}H_{22}F_3N_7O$: 433.2.

Example 45: Synthesis of (4S)-7-((S)-3-(dimethylamino)pyrrolidin-1-yl)-N-(pyridin-3-yl)-3,4-dihydro-1,4-methanopyrido[2,3-b][1,4]diazepine-5(2H)-carboxamide Step 1. Synthesis of (3S)—N,N-dimethyl-1-((4S)-2,3,4,5-tetrahydro-1,4-methanopyrido[2,3-b][1,4]diazepin-7-yl)pyrrolidin-3-amine

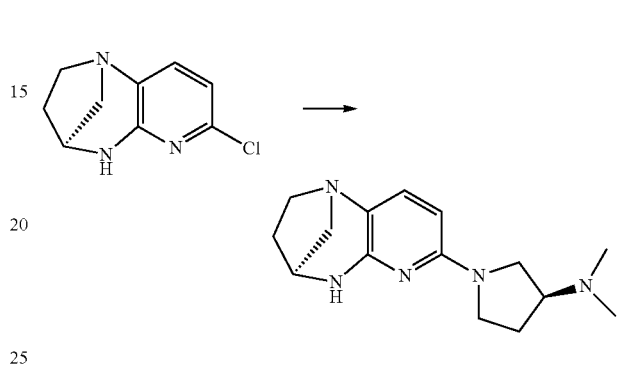

A 20 mL microwave vial was charged with a magnetic stir bar, (4S)-7-chloro-2,3,4,5-tetrahydro-1,4-methanopyrido[2,3-b][1,4]diazepine (978 mg, 5.00 mmol), [1,3-Bis(2,6-diisopropylphenyl)-4,5-dihydroimidazol-2-ylidene]chloro]allylpalladium(II) (51.7 mg, 0.100 mmol), (S)—N,N-dimethylpyrrolidin-3-amine (1.14 g, 10.00 mmol) and potassium tert-butoxide (1.12 mg, 10.00 mmol). DME (10.0 mL) was added, the microwave vial capped, and heated to 100° C. for 4 h. After cooling to room temperature, methanol (20 mL) and silica gel (5 g) were added, and all solvents were removed in vacuo. The remaining silica gel slurry was loaded atop a 40 g silica gel column, and flash chromatography (0% to 10% methanol in pentane) gave (3S)—N,N-dimethyl-1-((4S)-2,3,4,5-tetrahydro-1,4-methanopyrido[2,3-b][1,4]diazepin-7-yl)pyrrolidin-3-amine (524 mg, 1.92 mmol, 38% yield). MS (ESI) calcd for $C_{15}H_{23}N_5$: 273.2.

Step 2. Synthesis of (4S)-7-((S)-3-(dimethylamino)pyrrolidin-1-yl)-N-(pyridin-3-yl)-3,4-dihydro-1,4-methanopyrido[2,3-b][1,4]diazepine-5(2H)-carboxamide

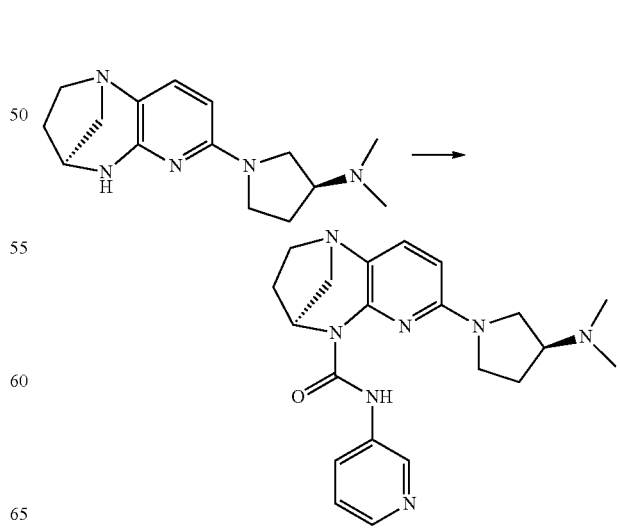

To a solution of (3S)—N,N-dimethyl-1-((4S)-2,3,4,5-tetrahydro-1,4-methanopyrido[2,3-b][1,4]diazepin-7-yl)pyrrolidin-3-amine (40.0 mg, 0.146 mmol) in acetonitrile (540 µL) and pyridine (150 µL) was added a solution of triphosgene (28.9 mg, 0.0975 mmol) in acetonitrile (310 µL). The reaction was stirred at 50° C. for 30 min, then triethylamine (40 µL) was added. 3-aminopyridine (94 mg, 1.00 mmol) was added as a solid, and the reaction stirred at 60° C. for 16 h. After 16 h, the reaction was cooled to room temperature, methanol (1 mL) was added, and the resulting solution purified by preparative HPLC. The isolated material was lyophilized from acetonitrile/aqueous 1N HCl to give (4S)-7-((S)-3-(dimethylamino)pyrrolidin-1-yl)-N-(pyridin-3-yl)-3,4-dihydro-1,4-methanopyrido[2,3-b][1,4]diazepine-5(2H)-carboxamide hydrochloride (30.6 mg, 0.0712 mmol, 49% yield). MS (ESI) calcd for $C_{21}H_{27}N_7O$: 393.2.

Example 46: Synthesis of tert-butyl 4-((9S)-10-(pyrimidin-4-ylcarbamoyl)-7,8,9,10-tetrahydro-6H-5,9-methanopyrido[2,3-b][1,4]diazocin-2-yl)-1,4-diazepane-1-carboxylate Step 1. Synthesis of tert-butyl 4-((9S)-7,8,9,10-tetrahydro-6H-5,9-methanopyrido[2,3-b][1,4]diazocin-2-yl)-1,4-diazepane-1-carboxylate

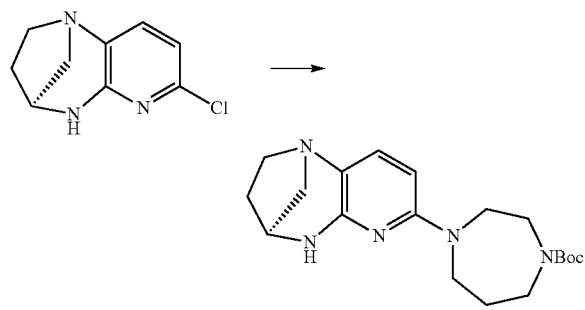

A 20 mL microwave vial was charged with a magnetic stir bar, (9S)-2-chloro-7,8,9,10-tetrahydro-6H-5,9-methanopyrido[2,3-b][1,4]diazocine (500 mg, 2.38 mmol), [1,3-Bis(2,6-di-isopropylphenyl)-4,5-dihydroimidazol-2-ylidene]chloro]allylpalladium(II) (12.4 mg, 0.0240 mmol), tert-butyl homopiperazine-1-carboxylate (953 mg, 4.76 mmol) and potassium tert-butoxide (534 mg, 4.76 mmol). DME (5.0 mL) was added, the vial was sealed, and heated in the microwave at 85° C. for 4 h. After cooling to room temperature, methanol (20 mL) and silica gel (5 g) were added, all solvents were removed in vacuo, and the remaining silica gel slurry was loaded atop a 40 g silica gel column. Flash chromatography (0% to 8% methanol in dichloromethane) gave tert-butyl 4-((9S)-7,8,9,10-tetrahydro-6H-5,9-methanopyrido[2,3-b][1,4]diazocin-2-yl)-1,4-diazepane-1-carboxylate (550 mg, 1.48 mmol, 62% yield). MS (ESI) calcd for $C_{20}H_{31}N_5O_2$: 373.2; found: 374.2 [M+H].

Step 2. Synthesis of tert-butyl 4-((9S)-10-(pyrimidin-4-ylcarbamoyl)-7,8,9,10-tetrahydro-6H-5,9-methanopyrido[2,3-b][1,4]diazocin-2-yl)-1,4-diazepane-1-carboxylate

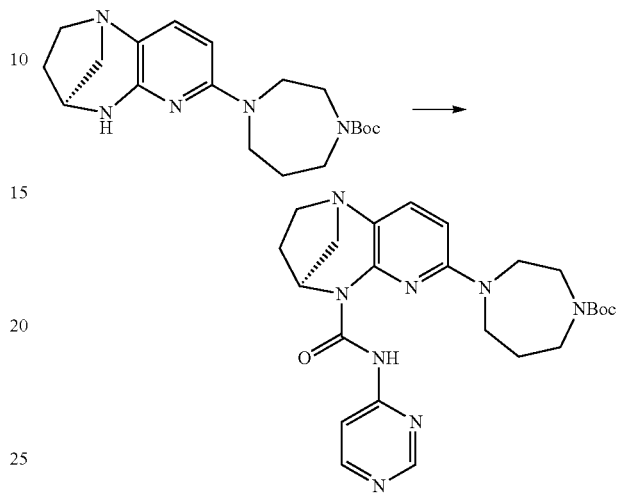

A mixture of tert-butyl 4-((9S)-7,8,9,10-tetrahydro-6H-5,9-methanopyrido[2,3-b][1,4]diazocin-2-yl)-1,4-diazepane-1-carboxylate (500 mg, 1.34 mmol), pyrimidin-4-yl-carbamic acid phenyl ester (570 mg, 2.65 mmol), 4-dimethylaminopyridine (190 mg, 1.56 mmol) in acetonitrile (30 mL) was stirred at 60° C. for 3.5 h. Solvent was removed under reduced pressure, the residue was dissolved in dichloromethane, washed with water, brine, and the organic layer dried over anhydrous Na2SO4. All solvent was removed in vacuo, and the remaining residue purified through silica gel chromatography with dichloromethane:ethyl acetate (2:1), then purified through preparative thin layer chromatography with 3% methanol in dichloromethane to give tert-butyl 4-((9S)-10-(pyrimidin-4-ylcarbamoyl)-7,8,9,10-tetrahydro-6H-5,9-methanopyrido[2,3-b][1,4]diazocin-2-yl)-1,4-diazepane-1-carboxylate (363 mg, 0.734 mmol, 55% yield). MS (ESI) calcd for $C_{25}H_{34}N_8O_3$: 494.3; found: 495.4 [M+H].

Example 47: Synthesis of (9S)-2-(1,4-diazepan-1-yl)-N-(pyrimidin-4-yl)-8,9-dihydro-6H-5,9-methanopyrido[2,3-b][1,4]diazocine-10(7H)-carboxamide

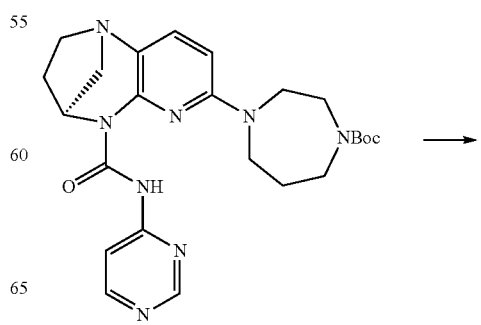

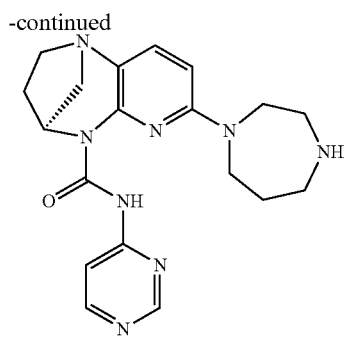

tert-butyl 4-((9S)-10-(pyrimidin-4-ylcarbamoyl)-7,8,9,10-tetrahydro-6H-5,9-methanopyrido[2,3-b][1,4]diazocin-2-yl)-1,4-diazepane-1-carboxylate (400 mg, 0.808 mmol) was dissolved in 1M HCl in MeOH (20 mL), and the reaction mixture was stirred at room temperature for 1.5 h. All solvent was removed in vacuo. Water (20 mL) and potassium carbonate (344 mg, 2.42 mmol) were added, and the mixture was stirred at room temperature for 1 h. Extraction with dichloromethane (3×5 mL) and drying the solvent in vacuo gave (9S)-2-(1,4-diazepan-1-yl)-N-(pyrimidin-4-yl)-8,9-dihydro-6H-5,9-methanopyrido[2,3-b][1,4]diazocine-10(7H)-carboxamide (300 mg, 0.761 mmol, 94% yield). MS (ESI) calcd for $C_{20}H_{26}N_8O$: 394.2.

Example 48: Synthesis of (9S)-2-(4-(methylsulfonyl)-1,4-diazepan-1-yl)-N-(pyrimidin-4-yl)-8,9-dihydro-6H-5,9-methanopyrido[2,3-b][1,4]diazocine-10(7H)-carboxamide

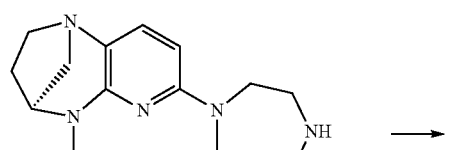

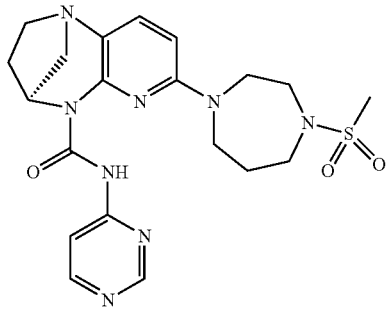

To a solution of (9S)-2-(1,4-diazepan-1-yl)-N-(pyrimidin-4-yl)-8,9-dihydro-6H-5,9-methanopyrido[2,3-b][1,4]diazocine-10(7H)-carboxamide (60.0 mg, 0.152 mmol) in dichloromethane (3 mL) was added triethylamine (46.1 mg, 0.457 mmol) and methanesulfonyl chloride (18.1 mg, 0.152 mmol). The mixture was stirred at 0° C. for 1 h. The solution was washed with water, brine, and the organic layer dried over anhydrous Na2SO4. The remaining solution was purified through preparative thin layer chromatography with 3% methanol in dichloromethane to give (9S)-2-(4-(methylsulfonyl)-1,4-diazepan-1-yl)-N-(pyrimidin-4-yl)-8,9-dihydro-6H-5,9-methanopyrido[2,3-b][1,4]diazocine-10(7H)-carboxamide (30.0 mg, 0.0635 mmol, 42% yield). MS (ESI) calcd for $C_{21}H_{28}N_8O_3S$: 472.2.

Example 49: Synthesis of (9S)-2-(4-methyl-1,4-diazepan-1-yl)-N-(pyrimidin-4-yl)-8,9-dihydro-6H-5,9-methanopyrido[2,3-b][1,4]diazocine-10(7H)-carboxamide

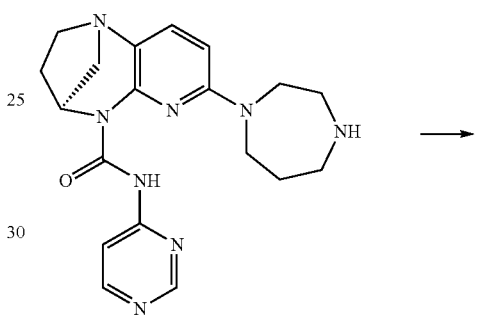

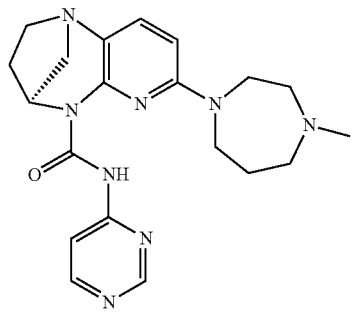

To a solution of (9S)-2-(1,4-diazepan-1-yl)-N-(pyrimidin-4-yl)-8,9-dihydro-6H-5,9-methanopyrido[2,3-b][1,4]diazocine-10(7H)-carboxamide (100 mg, 0.254 mmol) in methanol (3 mL) was added formaldehyde (37% in water, 20 µL) and 10% palladium on carbon (10 mg). The reaction was stirred under hydrogen atmosphere for 1 h. The solvent was removed in vacuo, and the remaining residue purified by preparative thin layer chromatography with 3% methanol in dichloromethane to give (9S)-2-(4-methyl-1,4-diazepan-1-yl)-N-(pyrimidin-4-yl)-8,9-dihydro-6H-5,9-methanopyrido[2,3-b][1,4]diazocine-10(7H)-carboxamide (22.2 mg, 0.0543 mmol, 21% yield). MS (ESI) calcd for $C_{21}H_{28}N_8O$: 408.2.

Example 50: Synthesis of (9S)-2-(4-isopropyl-1,4-diazepan-1-yl)-N-(pyrimidin-4-yl)-8,9-dihydro-6H-5,9-methanopyrido[2,3-b][1,4]diazocine-10(7H)-carboxamide

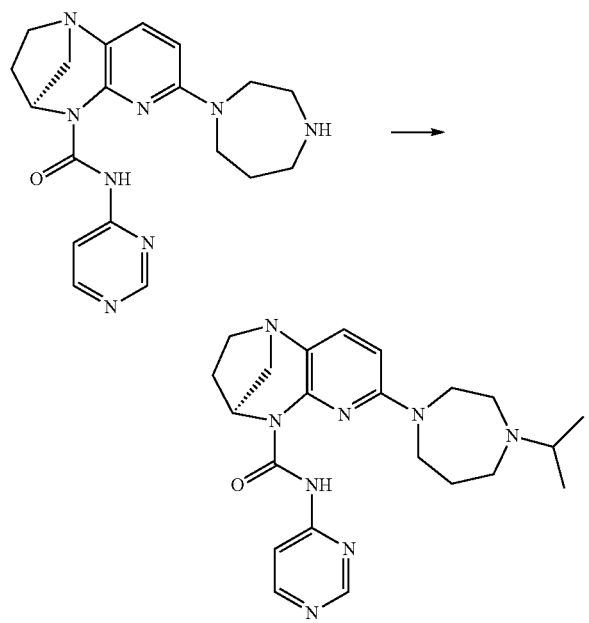

To a solution of (9S)-2-(1,4-diazepan-1-yl)-N-(pyrimidin-4-yl)-8,9-dihydro-6H-5,9-methanopyrido[2,3-b][1,4]diazocine-10(7H)-carboxamide (50.0 mg, 0.127 mmol) in dichloromethane (3 mL) was added acetone (12.9 mg, 0.254 mmol). The mixture was stirred for 30 min, and sodium cyanoborohydride (20.1 mg, 0.0759 mmol) was added as a solid, and the reaction stirred at room temperature overnight. All solvent was removed in vacuo, and the remaining residue purified by preparative thin layer chromatography (100% ethyl acetate) to give (9S)-2-(4-isopropyl-1,4-diazepan-1-yl)-N-(pyrimidin-4-yl)-8,9-dihydro-6H-5,9-methanopyrido[2,3-b][1,4]diazocine-10(7H)-carboxamide (16.8 mg, 0.0385 mmol, 30% yield). MS (ESI) calcd for $C_{23}H_{32}N_8O$: 436.3.

Example 51: Synthesis of (9S)—N-(pyrimidin-4-yl)-2-(4-(2,2,2-trifluoroethyl)-1,4-diazepan-1-yl)-8,9-dihydro-6H-5,9-methanopyrido[2,3-b][1,4]diazocine-10(7H)-carboxamide

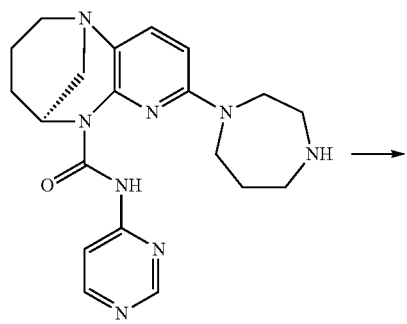

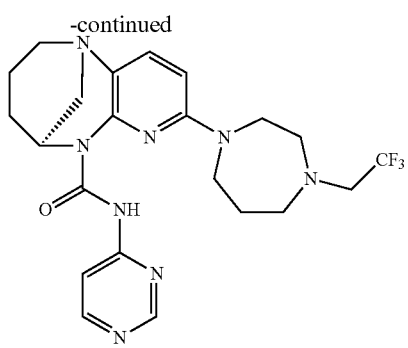

To a solution of (9S)-2-(1,4-diazepan-1-yl)-N-(pyrimidin-4-yl)-8,9-dihydro-6H-5,9-methanopyrido[2,3-b][1,4]diazocine-10(7H)-carboxamide (100 mg, 0.254 mmol) in DMF (3 mL) was added sodium carbonate (80.7 mg, 0.761 mmol) and 2,2,2-trifluoroethyl trifluoromethanesulfonate (163 mg, 0.508 mmol). The reaction was stirred at room temperature overnight, then diluted with dichloromethane (10 mL), and washed with water, brine, and dried with sodium sulfate. All solvent was removed in vacuo, and the remaining residue purified by preparative thin layer chromatography with 3% methanol in dichloromethane to give (9S)—N-(pyrimidin-4-yl)-2-(4-(2,2,2-trifluoroethyl)-1,4-diazepan-1-yl)-8,9-dihydro-6H-5,9-methanopyrido[2,3-b][1,4]diazocine-10(7H)-carboxamide (19.5 mg, 0.0409 mmol, 16% yield). MS (ESI) calcd for $C_{22}H_{27}F_3N_8O$: 476.2.

Example 52: Synthesis of (4S)-7-(4-(2,2,2-trifluoroethyl)-1,4-diazepan-1-yl)-2,3,4,5-tetrahydro-1,4-methanopyrido[2,3-b][1,4]diazepine Step 1. Synthesis of tert-butyl 4-((4S)-2,3,4,5-tetrahydro-1,4-methanopyrido[2,3-b][1,4]diazepin-7-yl)-1,4-diazepane-1-carboxylate

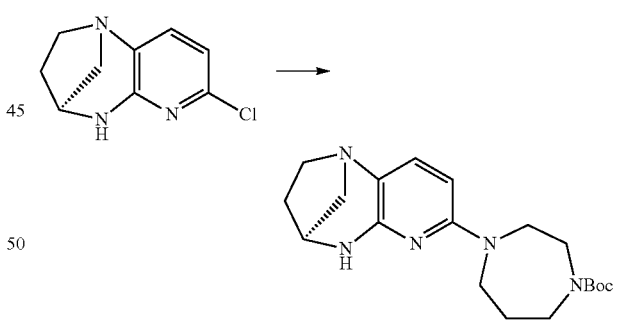

To a solution of (4S)-7-chloro-2,3,4,5-tetrahydro-1,4-methanopyrido[2,3-b][1,4]diazepine (500 mg, 2.56 mmol), N-Boc homopiperazine (953 mg, 4.76 mmol), potassium tert-butoxide (534 mg, 4.76 mmol) in DME (5 mL) was added [1,3-bis(2,6-di-isopropylphenyl)-4,5-dihydroimidazol-2-ylidene]chloro]allylpalladium(II) (12.4 mg, 0.0240 mmol). The mixture was heated to 90° C. for 3 h. After cooling, water was added, and the mixture extracted with ethyl acetate (3×15 mL). The combined organic layers were washed with brine, dried with sodium sulfate, filtered, and concentrated. The remaining residue was purified by silica gel chromatography (5:1 pentane:ethyl acetate) to give tert-butyl 4-((4S)-2,3,4,5-tetrahydro-1,4-methanopyrido[2,3-b]

[1,4]diazepin-7-yl)-1,4-diazepane-1-carboxylate (610 mg, 1.70 mmol, 66% yield). MS (ESI) calcd for $C_{19}H_{29}N_5O_2$: 359.2.

Step 2. Synthesis of (4S)-7-(1,4-diazepan-1-yl)-2,3,4,5-tetrahydro-1,4-methanopyrido[2,3-b][1,4]diazepine

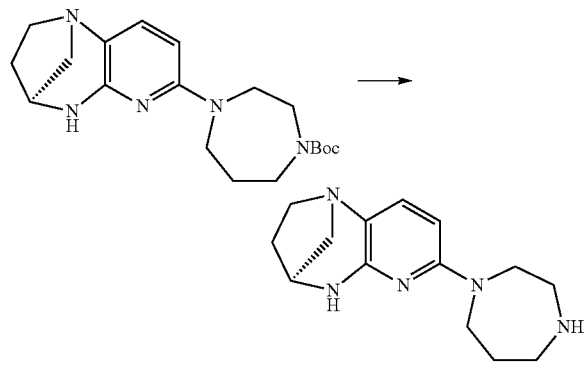

A mixture of tert-butyl 4-((4S)-2,3,4,5-tetrahydro-1,4-methanopyrido[2,3-b][1,4]diazepin-7-yl)-1,4-diazepane-1-carboxylate (610 mg, 1.70 mmol) and HCl in EtOAc (5M, 10 mL) was stirred at room temperature for 30 min. The solvent was removed to give (4S)-7-(1,4-diazepan-1-yl)-2,3,4,5-tetrahydro-1,4-methanopyrido[2,3-b][1,4]diazepine (418 mg, 1.61 mmol, 95% yield). MS (ESI) calcd for $C_{14}H_{21}N_5$: 259.2.

Step 3. Synthesis of (4S)-7-(4-(2,2,2-trifluoroethyl)-1,4-diazepan-1-yl)-2,3,4,5-tetrahydro-1,4-methanopyrido[2,3-b][1,4]diazepine

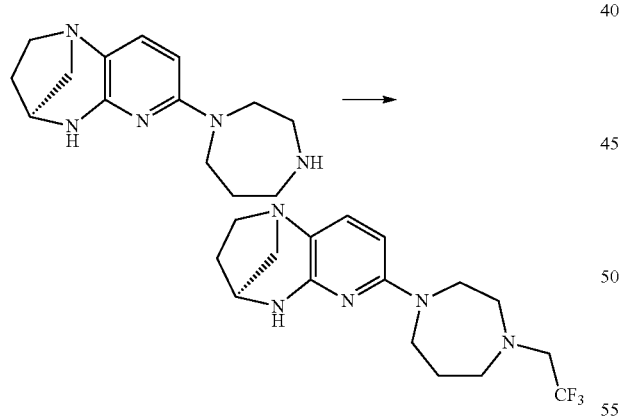

To a solution of (4S)-7-(1,4-diazepan-1-yl)-2,3,4,5-tetrahydro-1,4-methanopyrido[2,3-b][1,4]diazepine (418 mg, 1.61 mmol) in DMF (5 mL) was added 2,2,2-trifluoroethyltrifluoromethanesulfonate (748 mg, 3.23 mmol) and potassium carbonate (666 mg, 4.83 mmol). The reaction was stirred at room temperature overnight. The reaction was diluted with water, extracted with ethyl acetate (3×10 mL), and the combined organic layers washed with brine, dried with sodium sulfate, filtered, and concentrated. The remaining residue was purified by silica gel chromatography (6:1 pentane:ethyl acetate) to give (4S)-7-(4-(2,2,2-trifluoroethyl)-1,4-diazepan-1-yl)-2,3,4,5-tetrahydro-1,4-methanopyrido[2,3-b][1,4]diazepine (320 mg, 0.937 mmol, 58% yield). MS (ESI) calcd for $C_{16}H_{22}F_3N_5$: 341.2.

Example 53: Synthesis of (4S)—N-(3-(oxazol-5-yl)phenyl)-7-((R)-3-(trifluoromethyl)piperidin-1-yl)-3,4-dihydro-1,4-methanopyrido[2,3-b][1,4]diazepine-5(2H)-carboxamide and (4S)—N-(3-(oxazol-5-yl)phenyl)-7-((S)-3-(trifluoromethyl)piperidin-1-yl)-3,4-dihydro-1,4-methanopyrido[2,3-b][1,4]diazepine-5(2H)-carboxamide

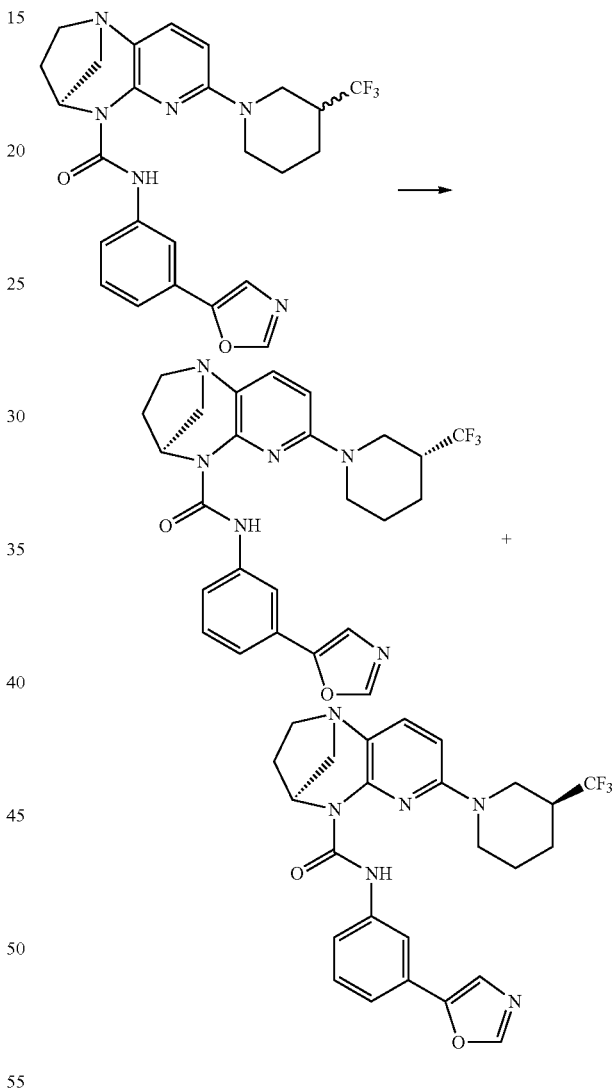

(4S)—N-(3-(oxazol-5-yl)phenyl)-7-(3-(trifluoromethyl)piperidin-1-yl)-3,4-dihydro-1,4-methanopyrido[2,3-b][1,4]diazepine-5(2H)-carboxamide (120 mg, 0.241 mmol) was loaded onto a 30×250 mm chiralcel OD-H column. Elution with 20:80 ethanol:heptanes first eluted (4S)—N-(3-(oxazol-5-yl)phenyl)-7-((R)-3-(trifluoromethyl)piperidin-1-yl)-3,4-dihydro-1,4-methanopyrido[2,3-b][1,4]diazepine-5(2H)-carboxamide (41.3 mg, 0.0828 mmol, 34% yield), $[\alpha]_D^{25}=+32$ (c, 0.09, MeOH), followed by (4S)—N-(3-(oxazol-5-yl)phenyl)-7-((S)-3-(trifluoromethyl)piperidin-1-yl)-3,4-dihydro-1,4-methanopyrido[2,3-b][1,4]diazepine-5(2H)-carboxamide (44.8 mg, 0.0899 mmol, 37% yield)

$[\alpha]_D^{25}$=+18.5 (c, 0.11, MeOH). MS (ESI) calcd for $C_{25}H_{25}F_3N_6O_2$: 498.2; found: 499.3 [M+H].

Example 54. Preparation of (5S)—N-(5-fluoropyridin-3-yl)-8-(3-(trifluoromethyl)phenyl)-4,5-dihydro-2,5-methanopyrido[2,3-g][1,2,6]thiadiazocine-6(3H)-carboxamide 1,1-dioxide Step 1. Synthesis of (S)-tert-butyl (1-((2,6-dichloropyridin-3-yl)sulfonyl)pyrrolidin-3-yl)carbamate

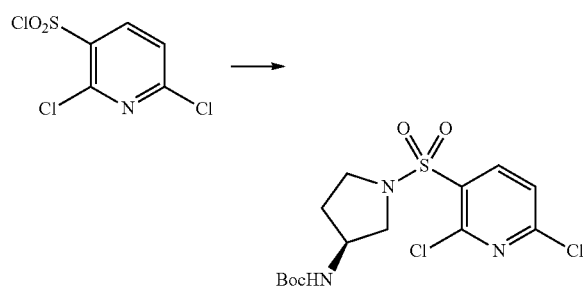

To a solution of 2,6-dichloropyridine-3-sulfonyl chloride (Org. Process Res. Dev. 2009, 13, 875-879) (3.40 g, 13.8 mmol) in dichloromethane (10 mL) was added (S)-tert-butyl pyrrolidin-3-ylcarbamate (2.82 g, 14.5 mmol), followed by triethylamine (3.00 mL, 21.5 mmol). The reaction was stirred at room temperature for 30 min, then poured into saturated sodium bicarbonate, and extracted with dichloromethane. The organic layer was washed with brine, dried with $Na_2SO_4$, and the solvent removed in vacuo, to give (S)-tert-butyl (1-((2,6-dichloropyridin-3-yl)sulfonyl)pyrrolidin-3-yl)carbamate (5.47 g, 13.8 mmol, 100% yield).

Step 2. Synthesis of (5S)-8-chloro-3,4,5,6-tetrahydro-2,5-methanopyrido[2,3-g][1,2,6]thiadiazocine 1,1-dioxide

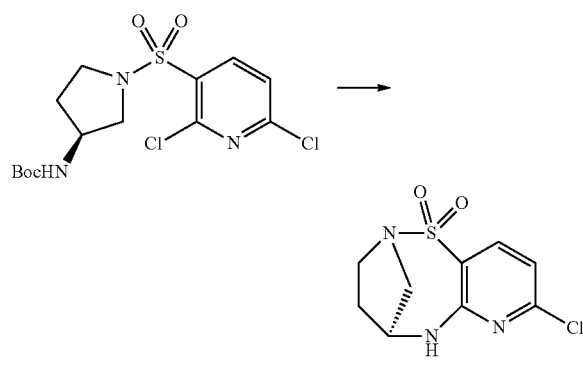

To a solution of (S)-tert-butyl (1-((2,6-dichloropyridin-3-yl)sulfonyl)pyrrolidin-3-yl)carbamate (5.47 g, 13.8 mmol) in dichloromethane (30 mL) was added trifluoroacetic acid (10 mL). The reaction was stirred at room temperature overnight, and all solvent removed in vacuo. The remaining residue was dissolved in DMF (30 mL), and sodium carbonate (10.0 g, 94.3 mmol) was added. The reaction was stirred at 90° C. for 2 h. The reaction was cooled to room temperature, poured into ice water, and the resulting solution was filtered, and the solids washed with water. The collected solid was dried, and purified by silica gel chromatography to give (5S)-8-chloro-3,4,5,6-tetrahydro-2,5-methanopyrido[2,3-g][1,2,6]thiadiazocine 1,1-dioxide (1.80 g, 6.93 mmol, 50% yield).

Step 3. Synthesis of (5S)-8-(3-(trifluoromethyl)phenyl)-3,4,5,6-tetrahydro-2,5-methanopyrido[2,3-g][1,2,6]thiadiazocine 1,1-dioxide

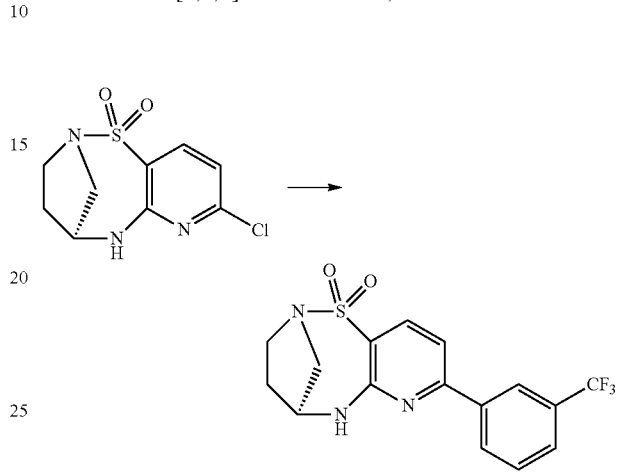

A mixture of (5S)-8-chloro-3,4,5,6-tetrahydro-2,5-methanopyrido[2,3-g][1,2,6]thiadiazocine 1,1-dioxide (800 mg, 3.08 mmol), 3-trifluoromethylbenzeneboronic acid (1.17 g, 6.16 mmol), cesium carbonate (3.00 g, 9.21 mmol) and [1,1'-bis(diphenylphosphino)ferrocene]dichloropalladium (II) (370 mg, 0.453 mmol) in 10:1 dioxane:water (45 mL) was stirred at 110° C. overnight. After cooling, the solvent was removed in vacuo, and the residue partitioned between dichloromethane and water. The organic layer was separated, washed with water, brine, dried with $Na_2SO_4$, and the solvent removed in vacuo. The remaining residue was purified by silica gel chromatography to give (5S)-8-(3-(trifluoromethyl)phenyl)-3,4,5,6-tetrahydro-2,5-methanopyrido[2,3-g][1,2,6]thiadiazocine 1,1-dioxide (1.00 g, 2.71 mmol, 88% yield).

Step 4. Synthesis of (5S)-8-((S)-3-fluoropyrrolidin-1-yl)-3,4,5,6-tetrahydro-2,5-methanopyrido[2,3-g][1,2,6]thiadiazocine 1,1-dioxide

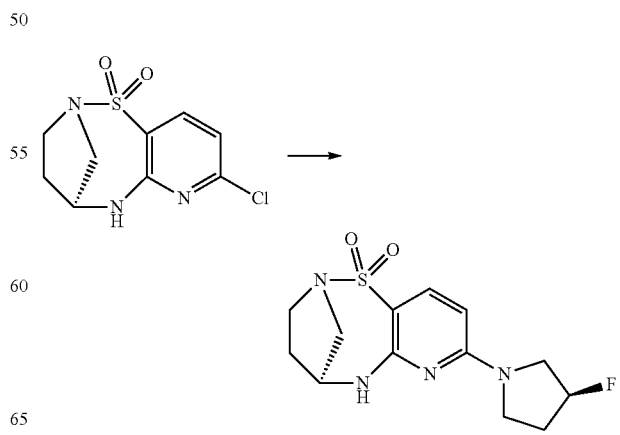

(S)-3-fluoropyrrolidine hydrochloride (1.10 g, 8.76 mmol) was added to a solution of (5S)-8-chloro-3,4,5,6-tetrahydro-2,5-methanopyrido[2,3-g][1,2,6]thiadiazocine 1,1-dioxide (800 mg, 3.08 mmol) and sodium carbonate (1.60 g, 15.1 mmol) in DMF (10 mL). The reaction was stirred at 90° C. for 6 h, then poured onto crushed ice, stirred, and filtered. The collected solid was washed with water, dried, and purified by silica gel chromatography to give (5S)-8-((S)-3-fluoropyrrolidin-1-yl)-3,4,5,6-tetrahydro-2,5-methanopyrido[2,3-g][1,2,6]thiadiazocine 1,1-dioxide (680 mg, 2.18 mmol, 71% yield).

Step 5. Synthesis of (5S)—N-(5-fluoropyridin-3-yl)-8-(3-(trifluoromethyl)phenyl)-4,5-dihydro-2,5-methanopyrido[2,3-g][1,2,6]thiadiazocine-6(3H)-carboxamide 1,1-dioxide

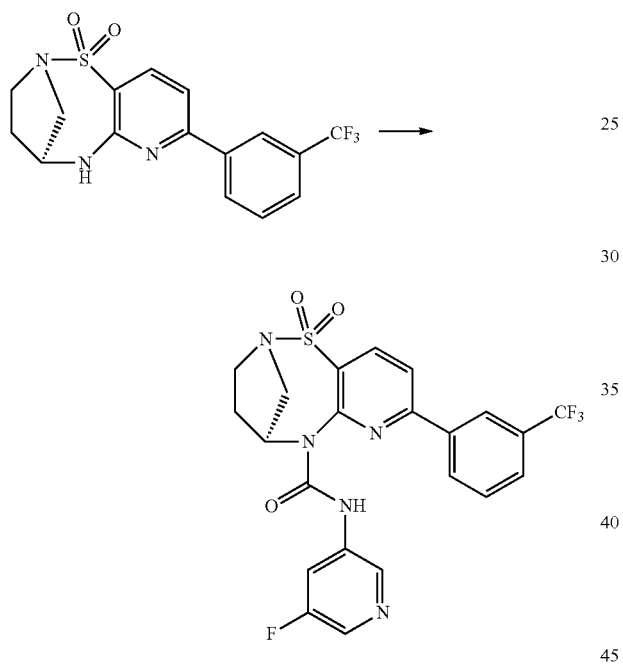

(5S)-8-(3-(trifluoromethyl)phenyl)-3,4,5,6-tetrahydro-2,5-methanopyrido[2,3-g][1,2,6]thiadiazocine 1,1-dioxide (70.0 mg, 0.190 mmol) was dissolved in DMF (3 mL), and sodium hydride (54 mg, 60% in oil, 1.35 mmol) was added. The reaction was stirred at room temperature for 2 h, and phenyl (5-fluoropyridin-3-yl)carbamate (176 mg, 0.768 mmol) was added. The reaction was stirred at room temperature for 1 h, poured into water, and extracted with dichloromethane. The organic layer was concentrated in vacuo, and the remaining residue purified by preparative thin-layer chromatography to give (5S)—N-(5-fluoropyridin-3-yl)-8-(3-(trifluoromethyl)phenyl)-4,5-dihydro-2,5-methanopyrido[2,3-g][1,2,6]thiadiazocine-6(3H)-carboxamide 1,1-dioxide (24.0 mg, 0.0473 mmol, 25% yield). MS (ESI) calcd for $C_{22}H_{17}F_4N_5O_3S$: 507.1; found: 508.1 $(M+H)^+$.

The following compound was made in an analogous manner: (5S)—N-(5-fluoropyridin-3-yl)-8-((S)-3-fluoropyrrolidin-1-yl)-4,5-dihydro-2,5-methanopyrido[2,3-g][1,2,6]thiadiazocine-6(3H)-carboxamide 1,1-dioxide.

Example 55. Synthesis of (4S)—N-(3-(4-((6-aminohexanamido)methyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide

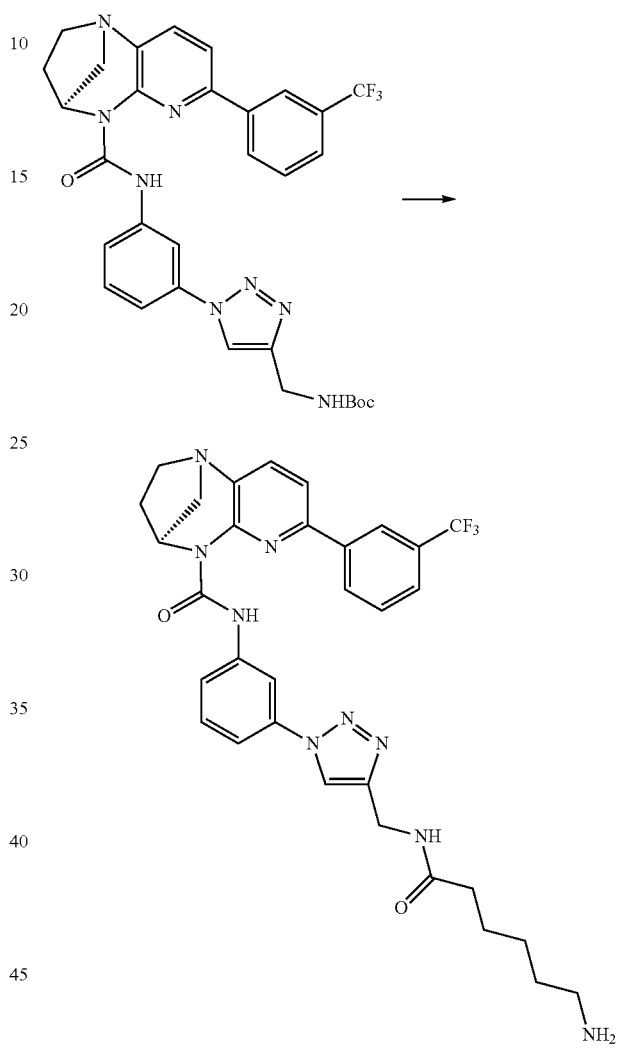

A solution of tert-butyl ((1-(3-((4S)-7-(3-(trifluoromethyl)phenyl)-2,3,4,5-tetrahydro-1,4-methanopyrido[2,3-b][1,4]diazepine-5-carboxamido)phenyl)-1H-1,2,3-triazol-4-yl)methyl)carbamate (190 mg, 0.306 mmol) in trifluoroacetic acid (3.0 mL) was stirred at room temperature for 1 h, then the excess trifluoroacetic acid removed in vacuo. The remaining residue was dissolved in DMF (5.0 mL) and triethylamine (1.0 mL), and 2,5-dioxopyrrolidin-1-yl 6-((tert-butoxycarbonyl)amino)hexanoate (250 mg, 0.761 mmol) was added. The reaction was stirred at 80° C. for 30 min, then cooled to 65° C. and 4N HCl (4 mL) was added. The reaction was stirred at 65° C. for 2 h, then filtered, and the filtrate purified by preparative HPLC. The isolated material was lyophilized from acetonitrile/1N HCl to give (4S)—N-(3-(4-((6-aminohexanamido)methyl)-1H-1,2,3-triazol-1-yl)phenyl)-7-(3-(trifluoromethyl)phenyl)-3,4-dihydro-1,4-methanopyrido[2,3-b][1,4]diazepine-5 (2H)- carboxamide hydrochloride (208 mg, 0.310 mmol, 100% yield). MS (ESI) calcd for $C_{32}H_{34}F_3N_9O_2$: 633.3; found: 634.3 (M+H)$^+$.

Example 56. Synthesis of (4S)—N-(3-(4-((6-(5-((3aS,4S,6aR)-2-oxohexahydro-1H-thieno[3,4-d]imidazol-4-yl)pentanamido)hexanamido)methyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide Example 57. Synthesis of (4S)—N-(3-(4-((3-(3',6'-dihydroxy-3-oxo-3H-spiro[isobenzofuran-1,9'-xanthen]-5-yl)thioureido)methyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide

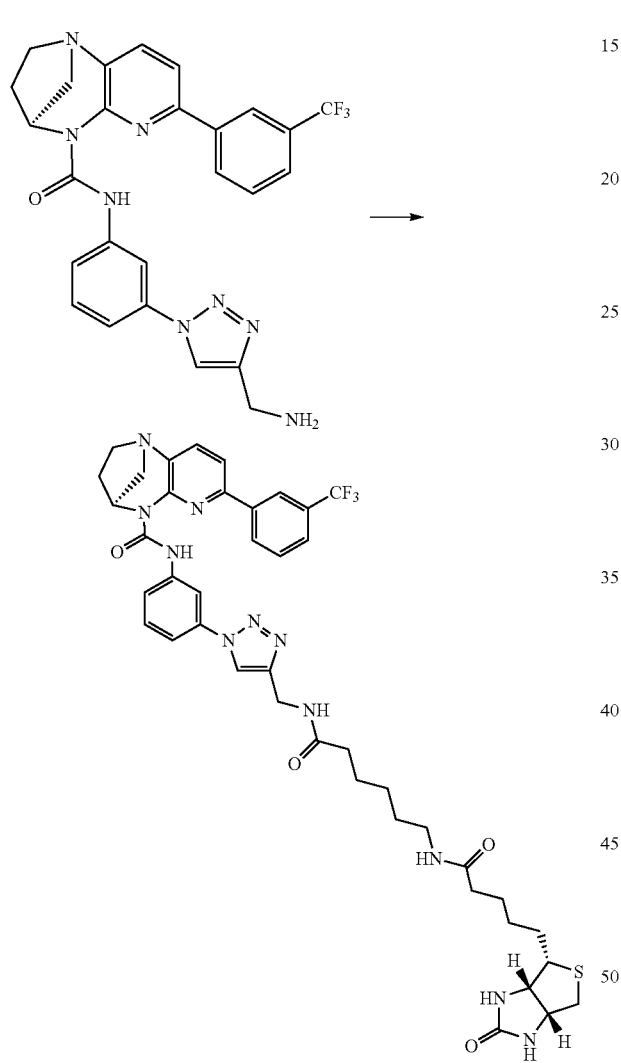

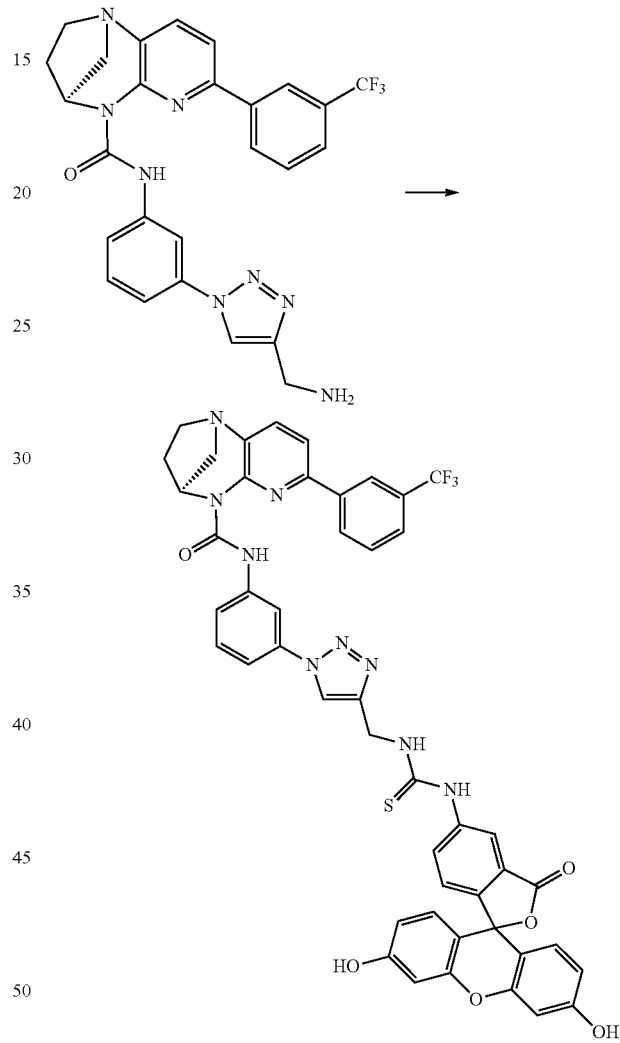

To a solution of (4S)—N-(3-(4-(aminomethyl)-1H-1,2,3-triazol-1-yl)phenyl)-7-(3-(trifluoromethyl)phenyl)-3,4-dihydro-1,4-methanopyrido[2,3-b][1,4]diazepine-5 (2H)-carboxamide (44.2 mg, 0.0850 mmol) in acetonitrile (1.3 mL) and triethylamine (0.13 mL, 0.933 mmol) was added biotinamidohexanoic acid N-hydroxysuccinimide ester (40.9 mg, 0.090 mmol). The reaction was stirred at 65° C. for 2 h, then DMF (1 mL) was added, and the resulting reaction mixture filtered, and the filtrate purified by preparative HPLC to give (4S)—N-(3-(4-((6-(5-((3aS,4S,6aR)-2-oxohexahydro-1H-thieno[3,4-d]imidazol-4-yl)pentanamido)hexanamido)methyl)-1H-1,2,3-triazol-1-yl)phenyl)-7-(3-(trifluorom-ethyl)phenyl)-3,4-dihydro-1,4-methanopyrido[2,3-b][1,4]diazepine-5 (2H)-carboxamide (43.6 mg, 0.0448 mmol, 53% yield).

To a solution of (4S)—N-(3-(4-(aminomethyl)-1H-1,2,3-triazol-1-yl)phenyl)-7-(3-(trifluoromethyl)phenyl)-3,4-dihydro-1,4-methanopyrido[2,3-b][1,4]diazepine-5 (2H)-carboxamide (44.2 mg, 0.0850 mmol) in acetonitrile (1.3 mL) and triethylamine (0.13 mL, 0.933 mmol) was added fluorescein isothiocyanate isomer I (35.0 mg, 0.090 mmol). The reaction was stirred at 65° C. for 2 h, then DMF (1 mL) was added, and the resulting reaction mixture filtered, and the filtrate purified by preparative HPLC to give (4S)—N-(3-(4-((3-(3',6'-dihydroxy-3-oxo-3H-spiro[isobenzofuran-1,9'-xanthen]-5-yl)thioureido)methyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide (51.0 mg, 0.0498 mmol, 58% yield).

207

Example 58. Synthesis of (4S)—N-(3-(4-((3-((Z)-2-((1-(difluoroboryl)-1H-pyrrol-2-yl)methylene)-2H-pyrrol-5-yl)propanamido)methyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide

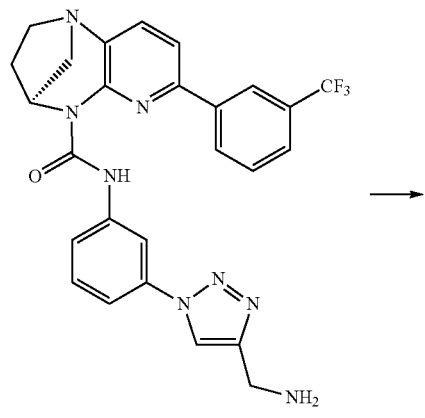

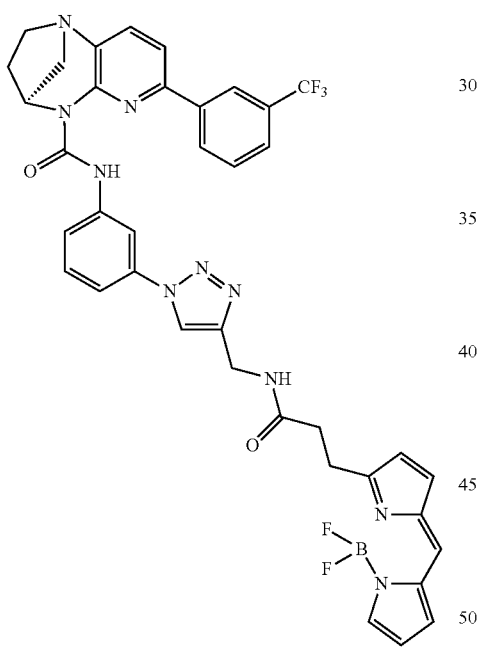

To a solution of (4S)—N-(3-(4-(aminomethyl)-1H-1,2,3-triazol-1-yl)phenyl)-7-(3-(trifluoromethyl)phenyl)-3,4-dihydro-1,4-methanopyrido[2,3-b][1,4]diazepine-5 (2H)-carboxamide (12.2 mg, 0.0234 mmol) in acetonitrile (0.35 mL) and triethylamine (0.035 mL, 0.251 mmol) was added 4,4-difluoro-5,7-dimethyl-4-bora-3a,4a-diaza-s-indacene-3-propionic acid, succinimidyl ester (10 mg, 0.0257 mmol). The reaction was stirred at 60° C. for 30 min, then the reaction mixture purified by preparative HPLC to give (4S)—N-(3-(4-((3-((Z)-2-((1-(difluoroboryl)-1H-pyrrol-2-yl)methylene)-2H-pyrrol-5-yl)propanamido)methyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide (5.8 mg, 0.0064 mmol, 27% yield).

208

Example 59. Synthesis of (9S)—N-(4-(acetamidomethyl)phenyl)-2-(3-(trifluoromethyl)phenyl)-8,9-dihydro-6H-5,9-methanopyrido[2,3-b][1,4]diazocine-10(7H)-carboxamide

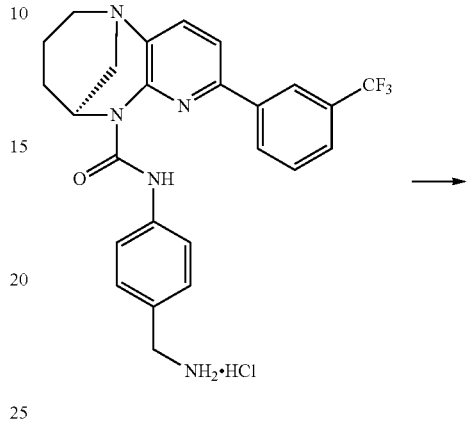

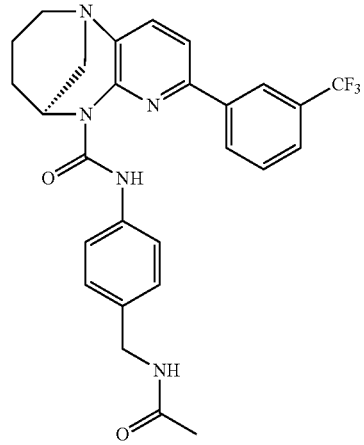

To a solution of (9S)—N-(4-(aminomethyl)phenyl)-2-(3-(trifluoromethyl)phenyl)-8,9-dihydro-6H-5,9-methanopyrido[2,3-b][1,4]diazocine-10(7H)-carboxamide hydrochloride (108 mg, 0.214 mmol) in pyridine (3.0 mL) was added acetic anhydride (28.0 µL, 0.300 mmol). The reaction was stirred at room temperature for 4 h, and the reaction mixture purified by preparative HPLC to give (9S)—N-(4-(acetamidomethyl)phenyl)-2-(3-(trifluoromethyl)phenyl)-8,9-dihydro-6H-5,9-methanopyrido[2,3-b][1,4]diazocine-10(7H)-carboxamide trifluoroacetate (111 mg, 0.178 mmol, 83% yield). MS (ESI) calcd for $C_{27}H_{26}F_3N_5O_2$: 509.2; found: 510.2 (M+H)$^+$.

Example 60. Preparation of (4S)—N-(3-(pyrrolidin-3-yl)phenyl)-7-(3-(trifluoromethyl)phenyl)-3,4-dihydro-1,4-methanopyrido[2,3-b][1,4]diazepine-5(2H)-carboxamide

Step 1: Synthesis of tert-butyl 3-(3-((4S)-7-(3-(trifluoromethyl)phenyl)-2,3,4,5-tetrahydro-1,4-methanopyrido[2,3-b][1,4]diazepine-5-carboxamido)phenyl)pyrrolidine-1-carboxylate

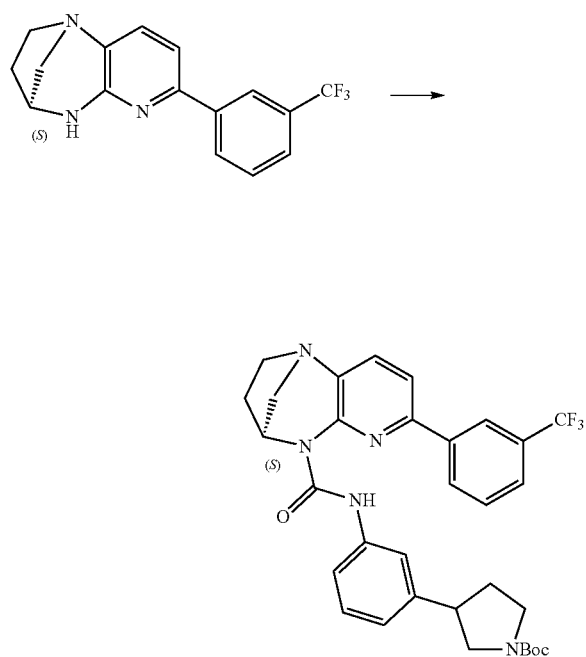

(4S)-7-(3-(trifluoromethyl)phenyl)-2,3,4,5-tetrahydro-1,4-methanopyrido[2,3-b][1,4]diazepine (A7, 0.150 g, 0.490 mmol) was dissolved in 5 ml methylene chloride and treated with DIEA (193 ul, 1.08 mmol). The mixture was stirred at room temperature for 30 minutes. Tert-butyl 3-(3-aminophenyl)pyrrolidine-1-carboxylate (0.141 g, 0.539 mmol) was then added and the solution was stirred over night at room temperature. The reaction was diluted with 5 ml methylene chloride and washed with 10 ml of a saturated solution of sodium hydrogen carbonate. Organics were collected and concentrated to dryness. Purification by silica column chromatography using 5-100% ethylacetate in pentane afforded tert-butyl 3-(3-((4S)-7-(3-(trifluoromethyl)phenyl)-2,3,4,5-tetrahydro-1,4-methanopyrido[2,3-b][1,4]diazepine-5-carboxamido)phenyl)pyrrolidine-1-carboxylate (0.077 g, 26%). MS (ESI) calcd for $C_{32}H_{34}F_3N_5O_3$: 593.3, found: 594 [M+H].

Step 2: Synthesis of (4S)—N-(3-(pyrrolidin-3-yl)phenyl)-7-(3-(trifluoromethyl)phenyl)-3,4-dihydro-1,4-methanopyrido[2,3-b][1,4]diazepine-5(2H)-carboxamide

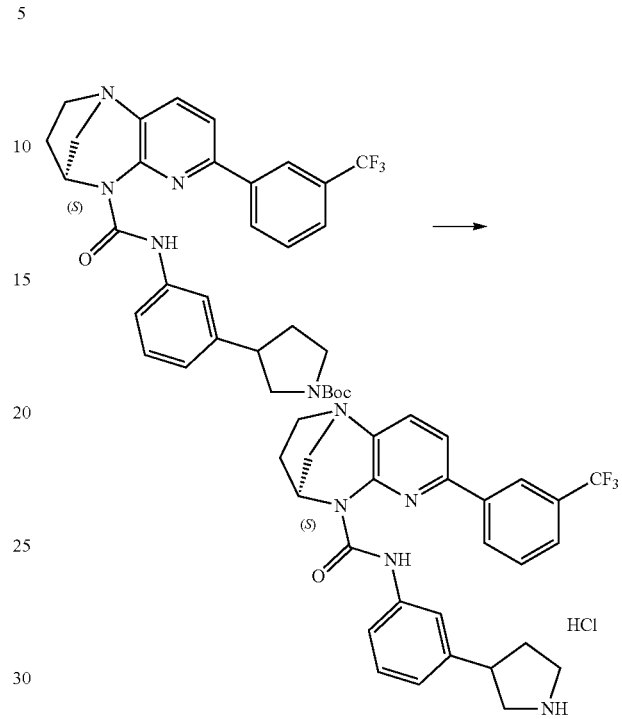

(S)Tert-butyl 3-(3-((4S)-7-(3-(trifluoromethyl)phenyl)-2,3,4,5-tetrahydro-1,4-methanopyrido[2,3-b][1,4]diazepine-5-carboxamido)phenyl)pyrrolidine-1-carboxylate: (0.077 g, 0.130 mmol) was dissolved in 5 mL of 4 N HCl in 1,4-dioxane and stirred under nitrogen for 3 hours at room temperature. All solvent was then removed under reduced pressure and the resulting solid was dried over night under vacuum to give (4S)—N-(3-(pyrrolidin-3-yl)phenyl)-7-(3-(trifluoromethyl)phenyl)-3,4-dihydro-1,4-methanopyrido[2,3-b][1,4]diazepine-5(2H)-carboxamide (0.078 g, 100%). MS (ESI) calcd for $C_{27}H_{26}F_3N_5O$: 493.21; found: 494 [M+H].

Example 61. Preparation of (4S)—N-(3-(1-(2-amino-2-oxoethyl)pyrrolidin-3-yl)phenyl)-7-(3-(trifluoromethyl)phenyl)-3,4-dihydro-1,4-methanopyrido[2,3-b][1,4]diazepine-5(2H)-carboxamide

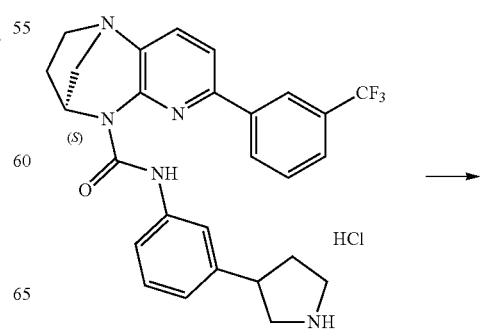

211
-continued

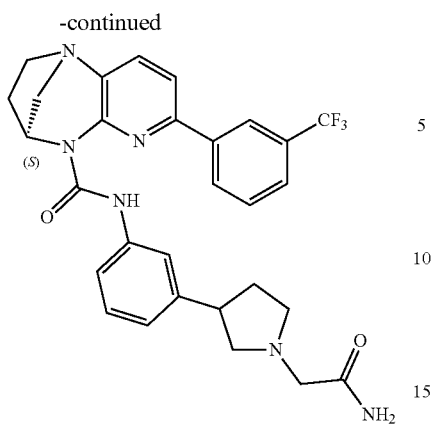

212
-continued

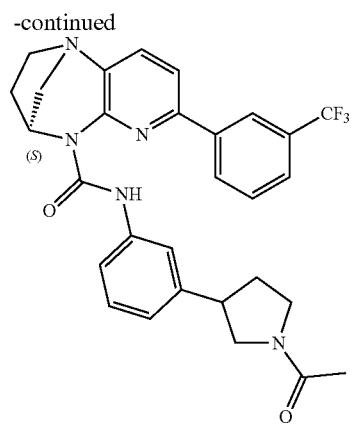

(4S)—N-(3-(pyrrolidin-3-yl)phenyl)-7-(3-(trifluoromethyl)-7-(3-(trifluoromethyl)phenyl)-3,4-dihydro-1,4-methanopyrido[2,3-b][1,4]diazepine-5(2H)-carboxamide (B579, 0.029 g, 0.058 mmol) was dissolved in 2 ml methylene chloride and then treated with DIEA (31 ul, 0.174 mmol). Chloroacetamide (0.006 g, 0.064 mmol) was then added and the reaction was heated to 60° C. over night. The reaction was then cooled to room temperature and diluted with 5 ml methylene chloride and washed with 10 ml of a saturated solution of sodium hydrogen carbonate. Organics were concentrated to dryness and purified via reverse phase chromatography on C18 using a gradient of 5-95% acetonitrile in water with 0.1% trifluroracetic acid as additive to give (4S)—N-(3-(1-(2-amino-2-oxoethyl)pyrrolidin-3-yl)phenyl)-7-(3-(trifluoromethyl)phenyl)-3,4-dihydro-1,4-methanopyrido[2,3-b][1,4]diazepine-5(2H)-carboxamide (0.008 g, 23%). MS (ESI) calcd for $C_{29}H_{29}F_3N_6O_2$: 550.2; found: 551 [M+H].

Example 62: Preparation of (4S)—N-(3-(1-(2-amino-2-oxoethyl)pyrrolidin-3-yl)phenyl)-7-(3-(trifluoromethyl)phenyl)-3,4-dihydro-1,4-methanopyrido[2,3-b][1,4]diazepine-5(2H)-carboxamide (4S)—N-(3-(pyrrolidin-3-yl)phenyl)-7-(3-(trifluoromethyl)phenyl)-3,4-dihydro-1,4-methanopyrido[2,3-b][1,4]diazepine-5(2H)-carboxamide (B579, 0.020 g, 0.038 mmol) was dissolved in 1.5 ml methylene chloride and then treated with DIEA (13 ul, 0.076 mmol). Acetylchloride (0.005 g, 0.042 mmol) was then added and the reaction was stirred at room temperature over night. The reaction was then diluted with 5 ml methylene chloride and washed with 10 ml of a saturated solution of sodium hydrogen carbonate. Organics were concentrated to dryness and purified via reverse phase chromatography on C18 to give (4S)—N-(3-(1-(2-amino-2-oxoethyl)pyrrolidin-3-yl)phenyl)-7-(3-(trifluoromethyl)phenyl)-3,4-dihydro-1,4-methanopyrido[2,3-b][1,4]diazepine-5 (2H)-carboxamide (0.023 g, 88%). MS (ESI) calcd for $C_{29}H_{28}F_3N_5O_2$: 535.2; found: 536 [M+H].

This general acylation procedure was used to prepare (4S)—N-(3-(1-propionylpyrrolidin-3-yl)phenyl)-7-(3-(trifluoromethyl)phenyl)-3,4-dihydro-1,4-methanopyrido[2,3-b][1,4]diazepine-5(2H)-carboxamide and (4S)—N-(3-(1-(cyclopropanecarbonyl)pyrrolidin-3-yl)phenyl)-7-(3-(trifluoromethyl)phenyl)-3,4-dihydro-1,4-methanopyrido[2,3-b][1,4]diazepine-5(2H)-carboxamide.

Example 63. Preparation of of benzyl ((5-(3-((4S)-7-(3-(trifluoromethyl)phenyl)-2,3,4,5-tetrahydro-1,4-methanopyrido[2,3-b][1,4]diazepine-5-carboxamido)phenyl)oxazol-2-yl)methyl)carbamate

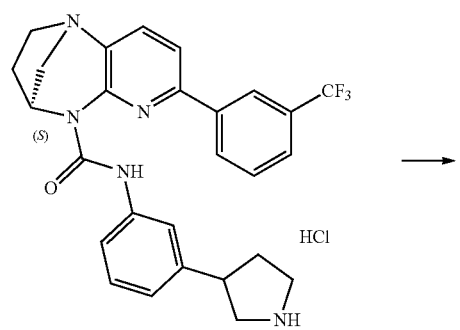

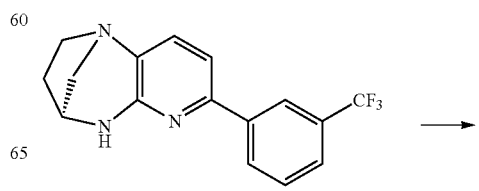

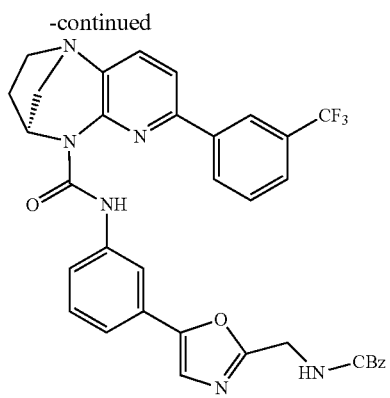

(4S)-7-(3-(trifluoromethyl)phenyl)-2,3,4,5-tetrahydro-1,4-methanopyrido[2,3-b][1,4]diazepine (0.276 g, 0.902 mmol) in 4 mL methylene chloride was combined with DIEA (400 uL, 2.261 mmol) and triphosgene (0.200 g, 0.676 mmol). The mixture was then heated to 65° C. at which point benzyl ((5-(3-aminophenyl)oxazol-2-yl)methyl)carbamate (0.321 g, 0.992 mmol) in 4 mL methylene chloride was added dropwise slowly. The mixture was then heated at 65° C. for 5 hours. The reaction was then cooled to RT and 10 mL methylene chloride was then added followed by wash with 50 mL of a saturated solution of sodium hydrogen carnonate. The organic layer was collected and concentrated to dryness under reduced pressure. Residue was then purified via silica gel chromatography to afford benzyl ((5-(3-((4S)-7-(3-(trifluoromethyl)phenyl)-2,3,4,5-tetrahydro-1,4-methanopyrido[2,3-b][1,4]diazepine-5-carboxamido)phenyl)oxazol-2-yl)methyl)carbamate (0.082 g, 14%). MS (ESI) calcd for $C_{35}H_{29}F_3N_6O_4$: 654.22; found: 655 [M+H].

Example 64. Preparation of (4S)—N-(3-(2-(aminomethyl)oxazol-5-yl)phenyl)-7-(3-(trifluoromethyl)phenyl)-3,4-dihydro-1,4-methanopyrido[2,3-b][1,4]diazepine-5(2H)-carboxamide

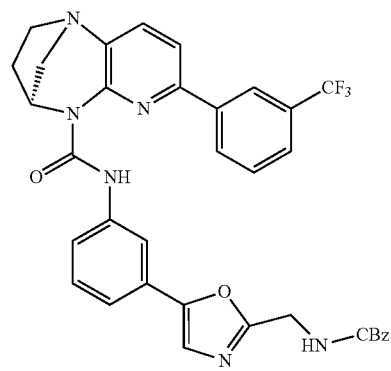

Benzyl((5-(3-((4S)-7-(3-(trifluoromethyl)phenyl)-2,3,4,5-tetrahydro-1,4-methanopyrido[2,3-b][1,4]diazepine-5-carboxamido)phenyl)oxazol-2-yl)methyl)carbamate (0.040 g, 0.06 mmol) was dissolved in 10 mL ethylacetate and degassed three times under vacuum. Approximately 5 mg of Palladium (10% on Carbon degaussa type) was then added and the reaction vessel was purged with nitrogen then fitted with a hydrogen ballon. Stirring was then initiated and the mixture was stirred under hydrogen for 2 hours. The reaction vessel was then evacuated and purged with nitrogen. The solids were removed via filtration and the solvent was removed under reduced pressure to give (4S)—N-(3-(2-(aminomethyl)oxazol-5-yl)phenyl)-7-(3-(trifluoromethyl)phenyl)-3,4-dihydro-1,4-methanopyrido[2,3-b][1,4]diazepine-5(2H)-carboxamide (0.032 g, 100%) that was used without purification. MS (ESI) calcd for $C_{27}H_{23}F_3N_6O_2$: 520.51; found: 521 [M+H].

Example 65. Preparation of (4S)—N-(5-phenyl-1,3,4-oxadiazol-2-yl)-7-(3-(trifluoromethyl)phenyl)-3,4-dihydro-1,4-methanopyrido[2,3-b][1,4]diazepine-5(2H)-carboxamide Step 1. Synthesis of (4S)-phenyl 7-(3-(trifluoromethyl)phenyl)-3,4-dihydro-1,4-methanopyrido[2,3-b][1,4]diazepine-5 (2H)-carboxylate

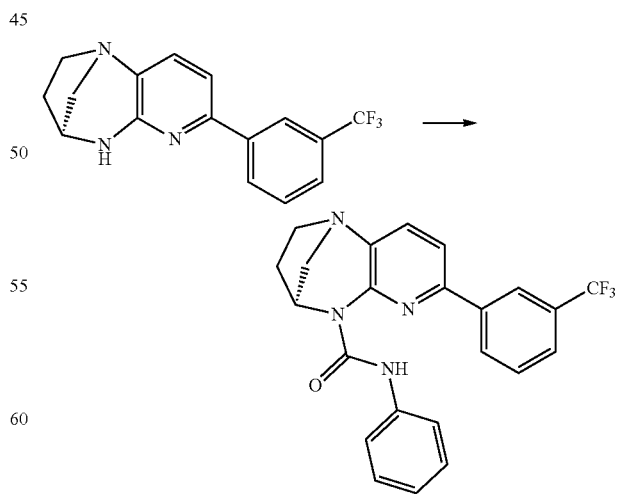

To a solution of (4S)-7-(3-(trifluoromethyl)phenyl)-2,3,4,5-tetrahydro-1,4-methanopyrido[2,3-b][1,4]diazepine (1.5 g, 4.92 mmol) and pyridine (0.74 mL, 9.84 mmol) in DCM (15 mL) was added phenyl chloroformate (1.1 mL, 8.85 mmol) at 0° C. dropwise. The resulting mixture was stirred at that temperature for 2 h, then washed with saturated aqueous NaHCO₃, dried over anhydrous Na₂SO₄, concentrated to afford the crude phenyl carbamate (1.8 g) as a brown oil, which was used in the next step without further purification.

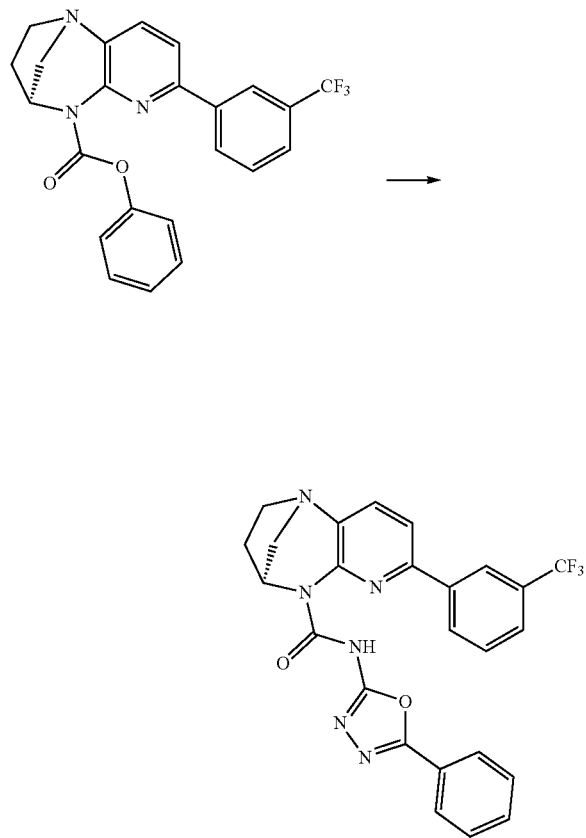

Step 2. Synthesis of (4S)—N-(5-phenyl-1,3,4-oxadiazol-2-yl)-7-(3-(trifluoromethyl)phenyl)-3,4-dihydro-1,4-methanopyrido[2,3-b][1,4]diazepine-5 (2H)-carboxamide To a solution of amine 5-phenyl-1,3,4-oxadiazol-2-amine (30 mg, 0.18 mmol) in dry THF (5 mL) was added NaH (18 mg, 0.75 mmol) in portions at 0° C., the reaction mixture was stirred at room temperature for 30 min. (4S)-phenyl 7-(3-(trifluoromethyl)phenyl)-3,4-dihydro-1,4-methanopyrido[2,3-b][1,4]diazepine-5(2H)-carboxylate (157 mg, 0.37 mmol) was then added and the mixture was stirred overnight. The resulting mixture was quenched with MeOH (2 mL), concentrated in vacuo by evaporator. The residue was purified by prep-TLC to give 2-(3-((2,2-dimethyl-1,3-dioxolan-4-yl)methyl)phenyl)-4,4,5,5-tetramethyl-1,3,2-dioxaborolane (50 mg, yield 54.9%) as a white solid.

This general procedure using (4S)-phenyl 7-(3-(trifluoromethyl)phenyl)-3,4-dihydro-1,4-methanopyrido[2,3-b][1,4]diazepine-5(2H)-carboxylate could be used to prepare a variety of carboxamides by using the appropriate arylamines in place of 5-phenyl-1,3,4-oxadiazol-2-amine.

Example 66. Preparation of (4S)—N-(3-(oxazol-5-yl)phenyl)-7-(3-(trifluoromethyl)phenyl)-3,4-dihydro-1,4-methanopyrido[2,3-b][1,4]diazepine-5 (2H)-carbothioamide Step 1. Synthesis of 5-(3-isothiocyanatophenyl)oxazole

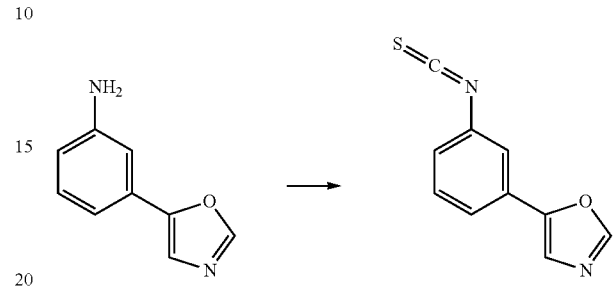

To a solution of 3-(oxazol-5-yl)aniline (160 mg, 1.0 mmol) and TEA (0.4 mL, 3.0 mmol) in dry THF (6 mL) was added a solution of thiophosgene (0.152 mL, 2.0 mmol) in dry THF (1.5 mL) dropwise over 10 min at 0° C. under Argon atmosphere. The reaction mixture was stirred at ambient temperature for 30 min, TLC showed 3-(oxazol-5-yl)aniline was fully consumed. The solvent was removed by evaporator under reduced pressure, the residue was diluted with water (10 mL) and ethyl acetate (25 mL), the organic layer was separated. The aqueous phase was extracted with ethyl acetate (3×30 mL), the combined organic layers were washed with saturated aqueous NaHCO₃ followed by water and brine, dried over anhydrous sodium sulfate, filtered and concentrated to give 5-(3-isothiocyanatophenyl)oxazole which was used for the next reaction without any further purification.

Step 2. Synthesis of (4S)—N-(3-(oxazol-5-yl)phenyl)-7-(3-(trifluoromethyl)phenyl)-3,4-dihydro-1,4-methanopyrido[2,3-b][1,4]diazepine-5(2H)-carbothioamide

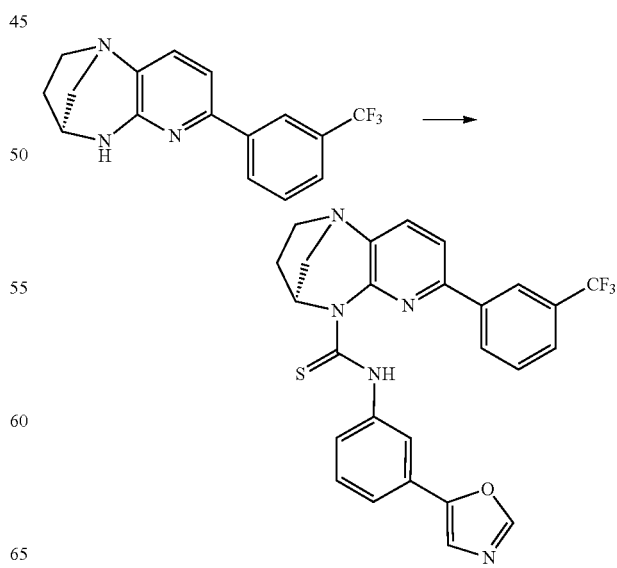

(4S)-7-(3-(trifluoromethyl)phenyl)-2,3,4,5-tetrahydro-1,4-methanopyrido[2,3-b][1,4]diazepine (244 mg, 0.8 mmol) was dissolved in dry DMF (5 mL) and NaH (128 mg, 60%, 3.2 mmol) was added in portions at 0° C. under Argon atmosphere. The mixture was warmed to room temperature and stirred for 1 h. A solution of 5-(3-isothiocyanatophenyl) oxazole prepared above in DMF (3 mL) was added dropwise and the reaction mixture was stirred at ambient temperature overnight. The resulting mixture was then quenched with saturated aqueous NH₄Cl, extracted with ethyl acetate (3×15 mL), washed with water and brine, dried over anhydrous Na₂SO₄, filtered and concentrated. The crude was purified through silica gel chromatography using DCM:MeOH=10:1 to give title compound (4S)—N-(3-(oxazol-5-yl)phenyl)-7-(3-(trifluoromethyl)phenyl)-3,4-dihydro-1,4-methanopyrido[2,3-b][1,4]diazepine-5(2H)-carbothioamide (186.1 mg, yield 46%).

Example 67. Preparation of (4S)—N-(3-(oxazol-5-yl)phenyl)-7-(3-(trifluoromethyl)phenyl)-3,4-dihydro-1,4-methanobenzo[b][1,4]diazepine-5(2H)-carboxamide Step 1. Synthesis of (S)-dimethyl 2-((5-bromo-2-nitrophenyl)amino)succinate

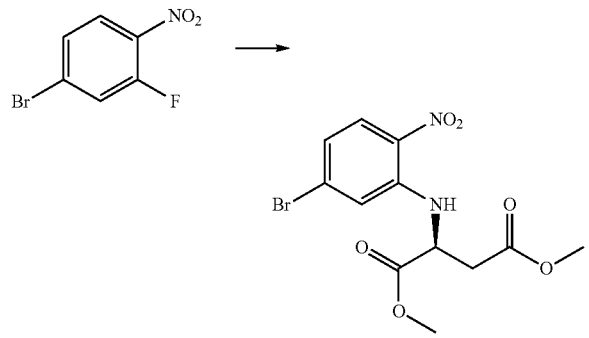

The mixture of 4-bromo-2-fluoro-1-nitrobenzene (15.0 g, 68 mmol), (S)-dimethyl 2-aminosuccinate hydrochloride (15 g, 75 mmol) and DIPEA (36 mL) in DMSO (127 mL) was stirred at 100° C. for 2 h. After cooling down, water (200 mL) was added and the mixture was extracted with ethyl acetate (3×300 mL). The combined organic layers were washed with water and brine, dried over anhydrous sodium sulfate, filtered and concentrated. The residue was purified by silica gel chromatography (petroleum ether/ethyl acetate=4/1) to give (S)-dimethyl 2-((5-bromo-2-nitrophenyl)amino)succinate (12.4 g, yield 51%)

Step 2. Synthesis of (S)-methyl 2-(7-bromo-3-oxo-1,2,3,4-tetrahydroquinoxalin-2-yl)acetate (Sundia E655-523-23)

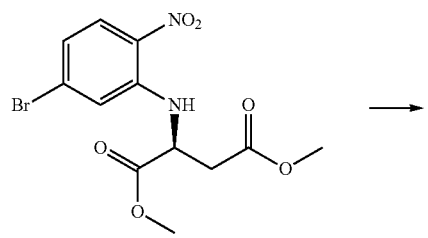

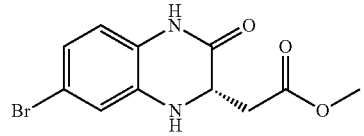

The mixture of (S)-dimethyl 2-((5-bromo-2-nitrophenyl)amino)succinate (12.4 g, 34.4 mmol), Fe (22 g, 392 mmol) and AcOH (1.2 mL) in i-PrOH (250 mL) and water (50 mL) was stirred at reflux for 2 h. After cooling, the solid was filtered and the filtrate was concentrated. The residue was diluted with DCM (300 mL) and water (300 mL), the organic layer was separated, and the aqueous phase was extracted with DCM (3×300 mL). The combined organic layers were washed with water and brine, dried over anhydrous sodium sulfate, filtered and concentrated. The residue was purified by silica gel chromatography (petroleum ether/ethyl acetate=4/1) to give (S)-methyl 2-(7-bromo-3-oxo-1,2,3,4-tetrahydroquinoxalin-2-yl)acetate (8.8 g, yield 86%) ¹H NMR (DMSO-d₆, 400 MHz): δ 10.43 (s, 1H), 6.84 (s, 1H), 6.75-6.73 (m, 1H), 6.66-6.63 (m, 1H), 6.32 (s, 1H), 4.19-4.16 (m, 1H), 3.60 (s, 3H), 2.78-2.72 (m, 1H), 2.68-2.61 (m, 1H).

Step 3. Synthesis of (S)-2-(7-bromo-1,2,3,4-tetrahydroquinoxalin-2-yl)ethanol

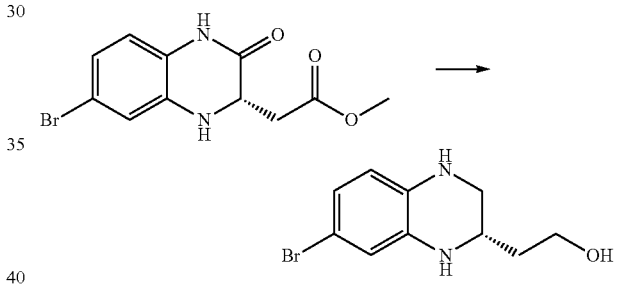

To the solution of (S)-methyl 2-(7-bromo-3-oxo-1,2,3,4-tetrahydroquinoxalin-2-yl)acetate (4.4 g, 14.7 mmol) in THF (30 mL) was added BH₃Me₂S (10 M, 10 mL) at 0° C. over 15 min in a dropwise fashion. The reaction was heated to reflux overnight. After cooling down, the mixture was quenched with 6N HCl (10 mL) and the resulting mixture stirred at 50° C. for 2 h. The mixture was then basified using 2N NaOH and brought to pH-8. The mixture was extracted with DCM (3×50 mL) and the combined organic layers were washed with water and brine, dried over anhydrous sodium sulfate, filtered and concentrated. The residue was purified by silica gel chromatography (DCM/MeOH=20/1) to give (S)-2-(7-bromo-1,2,3,4-tetrahydroquinoxalin-2-yl)ethanol (2.4 g, yield 63%).

Step 4. Synthesis of (4S)-7-bromo-2,3,4,5-tetrahydro-1,4-methanobenzo[b][1,4]diazepine

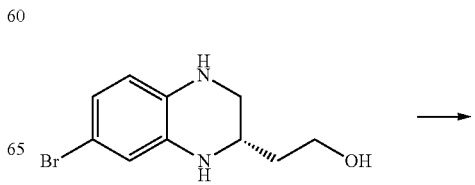

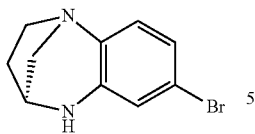

DDQ (2.7 g, 11.7 mmol) was added to a solution of PPh₃ (3.0 g, 11.7 mmol) in DCM (100 mL) at room temperature. (S)-2-(7-bromo-1,2,3,4-tetrahydroquinoxalin-2-yl)ethanol (2.0 g, 7.8 mmol) was added. The mixture was stirred at room temperature for 2 h. After removing the solvent, the residue was purified by silica gel chromatography (DCM/MeOH=40/1) to give (4S)-7-bromo-2,3,4,5-tetrahydro-1,4-methanobenzo[b][1,4]diazepine (1.5 g, yield 81%).

Step 5. Synthesis of (4S)-7-(3-(trifluoromethyl) phenyl)-2,3,4,5-tetrahydro-1,4-methanobenzo[b][1, 4]diazepine

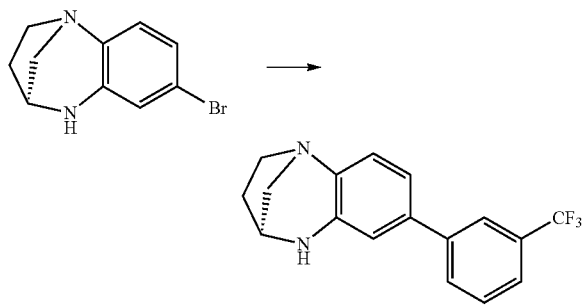

To the mixture of (4S)-7-bromo-2,3,4,5-tetrahydro-1,4-methanobenzo[b][1,4]diazepine (600 mg, 2.5 mmol), (3-(trifluoromethyl)phenyl)boronic acid (950 mg, 5.0 mmol), Cs₂CO₃ (2.4 g, 7.5 mmol) in dioxane (60 mL) and water (6 mL) was added Pd(dppf)Cl₂ (204 mg, 0.25 mmol) at room temperature under N₂ atmosphere. The mixture was stirred at 110° C. overnight. After cooling down, the solid was filtered and the filtrate was concentrated. The residue was diluted with DCM (30 mL) and water (30 mL), the organic layer was separated and the aqueous phase was extracted with DCM (3×30 mL). The combined organic layers were washed with water and brine, dried over anhydrous sodium sulfate, filtered and concentrated. The residue was purified by silica gel chromatography (DCM/MeOH=20/1) to give (4S)-7-(3-(trifluoromethyl)phenyl)-2,3,4,5-tetrahydro-1,4-methanobenzo[b][1,4]diazepine (700 mg, yield 95%).

Step 6. Synthesis of (4S)—N-(3-(oxazol-5-yl)phenyl)-7-(3-(trifluoromethyl)phenyl)-3,4-dihydro-1,4-methanobenzo[b][1,4]diazepine-5(2H)-carboxamide

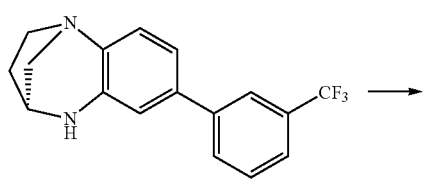

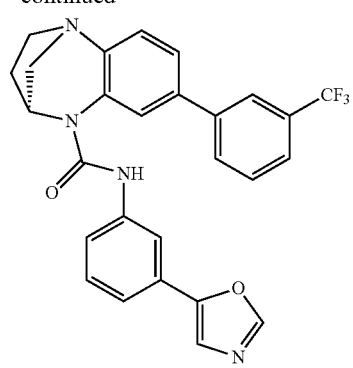

The mixture of (4S)-7-(3-(trifluoromethyl)phenyl)-2,3,4, 5-tetrahydro-1,4-methanobenzo[b][1,4]diazepine (50 mg, 0.16 mmol), TEA (0.1 mL) and triphosgene (40 mg, 0.13 mmol) in THF (5 mL) was stirred at 60° C. for 2 h. 3-(oxazol-5-yl)aniline (38 mg, 0.24 mmol) was added. The mixture was stirred at 60° C. overnight. After cooling down, the resulting mixture was concentrated, the residue was purified by prep-TLC (DCM/MeOH=20/1) to give (4S)—N-(3-(oxazol-5-yl)phenyl)-7-(3-(trifluoromethyl)phenyl)-3, 4-dihydro-1,4-methanobenzo[b][1,4]diazepine-5(2H)-carboxamide (26.1 mg, yield 33%).

Example 68. Preparation of (4S)—N-(pyridin-2-yl)-7-(3-(trifluoromethyl)phenyl)-3,4-dihydro-1,4-methanobenzo[b][1,4]diazepine-5(2H)-carboxamide

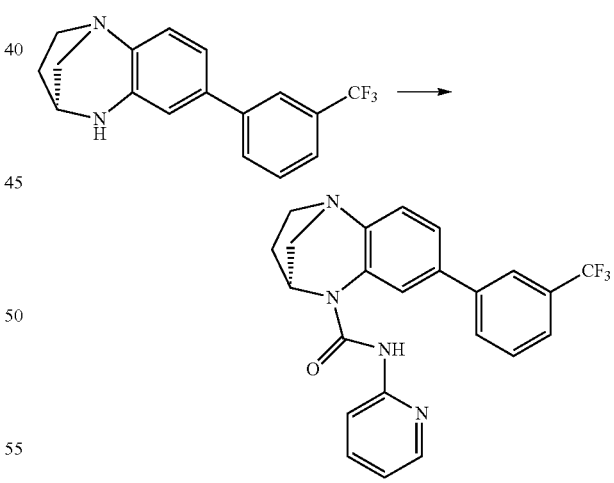

The mixture of (4S)-7-(3-(trifluoromethyl)phenyl)-2,3,4, 5-tetrahydro-1,4-methanobenzo[b][1,4]diazepine (50 mg, 0.16 mmol), DMAP (52 mg, 0.42 mmol) and phenyl pyridin-2-ylcarbamate (89 mg, 0.42 mmol) in CH₃CN (2.5 mL) was refluxed overnight. After cooling down, the solvent was removed. The residue was purified by prep-TLC (DCM/MeOH=20/1) to give (4S)—N-(pyridin-2-yl)-7-(3-(trifluoromethyl)phenyl)-3,4-dihydro-1,4-methanobenzo[b][1,4]diazepine-5(2H)-carboxamide (24.4 mg, yield 35%).

Example 69. Preparation of (4S)—N-(pyridin-3-yl)-7-(3-(trifluoromethyl)cyclohexyl)-3,4-dihydro-1,4-methanopyrido[2,3-b][1,4]diazepine-5(2H)-carboxamide Step 1. Synthesis of (4S)-7-(3-(trifluoromethyl)cyclohexyl)-2,3,4,5-tetrahydro-1,4-methanopyrido[2,3-b][1,4]diazepine

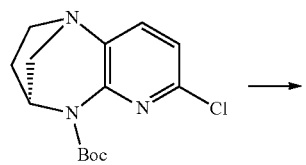

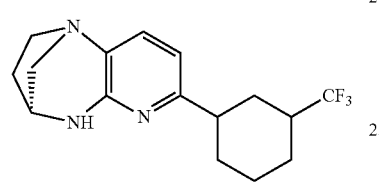

This moiety was made using the general Negishi coupling procedure above to give (4S)-7-(3-(trifluoromethyl)cyclohexyl)-2,3,4,5-tetrahydro-1,4-methanopyrido[2,3-b][1,4]diazepine as a 11:1 mixture of diastereomers (482 mg, 36%). MS (ESI) calcd for $C_{16}H_{20}F_3N_3$: 311.16; found: 312 [M+H].

Step 2. Synthesis of (4S)—N-(pyridin-3-yl)-7-(3-(trifluoromethyl)cyclohexyl)-3,4-dihydro-1,4-methanopyrido[2,3-b][1,4]diazepine-5(2H)-carboxamide

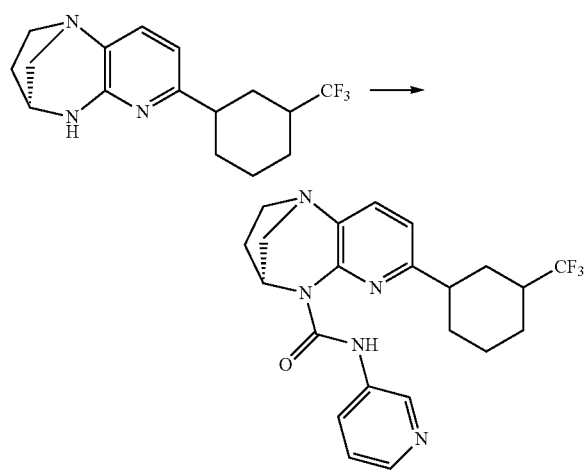

These compounds were made using the triphosgene urea coupling procedure above to give (4S)—N-(pyridin-3-yl)-7-(3-(trifluoromethyl)cyclohexyl)-3,4-dihydro-1,4-methanopyrido[2,3-b][1,4]diazepine-5(2H)-carboxamide as a 9:1 mixture of diastereomers (38 mg, 62%). MS (ESI) calcd for $C_{22}H_{24}F_3N_5O$: 431.19; found: 432 [M+H].

Example 70. Preparation of (4S)—N-(pyrimidin-4-yl)-7-(3-(trifluoromethyl)cyclohexyl)-3,4-dihydro-1,4-methanopyrido[2,3-b][1,4]diazepine-5(2H)-carboxamide

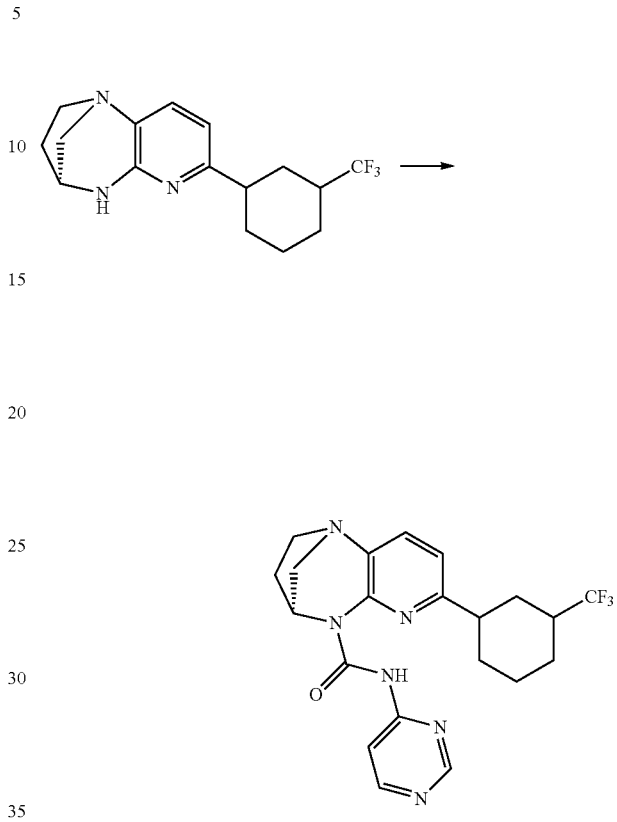

This mixture of diastereomers was made using the following protocol.

Carbonyldiimidazole (CDI, 21 mg, 0.13 mmol) was slurried in DCM (1.5 mL), followed by addition of 4-aminopyrimidine (13 mg, 0.13 mmol). To get everything into solution, dioxane was added (0.5 mL). The mixture was allowed to stir at room temp for 1 h under nitrogen atmosphere. (4S)-7-(3-(trifluoromethyl)cyclohexyl)-2,3,4,5-tetrahydro-1,4-methanopyrido[2,3-b][1,4]diazepine (41 mg, 0.13 mmol) was added in DCM (1 mL), and the reaction was allowed to stir overnight, then more CDI was added (21 mg) and the reaction heated to reflux for 4 h. The reaction was monitored by LCMS and the intermediate (before addition of 4-aminopyrimidine) was the major reaction component. The reaction was cooled to room temp, concentrated, then more 4-aminopyrimidine (25 mg) was added in 1 mL DMSO (for better solubility). The reaction was warmed to 60° C. overnight, then 100° C. in a sealed tube for a second night. More 4-aminopyrimidine (25 mg) was added and the reaction sealed and heated to 120° C. in microwave for 1 h. DCM (10 mL) was added, then 1 N HCl (3 mL). This was extracted with DCM (3×15 mL). Combined organics were washed with brine, dried with $Na_2SO_4$, filtered and concentrated. The crude product was purified by silica gel column chromatography (0-10% MeOH/DCM), then again by prep HPLC to give (4S)—N-(pyrimidin-4-yl)-7-(3-(trifluoromethyl)cyclohexyl)-3,4-dihydro-1,4-methanopyrido[2,3-b][1,4]diazepine-5(2H)-carboxamide (4 mg, 7%). MS (ESI) calcd for $C_{21}H_{23}F_3N_6O$: 432.19; found: 433 [M+H].

Example 71. Preparation of (4S)—N-(4,5-dimethyl-thiazol-2-yl)-7-(3-(trifluoromethyl)cyclohexyl)-3,4-dihydro-1,4-methanopyrido[2,3-b][1,4]diazepine-5(2H)-carboxamide

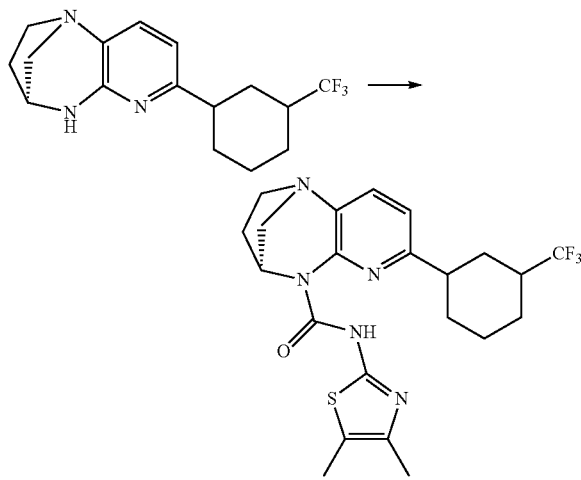

This mixture of diastereomers was made using the following protocol.

General Procedure for Carbamate Formation:
Phenyl chloroformate (2.09 g, 13.3 mmol, 1.05 equiv.) was added dropwise over 1.5 h to a cooled solution of 4,5-dimethylthiazol-2-amine (1.63 g, 12.7 mmol, 1.0 equiv.) and pyridine (3.01 g, 38.2 mmol, 3.0 equiv.) in DCM (16 mL). The reaction was stirred with continued cooling for 2 h. Water (15 mL) was added slowly over 30 min, and then the mixture was diluted with DCM. The layers were separated and the organic layer was washed with saturated aq. Sodium carbonate (20 mL), then brine (20 mL). The organic layer was then dried over Na$_2$SO$_4$, then concentrated under reduced pressure. The residue was suspended in EA/PE (1:5) for 30 min, then filtered to afford the phenyl (4,5-dimethylthiazol-2-yl)carbamate (1.7 g, 54%).

General Procedure for Urea Coupling Via Carbamate:
A mixture of phenyl (4,5-dimethylthiazol-2-yl)carbamate (80 mg, 0.322 mmol, 2.0 equiv.), (4S)-7-(3-(trifluoromethyl)cyclohexyl)-2,3,4,5-tetrahydro-1,4-methanopyrido[2,3-b][1,4]diazepine (75 mg, 0.161 mmol, 1.0 equiv.) and DMAP (24 mg, 0.193 mmol, 1.2 equiv.) in acetonitrile (4 mL) were stirred at 60° C. overnight. TLC and LC/MS were used to monitor reaction progress. The mixture was purified by prep HPLC to give (4S)—N-(4,5-dimethylthiazol-2-yl)-7-(3-(trifluoromethyl)cyclohexyl)-3,4-dihydro-1,4-methanopyrido[2,3-b][1,4]diazepine-5(2H)-carboxamide (14.5 mg, 12%). MS (ESI) calcd for C$_{22}$H$_{26}$F$_3$N$_5$OS: 465.18; found: 466 [M+H].

Example 72. Preparation of N-(pyridazin-3-yl)-7-(3-(trifluoromethyl)phenyl)-3,4-dihydro-1,4-ethano-pyrido[2,3-b][1,4]diazepine-5(2H)-carboxamide Step 1: Diethyl 3-aminopent-2-enedioate

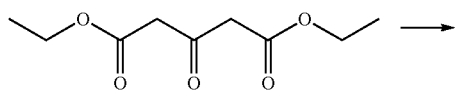

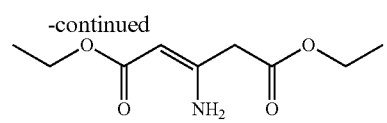

A 250 mL 3-necked flask was charged with 6.00 g (29.7 mmol) of 1,3-acetonedicarboxylate diethyl ester, 4.70 g (59.4 mmol) of ammonium bicarbonate, and 80 mL of ethanol. The reaction was stirred at ambient temperature for 24 h, then it was concentrated in vacuo. The residue was taken up in 100 mL of water and extracted with ethyl acetate (3×100 mL). The combined organic layers were back extracted with brine (1×200 mL), dried over Na$_2$SO$_4$, filtered, and concentrated to give 5 g (87%) of the product as a colorless oil. This was used in the next reaction without further purification.

Step 2: Diethyl 3-aminopentanedioate

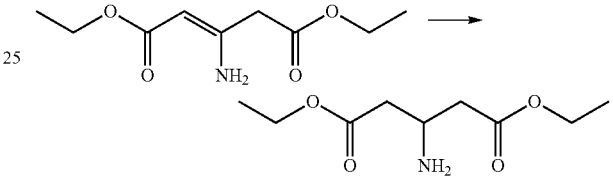

A 250 mL 3-necked flask was charged with 5.00 g (24.8 mmol) of diethyl 3-aminopent-2-enedioate, 40 mL of ethanol, 10 mL of glacial acetic acid, and 3.1 g (49.6 mmol) of NaBH$_3$CN. The reaction was stirred at ambient temperature for 2 h, then the solvents were removed in vacuo. The residue was taken up in water and extracted with ethyl acetate (3×100 mL). The combined ethyl acetate layers were back extracted with brine (1×200 mL), dried over Na$_2$SO$_4$, filtered, and concentrated in vacuo to give 4 g (80%) of the product as a colorless oil. This was used in the next reaction without further purification.

Step 3: Diethyl 3-((6-chloro-3-nitropyridin-2-yl)amino)pentanedioate

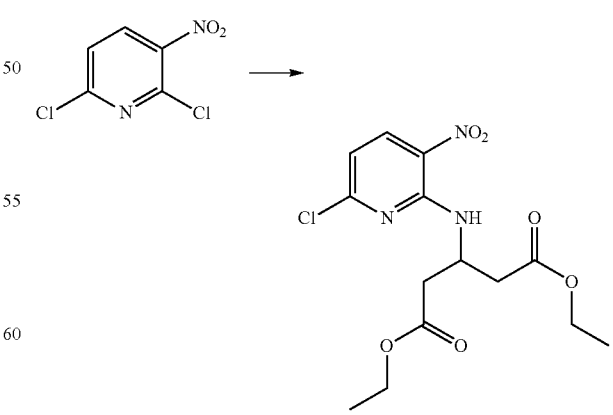

A 250 mL 3-necked flask was charged with 1.8 g (9.8 mmol) of 2,6-dichloro-3-nitropyridine, 4.0 g (19.7 mmol) of crude diethyl 3-aminopentanedioate, 3.2 g (39.0 mmol) of NaHCO₃, and 60 mL of tetrahydrofuran. The reaction was stirred at 40° C. for 24 h, then the solvent was removed in vacuo. The residue was dissolved in 100 mL of water, then extracted with ethyl acetate (3×100 mL). The combined organic phases were back extracted with brine (1×200 mL), dried over Na₂SO₄, filtered, and concentrated in vacuo.

The residue was purified via silica gel chromatography, eluting with 20/1 (v/v) hexanes/ethyl acetate to give 2.7 g (80%) of the product as a light yellow solid.

Step 4: Diethyl 3-((3-amino-6-chloropyridin-2-yl)amino)pentanedioate

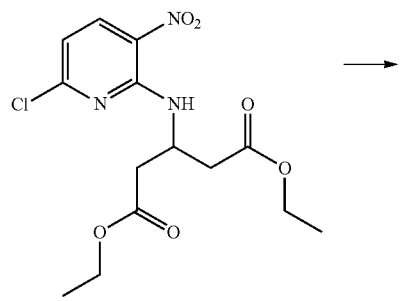

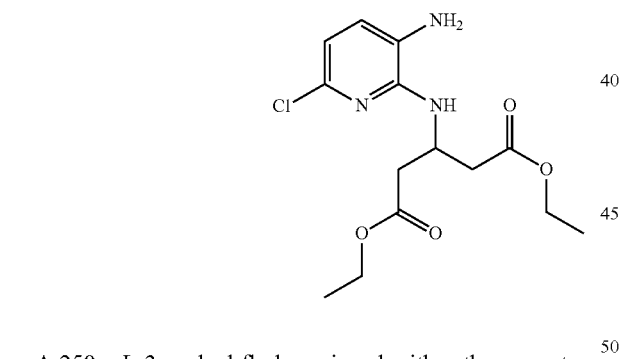

A 250 mL 3-necked flask equipped with a thermometer and a magnetic stir bar was charged with 2.7 g (7.5 mmol) of diethyl 3-((6-chloro-3-nitropyridin-2-yl)amino)pentanedioate, 2.1 g (37.5 mmol) of iron powder, 60 mL of 2-propanol, 20 mL of water, and 675 mg (11.0 mmol) of acetic acid. The mixture was stirred at 100 C for 1 h, monitoring by HPLC for the disappearance of the starting nitro compound. After the reaction was complete, the solids were filtered and washed with 2-propanol (3×50 mL), then the combined filtrate and washings was concentrated in vacuo. The residue was dissolved in 100 mL of water and extracted with dichloromethane (3×50 mL). The combined organic layers were back extracted with brine (1×50 mL), dried over Na₂SO₄, filtered, and concentrated to dryness. The crude product was purified via silica gel chromatography, eluting with 4/1 (v/v) hexanes/ethyl acetate to give 1.8 g (75%) of the product as a gray solid.

Step 5: Ethyl 2-(7-chloro-2-oxo-2,3,4,5-tetrahydro-1H-pyrido[2,3-b][1,4]diazepin-4-yl)acetate

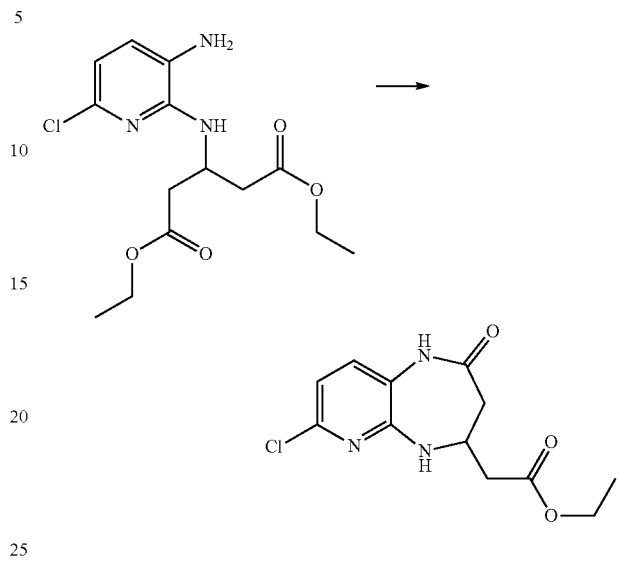

A 100 mL 3-necked flask equipped with a thermometer and a reflux condenser was charged with 1.8 g (5.4 mmol) of diethyl 3-((3-amino-6-chloropyridin-2-yl)amino)pentanedioate, 20 mL of toluene, and 1.0 mL (13.4 mmol) of trifluoroacetic acid. The mixture was stirred at reflux for 5 h, and the reaction was monitored by HPLC for the disappearance of starting material. After the reaction was complete, the solvents were removed in vacuo, then the residue was purified via silica gel chromatography, eluting with 3/1 (v/v) hexanes/ethyl acetate to give 1.1 g (70%) of the product as an off-white solid.

Step 6: 2-(7-chloro-2,3,4,5-tetrahydro-1H-pyrido[2,3-b][1,4]diazepin-4-yl)ethanol

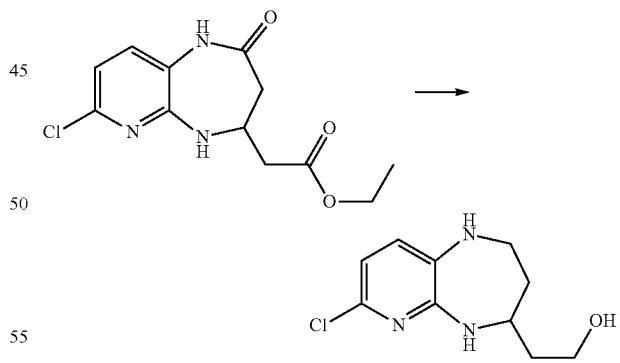

A 50 mL 3-necked flask equipped with a nitrogen inlet, a reflux condenser, and a thermometer was charged with 1.0 g (3.5 mmol) of ethyl 2-(7-chloro-2-oxo-2,3,4,5-tetrahydro-1H-pyrido[2,3-b][1,4]diazepin-4-yl)acetate, 530 mg (14.0 mmol) of LiAlH₄, and 10 mL of tetrahydrofuran. The reaction was stirred under N₂ at 60° C. for 6 h, monitoring for the appearance of product by HPLC. The ester was reduced rapidly, but the lactam required a longer time for complete reduction. When the reaction was complete, the mixture was cooled with an ice bath, 530 μL of water was added while keeping the internal temperature below 5° C., then the mixture was stirred for 15 min. Next, 530 µL of 15% (w/w) NaOH(aq.) was added while keeping the internal temperature below 5 C, then the mixture was stirred for 15 min. To complete the workup, 1590 µL water was added, then the mixture was stirred at ambient temperature for 30 min. The solids were filtered, then the precipitate was washed with tetrahydrofuran (3×50 mL). The filtrate was concentrated in vacuo, then the residue was purified via silica gel chromatography, eluting with 2/1 hexanes/ethyl acetate to give 520 mg (65%) of the product as a light yellow solid.

Step 7: 7-chloro-2,3,4,5-tetrahydro-1,4-ethanopyrido[2,3-b][1,4]diazepine

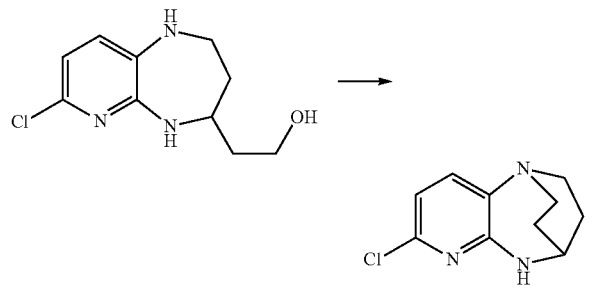

A 50 mL 3-necked flask was charged with 500 mg (2.2 mmol) of 2-(7-chloro-2,3,4,5-tetrahydro-1H-pyrido[2,3-b][1,4]diazepin-4-yl)ethanol, and 10 mL of 40% (w/w) HBr (aq.). The mixture was stirred at reflux for 18 h, then it was cooled to ambient temperature and neutralized with saturated NaHCO$_{3(aq.)}$. The aqueous mixture was extracted with ethyl acetate (3×50 mL), then the combined organic layers were back extracted with brine (1×50 mL), dried over Na$_2$SO$_4$, filtered, and concentrated in vacuo.

The residue was purified via silica gel chromatography, eluting with 3/1 hexanes/ethyl acetate to give 320 mg (70%) of the product as an off-white solid.

Step 8. Synthesis of 7-(3-(trifluoromethyl)phenyl)-2,3,4,5-tetrahydro-1,4-ethanopyrido[2,3-b][1,4]diazepine

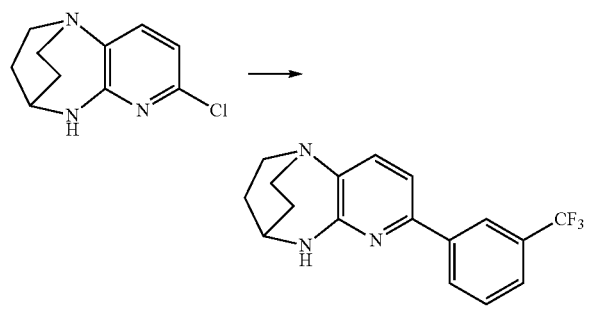

A dioxane/water mixture (10 mL/1 mL) was degassed and 7-chloro-2,3,4,5-tetrahydro-1,4-ethanopyrido[2,3-b][1,4]diazepine (250 mg, 1.196 mmol) was added, followed by 3-(trifluoromethyl)phenylboronic acid (454 mg, 2.392 mmol), Pd(dppf)Cl$_2$ (97 mg, 0.19 mmol), and Cs$_2$CO$_3$ (1.16 g, 3.588 mmol). The mixture was stirred at 110° C. for 12 hours, then concentrated and purified by column chromatography (PE/EtOAc=4/1) to give 7-(3-(trifluoromethyl)phenyl)-2,3,4,5-tetrahydro-1,4-ethanopyrido[2,3-b][1,4]diazepine (200 mg, 48%). MS (ESI) calcd for C$_{17}$H$_{16}$F$_3$N$_3$: 319.13.

Step 9. Synthesis of N-(pyridazin-3-yl)-7-(3-(trifluoromethyl)phenyl)-3,4-dihydro-1,4-ethanopyrido[2,3-b][1,4]diazepine-5(2H)-carboxamide

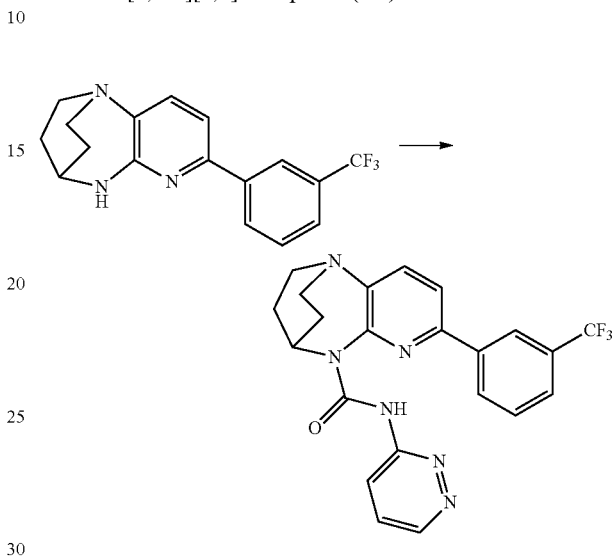

The following general urea coupling procedure was used: The carbamate of pyridazin-3-amine (53.9 mg, 0.25 mmol, 2.0 equiv.), 7-(3-(trifluoromethyl)phenyl)-2,3,4,5-tetrahydro-1,4-ethanopyrido[2,3-b][1,4]diazepine (40 mg, 0.12 mmol, 1.0 equiv.), and DMAP (18.4 mg, 0.15 mmol, 1.2 equiv.) in acetonitrile (5 mL) were stirred at 60° C. overnight. Reaction progress was monitored by TLC and LC/MS. The reaction mixture was loaded directly onto prep. TLC using 100% EtOAc as eluent to give N-(pyridazin-3-yl)-7-(3-(trifluoromethyl)phenyl)-3,4-dihydro-1,4-ethanopyrido[2,3-b][1,4]diazepine-5(2H)-carboxamide as a white solid (16.9 mg, 30.6%). MS (ESI) calcd for C$_{22}$H$_{19}$F$_3$N$_6$O: 440.16; found: 440.9 [M+H].

This general urea coupling procedure could be used to prepare a variety of 7-(3-(trifluoromethyl)phenyl)-, 7-(3-chlorophenyl)-, 7-(5-chloropyridin-3-yl)-, and 7-(5-fluoropyridin-3-yl)-3,4-dihydro-1,4-ethanopyrido[2,3-b][1,4]diazepine-5(2H)-carboxamides by substituting the appropriate amine moiety for pyridazin-3-amine.

Example 73. Preparation of 7-(3-chlorophenyl)-N-(pyridin-3-yl)-3,4-dihydro-1,4-ethanopyrido[2,3-b][1,4]diazepine-5(2H)-carboxamide Step 1. Synthesis of tert-butyl 7-chloro-3,4-dihydro-1,4-ethanopyrido[2,3-b][1,4]diazepine-5(2H)-carboxylate

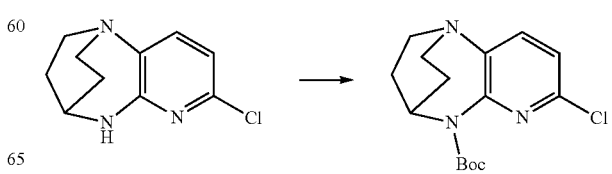

This moiety was made using the following protocol. A mixture of 7-chloro-2,3,4,5-tetrahydro-1,4-ethanopyrido[2,3-b][1,4]diazepine (3.0 g, 14.31 mmol), (Boc)₂O (4.6 g, 21.05 mmol, 1.5 equiv.), and DMAP (3.49 g, 28.62 mmol, 2.0 equiv.) in THF (5 mL) was stirred at 60° C. for 2 h. TLC and LC/MS were used to monitor reaction progress. Water (30 mL) was added and the mixture was extracted with DCM (3×15 mL). The organics were concentrated and the residue was purified by column chromatography to give tert-butyl 7-chloro-3,4-dihydro-1,4-ethanopyrido[2,3-b][1,4]diazepine-5(2H)-carboxylate as a white solid (4.5 g, 92%). MS (ESI) calcd for $C_{15}H_{20}ClN_3O_2$: 309.12.

Step 2. Synthesis of tert-butyl 7-(3-chlorophenyl)-3,4-dihydro-1,4-ethanopyrido[2,3-b][1,4]diazepine-5(2H)-carboxylate: (Sundia Prop. 455

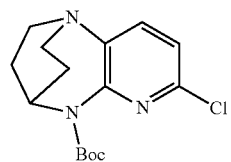
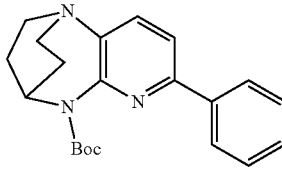

This moiety was made using the following protocol. To a degassed mixture of dioxane/water (20 mL/1 mL) was added tert-butyl 7-chloro-3,4-dihydro-1,4-ethanopyrido[2,3-b][1,4]diazepine-5(2H)-carboxylate (1.5 g, 4.85 mmol), (3-chlorophenyl)boronic acid (1.51 g, 9.70 mmol), Pd(dppf)Cl₂ (0.396 g, 0.485 mmol), and Cs₂CO₃ (4.74 g, 14.56 mmol). The mixture was stirred at 110° C. for 12 h, then concentrated and purified by column chromatography (PE/EA=2/1) to give tert-butyl 7-(3-chlorophenyl)-3,4-dihydro-1,4-ethanopyrido[2,3-b][1,4]diazepine-5(2H)-carboxylate (1.2 g, 89%). MS (ESI) calcd for $C_{21}H_{24}ClN_3O_2$: 385.16.

This general coupling procedure could be used to prepare a variety of 7-(3-substituted phenyl or pyridyl)-2,3,4,5-tetrahydro-1,4-ethanopyrido[2,3-b][1,4]diazepines by substituting the appropriate boronic acid or boronic ester moiety for (3-chlorophenyl)boronic acid.

Step 3. Synthesis of 7-(3-chlorophenyl)-2,3,4,5-tetrahydro-1,4-ethanopyrido[2,3-b][1,4]diazepine: (Sundia Prop. 455

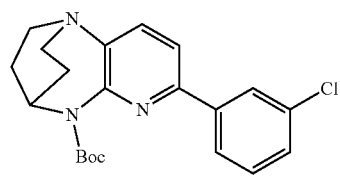

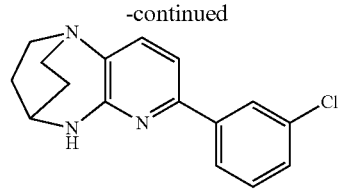

This moiety was made using the following protocol. Tert-butyl 7-(3-chlorophenyl)-3,4-dihydro-1,4-ethanopyrido[2,3-b][1,4]diazepine-5 (2H)-carboxylate (1.2 g, 3.1 mmol) was dissolved in HCl/MeOH (1 M, 20 mL) and the reaction mixture was stirred at room temp for 1.5 h, then concentrated in vacuo. Water (20 mL) and K₂CO₃ (3 g) were added. The mixture was stirred at room temp for 2 h, then extracted with DCM (3×15 mL). The organics were concentrated to give 7-(3-chlorophenyl)-2,3,4,5-tetrahydro-1,4-ethanopyrido[2,3-b][1,4]diazepine (800 mg, 90%). MS (ESI) calcd for $C_{16}H_{16}ClN_3$: 285.10.

Step 4. Synthesis of 7-(3-chlorophenyl)-N-(pyridin-3-yl)-3,4-dihydro-1,4-ethanopyrido[2,3-b][1,4]diazepine-5(2H)-carboxamide

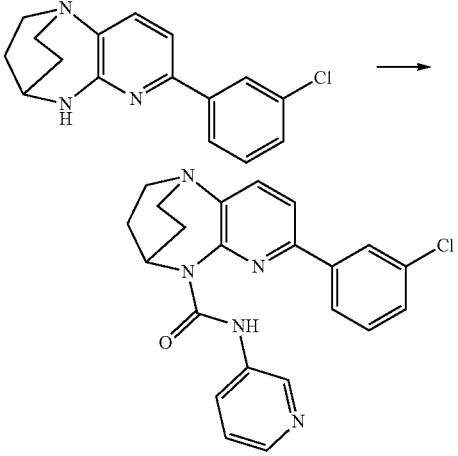

This compound was made using the general urea coupling procedure to give 7-(3-chlorophenyl)-N-(pyridin-3-yl)-3,4-dihydro-1,4-ethanopyrido[2,3-b][1,4]diazepine-5(2H)-carboxamide (20.4 mg, 24%). MS (ESI) calcd for $C_{22}H_{20}ClN_5O$: 405.14; found: 406 [M+H].

Example 74. Preparation of 7-(5-fluoropyridin-3-yl)-N-(pyridin-3-yl)-3,4-dihydro-1,4-ethanopyrido[2,3-b][1,4]diazepine-5(2H)-carboxamide

Step 1. Synthesis of tert-butyl 7-(5-fluoropyridin-3-yl)-3,4-dihydro-1,4-ethanopyrido[2,3-b][1,4]diazepine-5(2H)-carboxylate

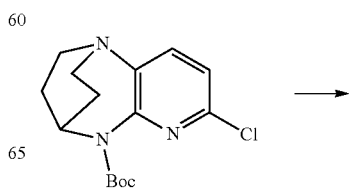

-continued

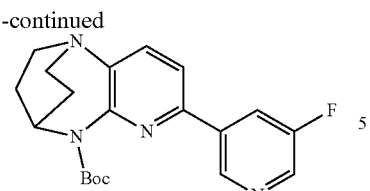

This moiety was made using the following protocol. To a degassed mixture of dioxane/water (30 mL/3 mL) was added tert-butyl 7-chloro-3,4-dihydro-1,4-ethanopyrido[2,3-b][1,4]diazepine-5(2H)-carboxylate (1.39 g, 4.5 mmol), (5-fluoropyridin-3-yl)boronic acid (1.27 g, 9.0 mmol), Pd(dppf)Cl$_2$ (0.37 g, 0.45 mmol), and Cs$_2$CO$_3$ (4.40 g, 13.5 mmol). The mixture was stirred at 110° C. for 12 h, then concentrated and purified by column chromatography (PE/EA=2/1) to give tert-butyl 7-(5-fluoropyridin-3-yl)-3,4-dihydro-1,4-ethanopyrido[2,3-b][1,4]diazepine-5(2H)-carboxylate (1.5 g, 89%). MS (ESI) calcd for C$_{20}$H$_{23}$FN$_4$O$_2$: 370.18.

Step 2. Synthesis of 7-(5-fluoropyridin-3-yl)-2,3,4,5-tetrahydro-1,4-ethanopyrido[2,3-b][1,4]diazepine

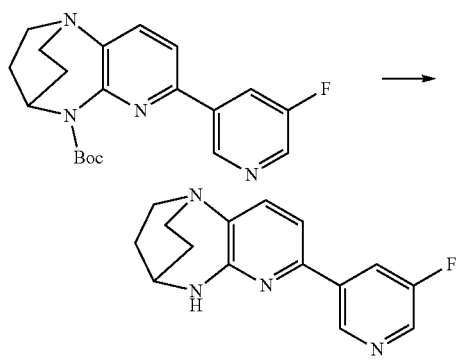

This moiety was made using the following protocol. TFA (20 mL) was added to a solution of tert-butyl 7-(5-fluoropyridin-3-yl)-3,4-dihydro-1,4-ethanopyrido[2,3-b][1,4]diazepine-5(2H)-carboxylate (1.50 g) in DCM (20 mL), and the reaction mixture was stirred at room temp for 3 h, then concentrated in vacuo. The residue was basified with saturated NaHCO$_3$ solution and extracted with DCM (3×15 mL). The organics were concentrated to give 7-(5-fluoropyridin-3-yl)-2,3,4,5-tetrahydro-1,4-ethanopyrido[2,3-b][1,4]diazepine (1.2 g, 100%). MS (ESI) calcd for C$_{15}$H$_{15}$FN$_4$: 270.13.

Step 3. Synthesis of 7-(5-fluoropyridin-3-yl)-N-(pyridin-3-yl)-3,4-dihydro-1,4-ethanopyrido[2,3-b][1,4]diazepine-5(2H)-carboxamide

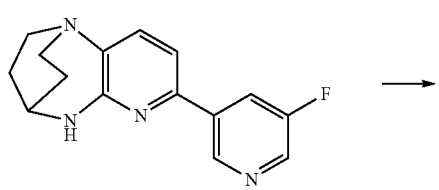

-continued

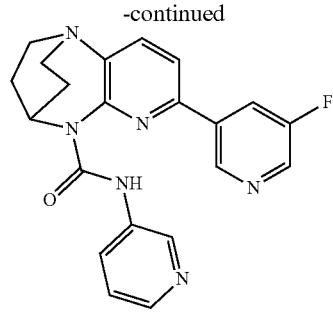

This compound was made using the general urea coupling procedure to give 7-(5-fluoropyridin-3-yl)-N-(pyridin-3-yl)-3,4-dihydro-1,4-ethanopyrido[2,3-b][1,4]diazepine-5(2H)-carboxamide (12.8 mg, 15%). MS (ESI) calcd for C$_{21}$H$_{19}$FN$_6$O: 390.16; found: 391 [M+H].

Example 75. Preparation of 3-bromo-5-(oxazol-5-yl)aniline

Step 1. Synthesis of 5-(3-bromo-5-nitrophenyl)oxazole

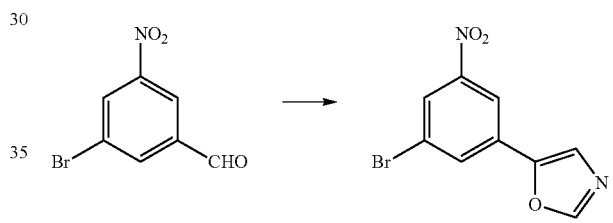

To a solution of 3-bromo-5-nitrobenzaldehyde (1 g, 4.34 mmol) in DME (10 mL) was added K$_2$CO$_3$ (1.2 g, 8.68 mmol), followed by 1-((isocyanomethyl)sulfonyl)-4-methylbenzene (891 mg, 4.56 mmol). The reaction mixture was stirred at reflux overnight. After cooling to room temp., EtOAc was added and the mixture was washed with H$_2$O twice then with brine. The organic layers were dried over MgSO$_4$, filtered, and concentrated. Purification by silica gel chromatography (0% to 100% EtOAc in pentane gradient) afforded 5-(3-bromo-5-nitrophenyl)oxazole (762 mg, 65%) as an orange solid. MS (ESI) calcd for C$_9$H$_5$BrN$_2$O$_3$: 268.0, 270.0.

Step 2. Synthesis of 3-bromo-5-(oxazol-5-yl)aniline

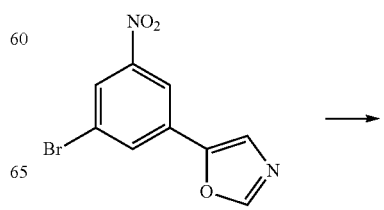

233
-continued

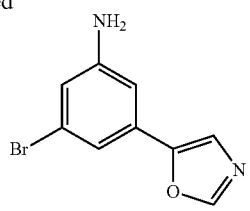

To a solution of 5-(3-bromo-5-nitrophenyl)oxazole (762 mg, 2.83 mmol) in THF (14 mL) was added acetic acid (13.6 mL), followed by iron powder (474 mg, 8.49 mmol). The reaction mixture was stirred at 60° C. overnight. After cooling to room temperature, the mixture was poured into a saturated $Na_2CO_3$ solution (175 mL) and extracted with EtOAc (50 mL×2). The combined organic layers were washed with brine, dried over $MgSO_4$, filtered, and concentrated to afford 3-bromo-5-(oxazol-5-yl)aniline (697 mg) as a brown oil. This material was used without further purification. MS (ESI) calcd for $C_9H7BrN_2O$: 238.0, 240.0.

This general two-step procedure of oxazole formation followed by nitro reduction could be used to prepare 4-bromo-5-(oxazol-5-yl)aniline by using 4-bromo-5-nitrobenzaldehyde.

Example 76. Preparation of 6-(oxazol-5-yl)pyridin-2-amine

Step 1. Synthesis of 6-amino-N-methoxy-N-methylpicolinamide

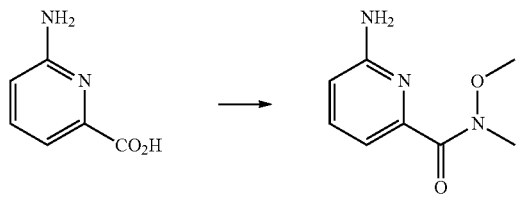

To a slurry of 6-aminopicolinic acid (10.0 g, 72.5 mmol) in acetonitrile (150 mL) was added N,O-dimethylhydroxylamine hydrochloride (8.52 g, 87.0 mmol), 1-hydroxybenzotriazole (11.8 g, 87.0 mmol), N-(3-dimethylamino)-N'-ethylcarbodiimide hydrochloride (16.7 g, 87.0 mmol), and N,N-diisopropylethylamine (37.7 mL, 217 mmol). The mixture was stirred at room temperature overnight, and the solvent removed in vacuo. The residue was partitioned between 1N NaOH and ethyl acetate, and the aqueous layer was extracted three times with ethyl acetate. The combined organic layers were washed with brine, dried with sodium sulfate, and the solvent removed in vacuo. The remaining residue was purified by flash chromatography (ethyl acetate with 0.1% triethylamine) to give 6-amino-N-methoxy-N-methylpicolinamide (4.30 g, 23.7 mmol, 33% yield). MS (ESI) calcd for $C_8H_{11}N_3O_2$: 181.1.

234
Step 2. Synthesis of 6-(oxazol-5-yl)pyridin-2-amine

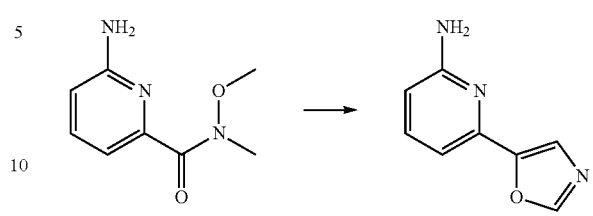

Lithium aluminum hydride (1.08 g, 28.5 mmol) was added to a solution of 6-amino-N-methoxy-N-methylpicolinamide (4.30 g, 23.7 mmol) in THF (30 mL). The reaction was stirred at room temperature for 90 min. Ethyl acetate (30 mL) was added slowly, the reaction was filtered, and the filtrate taken and all the solvent removed in vacuo to give 6-aminopicolinaldehyde, which was taken on crude to the next step.

To a solution of the above aldehyde in methanol (20 mL) was added p-toluenesulfonylmethyl isocyanide (13.9 g, 71.2 mmol) and potassium carbonate (19.4 g, 140 mmol). The reaction was stirred at reflux for 2 h, then all solvent removed in vacuo.

The residue was partitioned between ethyl acetate (150 mL) and water (70 mL). The organic layer was washed with brine, dried with sodium sulfate, and the solvent removed in vacuo. The remaining residue was purified by flash chromatography (10% methanol in dichloromethane) to give 6-(oxazol-5-yl)pyridin-2-amine (2.00 g, 12.4 mmol, 52% yield over two steps). MS (ESI) calcd for $C_8H_7N_3O$: 161.1.

The following compounds were prepared in an analogous manner: 4-(oxazol-5-yl)pyridin-2-amine; 5-(oxazol-5-yl)pyridin-3-amine.

Example 77: Synthesis of 3,5-bis(oxazol-5-yl)aniline

Step 1. Synthesis of $N^1,N^3$-dimethoxy-$N^1,N^3$-dimethyl-5-nitroisophthalamide

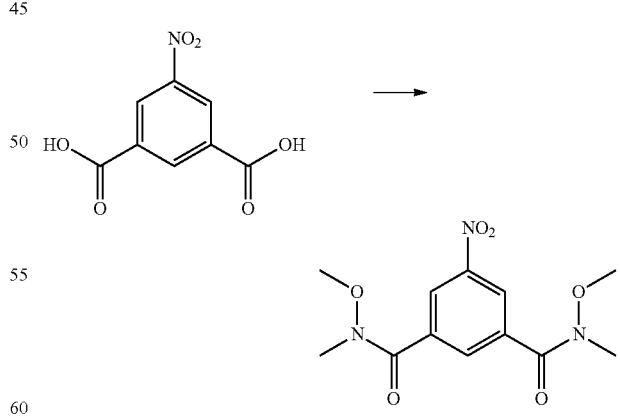

To a solution of 5-nitroisophthalic acid (5.00 g, 23.7 mmol) in dichloromethane (100 mL) was added oxalyl chloride (5.00 mL, 59.1 mmol), and the solution cooled to 0° C. DMF (1.0 mL) was added dropwise over 30 min. The mixture was warmed to room temperature and stirred for 4 h. All solvents were removed in vacuo.

To a mixture of N,O-dimethylhydroxylamine hydrochloride (4.6 g, 47.1 mmol) and triethylamine (6.60 mL, 47.4 mmol) in dichloromethane (80 mL) was added a solution of the above acid chloride in dichloromethane (20 mL) at 0° C. Once the reaction was complete, the reaction mixture was concentrated in vacuo. The residue was partitioned between IN sodium hydroxide and ethyl acetate, the organic layer separated, and the aqueous layer extracted with ethyl acetate. The combined organic layers were dried with sodium sulfate, the solvents removed in vacuo, and the residue purified by silica gel chromatography (1:1 petroleum ether:ethyl acetate) to give $N^1,N^3$-dimethoxy-$N^1,N^3$-dimethyl-5-nitroisophthalamide (4.00 g, 13.5 mmol, 57% yield). MS (ESI) calcd for $C_{12}H_{15}N_3O_6$: 297.1.

Step 2. Synthesis of 5-nitroisophthalaldehyde

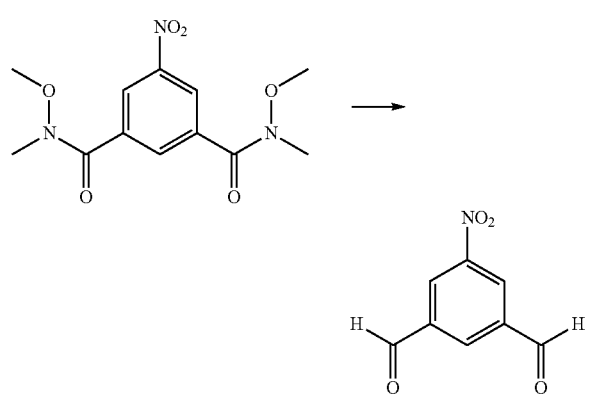

Lithium aluminum hydride (2.70 g, 71.1 mmol) was added to a stirred solution of $N^1,N^3$-dimethoxy-$N^1,N^3$-dimethyl-5-nitroisophthalamide (5.00 g, 16.9 mmol) in THF (150 mL) at −40° C. The reaction was stirred at −40° C. for 4 h. 10% sodium hydroxide solution (2.7 mL) was added slowly, followed by water (2.7 mL). The resulting solid was filtered, and the filtrate concentrated in vacuo to give 5-nitroisophthalaldehyde (1.37 g, 7.65 mmol, 45% yield). MS (ESI) calcd for $C_8H_5NO_4$: 179.0.

Step 3. Synthesis of 5,5'-(5-nitro-1,3-phenylene)bis(oxazole)

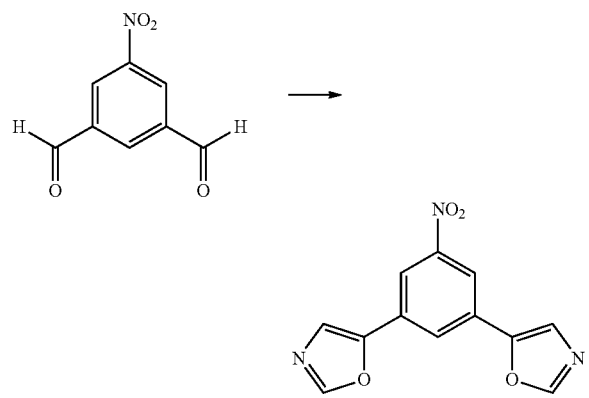

1-Isocyanomethanesulfonyl-4-methyl-benzene (7.40 g, 37.8 mmol) and anhydrous potassium carbonate (5.20 g, 37.8 mmol) were added to a solution of 5-nitroisophthalaldehyde (1.37 g, 7.65 mmol) in methanol (100 mL). The reaction was refluxed under nitrogen for 2 h. After cooling, the solvent was removed in vacuo. The residue was partitioned between ethyl acetate (150 mL) and water (70 mL). The organic layer was removed, and the aqueous layer extracted with ethyl acetate (3×150 mL). The combined organic layers were washed with brine, dried with sodium sulfate, and concentrated to give crude 5,5'-(5-nitro-1,3-phenylene)bis(oxazole) (1.70 g, 6.61 mmol, 86% yield). MS (ESI) calcd for $C_{12}H_7N_3O_4$: 257.0.

Step 4. Synthesis of 3,5-bis(oxazol-5-yl)aniline

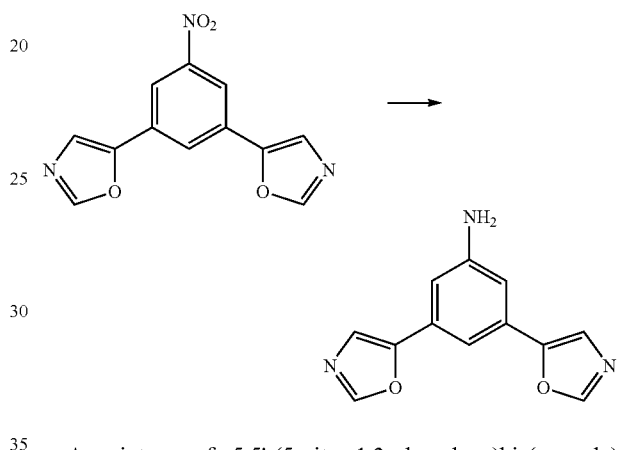

A mixture of 5,5'-(5-nitro-1,3-phenylene)bis(oxazole) (1.70 g, 6.61 mmol) and palladium on carbon (200 mg) in ethyl acetate (50 mL) was stirred under hydrogen for 4 h. The solid was filtered, and the filtrate concentrated in vacuo. The remaining residue was purified by silica gel chromatography (4:1 petroleum ether:ethyl acetate) to give 3,5-bis(oxazol-5-yl)aniline (1.30 g, 5.72 mmol, 87% yield). MS (ESI) calcd for $C_{12}H_9N_3O_2$: 227.1.

Example 78. Preparation of tert-butyl (2-(4-(3-aminophenyl)-1H-1,2,3-triazol-1-yl)ethyl)carbamate

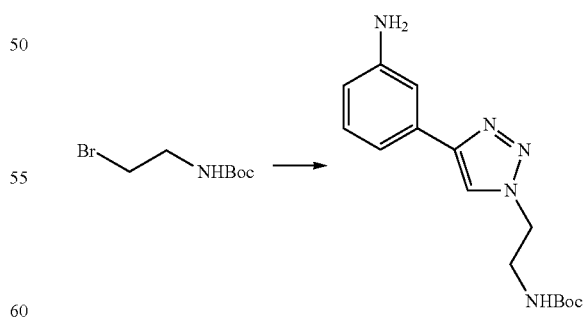

A 20 mL microwave vial was charged with tert-butyl (2-bromoethyl)carbamate (551 mg, 2.50 mmol), sodium azide (460 mg, 7.05 mmol), and DMF (5 mL). The vial was sealed, and heated in the microwave at 110° C. for 12 h. The reaction mixture was poured into water (8 mL), and extracted with ethyl acetate (2×10 mL). The combined organic layers were dried with magnesium sulfate, and all solvents removed in vacuo to give crude tert-butyl (2-azidoethyl)carbamate.

The crude tert-butyl (2-azidoethyl)carbamate was dissolved in THF (5 mL) and triethylamine (1 mL). 3-ethynylaniline (350 mg, 2.99 mmol) was added, followed by copper (I) iodide (15.0 mg, 0.0788 mmol). The reaction was stirred at 60° C. for 2 h, then all solvents removed in vacuo, and the remaining residue purified by flash chromatography (50% to 100% ethyl acetate in pentane) to give tert-butyl (2-(4-(3-aminophenyl)-1H-1,2,3-triazol-1-yl)ethyl)carbamate 415 mg, 1.37 mmol, 55% yield over 2 steps.) MS (ESI) calcd for $C_{15}H_{21}N_5O_2$: 303.2.

Example 79. Preparation of tert-butyl ((1-(3-aminophenyl)-1H-1,2,3-triazol-4-yl)methyl)carbamate

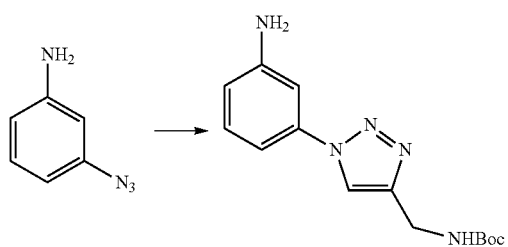 [SMILES: [N-]=[N+]=Nc1cccc(N)c1 ; CC(C)(C)OC(=O)NCc1cn(-c2cccc(N)c2)nn1]

To a solution of 3-azidoaniline (Chem. Commun. 2004, 888) (1.34 g, 9.99 mmol) in THF (9.0 mL) and triethylamine (1.0 mL) was added tert-butyl prop-2-yn-1-ylcarbamate (1.55 g, 9.99 mmol) and copper (I) iodide (40 mg, 0.210 mmol). The reaction was stirred at 60° C. for 1 h, then all solvents removed in vacuo. The remaining residue was purified by flash chromatography (0% to 80% ethyl acetate in pentane) to give tert-butyl ((1-(3-aminophenyl)-1H-1,2,3-triazol-4-yl)methyl)carbamate (Compound #; 1.71 g, 5.91 mmol, 59% yield). MS (ESI) calcd for $C_{14}H_{19}N_5O_2$: 289.1; found: 290.1 [M+H].

Example 80: Preparation of tert-butyl ((1-(3-aminophenyl)-1H-1,2,3-triazol-5-yl)methyl)carbamate

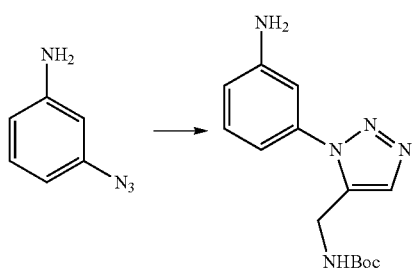 [SMILES: [N-]=[N+]=Nc1cccc(N)c1 ; CC(C)(C)OC(=O)NCc1cnnn1-c1cccc(N)c1]

To a vial with 3-azidoaniline (1.33 g, 9.92 mmol), tert-butyl prop-2-yn-1-ylcarbamate (1.55 g, 9.99 mmol), and pentamethylcyclopentadienylbis(triphenylphosphine)ruthenium(II) chloride (15.9 mg, 0.020 mmol) was added toluene (10 mL). The reaction was stirred at 100° C. for 72 h, then the reaction cooled to room temperature. Dichloromethane (5 mL) was added to dissolve any solids, and the remaining solution purified by silica gel chromatography (50% to 80% ethyl acetate in pentane) to give tert-butyl ((1-(3-aminophenyl)-1H-1,2,3-triazol-5-yl)methyl)carbamate (970 mg, 3.35 mmol, 34% yield). MS (ESI) calcd for $C_{14}H_{19}N_5O_2$: 289.2.

Example 81: Preparation of $N^4,N^4$-dimethylpyrimidine-2,4-diamine

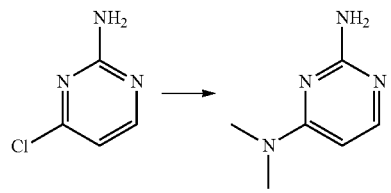

4-chloro-2-aminopyrimidine (495 mg, 3.82 mmol) was dissolved in aqueous dimethylamine (33%) in a sealed tube, and the reaction stirred at 100° C. overnight. After cooling, the reaction was diluted with water, and extracted with dichloromethane. The organic layer was washed with water and brine, and dried with sodium sulfate, and the solvents removed in vacuo to give $N^4,N^4$-dimethylpyrimidine-2,4-diamine (400 mg, 2.89 mmol, 76% yield). MS (ESI) calcd for $C_6H_{10}N_4$: 138.1.

Example 82: Preparation of tert-butyl 4-(2-aminopyrimidin-4-yl)piperazine-1-carboxylate

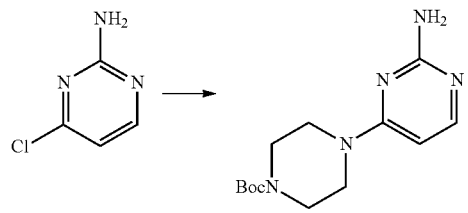 [SMILES: Nc1nccc(Cl)n1 ; CC(C)(C)OC(=O)N1CCN(c2ccnc(N)n2)CC1]

THF (20 mL) was added to a mixture of 4-chloro-2-aminopyrimidine (500 mg, 3.87 mmol) and N-Boc piperazine (7.21 g, 38.7 mmol). The reaction was stirred at 70° C. overnight. After cooling, the solvent was removed in vacuo and the remaining residue purified by silica gel chromatography (1:1 petroleum ether:ethyl acetate) to give tert-butyl 4-(2-aminopyrimidin-4-yl)piperazine-1-carboxylate (650 mg, 2.33 mmol, 60% yield). MS (ESI) calcd for $C_{13}H_{21}N_5O_2$: 279.2.

The following compound was made in an analogous manner: 4-(4-methylpiperazin-1-yl)pyrimidin-2-amine Example 83. Preparation of tert-butyl (3-(4-amino-2-(oxazol-5-yl)phenyl)prop-2-yn-1-yl)carbamate Step 1. Synthesis of 2-bromo-5-nitrobenzaldehyde

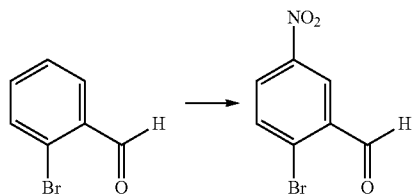 [SMILES: O=Cc1ccccc1Br ; O=Cc1cc([N+](=O)[O-])ccc1Br]

To a solution of 2-bromobenzaldehyde (10.0 g, 53.7 mmol) in H$_2$SO$_4$ (100 mL) was added KNO$_3$ (5.43 g, 53.7 mmol) in portions over 1 h at 0° C. The mixture was stirred for 40 min and additional KNO$_3$ (0.72 g) was added. The reaction mixture was stirred at 0° C. for 3 h then poured into ice water. The resulting precipitate was collected by filtration, rinsed with water and recrystallized from EtOAc/Pentane to give 2-bromo-5-nitrobenzaldehyde (11.7 g, 94% yield) as a white solid. MS (ESI) calcd for C$_7$H4BrNO$_3$: 228.9.

Step 2. Synthesis of
5-(2-bromo-5-nitrophenyl)oxazole

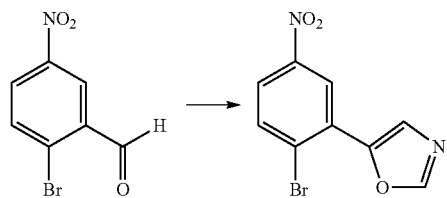 [SMILES: O=Cc1cc([N+](=O)[O-])ccc1Br ; O=[N+]([O-])c1ccc(Br)c(-c2cnco2)c1]

A mixture of 2-bromo-5-nitrobenzaldehyde (1.0 g, 4.33 mmol), K$_2$CO$_3$ (1.79 g, 12.9 mmol) and TosMIC (2.12 g, 10.8 mmmol) in MeOH was heated at 60° C. for 1.5 h. The mixture was concentrated. Water was added and the solid collected by filtration, rinsed with water, MeOH then petroleum ether to give 5-(2-bromo-5-nitrophenyl)oxazole (750 mg, yield 65%). as grey solid. MS (ESI) calcd for C$_9$H$_5$BrN$_{20}$O$_3$: 228.9.

Step 3. Synthesis of tert-butyl (3-(4-nitro-2-(oxazol-5-yl)phenyl)prop-2-yn-1-yl)carbamate

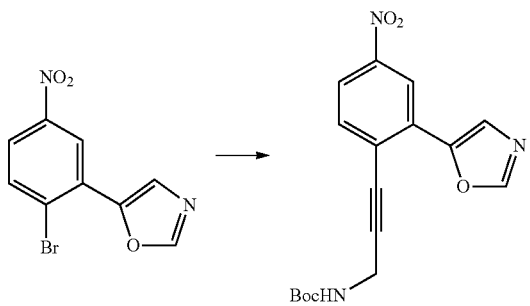 [SMILES: O=[N+]([O-])c1ccc(Br)c(-c2cnco2)c1 ; CC(C)(C)OC(=O)NCC#Cc1ccc([N+](=O)[O-])cc1-c1cnco1]

To a solution of 5-(2-bromo-5-nitrophenyl)oxazole (300 mg, 1.1 mmol) in DME (20 mL) was added tert-butyl prop-2-yn-1-ylcarbamate (431 mg, 2.77 mmol) under N$_2$. CuI (21 mg, 0.11 mmol) and Pd(dppf)Cl$_2$ (78 mg, 0.11 mmol) were added followed by TEA (0.5 mL). The reaction mixture was heated at 80° C. for 4 h, cooled to room temperature, poured into water, and extracted with EtOAc (3×50 mL). The combined organic layers were washed with brine, dried and concentrated. The residue was purified by silica gel column chromatography (EtOAc:Pentane=1:5) to give tert-butyl (3-(4-nitro-2-(oxazol-5-yl)phenyl)prop-2-yn-1-yl)carbamate (350 mg, yield 92%) as a yellow oil. MS (ESI) calcd for C$_{17}$H$_{17}$N$_3$O$_5$: 343.1.

Step 4. Synthesis of tert-butyl (3-(4-amino-2-(oxazol-5-yl)phenyl)prop-2-yn-1-yl)carbamate

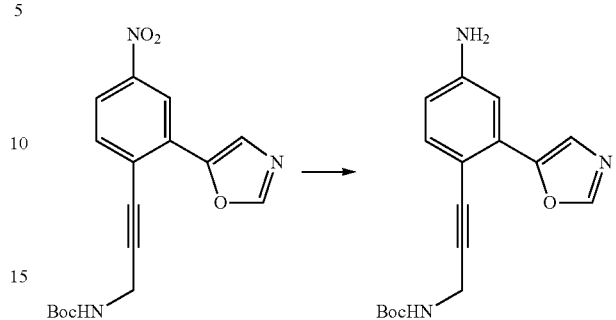

A suspension of tert-butyl (3-(4-nitro-2-(oxazol-5-yl)phenyl)prop-2-yn-1-yl)carbamate (3.8 g, 11.1 mmol) and Fe (4.96 g, 8.86 mmol) in sat.aq NH$_4$Cl/MeOH (V/V=1:3) was heated at 60° C. for 4.5 h. The mixture was cooled to room temperature, passed through a pad of celite and the filtrate was concentrated. The residue was dissolved in EtOAc, washed with water, dried (Na$_2$SO$_4$) and concentrated. The crude residue was purified by silica gel column chromatography to give tert-butyl (3-(4-amino-2-(oxazol-5-yl)phenyl)prop-2-yn-1-yl)carbamate (1.51 g, yield 44%) as a yellow oil. MS (ESI) calcd for C$_{17}$H$_{19}$N$_3$O$_3$: 228.9.

tert-butyl (3-(3-amino-5-(oxazol-5-yl)phenyl)prop-2-yn-1-yl)carbamate was prepared from 3-bromo-5-nitrobenzaldehyde in a similar manner to that described for tert-butyl (3-(4-amino-2-(oxazol-5-yl)phenyl)prop-2-yn-1-yl)carbamate.

Example 84. Preparation of tert-butyl (3-(4-amino-2-(oxazol-5-yl)phenyl)propyl)carbamate

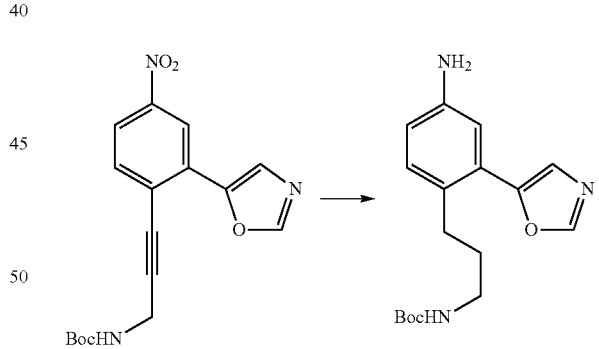

A mixture of tert-butyl (3-(4-nitro-2-(oxazol-5-yl)phenyl) prop-2-yn-1-yl)carbamate (3.0 g, 8.75 mmol) and 10 wt % Pd/C (1.0 g) in MeOH (100 mL) was stirred under H$_2$ atmosphere (50 psi) for 16 h. The mixture catalyst was removed by filtration, and the filtrate concentrated. The residue was purified by silica gel column chromatography to give tert-butyl (3-(4-amino-2-(oxazol-5-yl)phenyl)propyl) carbamate (940 mg, yield 35%) as a yellow oil. MS (ESI) calcd for C$_{17}$H$_{23}$N$_3$O$_3$: 228.9. tert-butyl (3-(3-amino-5-(oxazol-5-yl)phenyl)propyl)carbamate was prepared from tert-butyl (3-(3-nitro-5-(oxazol-5-yl)phenyl)prop-2-yn-1-yl)carbamate in a similar manner to that described for tert-butyl (3-(4-amino-2-(oxazol-5-yl)phenyl)propyl)carbamate.

Example 85. Preparation of 2-(3,3-difluoropyrrolidin-1-yl)-4-(4,4,5,5-tetramethyl-1,3,2-dioxaborolan-2-yl)pyridine

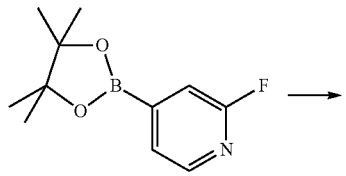

A mixture of 2-fluoro-4-(4,4,5,5-tetramethyl-1,3,2-dioxaborolan-2-yl)pyridine (1 g, 4.48 mmol), 3,3-difluoropyrrolidine hydrochloride (1.9 g, 13.4 mmol), and $K_2CO_3$ (3 g, 22.4 mmol) in NMP (13 mL) was stirred at 110° C. overnight. A second portion of 3,3-difluoropyrrolidine hydrochloride (0.5 g) was added and stirred overnight. The mixture was filtered, washed with $H_2O$, added 2N HCl to adjust pH to 1. The mixture was washed with EtOAc to remove residual 2-fluoro-4-(4,4,5,5-tetramethyl-1,3,2-dioxaborolan-2-yl)pyridine. The aqueous layer was adjusted to pH 13 with $K_2CO_3$ solution, then extracted with EtOAc to afford 2-(3,3-difluoropyrrolidin-1-yl)-4-(4,4,5,5-tetramethyl-1,3,2-dioxaborolan-2-yl)pyridine (220 mg, 17%). MS (ESI) calcd for $C_{15}H2_1BF_2N_2O_2$: 310.2.

This general procedure could be used to prepare 4-(4,4,5,5-tetramethyl-1,3,2-dioxaborolan-2-yl)-2-(3-(trifluoromethyl)pyrrolidin-1-yl)pyridine by using 3-(trifluoromethyl)pyrrolidine hydrochloride.

Example 86. Preparation of (S)-2-(3-fluoropyrrolidin-1-yl)-4-(4,4,5,5-tetramethyl-1,3,2-dioxaborolan-2-yl)pyridine

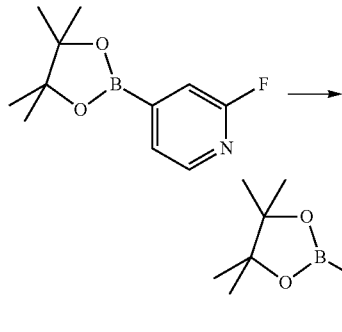

A mixture of 2-fluoro-4-(4,4,5,5-tetramethyl-1,3,2-dioxaborolan-2-yl)pyridine (200 mg), (S)-3-fluoropyrrolidine hydrochloride (350 mg), and $Na_2CO_3$ (480) in IPA (3.5 mL) was stirred at 91° C. for 17 hrs. The mixture was filtered and concentrated. 2N HCl was added to adjust pH to 1 and extracted with EtOAc. The aqueous layer was adjusted to pH 7 with $Na_2CO_3$ solution and the water was removed with toluene. The residue was taken up in EtOAc, filtered, and concentrated to afford (S)-2-(3-fluoropyrrolidin-1-yl)-4-(4,4,5,5-tetramethyl-1,3,2-dioxaborolan-2-yl)pyridine (95 mg, 36%). MS (ESI) calcd for $C_{15}H_{22}BFN_2O_2$: 292.2.

This general procedure could be used to prepare (R)-2-(3-fluoropyrrolidin-1-yl)-4-(4,4,5,5-tetramethyl-1,3,2-dioxaborolan-2-yl)pyridine by using (R)-3-fluoropyrrolidine hydrochloride.

Example 87. Preparation of 3,3-difluoro-1-(3-(4,4,5,5-tetramethyl-1,3,2-dioxaborolan-2-yl)phenyl)pyrrolidine

Step 1. Synthesis of 1-(3-bromophenyl)-3,3-difluoropyrrolidine

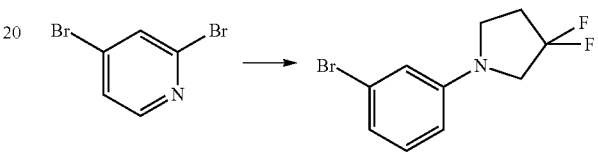

A mixture of 1,3-dibromobenzne (1 g, 4.24 mmol), 3,3-difluoropyrrolidine hydrochloride (669 mg, 4.66 mmol), $Pd_2(dba)3$ (134 mg, 0.233 mmol), $Cs_2CO_3$ (3.32 g, 10.2 mmol), and BINAP (264 mg, 0.424 mmol) in toluene (20 mL) was heated to reflux under a $N_2$ atmosphere. After stirring overnight, the mixture was cooled to room temp. and concentrated. The concentrate was suspended in EtOAc (50 mL), washed with water (20 mL×3) and brine (20 mL), dried over $Na_2SO_3$ and concentrated. Purification by column chromaotography (hexane/EtOAc=100/1) afforded 1-(3-bromophenyl)-3,3-difluoropyrrolidine (645 mg, >100%) as a colorless oil. MS (ESI) calcd for $C_{10}H_{10}BrF_2N$: 261.0.

Step 2. Synthesis of 3,3-difluoro-1-(3-(4,4,5,5-tetramethyl-1,3,2-dioxaborolan-2-yl)phenyl)pyrrolidine

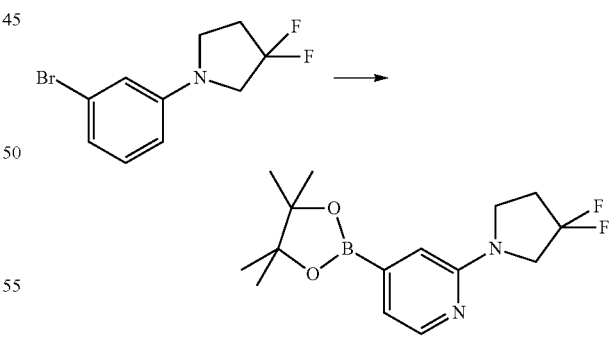

A suspension of 1-(3-bromophenyl)-3,3-difluoropyrrolidine (899 mg, 3.43 mmol), 4,4,4',4',5,5,5',5'-octamethyl-2,2'-bi(1,3,2-dioxaborolane) (957 mg, 3.77 mmol), Pd(dppf)C12 (75 mg, 0.103 mmol), KOAc (1 g, 10.29 mmol) in dioxane (18 mL) was heated to 85° C. under a $N_2$ atmosphere. After stirring overnight, the suspension was cooled to room temp. and filtered. The filtrate was concentrated and purified by column chromatography (hexane, then hexane/EtOAc=100/1) to afford 3,3-difluoro-1-(3-(4,4,5,5-tetramethyl-1,3,2-dioxaborolan-2-yl)phenyl)pyrrolidine (Compound A #; 873 mg, 82%) as a white solid. MS (ESI) calcd for $C_{16}H_{22}BF_2NO_2$: 309.2.

This general two-step procedure could be used to prepare 1-(3-(4,4,5,5-tetramethyl-1,3,2-dioxaborolan-2-yl)phenyl)-3-(trifluoromethyl)pyrrolidine by using 3-(trifluoromethyl) pyrrolidine hydrochloride.

Example 88. Preparation of 2-(3-((2,2-dimethyl-1,3-dioxolan-4-yl)methyl)phenyl)-4,4,5,5-tetramethyl-1,3,2-dioxaborolane Step 1. Synthesis of 1-allyl-3-bromobenzene

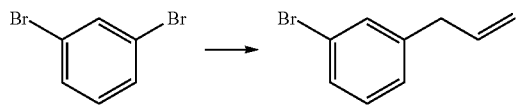

In a 3-neck flask, metal Mg (1.78 g, 73.76 mmol) was immersed in dry ether (20 mL) under $N_2$ atmosphere. One-third of the volume of 1,3-dibromobenzene (15 g, 63.58 mmol) in dry ether (20 mL) was added into the mixture. 1,2-Dibromoethane (0.1 mL) was added to initiate the reaction. After the reflux was steady, the remaining amount of the 1,3-dibromobenzene solution was added dropwise at a rate to maintain reflux. Upon completion of addition, the mixture was stirred at reflux for 1 hr. Then a solution of allylbromide (7.87 g, 65.12 mmol) in dry ether (20 mL) was added dropwise. Upon completion of addition, the suspension was stirred at reflux for 1 hr. The reaction was quenched with sat. $NH_4Cl$ (100 mL) and the mixture was separated. The aqueous phase was extracted with ether (20 mL×2). The combined organic phases were washed with water (70 mL×2) and brine (30 mL), dried over $Na_2SO_4$, and concentrated to afford 1-allyl-3-bromobenzene (146 g) as a colorless oil. This material was used without further purification. MS (ESI) calcd for $C_9H9Br$: 196.0.

Step 2. Synthesis of 3-(3-bromophenyl)propane-1,2-diol

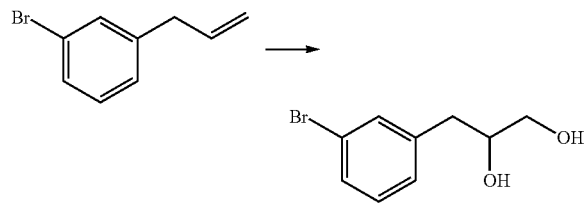

To a solution of 1-allyl-3-bromobenzene (A #; 1 g, 5.08 mmol) in $CH_3CN/H_2O$ (20 mL, v/v=4/1) were added NMO (1.3 g, 11.16 mmol) and $K_2OsO_4 \cdot 2H_2O$ (187 mg, 0.508 mmol).

The mixture was stirred at room temp. for 2 days. The $CH_3CN$ was removed under reduced pressure and the concentrate was diluted with EtOAc. The mixture was filtered through Celite and the filtrate was concentrated to afford 3-(3-bromophenyl)propane-1,2-diol (Compound A #). This material was used without further purification. MS (ESI) calcd for $C_9H_{11}BrO_2$: 230.0.

Step 3. Synthesis of 4-(3-bromobenzyl)-2,2-dimethyl-1,3-dioxolane

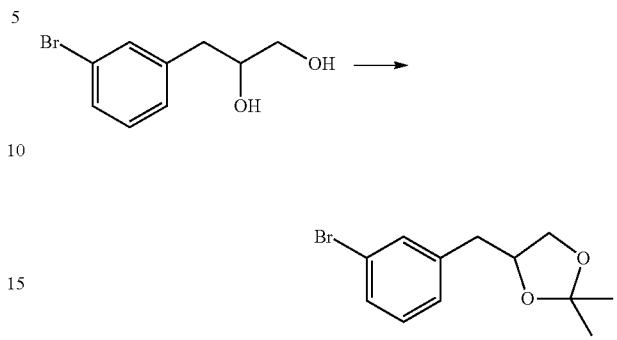

To a solution of 3-(3-bromophenyl)propane-1,2-diol (A #; 1.17 g, 5.06 mmol) in acetone (25 mL) were added 2,2-dimethoxypropane (1.8 mL, 15.18 mmol) and PTSA (96 mg, 0.506 mmol). The mixture was stirred at room temp. overnight. The reaction mixture was concentrated and purified by column chromatography (hexane/EtOAc=20/1) to afford 4-(3-bromobenzyl)-2,2-dimethyl-1,3-dioxolane (Compound A #; 200 mg, 15%) as a pale yellow oil. MS (ESI) calcd for $C_{12}H_{15}BrO_2$: 270.0.

Step 4. Synthesis of 2-(3-((2,2-dimethyl-1,3-dioxolan-4-yl)methyl)phenyl)-4,4,5,5-tetramethyl-1,3,2-dioxaborolane

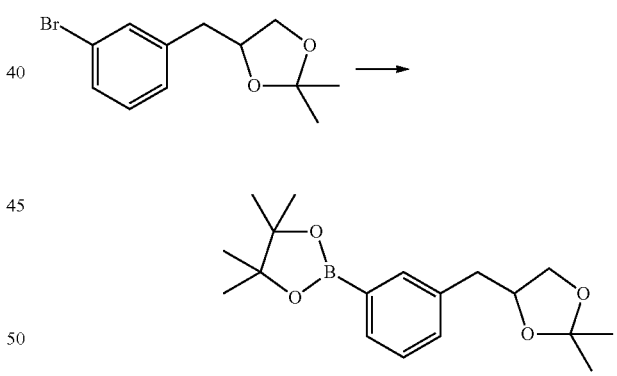

A mixture of 4-(3-bromo-benzyl)-2,2-dimethyl-[1,3]dioxolane (A #; 800 mg, 2.95 mmol) and bis(pinacolato) diboron (822 mg, 1.1 eq), Pd(dppf)Cl$_2$ (216 mg, 0.1 eq) and KOAc (868 mg, 3.0 eq) in dioxane (15 mL) was degassed and heated to 85° C. under $N_2$. After stirring overnight at 85° C., the black suspension was cooled to room temp. and filtered through Celite. The filtrate was concentrated and purified by column chromatography (hexane/EtOAc=40/1) to afford 2-(3-((2,2-dimethyl-1,3-dioxolan-4-yl)methyl)phenyl)-4,4,5,5-tetramethyl-1,3,2-dioxaborolane (Compound A #; 800 mg, 85%) as a colorless oil. MS (ESI) calcd for $C_{18}H_{27}BO_4$: 318.2.

Example 89. Preparation of (9S)—N-(4-(aminomethyl)phenyl)-2-(3-(trifluoromethyl)phenyl)-8,9-dihydro-6H-5,9-meth-anopyrido[2,3-b][1,4]diazocine-10(7H)-carboxamide hydrochloride and 2-(6-Hydroxy-3-oxo-3H-xanthen-9-yl)-5-((6-oxo-6-((4-((9S)-2-(3-(trifluoromethyl)phenyl)-7,8,9,10-tetrahydro-6H-5,9-methanopyrido[2,3-b][1,4]diazocine-10-carboxamido)benzyl) amino)hexyl)carbamoyl)benzoic acid

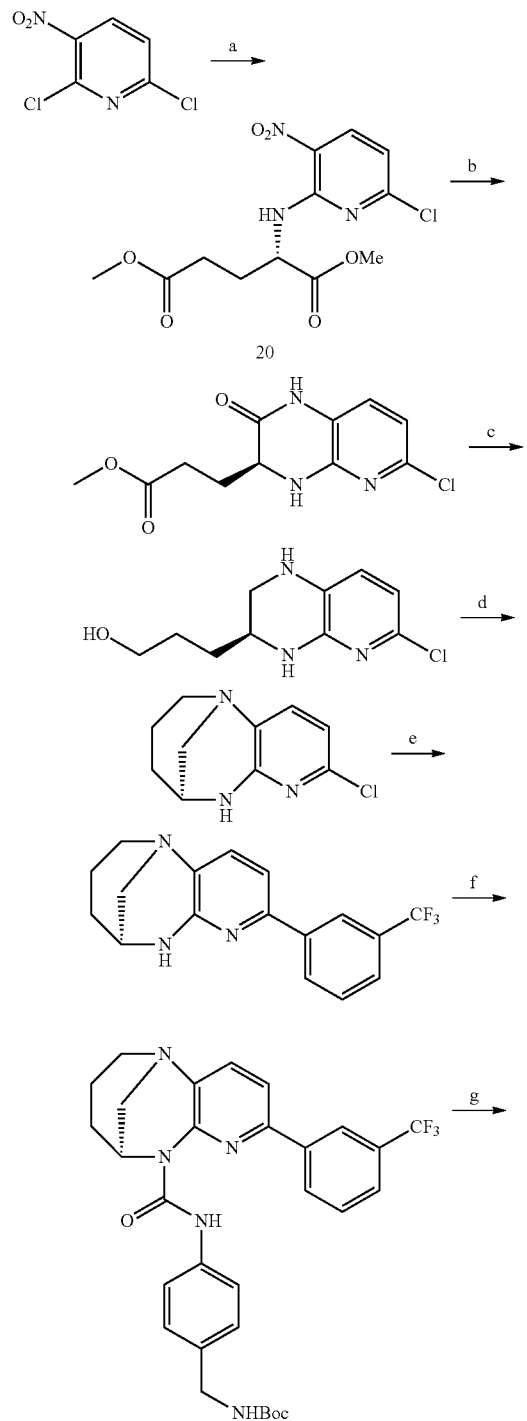

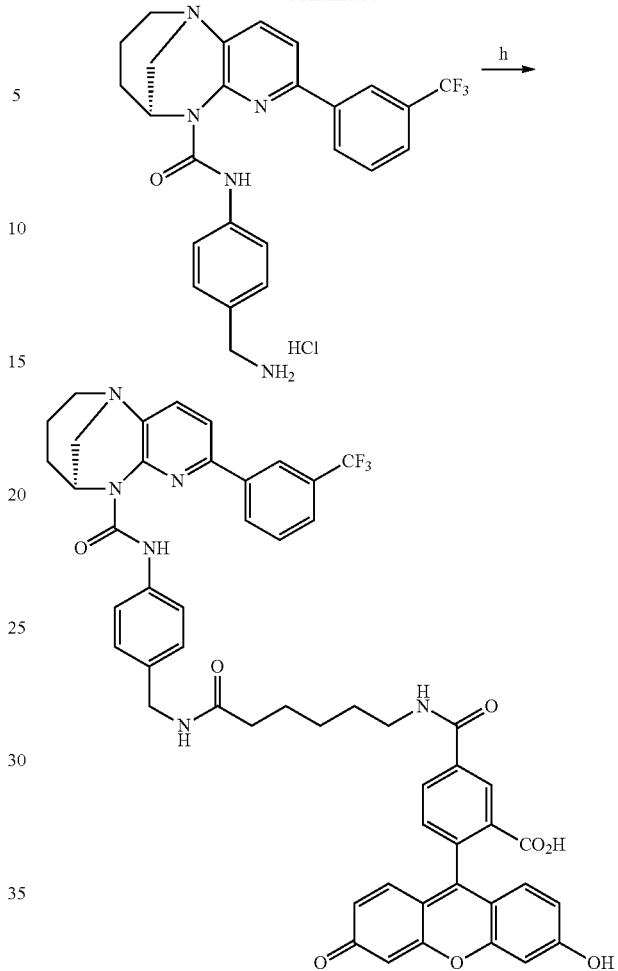

Reagents and conditions: a) NaHCO₃, THF, 40° C.; b) Fe, AcOH, IPA/Water, reflux; c) AlH₃, THF, -78° C. to rt; d) 48% HBr; e) 3-trifluorophrnylboronic acid, Pd(OAc)₂, X-Phos, Cs₂CO₃, dioxane/water; f) triphosgene, DIEA, CH₂Cl₂; g) 4N HCl, dioxane; h) DIEA, 6[fluorescein-5(6)-carboxamido]hexanoic acid N-hydroxysuccinimide ester, CH₃CN.

Step 1. Synthesis of (S)-Dimethyl 2-((6-chloro-3-nitropyridin-2-yl)amino)glutarate. To a mixture of 2,6-dichloro-3-nitropyridine (40.0 g, 207 mmol), L-glutamic acid dimethyl ester hydrochloride (87.7 g, 414 mmol) and NaHCO₃ (69.6 g, 829 mmol) was added tetrahydrofuran (600 mL). The mixture was stirred at 40° C. for 24 h, while monitoring for the disappearance of 2,6-dichloro-3-nitropyridine by HPLC. After the reaction was complete, the solids were filtered and washed with ethyl acetate (3×100 mL). The combined filtrate and washings were concentrated in vacuo, and the residue was purified via silica gel chromatography (eluting with 10:1 (v/v) hexanes/ethyl acetate) to obtain (S)-dimethyl 2-((6-chloro-3-nitropyridin-2-yl)amino)glutarate as a yellow solid. (60 g, 87%). LRMS (m/z) 332.1 [M+H]+; HRMS (m/z): [M+H]⁺ calcd for $C_{12}H_{15}N_3O_6Cl$, 332.0649; found, 332.0651.

Step 2. Synthesis of (S)-Methyl 3-(6-chloro-2-oxo-1,2,3,4-tetrahydropyrido[2,3-b]pyrazin-3-yl)propanoate To a mixture of (S)-dimethyl 2-((6-chloro-3-nitropyridin-2-yl)amino)pentanedioate (20 g, 60.2 mmol), and iron powder (16.8 g, 301 mmol) was added 2-propanol (375 mL) and water (125 mL). To the stirred mixture was added acetic acid (5.5 g, 90.3 mmol), and the reaction was stirred at reflux for 1 h while monitored for the disappearance of starting material by HPLC. After the reaction was complete, the solids were filtered and washed with 2-propanol (3×50 mL). The combined filtrate and washings were concentrated to dryness, then the residue was concentrated in vacuo to obtain (S)-methyl 3-(6-chloro-2-oxo-1,2,3,4-tetrahydropyrido[2,3-b]pyrazin-3-yl)propanoate as a dark yellow solid which was used in the next step without further purification (15 g, 81%). LRMS (m/z) 270.1 [M+H]+; HRMS (m/z): [M+H]+ calcd for $C_{11}H_{13}N_3O_3Cl$, 270.0645; found, 270.0645.

Step 3. Synthesis of (S)-3-(6-Chloro-1,2,3,4-tetrahydropyrido[2,3-b]pyrazin-3-yl)propan-1-ol To a solution of $AlCl_3$ (17.78 g, 133.3 mmol) in tetrahydrofuran (260 mL) under $N_2$ was added 2M $LiAlH_4$ in THF (200 mL, 400 mmol), dropwise, at a rate to control gas evolution. This gave a solution of alane ($AlH_3$) in THF. In a separate flask, a solution of (S)-methyl 3-(6-chloro-2-oxo-1,2,3,4-tetrahydropyrido[2,3-b]pyrazin-3-yl)propanoate (26.0 g, 96.4 mmol) in THF (460 mL) was prepared under $N_2$, then cooled with a dry ice/acetone bath. To this was added the alane solution, dropwise with stirring, over 2 h. When the addition was complete, the cooling bath was removed, and the reaction was allowed to warm to ambient temperature. After 1.5 h, LCMS analysis showed that the reaction was complete, and a solution of NaOH (17.6 g) in water (65 mL) was added slowly to control the evolution of $H_2$. The suspension was allowed to stir for 18 h, after which the solids were removed by filtration. The precipitate was washed with ethyl acetate, then the filtrate and washings were concentrated in vacuo. The product was purified via silica gel chromatography (0 to 10% gradient of MeOH in $CH_2Cl_2$) to obtain (S)-3-(6-chloro-1,2,3,4-tetrahydropyrido[2,3-b]pyrazin-3-yl)propan-1-ol as a yellow-orange solid (15.21 g, 69%). LRMS (m/z) 228.1 [M+H]+; HRMS (m/z): [M+H]+ calcd for $C_{10}H_{15}N_3OCl$, 228.0904; found, 228.0903.

Step 4. Synthesis of (5R,9S)-2-Chloro-7,8,9,10-tetrahydro-6H-5,9-methanopyrido[2,3-b][1,4]diazocine To (S)-3-(6-chloro-1,2,3,4-tetrahydropyrido[2,3-b]pyrazin-3-yl)propan-1-ol (12 g, 52.7 mmol) was added 48% (w/w) $HBr_{(aq.)}$ (160 mL), and the reaction was stirred at 90° C. for 18 h while monitoring the disappearance of the starting alcohol by HPLC. After the reaction was complete, it was cooled to ambient temperature, then 1.2 M aq. $NaHCO_3$ was added until pH 8 was achieved. The mixture was extracted with ethyl acetate (3×100 mL), then the organic phase was washed with brine (1×100 mL), dried ($Na_2SO_4$), filtered, and concentrated to dryness. The residue was purified by silica gel chromatography (eluting with 2:1 (v/v) hexanes/ethyl acetate) to obtain (5R,9S)-2-chloro-7,8,9,10-tetrahydro-6H-5,9-methanopyrido[2,3-b][1,4]diazocine as a light yellow solid (6.0 g, 55%). LRMS (m/z) 210.1 [M+H]+; HRMS (m/z): [M+H]+ calcd for $C_{10}H_{13}N_3Cl$, 210.0798; found, 210.0800.

Step 5. Synthesis of (9S)-2-(3-(Trifluoromethyl) phenyl)-7,8,9,10-tetrahydro-6H-5,9-methanopyrido [2,3-b][1,4] diazocine A solution of (9S)-2-chloro-7,8,9,10-tetrahydro-6H-5,9-methanopyrido[2,3-b][1,4]diazocine 3.0 g, 15.4 mmol), (3-(trifluoromethyl)phenyl)boronic acid (4.4 g, 23.1 mmol), palladium acetate (344 mg, 1.54 mmol), 2-dicyclohexylphosphino-2',4',6'-triisopropylbiphenyl (X-Phos, 476 mg, 3.08 mmol), and cesium carbonate (15 g, 46.2 mmol) in a 10 to 1 (v/v) mixture of 1,4-dioxane and water (60 mL) was heated at 90° C. for 24 hours. The reaction was then cooled to ambient temperature, and diluted with ethyl acetate (150 mL). The mixture was washed with sat. aq. $NaHCO_3$ (200 mL×3), then the organic layers was dried ($MgSO_4$) and concentrated to dryness. The resulting residue was purified by silica gel chromatography (10-100% ethyl acetate gradient in pentane) to obtain (9S)-2-(3-(trifluoromethyl)phenyl)-7,8,9,10-tetrahydro-6H-5,9-methanopyrido[2,3-b][1,4]diazocine as a light yellow solid (3.7 g, 75%). LRMS (m/z) 320.2 [M+H]+; HRMS (m/z): [M+H]+ calcd for $C_{17}H_{17}N_3F_3$, 320.1375; found, 320.1375.

Step 6. Synthesis of Tert-Butyl 4-((9S)-2-(3-(trifluoromethyl)phenyl)-7,8,9,10-tetrahydro-6H-5,9-methano-pyrido[2,3-b][1,4]diazocine-10-carboxamido)benzylcarbamate To a solution of (9S)-2-(3-(trifluoromethyl)phenyl)-7,8,9,10-tetrahydro-6H-5,9-methanopyrido[2,3-b][1,4]diazocine (999 mg, 3.23 mmol) in $CH_2Cl_2$ (30 mL) was added N,N-diisopropylethyl amine (1.7 mL, 9.78 mmol) and the reaction mixture was cooled to 0° C. with an ice bath. Triphosgene (482 mg, 1.63 mmol) was then added in four small portions. The ice bath was removed and the mixture was allowed to warm to room temperature. The reaction progress was monitored by removing a 500 uL aliquot and combining with methanol to assay for conversion to methyl carbamate via formation of the intermediate chloroformate. If any starting material remained, an additional portion of triphosgene (200 mg) was added and the reaction mixture stirred for five hours at room temperature. Next, tert-Butyl 4-aminobenzylcarbamate (800 mg, 3.60 mmol) was added in two equal portions (400 mg each) to the above mixture and the resulting mixture was stirred at room temperature for two hours. Saturated aqueous $NaHCO_3$ (30 mL) was added and the organic phase was then separated and concentrated to dryness under reduced pressure. The residue was purified by silica gel chromatography (15-100% ethyl acetate gradient in pentane) to obtain tert-butyl 4-((9S)-2-(3-(trifluoromethyl)phenyl)-7,8,9,10-tetrahydro-6H-5,9-methanopyrido [2,3-b][1,4]diazocine-10-carboxamido)benzyl-carbamate as a white solid. (761 mg, 42%). LRMS (m/z) 568.2 [M+H]+; HRMS (m/z): [M+H]+ calcd for $C_{30}H_{33}N_5O_3F_3$, 568.2536; found, 568.2538.

Step 7. Synthesis of (9S)—N-(4-(aminomethyl) phenyl)-2-(3-(trifluoromethyl)phenyl)-8,9-dihydro-6H-5,9-meth-anopyrido[2,3-b][1,4]diazocine-10 (7H)-carboxamide hydrochloride tert-Butyl 4-((9S)-2-(3-(trifluoromethyl)phenyl)-7,8,9,10-tetrahydro-6H-5,9-methanopyrido[2,3-b][1,4]diazocine-10-carboxamido)benzylcarbamate (759 mg, 1.34 mmol) was dissolved in 4N HCl (10 mL) and 1,4-dioxane and stirred under nitrogen for 1 hour at ambient temperature. The solvents were removed under reduced pressure and the resulting solid was dried overnight under vacuum to obtain (9S)—N-(4-(aminomethyl)phenyl)-2-(3-(trifluoromethyl) phenyl)-8,9-dihydro-6H-5,9-methanopyrido[2,3-b][1,4]diazocine-10(7H)-carboxamide hydrochloride as a light tan solid (763 mg, 100%). LRMS (m/z) 468.1 [M+H]+; HRMS (m/z): [M+H]$^+$ calcd for $C_{25}H_{25}N_5OF_3$, 468.2011; found, 468.2010.

Step 8. Synthesis of 2-(6-Hydroxy-3-oxo-3H-xanthen-9-yl)-5-((6-oxo-6-((4-((9S)-2-(3-(trifluoromethyl)phenyl)-7,8,9,10-tetrahydro-6H-5,9-methanopyrido[2,3-b][1,4]diazocine-10-carboxamido)benzyl)amino)hexyl)carbamoyl)benzoic Acid (9S)—N-(4-(aminomethyl)phenyl)-2-(3-(trifluoromethyl)phenyl)-8,9-dihydro-6H-5,9-methanopyrido[2,3-b][1,4]diazocine-10(7H)-carboxamide hydrochloride (39 mg, 0.10 mmol) was dissolved in acetonitrile (2 mL) and methanol (0.2 mL). N,N-diisopropylethylamine (32 µL, 0.20 mmol) was then added followed by 6-[fluorescein-5(6)-carboxamido]hexanoic acid N-hydroxysuccinimide ester (50 mg, 0.085 mmol). The mixture was stirred at room temperature overnight, then the product was isolated by reversed phase HPLC (5-95% acetonitrile gradient in water modified with 0.1% TFA) to obtain 2-(6-hydroxy-3-oxo-3H-xanthen-9-yl)-5-((6-oxo-6-((4-((9S)-2-(3-(trifluoromethyl)phenyl)-7,8,9,10-tetra-hydro-6H-5,9-methanopyrido[2,3-b][1,4]diazocine-10-carboxamido)benzyl)amino)hexyl)carbamoyl)benzoic acid as a brown solid (26 mg, 35%). LRMS (m/z) 939.2 [M+H]+; HRMS (m/z): [M+H]$^+$ calcd for $C_{52}H_{46}N_6O_8F_3$, 939.3329; found, 939.3328.

Example 90. Mini-hSIRT1 Design and Characterization

Proton-deuteron exchange mass spectrometry (HDX-MS) was performed on the full-length hSIRT1 protein to identify and characterize the key functional regions of hSIRT1.

The rate of H-D exchange is highly dependent on the dynamic properties of the protein, with faster exchange occurring at solvent exposed and/or flexible regions and slower exchange occurring at the more buried and/or structurally rigid regions (Hamuro, Y. et al. (2003) J biomol Techniques: JBT 14, 171). Consistent with the previous study on hSIRT1(19-747) (Hubbard, B. P. et al. (2013) Science 339, 1216), full-length hSIRT1 contains three major structured regions: the catalytic core region, residues 229-516 (referred to as hSIRT1cc hereafter) (Jin, L. et al. (2009) J Biol Chem 284, 24394 and Frye, R. A. (2000) Biochem Biophys Res Commun 273, 793), the N-terminal region of 190-230 immediately preceding the catalytic core and a remote region in the C-terminus following the catalytic core around 640-670.

To probe the STAC binding site on hSIRT1, HDX-MS was performed in the absence or presence of STAC 1. Addition of 1 reduces the H-D exchange rate around residues 190-230 in the N-terminal domain of hSIRT1, suggesting that this region is involved in STAC binding. Additionally, the $^1H$, $^{15}N$ HSQC spectrum of the $^{15}N$-labeled hSIRT1 (180-230) is well dispersed suggesting that it forms an autonomously folded domain. Addition of 1 to $^{15}N$-labeled hSIRT1(180-230) results in significant chemical shift perturbations and further supports direct interaction of 1 with this region, hereafter referred to as the STAC-binding domain (SBD). Addition of 1 to hSIRT1 in the presence of a p53-derived peptide substrate (Ac-p53(W5)) (Dai, H. et al. (2010) J Biol Chem 285, 32695) results in perturbation of the H-D exchange rates both around the SBD and at the presumed substrate binding site (residues 417-424) in the catalytic core, indicating that STAC binding in the N-terminal domain and substrate binding within the catalytic core of hSIRT1 are coupled. This is consistent with a previous observation that STACs enhance substrate binding to hSIRT1, thereby increasing hSIRT1 catalytic efficiency (Milne, J. C. et al. (2007) Nature 450, 712).

In contrast to the SBD, the C-terminal structural element (641-665) identified by HDX-MS is separated from the catalytic core by about 150 residues and is predicted to contain several β-strands, referred to here as C-terminal β-strands/sheet (CBS), similar to the previously reported murine Essential for SIRT1 Activity (ESA) peptide (19). hSIRT1cc only shows about one eighth of the activity of the full-length enzyme using deacetylation assay conditions previously reported (Dai, H. et al. (2010) J Biol Chem 285, 32695). The CBS peptide restores the catalytic activity of hSIRT1cc in trans, to 80% of that of full-length hSIRT1, with $EC_{50}$=59 nM, consistent with previous observations (Kang, H. et al. (2011) Mol Cell 44, 203 and Marmorstein, R. et al. (2012) J Biol Chem 287, 2468). We also designed a minimal CBS fragment covering only the β-stranded region (642-658), which behaves similarly to the parental CBS peptide. Kinetic characterization reveals that the CBS peptide restores activity by lowering the $K_M$ values for both peptide substrate and NAD$^+$ of hSIRT1cc by 4-5-fold (see Table 1).

TABLE 1

Steady-State Kinetics of hSIRT1 catalytic core in the absence or presence of CBS peptide.[a]

| Group | $k_{cat}$ (s$^{-1}$) | $K_M$ (µM) Ac-p53(W5)[b] | NAD$^{+c}$ |
|---|---|---|---|
| hSIRT1(229-516) | 0.29 ± 0.01 | 163 ± 8 | 988 ± 73 |
| hSIRT1(229-516) + CBS | 0.54 ± 0.01 | 37 ± 2.5 | 180 ± 14 |
| hSIRT1(229-516) + mini-CBS | 0.54 ± 0.01 | 49 ± 3 | 207 ± 19 |

[a]Data from PNC1/GDH assay.
[b]NAD$^+$ concentration fixed at 1 mM.
[c]Ac-p53(W) concentration fixed at 500 µM.

Taken together, the above data suggests a tri-partite architecture for a minimally functional hSIRT1 that includes; 1) the central core constituting the basic catalytic machinery, 2) the N-terminal SBD that mediates STAC binding and activation, and 3) the C-terminal CBS peptide which stabilizes the catalytic core resulting in more efficient deacetylase activity. Based on this, we designed hSIRT1 constructs encompassing all three of the minimal structural elements covalently bound, which we termed mini-hSIRT1s. The constructs span 183-505 or 183-516, which are connected to the CBS peptide via a flexible poly-glycine/serine linker (GS, (GGGS)$_2$, or (GGGS)$_3$) (Sauer, R. T. and Robinson, C. R. (1998) Proceedings of Nat Academy of Sciences of USA 95, 5929). The $K_M$ and $k_{cat}$ values are comparable between mini-hSIRT1 constructs and the full-length enzyme, as are the IC$_{50}$ values for the non-competitive hSIRT1 inhibitors EX-527 or nicotinamide (NAM) confirming functional fidelity of mini-hSIRT1s (see Table 2). In addition there is an excellent correlation between mini-hSIRT1 and the full length enzyme with respect to STAC-mediated activation across a broad set of chemotypes. Removal of the SBD completely abolishes STAC-mediated activation of mini-hSIRT1, confirming the critical importance of this domain for activation. In contrast, mini-hSIRT1 lacking the CBS retains a significant level of STAC activation demonstrating that the CBS enhances but, is not required for STAC-mediated activation. Finally, the E230K mutation also attenuates STAC-mediated activation in mini-hSIRT1 as in the full-length enzyme (Hubbard, B. P. et al. (2013) Science 339, 1216). Collectively, these observations demonstrate that at half the molecular size, mini-hSIRT1 is a fully functional and activatable surrogate for full-length hSIRT1.

TABLE 2

Steady-state kinetics of mini-hSIRT1 constructs.[a]

| hSIRT1 | $k_{cat}$ (s$^{-1}$) | $K_M$ (μM) Ac-p53(W5)[b] | NAD[+,c] |
|---|---|---|---|
| hSIRT1 (1-747) | 0.37 ± 0.01 | 3.7 ± 0.8[d] | 70 ± 6 |
| hSIRT1 (183-516) | 0.38 ± 0.01 | 42 ± 4.9 | 769 ± 97 |
| hSIRT1 (183-516-(GGGS)$_2$-641-665) | 0.44 ± 0.02 | 16 ± 2.2 | 82 ± 6 |
| hSIRT1 (183-516-(GS)-641-665) | 0.54 ± 0.01 | 14 ± 1.1 | 78 ± 8 |
| hSIRT1 (183-505-(GGGS)$_2$-641-665) | 0.54 ± 0.02 | 13 ± 2 | 112 ± 10 |
| hSIRT1 (229-516-(GGGS)$_2$-641-665) | 0.49 ± 0.01 | 13 ± 3 | 222 ± 25 |
| hSIRT1 (229-505-(GGGS)$_2$-641-665) | 0.43 ± 0.02 | 11 ± 3 | 218 ± 34 |
| hSIRT1 (183-505-(GGGS)$_2$-641-665) (R446A) | 0.54 ± 0.01 | 42 ± 4.1 | 170 ± 19 |
| hSIRT1 (183-505-(GGGS)$_2$-641-665) (R446E) | 0.21 ± 0.01 | 30 ± 3 | 375 ± 24 |
| hSIRT1 (183-505-(GGGS)$_2$-641-665) (E230K, R446E) | 0.30 ± 0.01 | 33 ± 2 | 423 ± 41 |
| hSIRT1 (183-505-(GGGS)$_2$-641-665) (P231G, P232G) | 0.65 ± 0.01 | 23.4 ± 1 | 273 ± 26 |

[a]Data from PNC1/GDH assay.
[b]NAD$^+$ concentration fixed at 2 mM.
[c]Ac-p53(W) concentration fixed at 400 μM.
[d]Value from (1)

Example 91. Structure of the Mini-hSIRT1/STAC Complex

While the x-ray crystallographic structure of the hSIRT1 catalytic core has been reported (Zhao, X. et al. (2013) J Med Chem 56, 963), no structure of the full-length enzyme exists to our knowledge. Structure of the full length hSIRT1 has been challenging, in part, due to the conformational flexibility of the extended N- and C-terminal domains. The mini-hSIRT1 constructs afforded us the opportunity to crystallize an equivalently functional surrogate of the full-length enzyme. We successfully crystallized mini-hSIRT1 (183-505-(GGGS)2-CBS) with STAC 1 used in the HDX-MS experiments and determined the structure of the complex (mini-hSIRT1/1) at 3.1 Å by molecular replacement using a search model based on the homolog model of SIRT3 (Jin, L. et al. (2009) J Biol chem 284, 24394). Mini-hSIRT1 is composed of a catalytic core that assumes a Rossmann-fold large lobe and a zinc-binding small lobe common to all sirtuins, an N-terminal three-helical bundle SBD and a C-terminal β-hairpin CBS. Interestingly, a STAC-mediated dimer of mini-hSIRT1 related by crystallographic symmetry was observed in the crystal lattices. Size exclusion chromatography (SEC) confirms that mini-hSIRT1 forms dimer in solution in the presence of STAC 1. However, no formation of mini-hSIRT1 dimer is observed for a similar STAC 7 of the same chemotype. Given this observation and the fact that the STAC concentration used for crystallization is much higher than that used in the biochemical assay measuring activation, it would appear that dimerization observed in the crystal structure is not a requirement for hSIRT1 activation by STACs.

The CBS mediates β-augmentation with the six-stranded β-sheet of the Rossmann-fold lobe of the catalytic domain, in agreement with the HDX-MS results of hSIRT1cc perturbation upon CBS binding. The CBS-mediated β-augmentation appears to stabilize the active site of the hSIRT1 catalytic core which restores the $K_M$ values observed for both acetylated peptide and NAD$^+$ substrates. The N-terminal SBD forms an independently folded three-helical bundle with 1 binding to the helix-turn-helix (H2-T-H3) motif within the SBD, consistent with the HDX-MS, NMR and enzyme kinetic results. The major mini-hSIRT1/1 binding site is a relatively shallow hydrophobic surface with an off-center, deeper hydrophobic pocket, that the CF$_3$ group of 1 occupies. This is consistent with the observed structure activity relationship (SAR) developed across multiple STAC chemotypes indicating the requirement of overall flatness of the core scaffold maintained by an intramolecular hydrogen bond (Vu, et al. (2009) J Med Chem, 52, 1275). A remarkable similarity in terms of domain configuration is observed between the mini-hSIRT1 structure and that of yeast Sir2 with both having an N-terminal helical bundle and the C-terminal β-augmentation by a β-hairpin beyond the typical Rossmann-fold large lobe (Hsu, H. C. et al. (2013) Genes & Dev 27, 64). However, yeast Sir2 doesn't include the 150 amino acid insertion observed in hSIRT1 and appears as a natural "mini-SIRT1" in yeast. The N-terminal domain in Sir2 appears to be important for the allosteric activation by another yeast protein Sir4 (Hsu, H. C. et al. (2013) Genes & Dev 27, 64). Though the architecture of the Sir2 N-terminal domain differs from the hSIRT1 SBD, the two appear to have functionally conserved roles in allosteric activation of the catalytic core.

Example 92. Site-Directed Mutagenesis of the STAC Binding Pocket

We used site-directed mutagenesis of full-length hSIRT1 to confirm the key residues of the SBD that were identified by the mini-hSIRT1 structures. The following point mutants of full-length hSIRT1 were generated probing three classes of residues: a) residues which appear to directly interact with activators (T219A, I223A, N226A, and I227A), b) coupling modulator Glu$^{230}$ (Hubbard, B. P. et al. (2013) Science 339, 1216) (E230K, E230A, and E230Q), and c) SBD residues with no apparent role in activator binding (Q222A and V224A). None of the mutants significantly impaired the basal catalytic activity using the Ac-p53(W5) substrate or affected inhibition by EX-527, a TFA-p53 peptide (Ac-RHK-K$^{TFA}$-L-Nle-F—NH$_2$), or nicotinamide (NAM) (see Tables 4 and 5).

The general impact of the mutations on activation was assessed by comparing the fold-activation of wild-type versus mutant full-length SIRT1 using a structurally diverse set of 246 STACs tested at a fixed concentration of 25 μM. Additionally, we investigated the effect of the mutations on STAC binding versus activation by monitoring shifts in their EC$_{50}$ and maximum activation values respectively using a panel of five compounds (STACs 1, 6-9). T219A, I223A, and I227A all exhibit broad impairment of activation with increases in EC$_{50}$ compared to wild-type hSIRT1, implicating impaired activator binding consistent with the structures (see Table 6). Interestingly, I223A was the most compound-dependent mutant with STAC-mediated activation ranging from attenuated to enhanced. STACs showing enhanced activation are enriched for structures containing an ortho-CF$_3$ substituted phenyl ring. In the crystal structures, Ile$^{223}$ lies directly beneath the activator and lines the pocket into which the meta-CF$_3$ of 1 inserts. The cavity created by mutation of Ile$^{223}$ to Ala would be expected to better accommodate an ortho substituent versus a meta-substitution. This observation further validates the key molecular interactions governing STAC binding and points to strategies for altering STAC interaction with the SBD.

TABLE 4

Steady-state substrate substrate kinetics for wild-type and mutant full-length hSIRT1.

| hSIRT1 | $k_{cat}$ (s$^{-1}$)$^a$ | Ac-p53(W5)$^a$ $K_M$ (μM) | Ac-p53(W5)$^b$ | NAD$^{+a}$ |
|---|---|---|---|---|
| wild-type | 0.37 ± 0.01 | 3.7 ± 0.8$^c$ | 2.7 ± 0.4$^c$ | 70 ± 6 |
| T219A | 0.35 ± 0.01 | 2.7 ± 0.5 | 1.7 ± 0.2 | 45 ± 4 |
| Q222A | 0.34 ± 0.01 | 7.1 ± 2.3 | 4.8 ± 0.6 | 35 ± 6 |
| I223A | 0.33 ± 0.02 | 2.5 ± 0.3 | 4.2 ± 0.4 | 96 ± 14 |
| V224A | 0.31 ± 0.01 | 6.2 ± 0.7 | 4.2 ± 0.3 | 43 ± 4 |
| N226A | 0.34 ± 0.02 | 1.8 ± 0.7 | 2.5 ± 0.2 | 85 ± 9 |
| I227A | 0.36 ± 0.01 | 5.3 ± 0.7 | 3.4 ± 0.4 | 43 ± 6 |
| E230K | 0.36 ± 0.01 | 7.0 ± 0.7 | 5.4 ± 0.2 | 70 ± 5 |
| E230A | 0.41 ± 0.01 | 6.2 ± 0.6 | 6.2 ± 0.5 | 57 ± 2 |
| E230Q | 0.38 ± 0.01 | 3.2 ± 0.7 | 7.5 ± 0.9 | 99 ± 17 |
| I223R | 0.27 ± 0.01 | 3.5 ± 0.5 | 1.4 ± 0.2 | 91 ± 13 |

$^a$Data from PNC1/GDH assay.
$^b$Data from OAcADPr assay.
$^c$Values from (1)

TABLE 5

Inhibition of wild-type and mutant full-length hSIRT1.

| hSIRT1 | EX-527 | TFA-p53 7-mer$^b$ IC$_{50}$ (μM)$^a$ | NAM |
|---|---|---|---|
| wild-type | 0.140 ± 0.020 | 0.680 ± 0.070 | 92 ± 6 |
| T219A | 0.310 ± 0.040 | 0.490 ± 0.020 | 53 ± 4 |
| Q222A | 0.110 ± 0.010 | 0.630 ± 0.050 | 53 ± 5 |
| I223A | 0.180 ± 0.020 | 0.540 ± 0.150 | 108 ± 10 |
| V224A | 0.140 ± 0.010 | 0.860 ± 0.080 | 64 ± 3 |
| N226A | 0.190 ± 0.010 | 0.350 ± 0.040 | 100 ± 9 |
| I227A | 0.220 ± 0.020 | 0.940 ± 0.060 | 92 ± 4 |
| E230K | 0.150 ± 0.020 | 1.6 ± 0.3 | 54 ± 3 |
| E230A | 0.100 ± 0.030 | 1.3 ± 0.4 | 60 ± 3 |
| E230Q | 0.240 ± 0.020 | 0.860 ± 0.060 | 56 ± 3 |
| I223R | 0.210 ± 0.020 | 0.660 ± 0.060 | 87 ± 6 |

$^a$Data from OAcADPr assay using the Ac-p53(W5) substrate.
$^b$TFA-p53 peptide sequence: Ac-RHKK(TFA)L-Nle-F-NH$_2$.

TABLE 6

Substrate concentrations used in full-length hSIRT1 activation or inhibition assays.

| | Activation assays | | Inhibition assays | |
|---|---|---|---|---|
| hSIRT1 | Ac-p53(W5) (μM) | NAD$^+$ (μM) | Ac-p53(W5) (μM) | NAD$^+$ (μM) |
| wild-type | 0.20 | 8.0 | 2 | 80 |
| T219A | 0.20 | 4.5 | 2 | 45 |
| Q222A | 0.70 | 4.5 | 6.5 | 45 |
| I223A | 0.25 | 10 | 2.5 | 100 |
| V224A | 0.60 | 4.5 | 6.5 | 45 |
| N226A | 0.20 | 8.0 | 2 | 80 |
| I227A | 0.40 | 4.5 | 4 | 45 |
| E230K | 0.40 | 8.0 | 4 | 80 |
| E230A | 0.40 | 8.0 | 4 | 80 |
| E230Q | 0.30 | 8.0 | 3 | 80 |
| I223R | 0.14 | 10 | 1.4 | 100 |

Asn$^{226}$ appears to form a hydrogen bond between its carboxamide nitrogen and the carbonyl oxygen of 1 on the surface of the protein. However, activation of N226A was only minimally impaired compared to wild-type. The small contribution from this H-bond is likely due to its high solvent exposure.

Mutation of Glu$^{230}$ to either Lys or Ala has been recently reported to broadly impair activation by STACs although the mechanism by which this occurs is unclear (Hubbard, B. P. et al. (2013) Science 339, 1216). We tested activation of E230K, E230A, and E230Q full-length hSIRT1 proteins. In all three Glu$^{230}$ mutants, the maximum activation is impaired without shifting the EC$_{50}$ (see Tables 7 and 8) suggesting a role for Glu$^{230}$ in the formation or stabilization of the activated conformation of hSIRT1. Activation of E230Q is also broadly impaired, indicating that the negative charge of Glu$^{230}$ is important for stabilizing the activated conformation of hSIRT1 and that Glu$^{230}$ likely interacts with a positively charged residue in the activated conformation.

TABLE 7

Effect of hSIRT1 mutations on activator EC$_{50}$ values.

| | compound | | | | | | | | | |
|---|---|---|---|---|---|---|---|---|---|---|
| | 1 | | 6 | | 7 | | 8 | | 9 | |
| hSIRT1 | EC$_{50}$ (μM) | fold shift$^a$ | EC$_{50}$ (μM) | fold shift$^a$ | EC$_{50}$ (μM) | fold shift$^a$ | EC$_{50}$ (μM) | fold shift$^a$ | EC$_{50}$ (μM) | fold shift$^a$ |
| WT | 0.30 | 1.00 | 0.77 | 1.00 | 2.20 | 1.00 | 0.48 | 1.00 | 0.77 | 1.00 |
| T219A | 1.00 | 3.30 | 2.38 | 3.10 | 8.83 | 4.01 | 3.96 | 8.26 | 4.12 | 5.36 |
| Q222A | 0.25 | 0.84 | 0.78 | 1.02 | 2.01 | 0.91 | 0.51 | 1.07 | 0.56 | 0.73 |
| I223A | 0.77 | 2.56 | 2.11 | 2.75 | 5.51 | 2.51 | 2.36 | 4.91 | 2.97 | 3.86 |
| V224A | 0.43 | 1.43 | 1.15 | 1.50 | 2.60 | 1.18 | 0.90 | 1.87 | 1.09 | 1.41 |
| N226A | 0.55 | 1.83 | 2.64 | 3.44 | 3.92 | 1.78 | 1.03 | 2.15 | 1.17 | 1.52 |
| I227A | 1.09 | 3.65 | 3.72 | 4.83 | 6.76 | 3.07 | 2.98 | 6.21 | 4.28 | 5.55 |
| E230A | 0.26 | 0.86 | 1.89 | 2.46 | 2.61 | 1.19 | 0.530 | 1.11 | 1.23 | 1.60 |
| E230K | 0.15 | 0.50 | 2.92 | 3.81 | 3.21 | 1.46 | 0.70 | 1.46 | 1.63 | 2.12 |
| E230Q | 0.37 | 1.23 | 2.15 | 2.80 | 3.36 | 1.53 | 0.58 | 1.21 | 1.34 | 1.74 |

$^a$Fold shift = (mutant EC$_{50}$/wild-type EC$_{50}$)

EC$_{50}$ values determined from activation dose-response curves using eq. 1. Activation was measured using the OAcADPr assay with Ac-p53(W5) substrate.

TABLE 8

Effect of hSIRT1 mutations on the maximum activation by STACs.

| | compound: | | | | | | | | |
|---|---|---|---|---|---|---|---|---|---|
| | 1 | | 6 | | 7 | | 8 | | 9 | |
| hSIRT1 | $RV_{max}$ | fold shift[a] | $RV_{max}$ | fold shift[a] | $RV_{max}$ | fold shift[a] | $RV_{max}$ | fold shift[a] | $RV_{max}$ | fold shift[a] |
| WT | 10.5 | 1.00 | 14.7 | 1.00 | 7.16 | 1.00 | 6.28 | 1.00 | 14.9 | 1.00 |
| T219A | 5.76 | 1.99 | 14.3 | 1.03 | 3.25 | 2.73 | 4.22 | 1.64 | 10.4 | 1.47 |
| Q222A | 7.58 | 1.44 | 10.9 | 1.39 | 7.27 | 0.98 | 5.32 | 1.22 | 10.4 | 1.48 |
| I223A | 4.52 | 2.69 | 9.85 | 1.55 | 1.89 | 6.90 | 6.45 | 0.97 | 8.00 | 1.98 |
| V224A | 9.56 | 1.11 | 12.9 | 1.15 | 9.58 | 0.72 | 7.71 | 0.79 | 14.5 | 1.03 |
| N226A | 7.82 | 1.39 | 11.2 | 1.34 | 5.68 | 1.32 | 4.95 | 1.34 | 13.4 | 1.12 |
| I227A | 5.22 | 2.25 | 6.14 | 2.67 | 8.25 | 0.85 | 5.98 | 1.06 | 12.5 | 1.20 |
| E230A | 2.64 | 5.81 | 6.15 | 2.66 | 2.72 | 3.58 | 3.21 | 2.39 | 6.91 | 2.35 |
| E230K | 1.39 | 24.3 | 3.83 | 4.84 | 1.71 | 8.67 | 1.99 | 5.36 | 2.96 | 7.06 |
| E230Q | 2.28 | 7.40 | 4.67 | 3.73 | 2.57 | 3.93 | 2.72 | 3.07 | 5.14 | 3.35 |

[a] Fold shift = (wild-type $RV_{max}$ − 1)/(mutant $RV_{max}$ − 1)
Maximum activation values ($RV_{max}$) determined from activation dose-response curves using Eq. 1. Activation was measured using the OAcADPr assay assay with Ac-p53(W5) substrate.

In contrast to the above mutants, Q222A and V224A displayed normal activation which is consistent with their positions away from the STAC in the mini-hSIRT1/1 structure. Importantly, all of these data obtained with full-length hSIRT1 are consistent with what the mini-SIRT1 crystal structures predict further validating the biochemical significance of these structures.

Despite the broad impact of the mutations described above, none of them completely abolished activation of hSIRT1 as seen with removal of the SBD. As Ile[223] lies directly beneath the bound STAC and activation of I223A is highly compound-dependent, we hypothesized that I223R hSIRT1 would constitute the most highly activation-impaired full-length enzyme to date. Substitution from Ile to Arg introduces bulk and charge into the hydrophobic STAC binding site which would be expected to disrupt compound binding based on the structure. I223R does not alter the basal catalytic activity with either the Ac-p53(W5) or FOXO-3a substrate peptides or inhibition by EX-527, TFA-p53 peptide, or NAM (see Tables 4, 5 and 9). However, activation is completely lost for all 246 activators for both substrates.

TABLE 9

Steady-state kinetics for full-length hSIRT1 with FOXO-3a 21-mer[a].

| hSIRT1 | $k_{cat}$ (s$^{-1}$) | $K_M$ peptide (μM) | $K_M$ NAD$^+$ (μM) |
|---|---|---|---|
| wild type | 0.39 ± 0.02 | 50 ± 6 | 280 ± 40 |
| I223R | 0.25 ± 0.01 | 90 ± 6 | 460 ± 50 |

[a]Data from PNC1/GDH assay.

Example 93. Allosteric Coupling Between STAC and Substrate Binding

We investigated the mechanism of activation of hSIRT1 by STACs. To that end, we determined a 2.73 Å structure of a quaternary complex of mini-hSIRT1, 1, a 7 amino acid peptide substrate derived from p53 (Ac-p53), and the non-hydrolyzable NAD$^+$ analog carbaNAD and a 2.74 Å structure mini-hSIRT1/1 in complex with a novel active-site directed inhibitor 2 that occupies the peptide and NAD$^+$ binding sites. In the quaternary complex structure, the Ac-p53 peptide and carbaNAD bind to the active site cleft between the large and small lobes. Ac-p53 adopts an extended conformation, with main chain amide group forming hydrogen bonds with the residues Gly[415] and Glu[416] from the small lobe and the residues Lys[444] and Arg[446] from the large lobe. The hydrogen bonds between the amide of the peptide +1 position and that of Arg[446] render a potential interaction between the side chains for a hydrophobic +1 residue, which may be important in STAC-mediated hSIRT1 activation (Dai, H. et al. (2010) J Biol Chem 285, 32695). The acetyllysine side chain inserts into a hydrophobic cavity lined by Phe[414], Leu[418] and Val[445]. The acetyl group is sandwiched between His[363] and Phe[297], with the ε-N of the acetyllysine hydrogen bonded with the carbonyl oxygen of Val[412], which maintains the orientation and the extended conformation of the acetyl-lysine side chain. CarbaNAD also makes multi-point contacts with hSIRT1, most of which are similar to those observed in the ternary complex of hSIRT1 catalytic core/NAD/EX-527 analog (Zhao, X. et al. (2013) J Med Chem 56, 963). Some differences were noted, such as the amide group of the nicotinamide ring forms hydrogen bonds with Ile[347] and Asp[348] in the C-pocket. In addition the 2' and 3' hydroxyl groups of the ribofuranose on the nicotinamide side form hydrogen bonds with the carbonyl oxygen atom of acetyl-lysine, which helps to orient the C-1' atom of NAD for subsequent nucleophilic attack by the peptide N-ε-acetyl group. Inhibitor 2 occupies both the acetyl-lysine binding site and the nicotinamide binding C-pocket of mini-hSIRT1, similar to the recently reported structure of the SIRT3/2 complex. Similar to SIRT3, binding of substrates or the active-site inhibitor leads to domain closure, bringing the small and large lobes together (Szczepankiewicz, B. G. et al. (2012) J Org chem 77, 7319 and Jin, L. et al. J Biol Chem (2009) 284, 24394). A more prominent conformational change upon active site occupancy is an upward movement of the N-terminal domain, which seems to hinge around Arg[234] and brings the SBD closer to the active site providing a potential mechanism for the allosteric coupling of STAC binding and substrate binding sites through concerted motions. The hinge residue, Arg[234], is located within the polybasic linker (residues 233-238) and anchors the N-terminal SBD to the catalytic core through a salt bridge formed between its guanidinium group and the carboxylate group of Asp[475] and hydrogen bonds to the carbonyl groups of His[473] and Val[459]. Comparison of the SBDs in these three structures shows that the domain is relatively rigid, with a superimposable STAC-binding helix-turn-helix (H2-T-H3) motif with only the first helix tilting out slightly in the mini-hSIRT1/1/2 complex structure. We assessed if the short linker (230-233) between the SBD and the anchoring $Arg^{234}$ might be important for the allosteric coupling by modulating the rigidity of the linker through mutating $Pro^{231}$ and $Pro^{232}$ to Gly. Indeed, P231G/P232G exhibits markedly attenuated STAC activation of mini-hSIRT1, supporting the importance of this short linker to mediate the movement of the SBD and the consequential coupling of STAC binding and substrate binding.

HDX-MS data reveal that, in contrast to wild-type hSIRT1, STAC binding to the E230K mutant no longer confers protection around the peptide binding site in the E230K/1/Ac-p53(W5) complex. This indicates that the E230K mutation likely compromises the coupling between the STAC and substrate binding sites. To explore this further, a fluorescence polarization (FP) assay was developed to measure STAC binding to hSIRT1 and investigate the coupling effect in the presence of substrate. A fluorescein-linked STAC (3) which binds to full-length hSIRT1 with a $K_d$ of 0.3 µM was used as an FP probe and was effectively competed off by its parent compound 4. Binding of 3 was severely impaired for I223R hSIRT1 confirming the role of this residue shown in the mini-hSIRT1/1 structures as being directly involved in STAC binding in the full-length enzyme. STACs were tested in the FP assay in the absence or presence of Ac-p53(W5) substrate exemplified by 5 which displayed enhanced binding affinity ($K_i$) in the presence of Ac-p53(W5) consistent with a $K_M$-lowering mechanism for activation. While the E230K mutant shows remarkably similar binding affinity for most STACs compared to the wild-type, enhancement of this binding by Ac-p53(W5) is absent or severely attenuated. The HDX-MS and activation data together suggest that $Glu^{230}$ is not directly involved in STAC binding but is instead, a critical residue mediating the coupling of STAC and substrate binding to promote activation. This was further verified by determining the structure of the E230K mini-hSIRT1 protein with compounds 1 and 2. The overall structures were similar to those of the wild-type mini-hSIRT1/1/2 ternary complexes, confirming that $Glu^{230}$ does not directly participate in STAC binding but instead likely plays a dynamic role during the allosteric coupling. Furthermore, a crystallographic dimer was observed with the E230K mini-hSIRT1/STAC structure, similar to that seen for the wild-type protein structures, further indicating that dimerization is unlikely to be required for the biochemical activation of hSIRT1 by STACs.

To assess the general requirement for a hydrophobic moiety on the acetyl-substrate for STAC-mediated SIRT1 activation (Dai, H. et al. (2010) J Biol Chem 285, 32695), we mutated the potential +1 Trp interacting residue $Arg^{446}$ to Ala based on the close proximity of $Arg^{446}$ to +1 position. R446A hSIRT1 has an increased $K_M$ value for Ac-p53(W5) (see Table 2) as expected. However, it also shows attenuated activation, similar to what is observed for E230K/A mutants. Given this observation, the cationic nature of $Arg^{446}$ and coupling between active site and STAC-binding site, we made the mini-hSIRT1 R446E/E230K double mutant to test if $Arg^{446}$ is a possible electrostatic partner for E230 with E230K and R446E mini-hSIRT1 as controls. Whereas either E230K or R446E results in significant attenuation of STAC activation of mini-hSIRT1, the R446E/E230K double mutant partially restores STAC-mediated activation of mini-hSIRT1 compared to E230K or R446E. These data support the existence of a salt bridge between $Glu^{230}$ and $Arg^{446}$ in the activated conformation and are consistent with the proposed movement of the SBD to interact with the catalytic core in the activated state.

All of mini-hSIRT1 constructs we discussed herein recapitulate three key features of full-length hSIRT1: 1) the steady state enzyme kinetics and inhibition, 2) the STAC activation profile across multiple chemotypes, 3) and STAC activation impairment by E230K. We then used the mini-hSIRT1 constructs to obtain the first reported structures of a fully functional form of hSIRT1 with a bound STAC. The biochemical and structural characterization reveals the hSIRT1 intra-molecular interactions between the CBS and catalytic core, which are essential for the basal deacetylation activity of hSIRT1. More importantly, the structures of the mini-hSIRT1/STAC complex reveal the detailed architecture of the STAC binding site providing important information for future structure-based drug design. The comparison of the hSIRT1 structures with different ligands bound suggests that the N-terminal SBD undergoes an upward movement along the conformational reaction coordinate, although the exact location of the SBD is likely influenced by crystal packing. A potential mechanism for STAC activation can thus be inferred, namely the concerted motions of an upward movement of the SBD and domain closure of the catalytic core to couple the STAC binding and the substrate binding. Biophysical characterization using FP and site-directed mutagenesis using full-length hSIRT1 are fully consistent with the structural observation of the mini-hSIRT1/STAC complex in support of this model of STAC binding and activation. To our knowledge, the structures of the mini-hSIRT1/STAC complexes reported here represent only the second example of a synthetic allosteric activator bound to an enzyme besides glucokinase (Grimsby, J. et al. (2005) Science 301, 370). In summary, the results presented here provide unambiguous visual and functional proof of direct allosteric activation of hSIRT1 by small molecules with peptide substrates and provide a basis for further elucidation of the mechanism of hSIRT1 activation by STACs, and potentially also by endogenous regulators of hSIRT1.

Example 94. Protein Cloning, Expression, and Purification

Mini-hSIRT1 constructs were cloned into a modified pET21b vector (Novagen). The protein was expressed in *E. coli* BL21-Gold (DE3) cells (Stratagene) as an N-terminal fusion to a hexahistidine affinity tag with integrated TEV protease site. A single colony was inoculated in LB media containing 100 µg/ml ampicillin at 37° C., 250 rpm until the $A_{600}$ reached 0.3. The culture was then transferred to 16° C., 250 rpm until the $A_{600}$ reached 0.6. Isopropyl 1-thio-β-D-galactopyranoside (IPTG) was added to a final concentration of 0.2 mM, and expression was continued at 16° C., 250 rpm overnight. Cells were collected by centrifugation, and the pellet was resuspended in lysis buffer (25 mM HEPES, pH 7.5, 200 mM NaCl, 5% glycerol, and 5 mM 2-mercaptoethanol) and sonicated to break the cells. Supernatant was separated from cell debris by centrifugation at 10,000×g for 40 min at 4° C. and loaded onto a Ni-NTA column (Qiagen) that equilibrated with the buffer containing 25 mM HEPES, pH 7.5, 200 mM NaCl, 5% glycerol, 5 mM 2-mercaptoethanol, and 20 mM imidazole. The column was washed with 5 column volumes of the buffer containing 25 mM HEPES, pH 7.5, 200 mM NaCl, 5% glycerol, 5 mM 2-mercaptoethanol, and 50 mM imidazole, and eluted with the buffer containing 25 mM HEPES, pH 7.5, 200 mM NaCl, 5% glycerol, 5 mM 2-mercaptoethanol, and 250 mM imidazole.

The eluted protein was dialyzed in lysis buffer and digested with TEV protease (Invitrogen) to remove the N-terminal His tag at 4° C. overnight. The protein was loaded on a second Ni-NTA column equilibrated with lysis buffer. The untagged protein was eluted by the buffer containing 25 mM HEPES, pH 7.5, 200 mM NaCl, 5% glycerol, 5 mM 2-mercaptoethanol, and 5 mM imidazole. The purified protein was dialyzed against the dialyzing buffer containing 20 mM Tris-HCl, pH 8.0, 250 mM NaCl, 5% glycerol, and 10 mM DTT, and concentrated. The protein was further purified by a S200 column (GE Healthcare) to 95% purity as assessed by SDS-PAGE analysis stained by Coomassie Brilliant Blue R-250 and concentrated to 10-15 mg/ml in the dialyzing buffer.

Human hsirt1 180-230 were cloned into a modified pET21b vector (Novagen) between BamHI and XhoI, which places expression under the control of the T7-lacO promoter. The protein was expressed in E. coli BL21-Gold(DE3) cells (Stratagene) as an N-terminal fusion to a hexahistidine affinity tag with integrated TEV protease site. A single colony was inoculated in 100 ml LB media containing 100 ug/ml ampicillin at 37° C., 250 rpm for overnight. Then 20 ml LB media was inoculated to 1 L M9 media which contained $^{15}NH_4Cl$ and Incubate them at 37° C. on an orbital shaker (200 rpm) until OD600 was about 0.8. The culture was then transferred to 16° C., 250 rpm until the A600 reached 1.0. Isopropyl 1-thio-β-D-galactopyranoside was added to a final concentration of 0.3 mM, and expression was continued at 16° C., 200 rpm overnight. Cells were collected by centrifugation, and the pellet was resuspended in lysis buffer (50 mM Hepes, 200 mM NaCl, 5% glycerol, 5 mM 3-ME, pH 7.5) and sonicated to open the cells. Supernatant was separated from cell debris by centrifugation at 10,000×g for 40 min at 4° C. and loaded onto a Ni-NTA column (Qiagen) that equilibrated with the buffer containing 50 mM Hepes, 200 mM NaCl, 5% glycerol, 5 mM β-ME, pH 7.5. The column was washed with 20 column volumes of the buffer containing 50 mM Hepes, 200 mM NaCl, 5% glycerol, 5m MB-ME and 20 mM imidazole, pH 7.5 and then eluted with the buffer containing 50 mM Hepes, 200 mM NaCl, 5% glycerol, 5 mM β-ME and 250 mM imidazole, pH 7.5. The eluted protein was dialyzed in lysis buffer and digested with TEV protease (Invitrogen) to remove the N-terminal His tag at 4° C. overnight. The protein was loaded on a second Ni-NTA column equilibrated with lysis buffer. The untagged protein was eluted by the buffer containing 50 mM Hepes, 200 mM NaCl, 5% glycerol, 5 mM β-ME and 10 mM imidazole, pH 7.5. The purified protein was concentrated and further purified by a S200 column (GE Healthcare) to get 95% purity as assessed by SDS-PAGE analysis stained by Coomassie Brilliant Blue R-250 and concentrated to 10 mg/ml in the 50 mM HEPES, 50 mM NaCl, 0.5 mM TCEP, pH 6.5.

Example 95. Full-Length SIRT1 Production

Full-length human SIRT1 (hSIRT1) proteins were expressed with a C-terminal $His_6$ tag and purified as described in Hubbard. et al. (2013) Science 339, 1216, except for Q222A, and I223R SIRT1 which were purified using an ÄKTAxpress™ (GE Lifesciences). Each cell paste was resuspended in buffer A (50 mM Tris-HCl pH 7.5, 250 mM NaCl, 25 mM imidazole, and 0.1 mM TCEP) with 1,000 U Benzonase nuclease (Sigma Aldrich) supplemented with cOmplete, EDTA-free Protease Inhibitor Cocktail Tablets (Roche) on ice. Cells were disrupted by pulse sonication with 50% on and 50% off for 12 minutes total at 40 W. Insoluble debris was removed by centrifugation. Clarified supernatant was directly loaded onto a 1 mL HisTrap FF Crude column (GE Lifesciences). After washing with buffer A, SIRT1 was eluted with buffer B (50 mM Tris-HCl pH 7.5, 250 mM NaCl, 500 mM imidazole and 0.1 mM TCEP). Protein was further purified by size exclusion chromatography in buffer C (50 mM Tris-HCl pH 7.5, 300 mM NaCl, 0.1 mM TCEP) using a Hi-load Superdex 200 16/60 column (GE Lifesciences). Enzyme concentrations were determined by Bradford assay using BSA as a standard. Final protein purity was assessed by gel densitometry. Proteins were confirmed by LC/MS. All proteins were greater than 90% pure except V224A and T219A (80%) and E230A (85%).

Example 96. SIRT1 Deacetylation Reactions

SIRT1 deacetylation reactions were performed in reaction buffer (50 mM HEPES-NaOH, pH 7.5, 150 mM NaCl, 1 mM DTT, and 1% DMSO) at 25° C. monitoring either nicotinamide production using the continuous PNC1/GDH coupled assay (Smith, B. C. et al. (2009) Anal Biochem 394, 101) or O-acetyl ADP ribose (OAcADPr) production by mass spectrometry (Hubbard. et al. (2013) Science 339, 1216). Final concentrations of the PNC1/GDH coupling system components used were 20 units/mL bovine GDH (Sigma-Aldrich), 1 uM yeast PNC1, 3.4 mM a-ketoglutarate, and 220 μM NADH or NADPH. An extinction coefficient of 6.22 $mM^{-1}$ $cm^{-1}$ and a pathlength of 0.81 cm was used to convert the absorbance at 340 nm to product concentration for the 150 uL reactions used. Assays monitoring OAcADPr production were performed in reaction buffer with 0.05% BSA and time points were taken by quenching the deacetylation reaction with a stop solution which gave a final concentration of 1% formic acid and 5 mM nicotinamide. Quenched reactions were diluted 5-fold with 1:1 acetonitrile:methanol and spun at 5,000×g for 10 minutes to precipitate protein before being analyzed with an Agilent RapidFire 200 High-Throughput Mass Spectrometry System (Agilent, Wakefield, Mass.) coupled to an ABSciex API 4000 mass spectrometer fitted with an electrospray ionization source. The p53-based Ac-p53(W5) (Ac—RHKK$^{Ac}$W—NH$_2$) and FOXO-3a 21-mer (Ac-SADDSPSQLSK$^{Ac}$WPGSPTSRSS-NH$_2$) peptides were obtained from Biopeptide, Inc. Deacetylation assays used the Ac-p53(W5) substrate unless otherwise noted.

Substrate $K_M$ determinations were performed by varying one substrate concentration at a fixed, saturating concentration of the second substrate. SIRT1 activation and inhibition assays were run in reaction buffer with 0.05% BSA at 25° C. and analyzed using the OAcADPr assay. Enzyme and compound were pre-incubated for 20 minutes before addition of substrates. For the activation screen of full-length hSIRT1, a structurally diverse set of 246 compounds was tested in duplicate at a final concentration of 25 μM each. In order to be sensitive to $K_M$-modulating activators, substrate concentrations of approximately one-tenth their $K_M$ values were used (see Table 5). The dose-dependence of five compounds was tested and the fold-activation data were described by Eq. 1

$$\frac{v_x}{v_o} = b + \frac{RV_{max} - b}{1 + \frac{EC_{50}}{[X]_o}} \quad \text{(Eq.1)}$$

where $v_x/v_0$ is the ratio of the reaction rate in the presence ($v_x$) versus absence ($v_0$) of activator (X), $RV_{max}$ is the relative velocity at infinite activator concentration, $EC_{50}$ is the concentration of activator required to produce one-half $RV_{max}$ and b is the minimum value of $v_x/v_0$.

TABLE 5

Inhibition of wild-type and mutant full-length hSIRT1

| hSIRT1 | $IC_{50}$ (μM)[a] | | |
| --- | --- | --- | --- |
| | EX-527 | TFA-p53 7-mer[b] | NAM |
| wild-type | 0.140 ± 0.020 | 0.680 ± 0.070 | 92 ± 6 |
| T219A | 0.310 ± 0.040 | 0.490 ± 0.020 | 53 ± 4 |
| Q222A | 0.110 ± 0.010 | 0.630 ± 0.050 | 53 ± 5 |
| I223A | 0.180 ± 0.020 | 0.540 ± 0.150 | 108 ± 10 |
| V224A | 0.140 ± 0.010 | 0.860 ± 0.080 | 64 ± 3 |
| N226A | 0.190 ± 0.010 | 0.350 ± 0.040 | 100 ± 9 |
| I227A | 0.220 ± 0.020 | 0.940 ± 0.060 | 92 ± 4 |
| E230K | 0.150 ± 0.020 | 1.6 ± 0.3 | 54 ± 3 |
| E230A | 0.100 ± 0.030 | 1.3 ± 0.4 | 60 ± 3 |
| E230Q | 0.240 ± 0.020 | 0.860 ± 0.060 | 56 ± 3 |
| I223R | 0.210 ± 0.020 | 0.660 ± 0.060 | 87 ± 6 |

[a]Data from OAcADPr assay using the Ac-p53(W5) substrate.
[b]TFA-p53 peptide sequence: Ac-RHKK(TFA)L-Nle-F-NH$_2$.

Example 97. Protein Crystallization, Data Collection and Structure Determination The crystals of mini-hSIRT1/1 binary complex were obtained by hanging drop vapor diffusion method at 18° C. The drop was composed of 1 μl of protein/compound mixture and 1 μl crystallization buffer of 0.2 M Magnesium chloride, 0.1 M Tris pH 8.5, and 16% w/v PEG 4000. The crystals of mini-hSIRT1/1/2 were obtained by hanging drop vapor diffusion method at 18° C. The drop was composed of 1 μl of protein/compound mixture and 1 μl crystallization buffer of 0.55 M Sodium chloride, 0.1 M MES pH 6.5, and 20% w/v PEG 4000. The crystals of mini-hSIRT1/1/p53-7mer/carbaNAD complex were obtained by hanging drop vapor diffusion method at 18° C. The drop was composed of 1 ul of the protein/substrate mixture and 1 ul of the crystallization buffer of 5% v/v Tacsimate, pH 0.00.1 M HEPES pH 7.0 and 10% w/v PEG 5000 MME. The crystals of mini-hSIRT1(E230K)/1/2 were obtained by hanging drop vapor diffusion method at 18° C. The drop was composed of 1 μl of protein/compound mixture and 1 μl crystallization buffer of 0.2 M Lithium Sulfate, 0.1 M Bis-Tris pH 6.5, 29% w/v PEG 3350.

The crystals were cryo-protected in mother liquor containing 20% glycerol before being flash-frozen in liquid nitrogen. Diffraction data were collected at SSRF BL17U1, APS 21-ID-D or APS 21-ID-G beamlines and processed using the Xia2 program (Winter, G. (2010) J Appl Crystallogr 43, 186). The molecular replacement software Phaser (McCoy, A. J. et al. (2007) J Appl Crystallogr 40, 658) was used to solve the structure with a search model containing residues 242-494 based on the homolog model of SIRT3 (PDB code: 3GLU). Iterative structure refinement and model building were performed between Refmac5 (Murshudov, A. A. et al. (1997) Acta Crystallogr D Biol Crystallogr 53, 240) of the CCP4 package ((1994) Acta Crystallogr D Biol Crystallogr 50, 760) and Coot et al. (2004) Acta Crystallogr D Biol Crystallogr 60, 2126. Detailed information regarding the diffraction data, refinement, and structure statistics is listed in Table 3.

TABLE 3

Data Processing and Refinement Statistics

| | Mini-SIRT1/1 | Mini-SIRT1/1/2 | Mini-SIRT1 (E230K)/1/2 | Mini-SIRT1/1/p53 7-mer/CarbaNAD |
| --- | --- | --- | --- | --- |
| Data Collection | | | | |
| Resolution (Å)* | 45.67-3.10 | 39.98-2.73 | 40.17-3.22 | 91.36-2.74 |
| | (3.18-3.10) | (2.81-2.73) | (3.30-3.22) | (2.81-2.74) |
| Space group | I2$_1$2$_1$2$_1$ | P6322 | P6322 | I4122 |
| Unit-cell parameters | | | | |
| a (Å) | 99.19 | 122.15 | 122.72 | 94.51 |
| b (Å) | 111.64 | 122.15 | 122.72 | 94.51 |
| c (Å) | 132.52 | 104.92 | 105.88 | 356.84 |
| α (°) | 90.00 | 90.00 | 90.00 | 90.00 |
| β (°) | 90.00 | 90.00 | 90.00 | 90.00 |
| γ (°) | 90.00 | 120.00 | 120.00 | 90.00 |
| Completeness (%)* | 99.5 (99.8) | 99.9 (100.0) | 99.9 (99.9) | 99.5 (99.4) |
| Redundancy* | 4.8 (4.9) | 17.6 (18.2) | 17.4 (18.4) | 9.6 (9.9) |
| Average I/σI* | 17.4 (2.0) | 38.8 (4.0) | 38.1 (4.4) | 20.7 (3.3) |
| Rmerge (%)* | 6.7 (78.1) | 5.3 (80.3) | 6.2 (80.6) | 8.2 (82.9) |
| Refinement | | | | |
| Resolution (Å)* | 45.71-3.10 | 40.01-2.74 | 40.17-3.22 | 91.36-2.74 |
| | (3.18-3.10) | (2.81-2.73) | (3.30-3.22) | (2.81-2.74) |
| $R_{work}$ (%)* | 21.2 (33.9) | 22.4 (33.6) | 22.8 (28.8) | 18.3 (31.8) |
| $R_{free}$ (%)* | 25.0 (37.6) | 27.1 (43.8) | 25.1 (40.3) | 23.5 (36.7) |
| R.M.S.D in bond lengths (Å) | 0.005 | 0.007 | 0.006 | 0.010 |
| R.M.S.D in bond angles (°) | 1.089 | 1.14 | 1.079 | 1.538 |
| Mean B factors (Å2) | 100.1 | 78.6 | 104.5 | 67.3 |

*Values in parentheses are for the highest-resolution shell

Example 98. Nuclear Magnetic Resonance (NMR) Spectroscopy

The $^1H$, $^{15}N$ HSQC NMR experiments were carried out at 25° C. on a Bruker AVANCE III 600 MHz NMR Spectrometer with cryoprobe using samples containing approximately 200 μM $^{15}N$-labeled SIRT1(180-230) in the presence or absence of 400 μM 1. All NMR data were processed with NMRPipe (Delaglio, F. et al. (1995) J Biomol NMR 6, 277) and analyzed with NMRView (Johnson, et al. (1994) J Biomol NMR 4, 603).

Example 99. Size Exclusion Chromatography (SEC) Assay

The assays were performed with a Superdex 75 10/300 GL column (GE healthcare) injecting 100 μL samples containing 10 NM mini-hSIRT1 in the absence or presence of 100 M STAC, dissolved in 50 mM HEPES-NaOH, pH 7.5, 150 mM NaCl, and 0.5 mM TCEP. Binding reactions were incubated for 1 h at RT before injection into the column.

Example 100. Fluorescence Polarization (FP) Assay

FP experiments were carried out in 20 μL assay buffer (50 mM HEPES-NaOH, pH 7.5, 150 mM NaCl, and 1 mM DTT) at 25° C. The 384-well plates were read on PHERAstar FS with excitation and emission wavelengths at 502 nm and 533 nm, respectively. For probe binding, increasing concentrations of SIRT1 were added into 10 nM probe 3. The Binding isotherm was described by Eq. 2. For competitive binding mode, increasing concentrations of competitors were added into the mixture of 10 nM 3 and 0.3 μM SIRT1 wild-type or E230K mutant in the absence or presence or 15 μM Ac-p53(W5). The competition data were described by Eq. 3. The conversion of $IC_{50}$ to $K_i$ was described by Eq. 4, where $K_d$ is the binding affinity of 3 to SIRT1, $F_0$ is the fraction of probe bound B/(B+F) and $L_0$ is the concentration of probe 3.

$$y = \frac{x(B-A)}{x+K_d} + Nx + A \quad (Eq.2)$$

$$y = \frac{1}{1+\frac{x}{IC_{50}}} \quad (Eq.3)$$

$$K_i = \frac{IC_{50}}{\frac{1}{1-F_0} + \frac{L_0(2-F_0)}{2K_d}} - K_d \frac{F_0}{2-F_0} \quad (Eq.4)$$

Example 101. Hydrogen-Deuterium Exchange Mass Spectrometry (HDX-MS) On-Exchange Experiment of SIRT1

H/D-exchange reactions followed by pepsin digestion, desalting, HPLC separation, and MS analysis were carried out using a fully automated system, described in detail elsewhere (Hamuro, Y. et al. (2003) J Biomol Techniques: JBT 14, 171). Particular to this set of experiments, on-exchange reactions were initiated by mixing 20 μL of a SIRT1 stock solution (0.77 mg/mL SIRT1, ±3.88 mM Ac-p53(W5), ±192 μM ligand, in 1.9% DMSO) and 20 μL of 100 mM phosphate, pH read 7.0 in D20. The 50% $D_2O$ mixture was incubated at 0° C. for 15, 50, 150, 500, 1,500, or 5,000 s. For SIRT1 (229-516), on-exchange reactions were initiated by mixing 4 μL of a SIRT1 stock solution (1.36 mg/mL SIRT1 (229-516), ±1.67 mM Trp-25mer) and 36 μL of 200 mM phosphate, pH read 7.0 in D20. The 90% $D_2O$ mixture was incubated at 0° C. for 15, 50, 150, 500, 1,500, or 5,000 s. Addition of 20 μL of 1.6 M guanidine hydrochloride (GuHCl), 0.8% formic acid, pH 2.3, quenched the on-exchange reaction immediately prior to being analyzed.

Example 102. General Protein Process for Standard HDX Sample

The quenched solution was passed through a pepsin column (104 μL bed volume) filled with porcine pepsin (Sigma, St Louis, Mo.) immobilized on Poros 20 AL media (Life Technologies, Carlsbad, Calif.) per the manufacturer's instructions, with 0.05% aqueous TFA (200 μL/min) for 2 min. The digested fragments were temporarily collected onto a reverse phase trap column (4 μL bed volume) and desalted. The peptide fragments were then eluted from the trap column and separated by a C18 column (BioBacis-18; Thermo Scientific, San Jose, Calif.) with a linear gradient of 13% solvent B to 40% solvent B over 23 min (solvent A, 0.05% TFA in water; solvent B, 95% acetonitrile, 5% buffer A; flow rate 10 μL/min). Mass spectrometric analyses were carried out using a LTQ OrbiTrap XL mass spectrometer (Thermo Fisher Scientific, San Jose, Calif.) with capillary temperature at 200° C.

Example 103. Digestion/Separation Optimization and Non-Deuterated Experiment of SIRT1

Prior to H/D-exchange experiment, digestion and separation conditions were optimized to yield high sequence coverage of SIRT1 by peptic fragments with high resolution under non-deuterated conditions. In this step, a mixture of 20 μL of 0.77 mg/mL (9.2 μM) SIRT1 and 20 μL of H2O was quenched by the addition of 20 μL of various acidic buffers. For SIRT1 (229-516), a mixture of 4 μL of a SIRT1 stock solution (1.36 mg/mL SIRT1 (229-516), ±1.67 mM Trp-25mer) and 36 μL of $H_2O$ was quenched by the addition of 20 μL of various acidic buffers. The quenched mixtures were subjected to aforementioned general protein process. The non-deuterated peptic fragments were identified by Sequest in Proteome Discoverer 1.1 (Thermo Fisher Scientific, San Jose, Calif.).

Example 104. Fully Deuterated Experiment of SIRT1

The fully deuterated sample was prepared by incubating a mixture of 45 μL of 0.77 mg/mL (9.2 μM) SIRT1 with 45 μL of 100 mM TCEP in $D_2O$, pH 2.5 at 60° C. for 3 h. For SIRT1 (229-516), the fully deuterated sample was prepared by incubating a mixture of 9 μL of 1.36 mg/mL (41.7 μM) SIRT1 (229-516) with 81 μL of 100 mM TCEP in $D_2O$, pH 2.5 at 60° C. for 3 h. After incubation, the sample was kept at 0° C. before being quenched identically to an on-exchanged solution and subjected to the general protein process.

Example 105. Determination of Deuteration Level of Each Peptide after On-Exchange Reaction The centroids of peptide isotopic envelopes were measured using the in-house-program developed in collaboration with Sierra Analytics (Modesto, Calif.). Corrections for back-exchange during the protein processing step were made employing the following standard equation Eq. 5 (Zhang, Z. et al. (1993) Protein Science 2, 522):

$$\text{Deuteration Level (\%)} = \frac{m(P) - m(N)}{m(F) - m(N)} \times 100 \quad \text{(Eq.5)}$$

where m(P), m(N), and m(F) are the centroid value of partially deuterated (on-exchanged) peptide, non-deuterated peptide, and fully deuterated peptide, respectively.

Example 106. Biological Activity

Mass spectrometry based assays were used to identify modulators of SIRT1 activity. The TAMRA based assay utilized a peptide having 20 amino acid residues as follows: Ac-EE-K(biotin)-GQSTSSHSK(Ac)NleSTEG-K(5TMR)-EE-NH$_2$ (SEQ ID NO: 1), wherein K(Ac) is an acetylated lysine residue and Nle is a norleucine. The peptide was labeled with the fluorophore 5TMR (excitation 540 nm/emission 580 nm) at the C-terminus. The sequence of the peptide substrate was based on p53 with several modifications. In addition, the methionine residue naturally present in the sequence was replaced with the norleucine because the methionine may be susceptible to oxidation during synthesis and purification. The Trp based assay utilized a peptide having an amino acid residues as follows: Ac—R—H—K—K(Ac)—W—NH2 (SEQ ID NO: 2).

The TAMRA based mass spectrometry assay was conducted as follows: 0.5 μM peptide substrate and 120 μM βNAD$^+$ was incubated with 10 nM SIRT1 for 25 minutes at 25° C. in a reaction buffer (50 mM Tris-acetate pH 8, 137 mM NaCl, 2.7 mM KCl, 1 mM MgCl$_2$, 5 mM DTT, 0.05% BSA). The SIRT1 protein was obtained by cloning the SirT1 gene into a T7-promoter containing vector, which was then transformed and expressed in BL21(DE3) bacterial cells. Test compound was added at varying concentrations to this reaction mixture and the resulting reactions were monitored. After the 25 minute incubation with SIRT1, 10 μL of 10% formic acid was added to stop the reaction. The resulting reactions were sealed and frozen for later mass spec analysis. Determination of the amount of deacetylated substrate peptide formed (or, alternatively, the amount of O-acetyl-ADP-ribose (OAADPR) generated) by the sirtuin-mediated NAD-dependent deacetylation reaction allowed for the precise measurement of relative SIRT1 activity in the presence of varying concentrations of the test compound versus control reactions lacking the test compound.

The Trp mass spectrometry assay was conducted as follows. 0.5 μM peptide substrate and 120 μM βNAD$^+$ were incubated with 10 nM SIRT1 for 25 minutes at 25° C. in a reaction buffer (50 mM HEPES pH 7.5, 1500 mM NaCl, 1 mM DTT, 0.05% BSA). The SIRT1 protein was obtained by cloning the SirT1 gene into a T7-promoter containing vector, which was then expressed in BL21(DE3) bacterial cells and purified as described in further detail below. Test compound was added at varying concentrations to this reaction mixture and the resulting reactions were monitored. After the 25 minute incubation with SIRT1, 10 μL of 10% formic acid was added to stop the reaction. The resulting reactions were sealed and frozen for later mass spec analysis. The relative SIRT1 activity was then determined by measuring the amount of O-acetyl-ADP-ribose (OAADPR) formed (or, alternatively, the amount of deacetylated Trp peptide generated) by the NAD-dependent sirtuin deacetylation reaction in the presence of varying concentrations of the test compound versus control reactions lacking the test compound. The degree to which the test agent activated deacetylation by SIRT1 was expressed as EC$_{1.5}$ (i.e., the concentration of compound required to increase SIRT1 activity by 50% over the control lacking test compound), and Percent Maximum Activation (i.e., the maximum activity relative to control (100%) obtained for the test compound).

A control for inhibition of sirtuin activity was conducted by adding 1 μL of 500 mM nicotinamide as a negative control at the start of the reaction (e.g., permits determination of maximum sirtuin inhibition). A control for activation of sirtuin activity was conducted using 10 nM of sirtuin protein, with 1 μL of DMSO in place of compound, to determine the amount of deacetylation of the substrate at a given time point within the linear range of the assay. This time point was the same as that used for test compounds and, within the linear range, the endpoint represents a change in velocity.

For the above assay, SIRT1 protein was expressed and purified as follows. The SirT1 gene was cloned into a T7-promoter containing vector and transformed into BL21 (DE3). The protein was expressed by induction with 1 mM IPTG as an N-terminal His-tag fusion protein at 18° C. overnight and harvested at 30,000×g. Cells were lysed with lysozyme in lysis buffer (50 mM Tris-HCl, 2 mM Tris[2-carboxyethyl] phosphine (TCEP), 10 μM ZnCl$_2$, 200 mM NaCl) and further treated with sonication for 10 min for complete lysis. The protein was purified over a Ni-NTA column (Amersham) and fractions containing pure protein were pooled, concentrated and run over a sizing column (Sephadex S200 26/60 global). The peak containing soluble protein was collected and run on an Ion-exchange column (MonoQ). Gradient elution (200 mM-500 mM NaCl) yielded pure protein. This protein was concentrated and dialyzed against dialysis buffer (20 mM Tris-HCl, 2 mM TCEP) overnight. The protein was aliquoted and frozen at −80° C. until further use.

Sirtuin-modulating compounds of Formula (I) that activated SIRT1 were identified using the assay described above and are shown below in Table 1 and Table 10 (i.e., additional representative compound examples), which recites additional representative compounds of the present invention.

The EC$_{1.5}$ values represent the concentration of test compounds that result in 150% activation of SIRT1. The EC$_{1.5}$ values for the activating compounds of Formula (I) are represented by A (EC$_{1.5}$<1 μM), B (EC$_{1.5}$ 1-25 μM), C (EC$_{1.5}$ >25 μM). The percent maximum fold activation is represented by A (Fold activation ≥150%) or B (Fold Activation <150%). "NT" means not tested; "ND" means not determinable. The compound numbering in the table starts with compound number 10, and parenthetic numbering (#) corresponding to the STAC numbering system in FIG. 4 and Examples 90-106 (i.e., compound no. 68 is also STAC 1, so it is shown as 68(1), and further STACs: 546(3), 444(4), 314(5), 816(7), 76(8), and 81(9)).

TABLE 1

Compounds of Formula (I).

| Compound No. | [M + H]+[calc] | Structure | Tyrp AVG EC$_{1.5}$ (μM) | Tyrp % Fold Act |
|---|---|---|---|---|
| 10 | 427 | 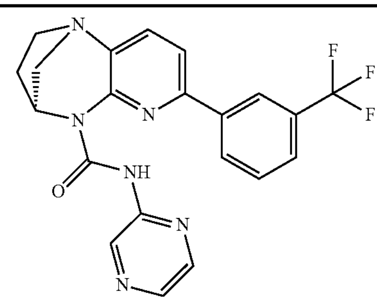 | A | A |
| 11 | 427 | 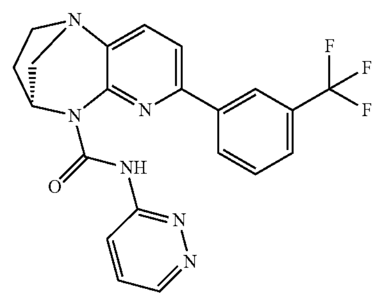 [SMILES: O=C(Nc1cccnn1)N1c2nc(-c3cccc(C(F)(F)F)c3)ccc2N2CC[C@H]1C2] | A | A |
| 12 | 427 | 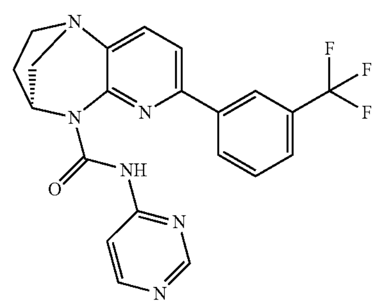 [SMILES: O=C(Nc1ccncn1)N1c2nc(-c3cccc(C(F)(F)F)c3)ccc2N2CC[C@H]1C2] | A | A |
| 13 | 454 | 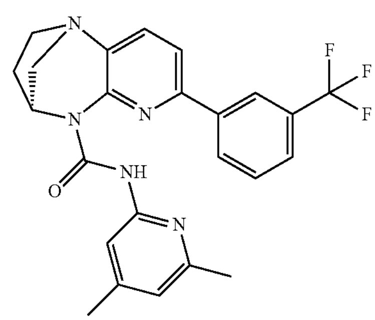 [SMILES: Cc1cc(C)nc(NC(=O)N2c3nc(-c4cccc(C(F)(F)F)c4)ccc3N3CC[C@H]2C3)c1] | B | A |
| 14 | 440 | 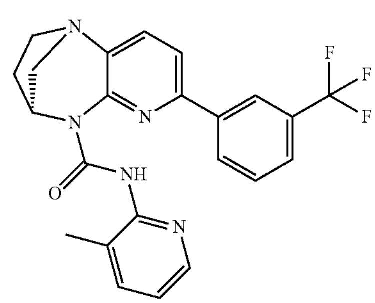 [SMILES: Cc1cccnc1NC(=O)N1c2nc(-c3cccc(C(F)(F)F)c3)ccc2N2CC[C@H]1C2] | C | B |

TABLE 1-continued

Compounds of Formula (I).

| Compound No. | [M + H]+[calc] | Structure | Tyrp AVG EC$_{1.5}$ (µM) | Tyrp % Fold Act |
|---|---|---|---|---|
| 15 | 444 | 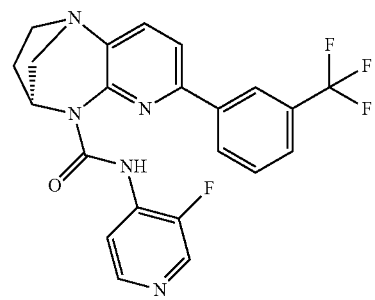 [SMILES: O=C(Nc1ccncc1F)N1c2nc(-c3cccc(C(F)(F)F)c3)ccc2N2CC[C@H]1C2] | A | A |
| 16 | 513 | 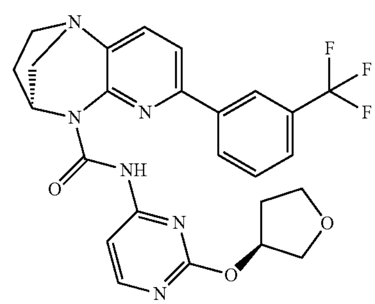 [SMILES: O=C(Nc1ccnc(O[C@H]2CCOC2)n1)N1c2nc(-c3cccc(C(F)(F)F)c3)ccc2N2CC[C@H]1C2] | A | A |
| 17 | 426 | 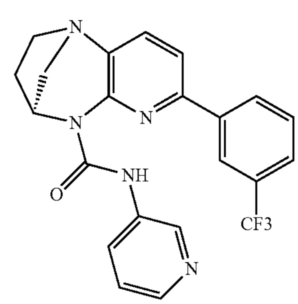 [SMILES: O=C(Nc1cccnc1)N1c2nc(-c3cccc(C(F)(F)F)c3)ccc2N2CC[C@H]1C2] | A | A |
| 18 | 517 | 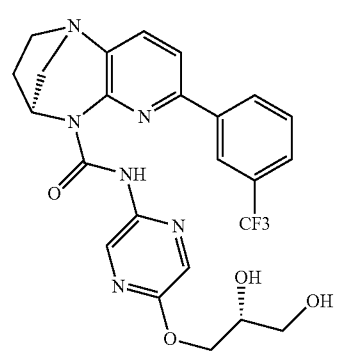 [SMILES: O=C(Nc1cnc(OC[C@H](O)CO)cn1)N1c2nc(-c3cccc(C(F)(F)F)c3)ccc2N2CC[C@H]1C2] | A | A |

TABLE 1-continued
Compounds of Formula (I).
| Compound No. | [M + H]+_{[calc]} | Structure | Tyrp AVG EC_{1.5} (μM) | Tyrp % Fold Act |
|---|---|---|---|---|
| 19 | 392 | 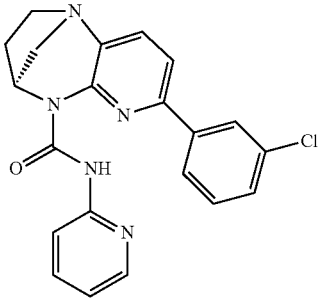 [SMILES: O=C(Nc1ccccn1)N1c2nc(-c3cccc(Cl)c3)ccc2N2CC[C@H]1C2] | A | A |
| 20 | 444 | 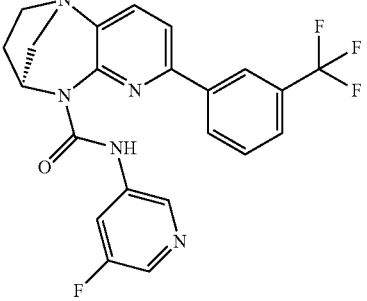 | A | A |
| 21 | 440 | 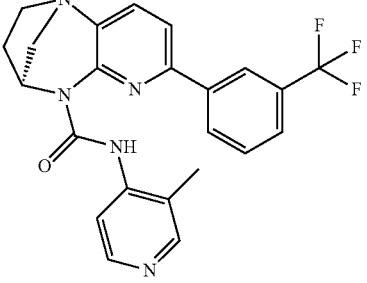 | B | A |
| 22 | 487 | 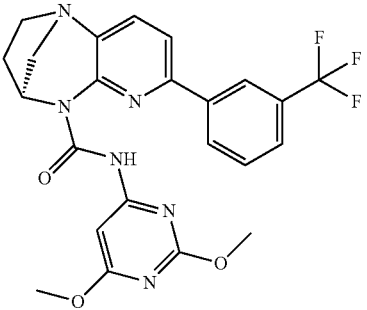 [SMILES: COc1cc(NC(=O)N2c3nc(-c4cccc(C(F)(F)F)c4)ccc3N3CC[C@H]2C3)nc(OC)n1] | B | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 23 | 427 | 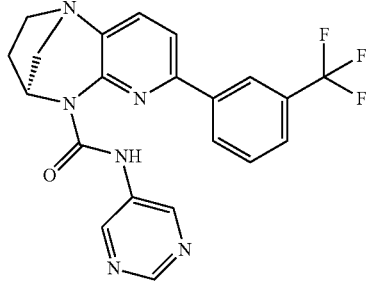 [SMILES: O=C(Nc1cncnc1)N1c2nc(-c3cccc(C(F)(F)F)c3)ccc2N2CC[C@H]1C2] | A | A |
| 24 | 410 | 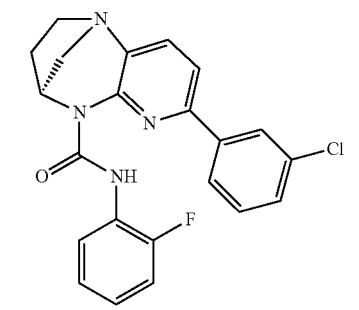 [SMILES: O=C(Nc1ccccc1F)N1c2nc(-c3cccc(Cl)c3)ccc2N2CC[C@H]1C2] | B | A |
| 25 | 429 | 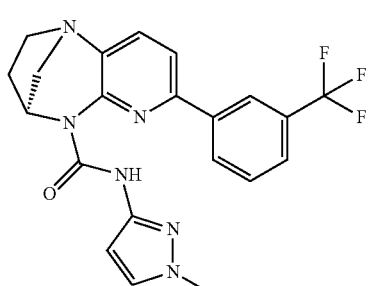 | A | A |
| 26 | 531 | 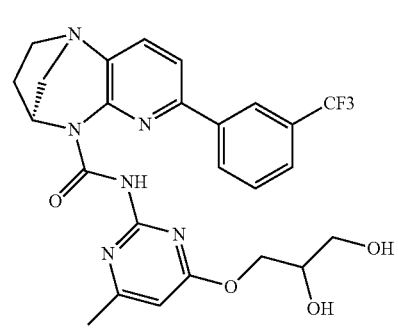 [SMILES: Cc1cc(OCC(O)CO)nc(NC(=O)N2c3nc(-c4cccc(C(F)(F)F)c4)ccc3N3CC[C@H]2C3)n1] | B | A |
| 27 | 441 | 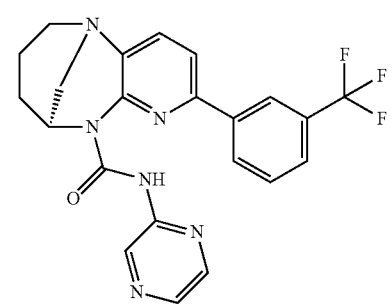 [SMILES: O=C(Nc1cnccn1)N1c2nc(-c3cccc(C(F)(F)F)c3)ccc2N2CCC[C@H]1C2] | A | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 28 | 441 | 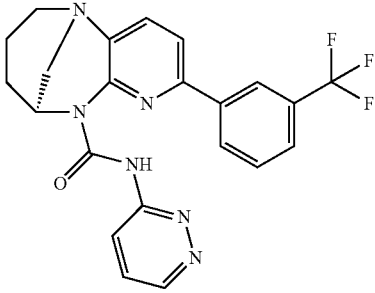 [SMILES: O=C(Nc1cccnn1)N1c2nc(-c3cccc(C(F)(F)F)c3)ccc2N2CCC[C@H]1C2] | A | A |
| 29 | 441 | 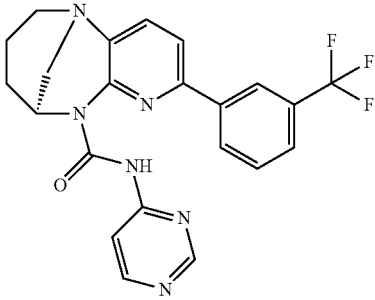 [SMILES: O=C(Nc1ccncn1)N1c2nc(-c3cccc(C(F)(F)F)c3)ccc2N2CCC[C@H]1C2] | A | A |
| 30 | 468 | 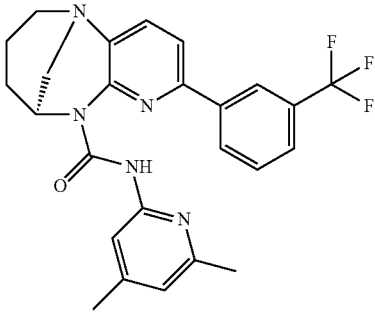 [SMILES: Cc1cc(C)nc(NC(=O)N2c3nc(-c4cccc(C(F)(F)F)c4)ccc3N3CCC[C@H]2C3)c1] | A | A |
| 31 | 501 | 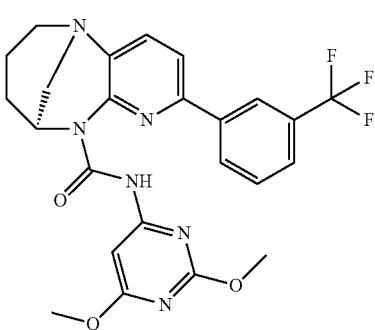 [SMILES: COc1cc(NC(=O)N2c3nc(-c4cccc(C(F)(F)F)c4)ccc3N3CCC[C@H]2C3)nc(OC)n1] | A | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 32 | 471 | 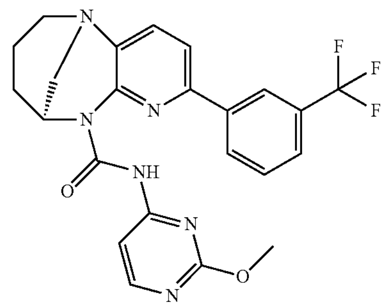 [SMILES: COc1nccc(NC(=O)N2c3nc(-c4cccc(C(F)(F)F)c4)ccc3N3CCC[C@H]2C3)n1] | A | A |
| 33 | 474 | 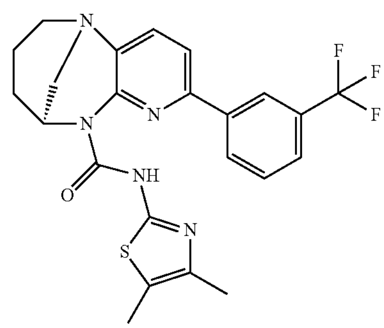 [SMILES: Cc1nc(NC(=O)N2c3nc(-c4cccc(C(F)(F)F)c4)ccc3N3CCC[C@H]2C3)sc1C] | A | A |
| 34 | 457 | 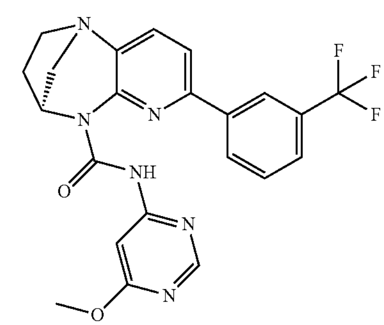 [SMILES: COc1cc(NC(=O)N2c3nc(-c4cccc(C(F)(F)F)c4)ccc3N3CC[C@H]2C3)ncn1] | A | A |
| 35 | 454 | 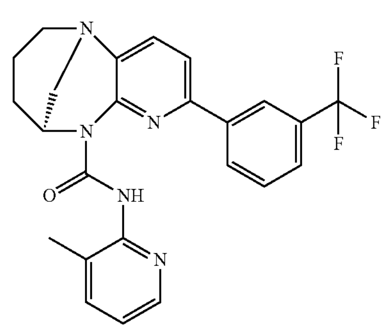 [SMILES: Cc1cccnc1NC(=O)N1c2nc(-c3cccc(C(F)(F)F)c3)ccc2N2CCC[C@H]1C2] | B | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 36 | 443 | 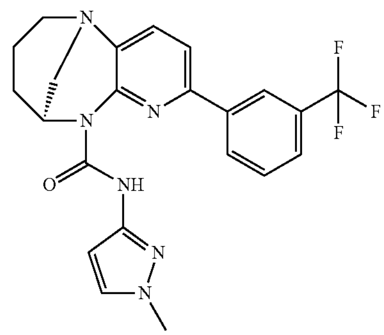 [SMILES: Cn1ccc(NC(=O)N2c3nc(-c4cccc(C(F)(F)F)c4)ccc3N3CCC[C@H]2C3)n1] | A | A |
| 37 | 454 | 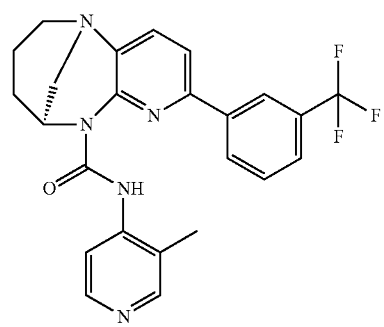 | B | A |
| 38 | 441 | 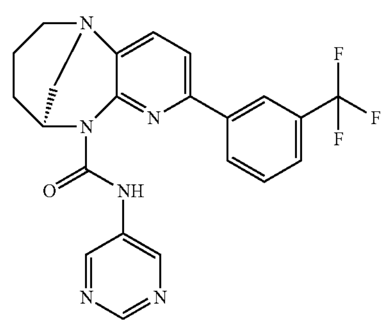 [SMILES: O=C(Nc1cncnc1)N1c2nc(-c3cccc(C(F)(F)F)c3)ccc2N2CCC[C@H]1C2] | A | A |
| 39 | 458 | 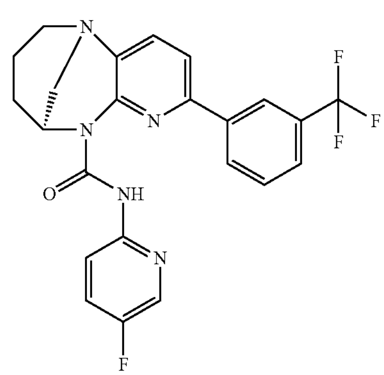 [SMILES: O=C(Nc1ccc(F)cn1)N1c2nc(-c3cccc(C(F)(F)F)c3)ccc2N2CCC[C@H]1C2] | A | A |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 40 | 443 | 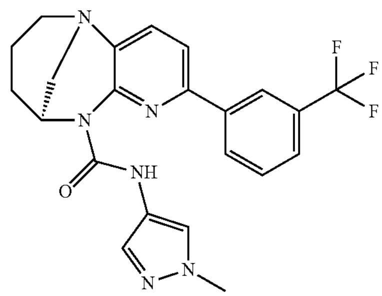 [SMILES: Cn1cc(NC(=O)N2c3nc(-c4cccc(C(F)(F)F)c4)ccc3N3CCC[C@H]2C3)cn1] | A | A |
| 41 | 471 | 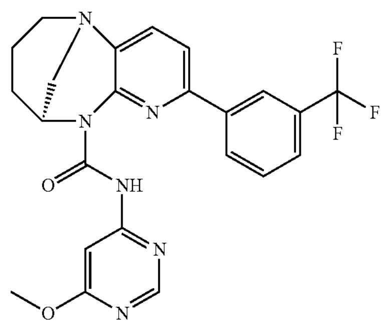 [SMILES: COc1cc(NC(=O)N2c3nc(-c4cccc(C(F)(F)F)c4)ccc3N3CCC[C@H]2C3)ncn1] | A | A |
| 42 | 458 | 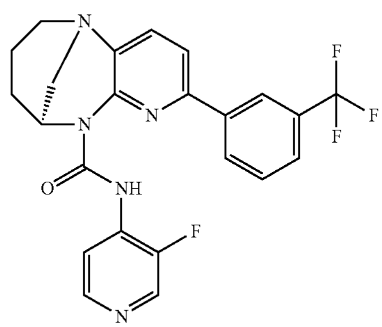 [SMILES: O=C(Nc1ccncc1F)N1c2nc(-c3cccc(C(F)(F)F)c3)ccc2N2CCC[C@H]1C2] | A | A |
| 43 | 410 | 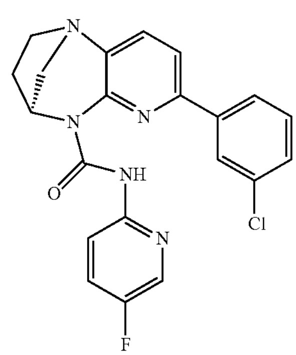 [SMILES: O=C(Nc1ccc(F)cn1)N1c2nc(-c3cccc(Cl)c3)ccc2N2CC[C@H]1C2] | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 44 | 406 | 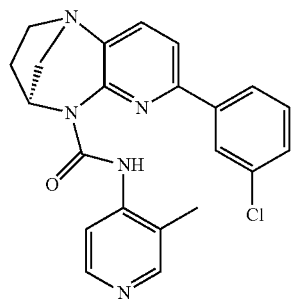 [SMILES: Cc1cnccc1NC(=O)N1c2nc(-c3cccc(Cl)c3)ccc2N2CC[C@H]1C2] | B | A |
| 45 | 458 | 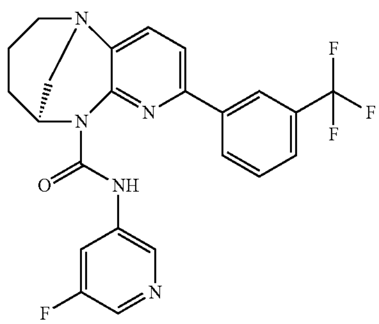 [SMILES: O=C(Nc1cncc(F)c1)N1c2nc(-c3cccc(C(F)(F)F)c3)ccc2N2CCC[C@H]1C2] | A | A |
| 46 | 444 | 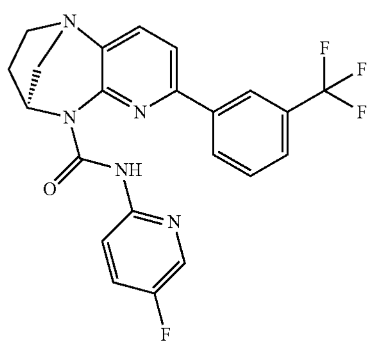 [SMILES: O=C(Nc1ccc(F)cn1)N1c2nc(-c3cccc(C(F)(F)F)c3)ccc2N2CC[C@H]1C2] | A | A |
| 47 | 457 | 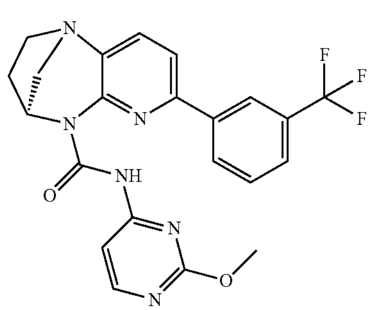 [SMILES: COc1nccc(NC(=O)N2c3nc(-c4cccc(C(F)(F)F)c4)ccc3N3CC[C@H]2C3)n1] | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 48 | 460 | 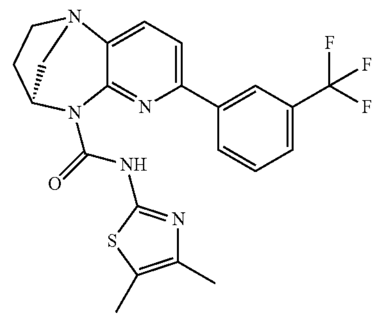 [SMILES: Cc1nc(NC(=O)N2c3nc(-c4cccc(C(F)(F)F)c4)ccc3N3CC[C@H]2C3)sc1C] | A | A |
| 49 | 429 | 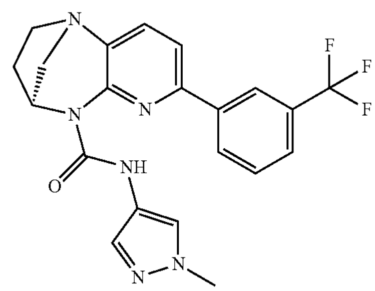 | A | A |
| 50 | 423 | 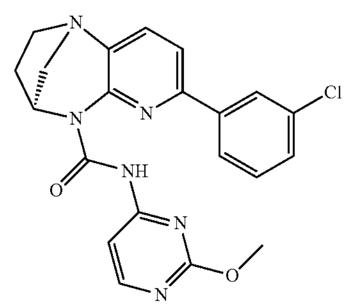 [SMILES: COc1nccc(NC(=O)N2c3nc(-c4cccc(Cl)c4)ccc3N3CC[C@H]2C3)n1] | B | A |
| 51 | 391 | 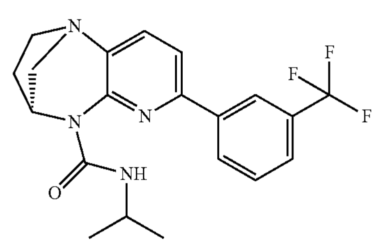 [SMILES: CC(C)NC(=O)N1c2nc(-c3cccc(C(F)(F)F)c3)ccc2N2CC[C@H]1C2] | B | A |
| 52 | 405 | 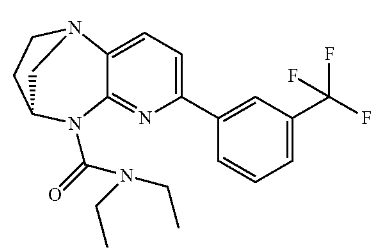 [SMILES: CCN(CC)C(=O)N1c2nc(-c3cccc(C(F)(F)F)c3)ccc2N2CC[C@H]1C2] | C | B |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 53 | 516 | 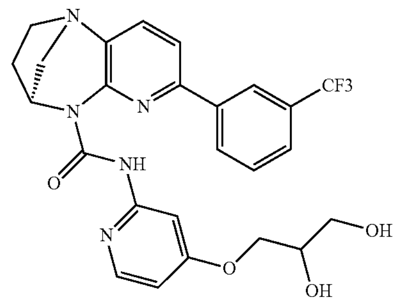 [SMILES: O=C(Nc1cc(OCC(O)CO)ccn1)N1c2nc(-c3cccc(C(F)(F)F)c3)ccc2N2CC[C@H]1C2] | A | A |
| 54 | 483 | 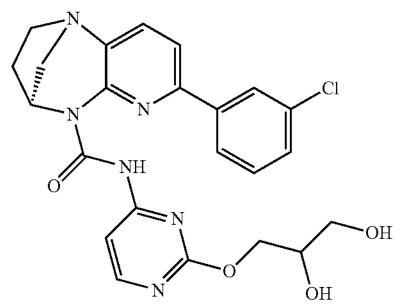 [SMILES: O=C(Nc1ccnc(OCC(O)CO)n1)N1c2nc(-c3cccc(Cl)c3)ccc2N2CC[C@H]1C2] | A | A |
| 55 | 497 | 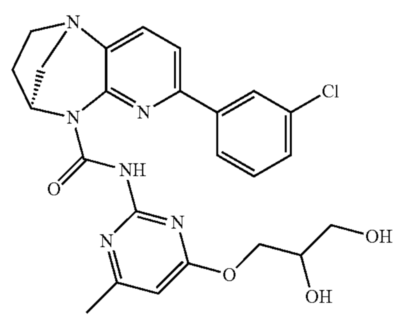 [SMILES: Cc1cc(OCC(O)CO)nc(NC(=O)N2c3nc(-c4cccc(Cl)c4)ccc3N3CC[C@H]2C3)n1] | B | A |
| 56 | 446 | 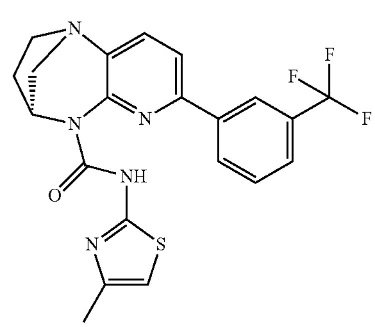 [SMILES: Cc1csc(NC(=O)N2c3nc(-c4cccc(C(F)(F)F)c4)ccc3N3CC[C@H]2C3)n1] | A | A |

TABLE 1-continued
Compounds of Formula (I).
| Compound No. | [M + H]+[calc] | Structure | Tyrp AVG EC_{1.5} (μM) | Tyrp % Fold Act |
|---|---|---|---|---|
| 57 | 376 | 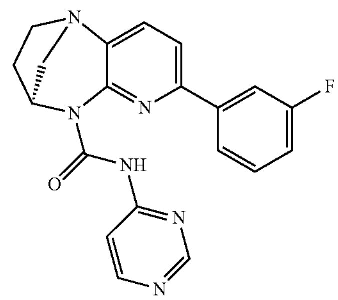 [SMILES: O=C(Nc1ccncn1)N1c2nc(-c3cccc(F)c3)ccc2N2CC[C@H]1C2] | A | A |
| 58 | 377 | 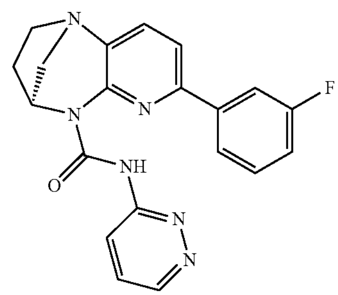 [SMILES: O=C(Nc1cccnn1)N1c2nc(-c3cccc(F)c3)ccc2N2CC[C@H]1C2] | B | A |
| 59 | 394 | 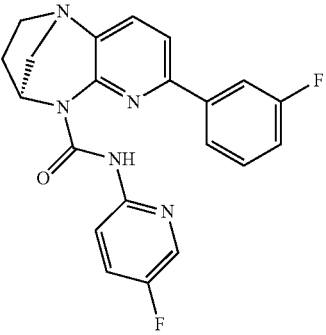 [SMILES: O=C(Nc1ccc(F)cn1)N1c2nc(-c3cccc(F)c3)ccc2N2CC[C@H]1C2] | A | A |
| 60 | 407 | 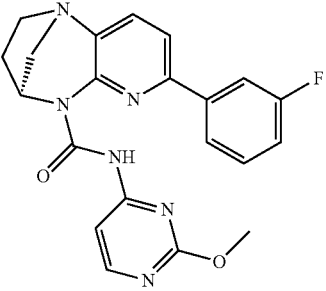 [SMILES: COc1nccc(NC(=O)N2c3nc(-c4cccc(F)c4)ccc3N3CC[C@H]2C3)n1] | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 61 | 440 | 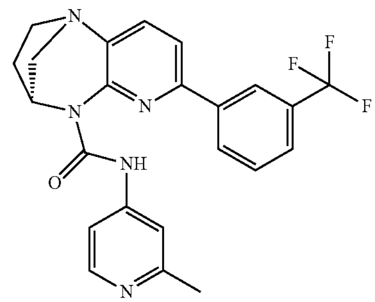 [SMILES: Cc1cc(NC(=O)N2c3nc(-c4cccc(C(F)(F)F)c4)ccc3N3CC[C@H]2C3)ccn1] | A | A |
| 62 | 390 | 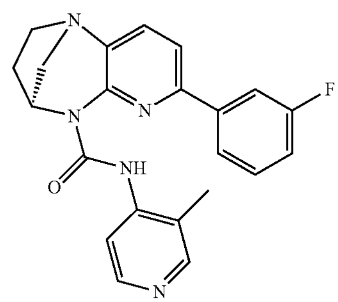 [SMILES: Cc1cnccc1NC(=O)N1c2nc(-c3cccc(F)c3)ccc2N2CC[C@H]1C2] | B | A |
| 63 | 483 | 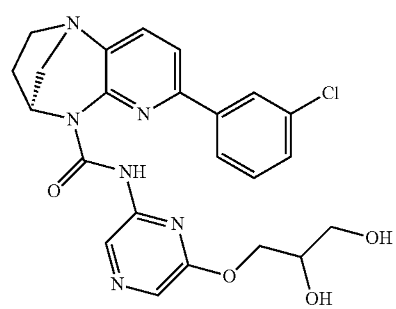 [SMILES: O=C(Nc1cncc(OCC(O)CO)n1)N1c2nc(-c3cccc(Cl)c3)ccc2N2CC[C@H]1C2] | A | A |
| 64 | 481 | 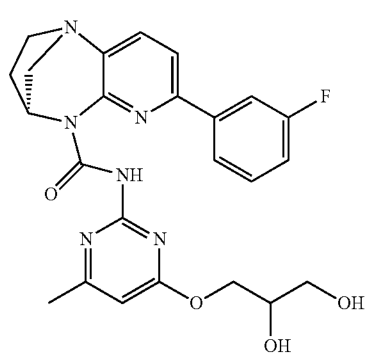 [SMILES: Cc1cc(OCC(O)CO)nc(NC(=O)N2c3nc(-c4cccc(F)c4)ccc3N3CC[C@H]2C3)n1] | B | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 65 | 467 | 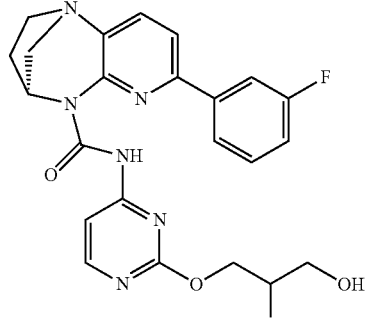 | B | A |
| 66 | 482 | 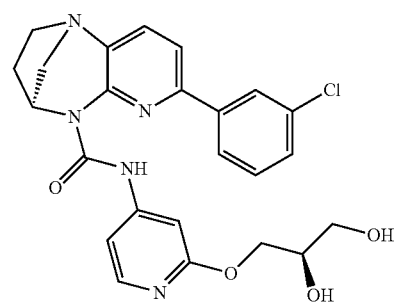 [SMILES: O=C(Nc1ccnc(OC[C@H](O)CO)c1)N1c2nc(-c3cccc(Cl)c3)ccc2N2CC[C@H]1C2] | A | A |
| 67 | 509 | 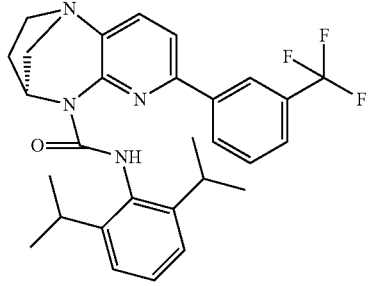 [SMILES: CC(C)c1cccc(C(C)C)c1NC(=O)N1c2nc(-c3cccc(C(F)(F)F)c3)ccc2N2CC[C@H]1C2] | C | B |
| 68 (1) | 492 | 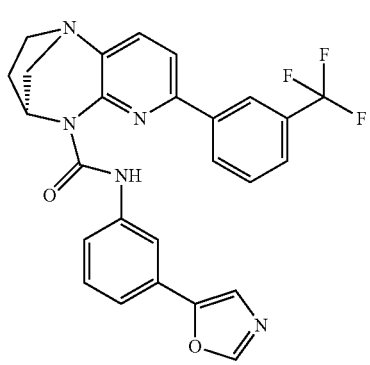 [SMILES: O=C(Nc1cccc(-c2cnco2)c1)N1c2nc(-c3cccc(C(F)(F)F)c3)ccc2N2CC[C@H]1C2] | A | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 69 | 467 | 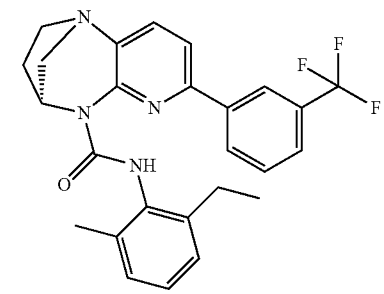 [SMILES: CCc1cccc(C)c1NC(=O)N1c2nc(-c3cccc(C(F)(F)F)c3)ccc2N2CC[C@H]1C2] | C | B |
| 70 | 481 | 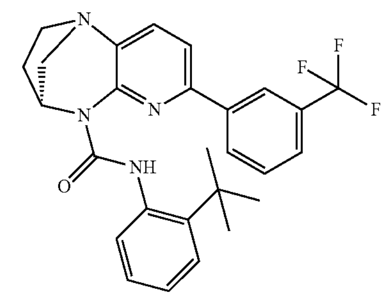 [SMILES: CC(C)(C)c1ccccc1NC(=O)N1c2nc(-c3cccc(C(F)(F)F)c3)ccc2N2CC[C@H]1C2] | C | B |
| 71 | 481 | 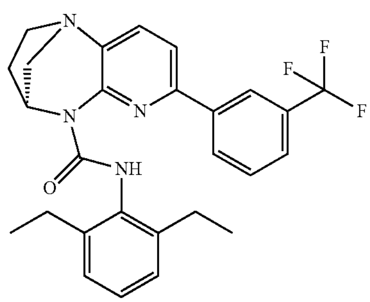 [SMILES: CCc1cccc(CC)c1NC(=O)N1c2nc(-c3cccc(C(F)(F)F)c3)ccc2N2CC[C@H]1C2] | C | B |
| 72 | 488 | 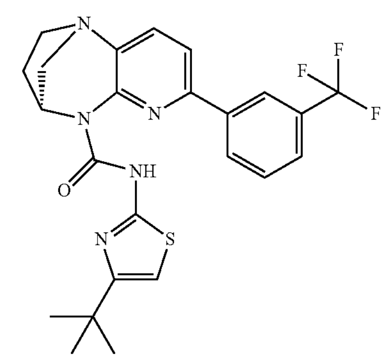 [SMILES: CC(C)(C)c1csc(NC(=O)N2c3nc(-c4cccc(C(F)(F)F)c4)ccc3N3CC[C@H]2C3)n1] | B | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 73 | 466 | 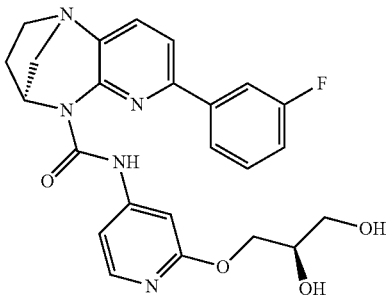 | B | A |
| 74 | 394 | 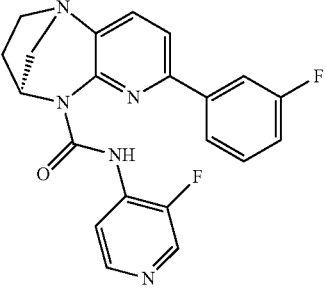 [SMILES: O=C(Nc1ccncc1F)N1c2nc(-c3cccc(F)c3)ccc2N2CC[C@H]1C2] | B | A |
| 75 | 488 | 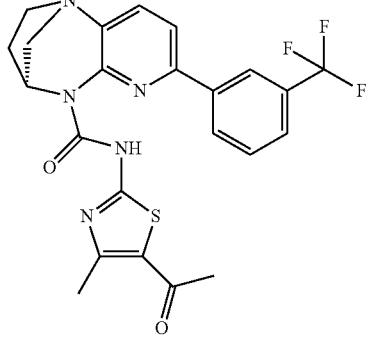 | A | A |
| 76 (8) | 491 | 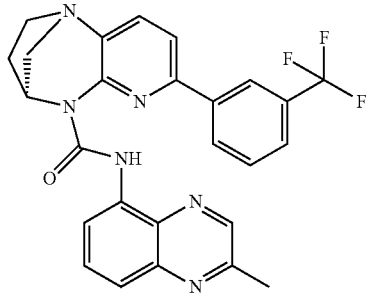 [SMILES: Cc1cnc2c(NC(=O)N3c4nc(-c5cccc(C(F)(F)F)c5)ccc4N4CC[C@H]3C4)cccc2n1] | A | A |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 77 | 470 | 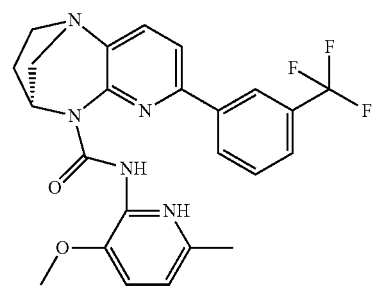 [SMILES: COc1ccc(C)nc1NC(=O)N1c2nc(-c3cccc(C(F)(F)F)c3)ccc2N2CC[C@H]1C2] | B | A |
| 78 | 503 | 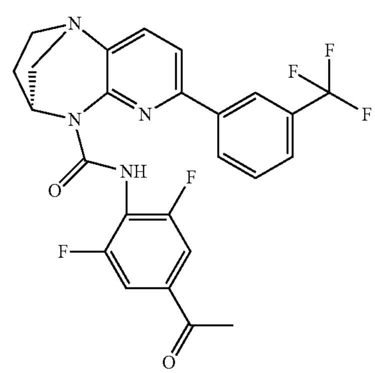 [SMILES: CC(=O)c1cc(F)c(NC(=O)N2c3nc(-c4cccc(C(F)(F)F)c4)ccc3N3CC[C@H]2C3)c(F)c1] | B | A |
| 79 | 517 | 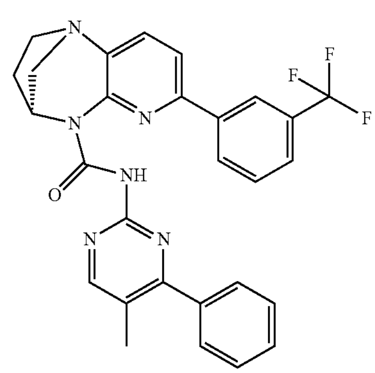 [SMILES: Cc1cnc(NC(=O)N2c3nc(-c4cccc(C(F)(F)F)c4)ccc3N3CC[C@H]2C3)nc1-c1ccccc1] | B | A |
| 80 | 486 | 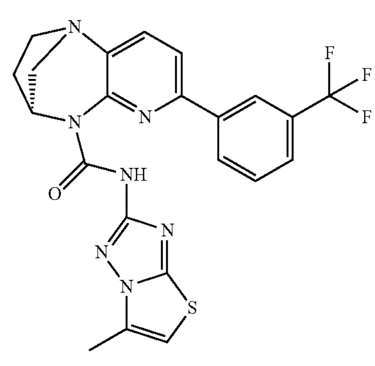 [SMILES: Cc1csc2nc(NC(=O)N3c4nc(-c5cccc(C(F)(F)F)c5)ccc4N4CC[C@H]3C4)nn12] | A | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 81 (9) | 493 | 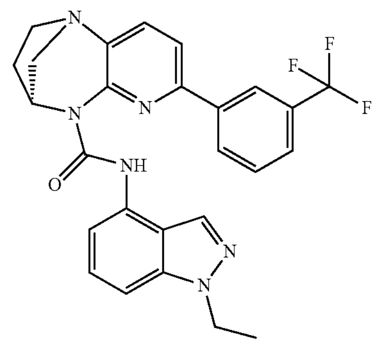 [SMILES: CCn1ncc2c(NC(=O)N3c4nc(-c5cccc(C(F)(F)F)c5)ccc4N4CC[C@H]3C4)cccc21] | A | A |
| 82 | 443 | 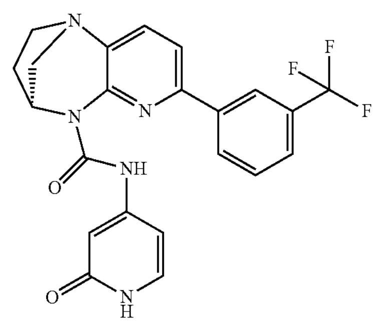 [SMILES: O=C(Nc1cc[nH]c(=O)c1)N1c2nc(-c3cccc(C(F)(F)F)c3)ccc2N2CC[C@H]1C2] | B | A |
| 83 | 477 | 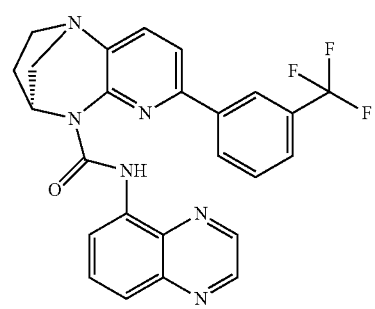 [SMILES: O=C(Nc1cccc2nccnc12)N1c2nc(-c3cccc(C(F)(F)F)c3)ccc2N2CC[C@H]1C2] | A | A |
| 84 | 490 | 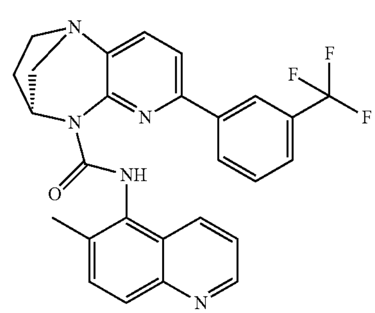 [SMILES: Cc1ccc2ncccc2c1NC(=O)N1c2nc(-c3cccc(C(F)(F)F)c3)ccc2N2CC[C@H]1C2] | C | B |

TABLE 1-continued
Compounds of Formula (I).
| Compound No. | [M + H]+$_{[calc]}$ | Structure | Tyrp AVG EC$_{1.5}$ (μM) | Tyrp % Fold Act |
|---|---|---|---|---|
| 85 | 442 | 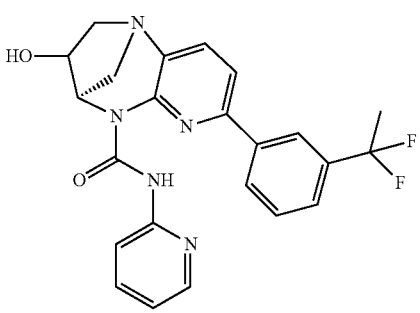 [SMILES: CC(F)(F)c1cccc(-c2ccc3c(n2)N(C(=O)Nc2ccccn2)[C@@H]2CN3CC2O)c1] | B | A |
| 86 | 491 | 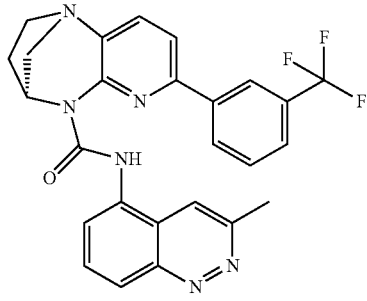 [SMILES: Cc1cc2c(NC(=O)N3c4nc(-c5cccc(C(F)(F)F)c5)ccc4N4CC[C@H]3C4)cccc2nn1] | A | A |
| 87 | 479 | 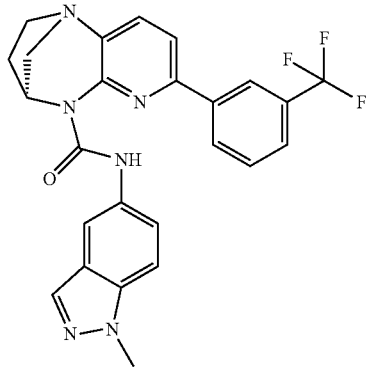 [SMILES: Cn1ncc2cc(NC(=O)N3c4nc(-c5cccc(C(F)(F)F)c5)ccc4N4CC[C@H]3C4)ccc21] | A | A |
| 90 | 482 | 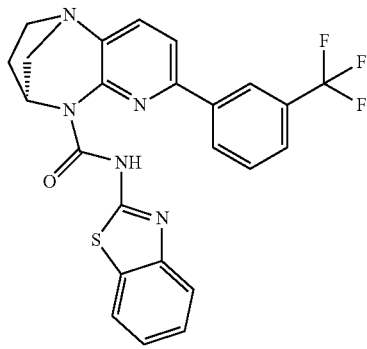 [SMILES: O=C(Nc1nc2ccccc2s1)N1c2nc(-c3cccc(C(F)(F)F)c3)ccc2N2CC[C@H]1C2] | A | A |

TABLE 1-continued

Compounds of Formula (I).

| Compound No. | [M + H]+$_{[calc]}$ | Structure | Tyrp AVG EC$_{1.5}$ (µM) | Tyrp % Fold Act |
|---|---|---|---|---|
| 91 | 481 | 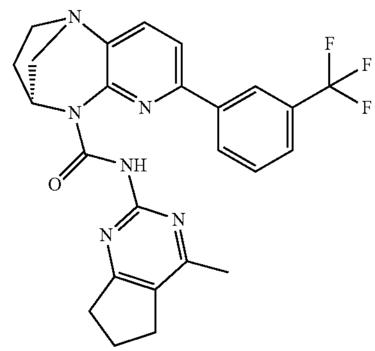 [SMILES: Cc1nc(NC(=O)N2c3nc(-c4cccc(C(F)(F)F)c4)ccc3N3CC[C@H]2C3)nc2c1CCC2] | B | A |
| 92 | 443 | 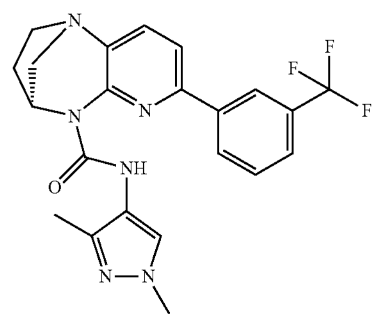 [SMILES: Cc1nn(C)cc1NC(=O)N1c2nc(-c3cccc(C(F)(F)F)c3)ccc2N2CC[C@H]1C2] | B | A |
| 93 | 481 | 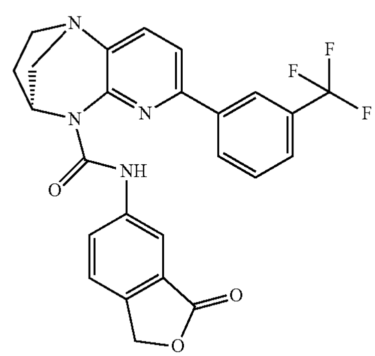 [SMILES: O=C1OCc2ccc(NC(=O)N3c4nc(-c5cccc(C(F)(F)F)c5)ccc4N4CC[C@H]3C4)cc21] | A | A |
| 94 | 509 | 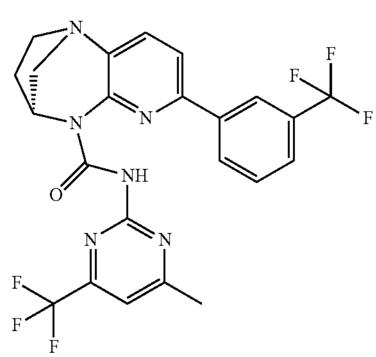 [SMILES: Cc1cc(C(F)(F)F)nc(NC(=O)N2c3nc(-c4cccc(C(F)(F)F)c4)ccc3N3CC[C@H]2C3)n1] | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 95 | 497 | 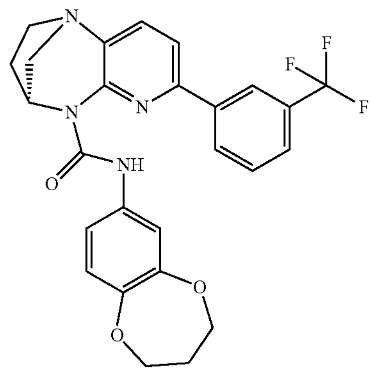 [SMILES: O=C(Nc1ccc2c(c1)OCCCO2)N1c2nc(-c3cccc(C(F)(F)F)c3)ccc2N2CC[C@H]1C2] | A | A |
| 96 | 460 | 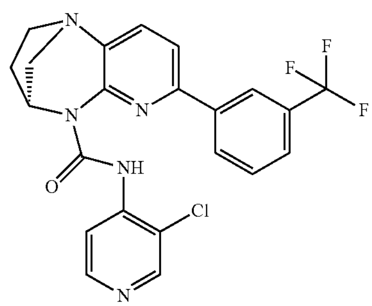 [SMILES: O=C(Nc1ccncc1Cl)N1c2nc(-c3cccc(C(F)(F)F)c3)ccc2N2CC[C@H]1C2] | B | A |
| 98 | 433 | 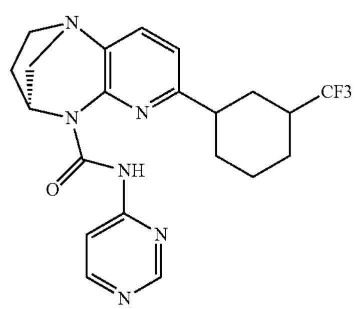 [SMILES: O=C(Nc1ccncn1)N1c2nc(C3CCCC(C(F)(F)F)C3)ccc2N2CC[C@H]1C2] | B | A |
| 99 | 432 | 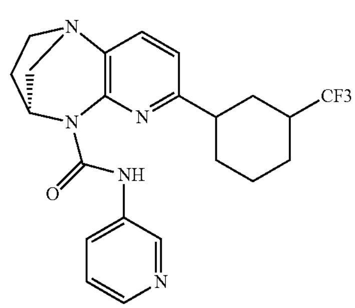 [SMILES: O=C(Nc1cccnc1)N1c2nc(C3CCCC(C(F)(F)F)C3)ccc2N2CC[C@H]1C2] | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 100 | 446 | 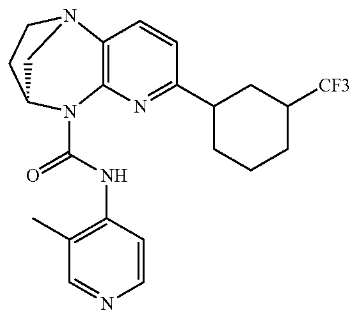 [SMILES: Cc1cnccc1NC(=O)N1c2nc(C3CCCC(C(F)(F)F)C3)ccc2N2CC[C@H]1C2] | B | A |
| 101 | 393 | 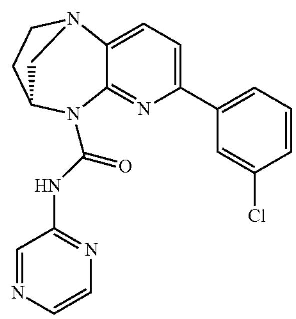 [SMILES: O=C(Nc1cnccn1)N1c2nc(-c3cccc(Cl)c3)ccc2N2CC[C@H]1C2] | A | A |
| 102 | 426 | 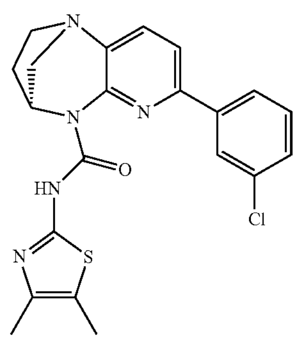 [SMILES: Cc1nc(NC(=O)N2c3nc(-c4cccc(Cl)c4)ccc3N3CC[C@H]2C3)sc1C] | A | A |
| 103 | 453 | 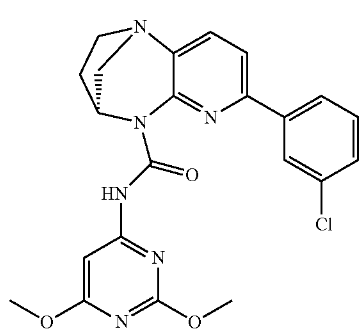 [SMILES: COc1cc(NC(=O)N2c3nc(-c4cccc(Cl)c4)ccc3N3CC[C@H]2C3)nc(OC)n1] | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 104 | 423 | 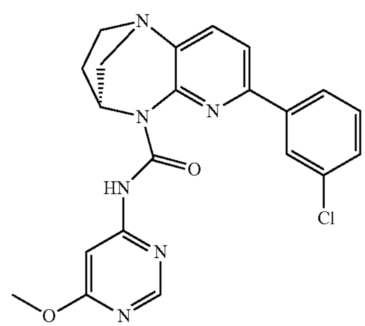 [SMILES: COc1cc(NC(=O)N2c3nc(-c4cccc(Cl)c4)ccc3N3CC[C@H]2C3)ncn1] | B | A |
| 105 | 420 | 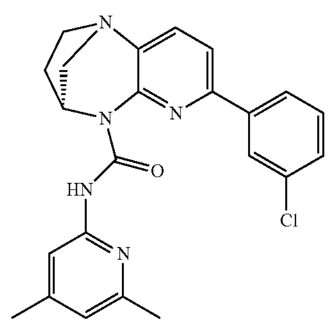 [SMILES: Cc1cc(C)nc(NC(=O)N2c3nc(-c4cccc(Cl)c4)ccc3N3CC[C@H]2C3)c1] | B | A |
| 106 | 406 | 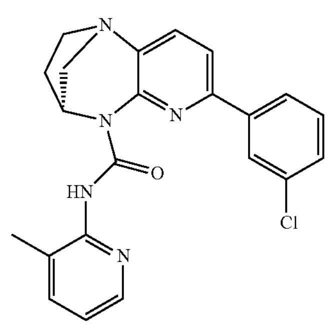 [SMILES: Cc1cccnc1NC(=O)N1c2nc(-c3cccc(Cl)c3)ccc2N2CC[C@H]1C2] | C | A |
| 107 | 392 | 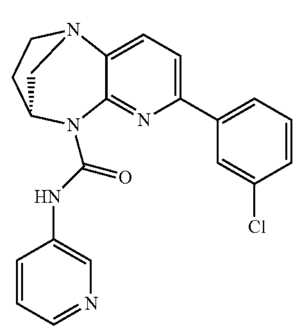 [SMILES: O=C(Nc1cccnc1)N1c2nc(-c3cccc(Cl)c3)ccc2N2CC[C@H]1C2] | A | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 108 | 395 | 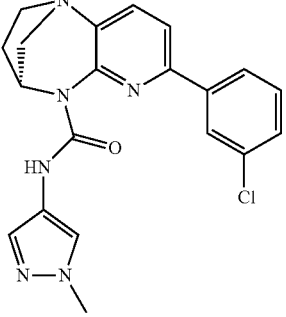 | B | A |
| 109 | 395 | 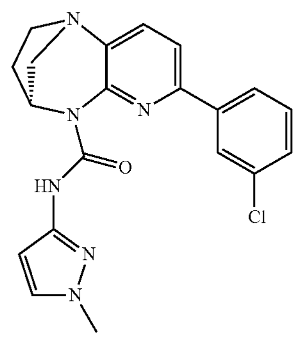 [SMILES: Cn1ccc(NC(=O)N2c3nc(-c4cccc(Cl)c4)ccc3N3CC[C@H]2C3)n1] | B | A |
| 110 | 393 | 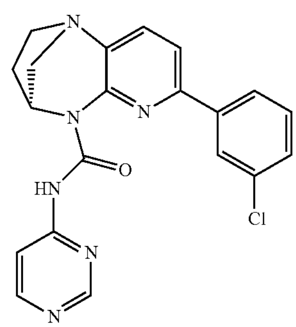 [SMILES: O=C(Nc1ccncn1)N1c2nc(-c3cccc(Cl)c3)ccc2N2CC[C@H]1C2] | A | A |
| 114 | 442 | 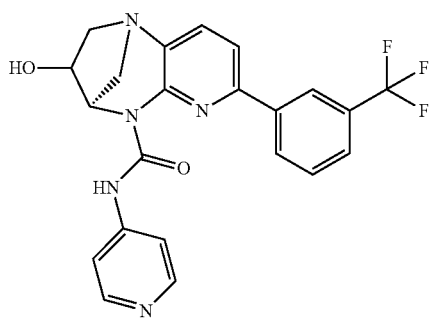 [SMILES: O=C(Nc1ccncc1)N1c2nc(-c3cccc(C(F)(F)F)c3)ccc2N2CC(O)[C@H]1C2] | B | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 118 | 445 | 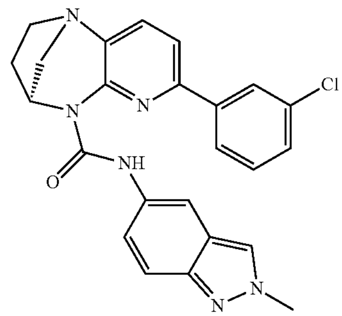 [SMILES: Cn1cc2cc(NC(=O)N3c4nc(-c5cccc(Cl)c5)ccc4N4CC[C@H]3C4)ccc2n1] | A | A |
| 119 | 410 | 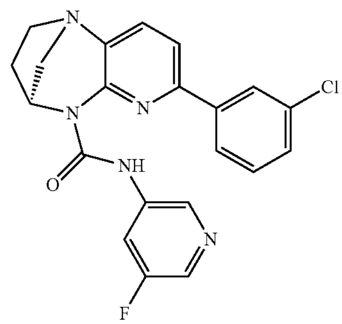 [SMILES: O=C(Nc1cncc(F)c1)N1c2nc(-c3cccc(Cl)c3)ccc2N2CC[C@H]1C2] | A | A |
| 120 | 393 | 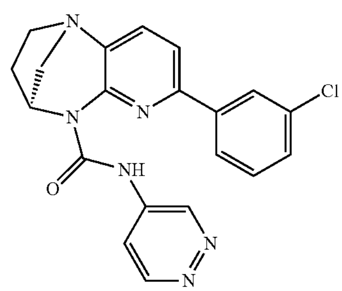 [SMILES: O=C(Nc1ccnnc1)N1c2nc(-c3cccc(Cl)c3)ccc2N2CC[C@H]1C2] | A | A |
| 121 | 423 | 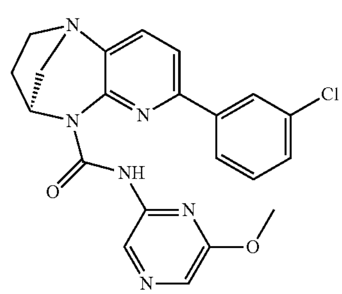 [SMILES: COc1cncc(NC(=O)N2c3nc(-c4cccc(Cl)c4)ccc3N3CC[C@H]2C3)n1] | A | A |

TABLE 1-continued
Compounds of Formula (I).
| Compound No. | [M + H]+[calc] | Structure | Tyrp AVG EC1.5 (µM) | Tyrp % Fold Act |
|---|---|---|---|---|
| 122 | 392 | 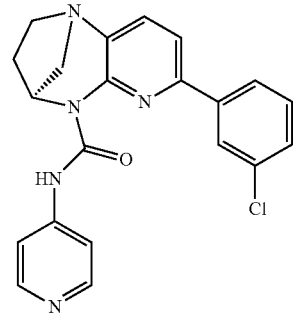 [SMILES: O=C(Nc1ccncc1)N1c2nc(-c3cccc(Cl)c3)ccc2N2CC[C@H]1C2] | A | A |
| 123 | 444 | 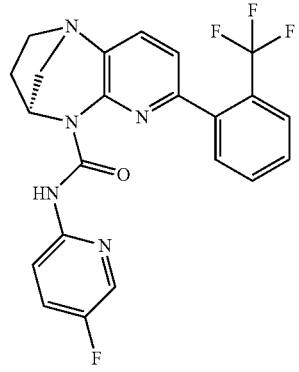 [SMILES: O=C(Nc1ccc(F)cn1)N1c2nc(-c3ccccc3C(F)(F)F)ccc2N2CC[C@H]1C2] | C | B |
| 124 | 423 | 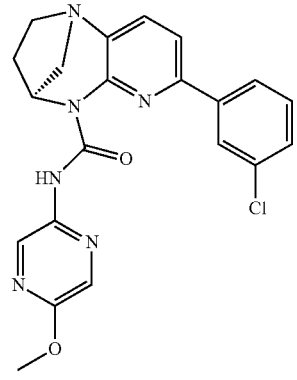 [SMILES: COc1cnc(NC(=O)N2c3nc(-c4cccc(Cl)c4)ccc3N3CC[C@H]2C3)cn1] | B | A |
| 128 | 445 | 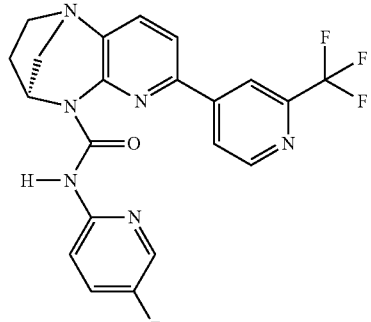 | A | A |

TABLE 1-continued
Compounds of Formula (I).
| Compound No. | [M + H]+<sub>[calc]</sub> | Structure | Tyrp AVG EC<sub>1.5</sub> (μM) | Tyrp % Fold Act |
|---|---|---|---|---|
| 129 | 460 | 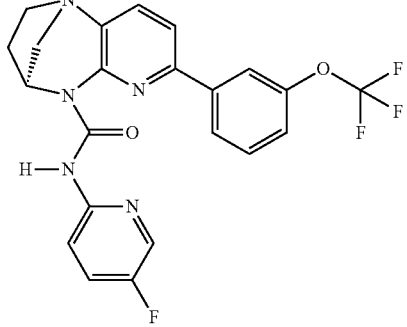 | A | A |
| 130 | 401 | 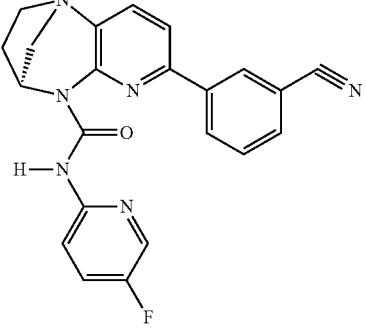 | A | A |
| 131 | 445 | 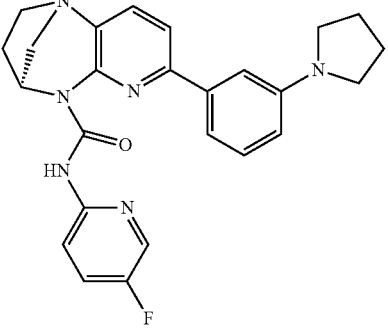 | B | A |
| 132 | 458 | 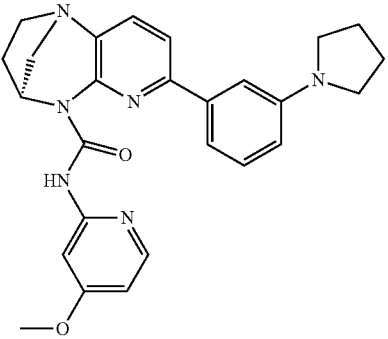 [SMILES: COc1ccnc(NC(=O)N2c3nc(-c4cccc(N5CCCC5)c4)ccc3N3CC[C@H]2C3)c1] | B | A |

TABLE 1-continued
Compounds of Formula (I).
| Compound No. | [M + H]+_{[calc]} | Structure | Tyrp AVG EC_{1.5} (μM) | Tyrp % Fold Act |
|---|---|---|---|---|
| 133 | 458 | 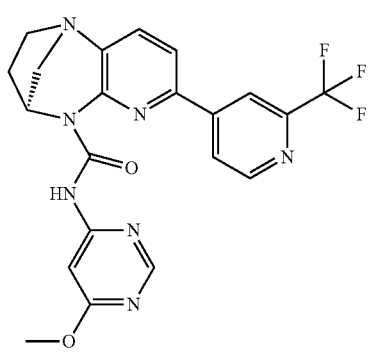 [SMILES: COc1cc(NC(=O)N2c3nc(-c4ccnc(C(F)(F)F)c4)ccc3N3CC[C@H]2C3)ncn1] | A | A |
| 134 | 457 | 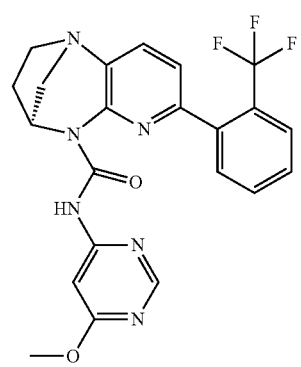 [SMILES: COc1cc(NC(=O)N2c3nc(-c4ccccc4C(F)(F)F)ccc3N3CC[C@H]2C3)ncn1] | C | B |
| 135 | 473 | 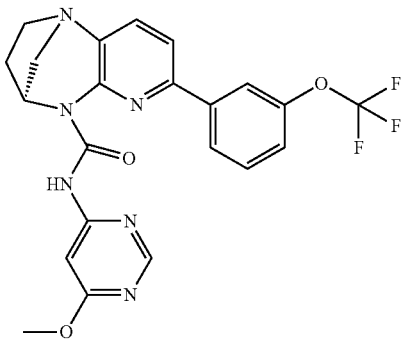 [SMILES: COc1cc(NC(=O)N2c3nc(-c4cccc(OC(F)(F)F)c4)ccc3N3CC[C@H]2C3)ncn1] | A | A |
| 136 | 427 | 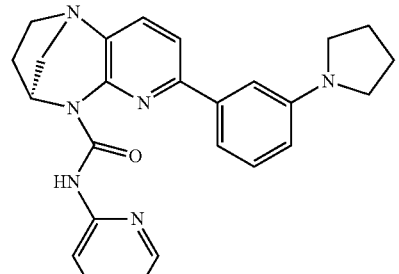 | A | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 137 | 426 | 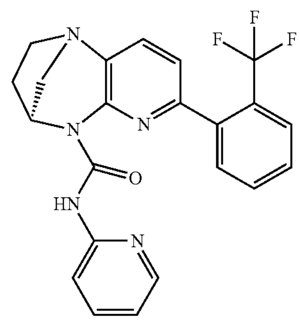 [SMILES: O=C(Nc1ccccn1)N1c2nc(-c3ccccc3C(F)(F)F)ccc2N2CC[C@H]1C2] | C | B |
| 138 | 442 | 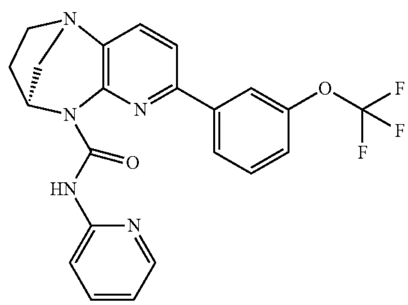 [SMILES: O=C(Nc1ccccn1)N1c2nc(-c3cccc(OC(F)(F)F)c3)ccc2N2CC[C@H]1C2] | A | A |
| 139 | 383 | 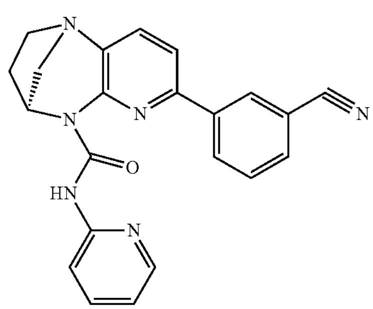 [SMILES: N#Cc1cccc(-c2ccc3c(n2)N(C(=O)Nc2ccccn2)[C@H]2CCN3C2)c1] | A | A |
| 140 | 414 | 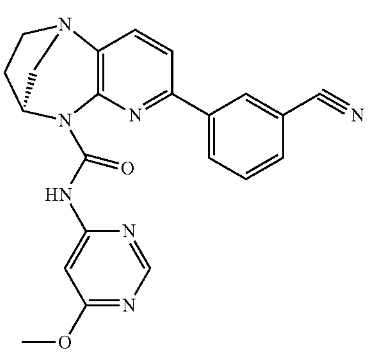 [SMILES: COc1cc(NC(=O)N2c3nc(-c4cccc(C#N)c4)ccc3N3CC[C@H]2C3)ncn1] | A | A |

TABLE 1-continued
| Compounds of Formula (I). | | | | |
|---|---|---|---|---|
| Compound No. | [M + H]+[calc] | Structure | Tyrp AVG EC1.5 (μM) | Tyrp % Fold Act |
| 141 | 424 | 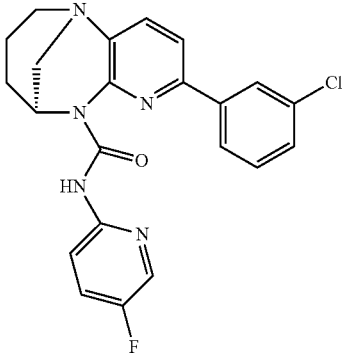 [SMILES: O=C(Nc1ccc(F)cn1)N1c2nc(-c3cccc(Cl)c3)ccc2N2CCC[C@H]1C2] | A | A |
| 142 | 427 | 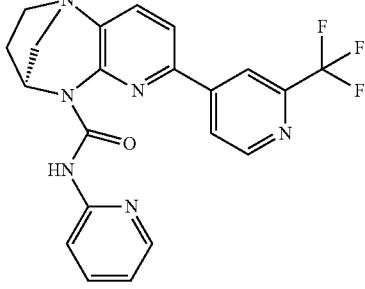 | A | A |
| 143 | 433 | 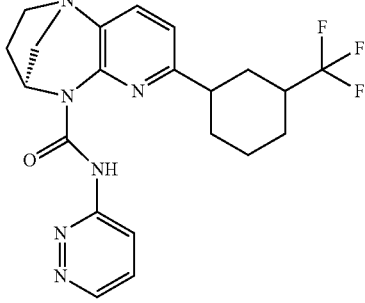 | B | A |
| 144 | 450 | 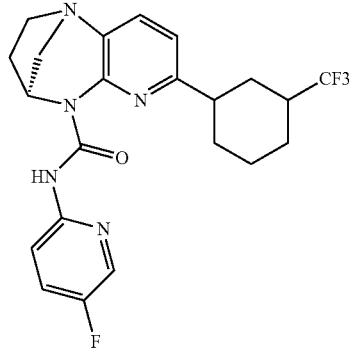 [SMILES: O=C(Nc1ccc(F)cn1)N1c2nc(C3CCCC(C(F)(F)F)C3)ccc2N2CC[C@H]1C2] | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 145 | 450 | 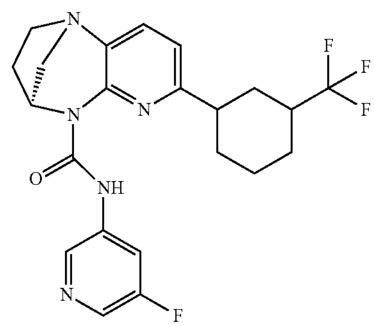 | A | A |
| 146 | 466 | 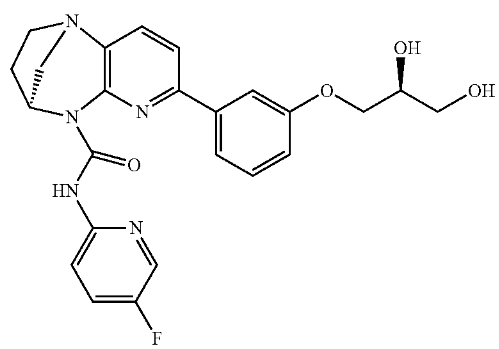 [SMILES: O=C(Nc1ccc(F)cn1)N1c2nc(-c3cccc(OC[C@@H](O)CO)c3)ccc2N2CC[C@H]1C2] | B | A |
| 147 | 401 | 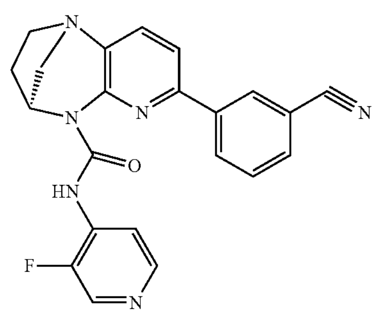 [SMILES: N#Cc1cccc(-c2ccc3c(n2)N(C(=O)Nc2ccncc2F)[C@H]2CCN3C2)c1] | B | A |
| 148 | 450 | 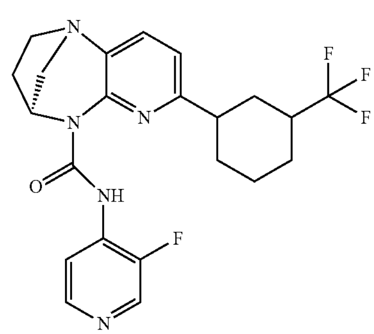 [SMILES: O=C(Nc1ccncc1F)N1c2nc(C3CCCC(C(F)(F)F)C3)ccc2N2CC[C@H]1C2] | B | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 149 | 466 | 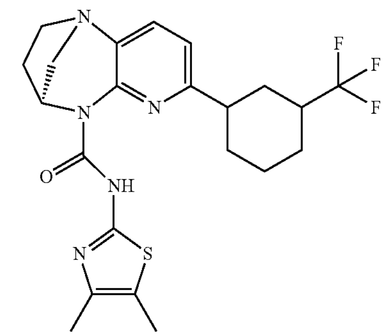 [SMILES: Cc1nc(NC(=O)N2c3nc(C4CCCC(C(F)(F)F)C4)ccc3N3CC[C@H]2C3)sc1C] | B | A |
| 150 | 445 | 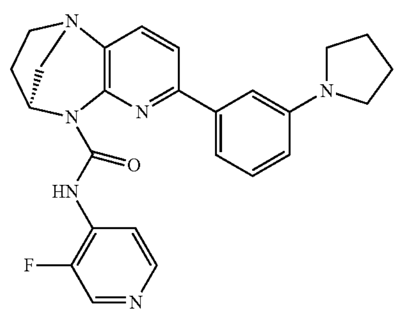 [SMILES: O=C(Nc1ccncc1F)N1c2nc(-c3cccc(N4CCCC4)c3)ccc2N2CC[C@H]1C2] | A | A |
| 151 | 445 | 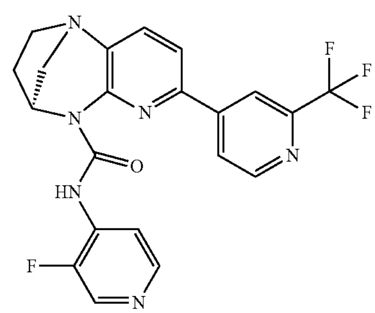 [SMILES: O=C(Nc1ccncc1F)N1c2nc(-c3ccnc(C(F)(F)F)c3)ccc2N2CC[C@H]1C2] | A | A |
| 152 | 444 | 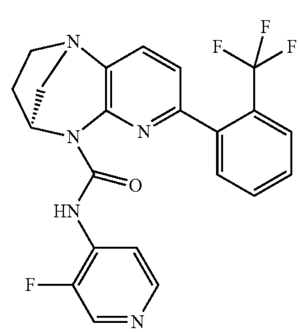 [SMILES: O=C(Nc1ccncc1F)N1c2nc(-c3ccccc3C(F)(F)F)ccc2N2CC[C@H]1C2] | C | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 153 | 460 | 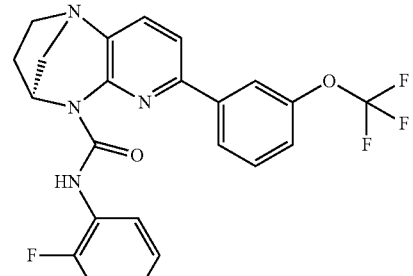 | A | A |
| 154 | 450 | 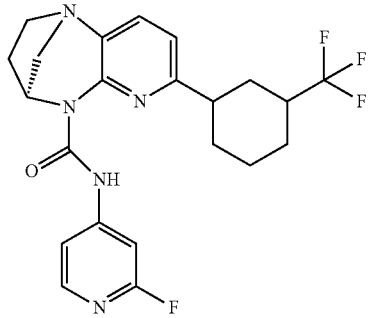 [SMILES: O=C(Nc1ccnc(F)c1)N1c2nc(C3CCCC(C(F)(F)F)C3)ccc2N2CC[C@H]1C2] | B | A |
| 155 | 448 | 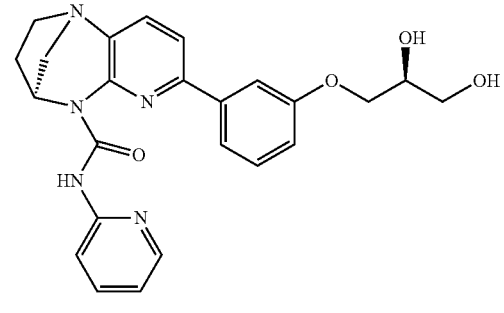 [SMILES: O=C(Nc1ccccn1)N1c2nc(-c3cccc(OC[C@@H](O)CO)c3)ccc2N2CC[C@H]1C2] | B | A |
| 156 | 479 | 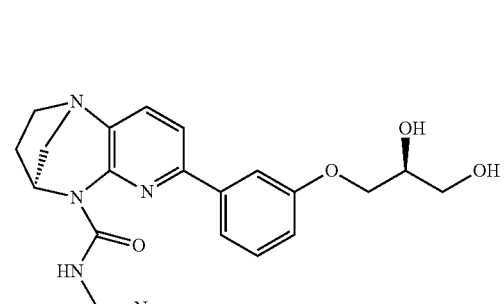 | A | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 157 | 466 | 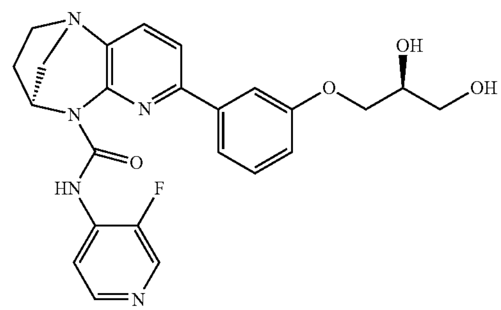 [SMILES: O=C(Nc1ccncc1F)N1c2nc(-c3cccc(OC[C@@H](O)CO)c3)ccc2N2CC[C@H]1C2] | B | A |
| 158 | 440 | 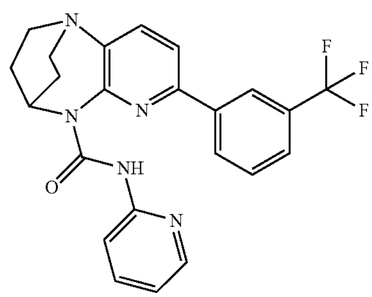 [SMILES: O=C(Nc1ccccn1)N1c2nc(-c3cccc(C(F)(F)F)c3)ccc2N2CCC1CC2] | B | A |
| 159 | 456 | 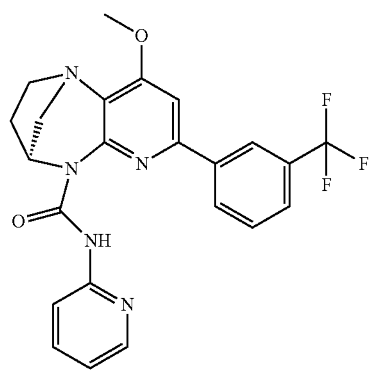 [SMILES: COc1cc(-c2cccc(C(F)(F)F)c2)nc2c1N1CC[C@@H](C1)N2C(=O)Nc1ccccn1] | A | A |
| 160 | 456 | 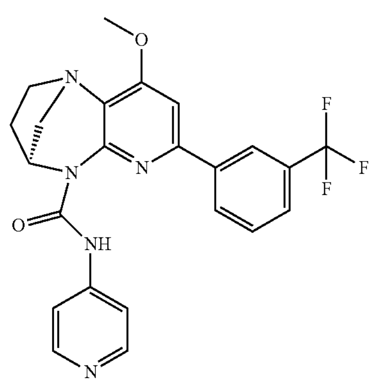 [SMILES: COc1cc(-c2cccc(C(F)(F)F)c2)nc2c1N1CC[C@@H](C1)N2C(=O)Nc1ccncc1] | A | A |

TABLE 1-continued
Compounds of Formula (I).
| Compound No. | [M + H]+[calc] | Structure | Tyrp AVG EC1.5 (μM) | Tyrp % Fold Act |
|---|---|---|---|---|
| 161 | 490 | 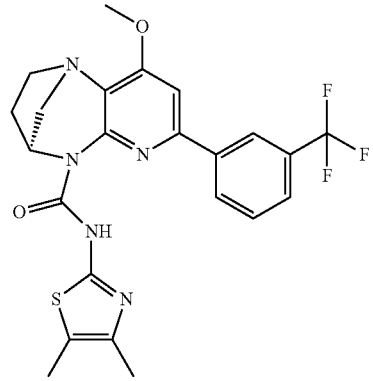 [SMILES: COc1cc(-c2cccc(C(F)(F)F)c2)nc2c1N1CC[C@@H](C1)N2C(=O)Nc1nc(C)c(C)s1] | A | A |
| 162 | 508 | 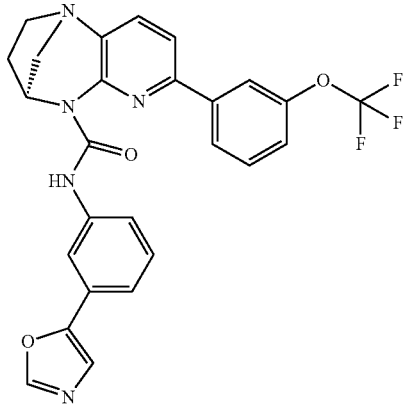 [SMILES: O=C(Nc1cccc(-c2cnco2)c1)N1c2nc(-c3cccc(OC(F)(F)F)c3)ccc2N2CC[C@H]1C2] | A | A |
| 163 | 442 | 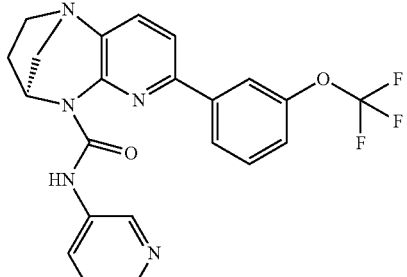 | A | A |
| 164 | 443 | 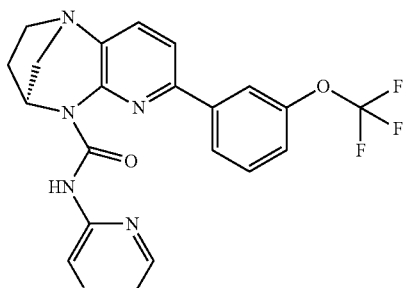 | A | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 165 | 476 | 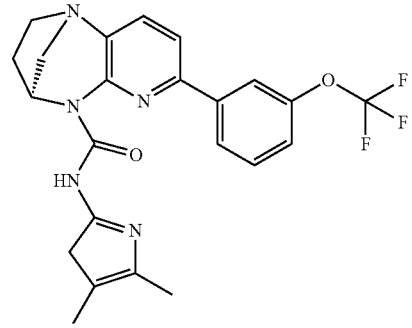 [SMILES: CC1=C(C)N=C(NC(=O)N2c3nc(-c4cccc(OC(F)(F)F)c4)ccc3N3CC[C@H]2C3)C1] | A | A |
| 166 | 443 | 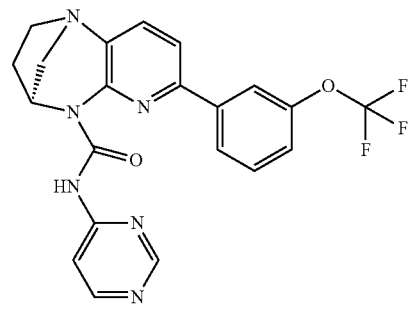 [SMILES: O=C(Nc1ccncn1)N1c2nc(-c3cccc(OC(F)(F)F)c3)ccc2N2CC[C@H]1C2] | A | A |
| 167 | 445 | 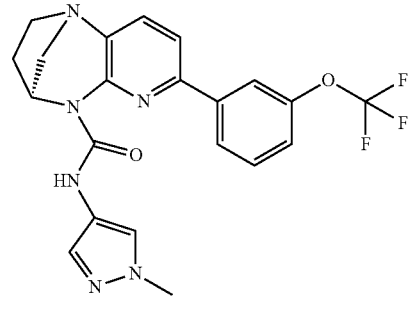 [SMILES: Cn1cc(NC(=O)N2c3nc(-c4cccc(OC(F)(F)F)c4)ccc3N3CC[C@H]2C3)cn1] | B | A |
| 168 | 471 | 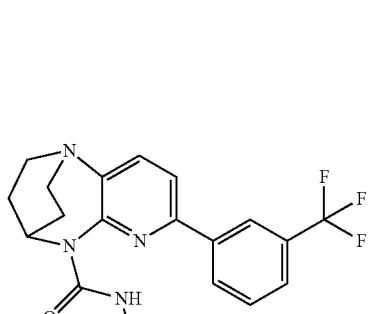 | A | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 169 | 471 | 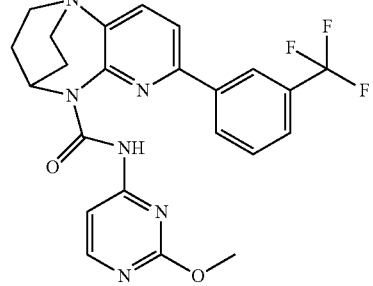 | B | A |
| 170 | 501 | 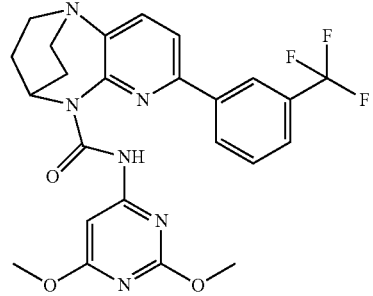 [SMILES: COc1cc(NC(=O)N2c3nc(-c4cccc(C(F)(F)F)c4)ccc3N3CCC2CC3)nc(OC)n1] | A | A |
| 171 | 441 | 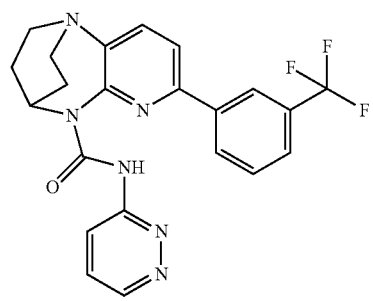 [SMILES: O=C(Nc1cccnn1)N1c2nc(-c3cccc(C(F)(F)F)c3)ccc2N2CCC1CC2] | B | A |
| 172 | 441 | 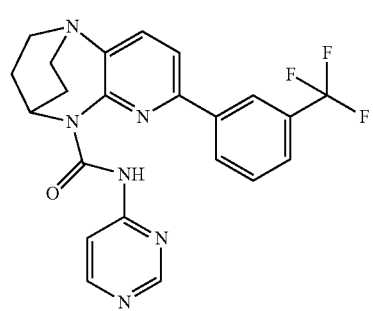 [SMILES: O=C(Nc1ccncn1)N1c2nc(-c3cccc(C(F)(F)F)c3)ccc2N2CCC1CC2] | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 173 | 474 | 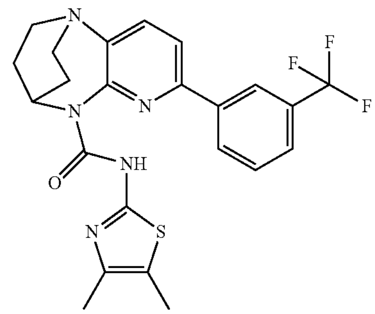 [SMILES: Cc1nc(NC(=O)N2c3nc(-c4cccc(C(F)(F)F)c4)ccc3N3CCC2CC3)sc1C] | A | A |
| 174 | 460 | 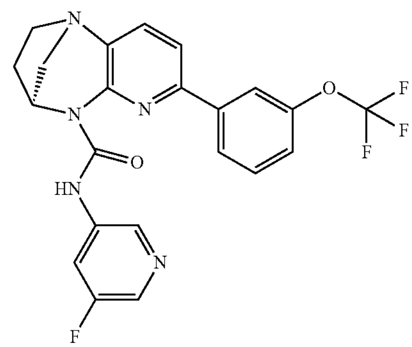 [SMILES: O=C(Nc1cncc(F)c1)N1c2nc(-c3cccc(OC(F)(F)F)c3)ccc2N2CC[C@H]1C2] | A | A |
| 175 | 495 | 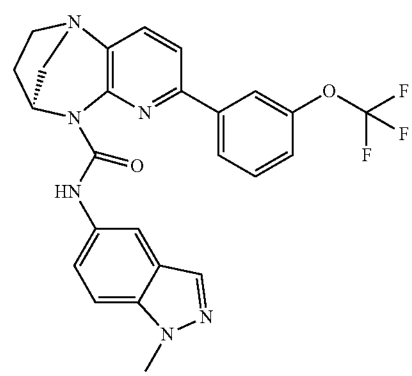 [SMILES: Cn1ncc2cc(NC(=O)N3c4nc(-c5cccc(OC(F)(F)F)c5)ccc4N4CC[C@H]3C4)ccc21] | A | A |
| 176 | 473 | 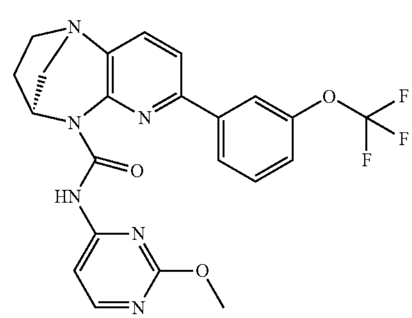 | A | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 177 | 445 | 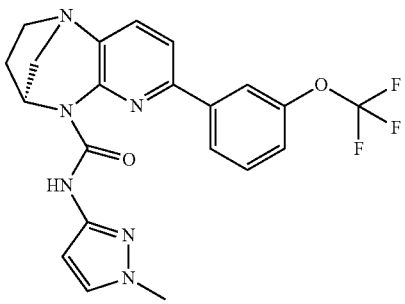 [SMILES: Cn1ccc(NC(=O)N2c3nc(-c4cccc(OC(F)(F)F)c4)ccc3N3CC[C@H]2C3)n1] | A | A |
| 178 | 449 | 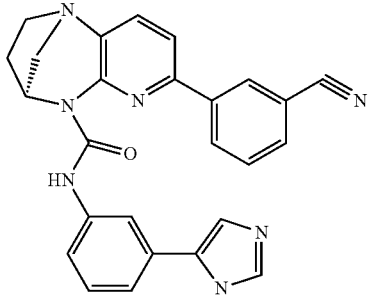 [SMILES: N#Cc1cccc(-c2ccc3c(n2)N(C(=O)Nc2cccc(-c4cnc[nH]4)c2)[C@H]2CCN3C2)c1] | A | A |
| 179 | 417 | 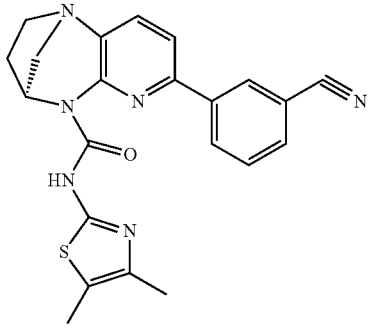 [SMILES: Cc1nc(NC(=O)N2c3nc(-c4cccc(C#N)c4)ccc3N3CC[C@H]2C3)sc1C] | A | A |
| 180 | 383 | 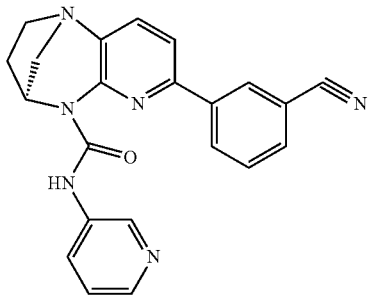 [SMILES: N#Cc1cccc(-c2ccc3c(n2)N(C(=O)Nc2cccnc2)[C@H]2CCN3C2)c1] | A | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 181 | 384 | 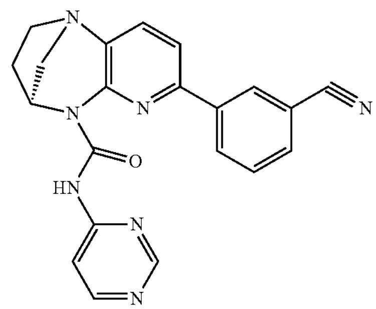 | A | A |
| 182 | 401 | 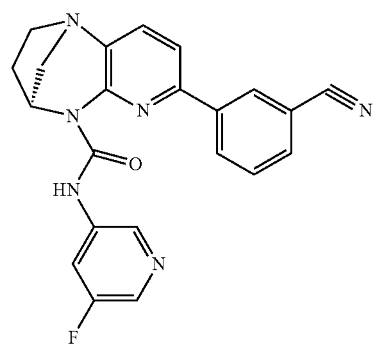 [SMILES: N#Cc1cccc(-c2ccc3c(n2)N(C(=O)Nc2cncc(F)c2)[C@H]2CCN3C2)c1] | A | A |
| 183 | 414 | 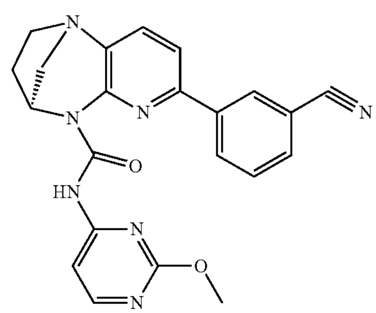 [SMILES: COc1nccc(NC(=O)N2c3nc(-c4cccc(C#N)c4)ccc3N3CC[C@H]2C3)n1] | B | A |
| 184 | 436 | 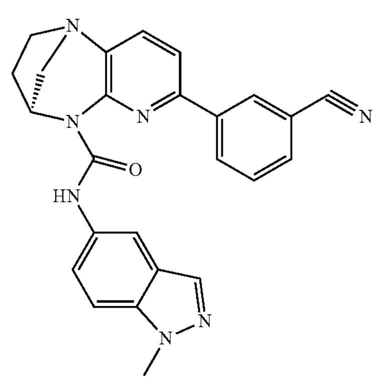 [SMILES: Cn1ncc2cc(NC(=O)N3c4nc(-c5cccc(C#N)c5)ccc4N4CC[C@H]3C4)ccc21] | A | A |

TABLE 1-continued

Compounds of Formula (I).

| Compound No. | [M + H]+[calc] | Structure | Tyrp AVG EC₁.₅ (μM) | Tyrp % Fold Act |
|---|---|---|---|---|
| 185 | 386 | 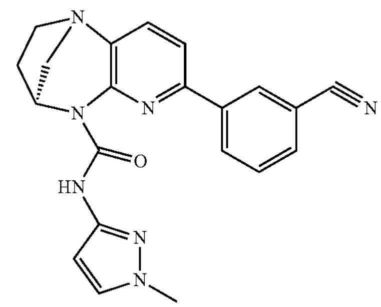 [SMILES: Cn1ccc(NC(=O)N2c3nc(-c4cccc(C#N)c4)ccc3N3CC[C@H]2C3)n1] | B | A |
| 186 | 386 | 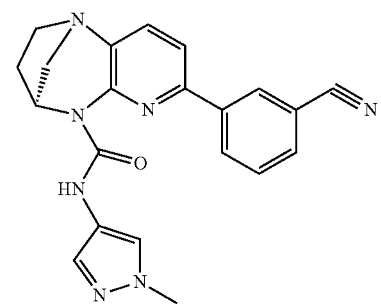 [SMILES: Cn1cc(NC(=O)N2c3nc(-c4cccc(C#N)c4)ccc3N3CC[C@H]2C3)cn1] | B | A |
| 187 | 461 | 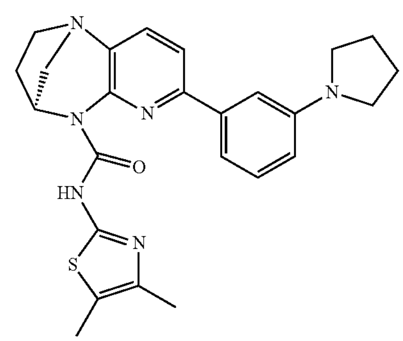 [SMILES: Cc1nc(NC(=O)N2c3nc(-c4cccc(N5CCCC5)c4)ccc3N3CC[C@H]2C3)sc1C] | B | A |
| 188 | 458 | 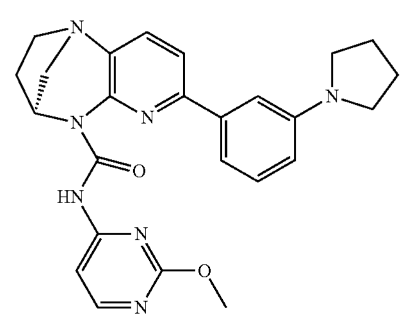 | B | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 189 | 384 | 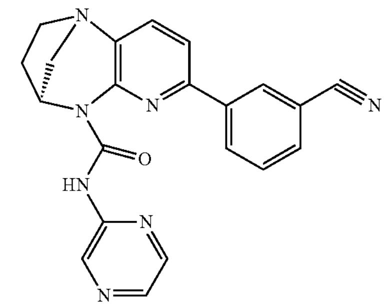 [SMILES: N#Cc1cccc(-c2ccc3c(n2)N(C(=O)Nc2cnccn2)[C@H]2CCN3C2)c1] | A | A |
| 190 | 414 | 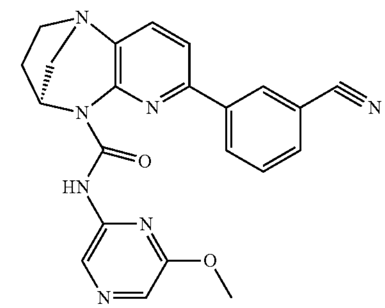 [SMILES: COc1cncc(NC(=O)N2c3nc(-c4cccc(C#N)c4)ccc3N3CC[C@H]2C3)n1] | B | A |
| 191 | 493 | 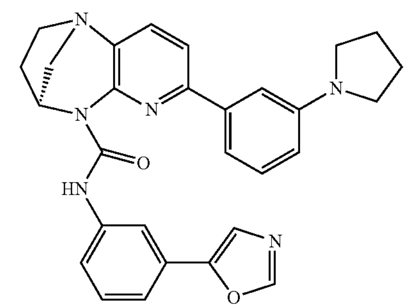 [SMILES: O=C(Nc1cccc(-c2cnco2)c1)N1c2nc(-c3cccc(N4CCCC4)c3)ccc2N2CC[C@H]1C2] | A | A |
| 192 | 427 | 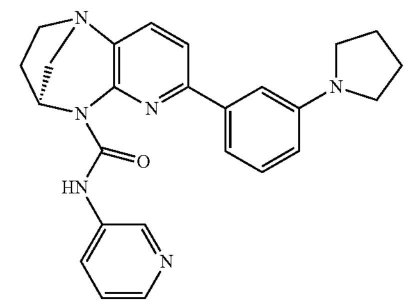 [SMILES: O=C(Nc1cccnc1)N1c2nc(-c3cccc(N4CCCC4)c3)ccc2N2CC[C@H]1C2] | B | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 193 | 428 | 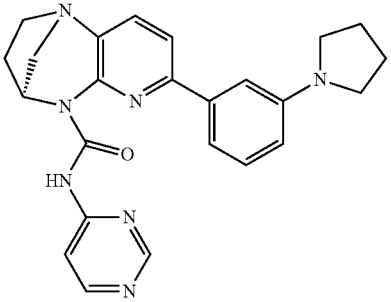 [SMILES: O=C(Nc1ccncn1)N1c2nc(-c3cccc(N4CCCC4)c3)ccc2N2CC[C@H]1C2] | B | A |
| 194 | 440 | 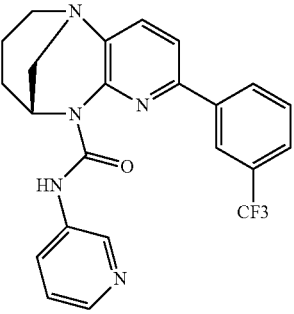 [SMILES: O=C(Nc1cccnc1)N1c2nc(-c3cccc(C(F)(F)F)c3)ccc2N2CCC[C@@H]1C2] | A | A |
| 195 | 440 | 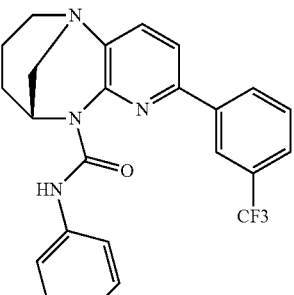 | B | A |
| 196 | 441 | 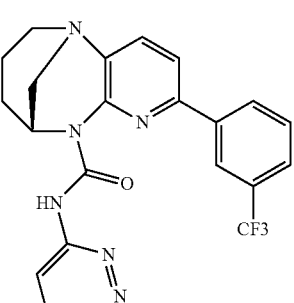 | B | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 197 | 473 | 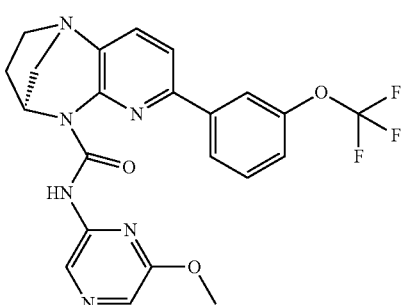 | A | A |
| 198 | 445 | 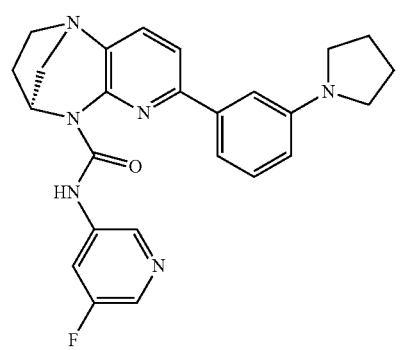 [SMILES: O=C(Nc1cncc(F)c1)N1c2nc(-c3cccc(N4CCCC4)c3)ccc2N2CC[C@H]1C2] | B | A |
| 199 | 430 | 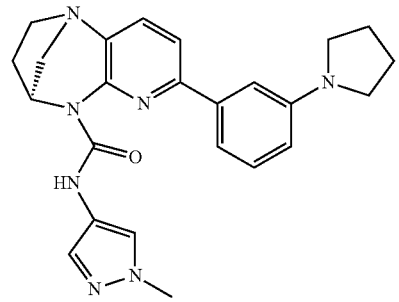 [SMILES: Cn1cc(NC(=O)N2c3nc(-c4cccc(N5CCCC5)c4)ccc3N3CC[C@H]2C3)cn1] | B | A |
| 200 | 440 | 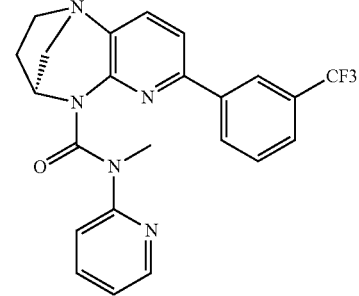 [SMILES: CN(C(=O)N1c2nc(-c3cccc(C(F)(F)F)c3)ccc2N2CC[C@H]1C2)c1ccccn1] | C | B |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 201 | 460 | 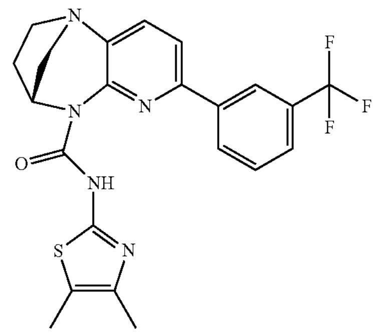 [SMILES: Cc1nc(NC(=O)N2c3nc(-c4cccc(C(F)(F)F)c4)ccc3N3CC[C@@H]2C3)sc1C] | B | A |
| 202 | 427 | 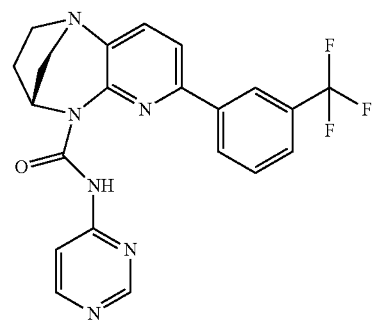 [SMILES: O=C(Nc1ccncn1)N1c2nc(-c3cccc(C(F)(F)F)c3)ccc2N2CC[C@@H]1C2] | B | A |
| 203 | 444 | 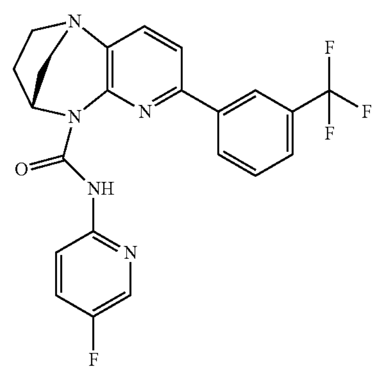 [SMILES: O=C(Nc1ccc(F)cn1)N1c2nc(-c3cccc(C(F)(F)F)c3)ccc2N2CC[C@@H]1C2] | B | A |
| 204 | 410 | 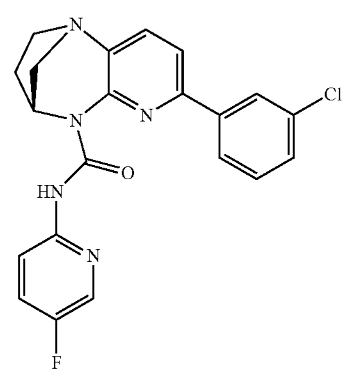 [SMILES: O=C(Nc1ccc(F)cn1)N1c2nc(-c3cccc(Cl)c3)ccc2N2CC[C@@H]1C2] | B | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 205 | 406 | 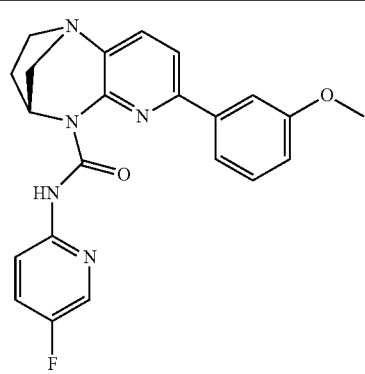 | B | A |
| 206 | 428 | 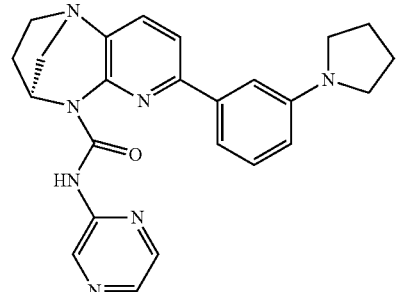 | B | A |
| 207 | 480 | 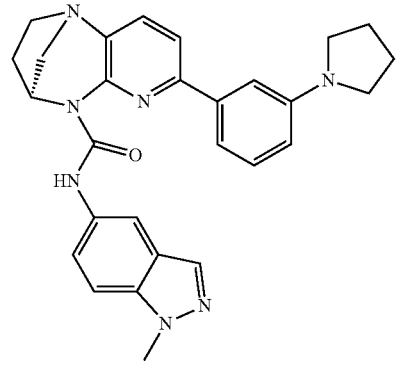 [SMILES: Cn1ncc2cc(NC(=O)N3c4nc(-c5cccc(N6CCCC6)c5)ccc4N4CC[C@H]3C4)ccc21] | A | A |
| 208 | 430 | 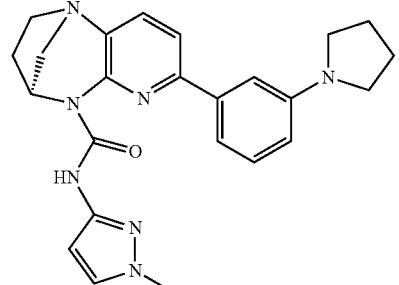 | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 209 | 428 | 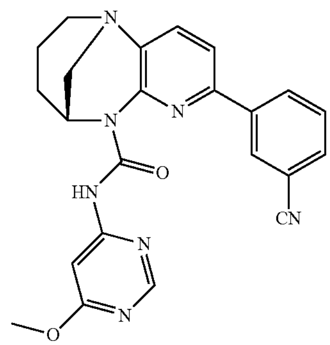 | C | B |
| 210 | 397 | 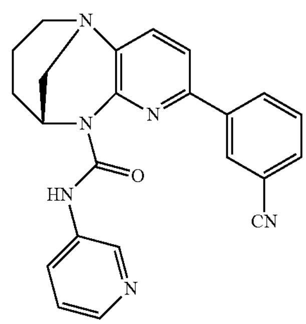 | B | A |
| 211 | 434 | 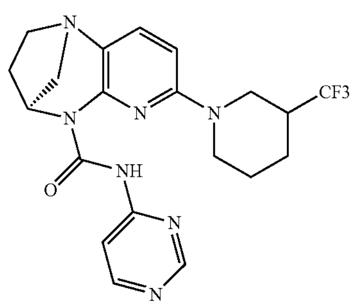 [SMILES: O=C(Nc1ccncn1)N1c2nc(N3CCCC(C(F)(F)F)C3)ccc2N2CC[C@H]1C2] | B | A |
| 212 | 499 | 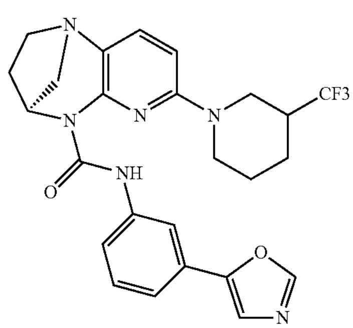 [SMILES: O=C(Nc1cccc(-c2cnco2)c1)N1c2nc(N3CCCC(C(F)(F)F)C3)ccc2N2CC[C@H]1C2] | A | A |

TABLE 1-continued

Compounds of Formula (I).

| Compound No. | [M + H]+<sub>[calc]</sub> | Structure | Tyrp AVG EC<sub>1.5</sub> (µM) | Tyrp % Fold Act |
|---|---|---|---|---|
| 213 | 461 | 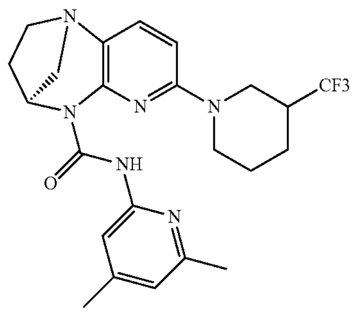 [SMILES: Cc1cc(C)nc(NC(=O)N2c3nc(N4CCCC(C(F)(F)F)C4)ccc3N3CC[C@H]2C3)c1] | B | A |
| 214 | 453 | 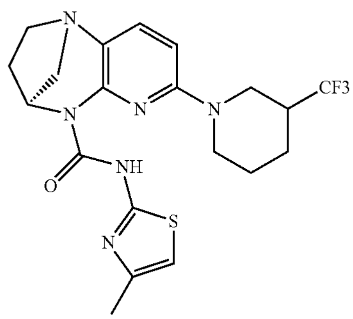 [SMILES: Cc1csc(NC(=O)N2c3nc(N4CCCC(C(F)(F)F)C4)ccc3N3CC[C@H]2C3)n1] | A | A |
| 215 | 467 | 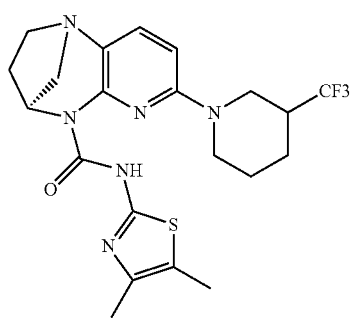 [SMILES: Cc1nc(NC(=O)N2c3nc(N4CCCC(C(F)(F)F)C4)ccc3N3CC[C@H]2C3)sc1C] | B | A |
| 216 | 476 | 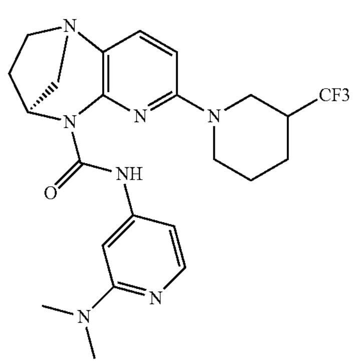 [SMILES: CN(C)c1cc(NC(=O)N2c3nc(N4CCCC(C(F)(F)F)C4)ccc3N3CC[C@H]2C3)ccn1] | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 217 | 477 | 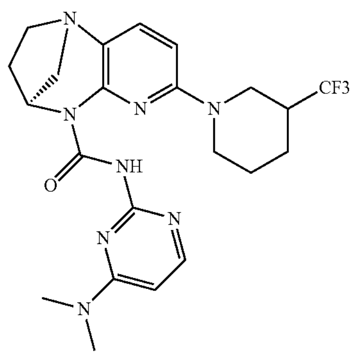 [SMILES: CN(C)c1ccnc(NC(=O)N2c3nc(N4CCCC(C(F)(F)F)C4)ccc3N3CC[C@H]2C3)n1] | B | A |
| 218 | 410 | 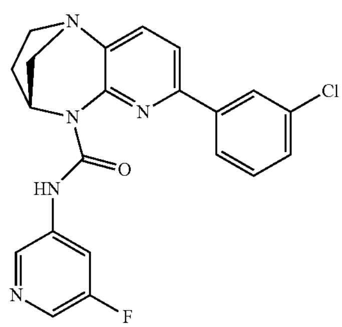 [SMILES: O=C(Nc1cncc(F)c1)N1c2nc(-c3cccc(Cl)c3)ccc2N2CC[C@@H]1C2] | A | A |
| 219 | 388 | 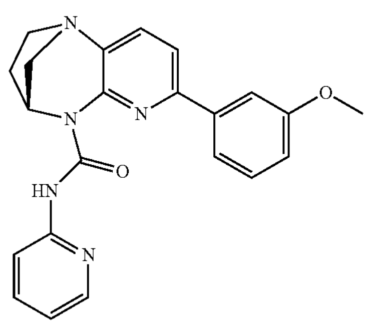 [SMILES: COc1cccc(-c2ccc3c(n2)N(C(=O)Nc2ccccn2)[C@@H]2CCN3C2)c1] | B | A |
| 220 | 373 | 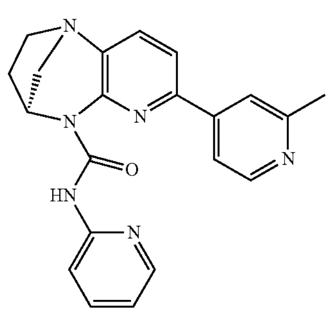 [SMILES: Cc1cc(-c2ccc3c(n2)N(C(=O)Nc2ccccn2)[C@H]2CCN3C2)ccn1] | A | A |

TABLE 1-continued
Compounds of Formula (I).
| Compound No. | [M + H]+[calc] | Structure | Tyrp AVG EC1.5 (µM) | Tyrp % Fold Act |
|---|---|---|---|---|
| 221 | 373 | 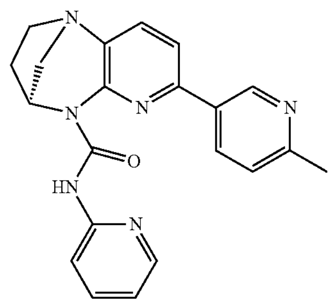 [SMILES: Cc1ccc(-c2ccc3c(n2)N(C(=O)Nc2ccccn2)[C@H]2CCN3C2)cn1] | B | A |
| 222 | 374 | 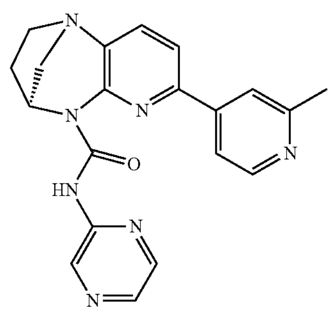 [SMILES: Cc1cc(-c2ccc3c(n2)N(C(=O)Nc2cnccn2)[C@H]2CCN3C2)ccn1] | A | A |
| 223 | 391 | 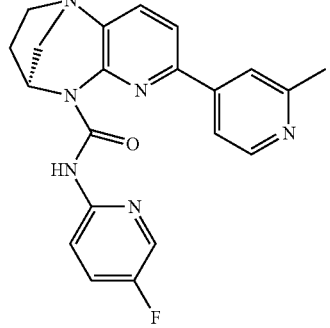 | A | A |
| 224 | 391 | 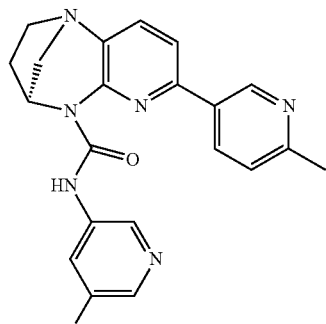 | B | A |

TABLE 1-continued

Compounds of Formula (I).

| Compound No. | [M + H]+<sub>[calc]</sub> | Structure | Tyrp AVG EC<sub>1.5</sub> (μM) | Tyrp % Fold Act |
|---|---|---|---|---|
| 225 | 397 | 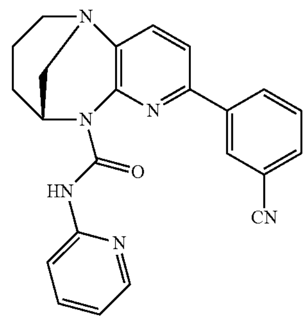 | B | A |
| 226 | 398 | 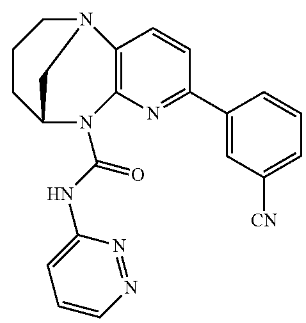 | B | A |
| 227 | 415 | 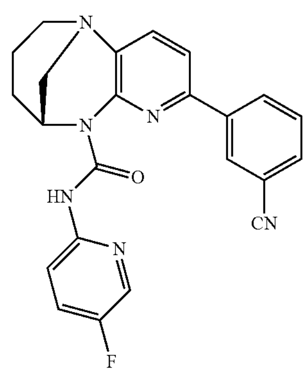 | B | A |
| 228 | 415 | 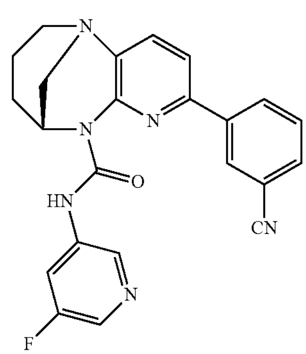 | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 229 | 433 | 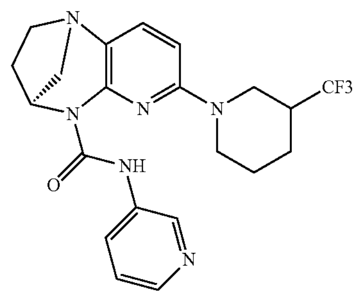 [SMILES: O=C(Nc1cccnc1)N1c2nc(N3CCCC(C(F)(F)F)C3)ccc2N2CC[C@H]1C2] | B | A |
| 230 | 447 | 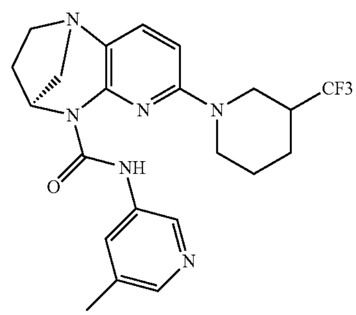 [SMILES: Cc1cncc(NC(=O)N2c3nc(N4CCCC(C(F)(F)F)C4)ccc3N3CC[C@H]2C3)c1] | A | A |
| 231 | 461 | 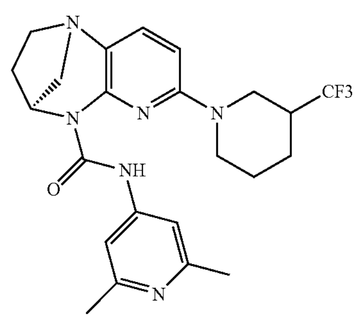 [SMILES: Cc1cc(NC(=O)N2c3nc(N4CCCC(C(F)(F)F)C4)ccc3N3CC[C@H]2C3)cc(C)n1] | B | A |
| 232 | 451 | 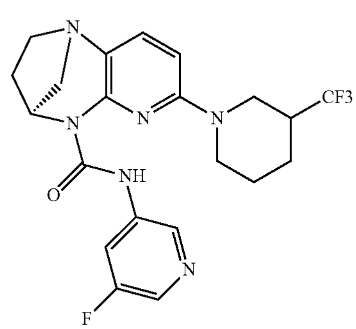 [SMILES: O=C(Nc1cncc(F)c1)N1c2nc(N3CCCC(C(F)(F)F)C3)ccc2N2CC[C@H]1C2] | B | A |

TABLE 1-continued

Compounds of Formula (I).

| Compound No. | [M + H]+<sub>[calc]</sub> | Structure | Tyrp AVG EC<sub>1.5</sub> (μM) | Tyrp % Fold Act |
|---|---|---|---|---|
| 233 | 492 | 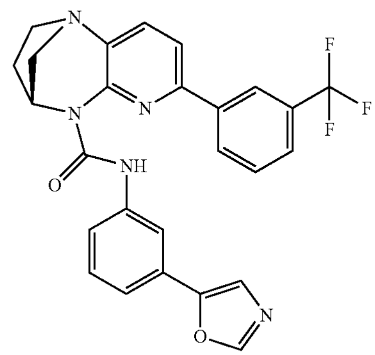 | A | A |
| 234 | 393 | 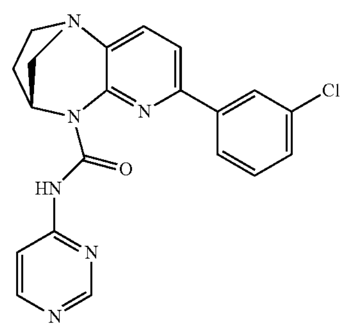 | B | A |
| 235 | 458 | 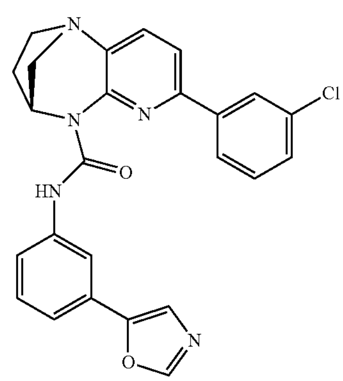 | A | A |
| 236 | 374 | 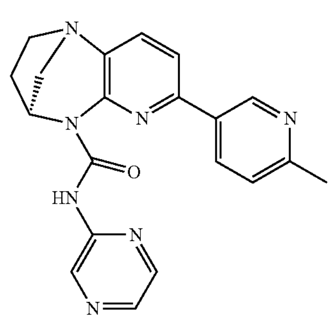 [SMILES: Cc1ccc(-c2ccc3c(n2)N(C(=O)Nc2cnccn2)[C@H]2CCN3C2)cn1] | B | A |

TABLE 1-continued
Compounds of Formula (I).
| Compound No. | [M + H]+[calc] | Structure | Tyrp AVG EC1.5 (μM) | Tyrp % Fold Act |
|---|---|---|---|---|
| 237 | 391 | 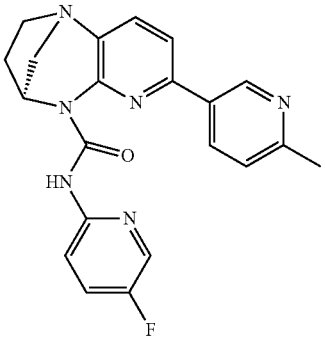 [SMILES: Cc1ccc(-c2ccc3c(n2)N(C(=O)Nc2ccc(F)cn2)[C@H]2CCN3C2)cn1] | B | A |
| 238 | 391 | 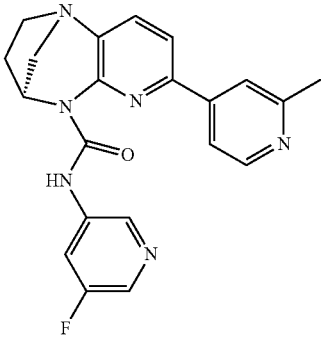 [SMILES: Cc1cc(-c2ccc3c(n2)N(C(=O)Nc2cncc(F)c2)[C@H]2CCN3C2)ccn1] | B | A |
| 239 | 464 | 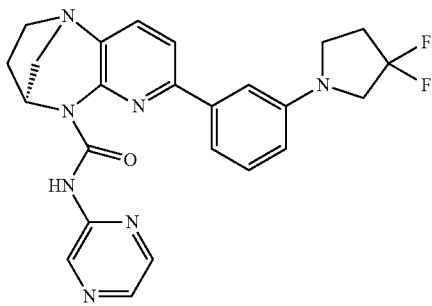 [SMILES: O=C(Nc1cnccn1)N1c2nc(-c3cccc(N4CCC(F)(F)C4)c3)ccc2N2CC[C@H]1C2] | A | A |
| 240 | 404 | 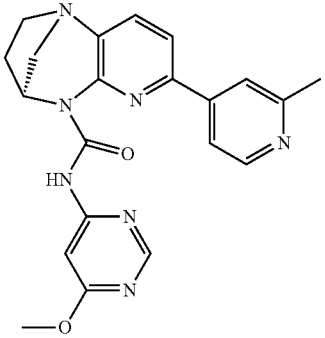 [SMILES: COc1cc(NC(=O)N2c3nc(-c4ccnc(C)c4)ccc3N3CC[C@H]2C3)ncn1] | B | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 241 | 404 | 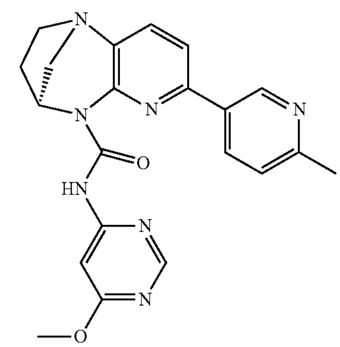 [SMILES: COc1cc(NC(=O)N2c3nc(-c4ccc(C)nc4)ccc3N3CC[C@H]2C3)ncn1] | B | A |
| 242 | 394 | 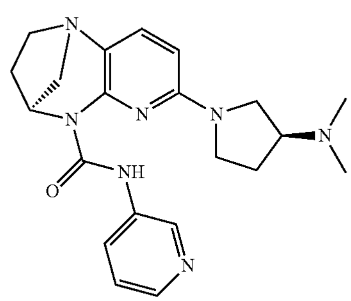 [SMILES: CN(C)[C@H]1CCN(c2ccc3c(n2)N(C(=O)Nc2cccnc2)[C@H]2CCN3C2)C1] | B | A |
| 243 | 408 | 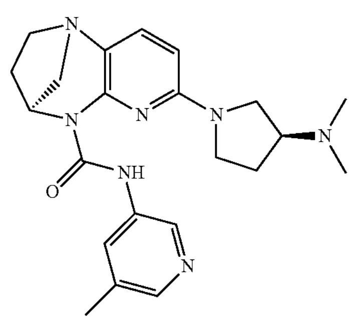 [SMILES: Cc1cncc(NC(=O)N2c3nc(N4CC[C@H](N(C)C)C4)ccc3N3CC[C@H]2C3)c1] | C | A |
| 244 | 412 | 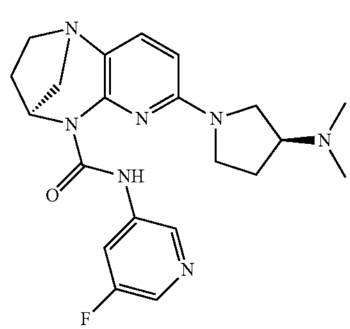 [SMILES: CN(C)[C@H]1CCN(c2ccc3c(n2)N(C(=O)Nc2cncc(F)c2)[C@H]2CCN3C2)C1] | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 245 | 422 | 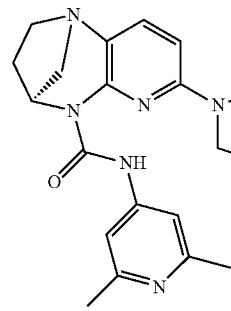 | B | A |
| 246 | 395 | 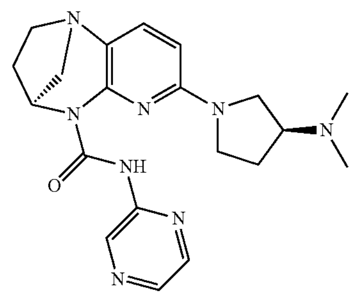 [SMILES: CN(C)[C@H]1CCN(c2ccc3c(n2)N(C(=O)Nc2cnccn2)[C@H]2CCN3C2)C1] | B | A |
| 247 | 400 | 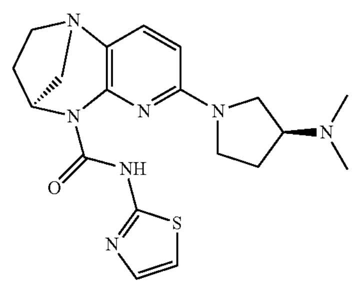 [SMILES: CN(C)[C@H]1CCN(c2ccc3c(n2)N(C(=O)Nc2nccs2)[C@H]2CCN3C2)C1] | B | A |
| 248 | 414 | 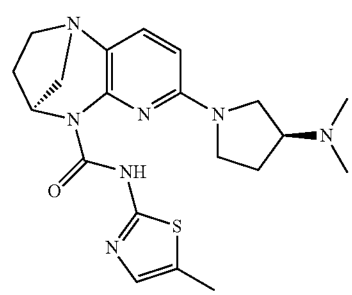 [SMILES: Cc1cnc(NC(=O)N2c3nc(N4CC[C@H](N(C)C)C4)ccc3N3CC[C@H]2C3)s1] | NT | NT |
| 249 | 394 | 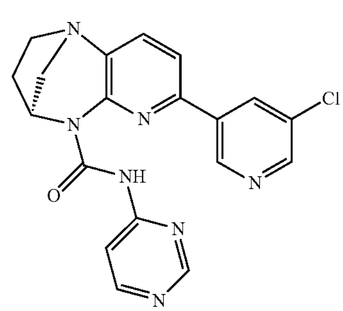 [SMILES: O=C(Nc1ccncn1)N1c2nc(-c3cncc(Cl)c3)ccc2N2CC[C@H]1C2] | B | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 250 | 424 | 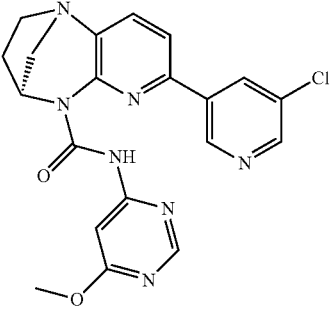 [SMILES: COc1cc(NC(=O)N2c3nc(-c4cncc(Cl)c4)ccc3N3CC[C@H]2C3)ncn1] | A | A |
| 251 | 415 | 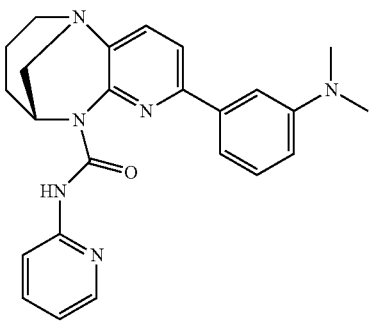 [SMILES: CN(C)c1cccc(-c2ccc3c(n2)N(C(=O)Nc2ccccn2)[C@@H]2CCCN3C2)c1] | C | A |
| 252 | 449 | 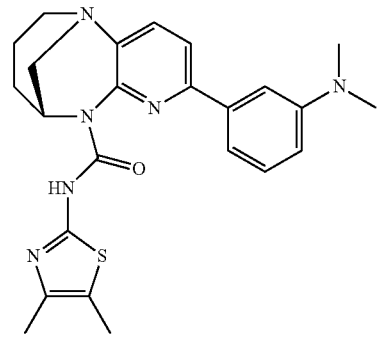 [SMILES: Cc1nc(NC(=O)N2c3nc(-c4cccc(N(C)C)c4)ccc3N3CCC[C@@H]2C3)sc1C] | C | A |
| 253 | 433 | 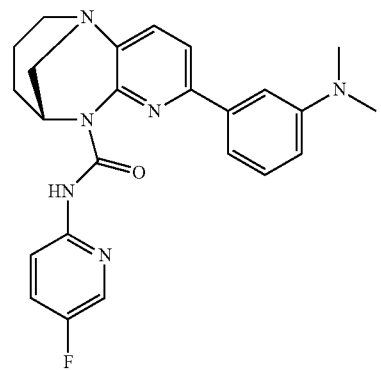 [SMILES: CN(C)c1cccc(-c2ccc3c(n2)N(C(=O)Nc2ccc(F)cn2)[C@@H]2CCCN3C2)c1] | C | B |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 254 | 463 | 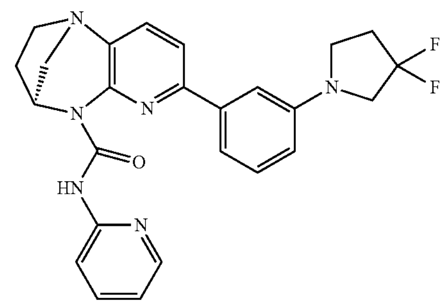 [SMILES: O=C(Nc1ccccn1)N1c2nc(-c3cccc(N4CCC(F)(F)C4)c3)ccc2N2CC[C@H]1C2] | A | A |
| 255 | 476 | 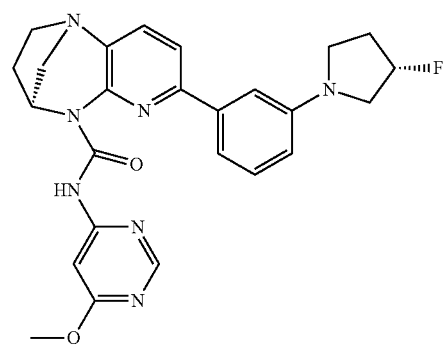 [SMILES: COc1cc(NC(=O)N2c3nc(-c4cccc(N5CC[C@H](F)C5)c4)ccc3N3CC[C@H]2C3)ncn1] | B | A |
| 256 | 494 | 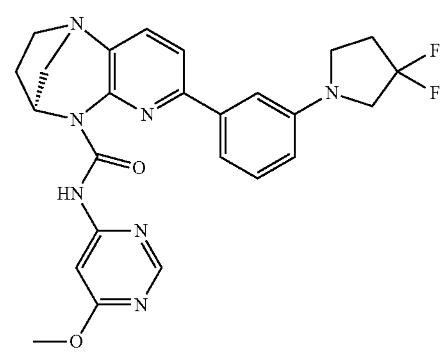 [SMILES: COc1cc(NC(=O)N2c3nc(-c4cccc(N5CCC(F)(F)C5)c4)ccc3N3CC[C@H]2C3)ncn1] | B | A |
| 257 | 481 | 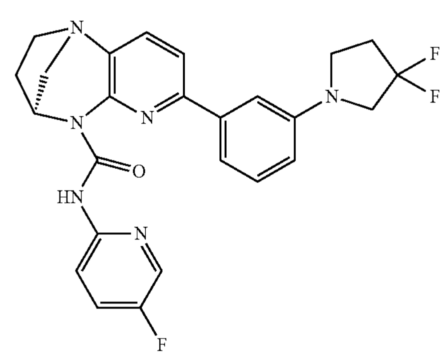 | B | A |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 258 | 316 | 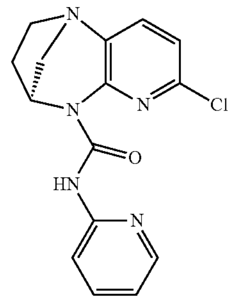 [SMILES: O=C(Nc1ccccn1)N1c2nc(Cl)ccc2N2CC[C@H]1C2] | C | A |
| 259 | 334 | 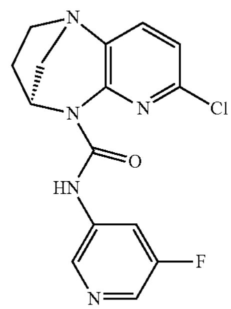 [SMILES: O=C(Nc1cncc(F)c1)N1c2nc(Cl)ccc2N2CC[C@H]1C2] | B | A |
| 260 | 393 | 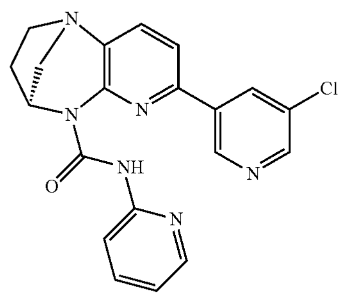 [SMILES: O=C(Nc1ccccn1)N1c2nc(-c3cncc(Cl)c3)ccc2N2CC[C@H]1C2] | A | A |
| 261 | 411 | 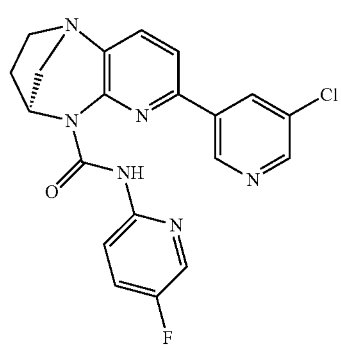 [SMILES: O=C(Nc1ccc(F)cn1)N1c2nc(-c3cncc(Cl)c3)ccc2N2CC[C@H]1C2] | A | A |

TABLE 1-continued

Compounds of Formula (I).

| Compound No. | [M + H]+<sub>[calc]</sub> | Structure | Tyrp AVG EC<sub>1.5</sub> (μM) | Tyrp % Fold Act |
|---|---|---|---|---|
| 262 | 438 | 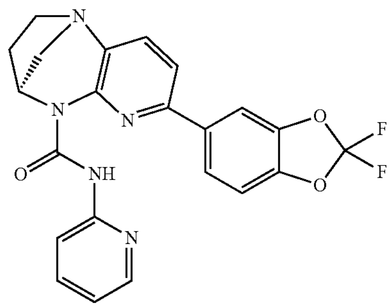 [SMILES: O=C(Nc1ccccn1)N1c2nc(-c3ccc4c(c3)OC(F)(F)O4)ccc2N2CC[C@H]1C2] | B | A |
| 263 | 420 | 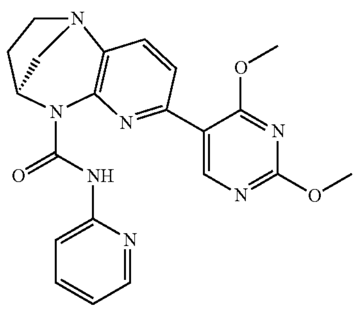 [SMILES: COc1ncc(-c2ccc3c(n2)N(C(=O)Nc2ccccn2)[C@H]2CCN3C2)c(OC)n1] | B | A |
| 264 | 481 | 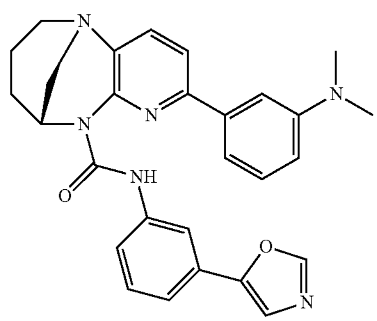 [SMILES: CN(C)c1cccc(-c2ccc3c(n2)N(C(=O)Nc2cccc(-c4cnco4)c2)[C@@H]2CCCN3C2)c1] | A | A |
| 265 | 446 | 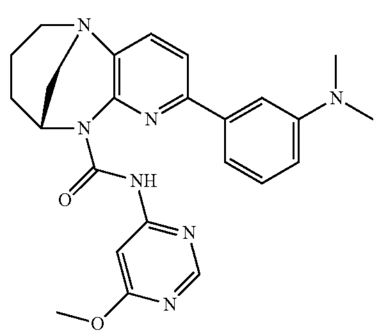 [SMILES: COc1cc(NC(=O)N2c3nc(-c4cccc(N(C)C)c4)ccc3N3CCC[C@@H]2C3)ncn1] | B | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 266 | 416 | 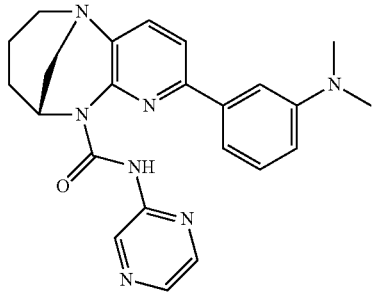 [SMILES: CN(C)c1cccc(-c2ccc3c(n2)N(C(=O)Nc2cnccn2)[C@@H]2CCCN3C2)c1] | B | A |
| 267 | 446 | 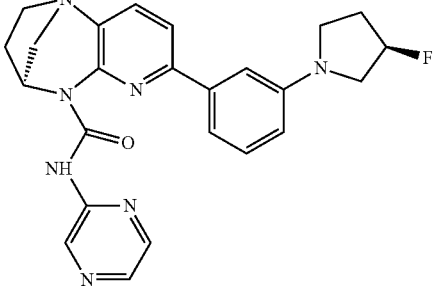 | B | A |
| 268 | 446 | 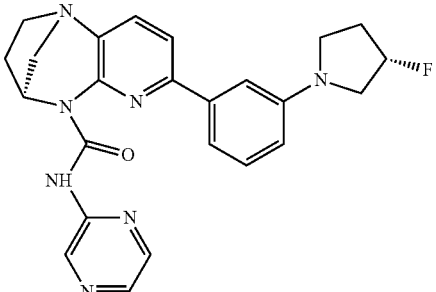 | A | A |
| 269 | 463 | 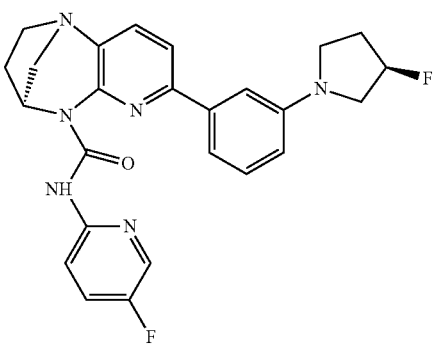 [SMILES: O=C(Nc1ccc(F)cn1)N1c2nc(-c3cccc(N4CC[C@@H](F)C4)c3)ccc2N2CC[C@H]1C2] | B | A |

TABLE 1-continued
Compounds of Formula (I).
| Compound No. | [M + H]+[calc] | Structure | Tyrp AVG EC1.5 (μM) | Tyrp % Fold Act |
|---|---|---|---|---|
| 270 | 463 | 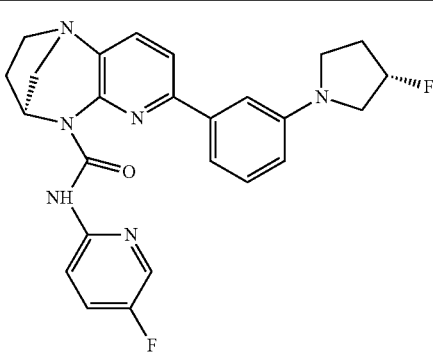 | B | A |
| 271 | 481 | 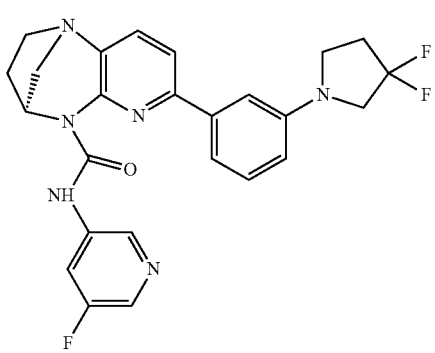 [SMILES: O=C(Nc1cncc(F)c1)N1c2nc(-c3cccc(N4CCC(F)(F)C4)c3)ccc2N2CC[C@H]1C2] | A | A |
| 272 | 440 | 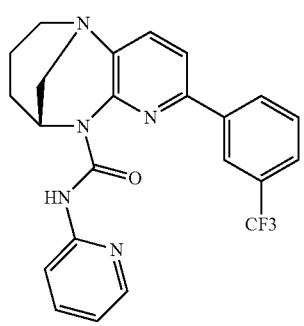 [SMILES: O=C(Nc1ccccn1)N1c2nc(-c3cccc(C(F)(F)F)c3)ccc2N2CCC[C@@H]1C2] | B | A |
| 273 | 458 | 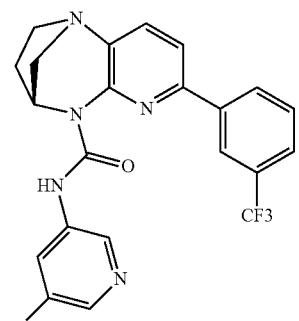 | A | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 274 | 471 | 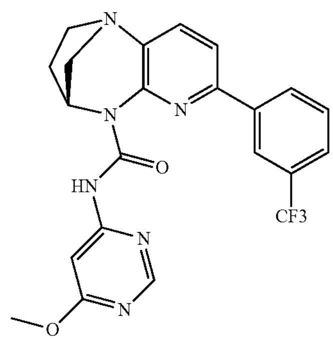 [SMILES: COc1cc(NC(=O)N2c3nc(-c4cccc(C(F)(F)F)c4)ccc3N3CC[C@@H]2C3)ncn1] | A | A |
| 275 | 394 | 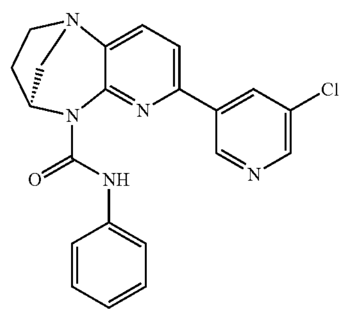 [SMILES: O=C(Nc1ccccc1)N1c2nc(-c3cncc(Cl)c3)ccc2N2CC[C@H]1C2] | A | A |
| 276 | 428 | 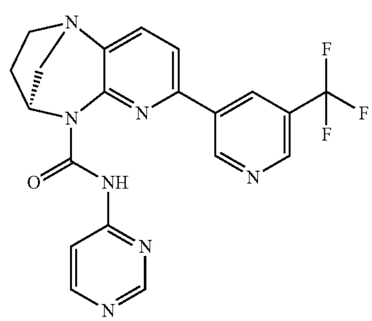 [SMILES: O=C(Nc1ccncn1)N1c2nc(-c3cncc(C(F)(F)F)c3)ccc2N2CC[C@H]1C2] | A | A |
| 277 | 455 | 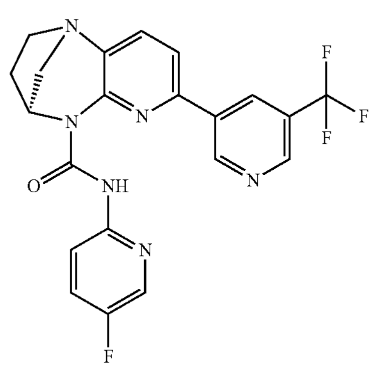 [SMILES: O=C(Nc1ccc(F)cn1)N1c2nc(-c3cncc(C(F)(F)F)c3)ccc2N2CC[C@H]1C2] | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 278 | 428 | 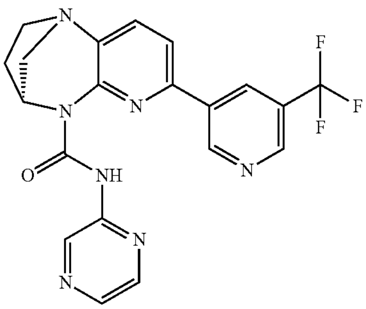 [SMILES: O=C(Nc1cnccn1)N1c2nc(-c3cncc(C(F)(F)F)c3)ccc2N2CC[C@H]1C2] | A | A |
| 279 | 445 | 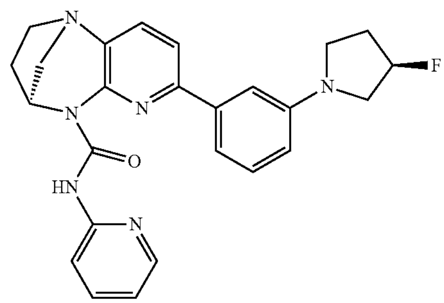 [SMILES: O=C(Nc1ccccn1)N1c2nc(-c3cccc(N4CC[C@@H](F)C4)c3)ccc2N2CC[C@H]1C2] | A | A |
| 280 | 445 | 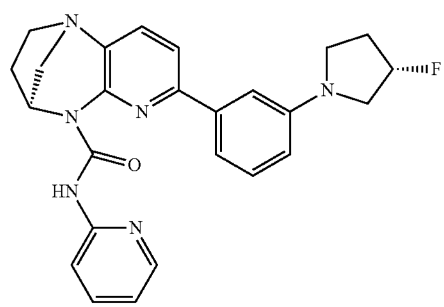 [SMILES: O=C(Nc1ccccn1)N1c2nc(-c3cccc(N4CC[C@H](F)C4)c3)ccc2N2CC[C@H]1C2] | A | A |
| 281 | 476 | 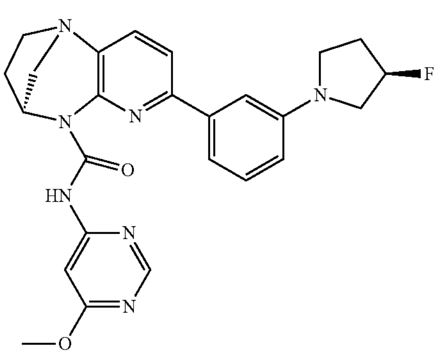 [SMILES: COc1cc(NC(=O)N2c3nc(-c4cccc(N5CC[C@@H](F)C5)c4)ccc3N3CC[C@H]2C3)ncn1] | A | A |

TABLE 1-continued

Compounds of Formula (I).

| Compound No. | [M + H]+[calc] | Structure | Tyrp AVG EC₁.₅ (μM) | Tyrp % Fold Act |
|---|---|---|---|---|
| 282 | 463 | 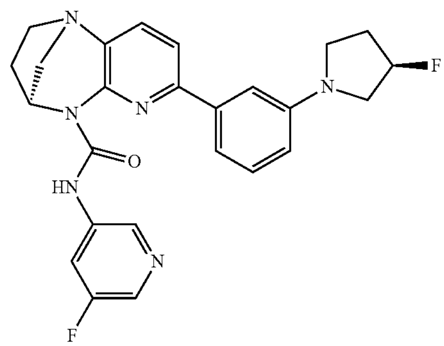 [SMILES: O=C(Nc1cncc(F)c1)N1c2nc(-c3cccc(N4CC[C@@H](F)C4)c3)ccc2N2CC[C@H]1C2] | A | A |
| 283 | 463 | 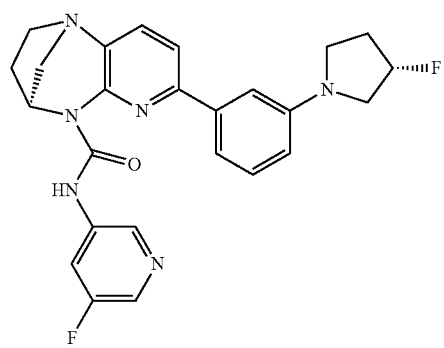 [SMILES: O=C(Nc1cncc(F)c1)N1c2nc(-c3cccc(N4CC[C@H](F)C4)c3)ccc2N2CC[C@H]1C2] | A | A |
| 284 | 378 | 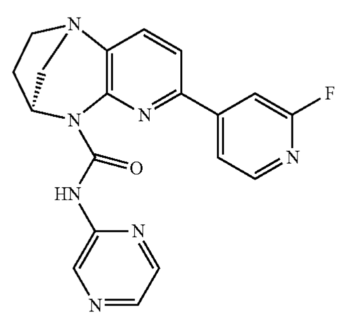 [SMILES: O=C(Nc1cnccn1)N1c2nc(-c3ccnc(F)c3)ccc2N2CC[C@H]1C2] | B | A |
| 285 | 513 | 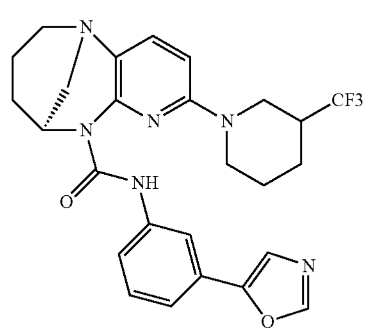 [SMILES: O=C(Nc1cccc(-c2cnco2)c1)N1c2nc(N3CCCC(C(F)(F)F)C3)ccc2N2CCC[C@H]1C2] | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 286 | 447 | 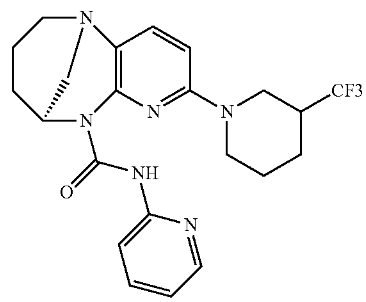 [SMILES: O=C(Nc1ccccn1)N1c2nc(N3CCCC(C(F)(F)F)C3)ccc2N2CCC[C@H]1C2] | A | A |
| 287 | 475 | 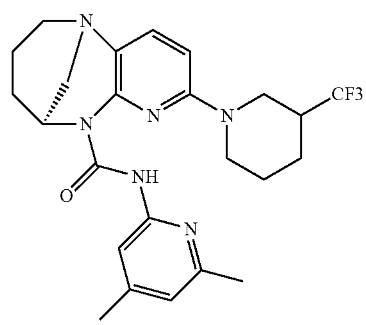 [SMILES: Cc1cc(C)nc(NC(=O)N2c3nc(N4CCCC(C(F)(F)F)C4)ccc3N3CCC[C@H]2C3)c1] | B | A |
| 288 | 447 | 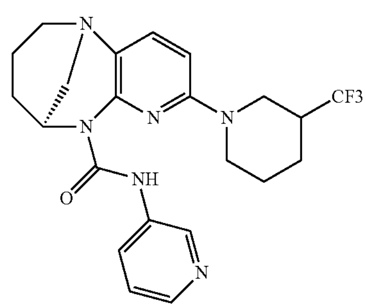 [SMILES: O=C(Nc1cccnc1)N1c2nc(N3CCCC(C(F)(F)F)C3)ccc2N2CCC[C@H]1C2] | A | A |
| 289 | 461 | 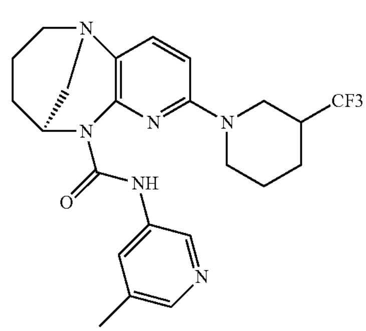 [SMILES: Cc1cncc(NC(=O)N2c3nc(N4CCCC(C(F)(F)F)C4)ccc3N3CCC[C@H]2C3)c1] | A | A |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 290 | 465 | 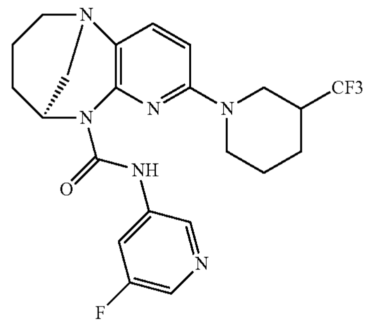 [SMILES: O=C(Nc1cncc(F)c1)N1c2nc(N3CCCC(C(F)(F)F)C3)ccc2N2CCC[C@H]1C2] | A | A |
| 291 | 465 | 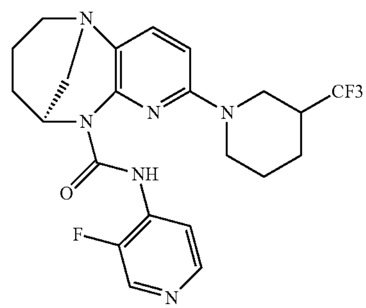 [SMILES: O=C(Nc1ccncc1F)N1c2nc(N3CCCC(C(F)(F)F)C3)ccc2N2CCC[C@H]1C2] | B | A |
| 292 | 448 | 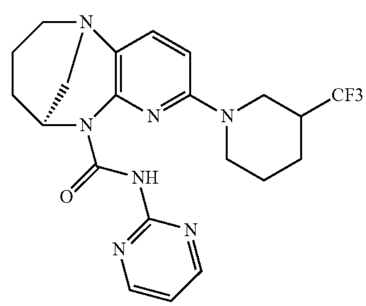 [SMILES: O=C(Nc1ncccn1)N1c2nc(N3CCCC(C(F)(F)F)C3)ccc2N2CCC[C@H]1C2] | A | A |
| 293 | 448 | 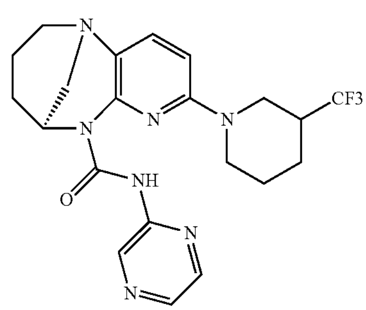 [SMILES: O=C(Nc1cnccn1)N1c2nc(N3CCCC(C(F)(F)F)C3)ccc2N2CCC[C@H]1C2] | A | A |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 294 | 448 | 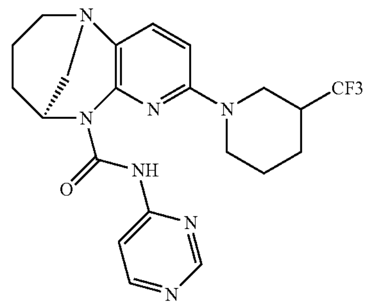 [SMILES: O=C(Nc1ccncn1)N1c2nc(N3CCCC(C(F)(F)F)C3)ccc2N2CCC[C@H]1C2] | B | A |
| 295 | 453 | 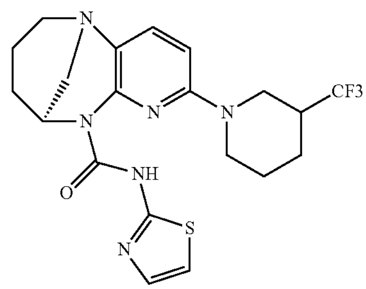 [SMILES: O=C(Nc1nccs1)N1c2nc(N3CCCC(C(F)(F)F)C3)ccc2N2CCC[C@H]1C2] | A | A |
| 296 | 467 | 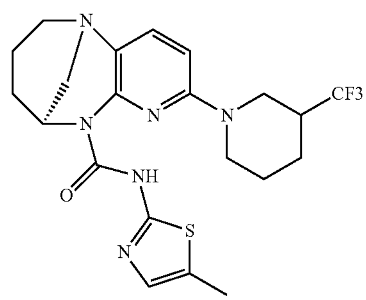 [SMILES: Cc1cnc(NC(=O)N2c3nc(N4CCCC(C(F)(F)F)C4)ccc3N3CCC[C@H]2C3)s1] | B | A |
| 297 | 467 | 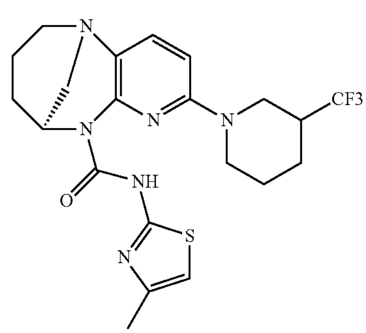 [SMILES: Cc1csc(NC(=O)N2c3nc(N4CCCC(C(F)(F)F)C4)ccc3N3CCC[C@H]2C3)n1] | B | A |

TABLE 1-continued

Compounds of Formula (I).

| Compound No. | [M + H]+[calc] | Structure | Tyrp AVG EC<sub>1.5</sub> (μM) | Tyrp % Fold Act |
|---|---|---|---|---|
| 298 | 481 | 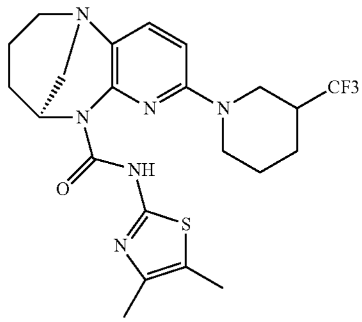 [SMILES: Cc1nc(NC(=O)N2c3nc(N4CCCC(C(F)(F)F)C4)ccc3N3CCC[C@H]2C3)sc1C] | B | A |
| 299 | 513 | 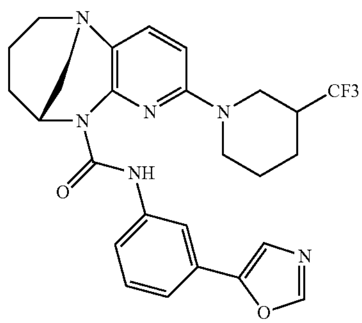 [SMILES: O=C(Nc1cccc(-c2cnco2)c1)N1c2nc(N3CCCC(C(F)(F)F)C3)ccc2N2CCC[C@@H]1C2] | A | A |
| 300 | 447 | 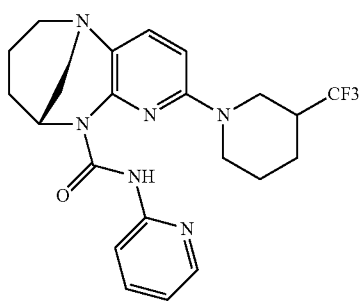 [SMILES: O=C(Nc1ccccn1)N1c2nc(N3CCCC(C(F)(F)F)C3)ccc2N2CCC[C@@H]1C2] | C | B |
| 301 | 475 | 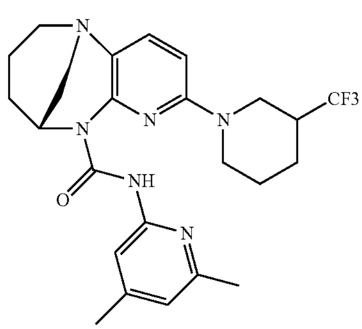 [SMILES: Cc1cc(C)nc(NC(=O)N2c3nc(N4CCCC(C(F)(F)F)C4)ccc3N3CCC[C@@H]2C3)c1] | C | B |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 302 | 447 | 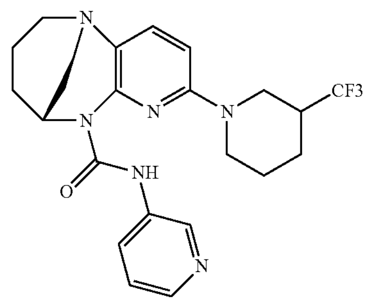 [SMILES: O=C(Nc1cccnc1)N1c2nc(N3CCCC(C(F)(F)F)C3)ccc2N2CCC[C@@H]1C2] | B | A |
| 303 | 461 | 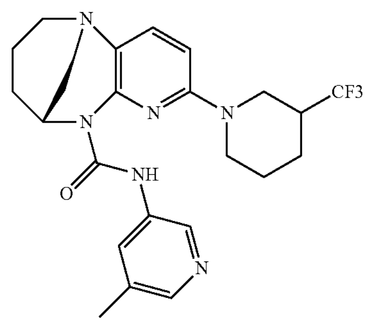 [SMILES: Cc1cncc(NC(=O)N2c3nc(N4CCCC(C(F)(F)F)C4)ccc3N3CCC[C@@H]2C3)c1] | B | A |
| 304 | 465 | 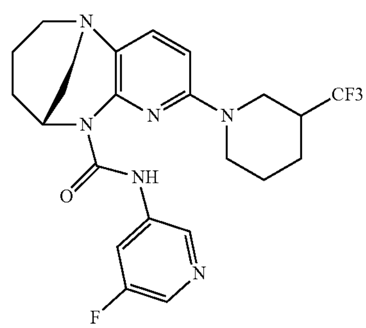 [SMILES: O=C(Nc1cncc(F)c1)N1c2nc(N3CCCC(C(F)(F)F)C3)ccc2N2CCC[C@@H]1C2] | B | A |
| 305 | 447 | 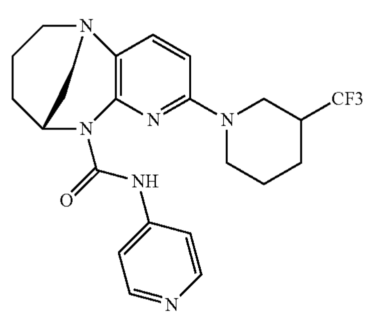 [SMILES: O=C(Nc1ccncc1)N1c2nc(N3CCCC(C(F)(F)F)C3)ccc2N2CCC[C@@H]1C2] | B | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 306 | 448 | 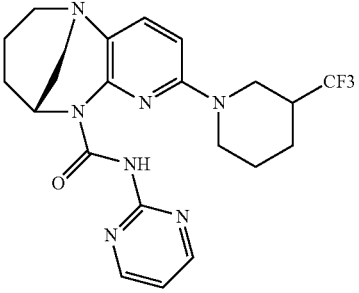 [SMILES: O=C(Nc1ncccn1)N1c2nc(N3CCCC(C(F)(F)F)C3)ccc2N2CCC[C@@H]1C2] | NT | NT |
| 307 | 448 | 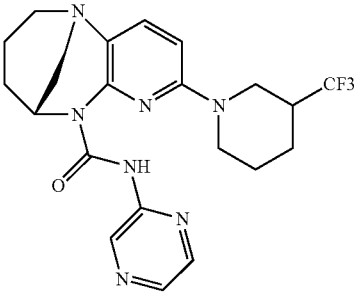 [SMILES: O=C(Nc1cnccn1)N1c2nc(N3CCCC(C(F)(F)F)C3)ccc2N2CCC[C@@H]1C2] | B | A |
| 308 | 448 | 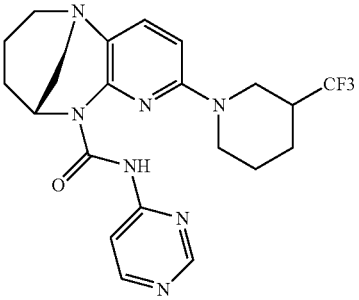 [SMILES: O=C(Nc1ccncn1)N1c2nc(N3CCCC(C(F)(F)F)C3)ccc2N2CCC[C@@H]1C2] | C | A |
| 309 | 477 | 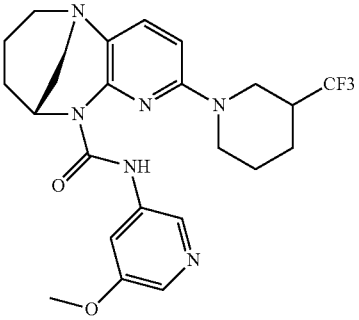 [SMILES: COc1cncc(NC(=O)N2c3nc(N4CCCC(C(F)(F)F)C4)ccc3N3CCC[C@@H]2C3)c1] | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 310 | 453 | 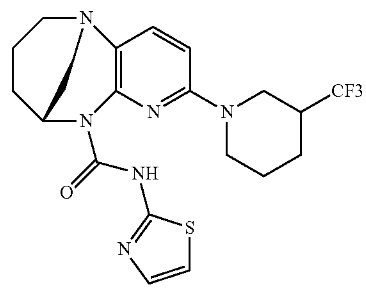 [SMILES: O=C(Nc1nccs1)N1c2nc(N3CCCC(C(F)(F)F)C3)ccc2N2CCC[C@@H]1C2] | B | A |
| 311 | 467 | 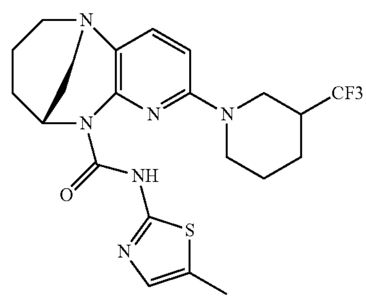 [SMILES: Cc1cnc(NC(=O)N2c3nc(N4CCCC(C(F)(F)F)C4)ccc3N3CCC[C@@H]2C3)s1] | C | B |
| 312 | 467 | 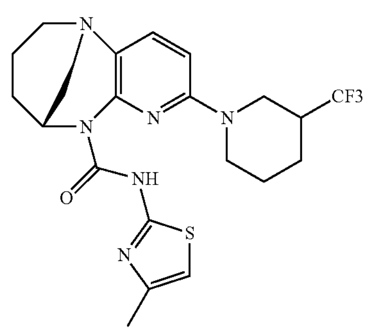 [SMILES: Cc1csc(NC(=O)N2c3nc(N4CCCC(C(F)(F)F)C4)ccc3N3CCC[C@@H]2C3)n1] | B | A |
| 313 | 481 | 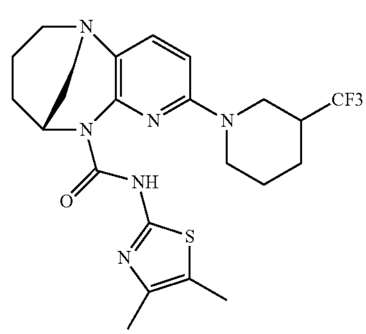 [SMILES: Cc1nc(NC(=O)N2c3nc(N4CCCC(C(F)(F)F)C4)ccc3N3CCC[C@@H]2C3)sc1C] | C | B |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 314 (5) | 440 | 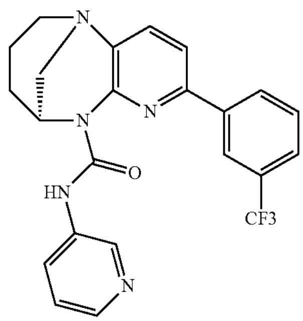 [SMILES: O=C(Nc1cccnc1)N1c2nc(-c3cccc(C(F)(F)F)c3)ccc2N2CCC[C@H]1C2] | A | A |
| 315 | 533 | 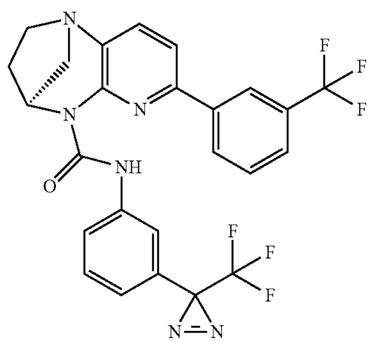 [SMILES: O=C(Nc1cccc(C2(C(F)(F)F)N=N2)c1)N1c2nc(-c3cccc(C(F)(F)F)c3)ccc2N2CC[C@H]1C2] | B | A |
| 316 | 427 | 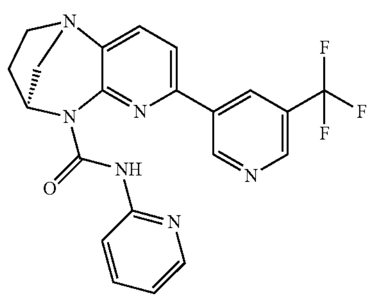 [SMILES: O=C(Nc1ccccn1)N1c2nc(-c3cncc(C(F)(F)F)c3)ccc2N2CC[C@H]1C2] | A | A |
| 317 | 458 | 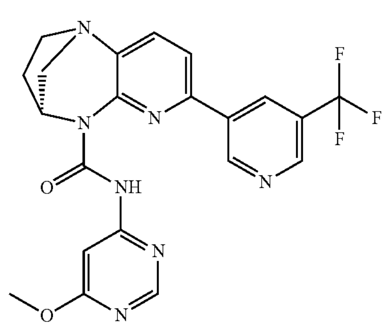 [SMILES: COc1cc(NC(=O)N2c3nc(-c4cncc(C(F)(F)F)c4)ccc3N3CC[C@H]2C3)ncn1] | B | A |

TABLE 1-continued
Compounds of Formula (I).
| Compound No. | [M + H]+[calc] | Structure | Tyrp AVG EC1.5 (μM) | Tyrp % Fold Act |
|---|---|---|---|---|
| 318 | 495 | 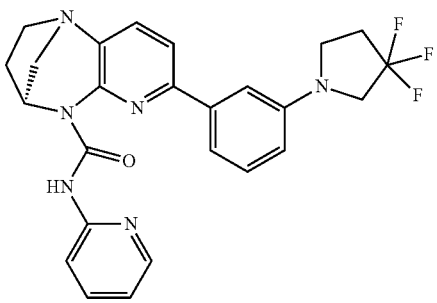 | B | A |
| 319 | 496 | 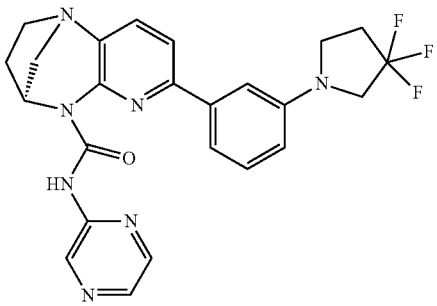 | B | A |
| 320 | 526 | 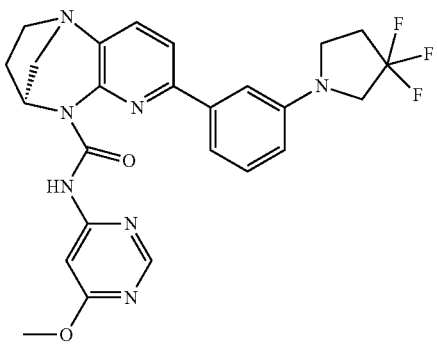 | B | A |
| 321 | 513 | 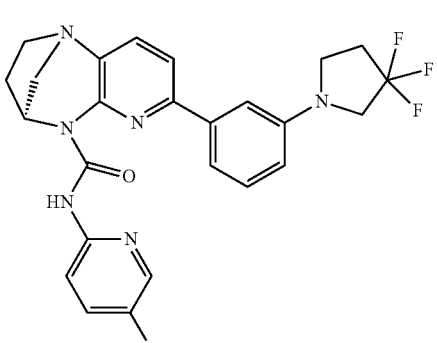 | B | A |

TABLE 1-continued
Compounds of Formula (I).
| Compound No. | [M + H]+$_{[calc]}$ | Structure | Tyrp AVG EC$_{1.5}$ (μM) | Tyrp % Fold Act |
|---|---|---|---|---|
| 322 | 482 | 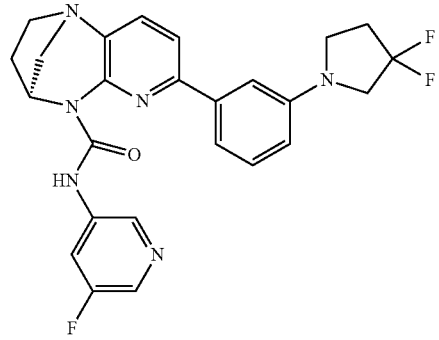 [SMILES: O=C(Nc1cncc(F)c1)N1c2nc(-c3cccc(N4CCC(F)(F)C4)c3)ccc2N2CC[C@H]1C2] | A | A |
| 323 | 513 | 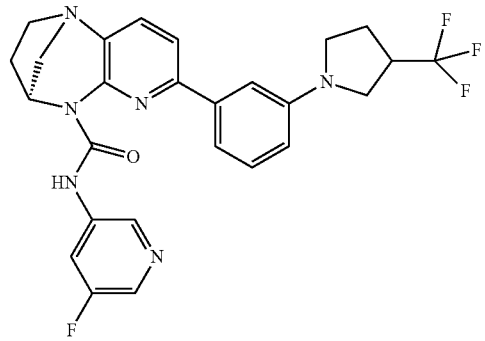 [SMILES: O=C(Nc1cncc(F)c1)N1c2nc(-c3cccc(N4CCC(C(F)(F)F)C4)c3)ccc2N2CC[C@H]1C2] | B | A |
| 324 | 426 | 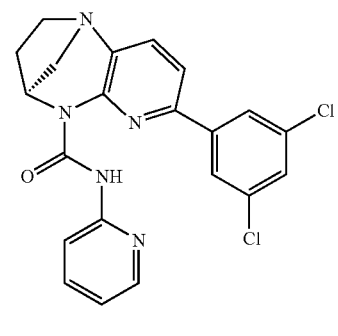 [SMILES: O=C(Nc1ccccn1)N1c2nc(-c3cc(Cl)cc(Cl)c3)ccc2N2CC[C@H]1C2] | A | A |
| 325 | 373 | 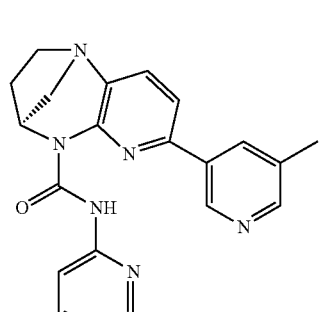 | A | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 326 | 436 | 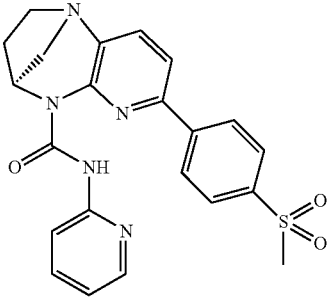 [SMILES: CS(=O)(=O)c1ccc(-c2ccc3c(n2)N(C(=O)Nc2ccccn2)[C@H]2CCN3C2)cc1] | B | A |
| 327 | 377 | 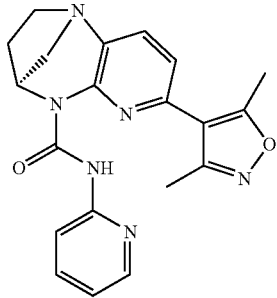 [SMILES: Cc1noc(C)c1-c1ccc2c(n1)N(C(=O)Nc1ccccn1)[C@H]1CCN2C1] | C | A |
| 328 | 437 | 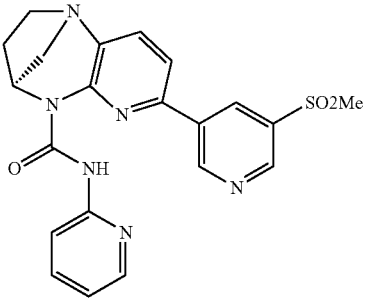 [SMILES: CS(=O)(=O)c1cncc(-c2ccc3c(n2)N(C(=O)Nc2ccccn2)[C@H]2CCN3C2)c1] | B | A |
| 329 | 410 | 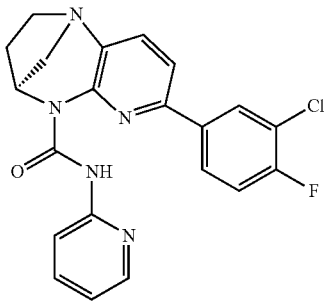 [SMILES: O=C(Nc1ccccn1)N1c2nc(-c3ccc(F)c(Cl)c3)ccc2N2CC[C@H]1C2] | A | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 330 | 400 | 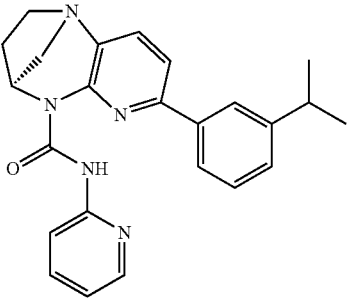 [SMILES: CC(C)c1cccc(-c2ccc3c(n2)N(C(=O)Nc2ccccn2)[C@H]2CCN3C2)c1] | A | A |
| 331 | 362 | 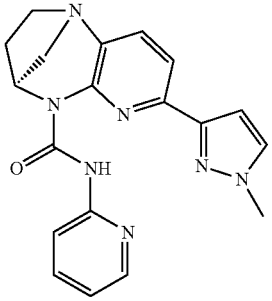 [SMILES: Cn1ccc(-c2ccc3c(n2)N(C(=O)Nc2ccccn2)[C@H]2CCN3C2)n1] | B | A |
| 332 | 426 | 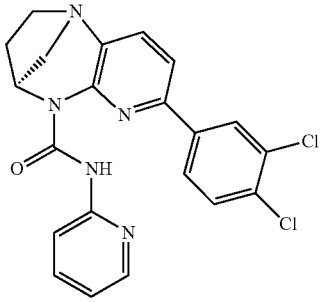 [SMILES: O=C(Nc1ccccn1)N1c2nc(-c3ccc(Cl)c(Cl)c3)ccc2N2CC[C@H]1C2] | A | A |
| 333 | 444 | 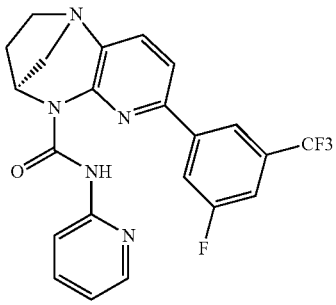 [SMILES: O=C(Nc1ccccn1)N1c2nc(-c3cc(F)cc(C(F)(F)F)c3)ccc2N2CC[C@H]1C2] | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 334 | 444 | 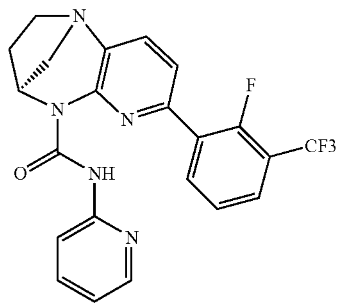 [SMILES: O=C(Nc1ccccn1)N1c2nc(-c3cccc(C(F)(F)F)c3F)ccc2N2CC[C@H]1C2] | B | A |
| 335 | 547 | 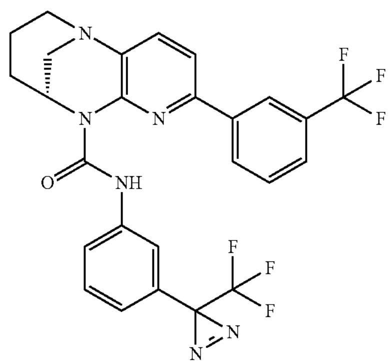 [SMILES: O=C(Nc1cccc(C2(C(F)(F)F)N=N2)c1)N1c2nc(-c3cccc(C(F)(F)F)c3)ccc2N2CCC[C@H]1C2] | A | A |
| 336 | 427 | 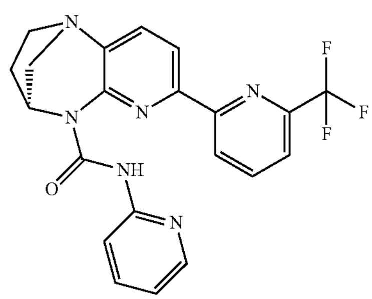 [SMILES: O=C(Nc1ccccn1)N1c2nc(-c3cccc(C(F)(F)F)n3)ccc2N2CC[C@H]1C2] | B | A |
| 337 | 428 | 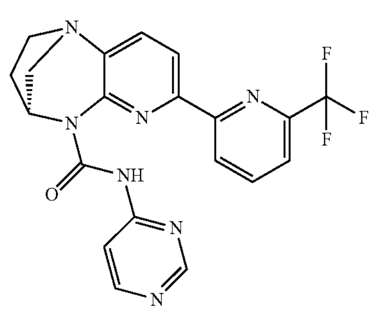 [SMILES: O=C(Nc1ccncn1)N1c2nc(-c3cccc(C(F)(F)F)n3)ccc2N2CC[C@H]1C2] | B | A |

TABLE 1-continued

Compounds of Formula (I).

| Compound No. | [M + H]+_{[calc]} | Structure | Tyrp AVG EC_{1.5} (μM) | Tyrp % Fold Act |
|---|---|---|---|---|
| 338 | 428 | 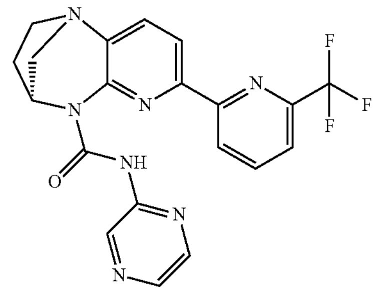 [SMILES: O=C(Nc1cnccn1)N1c2nc(-c3cccc(C(F)(F)F)n3)ccc2N2CC[C@H]1C2] | B | A |
| 339 | 458 | 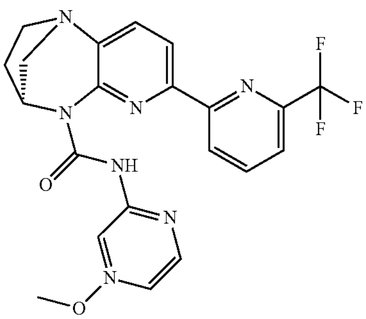 | B | A |
| 340 | 445 | 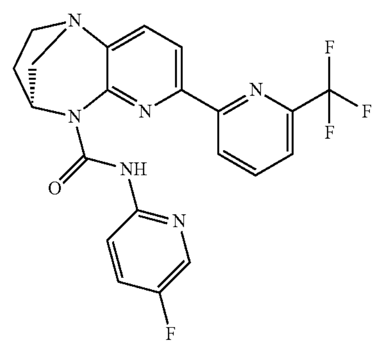 [SMILES: O=C(Nc1ccc(F)cn1)N1c2nc(-c3cccc(C(F)(F)F)n3)ccc2N2CC[C@H]1C2] | B | A |
| 341 | 401 | 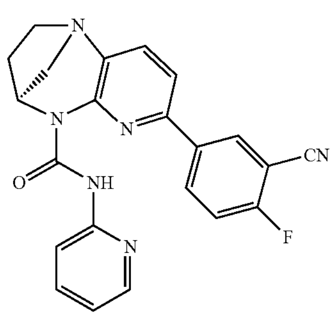 [SMILES: N#Cc1cc(-c2ccc3c(n2)N(C(=O)Nc2ccccn2)[C@H]2CCN3C2)ccc1F] | A | A |

TABLE 1-continued

Compounds of Formula (I).

| Compound No. | [M + H]+[calc] | Structure | Tyrp AVG EC$_{1.5}$ (µM) | Tyrp % Fold Act |
|---|---|---|---|---|
| 342 | 389 | 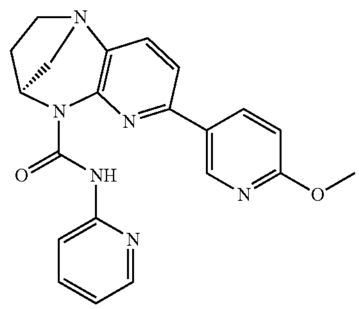 [SMILES: COc1ccc(-c2ccc3c(n2)N(C(=O)Nc2ccccn2)[C@H]2CCN3C2)cn1] | B | A |
| 343 | 415 | 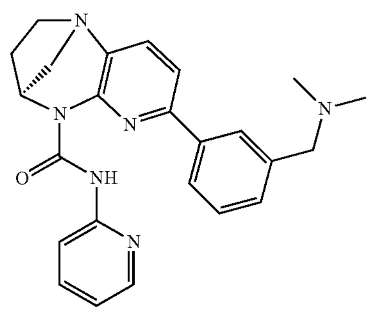 [SMILES: CN(C)Cc1cccc(-c2ccc3c(n2)N(C(=O)Nc2ccccn2)[C@H]2CCN3C2)c1] | B | A |
| 344 | 394 | 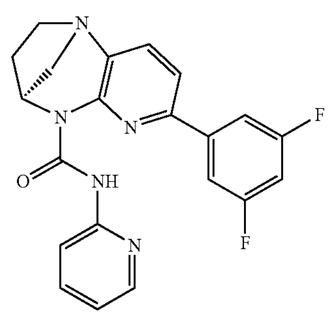 [SMILES: O=C(Nc1ccccn1)N1c2nc(-c3cc(F)cc(F)c3)ccc2N2CC[C@H]1C2] | A | A |
| 345 | 402 | 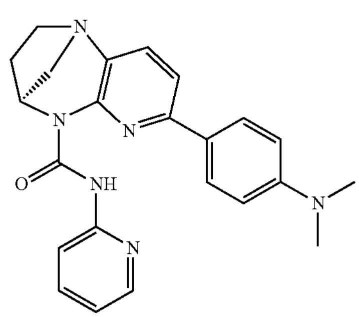 [SMILES: CN(C)c1ccc(-c2ccc3c(n2)N(C(=O)Nc2ccccn2)[C@H]2CCN3C2)cc1] | B | A |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 346 | 389 | 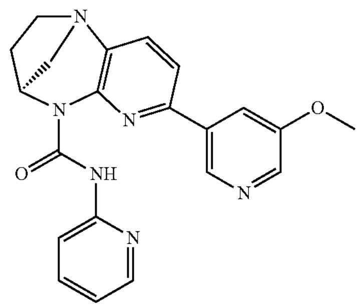 [SMILES: COc1cncc(-c2ccc3c(n2)N(C(=O)Nc2ccccn2)[C@H]2CCN3C2)c1] | B | A |
| 347 | 426 | 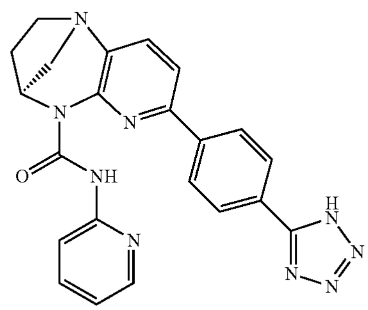 [SMILES: O=C(Nc1ccccn1)N1c2nc(-c3ccc(-c4nnn[nH]4)cc3)ccc2N2CC[C@H]1C2] | A | A |
| 348 | 397 | 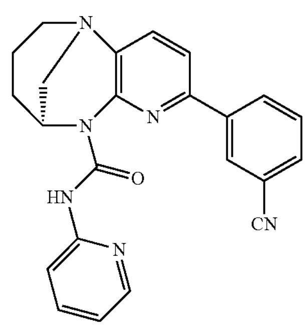 | A | A |
| 349 | 362 | 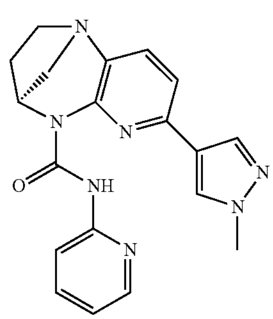 [SMILES: Cn1cc(-c2ccc3c(n2)N(C(=O)Nc2ccccn2)[C@H]2CCN3C2)cn1] | B | A |

TABLE 1-continued
Compounds of Formula (I).
| Compound No. | [M + H]+_[calc] | Structure | Tyrp AVG EC_{1.5} (μM) | Tyrp % Fold Act |
|---|---|---|---|---|
| 350 | 397 | 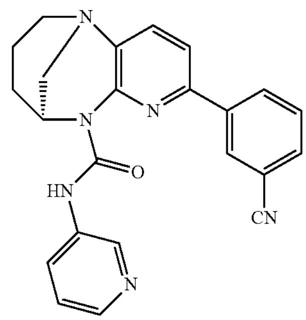 | A | A |
| 351 | 398 | 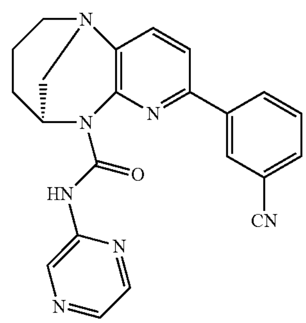 | A | A |
| 352 | 398 | 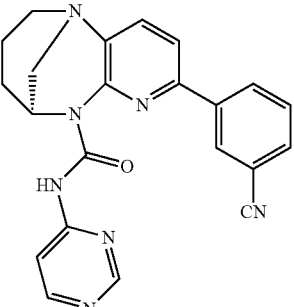 | A | A |
| 353 | 415 | 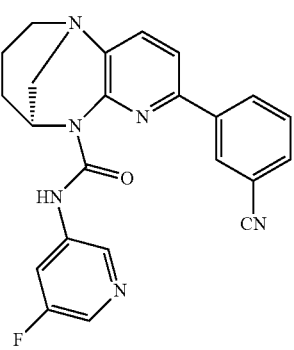 | A | A |

TABLE 1-continued
Compounds of Formula (I).
| Compound No. | [M + H]+_[calc] | Structure | Tyrp AVG EC_{1.5} (μM) | Tyrp % Fold Act |
|---|---|---|---|---|
| 354 | 432 | 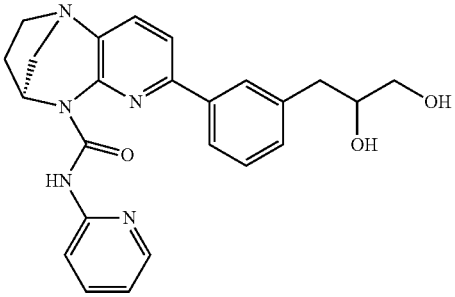 [SMILES: O=C(Nc1ccccn1)N1c2nc(-c3cccc(CC(O)CO)c3)ccc2N2CC[C@H]1C2] | A | A |
| 355 | 463 | 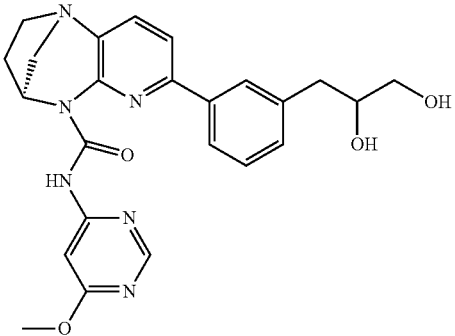 [SMILES: COc1cc(NC(=O)N2c3nc(-c4cccc(CC(O)CO)c4)ccc3N3CC[C@H]2C3)ncn1] | B | A |
| 356 | 450 | 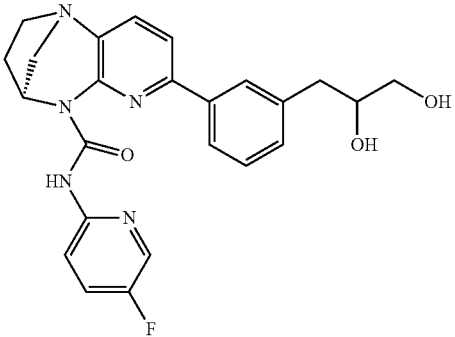 [SMILES: O=C(Nc1ccc(F)cn1)N1c2nc(-c3cccc(CC(O)CO)c3)ccc2N2CC[C@H]1C2] | A | A |
| 357 | 450 | 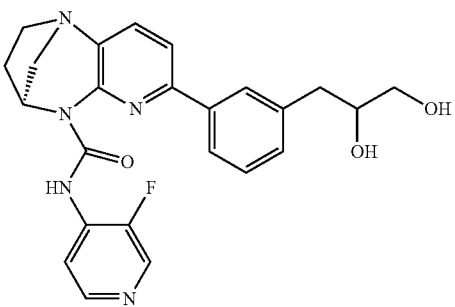 [SMILES: O=C(Nc1ccncc1F)N1c2nc(-c3cccc(CC(O)CO)c3)ccc2N2CC[C@H]1C2] | B | A |

US 10,590,135 B2
433                                                                                          434
TABLE 1-continued
Compounds of Formula (I).
| Compound No. | [M + H]+_[calc] | Structure | Tyrp AVG EC_{1.5} (μM) | Tyrp % Fold Act |
|---|---|---|---|---|
| 358 | 408 | 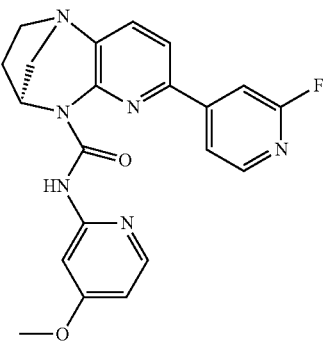 [SMILES: COc1ccnc(NC(=O)N2c3nc(-c4ccnc(F)c4)ccc3N3CC[C@H]2C3)c1] | C | B |
| 359 | 465 | 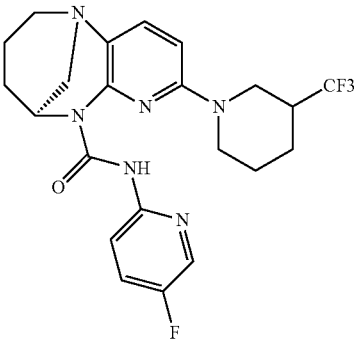 [SMILES: O=C(Nc1ccc(F)cn1)N1c2nc(N3CCCC(C(F)(F)F)C3)ccc2N2CCC[C@H]1C2] | A | A |
| 360 | 447 | 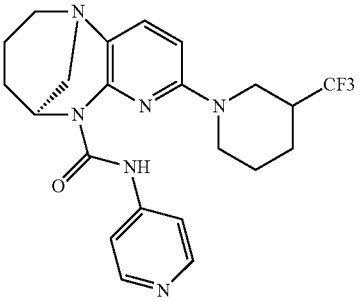 [SMILES: O=C(Nc1ccncc1)N1c2nc(N3CCCC(C(F)(F)F)C3)ccc2N2CCC[C@H]1C2] | A | A |
| 361 | 464 | 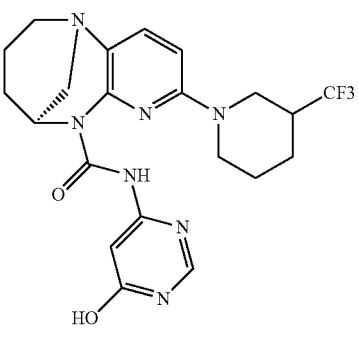 [SMILES: O=C(Nc1cc(O)ncn1)N1c2nc(N3CCCC(C(F)(F)F)C3)ccc2N2CCC[C@H]1C2] | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 362 | 465 | 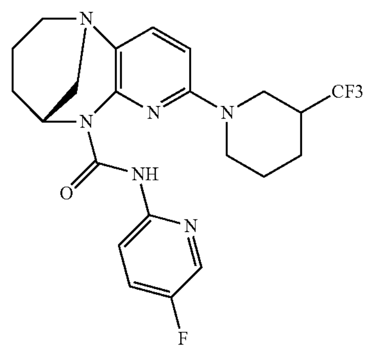 [SMILES: O=C(Nc1ccc(F)cn1)N1c2nc(N3CCCC(C(F)(F)F)C3)ccc2N2CCC[C@@H]1C2] | C | A |
| 363 | 495 | 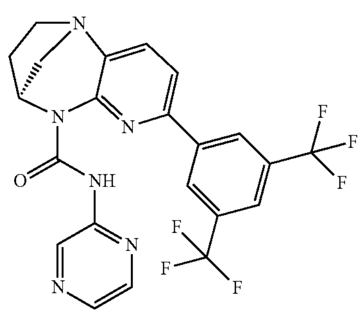 [SMILES: O=C(Nc1cnccn1)N1c2nc(-c3cc(C(F)(F)F)cc(C(F)(F)F)c3)ccc2N2CC[C@H]1C2] | B | A |
| 364 | 427 | 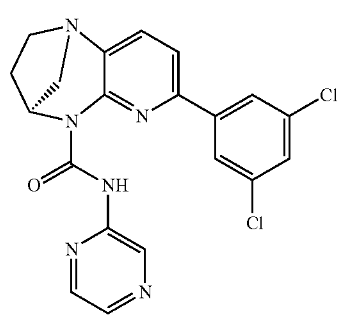 [SMILES: O=C(Nc1cnccn1)N1c2nc(-c3cc(Cl)cc(Cl)c3)ccc2N2CC[C@H]1C2] | B | A |
| 365 | 458 | 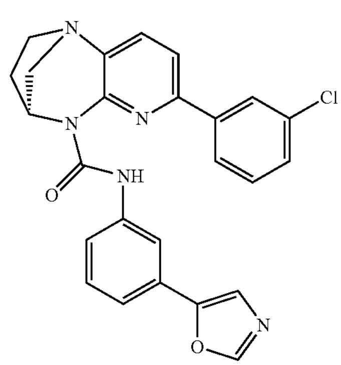 [SMILES: O=C(Nc1cccc(-c2cnco2)c1)N1c2nc(-c3cccc(Cl)c3)ccc2N2CC[C@H]1C2] | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 366 | 458 | 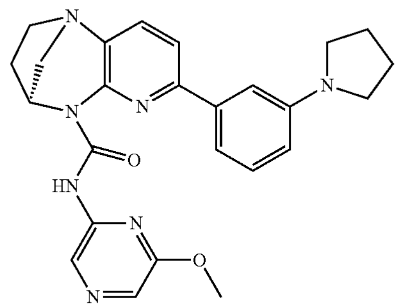 [SMILES: COc1cncc(NC(=O)N2c3nc(-c4cccc(N5CCCC5)c4)ccc3N3CC[C@H]2C3)n1] | A | A |
| 367 | 496 | 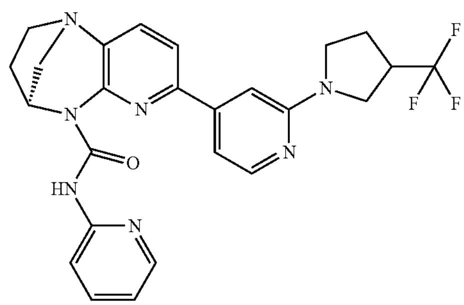 [SMILES: O=C(Nc1ccccn1)N1c2nc(-c3ccnc(N4CCC(C(F)(F)F)C4)c3)ccc2N2CC[C@H]1C2] | A | A |
| 368 | 527 | 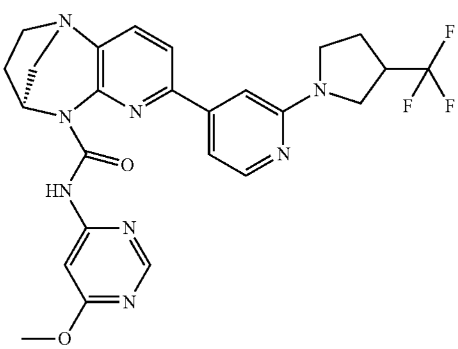 [SMILES: COc1cc(NC(=O)N2c3nc(-c4ccnc(N5CCC(C(F)(F)F)C5)c4)ccc3N3CC[C@H]2C3)ncn1] | B | A |
| 369 | 441 | 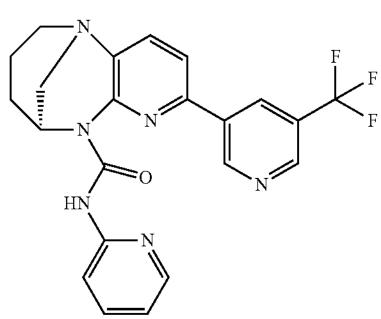 | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 370 | 362 | 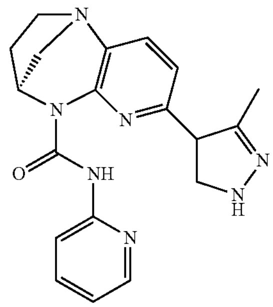 [SMILES: CC1=NNCC1c1ccc2c(n1)N(C(=O)Nc1ccccn1)[C@H]1CCN2C1] | B | A |
| 371 | 402 | 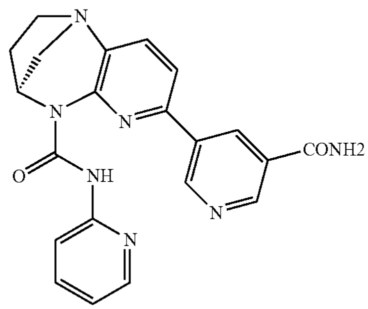 [SMILES: NC(=O)c1cncc(-c2ccc3c(n2)N(C(=O)Nc2ccccn2)[C@H]2CCN3C2)c1] | B | A |
| 372 | 400 | 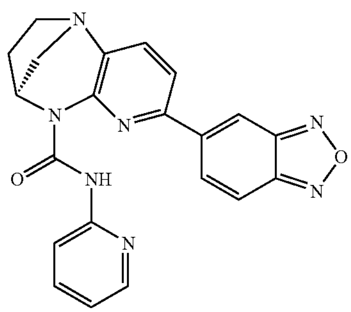 [SMILES: O=C(Nc1ccccn1)N1c2nc(-c3ccc4nonc4c3)ccc2N2CC[C@H]1C2] | B | A |
| 373 | 384 | 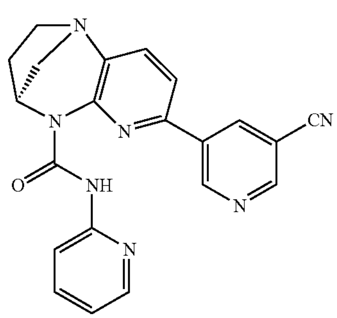 [SMILES: N#Cc1cncc(-c2ccc3c(n2)N(C(=O)Nc2ccccn2)[C@H]2CCN3C2)c1] | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 374 | 377 | 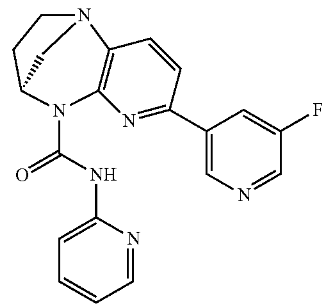 [SMILES: O=C(Nc1ccccn1)N1c2nc(-c3cncc(F)c3)ccc2N2CC[C@H]1C2] | B | A |
| 375 | 451 | 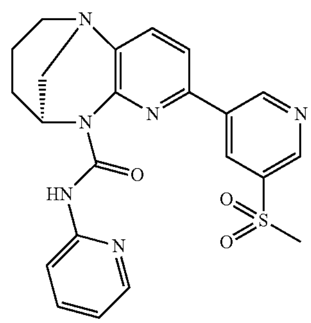 [SMILES: CS(=O)(=O)c1cncc(-c2ccc3c(n2)N(C(=O)Nc2ccccn2)[C@H]2CCCN3C2)c1] | A | A |
| 376 | 451 | 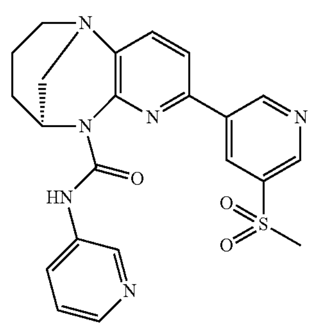 [SMILES: CS(=O)(=O)c1cncc(-c2ccc3c(n2)N(C(=O)Nc2cccnc2)[C@H]2CCCN3C2)c1] | A | A |
| 377 | 469 | 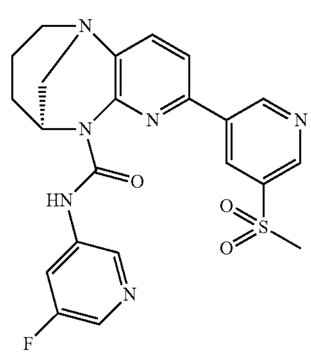 [SMILES: CS(=O)(=O)c1cncc(-c2ccc3c(n2)N(C(=O)Nc2cncc(F)c2)[C@H]2CCCN3C2)c1] | A | A |

TABLE 1-continued

Compounds of Formula (I).

| Compound No. | [M + H]+[calc] | Structure | Tyrp AVG EC1.5 (μM) | Tyrp % Fold Act |
|---|---|---|---|---|
| 378 | 452 | 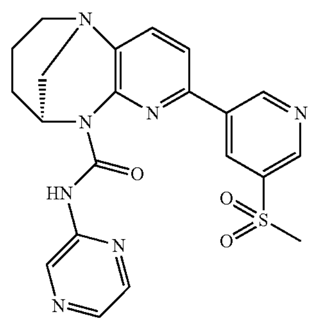 [SMILES: CS(=O)(=O)c1cncc(-c2ccc3c(n2)N(C(=O)Nc2cnccn2)[C@H]2CCCN3C2)c1] | A | A |
| 379 | 452 | 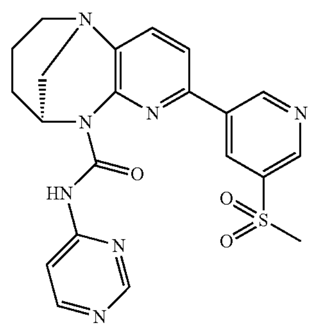 [SMILES: CS(=O)(=O)c1cncc(-c2ccc3c(n2)N(C(=O)Nc2ccncn2)[C@H]2CCCN3C2)c1] | A | A |
| 380 | 452 | 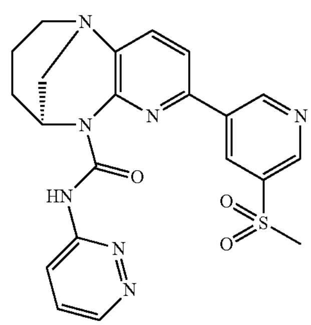 [SMILES: CS(=O)(=O)c1cncc(-c2ccc3c(n2)N(C(=O)Nc2cccnn2)[C@H]2CCCN3C2)c1] | A | A |
| 381 | 398 | 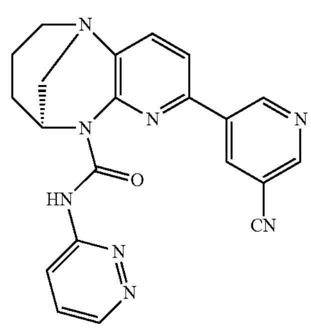 | B | A |

TABLE 1-continued

Compounds of Formula (I).

| Compound No. | [M + H]+_{[calc]} | Structure | Tyrp AVG EC_{1.5} (μM) | Tyrp % Fold Act |
|---|---|---|---|---|
| 382 | 495 | 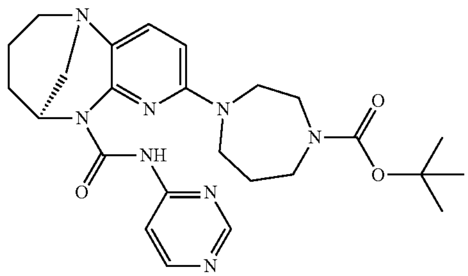 [SMILES: CC(C)(C)OC(=O)N1CCCN(c2ccc3c(n2)N(C(=O)Nc2ccncn2)[C@H]2CCCN3C2)CC1] | C | B |
| 383 | 449 | 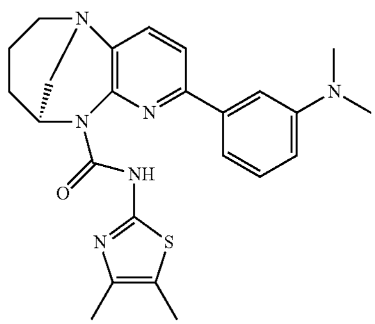 [SMILES: Cc1nc(NC(=O)N2c3nc(-c4cccc(N(C)C)c4)ccc3N3CCC[C@H]2C3)sc1C] | A | A |
| 384 | 433 | 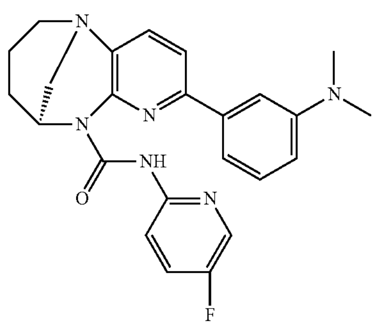 [SMILES: CN(C)c1cccc(-c2ccc3c(n2)N(C(=O)Nc2ccc(F)cn2)[C@H]2CCCN3C2)c1] | B | A |
| 385 | 446 | 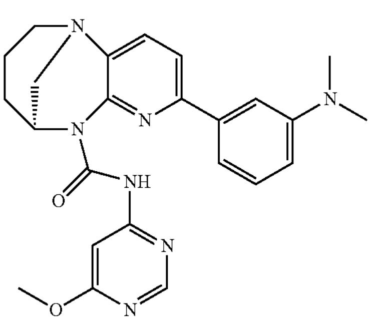 [SMILES: COc1cc(NC(=O)N2c3nc(-c4cccc(N(C)C)c4)ccc3N3CCC[C@H]2C3)ncn1] | A | A |

TABLE 1-continued

Compounds of Formula (I).

| Compound No. | [M + H]+<sub>[calc]</sub> | Structure | Tyrp AVG EC<sub>1.5</sub> (μM) | Tyrp % Fold Act |
|---|---|---|---|---|
| 386 | 415 | 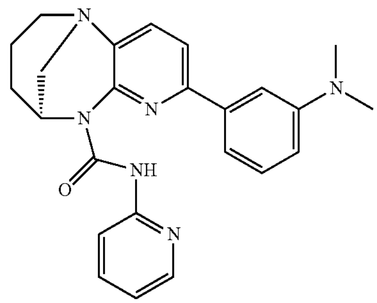 [SMILES: CN(C)c1cccc(-c2ccc3c(n2)N(C(=O)Nc2ccccn2)[C@H]2CCCN3C2)c1] | B | A |
| 387 | 406 | 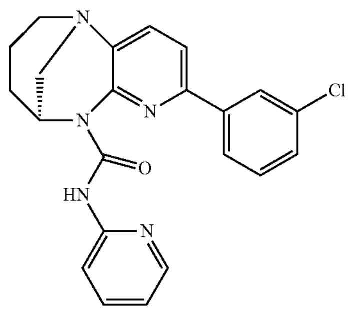 [SMILES: O=C(Nc1ccccn1)N1c2nc(-c3cccc(Cl)c3)ccc2N2CCC[C@H]1C2] | A | A |
| 388 | 464 | 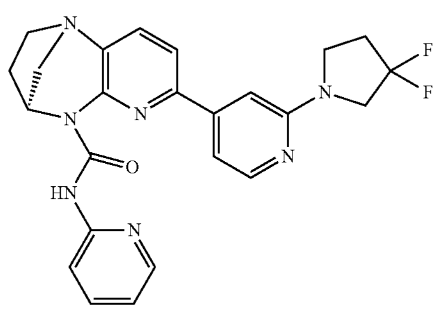 [SMILES: O=C(Nc1ccccn1)N1c2nc(-c3ccnc(N4CCC(F)(F)C4)c3)ccc2N2CC[C@H]1C2] | A | A |
| 389 | 497 | 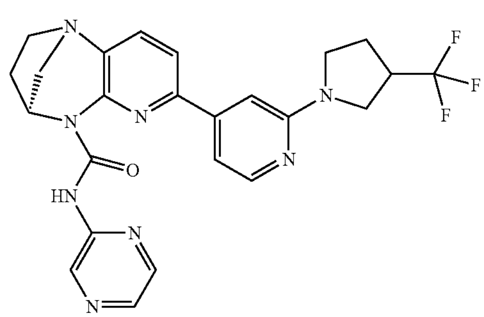 [SMILES: O=C(Nc1cnccn1)N1c2nc(-c3ccnc(N4CCC(C(F)(F)F)C4)c3)ccc2N2CC[C@H]1C2] | A | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 390 | 495 | 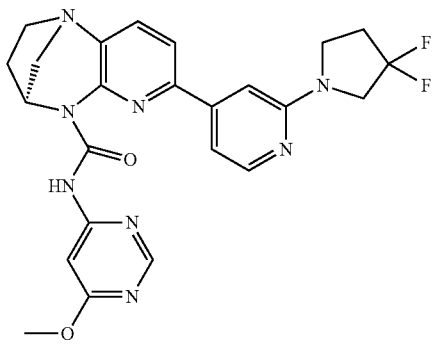 | B | A |
| 391 | 514 | 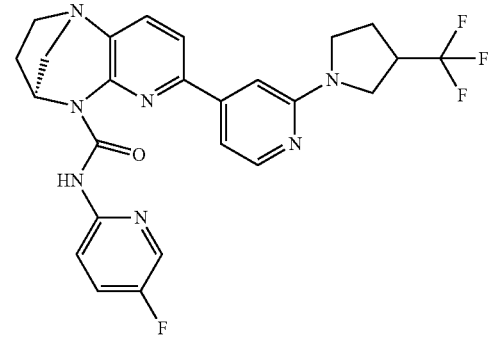 [SMILES: O=C(Nc1ccc(F)cn1)N1c2nc(-c3ccnc(N4CCC(C(F)(F)F)C4)c3)ccc2N2CC[C@H]1C2] | A | A |
| 392 | 441 | 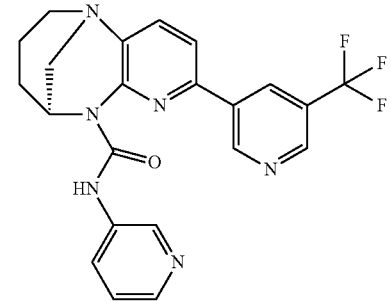 [SMILES: O=C(Nc1cccnc1)N1c2nc(-c3cncc(C(F)(F)F)c3)ccc2N2CCC[C@H]1C2] | A | A |
| 393 | 442 | 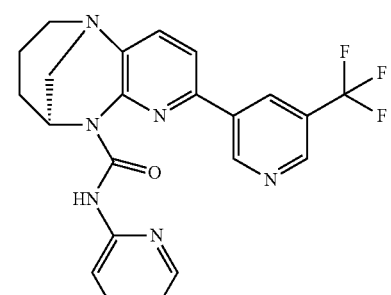 | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 394 | 472 | 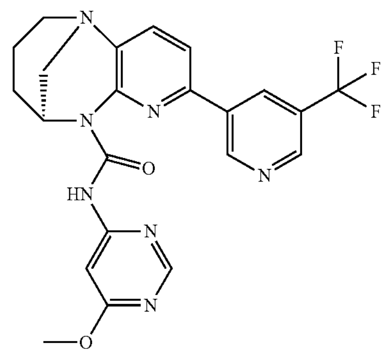 [SMILES: COc1cc(NC(=O)N2c3nc(-c4cncc(C(F)(F)F)c4)ccc3N3CCC[C@H]2C3)ncn1] | A | A |
| 395 | 362 | 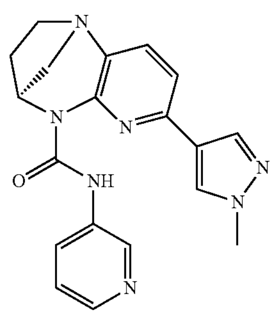 [SMILES: Cn1cc(-c2ccc3c(n2)N(C(=O)Nc2cccnc2)[C@H]2CCN3C2)cn1] | B | A |
| 396 | 423 | 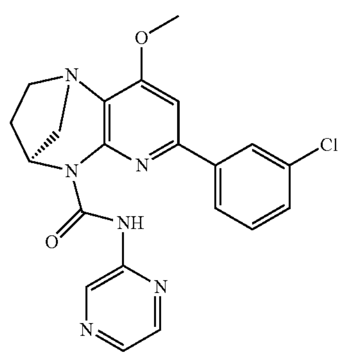 [SMILES: COc1cc(-c2cccc(Cl)c2)nc2c1N1CC[C@@H](C1)N2C(=O)Nc1cnccn1] | A | A |
| 397 | 395 | 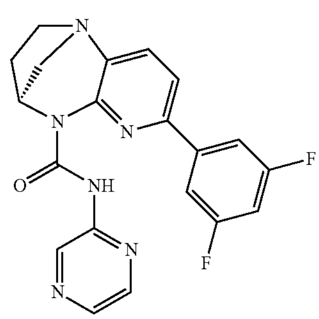 [SMILES: O=C(Nc1cnccn1)N1c2nc(-c3cc(F)cc(F)c3)ccc2N2CC[C@H]1C2] | C | A |

TABLE 1-continued
Compounds of Formula (I).
| Compound No. | [M + H]+$_{[calc]}$ | Structure | Tyrp AVG EC$_{1.5}$ (μM) | Tyrp % Fold Act |
|---|---|---|---|---|
| 398 | 421 | 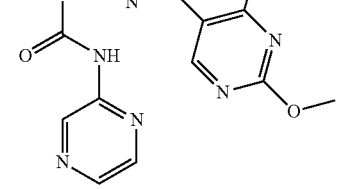 | B | A |
| 399 | 390 | 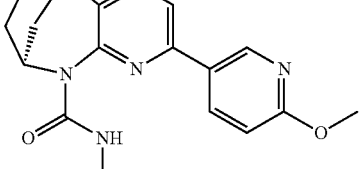 | B | A |
| 400 | 378 | 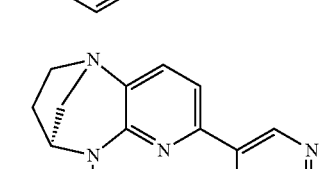 | B | A |
| 401 | 425 | 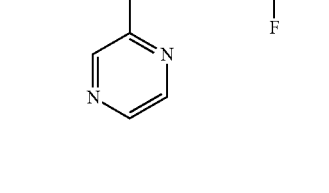 | A | A |

TABLE 1-continued
Compounds of Formula (I).
| Compound No. | [M + H]+_[calc] | Structure | Tyrp AVG EC_{1.5} (μM) | Tyrp % Fold Act |
|---|---|---|---|---|
| 402 | 441 | 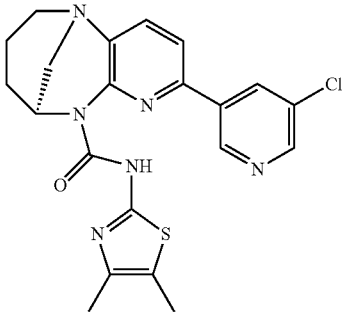 [SMILES: Cc1nc(NC(=O)N2c3nc(-c4cncc(Cl)c4)ccc3N3CCC[C@H]2C3)sc1C] | A | A |
| 403 | 416 | 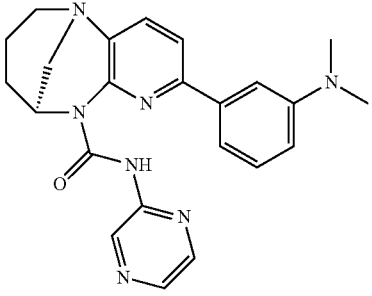 [SMILES: CN(C)c1cccc(-c2ccc3c(n2)N(C(=O)Nc2cnccn2)[C@H]2CCCN3C2)c1] | A | A |
| 404 | 422 | 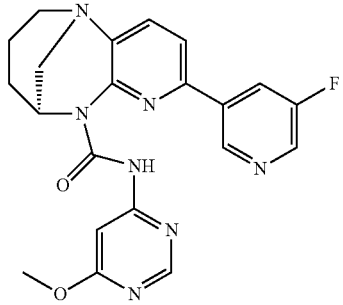 [SMILES: COc1cc(NC(=O)N2c3nc(-c4cncc(F)c4)ccc3N3CCC[C@H]2C3)ncn1] | A | A |
| 405 | 438 | 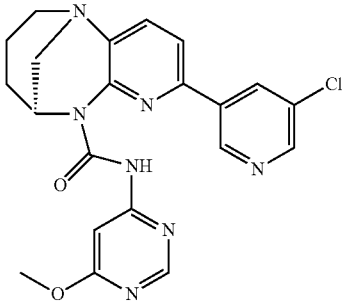 | A | A |

TABLE 1-continued

Compounds of Formula (I).

| Compound No. | [M + H]+[calc] | Structure | Tyrp AVG EC₁.₅ (μM) | Tyrp % Fold Act |
|---|---|---|---|---|
| 406 | 407 | 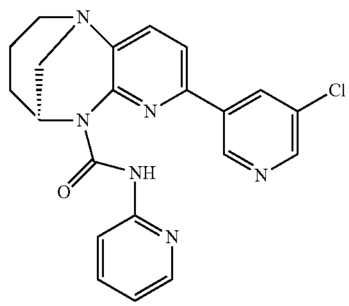 | A | A |
| 407 | 406 | 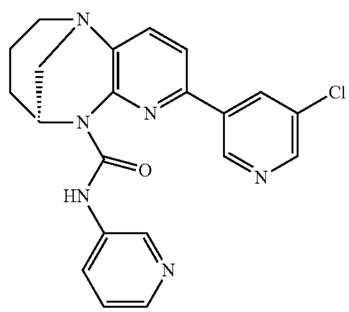 | A | A |
| 408 | 437 | 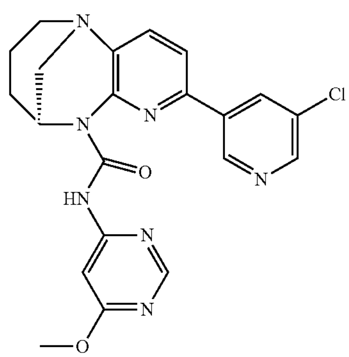 | A | A |
| 409 | 406 | 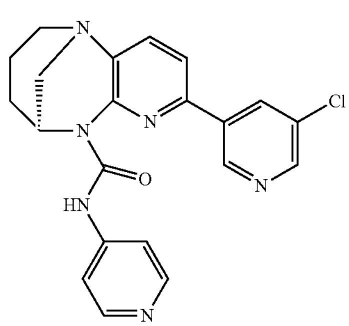 | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 410 | 514 | 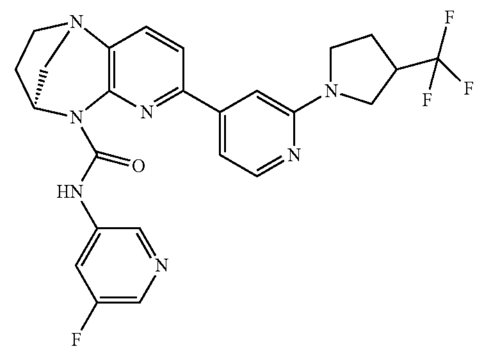 [SMILES: O=C(Nc1cncc(F)c1)N1c2nc(-c3ccnc(N4CCC(C(F)(F)F)C4)c3)ccc2N2CC[C@H]1C2] | A | A |
| 411 | 459 | 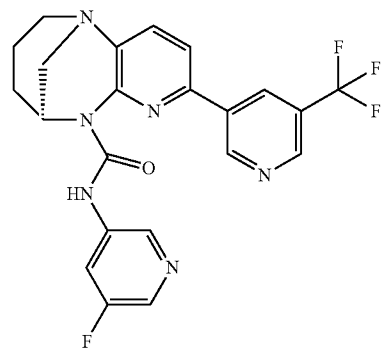 | A | A |
| 412 | 442 | 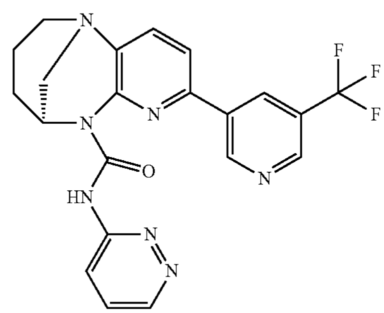 [SMILES: O=C(Nc1cccnn1)N1c2nc(-c3cncc(C(F)(F)F)c3)ccc2N2CCC[C@H]1C2] | A | A |
| 413 | 378 | 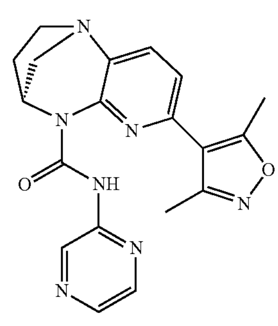 [SMILES: Cc1noc(C)c1-c1ccc2c(n1)N(C(=O)Nc1cnccn1)[C@H]1CCN2C1] | C | B |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 414 | 363 | 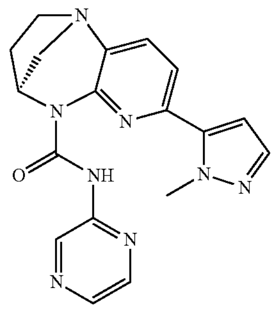 [SMILES: Cn1nccc1-c1ccc2c(n1)N(C(=O)Nc1cnccn1)[C@H]1CCN2C1] | B | A |
| 415 | 437 | 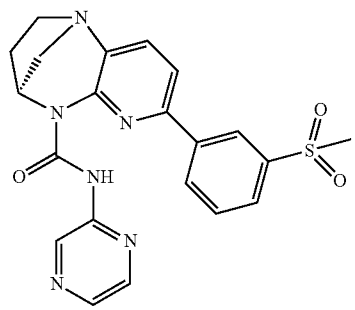 [SMILES: CS(=O)(=O)c1cccc(-c2ccc3c(n2)N(C(=O)Nc2cnccn2)[C@H]2CCN3C2)c1] | A | A |
| 416 | 413 | 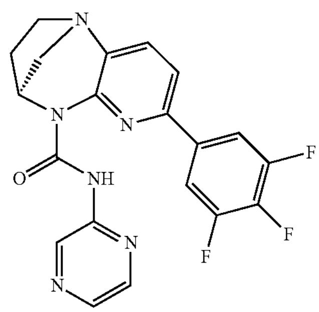 [SMILES: O=C(Nc1cnccn1)N1c2nc(-c3cc(F)c(F)c(F)c3)ccc2N2CC[C@H]1C2] | C | B |
| 417 | 408 | 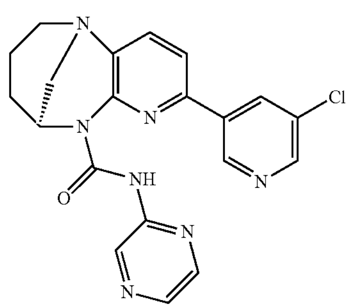 | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 418 | 452 | 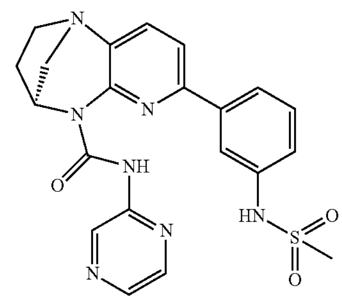 [SMILES: CS(=O)(=O)Nc1cccc(-c2ccc3c(n2)N(C(=O)Nc2cnccn2)[C@H]2CCN3C2)c1] | B | A |
| 419 | 402 | 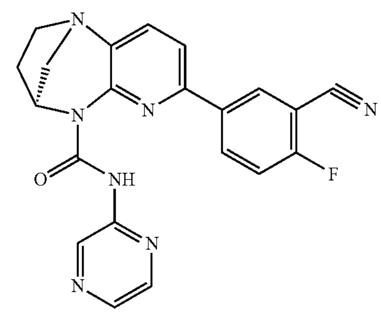 [SMILES: N#Cc1cc(-c2ccc3c(n2)N(C(=O)Nc2cnccn2)[C@H]2CCN3C2)ccc1F] | A | A |
| 420 | 395 | 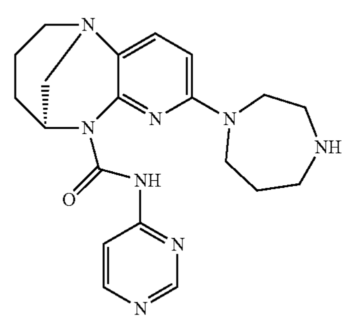 [SMILES: O=C(Nc1ccncn1)N1c2nc(N3CCCNCC3)ccc2N2CCC[C@H]1C2] | C | B |
| 421 | 424 | 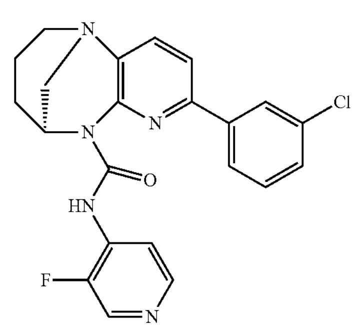 [SMILES: O=C(Nc1ccncc1F)N1c2nc(-c3cccc(Cl)c3)ccc2N2CCC[C@H]1C2] | A | A |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 422 | 446 | 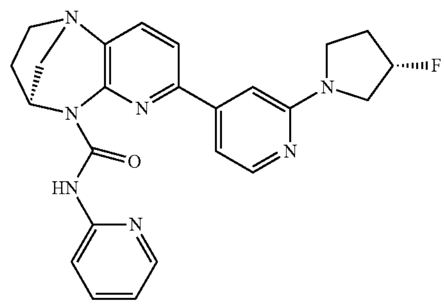 [SMILES: O=C(Nc1ccccn1)N1c2nc(-c3ccnc(N4CC[C@H](F)C4)c3)ccc2N2CC[C@H]1C2] | A | A |
| 423 | 465 | 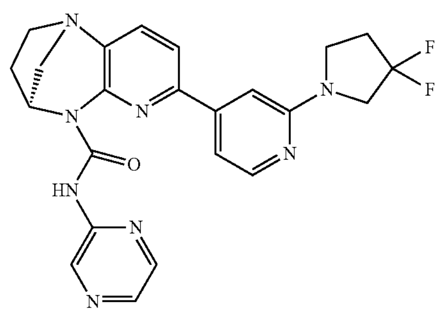 [SMILES: O=C(Nc1cnccn1)N1c2nc(-c3ccnc(N4CCC(F)(F)C4)c3)ccc2N2CC[C@H]1C2] | A | A |
| 424 | 477 | 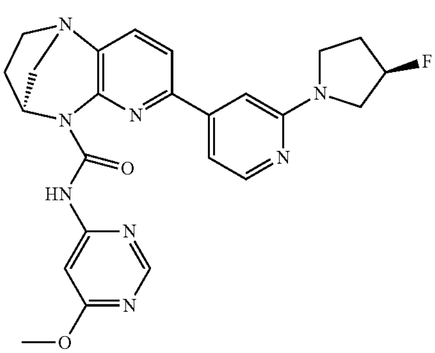 [SMILES: COc1cc(NC(=O)N2c3nc(-c4ccnc(N5CC[C@@H](F)C5)c4)ccc3N3CC[C@H]2C3)ncn1] | B | A |
| 425 | 482 | 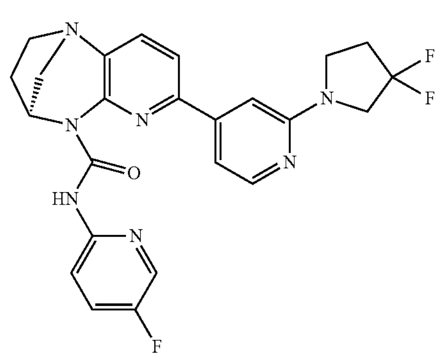 [SMILES: O=C(Nc1ccc(F)cn1)N1c2nc(-c3ccnc(N4CCC(F)(F)C4)c3)ccc2N2CC[C@H]1C2] | A | A |

TABLE 1-continued
Compounds of Formula (I).
| Compound No. | [M + H]+<sub>[calc]</sub> | Structure | Tyrp AVG EC<sub>1.5</sub> (μM) | Tyrp % Fold Act |
|---|---|---|---|---|
| 426 | 398 | 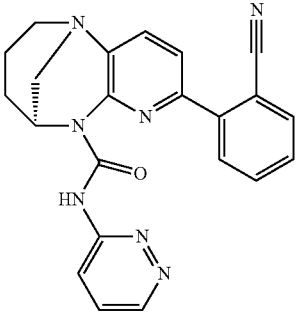 | B | A |
| 427 | 475 | 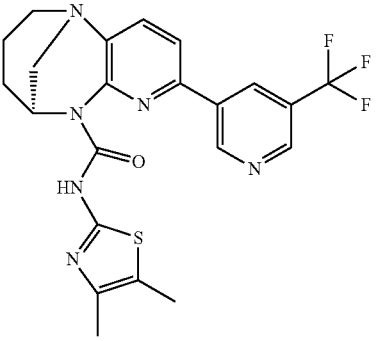 [SMILES: Cc1nc(NC(=O)N2c3nc(-c4cncc(C(F)(F)F)c4)ccc3N3CCC[C@H]2C3)sc1C] | A | A |
| 428 | 793 | 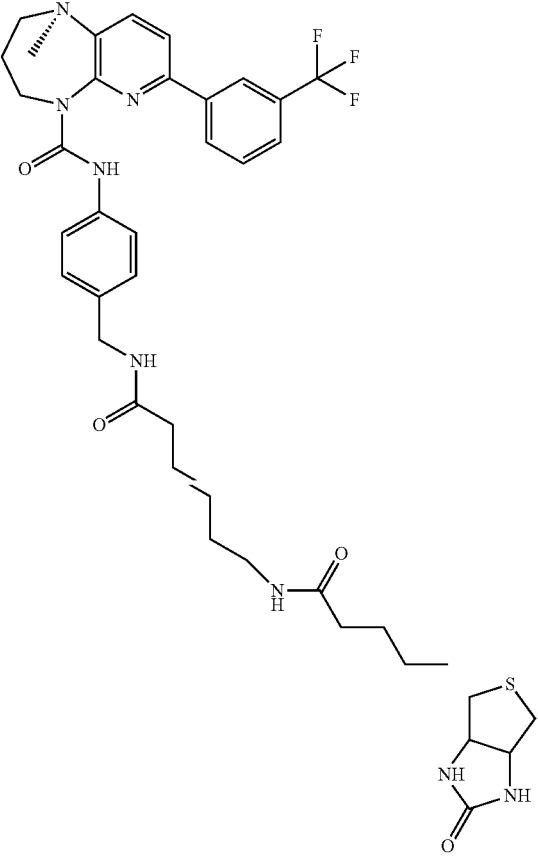 | A | A |

TABLE 1-continued

Compounds of Formula (I).

| Compound No. | [M + H]+$_{[calc]}$ | Structure | Tyrp AVG EC$_{1.5}$ (µM) | Tyrp % Fold Act |
|---|---|---|---|---|
| 429 | 454 | 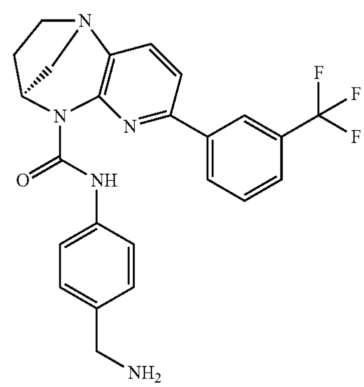 [SMILES: NCc1ccc(NC(=O)N2c3nc(-c4cccc(C(F)(F)F)c4)ccc3N3CC[C@H]2C3)cc1] | B | A |
| 430 | 807 | 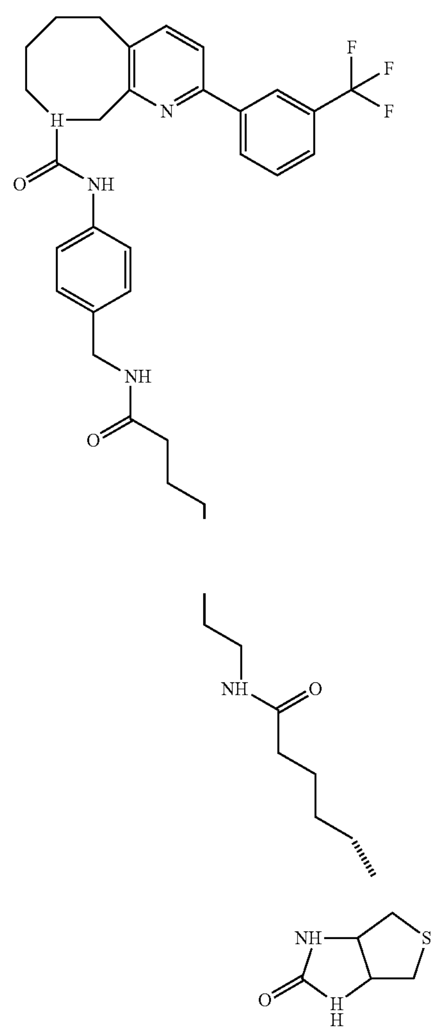 | A | A |

TABLE 1-continued

Compounds of Formula (I).

| Compound No. | [M + H]+<sub>[calc]</sub> | Structure | Tyrp AVG EC<sub>1.5</sub> (μM) | Tyrp % Fold Act |
|---|---|---|---|---|
| 431 | 409 | 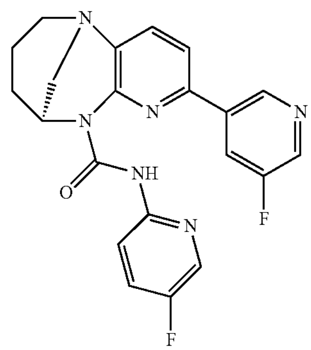 [SMILES: O=C(Nc1ccc(F)cn1)N1c2nc(-c3cncc(F)c3)ccc2N2CCC[C@H]1C2] | A | A |
| 432 | 392 | 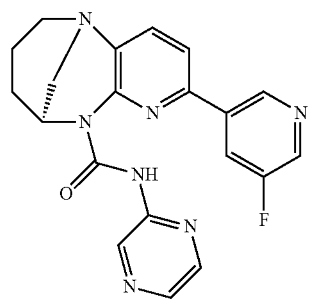 [SMILES: O=C(Nc1cnccn1)N1c2nc(-c3cncc(F)c3)ccc2N2CCC[C@H]1C2] | B | A |
| 433 | 473 | 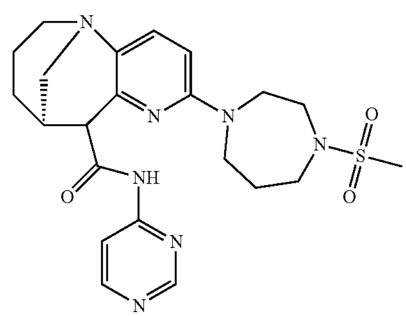 [SMILES: CS(=O)(=O)N1CCCN(c2ccc3c(n2)C(C(=O)Nc2ccncn2)[C@H]2CCCN3C2)CC1] | B | A |
| 434 | 437 | 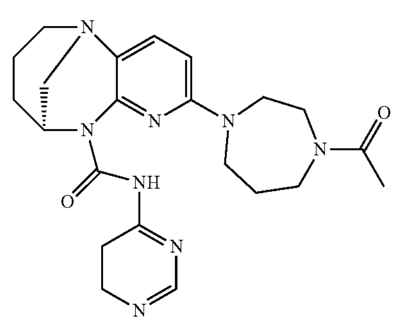 [SMILES: CC(=O)N1CCCN(c2ccc3c(n2)N(C(=O)NC2=NC=NCC2)[C@H]2CCCN3C2)CC1] | C | B |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 435 | 461 | 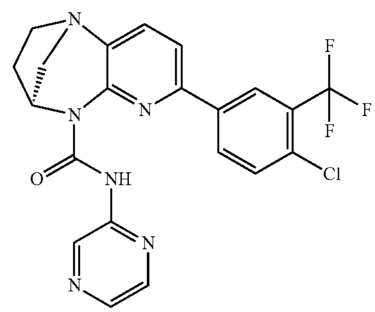 [SMILES: O=C(Nc1cnccn1)N1c2nc(-c3ccc(Cl)c(C(F)(F)F)c3)ccc2N2CC[C@H]1C2] | A | A |
| 436 | 447 | 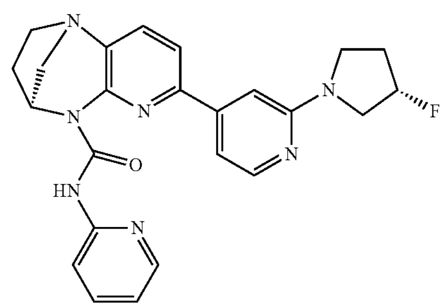 [SMILES: O=C(Nc1ccccn1)N1c2nc(-c3ccnc(N4CC[C@H](F)C4)c3)ccc2N2CC[C@H]1C2] | A | A |
| 437 | 477 | 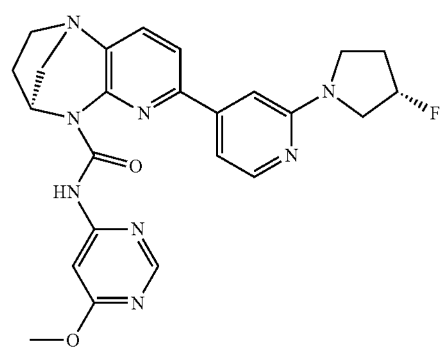 [SMILES: COc1cc(NC(=O)N2c3nc(-c4ccnc(N5CC[C@H](F)C5)c4)ccc3N3CC[C@H]2C3)ncn1] | B | A |
| 438 | 397 | 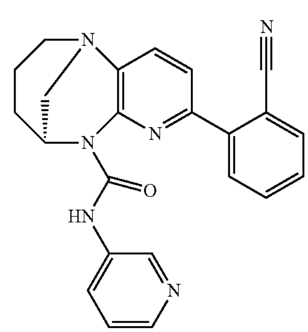 [SMILES: N#Cc1ccccc1-c1ccc2c(n1)N(C(=O)Nc1cccnc1)[C@H]1CCCN2C1] | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 439 | 415 | 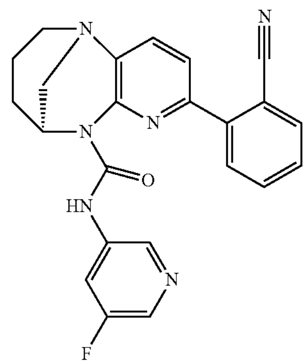 [SMILES: N#Cc1ccccc1-c1ccc2c(n1)N(C(=O)Nc1cncc(F)c1)[C@H]1CCCN2C1] | B | A |
| 440 | 428 | 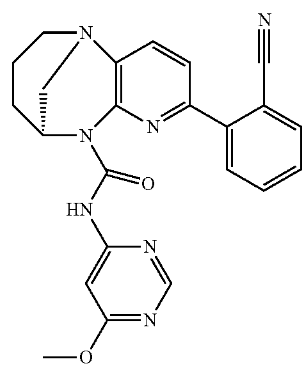 [SMILES: COc1cc(NC(=O)N2c3nc(-c4ccccc4C#N)ccc3N3CCC[C@H]2C3)ncn1] | C | B |
| 441 | 373 | 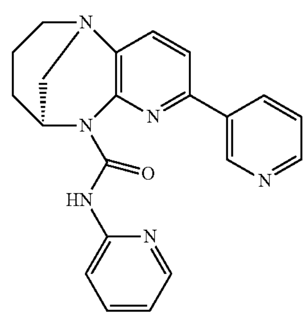 [SMILES: O=C(Nc1ccccn1)N1c2nc(-c3cccnc3)ccc2N2CCC[C@H]1C2] | B | A |
| 442 | 404 | 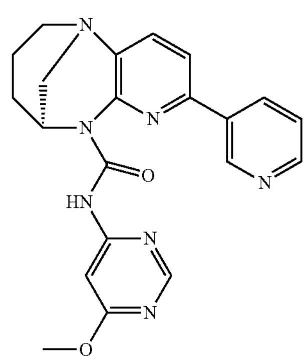 [SMILES: COc1cc(NC(=O)N2c3nc(-c4cccnc4)ccc3N3CCC[C@H]2C3)ncn1] | B | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 443 | 409 | 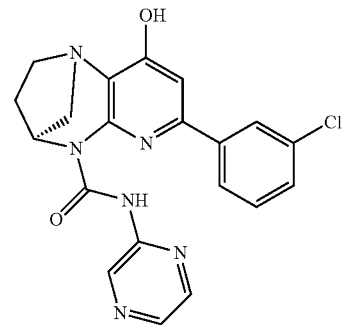 [SMILES: O=C(Nc1cnccn1)N1c2nc(-c3cccc(Cl)c3)cc(O)c2N2CC[C@H]1C2] | B | A |
| 444 (4) | 468 | 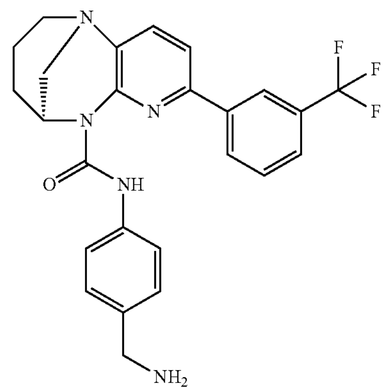 [SMILES: NCc1ccc(NC(=O)N2c3nc(-c4cccc(C(F)(F)F)c4)ccc3N3CCC[C@H]2C3)cc1] | A | A |
| 445 | 568 | 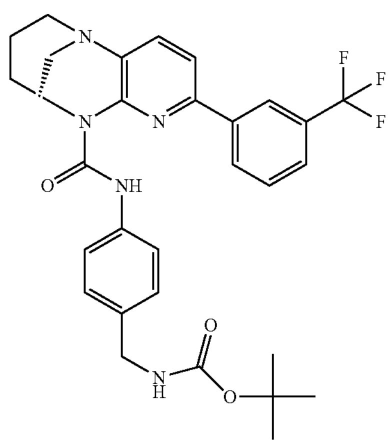 | A | A |
| 446 | 453 | 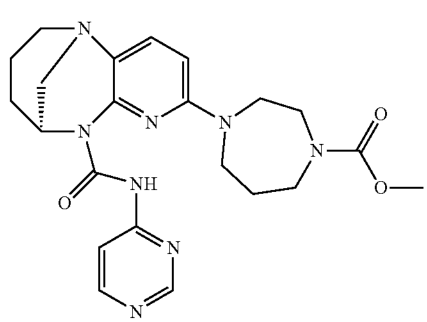 [SMILES: COC(=O)N1CCCN(c2ccc3c(n2)N(C(=O)Nc2ccncn2)[C@H]2CCCN3C2)CC1] | B | A |

TABLE 1-continued
Compounds of Formula (I).
| Compound No. | [M + H]+<sub>[calc]</sub> | Structure | Tyrp AVG EC<sub>1.5</sub> (μM) | Tyrp % Fold Act |
|---|---|---|---|---|
| 447 | 437 | 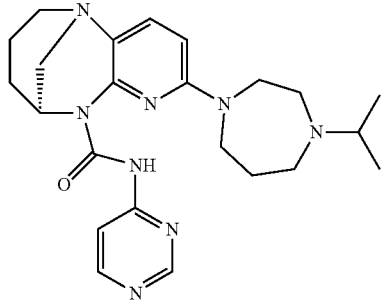 [SMILES: CC(C)N1CCCN(c2ccc3c(n2)N(C(=O)Nc2ccncn2)[C@H]2CCCN3C2)CC1] | C | B |
| 448 | 446 | 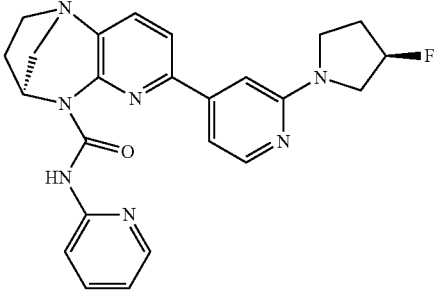 [SMILES: O=C(Nc1ccccn1)N1c2nc(-c3ccnc(N4CC[C@@H](F)C4)c3)ccc2N2CC[C@H]1C2] | B | A |
| 449 | 397 | 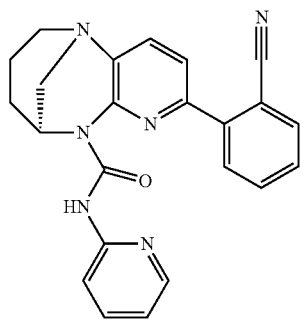 [SMILES: N#Cc1ccccc1-c1ccc2c(n1)N(C(=O)Nc1ccccn1)[C@H]1CCCN2C1] | B | A |
| 450 | 398 | 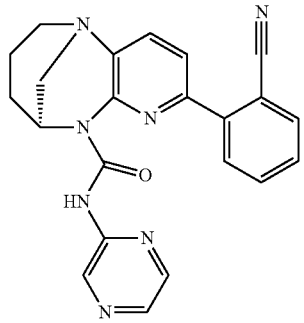 | B | A |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 451 | 398 | 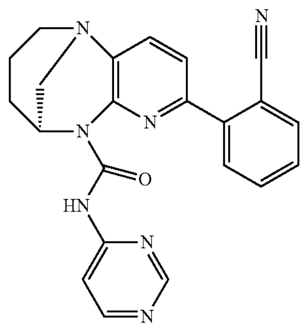 [SMILES: N#Cc1ccccc1-c1ccc2c(n1)N(C(=O)Nc1ccncn1)[C@H]1CCCN2C1] | B | A |
| 452 | 442 | 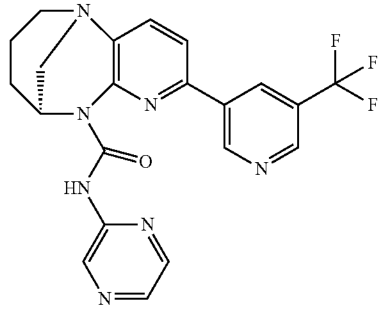 [SMILES: O=C(Nc1cnccn1)N1c2nc(-c3cncc(C(F)(F)F)c3)ccc2N2CCC[C@H]1C2] | A | A |
| 453 | 391 | 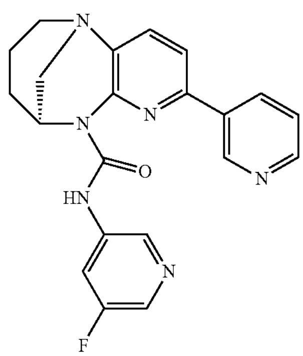 [SMILES: O=C(Nc1cncc(F)c1)N1c2nc(-c3cccnc3)ccc2N2CCC[C@H]1C2] | B | A |
| 454 | 374 | 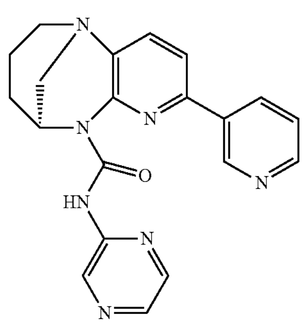 [SMILES: O=C(Nc1cnccn1)N1c2nc(-c3cccnc3)ccc2N2CCC[C@H]1C2] | B | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 455 | 373 | 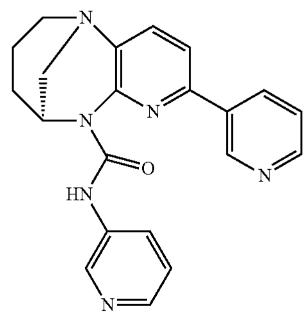 [SMILES: O=C(Nc1cccnc1)N1c2nc(-c3cccnc3)ccc2N2CCC[C@H]1C2] | B | A |
| 456 | 374 | 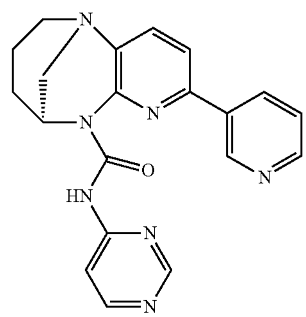 | B | A |
| 457 | 374 | 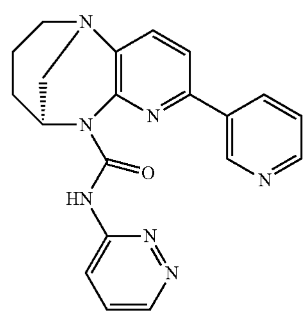 [SMILES: O=C(Nc1cccnn1)N1c2nc(-c3cccnc3)ccc2N2CCC[C@H]1C2] | B | A |
| 458 | 403 | 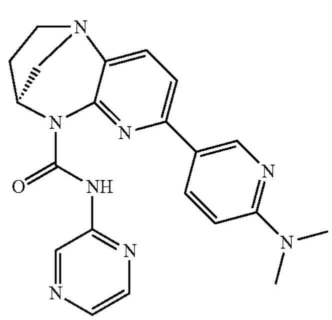 [SMILES: CN(C)c1ccc(-c2ccc3c(n2)N(C(=O)Nc2cnccn2)[C@H]2CCN3C2)cn1] | B | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 459 | 385 | 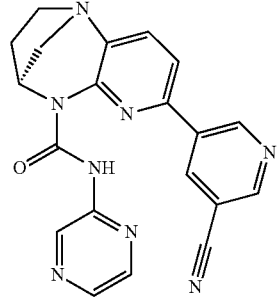 [SMILES: N#Cc1cncc(-c2ccc3c(n2)N(C(=O)Nc2cnccn2)[C@H]2CCN3C2)c1] | A | A |
| 460 | 508 | 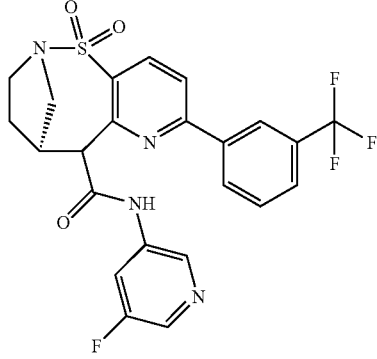 [SMILES: O=C(Nc1cncc(F)c1)C1c2nc(-c3cccc(C(F)(F)F)c3)ccc2S(=O)(=O)N2CC[C@H]1C2] | B | A |
| 461 | 427 | 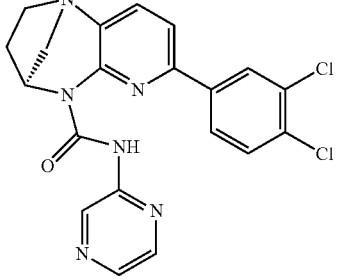 | A | A |
| 462 | 447 | 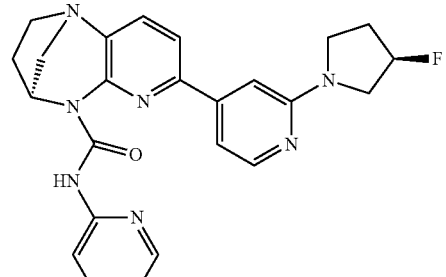 | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 463 | 464 | 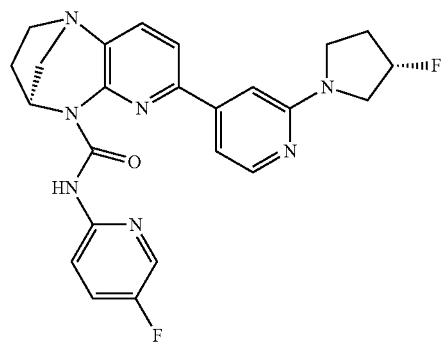 [SMILES: O=C(Nc1ccc(F)cn1)N1c2nc(-c3ccnc(N4CC[C@H](F)C4)c3)ccc2N2CC[C@H]1C2] | A | A |
| 464 | 464 | 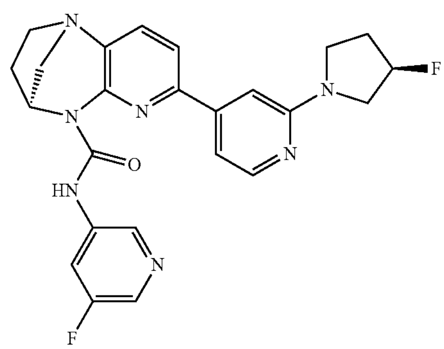 | B | A |
| 465 | 387 | 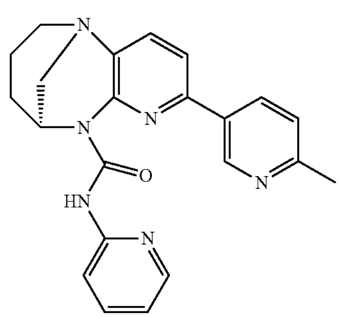 [SMILES: Cc1ccc(-c2ccc3c(n2)N(C(=O)Nc2ccccn2)[C@H]2CCCN3C2)cn1] | B | A |
| 466 | 407 | 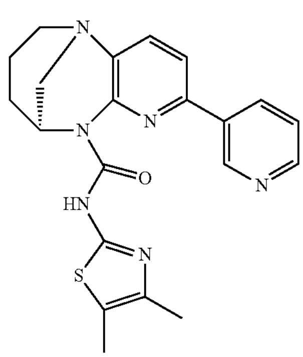 [SMILES: Cc1nc(NC(=O)N2c3nc(-c4cccnc4)ccc3N3CCC[C@H]2C3)sc1C] | B | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 467 | 388 | 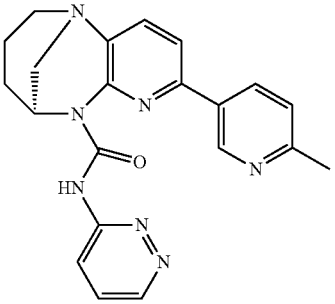 | B | A |
| 468 | 374 | 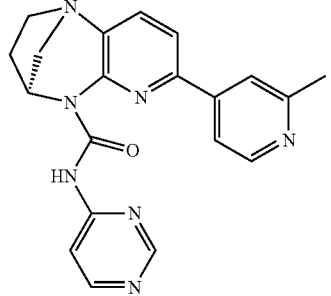 | B | A |
| 469 | 451 | 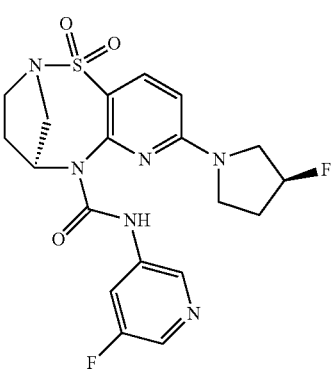 [SMILES: O=C(Nc1cncc(F)c1)N1c2nc(N3CC[C@H](F)C3)ccc2S(=O)(=O)N2CC[C@H]1C2] | C | B |
| 470 | 391 | 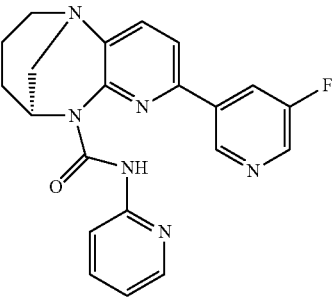 [SMILES: O=C(Nc1ccccn1)N1c2nc(-c3cncc(F)c3)ccc2N2CCC[C@H]1C2] | A | A |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 471 | 425 | 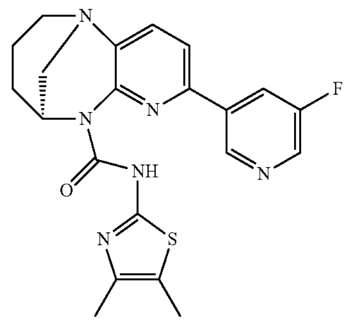 [SMILES: Cc1nc(NC(=O)N2c3nc(-c4cncc(F)c4)ccc3N3CCC[C@H]2C3)sc1C] | B | A |
| 472 | 441 | 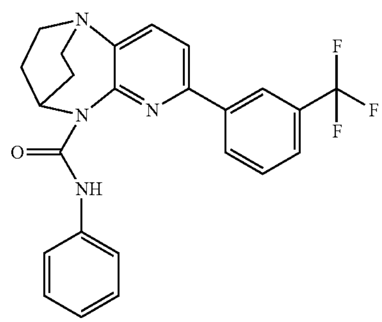 [SMILES: O=C(Nc1ccccc1)N1c2nc(-c3cccc(C(F)(F)F)c3)ccc2N2CCC1CC2] | A | A |
| 473 | 506 | 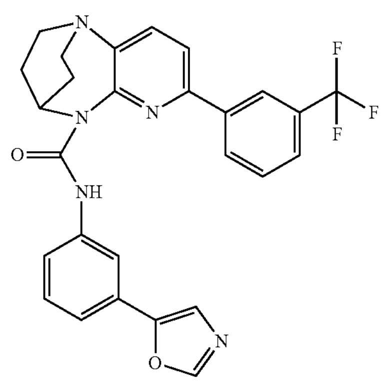 [SMILES: O=C(Nc1cccc(-c2cnco2)c1)N1c2nc(-c3cccc(C(F)(F)F)c3)ccc2N2CCC1CC2] | A | A |
| 474 | 464 | 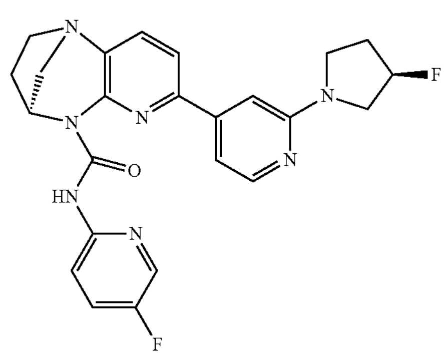 [SMILES: O=C(Nc1ccc(F)cn1)N1c2nc(-c3ccnc(N4CC[C@@H](F)C4)c3)ccc2N2CC[C@H]1C2] | A | A |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 475 | 464 | 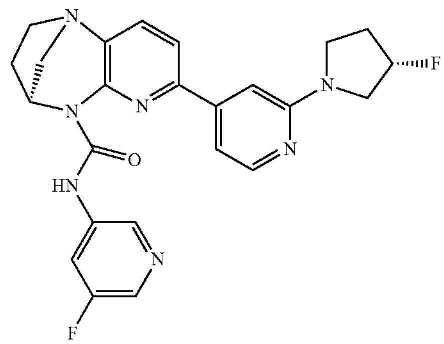 | A | A |
| 476 | 431 | 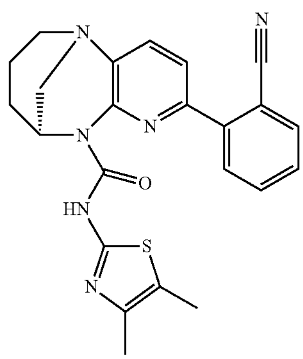 [SMILES: Cc1nc(NC(=O)N2c3nc(-c4ccccc4C#N)ccc3N3CCC[C@H]2C3)sc1C] | B | A |
| 477 | 405 | 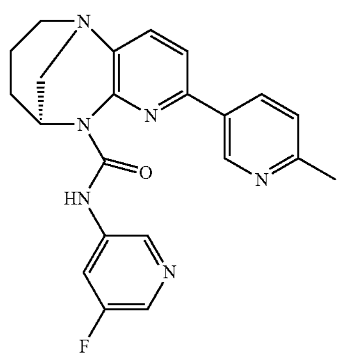 [SMILES: Cc1ccc(-c2ccc3c(n2)N(C(=O)Nc2cncc(F)c2)[C@H]2CCCN3C2)cn1] | B | A |
| 478 | 418 | 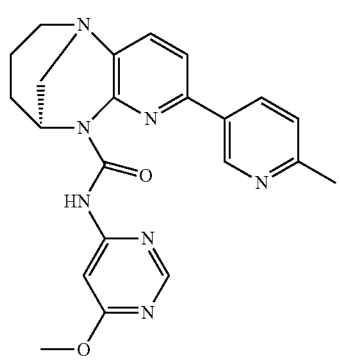 [SMILES: COc1cc(NC(=O)N2c3nc(-c4ccc(C)nc4)ccc3N3CCC[C@H]2C3)ncn1] | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 479 | 388 | 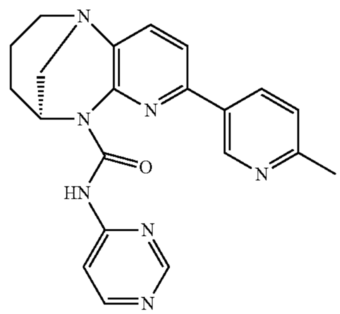 [SMILES: Cc1ccc(-c2ccc3c(n2)N(C(=O)Nc2ccncn2)[C@H]2CCCN3C2)cn1] | B | A |
| 480 | 439 | 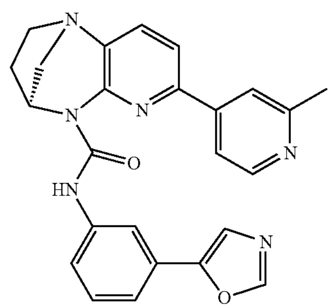 [SMILES: Cc1cc(-c2ccc3c(n2)N(C(=O)Nc2cccc(-c4cnco4)c2)[C@H]2CCN3C2)ccn1] | A | A |
| 481 | 407 | 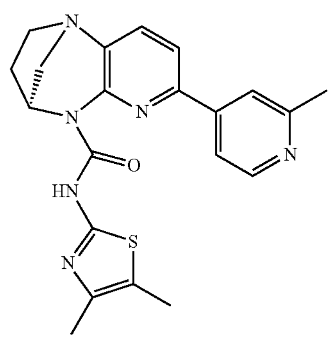 [SMILES: Cc1cc(-c2ccc3c(n2)N(C(=O)Nc2nc(C)c(C)s2)[C@H]2CCN3C2)ccn1] | A | A |
| 482 | 376 | 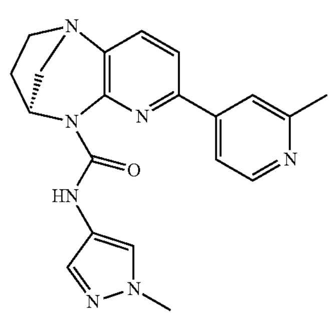 [SMILES: Cc1cc(-c2ccc3c(n2)N(C(=O)Nc2cnn(C)c2)[C@H]2CCN3C2)ccn1] | B | A |

TABLE 1-continued

Compounds of Formula (I).

| Compound No. | [M + H]+[calc] | Structure | Tyrp AVG EC1.5 (μM) | Tyrp % Fold Act |
|---|---|---|---|---|
| 483 | 426 | 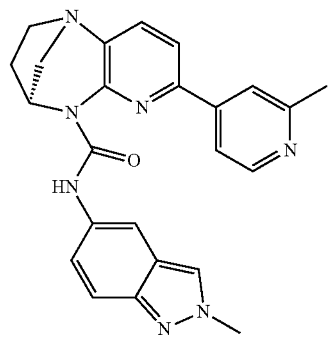 [SMILES: Cc1cc(-c2ccc3c(n2)N(C(=O)Nc2ccc4nn(C)cc4c2)[C@H]2CCN3C2)ccn1] | A | A |
| 484 | 409 | 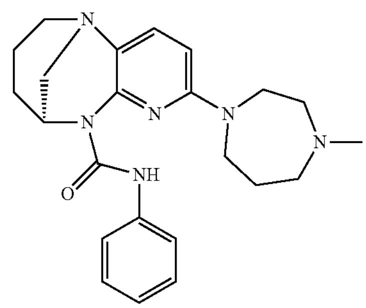 [SMILES: CN1CCCN(c2ccc3c(n2)N(C(=O)Nc2ccccc2)[C@H]2CCCN3C2)CC1] | C | B |
| 485 | 440 | 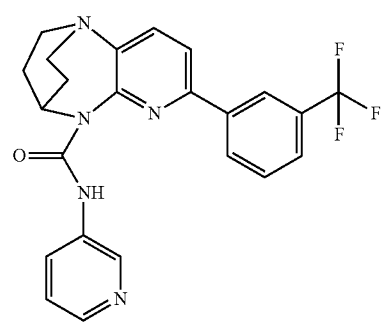 [SMILES: O=C(Nc1cccnc1)N1c2nc(-c3cccc(C(F)(F)F)c3)ccc2N2CCC1CC2] | A | A |
| 486 | 390 | 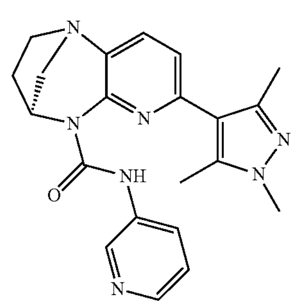 [SMILES: Cc1nn(C)c(C)c1-c1ccc2c(n1)N(C(=O)Nc1cccnc1)[C@H]1CCN2C1] | C | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 487 | 390 | 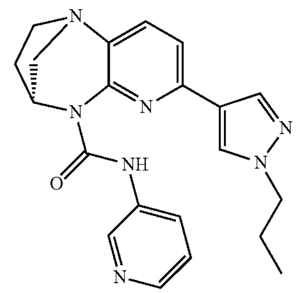 [SMILES: CCCn1cc(-c2ccc3c(n2)N(C(=O)Nc2cccnc2)[C@H]2CCN3C2)cn1] | B | A |
| 488 | 376 | 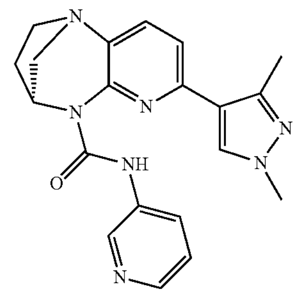 [SMILES: Cc1nn(C)cc1-c1ccc2c(n1)N(C(=O)Nc1cccnc1)[C@H]1CCN2C1] | B | A |
| 489 | 376 | 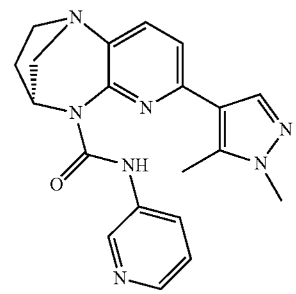 [SMILES: Cc1c(-c2ccc3c(n2)N(C(=O)Nc2cccnc2)[C@H]2CCN3C2)cnn1C] | B | A |
| 490 | 362 | 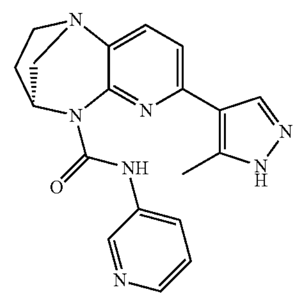 [SMILES: Cc1[nH]ncc1-c1ccc2c(n1)N(C(=O)Nc1cccnc1)[C@H]1CCN2C1] | B | A |
| 491 | 477 | 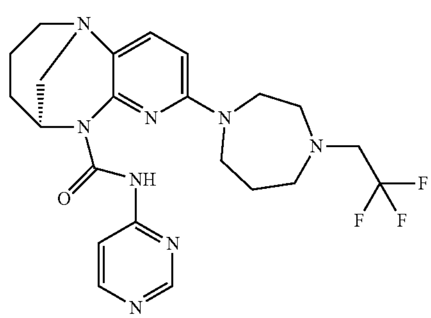 [SMILES: O=C(Nc1ccncn1)N1c2nc(N3CCCN(CC(F)(F)F)CC3)ccc2N2CCC[C@H]1C2] | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 492 | 458 | 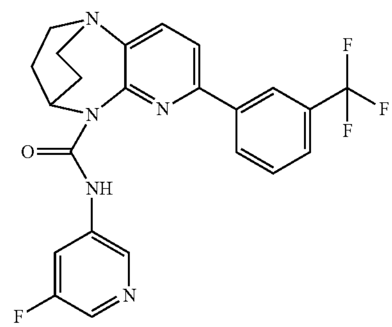 [SMILES: O=C(Nc1cncc(F)c1)N1c2nc(-c3cccc(C(F)(F)F)c3)ccc2N2CCC1CC2] | A | A |
| 493 | 348 | 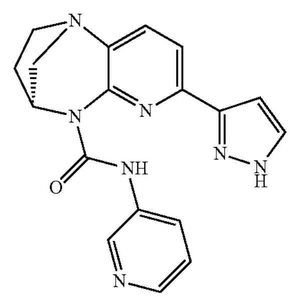 [SMILES: O=C(Nc1cccnc1)N1c2nc(-c3cc[nH]n3)ccc2N2CC[C@H]1C2] | B | A |
| 494 | 390 | 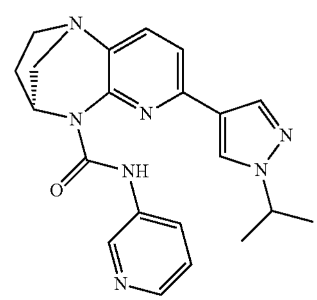 [SMILES: CC(C)n1cc(-c2ccc3c(n2)N(C(=O)Nc2cccnc2)[C@H]2CCN3C2)cn1] | B | A |
| 495 | 393 | 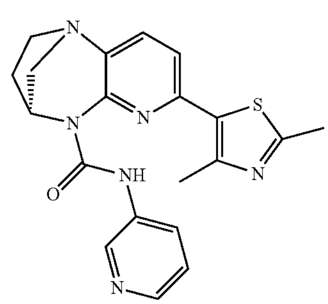 [SMILES: Cc1nc(C)c(-c2ccc3c(n2)N(C(=O)Nc2cccnc2)[C@H]2CCN3C2)s1] | B | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 496 | 406 | 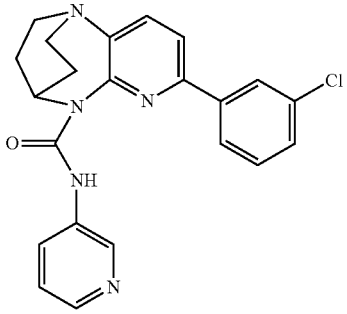 [SMILES: O=C(Nc1cccnc1)N1c2nc(-c3cccc(Cl)c3)ccc2N2CCC1CC2] | A | A |
| 497 | 472 | 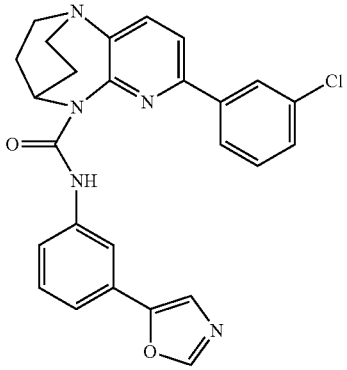 [SMILES: O=C(Nc1cccc(-c2cnco2)c1)N1c2nc(-c3cccc(Cl)c3)ccc2N2CCC1CC2] | A | A |
| 498 | 373 | 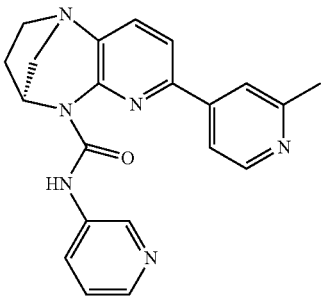 [SMILES: Cc1cc(-c2ccc3c(n2)N(C(=O)Nc2cccnc2)[C@H]2CCN3C2)ccn1] | A | A |
| 499 | 404 | 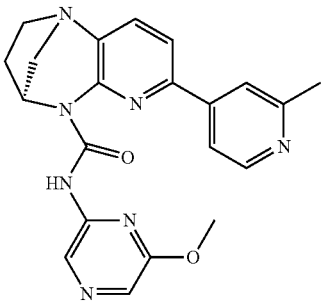 [SMILES: COc1cncc(NC(=O)N2c3nc(-c4ccnc(C)c4)ccc3N3CC[C@H]2C3)n1] | A | A |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 500 | 404 | 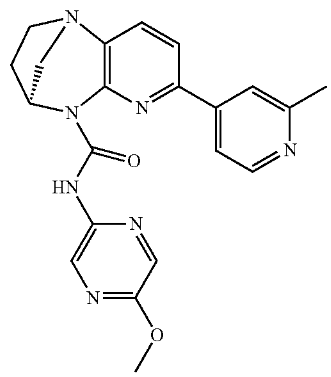 [SMILES: COc1cnc(NC(=O)N2c3nc(-c4ccnc(C)c4)ccc3N3CC[C@H]2C3)cn1] | A | A |
| 501 | 404 | 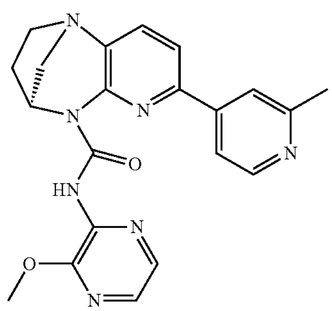 | B | A |
| 502 | 426 | 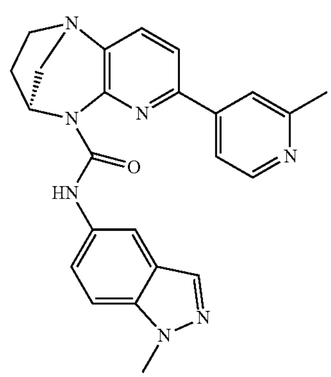 [SMILES: Cc1cc(-c2ccc3c(n2)N(C(=O)Nc2ccc4c(cnn4C)c2)[C@H]2CCN3C2)ccn1] | A | A |
| 503 | 388 | 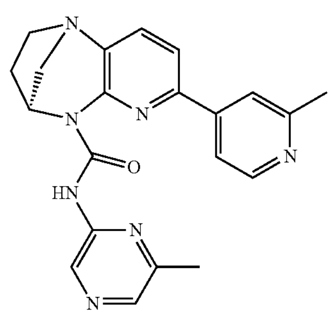 [SMILES: Cc1cc(-c2ccc3c(n2)N(C(=O)Nc2cncc(C)n2)[C@H]2CCN3C2)ccn1] | A | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 504 | 387 | 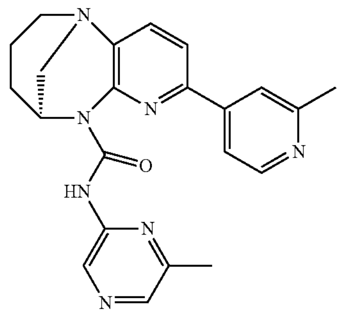 [SMILES: Cc1cc(-c2ccc3c(n2)N(C(=O)Nc2cncc(C)n2)[C@H]2CCCN3C2)ccn1] | A | A |
| 505 | 387 | 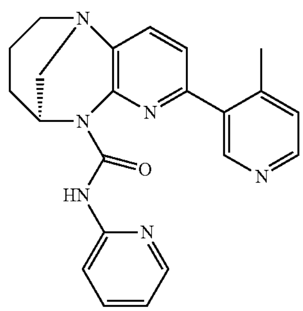 [SMILES: Cc1ccncc1-c1ccc2c(n1)N(C(=O)Nc1ccccn1)[C@H]1CCCN2C1] | C | B |
| 506 | 421 | 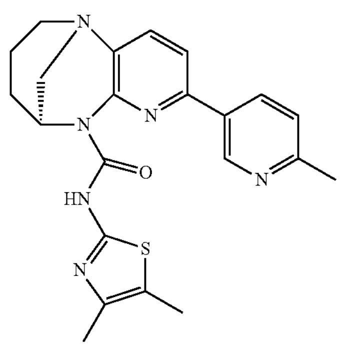 [SMILES: Cc1ccc(-c2ccc3c(n2)N(C(=O)Nc2nc(C)c(C)s2)[C@H]2CCCN3C2)cn1] | A | A |
| 507 | 421 | 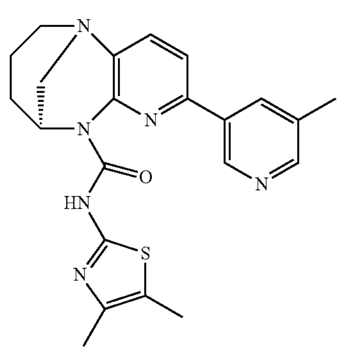 [SMILES: Cc1cncc(-c2ccc3c(n2)N(C(=O)Nc2nc(C)c(C)s2)[C@H]2CCCN3C2)c1] | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 508 | 421 | 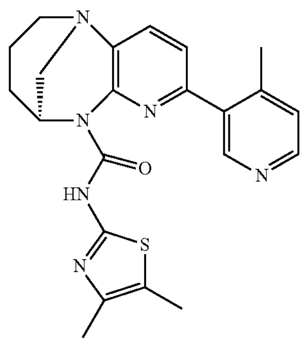 [SMILES: Cc1ccncc1-c1ccc2c(n1)N(C(=O)Nc1nc(C)c(C)s1)[C@H]1CCCN2C1] | C | A |
| 509 | 405 | 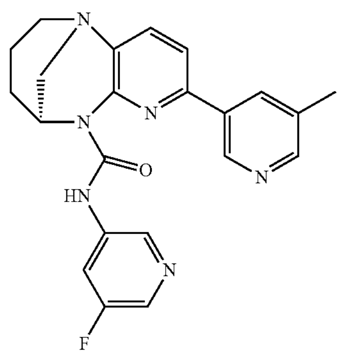 [SMILES: Cc1cncc(-c2ccc3c(n2)N(C(=O)Nc2cncc(F)c2)[C@H]2CCCN3C2)c1] | A | A |
| 510 | 405 | 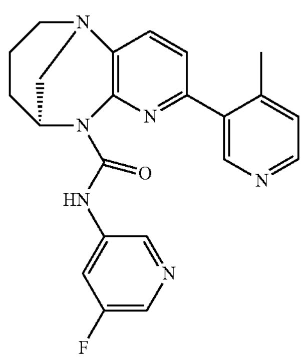 [SMILES: Cc1ccncc1-c1ccc2c(n1)N(C(=O)Nc1cncc(F)c1)[C@H]1CCCN2C1] | B | A |
| 511 | 418 | 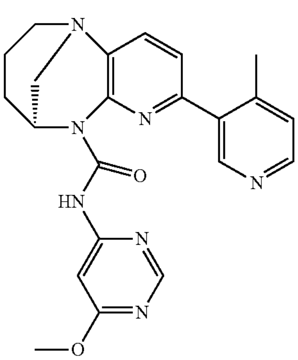 [SMILES: COc1cc(NC(=O)N2c3nc(-c4cnccc4C)ccc3N3CCC[C@H]2C3)ncn1] | C | B |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 512 | 388 | 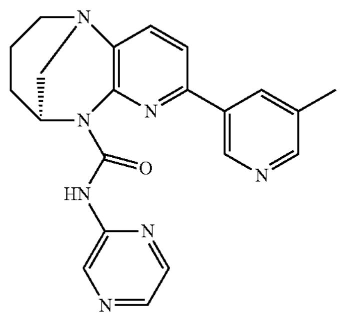 [SMILES: Cc1cncc(-c2ccc3c(n2)N(C(=O)Nc2cnccn2)[C@H]2CCCN3C2)c1] | B | A |
| 513 | 388 | 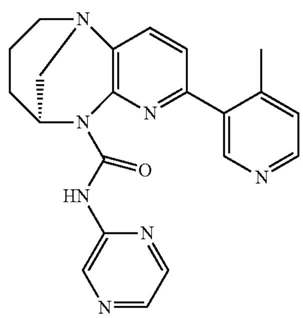 [SMILES: Cc1ccncc1-c1ccc2c(n1)N(C(=O)Nc1cnccn1)[C@H]1CCCN2C1] | C | A |
| 514 | 387 | 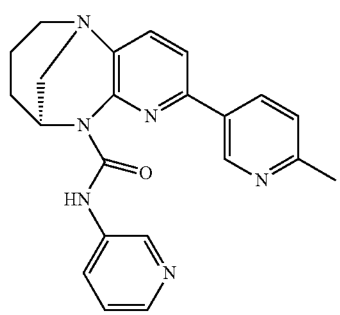 [SMILES: Cc1ccc(-c2ccc3c(n2)N(C(=O)Nc2cccnc2)[C@H]2CCCN3C2)cn1] | B | A |
| 515 | 387 | 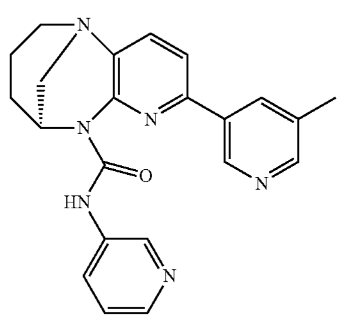 [SMILES: Cc1cncc(-c2ccc3c(n2)N(C(=O)Nc2cccnc2)[C@H]2CCCN3C2)c1] | A | A |

TABLE 1-continued
Compounds of Formula (I).
| Compound No. | [M + H]+_[calc] | Structure | Tyrp AVG EC_{1.5} (μM) | Tyrp % Fold Act |
|---|---|---|---|---|
| 516 | 387 | 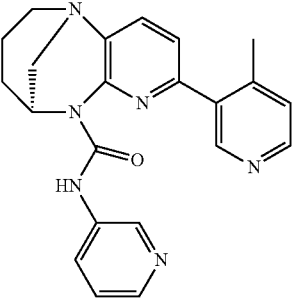 [SMILES: Cc1ccncc1-c1ccc2c(n1)N(C(=O)Nc1cccnc1)[C@H]1CCCN2C1] | B | A |
| 517 | 388 | 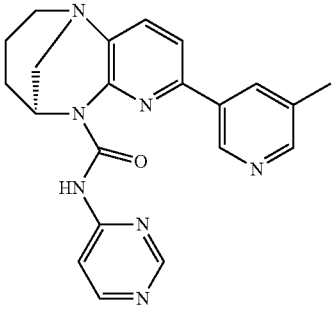 [SMILES: Cc1cncc(-c2ccc3c(n2)N(C(=O)Nc2ccncn2)[C@H]2CCCN3C2)c1] | A | A |
| 518 | 388 | 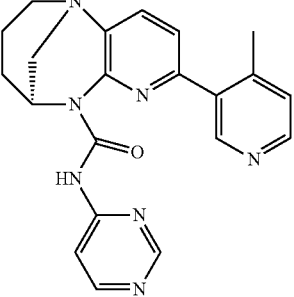 | C | B |
| 519 | 388 | 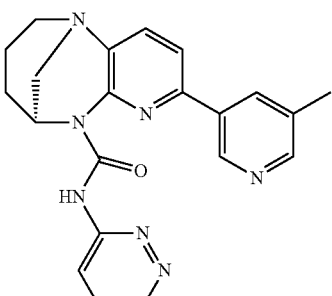 | A | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 520 | 388 | 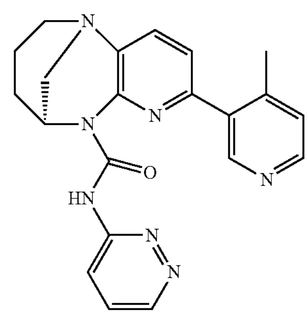 [SMILES: Cc1ccncc1-c1ccc2c(n1)N(C(=O)Nc1cccnn1)[C@H]1CCCN2C1] | C | A |
| 521 | 424 | 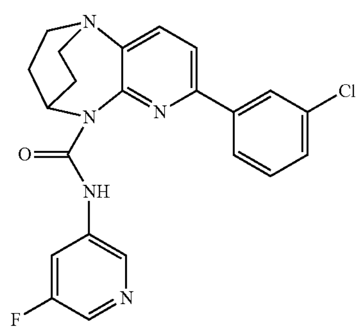 [SMILES: O=C(Nc1cncc(F)c1)N1c2nc(-c3cccc(Cl)c3)ccc2N2CCC1CC2] | B | A |
| 522 | 437 | 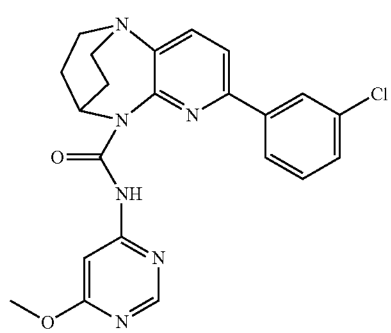 | B | A |
| 523 | 467 | 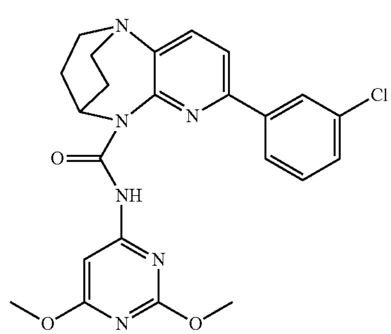 [SMILES: COc1cc(NC(=O)N2c3nc(-c4cccc(Cl)c4)ccc3N3CCC2CC3)nc(OC)n1] | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 524 | 362 | 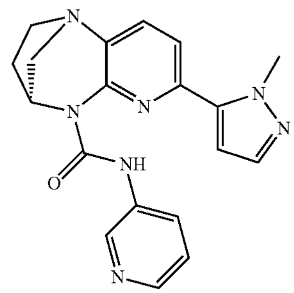 [SMILES: Cn1nccc1-c1ccc2c(n1)N(C(=O)Nc1cccnc1)[C@H]1CCN2C1] | B | A |
| 525 | 376 | 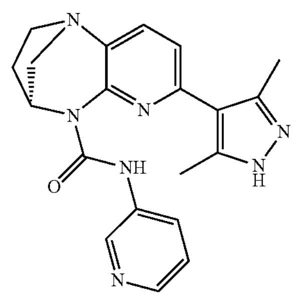 [SMILES: Cc1n[nH]c(C)c1-c1ccc2c(n1)N(C(=O)Nc1cccnc1)[C@H]1CCN2C1] | B | A |
| 526 | 393 | 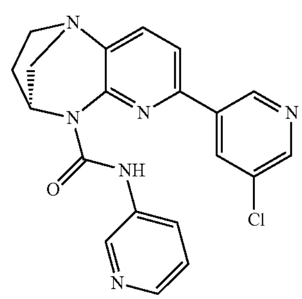 [SMILES: O=C(Nc1cccnc1)N1c2nc(-c3cncc(Cl)c3)ccc2N2CC[C@H]1C2] | A | A |
| 527 | 418 | 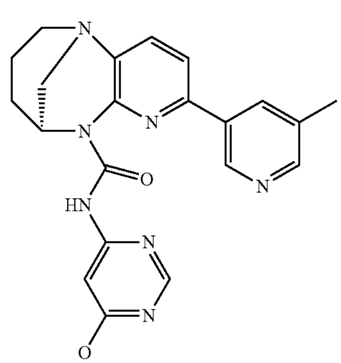 [SMILES: Cc1cncc(-c2ccc3c(n2)N(C(=O)Nc2cc(O)ncn2)[C@H]2CCCN3C2)c1] | A | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 528 | 488 | 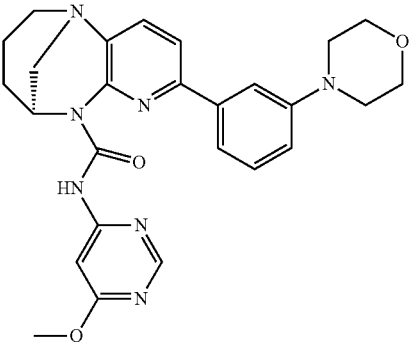 [SMILES: COc1cc(NC(=O)N2c3nc(-c4cccc(N5CCOCC5)c4)ccc3N3CCC[C@H]2C3)ncn1] | B | A |
| 529 | 458 | 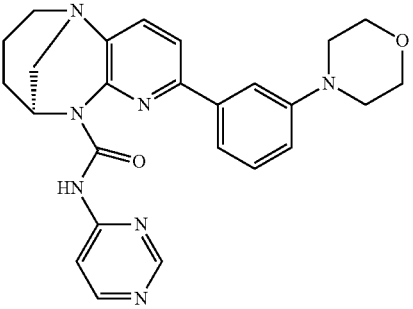 [SMILES: O=C(Nc1ccncn1)N1c2nc(-c3cccc(N4CCOCC4)c3)ccc2N2CCC[C@H]1C2] | B | A |
| 530 | 845 | 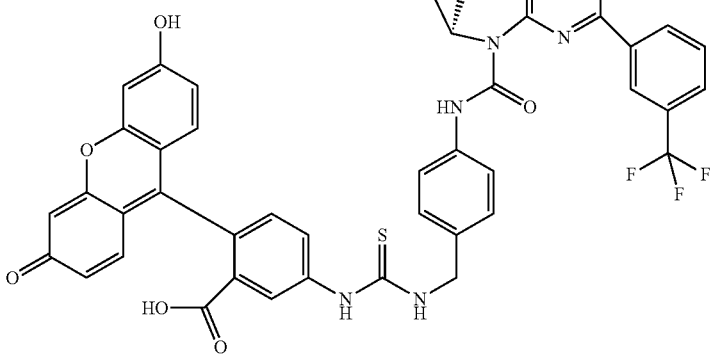 | A | A |
| 531 | 376 | 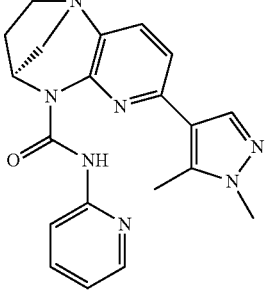 | B | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 532 | 377 | 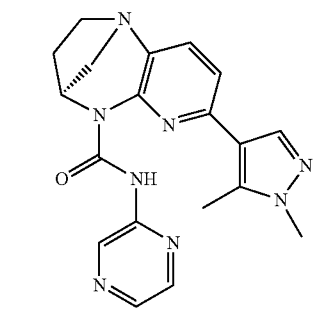 [SMILES: Cc1c(-c2ccc3c(n2)N(C(=O)Nc2ccccn2)[C@H]2CCN3C2)cnn1C] | B | A |
| 533 | 406 | 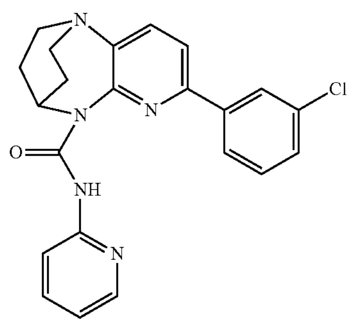 [SMILES: O=C(Nc1ccccn1)N1c2nc(-c3cccc(Cl)c3)ccc2N2CCC1CC2] | B | A |
| 534 | 407 | 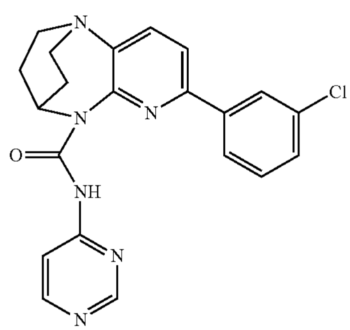 [SMILES: O=C(Nc1ccncn1)N1c2nc(-c3cccc(Cl)c3)ccc2N2CCC1CC2] | B | A |
| 535 | 416 | 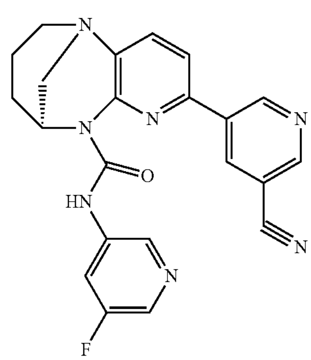 [SMILES: N#Cc1cncc(-c2ccc3c(n2)N(C(=O)Nc2cncc(F)c2)[C@H]2CCCN3C2)c1] | B | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 536 | 457 | 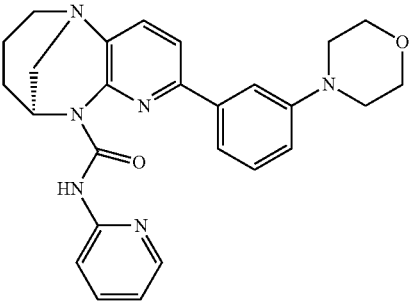 [SMILES: O=C(Nc1ccccn1)N1c2nc(-c3cccc(N4CCOCC4)c3)ccc2N2CCC[C@H]1C2] | B | A |
| 537 | 491 | 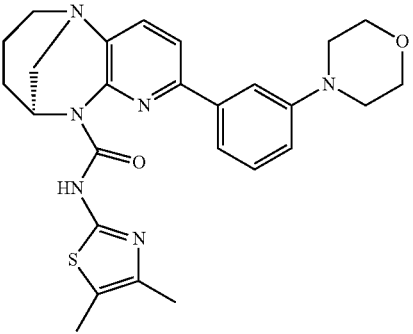 [SMILES: Cc1nc(NC(=O)N2c3nc(-c4cccc(N5CCOCC5)c4)ccc3N3CCC[C@H]2C3)sc1C] | B | A |
| 538 | 457 | 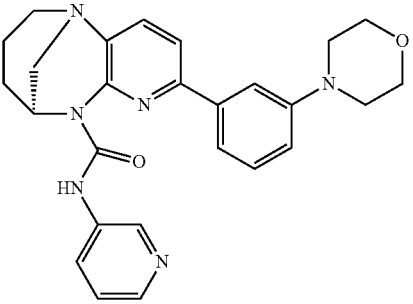 [SMILES: O=C(Nc1cccnc1)N1c2nc(-c3cccc(N4CCOCC4)c3)ccc2N2CCC[C@H]1C2] | A | A |
| 539 | 458 | 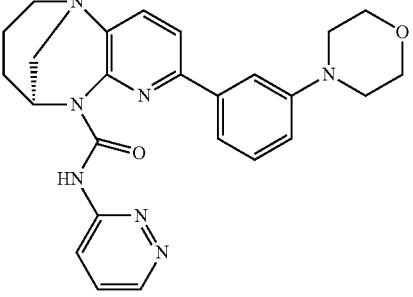 | B | A |

TABLE 1-continued

Compounds of Formula (I).

| Compound No. | [M + H]+<sub>[calc]</sub> | Structure | Tyrp AVG EC<sub>1.5</sub> (μM) | Tyrp % Fold Act |
|---|---|---|---|---|
| 540 | 518 | 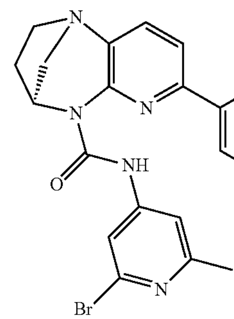 | A | A |
| 541 | 504 | 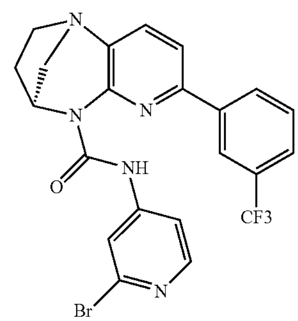 [SMILES: O=C(Nc1ccnc(Br)c1)N1c2nc(-c3cccc(C(F)(F)F)c3)ccc2N2CC[C@H]1C2] | A | A |
| 542 | 504 | 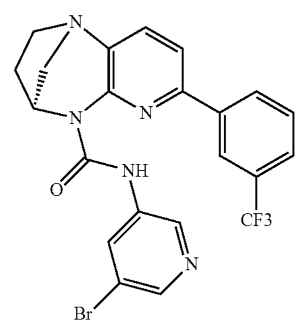 | A | A |
| 543 | 407 | 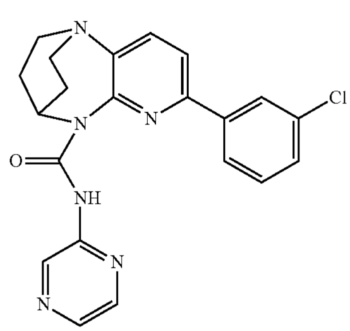 [SMILES: O=C(Nc1cnccn1)N1c2nc(-c3cccc(Cl)c3)ccc2N2CCC1CC2] | B | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 544 | 407 | 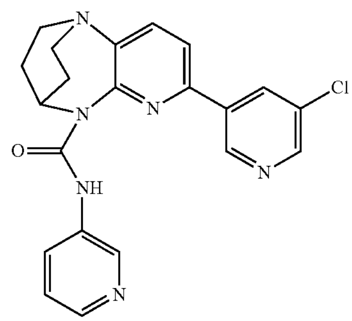 [SMILES: O=C(Nc1cccnc1)N1c2nc(-c3cncc(Cl)c3)ccc2N2CCC1CC2] | B | A |
| 545 | 425 | 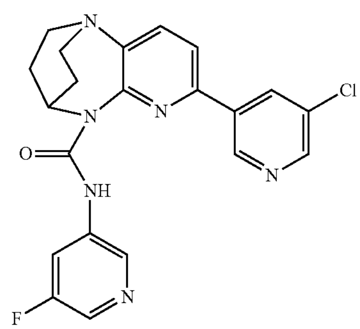 [SMILES: O=C(Nc1cncc(F)c1)N1c2nc(-c3cncc(Cl)c3)ccc2N2CCC1CC2] | B | A |
| 546 (3) | 939 | 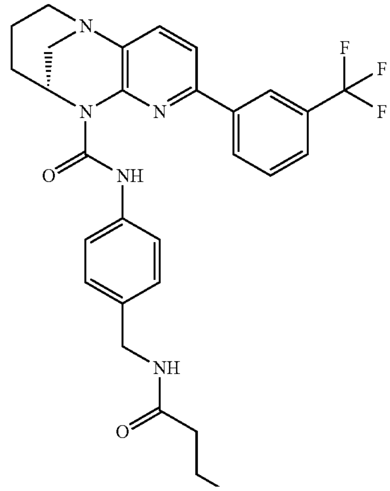 | B | B |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 547 | 925 | 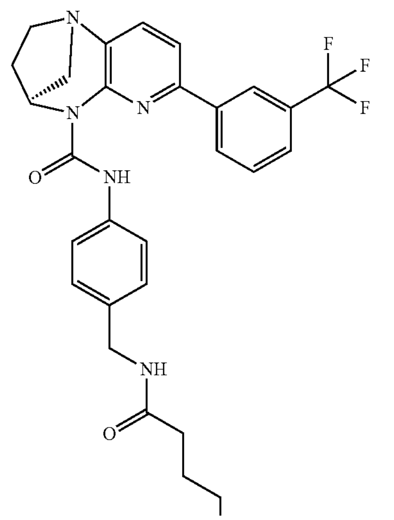 | C | B |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 548 | 564 | 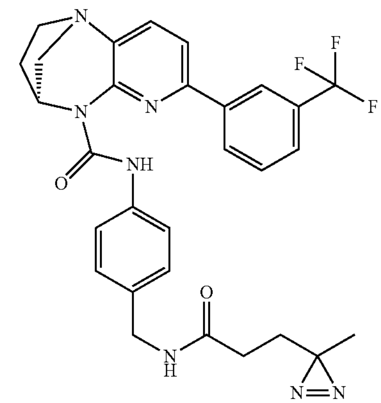 [SMILES: CC1(CCC(=O)NCc2ccc(NC(=O)N3c4nc(-c5cccc(C(F)(F)F)c5)ccc4N4CC[C@H]3C4)cc2)N=N1] | B | A |
| 549 | 424 | 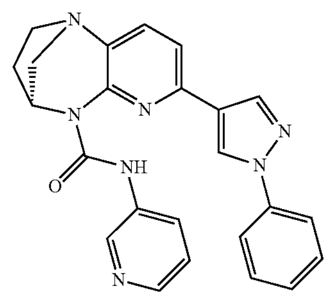 [SMILES: O=C(Nc1cccnc1)N1c2nc(-c3cnn(-c4ccccc4)c3)ccc2N2CC[C@H]1C2] | B | A |
| 550 | 408 | 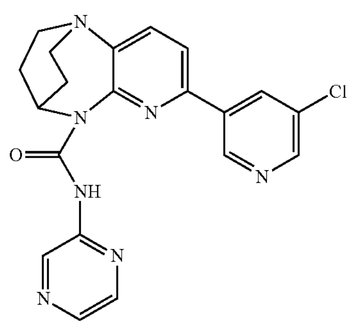 [SMILES: O=C(Nc1cnccn1)N1c2nc(-c3cncc(Cl)c3)ccc2N2CCC1CC2] | B | A |
| 551 | 407 | 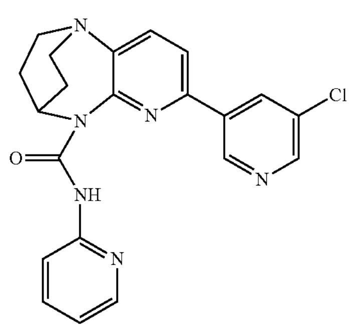 [SMILES: O=C(Nc1ccccn1)N1c2nc(-c3cncc(Cl)c3)ccc2N2CCC1CC2] | B | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 552 | 438 | 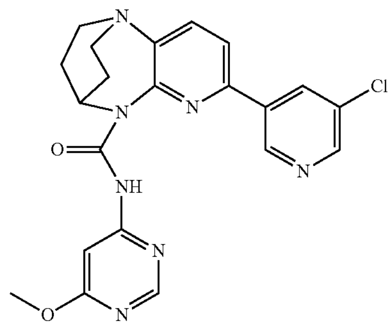 [SMILES: COc1cc(NC(=O)N2c3nc(-c4cncc(Cl)c4)ccc3N3CCC2CC3)ncn1] | C | B |
| 553 | 468 | 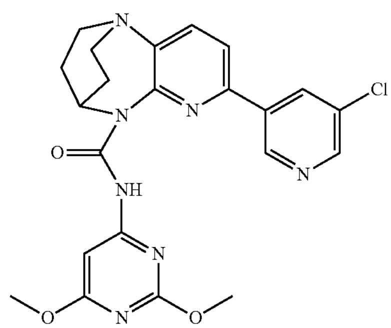 [SMILES: COc1cc(NC(=O)N2c3nc(-c4cncc(Cl)c4)ccc3N3CCC2CC3)nc(OC)n1] | B | A |
| 554 | 441 | 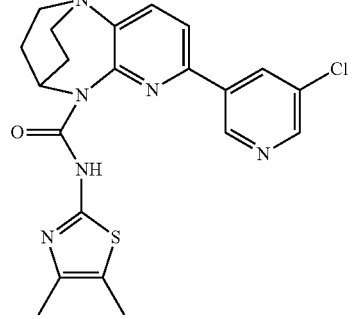 | B | A |
| 555 | 392 | 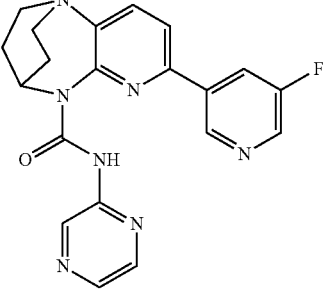 | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 556 | 427 | 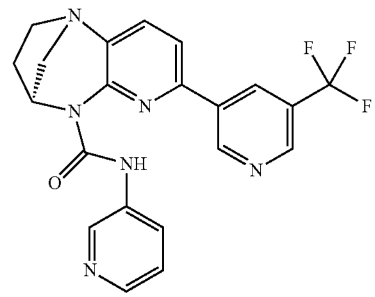 [SMILES: O=C(Nc1cccnc1)N1c2nc(-c3cncc(C(F)(F)F)c3)ccc2N2CC[C@H]1C2] | A | A |
| 557 | 398 | 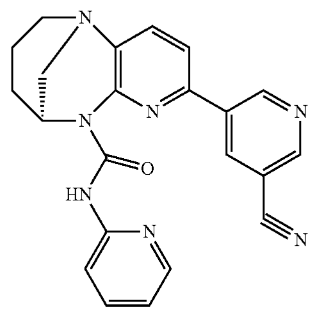 [SMILES: N#Cc1cncc(-c2ccc3c(n2)N(C(=O)Nc2ccccn2)[C@H]2CCCN3C2)c1] | A | A |
| 558 | 399 | 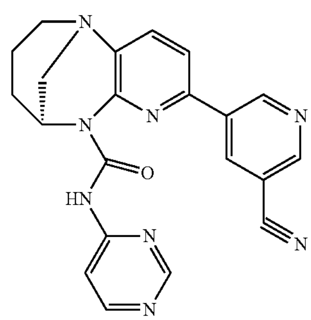 [SMILES: N#Cc1cncc(-c2ccc3c(n2)N(C(=O)Nc2ccncn2)[C@H]2CCCN3C2)c1] | B | A |
| 559 | 475 | 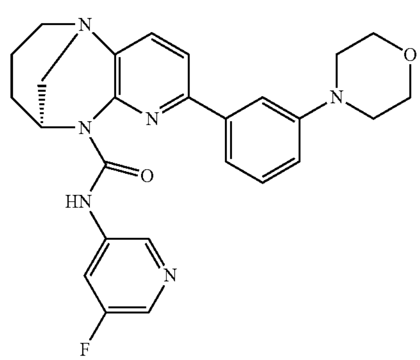 [SMILES: O=C(Nc1cncc(F)c1)N1c2nc(-c3cccc(N4CCOCC4)c3)ccc2N2CCC[C@H]1C2] | A | A |

TABLE 1-continued
Compounds of Formula (I).
| Compound No. | [M + H]+$_{[calc]}$ | Structure | Tyrp AVG EC$_{1.5}$ (μM) | Tyrp % Fold Act |
|---|---|---|---|---|
| 560 | 458 | 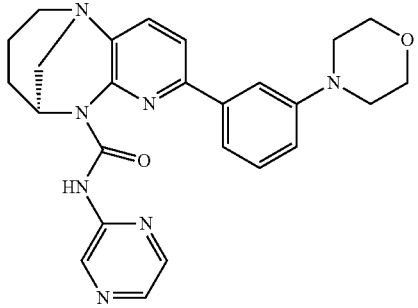 [SMILES: O=C(Nc1cnccn1)N1c2nc(-c3cccc(N4CCOCC4)c3)ccc2N2CCC[C@H]1C2] | B | A |
| 561 | 464 | 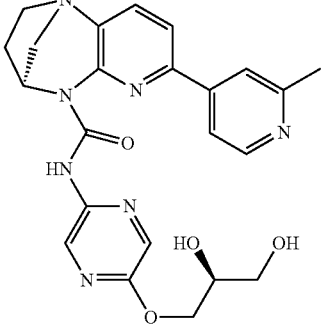 | B | A |
| 562 | 570 | 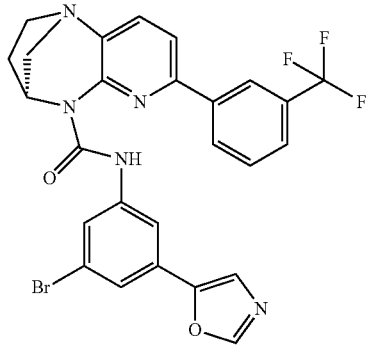 [SMILES: O=C(Nc1cc(Br)cc(-c2cnco2)c1)N1c2nc(-c3cccc(C(F)(F)F)c3)ccc2N2CC[C@H]1C2] | A | A |
| 563 | 857 | | A | A |
| 565 | 823 | | NT | NT |
| 569 | 440 | 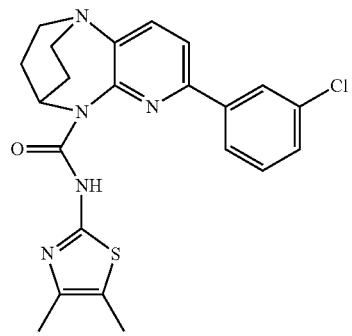 [SMILES: Cc1nc(NC(=O)N2c3nc(-c4cccc(Cl)c4)ccc3N3CCC2CC3)sc1C] | B | A |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 570 | 391 | 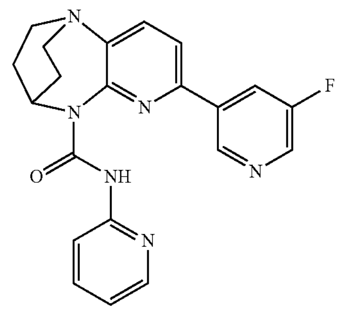 [SMILES: O=C(Nc1ccccn1)N1c2nc(-c3cncc(F)c3)ccc2N2CCC1CC2] | B | A |
| 571 | 409 | 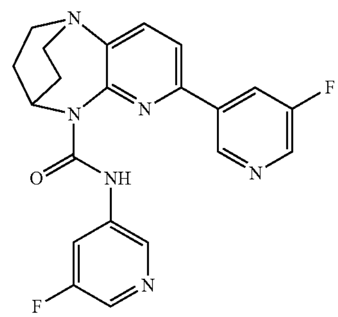 [SMILES: O=C(Nc1cncc(F)c1)N1c2nc(-c3cncc(F)c3)ccc2N2CCC1CC2] | B | A |
| 572 | 391 | 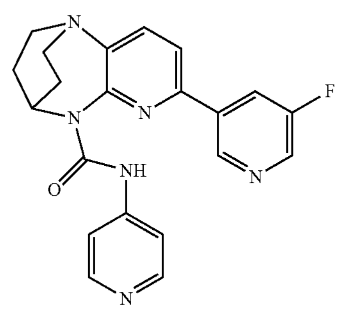 [SMILES: O=C(Nc1ccncc1)N1c2nc(-c3cncc(F)c3)ccc2N2CCC1CC2] | B | A |
| 573 | 392 | 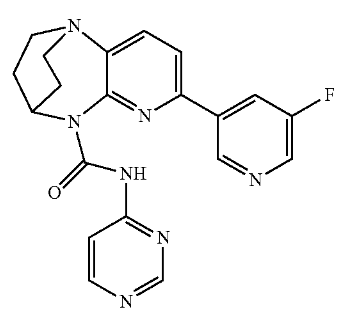 [SMILES: O=C(Nc1ccncn1)N1c2nc(-c3cncc(F)c3)ccc2N2CCC1CC2] | C | B |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 574 | 457 | 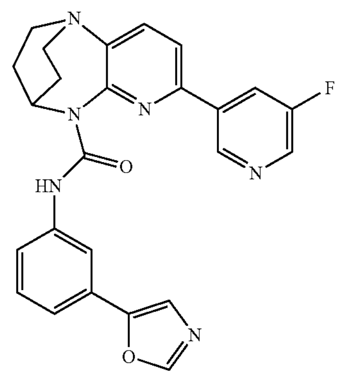 [SMILES: O=C(Nc1cccc(-c2cnco2)c1)N1c2nc(-c3cncc(F)c3)ccc2N2CCC1CC2] | A | A |
| 575 | 473 | 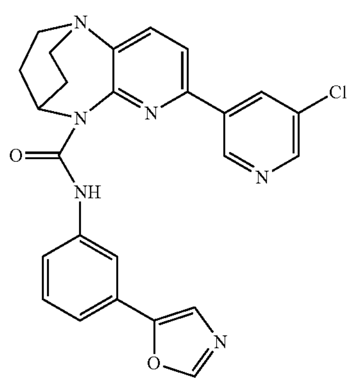 [SMILES: O=C(Nc1cccc(-c2cnco2)c1)N1c2nc(-c3cncc(Cl)c3)ccc2N2CCC1CC2] | A | A |
| 576 | 408 | 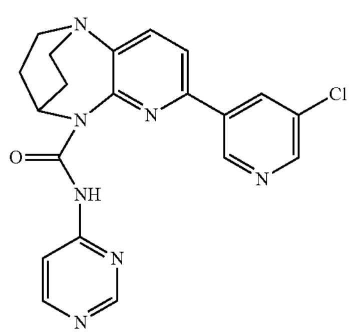 [SMILES: O=C(Nc1ccncn1)N1c2nc(-c3cncc(Cl)c3)ccc2N2CCC1CC2] | B | A |
| 577 | 425 | 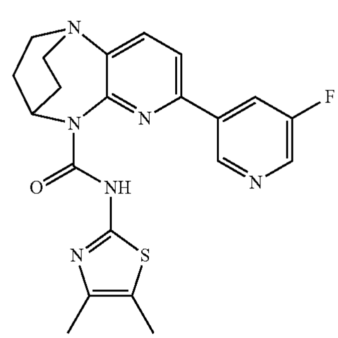 [SMILES: Cc1nc(NC(=O)N2c3nc(-c4cncc(F)c4)ccc3N3CCC2CC3)sc1C] | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 578 | 452 | 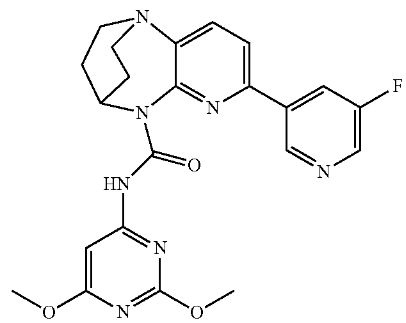 [SMILES: COc1cc(NC(=O)N2c3nc(-c4cncc(F)c4)ccc3N3CCC2CC3)nc(OC)n1] | B | A |
| 579 | 422 | 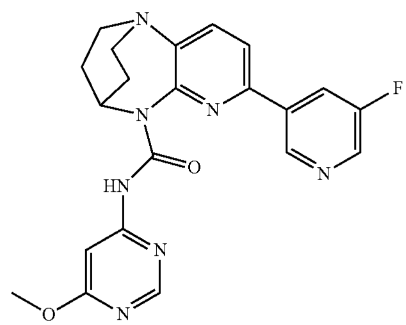 [SMILES: COc1cc(NC(=O)N2c3nc(-c4cncc(F)c4)ccc3N3CCC2CC3)ncn1] | B | A |
| 580 | 492 | 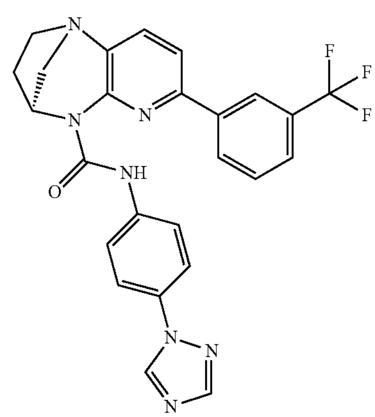 [SMILES: O=C(Nc1ccc(-n2cncn2)cc1)N1c2nc(-c3cccc(C(F)(F)F)c3)ccc2N2CC[C@H]1C2] | A | A |
| 581 | 492 | 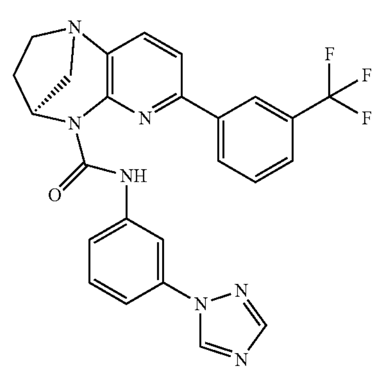 [SMILES: O=C(Nc1cccc(-n2cncn2)c1)N1c2nc(-c3cccc(C(F)(F)F)c3)ccc2N2CC[C@H]1C2] | A | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 582 | 505 | 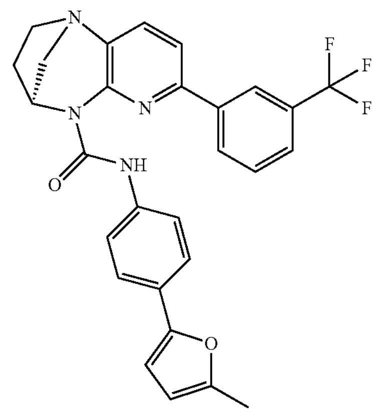 [SMILES: Cc1ccc(-c2ccc(NC(=O)N3c4nc(-c5cccc(C(F)(F)F)c5)ccc4N4CC[C@H]3C4)cc2)o1] | B | A |
| 583 | 522 | 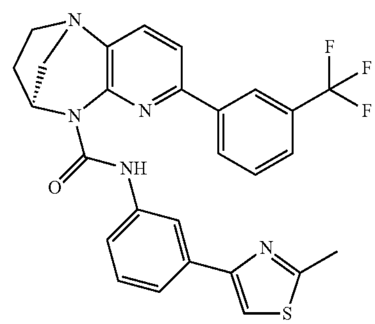 [SMILES: Cc1nc(-c2cccc(NC(=O)N3c4nc(-c5cccc(C(F)(F)F)c5)ccc4N4CC[C@H]3C4)c2)cs1] | A | A |
| 587 | 416 | 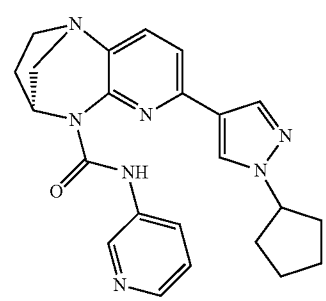 [SMILES: O=C(Nc1cccnc1)N1c2nc(-c3cnn(C4CCCC4)c3)ccc2N2CC[C@H]1C2] | B | A |
| 588 | 493 | 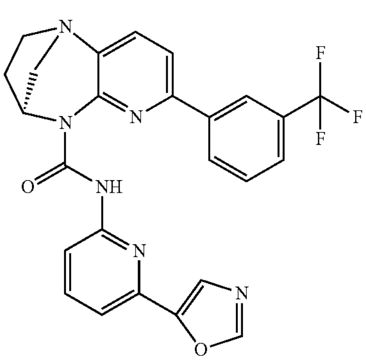 [SMILES: O=C(Nc1cccc(-c2cnco2)n1)N1c2nc(-c3cccc(C(F)(F)F)c3)ccc2N2CC[C@H]1C2] | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 589 | 493 | 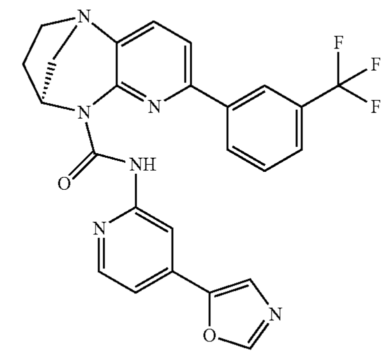 [SMILES: O=C(Nc1cc(-c2cnco2)ccn1)N1c2nc(-c3cccc(C(F)(F)F)c3)ccc2N2CC[C@H]1C2] | A | A |
| 590 | 507 | 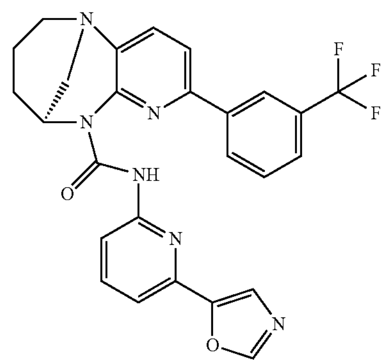 [SMILES: O=C(Nc1cccc(-c2cnco2)n1)N1c2nc(-c3cccc(C(F)(F)F)c3)ccc2N2CCC[C@H]1C2] | A | A |
| 591 | 507 | 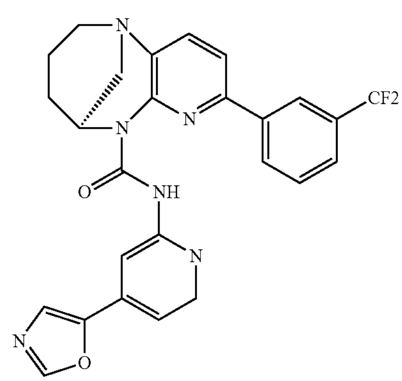 | A | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 592 | 594 | 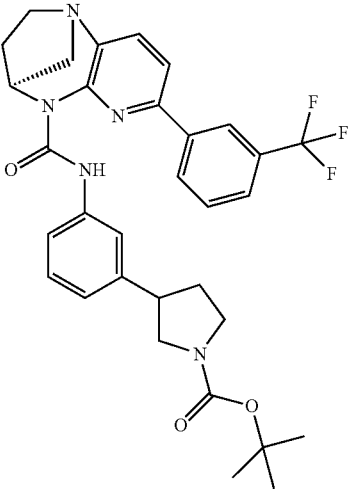 [SMILES: CC(C)(C)OC(=O)N1CCC(c2cccc(NC(=O)N3c4nc(-c5cccc(C(F)(F)F)c5)ccc4N4CC[C@H]3C4)c2)C1] | A | A |
| 593 | 494 | 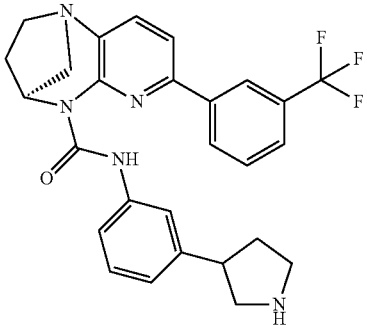 [SMILES: O=C(Nc1cccc(C2CCNC2)c1)N1c2nc(-c3cccc(C(F)(F)F)c3)ccc2N2CC[C@H]1C2] | A | A |
| 594 | 551 | 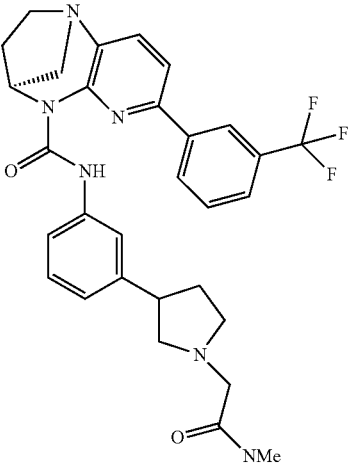 | A | A |

TABLE 1-continued

Compounds of Formula (I).

| Compound No. | [M + H]+[calc] | Structure | Tyrp AVG EC₁.₅ (μM) | Tyrp % Fold Act |
|---|---|---|---|---|
| 595 | 507 | 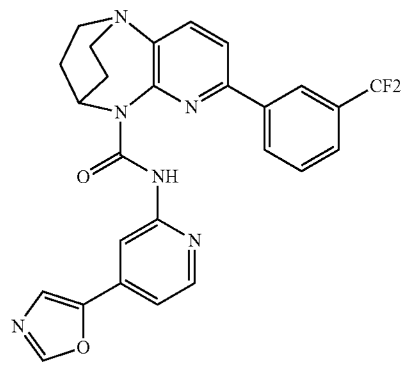 | A | A |
| 596 | 507 | 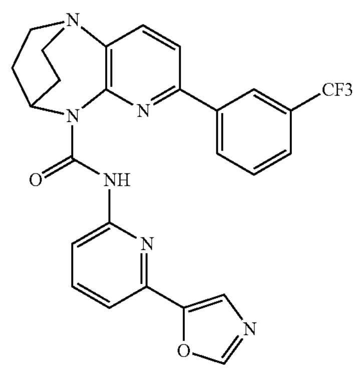 [SMILES: O=C(Nc1cccc(-c2cnco2)n1)N1c2nc(-c3cccc(C(F)(F)F)c3)ccc2N2CCC1CC2] | A | A |
| 597 | 439 | 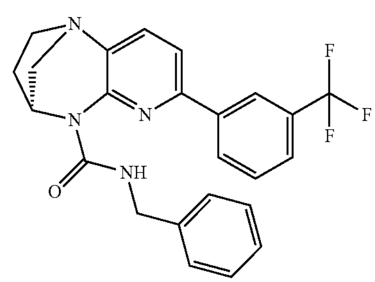 [SMILES: O=C(NCc1ccccc1)N1c2nc(-c3cccc(C(F)(F)F)c3)ccc2N2CC[C@H]1C2] | B | A |
| 598 | 453 | 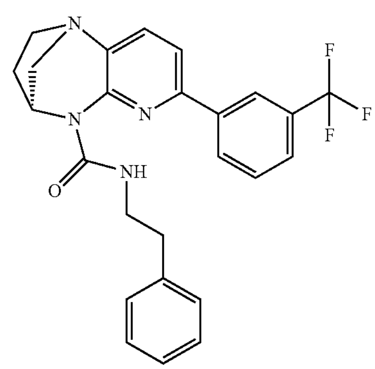 [SMILES: O=C(NCCc1ccccc1)N1c2nc(-c3cccc(C(F)(F)F)c3)ccc2N2CC[C@H]1C2] | B | A |

TABLE 1-continued

Compounds of Formula (I).

| Compound No. | [M + H]+[calc] | Structure | Tyrp AVG EC1.5 (μM) | Tyrp % Fold Act |
|---|---|---|---|---|
| 599 | 467 | 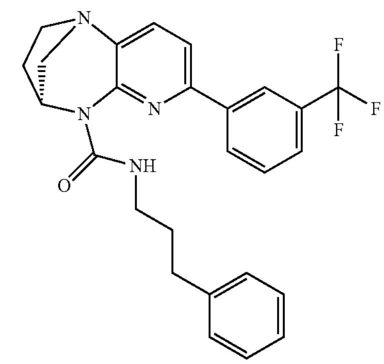 [SMILES: O=C(NCCCc1ccccc1)N1c2nc(-c3cccc(C(F)(F)F)c3)ccc2N2CC[C@H]1C2] | B | A |
| 600 | 481 | 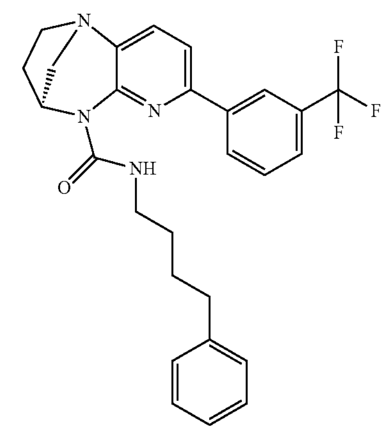 [SMILES: O=C(NCCCCc1ccccc1)N1c2nc(-c3cccc(C(F)(F)F)c3)ccc2N2CC[C@H]1C2] | B | A |
| 601 | 442 | 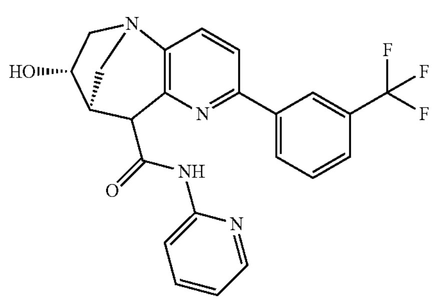 [SMILES: O=C(Nc1ccccn1)C1c2nc(-c3cccc(C(F)(F)F)c3)ccc2N2C[C@@H](O)[C@H]1C2] | A | A |
| 602 | 484 | 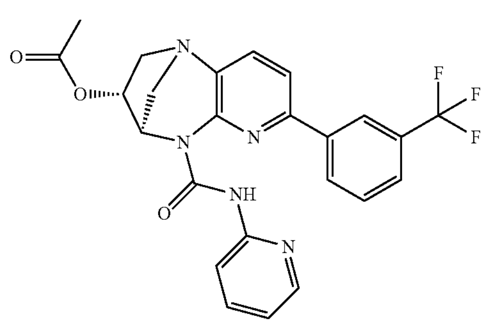 [SMILES: CC(=O)O[C@@H]1CN2C[C@H]1N(C(=O)Nc1ccccn1)c1nc(-c3cccc(C(F)(F)F)c3)ccc12] | B | A |

TABLE 1-continued

| | | Compounds of Formula (I). | | |
|---|---|---|---|---|
| Compound No. | [M + H]+_[calc] | Structure | Tyrp AVG EC_{1.5} (μM) | Tyrp % Fold Act |
| 603 | 546 | | C | B |
| 604 | 649 | | A | A |
| 605 | 621 | | A | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 606 | 521 | 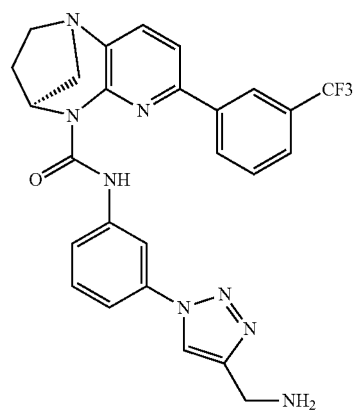 [SMILES: NCc1cn(-c2cccc(NC(=O)N3c4nc(-c5cccc(C(F)(F)F)c5)ccc4N4CC[C@H]3C4)c2)nn1] | A | A |
| 607 | 860 | 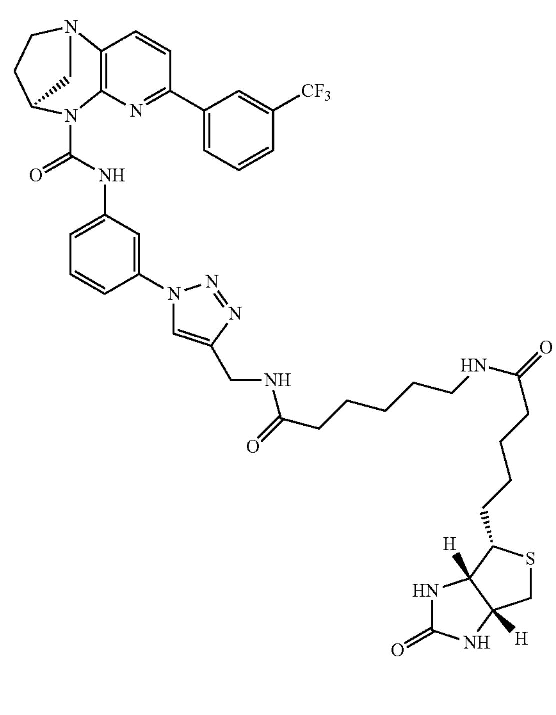 [SMILES: O=C(CCCC[C@@H]1SC[C@@H]2NC(=O)N[C@@H]21)NCCCCCC(=O)NCc1cn(-c2cccc(NC(=O)N3c4nc(-c5cccc(C(F)(F)F)c5)ccc4N4CC[C@H]3C4)c2)nn1] | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 608 | 910 | 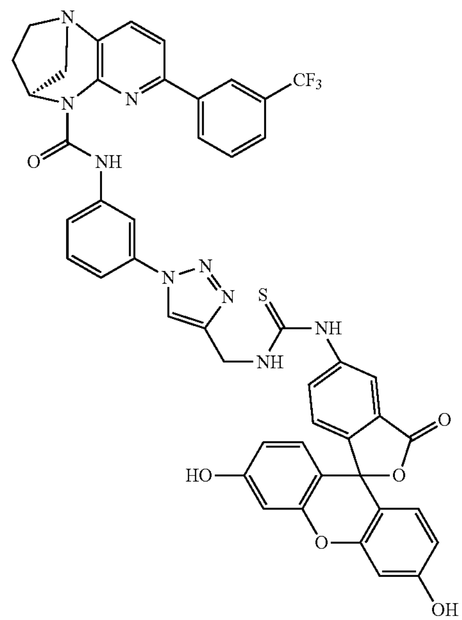 [SMILES: O=C1OC2(c3ccc(O)cc3Oc3cc(O)ccc32)c2ccc(NC(=S)NCc3cn(-c4cccc(NC(=O)N5c6nc(-c7cccc(C(F)(F)F)c7)ccc6N6CC[C@H]5C6)c4)nn3)cc21] | C | B |
| 609 | 580 | 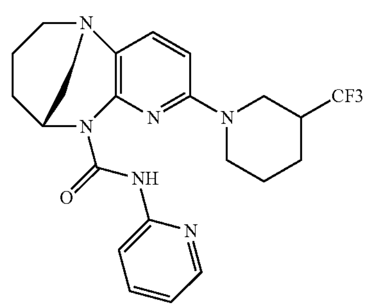 [SMILES: O=C(Nc1ccccn1)N1c2nc(N3CCCC(C(F)(F)F)C3)ccc2N2CCC[C@@H]1C2] | B | A |
| 610 | 580 | 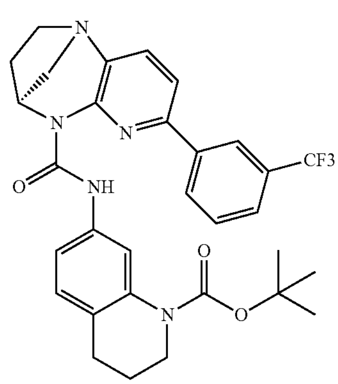 [SMILES: CC(C)(C)OC(=O)N1CCCc2ccc(NC(=O)N3c4nc(-c5cccc(C(F)(F)F)c5)ccc4N4CC[C@H]3C4)cc21] | B | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 611 | 580 | 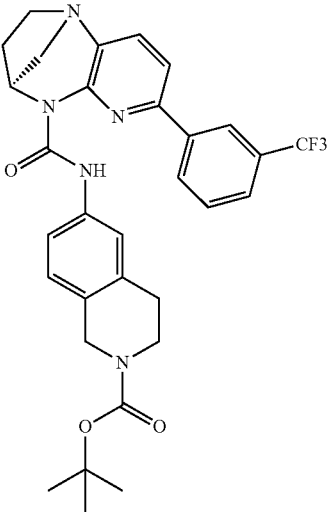 [SMILES: CC(C)(C)OC(=O)N1CCc2cc(NC(=O)N3c4nc(-c5cccc(C(F)(F)F)c5)ccc4N4CC[C@H]3C4)ccc2C1] | A | A |
| 612 | 476 | 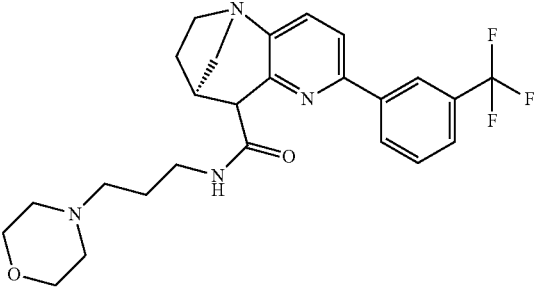 [SMILES: O=C(NCCCN1CCOCC1)C1c2nc(-c3cccc(C(F)(F)F)c3)ccc2N2CC[C@H]1C2] | B | A |
| 613 | 454 | 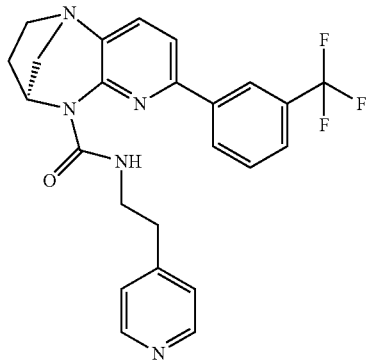 [SMILES: O=C(NCCc1ccncc1)N1c2nc(-c3cccc(C(F)(F)F)c3)ccc2N2CC[C@H]1C2] | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 614 | 454 | 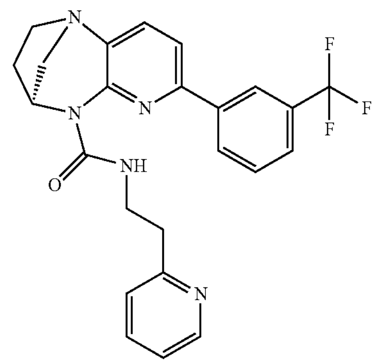 [SMILES: O=C(NCCc1ccccn1)N1c2nc(-c3cccc(C(F)(F)F)c3)ccc2N2CC[C@H]1C2] | B | A |
| 615 | 454 | 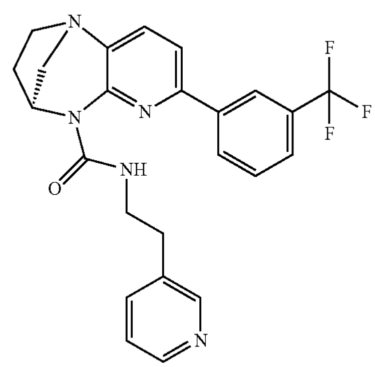 [SMILES: O=C(NCCc1cccnc1)N1c2nc(-c3cccc(C(F)(F)F)c3)ccc2N2CC[C@H]1C2] | B | A |
| 616 | 462 | 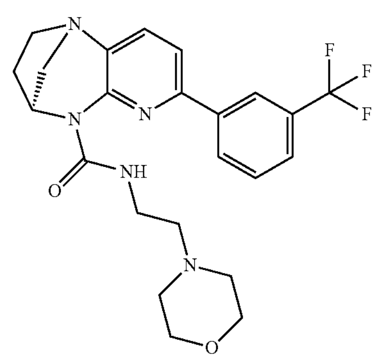 [SMILES: O=C(NCCN1CCOCC1)N1c2nc(-c3cccc(C(F)(F)F)c3)ccc2N2CC[C@H]1C2] | B | A |
| 617 | 493 | 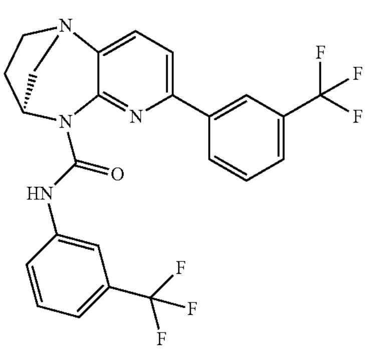 [SMILES: O=C(Nc1cccc(C(F)(F)F)c1)N1c2nc(-c3cccc(C(F)(F)F)c3)ccc2N2CC[C@H]1C2] | A | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 618 | 570 | 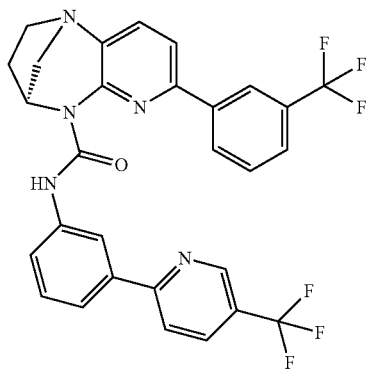 [SMILES: O=C(Nc1cccc(-c2ccc(C(F)(F)F)cn2)c1)N1c2nc(-c3cccc(C(F)(F)F)c3)ccc2N2CC[C@H]1C2] | B | A |
| 619 | 529 | 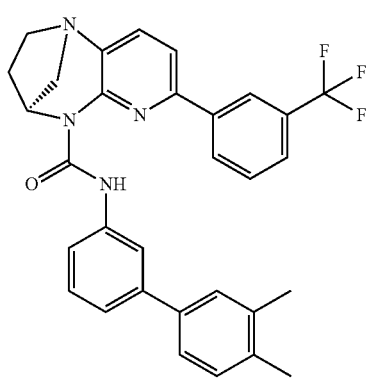 [SMILES: Cc1ccc(-c2cccc(NC(=O)N3c4nc(-c5cccc(C(F)(F)F)c5)ccc4N4CC[C@H]3C4)c2)cc1C] | C | B |
| 620 | 440 | 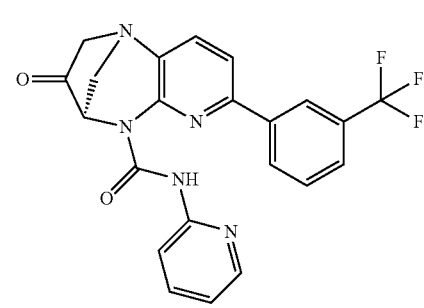 [SMILES: O=C1CN2C[C@H]1N(C(=O)Nc1ccccn1)c1nc(-c3cccc(C(F)(F)F)c3)ccc12] | B | A |
| 621 | 442 | 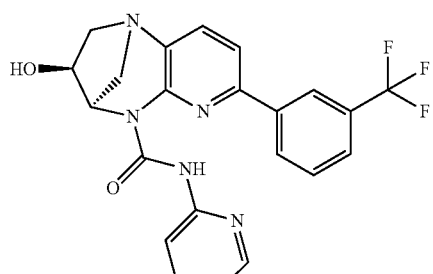 | NT | NT |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 622 | 795 | 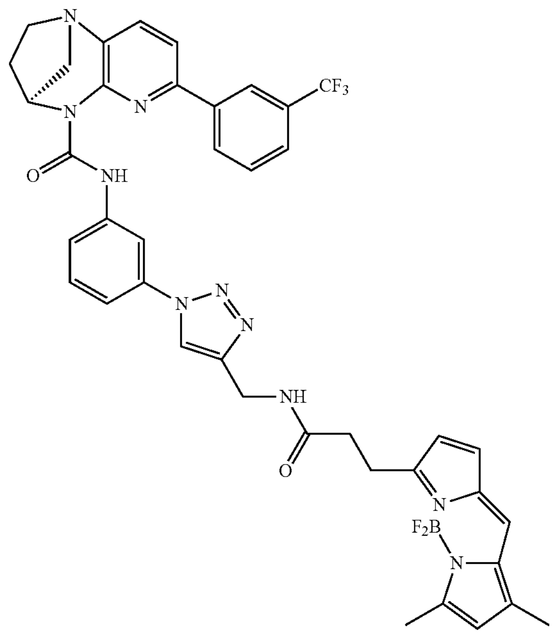 | C | B |
| 623 | 506 | 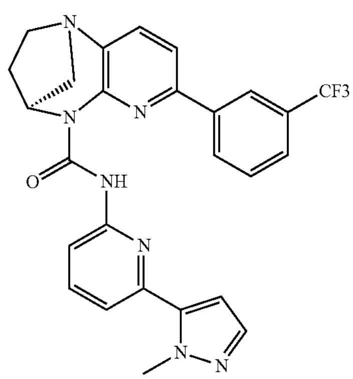 [SMILES: Cn1nccc1-c1cccc(NC(=O)N2c3nc(-c4cccc(C(F)(F)F)c4)ccc3N3CC[C@H]2C3)n1] | A | A |
| 624 | 465 | 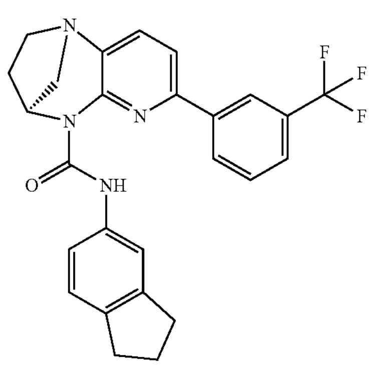 [SMILES: O=C(Nc1ccc2c(c1)CCC2)N1c2nc(-c3cccc(C(F)(F)F)c3)ccc2N2CC[C@H]1C2] | B | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 625 | 501 | 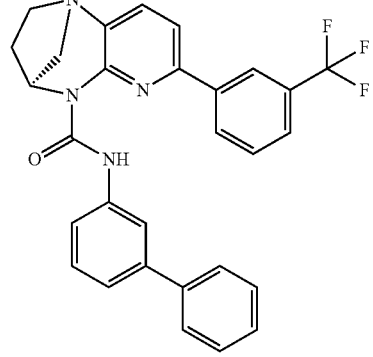 | A | A |
| 626 | 483 | 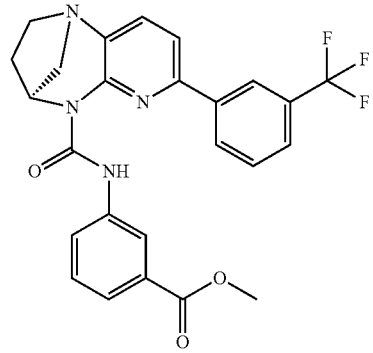 [SMILES: COC(=O)c1cccc(NC(=O)N2c3nc(-c4cccc(C(F)(F)F)c4)ccc3N3CC[C@H]2C3)c1] | A | A |
| 627 | 457 | 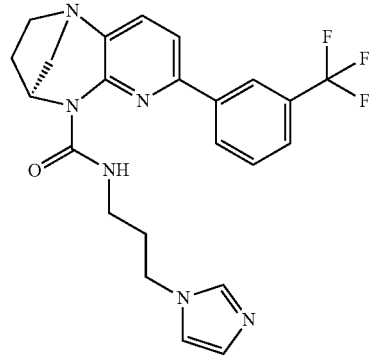 [SMILES: O=C(NCCCn1ccnc1)N1c2nc(-c3cccc(C(F)(F)F)c3)ccc2N2CC[C@H]1C2] | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 628 | 508 | 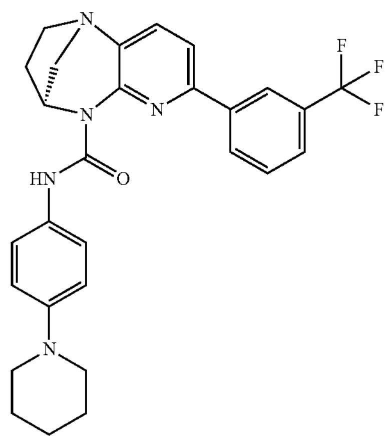 [SMILES: O=C(Nc1ccc(N2CCCCC2)cc1)N1c2nc(-c3cccc(C(F)(F)F)c3)ccc2N2CC[C@H]1C2] | B | A |
| 629 | 524 | 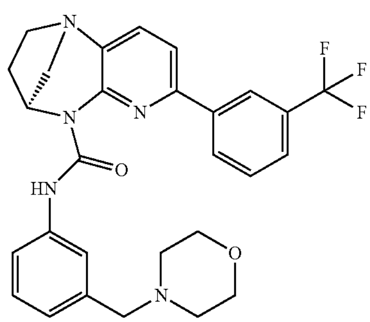 [SMILES: O=C(Nc1cccc(CN2CCOCC2)c1)N1c2nc(-c3cccc(C(F)(F)F)c3)ccc2N2CC[C@H]1C2] | A | A |
| 630 | 460 | 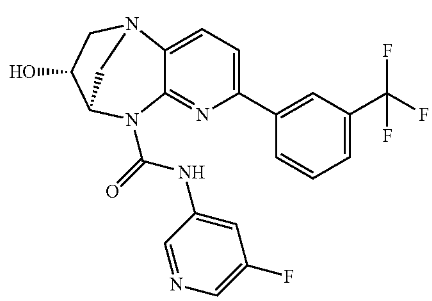 [SMILES: O=C(Nc1cncc(F)c1)N1c2nc(-c3cccc(C(F)(F)F)c3)ccc2N2C[C@@H](O)[C@H]1C2] | A | A |
| 631 | 443 | 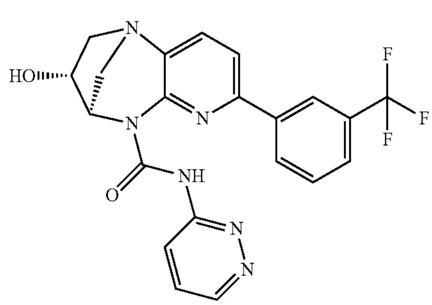 [SMILES: O=C(Nc1cccnn1)N1c2nc(-c3cccc(C(F)(F)F)c3)ccc2N2C[C@@H](O)[C@H]1C2] | B | A |

US 10,590,135 B2
TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 632 | 471 | 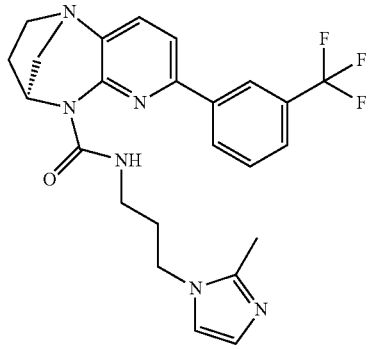 [SMILES: Cc1nccn1CCCNC(=O)N1c2nc(-c3cccc(C(F)(F)F)c3)ccc2N2CC[C@H]1C2] | C | A |
| 633 | 468 | 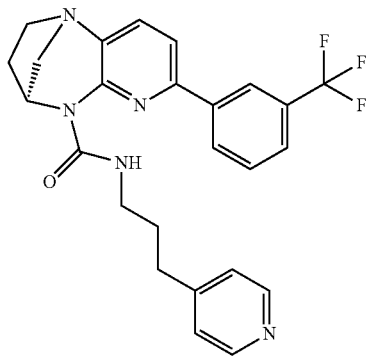 [SMILES: O=C(NCCCc1ccncc1)N1c2nc(-c3cccc(C(F)(F)F)c3)ccc2N2CC[C@H]1C2] | B | A |
| 634 | 484 | 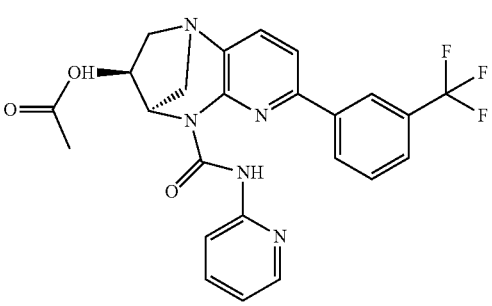 [SMILES: CC(=O)O[C@H]1CN2C[C@H]1N(C(=O)Nc1ccccn1)c1nc(-c3cccc(C(F)(F)F)c3)ccc12] | C | B |
| 635 | 536 | 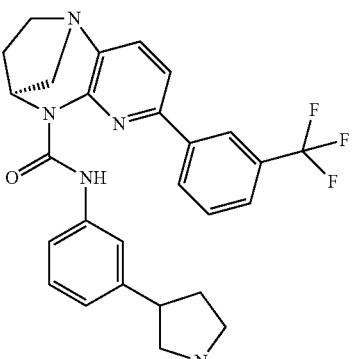 | A | A |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 636 | 550 | 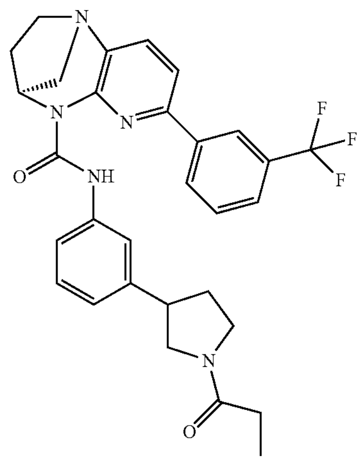 [SMILES: CCC(=O)N1CCC(c2cccc(NC(=O)N3c4nc(-c5cccc(C(F)(F)F)c5)ccc4N4CC[C@H]3C4)c2)C1] | A | A |
| 637 | 562 | 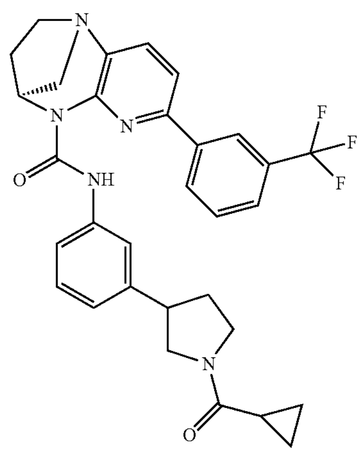 [SMILES: O=C(C1CC1)N1CCC(c2cccc(NC(=O)N3c4nc(-c5cccc(C(F)(F)F)c5)ccc4N4CC[C@H]3C4)c2)C1] | A | A |
| 638 | 621 | 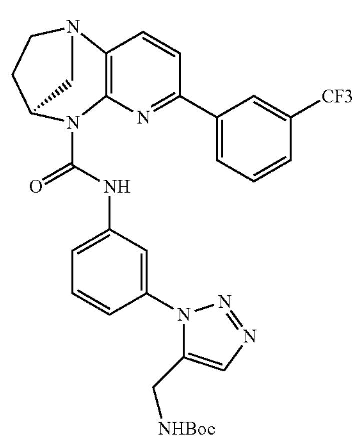 [SMILES: CC(C)(C)OC(=O)NCc1cnnn1-c1cccc(NC(=O)N2c3nc(-c4cccc(C(F)(F)F)c4)ccc3N3CC[C@H]2C3)c1] | A | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 639 | 634 | 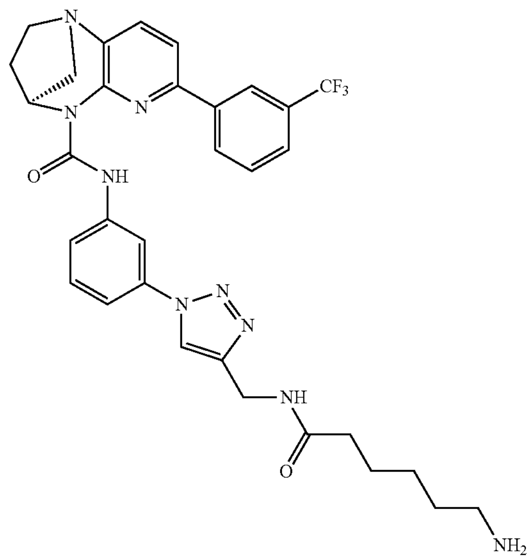 [SMILES: NCCCCCC(=O)NCc1cn(-c2cccc(NC(=O)N3c4nc(-c5cccc(C(F)(F)F)c5)ccc4N4CC[C@H]3C4)c2)nn1] | A | A |
| 640 | 521 | 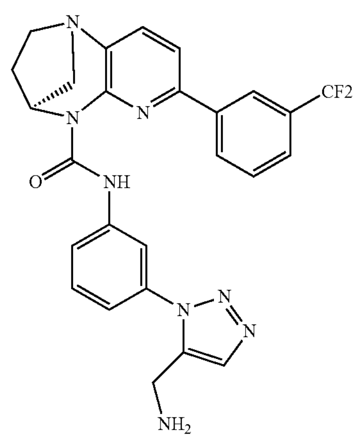 | A | A |
| 641 | 517 | 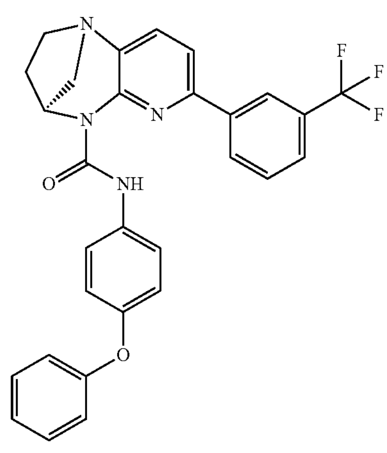 [SMILES: O=C(Nc1ccc(Oc2ccccc2)cc1)N1c2nc(-c3cccc(C(F)(F)F)c3)ccc2N2CC[C@H]1C2] | C | B |

TABLE 1-continued

Compounds of Formula (I).

| Compound No. | [M + H]+_{[calc]} | Structure | Tyrp AVG EC_{1.5} (μM) | Tyrp % Fold Act |
|---|---|---|---|---|
| 642 | 518 | 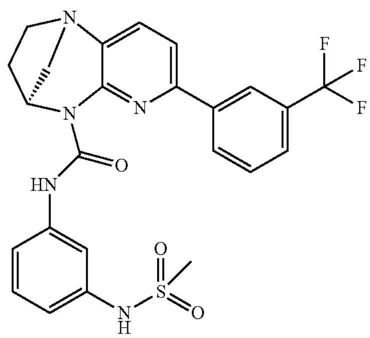 [SMILES: CS(=O)(=O)Nc1cccc(NC(=O)N2c3nc(-c4cccc(C(F)(F)F)c4)ccc3N3CC[C@H]2C3)c1] | A | A |
| 643 | 504 | 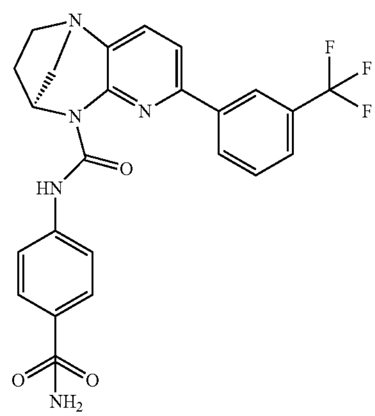 | A | A |
| 644 | 473 | 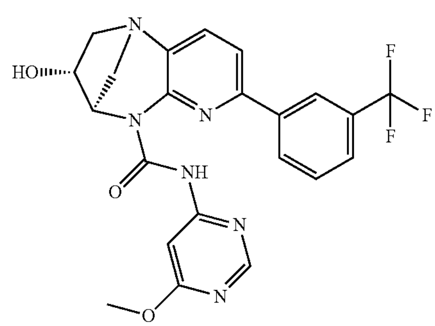 [SMILES: COc1cc(NC(=O)N2c3nc(-c4cccc(C(F)(F)F)c4)ccc3N3C[C@@H](O)[C@H]2C3)ncn1] | B | A |
| 645 | 443 | 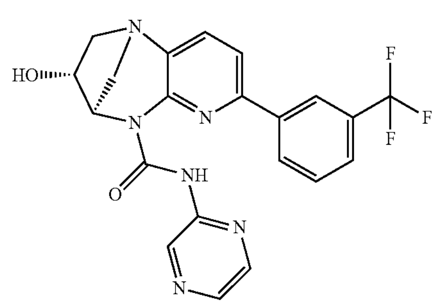 | A | A |

TABLE 1-continued
Compounds of Formula (I).
| Compound No. | [M + H]+_[calc] | Structure | Tyrp AVG EC_{1.5} (µM) | Tyrp % Fold Act |
|---|---|---|---|---|
| 646 | 433 | 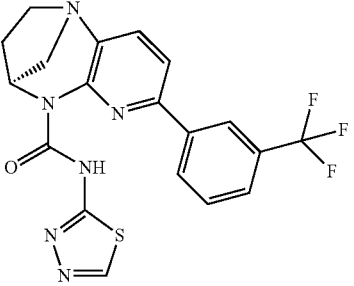 [SMILES: O=C(Nc1nncs1)N1c2nc(-c3cccc(C(F)(F)F)c3)ccc2N2CC[C@H]1C2] | A | A |
| 647 | 461 | 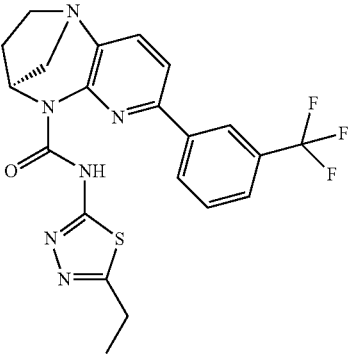 [SMILES: CCc1nnc(NC(=O)N2c3nc(-c4cccc(C(F)(F)F)c4)ccc3N3CC[C@H]2C3)s1] | A | A |
| 648 | 509 | 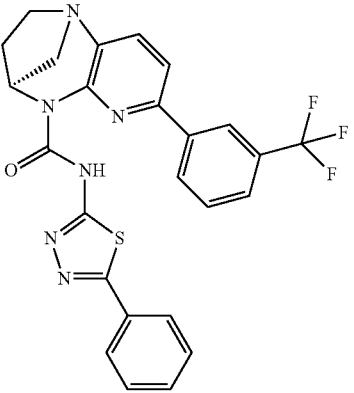 [SMILES: O=C(Nc1nnc(-c2ccccc2)s1)N1c2nc(-c3cccc(C(F)(F)F)c3)ccc2N2CC[C@H]1C2] | A | A |
| 649 | 489 | 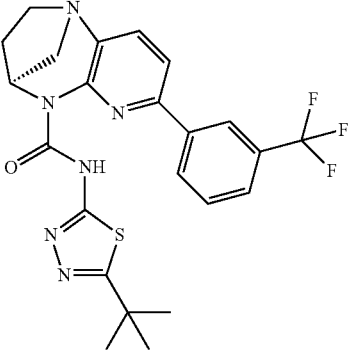 [SMILES: CC(C)(C)c1nnc(NC(=O)N2c3nc(-c4cccc(C(F)(F)F)c4)ccc3N3CC[C@H]2C3)s1] | B | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 650 | 501 | 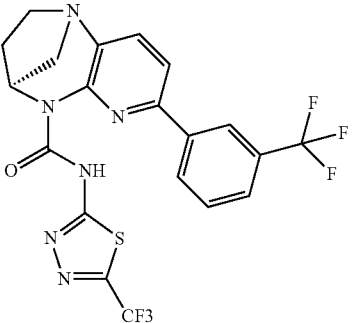 [SMILES: O=C(Nc1nnc(C(F)(F)F)s1)N1c2nc(-c3cccc(C(F)(F)F)c3)ccc2N2CC[C@H]1C2] | C | B |
| 651 | 510 | 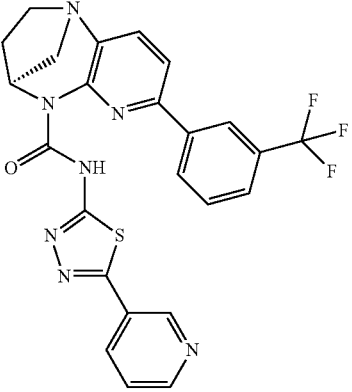 [SMILES: O=C(Nc1nnc(-c2cccnc2)s1)N1c2nc(-c3cccc(C(F)(F)F)c3)ccc2N2CC[C@H]1C2] | A | A |
| 652 | 504 | 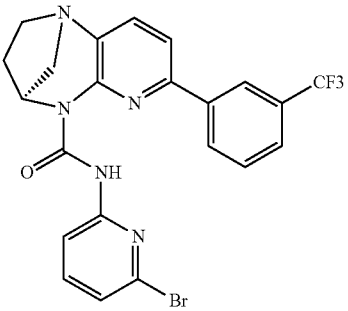 [SMILES: O=C(Nc1cccc(Br)n1)N1c2nc(-c3cccc(C(F)(F)F)c3)ccc2N2CC[C@H]1C2] | A | A |
| 653 | 508 | 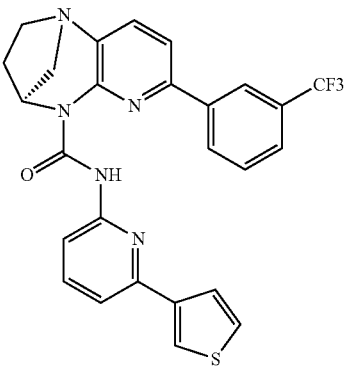 [SMILES: O=C(Nc1cccc(-c2ccsc2)n1)N1c2nc(-c3cccc(C(F)(F)F)c3)ccc2N2CC[C@H]1C2] | A | A |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 654 | 492 | 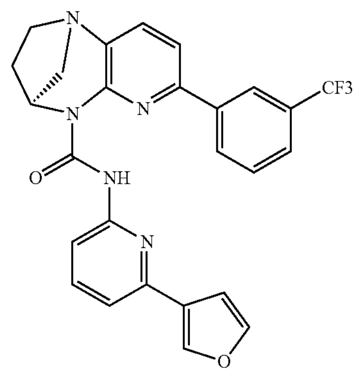 [SMILES: O=C(Nc1cccc(-c2ccoc2)n1)N1c2nc(-c3cccc(C(F)(F)F)c3)ccc2N2CC[C@H]1C2] | A | A |
| 655 | 503 | 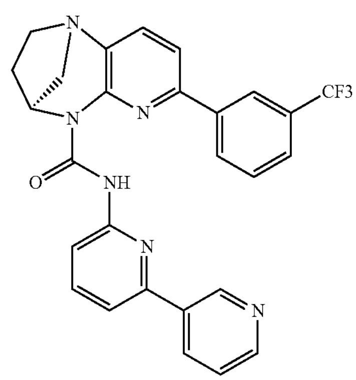 [SMILES: O=C(Nc1cccc(-c2cccnc2)n1)N1c2nc(-c3cccc(C(F)(F)F)c3)ccc2N2CC[C@H]1C2] | A | A |
| 656 | 534 | 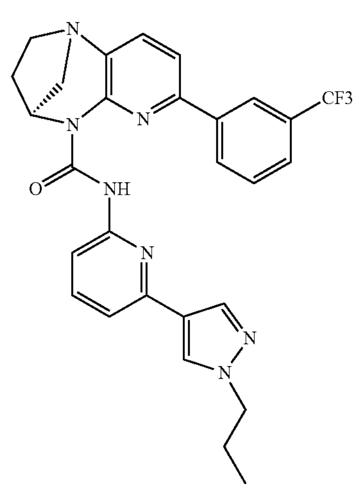 [SMILES: CCCn1cc(-c2cccc(NC(=O)N3c4nc(-c5cccc(C(F)(F)F)c5)ccc4N4CC[C@H]3C4)n2)cn1] | A | A |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 657 | 521 | 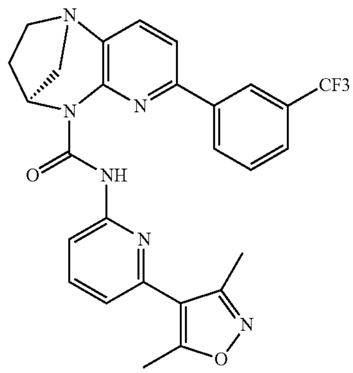 [SMILES: Cc1noc(C)c1-c1cccc(NC(=O)N2c3nc(-c4cccc(C(F)(F)F)c4)ccc3N3CC[C@H]2C3)n1] | A | A |
| 658 | 508 | 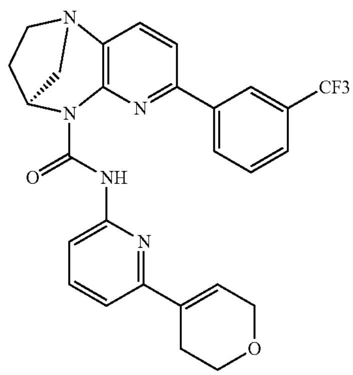 [SMILES: O=C(Nc1cccc(C2=CCOCC2)n1)N1c2nc(-c3cccc(C(F)(F)F)c3)ccc2N2CC[C@H]1C2] | A | A |
| 659 | 468 | 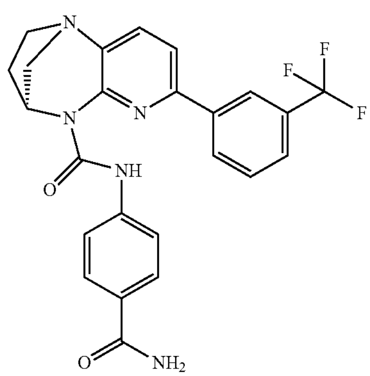 [SMILES: NC(=O)c1ccc(NC(=O)N2c3nc(-c4cccc(C(F)(F)F)c4)ccc3N3CC[C@H]2C3)cc1] | A | A |
| 660 | 502 | 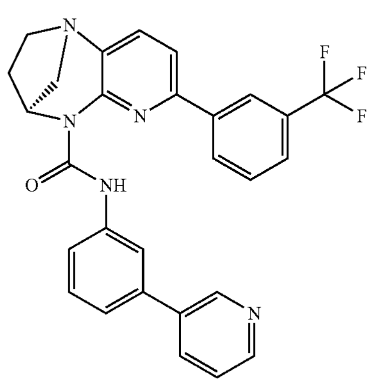 [SMILES: O=C(Nc1cccc(-c2cccnc2)c1)N1c2nc(-c3cccc(C(F)(F)F)c3)ccc2N2CC[C@H]1C2] | A | A |

TABLE 1-continued

Compounds of Formula (I).

| Compound No. | [M + H]+[calc] | Structure | Tyrp AVG EC1.5 (μM) | Tyrp % Fold Act |
|---|---|---|---|---|
| 661 | 443 | 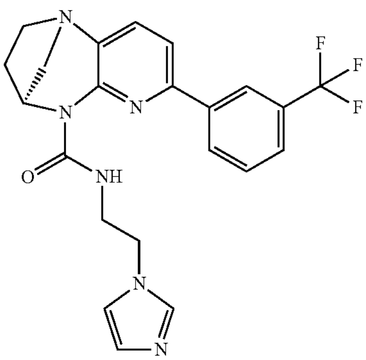 [SMILES: O=C(NCCn1ccnc1)N1c2nc(-c3cccc(C(F)(F)F)c3)ccc2N2CC[C@H]1C2] | C | A |
| 662 | 509 | 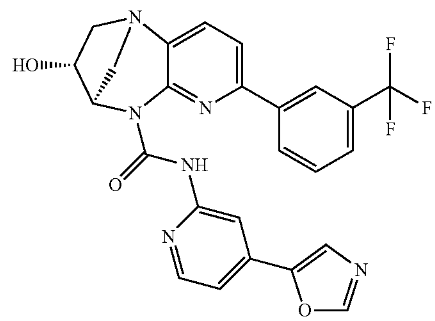 [SMILES: O=C(Nc1cc(-c2cnco2)ccn1)N1c2nc(-c3cccc(C(F)(F)F)c3)ccc2N2C[C@@H](O)[C@H]1C2] | B | A |
| 663 | 442 | 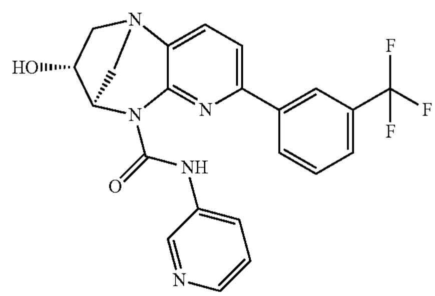 [SMILES: O=C(Nc1cccnc1)N1c2nc(-c3cccc(C(F)(F)F)c3)ccc2N2C[C@@H](O)[C@H]1C2] | A | A |
| 664 | 503 | 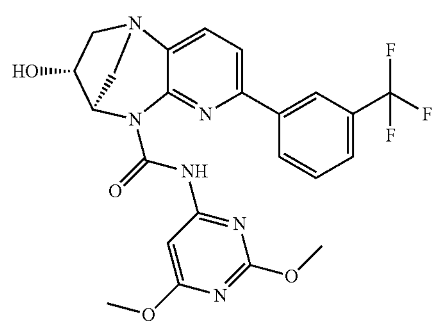 [SMILES: COc1cc(NC(=O)N2c3nc(-c4cccc(C(F)(F)F)c4)ccc3N3C[C@@H](O)[C@H]2C3)nc(OC)n1] | B | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 665 | 508 | 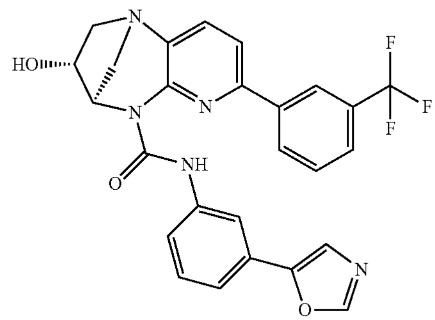 [SMILES: O=C(Nc1cccc(-c2cnco2)c1)N1c2nc(-c3cccc(C(F)(F)F)c3)ccc2N2C[C@@H](O)[C@H]1C2] | A | A |
| 666 | 465 | 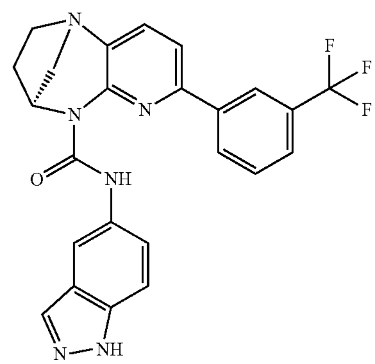 [SMILES: O=C(Nc1ccc2[nH]ncc2c1)N1c2nc(-c3cccc(C(F)(F)F)c3)ccc2N2CC[C@H]1C2] | A | A |
| 667 | 502 | 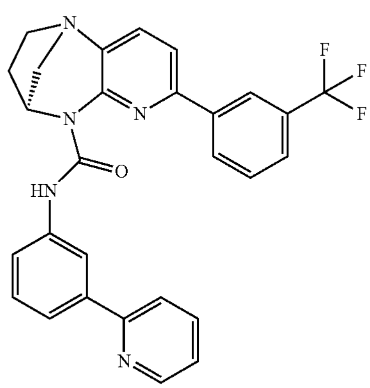 [SMILES: O=C(Nc1cccc(-c2ccccn2)c1)N1c2nc(-c3cccc(C(F)(F)F)c3)ccc2N2CC[C@H]1C2] | A | A |
| 668 | 467 | 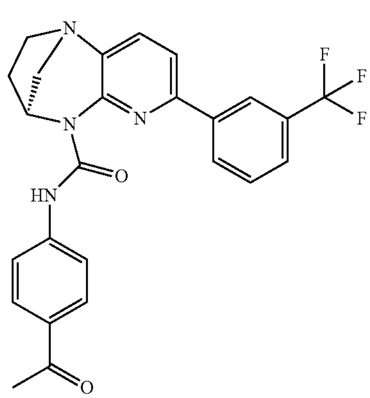 [SMILES: CC(=O)c1ccc(NC(=O)N2c3nc(-c4cccc(C(F)(F)F)c4)ccc3N3CC[C@H]2C3)cc1] | A | A |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 669 | 443 | 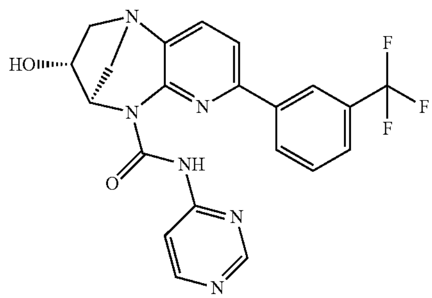 [SMILES: O=C(Nc1ccncn1)N1c2nc(-c3cccc(C(F)(F)F)c3)ccc2N2C[C@@H](O)[C@H]1C2] | B | A |
| 670 | 456 | 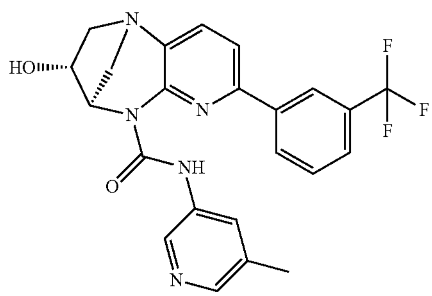 [SMILES: Cc1cncc(NC(=O)N2c3nc(-c4cccc(C(F)(F)F)c4)ccc3N3C[C@@H](O)[C@H]2C3)c1] | A | A |
| 671 | 467 | 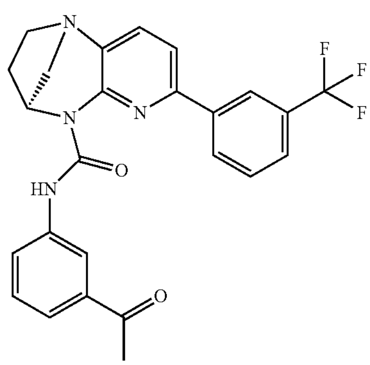 [SMILES: CC(=O)c1cccc(NC(=O)N2c3nc(-c4cccc(C(F)(F)F)c4)ccc3N3CC[C@H]2C3)c1] | A | A |
| 672 | 570 | 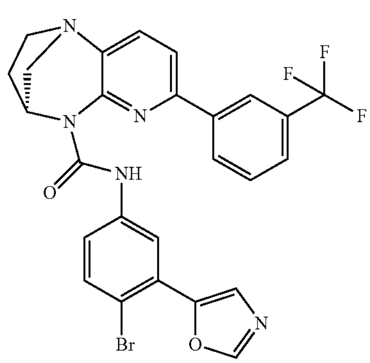 [SMILES: O=C(Nc1ccc(Br)c(-c2cnco2)c1)N1c2nc(-c3cccc(C(F)(F)F)c3)ccc2N2CC[C@H]1C2] | A | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 673 | 468 | 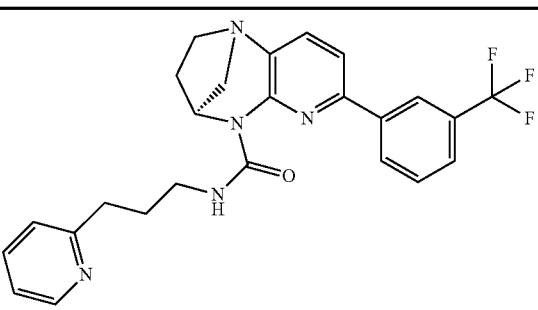 | B | A |
| 674 | 468 | 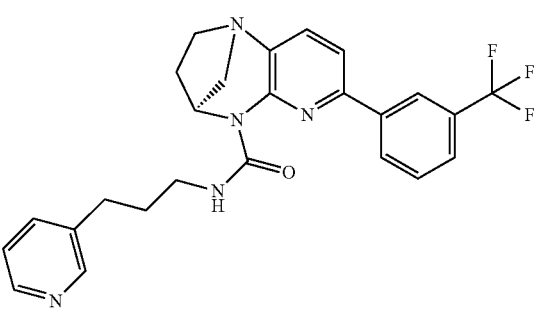 [SMILES: O=C(NCCCc1cccnc1)N1c2nc(-c3cccc(C(F)(F)F)c3)ccc2N2CC[C@H]1C2] | B | A |
| 675 | 408 | 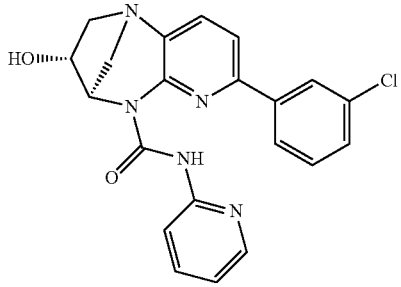 [SMILES: O=C(Nc1ccccn1)N1c2nc(-c3cccc(Cl)c3)ccc2N2C[C@@H](O)[C@H]1C2] | B | A |
| 676 | 422 | 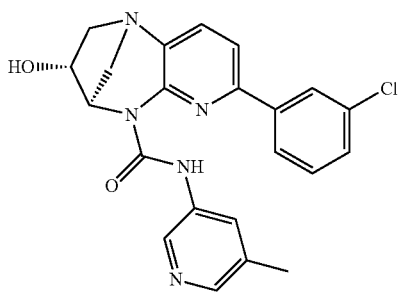 [SMILES: Cc1cncc(NC(=O)N2c3nc(-c4cccc(Cl)c4)ccc3N3C[C@@H](O)[C@H]2C3)c1] | A | A |
| 677 | 426 | 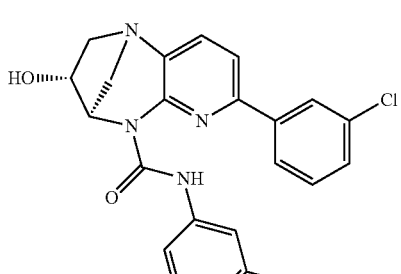 | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 678 | 409 | 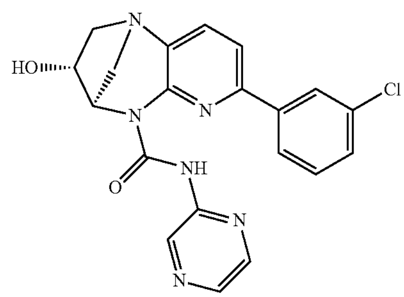 | C | B |
| 679 | 439 | 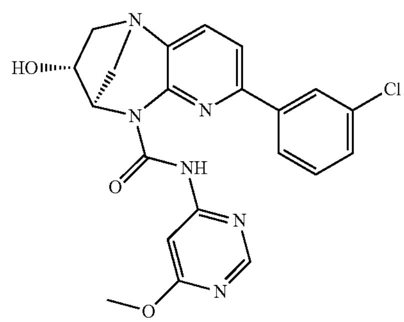 [SMILES: COc1cc(NC(=O)N2c3nc(-c4cccc(Cl)c4)ccc3N3C[C@@H](O)[C@H]2C3)ncn1] | B | A |
| 680 | 469 | 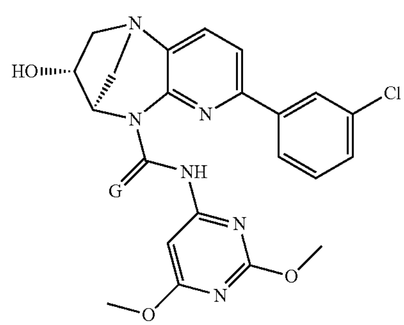 | B | A |
| 681 | 408 | 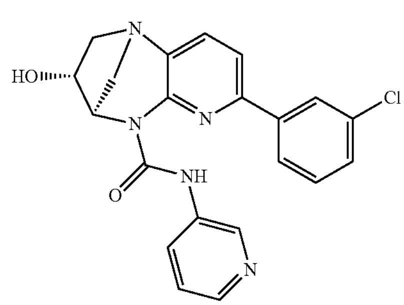 [SMILES: O=C(Nc1cccnc1)N1c2nc(-c3cccc(Cl)c3)ccc2N2C[C@@H](O)[C@H]1C2] | B | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 682 | 409 | 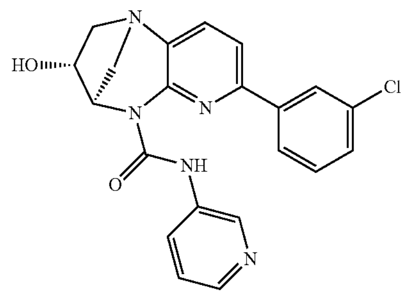 [SMILES: O=C(Nc1cccnc1)N1c2nc(-c3cccc(Cl)c3)ccc2N2C[C@@H](O)[C@H]1C2] | B | A |
| 683 | 474 | 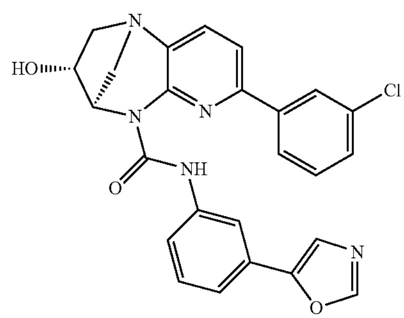 [SMILES: O=C(Nc1cccc(-c2cnco2)c1)N1c2nc(-c3cccc(Cl)c3)ccc2N2C[C@@H](O)[C@H]1C2] | A | A |
| 684 | 409 | 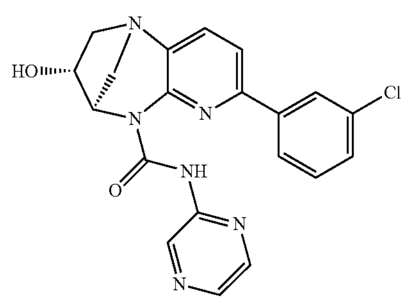 [SMILES: O=C(Nc1cnccn1)N1c2nc(-c3cccc(Cl)c3)ccc2N2C[C@@H](O)[C@H]1C2] | B | A |
| 685 | 475 | 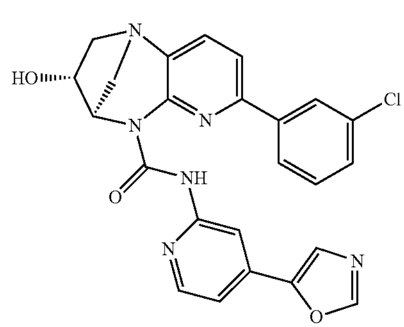 [SMILES: O=C(Nc1cc(-c2cnco2)ccn1)N1c2nc(-c3cccc(Cl)c3)ccc2N2C[C@@H](O)[C@H]1C2] | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 688 | 442 | 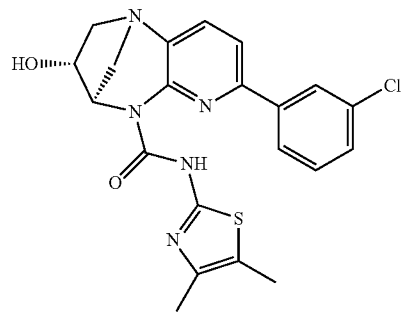 [SMILES: Cc1nc(NC(=O)N2c3nc(-c4cccc(Cl)c4)ccc3N3C[C@@H](O)[C@H]2C3)sc1C] | B | A |
| 689 | 471 | 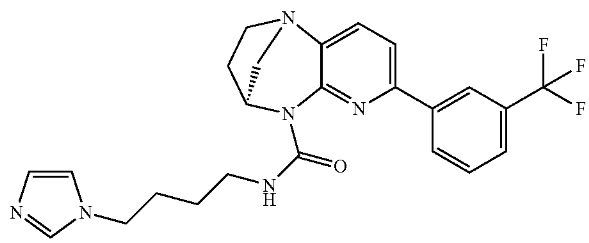 [SMILES: O=C(NCCCCn1ccnc1)N1c2nc(-c3cccc(C(F)(F)F)c3)ccc2N2CC[C@H]1C2] | B | A |
| 690 | 457 | 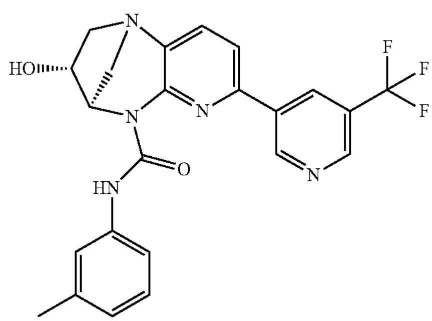 [SMILES: Cc1cccc(NC(=O)N2c3nc(-c4cncc(C(F)(F)F)c4)ccc3N3C[C@@H](O)[C@H]2C3)c1] | B | A |
| 691 | 461 | 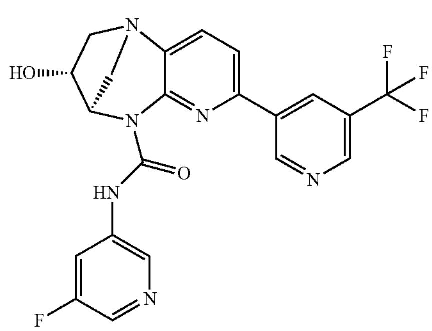 [SMILES: O=C(Nc1cncc(F)c1)N1c2nc(-c3cncc(C(F)(F)F)c3)ccc2N2C[C@@H](O)[C@H]1C2] | B | A |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 692 | 506 | 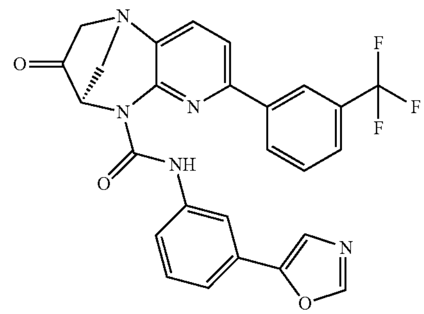 [SMILES: O=C1CN2C[C@H]1N(C(=O)Nc1cccc(-c3cnco3)c1)c1nc(-c3cccc(C(F)(F)F)c3)ccc12] | A | A |
| 693 | 475 | 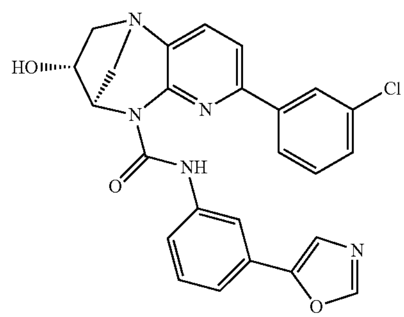 [SMILES: O=C(Nc1cccc(-c2cnco2)c1)N1c2nc(-c3cccc(Cl)c3)ccc2N2C[C@@H](O)[C@H]1C2] | A | A |
| 694 | 443 | 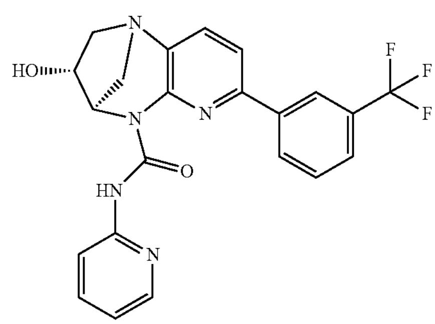 [SMILES: O=C(Nc1ccccn1)N1c2nc(-c3cccc(C(F)(F)F)c3)ccc2N2C[C@@H](O)[C@H]1C2] | A | A |
| 695 | 444 | 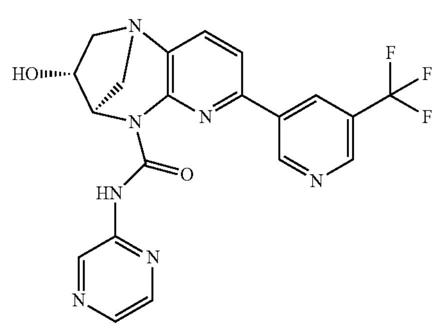 [SMILES: O=C(Nc1cnccn1)N1c2nc(-c3cncc(C(F)(F)F)c3)ccc2N2C[C@@H](O)[C@H]1C2] | B | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 696 | 474 | 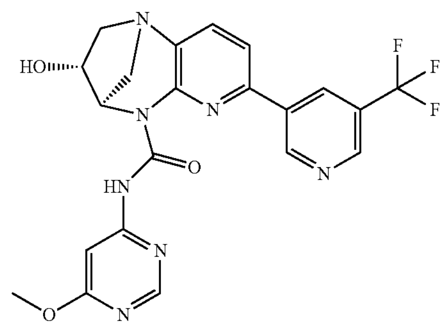 [SMILES: COc1cc(NC(=O)N2c3nc(-c4cncc(C(F)(F)F)c4)ccc3N3C[C@@H](O)[C@H]2C3)ncn1] | B | A |
| 697 | 477 | 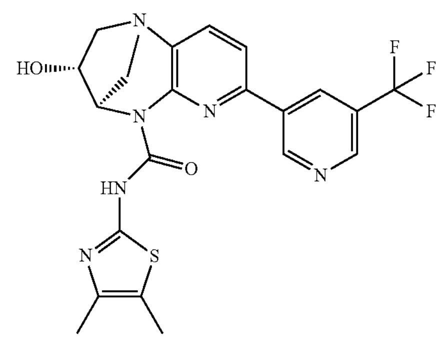 | B | A |
| 698 | 509 | 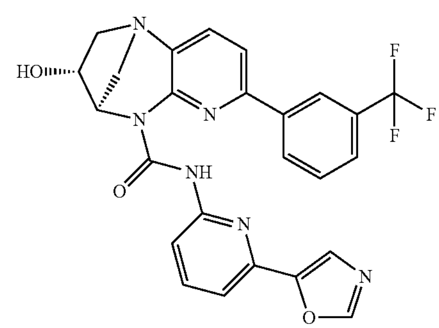 [SMILES: O=C(Nc1cccc(-c2cnco2)n1)N1c2nc(-c3cccc(C(F)(F)F)c3)ccc2N2C[C@@H](O)[C@H]1C2] | A | A |
| 699 | 476 | 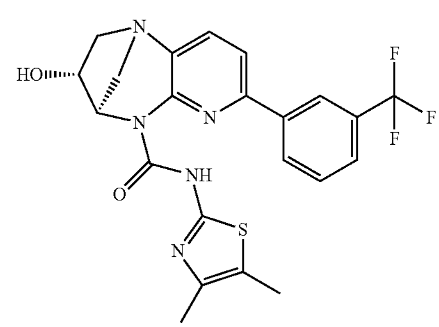 [SMILES: Cc1nc(NC(=O)N2c3nc(-c4cccc(C(F)(F)F)c4)ccc3N3C[C@@H](O)[C@H]2C3)sc1C] | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 700 | 444 | 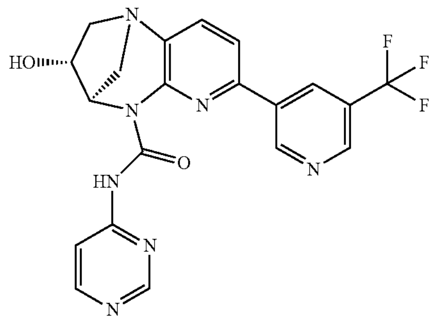 [SMILES: O=C(Nc1ccncn1)N1c2nc(-c3cncc(C(F)(F)F)c3)ccc2N2C[C@@H](O)[C@H]1C2] | B | A |
| 701 | 444 | 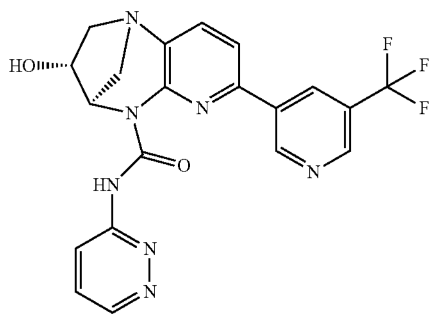 [SMILES: O=C(Nc1cccnn1)N1c2nc(-c3cncc(C(F)(F)F)c3)ccc2N2C[C@@H](O)[C@H]1C2] | B | A |
| 702 | 516 | 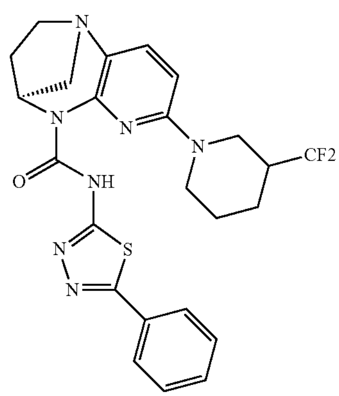 | NT | NT |
| 703 | 510 | 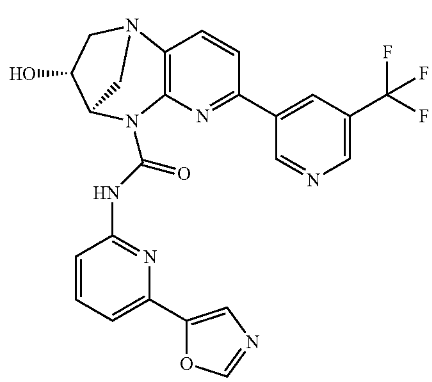 [SMILES: O=C(Nc1cccc(-c2cnco2)n1)N1c2nc(-c3cncc(C(F)(F)F)c3)ccc2N2C[C@@H](O)[C@H]1C2] | A | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 704 | 504 | 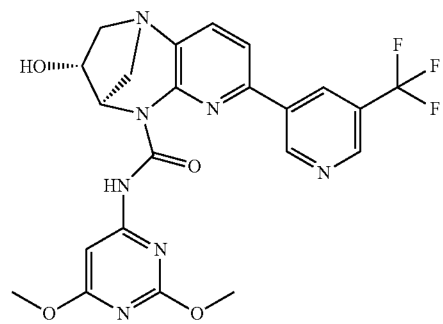 [SMILES: COc1cc(NC(=O)N2c3nc(-c4cncc(C(F)(F)F)c4)ccc3N3C[C@@H](O)[C@H]2C3)nc(OC)n1] | B | A |
| 705 | 443 | 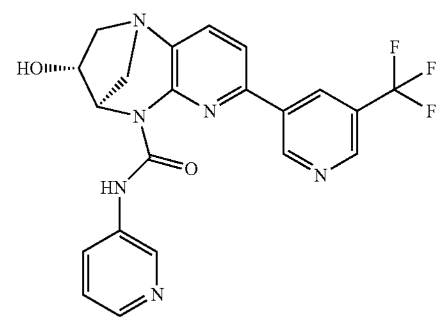 [SMILES: O=C(Nc1cccnc1)N1c2nc(-c3cncc(C(F)(F)F)c3)ccc2N2C[C@@H](O)[C@H]1C2] | B | A |
| 706 | 655 | 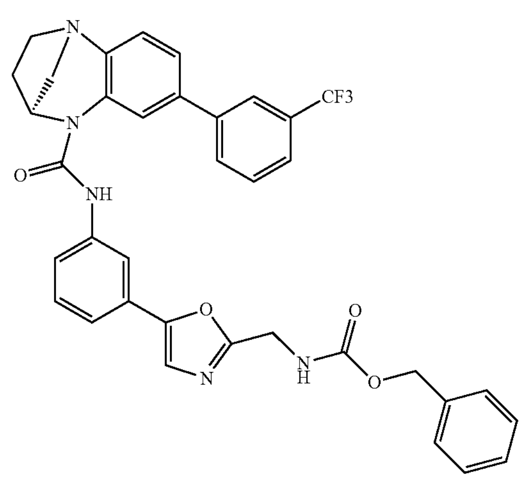 [SMILES: O=C(NCc1ncc(-c2cccc(NC(=O)N3c4cc(-c5cccc(C(F)(F)F)c5)ccc4N4CC[C@H]3C4)c2)o1)OCc1ccccc1] | A | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 708 | 992 | 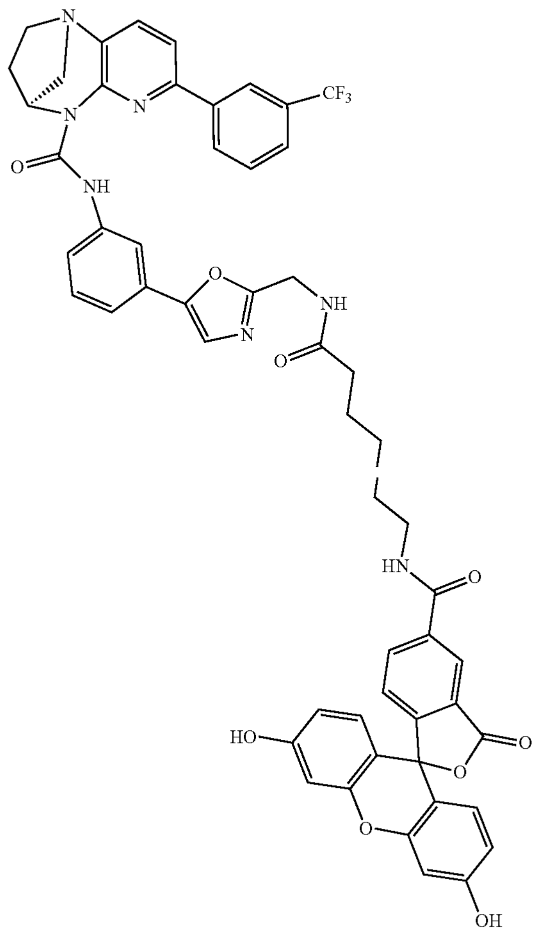 [SMILES: O=C(CCCCCNC(=O)c1ccc2c(c1)C(=O)OC21c2ccc(O)cc2Oc2cc(O)ccc21)NCc1ncc(-c2cccc(NC(=O)N3c4nc(-c5cccc(C(F)(F)F)c5)ccc4N4CC[C@H]3C4)c2)o1] | A | A |
| 709 | 509 | 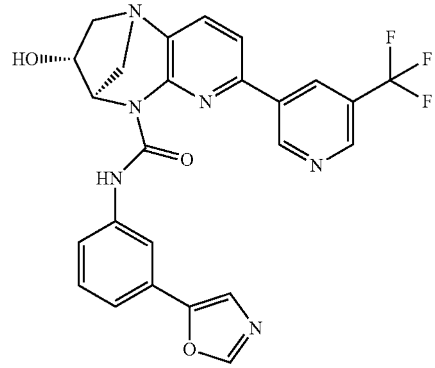 [SMILES: O=C(Nc1cccc(-c2cnco2)c1)N1c2nc(-c3cncc(C(F)(F)F)c3)ccc2N2C[C@@H](O)[C@H]1C2] | A | A |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 710 | 502 | 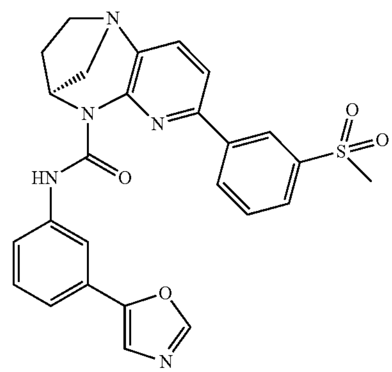 [SMILES: CS(=O)(=O)c1cccc(-c2ccc3c(n2)N(C(=O)Nc2cccc(-c4cnco4)c2)[C@H]2CCN3C2)c1] | A | A |
| 714 | 481 | 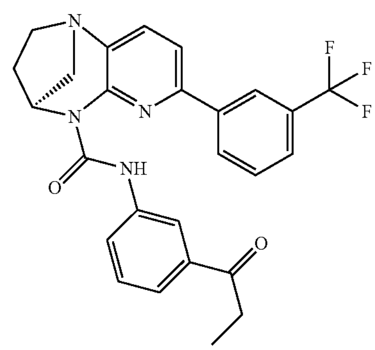 [SMILES: CCC(=O)c1cccc(NC(=O)N2c3nc(-c4cccc(C(F)(F)F)c4)ccc3N3CC[C@H]2C3)c1] | A | A |
| 715 | 503 | 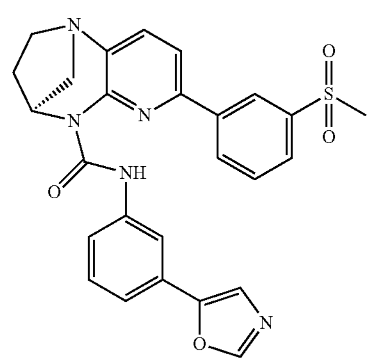 [SMILES: CS(=O)(=O)c1cccc(-c2ccc3c(n2)N(C(=O)Nc2cccc(-c4cnco4)c2)[C@H]2CCN3C2)c1] | B | A |
| 716 | 444 | 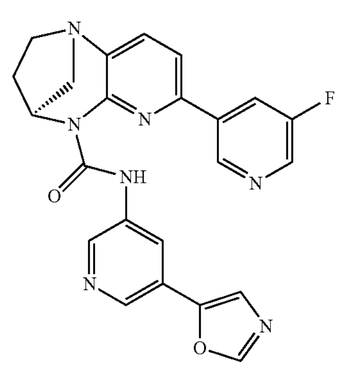 [SMILES: O=C(Nc1cncc(-c2cnco2)c1)N1c2nc(-c3cncc(F)c3)ccc2N2CC[C@H]1C2] | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 717 | 499 | 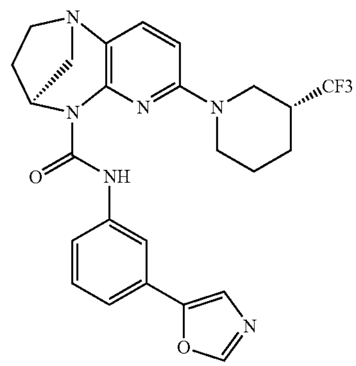 [SMILES: O=C(Nc1cccc(-c2cnco2)c1)N1c2nc(N3CCC[C@@H](C(F)(F)F)C3)ccc2N2CC[C@H]1C2] | A | A |
| 718 | 499 | 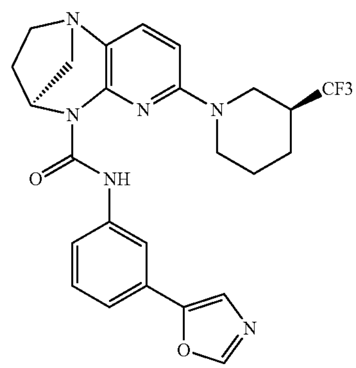 [SMILES: O=C(Nc1cccc(-c2cnco2)c1)N1c2nc(N3CCC[C@H](C(F)(F)F)C3)ccc2N2CC[C@H]1C2] | A | A |
| 719 | 493 | 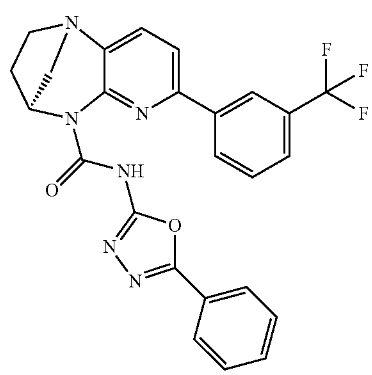 [SMILES: O=C(Nc1nnc(-c2ccccc2)o1)N1c2nc(-c3cccc(C(F)(F)F)c3)ccc2N2CC[C@H]1C2] | A | A |
| 720 | 494 | 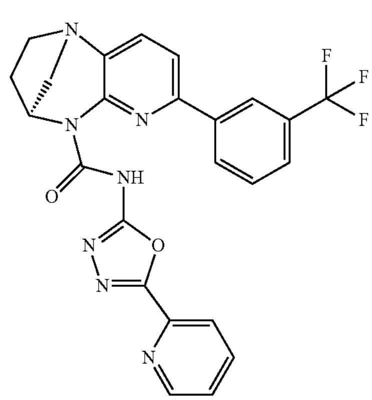 [SMILES: O=C(Nc1nnc(-c2ccccn2)o1)N1c2nc(-c3cccc(C(F)(F)F)c3)ccc2N2CC[C@H]1C2] | A | A |

TABLE 1-continued
Compounds of Formula (I).
| Compound No. | [M + H]+[calc] | Structure | Tyrp AVG EC$_{1.5}$ (µM) | Tyrp % Fold Act |
|---|---|---|---|---|
| 721 | 494 | 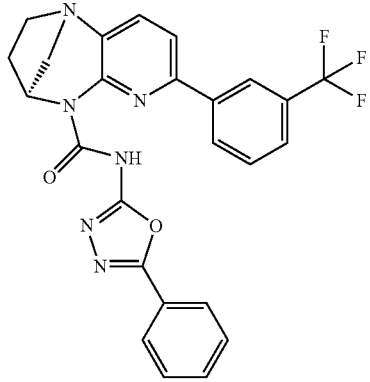 [SMILES: O=C(Nc1nnc(-c2ccccc2)o1)N1c2nc(-c3cccc(C(F)(F)F)c3)ccc2N2CC[C@H]1C2] | A | A |
| 722 | 443 | 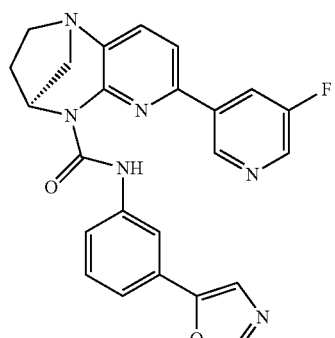 | A | A |
| 723 | 503 | 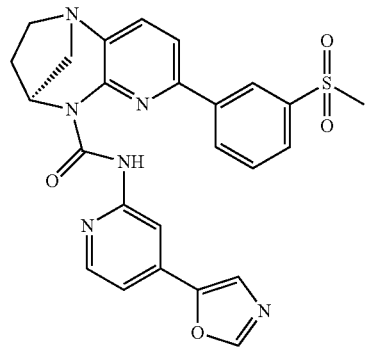 [SMILES: CS(=O)(=O)c1cccc(-c2ccc3c(n2)N(C(=O)Nc2cc(-c4cnco4)ccn2)[C@H]2CCN3C2)c1] | A | A |
| 724 | 503 | 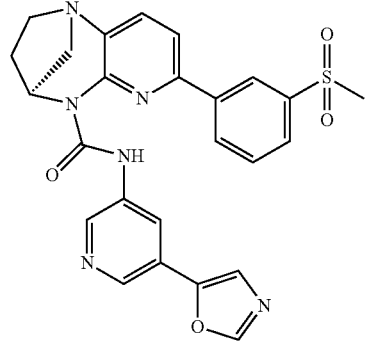 [SMILES: CS(=O)(=O)c1cccc(-c2ccc3c(n2)N(C(=O)Nc2cncc(-c4cnco4)c2)[C@H]2CCN3C2)c1] | A | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 725 | 521 | 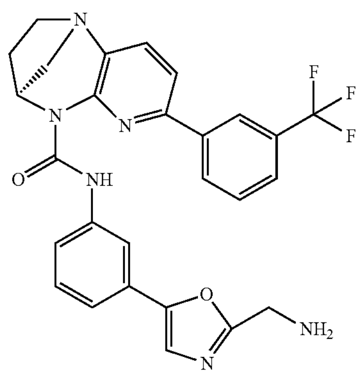 [SMILES: NCc1ncc(-c2cccc(NC(=O)N3c4nc(-c5cccc(C(F)(F)F)c5)ccc4N4CC[C@H]3C4)c2)o1] | A | A |
| 726 | 510 | 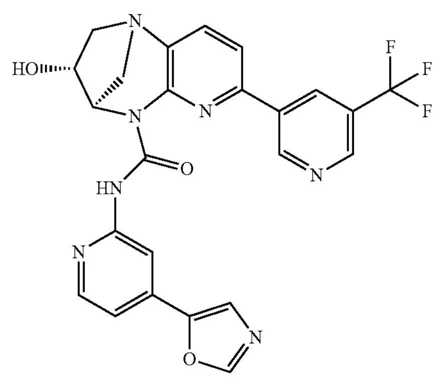 [SMILES: O=C(Nc1cc(-c2cnco2)ccn1)N1c2nc(-c3cncc(C(F)(F)F)c3)ccc2N2C[C@@H](O)[C@H]1C2] | B | B |
| 727 | 444 | 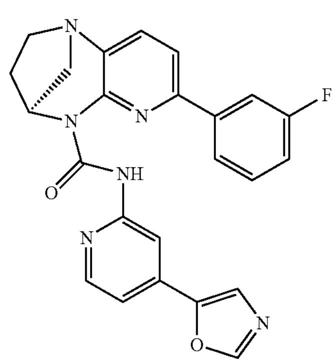 [SMILES: O=C(Nc1cc(-c2cnco2)ccn1)N1c2nc(-c3cccc(F)c3)ccc2N2CC[C@H]1C2] | A | A |

TABLE 1-continued

Compounds of Formula (I).

| Compound No. | [M + H]+_[calc] | Structure | Tyrp AVG EC_{1.5} (µM) | Tyrp % Fold Act |
|---|---|---|---|---|
| 730 | 1013 | 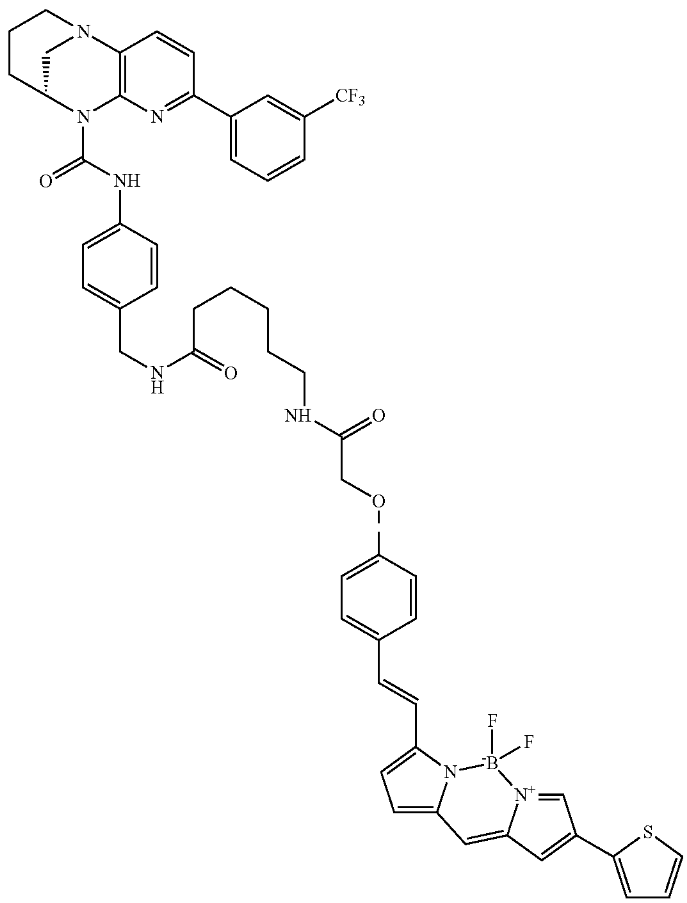 | A | A |
| 731 | 523 | 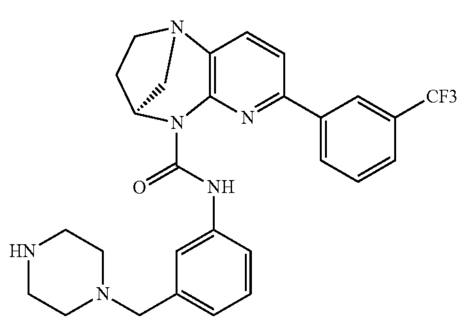 [SMILES: O=C(Nc1cccc(CN2CCNCC2)c1)N1c2nc(-c3cccc(C(F)(F)F)c3)ccc2N2CC[C@H]1C2] | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 733 | 510 | 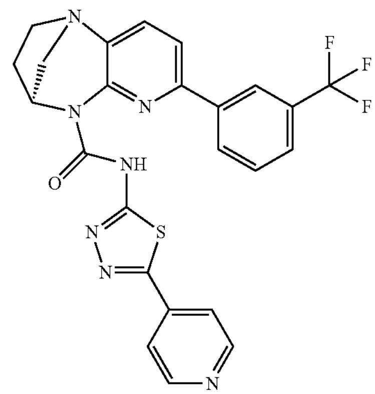 [SMILES: O=C(Nc1nnc(-c2ccncc2)s1)N1c2nc(-c3cccc(C(F)(F)F)c3)ccc2N2CC[C@H]1C2] | A | A |
| 734 | 508 | 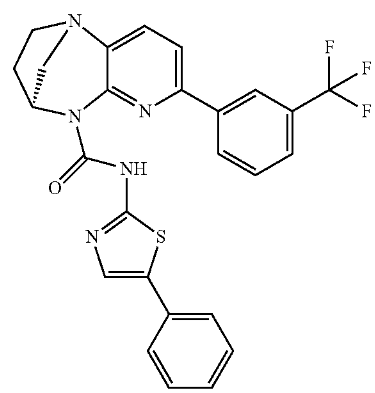 [SMILES: O=C(Nc1ncc(-c2ccccc2)s1)N1c2nc(-c3cccc(C(F)(F)F)c3)ccc2N2CC[C@H]1C2] | B | A |
| 736 | 495 | 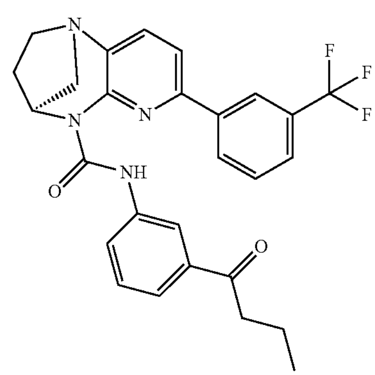 [SMILES: CCCC(=O)c1cccc(NC(=O)N2c3nc(-c4cccc(C(F)(F)F)c4)ccc3N3CC[C@H]2C3)c1] | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 737 | 509 | 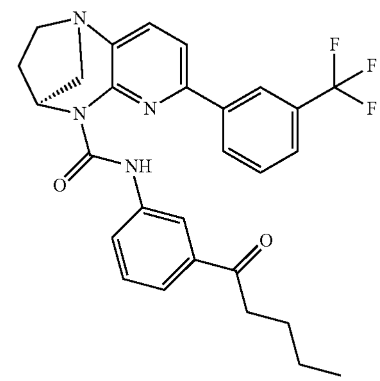 [SMILES: CCCCC(=O)c1cccc(NC(=O)N2c3nc(-c4cccc(C(F)(F)F)c4)ccc3N3CC[C@H]2C3)c1] | A | A |
| 739 | 444 | 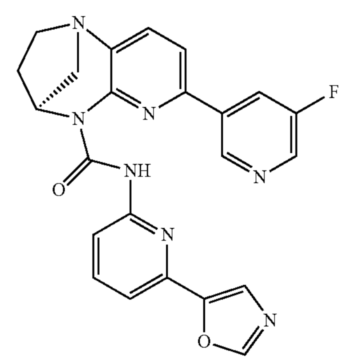 [SMILES: O=C(Nc1cccc(-c2cnco2)n1)N1c2nc(-c3cncc(F)c3)ccc2N2CC[C@H]1C2] | A | A |
| 740 | 495 | 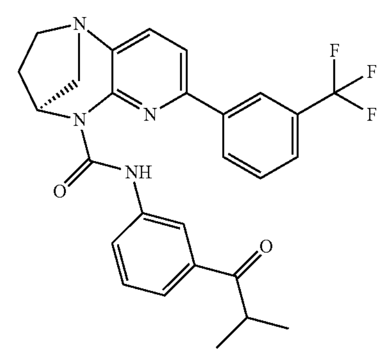 [SMILES: CC(C)C(=O)c1cccc(NC(=O)N2c3nc(-c4cccc(C(F)(F)F)c4)ccc3N3CC[C@H]2C3)c1] | A | A |
| 741 | 528 | 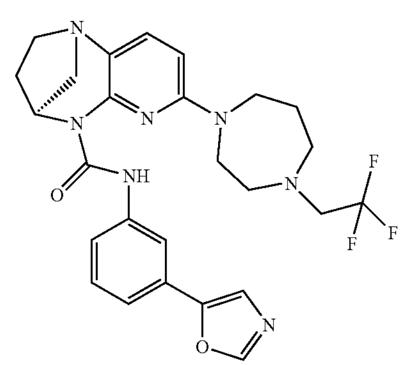 [SMILES: O=C(Nc1cccc(-c2cnco2)c1)N1c2nc(N3CCCN(CC(F)(F)F)CC3)ccc2N2CC[C@H]1C2] | A | A |

TABLE 1-continued
Compounds of Formula (I).
| Compound No. | [M + H]+$_{[calc]}$ | Structure | Tyrp AVG EC$_{1.5}$ (μM) | Tyrp % Fold Act |
|---|---|---|---|---|
| 742 | 525 | 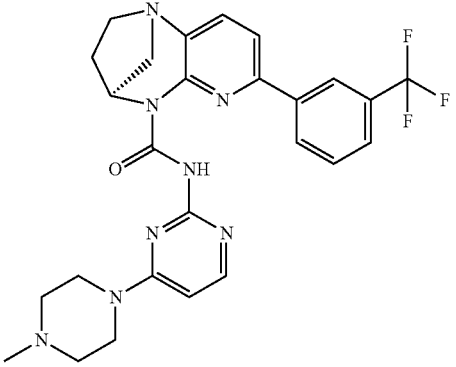 [SMILES: CN1CCN(c2ccnc(NC(=O)N3c4nc(-c5cccc(C(F)(F)F)c5)ccc4N4CC[C@H]3C4)n2)CC1] | A | A |
| 743 | 559 | 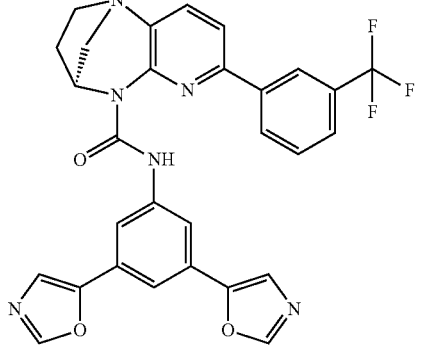 | A | A |
| 745 | 511 | 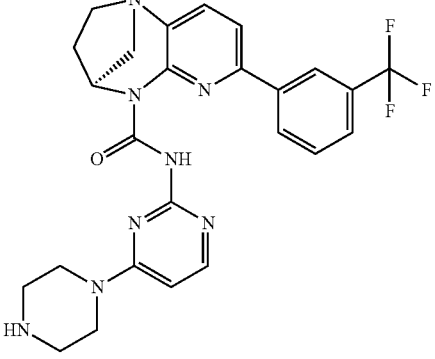 | B | A |
| 746 | 440 | 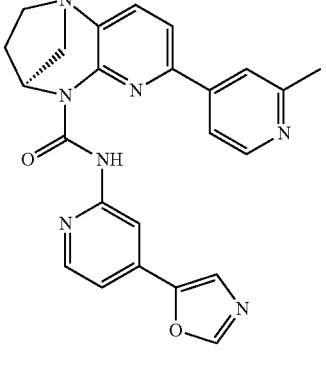 | A | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 747 | 470 | 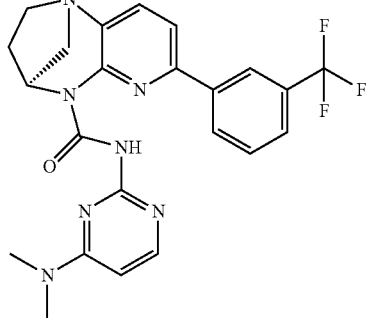 | A | A |
| 748 | 440 | 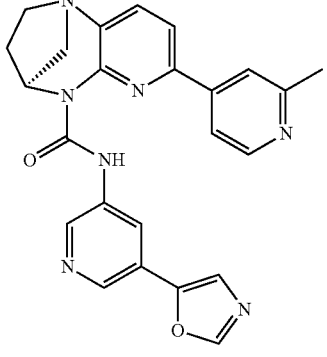 | A | A |
| 749 | 645 | 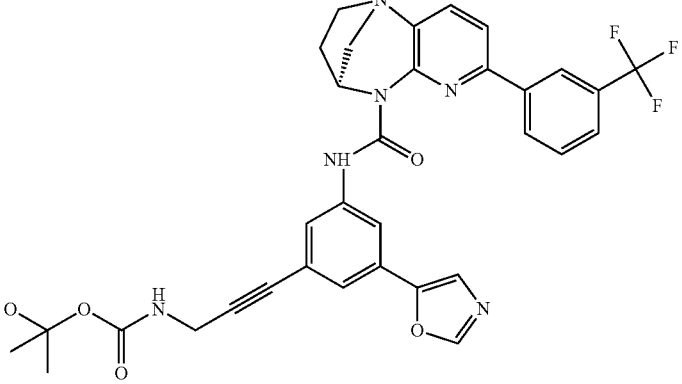 | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 750 | 649 | 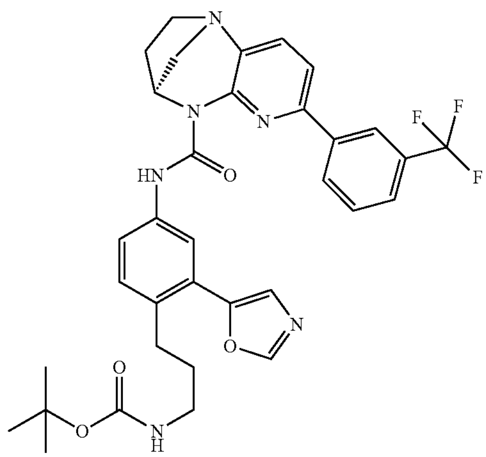 [SMILES: CC(C)(C)OC(=O)NCCCc1ccc(NC(=O)N2c3nc(-c4cccc(C(F)(F)F)c4)ccc3N3CC[C@H]2C3)cc1-c1cnco1] | A | A |
| 751 | 645 | 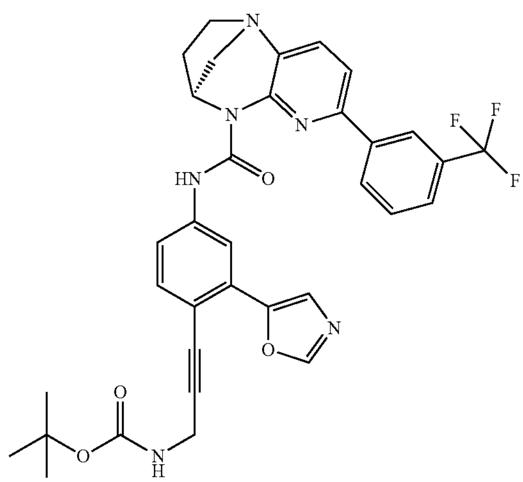 [SMILES: CC(C)(C)OC(=O)NCC#Cc1ccc(NC(=O)N2c3nc(-c4cccc(C(F)(F)F)c4)ccc3N3CC[C@H]2C3)cc1-c1cnco1] | A | A |
| 752 | 663 | 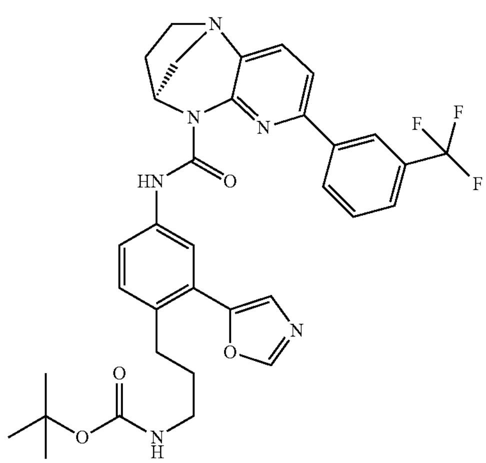 [SMILES: CC(C)(C)OC(=O)NCCCc1ccc(NC(=O)N2c3nc(-c4cccc(C(F)(F)F)c4)ccc3N3CC[C@H]2C3)cc1-c1cnco1] | A | A |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 753 | 659 | 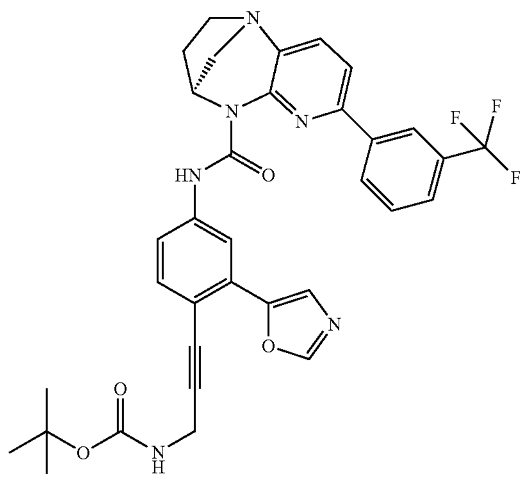 [SMILES: CC(C)(C)OC(=O)NCC#Cc1ccc(NC(=O)N2c3nc(-c4cccc(C(F)(F)F)c4)ccc3N3CC[C@H]2C3)cc1-c1cnco1] | A | A |
| 754 | 663 | 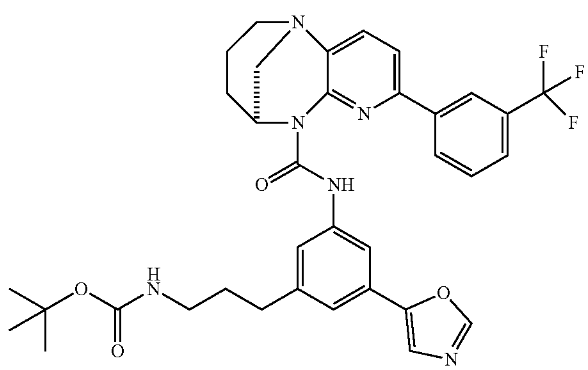 [SMILES: CC(C)(C)OC(=O)NCCCc1cc(NC(=O)N2c3nc(-c4cccc(C(F)(F)F)c4)ccc3N3CCC[C@H]2C3)cc(-c2cnco2)c1] | A | A |
| 755 | 454 | 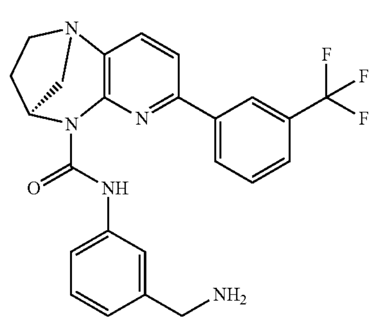 [SMILES: NCc1cccc(NC(=O)N2c3nc(-c4cccc(C(F)(F)F)c4)ccc3N3CC[C@H]2C3)c1] | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 756 | 581 | 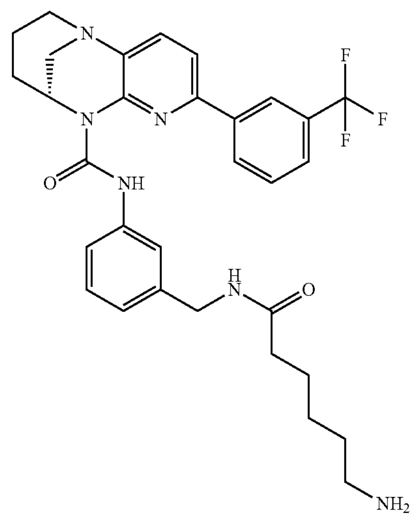 [SMILES: NCCCCCC(=O)NCc1cccc(NC(=O)N2c3nc(-c4cccc(C(F)(F)F)c4)ccc3N3CCC[C@H]2C3)c1] | A | A |
| 757 | 468 | 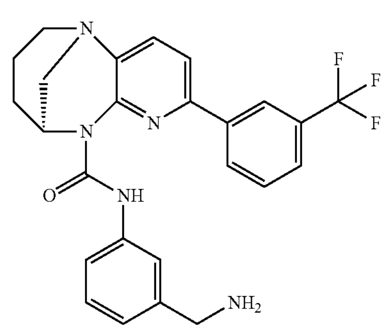 [SMILES: NCc1cccc(NC(=O)N2c3nc(-c4cccc(C(F)(F)F)c4)ccc3N3CCC[C@H]2C3)c1] | A | A |

TABLE 1-continued
Compounds of Formula (I).
| Compound No. | [M + H]+<sub>[calc]</sub> | Structure | Tyrp AVG EC<sub>1.5</sub> (μM) | Tyrp % Fold Act |
|---|---|---|---|---|
| 758 | 567 | 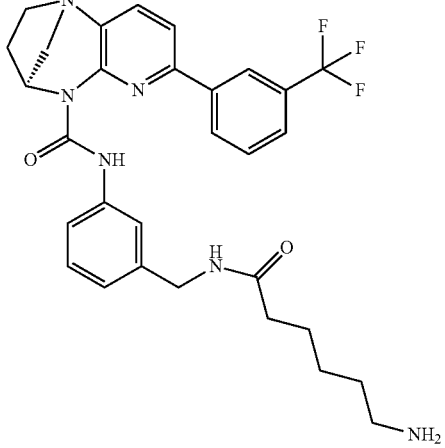 | A | A |
| 759 | 649 | 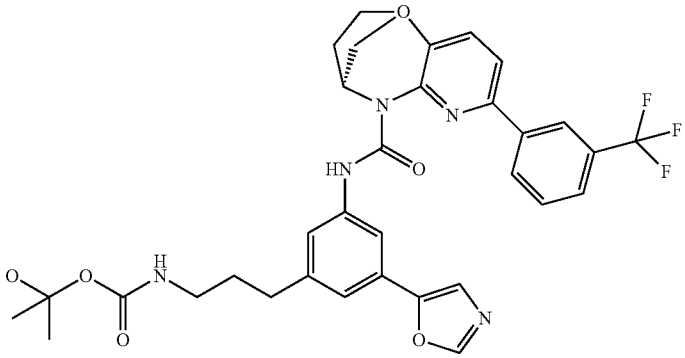 | B | A |
| 760 | 659 | 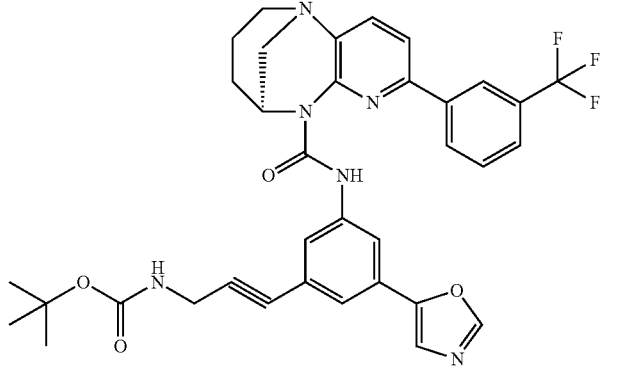 [SMILES: CC(C)(C)OC(=O)NCC#Cc1cc(NC(=O)N2c3nc(-c4cccc(C(F)(F)F)c4)ccc3N3CCC[C@H]2C3)cc(-c2cnco2)c1] | A | A |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 763 | 508 | 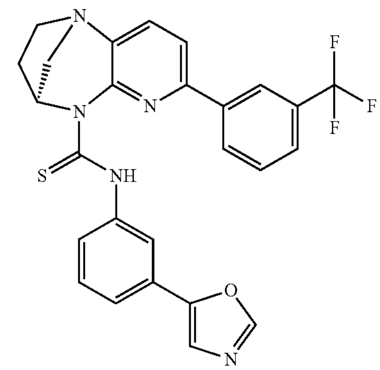 [SMILES: FC(F)(F)c1cccc(-c2ccc3c(n2)N(C(=S)Nc2cccc(-c4cnco4)c2)[C@H]2CCN3C2)c1] | A | A |
| 764 | 545 | 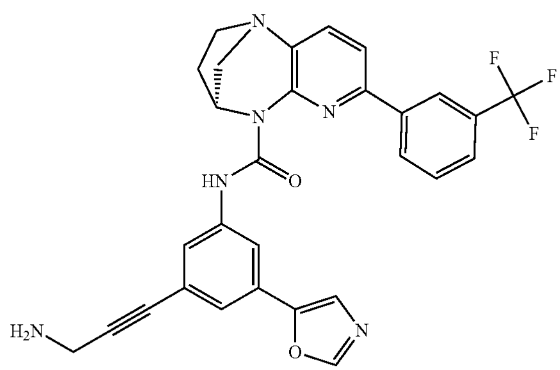 [SMILES: NCC#Cc1cc(NC(=O)N2c3nc(-c4cccc(C(F)(F)F)c4)ccc3N3CC[C@H]2C3)cc(-c2cnco2)c1] | NT | NT |
| 765 | 549 | 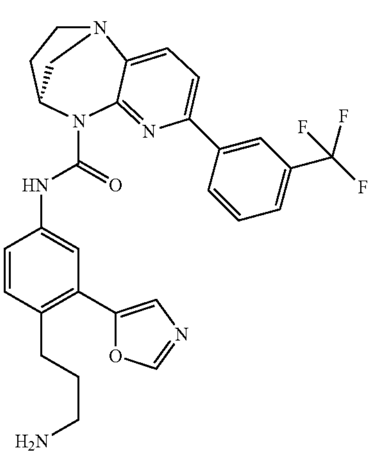 [SMILES: NCCCc1ccc(NC(=O)N2c3nc(-c4cccc(C(F)(F)F)c4)ccc3N3CC[C@H]2C3)cc1-c1cnco1] | A | A |

TABLE 1-continued

Compounds of Formula (I).

| Compound No. | [M + H]+$_{calc}$ | Structure | Tyrp AVG EC$_{1.5}$ (μM) | Tyrp % Fold Act |
|---|---|---|---|---|
| 766 | 545 | 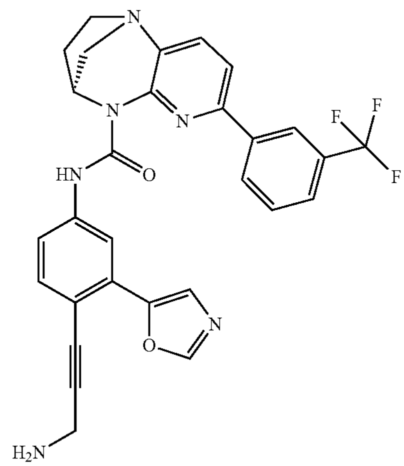 [SMILES: NCC#Cc1ccc(NC(=O)N2c3nc(-c4cccc(C(F)(F)F)c4)ccc3N3CC[C@H]2C3)cc1-c1cnco1] | A | A |
| 767 | 563 | 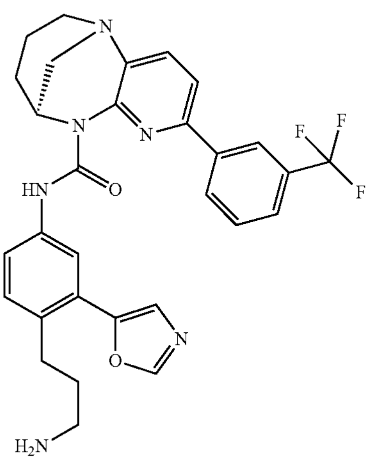 [SMILES: NCCCc1ccc(NC(=O)N2c3nc(-c4cccc(C(F)(F)F)c4)ccc3N3CCC[C@H]2C3)cc1-c1cnco1] | A | A |
| 768 | 559 | 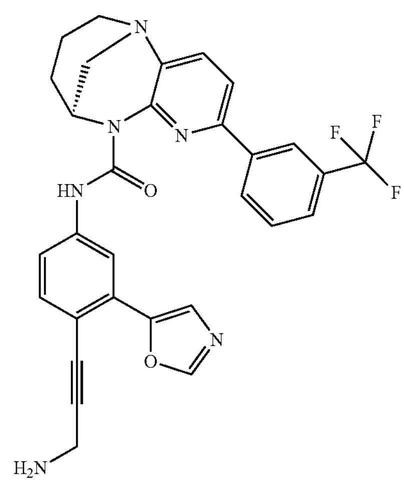 [SMILES: NCC#Cc1ccc(NC(=O)N2c3nc(-c4cccc(C(F)(F)F)c4)ccc3N3CCC[C@H]2C3)cc1-c1cnco1] | NT | NT |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 769 | 563 | 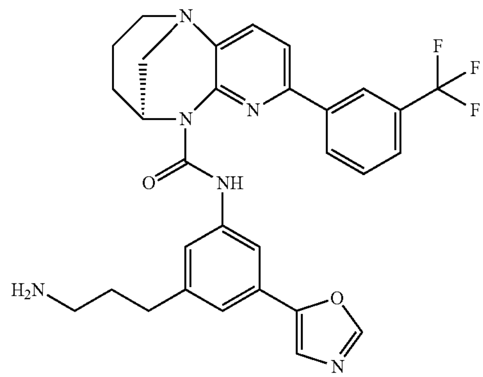 [SMILES: NCCCc1cc(NC(=O)N2c3nc(-c4cccc(C(F)(F)F)c4)ccc3N3CCC[C@H]2C3)cc(-c2cnco2)c1] | NT | NT |
| 770 | 549 | 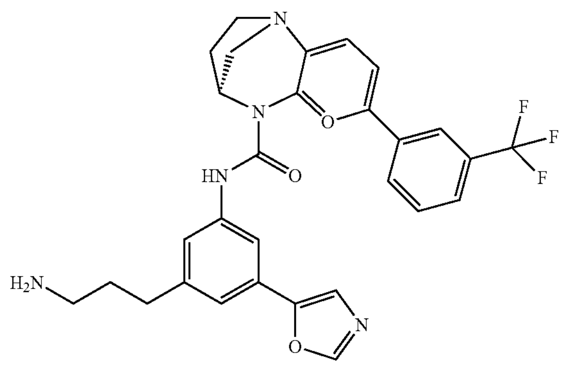 | A | A |
| 771 | 559 | 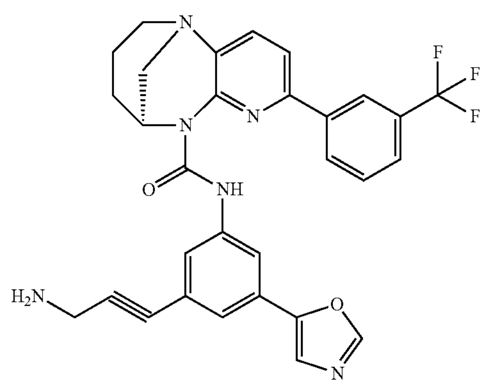 [SMILES: NCC#Cc1cc(NC(=O)N2c3nc(-c4cccc(C(F)(F)F)c4)ccc3N3CCC[C@H]2C3)cc(-c2cnco2)c1] | NT | NT |
| 776 | 563 | 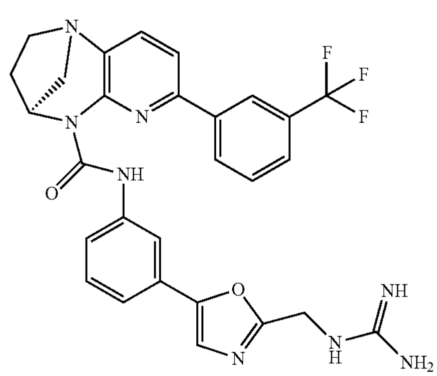 [SMILES: N=C(N)NCc1ncc(-c2cccc(NC(=O)N3c4nc(-c5cccc(C(F)(F)F)c5)ccc4N4CC[C@H]3C4)c2)o1] | A | A |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 777 | 510 | 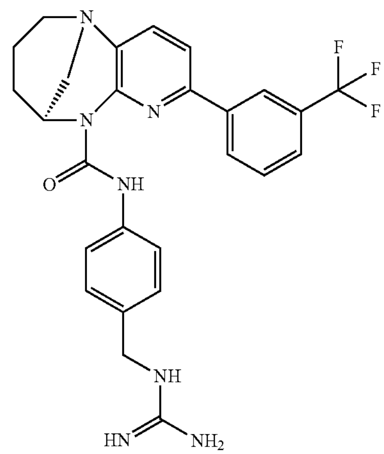 [SMILES: N=C(N)NCc1ccc(NC(=O)N2c3nc(-c4cccc(C(F)(F)F)c4)ccc3N3CCC[C@H]2C3)cc1] | A | A |
| 780 | 639 | 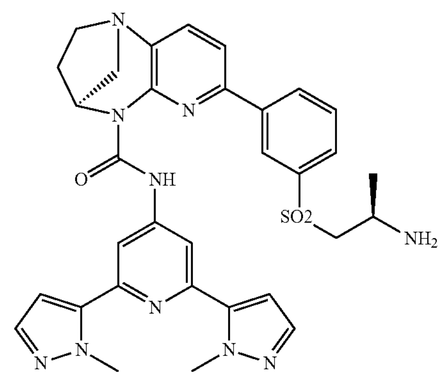 [SMILES: C[C@@H](N)CS(=O)(=O)c1cccc(-c2ccc3c(n2)N(C(=O)Nc2cc(-c4ccnn4C)nc(-c4ccnn4C)c2)[C@H]2CCN3C2)c1] | A | A |
| 785 | 425 | 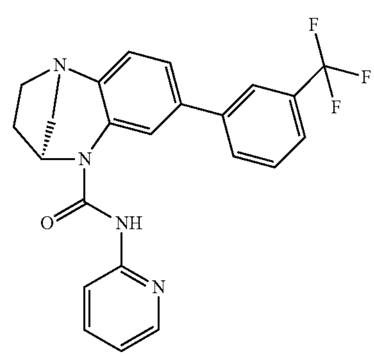 [SMILES: O=C(Nc1ccccn1)N1c2cc(-c3cccc(C(F)(F)F)c3)ccc2N2CC[C@H]1C2] | C | B |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 786 | 491 | 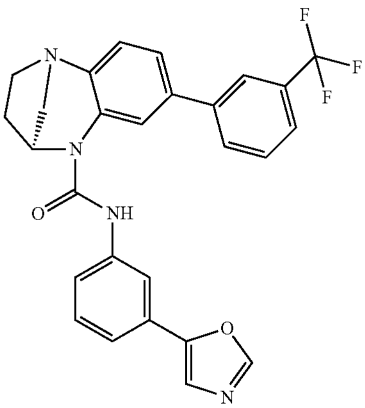 [SMILES: O=C(Nc1cccc(-c2cnco2)c1)N1c2cc(-c3cccc(C(F)(F)F)c3)ccc2N2CC[C@H]1C2] | B | A |
| 788 | 624 | 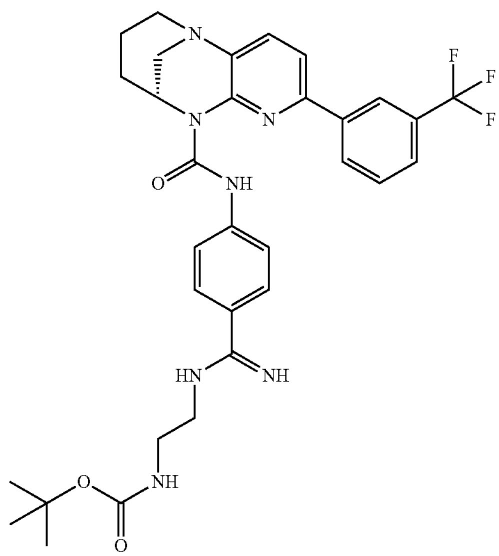 [SMILES: CC(C)(C)OC(=O)NCCNC(=N)c1ccc(NC(=O)N2c3nc(-c4cccc(C(F)(F)F)c4)ccc3N3CCC[C@H]2C3)cc1] | A | A |
| 790 | 510 | 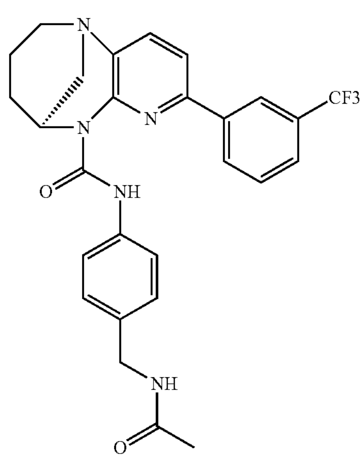 [SMILES: CC(=O)NCc1ccc(NC(=O)N2c3nc(-c4cccc(C(F)(F)F)c4)ccc3N3CCC[C@H]2C3)cc1] | A | A |

TABLE 1-continued

Compounds of Formula (I).

| Compound No. | [M + H]+<sub>[calc]</sub> | Structure | Tyrp AVG EC<sub>1.5</sub> (μM) | Tyrp % Fold Act |
|---|---|---|---|---|
| 792 | 524 | 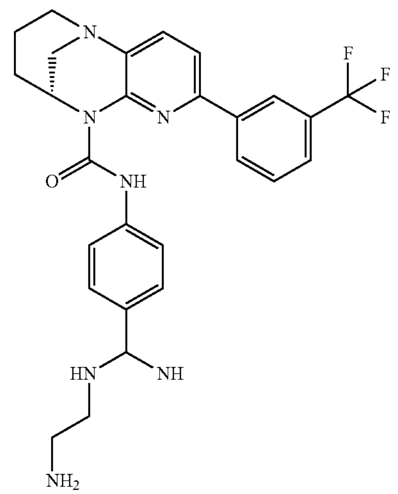 [SMILES: NCCNC(N)c1ccc(NC(=O)N2c3nc(-c4cccc(C(F)(F)F)c4)ccc3N3CCC[C@H]2C3)cc1] | A | A |
| 793 | 554 | 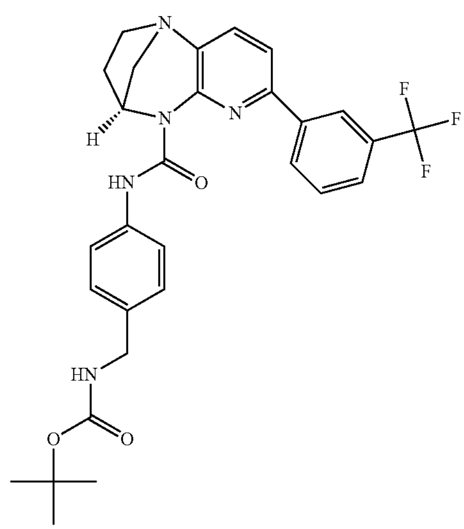 [SMILES: CC(C)(C)OC(=O)NCc1ccc(NC(=O)N2c3nc(-c4cccc(C(F)(F)F)c4)ccc3N3CC[C@H]2C3)cc1] | B | A |
| 794 | 487 | 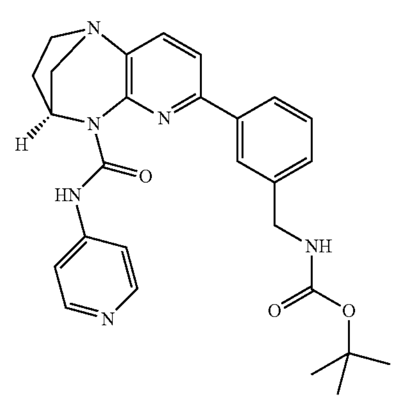 [SMILES: CC(C)(C)OC(=O)NCc1cccc(-c2ccc3c(n2)N(C(=O)Nc2ccncc2)[C@H]2CCN3C2)c1] | B | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 795 | 501 | 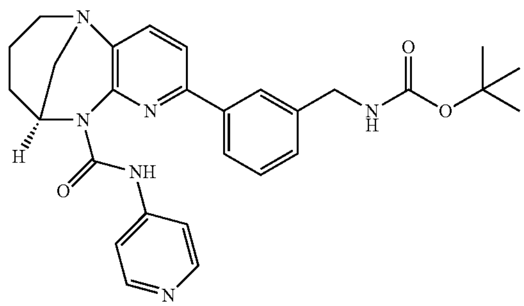 [SMILES: CC(C)(C)OC(=O)NCc1cccc(-c2ccc3c(n2)N(C(=O)Nc2ccncc2)[C@H]2CCCN3C2)c1] | B | A |
| 796 | 630 | 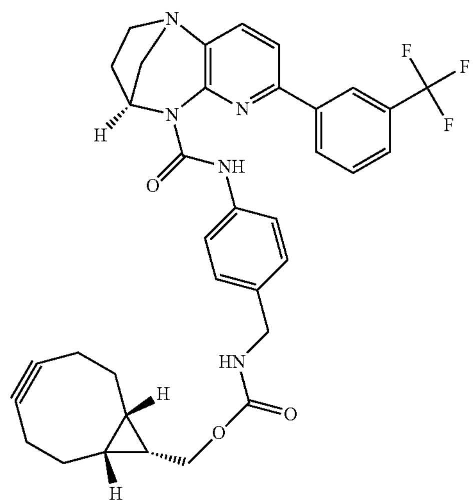 [SMILES: O=C(NCc1ccc(NC(=O)N2c3nc(-c4cccc(C(F)(F)F)c4)ccc3N3CC[C@H]2C3)cc1)OC[C@@H]1[C@@H]2CCC#CCC[C@@H]21] | B | A |
| 797 | 519 | 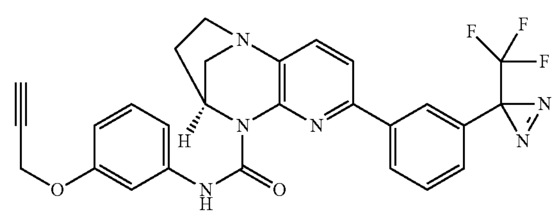 [SMILES: C#CCOc1cccc(NC(=O)N2c3nc(-c4cccc(C5(C(F)(F)F)N=N5)c4)ccc3N3CC[C@H]2C3)c1] | A | A |
| 798 | 548 | 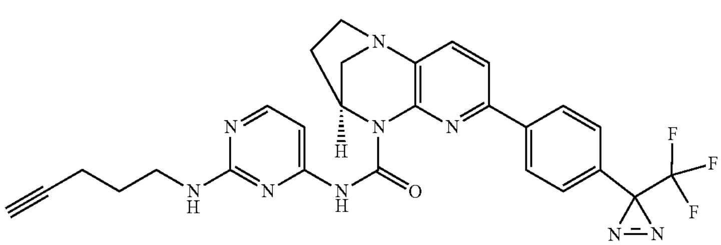 | A | A |

TABLE 1-continued

Compounds of Formula (I).

| Compound No. | [M + H]+[calc] | Structure | Tyrp AVG EC₁.₅ (μM) | Tyrp % Fold Act |
|---|---|---|---|---|
| 799 | 537 | 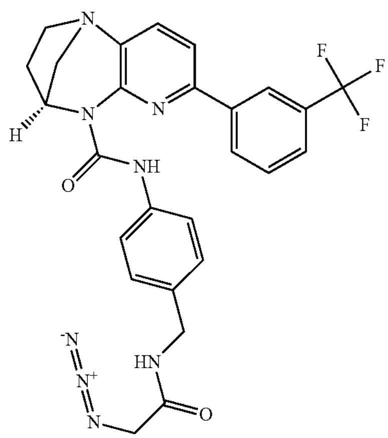 | A | A |
| 800 | 587 | 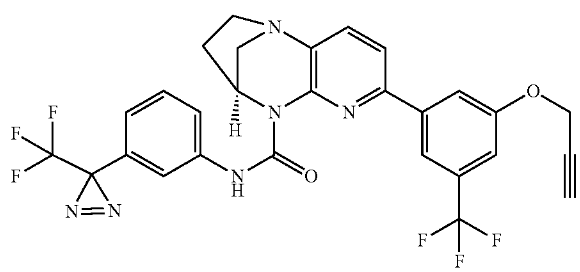 [SMILES: C#CCOc1cc(-c2ccc3c(n2)N(C(=O)Nc2cccc(C4(C(F)(F)F)N=N4)c2)[C@H]2CCN3C2)cc(C(F)(F)F)c1] | C | B |
| 801 | 548 | 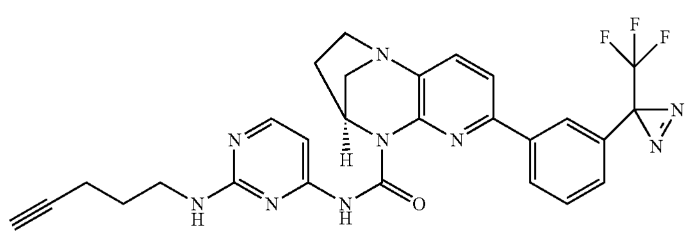 | A | A |
| 802 | 519 | 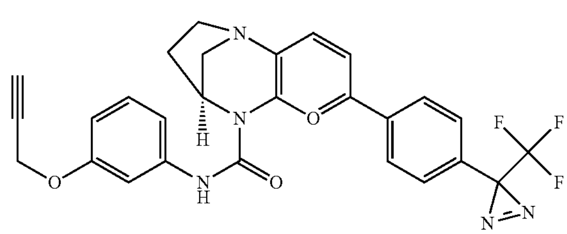 | B | A |
| 803 | 490 | 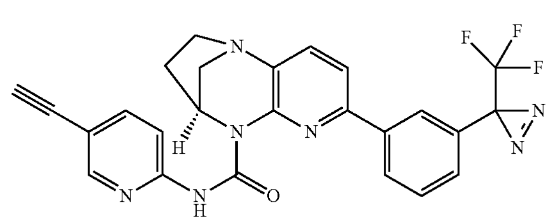 [SMILES: C#Cc1ccc(NC(=O)N2c3nc(-c4cccc(C5(C(F)(F)F)N=N5)c4)ccc3N3CC[C@H]2C3)nc1] | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 804 | 520 | 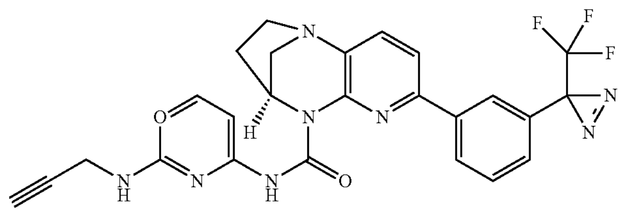 | A | A |
| 805 | 520 | 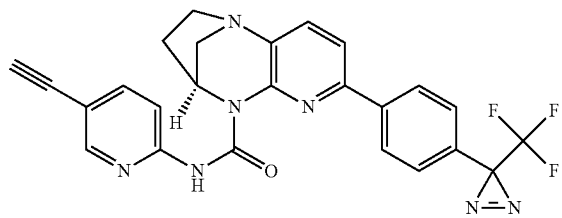 [SMILES: C#Cc1ccc(NC(=O)N2c3nc(-c4ccc(C5(C(F)(F)F)N=N5)cc4)ccc3N3CC[C@H]2C3)nc1] | B | A |
| 806 | 472 | 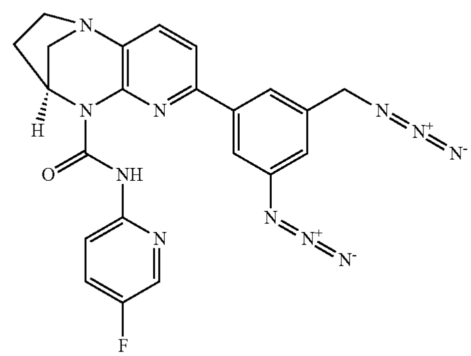 [SMILES: [N-]=[N+]=NCc1cc(N=[N+]=[N-])cc(-c2ccc3c(n2)N(C(=O)Nc2ccc(F)cn2)[C@H]2CCN3C2)c1] | A | A |
| 807 | 490 | 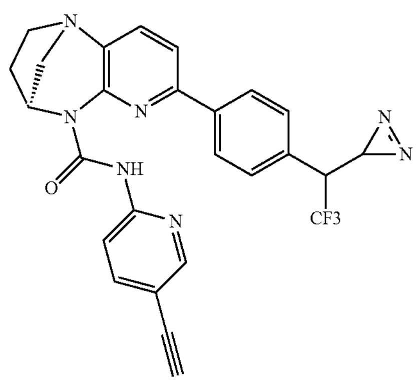 | C | B |
| 808 | 455 | 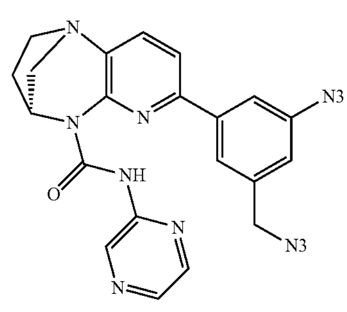 [SMILES: [N-]=[N+]=NCc1cc(N=[N+]=[N-])cc(-c2ccc3c(n2)N(C(=O)Nc2cnccn2)[C@H]2CCN3C2)c1] | A | A |

TABLE 1-continued
Compounds of Formula (I).
| Compound No. | [M + H]+$_{[calc]}$ | Structure | Tyrp AVG EC$_{1.5}$ (μM) | Tyrp % Fold Act |
|---|---|---|---|---|
| 809 | 520 | 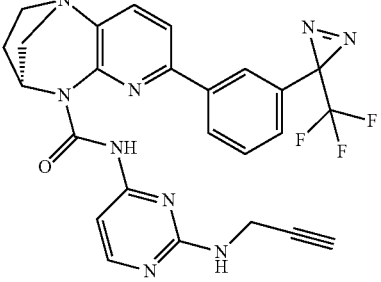 | B | A |
| 810 | 1308 | 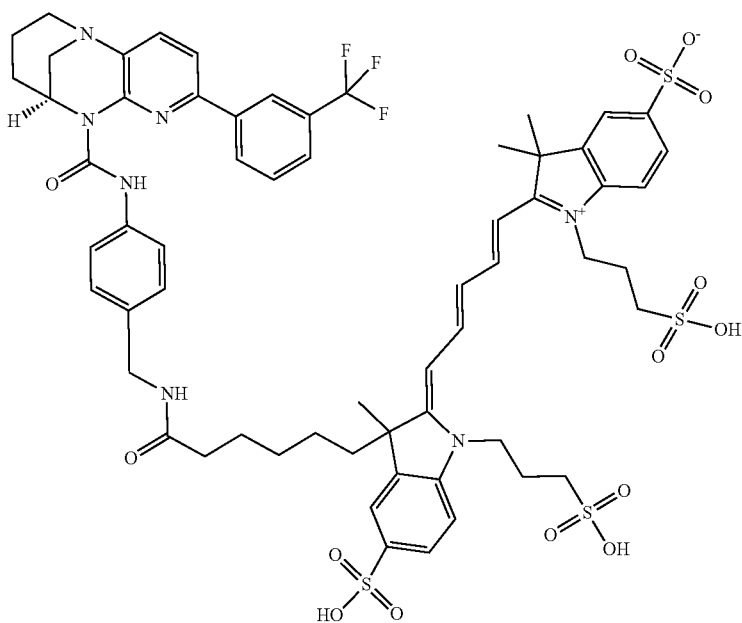 [SMILES: CC1(C)C(/C=C/C=C/C=C2\N(CCCS(=O)(=O)O)c3ccc(S(=O)(=O)O)cc3C2(C)CCCCCC(=O)NCc2ccc(NC(=O)N3c4nc(-c5cccc(C(F)(F)F)c5)ccc4N4CCC[C@H]3C4)cc2)=[N+](CCCS(=O)(=O)O)c2ccc(S(=O)(=O)[O-])cc21] | NT | NT |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 811 | 1294 | 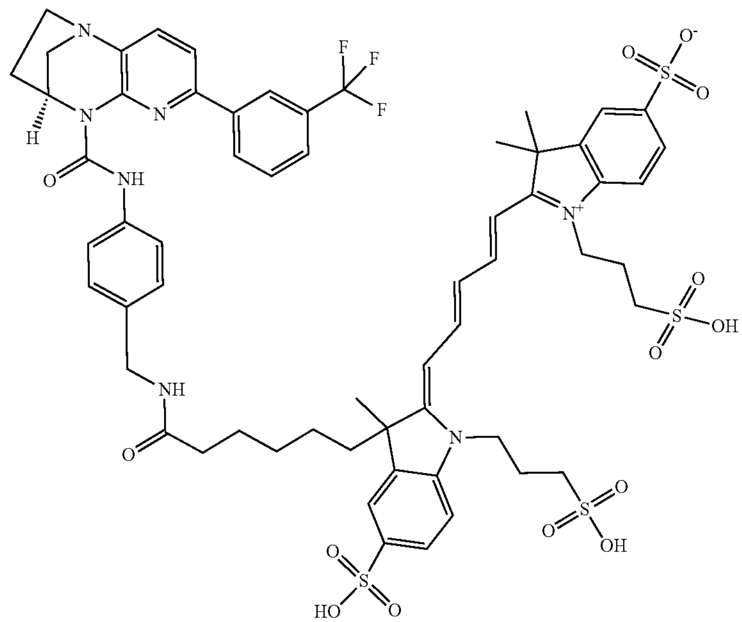 [SMILES: CC1(C)C(/C=C/C=C/C=C2\N(CCCS(=O)(=O)O)c3ccc(S(=O)(=O)O)cc3C2(C)CCCCCC(=O)NCc2ccc(NC(=O)N3c4nc(-c5cccc(C(F)(F)F)c5)ccc4N4CC[C@H]3C4)cc2)=[N+](CCCS(=O)(=O)O)c2ccc(S(=O)(=O)[O-])cc21] | NT | NT |
| 812 | 1473 | 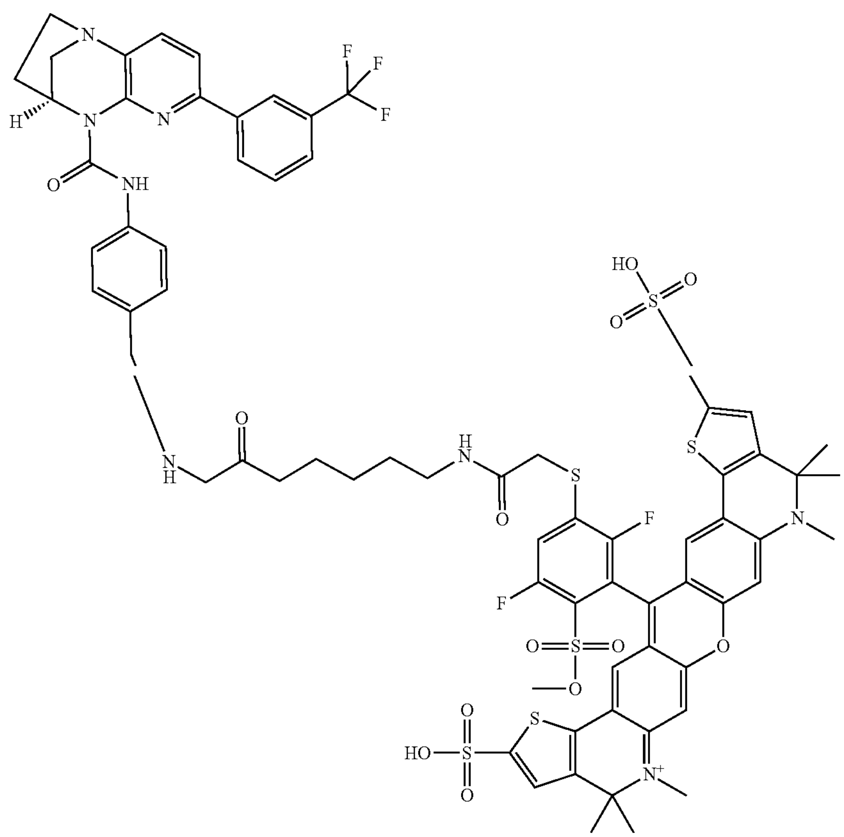 | NT | NT |

TABLE 1-continued
Compounds of Formula (I).
| Compound No. | [M + H]+<sub>[calc]</sub> | Structure | Tyrp AVG EC<sub>1.5</sub> (μM) | Tyrp % Fold Act |
|---|---|---|---|---|
| 813 | 1487 | 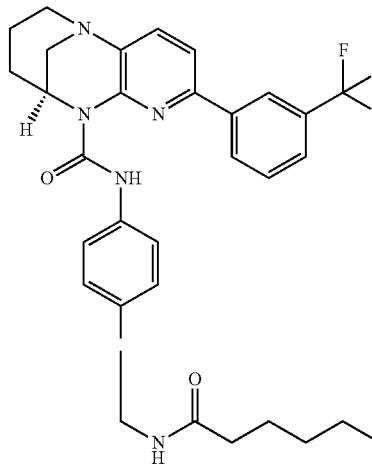 | NT | NT |
| 814 | 1109 | 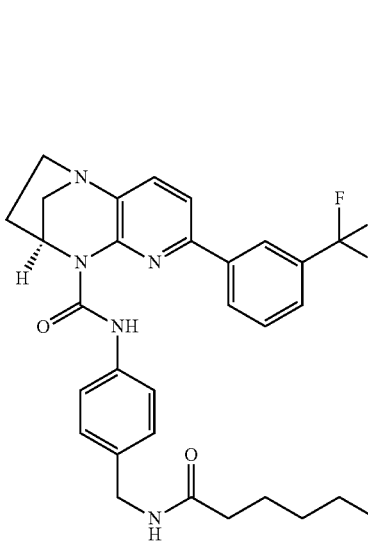 | NT | NT |

TABLE 1-continued

Compounds of Formula (I).

| Compound No. | [M + H]+_[calc] | Structure | Tyrp AVG EC_{1.5} (μM) | Tyrp % Fold Act |
|---|---|---|---|---|
| 815 | 1123 | 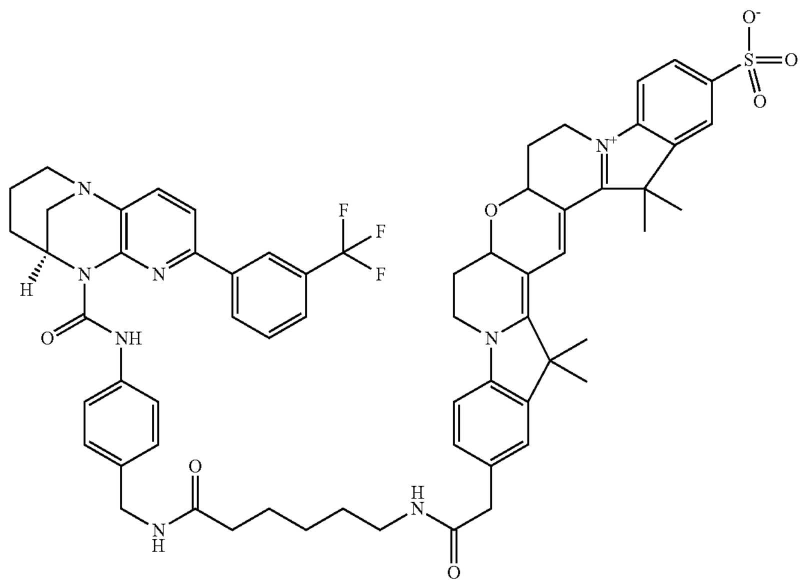 | NT | NT |
| 816 (7) | 426 | 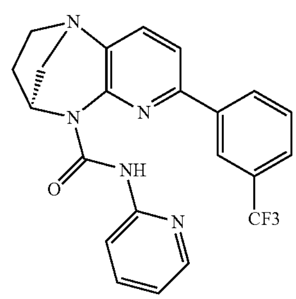 [SMILES: O=C(Nc1ccccn1)N1c2nc(-c3cccc(C(F)(F)F)c3)ccc2N2CC[C@H]1C2] | A | A |
| 817 | 426 | 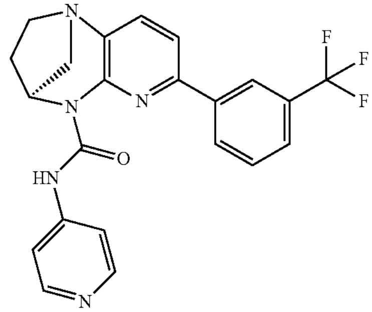 [SMILES: O=C(Nc1ccncc1)N1c2nc(-c3cccc(C(F)(F)F)c3)ccc2N2CC[C@H]1C2] | A | A |
| 818 | 517 | 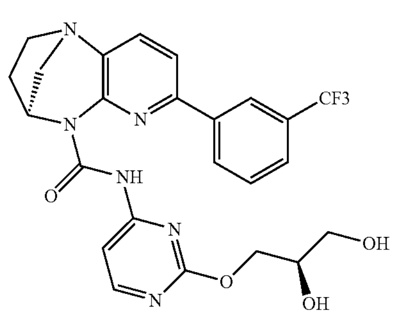 [SMILES: O=C(Nc1ccnc(OC[C@H](O)CO)n1)N1c2nc(-c3cccc(C(F)(F)F)c3)ccc2N2CC[C@H]1C2] | A | A |

TABLE 1-continued
Compounds of Formula (I).
| Compound No. | [M + H]+[calc] | Structure | Tyrp AVG EC$_{1.5}$ (μM) | Tyrp % Fold Act |
|---|---|---|---|---|
| 819 | 516 | 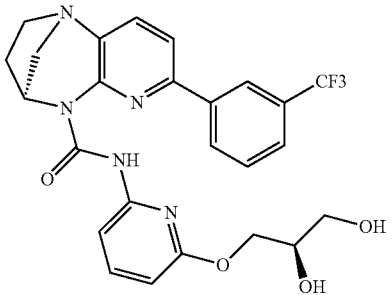 [SMILES: O=C(Nc1cccc(OC[C@H](O)CO)n1)N1c2nc(-c3cccc(C(F)(F)F)c3)ccc2N2CC[C@H]1C2] | A | A |
| 820 | 440 | 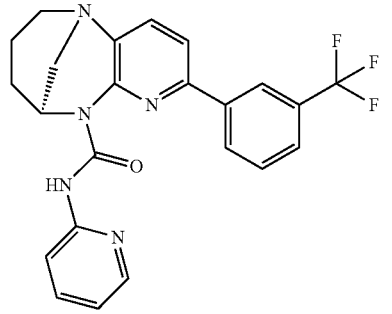 [SMILES: O=C(Nc1ccccn1)N1c2nc(-c3cccc(C(F)(F)F)c3)ccc2N2CCC[C@H]1C2] | A | A |
| 821 | 440 | 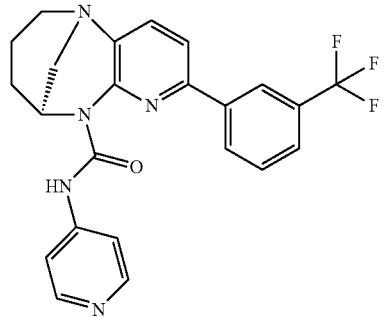 [SMILES: O=C(Nc1ccncc1)N1c2nc(-c3cccc(C(F)(F)F)c3)ccc2N2CCC[C@H]1C2] | A | A |
| 822 | 393 | 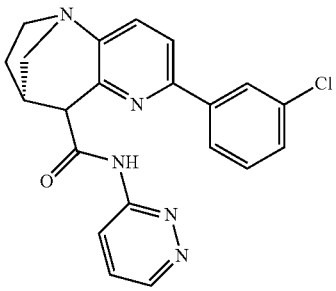 [SMILES: O=C(Nc1cccnn1)C1c2nc(-c3cccc(Cl)c3)ccc2N2CC[C@H]1C2] | A | A |

TABLE 1-continued

Compounds of Formula (I).

| Compound No. | [M + H]+[calc] | Structure | Tyrp AVG EC$_{1.5}$ (μM) | Tyrp % Fold Act |
|---|---|---|---|---|
| 823 | 426 | 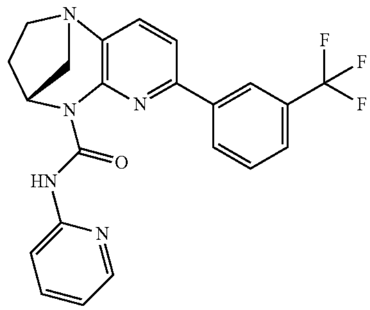 [SMILES: O=C(Nc1ccccn1)N1c2nc(-c3cccc(C(F)(F)F)c3)ccc2N2CC[C@@H]1C2] | A | A |
| 824 | 426 | 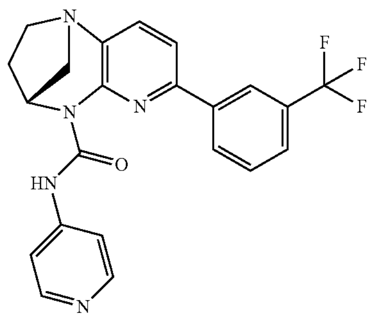 [SMILES: O=C(Nc1ccncc1)N1c2nc(-c3cccc(C(F)(F)F)c3)ccc2N2CC[C@@H]1C2] | A | A |
| 825 | 426 | 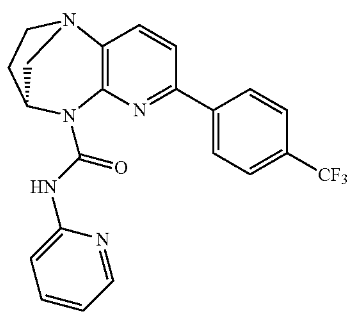 [SMILES: O=C(Nc1ccccn1)N1c2nc(-c3ccc(C(F)(F)F)cc3)ccc2N2CC[C@H]1C2] | NT | NT |
| 826 | 358 | 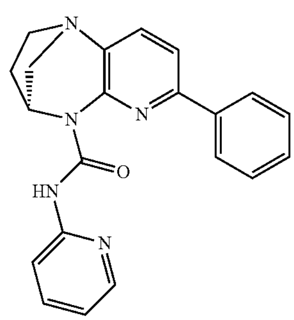 [SMILES: O=C(Nc1ccccn1)N1c2nc(-c3ccccc3)ccc2N2CC[C@H]1C2] | NT | NT |

TABLE 1-continued

Compounds of Formula (I).

| Compound No. | [M + H]+$_{[calc]}$ | Structure | Tyrp AVG EC$_{1.5}$ (μM) | Tyrp % Fold Act |
|---|---|---|---|---|
| 827 | 425 | (structure) | NT | NT |

In certain embodiments, the compound is any one of Compound Numbers 1, 3, 4, 5, 7, 8, 9, 10, 11, 12, 13, 14, 15, 16, 17, 18, 19, 20, 23, 25, 27, 28, 29, 30, 31, 32, 33, 34, 36, 38, 39, 40, 41, 42, 45, 46, 47, 48, 49, 53, 54, 56, 57, 59, 61, 63, 66, 68, 75, 76, 80, 81, 83, 86, 87, 90, 93, 95, 99, 101, 102, 107, 110, 118, 119, 120, 121, 122, 128, 129, 130, 133, 135, 136, 138, 139, 140, 141, 142, 145, 150, 151, 153, 156, 159, 160, 161, 162, 163, 164, 165, 166, 168, 170, 173, 174, 175, 176, 177, 178, 179, 180, 181, 182, 184, 189, 191, 194, 197, 207, 212, 214, 216, 218, 220, 222, 223, 230, 233, 235, 239, 250, 254, 260, 261, 264, 268, 271, 273, 274, 275, 276, 277, 278, 279, 280, 281, 282, 283, 285, 286, 288, 289, 290, 292, 293, 295, 299, 314, 316, 322, 324, 325, 329, 330, 332, 333, 335, 341, 344, 347, 348, 350, 351, 352, 353, 354, 356, 359, 360, 361, 365, 366, 367, 369, 373, 375, 376, 377, 378, 379, 380, 383, 385, 387, 388, 389, 391, 392, 393, 394, 396, 401, 402, 403, 404, 405, 406, 407, 408, 409, 410, 411, 412, 415, 417, 419, 421, 422, 423, 425, 427, 428, 430, 431, 435, 452, 459, 461, 463, 470, 472, 473, 474, 475, 480, 481, 483, 485, 491, 492, 496, 497, 498, 499, 500, 502, 503, 504, 505, 506, 507, 509, 515, 517, 519, 523, 526, 527, 530, 538, 540, 541, 542, 556, 557, 559, 562, 563, 574, 575, 580, 581, 583, 588, 589, 590, 591, 592, 593, 594, 595, 596, 601, 604, 605, 606, 607, 611, 617, 623, 625, 626, 629, 630, 635, 636, 637, 638, 639, 640, 642, 643, 645, 646, 647, 648, 651, 652, 653, 654, 655, 656, 657, 658, 659, 660, 663, 665, 666, 667, 668, 670, 671, 672, 676, 683, 692, 693, 694, 698, 703, 706, 708, 709, 710, 714, 717, 718, 719, 720, 721, 722, 723, 724, 725, 727, 730, 731, 733, 736, 737, 739, 740, 741, 742, 743, 746, 747, 748, 749, 750, 751, 752, 753, 754, 756, 757, 758, 760, 763, 765, 766, 767, 770, 776, 777, 780, 788, 790, 792, 797, 798, 799, 801, 803, 804, 806 and 808.

In one aspect or embodiments, a compound of the present invention is any one of compounds of the present invention as shown below in Table 10 and/or corresponding pharmaceutically acceptable salts thereof.

Table A—Additional Representative Compounds

TABLE A

Additional Representative Compounds

| Structure | Chemical Name | TRP Activity | TRP MAX RESP |
|---|---|---|---|
| (structure) | (9S)-5-chloro-N-[2-(3,3,3-trifluoropropyl)phenyl]-1,6,8-triazatricyclo[7.2.1.0 {2,7}]dodeca-2(7),3,5-triene-8-carboxamide | B | A |

TABLE A-continued

Additional Representative Compounds

| Structure | Chemical Name | TRP Activity | TRP MAX RESP |
|---|---|---|---|
| 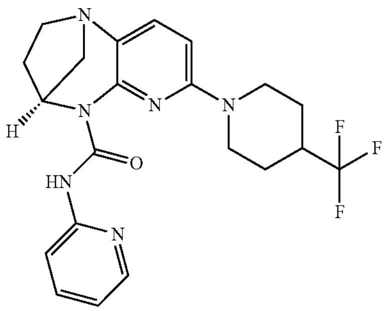 [SMILES: O=C(Nc1ccccn1)N1c2nc(N3CCC(C(F)(F)F)CC3)ccc2N2CC[C@H]1C2] | (9S)-N-(pyridin-2-yl)-5-[4-(trifluoromethyl)piperidin-1-yl]-1,6,8-triazatricyclo[7.2.1.0{2,7}]dodeca-2,4,6-triene-8-carboxamide | A | A |
| 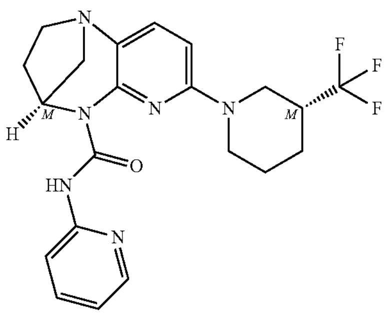 | (9S)-N-(pyridin-2-yl)-5-[(3R)-3-(trifluoromethyl)piperidin-1-yl]-1,6,8-triazatricyclo[7.2.1.0{2,7}]dodeca-2,4,6-triene-8-carboxamide | B | A |
| 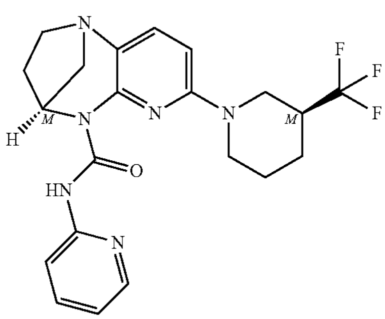 | (9S)-N-(pyridin-2-yl)-5-[(3S)-3-(trifluoromethyl)piperidin-1-yl]-1,6,8-triazatricyclo[7.2.1.0{2,7}]dodeca-2,4,6-triene-8-carboxamide | B | A |
| 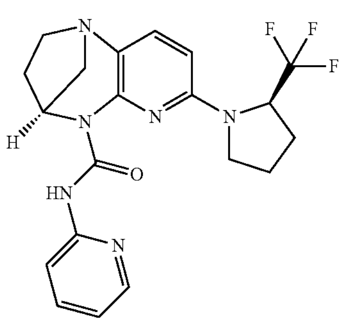 [SMILES: O=C(Nc1ccccn1)N1c2nc(N3CCC[C@@H]3C(F)(F)F)ccc2N2CC[C@H]1C2] | (9S)-N-(pyridin-2-yl)-5-[(2R)-2-(trifluoromethyl)pyrrolidin-1-yl]-1,6,8-triazatricyclo[7.2.1.0{2,7}]dodeca-2(7),3,5-triene-8-carboxamide | A | A |

TABLE A-continued

Additional Representative Compounds

| Structure | Chemical Name | TRP Activity | TRP MAX RESP |
|---|---|---|---|
| 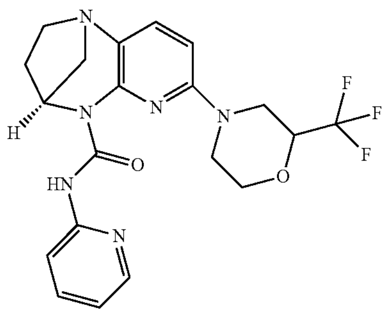 [SMILES: O=C(Nc1ccccn1)N1c2nc(N3CCOC(C(F)(F)F)C3)ccc2N2CC[C@H]1C2] | (9S)-N-(pyridin-2-yl)-5-[2-(trifluoromethyl)morpholin-4-yl]-1,6,8-triazatricyclo[7.2.1.0{2,7}]dodeca-2(7),3,5-triene-8-carboxamide | B | A |
| 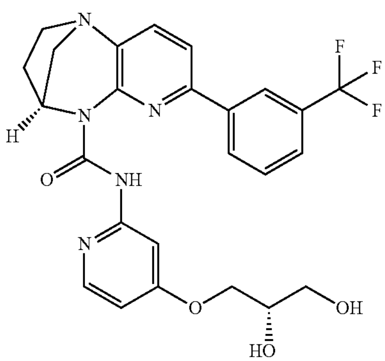 [SMILES: O=C(Nc1cc(OC[C@@H](O)CO)ccn1)N1c2nc(-c3cccc(C(F)(F)F)c3)ccc2N2CC[C@H]1C2] | (9S)-N-{4-[(2S)-2,3-dihydroxypropoxy]pyridin-2-yl}-5-[3-(trifluoromethyl)phenyl]-1,6,8-triazatricyclo[7.2.1.0 {2,7}]dodeca-2(7),3,5-triene-8-carboxamide | A | A |
| 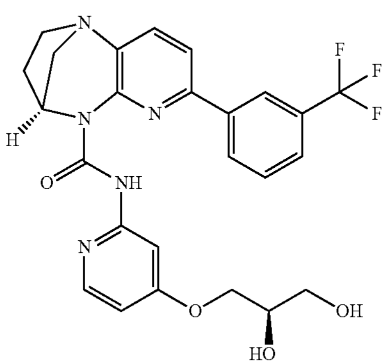 [SMILES: O=C(Nc1cc(OC[C@H](O)CO)ccn1)N1c2nc(-c3cccc(C(F)(F)F)c3)ccc2N2CC[C@H]1C2] | (9S)-N-{4-[(2R)-2,3-dihydroxypropoxy]pyridin-2-yl}-5-[3-(trifluoromethyl)phenyl]-1,6,8-triazatricyclo[7.2.1.0 {2,7}]dodeca-2(7),3,5-triene-8-carboxamide | A | A |
| 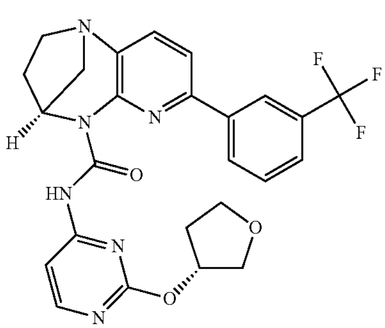 [SMILES: O=C(Nc1ccnc(O[C@@H]2CCOC2)n1)N1c2nc(-c3cccc(C(F)(F)F)c3)ccc2N2CC[C@H]1C2] | (9S)-N-{2-[(3R)-oxolan-3-yloxy]pyrimidin-4-yl}-5-[3-(trifluoromethyl)phenyl]-1,6,8-triazatricyclo[7.2.1.0 {2,7}]dodeca-2(7),3,5-triene-8-carboxamide | A | A |

TABLE A-continued

Additional Representative Compounds

| Structure | Chemical Name | TRP Activity | TRP MAX RESP |
|---|---|---|---|
| 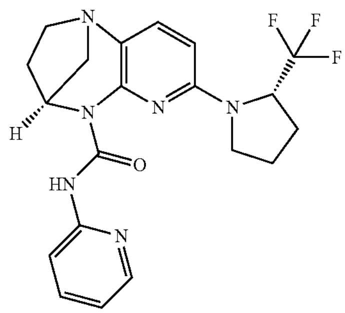 [SMILES: O=C(Nc1ccccn1)N1c2nc(N3CCC[C@H]3C(F)(F)F)ccc2N2CC[C@H]1C2] | (9S)-N-(pyridin-2-yl)-5-[(2S)-2-(trifluoromethyl)pyrrolidin-1-yl]-1,6,8-triazatricyclo[7.2.1.0{2,7}]dodeca-2(7),3,5-triene-8-carboxamide | B | A |
| 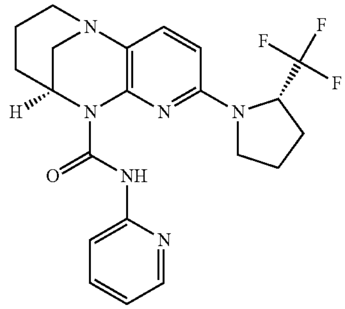 [SMILES: O=C(Nc1ccccn1)N1c2nc(N3CCC[C@H]3C(F)(F)F)ccc2N2CCC[C@H]1C2] | (9S)-N-(pyridin-2-yl)-5-[(2S)-2-(trifluoromethyl)pyrrolidin-1-yl]-1,6,8-triazatricyclo[7.3.1.0{2,7}]trideca-2(7),3,5-triene-8-carboxamide | B | A |
| 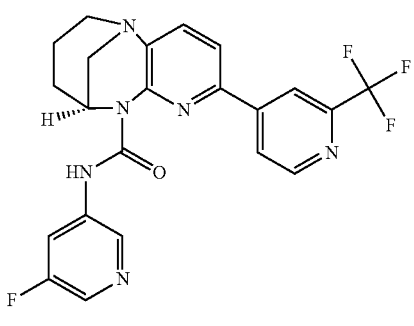 [SMILES: O=C(Nc1cncc(F)c1)N1c2nc(-c3ccnc(C(F)(F)F)c3)ccc2N2CCC[C@H]1C2] | (9S)-N-(5-fluoropyridin-3-yl)-5-[2-(trifluoromethyl)pyridin-4-yl]-1,6,8-triazatricyclo[7.3.1.0{2,7}]trideca-2(7),3,5-triene-8-carboxamide | A | A |
| 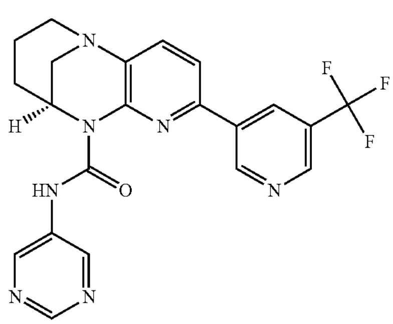 [SMILES: O=C(Nc1cncnc1)N1c2nc(-c3cncc(C(F)(F)F)c3)ccc2N2CCC[C@H]1C2] | (9S)-N-(pyrimidin-5-yl)-5-[5-(trifluoromethyl)pyridin-3-yl]-1,6,8-triazatricyclo[7.3.1.0{2,7}]trideca-2(7),3,5-triene-8-carboxamide | A | A |

TABLE A-continued

Additional Representative Compounds

| Structure | Chemical Name | TRP Activity | TRP MAX RESP |
|---|---|---|---|
| 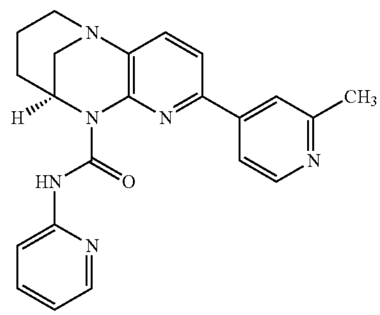 [SMILES: Cc1cc(-c2ccc3c(n2)N(C(=O)Nc2ccccn2)[C@H]2CCCN3C2)ccn1] | (9S)-5-(2-methylpyridin-4-yl)-N-(pyridin-2-yl)-1,6,8-triazatricyclo[7.3.1.0 {2,7}]trideca-2(7),3,5-triene-8-carboxamide | A | A |
| 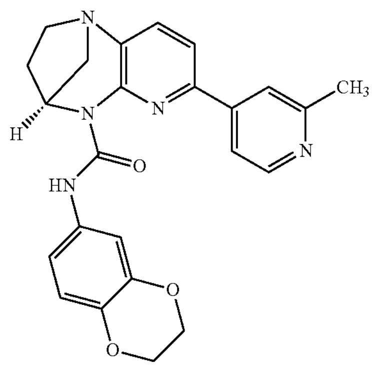 [SMILES: Cc1cc(-c2ccc3c(n2)N(C(=O)Nc2ccc4c(c2)OCCO4)[C@H]2CCN3C2)ccn1] | (9S)-N-(2,3-dihydro-1,4-benzodioxin-6-yl)-5-(2-methylpyridin-4-yl)-1,6,8-triazatricyclo[7.2.1.0 {2,7}]dodeca-2(7),3,5-triene-8-carboxamide | B | A |
| 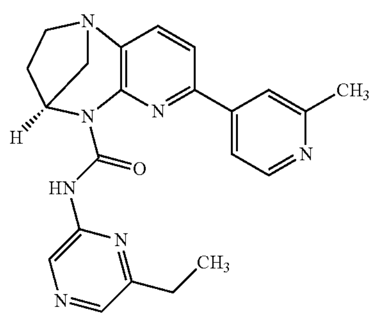 [SMILES: CCc1cncc(NC(=O)N2c3nc(-c4ccnc(C)c4)ccc3N3CC[C@H]2C3)n1] | (9S)-N-(6-ethylpyrazin-2-yl)-5-(2-methylpyridin-4-yl)-1,6,8-triazatricyclo[7.2.1.0 {2,7}]dodeca-2(7),3,5-triene-8-carboxamide | A | A |
| 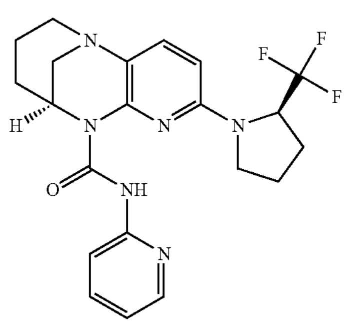 [SMILES: O=C(Nc1ccccn1)N1c2nc(N3CCC[C@@H]3C(F)(F)F)ccc2N2CCC[C@H]1C2] | (9S)-N-(pyridin-2-yl)-5-[(2R)-2-(trifluoromethyl)pyrrolidin-1-yl]-1,6,8-triazatricyclo[7.3.1.0 {2,7}]trideca-2(7),3,5-triene-8-carboxamide | A | A |

TABLE A-continued

Additional Representative Compounds

| Structure | Chemical Name | TRP Activity | TRP MAX RESP |
|---|---|---|---|
| 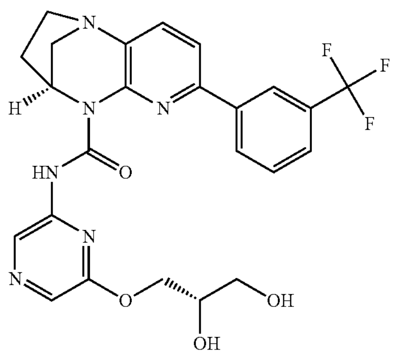 [SMILES: O=C(Nc1cncc(OC[C@@H](O)CO)n1)N1c2nc(-c3cccc(C(F)(F)F)c3)ccc2N2CC[C@H]1C2] | (9S)-N-{6-[(2S)-2,3-dihydroxypropoxy]pyrazin-2-yl}-5-[3-(trifluoromethyl)phenyl]-1,6,8-triazatricyclo[7.2.1.0 {2,7}]dodeca-2(7),3,5-triene-8-carboxamide | A | A |
| 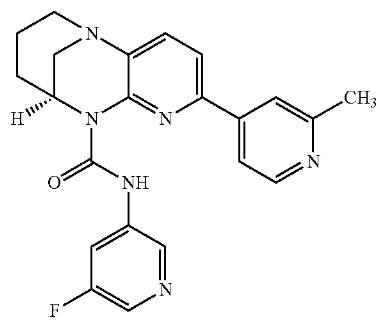 [SMILES: Cc1cc(-c2ccc3c(n2)N(C(=O)Nc2cncc(F)c2)[C@H]2CCCN3C2)ccn1] | (9S)-N-(5-fluoropyridin-3-yl)-5-(2-methylpyridin-4-yl)-1,6,8-triazatricyclo[7.3.1.0 {2,7}]trideca-2,4,6-triene-8-carboxamide | A | A |
| 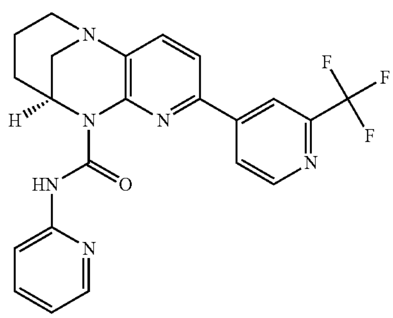 [SMILES: O=C(Nc1ccccn1)N1c2nc(-c3ccnc(C(F)(F)F)c3)ccc2N2CCC[C@H]1C2] | (9S)-N-(pyridazin-3-yl)-5-[2-(trifluoromethyl)pyridin-4-yl]-1,6,8-triazatricyclo[7.3.1.0 {2,7}]trideca-2(7),3,5-triene-8-carboxamide | A | A |
| 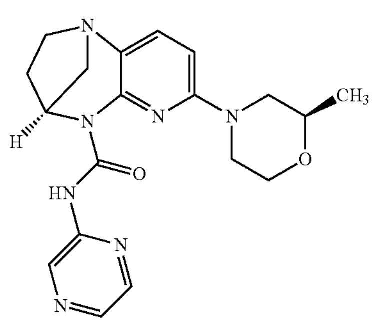 [SMILES: C[C@@H]1CN(c2ccc3c(n2)N(C(=O)Nc2cnccn2)[C@H]2CCN3C2)CCO1] | (9S)-5-[(2R)-2-methylmorpholin-4-yl]-N-(pyrazin-2-yl)-1,6,8-triazatricyclo[7.2.1.0 {2,7}]dodeca-2,4,6-triene-8-carboxamide | B | A |

TABLE A-continued

Additional Representative Compounds

| Structure | Chemical Name | TRP Activity | TRP MAX RESP |
|---|---|---|---|
| 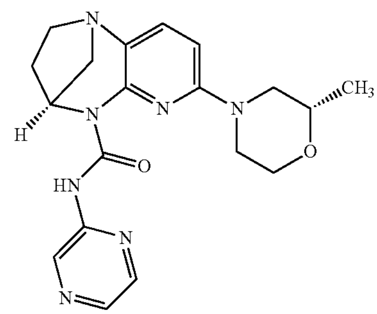 [SMILES: C[C@H]1CN(c2ccc3c(n2)N(C(=O)Nc2cnccn2)[C@H]2CCN3C2)CCO1] | (9S)-5-[(2S)-2-methylmorpholin-4-yl]-N-(pyrazin-2-yl)-1,6,8-triazatricyclo[7.2.1.0 {2,7}]dodeca-2,4,6-triene-8-carboxamide | B | A |
| 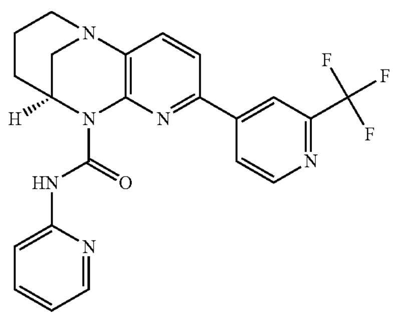 [SMILES: O=C(Nc1ccccn1)N1c2nc(-c3ccnc(C(F)(F)F)c3)ccc2N2CCC[C@H]1C2] | (9S)-N-(pyridin-2-yl)-5-[2-(trifluoromethyl)pyridin-4-yl]-1,6,8-triazatricyclo[7.3.1.0 {2,7}]trideca-2(7),3,5-triene-8-carboxamide | A | A |
| 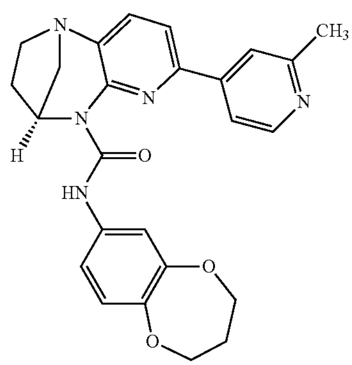 [SMILES: Cc1cc(-c2ccc3c(n2)N(C(=O)Nc2ccc4c(c2)OCCCO4)[C@H]2CCN3C2)ccn1] | (9S)-N-(3,4-dihydro-2H-1,5-benzodioxepin-7-yl)-5-(2-methylpyridin-4-yl)-1,6,8-triazatricyclo[7.2.1.0 {2,7}]dodeca-2,4,6-triene-8-carboxamide | A | A |
| 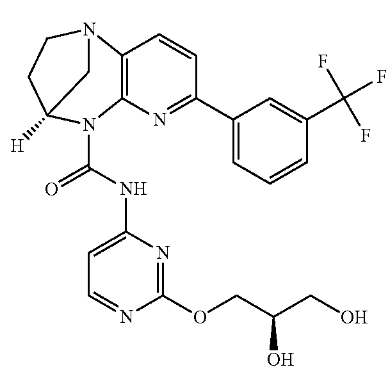 [SMILES: O=C(Nc1ccnc(OC[C@H](O)CO)n1)N1c2nc(-c3cccc(C(F)(F)F)c3)ccc2N2CC[C@H]1C2] | (9S)-N-{2-[(2R)-2,3-dihydroxypropoxy]pyrimidin-4-yl}-5-[3-(trifluoromethyl)phenyl]-1,6,8-triazatricyclo[7.2.1.0 {2,7}]dodeca-2(7),3,5-triene-8-carboxamide | A | A |

TABLE A-continued

Additional Representative Compounds

| Structure | Chemical Name | TRP Activity | TRP MAX RESP |
|---|---|---|---|
| 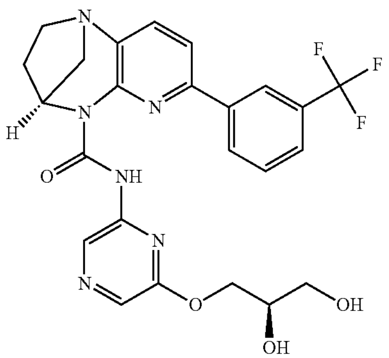 [SMILES: O=C(Nc1cncc(OC[C@H](O)CO)n1)N1c2nc(-c3cccc(C(F)(F)F)c3)ccc2N2CC[C@H]1C2] | (9S)-N-{6-[(2R)-2,3-dihydroxypropoxy]pyrazin-2-yl}-5-[3-(trifluoromethyl)phenyl]-1,6,8-triazatricyclo[7.2.1.0 {2,7}]dodeca-2(7),3,5-triene-8-carboxamide | A | A |
| ISOMER 1 | (9S)-N-(pyridin-2-yl)-5-[(3S)-3-(trifluoromethyl)pyrrolidin-1-yl]-1,6,8-triazatricyclo[7.3.1.0 {2,7}]trideca-2(7),3,5-triene-8-carboxamide | B | A |
| 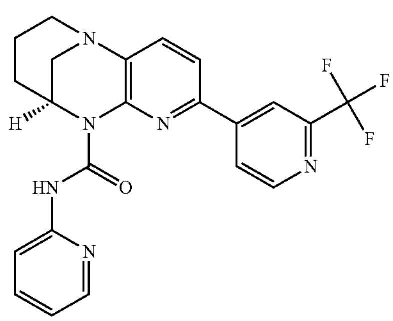 [SMILES: O=C(Nc1ccccn1)N1c2nc(-c3ccnc(C(F)(F)F)c3)ccc2N2CCC[C@H]1C2] | (9S)-N-(pyrimidin-4-yl)-5-[2-(trifluoromethyl)pyridin-4-yl]-1,6,8-triazatricyclo[7.3.1.0 {2,7}]trideca-2(7),3,5-triene-8-carboxamide | A | A |
| 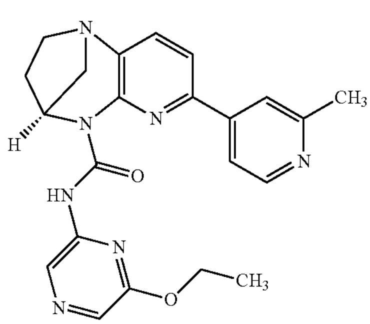 [SMILES: CCOc1cncc(NC(=O)N2c3nc(-c4ccnc(C)c4)ccc3N3CC[C@H]2C3)n1] | (9S)-N-(6-ethoxypyrazin-2-yl)-5-(2-methylpyridin-4-yl)-1,6,8-triazatricyclo[7.2.1.0 {2,7}]dodeca-2(7),3,5-triene-8-carboxamide | A | A |

TABLE A-continued

Additional Representative Compounds

| Structure | Chemical Name | TRP Activity | TRP MAX RESP |
|---|---|---|---|
| 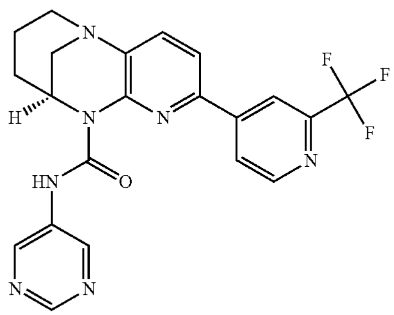 [SMILES: O=C(Nc1cncnc1)N1c2nc(-c3ccnc(C(F)(F)F)c3)ccc2N2CCC[C@H]1C2] | (9S)-N-(pyrimidin-5-yl)-5-[2-(trifluoromethyl)pyridin-4-yl]-1,6,8-triazatricyclo[7.3.1.0 {2,7}]trideca-2(7),3,5-triene-8-carboxamide | A | A |
| 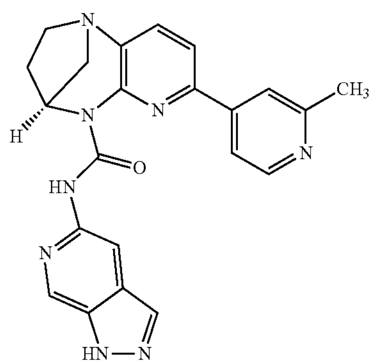 [SMILES: Cc1cc(-c2ccc3c(n2)N(C(=O)Nc2cc4cn[nH]c4cn2)[C@H]2CCN3C2)ccn1] | (9S)-5-(2-methylpyridin-4-yl)-N-{1H-pyrazolo[3,4-c]pyridin-5-yl}-1,6,8-triazatricyclo[7.2.1.0 {2,7}]dodeca-2(7),3,5-triene-8-carboxamide | A | A |
| 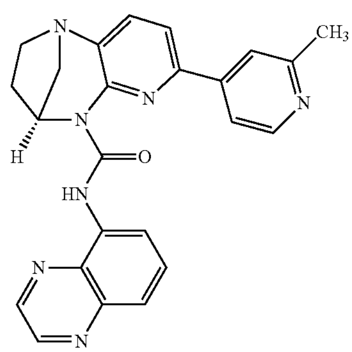 [SMILES: Cc1cc(-c2ccc3c(n2)N(C(=O)Nc2cccc4nccnc24)[C@H]2CCN3C2)ccn1] | (9S)-5-(2-methylpyridin-4-yl)-N-(quinoxalin-5-yl)-1,6,8-triazatricyclo[7.2.1.0 {2,7}]dodeca-2,4,6-triene-8-carboxamide | A | A |
| 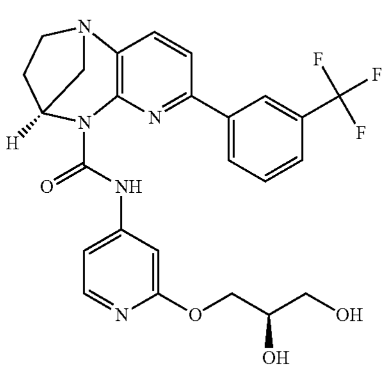 [SMILES: O=C(Nc1ccnc(OC[C@H](O)CO)c1)N1c2nc(-c3cccc(C(F)(F)F)c3)ccc2N2CC[C@H]1C2] | (9S)-N-{2-[(2R)-2,3-dihydroxypropoxy]pyridin-4-yl}-5-[3-(trifluoromethyl)phenyl]-1,6,8-triazatricyclo[7.2.1.0 {2,7}]dodeca-2(7),3,5-triene-8-carboxamide | A | A |

TABLE A-continued

Additional Representative Compounds

| Structure | Chemical Name | TRP Activity | TRP MAX RESP |
|---|---|---|---|
| 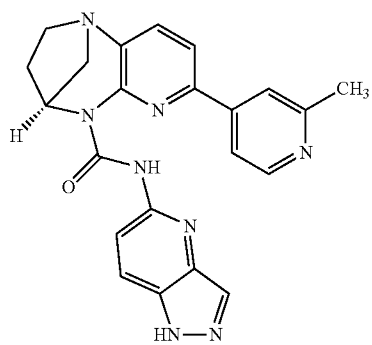 [SMILES: Cc1cc(-c2ccc3c(n2)N(C(=O)Nc2ccc4[nH]ncc4n2)[C@H]2CCN3C2)ccn1] | (9S)-5-(2-methylpyridin-4-yl)-N-{1H-pyrazolo[4,3-b]pyridin-5-yl}-1,6,8-triazatricyclo[7.2.1.0{2,7}]dodeca-2(7),3,5-triene-8-carboxamide | A | A |
| 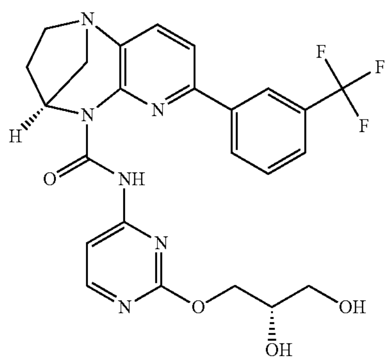 [SMILES: O=C(Nc1ccnc(OC[C@@H](O)CO)n1)N1c2nc(-c3cccc(C(F)(F)F)c3)ccc2N2CC[C@H]1C2] | (9S)-N-{2-[(2S)-2,3-dihydroxypropoxy]pyrimidin-4-yl}-5-[3-(trifluoromethyl)phenyl]-1,6,8-triazatricyclo[7.2.1.0 {2,7}]dodeca-2(7),3,5-triene-8-carboxamide | A | A |
| 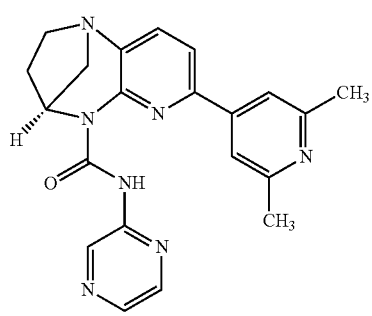 [SMILES: Cc1cc(-c2ccc3c(n2)N(C(=O)Nc2cnccn2)[C@H]2CCN3C2)cc(C)n1] | (9S)-5-(2,6-dimethylpyridin-4-yl)-N-(pyrazin-2-yl)-1,6,8-triazatricyclo[7.2.1.0^{2,7}]dodeca-2,4,6-triene-8-carboxamide | A | A |
| 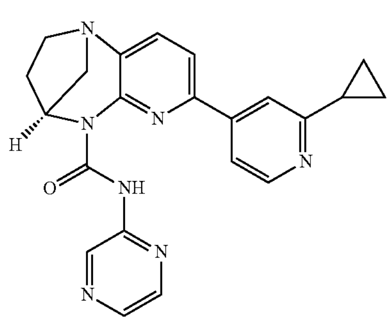 [SMILES: O=C(Nc1cnccn1)N1c2nc(-c3ccnc(C4CC4)c3)ccc2N2CC[C@H]1C2] | (9S)-5-(2-cyclopropylpyridin-4-yl)-N-(pyrazin-2-yl)-1,6,8-triazatricyclo[7.2.1.0 {2,7}]dodeca-2,4,6-triene-8-carboxamide | A | A |

TABLE A-continued

Additional Representative Compounds

| Structure | Chemical Name | TRP Activity | TRP MAX RESP |
|---|---|---|---|
| 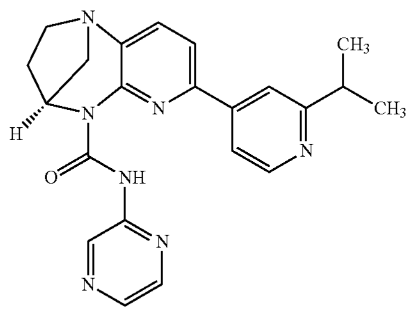 [SMILES: CC(C)c1cc(-c2ccc3c(n2)N(C(=O)Nc2cnccn2)[C@H]2CCN3C2)ccn1] | (9S)-5-[2-(propan-2-yl)pyridin-4-yl]-N-(pyrazin-2-yl)-1,6,8-triazatricyclo[7.2.1.0 {2,7}]dodeca-2,4,6-triene-8-carboxamide | A | A |
| 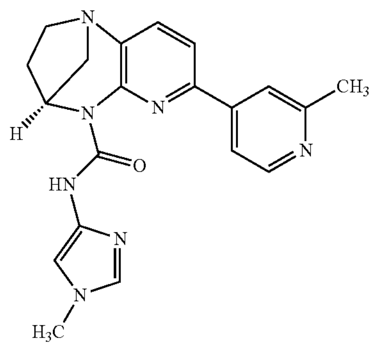 [SMILES: Cc1cc(-c2ccc3c(n2)N(C(=O)Nc2cn(C)cn2)[C@H]2CCN3C2)ccn1] | (9S)-N-(1-methyl-1H-1,2,3-triazol-4-yl)-5-(2-methylpyridin-4-yl)-1,6,8-triazatricyclo[7.2.1.0^{2,7}]dodeca-2(7),3,5-triene-8-carboxamide | B | A |
| 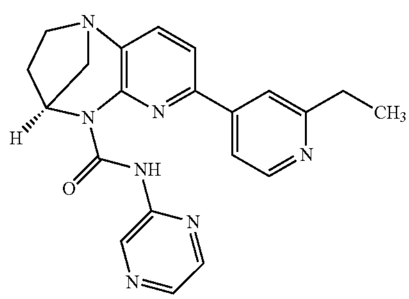 [SMILES: CCc1cc(-c2ccc3c(n2)N(C(=O)Nc2cnccn2)[C@H]2CCN3C2)ccn1] | (9S)-5-(2-ethylpyridin-4-yl)-N-(pyrazin-2-yl)-1,6,8-triazatricyclo[7.2.1.0 {2,7}]dodeca-2(7),3,5-triene-8-carboxamide | A | A |
| 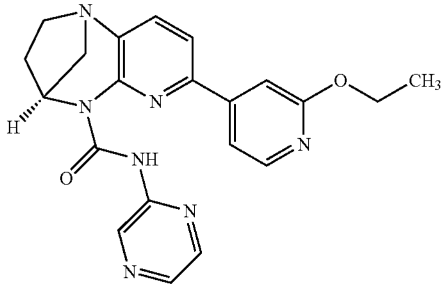 [SMILES: CCOc1cc(-c2ccc3c(n2)N(C(=O)Nc2cnccn2)[C@H]2CCN3C2)ccn1] | (9S)-5-(2-ethoxypyridin-4-yl)-N-(pyrazin-2-yl)-1,6,8-triazatricyclo[7.2.1.0 {2,7}]dodeca-2(7),3,5-triene-8-carboxamide | B | A |

TABLE A-continued

Additional Representative Compounds

| Structure | Chemical Name | TRP Activity | TRP MAX RESP |
|---|---|---|---|
| 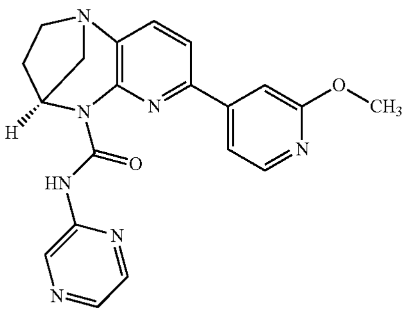 [SMILES: COc1cc(-c2ccc3c(n2)N(C(=O)Nc2cnccn2)[C@H]2CCN3C2)ccn1] | (9S)-5-(2-methoxypyridin-4-yl)-N-(pyrazin-2-yl)-1,6,8-triazatricyclo[7.2.1.0 {2,7}]dodeca-2(7),3,5-triene-8-carboxamide | B | A |
| 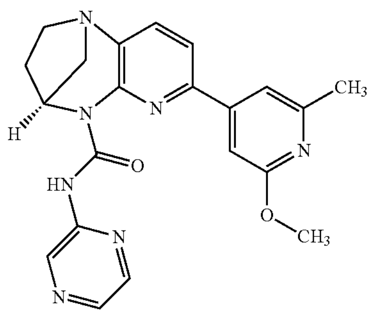 [SMILES: COc1cc(-c2ccc3c(n2)N(C(=O)Nc2cnccn2)[C@H]2CCN3C2)cc(C)n1] | (9S)-5-(2-methoxy-6-methylpyridin-4-yl)-N-(pyrazin-2-yl)-1,6,8-triazatricyclo[7.2.1.0 {2,7}]dodeca-2(7),3,5-triene-8-carboxamide | A | A |
| ISOMER 1 | (9S)-N-(pyridin-2-yl)-5-[(3S)-3-(trifluoromethyl)piperidin-1-yl]-1,6,8-triazatricyclo[7.3.1.0 {2,7}]trideca-2(7),3,5-triene-8-carboxamide | A | A |
| 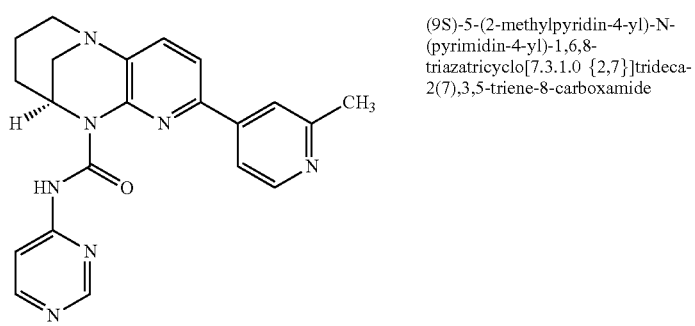 | (9S)-5-(2-methylpyridin-4-yl)-N-(pyrimidin-4-yl)-1,6,8-triazatricyclo[7.3.1.0 {2,7}]trideca-2(7),3,5-triene-8-carboxamide | A | A |

TABLE A-continued

Additional Representative Compounds

| Structure | Chemical Name | TRP Activity | TRP MAX RESP |
|---|---|---|---|
| 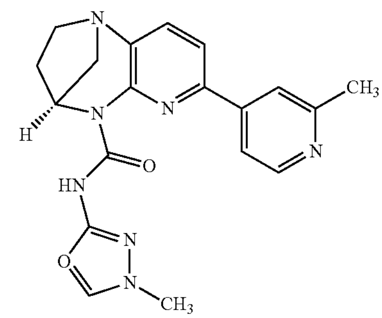 | (9S)-N-(1-methyl-1H-1,2,4-triazol-3-yl)-5-(2-methylpyridin-4-yl)-1,6,8-triazatricyclo[7.2.1.0 {2,7}]dodeca-2(7),3,5-triene-8-carboxamide | C | A |
| 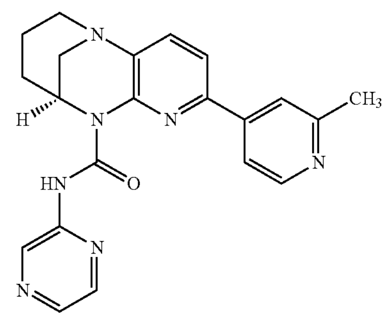 | (9S)-5-(2-methylpyridin-4-yl)-N-(pyrazin-2-yl)-1,6,8-triazatricyclo[7.3.1.0 {2,7}]trideca-2(7),3,5-triene-8-carboxamide | A | A |
| 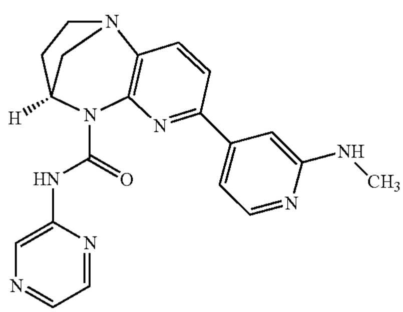 [SMILES: CNc1cc(-c2ccc3c(n2)N(C(=O)Nc2cnccn2)[C@H]2CCN3C2)ccn1] | (9S)-5-[2-(methylamino)pyridin-4-yl]-N-(pyrazin-2-yl)-1,6,8-triazatricyclo[7.2.1.0 {2,7}]dodeca-2(7),3,5-triene-8-carboxamide | B | A |
| 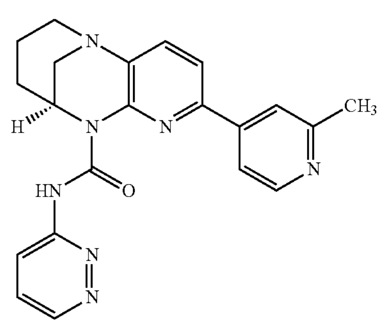 [SMILES: Cc1cc(-c2ccc3c(n2)N(C(=O)Nc2cccnn2)[C@H]2CCCN3C2)ccn1] | (9S)-5-(2-methylpyridin-4-yl)-N-(pyridazin-3-yl)-1,6,8-triazatricyclo[7.3.1.0 {2,7}]trideca-2(7),3,5-triene-8-carboxamide | A | A |

TABLE A-continued

Additional Representative Compounds

| Structure | Chemical Name | TRP Activity | TRP MAX RESP |
|---|---|---|---|
| 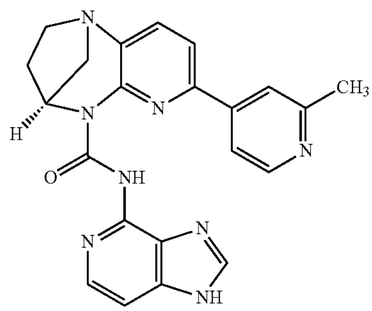 [SMILES: Cc1cc(-c2ccc3c(n2)N(C(=O)Nc2nccc4[nH]cnc24)[C@H]2CCN3C2)ccn1] | (9S)-N-{1H-imidazo[4,5-c]pyridin-4-yl}-5-(2-methylpyridin-4-yl)-1,6,8-triazatricyclo[7.2.1.0 {2,7}]dodeca-2,4,6-triene-8-carboxamide | B | A |
| 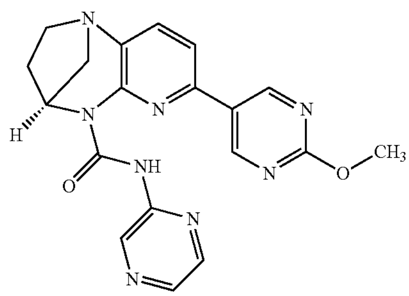 [SMILES: COc1ncc(-c2ccc3c(n2)N(C(=O)Nc2cnccn2)[C@H]2CCN3C2)cn1] | (9S)-5-(2-methoxypyrimidin-5-yl)-N-(pyrazin-2-yl)-1,6,8-triazatricyclo[7.2.1.0 {2,7}]dodeca-2(7),3,5-triene-8-carboxamide | B | A |
| 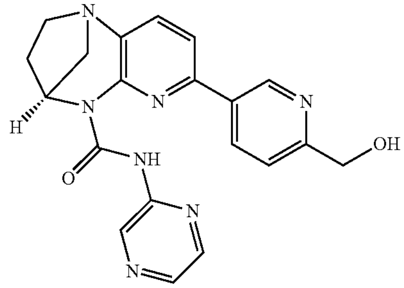 [SMILES: O=C(Nc1cnccn1)N1c2nc(-c3ccc(CO)nc3)ccc2N2CC[C@H]1C2] | (9S)-5-[6-(hydroxymethyl)pyridin-3-yl]-N-(pyrazin-2-yl)-1,6,8-triazatricyclo[7.2.1.0 {2,7}]dodeca-2(7),3,5-triene-8-carboxamide | B | A |
| 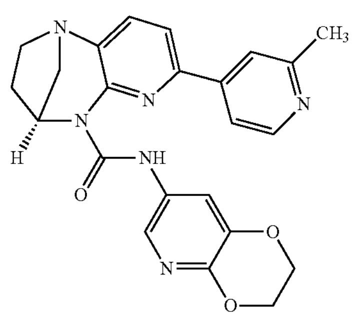 [SMILES: Cc1cc(-c2ccc3c(n2)N(C(=O)Nc2cnc4c(c2)OCCO4)[C@H]2CCN3C2)ccn1] | (9S)-N-{2H,3H-[1,4]dioxino[2,3-b]pyridin-7-yl}-5-(2-methylpyridin-4-yl)-1,6,8-triazatricyclo[7.2.1.0 {2,7}]dodeca-2,4,6-triene-8-carboxamide | B | A |

TABLE A-continued

Additional Representative Compounds

| Structure | Chemical Name | TRP Activity | TRP MAX RESP |
|---|---|---|---|
| 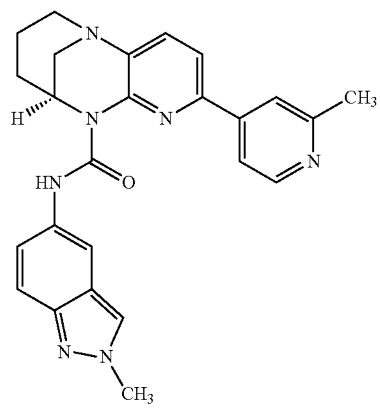 [SMILES: Cc1cc(-c2ccc3c(n2)N(C(=O)Nc2ccc4nn(C)cc4c2)[C@H]2CCCN3C2)ccn1] | (9S)-N-(2-methyl-2H-indazol-5-yl)-5-(2-methylpyridin-4-yl)-1,6,8-triazatricyclo[7.3.1.0 {2,7}]trideca-2,4,6-triene-8-carboxamide | A | A |
| 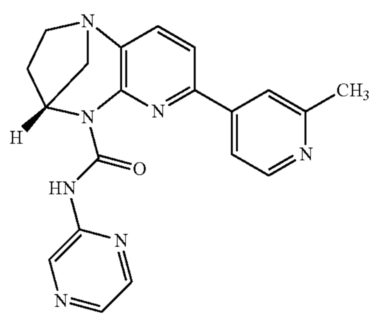 [SMILES: Cc1cc(-c2ccc3c(n2)N(C(=O)Nc2cnccn2)[C@@H]2CCN3C2)ccn1] | (9R)-5-(2-methylpyridin-4-yl)-N-(pyrazin-2-yl)-1,6,8-triazatricyclo[7.2.1.0 {2,7}]dodeca-2(7),3,5-triene-8-carboxamide | B | A |
| 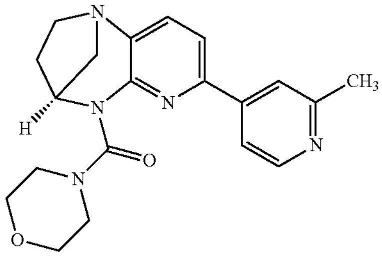 [SMILES: Cc1cc(-c2ccc3c(n2)N(C(=O)N2CCOCC2)[C@H]2CCN3C2)ccn1] | (9S)-5-(2-methylpyridin-4-yl)-8-[(morpholin-4-yl)carbonyl]-1,6,8-triazatricyclo[7.2.1.0 {2,7}]dodeca-2,4,6-triene | C | B |
| 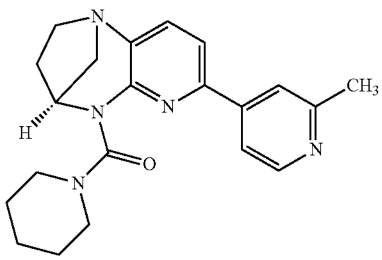 [SMILES: Cc1cc(-c2ccc3c(n2)N(C(=O)N2CCCCC2)[C@H]2CCN3C2)ccn1] | (9S)-5-(2-methylpyridin-4-yl)-8-[(piperidin-1-yl)carbonyl]-1,6,8-triazatricyclo[7.2.1.0 {2,7}]dodeca-2,4,6-triene | C | B |

TABLE A-continued

Additional Representative Compounds

| Structure | Chemical Name | TRP Activity | TRP MAX RESP |
|---|---|---|---|
| 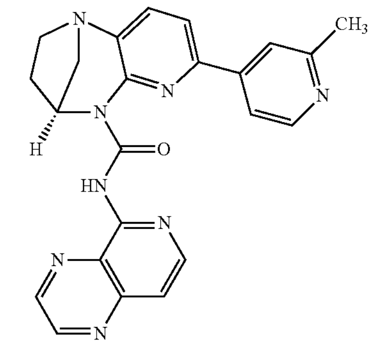 [SMILES: Cc1cc(-c2ccc3c(n2)N(C(=O)Nc2nccc4nccnc24)[C@H]2CCN3C2)ccn1] | (9S)-5-(2-methylpyridin-4-yl)-N-{pyrido[3,4-b]pyrazin-5-yl}-1,6,8-triazatricyclo[7.2.1.0 {2,7}]dodeca-2,4,6-triene-8-carboxamide | B | A |
| 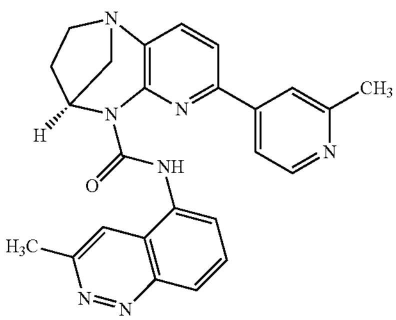 | (9S)-N-(3-methylcinnolin-5-yl)-5-(2-methylpyridin-4-yl)-1,6,8-triazatricyclo[7.2.1.0 {2,7}]dodeca-2(7),3,5-triene-8-carboxamide | B | A |
| 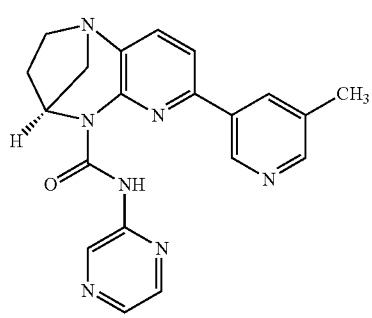 [SMILES: Cc1cncc(-c2ccc3c(n2)N(C(=O)Nc2cnccn2)[C@H]2CCN3C2)c1] | (9S)-5-(5-methylpyridin-3-yl)-N-(pyrazin-2-yl)-1,6,8-triazatricyclo[7.2.1.0 {2,7}]dodeca-2(7),3,5-triene-8-carboxamide | B | A |
| 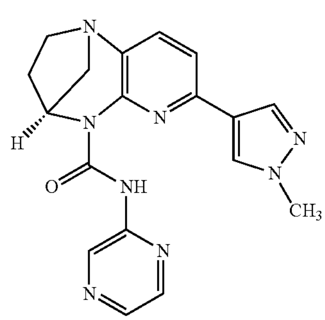 [SMILES: Cn1cc(-c2ccc3c(n2)N(C(=O)Nc2cnccn2)[C@H]2CCN3C2)cn1] | (9S)-5-(1-methyl-1H-pyrazol-4-yl)-N-(pyrazin-2-yl)-1,6,8-triazatricyclo[7.2.1.0 {2,7}]dodeca-2(7),3,5-triene-8-carboxamide | B | A |

TABLE A-continued

Additional Representative Compounds

| Structure | Chemical Name | TRP Activity | TRP MAX RESP |
|---|---|---|---|
| 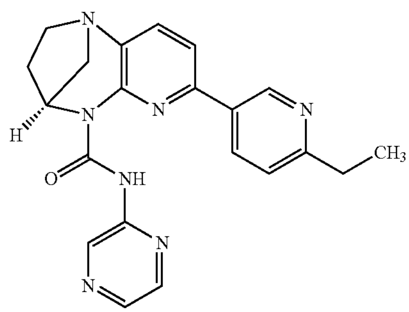 [SMILES: CCc1ccc(-c2ccc3c(n2)N(C(=O)Nc2cnccn2)[C@H]2CCN3C2)cn1] | (9S)-5-(6-ethylpyridin-3-yl)-N-(pyrazin-2-yl)-1,6,8-triazatricyclo[7.2.1.0 {2,7}]dodeca-2(7),3,5-triene-8-carboxamide | B | A |
| 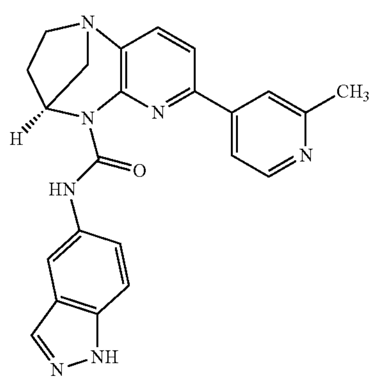 [SMILES: Cc1cc(-c2ccc3c(n2)N(C(=O)Nc2ccc4[nH]ncc4c2)[C@H]2CCN3C2)ccn1] | (9S)-N-(1H-indazol-5-yl)-5-(2-methylpyridin-4-yl)-1,6,8-triazatricyclo[7.2.1.0 {2,7}]dodeca-2(7),3,5-triene-8-carboxamide | A | A |
| 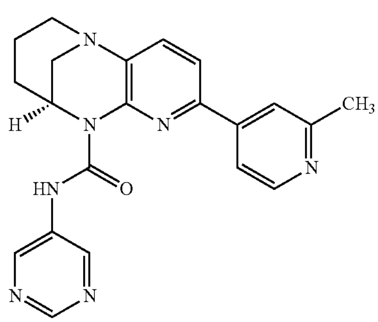 [SMILES: Cc1cc(-c2ccc3c(n2)N(C(=O)Nc2cncnc2)[C@H]2CCCN3C2)ccn1] | (9S)-5-(2-methylpyridin-4-yl)-N-(pyrimidin-5-yl)-1,6,8-triazatricyclo[7.3.1.0 {2,7}]trideca-2(7),3,5-triene-8-carboxamide | B | A |
| 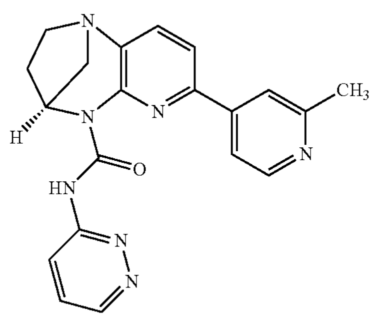 [SMILES: Cc1cc(-c2ccc3c(n2)N(C(=O)Nc2cccnn2)[C@H]2CCN3C2)ccn1] | (9S)-5-(2-methylpyridin-4-yl)-N-(pyridazin-3-yl)-1,6,8-triazatricyclo[7.2.1.0 {2,7}]dodeca-2(7),3,5-triene-8-carboxamide | B | A |

TABLE A-continued

Additional Representative Compounds

| Structure | Chemical Name | TRP Activity | TRP MAX RESP |
|---|---|---|---|
| 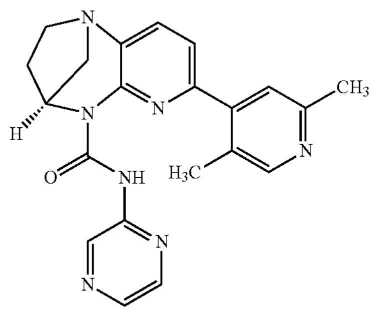 [SMILES: Cc1cc(-c2ccc3c(n2)N(C(=O)Nc2cnccn2)[C@H]2CCN3C2)c(C)cn1] | (9S)-5-(2,5-dimethylpyridin-4-yl)-N-(pyrazin-2-yl)-1,6,8-triazatricyclo[7.2.1.0 {2,7}]dodeca-2,4,6-triene-8-carboxamide | B | A |
| 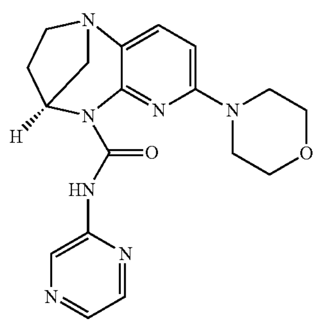 [SMILES: O=C(Nc1cnccn1)N1c2nc(N3CCOCC3)ccc2N2CC[C@H]1C2] | (9S)-5-(morpholin-4-yl)-N-(pyrazin-2-yl)-1,6,8-triazatricyclo[7.2.1.0 {2,7}]dodeca-2,4,6-triene-8-carboxamide | B | A |
| 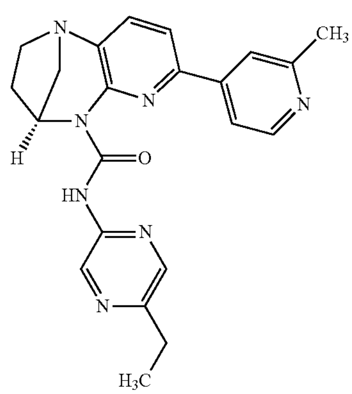 [SMILES: CCc1cnc(NC(=O)N2c3nc(-c4ccnc(C)c4)ccc3N3CC[C@H]2C3)cn1] | (9S)-N-(5-ethylpyrazin-2-yl)-5-(2-methylpyridin-4-yl)-1,6,8-triazatricyclo[7.2.1.0 {2,7}]dodeca-2(7),3,5-triene-8-carboxamide | A | A |
| 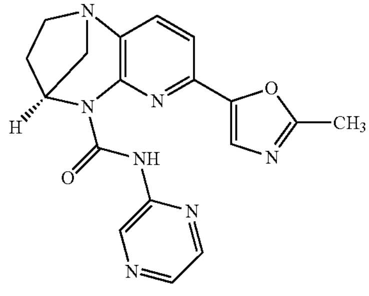 [SMILES: Cc1ncc(-c2ccc3c(n2)N(C(=O)Nc2cnccn2)[C@H]2CCN3C2)o1] | (9S)-5-(2-methyl-1,3-oxazol-5-yl)-N-(pyrazin-2-yl)-1,6,8-triazatricyclo[7.2.1.0 {2,7}]dodeca-2(7),3,5-triene-8-carboxamide | B | A |

TABLE A-continued

Additional Representative Compounds

| Structure | Chemical Name | TRP Activity | TRP MAX RESP |
|---|---|---|---|
| 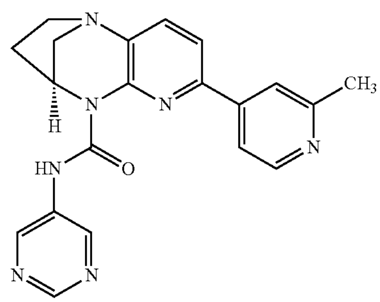 [SMILES: Cc1cc(-c2ccc3c(n2)N(C(=O)Nc2cncnc2)[C@H]2CCN3C2)ccn1] | (9S)-5-(2-methylpyridin-4-yl)-N-(pyrimidin-5-yl)-1,6,8-triazatricyclo[7.2.1.0 {2,7}]dodeca-2(7),3,5-triene-8-carboxamide | C | A |
| 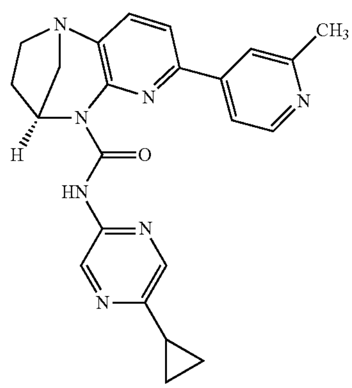 [SMILES: Cc1cc(-c2ccc3c(n2)N(C(=O)Nc2cnc(C4CC4)cn2)[C@H]2CCN3C2)ccn1] | (9S)-N-(5-cyclopropylpyrazin-2-yl)-5-(2-methylpyridin-4-yl)-1,6,8-triazatricyclo[7.2.1.0 {2,7}]dodeca-2(7),3,5-triene-8-carboxamide | A | A |
| 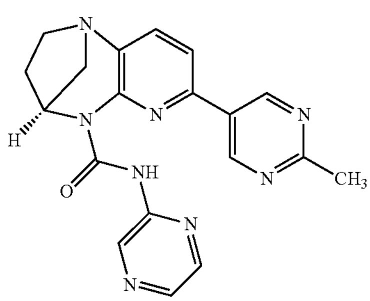 [SMILES: Cc1ncc(-c2ccc3c(n2)N(C(=O)Nc2cnccn2)[C@H]2CCN3C2)cn1] | (9S)-5-(2-methylpyrimidin-5-yl)-N-(pyrazin-2-yl)-1,6,8-triazatricyclo[7.2.1.0 {2,7}]dodeca-2(7),3,5-triene-8-carboxamide | B | A |
| 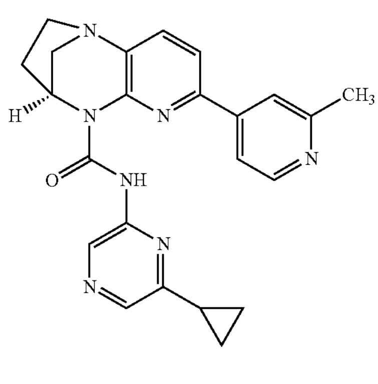 [SMILES: Cc1cc(-c2ccc3c(n2)N(C(=O)Nc2cncc(C4CC4)n2)[C@H]2CCN3C2)ccn1] | (9S)-N-(6-cyclopropylpyrazin-2-yl)-5-(2-methylpyridin-4-yl)-1,6,8-triazatricyclo[7.2.1.0 {2,7}]dodeca-2(7),3,5-triene-8-carboxamide | A | A |

TABLE A-continued

Additional Representative Compounds

| Structure | Chemical Name | TRP Activity | TRP MAX RESP |
|---|---|---|---|
| 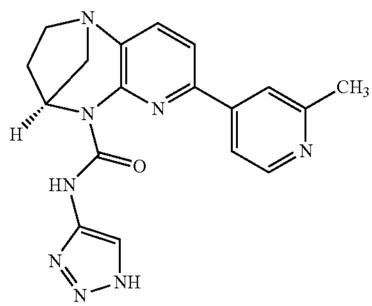 [SMILES: Cc1cc(-c2ccc3c(n2)N(C(=O)Nc2c[nH]nn2)[C@H]2CCN3C2)ccn1] | (9S)-5-(2-methylpyridin-4-yl)-N-(1H-1,2,3-triazol-4-yl)-1,6,8-triazatricyclo[7.2.1.0 {2,7}]dodeca-2(7),3,5-triene-8-carboxamide | B | A |
| 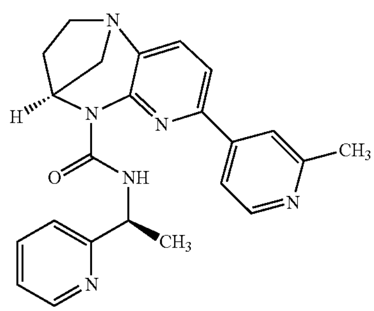 [SMILES: Cc1cc(-c2ccc3c(n2)N(C(=O)N[C@@H](C)c2ccccn2)[C@H]2CCN3C2)ccn1] | (9S)-5-(2-methylpyridin-4-yl)-N-[(1S)-1-(pyridin-2-yl)ethyl]-1,6,8-triazatricyclo[7.2.1.0 {2,7}]dodeca-2,4,6-triene-8-carboxamide | C | B |
| 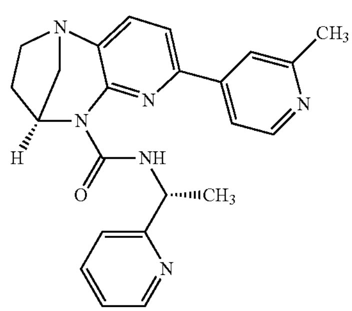 [SMILES: Cc1cc(-c2ccc3c(n2)N(C(=O)N[C@H](C)c2ccccn2)[C@H]2CCN3C2)ccn1] | (9S)-5-(2-methylpyridin-4-yl)-N-[(1R)-1-(pyridin-2-yl)ethyl]-1,6,8-triazatricyclo[7.2.1.0 {2,7}]dodeca-2,4,6-triene-8-carboxamide | C | B |
| 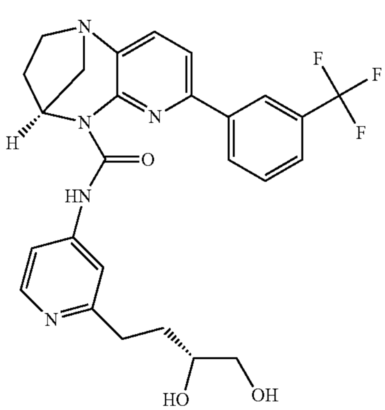 [SMILES: O=C(Nc1ccnc(CC[C@@H](O)CO)c1)N1c2nc(-c3cccc(C(F)(F)F)c3)ccc2N2CC[C@H]1C2] | (9S)-N-{2-[(2S)-2,3-dihydroxypropoxy]pyridin-4-yl}-5-[3-(trifluoromethyl)phenyl]-1,6,8-triazatricyclo[7.2.1.0 {2,7}]dodeca-2,4,6-triene-8-carboxamide | A | A |

TABLE A-continued

Additional Representative Compounds

| Structure | Chemical Name | TRP Activity | TRP MAX RESP |
|---|---|---|---|
| 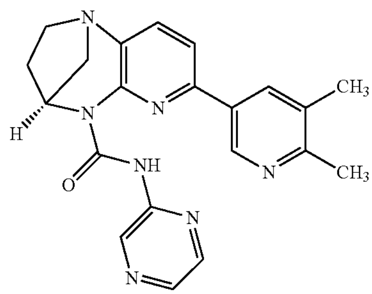 [SMILES: Cc1cc(-c2ccc3c(n2)N(C(=O)Nc2cnccn2)[C@H]2CCN3C2)cnc1C] | (9S)-5-(5,6-dimethylpyridin-3-yl)-N-(pyrazin-2-yl)-1,6,8-triazatricyclo[7.2.1.0 {2,7}]dodeca-2(7),3,5-triene-8-carboxamide | A | A |
| 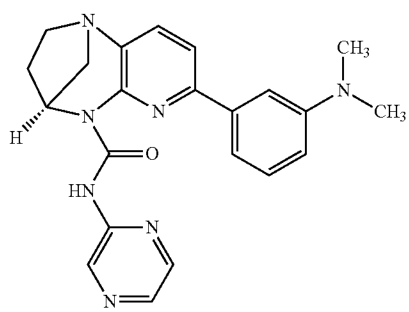 [SMILES: CN(C)c1cccc(-c2ccc3c(n2)N(C(=O)Nc2cnccn2)[C@H]2CCN3C2)c1] | (9S)-5-[3-(dimethylamino)phenyl]-N-(pyrazin-2-yl)-1,6,8-triazatricyclo[7.2.1.0 {2,7}]dodeca-2(7),3,5-triene-8-carboxamide | B | A |
| 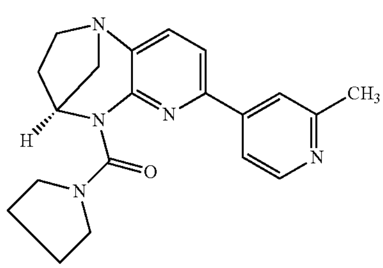 [SMILES: Cc1cc(-c2ccc3c(n2)N(C(=O)N2CCCC2)[C@H]2CCN3C2)ccn1] | (9S)-5-(2-methylpyridin-4-yl)-8-[(pyrrolidin-1-yl)carbonyl]-1,6,8-triazatricyclo[7.2.1.0 {2,7}]dodeca-2,4,6-triene | C | B |
| 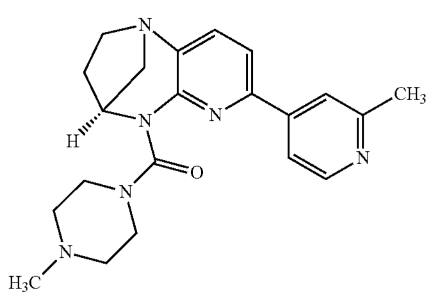 | (9S)-8-[(4-methylpiperazin-1-yl)carbonyl]-5-(2-methylpyridin-4-yl)-1,6,8-triazatricyclo[7.2.1.0 {2,7}]dodeca-2,4,6-triene | C | B |
| 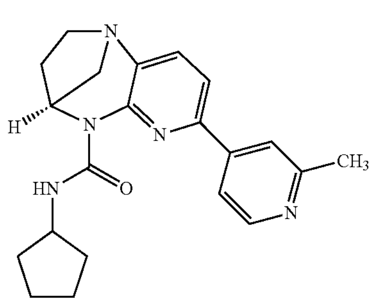 [SMILES: Cc1cc(-c2ccc3c(n2)N(C(=O)NC2CCCC2)[C@H]2CCN3C2)ccn1] | (9S)-N-cyclopentyl-5-(2-methylpyridin-4-yl)-1,6,8-triazatricyclo[7.2.1.0 {2,7}]dodeca-2,4,6-triene-8-carboxamide | B | A |

TABLE A-continued

Additional Representative Compounds

| Structure | Chemical Name | TRP Activity | TRP MAX RESP |
|---|---|---|---|
| 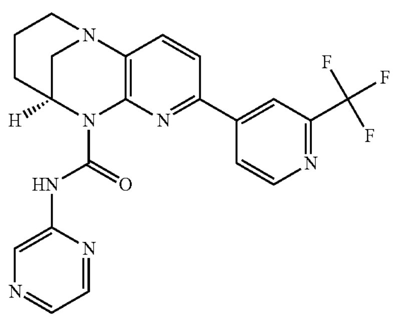 [SMILES: O=C(Nc1cnccn1)N1c2nc(-c3ccnc(C(F)(F)F)c3)ccc2N2CCC[C@H]1C2] | (9S)-N-(pyrazin-2-yl)-5-[2-(trifluoromethyl)pyridin-4-yl]-1,6,8-triazatricyclo[7.3.1.0 {2,7}]trideca-2(7),3,5-triene-8-carboxamide | A | A |
| 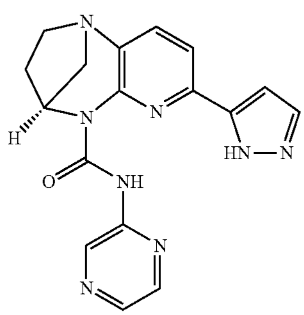 [SMILES: O=C(Nc1cnccn1)N1c2nc(-c3ccn[nH]3)ccc2N2CC[C@H]1C2] | (9S)-N-(pyrazin-2-yl)-5-(1H-pyrazol-5-yl)-1,6,8-triazatricyclo[7.2.1.0 {2,7}]dodeca-2(7),3,5-triene-8-carboxamide | B | A |
| ISOMER 1 | (9S)-N-(pyrimidin-2-yl)-5-[(3S)-3-(trifluoromethyl)piperidin-1-yl]-1,6,8-triazatricyclo[7.3.1.0 {2,7}]trideca-2(7),3,5-triene-8-carboxamide | A | A |
| 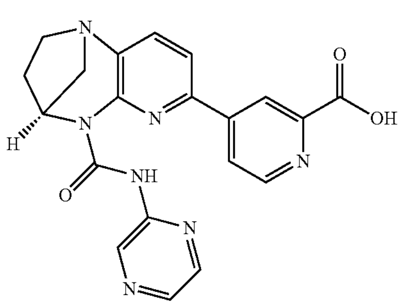 [SMILES: O=C(O)c1cc(-c2ccc3c(n2)N(C(=O)Nc2cnccn2)[C@H]2CCN3C2)ccn1] | 4-[(9S)-8-[(pyrazin-2-yl)carbamoyl]-1,6,8-triazatricyclo[7.2.1.0 {2,7}]dodeca-2(7),3,5-trien-5-yl]pyridine-2-carboxylic acid | C | B |

TABLE A-continued

Additional Representative Compounds

| Structure | Chemical Name | TRP Activity | TRP MAX RESP |
|---|---|---|---|
| 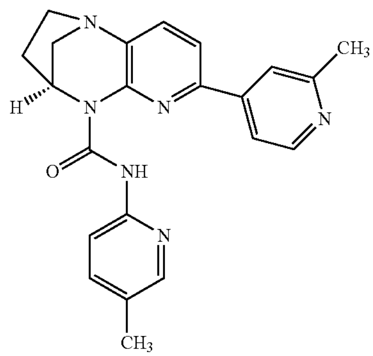 [SMILES: Cc1ccc(NC(=O)N2c3nc(-c4ccnc(C)c4)ccc3N3CC[C@H]2C3)nc1] | (9S)-N-(6-methylpyridin-3-yl)-5-(2-methylpyridin-4-yl)-1,6,8-triazatricyclo[7.2.1.0 {2,7}]dodeca-2(7),3,5-triene-8-carboxamide | B | A |
| 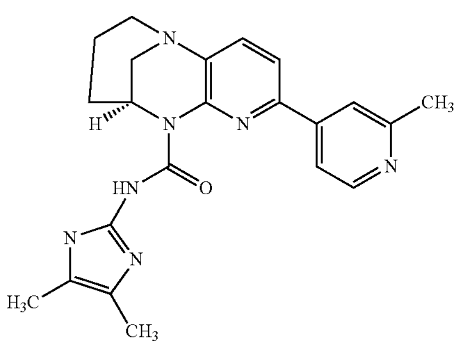 | (9S)-N-(dimethyl-1,3-thiazol-2-yl)-5-(2-methylpyridin-4-yl)-1,6,8-triazatricyclo[7.3.1.0 {2,7}]trideca-2(7),3,5-triene-8-carboxamide | A | A |
| 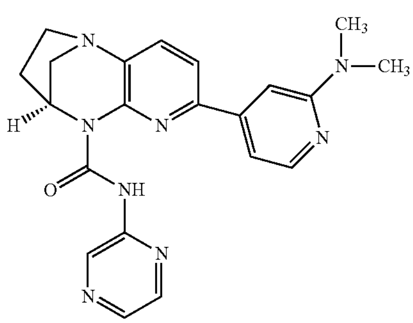 [SMILES: CN(C)c1cc(-c2ccc3c(n2)N(C(=O)Nc2cnccn2)[C@H]2CCN3C2)ccn1] | (9S)-5-[2-(dimethylamino)pyridin-4-yl]-N-(pyrazin-2-yl)-1,6,8-triazatricyclo[7.2.1.0 {2,7}]dodeca-2(7),3,5-triene-8-carboxamide | B | A |
| 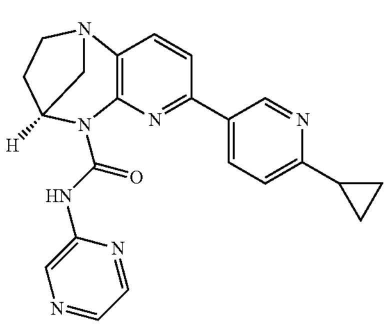 [SMILES: O=C(Nc1cnccn1)N1c2nc(-c3ccc(C4CC4)nc3)ccc2N2CC[C@H]1C2] | (9S)-5-(6-cyclopropylpyridin-3-yl)-N-(pyrazin-2-yl)-1,6,8-triazatricyclo[7.2.1.0 {2,7}]dodeca-2(7),3,5-triene-8-carboxamide | B | A |

TABLE A-continued

Additional Representative Compounds

| Structure | Chemical Name | TRP Activity | TRP MAX RESP |
|---|---|---|---|
| 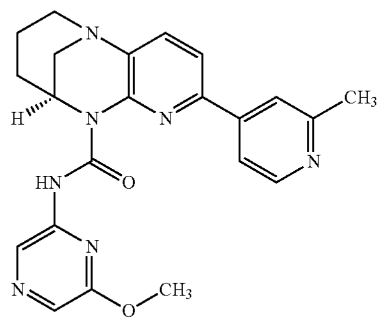 [SMILES: COc1cncc(NC(=O)N2c3nc(-c4ccnc(C)c4)ccc3N3CCC[C@H]2C3)n1] | (9S)-N-(6-methoxypyrazin-2-yl)-5-(2-methylpyridin-4-yl)-1,6,8-triazatricyclo[7.3.1.0 {2,7}]trideca-2(7),3,5-triene-8-carboxamide | A | A |
| 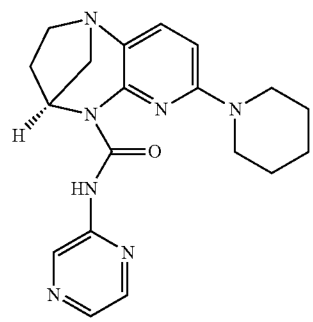 [SMILES: O=C(Nc1cnccn1)N1c2nc(N3CCCCC3)ccc2N2CC[C@H]1C2] | (9S)-5-(piperidin-1-yl)-N-(pyrazin-2-yl)-1,6,8-triazatricyclo[7.2.1.0 {2,7}]dodeca-2,4,6-triene-8-carboxamide | B | A |
| 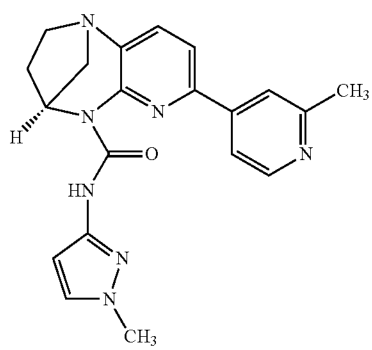 [SMILES: Cc1cc(-c2ccc3c(n2)N(C(=O)Nc2ccn(C)n2)[C@H]2CCN3C2)ccn1] | (9S)-N-(1-methyl-1H-pyrazol-3-yl)-5-(2-methylpyridin-4-yl)-1,6,8-triazatricyclo[7.2.1.0 {2,7}]dodeca-2,4,6-triene-8-carboxamide | B | A |
| 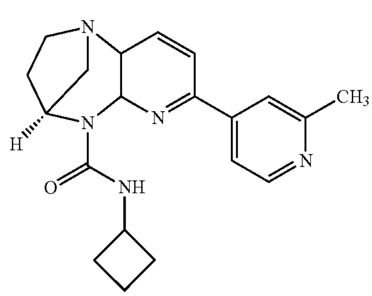 [SMILES: Cc1cc(C2=NC3C(C=C2)N2CC[C@@H](C2)N3C(=O)NC2CCC2)ccn1] | (9S)-N-cyclobutyl-5-(2-methylpyridin-4-yl)-1,6,8-triazatricyclo[7.2.1.0 {2,7}]dodeca-2(7),3,5-triene-8-carboxamide | B | A |

TABLE A-continued

Additional Representative Compounds

| Structure | Chemical Name | TRP Activity | TRP MAX RESP |
|---|---|---|---|
| 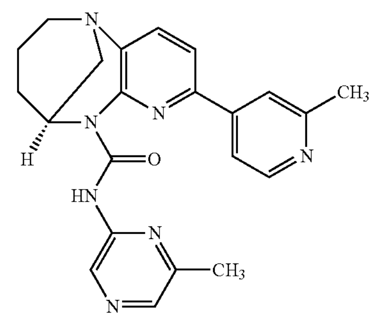 [SMILES: Cc1cc(-c2ccc3c(n2)N(C(=O)Nc2cncc(C)n2)[C@H]2CCCN3C2)ccn1] | (9S)-N-(6-methylpyrazin-2-yl)-5-(2-methylpyridin-4-yl)-1,6,8-triazatricyclo[7.3.1.0 {2,7}]trideca-2(7),3,5-triene-8-carboxamide | B | A |
| 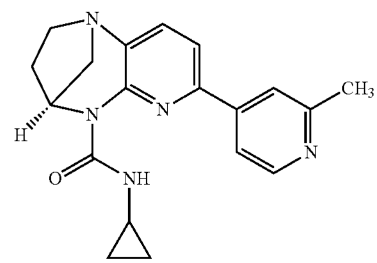 [SMILES: Cc1cc(-c2ccc3c(n2)N(C(=O)NC2CC2)[C@H]2CCN3C2)ccn1] | (9S)-N-cyclopropyl-5-(2-methylpyridin-4-yl)-1,6,8-triazatricyclo[7.2.1.0 {2,7}]dodeca-2,4,6-triene-8-carboxamide | B | A |
| ISOMER 2 | (9S)-N-(pyrimidin-2-yl)-5-[(3S)-3-(trifluoromethyl)piperidin-1-yl]-1,6,8-triazatricyclo[7.3.1.0 {2,7}]trideca-2(7),3,5-triene-8-carboxamide | A | A |
| ISOMER 2 | (9S)-N-(pyridin-2-yl)-5-[(3S)-3-(trifluoromethyl)piperidin-1-yl]-1,6,8-triazatricyclo[7.3.1.0 {2,7}]trideca-2(7),3,5-triene-8-carboxamide | B | A |

TABLE A-continued

Additional Representative Compounds

| Structure | Chemical Name | TRP Activity | TRP MAX RESP |
|---|---|---|---|
| 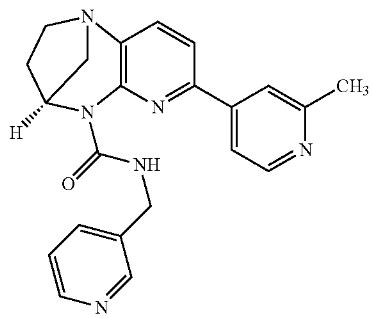 [SMILES: Cc1cc(-c2ccc3c(n2)N(C(=O)NCc2cccnc2)[C@H]2CCN3C2)ccn1] | (9S)-5-(2-methylpyridin-4-yl)-N-(pyridin-3-ylmethyl)-1,6,8-triazatricyclo[7.2.1.0 {2,7}]dodeca-2(7),3,5-triene-8-carboxamide | C | B |
| 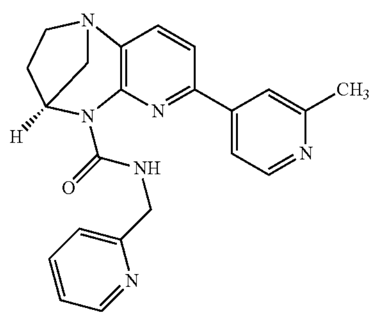 [SMILES: Cc1cc(-c2ccc3c(n2)N(C(=O)NCc2ccccn2)[C@H]2CCN3C2)ccn1] | (9S)-5-(2-methylpyridin-4-yl)-N-(pyridin-2-ylmethyl)-1,6,8-triazatricyclo[7.2.1.0 {2,7}]dodeca-2(7),3,5-triene-8-carboxamide | C | B |
| 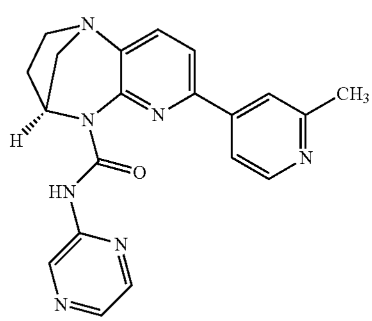 [SMILES: Cc1cc(-c2ccc3c(n2)N(C(=O)Nc2cnccn2)[C@H]2CCN3C2)ccn1] | (9S)-5-(2-methylpyridin-4-yl)-N-(1,2,4-triazin-5-yl)-1,6,8-triazatricyclo[7.2.1.0 {2,7}]dodeca-2,4,6-triene-8-carboxamide | C | B |
| 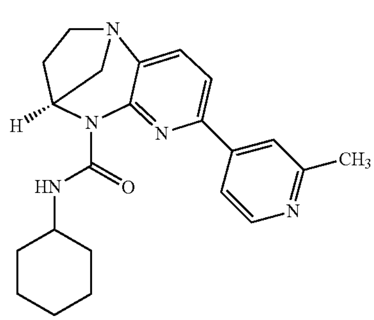 [SMILES: Cc1cc(-c2ccc3c(n2)N(C(=O)NC2CCCCC2)[C@H]2CCN3C2)ccn1] | (9S)-N-cyclohexyl-5-(2-methylpyridin-4-yl)-1,6,8-triazatricyclo[7.2.1.0 {2,7}]dodeca-2,4,6-triene-8-carboxamide | B | A |

TABLE A-continued

Additional Representative Compounds

| Structure | Chemical Name | TRP Activity | TRP MAX RESP |
|---|---|---|---|
| ISOMER 1 | (9S)-N-(5-fluoropyridin-2-yl)-5-[(3S)-3-(trifluoromethyl)piperidin-1-yl]-1,6,8-triazatricyclo[7.3.1.0{2,7}]trideca-2(7),3,5-triene-8-carboxamide | A | A |
| ISOMER 1 | (9S)-N-(pyridin-3-yl)-5-[(3S)-3-(trifluoromethyl)piperidin-1-yl]-1,6,8-triazatricyclo[7.3.1.0{2,7}]trideca-2(7),3,5-triene-8-carboxamide | A | A |
| 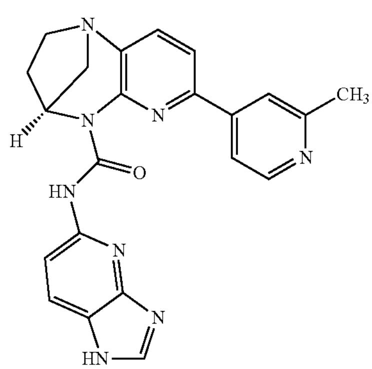 [SMILES: Cc1cc(-c2ccc3c(n2)N(C(=O)Nc2ccc4[nH]cnc4n2)[C@H]2CCN3C2)ccn1] | (9S)-N-{1H-imidazo[4,5-b]pyridin-5-yl}-5-(2-methylpyridin-4-yl)-1,6,8-triazatricyclo[7.2.1.0{2,7}]dodeca-2(7),3,5-triene-8-carboxamide | B | A |
| 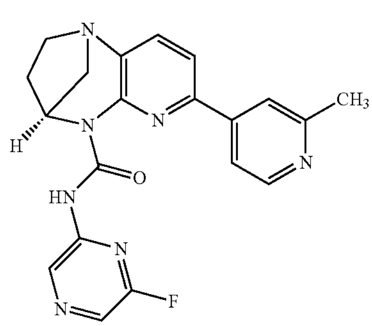 [SMILES: Cc1cc(-c2ccc3c(n2)N(C(=O)Nc2cncc(F)n2)[C@H]2CCN3C2)ccn1] | (9S)-N-(6-fluoropyrazin-2-yl)-5-(2-methylpyridin-4-yl)-1,6,8-triazatricyclo[7.2.1.0{2,7}]dodeca-2(7),3,5-triene-8-carboxamide | A | A |

TABLE A-continued

Additional Representative Compounds

| Structure | Chemical Name | TRP Activity | TRP MAX RESP |
|---|---|---|---|
| 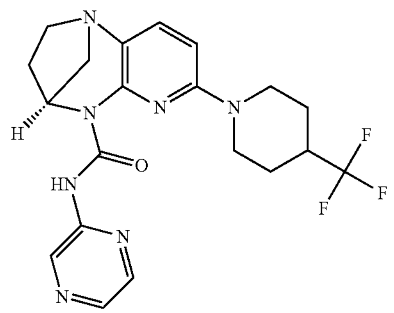 [SMILES: O=C(Nc1cnccn1)N1c2nc(N3CCC(C(F)(F)F)CC3)ccc2N2CC[C@H]1C2] | (9S)-N-(pyrazin-2-yl)-5-[4-(trifluoromethyl)piperidin-1-yl]-1,6,8-triazatricyclo[7.2.1.0{2,7}]dodeca-2(7),3,5-triene-8-carboxamide | A | A |
| 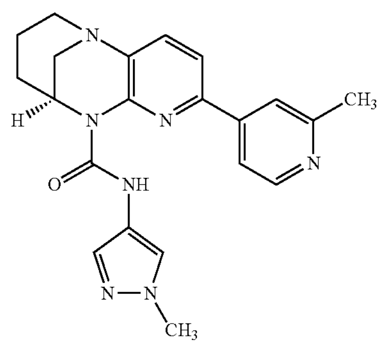 [SMILES: Cc1cc(-c2ccc3c(n2)N(C(=O)Nc2cnn(C)c2)[C@H]2CCCN3C2)ccn1] | (9S)-N-(1-methyl-1H-pyrazol-4-yl)-5-(2-methylpyridin-4-yl)-1,6,8-triazatricyclo[7.3.1.0{2,7}]trideca-2(7),3,5-triene-8-carboxamide | B | A |
| 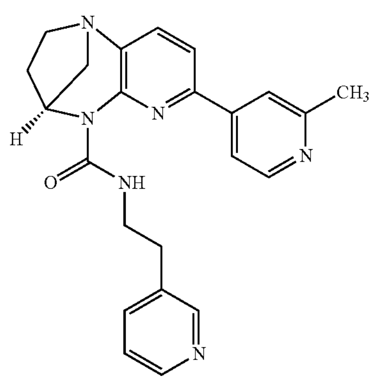 [SMILES: Cc1cc(-c2ccc3c(n2)N(C(=O)NCCc2cccnc2)[C@H]2CCN3C2)ccn1] | (9S)-5-(2-methylpyridin-4-yl)-N-[2-(pyridin-3-yl)ethyl]-1,6,8-triazatricyclo[7.2.1.0{2,7}]dodeca-2(7),3,5-triene-8-carboxamide hydrochloride | C | B |
| 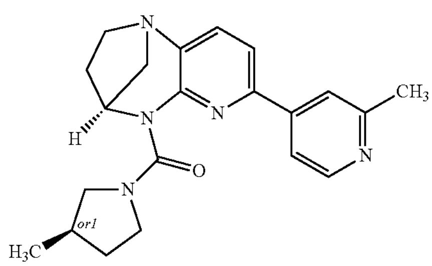 | (9S)-5-(2-methylpyridin-4-yl)-8-{[(3R)-3-methylpyrrolidin-1-yl]carbonyl}-1,6,8-triazatricyclo[7.2.1.0{2,7}]dodeca-2,4,6-triene | C | B |

ISOMER 1

TABLE A-continued

Additional Representative Compounds

| Structure | Chemical Name | TRP Activity | TRP MAX RESP |
|---|---|---|---|
| 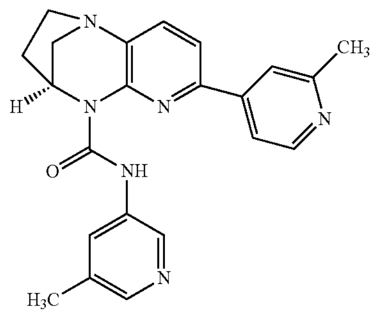 [SMILES: Cc1cncc(NC(=O)N2c3nc(-c4ccnc(C)c4)ccc3N3CC[C@H]2C3)c1] | (9S)-N-(5-methylpyridin-3-yl)-5-(2-methylpyridin-4-yl)-1,6,8-triazatricyclo[7.2.1.0 {2,7}]dodeca-2(7),3,5-triene-8-carboxamide | B | A |
| 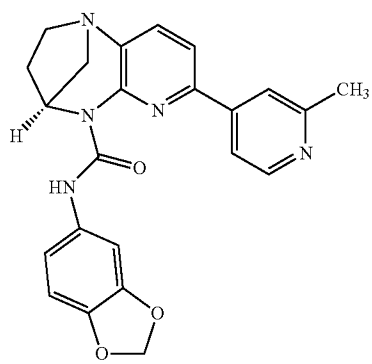 [SMILES: Cc1cc(-c2ccc3c(n2)N(C(=O)Nc2ccc4c(c2)OCO4)[C@H]2CCN3C2)ccn1] | (9S)-N-(2H-1,3-benzodioxol-5-yl)-5-(2-methylpyridin-4-yl)-1,6,8-triazatricyclo[7.2.1.0 {2,7}]dodeca-2(7),3,5-triene-8-carboxamide | A | A |
| 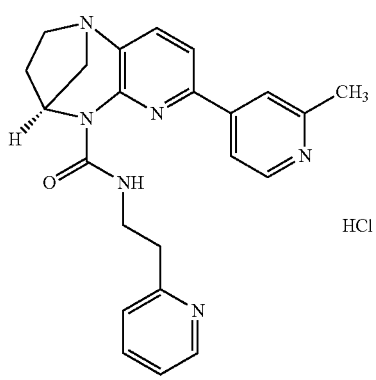 [SMILES: Cc1cc(-c2ccc3c(n2)N(C(=O)NCCc2ccccn2)[C@H]2CCN3C2)ccn1 ; Cl] | (9S)-5-(2-methylpyridin-4-yl)-N-[2-(pyridin-2-yl)ethyl]-1,6,8-triazatricyclo[7.2.1.0 {2,7}]dodeca-2(7),3,5-triene-8-carboxamide hydrochloride | C | B |
| 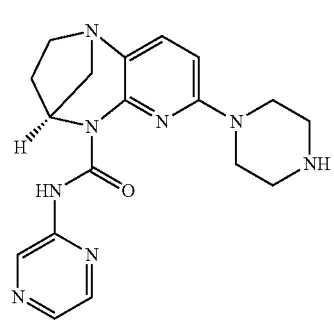 [SMILES: O=C(Nc1cnccn1)N1c2nc(N3CCNCC3)ccc2N2CC[C@H]1C2] | (9S)-5-(piperazin-1-yl)-N-(pyrazin-2-yl)-1,6,8-triazatricyclo[7.2.1.0 {2,7}]dodeca-2,4,6-triene-8-carboxamide | C | B |

TABLE A-continued

Additional Representative Compounds

| Structure | Chemical Name | TRP Activity | TRP MAX RESP |
|---|---|---|---|
| 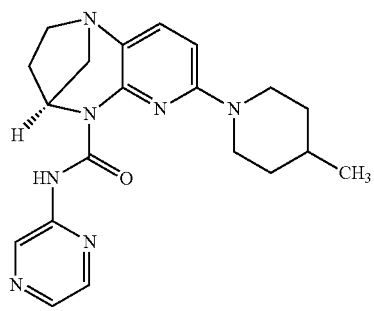 [SMILES: CC1CCN(c2ccc3c(n2)N(C(=O)Nc2cnccn2)[C@H]2CCN3C2)CC1] | (9S)-5-(4-methylpiperidin-1-yl)-N-(pyrazin-2-yl)-1,6,8-triazatricyclo[7.2.1.0 {2,7}]dodeca-2,4,6-triene-8-carboxamide | B | A |
| 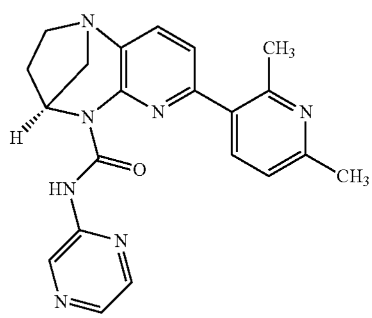 [SMILES: Cc1ccc(-c2ccc3c(n2)N(C(=O)Nc2cnccn2)[C@H]2CCN3C2)c(C)n1] | (9S)-5-(2,6-dimethylpyridin-3-yl)-N-(pyrazin-2-yl)-1,6,8-triazatricyclo[7.2.1.0 {2,7}]dodeca-2(7),3,5-triene-8-carboxamide | B | A |
| 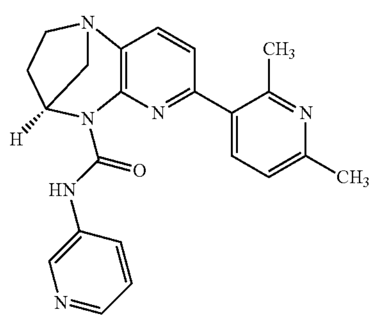 [SMILES: Cc1ccc(-c2ccc3c(n2)N(C(=O)Nc2cccnc2)[C@H]2CCN3C2)c(C)n1] | (9S)-5-(2,6-dimethylpyridin-3-yl)-N-(pyridin-3-yl)-1,6,8-triazatricyclo[7.2.1.0 {2,7}]dodeca-2(7),3,5-triene-8-carboxamide | B | A |
| 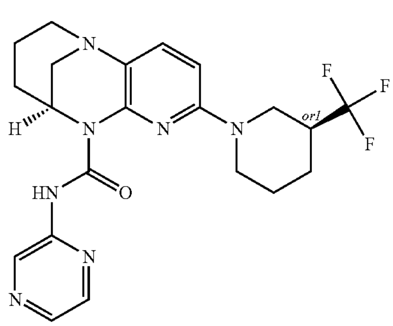 | (9S)-N-(pyrazin-2-yl)-5-[(3S)-3-(trifluoromethyl)piperidin-1-yl]-1,6,8-triazatricyclo[7.3.1.0 {2,7}]trideca-2(7),3,5-triene-8-carboxamide | A | A |

ISOMER 1

TABLE A-continued

Additional Representative Compounds

| Structure | Chemical Name | TRP Activity | TRP MAX RESP |
|---|---|---|---|
| 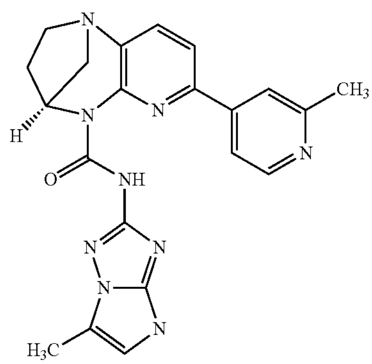 [SMILES: Cc1cc(-c2ccc3c(n2)N(C(=O)Nc2nc4[nH]cc(C)n4n2)[C@H]2CCN3C2)ccn1] | (9S)-N-{6-methyl-[1,2,4]triazolo[3,2-b][1,3]thiazol-2-yl}-5-(2-methylpyridin-4-yl)-1,6,8-triazatricyclo[7.2.1.0 {2,7}]dodeca-2(7),3,5-triene-8-carboxamide | B | A |
| 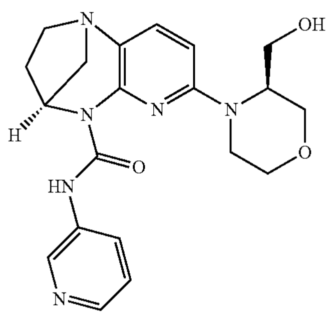 [SMILES: O=C(Nc1cccnc1)N1c2nc(N3CCOC[C@@H]3CO)ccc2N2CC[C@H]1C2] | (9S)-5-[(3S)-3-(hydroxymethyl)morpholin-4-yl]-N-(pyridin-3-yl)-1,6,8-triazatricyclo[7.2.1.0 {2,7}]dodeca-2(7),3,5-triene-8-carboxamide | C | B |
| 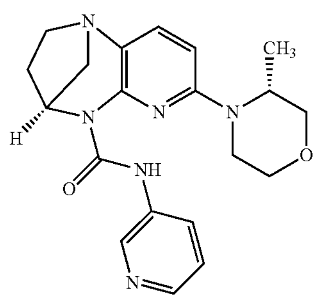 [SMILES: C[C@@H]1COCCN1c1ccc2c(n1)N(C(=O)Nc1cccnc1)[C@H]1CCN2C1] | (9S)-5-[(3R)-3-methylmorpholin-4-yl]-N-(pyridin-3-yl)-1,6,8-triazatricyclo[7.2.1.0 {2,7}]dodeca-2(7),3,5-triene-8-carboxamide | B | A |
| 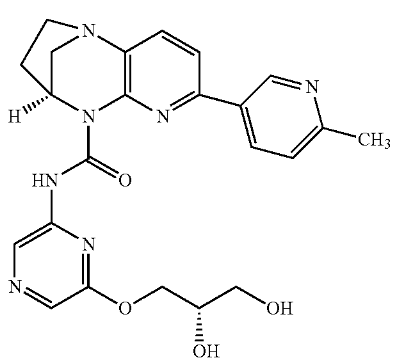 [SMILES: Cc1ccc(-c2ccc3c(n2)N(C(=O)Nc2cncc(OC[C@@H](O)CO)n2)[C@H]2CCN3C2)cn1] | (9S)-N-{6-[(2S)-2,3-dihydroxypropoxy]pyrazin-2-yl}-5-(6-methylpyridin-3-yl)-1,6,8-triazatricyclo[7.2.1.0 {2,7}]dodeca-2(7),3,5-triene-8-carboxamide | B | A |

TABLE A-continued

Additional Representative Compounds

| Structure | Chemical Name | TRP Activity | TRP MAX RESP |
|---|---|---|---|
| 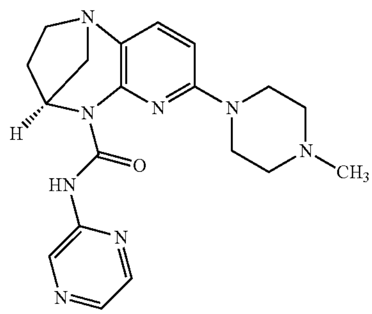 [SMILES: CN1CCN(c2ccc3c(n2)N(C(=O)Nc2cnccn2)[C@H]2CCN3C2)CC1] | (9S)-5-(4-methylpiperazin-1-yl)-N-(pyrazin-2-yl)-1,6,8-triazatricyclo[7.2.1.0 {2,7}]dodeca-2(7),3,5-triene-8-carboxamide | B | A |
| 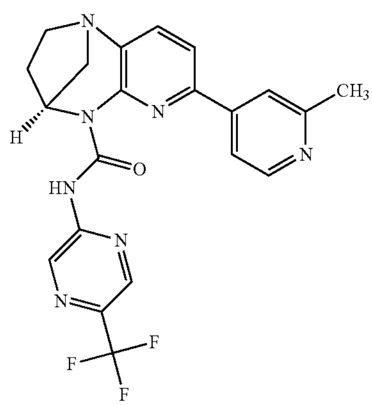 [SMILES: Cc1cc(-c2ccc3c(n2)N(C(=O)Nc2cnc(C(F)(F)F)cn2)[C@H]2CCN3C2)ccn1] | (9S)-5-(2-methylpyridin-4-yl)-N-[5-(trifluoromethyl)pyrazin-2-yl]-1,6,8-triazatricyclo[7.2.1.0 {2,7}]dodeca-2(7),3,5-triene-8-carboxamide | C | B |
| 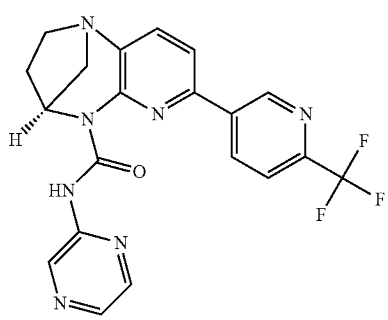 [SMILES: O=C(Nc1cnccn1)N1c2nc(-c3ccc(C(F)(F)F)nc3)ccc2N2CC[C@H]1C2] | (9S)-N-(pyrazin-2-yl)-5-[6-(trifluoromethyl)pyridin-3-yl]-1,6,8-triazatricyclo[7.2.1.0 {2,7}]dodeca-2(7),3,5-triene-8-carboxamide | B | A |
| 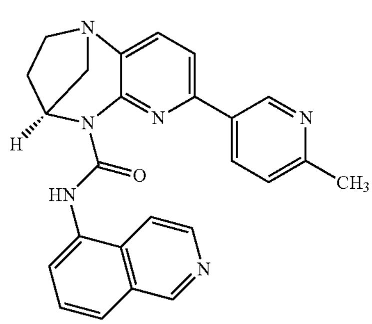 [SMILES: Cc1ccc(-c2ccc3c(n2)N(C(=O)Nc2cccc4cnccc24)[C@H]2CCN3C2)cn1] | (9S)-N-(isoquinolin-5-yl)-5-(6-methylpyridin-3-yl)-1,6,8-triazatricyclo[7.2.1.0 {2,7}]dodeca-2,4,6-triene-8-carboxamide | B | A |

TABLE A-continued

Additional Representative Compounds

| Structure | Chemical Name | TRP Activity | TRP MAX RESP |
|---|---|---|---|
| 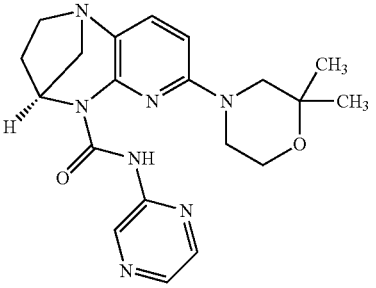 [SMILES: CC1(C)CN(c2ccc3c(n2)N(C(=O)Nc2cnccn2)[C@H]2CCN3C2)CCO1] | (9S)-5-(2,2-dimethylmorpholin-4-yl)-N-(pyrazin-2-yl)-1,6,8-triazatricyclo[7.2.1.0 {2,7}]dodeca-2(7),3,5-triene-8-carboxamide | A | A |
| 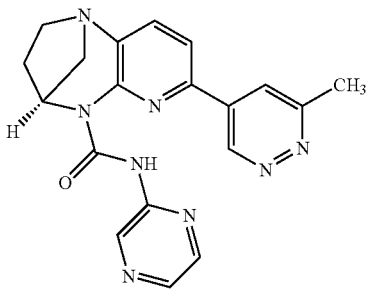 [SMILES: Cc1cc(-c2ccc3c(n2)N(C(=O)Nc2cnccn2)[C@H]2CCN3C2)cnn1] | (9S)-5-(6-methylpyridazin-4-yl)-N-(pyrazin-2-yl)-1,6,8-triazatricyclo[7.2.1.0 {2,7}]dodeca-2(7),3,5-triene-8-carboxamide | B | A |
| 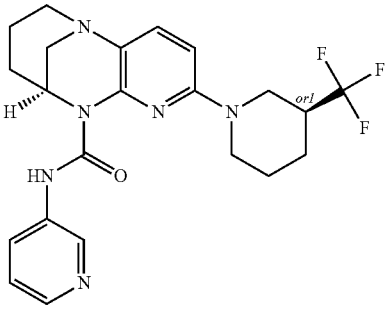 ISOMER 2 | (9S)-N-(pyridin-3-yl)-5-[(3S)-3-(trifluoromethyl)piperidin-1-yl]-1,6,8-triazatricyclo[7.3.1.0 {2,7}]trideca-2(7),3,5-triene-8-carboxamide | A | A |
| 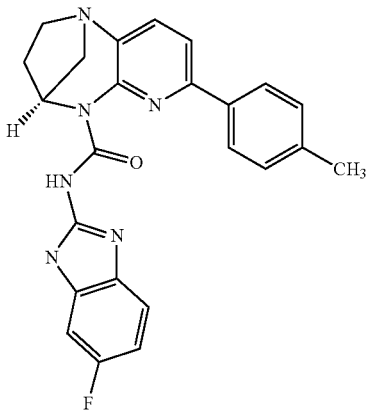 [SMILES: Cc1ccc(-c2ccc3c(n2)N(C(=O)Nc2nc4ccc(F)cc4[nH]2)[C@H]2CCN3C2)cc1] | (9S)-N-(6-fluoro-1,3-benzothiazol-2-yl)-5-(6-methylpyridin-3-yl)-1,6,8-triazatricyclo[7.2.1.0 {2,7}]dodeca-2,4,6-triene-8-carboxamide | B | A |

TABLE A-continued

Additional Representative Compounds

| Structure | Chemical Name | TRP Activity | TRP MAX RESP |
|---|---|---|---|
| 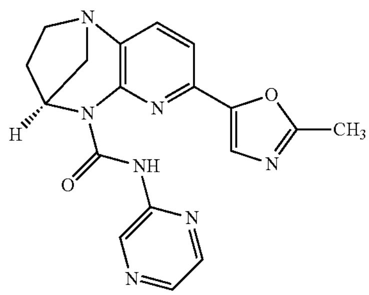 [SMILES: Cc1ncc(-c2ccc3c(n2)N(C(=O)Nc2cnccn2)[C@H]2CCN3C2)o1] | (9S)-5-(2-methyl-1,3-thiazol-5-yl)-N-(pyrazin-2-yl)-1,6,8-triazatricyclo[7.2.1.0 {2,7}]dodeca-2(7),3,5-triene-8-carboxamide | B | A |
| ISOMER 2 | (9S)-N-(5-fluoropyridin-2-yl)-5-[(3S)-3-(trifluoromethyl)piperidin-1-yl]-1,6,8-triazatricyclo[7.3.1.0 {2,7}]trideca-2(7),3,5-triene-8-carboxamide | B | A |
| 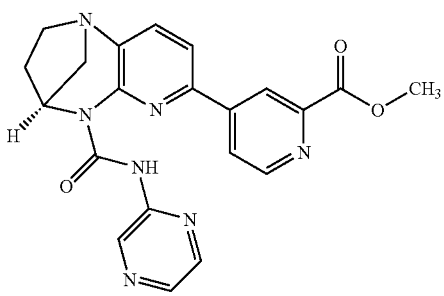 [SMILES: COC(=O)c1cc(-c2ccc3c(n2)N(C(=O)Nc2cnccn2)[C@H]2CCN3C2)ccn1] | methyl 4-[(9S)-8-[(pyrazin-2-yl)carbamoyl]-1,6,8-triazatricyclo[7.2.1.0 {2,7}]dodeca-2(7),3,5-trien-5-yl]pyridine-2-carboxylate | B | A |
| 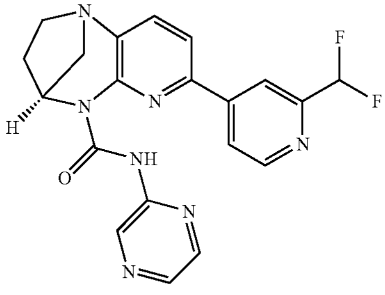 [SMILES: O=C(Nc1cnccn1)N1c2nc(-c3ccnc(C(F)F)c3)ccc2N2CC[C@H]1C2] | (9S)-5-[2-(difluoromethyl)pyridin-4-yl]-N-(pyrazin-2-yl)-1,6,8-triazatricyclo[7.2.1.0 {2,7}]dodeca-2(7),3,5-triene-8-carboxamide | A | A |

TABLE A-continued

Additional Representative Compounds

| Structure | Chemical Name | TRP Activity | TRP MAX RESP |
|---|---|---|---|
| ISOMER 1 | (9S)-N-(pyrazin-2-yl)-5-[(3S)-3-(trifluoromethyl)piperidin-1-yl]-1,6,8-triazatricyclo[7.3.1.0{2,7}]trideca-2(7),3,5-triene-8-carboxamide | A | A |
| 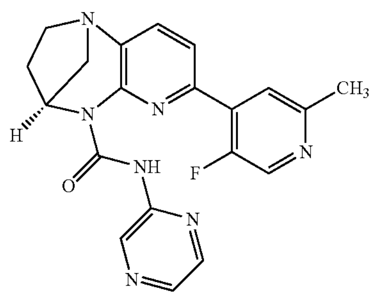 [SMILES: Cc1cc(-c2ccc3c(n2)N(C(=O)Nc2cnccn2)[C@H]2CCN3C2)c(F)cn1] | (9S)-5-(5-fluoro-2-methylpyridin-4-yl)-N-(pyrazin-2-yl)-1,6,8-triazatricyclo[7.2.1.0{2,7}]dodeca-2(7),3,5-triene-8-carboxamide | B | A |
| 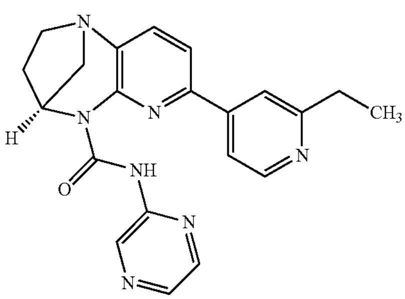 [SMILES: CCc1cc(-c2ccc3c(n2)N(C(=O)Nc2cnccn2)[C@H]2CCN3C2)ccn1] | (9S)-5-[2-(hydroxymethyl)pyridin-4-yl]-N-(pyrazin-2-yl)-1,6,8-triazatricyclo[7.2.1.0{2,7}]dodeca-2(7),3,5-triene-8-carboxamide | B | A |
| 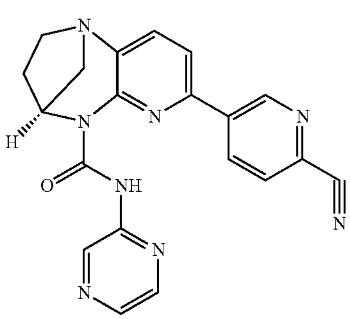 [SMILES: N#Cc1ccc(-c2ccc3c(n2)N(C(=O)Nc2cnccn2)[C@H]2CCN3C2)cn1] | (9S)-5-(6-cyanopyridin-3-yl)-N-(pyrazin-2-yl)-1,6,8-triazatricyclo[7.2.1.0{2,7}]dodeca-2,4,6-triene-8-carboxamide | C | B |

TABLE A-continued

Additional Representative Compounds

| Structure | Chemical Name | TRP Activity | TRP MAX RESP |
|---|---|---|---|
| 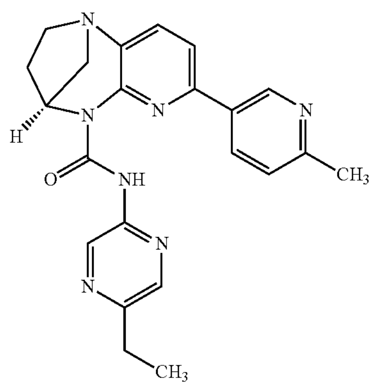 [SMILES: CCc1cnc(NC(=O)N2c3nc(-c4ccc(C)nc4)ccc3N3CC[C@H]2C3)cn1] | (9S)-N-(5-ethylpyrazin-2-yl)-5-(6-methylpyridin-3-yl)-1,6,8-triazatricyclo[7.2.1.0^{2,7}]dodeca-2,4,6-triene-8-carboxamide | B | A |
| 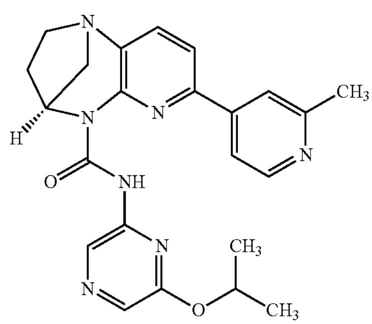 [SMILES: Cc1cc(-c2ccc3c(n2)N(C(=O)Nc2cncc(OC(C)C)n2)[C@H]2CCN3C2)ccn1] | (9S)-5-(2-methylpyridin-4-yl)-N-[6-(propan-2-yloxy)pyrazin-2-yl]-1,6,8-triazatricyclo[7.2.1.0 {2,7}]dodeca-2(7),3,5-triene-8-carboxamide | A | A |
| 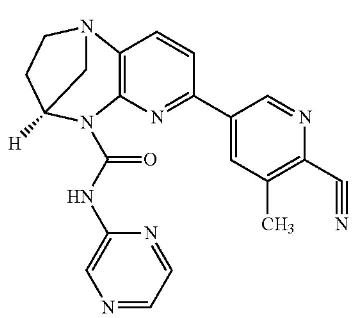 [SMILES: Cc1cc(-c2ccc3c(n2)N(C(=O)Nc2cnccn2)[C@H]2CCN3C2)cnc1C#N] | (9S)-5-(6-cyano-5-methylpyridin-3-yl)-N-(pyrazin-2-yl)-1,6,8-triazatricyclo[7.2.1.0 {2,7}]dodeca-2(7),3,5-triene-8-carboxamide | B | A |
| 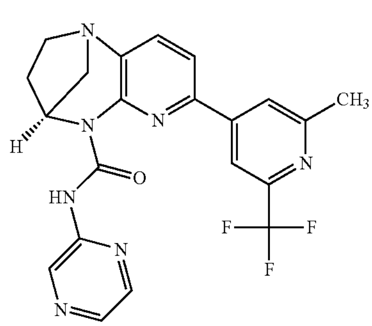 [SMILES: Cc1cc(-c2ccc3c(n2)N(C(=O)Nc2cnccn2)[C@H]2CCN3C2)cc(C(F)(F)F)n1] | (9S)-5-[2-methyl-6-(trifluoromethyl)pyridin-4-yl]-N-(pyrazin-2-yl)-1,6,8-triazatricyclo[7.2.1.0 {2,7}]dodeca-2(7),3,5-triene-8-carboxamide | A | A |

TABLE A-continued

Additional Representative Compounds

| Structure | Chemical Name | TRP Activity | TRP MAX RESP |
|---|---|---|---|
| 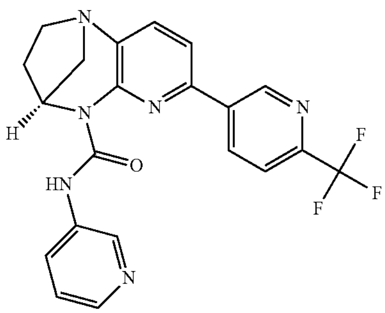 [SMILES: O=C(Nc1cccnc1)N1c2nc(-c3ccc(C(F)(F)F)nc3)ccc2N2CC[C@H]1C2] | (9S)-N-(pyridin-3-yl)-5-[6-(trifluoromethyl)pyridin-3-yl]-1,6,8-triazatricyclo[7.2.1.0^{2,7}]dodeca-2(7),3,5-triene-8-carboxamide | B | A |
| 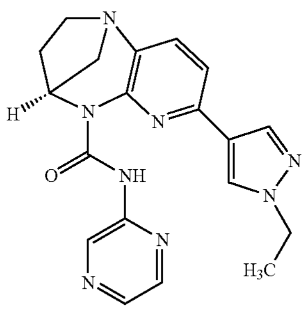 [SMILES: CCn1cc(-c2ccc3c(n2)N(C(=O)Nc2cnccn2)[C@H]2CCN3C2)cn1] | (9S)-5-(1-ethyl-1H-pyrazol-4-yl)-N-(pyrazin-2-yl)-1,6,8-triazatricyclo[7.2.1.0 {2,7}]dodeca-2(7),3,5-triene-8-carboxamide | B | A |
| 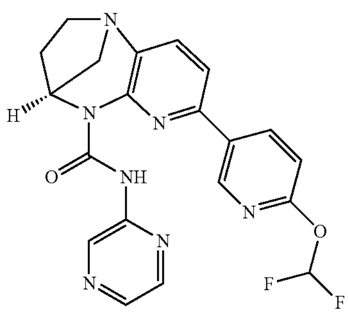 [SMILES: O=C(Nc1cnccn1)N1c2nc(-c3ccc(OC(F)F)nc3)ccc2N2CC[C@H]1C2] | (9S)-5-[6-(difluoromethoxy)pyridin-3-yl]-N-(pyrazin-2-yl)-1,6,8-triazatricyclo[7.2.1.0 {2,7}]dodeca-2(7),3,5-triene-8-carboxamide | B | A |
| 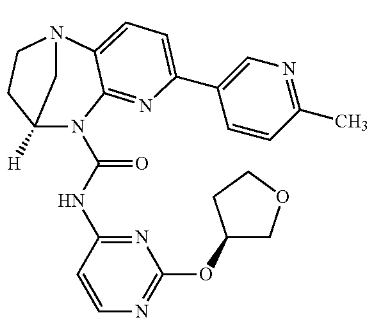 [SMILES: Cc1ccc(-c2ccc3c(n2)N(C(=O)Nc2ccnc(O[C@H]4CCOC4)n2)[C@H]2CCN3C2)cn1] | (9S)-5-(6-methylpyridin-3-yl)-N-{2-[(3S)-oxolan-3-yloxy]pyrimidin-4-yl}-1,6,8-triazatricyclo[7.2.1.0 {2,7}]dodeca-2,4,6-triene-8-carboxamide | B | A |

TABLE A-continued

Additional Representative Compounds

| Structure | Chemical Name | TRP Activity | TRP MAX RESP |
|---|---|---|---|
| ISOMER 1 | (9S)-5-[(2S)-2-methylpiperazin-1-yl]-N-(pyrazin-2-yl)-1,6,8-triazatricyclo[7.2.1.0 {2,7}]dodeca-2,4,6-triene-8-carboxamide | C | B |
| ISOMER 1 | (9S)-5-[(3R)-3-methylpiperazin-1-yl]-N-(pyrazin-2-yl)-1,6,8-triazatricyclo[7.2.1.0 {2,7}]dodeca-2,4,6-triene-8-carboxamide | C | B |
| ISOMER 2 | (9S)-N-(pyridin-2-yl)-5-[(3S)-3-(trifluoromethyl)pyrrolidin-1-yl]-1,6,8-triazatricyclo[7.3.1.0 {2,7}]trideca-2(7),3,5-triene-8-carboxamide hydrochloride | A | A |
| ISOMER 1 | (9S)-N-(pyrazin-2-yl)-5-[(2S)-2-(trifluoromethyl)morpholin-4-yl]-1,6,8-triazatricyclo[7.2.1.0 {2,7}]dodeca-2(7),3,5-triene-8-carboxamide | B | A |

TABLE A-continued

Additional Representative Compounds

| Structure | Chemical Name | TRP Activity | TRP MAX RESP |
|---|---|---|---|
| ISOMER 2 | (9S)-N-(pyrazin-2-yl)-5-[(2S)-2-(trifluoromethyl)morpholin-4-yl]-1,6,8-triazatricyclo[7.2.1.0{2,7}]dodeca-2(7),3,5-triene-8-carboxamide | A | A |
| HCl | (9S)-8-{[(2R)-2-methylmorpholin-4-yl]carbonyl}-5-(2-methylpyridin-4-yl)-1,6,8-triazatricyclo[7.2.1.0{2,7}]dodeca-2(7),3,5-triene hydrochloride | C | B |
| 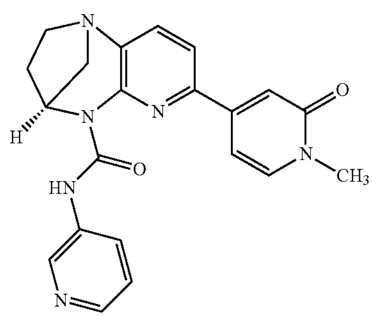 [SMILES: Cn1ccc(-c2ccc3c(n2)N(C(=O)Nc2cccnc2)[C@H]2CCN3C2)cc1=O] | (9S)-5-(1-methyl-2-oxo-1,2-dihydropyridin-4-yl)-N-(pyridin-3-yl)-1,6,8-triazatricyclo[7.2.1.0{2,7}]dodeca-2(7),3,5-triene-8-carboxamide | B | A |
| HCl | (9S)-8-{[(2S)-2-methylmorpholin-4-yl]carbonyl}-5-(2-methylpyridin-4-yl)-1,6,8-triazatricyclo[7.2.1.0{2,7}]dodeca-2(7),3,5-triene hydrochloride | C | B |
| 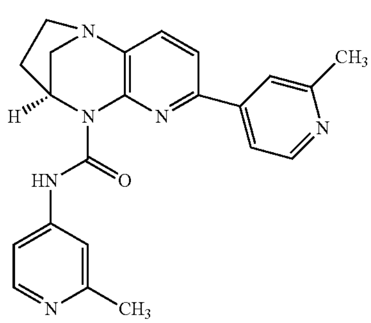 [SMILES: Cc1cc(NC(=O)N2c3nc(-c4ccnc(C)c4)ccc3N3CC[C@H]2C3)ccn1] | (9S)-N,5-bis(2-methylpyridin-4-yl)-1,6,8-triazatricyclo[7.2.1.0{2,7}]dodeca-2(7),3,5-triene-8-carboxamide | B | A |

TABLE A-continued

Additional Representative Compounds

| Structure | Chemical Name | TRP Activity | TRP MAX RESP |
|---|---|---|---|
| 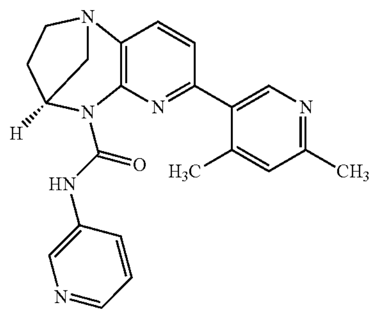 [SMILES: Cc1cc(C)c(-c2ccc3c(n2)N(C(=O)Nc2cccnc2)[C@H]2CCN3C2)cn1] | (9S)-5-(4,6-dimethylpyridin-3-yl)-N-(pyridin-3-yl)-1,6,8-triazatricyclo[7.2.1.0 {2,7}]dodeca-2(7),3,5-triene-8-carboxamide | B | A |
| 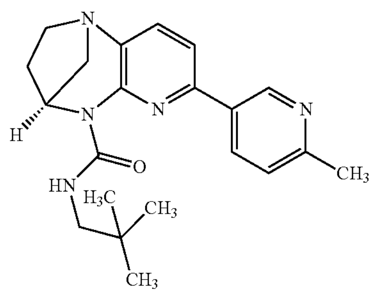 [SMILES: Cc1ccc(-c2ccc3c(n2)N(C(=O)NCC(C)(C)C)[C@H]2CCN3C2)cn1] | (9S)-N-(2,2-dimethylpropyl)-5-(6-methylpyridin-3-yl)-1,6,8-triazatricyclo[7.2.1.0 {2,7}]dodeca-2(7),3,5-triene-8-carboxamide | C | B |
| 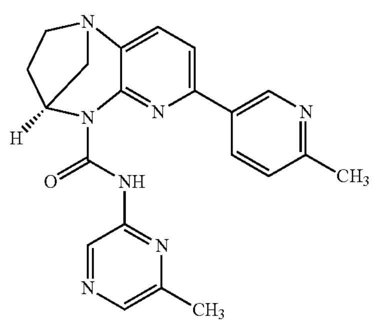 [SMILES: Cc1ccc(-c2ccc3c(n2)N(C(=O)Nc2cncc(C)n2)[C@H]2CCN3C2)cn1] | (9S)-N-(6-methylpyrazin-2-yl)-5-(6-methylpyridin-3-yl)-1,6,8-triazatricyclo[7.2.1.0 {2,7}]dodeca-2,4,6-triene-8-carboxamide | B | A |
| 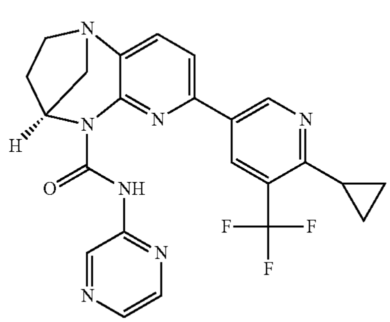 [SMILES: O=C(Nc1cnccn1)N1c2nc(-c3cnc(C4CC4)c(C(F)(F)F)c3)ccc2N2CC[C@H]1C2] | (9S)-5-[6-cyclopropyl-5-(trifluoromethyl)pyridin-3-yl]-N-(pyrazin-2-yl)-1,6,8-triazatricyclo[7.2.1.0 {2,7}]dodeca-2,4,6-triene-8-carboxamide | A | A |

TABLE A-continued

Additional Representative Compounds

| Structure | Chemical Name | TRP Activity | TRP MAX RESP |
|---|---|---|---|
| 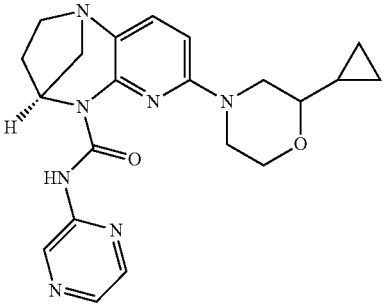 [SMILES: O=C(Nc1cnccn1)N1c2nc(N3CCOC(C4CC4)C3)ccc2N2CC[C@H]1C2] | (9S)-5-(2-cyclopropylmorpholin-4-yl)-N-(pyrazin-2-yl)-1,6,8-triazatricyclo[7.2.1.0 {2,7}]dodeca-2,4,6-triene-8-carboxamide | B | A |
| 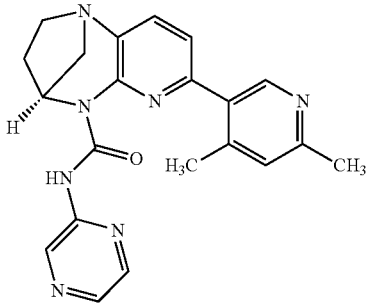 [SMILES: Cc1cc(C)c(-c2ccc3c(n2)N(C(=O)Nc2cnccn2)[C@H]2CCN3C2)cn1] | (9S)-5-(4,6-dimethylpyridin-3-yl)-N-(pyrazin-2-yl)-1,6,8-triazatricyclo[7.2.1.0 {2,7}]dodeca-2(7),3,5-triene-8-carboxamide | C | B |
| 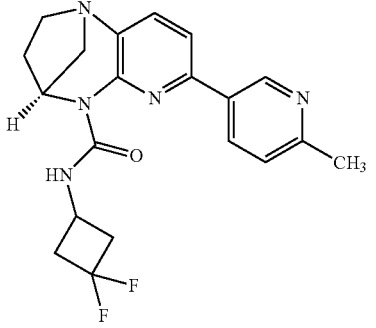 [SMILES: Cc1ccc(-c2ccc3c(n2)N(C(=O)NC2CC(F)(F)C2)[C@H]2CCN3C2)cn1] | (9S)-N-(3,3-difluorocyclobutyl)-5-(6-methylpyridin-3-yl)-1,6,8-triazatricyclo[7.2.1.0 {2,7}]dodeca-2(7),3,5-triene-8-carboxamide | B | A |
| 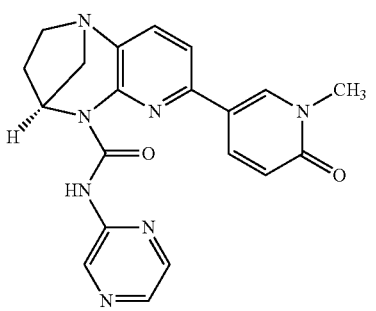 [SMILES: Cn1cc(-c2ccc3c(n2)N(C(=O)Nc2cnccn2)[C@H]2CCN3C2)ccc1=O] | (9S)-5-(1-methyl-6-oxo-1,6-dihydropyridin-3-yl)-N-(pyrazin-2-yl)-1,6,8-triazatricyclo[7.2.1.0$^{2,7}$]dodeca-2(7),3,5-triene-8-carboxamide | C | B |

TABLE A-continued

Additional Representative Compounds

| Structure | Chemical Name | TRP Activity | TRP MAX RESP |
|---|---|---|---|
| 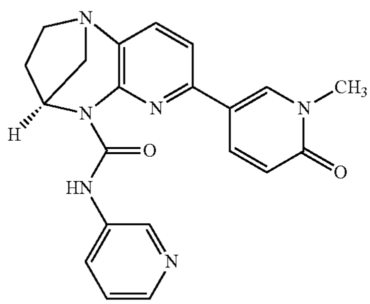 [SMILES: Cn1cc(-c2ccc3c(n2)N(C(=O)Nc2cccnc2)[C@H]2CCN3C2)ccc1=O] | (9S)-5-(1-methyl-6-oxo-1,6-dihydropyridin-3-yl)-N-(pyridin-3-yl)-1,6,8-triazatricyclo[7.2.1.0$^{2,7}$]dodeca-2(7),3,5-triene-8-carboxamide | B | A |
| 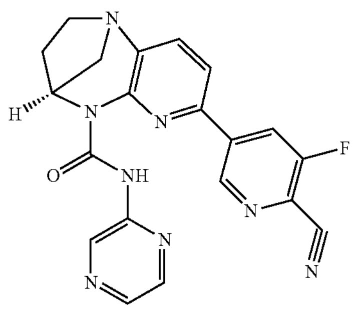 [SMILES: N#Cc1ncc(-c2ccc3c(n2)N(C(=O)Nc2cnccn2)[C@H]2CCN3C2)cc1F] | (9S)-5-(6-cyano-5-fluoropyridin-3-yl)-N-(pyrazin-2-yl)-1,6,8-triazatricyclo[7.2.1.0$^{2,7}$]dodeca-2(7),3,5-triene-8-carboxamide | C | B |
| 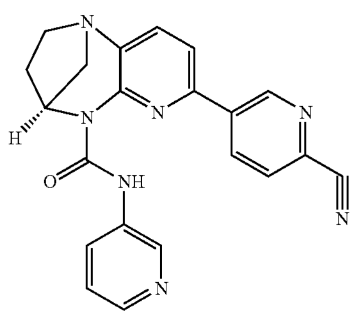 [SMILES: N#Cc1ccc(-c2ccc3c(n2)N(C(=O)Nc2cccnc2)[C@H]2CCN3C2)cn1] | (9S)-5-(6-cyanopyridin-3-yl)-N-(pyridin-3-yl)-1,6,8-triazatricyclo[7.2.1.0$^{2,7}$]dodeca-2,4,6-triene-8-carboxamide | B | A |
| 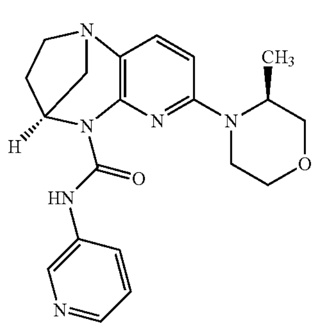 [SMILES: C[C@H]1COCCN1c1ccc2c(n1)N(C(=O)Nc1cccnc1)[C@H]1CCN2C1] | (9S)-5-[(3S)-3-methylmorpholin-4-yl]-N-(pyridin-3-yl)-1,6,8-triazatricyclo[7.2.1.0$^{2,7}$]dodeca-2(7),3,5-triene-8-carboxamide | B | A |

TABLE A-continued

Additional Representative Compounds

| Structure | Chemical Name | TRP Activity | TRP MAX RESP |
|---|---|---|---|
| 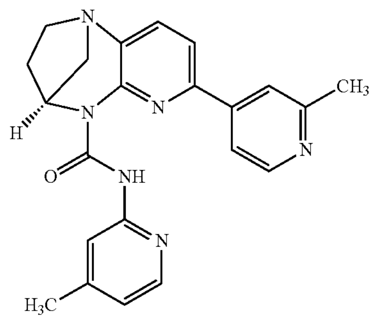 [SMILES: Cc1ccnc(NC(=O)N2c3nc(-c4ccnc(C)c4)ccc3N3CC[C@H]2C3)c1] | (9S)-N-(4-methylpyridin-2-yl)-5-(2-methylpyridin-4-yl)-1,6,8-triazatricyclo[7.2.1.0$^{2,7}$]dodeca-2,4,6-triene-8-carboxamide | B | A |
| 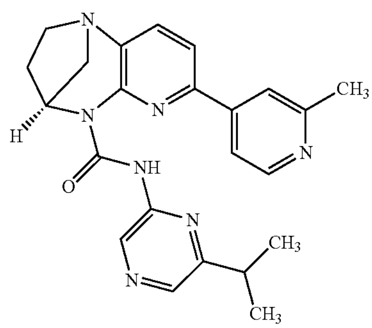 [SMILES: Cc1cc(-c2ccc3c(n2)N(C(=O)Nc2cncc(C(C)C)n2)[C@H]2CCN3C2)ccn1] | (9S)-5-(2-methylpyridin-4-yl)-N-[6-(propan-2-yl)pyrazin-2-yl]-1,6,8-triazatricyclo[7.2.1.0$^{2,7}$]dodeca-2(7),3,5-triene-8-carboxamide | A | A |
| ISOMER 1 | (9S)-N-(pyridin-2-yl)-5-[(3R)-3-(trifluoromethyl)pyrrolidin-1-yl]-1,6,8-triazatricyclo[7.2.1.0$^{2,7}$]dodeca-2,4,6-triene-8-carboxamide | A | A |
| 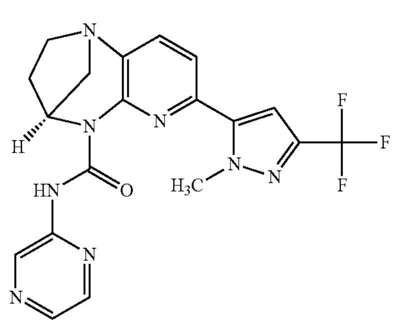 [SMILES: Cn1nc(C(F)(F)F)cc1-c1ccc2c(n1)N(C(=O)Nc1cnccn1)[C@H]1CCN2C1] | (9S)-5-[1-methyl-3-(trifluoromethyl)-1H-pyrazol-5-yl]-N-(pyrazin-2-yl)-1,6,8-triazatricyclo[7.2.1.0 {2,7}]dodeca-2(7),3,5-triene-8-carboxamide | B | A |

TABLE A-continued

Additional Representative Compounds

| Structure | Chemical Name | TRP Activity | TRP MAX RESP |
|---|---|---|---|
| 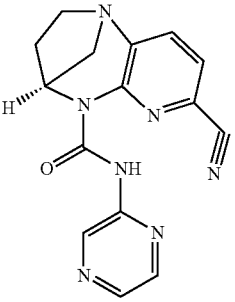 [SMILES: N#Cc1ccc2c(n1)N(C(=O)Nc1cnccn1)[C@H]1CCN2C1] | (9S)-5-cyano-N-(pyrazin-2-yl)-1,6,8-triazatricyclo[7.2.1.0 {2,7}]dodeca-2(7),3,5-triene-8-carboxamide | C | B |
| 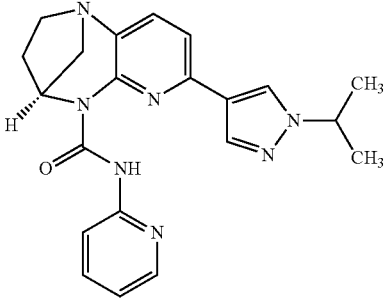 [SMILES: CC(C)n1cc(-c2ccc3c(n2)N(C(=O)Nc2ccccn2)[C@H]2CCN3C2)cn1] | (9S)-5-[1-(propan-2-yl)-1H-pyrazol-4-yl]-N-(pyrazin-2-yl)-1,6,8-triazatricyclo[7.2.1.0 {2,7}]dodeca-2,4,6-triene-8-carboxamide | A | A |
| 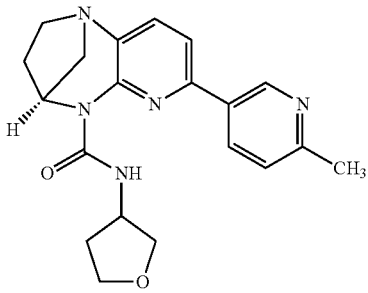 [SMILES: Cc1ccc(-c2ccc3c(n2)N(C(=O)NC2CCOC2)[C@H]2CCN3C2)cn1] | (9S)-5-(6-methylpyridin-3-yl)-N-(oxolan-3-yl)-1,6,8-triazatricyclo[7.2.1.0 {2,7}]dodeca-2,4,6-triene-8-carboxamide | C | B |
| 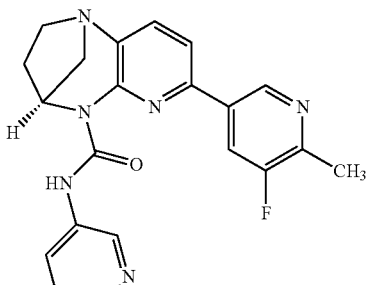 | (9S)-5-(5-fluoro-6-methylpyridin-3-yl)-N-(pyridin-3-yl)-1,6,8-triazatricyclo[7.2.1.0 {2,7}]dodeca-2(7),3,5-triene-8-carboxamide | B | A |

TABLE A-continued

Additional Representative Compounds

| Structure | Chemical Name | TRP Activity | TRP MAX RESP |
|---|---|---|---|
| 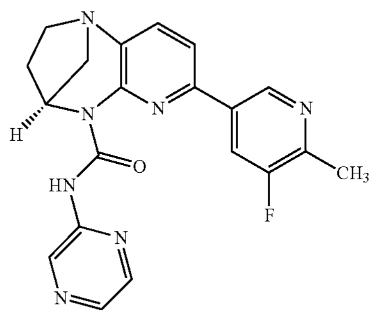 [SMILES: Cc1ncc(-c2ccc3c(n2)N(C(=O)Nc2cnccn2)[C@H]2CCN3C2)cc1F] | (9S)-5-(5-fluoro-6-methylpyridin-3-yl)-N-(pyrazin-2-yl)-1,6,8-triazatricyclo[7.2.1.0 {2,7}]dodeca-2(7),3,5-triene-8-carboxamide | B | A |
| 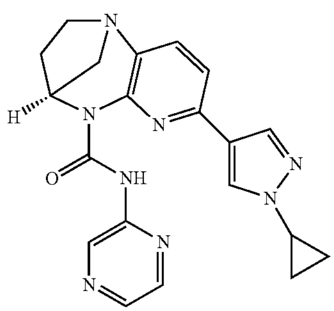 [SMILES: O=C(Nc1cnccn1)N1c2nc(-c3cnn(C4CC4)c3)ccc2N2CC[C@H]1C2] | (9S)-5-(1-cyclopropyl-1H-pyrazol-4-yl)-N-(pyrazin-2-yl)-1,6,8-triazatricyclo[7.2.1.0 {2,7}]dodeca-2(7),3,5-triene-8-carboxamide | A | A |
| 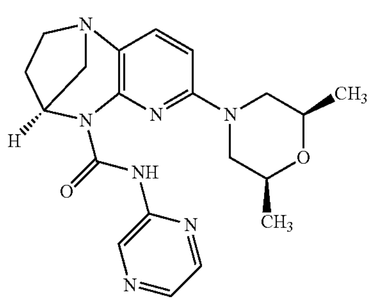 [SMILES: C[C@@H]1CN(c2ccc3c(n2)N(C(=O)Nc2cnccn2)[C@H]2CCN3C2)C[C@H](C)O1] | (9S)-5-[(2R,6S)-2,6-dimethylmorpholin-4-yl]-N-(pyrazin-2-yl)-1,6,8-triazatricyclo[7.2.1.0 {2,7}]dodeca-2(7),3,5-triene-8-carboxamide | B | A |
| 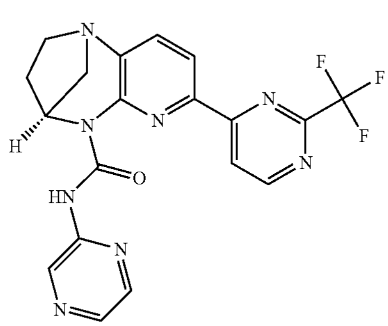 [SMILES: O=C(Nc1cnccn1)N1c2nc(-c3ccnc(C(F)(F)F)n3)ccc2N2CC[C@H]1C2] | (9S)-N-(pyrazin-2-yl)-5-[2-(trifluoromethyl)pyrimidin-4-yl]-1,6,8-triazatricyclo[7.2.1.0 {2,7}]dodeca-2(7),3,5-triene-8-carboxamide | B | A |

TABLE A-continued

Additional Representative Compounds

| Structure | Chemical Name | TRP Activity | TRP MAX RESP |
|---|---|---|---|
| 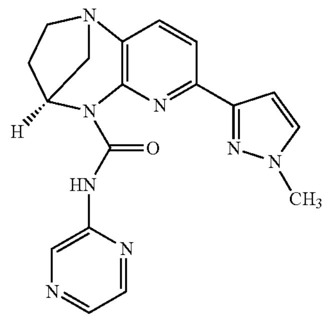 [SMILES: Cn1ccc(-c2ccc3c(n2)N(C(=O)Nc2cnccn2)[C@H]2CCN3C2)n1] | (9S)-5-(1-methyl-1H-pyrazol-3-yl)-N-(pyrazin-2-yl)-1,6,8-triazatricyclo[7.2.1.0 {2,7}]dodeca-2(7),3,5-triene-8-carboxamide | B | A |
| 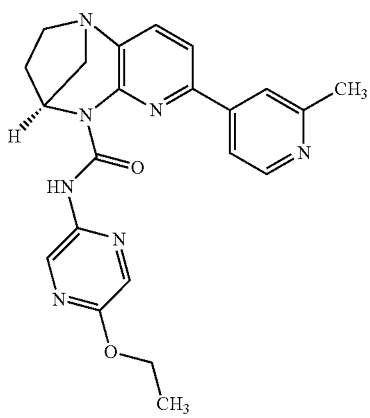 [SMILES: CCOc1cnc(NC(=O)N2c3nc(-c4ccnc(C)c4)ccc3N3CC[C@H]2C3)cn1] | (9S)-N-(5-ethoxypyrazin-2-yl)-5-(2-methylpyridin-4-yl)-1,6,8-triazatricyclo[7.2.1.0 {2,7}]dodeca-2(7),3,5-triene-8-carboxamide | B | A |
| 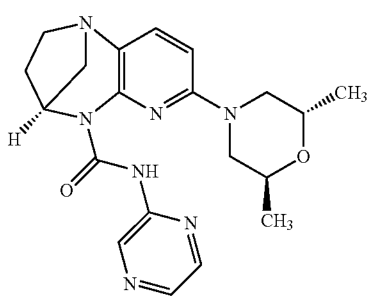 [SMILES: C[C@H]1CN(c2ccc3c(n2)N(C(=O)Nc2cnccn2)[C@H]2CCN3C2)C[C@H](C)O1] | (9S)-5-[(2S,6S)-2,6-dimethylmorpholin-4-yl]-N-(pyrazin-2-yl)-1,6,8-triazatricyclo[7.2.1.0^{2,7}]dodeca-2(7),3,5-triene-8-carboxamide | B | A |
|  | (9S)-5-(2-methylpyridin-4-yl)-N-(pyridazin-4-yl)-1,6,8-triazatricyclo[7.2.1.0^{2,7}]dodeca-2,4,6-triene-8-carboxamide | B | A |

TABLE A-continued

Additional Representative Compounds

| Structure | Chemical Name | TRP Activity | TRP MAX RESP |
|---|---|---|---|
| 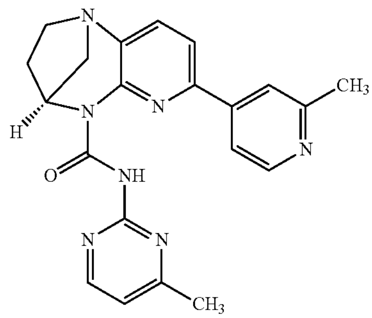 [SMILES: Cc1cc(-c2ccc3c(n2)N(C(=O)Nc2nccc(C)n2)[C@H]2CCN3C2)ccn1] | (9S)-5-(2-methylpyridin-4-yl)-N-(4-methylpyrimidin-2-yl)-1,6,8-triazatricyclo[7.2.1,0^{2,7}]dodeca-2,4,6-triene-8-carboxamide | B | A |
| 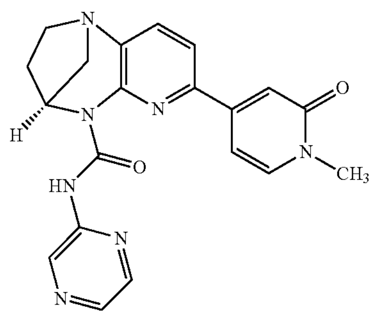 [SMILES: Cn1ccc(-c2ccc3c(n2)N(C(=O)Nc2cnccn2)[C@H]2CCN3C2)cc1=O] | (9S)-5-(1-methyl-2-oxo-1,2-dihydropyridin-4-yl)-N-(pyrazin-2-yl)-1,6,8-triazatricyclo[7.2.1.0^{2,7}]dodeca-2(7),3,5-triene-8-carboxamide | B | A |
| 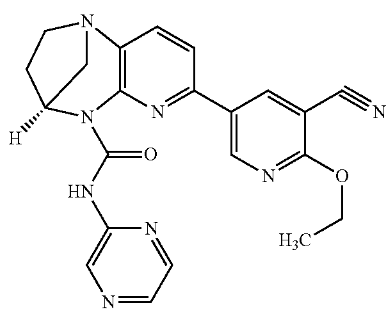 [SMILES: CCOc1ncc(-c2ccc3c(n2)N(C(=O)Nc2cnccn2)[C@H]2CCN3C2)cc1C#N] | (9S)-5-(5-cyano-6-ethoxypyridin-3-yl)-N-(pyrazin-2-yl)-1,6,8-triazatricyclo[7.2.1.0^{2,7}]dodeca-2(7),3,5-triene-8-carboxamide | C | B |
| 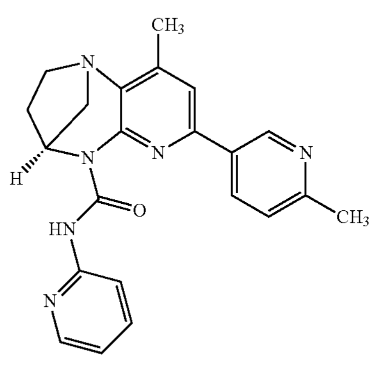 [SMILES: Cc1ccc(-c2cc(C)c3c(n2)N(C(=O)Nc2ccccn2)[C@H]2CCN3C2)cn1] | (9S)-3-methyl-5-(6-methylpyridin-3-yl)-N-(pyridin-2-yl)-1,6,8-triazatricyclo[7.2.1.0^{2,7}]dodeca-2,4,6-triene-8-carboxamide | B | A |

TABLE A-continued

Additional Representative Compounds

| Structure | Chemical Name | TRP Activity | TRP MAX RESP |
|---|---|---|---|
| 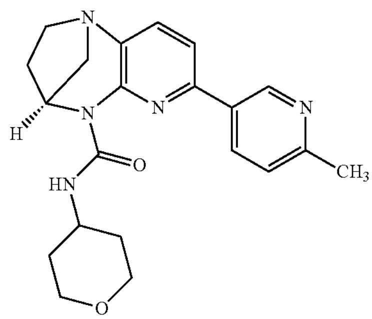 [SMILES: Cc1ccc(-c2ccc3c(n2)N(C(=O)NC2CCOCC2)[C@H]2CCN3C2)cn1] | (9S)-5-(6-methylpyridin-3-yl)-N-(oxan-4-yl)-1,6,8-triazatricyclo[7.2.1.0^{2,7}]dodeca-2(7),3,5-triene-8-carboxamide | C | B |
| 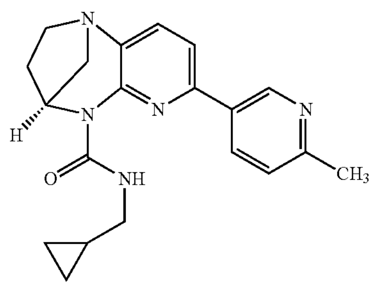 [SMILES: Cc1ccc(-c2ccc3c(n2)N(C(=O)NCC2CC2)[C@H]2CCN3C2)cn1] | (9S)-N-(cyclopropylmethyl)-5-(6-methylpyridin-3-yl)-1,6,8-triazatricyclo[7.2.1.0^{2,7}]dodeca-2,4,6-triene-8-carboxamide | B | A |
| 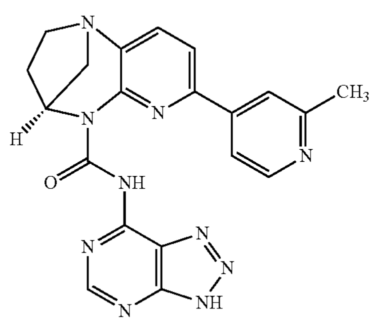 [SMILES: Cc1cc(-c2ccc3c(n2)N(C(=O)Nc2ncnc4[nH]nnc24)[C@H]2CCN3C2)ccn1] | (9S)-5-(2-methylpyridin-4-yl)-N-{3H-[1,2,3]triazolo[4,5-d]pyrimidin-7-yl}-1,6,8-triazatricyclo[7.2.1.0^{2,7}]dodeca-2,4,6-triene-8-carboxamide | C | B |
| 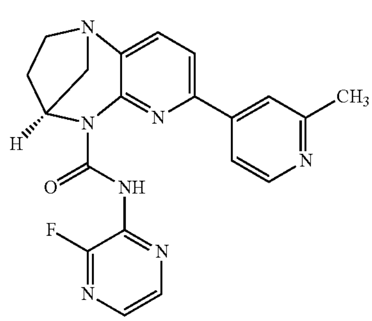 [SMILES: Cc1cc(-c2ccc3c(n2)N(C(=O)Nc2nccnc2F)[C@H]2CCN3C2)ccn1] | (9S)-N-(3-fluoropyrazin-2-yl)-5-(2-methylpyridin-4-yl)-1,6,8-triazatricyclo[7.2.1.0^{2,7}]dodeca-2,4,6-triene-8-carboxamide | B | A |

TABLE A-continued

Additional Representative Compounds

| Structure | Chemical Name | TRP Activity | TRP MAX RESP |
|---|---|---|---|
| ISOMER 2 | (9S)-N-(pyridin-2-yl)-5-[(3S)-3-(trifluoromethyl)pyrrolidin-1-yl]-1,6,8-triazatricyclo[7.2.1.0^{2,7}]dodeca-2(7),3,5-triene-8-carboxamide | B | A |
| 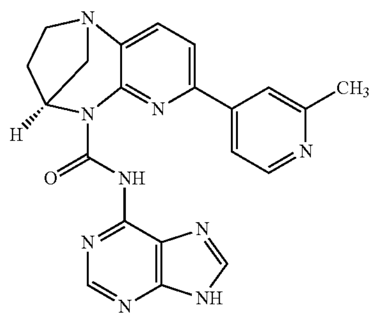 [SMILES: Cc1cc(-c2ccc3c(n2)N(C(=O)Nc2ncnc4[nH]cnc24)[C@H]2CCN3C2)ccn1] | (9S)-5-(2-methylpyridin-4-yl)-N-(9H-purin-6-yl)-1,6,8-triazatricyclo[7.2.1.0^{2,7}]dodeca-2,4,6-triene-8-carboxamide | B | A |
| 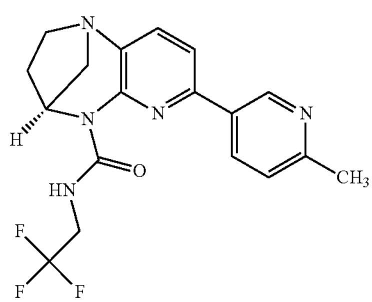 [SMILES: Cc1ccc(-c2ccc3c(n2)N(C(=O)NCC(F)(F)F)[C@H]2CCN3C2)cn1] | (9S)-5-(6-methylpyridin-3-yl)-N-(2,2,2-trifluoroethyl)-1,6,8-triazatricyclo[7.2.1.0^{2,7}]dodeca-2(7),3,5-triene-8-carboxamide | B | A |
| 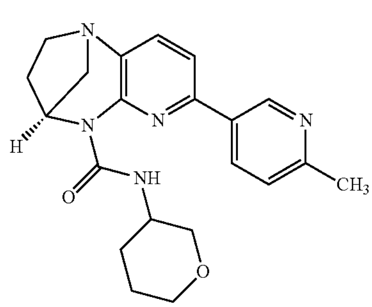 [SMILES: Cc1ccc(-c2ccc3c(n2)N(C(=O)NC2CCCOC2)[C@H]2CCN3C2)cn1] | (9S)-5-(6-methylpyridin-3-yl)-N-(oxan-3-yl)-1,6,8-triazatricyclo[7.2.1.0^{2,7}]dodeca-2(7),3,5-triene-8-carboxamide | C | B |

TABLE A-continued

Additional Representative Compounds

| Structure | Chemical Name | TRP Activity | TRP MAX RESP |
|---|---|---|---|
| 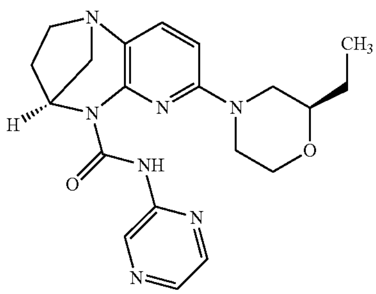 [SMILES: CC[C@@H]1CN(c2ccc3c(n2)N(C(=O)Nc2cnccn2)[C@H]2CCN3C2)CCO1] | (9S)-5-[(2R)-2-ethylmorpholin-4-yl]-N-(pyrazin-2-yl)-1,6,8-triazatricyclo[7.2.1.0^{2,7}]dodeca-2(7),3,5-triene-8-carboxamide | B | A |
| | (9S)-3-methyl-5-(6-methylpyridin-3-yl)-N-(pyridin-3-yl)-1,6,8-triazatricyclo[7.2.1.0^{2,7}]dodeca-2,4,6-triene-8-carboxamide | B | A |
| 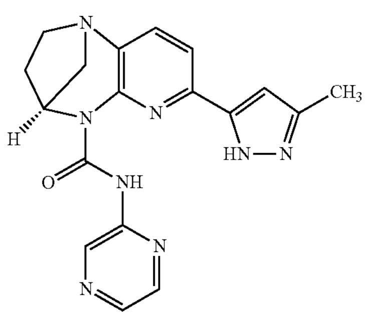 [SMILES: Cc1cc(-c2ccc3c(n2)N(C(=O)Nc2cnccn2)[C@H]2CCN3C2)[nH]n1] | (9S)-5-(3-methyl-1H-pyrazol-5-yl)-N-(pyrazin-2-yl)-1,6,8-triazatricyclo[7.2.1.0^{2,7}]dodeca-2(7),3,5-triene-8-carboxamide | B | A |
| 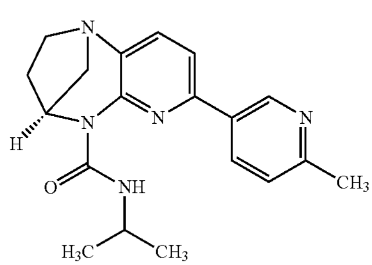 [SMILES: Cc1ccc(-c2ccc3c(n2)N(C(=O)NC(C)C)[C@H]2CCN3C2)cn1] | (9S)-5-(6-methylpyridin-3-yl)-N-(propan-2-yl)-1,6,8-triazatricyclo[7.2.1.0^{2,7}]dodeca-2,4,6-triene-8-carboxamide | B | A |

TABLE A-continued

Additional Representative Compounds

| Structure | Chemical Name | TRP Activity | TRP MAX RESP |
|---|---|---|---|
| 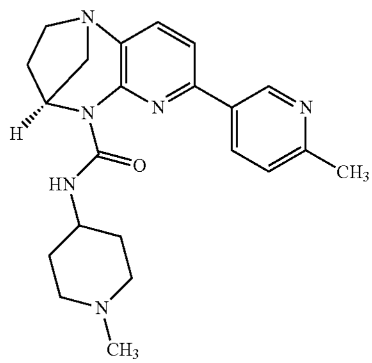 [SMILES: Cc1ccc(-c2ccc3c(n2)N(C(=O)NC2CCN(C)CC2)[C@H]2CCN3C2)cn1] | (9S)-N-(1-methylpiperidin-4-yl)-5-(6-methylpyridin-3-yl)-1,6,8-triazatricyclo[7.2.1.0^{2,7}]dodeca-2(7),3,5-triene-8-carboxamide | C | B |

In another aspect or embodiment, the present invention relates to a compound of Table 10 (i.e., additional representative compound examples) and at least one pharmaceutically acceptable carrier.

In another aspect, the present invention also relates to a pharmaceutical composition comprised of a compound of the present invention as defined herein (i.e., Formulas (I), (IIa), (IIb), (IIIa), (IIIb) and (IV), and which also include, but are not limited to compounds of Table 1 and Table 10, (i.e., additional representative compound examples) set forth herein), and additional active agent as defined in the present application.

In another aspect, the present invention relates to a pharmaceutical composition comprising a compound of the present invention and at least one pharmaceutically acceptable carrier.

In another aspect, the present invention relates to a pharmaceutical composition of the present invention further comprising an additional active agent.

In another aspect, the present invention relates to a method for treating insulin resistance, a metabolic syndrome, diabetes, or complications thereof, or for increasing insulin sensitivity in a subject, comprising administering a compound of the present invention to a subject in need thereof.

In another aspect, the present invention relates to a method for treating insulin resistance, a metabolic syndrome, diabetes, or complications thereof, or for increasing insulin sensitivity in a subject, comprising administering a pharmaceutical composition of the present invention to a subject in need thereof.

In another aspect, the present invention relates to a method of increasing sirtuin-1 activity in a cell comprising the step of contacting a cell with a compound of the present invention.

In another aspect, the present invention relates to a method of increasing sirtuin-1 activity in a cell comprising the step of contacting a cell with a pharmaceutical composition of the present invention.

In another aspect, the present invention relates to a method for treating metabolic dysfuntions comprising administering a compound or a pharmaceutically acceptable salt thereof of the present invention to a subject in need thereof.

In another aspect, the present invention relates to a method for treating metabolic dysfuntions comprising administering a pharmaceutical composition of the present invention to a subject in need thereof.

In another aspect, the present invention relates to a method for treating diseases or disorders resulting from diminished SIRT1 expression or activity, which comprises administering a compound or a pharmaceutically acceptable salt thereof of the present invention to a subject in need thereof.

In another aspect, the present invention relates to a method for treating diseases or disorders resulting from diminished SIRT1 expression or activity, which comprises administering a pharmaceutical composition of the present invention to a subject in need thereof.

In another aspect, the present invention relates to diseases or disorders resulting from diminished SIRT1 expression or activity are selected from, but not limited to aging or stress, diabetes, metabolic dysfunctions, neurodegenerative diseases, cardiovascular disease, cancer or inflammatory disease.

In another aspect, the present invention relates to diseases related to aging or stress, diabetes, metabolic dysfunctions, neurodegenerative diseases, cardiovascular disease, cance or inflammatory disease are selected from psoriasis, atopic dermatitis, acne, rosacea, inflammatory bowel disease, osteoporosis, sepsis, arthritis, COPD, systemic lupus erythematosus and ophthalmic inflammation.

In another aspect, the present invention relates to a method for treating psoriasis, which comprises administering a compound of the present invention to a subject in need thereof.

In another aspect, the present invention relates to a method for treating psoriasis, which comprises administering a pharmaceutical composition of the present invention to a subject in need thereof.

Example 107

(4S)—N-(pyridin-3-yl)-7-(4-(trifluoromethyl)piperidin-1-yl)-3,4-dihydro-1,4-methanopyrido[2,3-b][1,4]diazepine-5(2H)-carboxamide

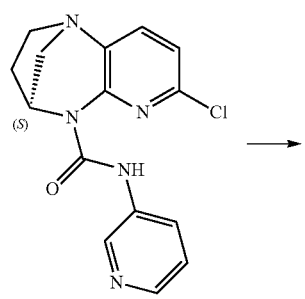

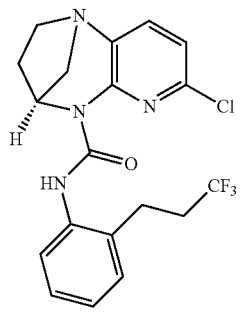

To a degassed solution of ((4S)-7-chloro-N-(pyridin-2-yl)-3,4-dihydro-1,4-methanopyrido[2,3-b][1,4]diazepine-5(2H)-carboxamide (700 mg, 2.217 mmol), 4-(trifluoromethyl)piperidine (679 mg, 4.43 mmol) in 1,4-Dioxane (20 mL) was added dicyclohexyl(2',4',6'-triisopropyl-[1,1'-biphenyl]-2-yl)phosphine (423 mg, 0.887 mmol), potassium carbonate (919 mg, 6.65 mmol) and palladium(II) acetate (100 mg, 0.443 mmol) subsequentially at 20° C. and the reaction mixture was stirred in a sealed tube at 90° C. for 16 hr. The reaction mixture was poured in to cold water (70 mL) and extracted with ethyl acetate (150 mL). The organics were separated and dried over anhydrous sodium sulphate, concentrated under reduced pressure to give the crude product. The crude product was added to a silica gel column and was eluted with 1% to 2% methanol in dichloro methane. Collected fractions to give 500 mg, It was again purified by GRACE reverse phase HPLC to give (4S)—N-(pyridin-3-yl)-7-(4-(trifluoromethyl)piperidin-1-yl)-3,4-dihydro-1,4-methanopyrido[2,3-b][1,4]diazepine-5(2H)-carboxamide (320 mg, 0.710 mmol, 32%). MS (ESI) calcd for $C_{21}H_{23}F_3N_6O$: 433.2.

ADDITIONAL NEW EXAMPLES

Example 108

Synthesis of (4S)-7-chloro-N-(2-(3,3,3-trifluoropropyl)phenyl)-3,4-dihydro-1,4-methano pyrido[2,3-b][1,4]diazepine-5(2H)-carboxamide

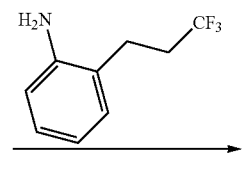

(4S)-7-chloro-2,3,4,5-tetrahydro-1,4-methanopyrido[2,3-b][1,4]diazepine (250 mg, 1.278 mmol) was dissolved in tetrahydrofuran (THF) (10 mL) stirred under nitrogen at room temperature were added triphosgene (190 mg, 0.639 mmol), TEA (0.534 mL, 3.83 mmol) sequentially. The reaction mixture was stirred for 30 min at room temperature. To this 2-(3, 3,3-trifluoropropyl) aniline (483 mg, 2.56 mmol) was added and stirred for 16 h at 80° C. in a sealed tube. The reaction mixture allowed to room temperature and quenched with 15 ml of water and extracted with 2×25 ml of ethyl acetate, organic layer was dried over sodium sulfate and concentrated under reduced pressure to obtain crude compound. The crude product was purified by column chromatography (silica-gel: 100-200 mesh) to afford (4S)-7-chloro-N-(2-(3,3,3-trifluoropropyl)phenyl)-3,4-dihydro-1,4-methanopyrido[2,3-b][1,4]diazepine-5(2H)-carboxamide (240 mg, 0.563 mmol, 44.1% yield) as a white solid, ($R_f$ value: 0.35, 10% Methanol in DCM), LCMS (m/z): 411.16 $[M+H]^+$.

$^1$H NMR (400 MHz, DMSO-$d_6$): δ ppm 11.49 (s, 1H), 7.79 (dd, J=8.00, 0.99 Hz, 1H), 7.61 (d, J=8.11 Hz, 1H), 7.35-7.31 (m, 1H), 7.24-7.29 (m, 1H), 7.17-7.09 (m, 2H), 5.44 (dd, J=5.92, 3.07 Hz, 1H), 3.21-2.90 (m, 6H), 2.66-2.53 (m, 2H), 2.20 (dddd, J=13.67, 9.95, 6.08, 3.62 Hz, 1H), 1.91 (dt, J=13.70, 6.96 Hz, 1H).

Example 109

Synthesis of (4S)—N-(pyridin-2-yl)-7-(4-(trifluoromethyl) piperidin-1-yl)-3,4-dihydro-1,4-methanopyrido[2,3-b][1,4]diazepine-5(2H)-carboxamide

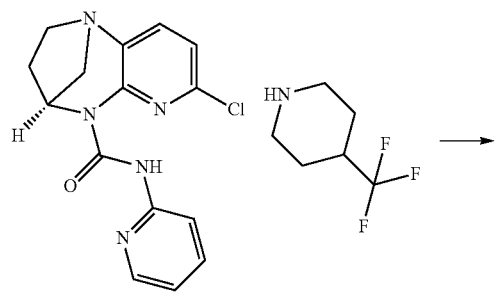

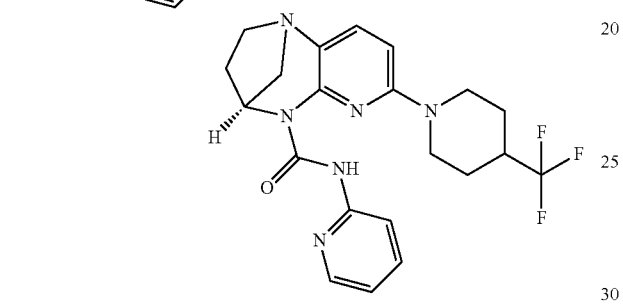

To a de-gassed solution of ((4S)-7-chloro-N-(pyridin-2-yl)-3,4-dihydro-1,4-methanopyrido[2,3-b][1,4]diazepine-5(2H)-carboxamide (700 mg, 2.217 mmol), 4-(trifluoromethyl)piperidine (679 mg, 4.43 mmol) in 1,4-dioxane (20 mL) were added dicyclohexyl(2',4',6'-triisopropyl-[1,1'-biphenyl]-2-yl)phosphine (423 mg, 0.887 mmol), potassium carbonate (919 mg, 6.65 mmol) and palladium(II) acetate (100 mg, 0.443 mmol) at 25° C. The reaction mixture was stirred at 90° C. for 16 h in sealed tube. Allowed to cool to room temperature and the mixture was poured in to cold water (70 mL) and extracted with ethyl acetate (3×50 mL). The combined organic layer was dried over anhydrous $Na_2SO_4$ and concentrated under reduced pressure to obtain the crude product. The crude mixture was purified by flash column chromatography (silica-gel; 100-200 mesh, eluted with 1 to 2% methanol in dichloromethane) to afford (4S)—N-(pyridin-2-yl)-7-(4-(trifluoromethyl) piperidin-1-yl)-3,4-dihydro-1,4-methanopyrido[2,3-b][1,4]diazepine-5(2H)-carboxamide (320 mg, 32% yield) as a white solid (TLC: eluent; ethyl acetate, $R_f$=0.4), LCMS (m/z): 433.22 [M+H]$^+$.

$^1$H NMR (400 MHz, DMSO-$d_6$): δ ppm 13.15 (s, 1H), 8.34-8.18 (m, 1H), 8.09 (dt, J=8.39, 0.96 Hz, 1H), 7.77 (ddd, J=8.55, 7.13, 1.86 Hz, 1H), 7.36 (d, J=8.77 Hz, 1H) 7.04 (ddd, J=7.29, 4.88, 0.99 Hz, 1H) 6.51 (d, J=8.55 Hz, 1H) 5.43 (dd, J=5.92, 3.07 Hz, 1H) 4.39 (d, J=12.93 Hz, 2H), 3.17-3.04 (m, 1H), 3.02-2.76 (m, 5H), 2.72-2.52 (m, 1H), 2.25-2.04 (m, 1H), 1.96-1.76 (m, 3H), 1.57-1.39 (m, 2H).

Example 110

Synthesis of (4S)—N-(pyridin-2-yl)-7-((R)-3-(trifluoromethyl) piperidin-1-yl)-3,4-dihydro-1,4-methanopyrido[2,3-b][1,4]diazepine-5(2H)-carboxamide

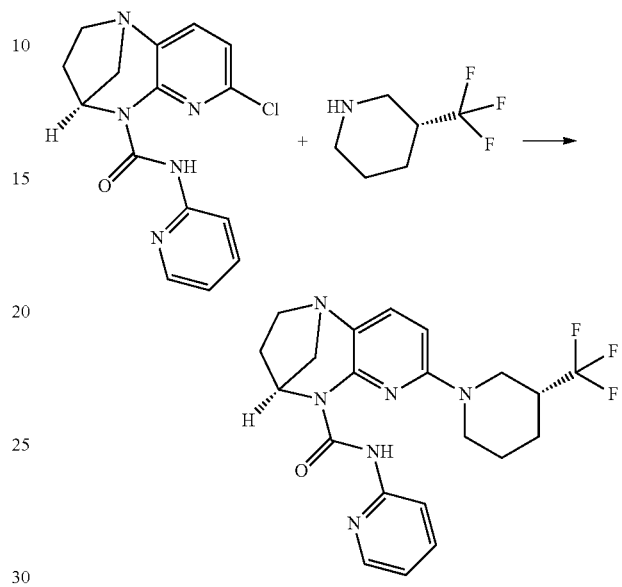

To a de-gassed solution of (4S)-7-chloro-N-(pyridin-2-yl)-3,4-dihydro-1,4-methanopyrido[2,3-b][1,4]diazepine-5(2H)-carboxamide (750 mg, 2.375 mmol) and (70:30-R/S)-3-(trifluoromethyl)piperidine (728 mg, 4.75 mmol) in 1,4-dioxane (20 mL) were added potassium carbonate (985 mg, 7.13 mmol) and palladium(II) acetate (107 mg, 0.475 mmol) at RT. The reaction mixture was stirred at 90° C. for 16 h in sealed tube. The reaction was allowed to cool down to room temperature and poured into cold water (70 mL) and extracted with ethyl acetate (3×50 mL). The combined organic layer was dried over anhydrous $Na_2SO_4$, concentrated under reduced pressure to obtain the crude product. The crude mixture was purified by flash column chromatography (silica-gel: 100-200 mesh, eluted with 1% to 2% methanol in dichloromethane) to afford (70:30, R:S) diastereometic mixture of (4S)—N-(pyridin-2-yl)-7-((R/S)-3-(trifluoromethyl) piperidin-1-yl)-3,4-dihydro-1,4-methanopyrido[2,3-b][1,4]diazepine-5(2H)-carboxamide (310 mg, yield 29.6%) as an off white solid (TLC: eluent, 100% ethyl acetate, $R_f$: 0.4), LCMS (m/z): 433.2 [M+H]$^+$.

$^1$H NMR (400 MHz, DMSO-$d_6$): δ ppm 13.10-12.94 (m, 1H), 8.22 (d, J=5.15 Hz, 1H), 8.15-7.98 (m, 1H), 7.76 (t, J=7.48 Hz, 1H), 7.45-7.28 (m, 1H), 7.04 (ddd, J=7.34, 4.93, 0.88 Hz, 1H), 6.54 (d, J=8.55 Hz, 1H), 5.48-5.32 (m, 1H), 4.35-4.12 (m, 2H), -3.12-2.89 (m, 5H), 2.88-2.78 (m, 1H), 2.61-2.52 (m, 1H), 2.25-2.04 (m, 1H), 2.04-1.92 (m, 1H), 1.90-1.74 (m, 2H), 1.71-1.46 (m, 2H).

Example 111

Synthesis of (4S)—N-(pyridin-2-yl)-7-((S)-3-(trifluoromethyl) piperidin-1-yl)-3,4-dihydro-1,4-methanopyrido[2,3-b][1,4]diazepine-5(2H)-carboxamide

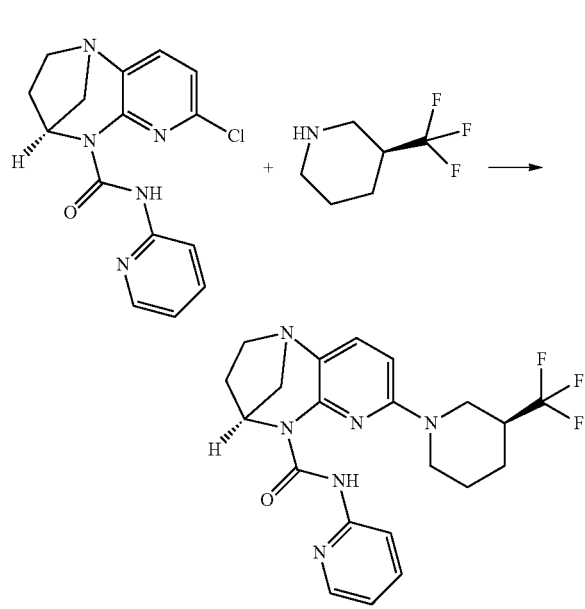

To a de-gassed solution of (4S)-7-chloro-N-(pyridin-2-yl)-3,4-dihydro-1,4-methanopyrido[2,3-b][1,4]diazepine-5(2H)-carboxamide (550 mg, 1.742 mmol) (33:66-R/S)-3-(trifluoromethyl) piperidine (534 mg, 3.48 mmol) in 1,4-dioxane (20 mL) were added potassium carbonate (722 mg, 5.23 mmol), dicyclohexyl(2',4',6'-triisopropyl-[1,1'-biphenyl]-2-yl)phosphine (332 mg, 0.697 mmol) and palladium (II) acetate (78 mg, 0.348 mmol) at RT. The reaction mixture was stirred at 90° C. for 16 h in sealed tube. The reaction was cooled to room temperature and poured into cold water (70 mL). The crude product was extracted with ethyl acetate (3×50 mL). The combined organic layer was dried over anhydrous $Na_2SO_4$, filtered, concentrated under reduced pressure to obtain the crude product. The crude mixture was purified by flash column chromatography (silica-gel: 100-200 mesh, eluted with 1 to 2% methanol in dichloromethane) to afford (33:67, S:R) diastereometic mixture of (4S)—N-(pyridin-2-yl)-7-((S/R)-3-(trifluoromethyl) piperidin-1-yl)-3,4-dihydro-1,4-methanopyrido[2,3-b][1,4]diazepine-5(2H)-carboxamide (250 mg, 33.2% yield) as a white solid (TLC: eluent, 100% ethyl acetate, $R_f$ 0.4), LCMS (m/z): 433.2 $[M+H]^+$.

$^1$H NMR (400 MHz, DMSO-$d_6$): δ ppm 13.06-12.99 (m, 1H), 8.22 (d, J=5.01 Hz, 1H), 8.07 (dt, J=8.33, 0.88 Hz, 1H), 7.76 (ddd, J=8.55, 7.13, 1.86 Hz, 1H), 7.47-7.29 (m, 1H), 7.04 (ddd, J=7.29, 4.88, 0.99 Hz, 1H), 6.54 (d, J=8.55 Hz, 1H), 5.51-5.36 (m, 1H), 4.37-4.15 (m, 2H), 3.12-2.80 (m, 6H), 2.60-2.52 (m, 1H), 2.25-2.04 (m, 1H), 2.04-1.93 (m, 1H), 1.90-1.74 (m, 2H), 1.72-1.48 (m, 2H).

Example 112

Synthesis of (4S)—N-(pyridin-2-yl)-7-((R)-2-(trifluoromethyl)pyrrolidin-1-yl)-3,4-dihydro-1,4-methanopyrido[2,3-b][1,4]diazepine-5(2H)-carboxamide

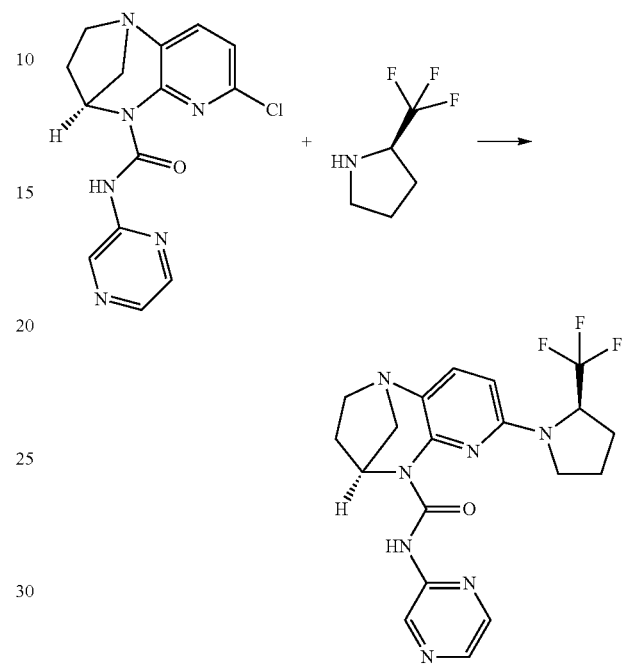

To a de-gassed solution of (4S)-7-chloro-N-(pyridin-2-yl)-3,4-dihydro-1,4-methanopyrido[2,3-b][1,4]diazepine-5(2H)-carboxamide (700 mg, 2.217 mmol), (R)-2-(trifluoromethyl)pyrrolidine (617 mg, 4.43 mmol) in 1,4-dioxane (20 mL) were added dicyclohexyl(2',4',6'-triisopropyl-[1,1'-biphenyl]-2-yl)phosphine (423 mg, 0.887 mmol), potassium carbonate (919 mg, 6.65 mmol) and palladium(II) acetate (100 mg, 0.443 mmol) at RT. The reaction mixture was heated at 90° C. for 16 h in sealed tube. The reaction mixture was poured in to cold water (70 mL) and extracted with ethyl acetate (3×50 mL). The combined organic layer was dried over anhydrous sodium sulfate and concentrated under reduced pressure to obtain crude compound. The crude mixture was purified by flash column chromatography (silica gel: 100-200 mesh, eluted with 1 to 2% methanol in dichloromethane) to afford (4S)—N-(pyridin-2-yl)-7-((R)-2-(trifluoromethyl)pyrrolidin-1-yl)-3,4-dihydro-1,4-methanopyrido[2,3-b][1,4]diazepine-5(2H)-carboxamide (220 mg, 0.52 mmol, 32% yield) as an off white solid (TLC: 100% ethyl acetate, $R_f$=0.4), LCMS (m/z): 419.21 $[M+H]^+$.

$^1$H NMR (400 MHz, DMSO-$d_6$): δ ppm 13.16 (s, 1H), 8.20 (d, J=6.33, 1H), 8.06 (d, J=8.33 Hz, 1H), 7.77 (td, J=7.84, 1.86 Hz, 1H), 7.40 (d, J=8.55 Hz, 1H), 7.05 (ddd, J=7.29, 4.88, 0.99 Hz, 1H), 6.36 (d, J=8.77 Hz, 1H), 5.40 (dd, J=5.92, 3.07 Hz, 1H), 5.28-5.06 (m, 1H), 3.84 (dt, J=10.14, 5.12 Hz, 1H), 3.65-3.36 (m, 1H), 3.17-2.91 (m, 2H), 2.90-2.80 (m, 2H), 2.25-2.04 (m, 5H), 1.84 (dt, J=13.65, 7.10 Hz, 1H).

Example 113

Synthesis of (4S)—N-(pyridin-2-yl)-7-(2-(trifluoromethyl)morpholino)-3,4-dihydro-1,4-methanopyrido[2,3-b][1,4]diazepine-5(2H)-carboxamide

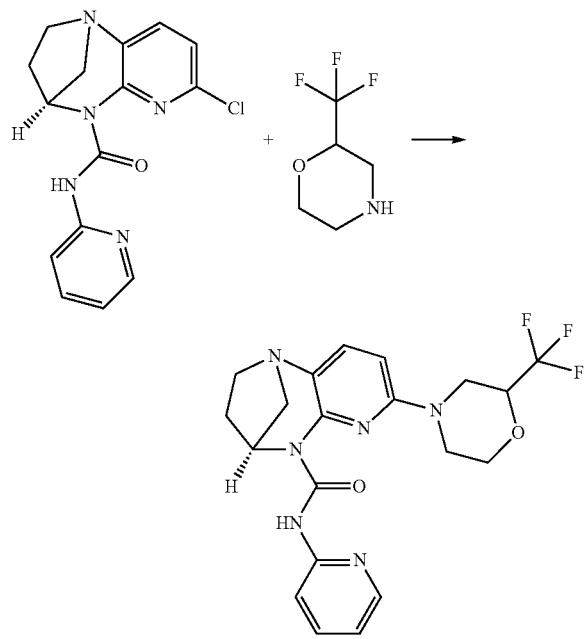

To a de-gassed solution of (4S)-7-chloro-N-(pyridin-2-yl)-3,4-dihydro-1,4-methanopyrido[2,3-b][1,4]diazepine-5(2H)-carboxamide (700 mg, 2.217 mmol), 2-(trifluoromethyl)morpholine (688 mg, 4.43 mmol) in 1,4-dioxane (20 mL) were added dicyclohexyl(2',4',6'-triisopropyl-[1,1'-biphenyl]-2-yl)phosphine (423 mg, 0.887 mmol), potassium carbonate (919 mg, 6.65 mmol) and palladium(II) acetate (100 mg, 0.443 mmol) at RT. The reaction mixture was heated at 90° C. for 16 h in sealed tube and cooled to RT then poured in to cold water (70 mL) and extracted with ethyl acetate (3×50 mL). The combined organic layer was dried over anhydrous sodium sulfate and concentrated under reduced pressure to obtain the crude product. The crude mixture was purified by flash column chromatography (silica-gel: 100-200 mesh, eluted with 1 to 2% of methanol in dichloromethane) to afford (4S)—N-(pyridin-2-yl)-7-(2-(trifluoromethyl)morpholino)-3,4-dihydro-1,4-methanopyrido[2,3-b][1,4]diazepine-5(2H)-carboxamide (300 mg, 0.69 mmol, 46% yield) as an off white solid (TLC: 100% ethyl acetate, $R_f$=0.4), LCMS (m/z): 435.20 [M+H]$^+$.

$^1$H NMR (400 MHz, DMSO-$d_6$): δ ppm 12.99 (d, J=4.82 Hz, 1H), 8.20 (dt, J=4.82, 0.88 Hz, 1H), 8.07 (dd, J=8.44, 0.77 Hz, 1H), 7.77 (td, J=7.84, 1.86 Hz, 1H), 7.43 (d, J=8.55 Hz, 1H), 7.05 (ddd, J=7.29, 4.88, 0.77 Hz, 1H), 6.62 (d, J=8.55 Hz, 1H), 5.44 (ddd, J=9.98, 6.25, 3.29 Hz, 1H), 4.34 (dd, J=7.13, 3.40 Hz, 1H), 4.25 (d, J=12.28 Hz, 1H), 4.14 (dd, J=11.62, 1.75 Hz, 1H), 4.10-3.94 (m, 1H), 3.87-3.67 (m, 1H), 3.15-2.91 (m, 6H), 2.30-2.14 (m, 1H), 1.72-1.65 (m, 1H).

Example 114

Synthesis of (4S)—N-(4-((S)-2,3-dihydroxypropoxy)pyridin-2-yl)-7-(3-(trifluoromethyl)phenyl)-3,4-dihydro-1,4-methanopyrido[2,3-b][1,4]diazepine-5(2H)-carboxamide

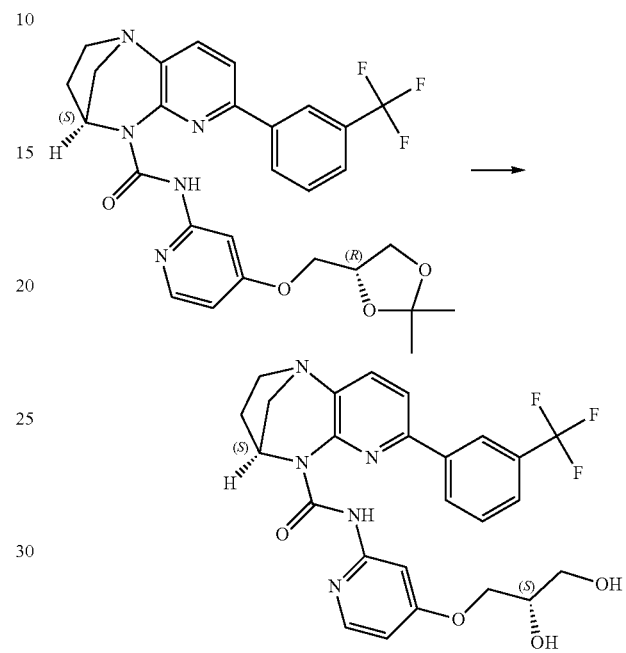

To a stirred solution of (4S)—N-(4-(((R)-2,2-dimethyl-1,3-dioxolan-4-yl)methoxy)pyridin-2-yl)-7-(3-(trifluoromethyl)phenyl)-3,4-dihydro-1,4-methanopyrido[2,3-b][1,4]diazepine-5(2H)-carboxamide (450 mg, 0.810 mmol) in dichloromethane (12 mL) and water (1.12 mL) at 0° C. was added 4.0 M hydrochloric acid in dioxane (1.68 mL, 0.810 mmol) dropwise over a period of 5 min. Then the reaction mixture was stirred at 30° C. for 3h and evaporated the solvent. The reaction mixture was neutralization with sodium bicarbonate solution and extracted with ethyl acetate (3×50 mL) then the combined organic layers was washed with water, brine solution & dried over sodium sulfate and evaporated to give crude as brown solid (TLC eluent: 5% MeOH in DCM: $R_f$=0.2; UV active). The crude compound was washed with n-pentane to afford pure (4S)—N-(4-((S)-2,3-dihydroxypropoxy)pyridin-2-yl)-7-(3-(trifluoro methyl)phenyl)-3,4-dihydro-1,4-methanopyrido[2,3-b][1,4]diazepine-5(2H)-carboxamide (340 mg, 0.635 mmol, 78.0% yield) as white solid, LCMS (m/z): 516.3 [M+H]$^+$.

$^1$H NMR (400 MHz, DMSO-$d_6$): δ ppm 13.42 (s, 1H) 8.54-8.44 (m, 2H) 8.10 (d, J=5.92 Hz, 1H) 7.85-7.81 (m, 1H) 7.80-7.68 (m, 4H) 6.71 (dd, J=5.70, 2.41 Hz, 1H) 5.51 (dd, J=5.92, 3.07 Hz, 1H) 5.01 (d, J=5.26 Hz, 1H) 4.70 (t, J=5.70 Hz, 1H) 4.11 (dd, J=9.76, 3.84 Hz, 1H) 3.96 (dd, J=9.87, 6.36 Hz, 1H) 3.87-3.79 (m, 1H) 3.51-3.42 (m, 2H) 3.26-3.17 (m, 1H) 3.15-3.06 (m, 2H) 2.96 (dd, J=12.06, 3.29 Hz, 1H) 2.25 (dddd, J=13.65, 9.92, 6.14, 3.62 Hz, 1H) 1.95 (dt, J=13.81, 6.91 Hz, 1H).

Example 115

Synthesis of (4S)—N-(4-((R)-2,3-dihydroxypropoxy)pyridin-2-yl)-7-(3-(trifluoromethyl)phenyl)-3,4-dihydro-1,4-methanopyrido[2,3-b][1,4]diazepine-5(2H)-carboxamide

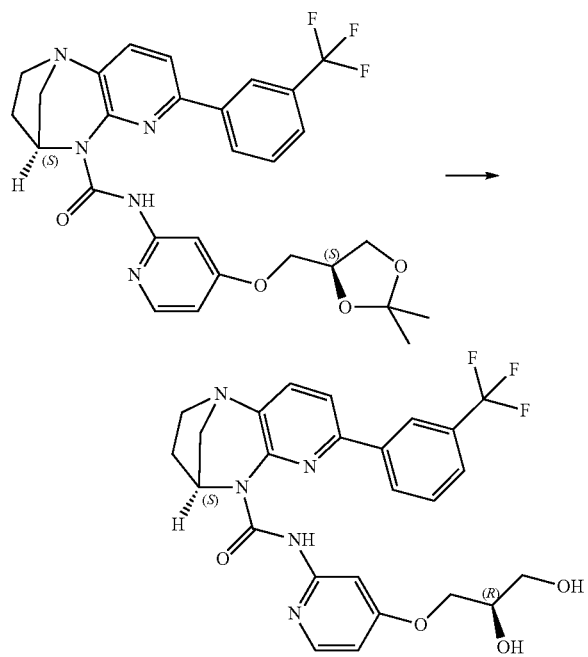

To a solution of (4S)—N-(4-(((S)-2,2-dimethyl-1,3-dioxolan-4-yl)methoxy)pyridin-2-yl)-7-(3-(trifluoromethyl)phenyl)-3,4-dihydro-1,4-methanopyrido[2,3-b][1,4]diazepine-5 (2H)-carboxamide (500 mg, 0.900 mmol), in dichloromethane (12.5 mL) and water (1.25 ml) stirred under nitrogen at 0° C. was added 4.0 M hydrochloric acid in dioxane (2 mL, 0.900 mmol) in one charge over 1 min. The reaction mixture was stirred at 30° C. for 3 h and evaporated the solvent. The reaction mixture was neutralized with sodium bi carbonate solution and extracted with ethyl acetate (3×50 mL). The combined organic layer was washed with water, brine solution & dried over anhydrous sodium sulfate and evaporated to give crude as brown solid (TLC eluent: 5% MeOH in DCM: $R_f$=0.2; UV active). The crude compound was washed with n-pentane to afford pure (4S)—N-(4-((R)-2,3-dihydroxypropoxy)pyridin-2-yl)-7-(3-(trifluoromethyl)phenyl)-3,4-dihydro-1,4-methanopyrido[2,3-b][1,4]diazepine-5(2H)-carboxamide (340 mg, 0.612 mmol 68.0% yield) as a white color solid, LCMS (m/z): 516.2 [M+H]$^+$.

$^1$H NMR (400 MHz, DMSO-d$_6$): δ ppm 13.42 (s, 1H) 8.58-8.44 (m, 2H) 8.10 (d, J=5.70 Hz, 1H) 7.85-7.68 (m, 5H) 6.71 (dd, J=5.81, 2.30 Hz, 1H) 5.52 (dd, J=5.70, 3.07 Hz, 1H) 5.01 (d, J=5.26 Hz, 1H) 4.70 (t, J=5.59 Hz, 1H) 4.11 (dd, J=9.76, 3.84 Hz, 1H) 3.96 (dd, J=9.76, 6.25 Hz, 1H) 3.87-3.79 (m, 1H) 3.50-3.43 (m, 2H) 3.27-3.17 (m, 1H) 3.16-3.05 (m, 2H) 2.96 (dd, J=12.06, 3.07 Hz, 1H) 2.30-2.20 (m, 1H) 1.95 (dt, J=13.92, 7.07 Hz, 1H).

Example 116

Synthesis of (4S)—N-(2-(((R)-tetrahydrofuran-3-yl)oxy)pyrimidin-4-yl)-7-(3-(trifluoromethyl)phenyl)-3,4-dihydro-1,4-methanopyrido[2,3-b][1,4]diazepine-5(2H)-carboxamide

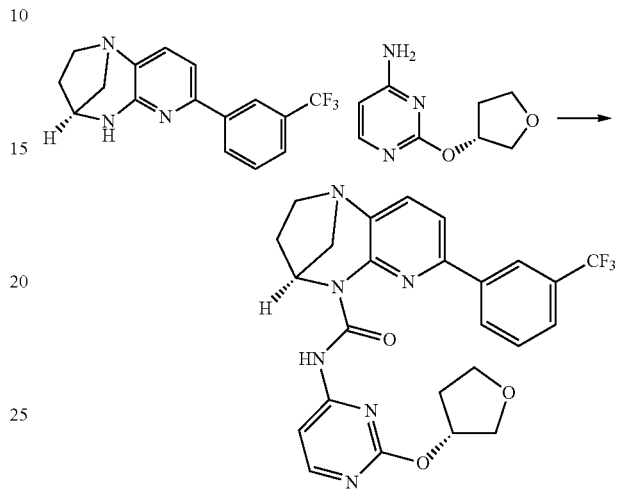

To a stirred solution of (4S)-7-(3-(trifluoromethyl)phenyl)-2,3,4,5-tetrahydro-1,4-methanopyrido[2,3-b][1,4]diazepine (600 mg, 1.965 mmol) in THF (20 mL) were added triethylamine (0.822 mL, 5.90 mmol) and triphosgene (292 mg, 0.983 mmol) at 30° C. and stirred at same temperature for 1 h. Then (R)-2-((tetrahydrofuran-3-yl)oxy)pyrimidin-4-amine (1068 mg, 5.90 mmol) was added at 30° C. and reaction was heated at 70° C. for 16 h. The reaction allowed to RT and solvent was evaporated under reduced pressure, the obtained residue was diluted with water (15 ml) and extracted with DCM (2×20 ml). The combined organic layer was washed with water, brine and dried over anhydrous sodium sulfate. The organic solvent was evaporated under reduced pressure to give crude product. The crude mixture was purified by prep HPLC (Formic acid in water and acetonitrile 30%) to afford (4S)—N-(2-(((R)-tetrahydrofuran-3-yl)oxy)pyrimidin-4-yl)-7-(3-(trifluoromethyl)phenyl)-3,4-dihydro-1,4-methanopyrido[2,3-b][1,4]diazepine-5(2H)-carboxamide (310 mg, 0.605 mmol, 30.6% yield) as an off white solid. (TLC: $R_f$=0.25, 10% MeOH in EtOAc), LCMS (m/z): 513.26 [M+H]$^+$.

$^1$H NMR (400 MHz, DMSO-d$_6$): δ ppm 13.61 (s, 1H), 8.50 (d, J=7.49 Hz, 1H), 8.45 (d, J=5.62 Hz, 1H), 8.25 (s, 1H), 7.87 (d, J=7.67 Hz, 1H), 7.81-7.68 (m, 4H), 5.47 (dd, J=5.92, 3.07 Hz, 1H), 5.32 (ddt, J=6.49, 4.36, 2.14, 2.14 Hz, 1H), 3.91-3.76 (m, 1H), 3.76-3.59 (m, 3H), 3.28-3.05 (m, 3H), 2.96 (dd, J=12.06, 3.29 Hz, 1H), 2.38-2.15 (m, 1H), 2.14-1.88 (m, 3H).

Example 117

Synthesis of (4S)—N-(pyridin-2-yl)-7-((S)-2-(trifluoromethyl)pyrrolidin-1-yl)-3,4-dihydro-1,4-methanopyrido[2,3-b][1,4]diazepine-5(2H)-carboxamide

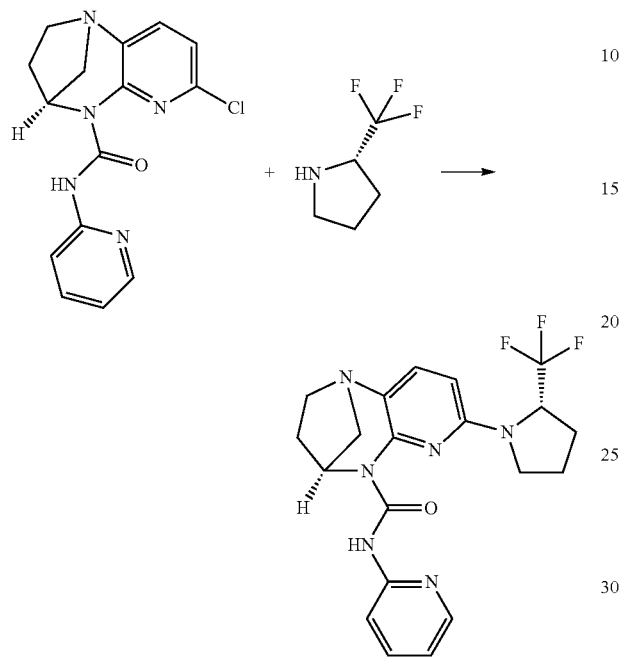

To a de-gassed solution of (4S)-7-chloro-N-(pyridin-2-yl)-3,4-dihydro-1,4-methanopyrido[2,3-b][1,4]diazepine-5(2H)-carboxamide (700 mg, 2.217 mmol), (S)-2-(trifluoromethyl)pyrrolidine (617 mg, 4.43 mmol) in 1,4-dioxane (20 mL) were added dicyclohexyl(2',4',6'-triisopropyl-[1,1'-biphenyl]-2-yl)phosphine (423 mg, 0.887 mmol) and palladium(II) acetate (100 mg, 0.443 mmol) at 25° C. The reaction mixture was heated at 90° C. for 16 h in sealed tube. The reaction mixture was poured in to cold water (70 mL) and extracted with ethyl acetate (3×50 mL). The combined organic layer was dried over anhydrous sodium sulfate and concentrated under reduced pressure to obtain the crude product. The crude mixture was purified by flash column chromatography (silica gel: 100-200 mesh, eluted with 1 to 2% of MeOH in DCM) to afford (4S)—N-(pyridin-2-yl)-7-((S)-2-(trifluoromethyl)pyrrolidin-1-yl)-3,4-dihydro-1,4-methanopyrido[2,3-b][1,4]diazepine-5(2H)-carboxamide (250 mg, 0.598 mmol, 35% yield) as a white solid (TLC: 100% ethyl acetate, $R_f$=0.4), LCMS (m/z): 419.18 [M+H]$^+$.

$^1$H NMR (400 MHz, DMSO-d$_6$): δ ppm 13.13 (s, 1H), 8.30-8.18 (d, J=7.2, 1H), 8.18-7.96 (d, J=8.40, 1H), 7.77 (ddd, J=8.55, 7.13, 1.86 Hz, 1H), 7.41 (d, J=8.55 Hz, 1H), 7.04 (ddd, J=7.23, 4.82, 1.10 Hz, 1H), 6.38 (d, J=8.55 Hz, 1H), 5.48 (dd, J=6.03, 3.18 Hz, 1H), 5.12-5.01 (m, 1H), 3.84 (m, 1H), 3.49 (q, J=9.65, J=5.70 Hz, 1H), 3.04-2.90 (m, 4H), 2.33-2.12 (m, 5H), 1.72-1.80 (m, 1H).

Example 118

Synthesis of (9S)—N-(pyridin-2-yl)-2-((S)-2-(trifluoromethyl)pyrrolidin-1-yl)-8,9-dihydro-6H-5,9-methanopyrido[2,3-b][1,4]diazocine-10(7H)-carboxamide

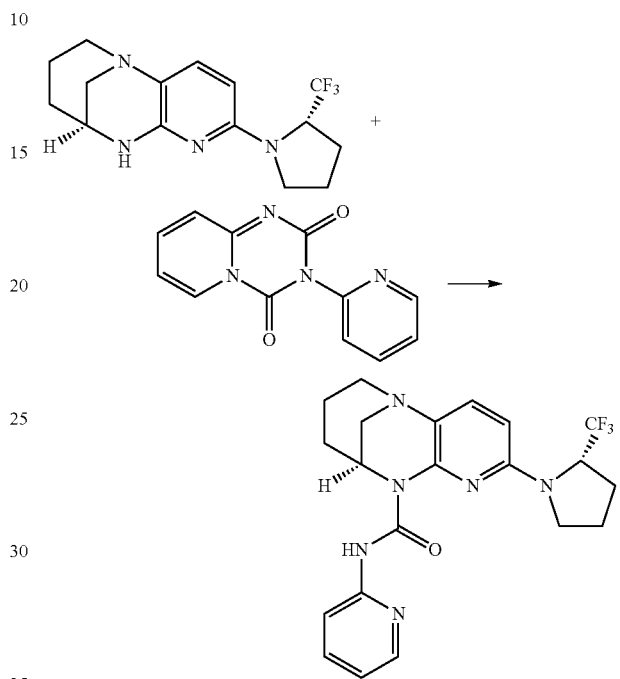

NaH (0.254 g, 10.57 mmol was added to a stirred solution of of (9S)-2-((S)-2-(trifluoromethyl)pyrrolidin-1-yl)-7,8,9,10-tetrahydro-6H-5,9-methanopyrido[2,3-b][1,4]diazocine (0.550 g, 1.761 mmol) in Tetrahydrofuran (THF) (30 mL) stirred under nitrogen at room temp. The reaction mixture was stirred at room temp for 30 minutes. Then 3-(pyridin-2-yl)-2H-pyrido[1,2-a][1,3,5]triazine-2,4(3H)-dione (0.635 g, 2.64 mmol) was added at room temp. Then reaction mixture was stirred at 65° C. for 24 hr. The reaction mixture was cooled to 28° C. and was partitioned between water (10 mL) and EtOAc (25 mL). Organic layer was separated and was dried over anhydrous Na$_2$SO$_4$, filtered and filtrate was evaporated to give crude as brown solid (TLC eluent: 100% EtOAc: $R_f$-0.3; UV active). The crude was purified by column chromatography using (100-200 mesh) silica gel and was eluted with 75-80% EtOAc in Hexane to afford pure (9S)—N-(pyridin-2-yl)-2-((S)-2-(trifluoromethyl)pyrrolidin-1-yl)-8,9-dihydro-6H-5,9-methanopyrido[2,3-b][1,4]diazocine-10(7H)-carboxamide (0.275 g, 0.631 mmol, 35.8% yield) as off-white solid, LCMS (m/z): 433.2 [M+H]$^+$.

$^1$H NMR (400 MHz, DMSO-d$_6$): δ ppm 13.60 (s, 1H), 8.20-8.29 (m, 1H), 8.09 (dt, J=8.33, 0.88 Hz, 1H), 7.72-7.81 (m, 1H), 7.37 (d, J=8.55 Hz, 1H), 7.05 (ddd, J=7.29, 4.88, 0.99 Hz, 1H), 6.45 (d, J=8.55 Hz, 1H), 5.11-5.19 (m, 1H), 4.74 (br s, 1H), 3.91 (dt, J=10.19, 5.21 Hz, 1H), 3.50-3.62 (m, 1H), 3.27 (d, J=1.75 Hz, 1H), 3.11-3.22 (m, 1H), 3.01-3.08 (m, 1H), 2.81 (br d, J=13.37 Hz, 1H), 2.07-2.28 (m, 4H), 1.94-2.02 (m, 1H), 1.81-1.92 (m, 1H), 1.21-1.40 (m, 2H)

Example 119

Synthesis of (9S)—N-(5-fluoropyridin-3-yl)-2-(2-(trifluoromethyl)pyridin-4-yl)-8,9-dihydro-6H-5,9-methanopyrido[2,3-b][1,4]diazocine-10(7H)-carboxamide

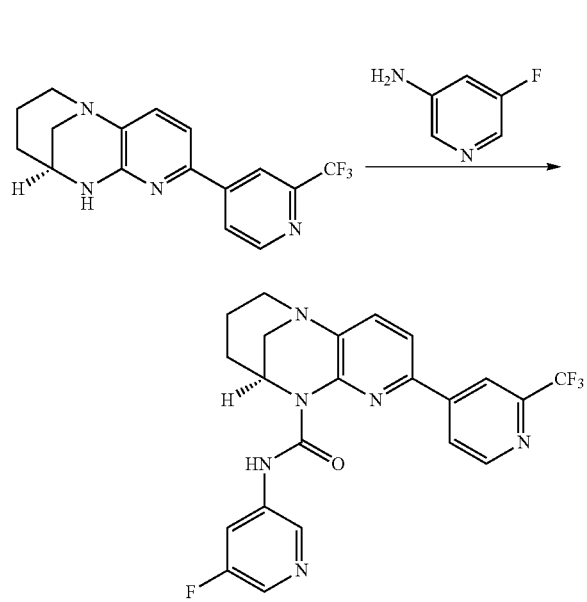

To a stirred solution of (9S)-2-(2-(trifluoromethyl)pyridin-4-yl)-7,8,9,10-tetrahydro-6H-5,9-methanopyrido[2,3-b][1,4]diazocine (500 mg, 1.561 mmol) in THF (15 mL) were added triethylamine (0.653 mL, 4.68 mmol) and triphosgene (232 mg, 0.780 mmol) at 30° C. and stirred at room temperature for 1 h. Then 5-fluoropyridin-3-amine (525 mg, 4.68 mmol) was added at 30° C. and reaction was heated at 70° C. for 16 h. The THF evaporated under reduced pressure and the obtained residue was diluted with water and extracted with $CH_2Cl_2$ (3×50 mL). The combined organic layer was washed with water, brine, dried over $Na_2SO_4$ and solvent was evaporated under reduced pressure to obtain the crude compound and it was purified by flash column chromatography (silica-gel: 100-200 mesh, eluent: 3% MeOH in DCM) to afford (9S)—N-(5-fluoropyridin-3-yl)-2-(2-(trifluoromethyl)pyridin-4-yl)-8,9-dihydro-6H-5,9-methanopyrido[2,3-b][1,4]diazocine-10(7H)-carboxamide (200 mg, 0.4366 mmol, 35% yield) as an off-white solid (TLC: $R_f$=0.3, 10% MeOH in EtOAc), LCMS (m/z): 459.25 $[M+H]^+$.

$^1$H NMR (400 MHz, DMSO-$d_6$): δ ppm 13.19 (s, 1H), 8.93 (d, J=5.04 Hz, 1H), 8.47 (s, 1H), 8.37 (s, 1H), 8.33-8.21 (m, 2H), 8.03 (d, J=11.18 Hz, 1H), 7.88 (d, J=8.11 Hz, 1H), 7.78 (d, J=8.11 Hz, 1H), 4.83 (s, 1H), 3.43 (d, J=12.06 Hz, 1H), 3.25 (s, 2H), 2.90 (d, J=13.81 Hz, 1H), 2.11-1.84 (m, 2H), 1.33 (s, 2H).

Example 120

Synthesis of (9S)—N-(pyrimidin-5-yl)-2-(5-(trifluoromethyl)pyridin-3-yl)-8,9-dihydro-6H-5,9-methanopyrido[2,3-b][1,4]diazocine-10(7H)-carboxamide

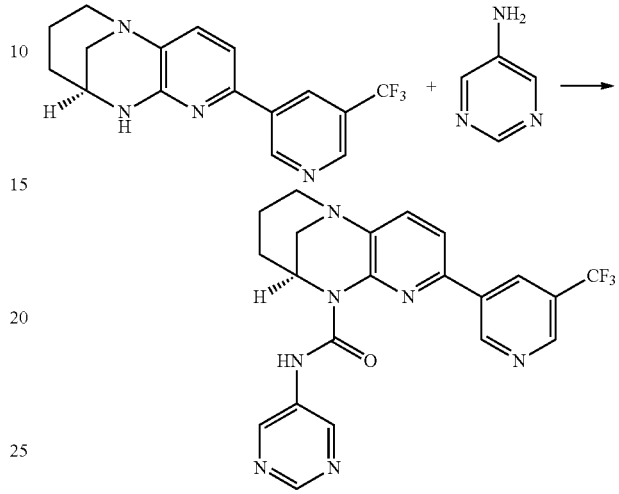

To a solution of (9S)-2-(5-(trifluoromethyl)pyridin-3-yl)-7,8,9,10-tetrahydro-6H-5,9-methanopyrido[2,3-b][1,4]diazocine (0.6 g, 1.873 mmol), triethylamine (0.783 mL, 5.62 mmol) in THF (12 mL) was added triphosgene (0.278 g, 0.937 mmol) at 0° C. and stirred at RT for 30 min. Then Pyrimidine-5-amine was added and the reaction mixture was stirred at 65° C. for 16 h. The solvent was removed under reduced pressure to obtain the crude and diluted with dichloromethane, washed with water and brine solution and dried over anhydrous $Na_2SO_4$, evaporated the organic layer under reduced pressure to obtain the crude product. The crude mixture was purified by flash column chromatography (silica-gel: 100-200 mesh, eluted with 2% MeOH in $CH_2Cl_2$) to afford (9S)—N-(pyrimidin-5-yl)-2-(5-(trifluoromethyl)pyridin-3-yl)-8,9-dihydro-6H-5,9-methanopyrido[2,3-b][1,4]diazocine-10(7H)-carboxamide (459 mg, 1.016 mmol, 54.2% yield) as a white solid (TLC: 80% EtOAc in Hexane, $R_f$=0.5), LCMS (m/z): 442.2 $[M+H]^+$.

$^1$H NMR (400 MHz, DMSO-$d_6$): δ ppm 13.19 (s, 1H), 9.48 (d, J=2.19 Hz, 1H), 9.08 (s, 1H), 8.96 (s, 1H), 8.88 (s, 1H), 8.71 (s, 1H), 7.85 (d, J=8.11 Hz, 1H), 7.77 (d, J=7.89 Hz, 1H), 4.84 (s, 1H), 3.43 (dd, J=13.59, 1.97 Hz, 1H), 3.33 (s, 2H), 2.90 (d, J=13.81 Hz, 2H), 1.95 (d, J=10.30 Hz, 2H), 1.33 (m, 2H).

Example 121

Synthesis of (9S)-2-(2-methylpyridin-4-yl)-N-(pyridin-2-yl)-8,9-dihydro-6H-5,9-methanopyrido[2,3-b][1,4]diazocine-10(7H)-carboxamide

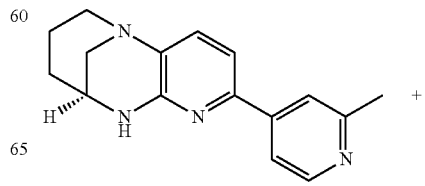 +

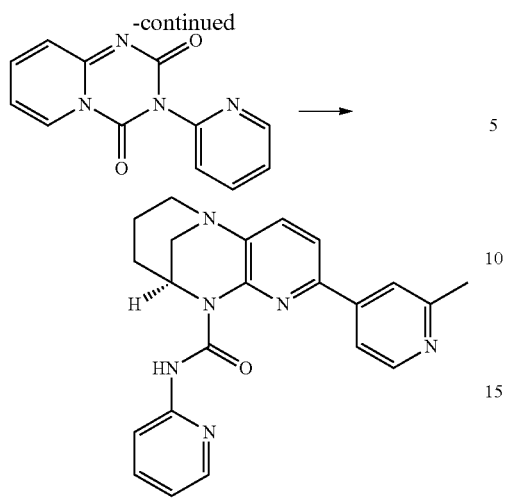

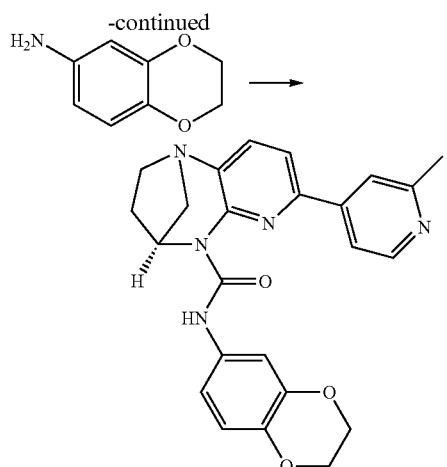

NaH (0.297 g, 12.39 mmol) was added to a stirred solution of (9S)-2-(2-methylpyridin-4-yl)-7,8,9,10-tetrahydro-6H-5,9-methanopyrido[2,3-b][1,4]diazocine (0.550 g, 2.065 mmol) in Tetrahydrofuran (THF) (30 mL) stirred under nitrogen at room temperature. Then the reaction mixture was stirred at room temperature for 30 minutes. 3-(pyridin-2-yl)-2H-pyrido[1,2-a][1,3,5]triazine-2,4(3H)-dione (0.744 g, 3.10 mmol) was added at was added at room temperature. Then the reaction mixture was stirred at 65° C. for 24 hr. The reaction mixture was cooled to 28° C. and was partitioned between water (20 mL) and EtOAc (50 mL). Organic layer was separated and was dried over anhydrous Na$_2$SO$_4$, filtered and filtrate was evaporated to give crude as brown solid (TLC eluent: 70% EtOAc in Hexane: R$_f$=0.3; UV active). The crude was purified by column chromatography using (100-200 mesh) silica gel and was eluted with 50-60% EtOAc in Hexane to afford pure (9S)-2-(2-methylpyridin-4-yl)-N-(pyridin-2-yl)-8,9-dihydro-6H-5,9-methanopyrido[2,3-b][1,4]diazocine-10(7H)-carboxamide (0.292 g, 0.751 mmol, 36.4% yield) as a pale yellow solid, LCMS (m/z): 387 [M+H]$^+$.

$^1$H NMR (400 MHz, DMSO-d$_6$): δ ppm 13.99 (s, 1H), 8.59 (d, J=5.48 Hz, 1H), 8.41-8.45 (m, 1H), 8.27 (s, 1H), 8.18 (d, J=8.33 Hz, 1H), 7.97 (br d, J=3.73 Hz, 1H), 7.82-7.86 (m, 2H), 7.71 (d, J=7.89 Hz, 1H), 7.11-7.16 (m, 1H), 4.86 (br s, 1H), 3.40 (br d, J=13.37 Hz, 1H), 3.29 (s, 2H), 2.91 (br d, J=13.15 Hz, 1H), 2.64 (s, 3H), 1.93-2.05 (m, 2H), 1.32 (br s, 2H)

Example 122

Synthesis of (4S)—N-(2,3-dihydrobenzo[b][1,4]dioxin-6-yl)-7-(2-methylpyridin-4-yl)-3,4-dihydro-1,4-methanopyrido[2,3-b][1,4]diazepine-5(2H)-carboxamide

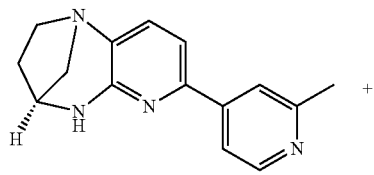

To a solution of (4S)-7-(2-methylpyridin-4-yl)-2,3,4,5-tetrahydro-1,4-methanopyrido[2,3-b][1,4]diazepine (500 mg, 1.982 mmol) in THF (30 ml) was added triphosgene (294 mg, 0.991 mmol) at 0° C. and stirred at RT for 1 h. Then 2,3-dihydrobenzo[b][1,4]dioxin-6-amine (899 mg, 5.94 mmol) and triethylamine (1.381 mL, 9.91 mmol) were added sequentially. The reaction mixture was heated at 70° C. for 16 h in sealed tube. The reaction mixture was poured in saturated NaHCO$_3$ solution (150 mL) and extracted with ethyl acetate (3×50 mL). The combined organic layer was dried over anhydrous Na$_2$SO$_4$ and concentrated under reduced pressure to obtain the crude compound. The crude mixture was purified by flash column chromatography (silica-gel: 100-200 mesh, using gradient mixture of 1% methanol in dichloromethane as eluent) to afford (4S)—N-(2,3-dihydrobenzo[b][1,4]dioxin-6-yl)-7-(2-methylpyridin-4-yl)-3,4-dihydro-1,4-methanopyrido[2,3-b][1,4]diazepine-5(2H)-carboxamide (315 mg, 0.734 mmol, 51% yield) as a brown solid (TLC: 5% Methanol in dichloromethane, R$_f$=0.3), LCMS (m/z): 430.0 [M+H]$^+$.

$^1$H NMR (400 MHz, DMSO-d$_6$): δ ppm 12.69 (s, 1H), 8.59 (d, J=5.26 Hz, 1H), 7.75-7.59 (m, 4H), 7.16 (s, 1H), 6.96-6.75 (dd, J=5.81, 2.41, 2H), 5.46 (dd, J=5.81, 3.18 Hz, 1H), 4.27-4.10 (m, 4H), 3.24-3.02 (m, 2H), 3.00-2.76 (m, 2H), 2.50 (s, 3H), 2.25-2.09 (m, 1H), 1.91-1.71 (m, 1H).

Example 123

Synthesis of (4S)—N-(6-ethylpyrazin-2-yl)-7-(2-methylpyridin-4-yl)-3,4-dihydro-1,4-methanopyrido[2,3-b][1,4]diazepine-5(2H)-carboxamide

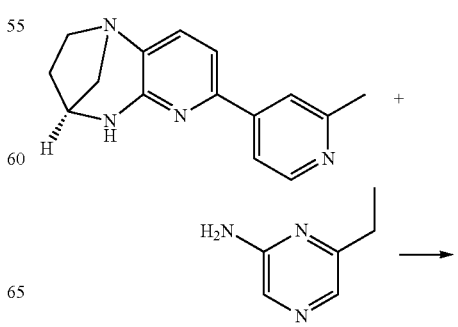

787

-continued

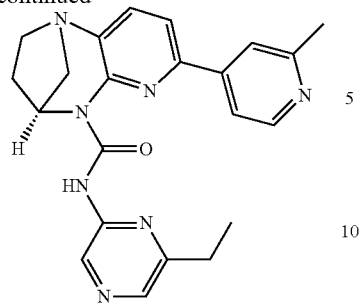

To a solution of (4S)-7-(2-methylpyridin-4-yl)-2,3,4,5-tetrahydro-1,4-methanopyrido[2,3-b][1,4]diazepine (500 mg, 1.982 mmol) in THF (25 ml) was added tri-phosgene (294 mg, 0.991 mmol) at 0° C. and stirred to RT for 1 h. Then 6-ethylpyrazin-2-amine (317 mg, 2.58 mmol), triethylamine (1.381 mL, 9.91 mmol) were added sequentially and heated the reaction mixture at 70° C. for 16 h in sealed tube. The reaction mixture was poured in saturated NaHCO$_3$ solution (150 mL) and extracted with ethyl acetate (3×50 mL). The combined organic layer was dried over anhydrous Na$_2$SO$_4$ and concentrated under reduced pressure to obtain the crude product. The crude mixture was purified by column chromatography (silica-gel: 100-200 mesh, eluent: 1% methanol in dichloromethane) to afford (4S)—N-(6-ethylpyrazin-2-yl)-7-(2-methylpyridin-4-yl)-3,4-dihydro-1,4-methanopyrido[2,3-b][1,4]diazepine-5(2H)-carboxamide (260 mg, 0.640 mmol, 32.3% yield) as a pale yellow solid (TLC: 5% MeOH in DCM, R$_f$=0.3), LCMS (m/z): 402.23 [M+H]$^+$.

$^1$H NMR (400 MHz, DMSO-d$_6$): δ ppm 13.47 (s, 1H), 9.23 (s, 1H), 8.59 (d, J=5.26 Hz, 1H), 8.29 (s, 1H), 8.02 (d, J=4.82 Hz, 2H), 7.88 (s, 1H), 7.64-7.84 (d, J=7.68 Hz, 1H), 5.52 (dd, J=6.03, 2.96 Hz, 1H), 3.08-3.33 (m, 2H), 2.89-3.08 (m, 2H), 2.78 (q, J=7.60 Hz, 2H), 2.57 (s, 3H), 2.39-2.13 (m, 1H), 2.12-1.88 (m, 1H) 1.21-1.30 (m, 3H).

Example 124

Synthesis of (9S)—N-(pyridin-2-yl)-2-((R)-2-(trifluoromethyl)pyrrolidin-1-yl)-8,9-dihydro-6H-5,9-methanopyrido[2,3-b][1,4]diazocine-10(7H)-carboxamide

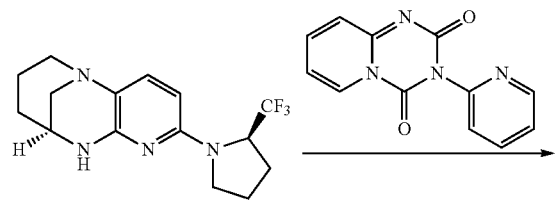

788

-continued

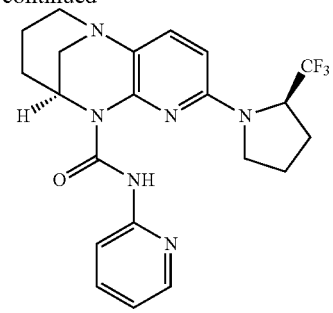

To a stirred solution of (9S)-2-((R)-2-(trifluoromethyl)pyrrolidin-1-yl)-7,8,9,10-tetrahydro-6H-5,9-methanopyrido[2,3-b][1,4]diazocine (500 mg, 1.601 mmol), in THF (10 mL) was added sodium hydride (419 mg, 9.61 mmol) portion wise during 5 min at 0° C. and stirred under nitrogen at room temp for 30 min. Then 3-(pyridin-2-yl)-2H-pyrido[1,2-a][1,3,5]triazine-2,4(3H)-dione (1154 mg, 4.80 mmol) was added and the reaction mixture was heated at 80° C. for 16 h. The reaction mixture was quenched with ice water and filtered through celite, the filtrate was extracted with EtOAc (2×50 ml). The combined organic layer was washed with water, brine solution and dried over anhydrous sodium sulfate, filtered and evaporated to obtain crude compound. The crude mixture was purified by flash column chromatography (silica-gel: 100-200 mesh, eluent: 2% MeOH in DCM) to afford (9S)—N-(pyridin-2-yl)-2-((R)-2-(trifluoromethyl)pyrrolidin-1-yl)-8,9-dihydro-6H-5,9-methanopyrido [2,3-b][1,4]diazocine-10(7H)-carboxamide (280 mg, 0.646 mmol, 40.3% yield) as an off-white solid (TLC: 10% MeOH in DCM, R$_f$: 0.4), LCMS (m/z): 433.3 [M+H]$^+$.

$^1$H NMR (400 MHz, DMSO-d$_6$): δ ppm 13.66 (s, 1H), 8.26 (dt, J=4.93, 0.93 Hz, 1H), 8.09 (d, J=8.33 Hz, 1H), 7.59-7.84 (m, 1H), 7.38 (d, J=8.77 Hz, 1H), 7.05 (ddd, J=7.23, 4.82, 0.66 Hz, 1H), 6.43 (d, J=8.55 Hz, 1H), 5.25 (br t, J=7.67 Hz, 1H), 4.70 (br s, 1H), 3.91 (dt, J=10.03, 5.18 Hz, 1H), 3.39-3.57 (m, 1H), 3.23-3.35 (m, 1H), 2.96-3.23 (m, 3H), 2.81 (br d, J=13.59 Hz, 1H), 2.14-2.34 (m, 2H), 2.10 (br s, 1H), 2.00 (d, J=13.81 Hz, 1H), 1.73-1.92 (m, 1H), 1.16-1.40 (m, 2H).

Example 125

Synthesis of (4S)—N-(6-((S)-2,3-dihydroxypropoxy) pyrazin-2-yl)-7-(3-(trifluoromethyl) phenyl)-3,4-dihydro-1,4-methanopyrido[2,3-b][1,4]diazepine-5(2H)-carboxamide

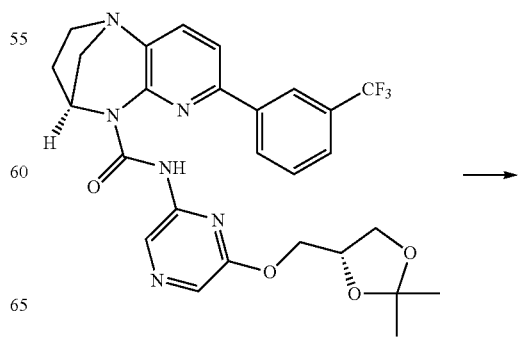

To a solution of (4S)—N-(6-(((R)-2,2-dimethyl-1,3-dioxolan-4-yl)methoxy)pyrazin-2-yl)-7-(3-(trifluoromethyl)phenyl)-3,4-dihydro-1,4-methanopyrido[2,3-b][1,4]diazepine-5 (2H)-carboxamide (600 mg, 1.078 mmol) in CH$_2$Cl$_2$ (16 mL) and water (1.6 mL) was added 4N HCl in dioxane (2.24 mL, 8.96 mmol) at 0° C. as dropwise over a period of 5 min. Then the reaction was stirred at RT for 3 h. The reaction mixture was concentrated under reduced pressure to obtain crude product. The crude product was diluted with water and neutralized with sodium bicarbonate (15 ml) and the aqueous layer was extracted with EtOAc (2×15 ml). The combined organic layer was washed with water, brine and dried over anhydrous Na$_2$SO$_4$, the organic solvent was evaporated under reduced pressure to afford the crude product. The crude product was triturated with di ethyl ether to afford (4S)—N-(6-((S)-2,3-dihydroxypropoxy)pyrazin-2-yl)-7-(3-(trifluoromethyl)phenyl)-3,4-dihydro-1,4-methanopyrido [2,3-b][1,4]diazepine-5(2H)-carboxamide (346 mg, 64% yield, 0.67 mmol) as an off white solid (TLC: 5% MeOH in CH$_2$Cl$_2$, R$_f$=0.3), LCMS (m/z): 517.18 [M+H]$^+$.
$^1$H NMR (400 MHz, DMSO-d6): δ 13.14 (s, 1H), 8.95 (s, 1H), 8.36 (d, J=7.7 Hz, 1H), 8.22 (s, 1H), 7.99 (s, 1H), 7.89-7.79 (m, 2H), 7.74 (q, J=8.0 Hz, 2H), 5.54 (s, 1H), 4.95 (d, J=5.1 Hz, 1H), 4.64 (t, J=5.5 Hz, 1H), 4.09 (qd, J=10.7, 5.1 Hz, 2H), 3.77 (d, J=5.2 Hz, 1H), 3.45-3.33 (m, 2H), 3.23-3.06 (m, 3H), 2.97 (dd, J=12.0, 3.3 Hz, 1H), 2.25 (ddt, J=14.0, 9.8, 4.8 Hz, 1H), 1.97 (dt, J=14.1, 7.3 Hz, 1H).

Example 126

Synthesis of (9S)—N-(5-fluoropyridin-3-yl)-2-(2-methylpyridin-4-yl)-8,9-dihydro-6H-5,9-methanopyrido[2,3-b][1,4]diazocine-10(7H)-carboxamide

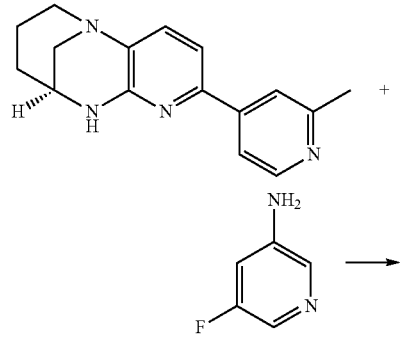

To a solution of (9S)-2-(2-methylpyridin-4-yl)-7,8,9,10-tetrahydro-6H-5,9-methanopyrido[2,3-b][1,4]diazocine (0.6 g, 2.253 mmol) in Tetrahydrofuran (THF) (30 mL) stirred under nitrogen at room temperature was added triethylamine (1.884 mL, 13.52 mmol) and triphosgene (0.669 g, 2.253 mmol). Then reaction mixture was stirred at rt for 30 minutes. Next, 5-fluoropyridin-3-amine (0.758 g, 6.76 mmol) was added at rt. and the reaction mixture was stirred at 65° C. for 16 hr. The reaction mixture was cooled to room temp. The reaction mixture concentrated under reduced pressure and then partitioned between water (20 mL) and Dichloromethane (50 mL). Organic layer was separated and was dried over anhydrous Na$_2$SO$_4$, filtered and filtrate was evaporated to give crude as brown solid (TLC eluent: 100% EtOAc: R$_f$-0.4; UV active). The crude was purified by column chromatography using (100-200 mesh) silica gel and was eluted with 100% EtOAc to afford pure (9S)—N-(5-fluoropyridin-3-yl)-2-(2-methylpyridin-4-yl)-8,9-dihydro-6H-5,9-methanopyrido[2,3-b][1,4]diazocine-10(7H)-carboxamide (0.314 g, 0.770 mmol, 34.2% yield) as a pale yellow solid, LCMS (m/z): 405.3 [M+H]$^+$.
$^1$H NMR (400 MHz, DMSO-d$_6$): δ 13.71 (s, 1H), 8.74-8.55 (m, 1H), 8.44 (d, J=1.7 Hz, 1H), 8.29 (d, J=2.6 Hz, 1H), 8.18-7.99 (m, 1H), 7.81 (d, J=1.7 Hz, 1H), 7.73 (d, J=2.8 Hz, 3H), 4.82 (s, 1H), 3.39 (d, J=1.9 Hz, 1H), 3.30 (s, 2H), 2.92 (s, 1H), 2.57 (s, 3H), 2.01 (s, 2H), 1.32 (s, 2H).

Example 127

Synthesis of (9S)—N-(pyridazin-3-yl)-2-(2-(trifluoromethyl)pyridin-4-yl)-8,9-dihydro-6H-5,9-methanopyrido[2,3-b][1,4]diazocine-10(7H)-carboxamide

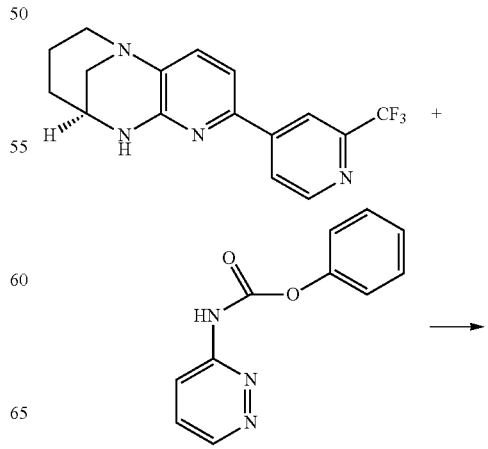

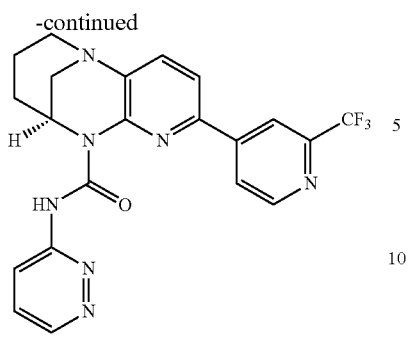

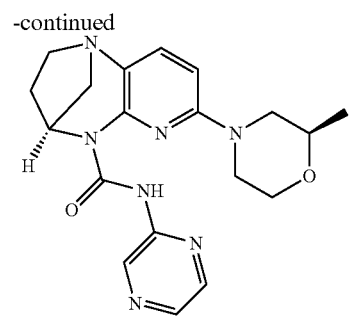

To a stirred solution of (9S)-2-(2-(trifluoromethyl)pyridin-4-yl)-7,8,9,10-tetrahydro-6H-5,9-methanopyrido[2,3-b][1,4]diazocine (0.4 g, 1.249 mmol), phenyl pyridazin-3-ylcarbamate (0.806 g, 3.75 mmol) in THF (8 mL) was added DMAP (0.458 g, 3.75 mmol) at 25° C. under nitrogen. The reaction mixture was heated at 80° C. for 16 h. Allowed to cool to RT and the solvent was removed in vacuo to obtain crude was diluted with $CH_2Cl_2$ and washed with water, brine solution, dried over anhydrous $Na_2SO_4$. The organic layer was concentrated in vacuo to obtain the crude compound. The crude mixture was purified by flash column chromatography (silica-gel: 100-200 mesh, eluent: 4% MeOH in $CH_2Cl_2$) to afford (9S)—N-(pyridazin-3-yl)-2-(2-(trifluoromethyl)pyridin-4-yl)-8,9-dihydro-6H-5,9-methanopyrido[2,3-b][1,4]diazocine-10(7H)-carboxamide (320 mg, 0.711 mmol, 56.9% yield) as a white solid (TLC: 80% EtOAc in Hexane $R_f$: 0.6), LCMS (m/z): 442.2 [M+H]⁺. ¹H NMR (400 MHz, DMSO-d6): δ 14.27 (s, 1H), 8.98 (dd, J=4.7, 1.5 Hz, 1H), 8.90 (d, J=5.1 Hz, 1H), 8.59-8.48 (m, 2H), 8.38 (dd, J=9.0, 1.5 Hz, 1H), 8.01 (d, J=8.1 Hz, 1H), 7.79 (d, J=8.1 Hz, 1H), 7.71 (dd, J=9.0, 4.7 Hz, 1H), 5.25-4.49 (m, 1H), 3.42 (dd, J=13.7, 1.9 Hz, 1H), 3.30 (s, 2H), 2.94 (dt, J=13.8, 2.5 Hz, 1H), 2.02 (m, 2H), 1.34 (q, J=5.2, 4.4 Hz, 2H).

To a degassed solution of (4S)-7-chloro-N-(pyrazin-2-yl)-3,4-dihydro-1,4-methanopyrido[2,3-b][1,4]diazepine-5(2H)-carboxamide (700 mg, 2.210 mmol), (R)-2-methylmorpholine Hydrochloride (335 mg, 2.431 mmol), $Cs_2CO_3$ (1440 mg, 4.42 mmol) and 2-dicyclohexylphosphino-2', 4', 6'-triisopropylbiphenyl (421 mg, 0.884 mmol) in 1,4-dioxane (10 mL) was added $Pd(OAc)_2$ (99 mg, 0.442 mmol) at RT. Then the reaction mixture was heated at 100° C. for 16 h. The reaction mixture was allowed to room temperature, quenched with 2×15 ml of water and extracted with 2×50 ml of ethyl acetate. The combined organic layer was dried over anhydrous sodium sulfate and concentrated under reduced pressure to obtain crude compound. The crude product was purified by column chromatography to afford (4S)-7-((R)-2-methylmorpholino)-N-(pyrazin-2-yl)-3,4-dihydro-1,4-methanopyrido[2,3-b][1,4]diazepine-5(2H)-carboxamide (275 mg, 0.696 mmol, 31.5% yield) as off white solid (TLC: $R_f$ value: 0.3, 5% Methanol in DCM), LCMS (m/z): 383.28 [M+H]⁺.

¹H NMR (400 MHz, DMSO-d₆): δ 13.40 (s, 1H), 9.38 (d, J=1.3 Hz, 1H), 8.46-8.17 (m, 2H), 7.40 (d, J=8.6 Hz, 1H), 6.53 (d, J=8.6 Hz, 1H), 5.44 (dd, J=6.1, 3.1 Hz, 1H), 4.20-4.04 (m, 1H), 4.00-3.93 (m, 1H), 3.91-3.80 (m, 1H), 3.70-3.53 (m, 2H), 3.17-3.05 (m, 1H), 3.03-2.92 (m, 2H), 2.87 (ddd, J=19.7, 11.9, 3.4 Hz, 2H), 2.58 (dd, J=12.6, 10.4 Hz, 1H), 2.21-2.12 (m, 1H), 1.86 (dd, J=14.3, 7.2 Hz, 1H), 1.22 (d, J=6.2 Hz, 3H).

Example 128

(4S)-7-((R)-2-methylmorpholino)-N-(pyrazin-2-yl)-3,4-dihydro-1,4-methanopyrido[2,3-b][1,4]diazepine-5(2H)-carboxamide Example 129

Synthesis of (4S)-7-((S)-2-methylmorpholino)-N-(pyrazin-2-yl)-3,4-dihydro-1,4-methano pyrido[2,3-b][1,4]diazepine-5(2H)-carboxamide

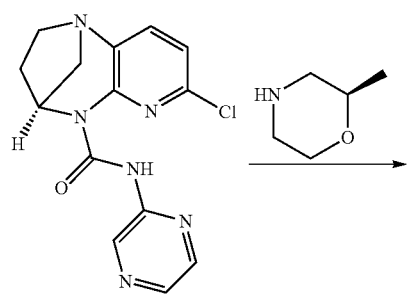

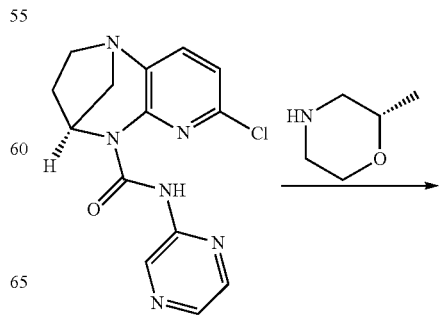

793

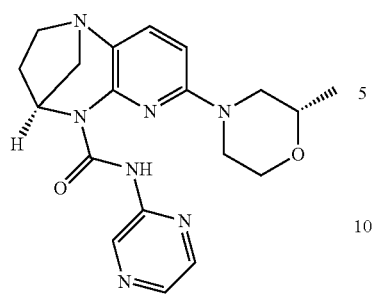

To a degassed solution of (4S)-7-chloro-N-(pyrazin-2-yl)-3,4-dihydro-1,4-methanopyrido[2,3-b][1,4]diazepine-5(2H)-carboxamide (700 mg, 2.210 mmol), (S)-2-methylmorpholine Hydrochloride (335 mg, 2.431 mmol), $Cs_2CO_3$ (1440 mg, 4.42 mmol) and 2-dicyclohexylphosphino-2', 4', 6'-triisopropylbiphenyl (421 mg, 0.884 mmol) in 1,4-dioxane (10 mL) was added $Pd(OAc)_2$ (99 mg, 0.442 mmol) at RT. Then the reaction mixture was heated at 100° C. for 16 h. The reaction mixture was allowed to room temperature, quenched with 2×15 ml of water and extracted with 2×50 ml of ethyl acetate. The combined organic layer was dried over anhydrous sodium sulfate and concentrated under reduced pressure to obtain crude compound. The crude product was purified by column chromatography to afford (4S)-7-((S)-2-methylmorpholino)-N-(pyrazin-2-yl)-3,4-dihydro-1,4-methanopyrido[2,3-b][1,4]diazepine-5(2H)-carboxamide (285 mg, 0.725 mmol, 32.8% yield) as off white solid (TLC: $R_f$ value: 0.3, 5% Methanol in DCM), LCMS (m/z): 383.28 $[M+H]^+$.

$^1$H NMR (400 MHz, DMSO-$d_6$): δ 13.40 (s, 1H), 9.38 (d, J=1.4 Hz, 1H), 8.40-8.14 (m, 2H), 7.40 (d, J=8.6 Hz, 1H), 6.53 (d, J=8.6 Hz, 1H), 5.44 (dd, J=6.0, 3.1 Hz, 1H), 4.12 (s, 1H), 3.96 (ddd, J=11.5, 3.6, 1.4 Hz, 1H), 3.86 (d, J=12.8 Hz, 1H), 3.62 (dd, J=11.8, 2.8 Hz, 2H), 3.09 (dd, J=11.4, 8.4 Hz, 1H), 2.96 (s, 2H), 2.93-2.78 (m, 2H), 2.58 (dd, J=12.6, 10.4 Hz, 1H), 2.17 (s, 1H), 1.85 (dt, J=14.3, 7.3 Hz, 1H), 1.23 (d, J=6.2 Hz, 3H).

Example 130

Synthesis of (9S)—N-(pyridin-2-yl)-2-(2-(trifluoromethyl)pyridin-4-yl)-8,9-dihydro-6H-5,9-methanopyrido[2,3-b][1,4]diazocine-10(7H)-carboxamide

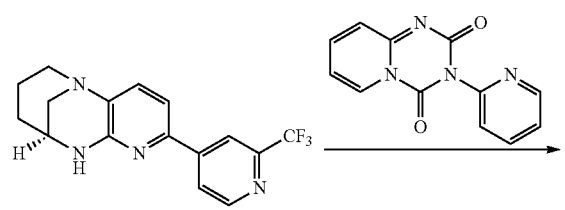

794

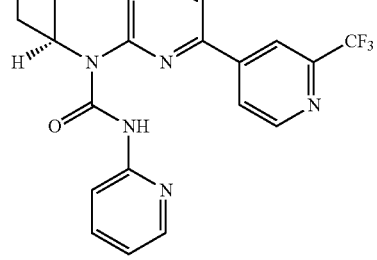

To a solution of (9S)-2-(2-(trifluoromethyl)pyridin-4-yl)-7,8,9,10-tetrahydro-6H-5,9-methanopyrido[2,3-b][1,4]diazocine (0.250 g, 0.780 mmol) in THF (5 mL) was added sodium hydride (0.156 g, 3.90 mmol) at RT in one charge. The reaction mixture was stirred at RT for 30 min. Then 3-(pyridin-2-yl)-2H-pyrido[1,2-a][1,3,5]triazine-2,4(3H)-dione (0.562 g, 2.341 mmol) was added and stirred the reaction mixture at 65° C. for 16 h. Allowed to cool to room temperature and quenched it with ice cold water, extracted with ethyl acetate (3×50 mL). The combined organic layer was washed with water, saturated brine solution, dried over sodium sulfate and concentrated under reduced pressure to obtain crude product. The crude mixture was purified by flash column chromatography (silica-gel: 100-200 mesh, eluent: 2% MeOH in $CH_2Cl_2$) to afford (9S)—N-(pyridin-2-yl)-2-(2-(trifluoromethyl)pyridin-4-yl)-8,9-dihydro-6H-5,9-methano pyrido[2,3-b][1,4]diazocine-10(7H)-carboxamide (302 mg, 0.681 mmol, 87% yield) as a white solid (TLC: 70% EtOAc in Hexane, $R_f$: 0.5), LCMS (m/z): 441.3 $[M+H]^+$.

$^1$H NMR (400 MHz, DMSO-d6): δ 13.85 (s, 1H), 8.94 (d, J=5.2 Hz, 1H), 8.64 (dd, J=1.7, 0.9 Hz, 1H), 8.55-8.50 (m, 1H), 8.34 (ddd, J=4.8, 2.0, 0.9 Hz, 1H), 8.15 (dt, J=8.3, 1.0 Hz, 1H), 7.98 (d, J=8.1 Hz, 1H), 7.86-7.79 (m, 1H), 7.77 (d, J=8.0 Hz, 1H), 7.12 (ddd, J=7.3, 4.9, 1.0 Hz, 1H), 4.87 (t, J=2.6 Hz, 1H), 3.41 (dd, J=13.6, 1.9 Hz, 1H), 3.30 (s, 2H), 2.92 (d, J=14.0 Hz, 1H), 2.09-1.86 (m, 2H), 1.34 (d, J=8.5 Hz, 2H).

Example 131

Synthesis of (4S)—N-(3,4-dihydro-2H-benzo[b][1,4]dioxepin-7-yl)-7-(2-methylpyridin-4-yl)-3,4-dihydro-1,4-methanopyrido[2,3-b][1,4]diazepine-5(2H)-carboxamide

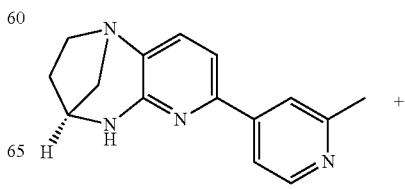

-continued

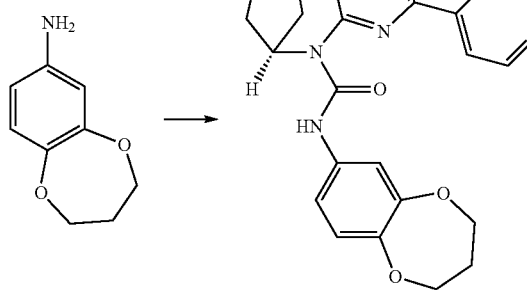

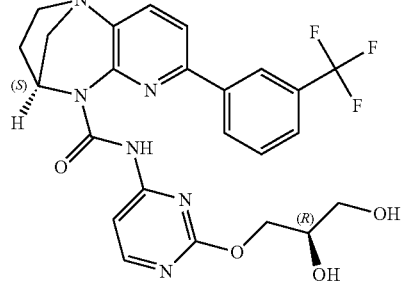

To a solution of (4S)-7-(2-methylpyridin-4-yl)-2,3,4,5-tetrahydro-1,4-methanopyrido[2,3-b][1,4]diazepine (500 mg, 1.982 mmol) in THF (30 ml) was added tri-phosgene (294 mg, 0.991 mmol) at 0° C. and stirred to RT for 1 h. Then 3,4-dihydro-2H-benzo[b][1,4]dioxepin-7-amine (426 mg, 2.58 mmol) and triethylamine (1.381 mL, 9.91 mmol) were added sequentially and heated the reaction mixture at 70° C. for 16 h in sealed tube. The reaction mixture was poured in saturated NaHCO$_3$ solution (150 mL) and extracted with ethyl acetate (3×50 mL). The combined organic layer was dried over anhydrous Na$_2$SO$_4$ and concentrated under reduced pressure to obtain the crude product. The crude mixture was purified by flash column chromatography (silica-gel; 100-200 mesh, using gradient mixture of 1% MeOH in DCM as eluent) to afford (4S)—N-(3,4-dihydro-2H-benzo[b][1,4]dioxepin-7-yl)-7-(2-methylpyridin-4-yl)-3,4-dihydro-1,4-methanopyrido[2,3-b][1,4]diazepine-5(2H)-carboxamide (394 mg, 0.889 mmol, 68% yield) as pale yellow solid (TLC: 5% MeOH in DCM, R$_f$=0.3), LCMS (m/z): 444.28 [M+H]$^+$.

$^1$H NMR (400 MHz, DMSO-d$_6$): δ ppm 12.76 (s, 1H), 8.59 (d, J=5.04 Hz, 1H), 7.79-7.58 (m, 3H), 7.24-7.06 (m, 2H), 6.96 (d, J=8.77 Hz, 1H), 5.46 (dd, J=5.70, 3.07 Hz, 1H), 4.10 (dt, J=19.51, 5.37 Hz, 4H), 3.15-3.02 (m, 1H), 3.02-2.77 (m, 3H), 2.50 (s, 3H), 2.46-2.18 (m, 1H), 2.17-2.01 (m, 2H), 2.01-1.83- (m, 2H).

Example 132

Synthesis of (4S)—N-(2-((R)-2,3-dihydroxypropoxy)pyrimidin-4-yl)-7-(3-(trifluoromethyl)phenyl)-3,4-dihydro-1,4-methanopyrido[2,3-b][1,4]diazepine-5(2H)-carboxamide

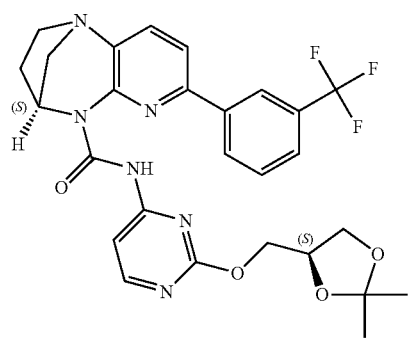

To a solution of (4S)—N-(2-(((S)-2,2-dimethyl-1,3-dioxolan-4-yl)methoxy)pyrimidin-4-yl)-7-(3-(trifluoromethyl)phenyl)-3,4-dihydro-1,4-methanopyrido[2,3-b][1,4]diazepine-5 (2H)-carboxamide (450 mg, 0.809 mmol) in dichloromethane (12 mL), water (1.2 mL) was added 4.0 M hydrochloric acid in 1,4-dioxane (1.68 mL, 0.809 mmol) at 0° C. The reaction mixture was stirred at 30° C. for 3 h and concentrated the solvent. The reaction mixture was partitioned between water (10 mL) and EtOAc (25 mL). Organic layers were washed with water, brine solution, dried over anhydrous Na$_2$SO$_4$ & filtered and filtrate was evaporated to give crude (TLC eluent: 5% MeOH in DCM: R$_f$-0.2; UV active). The crude was purified washed with n-pentane and suspended in water (5 mL), stirred for 15 min and filtered to afford pure (4S)—N-(2-((R)-2,3-dihydroxypropoxy)pyrimidin-4-yl)-7-(3-(trifluoromethyl) phenyl)-3,4-dihydro-1,4-methanopyrido[2,3-b][1,4]diazepine-5 (2H)-carboxamide (260 mg, 0.480 mmol, 59.4% yield) as off white solid, LCMS (m/z): 517.2 [M+H]$^+$.

$^1$H NMR (400 MHz, DMSO-d$_6$): δ 13.58 (s, 1H), 8.60 (d, J=7.5 Hz, 1H), 8.46 (d, J=5.6 Hz, 1H), 8.27 (s, 1H), 7.91-7.78 (m, 3H), 7.75-7.60 (m, 2H), 5.48 (dd, J=5.9, 3.0 Hz, 1H), 4.91 (d, J=4.8 Hz, 1H), 4.62 (t, J=5.5 Hz, 1H), 4.22 (dd, J=10.8, 4.4 Hz, 1H), 4.13 (dd, J=10.7, 5.9 Hz, 1H), 3.80 (q, J=5.4 Hz, 1H), 3.43 (t, J=5.7 Hz, 2H), 3.21 (s, 1H), 3.16-3.05 (m, 2H), 2.96 (dd, J=12.0, 3.3 Hz, 1H), 2.29-2.10 (m, 1H), 2.04-1.84 (m, 1H).

Example 133

Synthesis of (4S)—N-(6-((R)-2,3-dihydroxypropoxy)pyrazin-2-yl)-7-(3-(trifluoromethyl

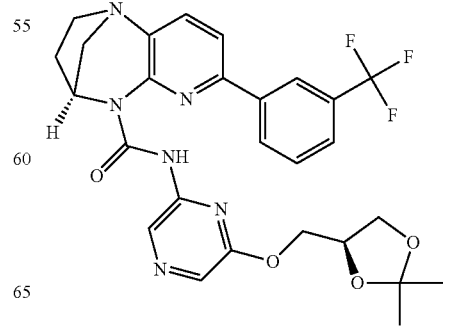

797

-continued

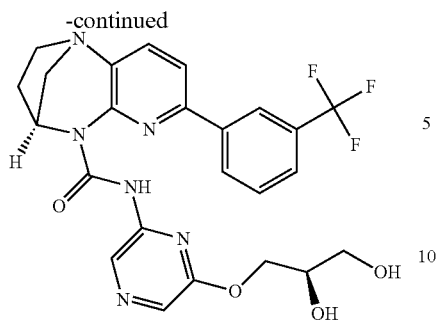

798

-continued

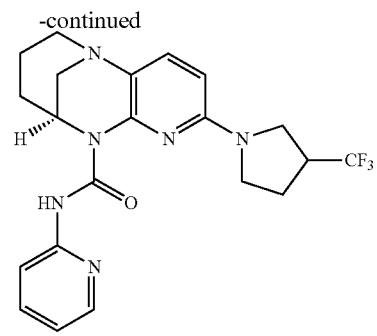

To a solution of (4S)—N-(6-(((S)-2,2-dimethyl-1,3-dioxolan-4-yl)methoxy)pyrazin-2-yl)-7-(3-(trifluoromethyl)phenyl)-3,4-dihydro-1,4-methanopyrido[2,3-b][1,4]diazepine-5 (2H)-carboxamide (300 mg, 0.539 mmol) in dichloromethane (8.0 mL), water (0.8 mL) was added 4.0 M hydrochloric acid in 1,4-dioxane (1.12 mL, 0.539 mmol) at 0° C. over 1 min (dropwise addition). The reaction mixture was stirred at 30° C. for 3 h and concentrated the solvent. The reaction mixture was partitioned between water (10 mL) and ethyl acetate (25 mL). Organic layers were washed with water, brine solution, dried over anhydrous $Na_2SO_4$ and evaporated to give crude compound (TLC eluent: 5% MeOH in DCM: $R_f$=0.2; UV active). The crude compound was washed with n-pentane and suspended in water (5 mL), stirred for 15 min and filtered to afford pure (4S)—N-(6-((R)-2,3-dihydroxypropoxy)pyrazin-2-yl)-7-(3-(trifluoromethyl)phenyl)-3,4-dihydro-1,4-methanopyrido[2,3-b][1,4]diazepine-5 (2H)-carboxamide (280 mg, 0.533 mmol, 99% yield) as off white solid, LCMS (m/z): 517.3 [M+H]$^+$.

$^1$H NMR (400 MHz, DMSO-d$_6$): δ 13.15 (s, 1H), 8.95 (s, 1H), 8.36 (d, J=7.7 Hz, 1H), 8.22 (s, 1H), 7.99 (s, 1H), 7.86 (t, J=7.8 Hz, 1H), 7.80 (d, J=7.8 Hz, 1H), 7.74 (q, J=8.0 Hz, 2H), 5.52 (dd, J=5.8, 3.0 Hz, 1H), 4.95 (d, J=5.1 Hz, 1H), 4.64 (t, J=5.5 Hz, 1H), 4.14 (dd, J=10.7, 4.0 Hz, 1H), 4.03 (dd, J=10.7, 6.1 Hz, 1H), 3.77 (q, J=5.2 Hz, 1H), 3.36 (hept, J=5.8 Hz, 2H), 3.22 (s, 1H), 3.12 (d, J=11.3 Hz, 2H), 2.97 (dd, J=11.9, 3.3 Hz, 1H), 2.26 (t, J=7.0 Hz, 1H), 2.03-1.90 (m, 1H).

Example 134

Synthesis of (9S)—N-(pyridin-2-yl)-2-(3-(trifluoromethyl)pyrrolidin-1-yl)-8,9-dihydro-6H-5,9-methanopyrido[2,3-b][1,4]diazocine-10(7H)-carboxamide

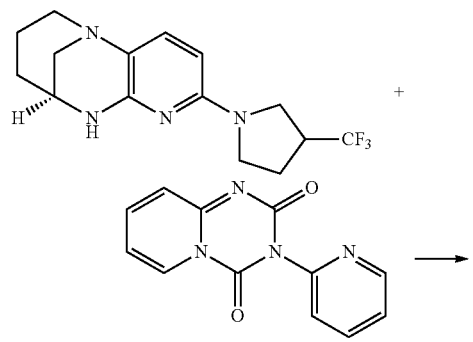

NaH (0.277 g, 11.53 mmol) was added to a solution of (9S)-2-(3)pyrrolidin-1-yl)-7,8,9,10-tetrahydro-6H-5,9-metha-(trifluoromethyl nopyrido[2,3-b][1,4]diazocine (0.6 g, 1.921 mmol) in Tetrahydrofuran (THF) (20 mL) and stirred for 30 min. Then 3-(pyridin-2-yl)-2H-pyrido[1,2-a][1,3,5]triazine-2,4(3H)-dione (0.692 g, 2.88 mmol) was added at room temp. Then reaction mixture was stirred at 65° C. for 24 h. The reaction mixture was cooled to RT and was partitioned between water (20 mL) and EtOAc (50 mL). Organic layer was separated and was dried over anhydrous $Na_2SO_4$, filtered and filtrate was evaporated to give crude as brown solid (TLC eluent: 70% EtOAc in Hexane: $R_f$-0.3; UV active). The crude was purified by column chromatography using (100-200 mesh) silica gel and was eluted with 50-60% EtOAc in hexane to afford mixture of stereoisomers (9:1) which on further SFC purification obtained pure (9S)—N-(pyridin-2-yl)-2-(3-(trifluoromethyl)pyrrolidin-1-yl)-8,9-dihydro-6H-5,9-methanopyrido[2,3-b][1,4]diazocine-10(7H)-carboxamide (0.422 g, 0.973 mmol, 50.6% yield) as an off-white solid, LCMS (m/z): 433.3 [M+H]$^+$.

Analytical SFC Conditions: Peak-I Column/dimensions: Chiralcel OX-H (250×4.6) mm, 5u
% $CO_2$: 60.0%
% Co solvent: 40.0% (0.5% DEA IN MeOH)
Total Flow: 4.0 g/min
Back Pressure: 100 bar
Temperature: 26.8° C.
UV: 263 nm $^1$H NMR (400 MHz, DMSO-d$_6$): δ 13.81 (s, 1H), 8.23-8.18 (m, 1H), 8.11 (dt, J=8.3, 1.0 Hz, 1H), 7.76 (ddd, J=8.5, 7.4, 1.9 Hz, 1H), 7.32 (d, J=8.5 Hz, 1H), 7.04 (ddd, J=7.3, 4.9, 1.0 Hz, 1H), 6.24 (d, J=8.5 Hz, 1H), 4.71 (s, 1H), 3.96 (d, J=8.5 Hz, 1H), 3.78 (d, J=7.0 Hz, 1H), 3.74 (s, 1H), 3.66 (d, J=4.1 Hz, 2H), 3.59-3.38 (m, 1H), 3.26 (d, J=1.9 Hz, 1H), 3.12 (dd, J=12.7, 3.5 Hz, 1H), 3.05 (s, 1H), 2.80 (d, J=13.4 Hz, 1H), 2.41-2.29 (m, 1H), 2.15 (dd, J=12.7, 8.1 Hz, 1H), 1.96 (s, 1H), 1.83 (s, 2H), 1.31 (s, 2H).

Example 135

Synthesis of (9S)—N-(pyrimidin-4-yl)-2-(2-(trifluoromethyl)pyridin-4-yl)-8,9-dihydro-6H-5,9-methanopyrido[2,3-b][1,4]diazocine-10(7H)-carboxamide

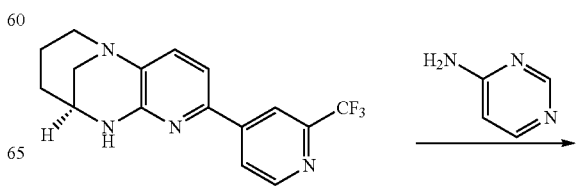

-continued

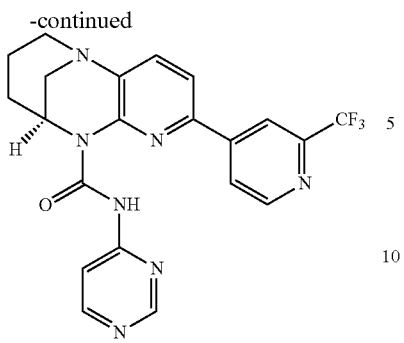

(9S)-2-(2-(trifluoromethyl)pyridin-4-yl)-7,8,9,10-tetrahydro-6H-5,9-methanopyrido[2,3-b][1,4]diazocine (0.5 g, 1.561 mmol), triethylamine (0.653 mL, 4.68 mmol) in THF (10 mL) stirred under nitrogen at 25° C. was added bis(trichloromethyl) carbonate (0.232 g, 0.780 mmol) in one charge. The reaction mixture was stirred at 25° C. for 30 min. Then pyrimidin-4-amine (0.445 g, 4.68 mmol) was added in a portion, reaction was stirred at 65° C. for 16 h. Allowed to cool to RT and solvent was removed under vacuo, crude was diluted with DCM, washed with water, brine solution, dried over sodium sulfate and concentrated under vacuum to obtain crude compound. The crude mixture was purified by prep HPLC to afford (9S)—N-(pyrimidin-4-yl)-2-(2-(trifluoromethyl)pyridin-4-yl)-8,9-dihydro-6H-5,9-methanopyrido[2,3-b][1,4]diazocine-10(7H)-carboxamide (199 mg, 0.446 mmol, 28.6% yield) as a white solid (TLC: 70% EtOAc in Hexane, $R_f$: 0.6), LCMS (m/z): 442.3 [M+H]$^+$. $^1$H NMR (400 MHz, DMSO-d6): δ 14.18 (s, 1H), 8.97 (d, J=5.1 Hz, 1H), 8.85 (d, J=1.2 Hz, 1H), 8.69 (d, J=5.8 Hz, 1H), 8.60 (dd, J=1.9, 0.8 Hz, 1H), 8.50 (dd, J=5.1, 1.7 Hz, 1H), 8.12 (dd, J=5.8, 1.3 Hz, 1H), 8.02 (d, J=8.1 Hz, 1H), 7.80 (d, J=8.1 Hz, 1H), 4.93-4.73 (m, 1H), 3.42 (dd, J=13.7, 1.9 Hz, 1H), 3.32 (d, J=8.2 Hz, 2H), 2.93 (dt, J=13.9, 2.5 Hz, 1H), 2.12-1.83 (m, 2H), 1.33 (d, J=7.8 Hz, 2H).

Example 136

Synthesis of (4S)—N-(6-ethoxypyrazin-2-yl)-7-(2-methylpyridin-4-yl)-3,4-dihydro-1,4-methanopyrido[2,3-b][1,4]diazepine-5(2H)-carboxamide

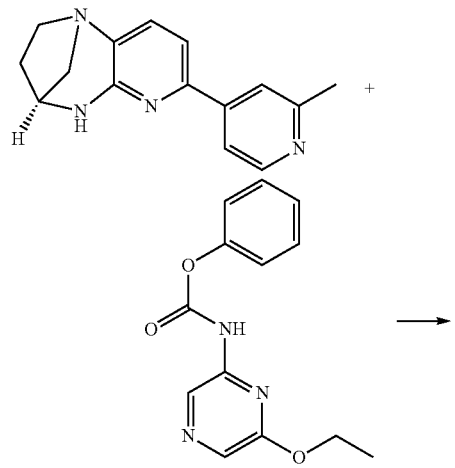

-continued

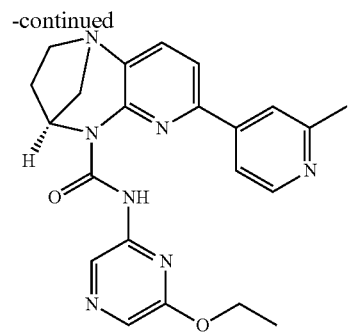

DMAP (726 mg, 5.94 mmol) and phenyl (6-ethoxypyrazin-2-yl)carbamate (1541 mg, 5.94 mmol) were added to a stirred solution of (4S)-7-(2-methylpyridin-4-yl)-2,3,4,5-tetrahydro-1,4-methanopyrido[2,3-b][1,4]diazepine (500 mg, 1.982 mmol) in THF at room temperature. The mixture was heated to 80° C. for 20 h in a sealed tube. After cooling to room temperature, the solvent was evaporated and crude product was purified by flash column chromatography (silica-gel: 100-200 mesh, 5% MeOH in DCM as an eluent). The recovered material was taken up in ethanol and the solid that separated was isolated by filtration to afford (4S)—N-(6-ethoxypyrazin-2-yl)-7-(2-methylpyridin-4-yl)-3,4-dihydro-1,4-methanopyrido[2,3-b][1,4]diazepine-5(2H)-carboxamide (416 mg, 0.978 mmol, 49.3% yield) as an off white solid (TLC eluent: 10% MeOH in DCM, $R_f$: 0.4), LCMS (m/z): 418.28 [M+H]$^+$.

$^1$H NMR (DMSO-d6, 400 MHz): δ 13.18 (s, 1H), 8.95 (s, 1H), 8.53 (dd, J=5.0, 1.0 Hz, 1H), 7.98 (d, J=0.5 Hz, 1H), 7.86-7.79 (m, 2H), 7.73 (s, 2H), 5.51 (dd, J=5.9, 3.1 Hz, 1H), 4.22 (qd, J=7.1, 2.3 Hz, 2H), 3.25-3.17 (m, 1H), 3.11 (dt, J=11.7, 2.4 Hz, 2H), 2.97 (dd, J=12.0, 3.3 Hz, 1H), 2.58 (s, 3H), 2.25 (dddd, J=13.7, 9.9, 6.2, 3.8 Hz, 1H), 2.04-1.90 (m, 1H), 1.27 (t, J=7.0 Hz, 3H).

Example 137

Synthesis of (9S)—N-(pyrimidin-5-yl)-2-(2-(trifluoromethyl)pyridin-4-yl)-8,9-dihydro-6H-5,9-methanopyrido[2,3-b][1,4]diazocine-10(7H)-carboxamide

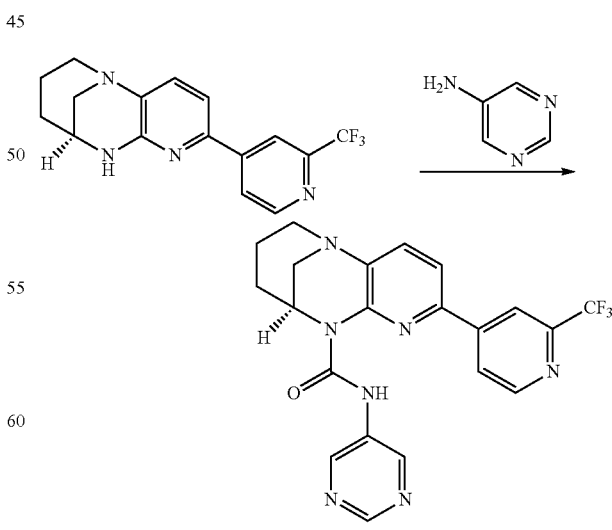

To a solution of (9S)-2-(2-(trifluoromethyl)pyridin-4-yl)-7,8,9,10-tetrahydro-6H-5,9-methanopyrido[2,3-b][1,4]diazocine (0.5 g, 1.561 mmol), triethylamine (0.653 mL, 4.68 mmol) in THF (10 mL) was added bis(trichloromethyl) carbonate (0.232 g, 0.780 mmol) at 25° C. under nitrogen atmosphere and stirred at RT for 30 min. Then pyrimidin-5-amine (0.445 g, 4.68 mmol) was added and heated the reaction mixture at 65° C. for 16 h. Allowed to cool to RT and solvent was removed on rota-vapour, the crude was diluted with $CH_2Cl_2$ (20 ml) and washed with water (5 ml), brine solution (5 ml) followed by dried over sodium sulfate. The organic solvent was evaporated under reduced pressure to obtain the crude product. The crude mixture was purified by prep-HPLC (formic acid, ACN 25%) to afford (9S)—N-(pyrimidin-5-yl)-2-(2-(trifluoromethyl)pyridin-4-yl)-8,9-dihydro-6H-5,9-methanopyrido[2,3-b][1,4]diazocine-10(7H)-carboxamide (250 mg, 0.56 mmol, 45% yield) as an off white solid (TLC: 80% EtOAc in Hexane, $R_f$: 0.5), LCMS (m/z): 442.3 [M+H]$^+$. $^1$H NMR (400 MHz, DMSO-d6): δ 13.07 (s, 1H), 9.08-8.72 (m, 4H), 8.38 (dd, J=1.7, 0.9 Hz, 1H), 8.28 (dd, J=5.2, 1.6 Hz, 1H), 7.90 (d, J=8.0 Hz, 1H), 7.79 (d, J=8.0 Hz, 1H), 4.85 (t, J=2.7 Hz, 1H), 3.43 (dd, J=13.7, 1.9 Hz, 1H), 3.33 (d, J=10.1 Hz, 2H), 2.91 (d, J=13.7 Hz, 1H), 2.15-1.79 (m, 2H), 1.33 (s, 2H).

Example 138

Synthesis of (4S)-7-(2-methylpyridin-4-yl)-N-(1H-pyrazolo[3,4-c]pyridin-5-yl)-3,4-dihydro-1,4-methanopyrido[2,3-b][1,4]diazepine-5(2H)-carboxamide

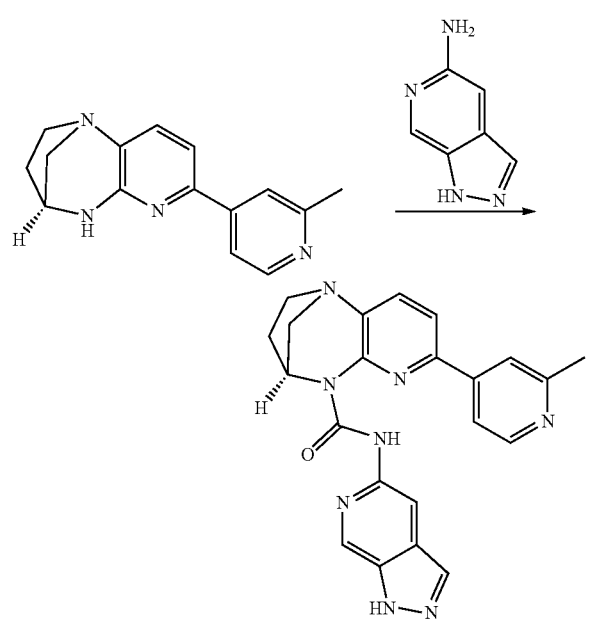

To a stirred solution of (4S)-7-(2-methylpyridin-4-yl)-2,3,4,5-tetrahydro-1,4-methanopyrido[2,3-b][1,4]diazepine (300 mg, 1.189 mmol) in THF (10 mL) was added triphosgene (176 mg, 0.594 mmol) at RT and stirred for 30 min. After 30 minutes triethylamine (0.829 mL, 5.94 mmol) and 1H-pyrazolo[3,4-c]pyridin-5-amine (191 mg, 1.427 mmol) were added. The reaction mixture was stirred at 65-70° C. for 16 h in sealed tube. Reaction mixture was quenched with 2×15 ml of water and extracted with 2×15 ml of ethyl acetate. The combined organic layer was dried over anhydrous sodium sulfate and concentrated under reduced pressure to obtain crude compound. The crude mixture was purified by column chromatography to afford (4S)-7-(2-methylpyridin-4-yl)-N-(1H-pyrazolo[3,4-c]pyridin-5-yl)-3,4-dihydro-1,4-methanopyrido[2,3-b][1,4]diazepine-5(2H)-carboxamide (330 mg, 0.764 mmol, 64.3% yield) as a pale yellow solid ($R_f$ value: 0.25, Neat Ethyl acetate), LCMS (m/z): 413.24[M+H]$^+$.

$^1$H NMR (400 MHz, DMSO-d$_6$): δ 13.47 (s, 2H), 8.89 (t, J=1.1 Hz, 1H), 8.71-8.57 (m, 1H), 8.44 (t, J=1.0 Hz, 1H), 8.28-8.10 (m, 2H), 8.05-7.93 (m, 1H), 7.79 (d, J=8.0 Hz, 1H), 7.71 (d, J=8.0 Hz, 1H), 5.56 (dd, J=5.9, 3.1 Hz, 1H), 3.22 (tt, J=8.1, 3.0 Hz, 1H), 3.15-3.04 (m, 2H), 2.97 (dd, J=12.0, 3.3 Hz, 1H), 2.67 (s, 3H), 2.36-2.16 (m, 1H), 1.96 (dd, J=14.0, 7.1 Hz, 1H).

Example 139

Synthesis of (4S)-7-(2-methylpyridin-4-yl)-N-(quinoxalin-5-yl)-3,4-dihydro-1,4-methanopyrido[2,3-b][1,4]diazepine-5(2H)-carboxamide

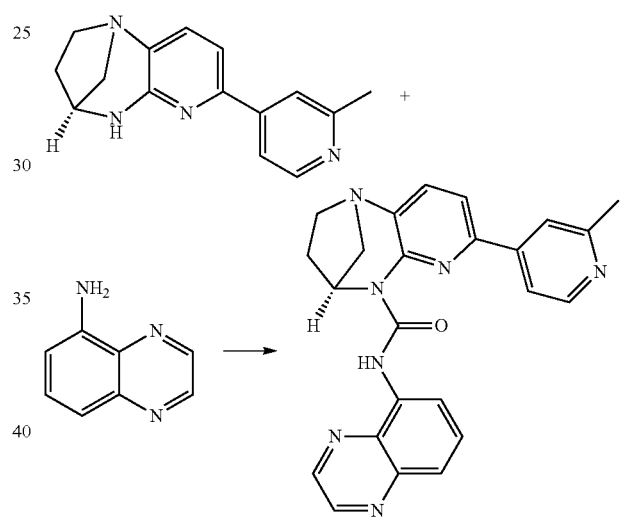

To a solution of (4S)-7-(2-methylpyridin-4-yl)-2,3,4,5-tetrahydro-1,4-methanopyrido[2,3-b][1,4]diazepine (500 mg, 1.982 mmol) in THF (30 ml) was added tri-phosgene (294 mg, 0.991 mmol) at 0° C. and stirred at RT for 1 h. Then quinoxalin-5-amine (374 mg, 2.58 mmol) and triethylamine (1.381 mL, 9.91 mmol) were added sequentially at RT and heated the reaction mixture at 70° C. for 16 h. The reaction mixture was poured in saturated NaHCO$_3$ solution (150 mL) and extracted with ethyl acetate (3×50 mL). The combined organic layer was dried over anhydrous Na$_2$SO$_4$ and concentrated under reduced pressure to obtain the crude product. The crude product was purified by flash column chromatography (silica-gel: 100-200 mesh, using gradient mixture of 1% MeOH in DCM as eluent) to afford (4S)-7-(2-methylpyridin-4-yl)-N-(quinoxalin-5-yl)-3,4-dihydro-1,4-methanopyrido[2,3-b][1,4]diazepine-5(2H)-carboxamide (300 mg, 0.709 mmol, 55% yield) as pale yellow solid (TLC: 5% MeOH in DCM, $R_f$=0.3), LCMS (m/z): 424.26 [M+H]$^+$.

$^1$H NMR (400 MHz, DMSO-d$_6$): δ ppm 13.50 (s, 1H), 8.91 (s, 1H), 8.68 (dd, J=7.89, 1.10 Hz, 1H), 8.48 (d, J=5.26 Hz, 1H), 7.92-7.80 (m, 2H), 7.80-7.62 (m, 4H), 5.58 (dd, J=5.81, 2.96 Hz, 1H), 3.20-3.08 (m, 4H), 3.08-2.86 (m, 1H), 2.26 (s, 4H), 2.00-1.95 (m, 1H).

Example 140

Synthesis of (4S)—N-(2-((R)-2,3-dihydroxy-propoxy)pyridin-4-yl)-7-(3-(trifluoromethyl)phenyl)-3,4-dihydro-1,4-methanopyrido[2,3-b][1,4]diazepine-5(2H)-carboxamide

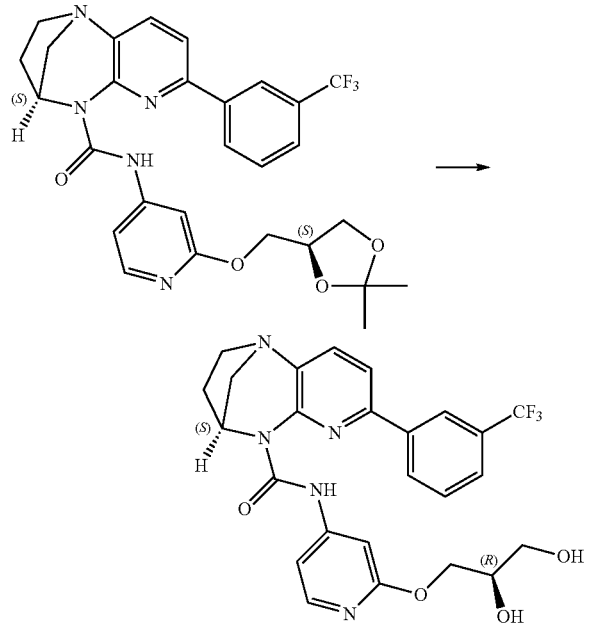

To a solution of (4S)—N-(2-(((S)-2,2-dimethyl-1,3-dioxolan-4-yl)methoxy)pyridin-4-yl)-7-(3-(trifluoromethyl)phenyl)-3,4-dihydro-1,4-methanopyrido[2,3-b][1,4]diazepine-5(2H)-carboxamide (450 mg, 0.810 mmol) in dichloromethane (12 mL), water (1.2 mL) was added 4.0 M hydrochloric acid in 1,4-dioxane (1.68 mL, 0.810 mmol) dropwise during 1 min at 0° C. The reaction mixture was stirred at 30° C. for 3 h and concentrated the solvent. The reaction mixture was partitioned between water (10 mL) and EtOAc (25 mL). Organic layers were washed with water, brine solution, dried over anhydrous $Na_2SO_4$ and evaporated to give crude compound (TLC eluent: 5% MeOH in DCM: $R_f$-0.2; UV active). The crude compound was washed with n-pentane and the compound was suspended in water (5 mL), stirred for 15 min and filtered to afford pure (4S)—N-(2-((R)-2,3-dihydroxypropoxy)pyridin-4-yl)-7-(3-(trifluoromethyl)phenyl)-3,4-dihydro-1,4-methanopyrido[2,3-b][1,4]diazepine-5(2H)-carboxamide (310 mg, 0.600 mmol, 74.0% yield) as white solid, LCMS (m/z): 516.3 [M+H]$^+$.

$^1$H NMR (400 MHz, DMSO-$d_6$): δ 13.02 (s, 1H), 8.27-8.15 (m, 2H), 7.94 (d, J=5.7 Hz, 1H), 7.89 (d, J=7.8 Hz, 1H), 7.82 (t, J=7.7 Hz, 1H), 7.72 (d, J=8.0 Hz, 1H), 7.66 (d, J=8.0 Hz, 1H), 7.11 (d, J=1.8 Hz, 1H), 6.80 (dd, J=5.8, 1.9 Hz, 1H), 5.47 (dd, J=5.9, 3.0 Hz, 1H), 4.85 (d, J=5.1 Hz, 1H), 4.59 (t, J=5.7 Hz, 1H), 4.23 (dd, J=10.9, 4.6 Hz, 1H), 4.13 (dd, J=10.9, 6.2 Hz, 1H), 3.81-3.65 (m, 1H), 3.43 (t, J=5.6, 1.3 Hz, 2H), 3.25-3.03 (m, 3H), 2.97 (dd, J=12.0, 3.3 Hz, 1H), 2.25 (m, J=13.8, 9.7, 4.7 Hz, 1H), 1.95 (m, J=14.3, 7.6 Hz, 1H).

Example 141

(4S)-7-(2-methylpyridin-4-yl)-N-(1H-pyrazolo[4,3-b]pyridin-5-yl)-3,4-dihydro-1,4-methanopyrido[2,3-b][1,4]diazepine-5(2H)-carboxamide

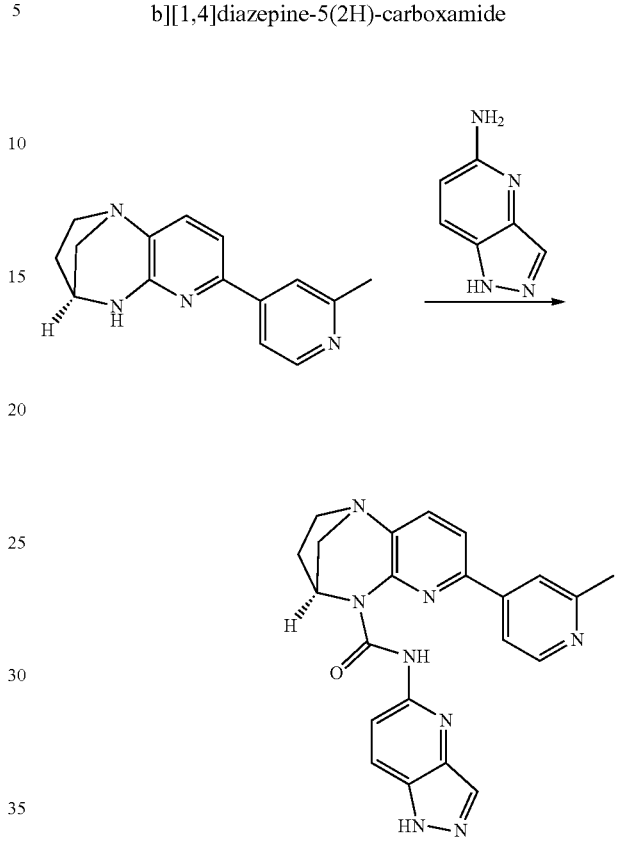

To a stirred solution of (4S)-7-(2-methylpyridin-4-yl)-2,3,4,5-tetrahydro-1,4-methanopyrido[2,3-b][1,4]diazepine (600 mg, 2.378 mmol) in THF (10 mL) was added triphosgene (353 mg, 1.189 mmol) at RT and stirred for 30 min, to this triethylamine (1.657 mL, 11.89 mmol) and 1H-pyrazolo[4,3-b] pyridin-5-amine (319 mg, 2.378 mmol) were added. The reaction mixture was stirred at 60° C. for 16 h. Reaction mixture was quenched with 2×15 ml of water and extracted with 2×15 ml of ethyl acetate. The combined organic layer was dried over anhydrous sodium sulfate and concentrated under reduced pressure to obtain crude compound. The crude product was purified by column chromatography (100-200 mesh) to afford (4S)-7-(2-methylpyridin-4-yl)-N-(1H-pyrazolo[4,3-b]pyridin-5-yl)-3,4-dihydro-1,4-methanopyrido[2,3-b][1,4]diazepine-5(2H)-carboxamide (265 mg, 0.622 mmol, 26.2% yield) as a pale yellow solid (TLC: $R_f$ value: 0.25, Neat ethyl acetate), LCMS (m/z): 413.28 [M+H]$^+$.

$^1$H NMR (400 MHz, DMSO-d6): δ 13.55 (s, 1H), 13.27 (s, 1H), 8.66 (dd, J=5.4, 0.8 Hz, 1H), 8.32 (d, J=9.2 Hz, 1H), 8.16-7.94 (m, 4H), 7.94-7.51 (m, 2H), 5.55 (dd, J=6.0, 3.1 Hz, 1H), 3.21 (d, J=8.7 Hz, 1H), 3.18-3.05 (m, 2H), 2.97 (dd, J=12.0, 3.3 Hz, 1H), 2.69 (s, 3H), 2.35-2.17 (m, 1H), 1.96 (dt, J=14.2, 7.6 Hz, 1H).

Example 142

Synthesis of (4S)—N-(2-((S)-2,3-dihydroxypropoxy)pyrimidin-4-yl)-7-(3-(trifluoromethyl)phenyl)-3,4-dihydro-1,4-methanopyrido[2,3-b][1,4]diazepine-5(2H)-carboxamide

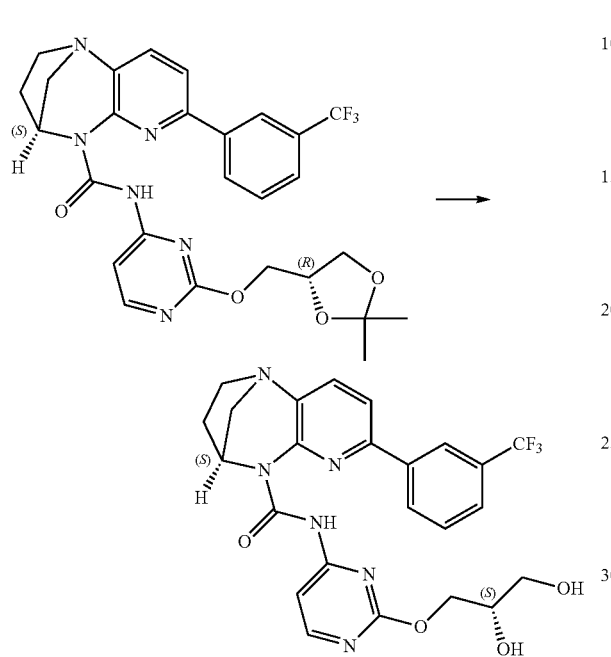

To a solution of (4S)—N-(2-(((R)-2,2-dimethyl-1,3-dioxolan-4-yl)methoxy)pyrimidin-4-yl)-7-(3-(trifluoromethyl)phenyl)-3,4-dihydro-1,4-methanopyrido[2,3-b][1,4]diazepine-5 (2H)-carboxamide (350 mg, 0.629 mmol) in dichloromethane (8 mL), water (0.8 mL) was added 4.0 M hydrochloric acid in 1,4-dioxane (1.12 mL, 0.629 mmol) dropwise over 1 min at 0° C. The reaction mixture was stirred at 30° C. for 3 h and concentrated the solvent. The reaction mixture was partitioned between water (10 mL) and EtOAc (25 mL). Organic layers were washed with water, brine solution, dried over anhydrous $Na_2SO_4$ and evaporated to give crude compound (TLC eluent: 5% MeOH in DCM: $R_f$=0.2; UV active). The crude was purified by chiral separation to get (4S)—N-(2-((S)-2,3-dihydroxypropoxy)pyrimidin-4-yl)-7-(3-(trifluoromethyl)phenyl)-3,4-dihydro-1,4-methanopyrido[2,3-b][1,4]diazepine-5 (2H)-carboxamide (210 mg, 0.405 mmol, 64.3% yield) as off white solid, LCMS (m/z): 517.3 $[M+H]^+$.

$^1$H NMR (400 MHz, DMSO-$d_6$): δ 13.59 (s, 1H), 8.60 (d, J=7.5 Hz, 1H), 8.46 (d, J=5.7 Hz, 1H), 8.27 (s, 1H), 7.90-7.78 (m, 3H), 7.76-7.69 (m, 2H), 5.48 (dd, J=5.8, 3.0 Hz, 1H), 4.91 (d, J=5.0 Hz, 1H), 4.63 (t, J=5.5 Hz, 1H), 4.46-4.01 (m, 2H), 3.80 (h, J=5.5 Hz, 1H), 3.44 (t, J=5.5 Hz, 2H), 3.21 (s, 1H), 3.12 (dd, J=10.1, 5.5 Hz, 2H), 2.96 (dd, J=12.0, 3.3 Hz, 1H), 2.24 (d, J=8.7 Hz, 1H), 2.03-1.90 (m, 1H).

Example 143

Synthesis of (4S)-7-(2,6-dimethylpyridin-4-yl)-N-(pyrazin-2-yl)-3,4-dihydro-1,4-methanopyrido[2,3-b][1,4]diazepine-5(2H)-carboxamide

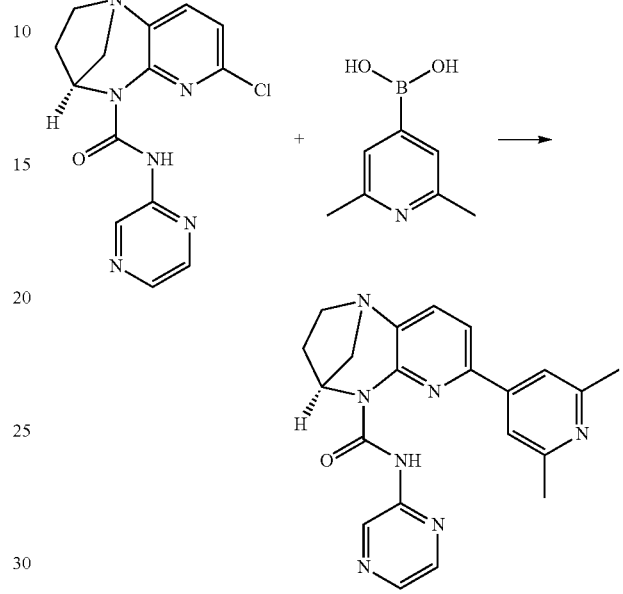

Tripotassium phosphate (804 mg, 3.79 mmol) was added to a stirred solution of (4S)-7-chloro-N-(pyrazin-2-yl)-3,4-dihydro-1,4-methanopyrido[2,3-b][1,4]diazepine-5(2H)-carboxamide (600 mg, 1.894 mmol), (2,6-dimethylpyridin-4-yl)boronic acid (343 mg, 2.273 mmol) in 1-butanol (10 mL), and water (1.667 mL) at 28° C. The reaction mixture was degassed for 15 min, was added $Pd_2(dba)_3$ (87 mg, 0.095 mmol), and X-phos (90 mg, 0.189 mmol). The reaction mixture was further degassed for 15 min, and the reaction mixture was stirred for 3 hr at 100° C. The reaction mixture was cooled to 28° C. and was partitioned between water (10 mL) and EtOAc (25 mL). Organic layer was separated and was dried over anhydrous $Na_2SO_4$, filtered and filtrate was evaporated to give crude as brown solid (TLC eluent: 10% MeOH in EtOAc; $R_f$=0.3; UV active). The crude was purified by column chromatography using (100-200 mesh) silica gel and was eluted with 5-10% MeOH in EtOAc to afford pure (4S)-7-(2,6-dimethylpyridin-4-yl)-N-(pyrazin-2-yl)-3,4-dihydro-1,4-methanopyrido[2,3-b][1,4]diazepine-5(2H)-carboxamide (355 mg, 0.916 mmol, 48.3% yield) as pale yellow solid, LCMS (m/z): 387.44 $[M+H]^+$.

$^1$H NMR (DMSO-$d_6$, 400 MHz,): δ 13.77 (s, 1H), 9.43 (d, J=1.5 Hz, 1H), 8.53-8.28 (m, 2H), 7.91-7.59 (m, 4H), 5.51 (dd, J=6.0, 3.1 Hz, 1H), 3.25-2.81 (m, 4H), 2.56-2.46 (m, 6H), 2.26 (dddd, J=13.7, 9.9, 6.1, 3.7 Hz, 1H), 1.97 (dq, J=14.4, 7.5, 6.8 Hz, 1H).

Example 144

Synthesis of (4S)-7-(2-cyclopropylpyridin-4-yl)-N-(pyrazin-2-yl)-3,4-dihydro-1,4-methanopyrido[2,3-b][1,4]diazepine-5(2H)-carboxamide

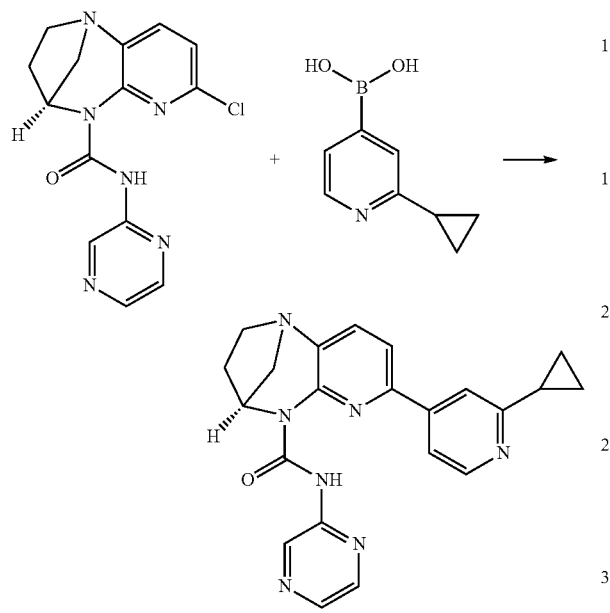

Tripotassium phosphate (670 mg, 3.16 mmol) was added to a stirred solution of (4S)-7-chloro-N-(pyrazin-2-yl)-3,4-dihydro-1,4-methanopyrido[2,3-b][1,4]diazepine-5(2H)-carboxamide (500 mg, 1.579 mmol), (2-cyclopropylpyridin-4-yl)boronic acid (309 mg, 1.894 mmol) in 1,4-dioxane (10 mL), and water (1.667 mL) at 28° C. The reaction mixture was degassed for 15 min, was added Pd$_2$(dba)$_3$ (72.3 mg, 0.079 mmol), and X-phos (75 mg, 0.158 mmol). The reaction mixture was further degassed for 15 min, and the reaction mixture was stirred for 3 hr at 100° C. The reaction mixture was cooled to 28° C. and was partitioned between water (10 mL) and EtOAc (25 mL). Organic layer was separated and was dried over anhydrous Na$_2$SO$_4$, filtered and filtrate was evaporated to give crude as brown solid (TLC eluent: 10% MeOH in EtOAc; R$_f$-0.3; UV active). The crude was purified by column chromatography using (100-200 mesh) silica gel and was eluted with 5-10% MeOH in EtOAc to afford pure (4S)-7-(2-cyclopropylpyridin-4-yl)-N-(pyrazin-2-yl)-3,4-dihydro-1,4-methanopyrido[2,3-b][1,4]diazepine-5(2H)-carboxamide (260 mg, 0.645 mmol, 40.8% yield) as off white solid, LCMS (m/z): 400.28 [M+H]$^+$.

$^1$H NMR (DMSO-d$_6$, 400 MHz): δ 13.75 (s, 1H), 9.43 (d, J=1.5 Hz, 1H), 8.54 (d, J=5.4 Hz, 1H), 8.46-8.28 (m, 2H), 8.19-8.01 (m, 1H), 7.89-7.62 (m, 3H), 5.52 (dd, J=6.0, 3.1 Hz, 1H), 3.30-2.86 (m, 4H), 2.27 (ddd, J=13.2, 6.4, 4.1 Hz, 2H), 1.98 (dt, J=14.5, 7.6 Hz, 1H), 1.17-0.88 (m, 4H).

Example 145

Synthesis of (4S)-7-(2-isopropylpyridin-4-yl)-N-(pyrazin-2-yl)-3,4-dihydro-1,4-methanopyrido[2,3-b][1,4]diazepine-5(2H)-carboxamide

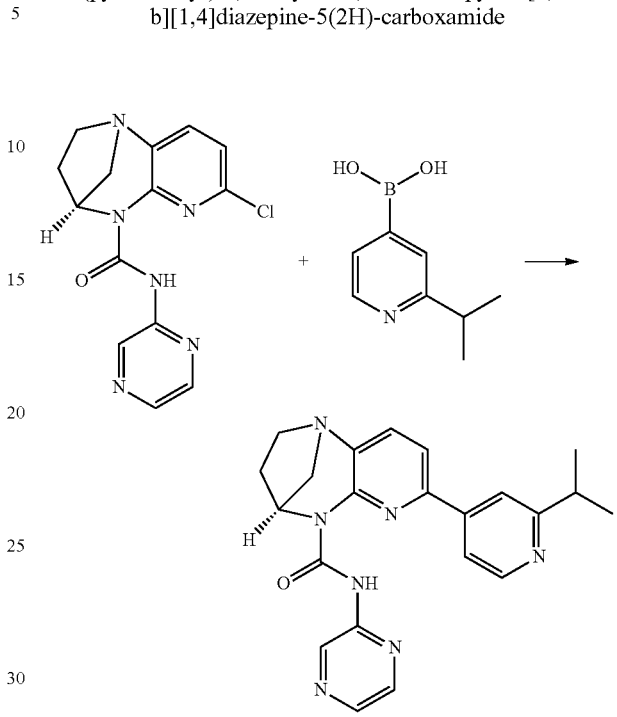

Tripotassium phosphate (670 mg, 3.16 mmol) was added to a stirred solution of (4S)-7-chloro-N-(pyrazin-2-yl)-3,4-dihydro-1,4-methanopyrido[2,3-b][1,4]diazepine-5(2H)-carboxa-mide (500 mg, 1.579 mmol), (2-isopropylpyridin-4-yl)boronic acid (313 mg, 1.894 mmol) in 1,4-dioxane (10 mL), and water (1.667 mL) at 28° C. The reaction mixture was degassed for 15 min, was added Pd$_2$(dba)$_3$ (72.3 mg, 0.079 mmol), and X-phos (75 mg, 0.158 mmol). The reaction mixture was further degassed for 15 min, and the reaction mixture was stirred for 3 hr at 100° C. The reaction mixture was cooled to 28° C. and was partitioned between water (10 mL) and EtOAc (25 mL). Organic layer was separated and was dried over anhydrous Na$_2$SO$_4$, filtered and filtrate was evaporated to give crude as brown solid (TLC eluent: 10% MeOH in EtOAc: R$_f$=0.3; UV active). The crude was purified by column chromatography using (100-200 mesh) silica gel and was eluted with 5-10% MeOH in EtOAc to afford pure (4S)-7-(2-isopropylpyridin-4-yl)-N-(pyrazin-2-yl)-3,4-dihydro-1,4-methanopyrido[2,3-b][1,4]diazepine-5(2H)-carboxamide (320 mg, 0.793 mmol, 50.2% yield) as Off white solid. LCMS (m/z): 402.33 [M+H]$^+$.

$^1$H NMR (CDCl$_3$, 400 MHz): δ 13.65 (s, 1H), 9.57 (d, J=1.5 Hz, 1H), 8.68 (d, J=5.2 Hz, 1H), 8.44-8.07 (m, 2H), 8.02-7.87 (m, 1H), 7.75-7.58 (m, 2H), 7.48 (d, J=8.0 Hz, 1H), 5.73 (dd, J=6.0, 3.2 Hz, 1H), 3.43-3.14 (m, 4H), 3.04 (dd, J=12.1, 3.3 Hz, 1H), 2.35 (dt, J=11.7, 5.0 Hz, 1H), 2.22-2.00 (m, 1H), 1.41 (dd, J=6.9, 0.9 Hz, 6H).

Example 146

Synthesis of (4S)—N-(1-methyl-1H-1,2,3-triazol-4-yl)-7-(2-methylpyridin-4-yl)-3,4-dihydro-1,4-methanopyrido[2,3-b][1,4]diazepine-5(2H)-carboxamide

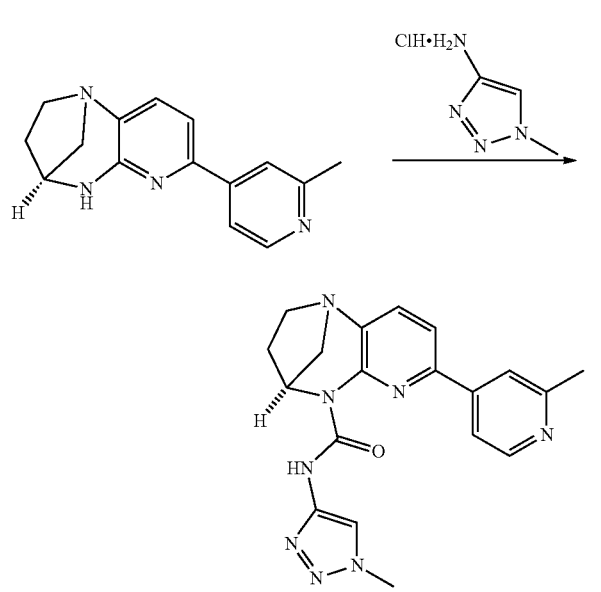

Triphosgene (0.588 g, 1.982 mmol) was added to a stirred solution of (4S)-7-(2-methylpyridin-4-yl)-2,3,4,5-tetrahydro-1,4-methanopyrido[2,3-b][1,4]diazepine (0.5 g, 1.982 mmol) in tetrahydrofuran (20 mL) at 0° C., followed by addition of triethylamine (0.829 mL, 5.94 mmol) and stirred for 30 min at 0° C. 1-Methyl-1H-1, 2,3-triazol-4-amine hydro-chloride (0.4 g, 2.97 mmol) was added and heated at 70° C. for 48h. The reaction mixture was cooled to 28° C. and was partitioned between water (10 mL) and ethyl acetate (50 mL). The organic layer was separated and washed with water and brine. The Organic layer was dried over anhydrous $Na_2SO_4$, filtered and filtrate was evaporated to afford crude yellow solid (TLC eluent: 10% MeOH in EtOAc: $R_f$=0.2; UV active). The crude compound was purified by 100-200 silica gel by eluting with 5% MeOH in ethyl acetate to afford (4S)—N-(1-methyl-1H-1,2,3-triazol-4-yl)-7-(2-methylpyridin-4-yl)-3,4-dihydro-1,4-methanopyrido[2,3-b][1,4]diazepine-5(2H)-carboxamide (0.260 g, 0.686 mmol, 34.6% yield) as an off white solid, LCMS (m/z): 377.28 $[M+H]^+$.

$^1$H NMR (400 MHz, DMSO-d6): δ 13.52 (s, 1H), 8.58 (dd, J=5.3, 0.8 Hz, 1H), 8.07 (s, 1H), 8.00 (d, J=1.7 Hz, 1H), 7.85-7.75 (m, 2H), 7.71 (d, J=8.0 Hz, 1H), 5.46 (dd, J=5.9, 3.0 Hz, 1H), 4.06 (s, 3H), 3.30 (s, 1H), 3.24-3.05 (m, 2H), 2.96 (dd, J=12.0, 3.2 Hz, 1H), 2.63 (s, 3H), 2.23 (dd, J=13.7, 9.8, 6.1, 3.7 Hz, 1H), 2.00-1.86 (m, 1H).

Example 147

Synthesis of (4S)-7-(2-ethylpyridin-4-yl)-N-(pyrazin-2-yl)-3,4-dihydro-1,4-methanopyrido[2,3-b][1,4]diazepine-5(2H)-carboxamide

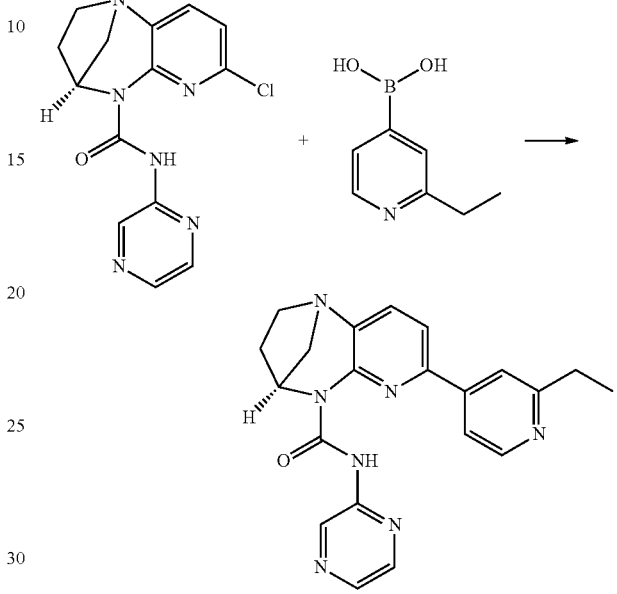

Tripotassium phosphate (804 mg, 3.79 mmol) was added to a stirred solution of (4S)-7-chloro-N-(pyrazin-2-yl)-3,4-dihydro-1,4-methanopyrido[2,3-b][1,4]diazepine-5(2H)-carboxa-mide (600 mg, 1.894 mmol), (2-ethylpyridin-4-yl) boronic acid (343 mg, 2.273 mmol) in n-butanol (10 mL) and water (1.667 mL). The reaction mixture was degassed for 15 min $Pd_2(dba)_3$ (87 mg, 0.095 mmol), and X-phos (90 mg, 0.189 mmol) were added. The reaction mixture was further degassed for 15 min, and was stirred at 100° C. for 5 hr. The reaction mixture was cooled to 28° C. and was partitioned between water (10 mL) and EtOAc (25 mL). Organic layer was separated and was dried over anhydrous $Na_2SO_4$, filtered. The filtrate was evaporated to get crude (TLC eluent: 10% MeOH in EtOAc: $R_f$ 0.2; UV active). The crude compound was purified by (100-200 mesh) silica gel eluting with 20% MeOH in EtOAc to afford (4S)-7-(2-ethylpyridin-4-yl)-N-(pyrazin-2-yl)-3,4-dihydro-1,4-methanopyrido[2,3-b][1,4]diazepine-5(2H)-carboxamide (418 mg, 1.074 mmol, 56.7% yield) as an off white solid, LCMS (m/z): 388.26 $[M+H]^+$.

$^1$H NMR (DMSO-$d_6$,400 MHz): δ 13.72 (s, 1H), 9.43 (d, J=1.5 Hz, 1H), 8.62 (dd, J=5.3, 0.8 Hz, 1H), 8.53-8.21 (m, 2H), 8.08 (d, J=1.7 Hz, 1H), 7.97-7.64 (m, 3H), 5.52 (dd, J=6.0, 3.1 Hz, 1H), 3.30 (s, 1H), 3.23-3.08 (m, 3H), 3.03-2.81 (m, 2H), 2.34-2.16 (m, 1H), 1.99 (d, J=6.8 Hz, 1H), 1.31 (t, J=7.6 Hz, 3H).

Example 148

Synthesis of (4S)-7-(2-ethoxypyridin-4-yl)-N-(pyrazin-2-yl)-3,4-dihydro-1,4-methanopyrido[2,3-b][1,4]diazepine-5(2H)-carboxamide

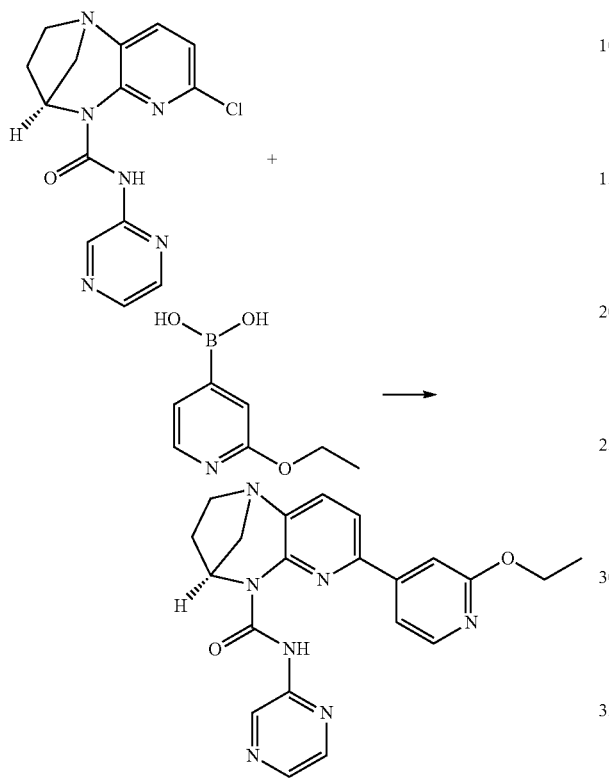

Tripotassium phosphate (804 mg, 3.79 mmol) was added to a stirred solution of (4S)-7-chloro-N-(pyrazin-2-yl)-3,4-dihydro-1,4-methanopyrido[2,3-b][1,4]diazepine-5(2H)-carbox-amide (600 mg, 1.894 mmol), (2-ethoxypyridin-4-yl)boronic acid (380 mg, 2.273 mmol) in 1-butanol (10 mL), and water (1.667 mL). The reaction mixture was degassed for 15 min $Pd_2(dba)_3$ (87 mg, 0.095 mmol), and X-phos (90 mg, 0.189 mmol) were added. The reaction mixture further degassed for 15 min, and was stirred at 100° C. for 4 hr. The reaction mixture was cooled to 28° C. and was partitioned between water (100 mL) and EtOAc (120 mL). EtOAc layer was separated and was dried over anhydrous $Na_2SO_4$, filtered and filtrate was evaporated to get crude (TLC eluent: 10% MeOH in EtOAc: $R_f$=0.4; UV active). The crude compound was purified by (100-200 mesh) silica gel, eluting with 10% MeOH in ethyl acetate to afford (4S)-7-(2-ethoxypyridin-4-yl)-N-(pyrazin-2-yl)-3,4-dihydro-1,4-methanopyrido[2,3-b][1,4]diazepine-5(2H)-carboxamide (435 mg, 1.063 mmol, 56.1% yield) as an off white solid, LCMS (m/z): 404.28 [M+H]$^+$.

$^1$H NMR (DMSO-d$_6$,400 MHz): δ 13.73 (s, 1H), 9.39 (d, J=1.5 Hz, 1H), 8.50-8.33 (m, 1H), 8.31-8.21 (m, 2H), 7.79 (d, J=8.0 Hz, 1H), 7.77-7.62 (m, 2H), 7.60 (d, J=2.2 Hz, 1H), 5.50 (dd, J=5.9, 3.0 Hz, 1H), 4.37 (q, J=7.0 Hz, 2H), 3.30 (s, 1H), 3.25-3.03 (m, 2H), 2.97 (dd, J=12.1, 3.3 Hz, 1H), 2.36-2.12 (m, 1H), 2.07-1.87 (m, 1H), 1.38 (t, J=7.0 Hz, 3H).

Example 149

Synthesis of (4S)-7-(2-methoxypyridin-4-yl)-N-(pyrazin-2-yl)-3,4-dihydro-1,4-methanopyrido[2,3-b][1,4]diazepine-5(2H)-carboxamide

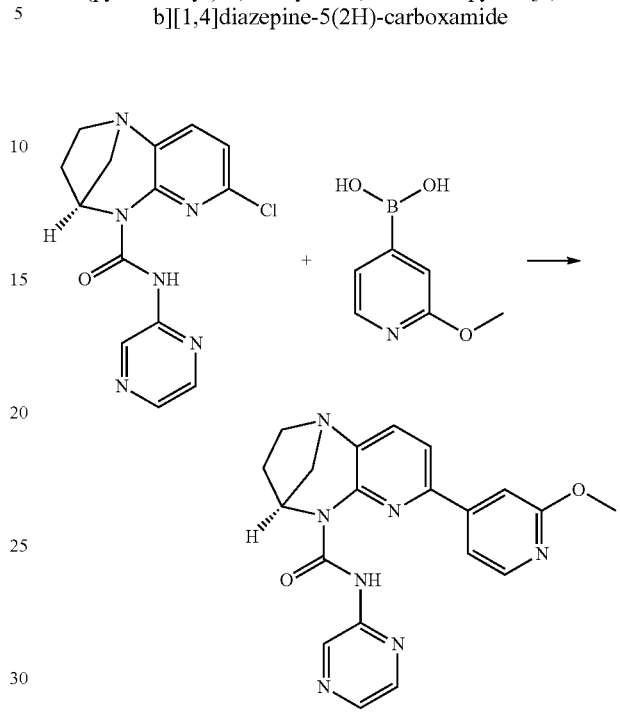

Tripotassium phosphate (804 mg, 3.79 mmol) was added to a stirred solution of (4S)-7-chloro-N-(pyrazin-2-yl)-3,4-dihydro-1,4-methanopyrido[2,3-b][1,4]diazepine-5(2H)-carboxamide (600 mg, 1.894 mmol), (2-methoxypyridin-4-yl) boronic acid (348 mg, 2.273 mmol) in 1,4-dioxane (12 mL), and water (2.000 mL). The reaction mixture was degassed for 15 min, $Pd_2(dba)_3$ (87 mg, 0.095 mmol), and X-phos (90 mg, 0.189 mmol) were added. The reaction mixture further degassed for 15 min, and was stirred at 100° C. for 5 hr. The reaction mixture was cooled to 28° C. and was partitioned between water (25 mL) and EtOAc (60 mL). Organic layer was separated and was dried over anhydrous $Na_2SO_4$, filtered and filtrate was evaporated to get crude (TLC eluent: 10% MeOH in EtOAc; $R_f$=0.2; UV active). The crude compound was purified by (100-200 mesh) silica gel eluting with 20% MeOH in ethyl acetate to afford (4S)-7-(2-methoxypyridin-4-yl)-N-(pyrazin-2-yl)-3,4-dihydro-1,4-methanopyrido[2,3-b][1,4]diazepine-5(2H)-carboxamide (310 mg, 0.793 mmol, 41.8% yield) as pale yellow solid, LCMS (m/z): 390.20 [M+H]$^+$.

$^1$H NMR (DMSO-d$_6$,400 MHz): δ 13.71 (s, 1H), 9.38 (d, J=1.5 Hz, 1H), 8.43 (dd, J=2.5, 1.5 Hz, 1H), 8.38 (s, 1H), 8.37 (d, J=2.5 Hz, 1H), 7.75 (d, J=22.0 Hz, 1H), 7.77-7.62 (m, 2H), 7.60 (s, 1H), 5.50 (dd, J=5.9, 3.0 Hz, 1H), 3.94 (s, 3H), 3.30 (s, 1H), 3.25-3.03 (m, 2H), 3.03-2.88 (m, 1H), 2.25 (dd, J=9.9, 3.9 Hz, 1H), 1.98 (dd, J=14.2, 7.2 Hz, 1H).

Example 150

Synthesis of (4S)-7-(2-methoxy-6-methylpyridin-4-yl)-N-(pyrazin-2-yl)-3,4-dihydro-1,4-methanopyrido[2,3-b][1,4]diazepine-5(2H)-carboxamide

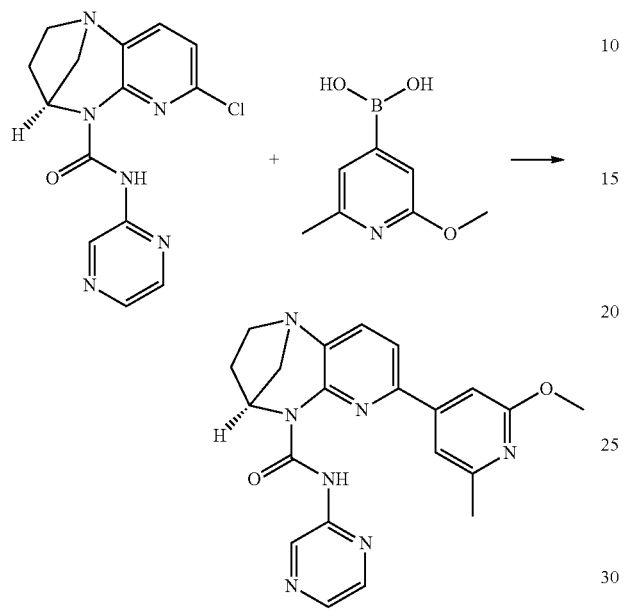

Tripotassium phosphate (804 mg, 3.79 mmol) was added to a stirred solution of (4S)-7-chloro-N-(pyrazin-2-yl)-3,4-dihydro-1,4-methanopyrido[2,3-b][1,4]diazepine-5(2H)-carboxamide (600 mg, 1.894 mmol), (2-methoxy-6-methylpyridin-4-yl)boronic acid (380 mg, 2.273 mmol) in 1,4-dioxane (12 mL), and water (2.000 mL). The reaction mixture was degassed for 15 min, $Pd_2(dba)_3$ (87 mg, 0.095 mmol), and X-phos (90 mg, 0.189 mmol) were added. The reaction mixture further degassed for 15 min, and was stirred at 100° C. for 5 hr. The reaction mixture was cooled to 28° C. and was partitioned between water (25 mL) and EtOAc (60 mL). Organic layer was separated and was dried over anhydrous $Na_2SO_4$, filtered. The filtrate was evaporated to get crude (TLC eluent: 10% MeOH in EtOAc; $R_f$=0.3; UV active). The crude compound was purified by (100-200 mesh) silica gel eluting with 20% MeOH in ethyl acetate to afford (4S)-7-(2-methoxy-6-methylpyridin-4-yl)-N-(pyrazin-2-yl)-3,4-dihydro-1,4-methanopyrido[2,3-b][1,4]diazepine-5(2H)-carboxamide (225 mg, 0.547 mmol, 28.9% yield) as an off white solid, LCMS (m/z): 404.24 $[M+H]^+$.

$^1$H NMR (DMSO-$d_6$, 400 MHz): δ 13.72 (s, 1H), 9.41 (d, J=1.5 Hz, 1H), 8.55-8.26 (m, 2H), 7.86-7.64 (m, 3H), 7.31 (dd, J=1.4, 0.7 Hz, 1H), 5.51 (dd, J=6.0, 3.1 Hz, 1H), 3.91 (s, 3H), 3.22-3.00 (m, 3H), 2.97 (dd, J=12.1, 3.3 Hz, 1H), 2.63-2.41 (m, 3H), 2.25 (dddd, J=13.8, 9.8, 6.1, 3.6 Hz, 1H), 1.97 (dt, J=14.3, 7.6 Hz, 1H).

Example 151

Synthesis of (9S)—N-(pyridin-2-yl)-2-(3-(trifluoromethyl)piperidin-1-yl)-8,9-dihydro-6H-5,9-methanopyrido[2,3-b][1,4]diazocine-10(7H)-carboxamide

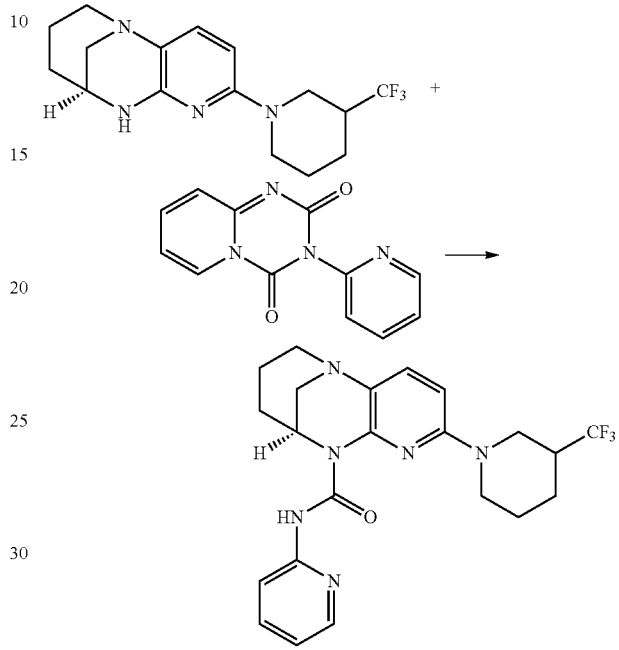

NaH (0.110 g, 4.60 mmol) was added to a stirred solution of (9S)-2-(3-(trifluoromethyl)piperidin-1-yl)-7,8,9,10-tetrahydro-6H-5,9-methanopyrido[2,3-b][1,4]diazocine (Peak-II from the intermediate SFC separation, 0.250 g, 0.766 mmol) in Tetrahydrofuran (THF) (20 mL) stirred under nitrogen at room temp. The reaction mixture was stirred at room temp for 30 minutes. Then 3-(pyridin-2-yl)-2H-pyrido[1,2-a][1,3,5]triazine-2,4(3H)-dione (0.276 g, 1.149 mmol) was added at room temp° C. Then reaction mixture was stirred at 65° C. for 24 hr. Reaction was cooled to room temperature and was partitioned between water (10 mL) and EtOAc (50 mL). Organic layer was separated and was dried over anhydrous $Na_2SO_4$, filtered and filtrate was evaporated to give crude as brown solid (TLC eluent: 70% EtOAc in Hexane: $R_f$-0.3; UV active). The crude was purified by column chromatography using (100-200 mesh) silica gel and was eluted with 50-60% EtOAc in Hexane to afford pure afford (9S)—N-(pyridin-2-yl)-2-(3-(trifluoromethyl)piperidin-1-yl)-8,9-dihydro-6H-5,9-methanopyrido[2,3-b][1,4]diazocine-10(7H)-carboxamide (0.2 g, 0.439 mmol, 57.3% yield) as a off-white solid, LCMS (m/z): 447.2 $[M+H]^+$.

$^1$H NMR (400 MHz, DMSO-$d_6$): δ 13.50 (s, 1H), 8.32-8.18 (m, 1H), 8.16-8.03 (m, 1H), 7.76 (ddd, J=8.8, 7.4, 2.0 Hz, 1H), 7.35 (d, J=8.6 Hz, 1H), 7.05 (dd, J=7.8, 4.5 Hz, 1H), 6.60 (d, J=8.7 Hz, 1H), 4.72 (d, J=2.7 Hz, 1H), 4.27 (s, 2H), 3.31-3.24 (m, 1H), 3.22-2.89 (m, 4H), 2.80 (d, J=13.3 Hz, 1H), 2.51 (s, 1H), 1.99 (t, J=12.7 Hz, 2H), 1.85 (d, J=11.6 Hz, 2H), 1.75-1.43 (m, 2H), 1.25 (s, 2H).

Example 152

Synthesis of (9S)-2-(2-methylpyridin-4-yl)-N-(pyrimidin-4-yl)-8,9-dihydro-6H-5,9-methanopyrido[2,3-b][1,4]diazocine-10(7H)-carboxamide

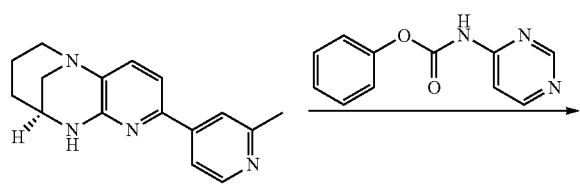

Example 153

Synthesis of (4S)—N-(1-methyl-1H-1,2,4-triazol-3-yl)-7-(2-methylpyridin-4-yl)-3,4-dihydro-1,4-methanopyrido[2,3-b][1,4]diazepine-5(2H)-carboxamide

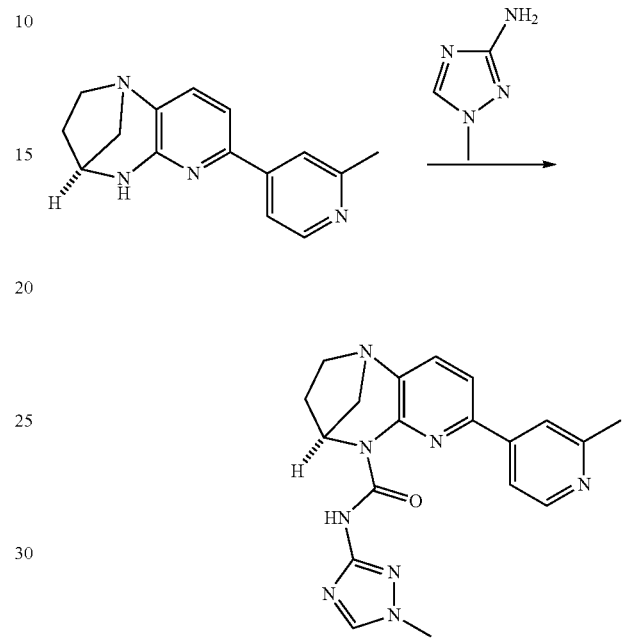

To a stirred solution of (9S)-2-(2-methylpyridin-4-yl)-7,8,9,10-tetrahydro-6H-5,9-methanopyrido[2,3-b][1,4]diazocine (0.350 g, 1.314 mmol), DMAP (0.482 g, 3.94 mmol) in THF (7 mL) was added phenyl pyrimidin-4-ylcarbamate (0.848 g, 3.94 mmol) at 25° C. The reaction mixture was stirred at 80° C. for 16 h. The solvent was removed under vacuo and crude was diluted with $CH_2Cl_2$ (20 ml) and washed with water (5 mL), saturated brine solution (5 mL) and dried over $Na_2SO_4$. The organic solvent was evaporated under reduced pressure to obtain the crude product. The crude mixture was purified by flash column chromatography (silica-gel: 100-200 mesh, eluted with 3% MeOH in $CH_2Cl_2$) to afford (9S)-2-(2-methylpyridin-4-yl)-N-(pyrimidin-4-yl)-8,9-dihydro-6H-5,9-methanopyrido[2,3-b][1,4]diazocine-10(7H)-carboxamide (207 mg, 0.529 mmol, 40.3% yield) as a white solid (TLC: 10% MeOH in DCM, $R_f$: 0.7), LCMS (m/z): 388.3 $[M+H]^+$.

$^1$H NMR (400 MHz, DMSO-d6): δ 14.32 (s, 1H), 8.95 (d, J=1.3 Hz, 1H), 8.69 (d, J=5.8 Hz, 1H), 8.61 (d, J=5.3 Hz, 1H), 8.17 (d, J=1.7 Hz, 1H), 8.15 (dd, J=5.8, 1.3 Hz, 1H), 7.95 (dd, J=5.3, 1.8 Hz, 1H), 7.86 (d, J=8.1 Hz, 1H), 7.74 (d, J=8.1 Hz, 1H), 4.90-4.67 (m, 1H), 3.40 (dd, J=13.7, 1.9 Hz, 1H), 3.28 (s, 2H), 3.00-2.81 (m, 1H), 2.64 (s, 3H), 2.13-1.71 (m, 2H), 1.41-1.14 (m, 2H).

Triphosgene (0.588 g, 1.982 mmol) was added to a stirred solution of (4S)-7-(2-methylpyridin-4-yl)-2,3,4,5-tetrahydro-1,4-methanopyrido[2,3-b][1,4]diazepine (0.5 g, 1.982 mmol) in tetrahydrofuran (20 mL) at 0° C. and stirred for 30 min. Triethylamine (0.829 mL, 5.94 mmol) and 1-methyl-1H-1,2,4-triazol-3-amine (0.486 g, 4.95 mmol) was added at 0° C. The reaction mixture was stirred for 48h at 70° C. The reaction mixture was cooled to 28° C., and was partitioned between water (50 mL) and DCM (50 mL). The separated organic layer was washed with water and brine. The organic layer was dried over anhydrous $Na_2SO_4$, filtered and filtrate was evaporated to afford crude yellow solid (TLC eluent: 10% MeOH in EtOAc: $R_f$-0.3; UV active). The crude compound was purified by (100-200 mesh) silica gel and was eluting with 5% MeOH in ethyl acetate to afford (4S)—N-(1-methyl-1H-1,2,4-triazol-3-yl)-7-(2-methylpyridin-4-yl)-3,4-dihydro-1,4-methanopyrido[2,3-b][1,4]diazepine-5(2H)-car-boxamide (0.215 g, 0.563 mmol, 28.4% yield) as light yellow solid, LCMS (m/z): 377.28 $[M+H]^+$.

$^1$H NMR (400 MHz, DMSO-d6): δ 13.44 (s, 1H), 8.55 (d, J=5.2 Hz, 1H), 8.36 (s, 1H), 7.96 (s, 1H), 7.86-7.61 (m, 3H), 5.44 (dd, J=5.8, 3.0 Hz, 1H), 3.83 (s, 3H), 3.27 (d, J=30.5 Hz, 3H), 2.95 (dd, J=12.0, 3.2 Hz, 1H), 2.59 (s, 3H), 2.23 (ddt, J=16.9, 9.7, 4.4 Hz, 1H), 1.91 (dt, J=14.7, 7.4 Hz, 1H).

Example 154

Synthesis of (9S)-2-(2-methylpyridin-4-yl)-N-(pyrazin-2-yl)-8, 9-dihydro-6H-5, 9-methanopyrido[2,3-b][1, 4] diazocine-10(7H)-carboxamide

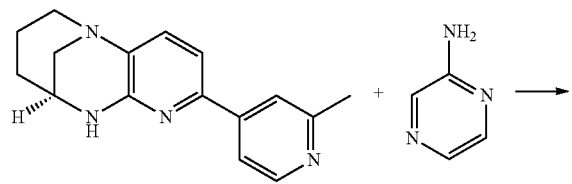

To a solution of (9S)-2-(2-methylpyridin-4-yl)-7,8,9,10-tetrahydro-6H-5,9-methanopyrido[2,3-b][1,4]diazocine (0.700 g, 2.63 mmol) in Tetrahydrofuran (THF) (30 mL) stirred under nitrogen at room temperature ° C. was added triethylamine (2.198 mL, 15.77 mmol) and triphosgene (0.780 g, 2.63 mmol). Then reaction mixture was stirred at room temperature for 30 minutes. pyrazin-2-amine (0.750 g, 7.88 mmol) was added at rt. Then the reaction mixture was stirred at 65° C. for 24 hr. The reaction mixture was concentrated to dryness and then partitioned between water (20 mL) and Dichloromethane (50 mL). Organic layer was separated and was dried over anhydrous $Na_2SO_4$, filtered and filtrate was evaporated to give crude as brown solid. The crude was purified by column chromatography using (100-200 mesh) silica gel to afford pure (9S)-2-(2-methylpyridin-4-yl)-N-(pyrazin-2-yl)-8,9-dihydro-6H-5,9-methanopyrido[2,3-b][1,4]diazocine-10(7H)-carboxamide as a pale yellow solid, LCMS (m/z): 388.3 $[M+H]^+$.

$^1$H NMR (400 MHz, $CDCl_3$): δ 14.27 (s, 1H), 9.59 (d, J=0.9 Hz, 1H), 8.67-8.60 (m, 1H), 8.32 (d, J=1.0 Hz, 2H), 8.10 (dt, J=1.9, 0.7 Hz, 1H), 7.74-7.67 (m, 1H), 7.62-7.50 (m, 2H), 5.06-5.00 (m, 1H), 3.51-3.27 (m, 3H), 3.03 (d, J=13.6 Hz, 1H), 2.74 (s, 3H), 2.26 (s, 3H), 2.08-1.84 (m, 1H), 1.43 (d, J=6.2 Hz, 2H).

Example 155

Synthesis of (4S)-7-(2-(methylamino)pyridin-4-yl)-N-(pyrazin-2-yl)-3,4-dihydro-1,4-meth anopyrido[2,3-b][1,4]diazepine-5(2H)-carboxamide

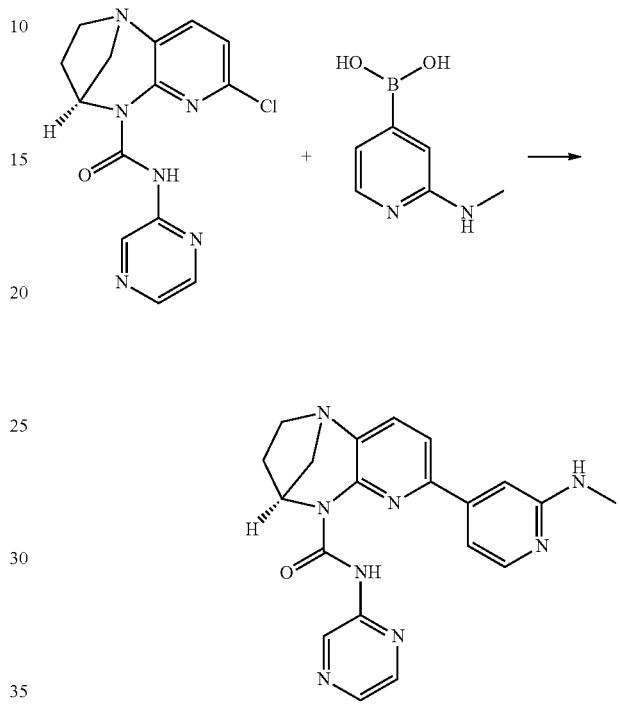

To a degassed solution of (4S)-7-chloro-N-(pyrazin-2-yl)-3,4-dihydro-1,4-methanopyrido[2,3-b][1,4]diazepine-5 (2H)-carboxamide (500 mg, 1.579 mmol), N-methyl-4-(4,4,5,5-tetramethyl-1,3,2-dioxaborolan-2-yl)pyridin-2-amine (443 mg, 1.894 mmol) and Potassium Phosphate tri basic (670 mg, 3.16 mmol) in 1,4-dioxane (15 mL) and water (2 mL) were added $Pd(OAc)_2$ (17.72 mg, 0.079 mmol) and dicyclohexyl(2',4',6'-triisopropyl-[1,1'-biphenyl]-2-yl)phosphine (75 mg, 0.158 mmol) at RT and the reaction mixture was heated at 120° C. for 4h. The n-butanol solvent was evaporated under reduced pressure and the obtained residue diluted with water and extracted with DCM (2×50 mL). The combined organic layer was washed with water, brine, dried over anhydrous sodium sulfate and solvent evaporated under reduced pressure to obtain crude product. The crude product was purified by flash column chromatography (silica-gel: 100-200 mesh, eluent: 3% MeOH in DCM) to afford (4S)-7-(2-(methylamino)pyridin-4-yl)-N-(pyrazin-2-yl)-3,4-dihydro-1,4-methanopyrido[2,3-b][1,4]diazepine-5(2H)-carboxamide (325 mg, 0.820 mmol, 51.9% yield) as a white solid (TLC: 10% MeOH in EtOAc, $R_f$: 0.2), LCMS (m/z): 389.2 $[M+H]^+$. $^1$H NMR (400 MHz, DMSO-$d_6$): δ ppm 13.64 (s, 1H), 9.40 (d, J=1.53 Hz, 1H), 8.46-8.31 (m, 2H), 8.14 (d, J=5.48 Hz, 1H), 7.71 (m, J=8.11 Hz, 1H), 7.61 (d, J=8.11 Hz, 1H), 7.22 (dd, J=5.37, 1.64 Hz, 1H), 7.03 (d, J=0.88 Hz, 1H), 6.40 (q, J=4.75 Hz, 1H), 5.51 (dd, J=5.92, 3.07 Hz, 1H), 3.35-3.04 (m, 3H), 2.96 (dd, J=12.06, 3.29 Hz, 1H), 2.85 (d, J=5.04 Hz, 3H), 2.25 (dddd, J=13.59, 9.87, 6.03, 3.62 Hz, 1H), 1.97 (dt, J=13.87, 6.99 Hz, 1H).

Example 156

Synthesis of (9S)-2-(2-methylpyridin-4-yl)-N-(pyridazin-3-yl)-8,9-dihydro-6H-5,9-methanopyrido[2,3-b][1,4]diazocine-10(7H)-carboxamide

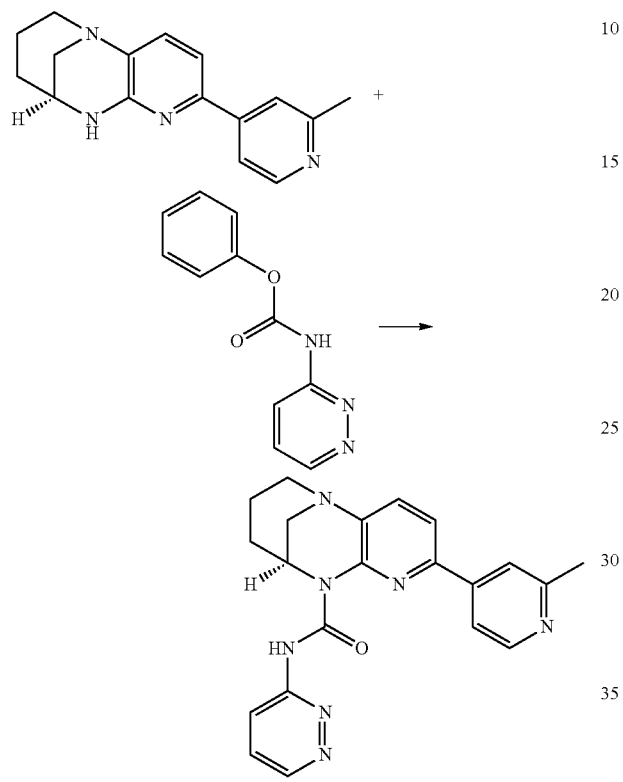

To a stirred solution of (9S)-2-(2-methylpyridin-4-yl)-7,8,9,10-tetrahydro-6H-5,9-methanopyrido[2,3-b][1,4]diazocine (0.150 g, 0.563 mmol), phenyl pyridazin-3-ylcarbamate (0.364 g, 1.690 mmol) in THF (3 mL) was added DMAP (0.206 g, 1.690 mmol) at 25° C. The reaction mixture was stirred at 80° C. for 16 h. Solvent was removed under reduced pressure, crude compound was diluted with DCM (10 ml), washed with water (3 ml), saturated brine solution (3 ml), dried over $Na_2SO_4$ and concentrated under reduced pressure to obtain crude product. The crude mixture was purified by flash column chromatography (silica-gel: 100-200 mesh, eluent: 2% MeOH in $CH_2Cl_2$) to afford (9S)-2-(2-methylpyridin-4-yl)-N-(pyridazin-3-yl)-8,9-dihydro-6H-5,9-methanopyrido[2,3-b][1,4]diazocine-10(7H)-carboxamide (271 mg, 0.692 mmol, 123% yield) as a white solid (TLC: 10% MeOH in $CH_2Cl_2$, $R_f$: 0.6), LCMS (m/z): 388.3 [M+H]$^+$.

$^1$H NMR (400 MHz, CDCl$_3$): δ 14.66 (s, 1H), 8.94 (dd, J=4.7, 1.5 Hz, 1H), 8.66 (dd, J=5.2, 0.8 Hz, 1H), 8.50 (dd, J=9.1, 1.5 Hz, 1H), 8.29 (d, J=1.8 Hz, 1H), 7.74 (dd, J=5.4, 1.8 Hz, 1H), 7.57 (d, J=4.3 Hz, 2H), 7.46 (dd, J=9.0, 4.7 Hz, 1H), 5.00 (p, J=2.6 Hz, 1H), 3.50-3.22 (m, 3H), 3.12-2.96 (m, 1H), 2.82 (s, 3H), 2.39-2.10 (m, 1H), 1.95 (tdd, J=14.2, 5.5, 3.0 Hz, 1H), 1.58-1.33 (m, 2H).

Example 157

(4S)—N-(1H-imidazo[4,5-c]pyridin-4-yl)-7-(2-methylpyridin-4-yl)-3,4-dihydro-1,4-methanopyrido[2,3-b][1,4]diazepine-5(2H)-carboxamide

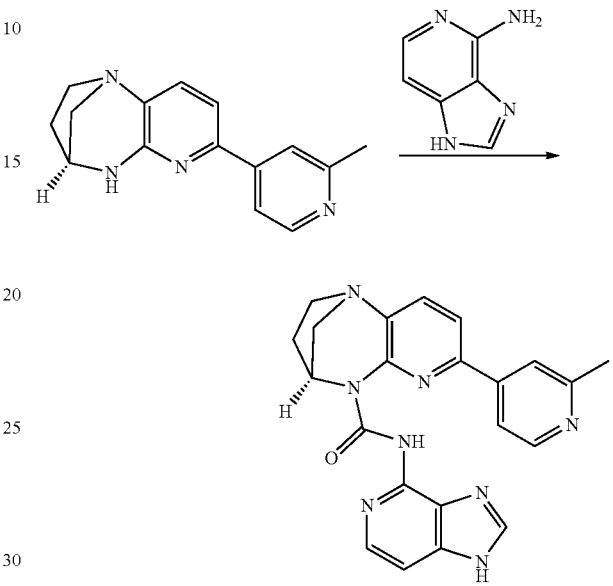

(4S)-7-(2-methylpyridin-4-yl)-2,3,4,5-tetrahydro-1,4-methanopyrido[2,3-b][1,4]diazepine (700 mg, 2.77 mmol) was dissolved in Tetrahydrofuran (THF) (10 mL) stirred under nitrogen at room temp was added triphosgene (412 mg, 1.387 mmol) and stirred for 30 min at RT, to this was added triethylamine (1.933 mL, 13.87 mmol) and 1H-imidazo[4,5-c]pyridin-4-amine (372 mg, 2.77 mmol) were added, then the reaction mixture was stirred at 60° C. for 16 hr. Reaction mixture was quenched with 2×15 ml of water and extracted with 2×15 ml of ethyl acetate, organic layer was dried over sodium sulfate and concentrated under reduced pressure to afford crude compound. The crude product was purified by column chromatography (100-200 mesh) to afford pure compound (4S)—N-(1H-imidazo[4,5-c]pyridin-4-yl)-7-(2-methylpyridin-4-yl)-3,4-dihydro-1,4-methanopyrido[2,3-b][1,4]diazepine-5(2H)-carboxamide (225 mg, 0.531 mmol, 19.14% yield) as pale yellow solid. ($R_f$ value: 0.4, 10% Methanol in DCM), LCMS (m/z): 413.1 [M+H]$^+$.

$^1$H NMR (400 MHz, CDCl$_3$): δ 14.03 (s, 1H), 11.93 (s, 1H), 8.65 (d, J=5.3 Hz, 1H), 8.35-7.86 (m, 3H), 7.86-7.37 (m, 4H), 5.72 (dd, J=5.9, 3.2 Hz, 1H), 3.21 (m, 3H), 3.06 (dd, J=12.2, 3.3 Hz, 1H), 2.78 (s, 3H), 2.38 (dddd, J=14.0, 9.9, 6.2, 4.2 Hz, 1H), 2.13 (dt, J=14.3, 7.2 Hz, 1H).

Example 158

Synthesis of (4S)-7-(2-methoxypyrimidin-5-yl)-N-(pyrazin-2-yl)-3,4-dihydro-1,4-methanopyrido[2,3-b][1,4]diazepine-5(2H)-carboxamide

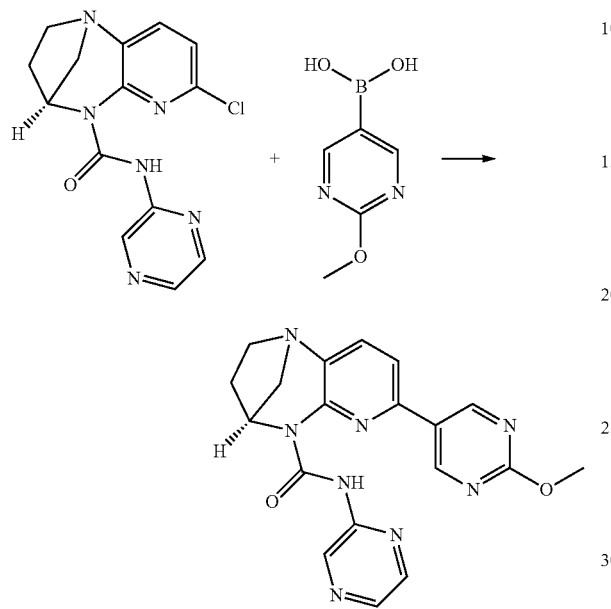

Potassium phosphate (402 mg, 1.894 mmol) and (2-methoxypyrimidin-5-yl)boronic acid (175 mg, 1.137 mmol) were added to a stirred solution of (4S)-7-chloro-N-(pyrazin-2-yl)-3,4-dihydro-1,4-methanopyrido[2,3-b][1,4]diazepine-5(2H)-carboxamide (300 mg, 0.947 mmol) in mixture of 1-Butanol (6 mL) and water (2.0 mL) at room temperature and de-gassed the mixture with Argon for 25 min, then added Pd$_2$(dba)$_3$ (43.4 mg, 0.047 mmol) and X-phos (45.2 mg, 0.095 mmol), heated at 120 C for 2h. Allowed the reaction mixture to room temperature, diluted with water (40 mL) and extracted with Ethyl acetate (3×30 mL), washed with brine (30 mL). The separated organic layer was concentrated and purified by flash column chromatography (silica-gel: 100-200 mesh, 80% Ethyl acetate in petroleum ether as an eluent). The recovered material was re-crystallized by using Ethanol and pentane to afford (4S)-7-(2-methoxypyrimidin-5-yl)-N-(pyrazin-2-yl)-3,4-dihydro-1,4-methanopyrido[2,3-b][1,4]diazepine-5(2H)-carboxamide (190 mg, 0.481 mmol, 50.8% yield) as an off white solid. (Mobile phase: 100% Ethyl acetate, R$_f$: 0.1), LCMS (m/z): 391.2 [M+H]$^+$.

$^1$H NMR (400 MHz, CDCl$_3$): δ 13.64 (s, 1H), 9.52 (d, J=1.5 Hz, 1H), 9.24 (s, 2H), 8.40-8.25 (m, 2H), 7.64 (d, J=7.9 Hz, 1H), 7.34 (d, J=8.0 Hz, 1H), 5.70 (dd, J=6.0, 3.1 Hz, 1H), 4.12 (s, 3H), 3.33-3.13 (m, 3H), 3.02 (d, J=3.3 Hz, 1H), 2.36 (dddd, J=13.9, 9.9, 5.9, 4.0 Hz, 1H), 2.17-2.04 (m, 1H).

Example 159

Synthesis of (4S)-7-(6-(hydroxymethyl)449yridine-3-yl)-N-(pyrazin-2-yl)-3,4-dihydro-1,4-methanopyrido[2,3-b][1,4]diazepine-5(2H)-carboxamide

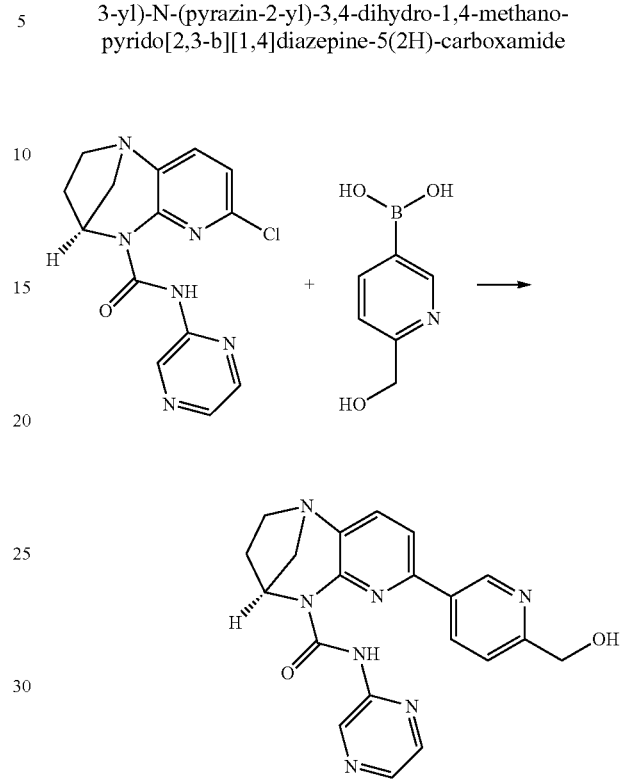

Potassium phosphate (535 mg, 2.53 mmol) and (6-(hydroxymethyl)pyridin-3-yl)boronic acid (232 mg, 1.515 mmol) were added to a stirred solution of (4S)-7-chloro-N-(pyrazin-2-yl)-3,4-dihydro-1,4-methanopyrido[2,3-b][1,4]diazepine-5(2H)-carboxamide (400 mg, 1.263 mmol) in mixture of 1-Butanol (6 mL) and water (2.0 mL) at room temperature. De-gassed the mixture with Argon for 10 min then added Pd$_2$(dba)$_3$ (57.8 mg, 0.063 mmol) and X-phos (60.2 mg, 0.126 mmol). The mixture was heated at 120 C for 20h. Allowed to cool the reaction mixture to room temperature and filtered through a pad of celite, washed with ethyl acetate (10 mL×2), filtrate solvent was removed under reduced pressure to afford crude compound. Above crude was purified by flash column chromatography (silica-gel: 100-200 mesh, eluted with 80% ethyl acetate in n-hexane) to afford (4S)-7-(6-(hydroxymethyl)pyridin-3-yl)-N-(pyrazin-2-yl)-3,4-dihydro-1,4-methanopyrido[2,3-b][1,4]diazepine-5(2H)-carboxamide (225 mg, 0.558 mmol, 44.2% yield) as an off white solid. (TLC: Eluent: 100% ethyl acetate R$_f$: 0.1), LCMS (m/z): 390.35 (M+H)$^+$.

$^1$HNMR (400 MHz, CDCl$_3$): δ 13.73 (s, 1H), 9.54 (d, J=1.3 Hz, 1H), 9.19 (dd, J=2.3, 0.9 Hz, 1H), 8.51 (dd, J=8.2, 2.3 Hz, 1H), 8.44-8.20 (m, 2H), 7.64 (d, J=8.0 Hz, 1H), 7.50-7.39 (m, 2H), 5.71 (dd, J=6.0, 3.2 Hz, 1H), 4.86 (d, J=2.4 Hz, 2H), 3.67 (s, 1H), 3.46-3.13 (m, 3H), 3.03 (dd, J=12.1, 3.3 Hz, 1H), 2.43-2.26 (m, 1H), 2.19-1.98 (m, 1H).

Example 160

Synthesis of (4S)—N-(2,3-dihydro-[1,4]dioxino[2,3-b]pyridin-7-yl)-7-(2-methylpyridin-4-yl)-3,4-dihydro-1,4-methanopyrido[2,3-b][1,4]diazepine-5(2H)-carboxamide

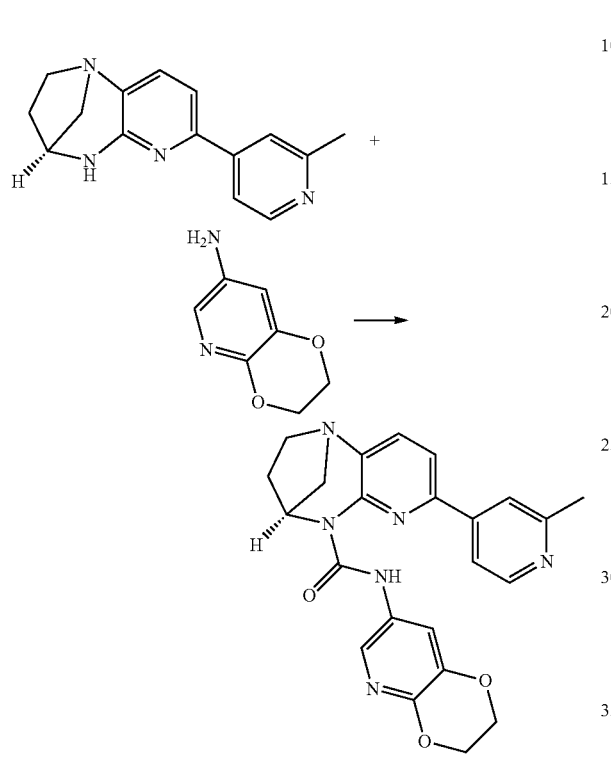

(4S)-7-(2-methylpyridin-4-yl)-2,3,4,5-tetrahydro-1,4-methanopyrido[2,3-b][1,4]diazepine (700 mg, 2.77 mmol) was dissolved in Tetrahydrofuran (THF) (10 mL) stirred under nitrogen at room temp was added triphosgene (412 mg, 1.387 mmol) and stirred for 30 min at RT, to this triethylamine (1.933 mL, 13.87 mmol) and 2,3-dihydro-[1,4]dioxino[2,3-b]pyridin-7-amine (422 mg, 2.77 mmol) were added. The reaction mixture was stirred at 60° C. for 16 hr. Reaction mixture was quenched with 2×15 ml of water and extracted with 2×20 ml of ethyl acetate, organic layer was dried over sodium sulfate and concentrated under reduced pressure to afford crude compound (800 mg). The crude product was purified by column chromatography to afford pure compound (4S)—N-(2,3-dihydro-[1,4]dioxino[2,3-b]pyridin-7-yl)-7-(2-methylpyridin-4-yl)-3,4-dihydro-1,4-methanopyrido[2,3-b][1,4]diazepine-5(2H)-carboxamide (325 mg, 0.732 mmol, 26.4% yield) as pale yellow solid. $R_f$ value: 0.4, 10% Methanol in DCM, LCMS (m/z): 413.28 [M+H]$^+$.

$^1$H NMR (400 MHz, DMSO-d$_6$): δ 12.81 (s, 1H), 8.58 (d, J=5.2 Hz, 1H), 7.82 (d, J=2.4 Hz, 1H), 7.78-7.40 (m, 5H), 5.45 (dd, J=5.9, 3.0 Hz, 1H), 4.46-4.31 (m, 2H), 4.29-4.16 (m, 2H), 3.19 (d, J=8.8 Hz, 1H), 3.14-3.03 (m, 2H), 2.96 (dd, J=12.0, 3.3 Hz, 1H), 2.55 (s, 3H), 2.23 (d, J=7.0 Hz, 1H), 1.93 (dd, J=14.1, 7.1 Hz, 1H).

Example 161

Synthesis of (9S)—N-(2-methyl-2H-indazol-5-yl)-2-(2-methylpyridin-4-yl)-8,9-dihydro-6H-5,9-methanopyrido[2,3-b][1,4]diazocine-10(7H)-carboxamide

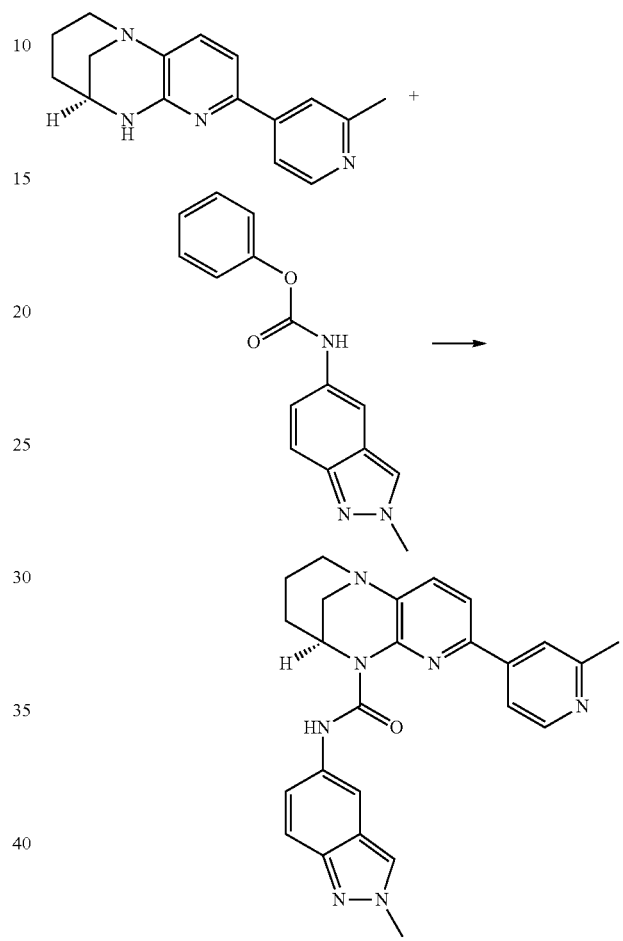

DMAP (0.550 g, 4.51 mmol) was added to a stirred solution of (9S)-2-(2-methylpyridin-4-yl)-7,8,9,10-tetrahydro-6H-5,9-methanopyrido[2,3-b][1,4]diazocine (0.4 g, 1.502 mmol) and phenyl (2-methyl-2H-indazol-5-yl)carbamate (0.803 g, 3.00 mmol) in Tetrahydrofuran (THF) (30 mL) under nitrogen atmosphere at room temp. The reaction was stirred at 70° C. for 48 hr. Reaction was cooled to room temperature and concentrated under reduced pressure. Added EtOAc to reaction mass and stirred for 10 minutes before being filtered and the solids washed with EtOAc. Take filtrate and concentrated to give the crude as brown solid (TLC eluent: 80% EtOAc: R$_f$-0.4; UV active). The crude was purified by column chromatography using neutral alumina and was eluted with 60% EtOAc in Hexane to afford pure afford (9S)—N-(2-methyl-2H-indazol-5-yl)-2-(2-methylpyridin-4-yl)-8,9-dihydro-6H-5,9-methanopyrido[2,3-b][1,4]diazocine-10(7H)-carboxamide (0.18 g, 0.406 mmol, 27.1% yield) as a off-white solid, LCMS (m/z): 440.4 [M+H]$^+$.

$^1$H NMR (400 MHz, CDCl$_3$): δ 13.44 (s, 1H), 8.66 (d, J=5.2 Hz, 1H), 8.18 (dd, J=1.9, 0.8 Hz, 1H), 7.82 (d, J=0.9 Hz, 1H), 7.69 (d, J=1.6 Hz, 1H), 7.63 (d, J=9.1 Hz, 1H), 7.60-7.50 (m, 2H), 7.40 (d, J=7.9 Hz, 1H), 7.27-7.19 (m, 1H), 5.05 (t, J=2.7 Hz, 1H), 4.20 (s, 3H), 3.50-3.23 (m, 3H), 3.01 (d, J=13.5 Hz, 1H), 2.67 (s, 3H), 2.28 (s, 1H), 1.93 (s, 1H), 1.58 (s, 2H).

Example 162

Synthesis of (4R)-7-(2-methylpyridin-4-yl)-N-(pyrazin-2-yl)-3,4-dihydro-1,4-methanopy-rido[2,3-b][1,4]diazepine-5(2H)-carboxamide

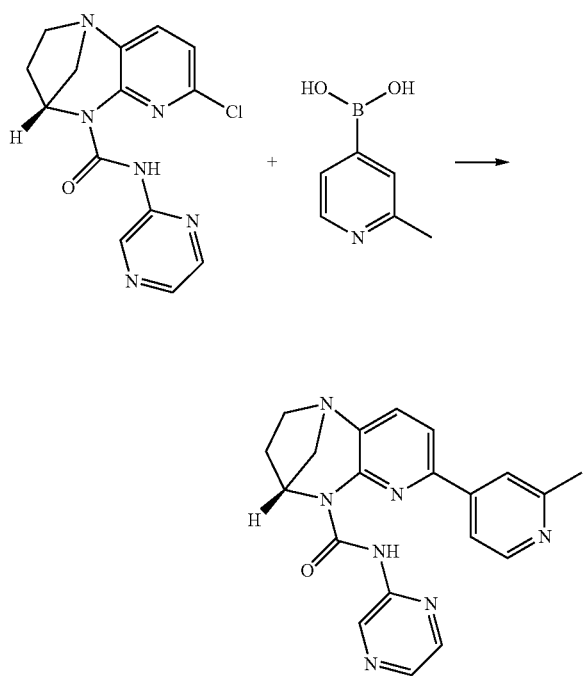

To a de-gassed solution of (4R)-7-chloro-N-(pyrazin-2-yl)-3,4-dihydro-1,4-methanopyrido[2,3-b][1,4]diazepine-5(2H)-carboxamide (700 mg, 2.210 mmol), (2-methylpyridin-4-yl)boronic acid (454 mg, 3.31 mmol) and $K_3PO_4$ (1825 mg, 6.63 mmol) in 1,4-dioxane (20 mL) and water (5.00 mL) were added X-Phos (211 mg, 0.442 mmol) and $Pd_2(dba)_3$ (202 mg, 0.221 mmol). The reaction mixture was heated at 110° C. for 2 h and allowed to cool to room temperature. Diluted with water (100 mL) and extracted with ethyl acetate (3×100 mL). The combined organic layer was dried over anhydrous $Na_2SO_4$ and concentrated under reduced pressure to obtain the crude product. The crude product was purified by flash column chromatography to afford (4R)-7-(2-methylpyridin-4-yl)-N-(pyrazin-2-yl)-3,4-dihydro-1,4-methanopyrido[2,3-b][1,4]diazepine-5(2H)-carboxamide (392 mg, 49.2% yield) as an off-white solid (TLC: eluent; 10% methanol in dichloromethane, $R_f$=0.3), LCMS (m/z): 374.18 [M+H]$^+$.

$^1$H NMR (400 MHz, DMSO-d$_6$): δ ppm 13.76 (s, 1H), 9.43 (d, J=1.53 Hz, 1H), 8.59 (d, J=5.26 Hz, 1H), 8.46 (dd, J=2.63, 1.53 Hz, 1H), 8.39 (d, J=2.41 Hz, 1H), 8.31 (s, 1H), 8.16-8.06 (m, 1H), 7.92-7.78 (m, 1H), 7.78-7.69 (m, 1H), 5.52 (dd, J=5.81, 3.18 Hz, 1H), 3.37 (m, 1H), 3.28-3.06 (m, 2H), 2.98 (dd, J=11.95, 3.18 Hz, 1H), 2.61 (s, 3H), 2.41-2.15 (m, 1H), 2.05-1.84 (m, 1H).

Example 163

((4S)-7-(2-methylpyridin-4-yl)-3, 4-dihydro-1, 4-methanopyrido [2, 3-b][1, 4] diazepine-5(2H)-yl) (Morpholino) methanone

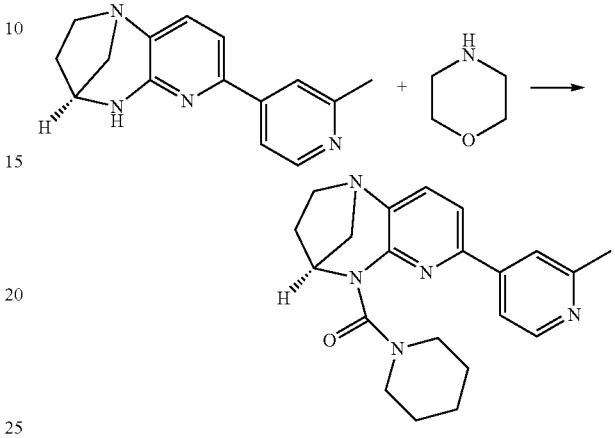

(4S)-7-(2-methylpyridin-4-yl)-2,3,4,5-tetrahydro-1,4-methanopyrido[2,3-b][1,4]diazepine (700 mg, 2.77 mmol) in Tetrahydrofuran (THF) (10 mL) stirred under nitrogen at room temp was added triphosgene (412 mg, 1.387 mmol) and stirred for 30 min at RT, To this triethylamine (1.933 mL, 13.87 mmol) and morpholine (314 mg, 3.61 mmol) were added. The reaction mixture was stirred at 60° C. for 16 hr. Reaction mixture was quenched with 2×15 ml of water and extracted with 2×20 ml of ethyl acetate, organic layer was dried over sodium sulfate and concentrated under reduced pressure to afford crude compound. The crude product was added to a 100-200 silica gel column and was eluted with 4% Methanol in DCM to afford pure compound ((4S)-7-(2-methylpyridin-4-yl)-3,4-dihydro-1,4-methanopyrido[2,3-b][1,4]diazepin-5(2H)-yl)(morpholino)methanone (270 mg, 0.735 mmol, 26.5% yield) as pale brown solid ($R_f$ value: 0.4, 10% Methanol in DCM), LCMS (m/z): 366.19 [M+H]$^+$.

$^1$H NMR (400 MHz, DMSO-d6) δ 8.52 (d, J=5.2 Hz, 1H), 7.85-7.75 (m, 1H), 7.70 (dd, J=5.2, 1.7 Hz, 1H), 7.57-7.30 (m, 1H), 4.38 (s, 1H), 3.50 (d, J=72.2 Hz, 8H), 3.23-2.95 (m, 1H), 2.89 (dd, J=11.6, 3.2 Hz, 1H), 2.58-2.32 (m, 6H), 2.33-1.92 (m, 2H).

Example 164

((4S)-7-(2-methylpyridin-4-yl)-3,4-dihydro-1,4-methanopyrido [2,3-b][1,4] diazepin-5(2H)-yl)(piperidin-1-yl) methanone

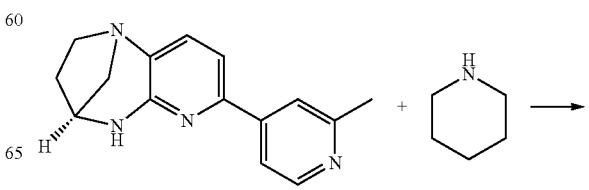

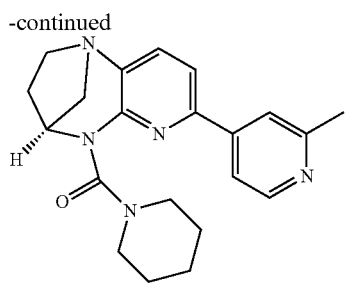

(4S)-7-(2-methylpyridin-4-yl)-2,3,4,5-tetrahydro-1,4-methanopyrido[2,3-b][1,4]diazepine (700 mg, 2.77 mmol) in Tetrahydrofuran (THF) (10 mL) stirred under nitrogen at room temp was added triphosgene (412 mg, 1.387 mmol) and stirred for 30 min at RT. To this triethylamine (1.933 mL, 13.87 mmol) and piperidine (236 mg, 2.77 mmol) were added. The reaction mixture was stirred at 60° C. for 16 hr. Reaction mixture was quenched with 2×15 ml of water and extracted with 2×20 ml of ethyl acetate, organic layer was dried over sodium sulfate and concentrated under reduced pressure to afford crude compound. The crude product was purified by column chromatography to afford pure compound ((4S)-7-(2-methylpyridin-4-yl)-3,4-dihydro-1,4-methanopyrido[2,3-b][1,4]diazepin-5 (2H)-yl)(piperidin-1-yl)methanone (220 mg, 0.583 mmol, 21.03% yield) as brown solid. ($R_f$ value: 0.4, 10% Methanol in DCM), LCMS (m/z): 364.21 [M+H]$^+$.

$^1$H NMR (400 MHz, DMSO-d6) δ 8.50 (d, J=5.2 Hz, 1H), 7.79 (d, J=1.8 Hz, 1H), 7.74-7.62 (m, 1H), 7.51-7.30 (m, 2H), 4.33 (t, J=4.2 Hz, 1H), 3.49 (d, J=71.1 Hz, 4H), 3.22-2.95 (m, 2H), 2.88 (dd, J=11.6, 3.2 Hz, 1H), 2.61-2.35 (m, 6H), 2.24-1.94 (m, 1H), 1.55 (s, 5H).

Example 165

Synthesis of (4S)-7-(2-methylpyridin-4-yl)-N-(pyrido[3,4-b]pyrazin-5-yl)-3,4-dihydro-1,4-methanopyrido[2,3-b][1,4]diazepine-5(2H)-carboxamide

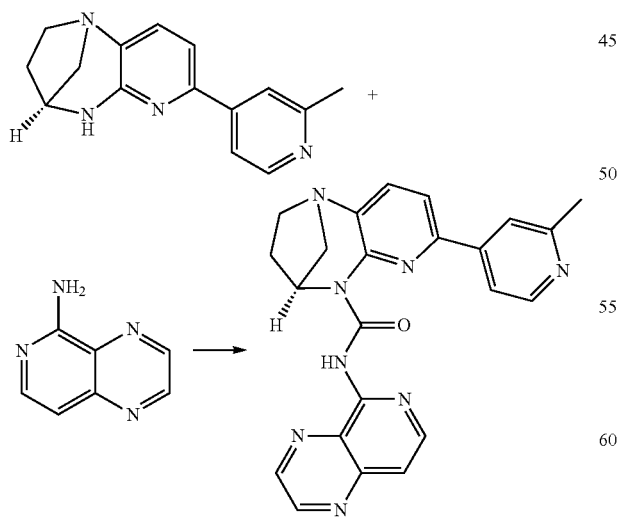

To a solution of (4S)-7-(2-methylpyridin-4-yl)-2,3,4,5-tetrahydro-1,4-methanopyrido[2,3-b][1,4]diazepine (600 mg, 2.378 mmol) in THF (30 ml) was added triphosgene (353 mg, 1.189 mmol) at 0° C. and stirred to RT for 1 h. Then pyrido[3,4-b]pyrazin-5-amine (452 mg, 3.09 mmol) and triethylamine (1.657 mL, 11.89 mmol) were added sequentially at RT and heated the reaction mixture at 70° C. for 16 h in sealed tube. The reaction mixture was poured in saturated NaHCO$_3$ solution (150 mL) and extracted with ethyl acetate (250 mL). The combined organic layer was dried over anhydrous Na$_2$SO$_4$ and concentrated under reduced pressure to obtain the crude product. The crude mixture was purified by flash column chromatography (silica-gel: 100-200 mesh, using gradient mixture of 1% MeOH in DCM as eluent) to afford (4S)-7-(2-methylpyridin-4-yl)-N-(pyrido[3,4-b]pyrazin-5-yl)-3,4-dihydro-1,4-methanopyrido[2,3-b][1,4]diazepine-5(2H)-carboxamide (260 mg, 0.613 mmol, 38% yield) as brown solid (TLC: 5% MeOH in DCM, $R_f$=0.3), LCMS (m/z): 425.27 [M+H]$^+$.

$^1$H NMR (400 MHz, DMSO-d$_6$): δ ppm 13.84 (s, 1H), 9.11 (d, J=1.97 Hz, 1H), 8.58 (d, J=5.70 Hz, 1H), 8.37-8.51 (m, 1H), 8.19 (d, J=1.97 Hz, 1H), 7.59-7.78 (m, 5H), 5.54-5.50 (m, 1H), 3.22-3.33 (m, 1H), 3.07-3.19 (m, 1H), 3.00 (dd, J=11.95, 3.18 Hz, 1H), 2.50 (dt, J=3.67, 1.78 Hz, 1H), 2.21-2.33 (m, 4H), 1.98 (dt, J=13.92, 7.07 Hz, 1H).

Example 166

Synthesis of (4S)—N-(3-methylcinnolin-5-yl)-7-(2-methylpyridin-4-yl)-3,4-dihydro-1,4-methanopyrido[2,3-b][1,4]diazepine-5(2H)-carboxamide

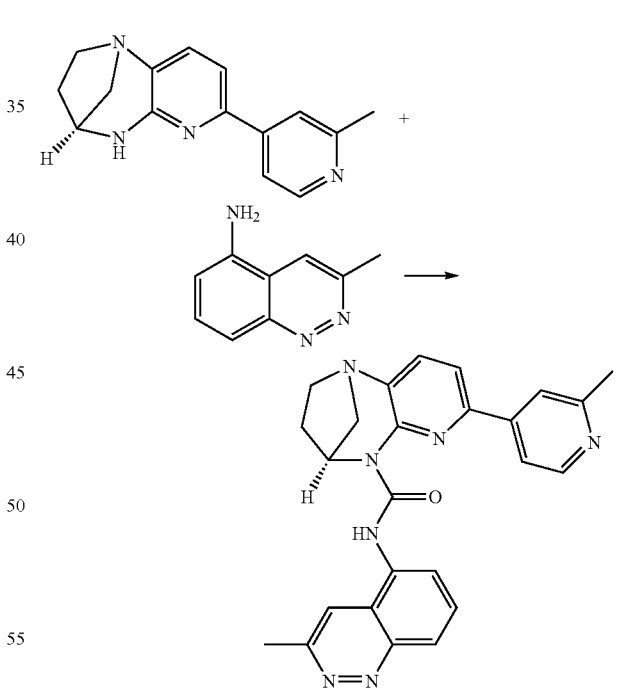

To a solution of (4S)-7-(2-methylpyridin-4-yl)-2,3,4,5-tetrahydro-1,4-methanopyrido[2,3-b][1,4]diazepine (600 mg, 2.378 mmol) in THF (30 ml) was added triphosgene (353 mg, 1.189 mmol) at 0° C. and stirred to RT for 1 h. Then 3-methylcinnolin-5-amine (492 mg, 3.09 mmol) and triethylamine (1.657 mL, 11.89 mmol) were added sequentially at RT and heated the reaction mixture at 70° C. for 16 h. The reaction mixture was poured in saturated NaHCO$_3$ solution (150 mL) and extracted with ethyl acetate (2×50 mL). The combined organic layer was dried over anhydrous $Na_2SO_4$ and concentrated under reduced pressure to obtain the crude product. The crude mixture was purified by flash column chromatography (silica-gel: 100-200 mesh, using gradient mixture of 1% MeOH in DCM as eluent) to afford (4S)—N-(3-methylcinnolin-5-yl)-7-(2-methylpyridin-4-yl)-3,4-dihydro-1,4-methanopyrido[2,3-b][1,4]diazepine-5(2H)-carboxamide (280 mg, 0.647 mmol, 42% yield) as pale yellow solid (TLC: 5% MeOH in DCM, $R_f$=0.25), LCMS (m/z): 438.26 [M+H]$^+$.

$^1$H NMR (400 MHz, CDCl$_3$): δ ppm 13.43 (s, 1H), 9.11 (s, 1H), 8.49 (d, J=5.92 Hz, 1H), 8.39 (d, J=7.45 Hz, 1H), 8.19 (s, 1H), 7.81 (t, J=8.11 Hz, 1H), 7.65 (d, J=7.5 Hz 1H), 7.35-7.31 (m, 3H), 5.77 (dd, J=5.81, 3.18 Hz, 1H), 3.41-3.15 (m, 3H), 2.91 (m, 1H), 2.30-2.25 (m, 3H), 2.24 (s, 3H), 2.10-1.92 (m, 1H).

Example 167

Synthesis of (4S)-7-(5-methylpyridin-3-yl)-N-(pyrazin-2-yl)-3,4-dihydro-1,4-methanopyrido[2,3-b][1,4]diazepine-5(2H)-carboxamide

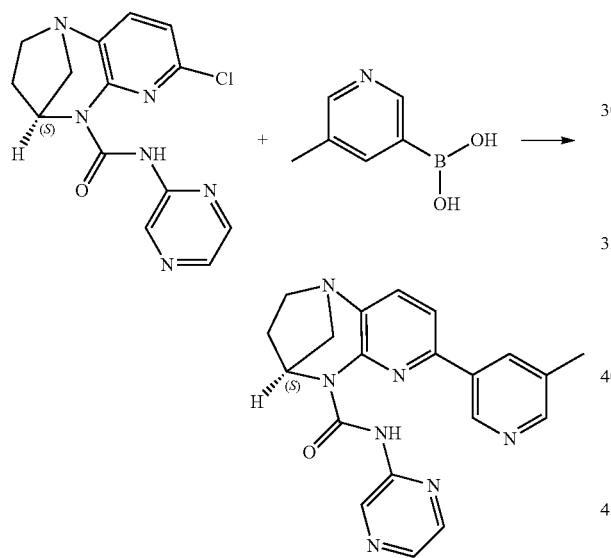

To a solution of (4S)-7-chloro-N-(pyrazin-2-yl)-3,4-dihydro-1,4-methanopyrido[2,3-b][1,4]diazepine-5(2H)-carboxamide (600 mg, 1.894 mmol), (5-methylpyridin-3-yl)boronic acid (311 mg, 2.273 mmol) and K$_3$PO$_4$ (804 mg, 3.79 mmol) in 1,4-dioxane (12.00 mL), water (4.00 mL) and degassed with argon for 20 min was added X-Phos (90 mg, 0.189 mmol), tris(dibenzylideneacetone)dipalladium(0) (87 mg, 0.095 mmol) again degassed with argon for 10 min. The reaction mixture was stirred at 100° C. for 4 h and cooled to room temperature. The reaction mixture was filtered through celite then the filtrate was diluted with water and extracted with EtOAc (3×10 mL). The combined organic layers were washed with water, brine solution & dried over sodium sulfate and evaporated to give crude compound (TLC eluent: 5% MeOH in DCM: $R_f$-0.3; UV active). The crude compound was purified by column chromatography using 100-200 silica gel mesh and eluted with 1 to 3% MeOH/DCM to afford pure (4S)-7-(5-methylpyridin-3-yl)-N-(pyrazin-2-yl)-3,4-dihydro-1,4-methanopyrido[2,3-b][1,4]diazepine-5(2H)-carboxamide (356 mg, 0.938 mmol, 49.5% yield) as off white solid, LCMS (m/z): 374.3 [M+H]$^+$.

$^1$H NMR (400 MHz, CDCl$_3$): δ 13.81 (s, 1H), 9.57 (d, J=1.4 Hz, 1H), 8.99 (dd, J=2.1, 0.8 Hz, 1H), 8.52 (dd, J=2.0, 0.9 Hz, 1H), 8.47 (m, J=2.2, 1.1 Hz, 1H), 8.32-8.28 (m, 2H), 7.64 (d, J=8.0 Hz, 1H), 7.47 (d, J=8.0 Hz, 1H), 5.71 (dd, J=6.1, 3.2 Hz, 1H), 3.35-3.16 (m, 3H), 3.03 (dd, J=12.1, 3.3 Hz, 1H), 2.51 (s, 3H), 2.35 (dddd, J=14.0, 9.9, 6.1, 4.0 Hz, 1H), 2.15-2.03 (m, 1H).

Example 168

Synthesis of (4S)-7-(1-methyl-1H-pyrazol-4-yl)-N-(pyrazin-2-yl)-3,4-dihydro-1,4-methanopyrido[2,3-b][1,4]diazepine-5(2H)-carboxamide

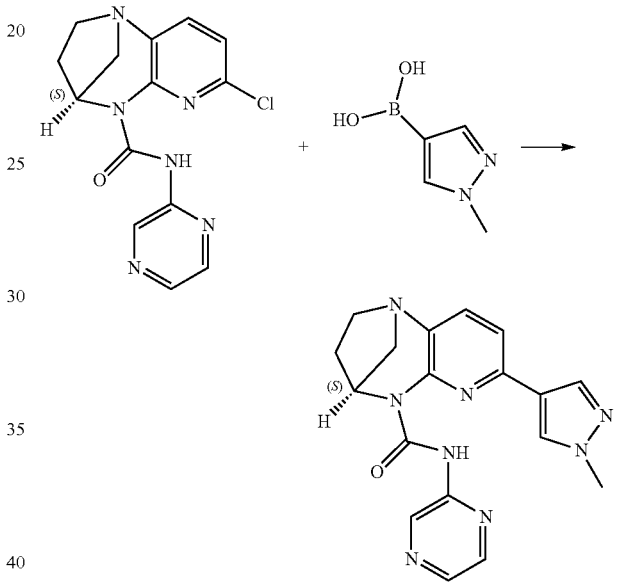

To a solution of (4S)-7-chloro-N-(pyrazin-2-yl)-3,4-dihydro-1,4-methanopyrido[2,3-b][1,4]diazepine-5(2H)-carboxamide (600 mg, 1.894 mmol), (1-methyl-1H-pyrazol-4-yl)boronic acid (286 mg, 2.273 mmol) and K$_3$PO$_4$ (804 mg, 3.79 mmol) in 1,4-dioxane (12.00 mL), water (4.00 mL) and degassed with Argon for 20 min was added X-Phos (90 mg, 0.189 mmol), tris(dibenzylideneacetone)dipalladium(0) (87 mg, 0.095 mmol) again degassed with argon for 10 min. The reaction mixture was stirred at 100° C. for 4 h and cooled to room temperature. The reaction mixture was filtered through celite then the filtrate was diluted with water and extracted with EtOAc (3×10 mL). The combined organic layers were washed with water, brine solution, dried over sodium sulfate and evaporated to give crude compound (TLC eluent: 5% MeOH in DCM: $R_f$-0.3; UV active). The crude compound was purified by column chromatography using 100-200 silica gel mesh and eluted with 1.5-3% MeOH/DCM to afford pure (4S)-7-(1-methyl-1H-pyrazol-4-yl)-N-(pyrazin-2-yl)-3,4-dihydro-1,4-methanopyrido[2,3-b][1,4]diazepine-5(2H)-carboxamide (354 mg, 0.963 mmol, 50.9% yield) as pale yellow solid, LCMS (m/z): 363.1 [M+H]$^+$.

$^1$H NMR (400 MHz, DMSO-d$_6$): δ 14.09 (s, 1H), 9.39 (d, J=1.5 Hz, 1H), 8.51 (d, J=0.8 Hz, 1H), 8.47 (dd, J=2.6, 1.6 Hz, 1H), 8.37-8.36 (m, 1H), 8.26 (d, J=0.8 Hz, 1H), 7.56 (d, J=8.0 Hz, 1H), 7.34 (d, J=8.0 Hz, 1H), 5.46 (dd, J=6.0, 3.1

Hz, 1H), 3.92 (s, 3H), 3.22-3.13 (m, 1H), 3.12-3.02 (m, 2H), 2.94 (dd, J=12.0, 3.3 Hz, 1H), 2.24 (dddd, J=13.6, 9.8, 6.1, 3.8 Hz, 1H), 1.92 (m, J=14.4, 7.4 Hz, 1H).

Example 169

Synthesis of (4S)-7-(6-ethylpyridin-3-yl)-N-(pyrazin-2-yl)-3,4-dihydro-1,4-methanopyrido[2,3-b][1,4]diazepine-5(2H)-carboxamide

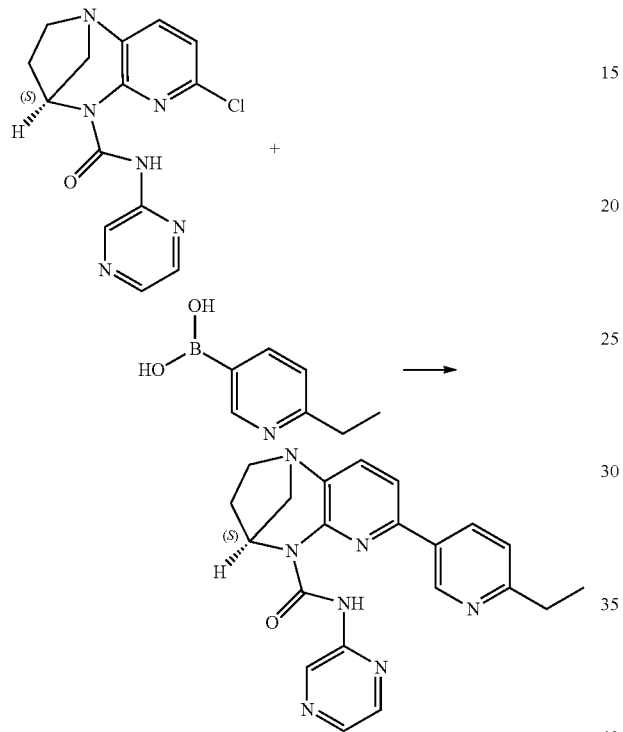

To a solution of (4S)-7-chloro-N-(pyrazin-2-yl)-3,4-dihydro-1,4-methanopyrido[2,3-b][1,4]diazepine-5(2H)-carboxamide (600 mg, 1.894 mmol), (6-ethylpyridin-3-yl)boronic acid (343 mg, 2.273 mmol) and $K_3PO_4$ (804 mg, 3.79 mmol) in 1,4-dioxane (12.00 mL), water (3.00 mL) degassed with argon for 20 min was added X-Phos (90 mg, 0.189 mmol), tris(dibenzylideneacetone)dipalladium(0) (87 mg, 0.095 mmol) and again degassed with argon for 10 min. The reaction mixture was stirred at 100° C. for 4 h and cooled to room temperature. The reaction mixture was filtered through celite then the filtrate was diluted with water and extracted with EtOAc (3×10 mL). The combined organic layers were washed with water, brine solution, dried over sodium sulfate and evaporated to give crude compound (TLC eluent: 5% MeOH in DCM: $R_f$-0.3; UV active). The crude compound was purified by column chromatography using 100-200 silica gel mesh and eluted with 1.5-3% MeOH/DCM to afford pure (4S)-7-(6-ethylpyridin-3-yl)-N-(pyrazin-2-yl)-3,4-dihydro-1,4-methanopyrido [2,3-b][1,4]diazepine-5(2H)-carboxamide (354 mg, 0.883 mmol, 46.6% yield) as off white solid, LCMS (m/z): 388.3 [M+H]$^+$.

$^1$H NMR (400 MHz, CDCl$_3$): δ 13.77 (s, 1H), 9.54 (d, J=1.5 Hz, 1H), 9.22-9.01 (d, 1H), 8.47 (dd, J=2.5 Hz, 1H), 8.35 (d, J=2.4 Hz, 1H), 8.29 (d, J=2.6 Hz, 1H), 7.63 (d, J=8.0 Hz, 1H), 7.42 (d, J=8.0 Hz, 1H), 7.35-7.32 (d, 1H), 5.70 (dd, J=6.0, 3.2 Hz, 1H), 3.39-3.13 (m, 3H), 3.02 (dd, J=12.1, 3.3 Hz, 1H), 2.92 (q, J=7.6 Hz, 2H), 2.35 (dddd, J=13.9, 9.9, 6.1, 4.0 Hz, 1H), 2.21-1.98 (m, 1H), 1.38 (t, J=7.6 Hz, 3H).

Example 170

Synthesis of (4S)—N-(1H-indazol-5-yl)-7-(2-methylpyridin-4-yl)-3,4-dihydro-1,4-methano pyrido[2,3-b][1,4]diazepine-5(2H)-carboxamide

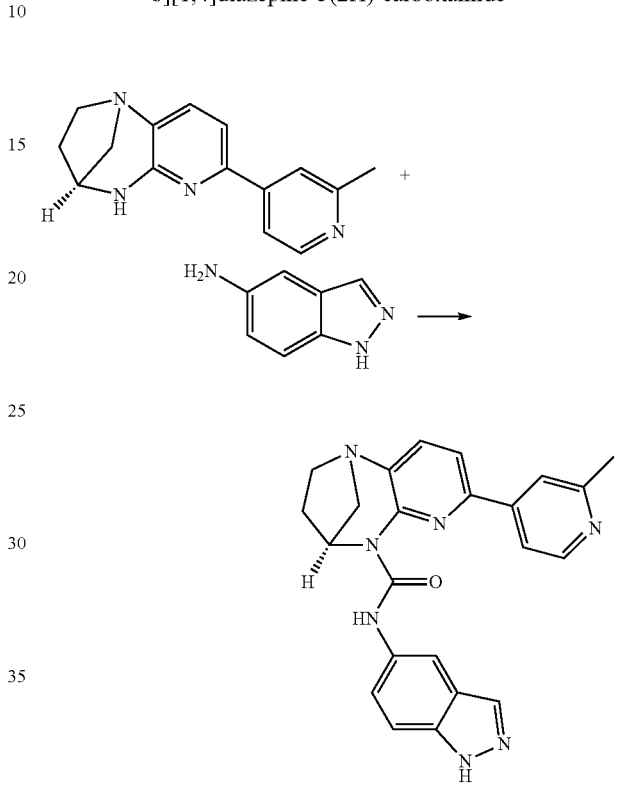

To a solution of (4S)-7-(2-methylpyridin-4-yl)-2,3,4,5-tetrahydro-1,4-methanopyrido[2,3-b][1,4]diazepine (600 mg, 2.378 mmol) in THF (30 ml) was added tri-phosgene (353 mg, 1.189 mmol) at 0° C. and stirred to RT for 1 h. Then 1H-indazol-5-amine (412 mg, 3.09 mmol) and triethylamine (1.657 mL, 11.89 mmol) were added sequentially at RT. The reaction mixture was heated at 70° C. for 16 h in sealed tube and was poured in saturated NaHCO$_3$ solution (180 mL), extracted with ethyl acetate (3×50 mL). The combined organic layer was dried over anhydrous Na$_2$SO$_4$ and concentrated under reduced pressure to obtain the crude product. The crude mixture was purified by prep HPLC (ammonium bicarbonate and Acetonitrile) to afford (4S)—N-(1H-indazol-5-yl)-7-(2-methylpyridin-4-yl)-3,4-dihydro-1,4-methanopyrido [2,3-b][1,4]diazepine-5(2H)-carboxamide (210 mg, 0.489 mmol, 20.54% yield) as a pale brown solid (TLC: 5% MeOH in DCM, $R_f$=0.3), LCMS (m/z): 412.27 [M+H]$^+$.

$^1$H NMR (400 MHz, CDCl$_3$): δ ppm 12.98 (s, 1H), 12.92 (s, 1H), 8.65 (d, J=5.04 Hz, 1H), 8.09-7.94 (d, J=4.5 Hz, 1H), 7.58-7.47 (m, 2H), 7.47-7.41 (m, 2H), 7.41-7.32 (d, J=8.4 Hz, 1H), 7.32-7.17 (d, J=8.3 Hz, 1H), 5.74 (dd, J=5.70, 3.07 Hz, 1H), 3.37-3.11 (m, 3H), 3.11-2.86 (m, 1H), 2.60 (s, 3H), 2.22 (dt, J=14.03, 7.02 Hz, 2H), 1.99-1.81 (m, 1H).

Example 171

Synthesis of (9S)-2-(2-methylpyridin-4-yl)-N-(pyrimidin-5-yl)-8,9-dihydro-6H-5,9-methanopyrido[2,3-b][1,4]diazocine-10(7H)-carboxamide

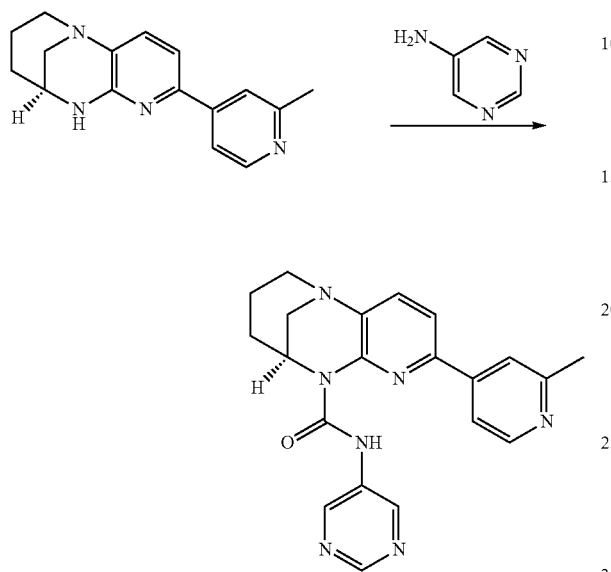

(9S)-2-(2-methylpyridin-4-yl)-7,8,9,10-tetrahydro-6H-5,9-methanopyrido[2,3-b][1,4]diazocine (0.6 g, 2.253 mmol), triethylamine (0.942 mL, 6.76 mmol) and bis(trichloromethyl) carbonate (0.334 g, 1.126 mmol) in THF (12 mL) stirred under nitrogen at room temperature for 30 min. min and then added pyrimidin-5-amine (0.643 g, 6.76 mmol) in one charge. The reaction mixture was stirred at 65° C. for 16 h. The solvent was removed under reduced pressure and the obtained crude was diluted with $CH_2Cl_2$(35 ml), washed with water (5 mL), saturated brine solution (5 mL), dried over anhydrous $Na_2SO_4$ and concentrated under reduced pressure to obtain the crude product. The crude mixture was purified by flash column chromatography (silica-gel: 100-200 mesh, eluent: 3% MeOH in $CH_2Cl_2$) to obtained semi pure compound. The semi pure compound was again purified by Prep HPLC (30% ACN/Water) to afford (9S)-2-(2-methylpyridin-4-yl)-N-(pyrimidin-5-yl)-8,9-dihydro-6H-5,9-methanopyrido[2,3-b][1,4]diazocine-10(7H)-carboxamide (261 mg, 0.667 mmol, 29.6% yield) as an white solid (TLC: 10% MeOH in $CH_2Cl_2$, $R_f$: 0.4), LCMS (m/z): 388 [M+H]$^+$.

$^1$H NMR (400 MHz, CDCl$_3$): δ 13.81 (s, 1H), 9.03 (s, 2H), 8.94 (s, 1H), 8.69 (dd, J=5.2, 0.9 Hz, 1H), 7.75-7.55 (m, 2H), 7.55-7.46 (m, 1H), 7.43 (d, J=8.0 Hz, 1H), 5.08-4.89 (m, 1H), 3.49-3.17 (m, 3H), 3.02 (d, J=13.7 Hz, 1H), 2.69 (s, 3H), 2.36-2.13 (m, 1H), 2.06-1.79 (m, 1H), 1.59-1.32 (m, 2H).

Example 172

Synthesis of (4S)-7-(2-methylpyridin-4-yl)-N-(pyridazin-3-yl)-3,4-dihydro-1,4-methanopyrido[2,3-b][1,4]diazepine-5(2H)-carboxamide

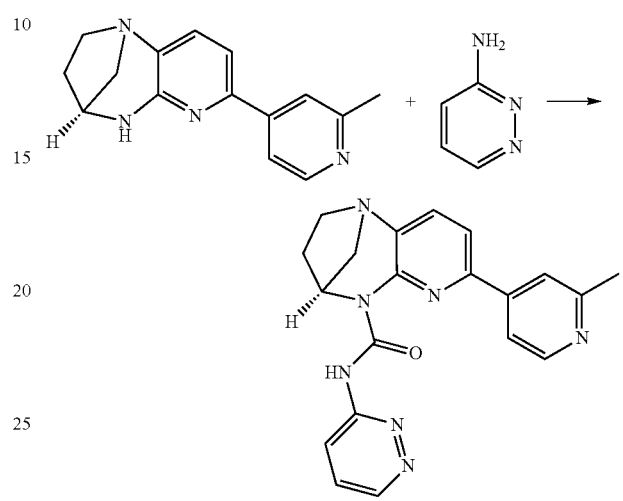

To a stirred solution of (4S)-7-(2-methylpyridin-4-yl)-2,3,4,5-tetrahydro-1,4-methanopyrido[2,3-b][1,4]diazepine (700 mg, 2.77 mmol) in THF (15 mL) was added triphosgene (412 mg, 1.387 mmol) at 30° C. and stirred for 1h. Then pyridazin-3-amine (792 mg, 8.32 mmol) and triethylamine (1.160 mL, 8.32 mmol) were added at 30° C. and heated the reaction mixture at 75° C. for 16 h. The reaction was allowed to 30° C. and poured in to cold water (30 mL), extracted with DCM (2×35 ml). The combined organic layer was washed with brine, dried over sodium sulfate and solvent was evaporated under reduced pressure to obtain crude product. The crude mixture was purified by flash column chromatography (silica-gel: 100-200 mesh, solvent system) and prep HPLC ((10 mM Ammonium Bicarbonate (Aq) MP-B: Acetonitrile Column: xbridge C18 (150×30) mm 5μ Method -t % b 0/60, 13.5/60, 14/100, 17/100, 17.1/60 Flow: 30 ml/min, Solubility: THF+ACN.+WATER) to afford (4S)-7-(2-methylpyridin-4-yl)-N-(pyridazin-3-yl)-3,4-dihydro-1,4-methanopyrido[2,3-b][1,4]diazepine-5(2H)-carboxamide (270 mg, 0.723 mmol, 25.7%) as a pale yellow solid (TLC: $R_f$: 0.4, 10% MeOH in EtOAc), LCMS (m/z): 374.26 [M+H]$^+$.

$^1$H NMR (400 MHz, CDCl$_3$): δ 14.16 (s, 1H), 8.94 (dd, J=4.7, 1.5 Hz, 1H), 8.66 (d, J=5.3 Hz, 1H), 8.48 (dd, J=9.1, 1.5 Hz, 1H), 8.38-830 (m, 1H), 8.22 (s, 1H), 7.83-7.50 (m, 3H), 5.69 (dd, J=6.0, 3.2 Hz, 1H), 3.41-3.16 (m, 3H), 3.03 (dd, J=12.1, 3.3 Hz, 1H), 2.81 (s, 3H), 2.35 (dddd, J=13.9, 10.0, 6.1, 4.0 Hz, 1H), 2.22-2.00 (m, 1H).

Example 173

Synthesis of (4S)-7-(2,5-dimethylpyridin-4-yl)-N-(pyrazin-2-yl)-3,4-dihydro-1,4-methanopyrido[2,3-b][1,4]diazepine-5(2H)-carboxamide

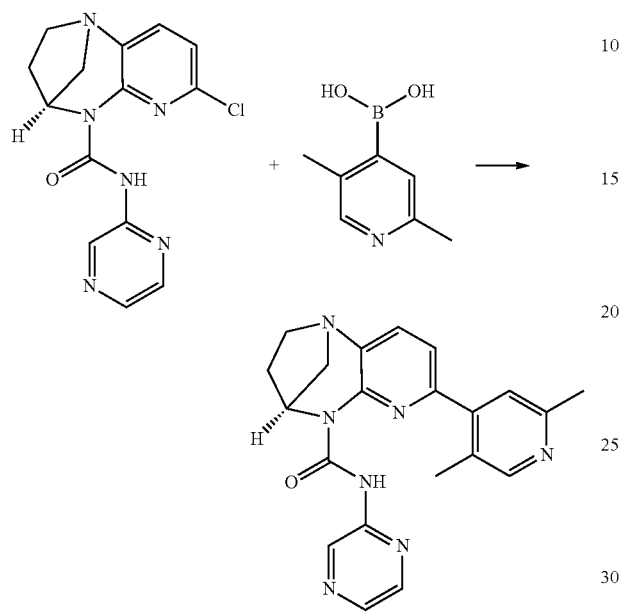

Tripotassium phosphate (804 mg, 3.79 mmol) was added to a stirred solution of (4S)-7-chloro-N-(pyrazin-2-yl)-3,4-dihydro-1,4-methanopyrido[2,3-b][1,4]diazepine-5(2H)-carbo-xamide (600 mg, 1.894 mmol), 2,5-dimethyl-4-(4,4,5,5-tetramethyl-1,3,2-dioxaborolan-2-yl)pyridine (662 mg, 2.84 mmol) in 1,4-dioxane (10 mL), and water (1.667 mL) at 28° C. The reaction mixture was degassed for 15 min, was added $Pd_2(dba)_3$ (87 mg, 0.095 mmol), and X-phos (90 mg, 0.189 mmol). The reaction mixture was further degassed for 15 min, and the reaction mixture was stirred for 3 hr at 100° C. The reaction mixture was cooled to 28° C. and was partitioned between water (10 mL) and EtOAc (25 mL). Organic layer was separated and was dried over anhydrous $Na_2SO_4$, filtered and filtrate was evaporated to give crude as pink solid (TLC eluting system: 10% Methanol in EtOAc; $R_f$=0.3). The crude was purified by column chromatography using (100-200 mesh) silica gel and was eluted with 5-8% methanol in EtOAc to afford pure (4S)-7-(2,5-dimethylpyridin-4-yl)-N-(pyrazin-2-yl)-3,4-dihydro-1,4-methanopyrido[2,3-b][1,4]diazepine-5(2H)-carboxamide (337 mg, 0.860 mmol, 45.4% yield) as off white solid, LCMS (m/z): 388.19 $[M+H]^+$.

$^1$H NMR (CDCl$_3$, 400 MHz): δ 13.48 (s, 1H), 9.49 (d, J=1.6 Hz, 1H), 8.46 (s, 1H), 8.34-8.10 (m, 2H), 7.63 (d, J=7.8 Hz, 1H), 7.45 (s, 1H), 7.15 (d, J=7.9 Hz, 1H), 5.71 (dd, J=6.0, 3.2 Hz, 1H), 3.51-3.09 (m, 3H), 3.04 (dd, J=12.1, 3.3 Hz, 1H), 2.63 (s, 3H), 2.43 (s, 3H), 2.40-2.27 (m, 1H), 2.20-1.96 (m, 1H).

Example 174

Synthesis of (4S)-7-morpholino-N-(pyrazin-2-yl)-3,4-dihydro-1,4-methanopyrido[2,3-b][1,4]diazepine-5(2H)-carboxamide

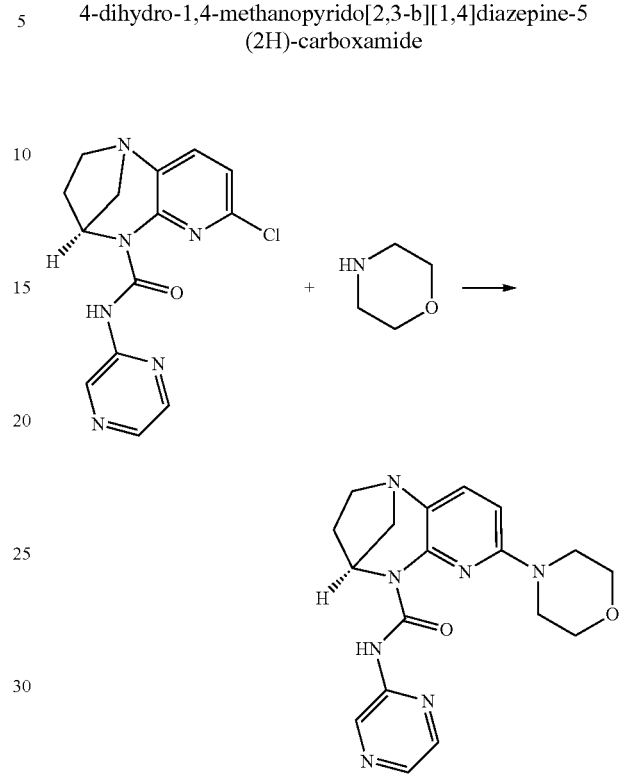

To a degassed solution of (4S)-7-chloro-N-(pyrazin-2-yl)-3,4-dihydro-1,4-methanopyrido[2,3-b][1,4]diazepine-5(2H)-carboxamide (600 mg, 1.894 mmol) and morpholine (0.330 mL, 3.79 mmol) in 1,4-dioxane (6 mL) were added $Cs_2CO_3$ (1234 mg, 3.79 mmol), x-phos (361 mg, 0.758 mmol) and Pd(OAc)$_2$ (85 mg, 0.379 mmol). The reaction mixture was stirred at 110° C. for 16 h. The reaction mixture was poured in to cold water (50 mL) and extracted with ethyl acetate (2×50 mL). The combined organic layer was dried over anhydrous sodium sulfate, concentrated under reduced pressure to obtain the crude product. The crude product was purified by flash column chromatography (silica-gel: 100-200 mesh, eluent: 2% MeOH/DCM) to afford (4S)-7-morpholino-N-(pyrazin-2-yl)-3,4-dihydro-1,4-methanopyrido[2,3-b][1,4]diazepine-5(2H)-carboxamide (268 mg, 0.707 mmol, 37.3% yield) as a pale yellow solid (TLC: $R_f$: 0.2, neat EtOAc), LCMS (m/z): 368 $[M+H]^+$.

$^1$H NMR (400 MHz, CDCl$_3$): δ 13.41 (s, 1H), 9.53 (d, J=1.5 Hz, 1H), 8.37-7.90 (m, 2H), 7.39 (d, J=8.6 Hz, 1H), 6.29 (d, J=8.6 Hz, 1H), 5.62 (dd, J=6.0, 3.2 Hz, 1H), 3.98-3.72 (m, 4H), 3.62-3.46 (m, 4H), 3.22 (dddd, J=12.2, 8.5, 3.7, 2.2 Hz, 1H), 3.18-3.05 (m, 2H), 2.93 (dd, J=11.8, 3.3 Hz, 1H), 2.27 (dd, J=10.1, 4.0 Hz, 1H), 2.01 (d, J=6.9 Hz, 1H).

Example 175

Synthesis of (4S)—N-(5-ethylpyrazin-2-yl)-7-(2-methylpyridin-4-yl)-3,4-dihydro-1,4-methanopyrido[2,3-b][1,4]diazepine-5(2H)-carboxamide

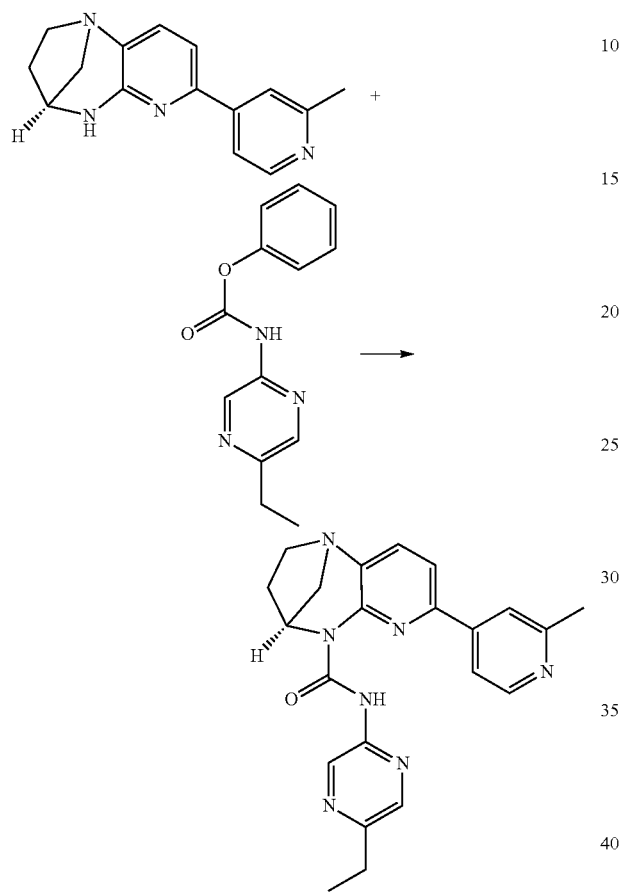

phenyl (5-ethylpyrazin-2-yl)carbamate (1446 mg, 5.94 mmol) and DMAP (726 mg, 5.94 mmol) were added to a stirred solution of (4S)-7-(2-methylpyridin-4-yl)-2,3,4,5-tetrahydro-1,4-methanopyrido[2,3-b][1,4]diazepine (500 mg, 1.982 mmol) in Tetrahydrofuran (THF) (15 mL) at RT and stirred the reaction mixture at 80° C. for 16 h. Allowed the reaction mixture to RT, diluted with ethyl acetate (2×30 mL) washed with water (40 mL) and brine (20 mL). The organic layer was separated and dried over sodium sulfate, filtered and concentrated. Residue was purified by column chromatography using silica gel (100-200 mesh) 1% Methanol in DCM as a eluent to get the desired product. Compound was re-crystallized by using ethanol and pentane (4S)—N-(5-ethylpyrazin-2-yl)-7-(2-methylpyridin-4-yl)-3,4-dihydro-1,4-methanopyrido[2,3-b][1,4]diazepine-5(2H)-carboxamide (245 mg, 0.602 mmol, 30.4% yield) as a off white Solid. (TLC: 5% Methanol in DCM. $R_f$: 0.4 UV), LCMS (m/z): 402.3 [M+H]$^+$.

$^1$H NMR (400 MHz, CDCl$_3$) δ 13.46 (s, 1H), 9.37 (s, 1H), 8.67 (dd, J=5.3, 0.8 Hz, 1H), 8.20 (d, J=0.6 Hz, 1H), 7.98 (ddd, J=5.4, 1.8, 0.7 Hz, 1H), 7.74-7.54 (m, 2H), 7.48 (d, J=7.9 Hz, 1H), 5.72 (dd, J=6.0, 3.2 Hz, 1H), 3.37-3.17 (m, 1H), 3.03 (dd, J=12.1, 3.3 Hz, 1H), 2.80 (q, J=7.6 Hz, 2H), 2.62 (s, 3H), 2.35 (dddd, J=14.0, 9.9, 6.1, 4.1 Hz, 1H), 2.22-1.92 (m, 3H), 1.32 (t, J=7.6 Hz, 3H).

Example 176

Synthesis of (4S)-7-(2-methyloxazol-5-yl)-N-(pyrazin-2-yl)-3,4-dihydro-1,4-methanopyrido[2,3-b][1,4]diazepine-5(2H)-carboxamide

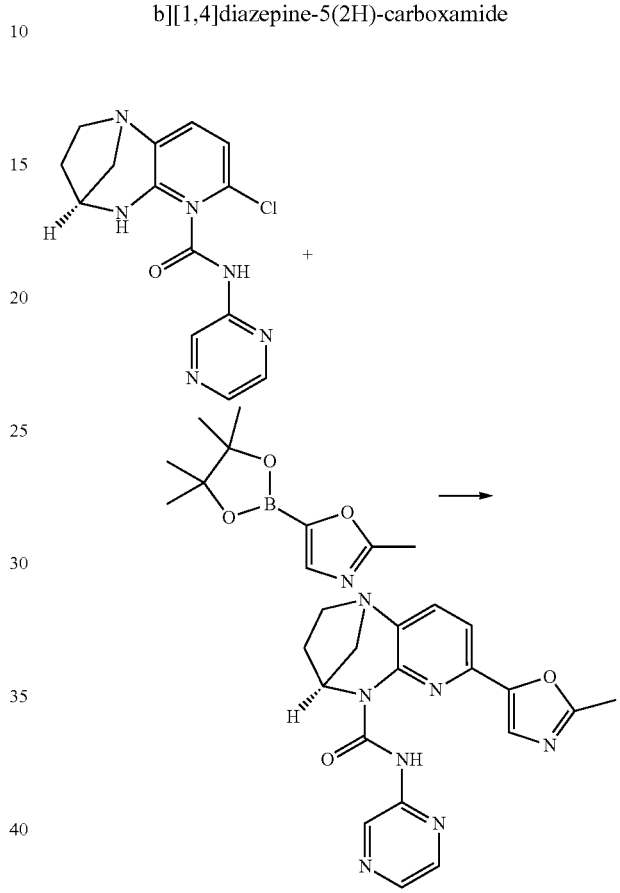

Tripotassium phosphate (804 mg, 3.79 mmol) was added to a stirred solution of (4S)-7-chloro-N-(pyrazin-2-yl)-3,4-dihydro-1,4-methanopyrido[2,3-b][1,4]diazepine-5(2H)-carboxamide (600 mg, 1.894 mmol), 2-methyl-5-(4,4,5,5-tetramethyl-1,3,2-dioxaborolan-2-yl)oxazole (475 mg, 2.273 mmol) in 1,4-dioxane (10 mL), and water (1.667 mL) at 28° C. The reaction mixture was degassed for 15 min, was added Pd$_2$(dba)$_3$ (87 mg, 0.095 mmol), and X-phos (90 mg, 0.189 mmol). The reaction mixture was further degassed for 15 min, and the reaction mixture was stirred for 3 hr at 100° C. The reaction mixture was cooled to 28° C. and was partitioned between water (10 mL) and EtOAc (25 mL). Organic layer was separated and was dried over anhydrous Na$_2$SO$_4$, filtered and filtrate was evaporated to give crude as brown solid (TLC eluent: 10% MeOH in EtOAc; $R_f$=0.2; UV active). The crude was purified by prep HPLC to give the desired product (4S)-7-(2-methyloxazol-5-yl)-N-(pyrazin-2-yl)-3,4-dihydro-1,4-methanopyrido[2,3-b][1,4]diazepine-5(2H)-carboxamide (153 mg, 0.418 mmol, 22.04% yield) as white solid, LCMS (m/z): 364.32 [M+H]$^+$.

$^1$H NMR (CDCl$_3$, 400 MHz): δ 13.72 (s, 1H), 9.54 (d, J=1.5 Hz, 1H), 8.44-8.17 (m, 2H), 8.07 (s, 1H), 7.57 (d, J=7.9 Hz, 1H), 7.30-7.13 (m, 1H), 5.67 (dd, J=6.0, 3.2 Hz,

1H), 3.45-3.08 (m, 3H), 3.01 (dd, J=12.1, 3.3 Hz, 1H), 2.58 (s, 3H), 2.34 (dddd, J=14.1, 9.9, 6.1, 4.2 Hz, 1H), 2.22-1.95 (m, 1H).

Example 177

Synthesis of (4S)-7-(2-methylpyridin-4-yl)-N-(pyrimidin-5-yl)-3,4-dihydro-1,4-methanopyrido[2,3-b][1,4]diazepine-5(2H)-carboxamide

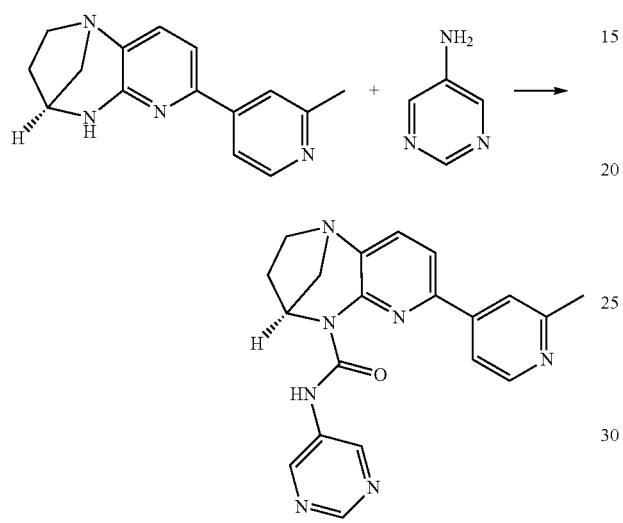

To a stirred solution of (4S)-7-(2-methylpyridin-4-yl)-2,3,4,5-tetrahydro-1,4-methanopyrido[2,3-b][1,4]diazepine (700 mg, 2.77 mmol) in THF (15 mL) was added triphosgene (823 mg, 2.77 mmol) at 30° C. and stirred for 1h. Then pyrimidin-5-amine (317 mg, 3.33 mmol) and TEA (0.387 mL, 2.77 mmol) were added at 30° C. and heated the reaction mixture at 75° C. for 16 h. The reaction was allowed to 30° C. and poured in to cold water (30 mL), extracted with DCM (2×50 ml). The combined organic layer was washed with brine, dried over sodium sulfate and solvent was evaporated under reduced pressure to obtain crude product. The crude mixture was purified by flash column chromatography (silica-gel: 100-200 mesh, 3% MeOH in Ethyl acetate) to afford (4S)-7-(2-methylpyridin-4-yl)-N-(pyrimidin-5-yl)-3,4-dihydro-1,4-methanopyrido[2,3-b][1,4] diazepine-5(2H)-carboxamide (275 mg, 0.737 mmol, 32%) as a pale yellow solid (TLC: $R_f$: 0.4, 10% MeOH in EtOAc), LCMS (m/z): 374.22 [M+H]$^+$.

$^1$H NMR (400 MHz, CDCl$_3$): δ 13.25 (s, 1H), 9.01 (s, 2H), 8.94 (s, 1H), 8.68 (d, J=0.8 Hz, 1H), 7.67 (d, J=7.9 Hz, 1H), 7.55 (dt, J=1.6, 0.8 Hz, 1H), 7.47 (ddd, J=5.2, 1.7, 0.7 Hz, 1H), 7.39 (s, 1H), 5.69 (dd, J=5.9, 3.2 Hz, 1H), 3.33-3.13 (m, 3H), 3.04 (dd, J=12.2, 3.2 Hz, 1H), 2.69 (s, 3H), 2.36 (dd, J=10.1, 4.1 Hz, 1H), 2.15-2.04 (m, 1H).

Example 178

Synthesis of (4S)—N-(5-cyclopropylpyrazin-2-yl)-7-(2-methylpyridin-4-yl)-3,4-dihydro-1,4-methanopyrido[2,3-b][1,4]diazepine-5(2H)-carboxamide

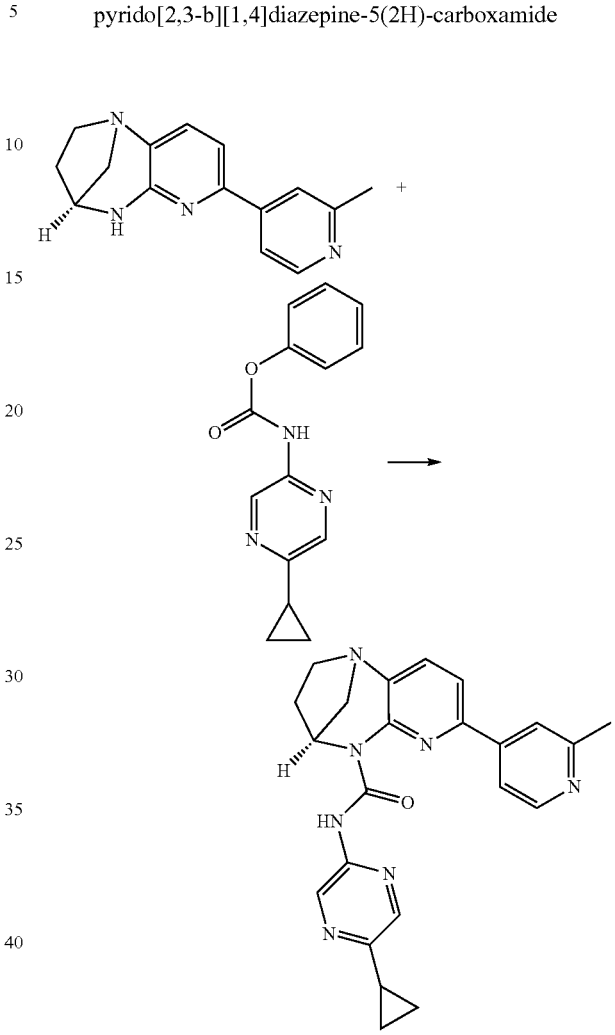

Phenyl (5-cyclopropylpyrazin-2-yl)carbamate (1214 mg, 4.76 mmol) and DMAP (581 mg, 4.76 mmol) were added to a stirred solution of (4S)-7-(2-methylpyridin-4-yl)-2,3,4,5-tetrahydro-1,4-methanopyrido[2,3-b][1,4]diazepine (400 mg, 1.585 mmol) in THF (15 mL) at RT and stirred the reaction mixture at 80° C. for 16 h. Allowed the reaction mixture to RT, diluted with Ethyl acetate (2×30 mL) washed with water (20 mL) and brine (20 mL). The organic layer was separated and dried over sodium sulfate, filtered and concentrated. Residue was purified by column chromatography using silica gel (100-200 mesh), 2% methanol in DCM as the eluent to give the desired product. Compound was re-crystallized by ethanol and pentane to afforded (4S)—N-(5-cyclopropylpyrazin-2-yl)-7-(2-methylpyridin-4-yl)-3,4-dihydro-1,4-methanopyrido[2,3-b][1,4]diazepine-5(2H)-carboxamide (260 mg, 0.623 mmol, 45.2%) as an off white solid, ($R_f$: 0.4, TLC: 5% methanol in DCM), LCMS (m/z): 414.3 [M+H]$^+$.

$^1$H NMR (400 MHz, CDCl$_3$): δ 13.59 (s, 1H), 9.35 (d, J=1.5 Hz, 1H), 8.62 (dd, J=5.3, 0.8 Hz, 1H), 8.20 (d, J=1.5 Hz, 1H), 8.07 (q, J=0.9 Hz, 1H), 7.71-7.59 (m, 2H), 7.48 (d, J=8.0 Hz, 1H), 5.71 (dd, J=6.0, 3.2 Hz, 1H), 3.37-3.10 (m,

3H), 3.02 (dd, J=12.1, 3.3 Hz, 1H), 2.74 (s, 3H), 2.34 (dd, J=10.1, 4.1 Hz, 1H), 2.07 (d, J=8.0 Hz, 1H), 1.21-0.66 (m, 5H).

Example 179

Synthesis of (4S)-7-(2-methylpyrimidin-5-yl)-N-(pyrazin-2-yl)-3,4-dihydro-1,4-methanopyrido[2,3-b][1,4]diazepine-5(2H)-carboxamide

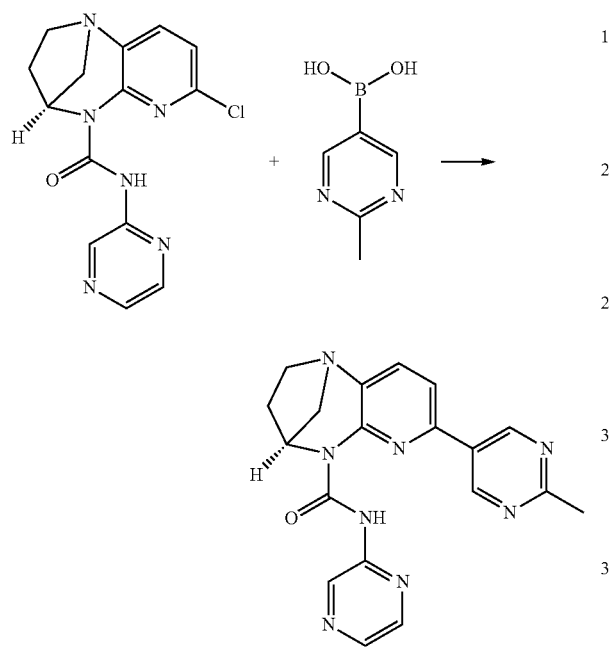

Tripotassium phosphate (804 mg, 3.79 mmol) was added to a stirred solution of (4S)-7-chloro-N-(pyrazin-2-yl)-3,4-dihydro-1,4-methanopyrido[2,3-b][1,4]diazepine-5(2H)-carboxamide (600 mg, 1.894 mmol), (2-methylpyrimidin-5-yl)boronic acid (314 mg, 2.273 mmol) in 1,4-dioxane (12 mL) and water (2.000 mL). The reaction mixture was degassed for 15 min X-phos (90 mg, 0.189 mmol), and Pd$_2$(dba)$_3$ (87 mg, 0.095 mmol) were added. The reaction mixture was further degassed for 15 min, and was stirred at 100° C. for 6 hr. The reaction mixture was cooled to 28° C. and was partitioned between water (30 mL) and EtOAc (70 mL). Organic layer was separated and was dried over anhydrous Na$_2$SO$_4$, filtered. The filtrate was evaporated to get crude (TLC eluent: 5% MeOH in CHCl$_3$: R$_f$=0.2; UV active). The crude compound was purified by 100-200 silica gel by eluting 20% MeOH in ethyl acetate to afford (4S)-7-(2-methylpyrimidin-5-yl)-N-(pyrazin-2-yl)-3,4-dihydro-1,4-methanopyrido[2,3-b][1,4]diazepine-5(2H)-carboxamide (353 mg, 0.938 mmol, 49.5% yield) as pale yellow solid, LCMS (m/z): 375.19 [M+H]$^+$.

$^1$H NMR (CDCl$_3$, 400 MHz): δ 13.57 (s, 1H), 9.53 (d, J=1.5 Hz, 1H), 9.33 (s, 2H), 8.38 (d, J=1.6 Hz, 1H), 8.30 (s, 1H), 7.66 (d, J=8.0 Hz, 1H), 7.40 (d, J=8.0 Hz, 1H), 5.71 (dd, J=5.9, 3.2 Hz, 1H), 3.41-3.11 (m, 3H), 3.04 (dd, J=12.1, 3.3 Hz, 1H), 2.84 (s, 3H), 2.36 (dddd, J=14.0, 9.9, 6.1, 4.1 Hz, 1H), 2.11 (d, J=7.1 Hz, 1H).

Example 180

Synthesis of (4S)—N-(6-cyclopropylpyrazin-2-yl)-7-(2-methylpyridin-4-yl)-3,4-dihydro-1,4-methanopyrido[2,3-b][1,4]diazepine-5(2H)-carboxamide

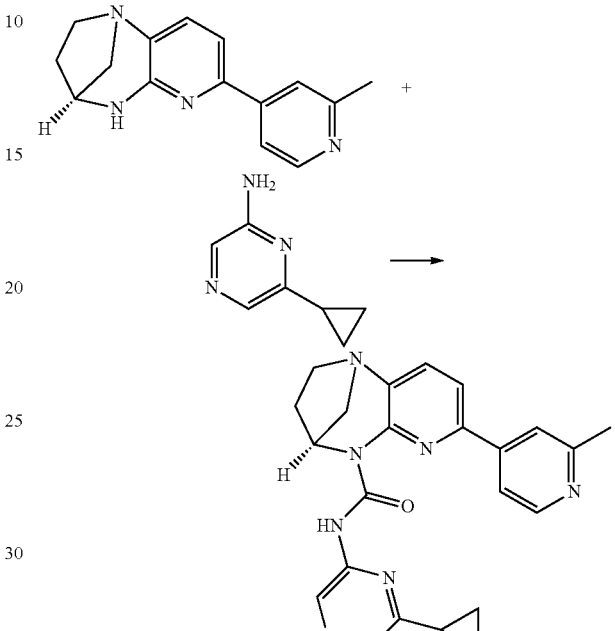

To a stirred solution of 7-(2-methylpyridin-4-yl)-2,3,4,5-tetrahydro-1,4-methanopyrido[2,3-b][1,4]diazepine (600 mg, 0.198 mmol) in THF (30 mL) was added triphosgene (353 mg, 0.099 mmol) at RT and stirred for 30 min. Then 6-cyclopropylpyrazin-2-amine (321 mg, 2.378 mmol) and Et$_3$N (1.657 mL, 0.991 mmol) were added at RT. The reaction mixture was stirred at 65° C. for 16 h. The Reaction mixture was poured in NaHCO$_3$ solution and extracted with CH$_2$Cl$_2$ (3×50 mL). The combined organic layer was dried over anhydrous Na$_2$SO$_4$ and concentrated under reduced pressure to obtain the crude product. The crude mixture was purified by flash column chromatography (silica-gel: 100-200 mesh, eluted with 2% MeOH in CH$_2$Cl$_2$) to afford (4S)—N-(6-cyclopropylpyrazin-2-yl)-7-(2-methylpyridin-4-yl)-3,4-dihydro-1,4-methanopyrido[2,3-b][1,4]diazepine-5(2H)-carboxamide (208 mg, 0.479 mmol, 30.2% yield) as a white solid (TLC: 10% MeOH in CH$_2$Cl$_2$, R$_f$: 0.5), LCMS (m/z): 414.29 [M+H]$^+$.

$^1$H NMR (400 MHz, CDCl$_3$): δ ppm 13.11 (s, 1H), 9.29 (s, 1H), 8.80 (d, J=5.26 Hz, 1H), 8.57 (d, J=4.60 Hz, 1H), 8.15 (s, 1H), 7.97-7.67 (m, 1H), 7.64 (d, J=7.89 Hz, 1H), 7.59-7.42 (m, 1H), 5.72 (dd, J=5.92, 3.29 Hz, 1H), 3.34-3.10 (m, 3H), 3.39-3.09 (m, 1H), 2.62 (s, 3H), 2.44-2.18 (m, 1H), 2.17-1.97 (m, 1H), 1.13-0.93 (m, 4H).

Example 181

(4S)-7-(2-methylpyridin-4-yl)-N-(1H-1,2,3-triazol-4-yl)-3,4-dihydro-1,4-methanopyrido[2,3-b][1,4]diazepine-5(2H)-carboxamide

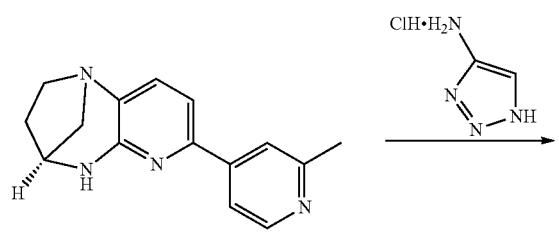

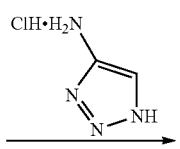

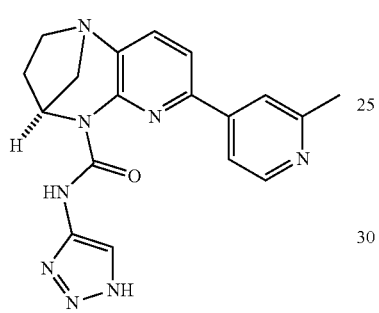

Triphosgene (0.588 g, 1.982 mmol) was added to a stirred solution of (4S)-7-(2-methylpyridin-4-yl)-2,3,4,5-tetrahydro-1,4-methanopyrido[2,3-b][1,4]diazepine (0.5 g, 1.982 mmol) in tetrahydrofuran (50 mL) at 0° C., followed by addition of triethylamine (0.829 mL, 5.94 mmol) and 1H-1,2,3-triazol-4-amine hydrochloride (0.597 g, 4.95 mmol) at 0° C. The reaction mixture was stirred for 48h at 70° C. The reaction mixture was cooled to 28° C. and was partitioned between water (50 mL) and EtOAc (50 mL). The organic layer was separated and was washed with water and brine. The Organic layer was dried over anhydrous Na$_2$SO$_4$, filtered and filtrate was evaporated to afford crude yellow solid (TLC eluent: 10% MeOH in EtOAc: R$_f$=0.35; UV active). The crude compound was purified by 100-200 silica gel by eluting with 5% MeOH in ethyl acetate to afford (4S)-7-(2-methylpyridin-4-yl)-N-(1H-1,2,3-triazol-4-yl)-3,4-dihydro-1,4-methanopyrido[2,3-b][1,4]dia-zepine-5(2H)-carboxamide (0.21 g, 0.558 mmol, 28.2% yield) as light yellow solid, LCMS (m/z): 363.24 [M+H]$^+$.

$^1$H NMR (400 MHz, DMSO-d6): δ 14.58 (s, 1H), 13.55 (s, 1H), 8.58 (d, J=5.2 Hz, 1H), 7.94 (s, 2H), 7.84-7.75 (m, 2H), 7.71 (d, J=8.0 Hz, 1H), 5.47 (dd, J=5.8, 3.0 Hz, 1H), 3.27-3.16 (m, 1H), 3.16-3.01 (m, 2H), 2.97 (dd, J=12.0, 3.2 Hz, 1H), 2.64 (s, 3H), 2.24 (dddd, J=13.7, 9.8, 5.9, 3.7 Hz, 1H), 1.94 (dddd, J=14.5, 8.7, 4.5 Hz, 1H).

Example 182

Synthesis of (4S)-7-(2-methylpyridin-4-yl)-N—((S)-1-(pyridin-2-yl)ethyl)-3,4-dihydro-1,4-methanopyrido[2,3-b][1,4]diazepine-5(2H)-carboxamide

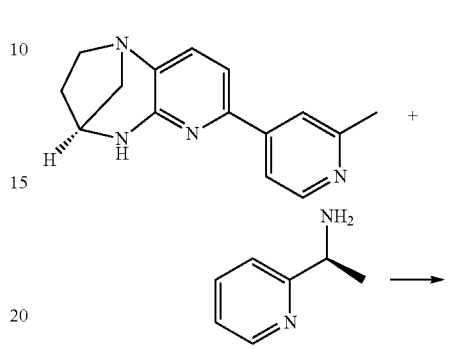

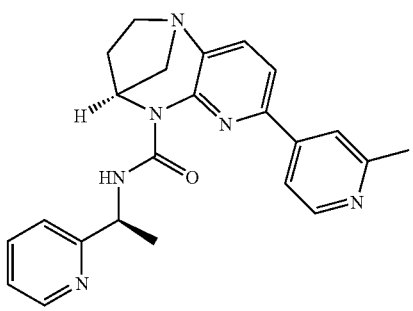

To a solution of (4S)-7-(2-methylpyridin-4-yl)-2,3,4,5-tetrahydro-1,4-methanopyrido[2,3-b][1,4]diazepine (500 mg, 1.982 mmol) in tetrahydrofuran (10 mL) was added triphosgene (588 mg, 1.982 mmol) and triethylamine (1.657 mL, 11.89 mmol). The reaction mixture was stirred at room temp for 30 min, was added (S)-1-(pyridin-2-yl)ethanamine and stirred at 70° C. for 16 h. The solvent was removed under reduced pressure and diluted with water and extracted with ethyl acetate (2×50 mL). The combined organic layer was washed with water (30 mL), saturated brine solution. Organic layer was dried over anhydrous sodium sulfate, filtered and filtrate was evaporated to give the crude product as a brown solid. (TLC eluent: 10% Methanol in dichloromethane, R$_f$=0.3; UV active). The crude compound was purified by column chromatography (neutral alumina) product was eluted with 55-60% ethyl acetate in hexane. Collected fractions evaporated under reduce pressure to afford pure (4S)-7-(2-methylpyridin-4-yl)-N—((S)-1-(pyridin-2-yl)ethyl)-3,4-dihydro-1,4-methanopyrido[2,3-b][1,4]diazepine-5(2H)-carboxamide (277 mg, 0.684 mmol, 34.5% yield) as Off-White solid, LCMS (m/z): 401.2 [M+H]$^+$.

$^1$H NMR (400 MHz, CDCl$_3$): δ 11.09 (d, J=7.6 Hz, 1H), 8.56 (dd, J=5.3, 0.8 Hz, 1H), 8.36 (ddd, J=4.8, 1.8, 0.9 Hz, 1H), 7.78 (dt, J=1.4, 0.7 Hz, 1H), 7.63-7.60 (m, 2H), 7.59 (dd, J=7.7, 1.9 Hz, 1H), 7.31-7.29 (m, 2H), 7.11 (ddd, J=7.6, 4.8, 1.2 Hz, 1H), 5.64 (dd, J=6.0, 3.2 Hz, 1H), 5.32-5.23 (m, 1H), 3.27-3.06 (m, 3H), 2.95 (dd, J=12.0, 3.3 Hz, 1H), 2.60 (s, 3H), 2.22 (dd, J=10.0, 4.0 Hz, 1H), 2.03-1.89 (m, 1H), 1.62 (d, J=6.9 Hz, 3H).

Example 183

Synthesis of (4S)-7-(2-methylpyridin-4-yl)-N—((R)-1-(pyridin-2-yl)ethyl)-3,4-dihydro-1,4-methanopyrido[2,3-b][1,4]diazepine-5(2H)-carboxamide

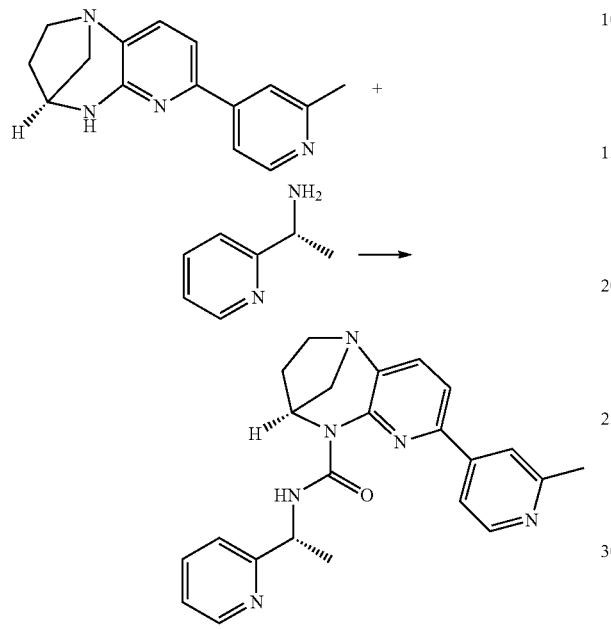

To a solution of (4S)-7-(2-methylpyridin-4-yl)-2,3,4,5-tetrahydro-1,4-methanopyrido[2,3-b][1,4]diazepine (500 mg, 1.982 mmol) in tetrahydrofuran (10 mL) was added triphosgene (588 mg, 1.982 mmol) and triethylamine (1.657 mL, 11.89 mmol) at room temperature. The reaction mixture was stirred at room temp for 30 min, was added (R)-1-(pyridin-2-yl) ethanamine (726 mg, 5.94 mmol) and stirred at 70° C. for 16 h. The solvent was removed under reduced pressure, diluted with water (15 mL), and was extracted with ethyl acetate (2×50 mL). The combined organic layers were washed with water (30 mL), saturated brine solution then dried over anhydrous sodium sulfate. The solution was filtered and concentrated to give the crude product as a brown solid. (TLC eluent: 10% methanol in dichloromethane, $R_f$=0.3; UV active). The crude compound was purified by column chromatography (neutral alumina) product was eluted with 55-60% ethyl acetate in hexane to afford (4S)-7-(2-methylpyridin-4-yl)-N—((R)-1-(pyridin-2-yl)ethyl)-3,4-dihydro-1,4-methanopyrido[2,3-b][1,4]diazepine-5(2H)-carboxamide (240 mg, 0.595 mmol, 30.0% yield) as yellow gum, LCMS (m/z): 401.2 [M+H]$^+$.

$^1$H NMR (400 MHz, CDCl$_3$): δ 11.06 (d, J=7.5 Hz, 1H), 8.57 (dd, J=5.2, 0.8 Hz, 1H), 8.43 (ddd, J=4.8, 1.8, 0.9 Hz, 1H), 7.78 (q, J=0.9 Hz, 1H), 7.63 (ddd, J=5.1, 1.9, 0.7 Hz, 1H), 7.61 (dd, J=7.8, 1.9 Hz, 1H), 7.55 (d, J=7.9 Hz, 1H), 7.36-7.30 (m, 2H), 7.13 (ddd, J=7.6, 4.8, 1.2 Hz, 1H), 5.62 (dd, J=5.9, 3.2 Hz, 1H), 5.27 (p, J=7.0 Hz, 1H), 3.30-3.21 (m, 1H), 3.18 (ddd, J=12.2, 9.9, 6.9 Hz, 1H), 3.06 (dt, J=12.0, 2.1 Hz, 1H), 2.92 (dd, J=11.9, 3.3 Hz, 1H), 2.60 (s, 3H), 2.27 (dddd, J=13.9, 9.9, 6.1, 3.9 Hz, 1H), 2.07 (dt, J=14.0, 7.5 Hz, 1H), 1.62 (d, J=6.9 Hz, 3H).

Example 184

Synthesis of (4S)—N-(2-((S)-2,3-dihydroxypropoxy)pyridin-4-yl)-7-(3-(trifluoromethyl)phenyl)-3,4-dihydro-1,4-methanopyrido[2,3-b][1,4]diazepine-5(2H)-carboxamide

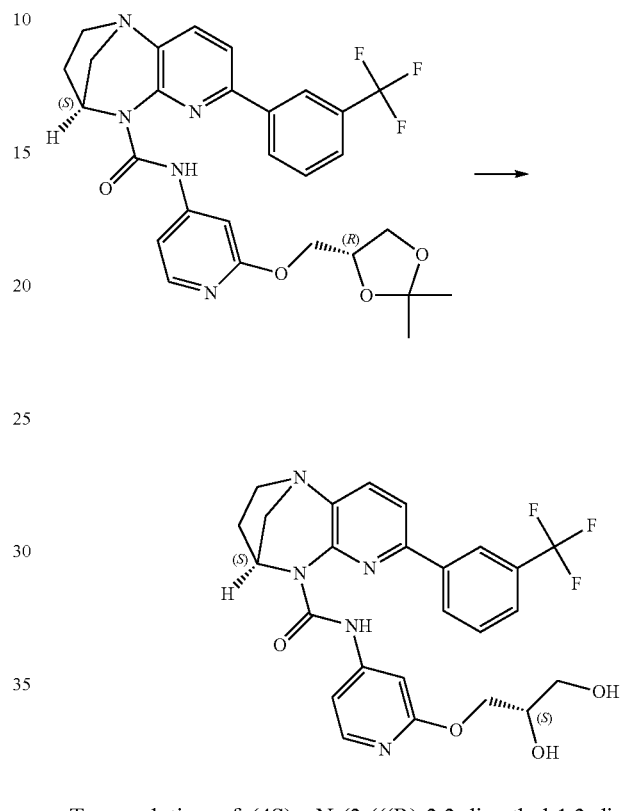

To a solution of (4S)—N-(2-(((R)-2,2-dimethyl-1,3-dioxolan-4-yl)methoxy)pyridin-4-yl)-7-(3-(trifluoromethyl)phenyl)-3,4-dihydro-1,4-methanopyrido[2,3-b][1,4]diazepine-5(2H)-carboxamide (600 mg, 1.080 mmol), was added a solution of 4.0 M Hydrochloric acid in Dioxane (10 mL, 1.080 mmol) at 0° C. The reaction mixture was stirred at room-temp for 3 h. The reaction mixture was evaporated the solvent and neutralized with sodium bicarbonate and extracted with EtOAc (3×50 mL), the combined organic layer was washed with brine solution and dried over sodium sulfate and evaporated to give 350 mg of crude compound. The crude product was added to a silica gel column and was eluted with 2% MeOH/DCM Collected fractions were evaporated to give (4S)—N-(2-((S)-2,3-dihydroxypropoxy)pyridin-4-yl)-7-(3-(trifluoromethyl)phenyl)-3,4-dihydro-1,4-methano pyrido[2,3-b][1,4]diazepine-5(2H)-carboxamide (253 mg, 0.487 mmol, 45.1% yield) as an off white solid. (TLC: $R_f$: 0.2, 5% MeOH/DCM), LCMS (m/z): 516.3 [M+H]$^+$.

$^1$H NMR (400 MHz, DMSO-d$_6$) δ ppm 13.02 (s, 1H), 8.08-8.33 (m, 2H), 7.77-8.00 (m, 3H), 7.76-7.59 (m, 2H), 7.11 (d, J=1.53 Hz, 1H), 6.80 (dd, J=5.70, 1.75 Hz, 1H), 5.47 (dd, J=5.92, 3.07 Hz, 1H), 4.85 (d, J=5.26 Hz, 1H), 4.58 (t, J=5.70 Hz, 1H), 4.23 (dd, J=10.85, 4.49 Hz, 1H), 4.12 (dd, J=10.74, 6.14 Hz, 1H), 3.78 (dq, J=10.69, 5.43 Hz, 1H), 3.53-3.32 (m, 1H), 3.25-3.05 (m, 3H), 2.97 (dd, J=11.95, 3.18 Hz, 2H), 2.37-2.18 (m, 1H), 2.03-1.86 (m, 1H).

Example 185

Synthesis of (4S)-7-(5,6-dimethylpyridin-3-yl)-N-(pyrazin-2-yl)-3,4-dihydro-1,4-methanopyrido[2,3-b][1,4]diazepine-5(2H)-carboxamide

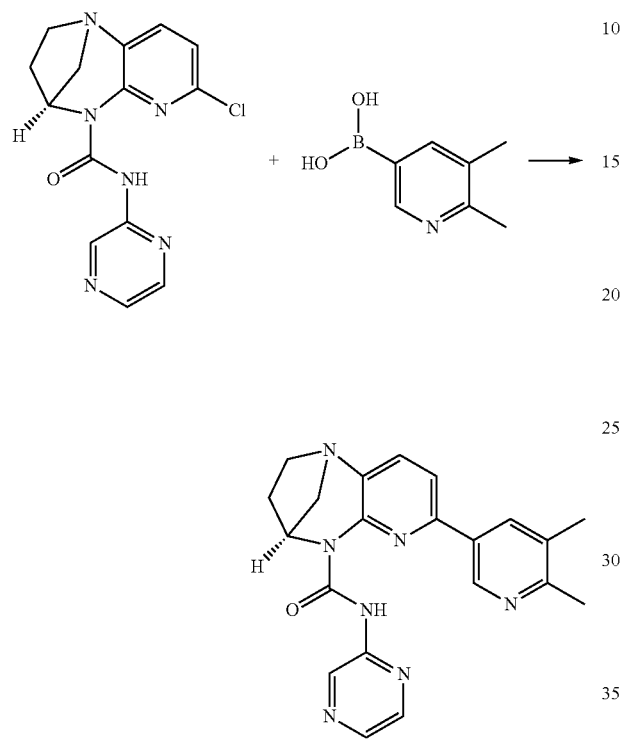

Tripotassium phosphate (804 mg, 3.79 mmol) was added to a stirred solution of (4S)-7-chloro-N-(pyrazin-2-yl)-3,4-dihydro-1,4-methanopyrido[2,3-b][1,4]diazepine-5(2H)-carbox-amide (600 mg, 1.894 mmol), (5,6-dimethylpyridin-3-yl)boronic acid (343 mg, 2.273 mmol) in 1,4-dioxane (10 mL), and water (1.667 mL) at 28° C. The reaction mixture was degassed for 15 min, was added $Pd_2(dba)_3$ (87 mg, 0.095 mmol), and X-phos (90 mg, 0.189 mmol). The reaction mixture was further degassed for 15 min, and the reaction mixture was stirred for 3 hr at 100° C. The reaction mixture was cooled to 28° C. and was partitioned between water (10 mL) and EtOAc (25 mL). Organic layer was separated and was dried over anhydrous $Na_2SO_4$, filtered and filtrate was evaporated to give crude as brown solid (TLC eluent: 10% MeOH in EtOAc; $R_f$=0.3; UV active). The crude was purified by column chromatography using (100-200 mesh) silica gel and was eluted with 5-10% MeOH in EtOAc to afford pure (4S)-7-(5,6-dimethylpyridin-3-yl)-N-(pyrazin-2-yl)-3,4-dihydro-1,4-methanopyrido[2,3-b][1,4]diazepine-5 (2H)-carboxamide (420 mg, 1.078 mmol, 56.9% yield) as off white solid, LCMS (m/z): 388.19 $[M+H]^+$. $^1H$ NMR ($CDCl_3$, 400 MHz): δ 13.85 (s, 1H), 9.57 (d, J=1.4 Hz, 1H), 8.86 (d, J=2.3 Hz, 1H), 8.54-8.34 (m, 1H), 8.34-8.19 (m, 2H), 7.62 (d, J=8.0 Hz, 1H), 7.44 (d, J=8.0 Hz, 1H), 5.71 (dd, J=6.0, 3.2 Hz, 1H), 3.45-3.08 (m, 3H), 3.02 (dd, J=12.1, 3.3 Hz, 1H), 2.59 (s, 3H), 2.47 (d, J=0.8 Hz, 3H), 2.35 (dddd, J=14.0, 10.0, 6.1, 4.0 Hz, 1H), 2.22-2.00 (m, 1H).

Example 186

Synthesis of (4S)-7-(3-(dimethylamino)phenyl)-N-(pyrazin-2-yl)-3,4-dihydro-1,4-methanopyrido[2,3-b][1,4]diazepine-5(2H)-carboxamide

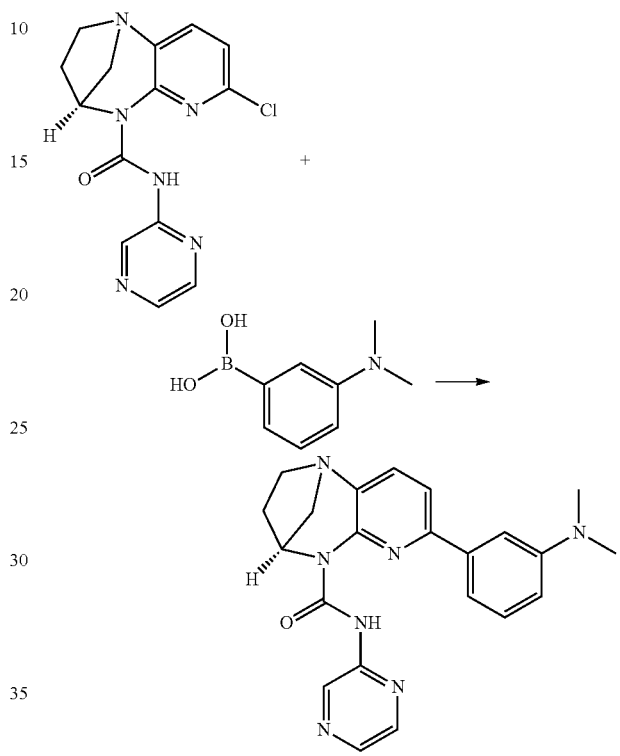

Tripotassium phosphate (804 mg, 3.79 mmol) was added to a stirred solution of (4S)-7-chloro-N-(pyrazin-2-yl)-3,4-dihydro-1,4-methanopyrido[2,3-b][1,4]diazepine-5(2H)-carbox amide (600 mg, 1.894 mmol), (3-(dimethyl amino)phenyl)boronic acid (469 mg, 2.84 mmol) in 1,4-dioxane (10 mL), and water (1.667 mL) at 28° C. The reaction mixture was degassed for 15 min, was added $Pd_2(dba)_3$ (87 mg, 0.095 mmol), and X-phos (90 mg, 0.189 mmol). The reaction mixture was further degassed for 15 min, and the reaction mixture was stirred for 3 hr at 100° C. The reaction mixture was cooled to 28° C. and was partitioned between water (10 mL) and EtOAc (25 mL). Organic layer was separated and was dried over anhydrous $Na_2SO_4$, filtered and the filtrate was evaporated to give crude as brown solid (TLC eluent: 10% MeOH in EtOAc; $R_f$=0.5; UV active). The crude was purified by using column chromatography using (100-200 mesh) silica gel and was eluted with 0-5% MeOH in EtOAc to afford pure (4S)-7-(3-(dimethylamino)phenyl)-N-(pyrazin-2-yl)-3,4-dihydro-1,4-methanopyrido[2,3-b][1,4]diazepine-5(2H)-carboxamide (273 mg, 0.660 mmol, 34.8% yield) as off white solid, LCMS (m/z): 402.26 $[M+H]^+$.

$^1H$ NMR (DMSO-$d_6$, 400 MHz): δ 13.66 (s, 1H), 9.39 (s, 1H), 8.35 (q, J=2.7 Hz, 2H), 7.81-7.42 (m, 1H), 7.44-7.19 (m, 4H), 6.92-6.77 (m, 1H), 5.53 (dd, J=5.9, 3.1 Hz, 1H), 3.29-3.00 (m, 3H), 2.98 (s, 7H), 2.25 (ddd, J=13.8, 10.3, 5.4 Hz, 1H), 1.96 (dt, J=14.9, 7.8 Hz, 1H).

Example 187

Synthesis of ((4S)-7-(2-methylpyridin-4-yl)-3,4-dihydro-1,4-methanopyrido[2,3-b][1,4]diazepin-5(2H)-yl)(pyrrolidin-1-yl)methanone

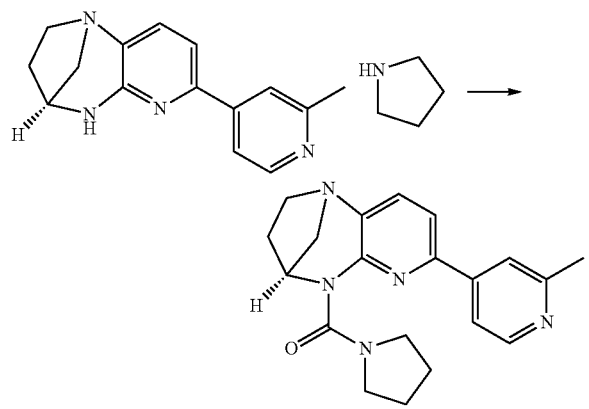

(4S)-7-(2-methylpyridin-4-yl)-2,3,4,5-tetrahydro-1,4-methanopyrido[2,3-b][1,4]diazepine (500 mg, 1.982 mmol) in Tetrahydrofuran (THF) (10 mL) stirred under nitrogen at room temperature was added triphosgene (294 mg, 0.991 mmol) and stirred for 30 min at RT. After 30 minutes triethylamine (1.381 mL, 9.91 mmol) and pyrrolidine (183 mg, 2.58 mmol) were added. The reaction mixture was stirred at 60° C. for 16 hr. Reaction mixture was quenched with 2×15 ml of water and extracted with 2×20 ml of ethyl acetate, organic layer was washed with water and dried over sodium sulfate and concentrated under reduced pressure to afford crude compound. The crude product was purified by 100-200 silica gel column and was eluted with 4% Methanol in DCM to afford pure compound ((4S)-7-(2-methylpyridin-4-yl)-3,4-dihydro-1,4-methanopyrido[2,3-b][1,4]diazepin-5(2H)-yl)(pyrrolidin-1-yl)methanone (350 mg, 0.993 mmol, 50.1% yield) as yellow solid ($R_f$ value: 0.4, 10% Methanol in DCM), LCMS (m/z): 350.25 [M+H]$^+$.

$^1$H NMR (400 MHz, DMSO-d6) δ 8.49 (dd, J=5.2, 0.8 Hz, 1H), 7.75 (dt, J=1.4, 0.7 Hz, 1H), 7.67 (ddd, J=5.4, 1.7, 0.7 Hz, 1H), 7.50 (d, J=7.9 Hz, 1H), 7.44 (d, J=7.9 Hz, 1H), 4.42 (d, J=3.8 Hz, 1H), 3.44-3.24 (m, 4H), 3.14 (ddt, J=12.0, 6.1, 3.3 Hz, 1H), 3.03 (dd, J=13.8, 5.2 Hz, 2H), 2.89 (dd, J=11.6, 3.3 Hz, 1H), 2.55 (s, 3H), 2.23-2.01 (m, 2H), 1.99-1.86 (m, 4H).

Example 188

Synthesis of (4-methylpiperazin-1-yl)((4S)-7-(2-methylpyridin-4-yl)-3,4-dihydro-1,4-methanopyrido[2,3-b][1,4]diazepin-5(2H)-yl)methanone

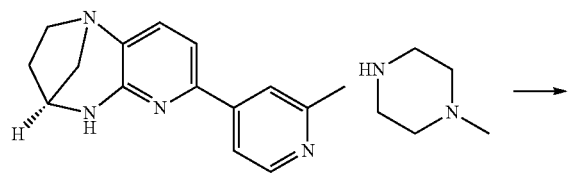

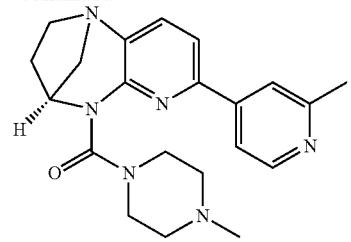

(4S)-7-(2-methylpyridin-4-yl)-2,3,4,5-tetrahydro-1,4-methanopyrido[2,3-b][1,4]diazepine (500 mg, 1.982 mmol) in Tetrahydrofuran (THF) (10 mL) stirred under nitrogen at room temp was added triphosgene (294 mg, 0.991 mmol) and stirred for 30 min at room temperature. After 30 minutes triethylamine (1.381 mL, 9.91 mmol) and 1-methylpiperazine (258 mg, 2.58 mmol) were added. The reaction mixture was stirred at 60° C. for 16 hr. The reaction mixture was allowed to room temperature and quenched with 2×15 ml of water and extracted with 2×20 ml of ethyl acetate, organic layer was washed with water and dried over sodium sulfate and concentrated under reduced pressure to afford crude compound 500 mg. The crude product was purified by column chromatography to afford pure compound (4-methylpiperazin-1-yl)((4S)-7-(2-methylpyridin-4-yl)-3,4-dihydro-1,4-methanopyrido[2,3-b][1,4]diazepin-5(2H)-yl)methanone (280 mg, 0.725 mmol, 36.6% yield) as yellow solid, ($R_f$ value: 0.25, 10% Methanol in DCM), LCMS (m/z): 379.1 [M+H]$^+$.

$^1$H NMR (400 MHz, DMSO-d6) δ 8.51 (dd, J=5.3, 0.8 Hz, 1H), 7.83-7.72 (m, 1H), 7.70 (ddd, J=5.2, 1.7, 0.7 Hz, 1H), 7.53-7.36 (m, 2H), 4.36 (d, J=3.9 Hz, 1H), 3.60 (s, 1H), 3.42 (s, 2H), 3.22-2.90 (m, 3H), 2.61-2.44 (m, 9H), 2.15 (d, J=10.0 Hz, 5H).

Example 189

Synthesis of (4S)—N-cyclopentyl-7-(2-methylpyridin-4-yl)-3, 4-dihydro-1,4-methanopyrido [2, 3-b] [1, 4] diazepine-5(2H)-carboxamide

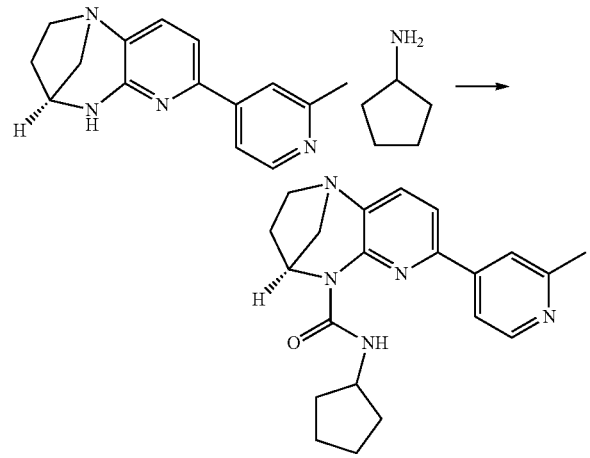

(4S)-7-(2-methylpyridin-4-yl)-2,3,4,5-tetrahydro-1,4-methanopyrido[2,3-b][1,4]diazepine (500 mg, 1.982 mmol) in Tetrahydrofuran (THF) (10 mL) stirred under nitrogen at room temp was added triphosgene (294 mg, 0.991 mmol)

and stirred for 30 min at RT. To this triethylamine (1.381 mL, 9.91 mmol) and cyclopentanamine (219 mg, 2.58 mmol) were added. The reaction mixture was stirred at 60° C. for 16 hr. Reaction mixture was quenched with 2×15 ml of water and extracted with 2×20 ml of ethyl acetate, organic layer was washed with water and dried over sodium sulfate and concentrated under reduced pressure to afford crude compound 500 mg. The crude product was purified by column chromatography to afford pure compound (4S)—N-cyclopentyl-7-(2-methylpyridin-4-yl)-3,4-dihydro-1,4-methanopyrido[2,3-b][1,4]diazepine-5(2H)-carboxamide (275 mg, 0.727 mmol, 36.7% yield) as yellow solid, ($R_f$ value: 0.4, 10% Methanol in DCM), LCMS (m/z): 364.29 (M+H)$^+$.

$^1$H NMR (400 MHz, DMSO-d$_6$) δ ppm 10.30 (d, J=6.58 Hz, 1H), 8.56 (d, J=5.04 Hz, 1H), 7.67-7.52 (m, 4H), 5.41 (dd, J=5.81, 2.96 Hz, 1H), 4.14-4.06 (m, 1H), 3.21-3.02 (m, 2H), 2.99-2.85 (m, 2H), 2.54 (s, 3H), 2.17 (dd, J=9.76, 3.84 Hz, 1H), 2.03-1.79 (m, 3H), 1.64-1.43 (m, 6H).

Example 190

Synthesis of (9S)—N-(pyrazin-2-yl)-2-(2-(trifluoromethyl)pyridin-4-yl)-8,9-dihydro-6H-5,9-methanopyrido[2,3-b][1,4]diazocine-10(7H)-carboxamide

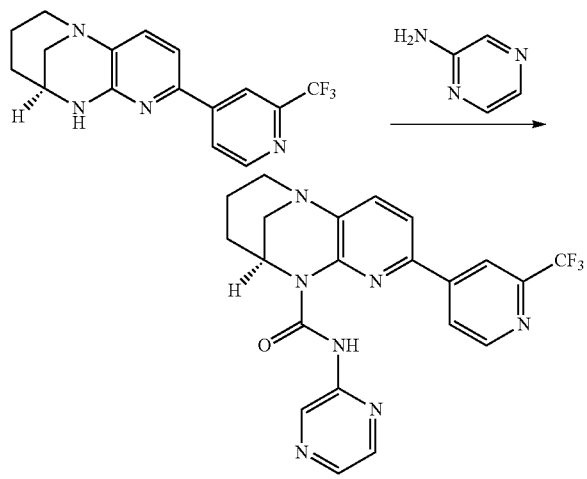

To a stirred solution of (9S)-2-(2-(trifluoromethyl)pyridin-4-yl)-7,8,9,10-tetrahydro-6H-5,9-methanopyrido[2,3-b][1,4]diazocine (0.9 g, 2.81 mmol) in THF (18 mL) was added bis(trichloromethyl) carbonate (0.417 g, 1.405 mmol) at RT and stirred for 30 min. Then Pyrazine-2-amine and Et$_3$N (2.94 ml, 21.8 mmol) were added. The reaction mixture was stirred at 65° C. for 16 h. The organic solvent was removed under reduced pressure and CH$_2$Cl$_2$(30 ml). The organic layer was washed with water (5 ml), saturated brine solution (5 ml), dried over anhydrous Na$_2$SO$_4$ and concentrated under reduced pressure to obtain the crude product. The crude mixture was purified by flash column chromatography (silica-gel: 100-200 mesh, eluent: 4% MeOH in DCM) to afford (9S)—N-(pyrazin-2-yl)-2-(2-(trifluoromethyl)pyridin-4-yl)-8,9-dihydro-6H-5,9-methanopyrido[2,3-b][1,4]diazocine-10(7H)-carboxamide (476 mg, 1.059 mmol, 37.7% yield) as a white solid (TLC: 80% EtOAc in Hexane, $R_f$: 0.5), LCMS (m/z): 442.2 [M+H]$^+$.

$^1$H NMR (400 MHz, CDCl$_3$): δ 14.06 (s, 1H), 9.56 (d, J=1.4 Hz, 1H), 8.87 (d, J=5.1 Hz, 1H), 8.46 (dd, J=1.8, 0.9 Hz, 1H), 8.37-8.23 (m, 2H), 8.14 (dd, J=5.1, 1.7 Hz, 1H), 7.63 (d, J=8.0 Hz, 1H), 7.56 (s, 1H), 5.15-4.92 (m, 1H), 3.52-3.26 (m, 3H), 3.03 (d, J=14.0 Hz, 1H), 2.26 (s, 1H), 2.05-1.88 (m, 1H), 1.53-1.29 (m, 2H).

Example 191

Synthesis of (4S)—N-(pyrazin-2-yl)-7-(1H-pyrazol-5-yl)-3,4-dihydro-1,4-methanopyrido[2,3-b][1,4]diazepine-5(2H)-carboxamide

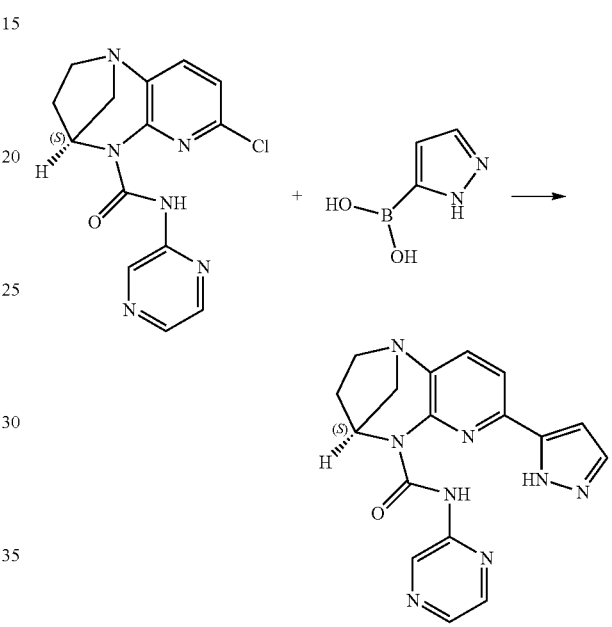

To a solution of (4S)-7-chloro-N-(pyrazin-2-yl)-3,4-dihydro-1,4-methanopyrido[2,3-b][1,4]diazepine-5(2H)-carboxamide (300 mg, 0.947 mmol), (1H-pyrazol-5-yl)boronic acid (127 mg, 1.137 mmol) and K$_3$PO$_4$ (402 mg, 1.894 mmol) in 1,4-dioxane (9 mL), water (3 mL) degassed with argon for 20 min was added X-phos (45.2 mg, 0.095 mmol), tris(dibenzylideneacetone)dipalladium(0) (43.4 mg, 0.047 mmol) again degassed with argon for 10 min. The reaction mixture was stirred at 100° C. for 4 h and cooled to room temperature. The reaction mixture was filtered through celite then the filtrate was diluted with water and extracted with EtOAc (3×10 mL). The combined organic layers were washed with water, brine solution, dried over sodium sulfate and evaporated to give crude compound (TLC eluent: 5% MeOH in DCM: $R_f$-0.3; UV active). The crude compound was purified by column chromatography using 100-200 silica gel mesh and eluted with 2-3% MeOH/DCM to afford pure (4S)—N-(pyrazin-2-yl)-7-(1H-pyrazol-5-yl)-3,4-dihydro-1,4-methanopyrido[2,3-b][1,4]diazepine-5(2H)-carboxamide (100 mg, 0.280 mmol, 29.5% yield) as pale yellow solid, LCMS (m/z): 349.2 [M+H]$^+$.

$^1$H NMR (400 MHz, CDCl$_3$): δ 14.58 (s, 1H), 12.8-11.0 (br, 1H), 9.50 (d, J=1.5 Hz, 1H), 8.41 (dd, J=2.6, 1.5 Hz, 1H), 8.34 (d, J=2.6 Hz, 1H), 7.69 (d, J=2.0 Hz, 1H), 7.60 (d, J=7.9 Hz, 1H), 7.41 (d, J=7.6 Hz, 1H), 6.97 (d, J=17.7 Hz, 1H), 5.63 (dd, J=6.0, 3.2 Hz, 1H), 3.33-3.14 (m, 3H), 3.03 (dd, J=12.1, 3.3 Hz, 1H), 2.35 (dddd, J=14.0, 9.9, 6.1, 4.1 Hz, 1H), 2.17-2.02 (m, 1H).

Example 192

Synthesis of (9S)—N-(pyrimidin-2-yl)-2-(3-(trifluoromethyl)piperidin-1-yl)-8,9-dihydro-6H-5,9-methanopyrido[2,3-b][1,4]diazocine-10(7H)-carboxamide

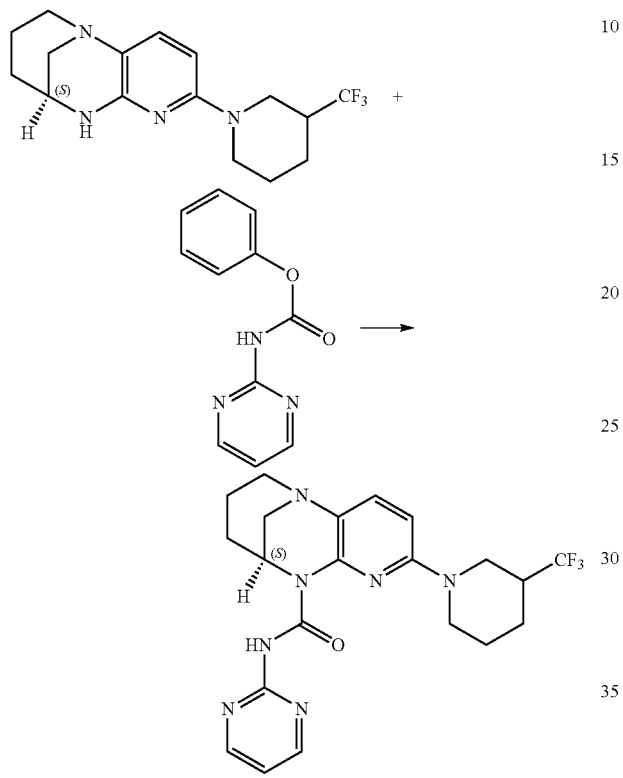

To a solution of (9S)-2-(3-(trifluoromethyl)piperidin-1-yl)-7,8,9,10-tetrahydro-6H-5,9-methanopyrido[2,3-b][1,4]diazocine (Peak1 from the intermediate SFC separation 500 mg, 1.532 mmol) in tetrahydrofuran (500 mL), DMAP (562 mg, 4.60 mmol) and phenyl 2-(pyrimidin-2-yl)acetate (985 mg, 4.60 mmol) were added. The reaction mixture was stirred at 65° C. for 28 hr. The reaction mixture was diluted with water (50 mL) and extracted with EtOAc (2×75 mL). The combined organic layer was washed with water and saturated with brine solution and dried over anhydrous $Na_2SO_4$, filtered and concentrated to give the crude as white solid (TLC eluent: 10% MeOH in DCM: $R_f$-0.4; UV active). The crude product was purified by column chromatography (neutral alumina) and the product was eluted with 25% ethyl acetate in hexane to afford (9S)—N-(pyrimidin-2-yl)-2-(3-(trifluoromethyl)piperidin-1-yl)-8,9-dihydro-6H-5,9-methano-pyrido [2,3-b][1,4]diazocine-10(7H)-carboxamide (320 mg, 0.711 mmol, 46.4% yield) as off white solid. LCMS (m/z) 448.3 [M+H]⁺.

¹H NMR (400 MHz, DMSO-$d_6$): δ 13.80 (s, 1H), 8.62 (d, J=4.8 Hz, 2H), 7.36 (d, J=8.6 Hz, 1H), 7.15 (t, J=4.8 Hz, 1H), 6.61 (d, J=8.6 Hz, 1H), 4.69 (s, 1H), 4.30 (d, J=12.7 Hz, 1H), 4.20 (d, J=13.0 Hz, 1H), 3.26 (d, J=1.9 Hz, 1H), 3.20-2.89 (m, 4H), 2.79 (d, J=13.4 Hz, 1H), 2.55 (d, J=10.8 Hz, 1H), 1.99 (d, J=12.6 Hz, 2H), 1.82 (h, J=6.1 Hz, 2H), 1.72-1.44 (m, 2H), 1.42-1.15 (m, 2H).

Example 193

Synthesis of 4-((4S)-5-(pyrazin-2-ylcarbamoyl)-2,3,4,5-tetrahydro-1,4-methanopyrido[2,3-b][1,4]diazepin-7-yl)picolinic Acid

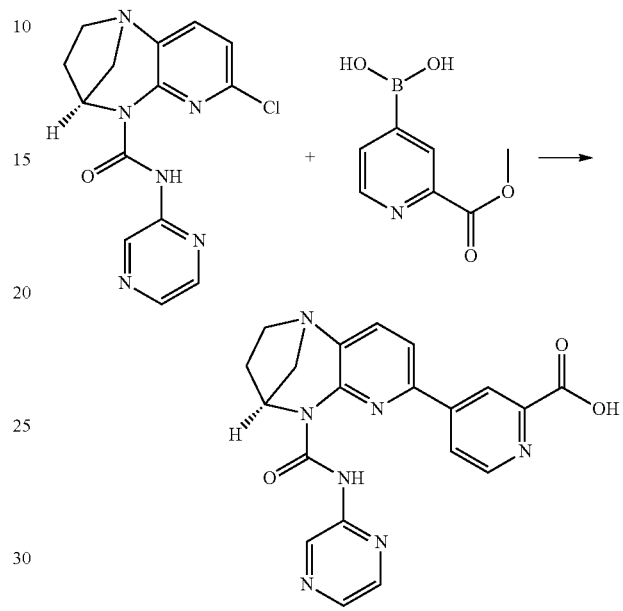

Tripotassium phosphate (6.03 g, 28.4 mmol) was added to a stirred solution of (4S)-7-chloro-N-(pyrazin-2-yl)-3,4-dihydro-1,4-methanopyrido[2,3-b][1,4]diazepine-5(2H)-carboxamide (3 g, 9.47 mmol), methyl 4-(4,4,5,5-tetramethyl-1,3-dioxolan-2-yl)picolinate (3.02 g, 11.37 mmol) in 1,4-dioxane (25 mL), and water (4.17 mL). The reaction mixture was degassed for 15 min, $Pd_2(dba)_3$ (0.434 g, 0.474 mmol) and X-phos (0.452 g, 0.947 mmol) were added. The reaction mixture was further degassed for 15 min, and was stirred at 100° C. for 24 hr. The reaction mixture was cooled to 28° C. and was partitioned between water (50 mL) and EtOAc (200 mL). Aqueous layer neutralized with saturated citric acid solution, precipitated solid was filtered and dried. The crude solid was triturated with methanol and water to afford 4-((4S)-5-(pyrazin-2-ylcarbamoyl)-2,3,4,5-tetrahydro-1,4-methanopyrido[2,3-b][1,4]diazepin-7-yl)picolinic acid (272 mg, 0.667 mmol, 7.04% yield) as an off white solid. (TLC eluent: 20% MeOH in DCM: $R_f$: 0.1; UV active), LCMS (m/z): 404.1 [M+H]⁺.

¹H NMR (DMSO-$d_6$, 400 MHz): δ 13.66 (s, 1H), 9.37 (d, J=0.8 Hz, 1H), 8.87 (d, J=4.8 Hz, 1H), 8.62 (s, 1H), 8.42 (s, 1H), 8.38-8.34 (dd, J=8.4, 2.4 Hz, 2H), 7.887 (d, J=8 Hz, 1H), 7.762 (d, J=8.4 Hz, 1H) 5.53-5.51 (dd, J=5.6, 2.8 Hz, 1H), 3.31-3.23 (m, 1H), 3.15-3.09 (m, 2H), 3.08-2.97 (dd, J=12, 2.8 Hz, 1H), 2.28-2.24 (m, 1H), 2.02-1.97 (m, 1H).

Example 194

Synthesis of (4S)—N-(6-methylpyridin-3-yl)-7-(2-methylpyridin-4-yl)-3,4-dihydro-1,4-methanopyrido[2,3-b][1,4]diazepine-5(2H)-carboxamide

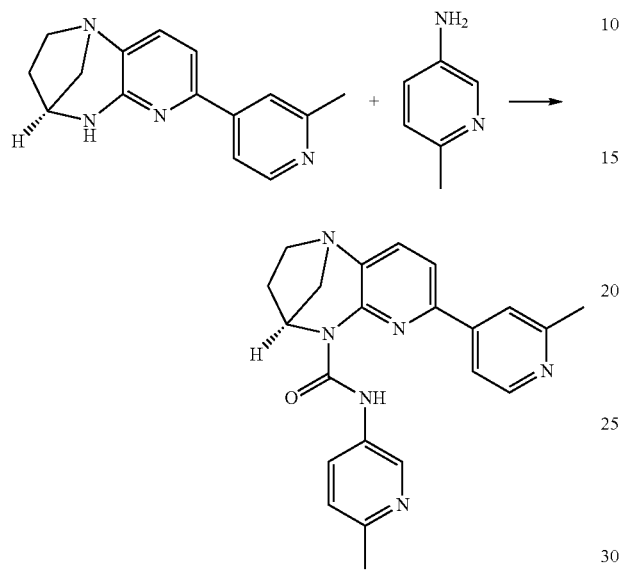

To a stirred solution of (4S)-7-(2-methylpyridin-4-yl)-2,3,4,5-tetrahydro-1,4-methanopyrido[2,3-b][1,4]diazepine (400 mg, 1.585 mmol) in THF (15 mL) was added triphosgene (282 mg, 0.951 mmol) at 30° C. and stirred for 1 h. Then Et₃N (1.105 mL, 7.93 mmol) and 6-methylpyridin-3-amine (257 mg, 2.378 mmol) were added at 30° C. and heated the reaction mixture at 65° C. for 16h. The reaction mixture was poured in to cold water (50 ml) and extracted with DCM (2×50 ml). The combined organic layer was washed with water, brine, dried over sodium sulfate and solvent evaporated under reduced pressure to obtain crude product. The crude mixture was purified by flash column chromatography (silica-gel: 100-200 mesh, eluent: 0-15% MeOH in DCM) to afford (4S)—N-(6-methylpyridin-3-yl)-7-(2-methylpyridin-4-yl)-3,4-dihydro-1,4-methanopyrido[2,3-b][1,4]diazepine-5(2H)-carboxamide (320 mg, 0.829 mmol, 52% yield) as an off-white solid (TLC: 4% MeOH in DCM, $R_f$: 0.35), LCMS (m/z): 387.25 [M+H]⁺.

¹H NMR (400 MHz, CDCl₃): δ ppm 12.94 (s, 1H), 8.66 (d, J=5.26 Hz, 1H), 8.56 (d, J=2.63 Hz, 1H), 8.00 (dd, J=8.44, 2.74 Hz, 1H), 7.63 (d, J=8.14 Hz, 1H), 7.57 (s, 1H), 7.50 (d, J=5.35 Hz, 1H), 7.25-7.38 (m, 1H), 7.13 (d, J=8.55 Hz, 1H), 5.70 (dd, J=5.92, 3.29 Hz, 1H), 3.10-3.35 (m, 3H), 3.02 (dd, J=12.06, 3.29 Hz, 1H), 2.58 (s, 3H), 2.48 (s, 3H) 2.03-2.22 (m, 1H) 2.34 (dddd, J=14.03, 9.87, 5.92, 4.17 Hz, 1H).

Example 195

Synthesis of (9S)—N-(4,5-dimethylthiazol-2-yl)-2-(2-methylpyridin-4-yl)-8,9-dihydro-6H-5,9-methanopyrido[2,3-b][1,4]diazocine-10(7H)-carboxamide

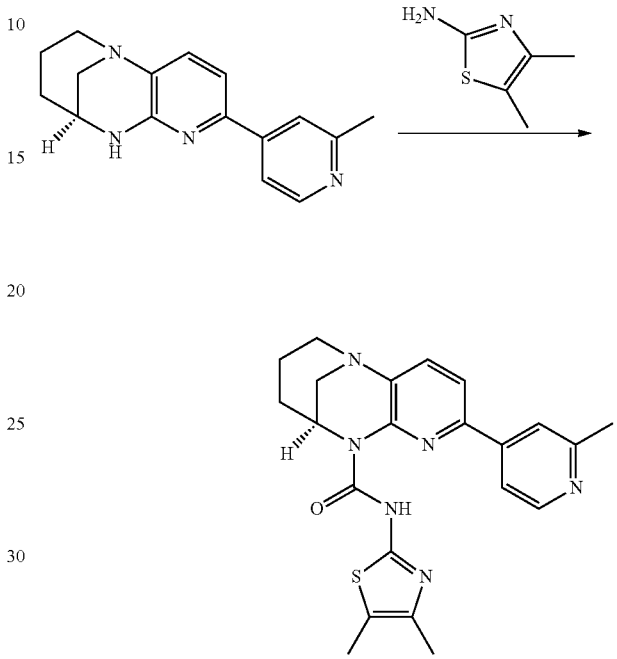

To a solution of (9S)-2-(2-methylpyridin-4-yl)-7,8,9,10-tetrahydro-6H-5,9-methanopyrido[2,3-b][1,4]diazocine (600 mg, 2.253 mmol) in THF (15 mL) were added triethylamine (0.942 mL, 6.76 mmol) and triphosgene (334 mg, 1.126 mmol) at 30° C. and stirred for 1 h. Then 4,5-dimethylthiazol-2-amine hydrochloride (556 mg, 3.38 mmol) was added at 30° C. and reaction was heated at 70° C. for 16h. The solvent evaporated under reduced pressure, residue diluted with water (40 ml) and extracted with DCM (2×40 ml). The combined organic layer was washed with water, brine, dried over anhydrous sodium sulfate and the solvent was evaporated under reduced pressure to obtain crude compound. The crude mixture was purified by flash column chromatography and prep HPLC to afford (9S)—N-(4,5-dimethylthiazol-2-yl)-2-(2-methylpyridin-4-yl)-8,9-dihydro-6H-5,9-methanopyrido[2,3-b][1,4]diazocine-10(7H)-carboxamide (275 mg, 0.655 mmol, 42% yield) as a pale yellow solid (TLC: 10% MeOH in EtOAc, $R_f$: 0.3), LCMS (m/z): 421.27 [M+H]⁺.

¹H NMR (400 MHz, CDCl₃): δ ppm 14.79 (s, 2H), 8.64 (d, J=5.26 Hz, 2H), 8.02 (s, 1H), 7.64 (dd, J=5.26, 1.53 Hz, 1H), 7.54 (q, J=8.11 Hz, 1H), 4.99 (s, 1H), 3.42-3.18 (m, 3H), 3.12-2.89 (m, 1H), 2.79 (s, 3H), 2.28 (s, 3H), 2.22 (s, 3H), 2.00-1.75 (m, 1H), 1.52-1.35 (m, 2H).

Example 196

Synthesis of (4S)-7-(2-(dimethylamino)pyridin-4-yl)-N-(pyrazin-2-yl)-3,4-dihydro-1,4-methanopyrido[2,3-b][1,4]diazepine-5(2H)-carboxamide

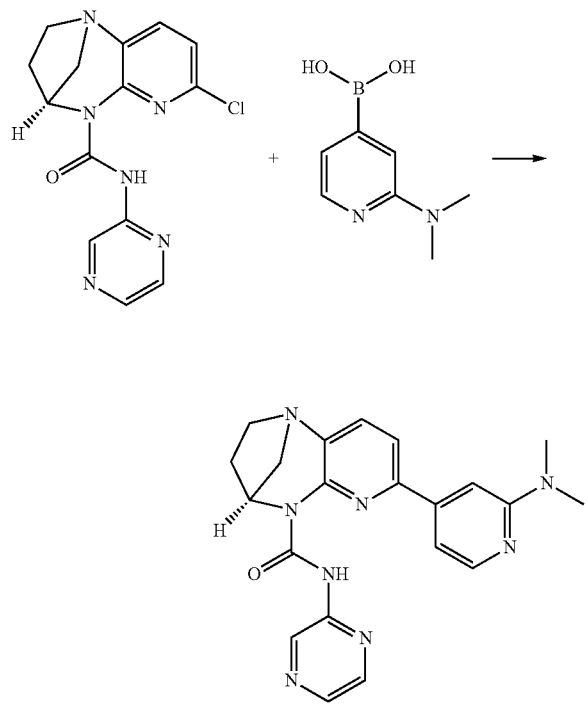

To a degassed solution of (4S)-7-chloro-N-(pyrazin-2-yl)-3,4-dihydro-1,4-methanopyrido[2,3-b][1,4]diazepine-5(2H)-carboxamide (300 mg, 0.947 mmol) $K_3PO_4$ (603 mg, 2.84 mmol) in 1,4-dioxane (30 mL) and water (0.3 mL) were added x-phos (45.2 mg, 0.095 mmol) and palladium(II) acetate (10.63 mg, 0.047 mmol). Then the reaction mixture was heated at 120° C. for 12h. The solvent was evaporated under reduced pressure and extracted with DCM (2×40 ml). The combined organic layer was washed with water, brine, dried over anhydrous sodium sulfate and the solvent was evaporated under reduced pressure to obtain crude product. The crude mixture was purified by flash column chromatography (silica-gel: 100-200 mesh, eluent: 3% MeOH in DCM) to afford (4S)-7-(2-(dimethylamino)pyridin-4-yl)-N-(pyrazin-2-yl)-3,4-dihydro-1,4-methanopyrido [2,3-b][1,4]diazepine-5(2H)-carboxamide (210 mg, 0.496 mmol, 52.3% yield) as an off white solid (TLC: 10% MeOH in EtOAc, $R_f$: 0.2), LCMS (m/z): 403.31 [M+H]$^+$.

$^1$H NMR (400 MHz, CDCl$_3$): δ ppm 13.56 (s, 1H), 9.54 (s, 1H), 8.25-8.11 (m, 3H), 7.62 (m, J=7.89 Hz, 1H), 7.41 (d, J=7.89 Hz, 1H), 7.19-7.01 (m, 2H), 5.72 (dd, J=5.81, 3.18 Hz, 1H), 3.31-3.14 (m, 9H), 3.02 (dd, J=12.17, 3.18 Hz, 1H), 2.50-2.23 (m, 1H), 2.10 (d, J=7.02 Hz, 1H).

Example 197

Synthesis of (4S)-7-(6-cyclopropylpyridin-3-yl)-N-(pyrazin-2-yl)-3,4-dihydro-1,4-methanopyrido[2,3-b][1,4]diazepine-5(2H)-carboxamide

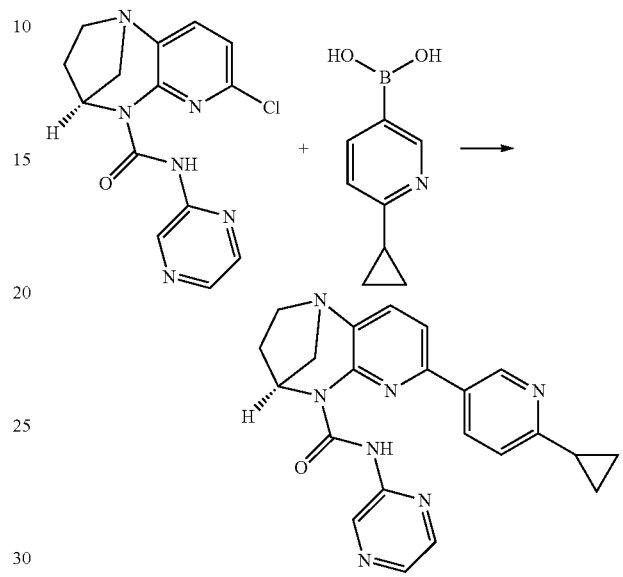

Potassium phosphate (402 mg, 1.894 mmol) and (6-cyclopropylpyridin-3-yl)boronic acid (185 mg, 1.137 mmol) were added to a stirred solution of (4S)-7-chloro-N-(pyrazin-2-yl)-3,4-dihydro-1,4-methanopyrido[2,3-b][1,4]diazepine-5(2H)-carboxamide (300 mg, 0.947 mmol) in a mixture of 1-Butanol (6 mL) and Water (2.0 mL) at RT. Purged with Argon for 30 min, then added Pd$_2$(dba)$_3$ (43.4 mg, 0.047 mmol) and x-phos (45.2 mg, 0.095 mmol)) stirred the reaction mixture at 120 C for 3h. Allowed the reaction mixture to RT, diluted with ethyl acetate (100 mL) washed with water (30 mL) and brine (40 mL). The organic layer was dried over Na$_2$SO$_4$ and concentrated. The residue was purified by flash column chromatography (silica-gel: 100-200 mesh, 80% Ethyl acetate in petroleum ether as an eluent). The recovered material was re-crystallized by using Ethanol and pentane to afford (4S)-7-(6-cyclopropylpyridin-3-yl)-N-(pyrazin-2-yl)-3,4-dihydro-1,4-methanopyrido[2,3-b][1,4]diazepine-5(2H)-carboxamide (130 mg, 0.322 mmol, 34.0% yield) as an off white solid (TLC Eluent: 100% Ethyl acetate, $R_f$: 0.2), LCMS (m/z): 400.25 [M+H]$^+$.

$^1$H NMR (400 MHz, CDCl$_3$): δ 13.79 (s, 1H), 9.53 (d, J=1.5 Hz, 1H), 9.01 (dd, J=2.4, 0.8 Hz, 1H), 8.42-8.22 (m, 3H), 7.61 (d, J=8.0 Hz, 1H), 7.45-7.19 (m, 2H), 5.70 (dd, J=5.9, 3.2 Hz, 1H), 3.34-3.16 (m, 3H), 3.02 (dd, J=12.1, 3.3 Hz, 1H), 2.34 (dd, J=10.1, 4.1 Hz, 1H), 2.19-2.02 (m, 2H), 1.20-0.96 (m, 4H).

Example 198

Synthesis of (9S)—N-(6-methoxypyrazin-2-yl)-2-(2-methylpyridin-4-yl)-8,9-dihydro-6H-5,9-methanopyrido[2,3-b][1,4]diazocine-10(7H)-carboxamide

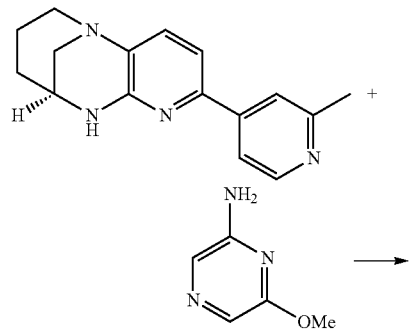

To a solution of (9S)-2-(2-methylpyridin-4-yl)-7,8,9,10-tetrahydro-6H-5,9-methanopyrido[2,3-b][1,4]diazocine (0.6 g, 2.253 mmol) in Tetrahydrofuran (THF) (30 mL) stirred under nitrogen at room temperature was added triethylamine (1.884 mL, 13.52 mmol) and triphosgene (0.669 g, 2.253 mmol). Then reaction mixture was stirred at room temperature for 30 minutes. 6-methoxypyrazin-2-amine (0.846 g, 6.76 mmol) was added at rt. Then the reaction mixture was stirred at 65° C. for 16 hr. The reaction mixture was cooled to room temperature and concentrated under reduced pressure and was partitioned between water (20 mL) and EtOAc (50 mL). Organic layer was separated and was dried over anhydrous $Na_2SO_4$, filtered and filtrate was evaporated to give crude as brown solid (TLC eluent: 100% EtOAc: $R_f$-0.3; UV active). The crude was purified by column chromatography using neutral alumina and was eluted with 50% EtOAc in Hexane to afford pure (9S)—N-(6-methoxypyrazin-2-yl)-2-(2-methylpyridin-4-yl)-8,9-dihydro-6H-5,9-methanopyrido[2,3-b][1,4]diazocine-10(7H)-carboxamide (0.220 g, 0.526 mmol, 23.34% yield) as a off-white solid, LCMS (m/z): 418.3 [M+H]$^+$.

$^1$H NMR (400 MHz, CDCl$_3$): δ 13.64 (s, 1H), 9.45-8.78 (m, 1H), 8.60 (dd, J=5.3, 0.8 Hz, 1H), 7.96 (d, J=0.5 Hz, 1H), 7.80 (ddd, J=5.3, 1.7, 0.7 Hz, 1H), 7.62 (dt, J=1.8, 0.7 Hz, 1H), 7.59 (s, 1H, 7.57 (s, 1H), 7.46 (d, J=8.0 Hz, 1H), 5.04 (t, J=2.6 Hz, 1H), 3.84 (s, 3H), 3.57-3.26 (m, 3H), 3.15-2.91 (m, 1H), 2.64 (s, 3H), 2.28 (d, J=14.3 Hz, 1H), 2.12-1.85 (m, 1H), 1.43 (s, 2H)

Example 199

Synthesis of (4S)-7-(piperidin-1-yl)-N-(pyrazin-2-yl)-3,4-dihydro-1,4-methanopyrido[2,3-b][1,4]diazepine-5(2H)-carboxamide

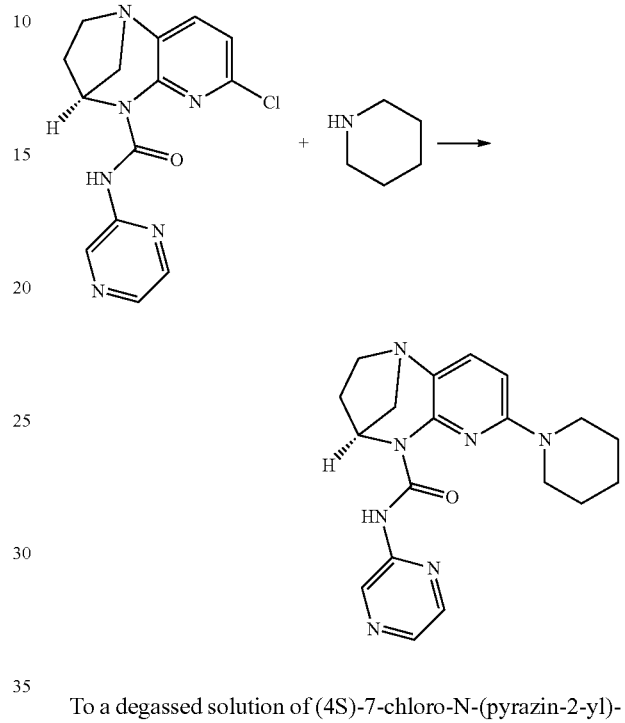

To a degassed solution of (4S)-7-chloro-N-(pyrazin-2-yl)-3,4-dihydro-1,4-methanopyrido[2,3-b][1,4]diazepine-5(2H)-carboxamide (600 mg, 1.894 mmol) and piperidine (0.375 mL, 3.79 mmol) in 1,4-dioxane (10 mL) were added Cs$_2$CO$_3$ (1852 mg, 5.68 mmol), x-phos (361 mg, 0.758 mmol) and Pd(OAc)$_2$ (85 mg, 0.379 mmol). The reaction mixture was stirred at 100° C. for 16 h and poured it in to cold water (20 mL), extracted with ethyl acetate (2×50 mL). The combined organic layer was dried over anhydrous sodium sulfate and concentrated under reduced pressure to obtain the crude product. The crude product was purified by flash column chromatography (silica-gel: 100-200 mesh, eluent: 5% methanol in DCM) to obtain (4S)-7-(piperidin-1-yl)-N-(pyrazin-2-yl)-3,4-dihydro-1,4-methanopyrido[2,3-b][1,4]diazepine-5(2H)-carboxamide (284 mg, 0.762 mmol, 40.2% yield) as a pale yellow solid (TLC: R$_f$: 0.2, neat EtOAc), LCMS (m/z): 366.3 [M+H]$^+$.

$^1$H NMR (400 MHz, CDCl$_3$): δ 13.51 (s, 1H), 9.52 (d, J=1.5 Hz, 1H), 8.29-8.19 (m, 1H), 8.18 (s, 1H), 7.33 (d, J=8.6 Hz, 1H), 6.29 (d, J=8.6 Hz, 1H), 5.61 (dd, J=6.1, 3.3 Hz, 1H), 3.55 (t, J=4.9 Hz, 4H), 3.22 (dddd, J=12.2, 8.6, 3.7, 2.3 Hz, 1H), 3.16-3.07 (m, 2H), 2.90 (dd, J=11.8, 3.3 Hz, 1H), 2.34-2.22 (m, 1H), 2.00 (dddd, J=14.1, 8.7, 6.8, 2.0 Hz, 1H), 1.78-1.64 (m, 6H).

Example 200

Synthesis of (4S)—N-(1-methyl-1H-pyrazol-3-yl)-7-(2-methylpyridin-4-yl)-3,4-dihydro-1,4-methano-pyrido[2,3-b][1,4]diazepine-5(2H)-carboxamide

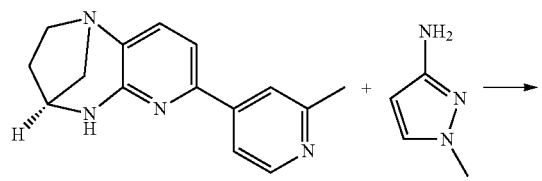

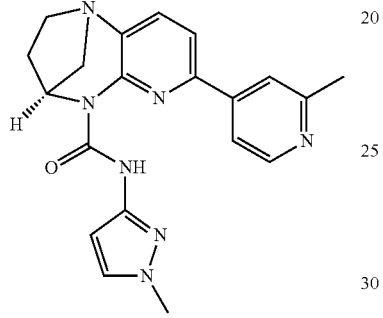

To a stirred solution of (4S)-7-(2-methylpyridin-4-yl)-2,3,4,5-tetrahydro-1,4-methanopyrido[2,3-b][1,4]diazepine (200 mg, 0.793 mmol), Et$_3$N (0.331 mL, 2.378 mmol) in THF (10 mL) was added triphosgene (118 mg, 0.396 mmol) at 25° C. and stirred the reaction mixture for 30 minutes at RT. Then 1-methyl-1H-pyrazol-3-amine (231 mg, 2.378 mmol) in THF (2 ml) was added dropwise. The reaction mixture was stirred at 65° C. for 16 h. The organic solvent was evaporated in vacuo and the crude was diluted with DCM (20 ml). The organic layer was washed with water (5 mL), saturated brine (5 mL), dried over anhydrous Na$_2$SO$_4$ and evaporated in vacuo to obtain the crude product. The crude mixture was purified by flash column chromatography (silica-gel: 100-200 mesh, eluent: 2% MeOH in DCM) to afford (4S)—N-(1-methyl-1H-pyrazol-3-yl)-7-(2-methyl-pyridin-4-yl)-3,4-dihydro-1,4-methanopyrido[2,3-b][1,4]diazepine-5(2H)-carboxamide (185 mg, 0.490 mmol, 61.8% yield) as a white solid (TLC: 5% MeOH in DCM, R$_f$: 0.5), LCMS (m/z): 376.3 [M+H]$^+$.

$^1$H NMR (400 MHz, CDCl$_3$): δ ppm 13.37 (s, 1H), 8.61 (d, J=5.26 Hz, 1H), 8.05-7.83 (m, 1H), 7.68-7.55 (m, 2H), 7.43 (d, J=7.89 Hz, 1H), 7.35-7.17 (m, 1H), 6.63 (d, J=2.19 Hz, 1H), 5.69 (dd, J=5.92, 3.07 Hz, 1H), 3.84 (s, 3H), 3.34-3.10 (m, 3H), 3.00 (dd, J=12.06, 3.29 Hz, 1H), 2.75 (s, 3H), 2.32 (dddd, J=14.03, 9.92, 5.97, 4.06 Hz, 1H) 2.21-1.99 (m, 1H).

Example 201

Synthesis of (4S)—N-cyclobutyl-7-(2-methylpyridin-4-yl)-3,4-dihydro-1,4-methano-pyrido[2,3-b][1,4]diazepine-5(2H)-carboxamide

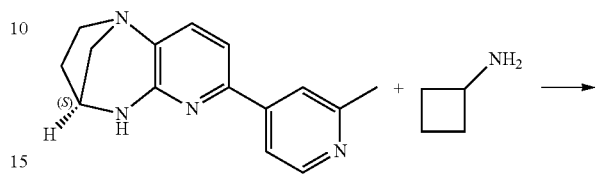

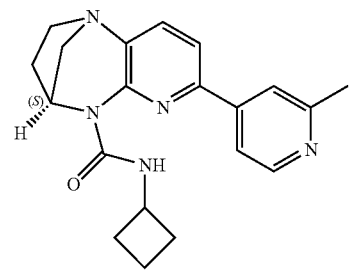

To a solution of (4S)-7-(2-methylpyridin-4-yl)-2,3,4,5-tetrahydro-1,4-methanopyrido[2,3-b][1,4]diazepine (400 mg, 1.585 mmol), triethylamine (1.105 mL, 7.93 mmol) and triphosgene (282 mg, 0.951 mmol) in tetrahydrofuran (20 mL) stirred under nitrogen at room temp for 30 min was added a solution of cyclobutanamine (225 mg, 3.17 mmol) in THF (5 mL). The reaction mixture was stirred at 65° C. for 16 h and cooled to room temperature. The reaction mixture was poured in to ice water and extracted with EtOAc (3×15 mL). The combined organic layers were washed with water, brine solution, dried over sodium sulfate and evaporated to give crude compound (TLC eluent: 5% MeOH in DCM: R$_f$-0.3; UV active). The crude compound was purified by Grace reverse phase column and eluted with 30% (0.1% HCOOH in Water)/MeOH to get (4S)—N-cyclobutyl-7-(2-methylpyridin-4-yl)-3,4-dihydro-1,4-methanopyrido[2,3-b][1,4]diazepine-5 (2H)-carboxamide (369 mg, 1.053 mmol, 66.4% yield) as pale yellow solid, LCMS (m/z): 350.3 [M+H]$^+$.

$^1$H NMR (400 MHz, CDCl$_3$): δ 10.76-10.60 (m, 1H), 8.61 (dd, J=5.3, 0.8 Hz, 1H), 7.60 (dt, J=1.6, 0.7 Hz, 1H), 7.55 (d, J=7.8 Hz, 1H), 7.49 (ddd, J=5.3, 1.7, 0.7 Hz, 1H), 7.32 (d, J=7.9 Hz, 1H), 5.62 (dd, J=6.0, 3.2 Hz, 1H), 4.52-4.36 (m, 1H), 3.28-3.13 (m, 2H), 3.07 (dt, J=11.9, 2.1 Hz, 1H), 2.94 (dd, J=12.0, 3.3 Hz, 1H), 2.65 (s, 3H), 2.51-2.39 (m, 2H), 2.26 (dddd, J=13.9, 10.0, 6.1, 4.1 Hz, 1H), 2.08-1.90 (m, 3H), 1.84-1.72 (m, 2H).

Example 202

Synthesis of ((9S)—N-(6-methylpyrazin-2-yl)-2-(2-methylpyridin-4-yl)-8,9-dihydro-6H-5,9-methanopyrido[2,3-b][1,4]diazocine-10(7H)-carboxamide

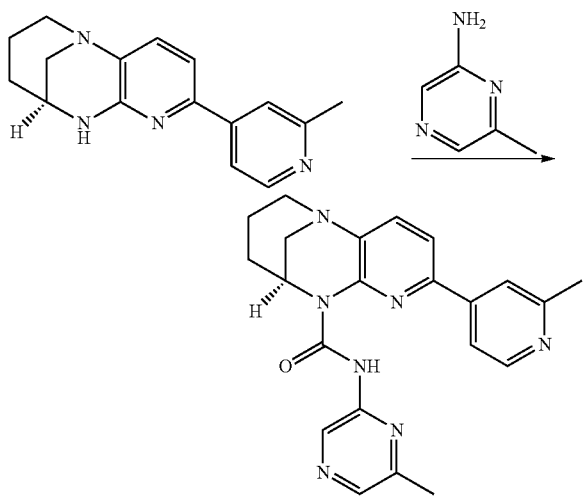

Triphosgene (0.279 g, 0.939 mmol) was added to a stirred solution of (9S)-2-(2-methylpyridin-4-yl)-7,8,9,10-tetrahydro-6H-5,9-methanopyrido[2,3-b][1,4]diazocine (0.25 g, 0.939 mmol) in tetrahydrofuran (50 mL) at 25° C. Triethylamine (0.654 mL, 4.69 mmol) was added and followed by addition of 6-methylpyrazin-2-amine (0.410 g, 3.75 mmol). The reaction mixture was stirred for 15h at 70° C. The reaction mixture was cooled to 28° C. and was partitioned between water (50 mL) and dichloromethane (50 mL). The separated organic layer was washed with water and brine. The organic layer was dried over sodium sulfate filtered and filtrate was evaporated to get crude compound (TLC eluent: 10% MeOH in EtOAc; $R_f$=0.4; UV active). The crude compound was purified by using neutral alumina and eluted in 100% ethyl acetate to afford (9S)—N-(6-methylpyrazin-2-yl)-2-(2-methylpyridin-4-yl)-8,9-dihydro-6H-5,9-methanopyrido[2,3-b][1,4]diazocine-10(7H)-carboxamide (0.11 g, 0.272 mmol, 29.0% yield) as yellow solid, LCMS (m/z): 402.26 [M+H]$^+$.

$^1$H NMR (CDCl$_3$, 400 MHz): δ 14.02 (s, 1H), 9.37 (s, 1H), 8.68 (d, J=5.26 Hz, 1H), 8.13-8.26 (m, 1H), 7.98 (dd, J=5.26, 1.75 Hz, 1H), 7.69-7.80 (m, 1H), 7.49-7.63 (m, 2H), 5.03 (t, J=2.19 Hz, 1H), 3.30-3.47 (m, 2H), 3.03 (br d, J=13.81 Hz, 1H), 2.69 (s, 2H), 2.49-2.59 (m, 2H), 2.15-2.30 (m, 1H), 1.84-1.99 (m, 1H), 1.24-1.66 (m, 3H).

Example 203

Synthesis of (4S)—N-cyclopropyl-7-(2-methylpyridin-4-yl)-3,4-dihydro-1,4-methanopyrido[2,3-b][1,4]diazepine-5(2H)-carboxamide

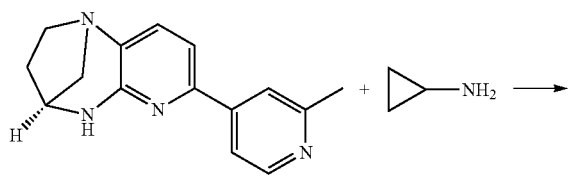

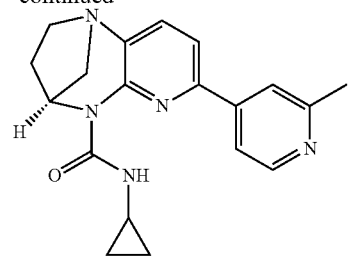

Triphosgene (706 mg, 2.378 mmol) was added to a stirred solution of (4S)-7-(2-methylpyridin-4-yl)-2,3,4,5-tetrahydro-1,4-methanopyrido[2,3-b][1,4]diazepine (600 mg, 2.378 mmol), and TEA (1.657 mL, 11.89 mmol) in tetrahydrofuran (25 mL) at 0° C. The reaction mixture was stirred for 1 hr and was added cyclopropanamine (272 mg, 4.76 mmol), and was stirred for 16 hr at 60° C. The reaction mixture was cooled to 28° C. and was partitioned between water (10 mL) and EtOAc (25 mL). Organic layer was separated and was dried over anhydrous Na$_2$SO$_4$, filtered and filtrate was evaporated to afford crude yellow solid (TLC eluent: 10% MeOH in EtOAc: $R_f$-0.2; UV active). The crude was purified by column chromatography using (100-200 mesh) silica gel and was eluted with 10% MeOH in EtOAc to afford pure (4S)—N-cyclopropyl-7-(2-methylpyridin-4-yl)-3,4-dihydro-1,4-methanopyrido[2,3-b][1,4]diazepine-5(2H)-carboxamide (218 mg, 0.638 mmol, 26.8% yield) as yellow solid, LCMS (m/z): 336.24 [M+H]$^+$.

$^1$H NMR (CDCl$_3$, 400 MHz): δ 10.59 (s, 1H), 8.60 (d, J=5.4 Hz, 1H), 7.68-7.50 (m, 2H), 7.42 (dd, J=5.2, 1.7 Hz, 1H), 7.38-7.21 (m, 1H), 5.66 (dd, J=5.9, 3.2 Hz, 1H), 3.36-3.12 (m, 2H), 3.07 (dt, J=12.0, 2.1 Hz, 1H), 3.01-2.82 (m, 2H), 2.66 (s, 3H), 2.27 (dddd, J=13.8, 9.9, 6.0, 4.0 Hz, 1H), 2.02 (dt, J=14.6, 7.3 Hz, 1H), 0.91-0.79 (m, 2H), 0.69-0.51 (m, 2H).

Example 204

Synthesis of (9S)—N-(pyrimidin-2-yl)-2-(3-(trifluoromethyl)piperidin-1-yl)-8,9-dihydro-6H-5,9-methanopyrido[2,3-b][1,4]diazocine-10(7H)-carboxamide

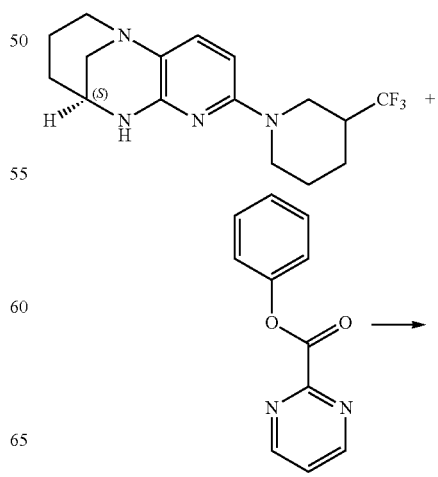

865

-continued

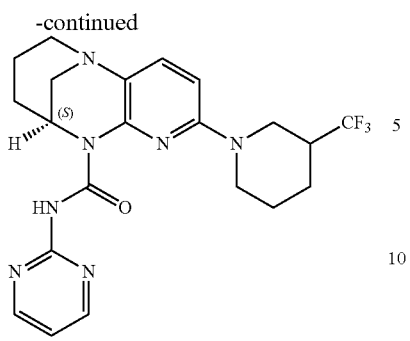

866

-continued

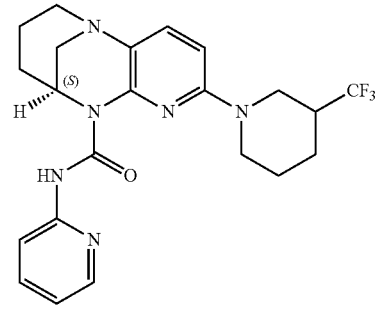

To a solution of (9S)-2-(3-(trifluoromethyl)piperidin-1-yl)-7,8,9,10-tetrahydro-6H-5,9-methanopyrido[2,3-b][1,4]diazocine (Peak II from the intermediate SFC separation 0.600 g, 1.838 mmol) in Tetrahydrofuran (THF) (30 mL) was added DMAP (0.674 g, 5.52 mmol) and phenyl pyrimidin-2-ylcarbamate (1.187 g, 5.52 mmol) stirred at 65° C. for 36 hr. Reaction was cooled to room temperature and then concentrated under reduced pressure. The residue was partitioned between water (10 mL) and EtOAc (50 mL). Organic layer was separated and was dried over anhydrous Na$_2$SO$_4$, filtered and filtrate was evaporated to give crude as brown solid (TLC eluent: 80% EtOAc in Hexane: R$_f$-0.3; UV active). The crude was purified by column chromatography using neutral alumina and was eluted with 35-40% EtOAc in Hexane to afford pure 9S)—N-(pyrimidin-2-yl)-2-(3-(trifluoromethyl)piperidin-1-yl)-8,9-dihydro-6H-5,9-methanopyrido[2,3-b][1,4]diazocine-10(7H)-carboxamide (0.375 g, 0.834 mmol, 45.4% yield) as a off-white solid, LCMS (m/z): 448.3 [M+H]$^+$.

$^1$H NMR (400 MHz, CDCl$_3$): δ 13.97 (s, 1H), 8.59 (d, J=4.8 Hz, 2H), 7.31 (d, J=8.6 Hz, 1H), 6.93 (t, J=4.8 Hz, 1H), 6.40 (d, J=8.6 Hz, 1H), 4.93 (q, J=2.6 Hz, 1H), 4.44-4.07 (m, 2H), 3.31 (d, J=1.9 Hz, 1H), 3.19 (d, J=3.4 Hz, 2H), 3.10-2.81 (m, 3H), 2.44 (dtt, J=15.6, 7.7, 3.9 Hz, 1H), 2.29 (d, J=13.4 Hz, 1H), 2.17-2.07 (m, 1H), 1.93 (dt, J=13.2, 3.3 Hz, 1H), 1.85 (ddd, J=13.8, 5.3, 3.1 Hz, 2H), 1.77-1.68 (m, 1H), 1.55-1.43 (m, 1H), 1.31 (d, J=14.0 Hz, 1H).

Example 205

Synthesis of (9S)—N-(pyridin-2-yl)-2-(3-(trifluoromethyl)piperidin-1-yl)-8,9-dihydro-6H-5,9-methanopyrido[2,3-b][1,4]diazocine-10(7H)-carboxamide

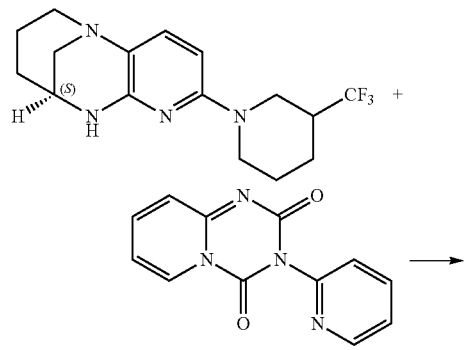

NaH (0.154 g, 6.43 mmol) was added to a solution of (9S)-2-(3-(trifluoromethyl)piperidin-1-yl)-7,8,9,10-tetrahydro-6H-5,9-methanopyrido[2,3-b][1,4]diazocine (Peak-I from intermediate SFC Separation, 0.350 g, 1.072 mmol) in tetrahydrofuran (25 mL) stirred under nitrogen at 0° C. The reaction mixture was stirred at 30° C. for 30 minutes and 3-(pyridin-2-yl)-2H-pyrido[1,2-a][1,3,5]triazine-2,4(3H)-dione (0.386 g, 1.609 mmol) was added. The reaction mixture was stirred at 65° C. for 24 hrs. The reaction mixture was cooled to room temperature and quenched with methanol (5 mL). The reaction mixture was diluted with water and extracted with EtOAc (2×100 mL). The organic layers were washed with water and followed by brine solution and dried over with Na$_2$SO$_4$ filtered and concentrated under reduced pressure to get crude as a brown solid. The crude was purified by column chromatography using Neutral Alumina and was eluted with 60% ethyl acetate in hexane to afford pure (9S)—N-(pyridin-2-yl)-2-(3-(trifluoromethyl)piperidin-1-yl)-8,9-dihydro-6H-5,9-methanopyrido[2,3-b][1,4]diazocine-10(7H)-carboxamide (0.320 g, 0.708 mmol, 66.0% yield) as off white solid, LCMS (m/z): 447.34 [M+H]$^+$.

$^1$H NMR (400 MHz, CDCl$_3$): δ 13.58 (s, 1H), 8.46-8.04 (m, 2H), 7.65 (ddd, J=8.9, 7.3, 1.9 Hz, 1H), 7.35-7.10 (m, 1H), 6.94 (ddd, J=7.3, 4.9, 1.1 Hz, 1H), 6.38 (d, J=8.6 Hz, 1H), 5.10-4.73 (m, 1H), 4.59-4.37 (m, 1H), 4.31-4.19 (m, 1H), 3.30 (dd, J=13.4, 1.9 Hz, 1H), 3.26-3.13 (m, 2H), 3.06-2.88 (m, 3H), 2.48-2.36 (m, J=16.3, 8.3, 4.1 Hz, 1H), 2.21 (d, J=14.4 Hz, 1H), 2.12 (d, J=12.1 Hz, 1H), 1.94 (s, 1H), 1.88-1.68 (m, 2H), 1.67-1.57 (m, 1H), 1.50 (s, 1H), 1.31 (d, J=13.6 Hz, 1H).

Example 206

Synthesis of (4S)-7-(2-methylpyridin-4-yl)-N-(pyridin-3-ylmethyl)-3,4-dihydro-1,4-methanopyrido[2,3-b][1,4]diazepine-5(2H)-carboxamide

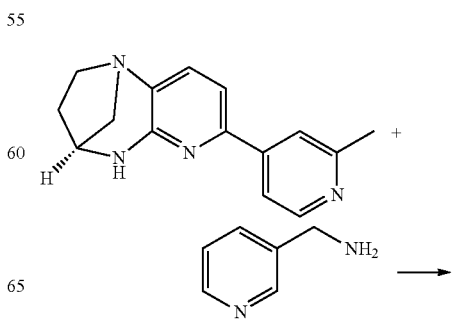

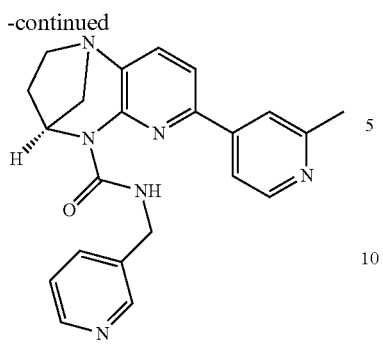

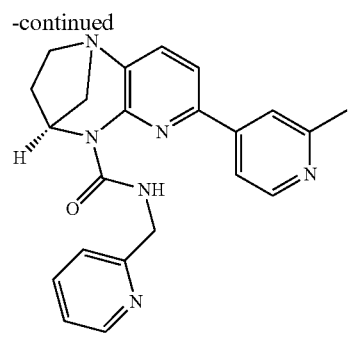

Triphosgene (706 mg, 2.378 mmol) was added to a stirred solution of (4S)-7-(2-methylpyridin-4-yl)-2,3,4,5-tetrahydro-1,4-methanopyrido[2,3-b][1,4]diazepine (600 mg, 2.378 mmol), and TEA (1.657 mL, 11.89 mmol) in tetrahydrofuran (30 mL) at 0° C. The reaction mixture was stirred for 1 hr and was added pyridin-3-ylmethanamine (514 mg, 4.76 mmol), and was stirred for 16 hr at 60° C. The reaction mixture was cooled to 28° C. and was partitioned between water (10 mL) and EtOAc (25 mL). Organic layer was separated and was dried over anhydrous $Na_2SO_4$, filtered and filtrate was evaporated to afford crude yellow solid (TLC eluent: 10% MeOH in EtOAc: $R_f$=0.2; UV active). The crude compound was purified by reverse phase column (Column: C18, 40 μm) and eluted with 20% (0.1% HCOOH&Water)/MeOH to afford pure (4S)-7-(2-methyl-pyridin-4-yl)-N-(pyridin-3-ylmethyl)-3,4-dihydro-1,4-methanopyrido[2,3-b][1,4]diazepine-5(2H)-carboxamide (193 mg, 0.498 mmol, 20.93% yield) as yellow solid, LCMS (m/z): 387.32 $[M+H]^+$.

$^1$H NMR (CDCl$_3$, 400 MHz): δ 10.89 (t, J=5.7 Hz, 1H), 8.75-8.60 (m, 1H), 8.56 (dd, J=4.8, 1.7 Hz, 1H), 8.40 (d, J=5.3 Hz, 1H), 7.72 (dt, J=7.9, 2.0 Hz, 1H), 7.57 (d, J=7.9 Hz, 1H), 7.44-7.21 (m, 3H), 7.15 (dd, J=5.3, 1.8 Hz, 1H), 5.66 (dd, J=5.9, 3.2 Hz, 1H), 4.63 (d, J=5.4 Hz, 2H), 3.37-3.15 (m, 2H), 3.11 (dt, J=12.2, 2.1 Hz, 1H), 2.98 (dd, J=12.0, 3.3 Hz, 1H), 2.49 (s, 3H), 2.39-2.23 (m, 1H), 2.05 (dt, J=14.6, 7.8 Hz, 1H).

Example 207

Synthesis of (4S)-7-(2-methylpyridin-4-yl)-N-(pyridin-3-ylmethyl)-3,4-dihydro-1,4-methanopyrido[2,3-b][1,4]diazepine-5(2H)-carboxamide

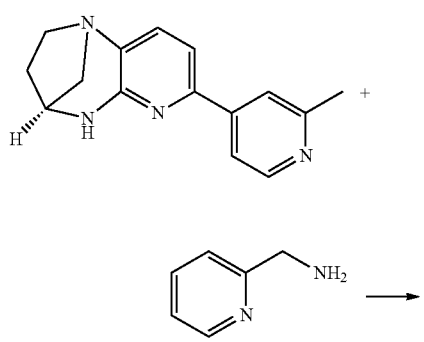

Triphosgene (706 mg, 2.378 mmol) was added to a stirred solution of (4S)-7-(2-methylpyridin-4-yl)-2,3,4,5-tetrahydro-1,4-methanopyrido[2,3-b][1,4]diazepine (600 mg, 2.378 mmol), and TEA (1.657 mL, 11.89 mmol) in tetrahydrofuran (25 mL) at 0° C. The reaction mixture was stirred for 1 hr and was added pyridin-2-ylmethanamine (514 mg, 4.76 mmol), and was stirred for 16 hr at 60° C. The reaction mixture was cooled to 28° C. and was partitioned between water (10 mL) and EtOAc (25 mL). EtOAc layer was separated and was dried over anhydrous $Na_2SO_4$, filtered and filtrate was evaporated to afford crude as yellow solid (TLC eluent: 10% MeOH in EtOAc: $R_f$=0.2; UV active). The crude compound was purified by reverse phase column (Column: C18, 40 am) and eluted with 20% (0.1% HCOOH&water)/MeOH to afford pure (4S)-7-(2-methyl-pyridin-4-yl)-N-(pyridin-2-ylmethyl)-3,4-dihydro-1,4-methanopyrido[2,3-b][1,4]diazepine-5 (2H)-carboxamide (190 mg, 0.492 mmol, 20.67% yield) as off-white solid, LCMS (m/z): 387.22 $[M+H]^+$.

$^1$H NMR (CDCl$_3$, 400 MHz): δ 11.04 (t, J=5.4 Hz, 1H), 8.45 (d, J=5.2 Hz, 1H), 8.40 (dt, J=4.7, 1.5 Hz, 1H), 7.64 (td, J=7.7, 1.9 Hz, 1H), 7.60-7.49 (m, 2H), 7.44 (dd, J=5.3, 1.7 Hz, 1H), 7.36 (d, J=7.8 Hz, 1H), 7.33-7.22 (m, 1H), 7.22-7.10 (m, 1H), 5.68 (dd, J=6.0, 3.2 Hz, 1H), 4.78 (d, J=5.0 Hz, 2H), 3.34-3.04 (m, 3H), 2.97 (dd, J=12.0, 3.3 Hz, 1H), 2.49 (s, 3H), 2.28 (dddd, J=13.8, 10.0, 5.9, 4.0 Hz, 1H), 2.06 (dt, J=14.5, 7.3 Hz, 1H).

Example 208

Synthesis of (4S)-7-(2-methylpyridin-4-yl)-N-(1,2,4-triazin-5-yl)-3,4-dihydro-1,4-methanopyrido[2,3-b][1,4]diazepine-5(2H)-carboxamide

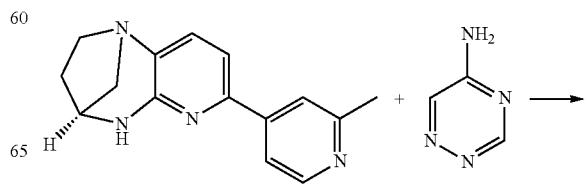

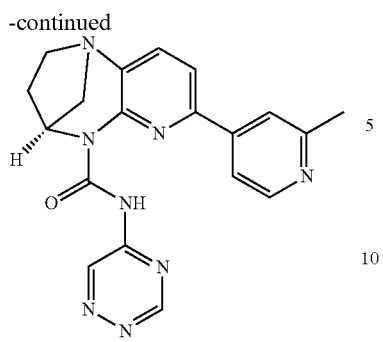

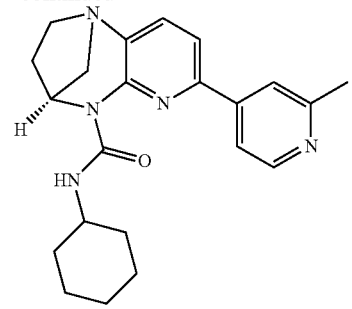

To a solution of (4S)-7-(2-methylpyridin-4-yl)-2,3,4,5-tetrahydro-1,4-methanopyrido[2,3-b][1,4]diazepine (0.250 g, 0.991 mmol) in tetrahydrofuran (30 mL) stirred under nitrogen at room temperature was added triethylamine (2.486 mL, 17.83 mmol) and triphosgene (0.294 g, 0.991 mmol). Then reaction mixture was stirred at room temperature for 30 minutes. 1,2,4-triazin-5-amine (0.286 g, 2.97 mmol) was added at rt. Then the reaction mixture was stirred at 65° C. for 16 hr. The reaction mixture was cooled to room temperature and distilled out the solvent completely and was partitioned between water (20 mL) and EtOAc (50 mL). Organic layer was separated and was dried over anhydrous Na₂SO₄, filtered and filtrate was evaporated to give crude as brown solid (TLC eluent: 100% EtOAc: R$_f$-0.4; UV active). The crude was purified by column chromatography using (100-200 mesh) silica gel and was eluted with 100% EtOAc to afford pure get (4S)-7-(2-methylpyridin-4-yl)-N-(1,2,4-triazin-5-yl)-3,4-dihydro-1,4-methanopyrido[2,3-b][1,4]diazepine-5(2H)-carboxamide (0.044 g, 0.117 mmol, 11.76% yield) as off-white solid, LCMS (m/z): 375.2 [M+H]⁺.

¹H NMR (400 MHz, CDCl₃): δ 14.23 (s, 1H), 10.27 (d, J=2.0 Hz, 1H), 9.27 (d, J=2.1 Hz, 1H), 8.65 (dd, J=5.3, 0.8 Hz, 1H), 7.96 (dt, J=1.9, 0.7 Hz, 1H), 7.73-7.61 (m, 2H), 7.54 (d, J=8.0 Hz, 1H), 5.69 (dd, J=6.0, 3.2 Hz, 1H), 3.31-3.14 (m, 3H), 3.05 (dd, J=12.2, 3.3 Hz, 1H), 2.73 (s, 3H), 2.38 (dddd, J=13.9, 9.9, 6.1, 4.2 Hz, 1H), 2.15-2.02 (m, 1H).

Example 209

(4S)—N-cyclohexyl-7-(2-methylpyridin-4-yl)-3,4-dihydro-1,4-methanopyrido [2, 3-b][1, 4] diazepine-5(2H)-carboxamide

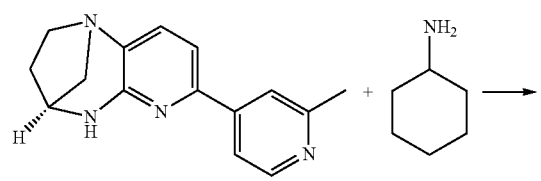

(4S)-7-(2-methylpyridin-4-yl)-2,3,4,5-tetrahydro-1,4-methanopyrido[2,3-b][1,4]diazepine (500 mg, 1.982 mmol) in Tetrahydrofuran (THF) (10 mL) stirred under nitrogen at room temp was added triphosgene (294 mg, 0.991 mmol) and stirred for 30 min at RT. To this triethylamine (1.381 mL, 9.91 mmol) and cyclohexanamine (255 mg, 2.58 mmol) were added and the reaction mixture was stirred at 60° C. for 16 hr. Reaction mixture was quenched with 2×15 ml of water and extracted with 2×20 ml of ethyl acetate, organic layer was dried over sodium sulfate and concentrated under reduced pressure to afford crude compound. The crude product was purified by column chromatography to afford pure compound (4S)—N-cyclohexyl-7-(2-methylpyridin-4-yl)-3,4-dihydro-1,4-methanopyrido[2,3-b][1,4]diazepine-5(2H)-carboxamide (265 mg, 0.701 mmol, 35.4% yield) as off white solid, (R$_f$ value: 0.4, 10% Methanol in DCM), LCMS (m/z): 378.36 [M+H]⁺.

¹H NMR (400 MHz, CDCl₃) δ ppm 10.36 (d, J=7.02 Hz, 1H), 8.59 (d, J=5.26 Hz, 1H), 7.56 (d, J=5.26 Hz, 1H), 7.54-7.52 (m, 1H), 7.45 (dd, J=5.15, 1.21 Hz, 1H), 7.29 (d, J=7.89 Hz, 1H), 5.64 (dd, J=5.92, 3.29 Hz, 1H), 3.87-3.74 (m, 1H), 3.06-3.30 (m, 3H), 2.95 (dd, J=12.06, 3.29 Hz, 1H), 2.65 (s, 3H), 2.26 (dddd, J=14.00, 9.89, 5.92, 4.17 Hz, 1H), 2.14-1.98 (m, 3H), 1.81-1.61 (m, 3H), 1.45-1.14 (m, 5H)

Example 210

Synthesis of (9S)—N-(5-fluoropyridin-2-yl)-2-(3-(trifluoromethyl)piperidin-1-yl)-8,9-dihydro-6H-5,9-methanopyrido[2,3-b][1,4]diazocine-10(7H)-carboxamide

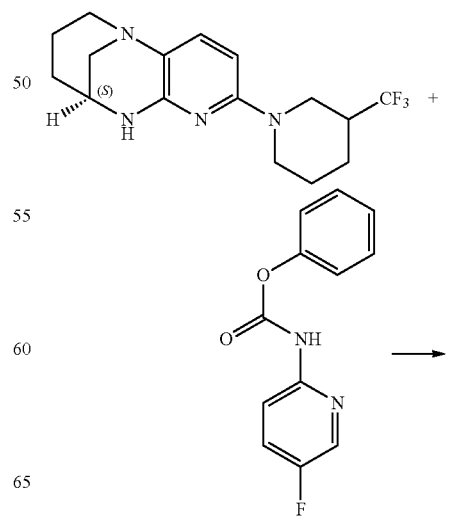

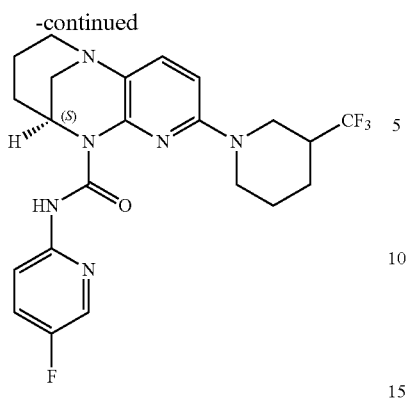

To a solution of (9S)-2-(3-(trifluoromethyl)piperidin-1-yl)-7,8,9,10-tetrahydro-6H-5,9-methanopyrido[2,3-b][1,4]diazocine (Peak-II of the intermediate SFC separation, 0.600 g, 1.838 mmol) in Tetrahydrofuran (THF) (30 mL) was added DMAP (0.674 g, 5.52 mmol) and phenyl (5-fluoropyridin-2-yl)carbamate (1.281 g, 5.52 mmol). The reaction mixture was stirred at 65° C. for 36 hr. Reaction was cooled to room temperature and concentrated under reduced pressure. The residue was partitioned between water (10 mL) and EtOAc (50 mL). Organic layer was separated and was dried over anhydrous Na$_2$SO$_4$, filtered and filtrate was evaporated to give crude as brown solid (TLC eluent: 80% EtOAc in Hexane: R$_f$-0.3; UV active). The crude was purified by column chromatography using neutral alumina and was eluted with 25-30% EtOAc in Hexane to afford pure (9S)—N-(5-fluoropyridin-2-yl)-2-(3-(trifluoromethyl)piperidin-1-yl)-8,9-dihydro-6H-5,9-methanopyrido[2,3-b][1,4]diazocine-10(7H)-carboxamide (0.288 g, 0.608 mmol, 33.1% yield) as a white solid, LCMS (m/z): 465.3 [M+H]$^+$.

$^1$H NMR (400 MHz, CDCl$_3$): δ 13.62 (s, 1H), 8.20 (ddd, J=9.2, 4.1, 0.6 Hz, 1H), 8.09 (s, 1H), 7.39 (ddd, J=9.1, 7.8, 3.0 Hz, 1H), 7.30 (d, J=8.5 Hz, 1H), 6.39 (d, J=8.6 Hz, 1H), 4.87 (p, J=2.8 Hz, 1H), 4.30 (dtt, J=12.5, 3.7, 1.8 Hz, 2H), 3.31 (dd, J=13.4, 1.9 Hz, 1H), 3.25-3.13 (m, 2H), 3.07-2.85 (m, 3H), 2.44 (dt, J=7.4, 3.6 Hz, 1H), 2.26-2.05 (m, 2H), 1.99-1.83 (m, 2H), 1.78-1.66 (m, 1H), 1.62 (dd, J=12.4, 3.8 Hz, 1H), 1.53-1.44 (m, 1H), 1.37-1.26 (m, 1H).

Example 211

Synthesis of (9S)—N-(pyridin-3-yl)-2-(3-(trifluoromethyl)piperidin-1-yl)-8,9-dihydro-6H-5,9-methanopyrido[2,3-b][1,4]diazocine-10(7H)-carboxamide

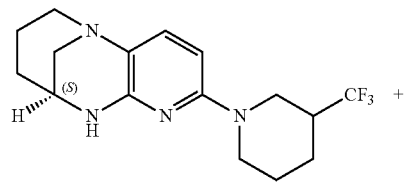

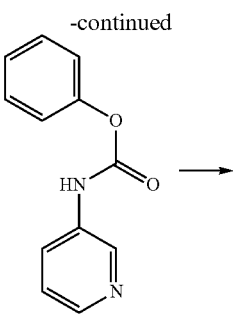

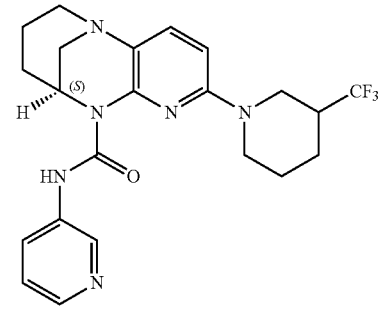

To a solution of (9S)-2-(3-(trifluoromethyl)piperidin-1-yl)-7,8,9,10-tetrahydro-6H-5,9-methanopyrido[2,3-b][1,4]diazocine (Peak-I of the intermediate SFC separation, 600 mg, 1.838 mmol) in tetrahydrofuran (30 mL), DMAP (674 mg, 5.52 mmol) and phenyl pyridin-3-ylcarbamate (1182 mg, 5.52 mmol) were added. The reaction mixture was stirred at 65° C. for 16 hr. The reaction mixture was diluted with water (50 mL) and extracted with ethyl acetate (2×75 mL). The combined organic layers were washed with water and saturated with brine solution and dried over anhydrous sodium sulfate, filtered and concentrated to give crude as a white solid. (TLC eluent: 100% pure Ethyl Acetate; R$_f$ value: 0.4; UV active). The crude product was purified by column chromatography (neutral alumina) product was eluted with 25% ethyl acetate in hexane to afford (9S)—N-(pyridin-3-yl)-2-(3-(trifluoromethyl)piperidin-1-yl)-8,9-dihydro-6H-5,9-metha-nopyrido[2,3-b][1,4]diazocine-10(7H)-carboxamide (350 mg, 0.782 mmol, 42.5% yield) as off white solid, LCMS (m/z): 447.26 [M+H]$^+$.

$^1$H NMR (400 MHz, CDCl$_3$): δ 12.94 (s, 1H), 8.62 (dd, J=2.6, 0.7 Hz, 1H), 8.32 (dd, J=4.7, 1.5 Hz, 1H), 8.15 (ddd, J=8.4, 2.7, 1.5 Hz, 1H), 7.33 (d, J=8.5 Hz, 1H), 7.29-7.24 (m, 1H), 6.41 (d, J=8.6 Hz, 1H), 4.90 (t, J=2.6 Hz, 1H), 4.22-4.04 (m, 2H), 3.31 (dd, J=13.5, 1.9 Hz, 1H), 3.25-3.14 (m, 2H), 2.99-2.88 (m, 3H), 2.48-2.36 (m, 1H), 2.25-2.18 (m, 1H), 2.13 (dd, J=13.2, 4.0 Hz, 1H), 1.98-1.92 (m, 1H), 1.85 (tdd, J=13.9, 5.2, 2.9 Hz, 1H), 1.71 (dtd, J=16.5, 8.3, 7.7, 4.3 Hz, 1H), 1.63 (d, J=3.8 Hz, 1H), 1.57-1.44 (m, 1H), 1.33 (d, J=14.2 Hz, 1H).

Example 212

Synthesis of (4S)—N-(1H-imidazo[4, 5-b]pyridin-5-yl)-7-(2-methylpyridin-4-yl)-3,4-dihydro-1,4-methanopyrido[2,3-b][1, 4]diazepine-5(2H)-carboxamide

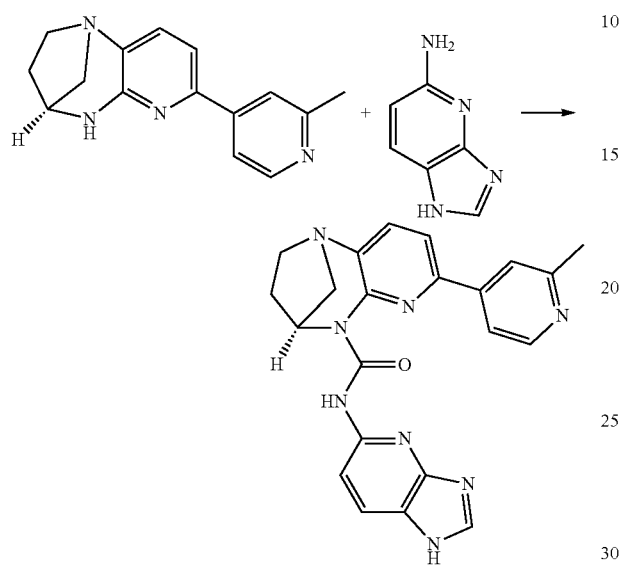

To a solution of (4S)-7-(2-methylpyridin-4-yl)-2,3,4,5-tetrahydro-1,4-methanopyrido[2,3-b][1,4]diazepine (600 mg, 2.378 mmol) in THF (30 ml) was added triphosgene (353 mg, 1.189 mmol) at 0° C. and stirred at room temperature for 1 h. Then 1H-imidazo[4,5-b]pyridin-5-amine (415 mg, 3.09 mmol) and triethylamine (1.657 mL, 11.89 mmol) were added sequentially and the reaction was heated at 70° C. for 16 h in sealed tube. The reaction mixture was allowed to cool to room temperature, poured in saturated NaHCO$_3$ solution (150 mL) and extracted with ethyl acetate (3×50 mL). The combined organic layer was dried over anhydrous Na$_2$SO$_4$ and concentrated under reduced pressure to obtain crude product. The crude mixture was purified by flash column chromatography (silica-gel: 100-200 mesh, using gradient mixture of 1% methanol in dichloromethane as eluent) to afford (4S)—N-(1H-imidazo[4, 5-b]pyridin-5-yl)-7-(2-methylpyridin-4-yl)-3,4-dihydro-1,4-methanopyrido[2,3-b][1, 4]diazepine-5(2H)-carboxamide (160 mg, 0.388 mmol, 25%) as pale yellow solid (TLC: 5% methanol in DCM, R$_f$=0.3), LCMS (m/z): 413.28 [M+H]$^+$.

$^1$H NMR (400 MHz, DMSO-d6): δ 13.43 (s, 1H), 12.30-11.54 (m, 1H), 8.72 (d, J=5.4 Hz, 1H), 8.34 (s, 1H), 8.19-8.10 (m, 3H), 8.04 (d, J=8.7 Hz, 1H), 7.80 (d, J=8.0 Hz, 1H), 7.72 (d, J=8.0 Hz, 1H), 5.55 (dd, J=6.0, 3.1 Hz, 1H), 3.12 (d, J=11.5 Hz, 2H), 2.98 (d, J=3.3 Hz, 1H), 2.95 (d, J=3.3 Hz, 1H), 2.70 (s, 3H), 2.25 (m, J=13.9, 4.7 Hz, 1H), 1.96 (dt, J=14.3, 7.4 Hz, 1H).

Example 213

Synthesis of (4S)—N-(6-fluoropyrazin-2-yl)-7-(2-methylpyridin-4-yl)-3,4-dihydro-1,4-methanopyrido[2,3-b][1,4]diazepine-5(2H)-carboxamide

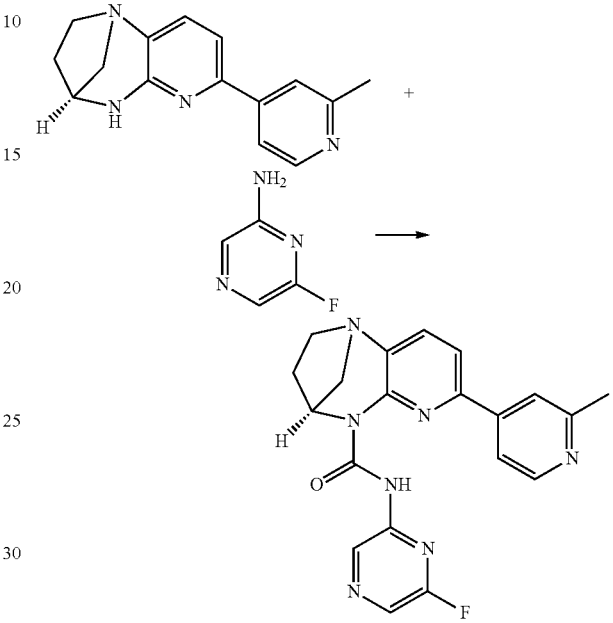

Triethylamine (1.105 mL, 7.93 mmol) and triphosgene (235 mg, 0.793 mmol) were added to a stirred solution of (4S)-7-(2-methylpyridin-4-yl)-2,3,4,5-tetrahydro-1,4-methanopyrido[2,3-b][1,4]diazepine (400 mg, 1.585 mmol) in Tetrahydrofuran (THF) (20 mL) at 25° C., after 30 min, 6-fluoropyrazin-2-amine (359 mg, 3.17 mmol) was added and heated to 70° C. for 16 h. Allowed the reaction mixture to room temperature, organic solvent was removed by rotary evaporation. Residue was diluted with water (50 mL) and extracted with ethyl acetate (3×60 mL). The combined organic layers washed with brine (60 mL) and dried over Na$_2$SO$_4$, filtered and concentrated to get crude compound. Crude compound was purified by flash column chromatography (silica gel: 100-200 mesh, 2% MeOH in DCM as an eluent) to get (4S)—N-(6-fluoropyrazin-2-yl)-7-(2-methylpyridin-4-yl)-3,4-dihydro-1,4-methanopyrido[2,3-b][1,4]diazepine-5(2H)-carboxamide (210 mg, 0.522 mmol, 32.9% yield) as a pale yellow solid (TLC Eluent: 10% MeOH in DCM, R$_f$: 0.4), LCMS (m/z): 392.26 [M+H]$^+$.

$^1$H NMR (400 MHz, CDCl$_3$): δ 13.82 (s, 1H), 9.48 (d, J=4.6 Hz, 1H), 8.66 (d, J=5.3 Hz, 1H), 8.15 (d, J=8.4 Hz, 1H), 7.92 (d, J=2.2 Hz, 1H), 7.71-7.40 (m, 2H), 7.26 (s, 1H), 5.75-5.63 (m, 1H), 3.26 (dd, J=9.7, 6.9 Hz, 3H), 3.05 (d, J=3.3 Hz, 1H), 2.75 (s, 3H), 2.36 (dddd, J=13.9, 9.9, 5.9, 3.9 Hz, 1H), 2.16-1.93 (m, 1H).

Example 214

Synthesis of (4S)—N-(pyrazin-2-yl)-7-(4-(trifluoromethyl)piperidin-1-yl)-3,4-dihydro-1,4-methanopyrido[2,3-b][1,4]diazepine-5(2H)-carboxamide

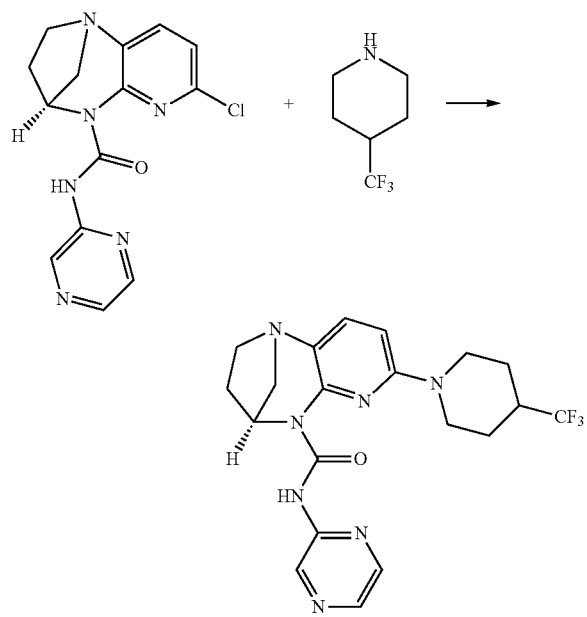

To a de-gassed solution of (4S)-7-chloro-N-(pyrazin-2-yl)-3,4-dihydro-1,4-methanopyrido[2,3-b][1,4]diazepine-5(2H)-carboxamide (800 mg, 2.53 mmol) and 4-(trifluoromethyl)piperidine (580 mg, 3.79 mmol) in 1,4-dioxane (15 mL) was added $Cs_2CO_3$ (2469 mg, 7.58 mmol) and purged with argon gas for 15 min and followed by x-phos (241 mg, 0.505 mmol), palladium(II) acetate (56.7 mg, 0.253 mmol) were added. The reaction mixture was stirred at 100° C. for 16 h in sealed tube. The reaction mixture was allowed to cool to room temperature, poured in to cold water (30 mL) and extracted with ethyl acetate (2×50 mL). The combined organic layer was dried over anhydrous sodium sulfate, concentrated under reduced pressure to obtain crude product. The crude mixture was purified by flash column chromatography (silica-gel: 100-200 mesh, using gradient mixture of 2% MeOH in DCM as eluent) to afford (4S)—N-(pyrazin-2-yl)-7-(4-(trifluoromethyl)piperidin-1-yl)-3,4-dihydro-1,4-methanopyrido [2,3-b][1,4]diazepine-5(2H)-carboxamide (255 mg, 0.559 mmol, 22.13% yield) as an off white solid (TLC: 100% ethyl acetate, $R_f$=0.3), LCMS (m/z): 434.1 $[M+H]^+$.

$^1H$ NMR (400 MHz, $CDCl_3$): δ 13.39 (s, 1H), 9.54 (d, J=1.5 Hz, 1H), 8.25 (d, J=2.5 Hz, 1H), 8.19 (dd, J=2.6, 1.6 Hz, 1H), 7.37 (d, J=8.6 Hz, 1H), 6.32 (d, J=8.6 Hz, 1H), 5.62 (dd, J=6.0, 3.2 Hz, 1H), 4.41-4.30 (m, 2H), 3.30-3.18 (m, 1H), 3.16-3.08 (m, 2H), 3.00-2.88 (m, 3H), 2.37-2.19 (m, 2H), 2.09-1.97 (m, 3H), 1.75-1.61 (m, 2H).

Example 215

Synthesis of (9S)—N-(1-methyl-1H-pyrazol-4-yl)-2-(2-methylpyridin-4-yl)-8,9-dihydro-6H-5,9-methanopyrido[2,3-b][1,4]diazocine-10(7H)-carboxamide

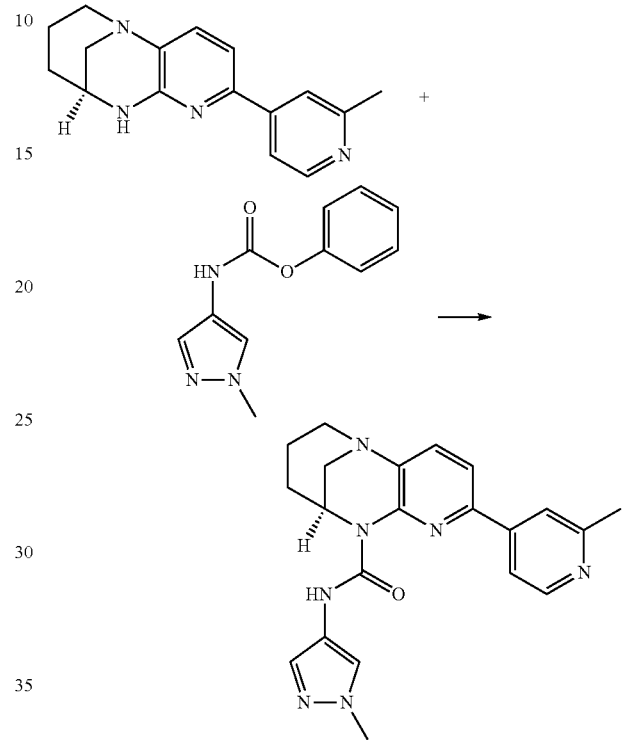

DMAP (0.573 g, 4.69 mmol) was added to a stirred solution of (9S)-2-(2-methylpyridin-4-yl)-7,8,9,10-tetrahydro-6H-5,9-methanopyrido[2,3-b][1,4]diazocine (0.5 g, 1.877 mmol), and phenyl (1-methyl-1H-pyrazol-4-yl)carbamate (1.01 g, 4.692 mmol) in tetrahydrofuran (10 mL) at room temperature and heated to 24h at 80° C. in sealed tube. The reaction mixture was cooled to 28° C., and was diluted with ethyl acetate and water. The organic layer was separated and was washed with water and brine. The organic layer was dried over sodium sulfate and evaporated under reduced pressure to get crude compound (TLC eluent: 10% MeOH in EtOAc; $R_f$-0.4; UV active). The crude compound was purified by using neutral alumina and was eluted with 75% ethyl acetate in hexane to afford (9S)—N-(1-methyl-1H-pyrazol-4-yl)-2-(2-methylpyridin-4-yl)-8,9-dihydro-6H-5,9-methanopyrido[2,3-b][1,4]diazocine-10(7H)-carboxamide (0.17 g, 0.430 mmol, 22.89% yield) as an off-white solid, LCMS (m/z): 390.28 $[M+H]^+$.

$^1H$ NMR ($CDCl_3$, 400 MHz): δ 13.27 (s, 1H), 8.67 (d, J=5.26 Hz, 1H), 7.87 (s, 1H), 7.63 (d, J=1.53 Hz, 1H), 7.53-7.57 (m, 2H), 7.43 (d, J=0.66 Hz, 1H), 7.40 (s, 1H), 4.99 (t, J=2.30 Hz, 1H), 3.89 (s, 3H), 3.22-3.42 (m, 3H), 2.98 (br d, J=13.59 Hz, 1H), 2.70 (s, 3H), 2.20-2.28 (m, 1H), 1.92 (tdd, J=13.67, 13.67, 5.54, 3.07 Hz, 1H), 1.32-1.50 (m, 2H).

Example 216

Synthesis of (4S)-7-(2-methylpyridin-4-yl)-N-(2-(pyridin-3-yl)ethyl)-3,4-dihydro-1,4-me-thanopyrido[2,3-b][1,4]diazepine-5(2H)-carboxamide hydrochloride

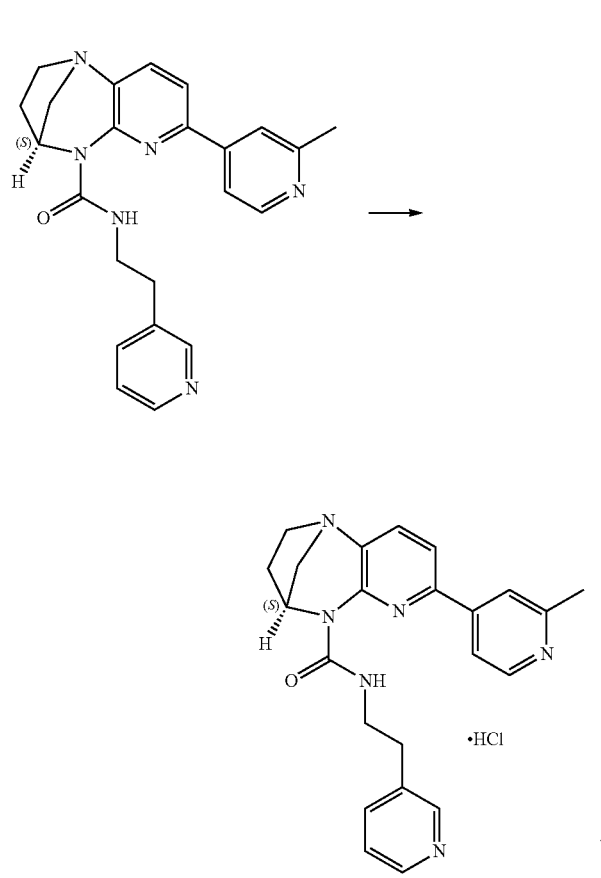

2.0 M Hydrochloric acid in diethyl ether (2 mL, 4.00 mmol) was added to (4S)-7-(2-methylpyridin-4-yl)-N-(2-(pyridin-3-yl)ethyl)-3,4-dihydro-1,4-methanopyrido[2,3-b][1,4]diazepine-5(2H)-carboxamide (250 mg, 0.624 mmol) at 0° C. The reaction mixture was stirred at 28° C. for 4 h and concentrated to give crude compound (TLC eluent: 5% MeOH in DCM: $R_f$-0.1; UV active). The crude compound was washed with diethyl ether (2×5 mL) to afford pure (4S)-7-(2-methylpyridin-4-yl)-N-(2-(pyridin-3-yl)ethyl)-3,4-dihydro-1,4-methanopyrido[2,3-b][1,4]diazepine-5(2H)-carboxamide hydrochloride (274 mg, 0.606 mmol, 97% yield) as yellow solid, LCMS (m/z): 401.1 [M+H]$^+$.

$^1$H NMR (400 MHz, CD$_3$OD): δ 8.89 (s, 2H), 8.72 (d, J=4.7 Hz, 1H), 8.65 (d, J=6.7 Hz, 1H), 8.44 (s, 1H), 8.32 (s, 1H), 8.17 (d, J=7.1 Hz, 1H), 8.06-7.92 (m, 2H), 5.67 (d, J=5.2 Hz, 1H), 3.99-3.75 (m, 6H), 3.32-3.20 (m, 2H), 2.93 (s, 3H), 2.72-2.53 (m, 1H), 2.42-2.37 (s, 1H).

Example 217

Synthesis of ((4S)-7-(2-methylpyridin-4-yl)-3,4-dihydro-1,4-methanopyrido[2,3-b][1,4]diazepin-5(2H)-yl)(3-methylpyrrolidin-1-yl)methanone

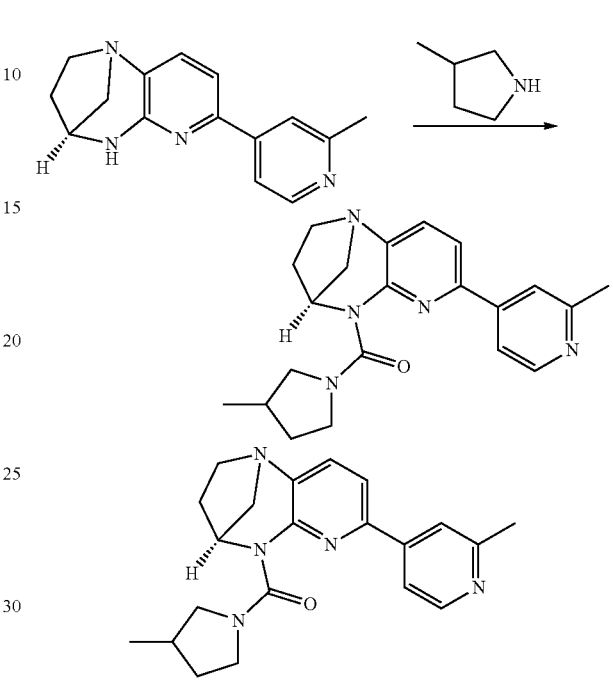

(4S)-7-(2-methylpyridin-4-yl)-2,3,4,5-tetrahydro-1,4-methanopyrido[2,3-b][1,4]diazepine (1.5 g, 5.94 mmol) in Tetrahydrofuran (THF) (20 mL) stirred under nitrogen at room temp was added triphosgene (0.882 g, 2.97 mmol) and stirred for 30 min at room temperature. After 30 minutes triethylamine (4.14 mL, 29.7 mmol) and 3-methylpyrrolidine (0.658 g, 7.73 mmol) were added, then the reaction mixture was stirred at 60° C. for 16 hr. Reaction mixture was quenched with 2×25 ml of water and extracted with 2×50 ml of ethyl acetate, organic layer was dried over sodium sulfate and concentrated under reduced pressure to afford crude compound. The crude product was purified by column chromatography and was submitted for SFC, separated peaks as peak-I isolated yield ((4S)-7-(2-methylpyridin-4-yl)-3,4-dihydro-1,4-methanopyrido[2,3-b][1,4]diazepin-5(2H)-yl)(3-methylpyrrolidin-1-yl)methanone (210 mg, 0.574 mmol, 9.65% yield) as pale brown solid and peak-II isolated yield ((4S)-7-(2-methylpyridin-4-yl)-3,4-dihydro-1,4-methanopyrido[2,3-b][1,4]diazepin-5(2H)-yl)(3-methylpyrrolidin-1-yl)methanone (180 mg, 0.494 mmol, 6.79% yield) as pale brown solid, ($R_f$ value: 0.4, 10% Methanol in DCM), LCMS (m/z): 364.32 [M+H]$^+$.

Peak-1

$^1$H NMR (400 MHz, DMSO-d$_6$) δ ppm 8.50 (d, J=5.04 Hz, 1H), 7.76 (d, J=0.66 Hz, 1H), 7.68 (dd, J=5.26, 1.10 Hz, 1H), 7.52-7.48 (m, 1H), 7.47-7.38 (m, 1H), 4.40 (br d, J=2.85 Hz, 1H), 3.48 (br s, 3H), 3.16-2.98 (m, 4H), 2.89 (dd, J=11.62, 3.29 Hz, 1H), 2.53-2.46 (m, 3H), 2.32-2.20 (m, 3H), 2.14 (br d, J=4.60 Hz, 2H), 1.48 (dt, J=19.51, 9.76 Hz, 1H), 1.12-0.98 (m, 2H).

Peak-II $^1$H NMR (400 MHz, DMSO-d$_6$) δ ppm 8.48 (d, J=5.26 Hz, 1H), 7.76 (s, 1H), 7.68 (dd, J=5.26, 1.32 Hz, 1H), 7.40-7.54 (m, 2H), 4.44 (br s, 1H), 3.36-3.69 (m, 3H), 2.99-3.18 (m, 4H), 2.89 (dd, J=11.62, 3.29 Hz, 1H), 2.03-2.33 (m, 4H), 1.81-1.52 (m, 2H), 1.01 (br s, 2H).

Example 218

Synthesis of (4S)—N-(5-methylpyridin-3-yl)-7-(2-methylpyridin-4-yl)-3,4-dihydro-1,4-methanopyrido[2,3-b][1,4]diazepine-5(2H)-carboxamide

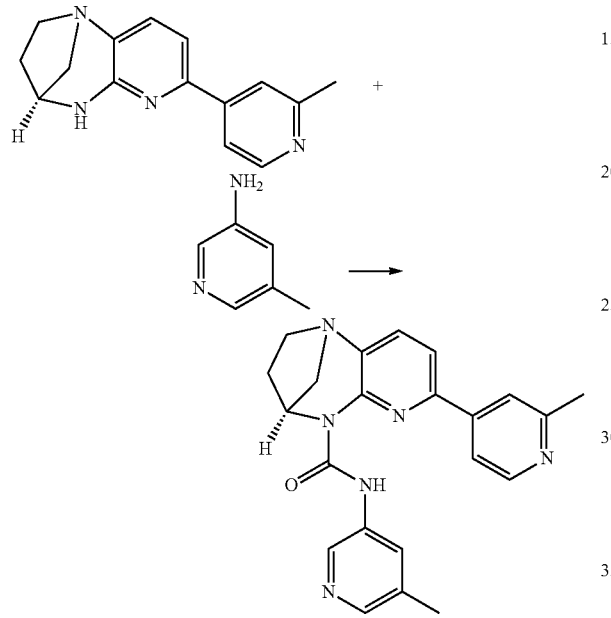

To a stirred solution of (4S)-7-(2-methylpyridin-4-yl)-2,3,4,5-tetrahydro-1,4-methanopyrido[2,3-b][1,4]diazepine (600 mg, 2.378 mmol) in THF (15 mL) was added triphosgene (423 mg, 1.427 mmol) at 30° C. and stirred for 1 h. Then Et₃N (1.657 mL, 11.89 mmol) and 5-methylpyridin-3-amine (771 mg, 7.13 mmol) were added at 30° C. and heated the reaction mixture at 65° C. for 16h. The reaction mixture was poured in to cold water (50 ml) and extracted with DCM (2×50 ml). The combined organic layer was washed with water, brine, dried over sodium sulfate and solvent evaporated under reduced pressure to obtain crude product. The crude mixture was purified by flash column chromatography (silica-gel: 100-200 mesh, eluent: 0-15% MeOH in DCM) to afford (4S)—N-(5-methylpyridin-3-yl)-7-(2-methylpyridin-4-yl)-3,4-dihydro-1,4-methanopyrido[2,3-b][1,4]diazepine-5(2H)-carboxamide (300 mg, 0.777 mmol, 45% yield) as a yellow solid (TLC: 10% MeOH in EtOAc, $R_f$: 0.4), LCMS (m/z): 387.36 [M+H]⁺.

¹H NMR (400 MHz, CDCl₃): δ ppm 13.00 (s, 1H), 8.66 (d, J=5.04 Hz, 1H), 8.47 (s, 1H), 8.16 (s, 1H), 7.99 (s, 1H), 7.71-7.57 (m, 2H), 7.50 (d, J=5.26 Hz, 1H), 7.38 (d, J=7.89 Hz, 1H), 5.70 (dd, J=5.81, 3.18 Hz, 1H), 3.37-3.10 (m, 3H), 3.03 (dd, J=12.06, 3.07 Hz, 1H), 2.68 (s, 3H), 2.45-2.25 (m, 4H), 2.22-1.98 (m, 1H).

Example 219

Synthesis of (4S)—N-(benzo[d][1,3]dioxol-5-yl)-7-(2-methylpyridin-4-yl)-3,4-dihydro-1,4-methanopyrido[2,3-b][1,4]diazepine-5(2H)-carboxamide

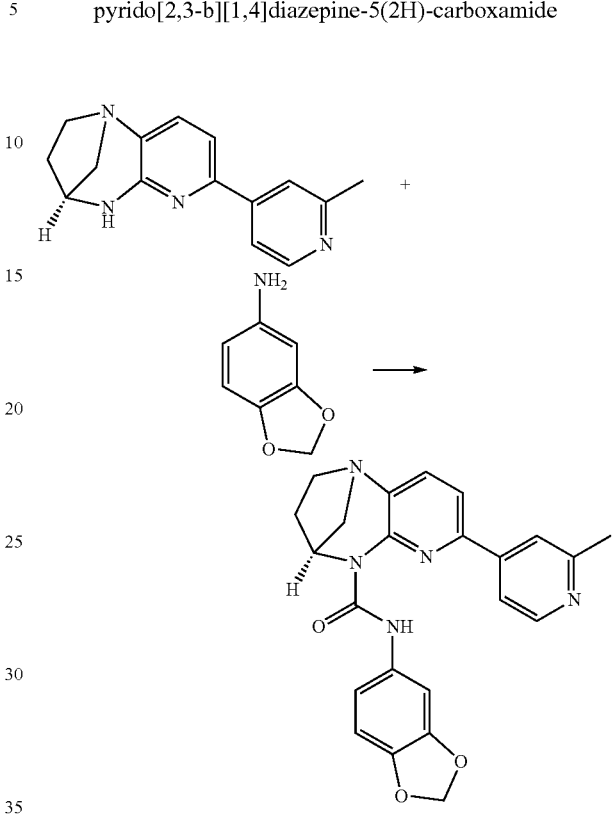

To a solution of (4S)-7-(2-methylpyridin-4-yl)-2,3,4,5-tetrahydro-1,4-methanopyrido[2,3-b][1,4]diazepine (600 mg, 2.378 mmol) in THF (15 mL), was added triphosgene (353 mg, 1.189 mmol) at 0° C. and stirred at 27° C. for 2 h, then benzo[d][1,3]dioxol-5-amine (391 mg, 2.85 mmol) and N-ethyl-N-isopropylpropan-2-amine (307 mg, 2.378 mmol) were added at 27° C., heated to 50° C. for 16 h. The reaction was allowed to room temperature and the reaction mixture was poured in to saturated NaHCO₃ solution and extracted with ethyl acetate (3×50 mL). The combined organic layer was dried over anhydrous Na₂SO₄ and concentrated under reduced pressure to obtain the crude product. The crude mixture was purified by flash column chromatography (silica-gel: 100-200 mesh, eluted with 2% methanol in dichloromethane) to afford (4S)—N-(benzo[d][1,3]dioxol-5-yl)-7-(2-methylpyridin-4-yl)-3,4-dihydro-1,4-methanopyrido[2,3-b][1,4]diazepine-5(2H)-carboxamide (270 mg, 26.2% yield) (TLC: eluent, 5% Methanol in DCM; $R_f$-0.4), LCMS (m/z): 416.30 [M+H]⁺.

¹H NMR (400 MHz, CDCl₃): δ ppm 12.81 (s, 1H), 8.63 (d, J=5.26 Hz, 1H), 7.64-7.59 (m, 2H), 7.49 (dd, J=5.15, 1.43 Hz, 1H), 7.37-7.31 (m, 2H), 6.85 (dd, J=8.33, 2.19 Hz, 1H), 6.75 (d, J=8.33 Hz, 1H), 5.97-5.92 (m, 2H), 5.73-5.66 (m, 1H), 3.33-3.10 (m, 3H), 3.01 (dd, J=12.06, 3.29 Hz, 1H), 2.65 (s, 3H), 2.32 (dddd, J=14.11, 9.84, 5.86, 4.17 Hz, 1H), 2.09 (dt, J=14.03, 6.80 Hz, 1H).

Example 220

Synthesis of (4S)-7-(2-methylpyridin-4-yl)-N-(2-(pyridin-2-yl)ethyl)-3,4-dihydro-1,4-methanopyrido[2,3-b][1,4]diazepine-5(2H)-carboxamide hydrochloride

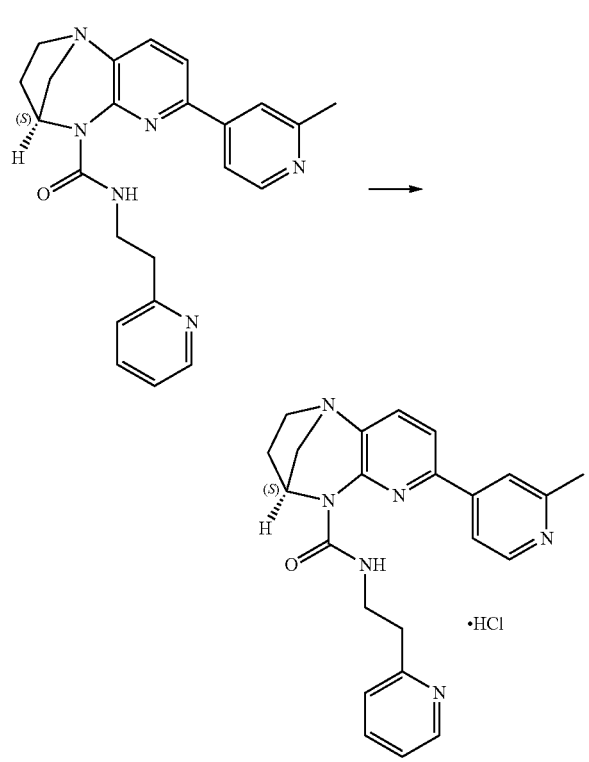

2.0 M Hydrochloric acid in diethyl ether (2 mL, 4.00 mmol) was added to (4S)-7-(2-methylpyridin-4-yl)-N-(2-(pyridin-2-yl)ethyl)-3,4-dihydro-1,4-methanopyrido[2,3-b][1,4]diazepine-5(2H)-carboxamide (300 mg, 0.749 mmol) at 0° C. The reaction mixture was stirred at 28° C. for 4 h and concentrated to give crude compound (TLC eluent: 5% MeOH in DCM: $R_f$-0.1; UV active). The crude compound was washed with diethyl ether (3×5 mL) to afford pure (4S)-7-(2-methylpyridin-4-yl)-N-(2-(pyridin-2-yl)ethyl)-3,4-dihydro-1,4-methanopyrido[2,3-b][1,4]diazepine-5(2H)-carboxamide hydrochloride (296 mg, 0.675 mmol, 90% yield) as yellow solid, LCMS (m/z) 401.2 [M+H]$^+$.

$^1$H NMR (400 MHz, DMSO-d$_6$): δ 9.88 (t, J=5.9 Hz, 1H), 8.89 (d, J=6.1 Hz, 1H), 8.66 (dd, J=5.6, 1.7 Hz, 1H), 8.40-8.35 (m, 1H), 8.31-8.29 (m, 1H), 8.14 (dd, J=6.2, 1.9 Hz, 1H), 8.08 (d, J=7.8 Hz, 1H), 7.95 (dd, J=7.9, 4.9 Hz, 2H), 7.74 (t, J=6.7 Hz, 1H), 5.40 (dd, J=5.6, 2.9 Hz, 1H), 3.97-3.78 (m, 2H), 3.58-3.26 (m, 6H), 2.84 (s, 3H), 2.32-2.25 (m, 1H), 2.19-2.03 (m, 1H).

Example 221

Synthesis of (4S)-7-(piperazin-1-yl)-N-(pyrazin-2-yl)-3,4-dihydro-1,4-methanopyrido[2,3-b][1,4]diazepine-5(2H)-carboxamide

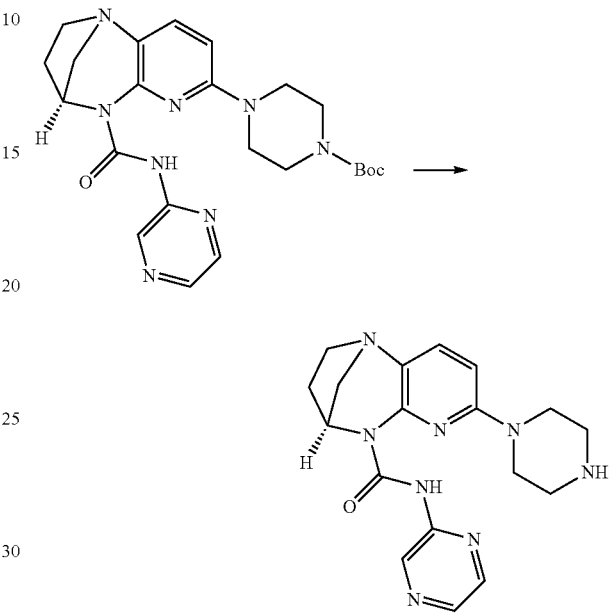

To a solution of tert-butyl 4-((4S)-5-(pyrazin-2-ylcarbamoyl)-2,3,4,5-tetrahydro-1,4-methanopyrido[2,3-b][1,4]diazepin-7-yl)piperazine-1-carboxylate (359 mg, 0.770 mmol) in THF (5 mL) was added a 2M solution of HCl in diethyl ether (1.924 mL, 3.85 mmol) at 0° C. and the reaction mixture was stirred at 35° C. for 4 h and the reaction mixture was cooled to 0° C., neutralized with aq NaHCO$_3$ solution and extracted with CH$_2$Cl$_2$ (2×50 mL). The combined organic layer was washed with water, brine, dried over anhydrous Na$_2$SO$_4$ and concentrated under reduced pressure to obtain the crude product. The crude mixture was purified by flash column chromatography (silica-gel: 100-200 mesh, eluent: 3% MeOH in DCM) to afford (4S)-7-(piperazin-1-yl)-N-(pyrazin-2-yl)-3,4-dihydro-1,4-methanopyrido[2,3-b][1,4]diazepine-5(2H)-carboxamide (277 mg, 0.741 mmol, 96% yield) as an off white solid (TLC: $R_f$: 0.3; 5% MeOH in DCM), LCMS (m/z): 367.2 [M+H]$^+$.

$^1$H NMR (400 MHz, CDCl$_3$): δ 13.41 (s, 1H), 9.53 (d, J=1.5 Hz, 1H), 8.24 (d, J=2.5 Hz, 1H), 8.17 (dd, J=2.5, 1.5 Hz, 1H), 7.38 (d, J=8.6 Hz, 1H), 6.30 (d, J=8.6 Hz, 1H), 5.62-5.55 (m, 1H), 3.63 (t, J=5.2 Hz, 4H), 3.26-3.17 (m, 1H), 3.17-3.06 (m, 6H), 2.92 (dd, J=11.9, 3.3 Hz, 1H), 2.27 (dddd, J=13.7, 9.9, 6.2, 3.8 Hz, 1H), 2.07-1.96 (m, 2H).

Example 222

Synthesis of (4S)-7-(4-methylpiperidin-1-yl)-N-(pyrazin-2-yl)-3,4-dihydro-1,4-methanopyrido[2,3-b][1,4]diazepine-5(2H)-carboxamide

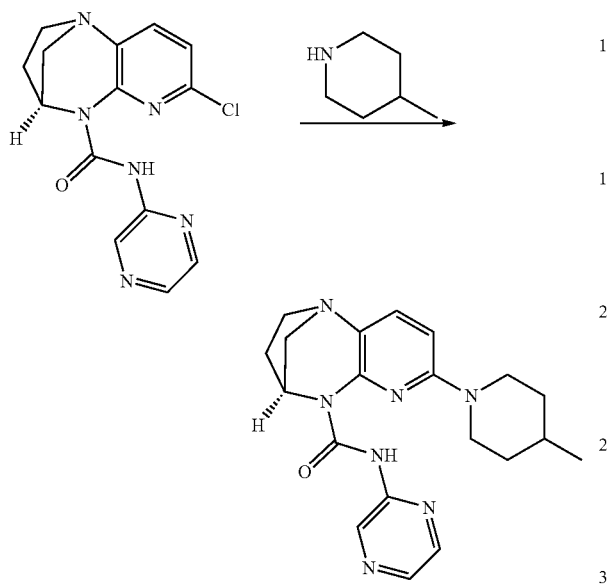

To a degassed solution of (4S)-7-chloro-N-(pyrazin-2-yl)-3,4-dihydro-1,4-methanopyrido[2,3-b][1,4]diazepine-5(2H)-carboxamide (600 mg, 1.894 mmol), 4-methylpiperidine (376 mg, 3.79 mmol) in 1,4-dioxane (10 mL) were added Cs$_2$CO$_3$ (1852 mg, 5.68 mmol), x-phos (361 mg, 0.758 mmol) and Pd(OAc)$_2$ (106 mg, 0.474 mmol) at RT. The reaction mixture was stirred at 110° C. for 16 h and was poured in to cold water (20 mL), extracted with ethyl acetate (2×50 mL). The combined organic layer was dried over anhydrous sodium sulfate and concentrated under reduced pressure to obtain the crude product. The crude mixture was purified by flash column chromatography (silica-gel: 100-200 mesh, eluent: 4% MeOH in DCM) to afford (4S)-7-(4-methylpiperidin-1-yl)-N-(pyrazin-2-yl)-3,4-dihydro-1,4-methanopyrido[2,3-b][1,4]diazepine-5(2H)-carboxamide (300 mg, 0.775 mmol, 40.9% yield) as an off white solid (TLC: R$_f$: 0.4; neat EtOAc), LCMS (m/z): 380.3 [M+H]$^+$.

$^1$H NMR (400 MHz, CDCl$_3$): δ 13.51 (s, 1H), 9.52 (d, J=1.5 Hz, 1H), 8.23 (dd, J=2.5, 0.4 Hz, 1H), 8.20 (dd, J=2.5, 1.5 Hz, 1H), 7.33 (d, J=8.6 Hz, 1H), 6.30 (d, J=8.7 Hz, 1H), 5.61 (dd, J=6.1, 3.2 Hz, 1H), 4.20 (ddd, J=11.4, 3.6, 2.1 Hz, 2H), 3.22 (dddd, J=12.3, 8.6, 3.7, 2.2 Hz, 1H), 3.15-3.05 (m, 2H), 3.00-2.86 (m, 3H), 2.26 (dddd, J=13.8, 9.9, 6.2, 3.8 Hz, 1H), 2.04-1.94 (m, 1H), 1.84-1.72 (m, 2H), 1.68-1.60 (m, 1H), 1.33-1.18 (m, 2H), 0.99 (d, J=6.5 Hz, 3H).

Example 223

Synthesis of (4S)-7-(2,6-dimethylpyridin-3-yl)-N-(pyrazin-2-yl)-3,4-dihydro-1,4-methanopyrido[2,3-b][1,4]diazepine-5(2H)-carboxamide

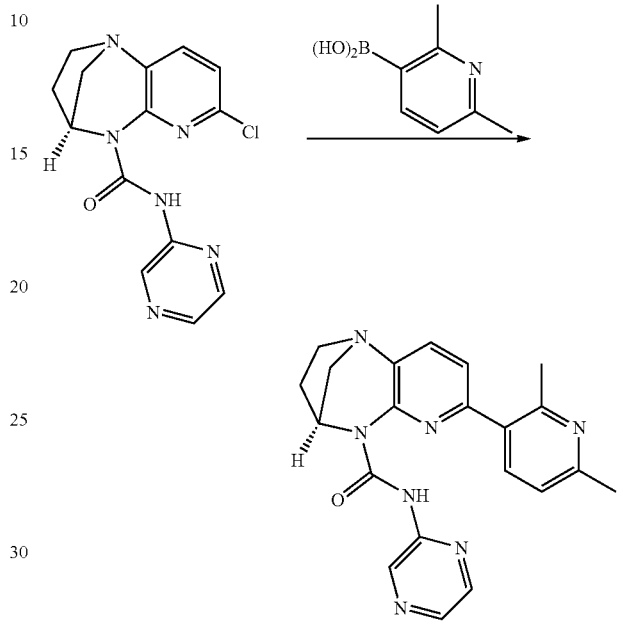

K$_3$PO$_4$ (535 mg, 2.53 mmol) was added to a stirred solution of (4S)-7-chloro-N-(pyrazin-2-yl)-3,4-methanopyrido[2,3-b][1,4]diazepine-5(2H)-carboxamide (400 mg, 1.263 mmol) & (2,6-dimethylpyridin-3-yl)boronic acid (248 mg, 1.642 mmol) in 1,4-Dioxane (20 mL) and Water (1 mL) then de-gassed for 15 min and x-phos (60.2 mg, 0.126 mmol) followed by Pd$_2$(dba)$_3$ (57.8 mg, 0.063 mmol) were added and then the reaction was heated at 90° C. for 2 h 45 min before being allowed to cool to room temperature, filtered through a pad of celite, washed with ethyl acetate (10 mL×2), from filtrate organic solvent was removed under reduced pressure. The aqueous layer was extracted with ethyl acetate (20 mL×2), washed with water (20 mL×2), brine (20 mL) and dried over Na$_2$SO$_4$. Organic solvent was removed in vacuum to afford crude compound. Above compound was purified by flash column chromatography (silica-gel: 100-200 mesh, eluted with 80% ethyl acetate in hexane) to afford the (4S)-7-(2,6-dimethylpyridin-3-yl)-N-(pyrazin-2-yl)-3,4-dihydro-1,4-methanopyrido[2,3-b][1,4]diazepine-5(2H)-carboxamide (330 mg, 0.848 mmol, 67.2% yield) as an off white solid (TLC: Eluent: 100% ethyl acetate R$_f$: 0.3, UV active), LCMS (m/z): 388.28 [M+H]$^+$.

$^1$H-NMR (CDCl$_3$, 400 MHz): δ 13.5 (s, 1H), 9.45 (s, 1H), 8.22-8.25 (m, 1H), 8.18-8.20 (m, 1H), 7.77 (d, 1H, J=7.6 Hz), 7.6 (d, 1H, J=8 Hz), 7.08-7.14 (m, 2H), 5.68-5.72 (m, 1H), 3.18-3.34 (m, 3H), 3.01-3.06 (m, 1H), 2.65 (s, 3H), 2.5 (s, 3H), 2.31-2.39 (m, 1H), 2.08-2.15 (m, 1H).

Example 224

Synthesis of (4S)-7-(2,6-dimethylpyridin-3-yl)-N-(pyridin-3-yl)-3,4-dihydro-1,4-methanopyrido[2,3-b][1,4]diazepine-5(2H)-carboxamide

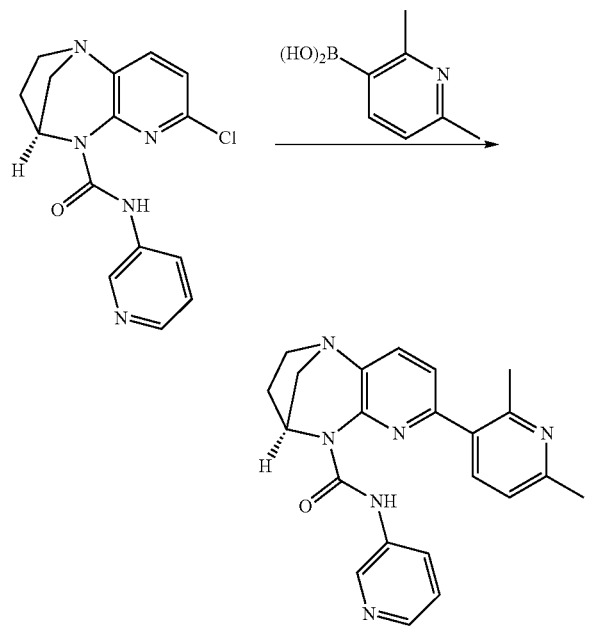

K₃PO₄ (537 mg, 2.53 mmol) was added to a stirred solution of (4S)-7-chloro-N-(pyridin-3-yl)-3,4-dihydro-1,4-methanopyrido[2,3-b][1,4]diazepine-5(2H)-carboxamide (400 mg, 1.267 mmol) &(2,6-dimethylpyridin-3-yl)boronic acid (249 mg, 1.647 mmol) in 1,4-Dioxane (15 mL) and water (1 mL) then de-gassed for 15 min and dicyclohexyl (2',4',6'-triisopropyl-[1,1'-biphenyl]-2-yl)phosphine (60.4 mg, 0.127 mmol), followed by Pd₂(dba)₃ (58.0 mg, 0.063 mmol) were added and heated at 100° C. for 2 h 45 min. Allowed the reaction mixture to RT, filtered through a pad of celite, washed with ethyl acetate (10 mL×2), filtrate solvent removed under reduced pressure. Organic compound was extracted with ethyl acetate (20 mL×2). The combined organic layers were washed with water (20 mL×2), brine (20 mL) and dried over Na₂SO₄. Organic solvent was removed under vacuum to afford crude compound. Above crude compound was purified by flash column chromatography (silica-gel: 100-200 mesh, Compound eluted with 90% ethyl acetate in hexane) to afford the (4S)-7-(2,6-dimethylpyridin-3-yl)-N-(pyridin-3-yl)-3,4-dihydro-1,4-methanopyrido[2,3-b][1,4]diazepine-5(2H)-carboxamide (304 mg, 0.777 mmol, 61.3% yield) as an off white solid (TLC: Eluent: 100% ethyl acetate R$_f$: 0.4, UV active), LCMS (m/z): 387.31 [M+H]⁺.

¹H-NMR (CDCl₃, 400 MHz): δ 13.13 (s, 1H), 8.33-8.35 (m, 1H), 8.24-8.26 (m, 1H), 8.10-8.14 (m, 1H), 7.6 (d, 1H, J=7.6 Hz), 7.59 (d, 1H, J=8 Hz), 7.19-7.24 (m, 1H), 7.15 (d, 1H, J=8 Hz), 7.05 (d, 1H, J=7.6 Hz), 5.67-5.71 (m, 1H), 3.35-3.4 (m, 1H), 3.19-3.25 (m, 2H), 3.1-3.36 (m, 1H), 2.6 (s, 6H), 2.29-2.38 (m, 1H), 2.17-2.26 (m, 1H).

Example 225

Synthesis of (9S)-N-(pyrazin-2-yl)-2-(3-(trifluoromethyl)piperidin-1-yl)-8,9-dihydro-6H-5,9-methanopyrido[2,3-b][1,4]diazocine-10(7H)-carboxamide

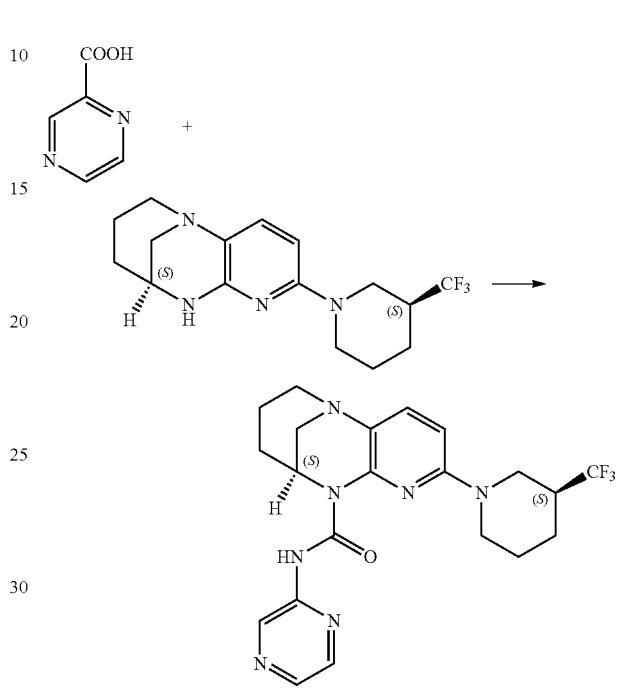

Diphenyl phosphorazidate (1.996 g, 7.25 mmol) added to a stirred solution of pyrazine-2-carboxylic acid (Peak-II of the intermediate SFC separation, 0.600 g, 4.83 mmol) and DIPEA (4.22 mL, 24.17 mmol) in Tetrahydrofuran (THF) (60 mL) stirred with argon at room temp. The reaction mixture was stirred 2 hr at room temperature and added (9S)-2-(3-(trifluoromethyl)piperidin-1-yl)-7,8,9,10-tetrahydro-6H-5,9-methanopyrido[2,3-b][1,4]diazocine (1.105 g, 3.38 mmol). The reaction mixture was stirred 16 hr at 65° C. The reaction mixture was cooled to room temperature and concentrated under reduced pressure. The residue was partitioned between water (30 mL) and EtOAc (100 mL). Organic layer was separated and was dried over anhydrous Na₂SO₄, filtered and filtrate was evaporated to give crude as brown solid (TLC eluent: 100% EtOAc: R$_f$-0.3; UV active). The crude was purified by column chromatography using neutral alumina and was eluted with 50% EtOAc in Hexane to afford pure (9S)-N-(pyrazin-2-yl)-2-(3-(trifluoromethyl)piperidin-1-yl)-8,9-dihydro-6H-5,9-methanopyrido[2,3-b][1,4]diazocine-10(7H)-carboxamide (0.367 g, 0.815 mmol, 16.86% yield) as a pale yellow solid, LCMS (m/z): 448.3 [M+H]⁺.

¹H NMR (400 MHz, CDCl₃): δ 13.79 (s, 1H), 9.53 (d, J=1.5 Hz, 1H), 8.25 (d, J=2.5 Hz, 1H), 8.20 (d, J=1.6 Hz, 1H), 7.32 (d, J=8.6 Hz, 1H), 6.42 (d, J=8.6 Hz, 1H), 4.90 (s, 1H), 4.28 (s, 2H), 3.32 (dd, J=13.5, 1.9 Hz, 1H), 3.21 (dd, J=12.5, 3.3 Hz, 2H), 3.10-2.86 (m, 3H), 2.44 (dt, J=7.6, 3.6 Hz, 1H), 2.28-2.18 (m, 1H), 2.11 (d, J=3.6 Hz, 1H), 1.99-1.80 (m, 2H), 1.78-1.65 (m, 1H), 1.65-1.60 (m, 1H), 1.49 (s, 1H), 1.35 (s, 1H).

Example 226

Synthesis of (4S)-7-(2-methylpyridin-4-yl)-N-(6-methylthiazolo[3,2-b][1,2,4]triazol-2-yl)-3,4-dihydro-1,4-methanopyrido[2,3-b][1,4]diazepine-5(2H)-carboxamide

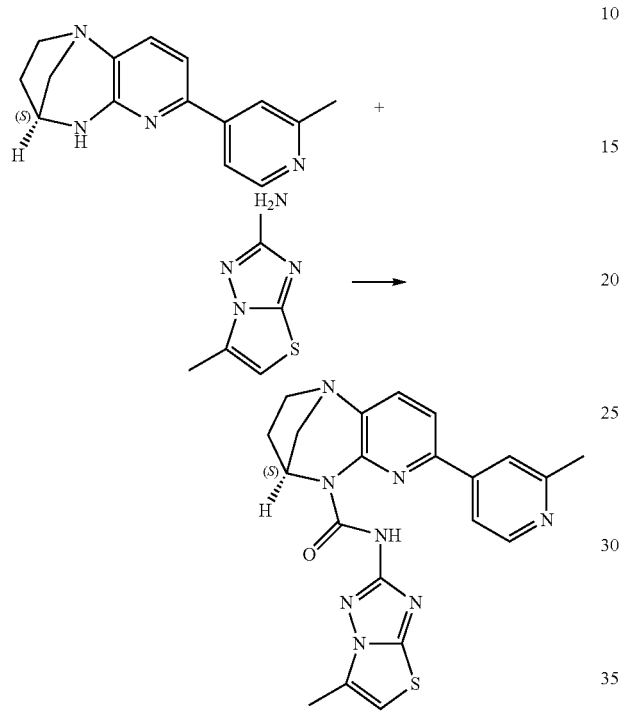

To a solution of (4S)-7-(2-methylpyridin-4-yl)-2,3,4,5-tetrahydro-1,4-methanopyrido[2,3-b][1,4]diazepine (300 mg, 1.189 mmol), triethylamine (0.829 mL, 5.94 mmol) and triphosgene (212 mg, 0.713 mmol) in tetrahydrofuran (10 mL) stirred under nitrogen at room temp for 30 min was added a solution of 6-methylthiazolo[3,2-b][1,2,4]triazol-2-amine (367 mg, 2.378 mmol) in THF (2 mL) dropwise during 1 min. The reaction mixture was stirred at 65° C. for 16 h and cooled to room temperature. The reaction mixture was poured in to water and extracted with EtOAc (3×10 mL). Then the combined organic layers were washed with water, brine solution, dried over sodium sulfate and evaporated to give crude compound (TLC eluent: 10% MeOH in DCM: $R_f$-0.1; UV active). The crude compound was purified by reverse phase column and eluted with 90% (0.1% HCOOH in Water)/MeOH to afford pure (4S)-7-(2-methylpyridin-4-yl)-N-(6-methylthiazolo[3,2-b][1,2,4]triazol-2-yl)-3,4-dihydro-1,4-methanopyrido[2,3-b][1,4]diazepine-5(2H)-carboxamide (390 mg, 0.892 mmol, 75% yield) as pale yellow solid, LCMS (m/z): 433.2 [M+H]$^+$.

$^1$H NMR (400 MHz, CDCl$_3$): δ 13.88 (s, 1H), 8.63 (d, J=5.2 Hz, 1H), 7.91 (d, J=1.9 Hz, 1H), 7.69-7.52 (m, 2H), 7.46 (d, J=8.0 Hz, 1H), 6.48 (d, J=1.6 Hz, 1H), 5.75 (dd, J=5.9, 3.1 Hz, 1H), 3.35-3.10 (m, 3H), 3.02 (dd, J=12.1, 3.3 Hz, 1H), 2.72 (s, 3H), 2.57 (d, J=1.4 Hz, 3H), 2.40-2.25 (m, 1H), 2.19-2.05 (m, 1H).

Example 227

Synthesis of (4S)-7-((S)-3-(hydroxymethyl)morpholino)-N-(pyridin-3-yl)-3,4-dihydro-1,4-methanopyrido[2,3-b][1,4]diazepine-5(2H)-carboxamide

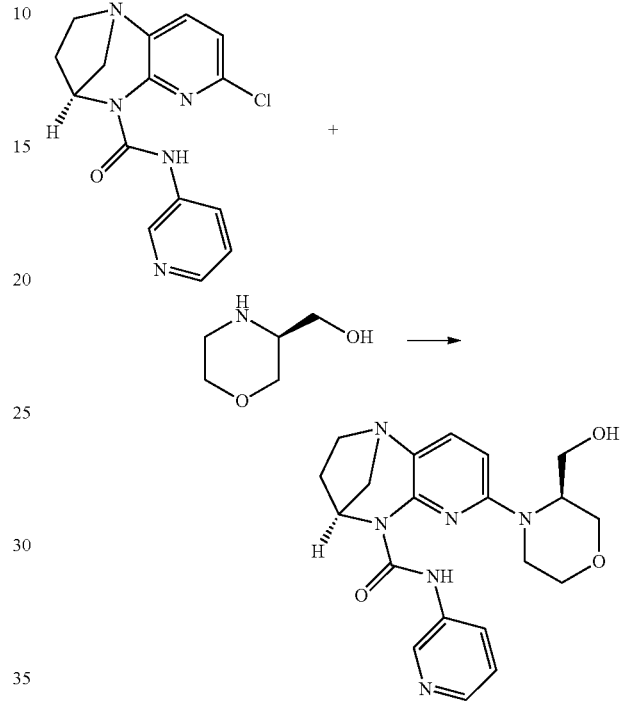

Cs$_2$CO$_3$ (5778 mg, 17.74 mmol) and (S)-morpholin-3-ylmethanol (390 mg, 3.33 mmol) were added to a stirred solution of (4S)-7-chloro-N-(pyridin-3-yl)-3,4-dihydro-1,4-methanopyrido[2,3-b][1,4]diazepine-5(2H)-carboxamide (700 mg, 2.217 mmol) in 1,4-Dioxane (10 mL) at room temperature and purged with argon for 25 min then palladium(II) acetate (49.8 mg, 0.222 mmol) and X-phos (211 mg, 0.443 mmol) were added. The reaction was stirred at 100° C. for 8h before allowing reaction mixture to warm to room temperature. Organic solvent was removed by rotary evaporation, diluted with water (60 mL) and extracted with ethyl acetate (3×50 mL). The combined organic layers were washed with brine (50 mL), dried over Na$_2$SO$_4$, filtered and concentrated to get the crude residue. The crude residue was purified by column chromatography (Silica-gel: 100-200 mesh, 2% methanol in dichloromethane as an eluent) to afford (4S)-7-((S)-3-(hydroxymethyl)morpholino)-N-(pyridin-3-yl)-3,4-dihydro-1,4-methanopyrido[2,3-b][1,4]diazepine-5(2H)-carboxamide (275 mg, 0.691 mmol, 31.2% yield) as an off white solid (TLC eluent: 10% MeOH in DCM $R_f$: 0.4), LCMS (m/z): 397.28 [M+H]$^+$.

$^1$H NMR (400 MHz, CDCl$_3$): δ 12.38 (s, 1H), 8.51 (d, J=2.6 Hz, 1H), 8.36-8.24 (m, 1H), 8.16 (ddd, J=8.4, 2.7, 1.5 Hz, 1H), 7.44-7.16 (m, 2H), 6.25 (d, J=8.6 Hz, 1H), 5.63 (dd, J=6.2, 3.2 Hz, 1H), 4.06 (d, J=7.4 Hz, 2H), 3.81 (t, J=2.7 Hz, 2H), 3.69-3.48 (m, 2H), 3.38-3.03 (m, 4H), 2.90 (dd, J=11.8, 3.3 Hz, 1H), 2.26 (dd, J=10.1, 3.9 Hz, 1H), 2.11-1.87 (m, 1H), 1.26 (d, J=6.6 Hz, 3H).

Example 228

Synthesis of (4S)-7-((R)-3-methylmorpholino)-N-(pyridin-3-yl)-3,4-dihydro-1,4-methano-pyrido[2,3-b][1,4]diazepine-5(2H)-carboxamide

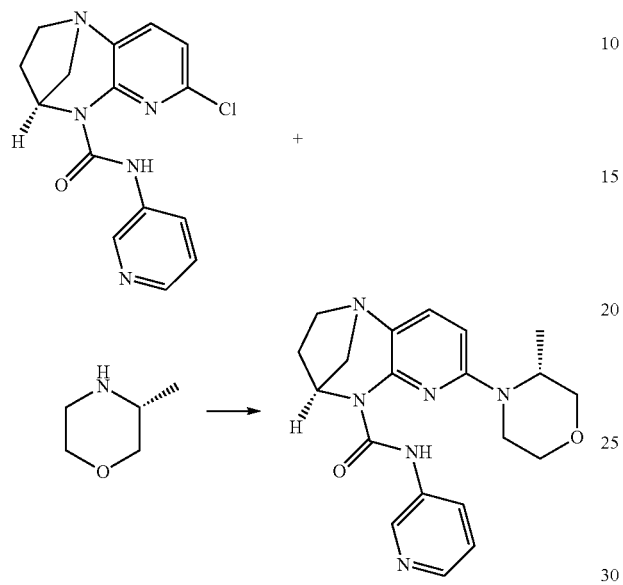

(R)-3-methylmorpholine (320 mg, 3.17 mmol) followed by cesium carbonate (516 mg, 1.583 mmol) were added to a stirred solution of (4S)-7-chloro-N-(pyridin-3-yl)-3,4-dihydro-1,4-methanopyrido[2,3-b][1,4]diazepine-5(2H)-carboxamide (500 mg, 1.583 mmol) in 1,4-dioxane (8 mL) at RT and degassed for 30 min. Then Pd(OAc)$_2$ (71.1 mg, 0.317 mmol) and X-phos (755 mg, 1.583 mmol) were added to the reaction mixture at RT and again degassed for 15 min. The reaction mixture was stirred at 110° C. for 6 h and was then cooled to RT, diluted with water (30 mL), extracted with ethyl acetate (2×50 mL). The combined organic layer was washed with brine (20 mL), dried over sodium sulfate, filtered and concentrated to obtain the crude product. The crude mixture was purified by flash column chromatography (silica-gel: 100-200 mesh, eluent: 2% MeOH in DCM) to afford (4S)-7-((R)-3-methylmorpholino)-N-(pyridin-3-yl)-3,4-dihydro-1,4-methanopyrido[2,3-b][1,4]diazepine-5(2H)-carboxamide (100 mg, 0.258 mmol, 16.27% yield) as an off white solid (TLC: R$_f$ 0.4, 10% MeOH in DCM), LCMS (m/z): 381.26 [M+H]$^+$.

$^1$H NMR (400 MHz, CDCl$_3$): δ 12.38 (s, 1H), 8.51 (d, J=2.6 Hz, 1H), 8.36-8.24 (m, 1H), 8.16 (ddd, J=8.4, 2.7, 1.5 Hz, 1H), 7.44-7.16 (m, 2H), 6.25 (d, J=8.6 Hz, 1H), 5.63 (dd, J=6.2, 3.2 Hz, 1H), 4.06 (d, J=7.4 Hz, 2H), 3.81 (t, J=2.7 Hz, 2H), 3.69-3.48 (m, 2H), 3.38-3.03 (m, 4H), 2.90 (dd, J=11.8, 3.3 Hz, 1H), 2.26 (dd, J=10.1, 3.9 Hz, 1H), 2.11-1.87 (m, 1H), 1.26 (d, J=6.6 Hz, 3H).

Example 229

Synthesis of (4S)—N-(6-((S)-2,3-dihydroxypropoxy)pyrazin-2-yl)-7-(6-methylpyridin-3-yl)-3,4-dihydro-1,4-methanopyrido[2,3-b][1,4]diazepine-5(2H)-carboxamide

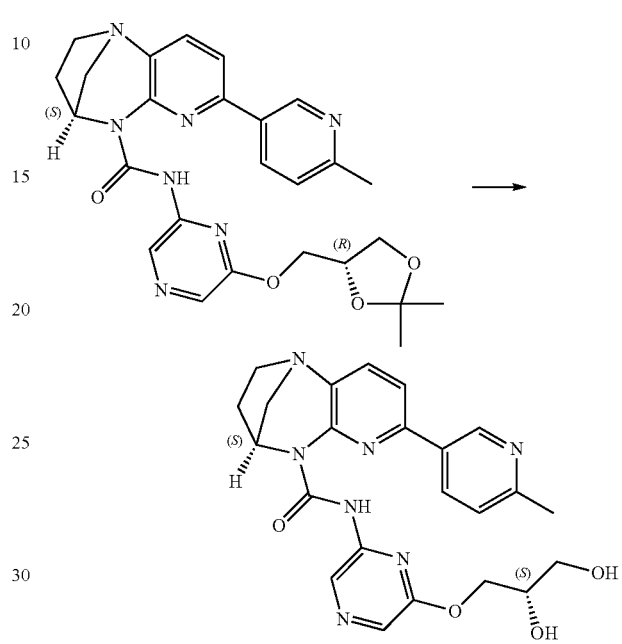

To a solution of (4S)—N-(6-(((R)-2,2-dimethyl-1,3-dioxolan-4-yl)methoxy)pyrazin-2-yl)-7-(6-methylpyridin-3-yl)-3,4-dihydro-1,4-methanopyrido[2,3-b][1,4]diazepine-5(2H)-carboxamide (0.4 g, 0.794 mmol) in dichloromethane (10 mL) was added 4M HCl in dioxane (0.198 g, 1.589 mmol) at 0° C. Then the reaction mixture was stirred at 35° C. for 6h. Reaction mixture was neutralized with NaHCO$_3$ solution and extracted with DCM (2×30 ml). The combined organic layer was washed with water (20 ml), brine, dried over anhydrous Na$_2$SO$_4$ and evaporated under reduced pressure to obtain crude product. The crude compound was triturated with diethylether (40 ml) and pentane (20 ml) to afford pure product (4S)—N-(6-((S)-2,3-dihydroxypropoxy)pyrazin-2-yl)-7-(6-methylpyridin-3-yl)-3,4-dihydro-1,4-methanopyrido[2,3-b][1,4]diazepine-5(2H)-carboxamide (0.21 g, 0.453 mmol, 65% yield) as a white solid (TLC: 10% MeOH in Ethyl acetate, R$_f$: 0.2), LCMS (m/z): 464.27 [M+H]$^+$.

$^1$H NMR (400 MHz, CDCl$_3$): δ ppm 12.99 (s, 1H), 9.33 (d, J=2.19 Hz, 1H), 9.13 (s, 1H), 8.00 (d, J=7.78 Hz, 2H), 7.97 (s, 1H), 7.64 (d, J=8.11 Hz, 1H), 7.19-7.37 (m, 2H), 5.87 (br s, 1H), 5.73 (dd, J=5.92, 3.29 Hz, 1H), 4.74 (dd, J=10.96, 5.70 Hz, 1H), 4.40 (dd, J=10.96, 7.45 Hz, 1H), 4.08-4.30 (m, 1H), 3.65-3.90 (m, 2H), 3.10-3.34 (m, 4H), 3.02 (dd, J=12.28, 3.29 Hz, 1H), 2.62 (s, 3H), 2.36 (dddd, J=14.14, 9.87, 5.81, 4.17 Hz, 1H), 2.00-2.22 (m, 1H).

Example 230

Synthesis of (4S)-7-(2-methylpyridin-4-yl)-N-(pyrido[3,4-b]pyrazin-5-yl)-3,4-dihydro-1,4-methanopyrido[2,3-b][1,4]diazepine-5(2H)-carboxamide

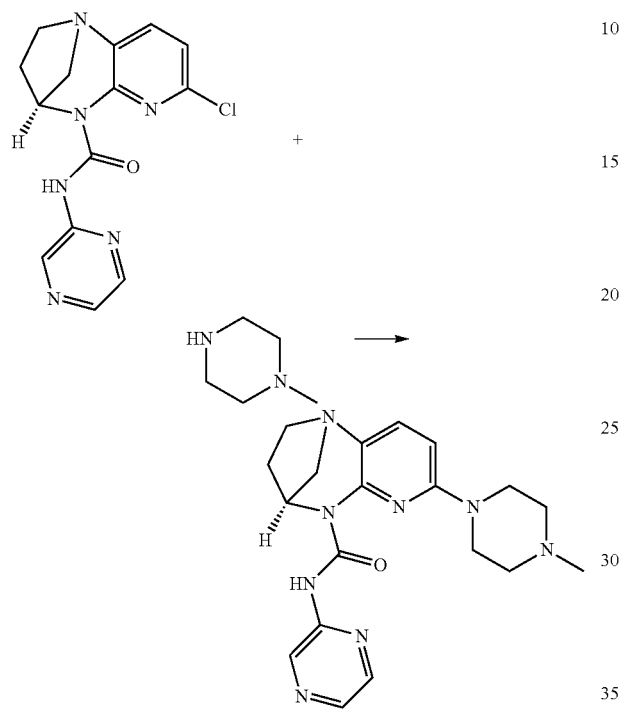

Example 231

Synthesis of (4S)-7-(2-methylpyridin-4-yl)-N-(5-(trifluoromethyl)pyrazin-2-yl)-3,4-dihydro-1,4-methanopyrido[2,3-b][1,4]diazepine-5(2H)-carboxamide

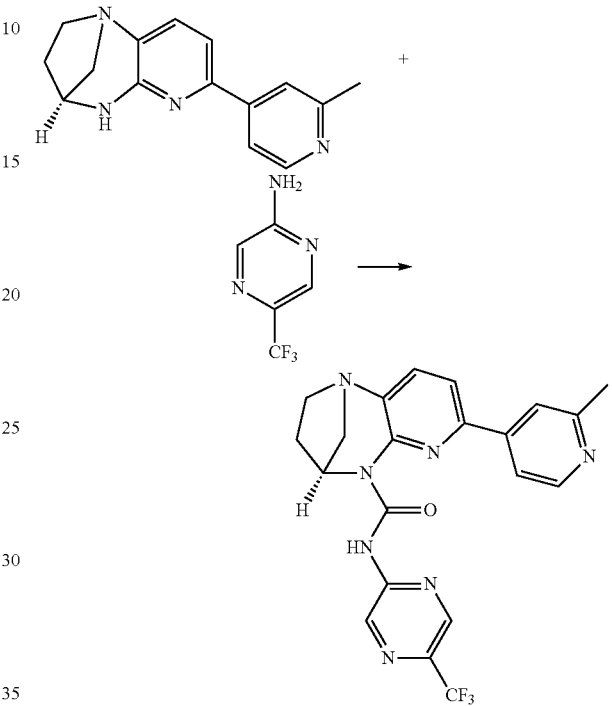

To a de-gassed solution of (4S)-7-chloro-N-(pyrazin-2-yl)-3,4-dihydro-1,4-methanopyrido[2,3-b][1,4]diazepine-5(2H)-carboxamide (800 mg, 2.53 mmol) and 1-methylpiperazine (379 mg, 3.79 mmol) in 1,4-dioxane (15 mL) were added cesium carbonate (2469 mg, 7.58 mmol), x-phos (241 mg, 0.505 mmol) and palladium(II) acetate (56.7 mg, 0.253 mmol). The reaction mixture was heated at 100° C. for 16 h and poured in to cold water (45 mL), extracted with ethyl acetate (2×100 mL). The combined organic layer was dried over anhydrous sodium sulfate and concentrated under reduced pressure to obtain the crude product. The crude mixture was purified by flash column chromatography (silica-gel: 100-200 mesh, eluted with 2% MeOH in DCM) to afford (4S)-7-(4-methylpiperazin-1-yl)-N-(pyrazin-2-yl)-3,3,4-dihydro-1,4-methanopyrido[2,3-b][1,4]diazepine-5(2H)-carboxamide (268 mg, 0.693 mmol, 27.5% yield) as a yellow solid (TLC: 100% ethyl acetate, $R_f$=0.23), LCMS (m/z): 381.3 [M+H]$^+$. $^1$H NMR (400 MHz, CDCl$_3$): δ ppm 13.46 (s, 2H), 9.53 (s, 1H), 8.29-8.12 (m, 2H), 7.36 (d, J=8.55 Hz, 1H), 6.30 (d, J=8.55 Hz, 2H), 5.61 (dd, J=5.92, 3.29 Hz, 2H), 3.65-3.63 (m, 4H), 3.27-3.03 (m, 3H), 2.91 (dd, J=11.73, 3.40 Hz, 1H), 2.42-2.39 (m, 1H), 2.39 (s, 3H), 2.33-2.14- (m, 1H), 2.13-1.93 (m, 1H).

To a stirred solution of 5-(trifluoromethyl)pyrazin-2-amine (1164 mg, 7.13 mmol) in THF (10 mL) were added triethylamine (1.989 mL, 14.27 mmol) and triphosgene (706 mg, 2.378 mmol) at 25° C. and stirred for 1h. Then (4S)-7-(2-methylpyridin-4-yl)-2,3,4,5-tetrahydro-1,4-methanopyrido[2,3-b][1,4]diazepine (600 mg, 2.378 mmol) was added and heated at 100° C. for 15 h in sealed tube. The reaction mixture was cooled to room temperature and extracted with ethyl acetate (2×50 mL). The combined organic layer was washed with water (20 mL×2), brine (10 mL), dried over anhydrous Na$_2$SO$_4$ and concentrated under pressure to obtain the crude product. The crude product was purified by flash column chromatography (silica-gel: 100-200 mesh, eluent: 2% MeOH in DCM) to afford (4S)-7-(2-methylpyridin-4-yl)-N-(5-(trifluoromethyl)pyrazin-2-yl)-3,4-dihydro-1,4-methanopyrido[2,3-b][1,4]diazepine-5(2H)-carboxamide (125 mg, 0.283 mmol, 32% yield) as an off white solid (TLC: Eluent: 5% methanol in DCM, $R_f$: 0.3), LCMS (m/z): 442.24 [M+H]$^+$.

$^1$H-NMR (CDCl$_3$, 400 MHz): 14.1 (s, 1H), 9.7 (s, 1H), 8.66-8.62 (m, 2H), 8.0 (s, 1H), 7.69-7.64 (m, 2H), 7.5 (d, J=8 Hz, 1H), 5.74-5.69 (m, 1H), 3.34-3.16 (m, 3H), 3.08-3.02 (m, 1H), 2.75 (s, 3H), 2.32-2.42 (m, 1H), 2.14-2.06 (m, 1H).

Example 232

Synthesis of (4S)—N-(pyrazin-2-yl)-7-(6-(trifluoromethyl)pyridin-3-yl)-3,4-dihydro-1,4-methanopyrido[2,3-b][1,4]diazepine-5(2H)-carboxamide

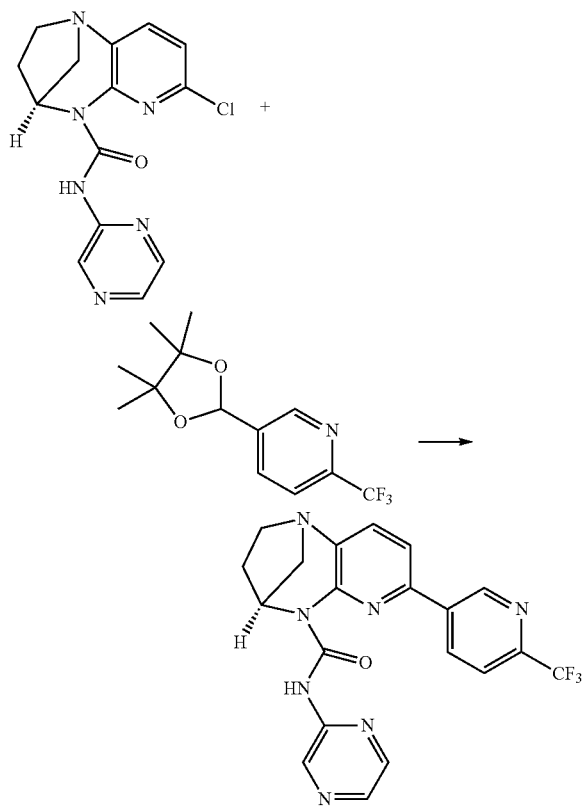

A solution of (4S)-7-chloro-N-(pyrazin-2-yl)-3,4-dihydro-1,4-methanopyrido[2,3-b][1,4]diazepine-5(2H)-carboxamide (600 mg, 1.894 mmol), 5-(4,4,5,5-tetramethyl-1,3,2-dioxaborolan-2-yl)-2-(trifluoromethyl)pyridine (776 mg, 2.84 mmol) and $K_3PO_4$ (804 mg, 3.79 mmol) in 1,4-dioxane (20 mL) and water (3 mL) was degassed with argon at room temp for 15 mins. X-phos (90 mg, 0.189 mmol), and $Pd_2(dba)_3$ (87 mg, 0.095 mmol) was added to reaction mixture. The reaction mixture was further degassed for 15 min and was stirred for 16 h at 90° C. The reaction mixture was cooled to 28° C. and was filtered through a pad of celite and the filtrate was evaporated to give crude residue. The crude residue was diluted with water (20 mL) and extracted with ethyl acetate (2×80 mL). The combined organic layers were washed with water (20 mL) followed by brine solution (10 mL). The organic layer was dried over sodium sulfate, filtered and filtrate was evaporated to give as a brown solid. (TLC eluent: 100% ethyl acetate, $R_f$-0.3; UV active). The Crude compound was purified by column chromatography (neutral alumina), product was eluted with 45-50% ethyl acetate in hexane to afford (4S)—N-(pyrazin-2-yl)-7-(6-(trifluoromethyl)pyridin-3-yl)-3,4-dihydro-1,4-methanopyrido[2,3-b][1,4]diazepine-5 (2H)-carboxamide (360 mg, 0.824 mmol, 43.5% yield) as a off white solid, LCMS (m/z): 428.17 $[M+H]^+$.

$^1H$ NMR (400 MHz, $CDCl_3$): δ 13.60 (s, 1H), 9.52 (d, J=1.1 Hz, 1H), 9.28 (d, J=2.2 Hz, 1H), 8.71 (dd, J=8.1, 1.97 Hz, 1H), 8.25-8.33 (m, 2H), 7.84 (d, J=8.3 Hz, 1H), 7.67 (d, J=7.9 Hz, 1H), 7.5 (d, J=8 Hz, 1H), 5.70 (dd, J=6.03, 3.18 Hz, 1H), 3.11-3.36 (m, 3H), 2.96-3.11 (m, 1H), 2.22-2.43 (m, 1H), 1.97-2.21 (m, 1H).

Example 233

Synthesis of (4S)—N-(isoquinolin-5-yl)-7-(6-methylpyridin-3-yl)-3,4-dihydro-1,4-methanopyrido[2,3-b][1,4]diazepine-5(2H)-carboxamide

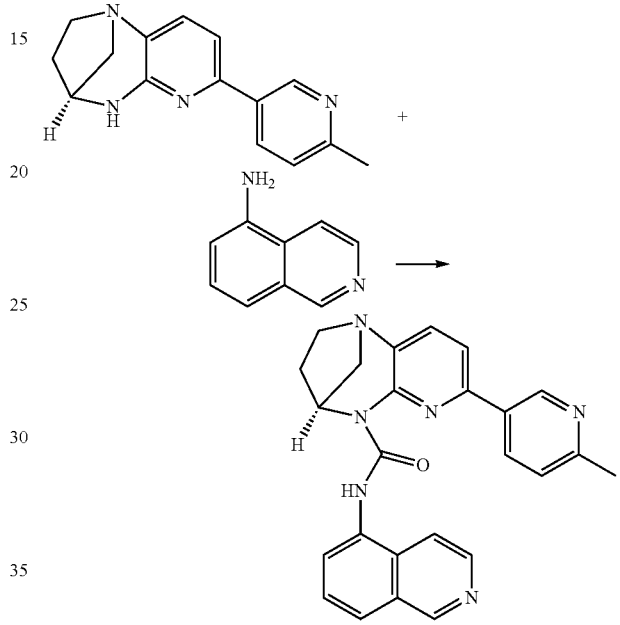

To a solution of (4S)-7-(6-methylpyridin-3-yl)-2,3,4,5-tetrahydro-1,4-methanopyrido[2,3-b][1,4]diazepine (0.750 g, 2.97 mmol) in Tetrahydrofuran (THF) (40 mL) stirred under nitrogen at room temperature was added triethylamine (2.486 mL, 17.83 mmol) and triphosgene (0.882 g, 2.97 mmol). The reaction mixture was stirred at room temperature for 30 minutes before isoquinolin-5-amine (1.286 g, 8.92 mmol) was added. The reaction mixture was stirred at 65° C. for 16 hr and then the reaction mixture was cooled to room temperature and concentrated under reduced pressure. The residue was partitioned between water (30 mL) and Dichloromethane (100 mL). Organic layer was separated and was dried over anhydrous $Na_2SO_4$, filtered and filtrate was evaporated to give crude as brown solid (TLC eluent: 100% EtOAc: $R_f$-0.2; UV active). The crude was purified by column chromatography using neutral alumina and was eluted with 100% Dichloromethane to afford pure (4S)—N-(isoquinolin-5-yl)-7-(6-methylpyridin-3-yl)-3,4-dihydro-1,4-methanopyrido[2,3-b][1,4]diazepine-5(2H)-carboxamide (0.315 g, 0.743 mmol, 25.00% yield) as a off-white solid, LCMS (m/z): 423.3 $[M+H]^+$.

$^1H$ NMR (400 MHz, $CDCl_3$): δ ppm 13.21 (s, 1H), 9.20 (s, 1H), 8.88 (d, J=2.19 Hz, 1H), 8.37 (d, J=7.23 Hz, 1H), 7.94 (d, J=6.14 Hz, 1H), 7.88 (dd, J=8.11, 2.41 Hz, 1H), 7.75 (d, J=8.11 Hz, 1H), 7.61-7.69 (m, 2H), 7.47 (d, J=5.92 Hz, 1H), 7.31 (d, J=7.89 Hz, 1H), 7.08 (d, J=7.89 Hz, 1H), 5.77 (dd, J=5.92, 3.29 Hz, 1H), 3.21-3.36 (m, 3H), 3.06 (dd, J=12.06, 3.07 Hz, 1H), 2.59 (s, 3H), 2.32-2.43 (m, 1H), 2.17 (dt, J=14.03, 7.02 Hz, 1H

Example 234

Synthesis of (4S)-7-(2,2-dimethylmorpholino)-N-(pyrazin-2-yl)-3,4-dihydro-1,4-methanopyrido[2,3-b][1,4]diazepine-5(2H)-carboxamide

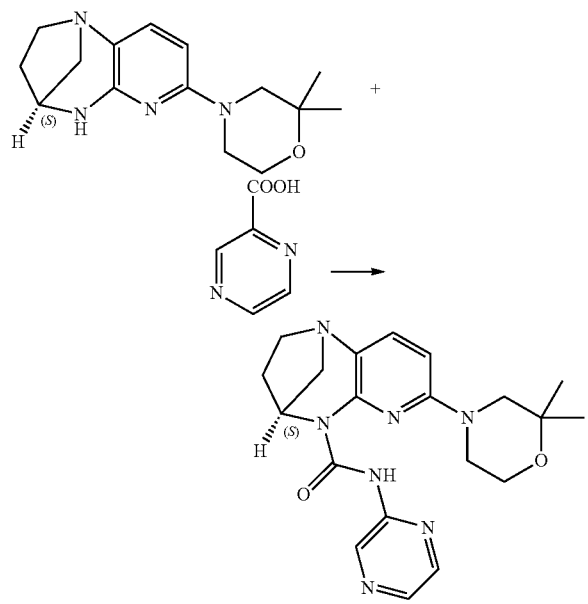

To a solution of pyrazine-2-carboxylic acid (350 mg, 2.82 mmol) in THF (15 mL) was added diphenyl phosphorazidate (1164 mg, 4.23 mmol) and DIPEA (2.463 mL, 14.10 mmol) at at 0° C. The reaction mixture was stirred under nitrogen for 2 h at 30° C. 2,2-dimethyl-4-((4S)-2, 3, 4,5-tetrahydro-1,4-methanopyrido[2,3-b][1,4]diazepin-7-yl)morpholine (542 mg, 1.974 mmol) was added and reaction mixture was stirred at 65° C. for 16 h. The solvent was removed under reduced pressure. The crude was diluted with water (20 mL) and extracted with ethyl acetate (2×30 mL). The combined organic layers were washed with water (10 mL), saturated brine solution. The organic layer was dried over anhydrous sodium sulfate, filtered and filtrate was evaporated to give crude. The crude compound was purified by column chromatography (neutral alumina) product was eluted with 10% ethyl acetate in hexane. Collected fractions were concentrated under reduced pressure to afford (4S)-7-(2,2-dimethylmorpholino)-N-(pyrazin-2-yl)-3,4-dihydro-1,4-methanopyrido[2,3-b][1,4]diazepine-5(2H)-carboxamide (120 mg, 0.303 mmol, 10.74% yield) as off-white solid, LCMS (m/z): 396.3 [M+H]$^+$.

$^1$H-NMR (400 MHz, CDCl$_3$): δ 13.40 (s, 1H), 9.56 (d, J=1.2 Hz, 1H), 8.26 (d, J=2.41 Hz, 1H), 8.06-8.22 (m, 1H), 7.38 (d, J=8.8 Hz, 1H), 6.28 (d, J=8.5 Hz, 1H), 5.63 (dd, J=5.7, 3.3 Hz, 1H), 3.90 (t, J=5 Hz, 2H), 3.47 (s, 2H), 3.41 (t, J=5 Hz, 2H), 3.04-3.31 (m, 3H), 2.92 (dd, J=11.9, 3.18 Hz, 1H), 2.14-2.35 (m, 1H), 1.89-2.12 (m, 1H), 1.36 (s, 6H).

Example 235

Synthesis of (4S)-7-(6-methylpyridazin-4-yl)-N-(pyrazin-2-yl)-3,4-dihydro-1,4-methanopyrido[2,3-b][1,4]diazepine-5(2H)-carboxamide

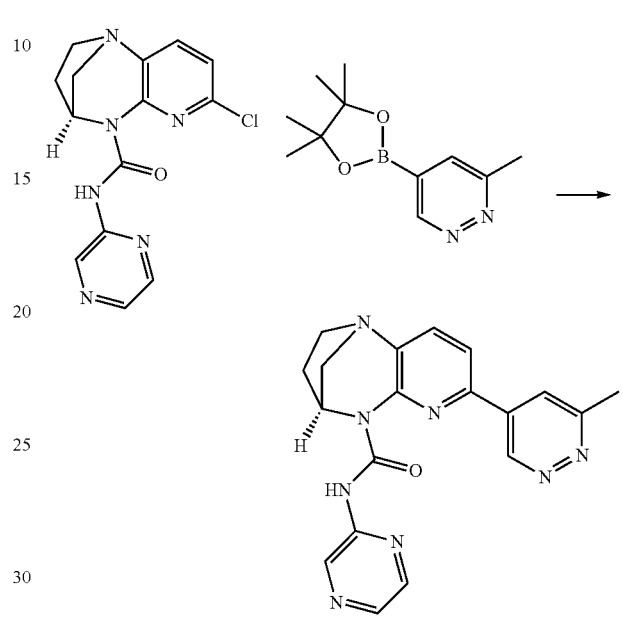

To a de-gassed solution of (4S)-7-chloro-N-(pyrazin-2-yl)-3,4-dihydro-1,4-methanopyrido[2,3-b][1,4]diazepine-5(2H)-carboxamide (400 mg, 1.263 mmol), 3-methyl-5-(4,4,5,5-tetramethyl-1,3,2-dioxaborolan-2-yl)pyridazine (306 mg, 1.389 mmol) and K$_3$PO$_4$ (536 mg, 2.53 mmol) in 1,4-dioxane (15 mL) and water (2 mL) were added Pd(OAc)$_2$ (14.18 mg, 0.063 mmol) and x-phos (60.2 mg, 0.126 mmol) at 25° C. Then the reaction mixture was stirred at 100° C. for 8 hr and then allowed the reaction mixture to cool to RT and evaporated the dioxane under vacuo. Then it was diluted with water and extracted with DCM (3×50 mL). The combined organic layer was dried over hydrous Na$_2$SO$_4$ and the solvent was removed under reduced pressure to obtain crude product. The crude mixture was purified by flash column chromatography (silica-gel: 100-200 mesh, eluent: 2-3% of MeOH in EtOAc) to afford (4S)-7-(6-methylpyridazin-4-yl)-N-(pyrazin-2-yl)-3,4-dihydro-1,4-methanopyrido[2,3-b][1,4]diazepine-5(2H)-carboxamide (260 mg, 0.689 mmol, 54.6% yield) as an off white solid (TLC: 10% MeOH in EtOAc, R$_f$: 0.4), LCMS (m/z): 375.25 [M+H]$^+$.

$^1$H NMR (400 MHz, CDCl$_3$): δ ppm 13.69 (s, 1H), 9.62-9.53 (s, 2H), 8.38-8.29 (m, 3H), 7.71 (d, J=8.11 Hz, 1H), 7.59 (d, J=8.11 Hz, 1H), 5.72 (dd, J=5.92, 3.29 Hz, 1H), 3.35-3.15 (m, 2H), 3.12-3.00 (m, 2H), 2.90 (s, 3H), 2.48-2.25 (m, 1H), 2.11 (dt, J=14.03, 6.80 Hz, 1H).

Example 236

Synthesis of (9S)—N-(pyridin-3-yl)-2-(3-(trifluoromethyl)piperidin-1-yl)-8,9-dihydro-6H-5,9-methanopyrido[2,3-b][1,4]diazocine-10(7H)-carboxamide

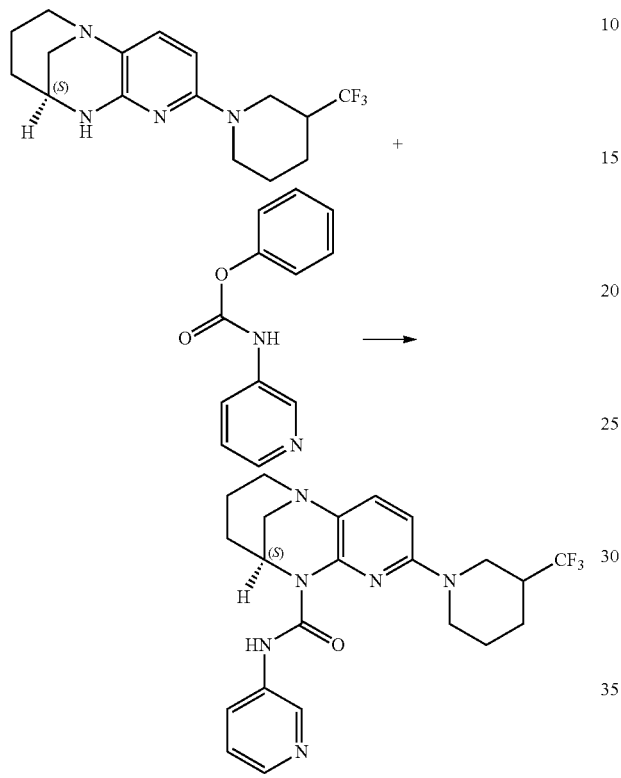

To a solution of (9S)-2-(3-(trifluoromethyl)piperidin-1-yl)-7,8,9,10-tetrahydro-6H-5,9-methanopyrido[2,3-b][1,4]diazocine (Peak-II of the intermediate SFC separation, (Peak-II from intermediate SFC separation, 0.700 g, 2.145 mmol) in Tetrahydrofuran (THF) (70 mL) was added DMAP (0.786 g, 6.43 mmol) and phenyl pyridin-3-ylcarbamate (1.378 g, 6.43 mmol) stirred at 65° C. for 36 hr before the reaction was cooled to room temperature and concentrated under reduced pressure. The residue was partitioned between water (20 mL) and EtOAc (75 mL). Organic layer was separated and was dried over anhydrous Na$_2$SO$_4$, filtered and filtrate was evaporated to give crude as brown solid (TLC eluent: 80% EtOAc in Hexane: R$_f$-0.3; UV active). The crude was purified by column chromatography using neutral alumina and was eluted with 50% EtOAc in Hexane to afford pure (9S)—N-(pyridin-3-yl)-2-(3-(trifluoromethyl)piperidin-1-yl)-8,9-dihydro-6H-5,9-methanopyrido[2,3-b][1,4]diazocine-10(7H)-carboxamide (0.355 g, 0.794 mmol, 37.0% yield) as a white solid, LCMS (m/z): 447.3 [M+H]$^+$.

$^1$H-NMR (400 MHz, CDCl$_3$): δ ppm 12.92 (s, 1H), 8.62 (d, J=2.63 Hz, 1H), 8.32 (dd, J=4.71, 1.43 Hz, 1H), 8.08-8.21 (m, 1H), 7.33 (d, J=8.55 Hz, 1H), 7.20-7.29 (m, 1H), 6.40 (d, J=8.55 Hz, 1H), 4.90 (br s, 1H), 4.00-4.21 (m, 2H), 3.31 (dd, J=13.48, 1.86 Hz, 1H), 3.17-3.26 (m, 2H), 2.88-3.03 (m, 3H), 2.36-2.49 (m, 1H), 2.19-2.25 (m, 1H), 2.10-2.16 (m, 1H), 1.92-1.99 (m, 1H), 1.86 (tdd, J=13.84, 13.84, 5.10, 2.96 Hz, 1H), 1.65-1.76 (m, 1H), 1.46-1.58 (m, 2H), 1.29-1.38 (m, 1H)

Example 237

Synthesis of (4S)—N-(6-fluorobenzo[d]thiazol-2-yl)-7-(6-methylpyridin-3-yl)-3,4-dihydro-1,4-methanopyrido[2,3-b][1,4]diazepine-5(2H)-carboxamide

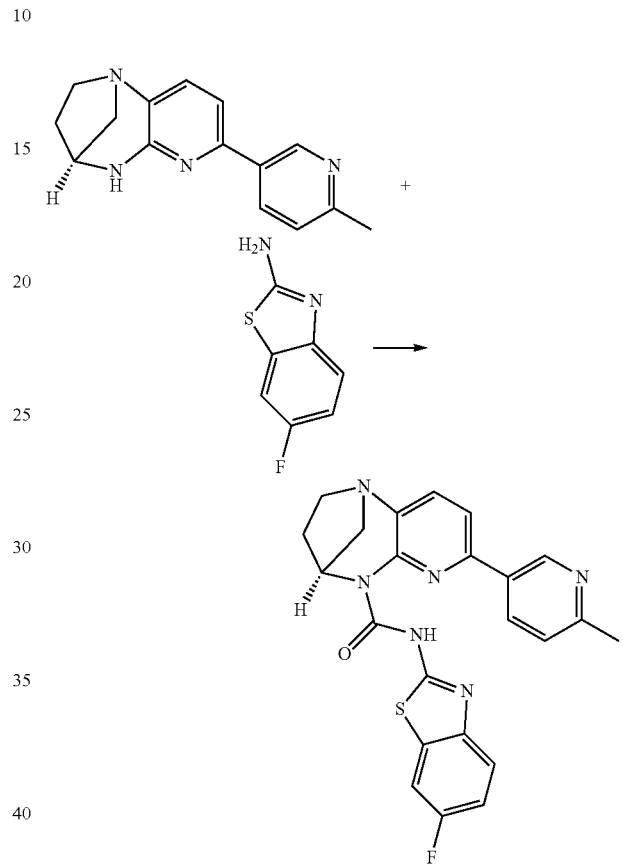

To a solution of (4S)-7-(6-methylpyridin-3-yl)-2,3,4,5-tetrahydro-1,4-methanopyrido[2,3-b][1,4]diazepine (0.750 g, 2.97 mmol) in Tetrahydrofuran (THF) (40 mL) stirred under nitrogen at room temperature was added triethylamine (2.486 mL, 17.83 mmol) and triphosgene (0.882 g, 2.97 mmol). The reaction mixture was stirred at room temperature for 30 minutes before 6-fluorobenzo[d]thiazol-2-amine (1.500 g, 8.92 mmol) was added at room temperature and the reaction mixture was stirred at 65° C. for 16 hr and then cooled to room temperature and the solvent removed under reduced pressure. The resulting residue was partitioned between water (30 mL) and EtOAc (100 mL). Organic layer was separated and was dried over anhydrous Na$_2$SO$_4$, filtered and filtrate was evaporated to give crude as brown solid (TLC eluent: 100% EtOAc: R$_f$-0.2; UV active). The crude was purified by column chromatography using neutral alumina and was eluted with 100% Dichloromethane to afford pure (4S)—N-(6-fluorobenzo[d]thiazol-2-yl)-7-(6-methylpyridin-3-yl)-3,4-dihydro-1,4-methanopyrido[2,3-b][1,4]diazepine-5(2H)-carboxamide (0.313 g, 0.700 mmol, 23.53% yield) as a pale yellow solid, LCMS (m/z): 447.2 [M+H]$^+$.

$^1$H NMR (400 MHz, CDCl$_3$): δ ppm 14.74 (s, 1H), 9.06 (d, J=2.19 Hz, 1H), 8.43 (dd, J=8.11, 2.41 Hz, 1H), 7.75 (dd, J=8.88, 4.71 Hz, 1H), 7.66 (d, J=8.11 Hz, 1H), 7.41-7.52 (m, 3H), 7.14 (td, J=8.99, 2.63 Hz, 1H), 5.68 (dd, J=5.92, 3.07 Hz, 1H), 3.17-3.33 (m, 3H), 3.04 (dd, J=12.17, 3.18 Hz, 1H), 2.68 (s, 3H), 2.32-2.43 (m, 1H), 2.12 (dt, J=14.20, 7.04 Hz, 1H)

Example 238

Synthesis of (4S)-7-(2-methylthiazol-5-yl)-N-(pyrazin-2-yl)-3,4-dihydro-1,4-methanopyrido[2,3-b][1,4]diazepine-5(2H)-carboxamide

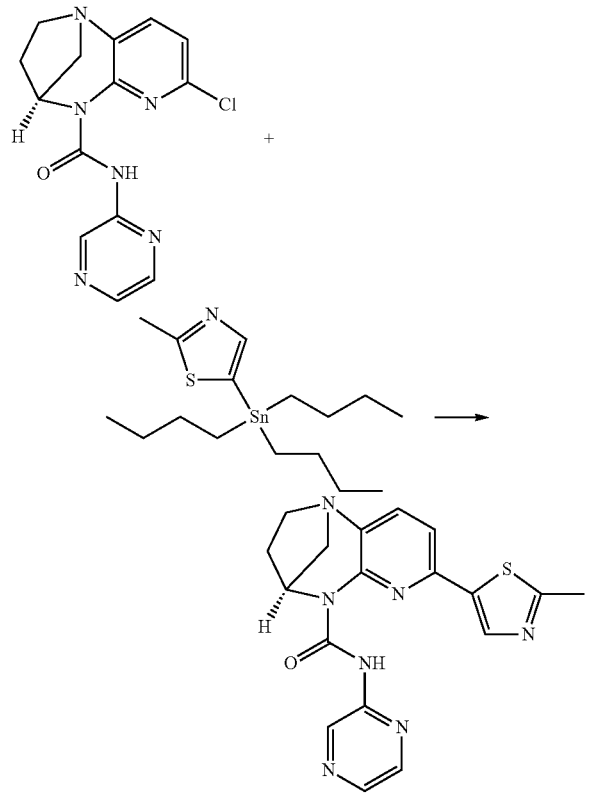

Cesium fluoride (767 mg, 5.05 mmol) was added to a stirred solution of (4S)-7-chloro-N-(pyrazin-2-yl)-3,4-dihydro-1,4-methanopyrido[2,3-b][1,4]diazepine-5 (2H)-carboxamide (800 mg, 2.53 mmol), 2-methyl-5-(tributylstannyl)thiazole (1177 mg, 3.03 mmol) and tri-t-butyl phosphine (511 mg, 2.53 mmol) in 1,4-Dioxane (40 mL) was degassed for 15 min, palladium (II) acetate (11.34 mg, 0.051 mmol), and copper (I) iodide (19.24 mg, 0.101 mmol) were added. The reaction mixture was further degassed for 10 min, and was stirred at 100° C. for 15 hr. The reaction mixture was cooled to 28° C. and was partitioned between water (50 mL) and EtOAc (125 mL). Organic layer was separated and was dried over anhydrous $Na_2SO_4$, filtered. The filtrate was evaporated to get crude. The crude was purified by column chromatography using (100-200 mesh) silica gel eluting with 5% MeOH in EtOAc to afford (4S)-7-(2-methylthiazol-5-yl)-N-(pyrazin-2-yl)-3,4-dihydro-1,4-methanopyrido[2,3-b][1,4]diazepine-5(2H)-carboxamide (230 mg, 0.600 mmol, 23.77% yield) as off-white solid, LCMS (m/z): 380.18 [M+H]$^+$.

$^1$H-NMR (CDCl$_3$, 400 MHz): δ 13.30 (s, 1H), 9.53 (d, J=1.6 Hz, 1H), 8.43 (s, 1H), 8.36-8.35 (dd, J=2.4, 1.6 Hz, 1H), 8.30 (d, J=2.8 Hz 1H), 7.53 (d, J=8.0 Hz, 1H), 7.18 (d, J=8.0 Hz, 1H), 5.68 (dd, J=6, 3.2 Hz, 1H), 3.28-3.22 (m, 2H), 3.20-3.13 (m, 1H), 3.02-2.98 (dd, J=12.4, 3.6 Hz, 1H), 2.78 (s, 3H), 2.35-2.32 (m, 1H), 2.10-2.04 (m, 1H).

Example 239

Synthesis of (9S)—N-(5-fluoropyridin-2-yl)-2-(3-(trifluoromethyl)piperidin-1-yl)-8,9-dihydro-6H-5,9-methanopyrido[2,3-b][1,4]diazocine-10(7H)-carboxamide

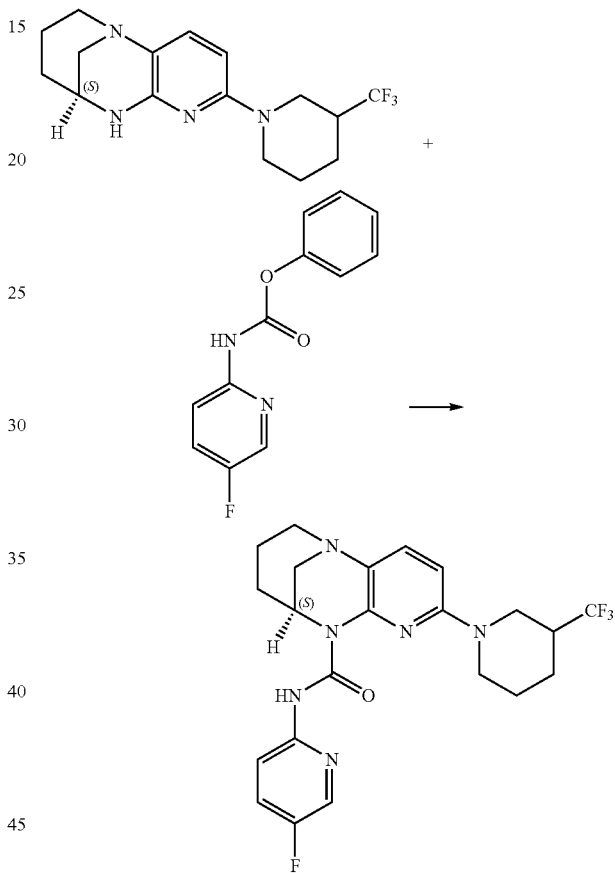

To a solution of (9S)-2-(3-(trifluoromethyl)piperidin-1-yl)-7,8,9,10-tetrahydro-6H-5,9-methanopyrido[2,3-b][1,4]diazocine (Peak-I from SFC separation, 450 mg, 1.379 mmol) in tetrahydrofuran (30 mL), DMAP (505 mg, 4.14 mmol) and phenyl (5-fluoropyridin-2-yl)carbamate (961 mg, 4.14 mmol) were added. The reaction mixture was stirred at 65° C. for 16 hr. The reaction mixture was diluted with water (50 mL) and extracted with ethyl acetate (2×75 mL). The combined organic layers were washed with water and saturated with brine solution and dried over anhydrous sodium sulfate, filtered and concentrated to give the crude as off white solid. (TLC Eluent: 100% Ethyl Acetate; $R_f$ value: 0.4; UV active). The crude product was purified by column chromatography (neutral alumina) product was eluted with 25% ethyl acetate in hexane to afford (9S)—N-(5-fluoropyridin-2-yl)-2-(3-(trifluoromethyl)piperidin-1-yl)-8,9-dihydro-6H-5,9-methanopyrido[2,3-b][1,4]diazocine-10(7H)-carboxamide (140 mg, 0.296 mmol, 21.46% yield) as a white solid, LCMS (m/z): 465.21 [M+H]$^+$.

901

¹H NMR (400 MHz, CDCl₃): δ ppm 1.15-1.43 (m, 1H) 1.43-1.68 (m, 2H) 1.68-1.89 (m, 3H) 2.04-2.28 (m, 2H) 2.42 (dtd, J=11.67, 7.92, 7.92, 4.06 Hz, 1H) 2.86-3.09 (m, 3H) 3.10-3.36 (m, 3H) 4.23-4.47 (m, 2H) 4.87 (br s, 1H) 6.39 (d, J=8.55 Hz, 1H) 7.3 (d, J=8.8 Hz, 1H) 7.34-7.59 (m, 1H) 8.09 (d, J=2.8 Hz, 1H) 8.20 (dd, J=9.21, 4.17 Hz, 1H) 13.65 (s, 1H).

Example 240

Synthesis of methyl 4-((4S)-5-(pyrazin-2-ylcarbamoyl)-2,3,4,5-tetrahydro-1,4-methanopyrido[2,3-b][1,4]diazepin-7-yl)picolinate

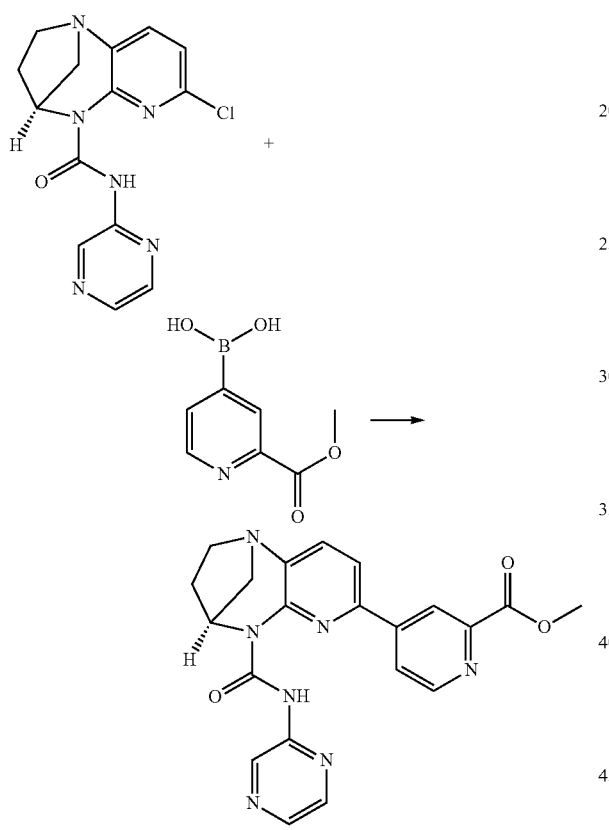

Tripotassium phosphate (2.68 g, 12.63 mmol) was added to a stirred solution of (4S)-7-chloro-N-(pyrazin-2-yl)-3,4-dihydro-1,4-methanopyrido[2,3-b][1,4]diazepine-5(2H)-carboxamide (2 g, 6.31 mmol), methyl 4-(4,4,5,5-tetramethyl-1,3,2-dioxaborolan-2-yl)picolinate (1.994 g, 7.58 mmol) in 1,4-dioxane (60 mL). The reaction mixture was degassed for 15 min. Pd₂(dba)₃ (0.289 g, 0.316 mmol) and X-phos (0.301 g, 0.631 mmol) were added. The reaction mixture was further degassed for 15 min, and was stirred at 100° C. for 18 hr. The reaction mixture was cooled to 28° C. and was partitioned between water (50 mL) and EtOAc (200 mL). Organic layer was separated and concentrated in vacuo to get crude (TLC eluent: 5% MeOH in DCM: $R_f$=0.3; UV active). The crude was purified by column chromatography using (100-200 mesh) silica gel eluting with 10% MeOH in EtOAc to afford methyl 4-((4S)-5-(pyrazin-2-ylcarbamoyl)-2,3,4,5-tetrahydro-1,4-methanopyrido[2,3-b][1,4]diazepin-7-yl)picolinate (780 mg, 1.806 mmol, 28.6% yield) as off white solid, LCMS (m/z): 418.23 [M+H]⁺.

902

¹H NMR (CDCl₃, 400 MHz): δ 13.63 (s, 1H), 9.54 (d, J=1.2 Hz, 1H), 8.91-8.89 (dd, J=5.2, 0.8 Hz, 1H), 8.68-8.68 (dd, J=2, 0.4 Hz, 1H), 8.34-8.29 (m, 3H), 7.69 (d, J=8.0 Hz, 1H), 7.59 (d, J=8.0 Hz, 1H), 4.05 (s, 3H), 3.34-3.16 (m, 3H), 3.07-3.03 (dd, J=12.4, 3.2 Hz, 1H), 2.41-2.33 (m, 1H), 2.15-2.07 (m, 1H).

Example 241

Synthesis of (4S)-7-(2-(difluoromethyl)pyridin-4-yl)-N-(pyrazin-2-yl)-3,4-dihydro-1,4-methanopyrido[2,3-b][1,4]diazepine-5(2H)-carboxamide

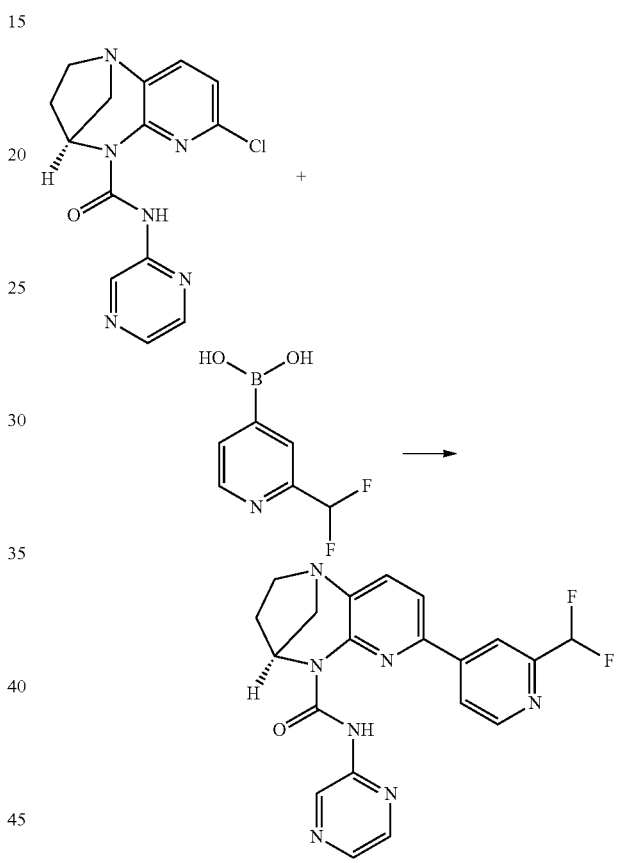

Tripotassium phosphate (670 mg, 3.16 mmol) was added to a stirred solution of (4S)-7-chloro-N-(pyrazin-2-yl)-3,4-dihydro-1,4-methanopyrido[2,3-b][1,4]diazepine-5(2H)-carboxa-mide (500 mg, 1.579 mmol), (2-(difluoromethyl) pyridin-4-yl)boronic acid (328 mg, 1.894 mmol) in 1,4-dioxane (10 mL), and water (1.667 mL) at 28° C. The reaction mixture was degassed for 15 min, was added Pd₂(dba)₃ (145 mg, 0.158 mmol), and X-phos (75 mg, 0.158 mmol). The reaction mixture was further degassed for 15 min and the reaction mixture was stirred for 1 hr under microwave at 100° C. The reaction mixture was cooled to 28° C. and was partitioned between water (10 mL) and EtOAc (25 mL). Organic layer was separated and was dried over anhydrous Na₂SO₄, filtered and filtrate was evaporated to give crude as brown solid (TLC eluent: 10% MeOH in EtOAc: $R_f$=0.3; UV active). The crude was purified by column chromatography using (100-200 mesh) silica gel and was eluted with 5-10% MeOH in EtOAc to afford pure (4S)-7-(2-(difluoromethyl)pyridin-4-yl)-N-(pyrazin-2-yl)-3, 4-dihydro-1,4-methanopyrido[2,3-b][1,4]diazepine-5(2H)-carboxamide (112 mg, 0.273 mmol, 17.27% yield) as off white solid, LCMS (m/z): 410.17 [M+H]$^+$.

$^1$H NMR (CDCl$_3$, 400 MHz): δ 13.63 (s, 1H), 9.54 (s, 1H), 8.79 (d, J=5.2 Hz, 1H), 8.40 (s, 1H), 8.32 (d, J=3.2 Hz, 2H), 8.06 (dd, J=5.2, 0.8 Hz, 1H), 7.68 (d, J=7.6 Hz, 1H), 7.54 (d, J=8 Hz, 1H), 6.90-6.62 (t, J=55.2 Hz, 1H), 5.73-5.71 (dd, J=5.6, 2.8 Hz, 1H), 3.33-3.16 (m, 3H), 3.06-3.03 (dd, J=12.0, 3.2 Hz, 1H), 2.41-2.33 (m, 1H), 2.14-2.07 (m, 1H).

Example 242

Synthesis of (9S)—N-(pyrazin-2-yl)-2-(3-(trifluoromethyl)piperidin-1-yl)-8,9-dihydro-6H-5,9-methanopyrido[2,3-b][1,4]diazocine-10(7H)-carboxamide

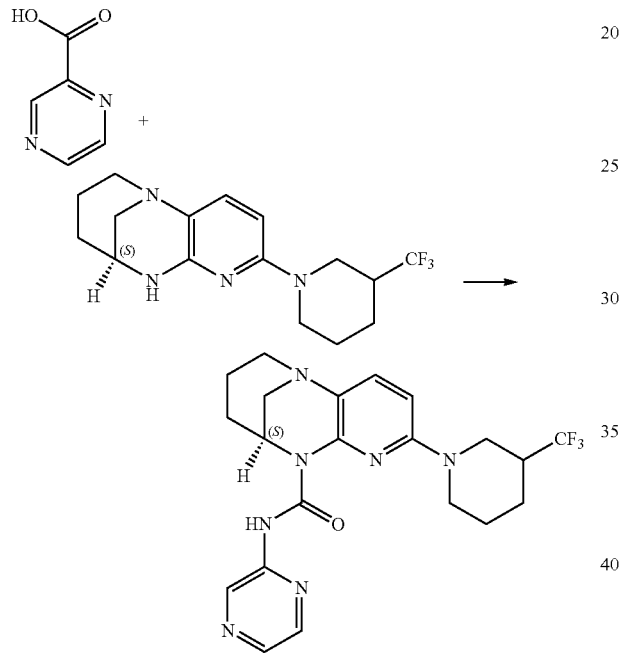

A suspension of pyrazine-2-carboxylic acid (0.6 g, 4.83 mmol) in tetrahydrofuran (50 mL) diphenylphosphoryl azide (1.996 g, 7.25 mmol) and DIPEA (4.22 mL, 24.17 mmol) added to the reaction mixture. The reaction mixture was stirred for 2 hr at 28° C. (9S)-2-(3-(trifluoromethyl)piperidin-1-yl)-7,8,9,10-tetrahydro-6H-5,9-methanopyrido[2,3-b][1,4]diaz-ocine (Peak-I from intermediate SFC Separation 1.105 g, 3.38 mmol) was added to the reaction mixture. The reaction mixture was stirred 16 hr at 65° C. The reaction mixture was diluted with water (50 mL) and extracted with ethyl acetate (2×75 mL). The combined organic layer was washed with water and saturated with brine solution and dried over anhydrous Na$_2$SO$_4$, filtered and concentrated to give the crude as a off white solid. (TLC eluent: 100% ethyl acetate; R$_f$ value: 0.3; UV active). The crude product was purified by column chromatography (neutral alumina) product was eluted with 30% ethyl acetate in hexane to afford (9S)—N-(pyrazin-2-yl)-2-(3-(trifluoromethyl)-piperidin-1-yl)-8,9-dihydro-6H-5,9-methanopyrido[2,3-b][1,4]diazocine-10(7H)-carboxami-de (0.330 g, 0.728 mmol, 15.05% yield) as a white solid, LCMS (m/z): 448.25 [M+H]$^+$.

$^1$H NMR (400 MHz, CDCl$_3$): δ ppm 1.31-1.34 (m, 1H) 1.45-1.67 (m, 2H) 1.68-1.79 (m, 1H) 1.82-1.99 (m, 2H) 2.05-2.18 (m, 2H) 2.42 (dddt, J=15.65, 11.78, 8.03, 3.97, 3.97 Hz, 1H) 2.86-3.09 (m, 3H) 3.11-3.35 (m, 3H) 4.21-4.39 (m, 2H) 4.89 (br s, 1H) 6.42 (d, J=8.55 Hz, 1H) 7.32 (d, J=8.4 Hz, 1H) 8.14-8.20 (m, 1H) 8.24 (d, J=2.8 Hz, 1H) 9.53 (d, J=1.53 Hz, 1H) 13.81 (s, 1H)

Example 243

Synthesis of (4S)-7-(5-fluoro-2-methylpyridin-4-yl)-N-(pyrazin-2-yl)-3,4-dihydro-1,4-methanopyrido[2,3-b][1,4]diazepine-5(2H)-carboxamide

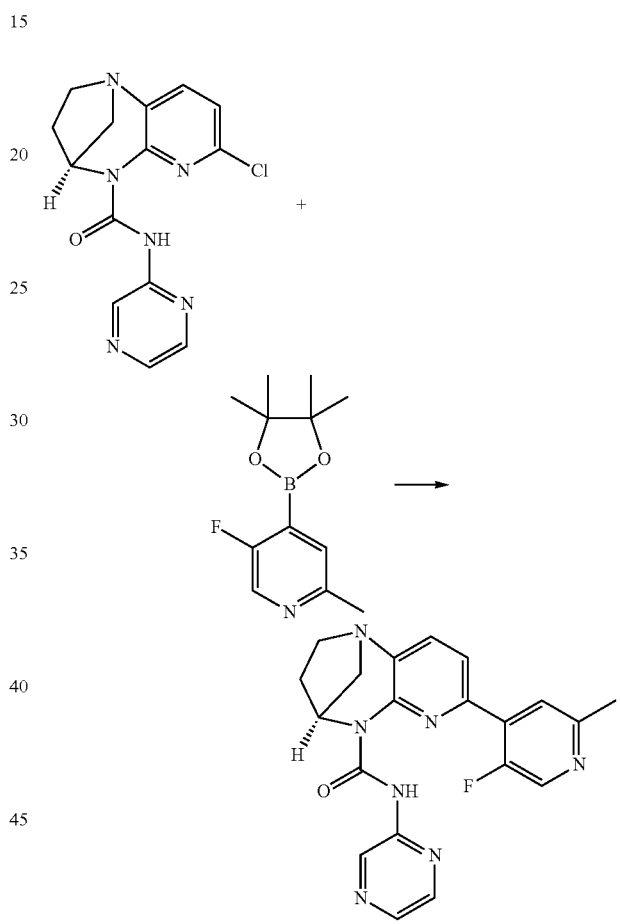

Tripotassium phosphate (804 mg, 3.79 mmol) was added to a stirred solution of (4S)-7-chloro-N-(pyrazin-2-yl)-3,4-dihydro-1,4-methanopyrido[2,3-b][1,4]diazepine-5(2H)-carboxa amide (600 mg, 1.894 mmol), 5-fluoro-2-methyl-4-(4,4,5,5-tetramethyl-1,3,2-dioxaborolan-2-yl) pyridine (674 mg, 2.84 mmol) in 1,4-dioxane (20 mL), and water (3.33 mL) at 28° C. The reaction mixture was degassed for 15 min, was added Pd$_2$(dba)$_3$ (173 mg, 0.189 mmol), and X-phos (90 mg, 0.189 mmol). The reaction mixture was further degassed for 15 min, and the reaction mixture was stirred for 1 hr in microwave at 100° C. The reaction mixture was cooled to 28° C. and was partitioned between water (10 mL) and EtOAc (25 mL). Organic layer was separated and was dried over anhydrous Na$_2$SO$_4$, filtered and filtrate was evaporated to give crude as brown solid (TLC eluent: 10% MeOH in EtOAc; R$_f$=0.3; UV active). The crude product was washed with methanol and ether to afford (4S)-7-(5- fluoro-2-methylpyridin-4-yl)-N-(pyrazin-2-yl)-3,4-dihydro-1,4methanopyrido[2,3-b][1,4]diazepine-5(2H)-carboxamide (317 mg, 0.788 mmol, 41.6% yield) as off white solid, LCMS (m/z): 392.20 [M+H]$^+$.

$^1$H NMR (CDCl$_3$, 400 MHz): δ 13.54 (s, 1H), 9.57 (d, J=1.6 Hz, 1H), 8.45 (d, J=3.2 Hz, 1H), 8.31 (d, J=2.8 Hz, 1H), 8.27-8.26 (t, J=1.6 Hz, 1H), 8.09 (d, J=6.8 Hz, 1H), 7.66-7.62 (t, J=8 Hz, 2H), 5.73-5.71 (dd, J=6.0, 3.2 Hz, 1H), 3.34-3.17 (m, 3H), 3.06-3.02 (dd, J=12.0, 3.2 Hz, 1H), 2.71 (s, 3H), 2.40-2.33 (m, 1H), 2.13-2.06 (m, 1H).

Example 244

Synthesis of methyl 4-((4S)-5-(pyrazin-2-ylcarbamoyl)-2,3,4,5-tetrahydro-1,4-methanopyrido[2,3-b][1,4]diazepin-7-yl)picolinate

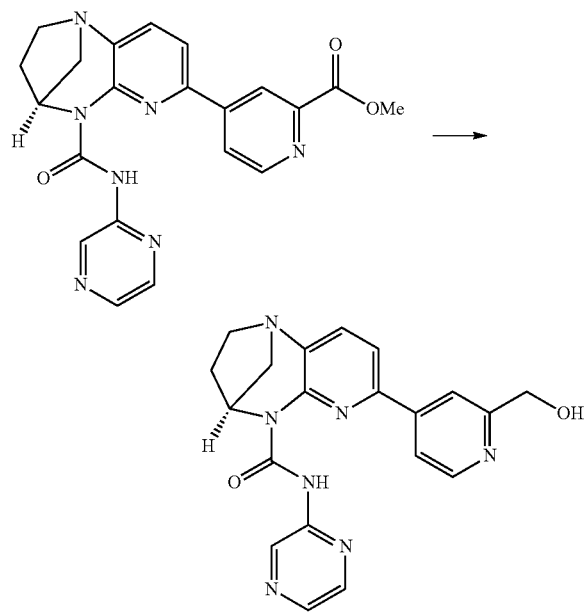

NaBH$_4$ (136 mg, 3.59 mmol) was added to a solution of methyl 4-((4S)-5-(pyrazin-2-ylcarbamoyl)-2,3,4,5-tetrahydro-1,4-methanopyrido[2,3-b][1,4]diazepin-7-yl)picolinate (600 mg, 1.437 mmol) in THF (100 mL) at 0° C. The reaction mixture was stirred at 28° C. for 8 h. The solvent was removed by rotary evaporation, and the residue was partitioned between ethyl acetate (40 mL) and water (20 mL). Organic layer was separated, dried over anhydrous Na$_2$SO$_4$ and filtered; filtrate was evaporated in vacuo to give crude. The crude was purified by prep HPLC to afford (4S)-7-(2-(Hydroxymethyl)pyridin-4-yl)-N-(pyrazin-2-yl)-3,4-dihydro-1,4 methanopyrido[2,3-b][1,4]diazepine-5(2H)-carboxamide (135 mg, 0.345 mmol, 24.00%) as off-white solid, LCMS (m/z): 390.22 [M+H]$^+$.

$^1$H NMR (CDCl$_3$, 400 MHz): δ 13.66 (s, 1H), 9.60 (s, 1H), 8.68 (d, J=5.2 Hz, 1H), 8.33 (s, 2H), 8.19 (s, 1H) 7.74-7.72 (dd, J=5.2, 1.6 Hz, 1H), 7.67 (d, J=8.0 Hz, 1H), 7.52 (d, J=8.0 Hz, 1H), 5.73-5.70 (dd, J=6.0, 3.6 Hz, 1H), 4.93 (s, 2H), 3.31-3.16 (m, 3H), 3.06-3.02 (dd, J=12.4, 3.2 Hz, 1H), 2.38-2.35 (m, 1H), 2.12-2.08 (t, J=7.6 Hz, 1H).

Example 245

Synthesis of (4S)-7-(6-cyanopyridin-3-yl)-N-(pyrazin-2-yl)-3,4-dihydro-1,4-methanopyrido[2,3-b][1,4]diazepine-5(2H)-carboxamide

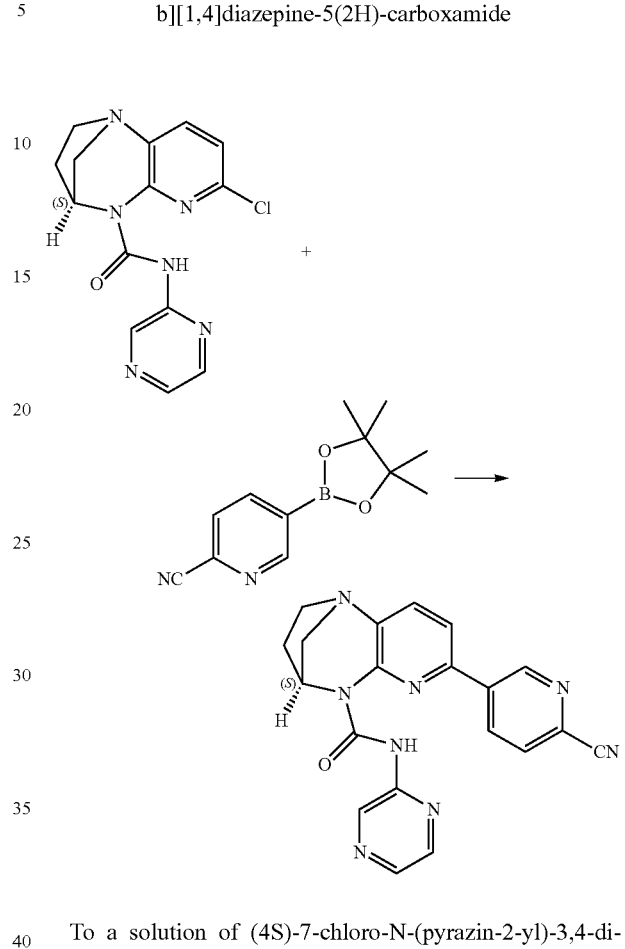

To a solution of (4S)-7-chloro-N-(pyrazin-2-yl)-3,4-dihydro-1,4-methanopyrido[2,3-b][1,4]diazepine-5(2H)-carboxamide (600 mg, 1.894 mmol), 5-(4,4,5,5-tetramethyl-1,3,2-dioxaborolan-2-yl)picolinonitrile (523 mg, 2.273 mmol) and K$_3$PO$_4$ (804 mg, 3.79 mmol) in 1,4-Dioxane (20 mL), Water (3 mL) was degassed with Argon for 20 min was added X-Phos (90 mg, 0.189 mmol), Tris(dibenzylideneacetone)dipalladium(0) (87 mg, 0.095 mmol) and again degassed with Argon for 10 min. The reaction mixture was stirred at 100° C. for 16 h and cooled to room temperature. The reaction mixture was filtered through celite then the filtrate was diluted with water and extracted with EtOAc (3×15 mL). The combined organic layers were washed with water, brine solution, dried over sodium sulfate and evaporated to give crude compound (TLC eluent: 5% MeOH in DCM: R$_f$-0.1; UV active). The crude compound was purified by column chromatography using Neutral Alumina and eluted with 30% EtOAc/Pet ether to afford pure (4S)-7-(6-cyanopyridin-3-yl)-N-(pyrazin-2-yl)-3,4-dihydro-1,4-methanopyrido[2,3-b][1,4]diazepine-5(2H)-carboxamide (220 mg, 0.568 mmol, 30.0% yield) as off white solid, LCMS (m/z): 385.3 [M+H]$^+$.

$^1$H NMR (400 MHz, CDCl$_3$): δ ppm 13.54 (s, 1H) 9.54 (d, J=1.32 Hz, 1H) 9.34 (dd, J=2.30, 0.77 Hz, 1H) 8.66 (dd, J=8.11, 2.41 Hz, 1H) 8.35-8.30 (m, 2H) 7.86 (dd, J=8.11, 0.88 Hz, 1H) 7.70 (d, J=7.89 Hz, 1H) 7.50 (d, J=8.11 Hz, 1H) 5.71 (dd, J=5.92, 3.29 Hz, 1H) 3.35-3.14 (m, 3H) 3.09-3.02 (m, 1H) 2.43-2.32 (m, 1H) 2.16-2.05 (m, 1H).

Example 246

Synthesis of (4S)—N-(5-ethylpyrazin-2-yl)-7-(6-methylpyridin-3-yl)-3,4-dihydro-1,4-methanopyrido[2,3-b][1,4]diazepine-5(2H)-carboxamide

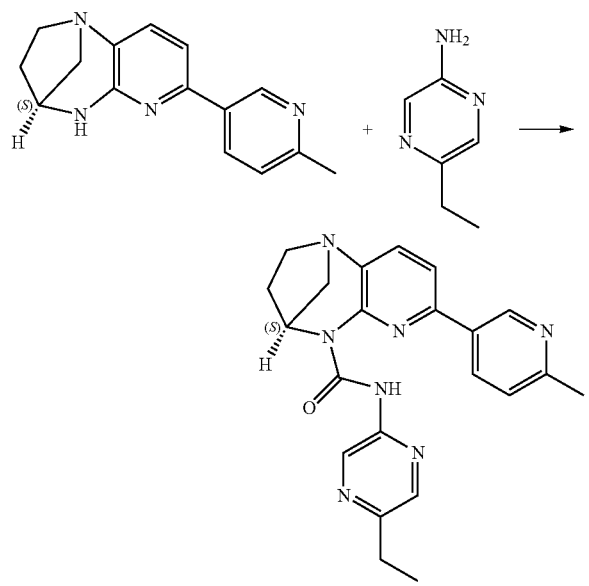

To a solution of (4S)-7-(6-methylpyridin-3-yl)-2,3,4,5-tetrahydro-1,4-methanopyrido[2,3-b][1,4]diazepine (600 mg, 2.378 mmol), triphosgene (706 mg, 2.378 mmol) and triethylamine (1.989 mL, 14.27 mmol) in tetrahydrofuran (THF) (15 mL) stirred under nitrogen at room temperature for 30 min was added 5-ethylpyrazin-2-amine (879 mg, 7.13 mmol). The reaction mixture was stirred at 70° C. for 16 h and cooled to room temperature and then the reaction mixture was poured in to water and extracted with EtOAc (3×15 mL). The combined organic layers were washed with water, brine solution, dried over sodium sulfate and evaporated to give crude compound (TLC eluent: 5% MeOH in DCM: $R_f$-0.1; UV active). The crude compound was purified by column chromatography using Neutral Alumina and eluted with 30% EtOAc/Pet ether to afford pure (4S)—N-(5-ethylpyrazin-2-yl)-7-(6-methylpyridin-3-yl)-3,4-dihydro-1,4-methanopyrido[2,3-b][1,4]diazepine-5(2H)-carboxamide (383 mg, 0.953 mmol, 40.1% yield), LCMS (m/z): 402.3 [M+H]$^+$.

$^1$H NMR (400 MHz, CDCl$_3$): δ ppm 13.65 (s, 1H) 9.41 (d, J=1.53 Hz, 1H) 9.11 (d, J=2.19 Hz, 1H) 8.41 (dd, J=8.22, 2.52 Hz, 1H) 8.22 (d, J=1.32 Hz, 1H) 7.61 (d, J=7.89 Hz, 1H) 7.40 (d, J=8.11 Hz, 1H) 7.32 (d, J=8.11 Hz, 1H) 5.70 (dd, J=6.03, 3.18 Hz, 1H) 3.34-3.13 (m, 3H) 3.02 (dd, J=12.06, 3.29 Hz, 1H) 2.83 (q, J=7.53 Hz, 2H) 2.64 (s, 3H) 2.40-2.34 (m, 1H) 2.15-2.03 (m, 1H) 1.33 (t, J=7.56 Hz, 3H).

Example 247

Synthesis of (4S)—N-(6-isopropoxypyrazin-2-yl)-7-(2-methylpyridin-4-yl)-3,4-dihydro-1,4-methanopyrido[2,3-b][1,4]diazepine-5(2H)-carboxamide

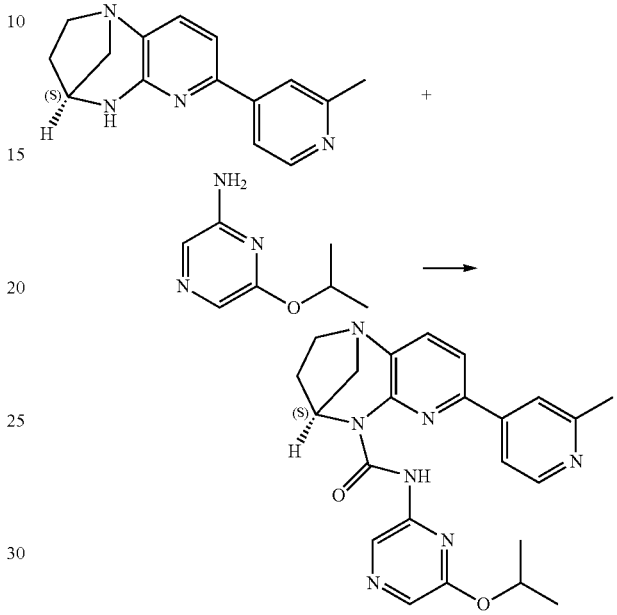

Triethylamine (1.326 mL, 9.51 mmol) followed by triphosgene (470 mg, 1.585 mmol) were added to a stirred solution of (4S)-7-(2-methylpyridin-4-yl)-2,3,4,5-tetrahydro-1,4-methanopyrido[2,3-b][1,4]diazepine (400 mg, 1.585 mmol) in tetrahydrofuran (THF) (8 mL) at RT and stirred for 30 min before 6-isopropoxypyrazin-2-amine (486 mg, 3.17 mmol) was added to the reaction mixture and stirred to 80° C. for 16 h. Reaction mixture was cooled to RT, diluted with water (50 mL), extracted with Ethyl acetate (2×40 mL), washed with brine (30 mL). Organic layer was separated, dried over sodium sulfate, filtered and concentrated. Residue was purified by flash chromatography using silica gel (100-200 mesh), 2% methanol in DCM to get (4S)—N-(6-isopropoxypyrazin-2-yl)-7-(2-methylpyridin-4-yl)-3,4-dihydro-1,4-methanopyrido[2,3-b][1,4]diazepine-5(2H)-carboxamide (60 mg, 0.132 mmol, 8.33% yield) as off-white solid (TLC: $R_f$: 0.4, 5% methanol in DCM), LCMS (m/z): 432.27 [M+H]$^+$.

$^1$H NMR (400 MHz, CDCl$_3$) δ ppm 1.24 (dd, J=13.15, 6.14 Hz, 6H) 2.09 (dt, J=14.14, 6.96 Hz, 1H) 2.22-2.45 (m, 1H) 2.65 (s, 3H) 3.03 (dd, J=12.06, 3.29 Hz, 1H) 3.13-3.38 (m, 3H) 5.10 (dt, J=12.44, 6.17 Hz, 1H) 5.71 (dd, J=6.03, 3.18 Hz, 1H) 7.27-7.46 (m, 1H) 7.51-7.68 (m, 2H) 7.73 (dd, J=5.15, 1.43 Hz, 1H) 7.88 (s, 1H) 8.58 (d, J=5.26 Hz, 1H) 9.03 (s, 1H) 13.04 (s, 1H).

Example 248

Synthesis of (4S)-7-(6-cyano-5-methylpyridin-3-yl)-N-(pyrazin-2-yl)-3, 4-dihydro-1,4-methanopyrido[2,3-b][1,4]diazepine-5(2H)-carboxamide

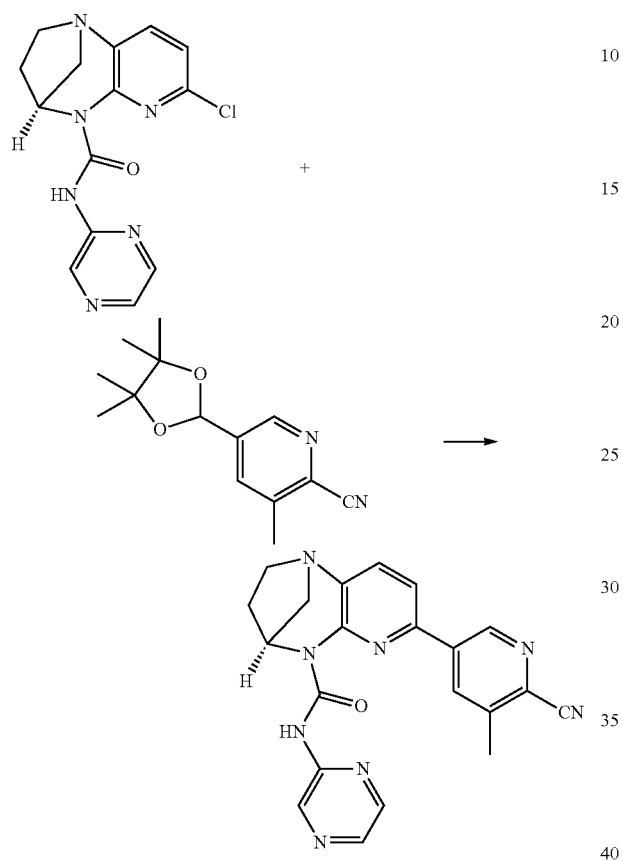

To a degassed solution of (4S)-7-chloro-N-(pyrazin-2-yl)-3,4-dihydro-1,4-methanopyrido[2,3-b][1,4]diazepine-5(2H)-carboxamide (500 mg, 1.579 mmol), 3-methyl-5-(4,4,5,5-tetramethyl-1,3,2-dioxaborolan-2-yl)picolinonitrile (501 mg, 2.052 mmol) and $K_3PO_4$ (1.005 g, 4.74 mmol) in 1,4-dioxane (20 mL) and water (3 mL), was added X-phos (75 mg, 0.158 mmol) and Pd(OAc)$_2$ (17.72 mg, 0.079 mmol). The reaction mixture was further degassed for 15 min and the reaction mixture was stirred for 16 h at 90° C. The reaction mixture was cooled to 28° C. and filtered through a pad of celite and filtrate was evaporated to give residue. The residue was diluted with water (20 mL) and extracted with ethyl acetate (2×70 mL). The combined organic layer was washed with water (10 mL) followed by brine solution (10 mL). Organic layer was dried over anhydrous sodium sulfate, filtered and filtrate was evaporated to give crude. (TLC eluent: 100% Ethyl acetate, $R_f$-0.3; UV active). The crude compound was purified by column chromatography using neutral alumina, and the product was eluted with 55-60% ethyl acetate in hexane to afford pure (4S)-7-(6-cyano-5-methylpyridin-3-yl)-N-(pyrazin-2-yl)-3,4-dihydro-1,4-methanopyrido[2,3-b][1,4]diazepine-5(2H)-carboxamide (350 mg, 0.835 mmol, 52.9% yield) as pale yellow solid, LCMS (m/z): 399.22 [M+H]$^+$.

$^1$H NMR (400 MHz, CDCl$_3$): δ 13.61 (s, 1H), 9.58 (d, J=1.5 Hz, 1H), 9.07 (d, J=2.2 Hz, 1H), 8.63-8.69 (m, 1H), 8.33 (d, J=2.8 Hz, 1H), 8.28 (dd, J=1.4, 2.6 Hz, 1H), 7.69 (d, J=8.1 Hz, 1H), 7.52 (m, J=8.1 Hz, 1H), 5.72 (dd, J=5.9, 3.07 Hz, 1H), 3.13-3.36 (m, 3H), 3.05 (dd, J=12.28, 3.3 Hz, 1H), 2.73 (S, 3H), 2.25-2.44 (m, 1H), 2.04-2.24 (m, 1H).

Example 249

Synthesis of (4S)-7-(2-methyl-6-(trifluoromethyl)pyridin-4-yl)-N-(pyrazin-2-yl)-3,4-dihydro-1,4-methanopyrido[2,3-b][1,4]diazepine-5(2H)-carboxamide

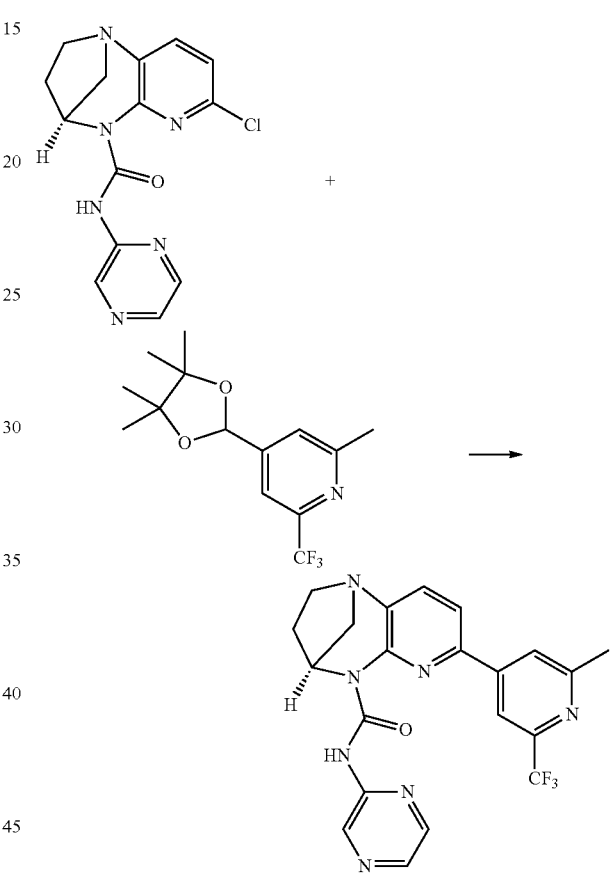

To a degassed solution of (4S)-7-chloro-N-(pyrazin-2-yl)-3,4-dihydro-1,4-methanopyrido[2,3-b][1,4]diazepine-5(2H)-carboxamide (400 mg, 1.263 mmol), 2-methyl-4-(4,4,5,5-tetramethyl-1,3,2-dioxaborolan-2-yl)-6-(trifluoromethyl)pyridine (471 mg, 1.642 mmol) and $K_3PO_4$ (804 mg, 3.79 mmol) in 1,4-dioxane (20 mL) and water (3 mL) was added X-phos (60.2 mg, 0.126 mmol) and Pd$_2$(dba)$_3$ (57.8 mg, 0.063 mmol). The reaction mixture was further degassed for 15 min and the reaction mixture was stirred for 16 h at 90° C. The reaction mixture was cooled to 28° C. and filtered through a pad of celite and the filtrate was evaporated to give residue. The residue was diluted with water (20 mL) and extracted with ethyl acetate (2×70 mL). The combined organic layer was washed with water (10 mL) followed by brine solution (10 mL). The organic layer was dried over sodium sulfate, filtered and filtrate was evaporated to give crude (TLC eluent: 100% Ethyl acetate, $R_f$=0.4; UV active). The Crude compound was purified by column chromatography (neutral alumina), and the product was eluted with 45-50% ethyl acetate in hexane to afford (4S)-7-(2-methyl-6-(trifluoromethyl)pyridin-4-yl)-N-(pyrazin-2-yl)-3,4-dihydro-1,4-methanopyrido[2,3-b][1,4]diazepine-5(2H)-carboxamide (318 mg, 0.719 mmol, 56.9% yield) as off-white solid, LCMS (m/z): 442.24 [M+H]+.

$^1$H NMR (400 MHz, CDCl$_3$): δ 13.63 (s, 1H), 9.57 (d, J=1.3 Hz, 1H), 8.22-8.40 (m, 2H), 8.14 (s, 1H), 8.11 (s, 1H), 7.69 (d, J=8.1 Hz, 1H), 7.53 (d, J=7.9 Hz, 1H), 5.73 (dd, J=5.9, 3.0 Hz, 1H), 3.12-3.37 (m, 3H), 2.95-3.12 (m, 1H), 2.79 (S, 3H), 2.25-2.46 (m, 1H), 2.00-2.21 (m, 1H).

Example 250

Synthesis of (4S)—N-(pyridin-3-yl)-7-(6-(trifluoromethyl)pyridin-3-yl)-3,4-dihydro-1,4-methanopyrido[2,3-b][1,4]diazepine-5(2H)-carboxamide give as a brown solid (TLC eluent: 100% ethyl acetate, R$_f$-0.4; UV active). The crude compound was purified by column chromatography using neutral alumina, and the product was eluted with 35-40% ethyl acetate in hexane to afford (4S)—N-(pyridin-3-yl)-7-(6-(trifluoromethyl)pyridin-3-yl)-3,4-dihydro-1,4-methanopyrido[2,3-b][1,4]diazepine-5(2H)-carboxamide (400 mg, 0.924 mmol, 58.3% yield) as off white solid, LCMS (m/z): 427.20 [M+H]+.

$^1$H NMR (400 MHz, CDCl$_3$): δ 12.79 (s, 1H), 9.16 (d, J=1.9 Hz, 1H), 8.54 (d, J=2.4 Hz, 1H), 8.32 (dd, J=1.2, 4.8 Hz, 1H), 8.29 (dd, J=2, 8.4 Hz, 1H), 7.99-8.19 (m, 1H), 7.87 (d, J=8.3 Hz, 1H), 7.69 (d, J=7.6 Hz, 1H), 7.38 (d, J=7.9 Hz, 1H), 7.28-7.30 (m, 1H), 5.71 (dd, J=5.8, 3.2 Hz, 1H), 3.12-3.36 (m, 3H), 2.94-3.12 (m, 1H), 2.25-2.43 (m, 1H), 2.00-2.23 (m, 1H).

Example 251

Synthesis of (4S)-7-(2,5-dimethylpyridin-4-yl)-N-(pyrazin-2-yl)-3,4-dihydro-1,4-methanopyrido[2,3-b][1,4]diazepine-5(2H)-carboxamide

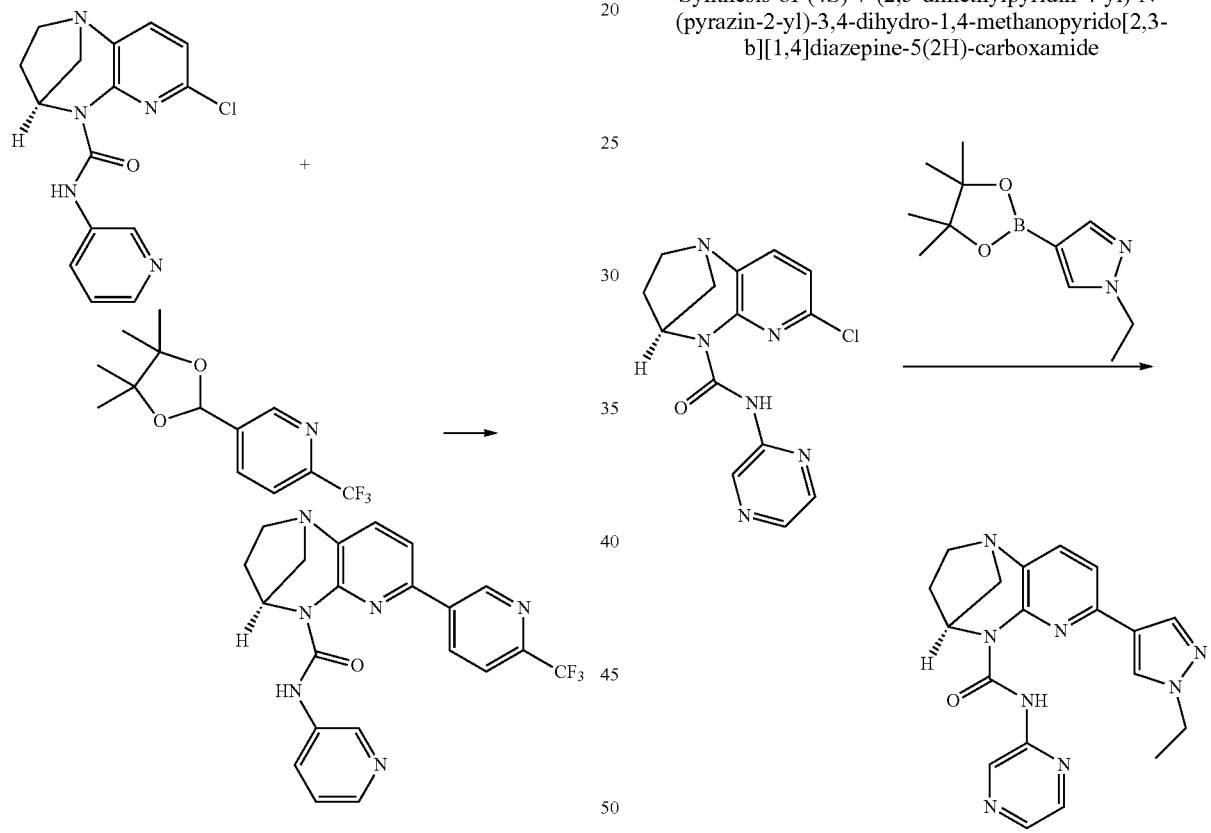

To a degassed solution of (4S)-7-chloro-N-(pyridin-3-yl)-3,4-dihydro-1,4-methanopyrido[2,3-b][1,4]diazepine-5(2H)-carboxamide (500 mg, 1.583 mmol), 5-(4,4,5,5-tetramethyl-1,3,2-dioxaborolan-2-yl)-2-(trifluoromethyl)pyridine (562 mg, 2.059 mmol) and K$_3$PO$_4$ (1008 mg, 4.75 mmol) in 1,4-dioxane (20 mL), and water (3 mL), was added X-phos (75 mg, 0.158 mmol) and Pd$_2$(dba)$_3$ (72.5 mg, 0.079 mmol). The reaction mixture was further degassed for 15 min and the reaction mixture was stirred for 16 h at 90° C. The reaction mixture was cooled to 28° C. and filtered through a pad of celite and the filtrate was evaporated to give crude residue. The crude residue was diluted with water (20 mL) and extracted with ethyl acetate (2×70 mL). The combined organic layer was washed with water (10 mL) followed by brine solution (10 mL). Organic layer was dried over sodium sulfate, filtered and filtrate was evaporated to Pd$_2$(dba)$_3$ (0.087 g, 0.095 mmol) and X-phos (0.018 g, 0.047 mmol) was added to degassed (argon) solution of (4S)-7-chloro-N-(pyrazin-2-yl)-3,4-dihydro-1,4-methanopyrido[2,3-b][1,4]diazepine-5(2H)-carboxamide (0.3 g, 0.947 mmol), 1-ethyl-4-(4,4,5,5-tetramethyl-1,3,2-dioxaborolan-2-yl)-1H-pyrazole (0.316 g, 1.421 mmol) and potassium dihydrogen phosphate (0.258 g, 1.894 mmol) in 1,4-dioxane (5 mL): water (1 mL). The reaction mixture was further degassed for 10 min and was stirred for 15h at 90° C. The reaction mixture was cooled to 28° C. and was filtered through a pad of celite. The filtrate was diluted with water (50 mL) and ethyl acetate (50 mL). The organic layer was separated and was washed with water and brine. The organic layer was dried over anhydrous sodium sulfate, filtered and filtrate was evaporated to get crude compound (TLC eluent: 10% MeOH in EtOAc; R$_f$-0.35 UV active). The crude compound was purified by column chromatography using neutral alumina and was eluted with 75% ethyl acetate in hexane to afford (4S)-7-(1-ethyl-1H-pyrazol-4-yl)-N-(pyrazin-2-yl)-3,4-dihydro-1,4-methanopyrido[2,3-b][1,4]diazepine-5(2H)-carboxamide (0.26 g, 0.688 mmol, 72.6% yield) as off-white solid, LCMS (m/z): 377.30 [M+H]$^+$.

$^1$H NMR (CDCl$_3$, 400 MHz): δ 14.15 (s, 1H), 9.60 (d, J=1.53 Hz, 1H), 8.56 (s, 1H), 8.22-8.30 (m, 2H), 8.07 (s, 1H), 7.50 (d, J=7.89 Hz, 1H), 7.14 (d, J=7.89 Hz, 1H), 5.66 (dd, J=6.03, 3.18 Hz, 1H), 4.28 (q, J=7.38 Hz, 2H), 3.11-3.38 (m, 3H), 2.97-3.07 (m, 1H), 2.32 (dddd, J=14.03, 9.98, 6.03, 3.95 Hz, 1H), 1.97-2.13 (m, 1H), 1.60 (d, J=7.20 Hz, 3H).

Example 252

Synthesis of (4S)-7-(6-(difluoromethoxy)pyridin-3-yl)-N-(pyrazin-2-yl)-3,4-dihydro-1,4-methanopyrido[2,3-b][1,4]diazepine-5(2H)-carboxamide

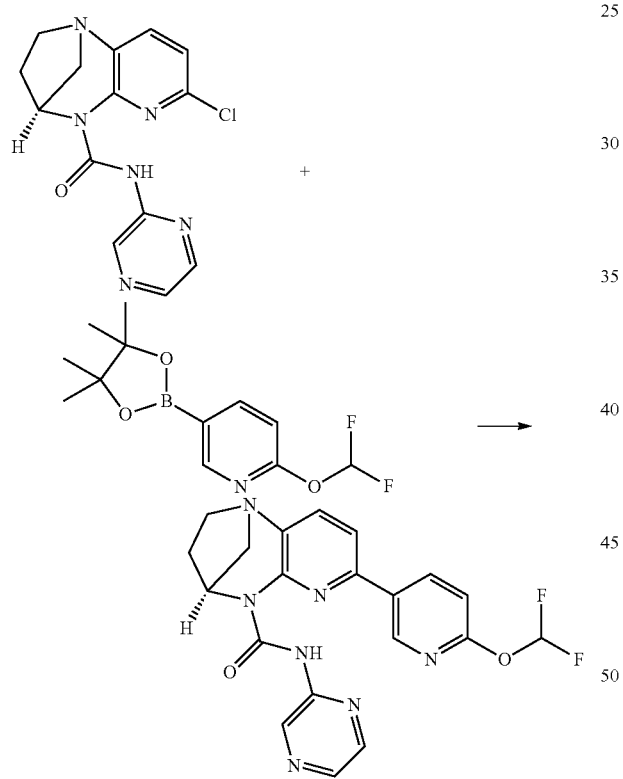

Pd$_2$(dba)$_3$ (0.087 g, 0.095 mmol) and X-phos (0.018 g, 0.047 mmol) was added to degassed solution of (4S)-7-chloro-N-(pyrazin-2-yl)$_{3,4}$dihydro1,4methanopyrido[2,3-b][1,4]diazepine-5(2H)-carboxamide (0.3 g, 0.947 mmol), 2-(difluoromethoxy)-5-(4,4,5,5-tetramethyl-1,3,2-dioxaborolan-2-yl)pyridine (0.385 g, 1.421 mmol) and potassium dihydrogen phosphate (0.258 g, 1.894 mmol) in 1,4-dioxane (5 mL): water (1 mL). The reaction mixture was further degassed for 10 min and was stirred for 15h at 90° C. The reaction mixture was cooled to 28° C. and was filtered through a pad of celite. The filtrate was diluted with water (50 mL) and ethyl acetate (50 mL). The organic layer was separated and was washed with water and brine. The organic layer was dried over anhydrous sodium sulfate, filtered, and filtrate was evaporated get crude compound (TLC eluent: 10% MeOH in EtOAc: R$_f$-0.4 UV active). The crude compound was purified by column chromatography using neutral alumina and was eluted with 75% ethyl acetate in hexane to afford (4S)-7-(6-(difluoromethoxy)pyridin-3-yl)-N-(pyrazin-2-yl)-3,4-dihydro-1,4-methanopyrido[2,3-b][1,4]diazepine-5(2H)-carboxamide (0.210 g, 0.493 mmol, 52.1% yield) as Off-white solid, LCMS (m/z): 426.22 [M+H]$^+$.

$^1$H NMR (CDCl$_3$, 400 MHz): δ 13.70 (s, 1H), 9.54 (d, J=1.53 Hz, 1H), 8.81 (dd, J=2.63, 0.66 Hz, 1H), 8.57 (dd, J=8.55, 2.63 Hz, 1H), 8.27-8.32 (m, 2H), 7.74 (s, 1H), 7.63 (d, J=8.11 Hz, 1H), 7.37-7.75 (m, 1H), 7.06 (dd, J=8.55, 0.66 Hz, 1H), 5.70 (dd, J=5.92, 3.29 Hz, 1H), 3.13-3.33 (m, 3H), 3.03 (dd, J=12.17, 3.18 Hz, 1H), 2.29-2.41 (m, 1H), 2.07-2.13 (m, 1H).

Example 253

Synthesis of (4S)-7-(6-methylpyridin-3-yl)-N-(2-(((S)-tetrahydrofuran-3-yl)oxy) pyrimidin-4-yl)-3,4-dihydro-1,4-methanopyrido[2,3-b][1,4]diazepine-5(2H)-carboxamide

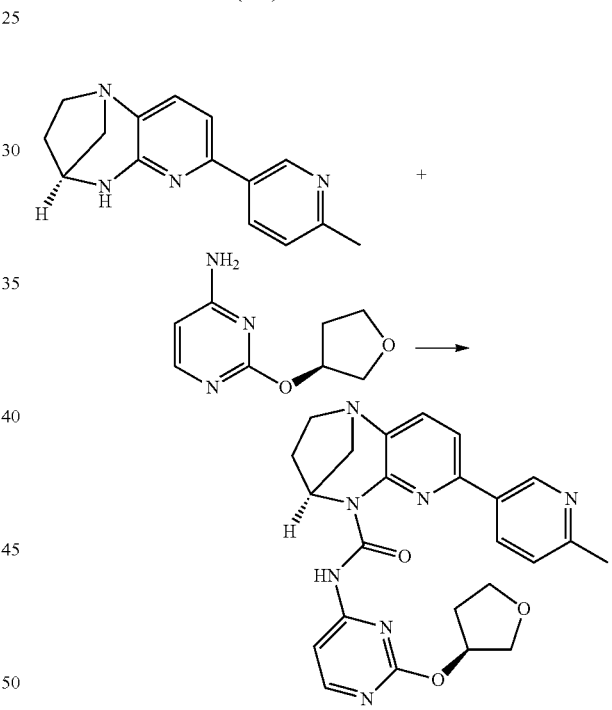

To a solution of (S)-2-((tetrahydrofuran-3-yl)oxy)pyrimidin-4-amine (862 mg, 4.76 mmol), triphosgene (423 mg, 1.427 mmol) in THF (15 mL) were added DIPEA (2.077 mL, 11.89 mmol) and (4S)-7-(6-methylpyridin-3-yl)-2,3,4,5-tetrahydro-1,4-methanopyrido[2,3-b][1,4]diazepine (600 mg, 2.378 mmol) at RT. The reaction mixture was stirred at 80° C. for 16h before the THF was evaporated under reduced pressure and the residue diluted with water and extracted with DCM (2×25 mL). The combined organic layer was dried over anhydrous Na$_2$SO$_4$ and evaporated under reduced pressure to afford the crude compound. The crude compound was purified by using Prep HPLC to afford (4S)-7-(6-methylpyridin-3-yl)-N-(2-(((S)-tetrahydrofuran-3-yl)oxy)pyrimidin-4-yl)-3,4-dihydro-1,4-methanopyrido[2,3-b][1,4]diazepine-5(2H)-carboxamide (195 mg, 0.421 mmol, 17.72% yield) as a white solid (TLC: 10% MeOH in EtOAc, R$_f$: 0.4), LCMS (m/z): 460.28 [M+H]$^+$.

$^1$H NMR (400 MHz, CDCl$_3$): δ ppm 13.67 (s, 1H), 9.16 (d, J=2.19 Hz, 1H), 8.38 (d, J=5.70 Hz, 1H), 8.34-8.07 (m, 1H), 7.80 (d, J=5.70 Hz, 1H), 7.63 (d, J=7.89 Hz, 1H), 7.39 (d, J=8.11 Hz, 1H), 7.33-7.23 (m, 1H), 5.76-5.58 (m, 1H), 4.03-3.83 (m, 4H), 3.35-3.10 (m, 3H), 2.49-2.24 (m, 1H), 2.23-2.00 (m, 3H).

Example 254

Synthesis of (4S)-7-(2-methylpiperazin-1-yl)-N-(pyrazin-2-yl)-3,4-dihydro-1,4-methanopyrido[2,3-b][1,4]diazepine-5(2H)-carboxamide

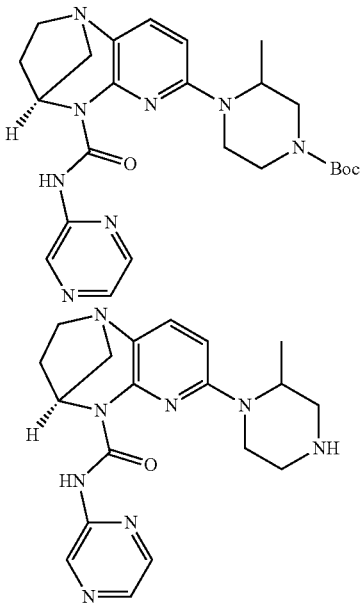

To a stirred solution of Tert-butyl3-methyl-4-((4S)-5-(pyrazin-2-ylcarbamoyl)-2,3,4,5-tetrahydro-1,4-methanopyrido [2,3-b][1,4]diazepin-7-yl)piperazine-1-carboxylate (397 mg, 0.826 mmol) in THF (5 mL) was added 2M HCl solution in diethyl ether (2.065 mL, 4.13 mmol) at 0° C. and the reaction mixture was stirred at 35° C. for 4 h. The reaction mixture was neutralized with aq NaHCO$_3$ solution and extracted with CH$_2$Cl$_2$ (3×50 mL). The combined organic layer was washed with water, brine, dried over Na$_2$SO$_4$ and concentrated under reduced pressure to obtain the crude product. The crude mixture was purified by Prep HPLC to afford (4S)-7-(2-methylpiperazin-1-yl)-N-(pyrazin-2-yl)-3,4-dihydro-1,4-methanopyrido[2,3-b][1,4]diazepine-5(2H)-carboxamide (270 mg, 0.710 mmol, 85% yield) as an off white solid (TLC: 5% MeOH in DCM, R$_f$: 0.3), LCMS (m/z): 381 [M+H]$^+$.

$^1$H NMR (400 MHz, DMSO-d$_6$): δ ppm 13.36-13.49 (m, 1H), 9.39 (m, 1H), 8.41-8.22 (m, 2H), 7.44-7.29 (m, 1H), 6.41 (dd, J=8.77, 2.63 Hz, 1H), 5.44 (dd, J=5.26, 2.63 Hz, 1H), 4.42-4.25 (m, 1H), 3.93-3.68 (m, 1H), 3.16-2.98 (m, 4H), 2.90-2.73 (m, 3H), 2.69-2.53 (m, 1H), 2.37-2.27 (m, 2H), 2.26-2.10 (m, 1H), 1.99-1.79 (m, 1H), 1.12 (dd, J=6.58, 3.95 Hz, 3H).

Example 255

Synthesis of (4S)-7-(3-methylpiperazin-1-yl)-N-(pyrazin-2-yl)-3,4-dihydro-1,4-methanopyrido [2,3-b][1,4]diazepine-5(2H)-carboxamide

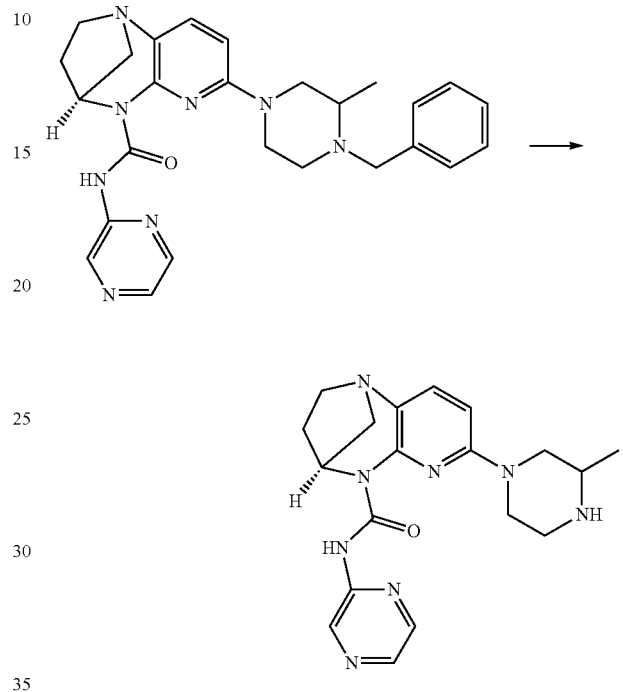

To a stirred solution of (4S)-7-(4-benzyl-3-methylpiperazin-1-yl)-N-(pyrazin-2-yl)-3,4-dihydro-1,4-methanopyrido [2,3-b][1,4]diazepine-5(2H)-carboxamide (450 mg, 0.956 mmol) in Methanol (10 mL) were added acetic acid (0.027 mL, 0.478 mmol) and 10% palladium hydroxide on carbon (67.1 mg, 0.096 mmol) at RT under hydrogen atmosphere (balloon pressure) and the reaction mixture was stirred at 35° C. for 4 h. After completion of reaction the reaction mixture was filtered through celite pad, the filtrate was evaporated in vacuo to give the crude product. The crude mixture was purified by Prep HPLC to afford (4S)-7-(3-methylpiperazin-1-yl)-N-(pyrazin-2-yl)-3,4-dihydro-1,4-methanopyrido [2,3-b][1,4]diazepine-5(2H)-carboxamide (280 mg, 0.736 mmol, 76% yield) as pale brown solid (TLC: R$_f$: 20% MeOH in DCM, 0.4), LCMS (m/z): 381.3 [M+H]$^+$.

$^1$H NMR (400 MHz, CDCl$_3$): δ ppm 13.43 (s, 1H), 9.55 (d, J=1.53 Hz, 1H), 8.24 (d, J=2.63 Hz, 1H), 8.09-8.20 (m, 2H), 7.36 (d, J=8.55 Hz, 1H), 6.30 (d, J=8.55 Hz, 1H), 5.62 (dd, J=5.92, 3.07 Hz, 1H), 4.20 (d, J=12.06 Hz, 1H), 3.95 (d, J=11.84 Hz, 1H), 3.08-2.87 (m, 4H) 3.25-3.08 (m, 4H), 2.57 (ddd, J=12.33, 10.25, 2.19 Hz, 1H), 2.27 (dddd, J=13.92, 9.98, 6.14, 3.73 Hz, 1H), 2.00 (dt, J=14.41, 7.37 Hz, 1H), 1.21 (d, J=6.14 Hz, 3H).

Example 256

Synthesis of (9S)—N-(pyridine-2-yl)-2-(3-(trifluoromethyl)pyrrolidin-1-yl)-8,9-dihydro-6H-5,9-methanopyrido[2,3-b][1,4]diazocine-10(7H)-carboxamide hydrochloride

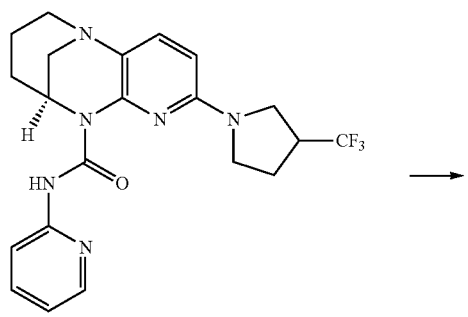

2.0 M Hydrochloric acid in Diethyl ether (2 mL, 4.00 mmol) was added to (9S)—N-(Pyridine-2-yl)-2-(3-(trifluoromethyl)pyrrolidine-1-yl)-8,9-dihydro-6H-5,9-methanopyrido[2,3-b][1,4]diazocine-10(7H)-carboxamide (180 mg, 0.416 mmol) at 0° C. The reaction mixture was stirred at 28° C. for 4 h and concentrated to give crude compound (TLC eluent: 5% MeOH in DCM: $R_f$-0.1; UV active). The crude compound was washed with Diethyl ether (2×5 mL) to afford pure (9S)—N-(pyridine-2-yl)-2-(3-(trifluoromethyl)pyrrolidin-1-yl)-8,9-dihydro-6H-5,9-methanopyrido[2,3-b][1,4]diazocine-10(7H)-carboxamide hydrochloride (83 mg, 0.177 mmole, 42.78% yield) as pale brown solid, LCMS (m/z): 433.28 [M+H]$^+$.

$^1$H NMR (400 MHz, CDCl$_3$): δ 15.02 (br s, 1H), 13.34 (br s, 1H), 8.25 (br d, J=3.73 Hz, 1H), 8.13 (br d, J=8.33 Hz, 1H), 8.06 (d, J=8.77 Hz, 1H), 7.75-7.68 (m, 1H), 7.04-6.98 (m, 1H), 6.15 (s, 1H), 5.30-5.24 (b, s, 1H), 4.12-3.94 (m, 2H), 3.73-3.59 (m, 4H), 3.49-3.37 (m, 2H), 3.18-3.04 (m, 1H), 2.45-2.25 (m, 3H), 1.86 (d, J=12.50 Hz, 2H).

Example 257,258

(4S)—N-(pyrazin-2-yl)-7-((+)-2-(trifluoromethyl)morpholino)-3,4-dihydro-1,4-methanopyrido[2,3-b][1,4] diazepine-5 (2H)-carboxamide

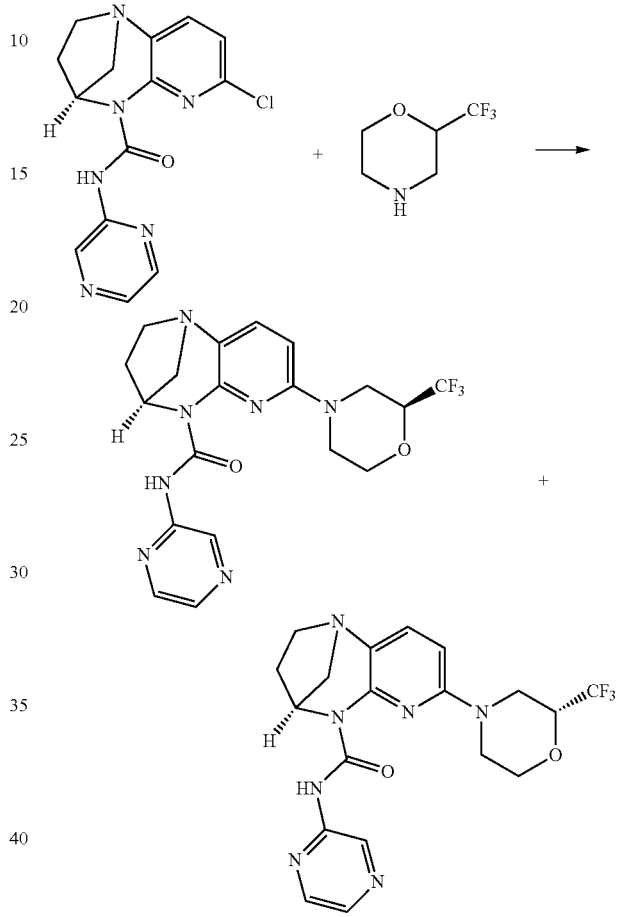

To a degassed solution of (4S)-7-chloro-N-(pyrazin-2-yl)-3,4-dihydro-1,4-methanopyrido[2,3-b][1,4]diazepine-5 (2H)-carboxamide (2 g, 6.31 mmol) and 2-(trifluoromethyl) morpholine (1.469 g, 9.47 mmol) in 1,4-dioxane (30 mL) were added cesium carbonate (6.17 g, 18.94 mmol), x-phos (1.204 g, 2.53 mmol) and palladium(II) acetate (0.284 g, 1.263 mmol). The reaction mixture was stirred at 100° C. for 16 h in sealed tube. The reaction mixture was poured in to cold water (80 mL) and extracted with ethyl acetate (3×100 mL). The combined organic layer was dried over anhydrous sodium sulfate and concentrated under reduced pressure to obtain the crude product. The crude mixture was purified by flash column chromatography (silica-gel: 100-200 mesh, eluent: 2% MeOH in CH$_2$Cl$_2$) to afford enantiomeric mixture of (4S)—N-(pyrazin-2-yl)-7-((+)-2-(trifluoromethyl) morpholino)-3,4-dihydro-1,4-methanopyrido[2,3-b][1,4] diazepine-5 (2H)-carboxamide. The mixture was separated by chiral prep-SFC (conditions: (Cellulose-2 (250×30) mm, 55.0% (100% MeOH), 90.0 g/min, 100.0 bar, 42 nm, 8.5 min)) as peak-I (fastest eluent: 320 mg, 0.736 mmol, 42% yield) and peak-II (slowest eluent: 305 mg, 0.701 mmol, 40.5% yield) as an off white solids (TLC: neat EtOAc, $R_f$: -0.21), LCMS (m/z): 436.25 [M+H]$^+$.

Fastest eluent peak: ¹H NMR (400 MHz, CDCl₃): δ ppm 13.19 (s, 1H), 9.52 (s, 1H), 8.25 (d, J=2.41 Hz, 1H), 8.21-8.09 (m, 1H), 7.43 (d, J=8.33 Hz, 1H), 6.35 (d, J=8.55 Hz, 1H), 5.64 (dd, J=6.03, 3.18 Hz, 1H), 4.21 (dd, J=11.84, 1.97 Hz, 1H), 4.15-4.00 (m, 1H), 4.00-3.77 (m, 3H), 3.26-3.04 (m, 5H), 3.04-2.82 (m, 1H), 2.28 (dddd, J=13.95, 10.00, 6.19, 3.84 Hz, 1H), 2.07-1.92 (m, 1H).

Slowest eluent peak: ¹H NMR (400 MHz, CDCl₃): δ ppm 13.20 (s, 1H), 9.52 (d, J=1.53 Hz, 1H), 8.26 (d, J=2.41 Hz, 1H), 8.16 (dd, J=2.41, 1.53 Hz, 1H), 7.43 (d, J=8.55 Hz, 1H), 6.35 (d, J=8.55 Hz, 1H), 5.63 (dd, J=6.03, 3.18 Hz, 1H), 4.21 (d, J=12.06 Hz, 1H), 4.08 (ddd, J=10.69, 6.19, 2.85 Hz, 1H), 4.00-3.92 (m, 2H), 3.84 (td, J=11.56, 2.96 Hz, 1H), 3.26-3.07 (m, 5H), 3.07-2.82 (m, 1H), 2.43-2.24 (m, 1H), 2.21-1.95 (m, 1H).

Example 259

Synthesis of ((R)-2-methylmorpholino)((4S)-7-(2-methylpyridin-4-yl)-3,4-dihydro-1,4-methanopyrido[2,3-b][1,4]diazepin-5(2H)-yl)methanone hydrochloride

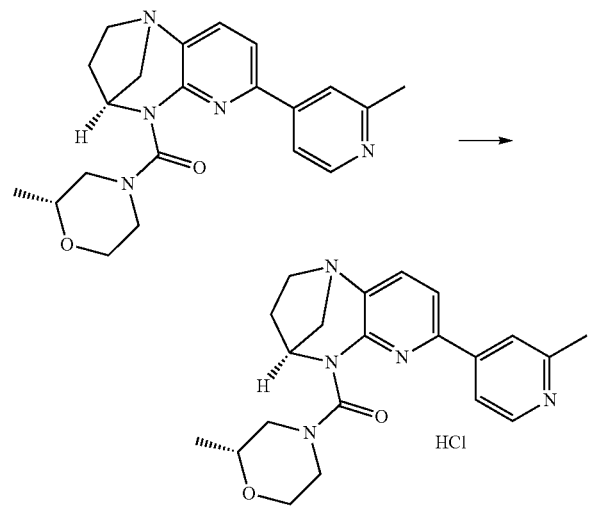

1.0 M Hydrochloric acid in dioxane (1.6 mL) was added to a stirred solution of (R)-2-methylmorpholino)((4S)-7-(2-methylpyridin-4-yl)-3,4-dihydro-1,4-methanopyrido[2,3-b][1, 4]diazepin-5(2H)-yl)methanone (0.21 g, 0.544 mmol) in methanol (5 mL) at 0° C. The reaction mixture was evaporated to give crude compound. The crude compound was triturated with diethyl ether (3×5 mL) to afford pure ((R)-2-methylmorpholino)((4S)-7-(2-methylpyridin-4-yl)-3,4dihydro 1,4methanopyrido[2,3-b][1,4]diazepin-5(2H)-yl) methanone hydrochloride (105 mg, 0.253 mmol, 45% yield) as yellow solid, LCMS (m/z): 380.25 [M+H]⁺.

¹H NMR (400 MHz, DMSO-d₆): δ 8.86 (br d, J=5.92 Hz, 1H), 8.41 (br s, 1H), 8.28 (br s, 1H), 7.82-8.07 (m, 2H), 4.64 (br s, 1H), 3.23-4.11 (m, 9H), 2.99-3.14 (m, 1H), 2.53-2.87 (m, 4H), 2.19-2.43 (m, 2H), 0.89-1.15 (m, 3H)

Example 260

Synthesis of (4S)-7-(1-methyl-2-oxo-1,2-dihydropyridin-4-yl)-N-(pyridin-3-yl)-3,4-dihydro-1,4-methanopyrido[2,3-b][1,4]diazepine-5(2H)-carboxamide

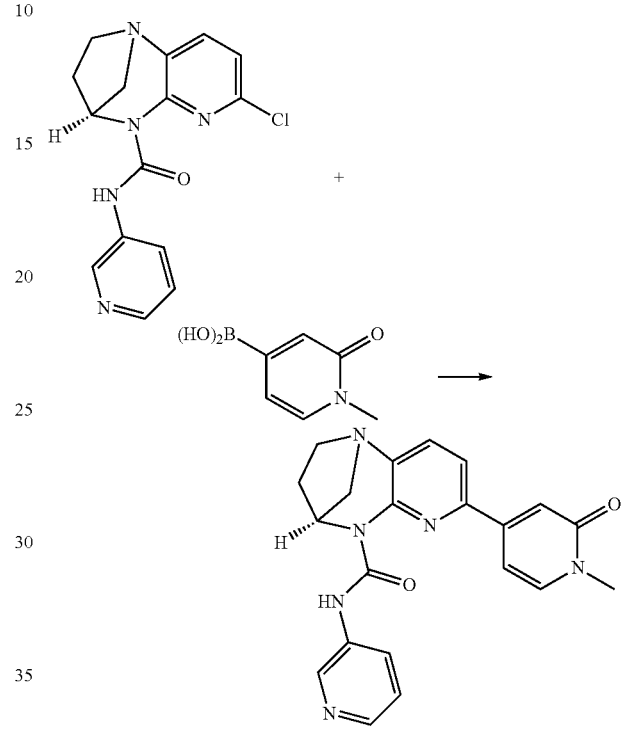

To a degassed solution of (4S)-7-chloro-N-(pyridin-3-yl)-3,4-dihydro-1,4-methanopyrido[2,3-b][1,4]diazepine-5(2H)-carboxamide (400 mg, 1.267 mmol), potassium phosphate (537 mg, 2.53 mmol) and (1-methyl-2-oxo-1,2-dihydropyridin-4-yl)boronic acid (291 mg, 1.900 mmol) in mixture of 1,4-dioxane (9 mL) and water (1 mL) were added X-Phos (60.4 mg, 0.127 mmol) and Pd(OAc)₂ (14.22 mg, 0.063 mmol) at RT and heated at 100° C. for 16h. Allowed the reaction mixture to RT, organic solvent was removed by rotary evaporation and diluted with water (50 mL), extracted with ethyl acetate (3×50 mL). The combined organic layer was washed with brine (50 mL), dried over anhydrous Na₂SO₄ and concentrated to obtain the crude product. The crude product was purified by flash column chromatography (silica-gel: 100-200 mesh, eluent: 03% MeOH in DCM) to afford (4S)-7-(1-methyl-2-oxo-1,2-dihydropyridin-4-yl)-N-(pyridin-3-yl)-3,4-dihydro-1,4-methanopyrido[2,3-b][1,4]diazepine-5(2H)-carboxamide (150 mg, 0.383 mmol, 30.2% yield) as an off white solid (TLC: R_f 0.4, 10% MeOH/DCM), LCMS (m/z): 389.22 [M+H]⁺.

¹H NMR (400 MHz, CDCl₃): δ ppm 12.92 (s, 1H), 8.57 (d, J=2.63 Hz, 1H), 8.06-8.32 (m, 2H), 7.62 (d, J=7.89 Hz, 1H), 7.48 (d, J=7.02 Hz, 1H), 7.25-7.32 (m, 2H), 6.95 (d, J=1.75 Hz, 1H), 6.63 (dd, J=7.02, 1.97 Hz, 1H), 5.68 (dd, J=5.92, 3.29 Hz, 1H), 3.62 (s, 3H), 3.19-3.39 (m, 2H), 3.15 (d, J=12.06 Hz, 1H), 2.84-3.09 (m, 1H), 2.19-2.39 (m, 1H), 2.05-2.19 (m, 1H).

Example 261

Synthesis of ((S)-2-methylmorpholino)((4S)-7-(2-methylpyridin-4-yl)-3,4-dihydro-1,4-methanopyrido[2,3-b][1,4]diazepin-5(2H)-yl)methanone hydrochloride

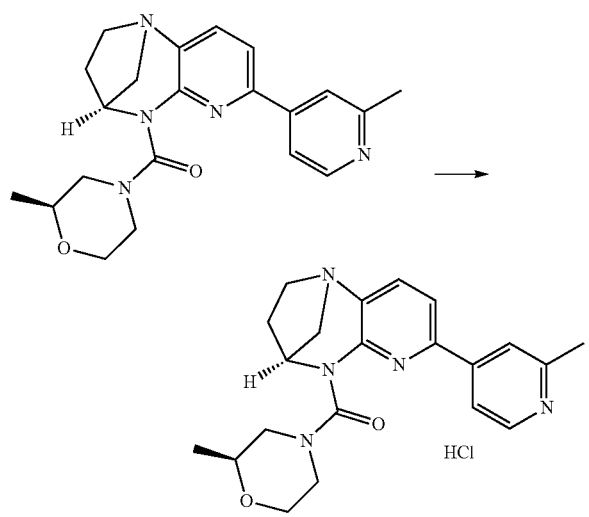

1.0 M Hydrochloric acid in dioxane (1.74 mL) was added to a stirred solution of(S)-2-methylmorpholino)(4S)-7-(2-methylpyridin-4-yl)-3,4-dihydro-1,4-methanopyrido[2,3-b][1,4]diazepin-5(2H)-yl)methanone (0.22 g, 0.580 mmol) in methanol (5 mL) at 0° C. The reaction mixture was stirred at 28° C. for 4 h. The reaction mixture was evaporated to give crude compound. The crude compound was triturated with diethyl ether (3×5 mL) to afford pure ((S)-2-methylmorpholino)((4S)-7-(2-methylpyridin-4-yl)-3,4-dihydro-1,4methanopyrido [2,3-b][1,4]diazepin-5(2H)-yl)methanone hydrochloride (110 mg, 0.265 mmol, 45% yield) as yellow solid, LCMS (m/z): 380.25 [M+H]$^+$.

$^1$H NMR (400 MHz, DMSO-d$_6$): δ 8.86 (d, J=6.36 Hz, 1H), 8.38-8.45 (m, 1H), 8.24-8.34 (m, 1H), 7.86-7.99 (m, 2H), 4.57-4.64 (m, 1H), 4.07 (br d, J=10.30 Hz, 1H), 3.35-3.85 (m, 10H), 3.07 (br t, J=12.06 Hz, 1H), 2.81 (s, 4H), 2.39 (s, 2H), 0.96-1.17 (m, 3H).

Example 262 e-LNB No: N33406-70-A2, GSK3397559A

Synthesis of (4S)—N-7-bis(2-methylpyridin-4-yl)-3,4-dihydro-1,4-methanopyrido[2,3-b][1,4] diazepine-5(2H)-carboxamide

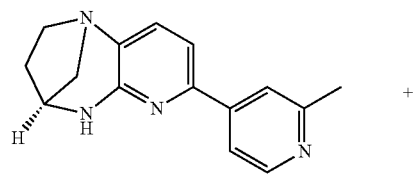

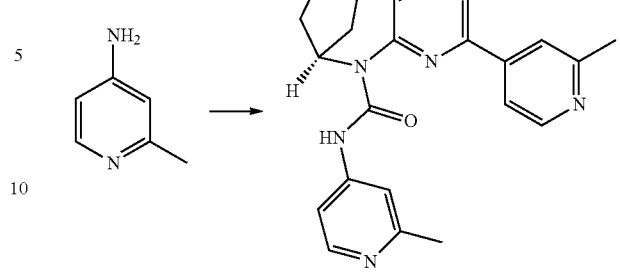

To a stirred solution of (4S)-7-(2-methylpyridin-4-yl)-2,3,4,5-tetrahydro-1,4-methanopyrido[2,3-b][1,4]diazepine (0.8 g, 3.17 mmol) in THF (15 mL) was added triphosgene (0.565 g, 1.902 mmol) at room temp and stirred for 30 min. Then 2-methylpyridin-4-amine (0.686 g, 6.34 mmol) and DIPEA (1.661 mL, 9.51 mmol) were added at room temperature. The reaction mixture was heated at 80° C. for 15 h. THF evaporated under reduced pressure and diluted with water (15 ml) and extracted with DCM (2×20 ml). The combined organic layer was dried over anhydrous Na$_2$SO$_4$ and evaporated under reduced pressure to obtain crude compound. The crude compound was purified by flash column chromatography to afford (4S)—N-7-bis(2-methylpyridin-4-yl)-3,4-dihydro-1,4-methanopyrido[2,3-b][1,4]diazepine-5(2H)-carboxamide (120 mg, 0.31 mmol, 22%) as a white solid (TLC: 10% MeOH in EtoAc, R$_f$: 0.4), LCMS (m/z): 387.28 [M+H]$^+$.

$^1$H NMR (400 MHz, CDCl$_3$): δ ppm 13.15 (s, 1H), 8.68 (d, J=5.26 Hz, 1H), 8.36 (d, J=5.48 Hz, 1H), 7.70-7.56 (m, 1H), 7.56-7.47 (m, 1H), 7.34-7.42 (m, 2H), 7.31-7.25 (m, 2H), 5.68 (dd, J=5.92, 3.07 Hz, 1H), 3.20-3.11 (m, 3H), 3.03 (dd, J=12.06, 3.29 Hz, 1H), 2.63 (s, 3H), 2.52 (s, 3H), 2.43-2.25 (m, 1H), 2.15-2.03 (m, 1H).

Example 263

Synthesis of (4S)-7-(4,6-dimethylpyridin-3-yl)-N-(pyridin-3-yl)-3,4-dihydro-1,4-methano pyrido[2,3-b][1,4]diazepine-5(2H)-carboxamide

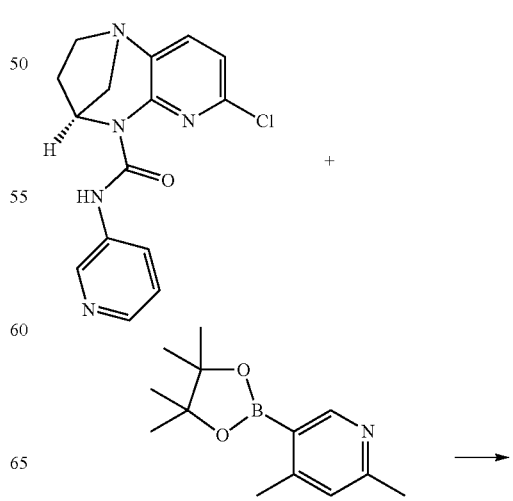

923

-continued

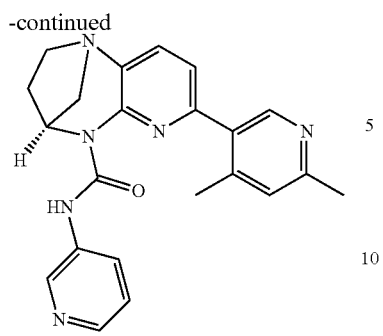

To a degassed solution of (4S)-7-chloro-N-(pyridin-3-yl)-3,4-dihydro-1,4-methanopyrido[2,3-b][1,4]diazepine-5(2H)-carboxamide (400 mg, 1.267 mmol), 2,4-dimethyl-5-(4,4,5,5-tetramethyl-1,3,2-dioxaborolan-2-yl)pyridine (591 mg, 2.53 mmol) and Cs$_2$CO$_3$ (1238 mg, 3.80 mmol) in mixture of 1,4-dioxane (9 mL) and water (1 mL) were added Pd(OAc)$_2$ (14.22 mg, 0.063 mmol) and X-Phos (60.4 mg, 0.127 mmol) at RT and heated at 100° C. for 16h. Allowed the reaction mixture to RT, organic solvent was removed by rotary evaporation and diluted with water (50 mL), extracted with ethyl acetate (3×50 mL). The combined organic layer was washed with brine (50 mL), dried over anhydrous Na$_2$SO$_4$, filtered and concentrated to obtain crude product. The crude mixture was purified by flash column chromatography (silica-gel: 100-200 mesh, eluent: 3% MeOH in DCM) to afford (4S)-7-(4,6-dimethylpyridin-3-yl)-N-(pyridin-3-yl)-3,4-dihydro-1,4-methanopyrido[2,3-b][1,4]diazepine-5(2H)-carboxamide (115 mg, 0.295 mmol, 23.30% yield) as an off white solid (TLC: R$_f$: 0.4, 10% MeOH in DCM), LCMS (m/z): 387.25 [M+H]$^+$.

$^1$H NMR (400 MHz, CDCl$_3$): δ ppm 13.07 (br s, 1H), 8.51 (s, 1H), 8.24 (br d, J=4.17 Hz, 1H), 8.18-7.97 (m, 1H), 7.61 (br d, J=7.67 Hz, 1H), 7.34-7.16 (m, 2H), 7.13 (m, 1H), 5.68 (br d, J=2.19 Hz, 1H), 3.38-3.11 (m, 3H), 3.11-2.89 (m, 1H), 2.60 (s, 3H), 2.36 (s, 4H) 2.30-2.03 (m, 1H), 1.36-1.12- (m, 1H).

Example 264

Synthesis of (4S)-7-(6-methylpyridin-3-yl)-N-neopentyl-3,4-dihydro-1,4-methanopyrido[2,3-b][1,4]diazepine-5(2H)-carboxamide

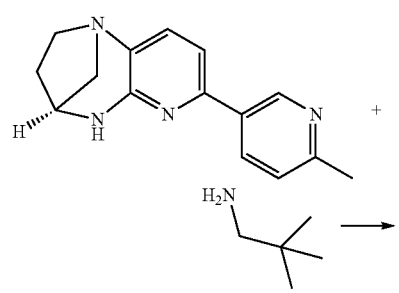

924

-continued

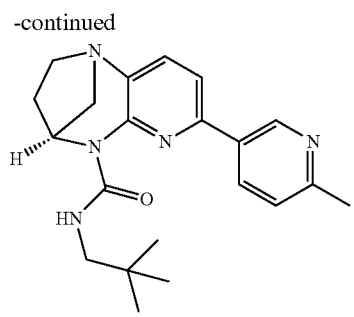

To a stirred solution of (4S)-7-(6-methylpyridin-3-yl)-2,3,4,5-tetrahydro-1,4-methano benzo[b][1,4]diazepine (250 mg, 0.991 mmol) in THF (10 mL) was added triphosgene (176 mg, 0.594 mmol) at RT and stirred for 30 min. Then DIPEA (0.519 mL, 2.97 mmol) and 2,2-dimethylpropan-1-amine (130 mg, 1.486 mmol) were added to above reaction mixture and stirred at 80° C. for 16 h. Allowed the reaction mixture to warm to RT, diluted with water (60 mL) and extracted with ethyl acetate (3×50 mL). The combined organic layer was washed with brine (60 mL), dried over anhydrous Na$_2$SO$_4$, filtered and concentrated to obtain the crude product. The crude was purified by flash column chromatography (silica-gel 100-200 mesh, eluent: 2% MeOH in DCM) to afford (4S)-7-(6-methylpyridin-3-yl)-N-neopentyl-3,4-dihydro-1,4-methanopyrido[2,3-b][1,4]diazepine-5(2H)-carboxamide (163 mg, 0.441 mmol, 44.5% yield) as a pale yellow solid (TLC: R$_f$: 0.4, 10% MeOH in DCM), LCMS (m/z): 366.29 [M+H]$^+$.

$^1$H NMR (400 MHz, CDCl$_3$): δ ppm 10.45 (br s, 1H), 8.88 (s, 1H), 7.93 (br d, J=7.89 Hz, 1H), 7.54 (d, J=7.89 Hz, 1H), 7.34-7.11 (m, 2H), 5.77-5.51 (m, 1H), 3.33-3.14 (m, 5H), 2.95 (brdd, J=11.84, 3.07 Hz, 1H), 2.61 (s, 3H), 2.35-2.18 (m, 1H), 2.18-1.89 (m, 1H), 0.90 (s, 9H).

Example 265

Synthesis of (4S)—N-(6-methylpyrazin-2-yl)-7-(6-methylpyridin-3-yl)-3,4-dihydro-1,4-methanopyrido[2,3-b][1,4]diazepine-5(2H)-carboxamide

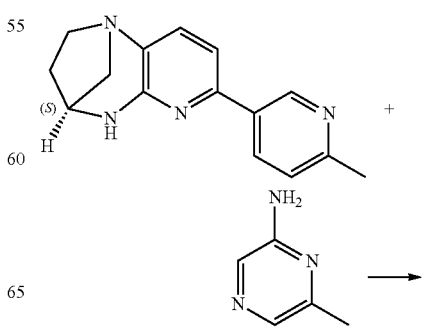

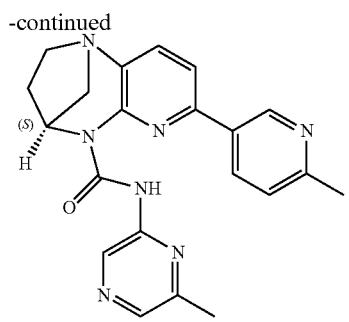
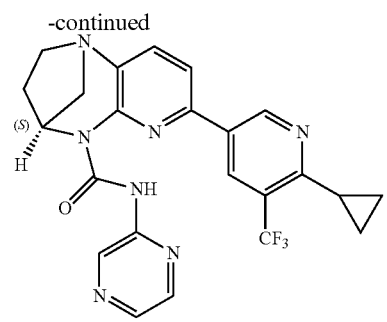

To a solution of (4S)-7-(6-methylpyridin-3-yl)-2,3,4,5-tetrahydro-1,4-methanopyrido[2,3-b][1,4]diazepine (600 mg, 2.378 mmol), triphosgene (706 mg, 2.378 mmol) and triethylamine (1.989 mL, 14.27 mmol) in tetrahydrofuran (15 mL) stirred under nitrogen at room temp for 30 min was added 6-methylpyrazin-2-amine (778 mg, 7.13 mmol). The reaction mixture was stirred at 70° C. for 16 h and cooled to room temperature. The reaction mixture was poured in to water and extracted with EtOAc (3×15 mL). The combined organic layers were washed with water, brine solution, dried over sodium sulfate and evaporated to give crude compound (TLC eluent: 5% MeOH in DCM: $R_f$-0.1; UV active). The crude compound was purified by column chromatography using neutral alumina and eluted with 30% EtOAc/pet ether to afford pure (4S)—N-(6-methylpyrazin-2-yl)-7-(6-methylpyridin-3-yl)-3,4-dihydro-1,4-methanopyrido[2,3-b][1,4]diazepine-5(2H)-carboxamide (151 mg, 0.389 mmol, 16.38% yield) as off white solid. LCMS (m/z): 388.2 [M+H]$^+$.

$^1$H NMR (400 MHz, CDCl$_3$): δ ppm 13.79 (s, 1H) 9.33 (s, 1H) 9.10 (d, J=2.41 Hz, 1H) 8.55 (dd, J=8.11, 2.41 Hz, 1H) 8.19 (s, 1H) 7.62 (d, J=7.89 Hz, 1H) 7.43 (d, J=7.89 Hz, 1H) 7.31 (d, J=8.11 Hz, 1H) 5.70 (dd, J=5.92, 3.07 Hz, 1H) 3.36-3.14 (m, 3H) 3.02 (dd, J=11.95, 3.40 Hz, 1H) 2.65 (s, 3H) 2.56 (s, 3H) 2.42-2.32 (m, 1H) 2.18-2.01 (m, 1H).

Example 266

Synthesis of (4S)-7-(6-cyclopropyl-5-(trifluoromethyl)pyridin-3-yl)-N-(pyrazin-2-yl)-3,4-dihydro-1,4-methanopyrido[2,3-b][1,4]diazepine-5(2H)-carboxamide

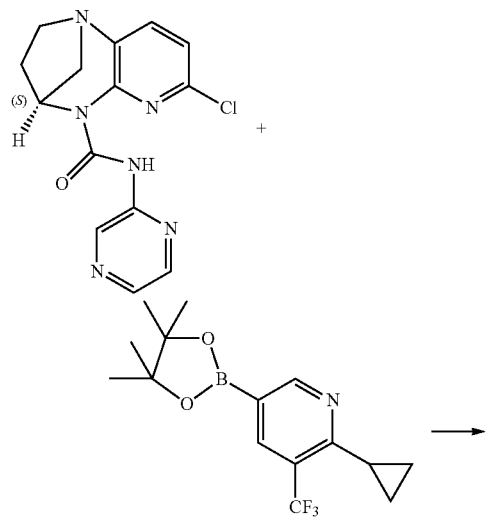

To a solution of (4S)-7-chloro-N-(pyrazin-2-yl)-3,4-dihydro-1,4-methanopyrido[2,3-b][1,4]diazepine-5(2H)-carboxamide (600 mg, 1.894 mmol), 2-cyclopropyl-5-(4,4,5,5-tetramethyl-1,3,2-dioxaborolan-2-yl)-3-(trifluoromethyl)pyridine (mg, mmol) and K$_3$PO$_4$ (804 mg, 3.79 mmol) in 1,4-dioxane (20 mL), water (3 mL) degassed with argon for 20 min was added X-Phos (90 mg, 0.189 mmol), tris(dibenzylideneacetone)dipalladium(0) (87 mg, 0.095 mmol) and again degassed with argon for 10 min. The reaction mixture was stirred at 100° C. for 16 h and cooled to room temperature. The reaction mixture was filtered through celite then the filtrate was diluted with water and extracted with EtOAc (3×15 mL). The combined organic layers was washed with water, brine solution, dried over sodium sulfate and evaporated to give crude compound (TLC eluent: 5% MeOH in DCM: $R_f$-0.2; UV active). The crude compound was purified by column chromatography using neutral alumina and eluted with 30% EtOAc/pet ether to afford pure (4S)-7-(6-cyclopropyl-5-(trifluoromethyl)pyridin-3-yl)-N-(pyrazin-2-yl)-3,4-dihydro-1,4-methanopyrido[2,3-b][1,4]diazepine-5(2H)-carboxamide (380 mg, 0.813 mmol, 42.85% yield) as off white solid, LCMS (m/z): 468.2 [M+H]$^+$.

$^1$H NMR (400 MHz, CDCl$_3$): δ ppm 13.66 (s, 1H) 9.51 (d, J=1.53 Hz, 1H) 9.08 (d, J=1.97 Hz, 1H) 8.58 (d, J=2.19 Hz, 1H) 8.31-8.24 (m, 2H) 7.64 (d, J=7.89 Hz, 1H) 7.38 (d, J=7.89 Hz, 1H) 5.71 (dd, J=5.92, 3.07 Hz, 1H) 3.34-3.14 (m, 3H) 3.03 (dd, J=12.06, 3.29 Hz, 1H) 2.47-2.30 (m, 2H) 2.15-2.04 (m, 1H) 1.33-1.28 (m, 2H) 1.16-1.10 (m, 2H).

Example 267

Synthesis of (4S)-7-(2-cyclopropylmorpholino)-N-(pyrazin-2-yl)-3, 4-dihydro-1,4-methanopyrido [2,3-b][1, 4] diazepine-5(2H)-carboxamide

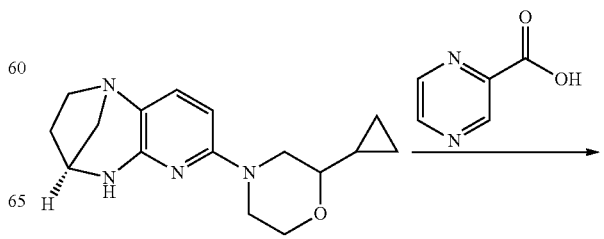

927                                                     928
-continued                                       -continued

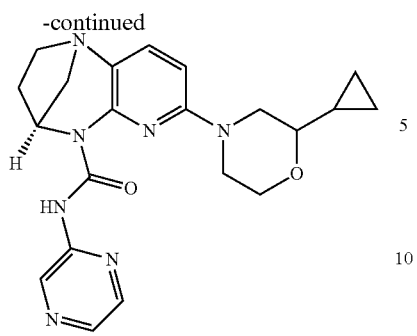

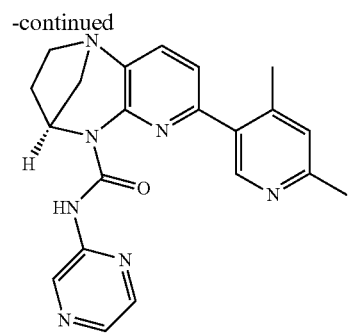

To a solution of Pyrazine-2-carboxylic acid (550 mg, 4.43 mmol) in THF (10 mL) under nitrogen at 0° C. diphenyl phosphorazidate (2439 mg, 8.86 mmol) and TEA were added (3.09 mL, 22.16 mmol) and stirred for 2 h at RT. To this reaction mixture 2-cyclopropyl-4-((4S)-2,3,4,5-tetrahydro-1,4-methanopyrido [2,3-b][1,4]diazepin-7-yl)morpholine (888 mg, 3.10 mmol) was added and stirred at 100° C. for 16 h. The reaction mixture was diluted with water and extracted with ethyl acetate (2×25 ml). The combined organic layer was washed with brine solution, dried over anhydrous sodium sulfate and concentrated under reduced pressure to afford crude compound. The crude product was purified by flash column chromatography (100-200 silica gel eluted with 2% of MeOH in $CH_2Cl_2$) to afford compound (4S)-7-(2-cyclopropylmorpholino)-N-(pyrazin-2-yl)-3, 4-dihydro-1, 4-methanopyrido [2, 3-b][1, 4] diazepine-5 (2H)-carboxamide (90 mg, 0.219 mmol, 4.95% yield) as a pale brown solid. (TLC system: 5% Methanol in DCM. $R_f$ value: 0.3), LCMS (m/z): 408.33 $[M+H]^+$.

$^1$H NMR (400 MHz, DMSO-$d_6$): δ ppm 13.32 (s, 1H), 9.37 (d, J=1.32 Hz, 1H), 8.43-8.13 (m, 2H), 7.41 (d, J=8.55 Hz, 1H), 6.56 (d, J=8.77 Hz, 1H), 5.56-5.28 (m, 1H), 4.13-3.73 (m, 3H), 3.55 (td, J=11.56, 2.52 Hz, 1H), 3.16-2.63 (m, 7H), 2.31-1.99 (m, 1H), 1.85 (dt, J=13.92, 6.85 Hz, 1H), 1.08-0.76 (m, 1H), 0.59-0.12 (m, 4H)

Example 268

Synthesis of (4S)-7-(4,6-dimethylpyridin-3-yl)-N-(pyrazin-2-yl)-3,4-dihydro-1,4-methanopyrido[2,3-b][1,4]diazepine-5(2H)-carboxamide $Cs_2CO_3$ (1237 mg, 3.797 mmol) and 2,4-dimethyl-5-(4,4,5,5-tetramethyl-1,3,2-dioxaborolan-2-yl)pyridine (590 mg, 2.531 mmol) were added to a solution of (4S)-7-chloro-N-(pyrazin-2-yl)-3,4-dihydro-1,4-methanopyrido[2,3-b][1,4]diazepine-5(2H)-carboxamide (400 mg, 1.265 mmol) in mixture of 1,4-Dioxane (9 mL) and water (1 mL). The reaction mixture was purged with argon for 30 min. $PdOAc_2$ (28.3 mg, 0.126 mmol) and X-Phos (120.6 mg, 0.253 mmol) were added to above reaction mixture, stirred at 100° C. for 16h. The reaction mixture was cooled to room temperature, concentrated in vacuo and the residue was partitioned between water (40 mL) and EtOAc (80 mL). Organic layer was separated and dried over anhydrous $Na_2SO_4$, filtered and filtrate was evaporated to get crude compound. The crude compound was purified by column chromatography using silica gel (100-200 mesh) 2% methanol in dichloromethane as a eluent to afford (4S)-7-(4,6-dimethylpyridin-3-yl)-N-(pyrazin-2-yl)-3,4-dihydro-1,4-methanopyrido[2,3-b][1,4]diazepine-5(2H)-carboxamide (135 mg, 0.332 mmol, 52.5% yield) as an off white solid. (TLC eluent: 10% MeOH in DCM $R_f$: 0.4; UV active), LCMS (m/z): 388.28 $[M+H]^+$.

$^1$H NMR (400 MHz, CDCl$_3$): δ ppm 13.37 (s, 1H), 9.45 (d, J=1.32 Hz, 1H), 8.54 (s, 1H), 8.22 (d, J=2.63 Hz, 1H), 8.16-8.20 (m, 1H), 7.62 (d, J=7.67 Hz, 1H), 7.12 (s, 1H), 7.07 (d, J=7.89 Hz, 1H), 5.71 (dd, J=5.81, 2.96 Hz, 1H), 3.15-3.36 (m, 3H), 3.03 (dd, J=12.17, 3.40 Hz, 1H), 2.59 (s, 3H), 2.46 (s, 3H), 2.28-2.38 (m, 1H), 2.04-2.17 (m, 1H).

Example 269

Synthesis of (4S)—N-(3,3-difluorocyclobutyl)-7-(6-methylpyridin-3-yl)-3,4-dihydro-1,4-methanopyrido[2,3-b][1,4]diazepine-5(2H)-carboxamide

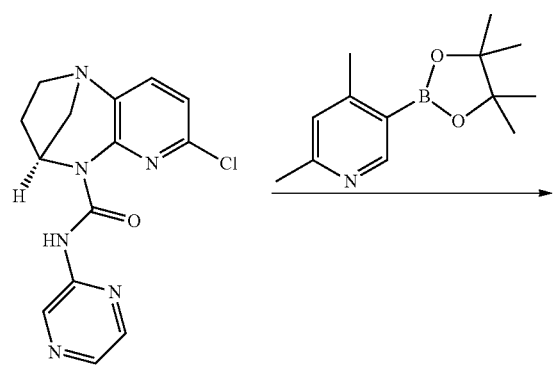

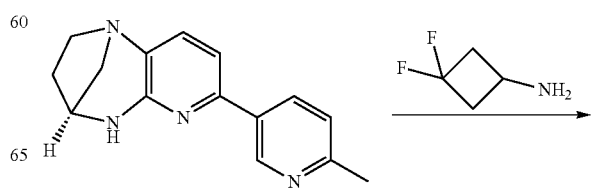

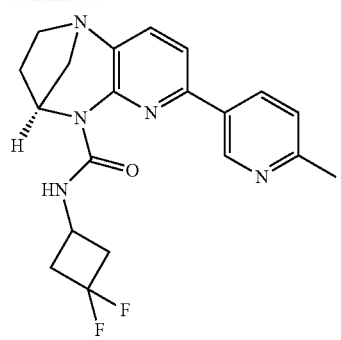

Triphosgene (212 mg, 0.714 mmol) was added slowly in portions to a stirred solution of (4S)-7-(6-methylpyridin-3-yl)-2,3,4,5-tetrahydro-1,4-methanopyrido[2,3-b][1,4]diazepine (300 mg, 1.190 mmol) in Tetrahydrofuran (THF) (15 mL) at RT. This reaction mixture was stirred for 30 min. DIPEA (0.623 mL, 3.57 mmol) and 3,3-difluorocyclobutanamine (191 mg, 1.785 mmol) were added to above reaction mixture, stirred at 80° C. for 16 h. The reaction mixture was cooled to room temperature, concentrated in vacuo and the residue was partitioned between water (40 mL) and EtOAc (80 mL). Organic layer was separated and dried over anhydrous $Na_2SO_4$, filtered and filtrate was evaporated to get crude compound. The crude compound was purified by column chromatography using silica gel (100-200 mesh) 2% methanol in dichloromethane as a eluent to afford (4S)—N-(3,3-difluorocyclobutyl)-7-(6-methylpyridin-3-yl)-3,4-dihydro-1,4-methanopyrido[2,3-b][1,4]diazepine-5(2H)-carboxamide (113 mg, 0.283 mmol, 28.5% yield) as an off white solid. (TLC eluent: 10% MeOH in DCM $R_f$: 0.4; UV active), LCMS (m/z): 386.27 [M+H]$^+$.

$^1$H NMR (400 MHz, CDCl$_3$): δ ppm 10.93 (br d, J=5.92 Hz, 1H), 8.88 (d, J=2.19 Hz, 1H), 7.94 (dd, J=8.11, 2.41 Hz, 1H), 7.56 (d, J=7.67 Hz, 1H), 7.31-7.22 (m, 2H), 5.59 (dd, J=5.92, 3.29 Hz, 1H), 4.29 (br s, 1H), 3.00-3.29 (m, 5H), 2.95 (dd, J=11.95, 3.40 Hz, 1H), 2.66-2.50 (m, 5H), 2.31-2.21 (m, 1H), 2.06-1.98 (m, 1H)

Example 270

Synthesis of (4S)-7-(1-methyl-6-oxo-1,6-dihydropyridin-3-yl)-N-(pyrazin-2-yl)-3,4-dihydro-1,4-methanopyrido[2,3-b][1,4]diazepine-5(2H)-carboxamide

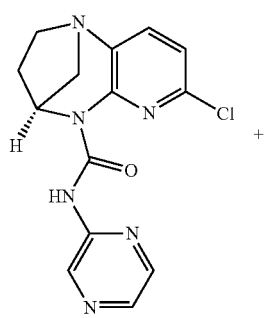

+

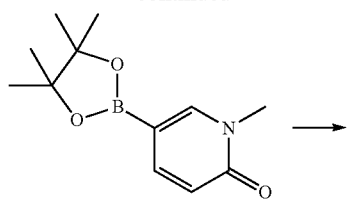

→

Tripotassium phosphate (804 mg, 3.79 mmol) was added to a stirred solution of (4S)-7-chloro-N-(pyrazin-2-yl)-3,4-dihydro-1,4-methanopyrido[2,3-b][1,4]diazepine-5(2H)-carboxa-mide (500 mg, 1.579 mmol), and 1-methyl-5-(4,4,5,5-tetramethyl-1,3,2-dioxaborolan-2-yl)pyridin-2(1H)-one (445 mg, 1.894 mmol) in 1,4-dioxane (10 mL), and water (2.000 mL) at 28° C. The reaction mixture was degassed for 10 min then was added Pd$_2$(dba)$_3$ (72.3 mg, 0.079 mmol), and X-phos (75 mg, 0.158 mmol). The reaction mixture was further degassed for 15 min. The reaction mixture was stirred for 1 hour in microwave at 100° C. The reaction mixture was cooled to 28° C. and was partitioned between water (10 mL) and ethyl acetate (2×15 mL). Ethyl acetate layer was separated and was dried over anhydrous Na$_2$SO$_4$, filtered and filtrate was evaporated to afford crude brown solid (TLC eluent: 10% MeOH in EtOAc: $R_f$-0.2; UV active). The crude was purified by column chromatography using (100-200 mesh) silica gel and was eluted with 2% MeOH in EtOAc to afford (4S)-7-(1-methyl-6-oxo-1,6-dihydropyridin-3-yl)-N-(pyrazin-2-yl)-3,4-dihydro-1,4-methanopy-rido[2,3-b][1,4]diazepine-5(2H)-carboxamide (330 mg, 0.840 mmol, 53.2% yield) as off-white solid, LCMS (m/z): 390.26 [M+H]$^+$.

$^1$H NMR (400 MHz, CDCl$_3$): δ ppm 13.78 (s, 1H), 9.61 (d, J=1.53 Hz, 1H), 8.57 (d, J=2.63 Hz, 1H), 8.33 (d, J=2.63 Hz, 1H), 8.22 (dd, J=2.52, 1.64 Hz, 1H), 7.88 (dd, J=9.54, 2.74 Hz, 1H), 7.57 (d, J=7.89 Hz, 1H), 7.18 (d, J=8.11 Hz, 1H), 6.69 (d, J=9.43 Hz, 1H), 5.69 (dd, J=5.92, 3.07 Hz, 1H), 3.78 (s, 3H), 3.12-3.30 (m, 3H), 3.01 (dd, J=12.06, 3.29 Hz, 1H), 2.28-2.41 (m, 1H), 2.00-2.13 (m, 1H)

Example 271

Synthesis of (4S)-7-(1-methyl-6-oxo-1,6-dihydropyridin-3-yl)-N-(pyridin-3-yl)-3,4-dihydro-1,4-methanopyrido[2,3-b][1,4]diazepine-5(2H)-carboxamide

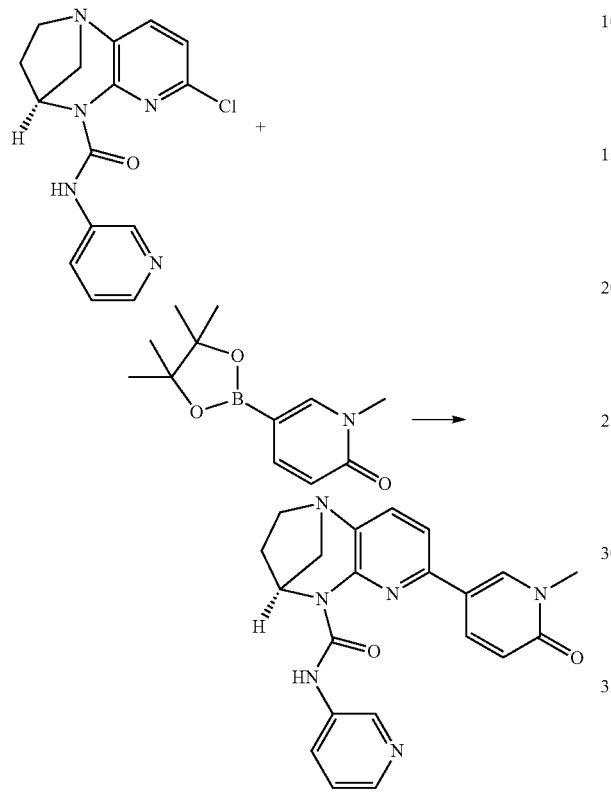

Tripotassium phosphate (672 mg, 3.17 mmol) was added to a stirred solution of (4S)-7-chloro-N-(pyridin-3-yl)-3,4-dihydro-1,4-methanopyrido[2,3-b][1,4]diazepine-5(2H)-carboxa-mide (500 mg, 1.583 mmol), and 1-methyl-5-(4,4,5,5-tetramethyl-1,3,2-dioxaborolan-2-yl)pyridin-2(1H)-one (447 mg, 1.900 mmol) in 1,4-dioxane (10 mL), and water (2.000 mL) at 28° C. The reaction mixture was degassed for 10 min then was added Pd$_2$(dba)$_3$ (72.5 mg, 0.079 mmol), and X-phos (75 mg, 0.158 mmol). The reaction mixture was further degassed for 15 min. The reaction mixture was stirred for 1 hr in Microwave at 100° C. The reaction mixture was cooled to 28° C. and was partitioned between water (10 mL) and EtOAc (25 mL). EtOAc layer was separated and was dried over anhydrous Na$_2$SO$_4$, filtered and filtrate was evaporated to afford crude as brown solid (TLC eluent: 10% MeOH in EtOAc: R$_f$-0.2; UV active). The crude was purified by column chromatography using silica gel (100-200 mesh), and the product was eluting with 2% MeOH in Ethyl acetate to afford (4S)-7-(1-methyl-6-oxo-1,6-dihydropyridin-3-yl)-N-(pyridin-3-yl)-3,4-dihydro-1,4-methanopyrido[2,3-b][1, 4]diazepine-5(2H)-carboxamide (272 mg, 0.679 mmol, 42.9% yield) as off white solid, LCMS (m/z): 389.27 [M+H]$^+$.

$^1$H NMR (400 MHz, CDCl$_3$): δ ppm 12.93 (s, 1H), 8.61 (d, J=2.41 Hz, 1H), 8.33 (dd, J=4.71, 1.43 Hz, 1H), 8.05-8.20 (m, 1H), 7.74-7.87 (m, 2H), 7.57 (d, J=7.89 Hz, 1H), 7.22-7.33 (m, 1H), 7.09 (d, J=7.89 Hz, 1H), 6.65-6.82 (m, 1H), 5.67 (dd, J=5.81, 3.18 Hz, 1H), 3.64 (s, 3H), 3.08-3.28 (m, 3H), 3.00 (dd, J=12.06, 3.29 Hz, 1H), 2.33 (qd, J=9.98, 4.49 Hz, 1H), 2.00-2.12 (m, 1H).

Example 272

Synthesis of (4S)—N-(1-methyl-1H-1,2,3-triazol-4-yl)-7-(2-methylpyridin-4-yl)-3,4-dihydro-1,4-methanopyrido[2,3-b][1,4]diazepine-5(2H)-carboxamide

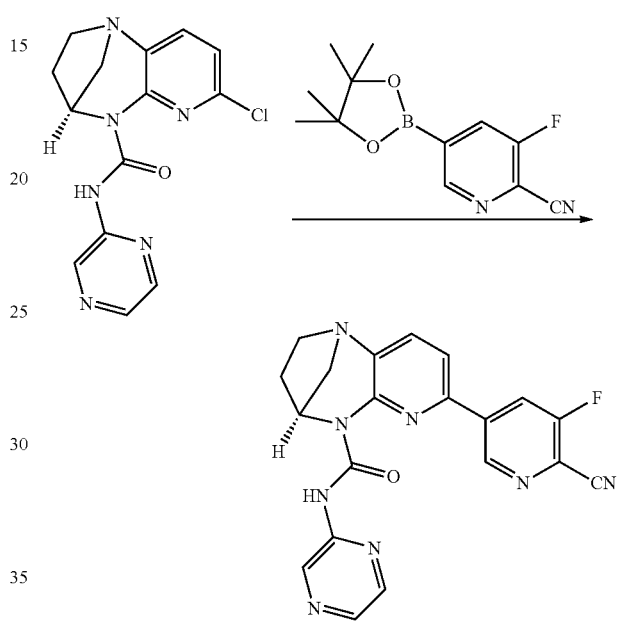

Pd$_2$(dba)$_3$ (0.043 g, 0.047 mmol) and X-phos (0.036 g, 0.095 mmol) was added to degassed solution of (4S)-7-chloro-N-(pyrazin-2-yl)-3,4-dihydro-1,4-methanopyrido[2,3-b][1,4]diazepine-5(2H)-carboxamide (0.3 g, 0.947 mmol), 3-fluoro-5-(4,4,5,5-tetramethyl-1,3,2-dioxaborolan-2-yl)picolinonitrile (0.352 g, 1.421 mmol) and potassium dihydrogen phosphate (0.258 g, 1.894 mmol) in 1,4-dioxane (5 mL):water (1 mL) and heated to 90° C. for 15 hours. Cooled to room temperature and filtered through pad of celite. The filtrate was diluted with water (25 mL) and ethyl acetate (50 mL). The separated organic layer was dried over anhydrous sodium sulfate, filtered and evaporated to get crude (TLC eluent: 10% MeOH in ethyl acetate; UV active; R$_f$: 0.25). Crude compound was purified by column chromatography using neutral alumina and eluted in 75% ethyl acetate in hexane to afford (4S)-7-(6-cyano-5-fluoropyridin-3-yl)-N-(pyrazin-2-yl)-3,4-dihydro-1,4-methanopyrido[2,3-b][1,–4]diazepine-5(2H)-carboxamide (0.105 g, 0.251 mmol, 26.5% yield) as off-white solid, LCMS (m/z): 403.18 [M+H]$^+$.

$^1$H NMR (400 MHz, CDCl$_3$): δ 13.57 (s, 1H), 9.53 (d, J=1.53 Hz, 1H), 9.11 (t, J=1.43 Hz, 1H), 8.69 (dd, J=9.87, 1.75 Hz, 1H), 8.27-8.40 (m, 2H), 7.71 (d, J=8.11 Hz, 1H), 7.54 (d, J=8.11 Hz, 1H), 5.71 (dd, J=5.81, 3.18 Hz, 1H), 3.01-3.37 (m, 4H), 2.32-2.45 (m, 1H), 2.01-2.21 (m, 1H).

Example 273

Synthesis of (4S)-7-(6-cyanopyridin-3-yl)-N-(pyridin-3-yl)-3,4-dihydro-1,4-methano-pyrido[2,3-b][1,4]diazepine-5(2H)-carboxamide

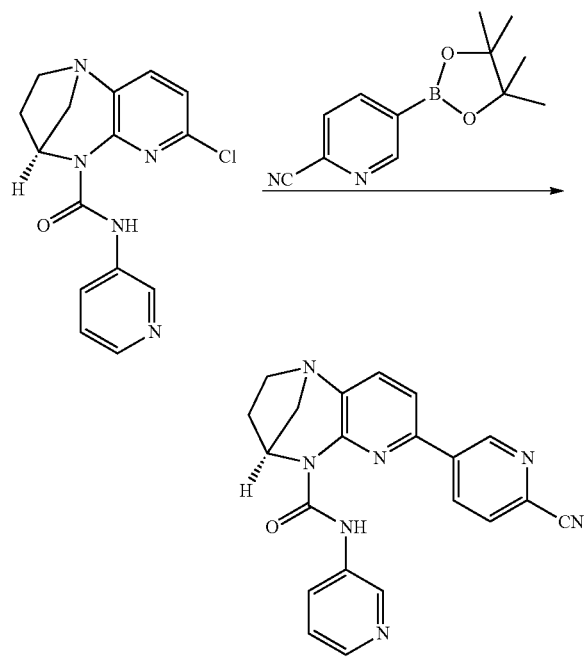

To a solution of (4S)-7-chloro-N-(pyridin-3-yl)-3,4-dihydro-1,4-methanopyrido[2,3-b][1,4]diazepine-5(2H)-carboxamide (600 mg, 1.900 mmol), 5-(4,4,5,5-tetramethyl-1,3,2-dioxaborolan-2-yl)picolinonitrile (525 mg, 2.280 mmol) and $K_3PO_4$ (807 mg, 3.80 mmol) in 1,4-dioxane (20 mL), water (3 mL) degassed with argon for 20 min was added X-phos (91 mg, 0.190 mmol), tris(dibenzylideneacetone)dipalladium(0) (87 mg, 0.095 mmol) again degassed with argon for 10 min. The reaction mixture was stirred at 100° C. for 16 hours and cooled to room temperature. The reaction mixture was filtered through celite then the filtrate was diluted with water and extracted with EtOAc (3×20 mL). The combined organic layers were washed with water, brine solution, dried over sodium sulfate and evaporated to give crude compound (TLC eluent: 5% MeOH in DCM: $R_f$-0.3; UV active). The crude compound was purified by column chromatography using neutral alumina and eluted with 30-40% EtOAc/hexane to afford pure (4S)-7-(6-cyanopyridin-3-yl)-N-(pyridin-3-yl)-3,4-dihydro-1,4-methano-pyrido[2,3-b][1,4]diazepine-5(2H)-carboxamide (399 mg, 1.033 mmol, 54.4% yield) as off white solid, LCMS (m/z): 384.3 [M+H]$^+$.

$^1$H NMR (400 MHz, CDCl$_3$): δ 12.71 (s, 1H), 9.17 (dd, J=2.2, 0.7 Hz, 1H), 8.54 (d, J=2.4 Hz, 1H), 8.33 (dd, J=4.7, 1.4 Hz, 1H), 8.23 (dd, J=8.0, 2.3 Hz, 1H), 8.07-8.12 (m, 1H), 7.87 (d, J=8.1 Hz, 1H), 7.69 (d, J=8.1 Hz, 1H), 7.38 (d, J=7.9 Hz, 1H), 7.26-7.31 (m, 1H), 5.71 (dd, J=5.9, 2.8 Hz, 1H), 3.12-3.34 (m, 3H), 3.01-3.09 (m, 1H), 2.36 (m, 1H), 2.1 (m, 1H).

Example 274 e-LNB No: N33789-17-A2, GSK3400265A

Synthesis of (4S)-7-((S)-3-methylmorpholino)-N-(pyridin-3-yl)-3,4-dihydro-1,4-methanopyrido[2,3-b][1,4]diazepine-5(2H)-carboxamide

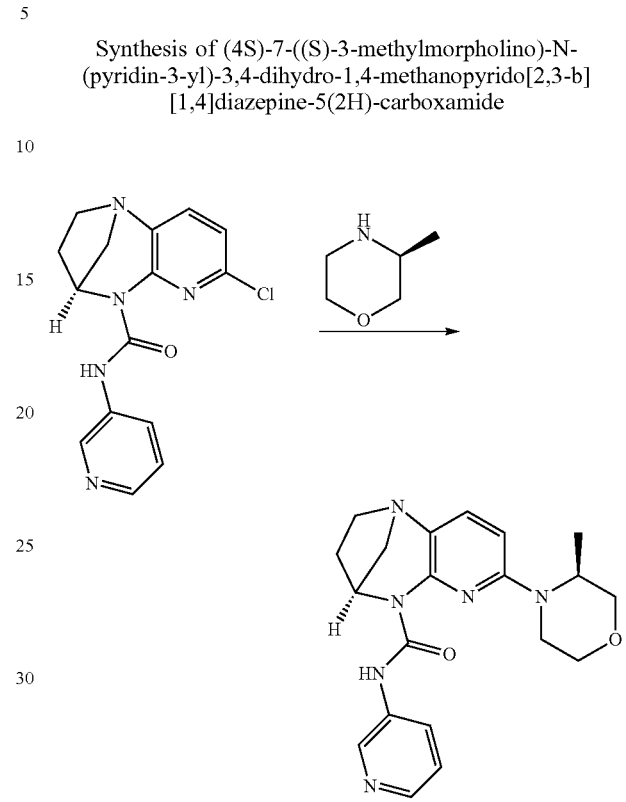

$Cs_2CO_3$ (3.10 g, 9.50 mmol), (S)-3-methylmorpholine (0.641 g, 6.33 mmol) were added to a solution of (4S)-7-chloro-N-(pyridin-3-yl)-3,4-dihydro-1,4-methanopyrido[2,3-b][1,4]diazepine-5(2H)-carboxamide (1.0 g, 3.17 mmol) in 1,4-Dioxane (10 mL) in a sealed tube while purging with argon for 25 min. Subsequently PdOAc$_2$ (0.142 g, 0.633 mmol) and X-phos (0.604 g, 1.267 mmol) were added to the reaction mixture and stirred at 100° C. for 4h. The reaction was cooled to RT, solvent removed under reduced pressure, residue was partitioned between water (40 mL) and EtOAc (80 mL). Organic layer was separated and dried over anhydrous Na$_2$SO$_4$, filtered and filtrate was evaporated to yield crude compound. It was purified by column chromatography using silica gel (100-200 mesh) 2% methanol in dichloromethane as an eluent to afford (4S)-7-((S)-3-methylmorpholino)-N-(pyridin-3-yl)-3,4-dihydro-1,4-methanopyrido[2,3-b][1,4]diazepine-5(2H)-carboxamide (140 mg, 0.366 mmol, 11.56% yield) as an off white solid. (TLC eluent: 10% MeOH in DCM, $R_f$: 0.4; UV active), LCMS (m/z): 381.30 [M+H]$^+$.

$^1$H NMR (400 MHz, CDCl$_3$): δ ppm 12.42 (s, 1H), 8.50 (d, J=2.41 Hz, 1H), 8.31 (d, J=4.60 Hz, 1H), 8.16 (br d, J=8.55 Hz, 1H), 7.39 (d, J=8.55 Hz, 1H), 7.31-7.26 (m, 1H), 6.24 (d, J=8.55 Hz, 1H), 5.60 (dd, J=5.92, 3.29 Hz, 1H), 4.06 (brdd, J=11.18, 3.51 Hz, 2H), 3.85-3.79 (m, 2H), 3.69-3.51 (m, 2H), 3.37-3.04 (m, 4H), 2.91 (dd, J=11.84, 3.29 Hz, 1H), 2.31-2.18 (m, 1H), 2.07-1.97 (m, 1H), 1.27 (d, J=6.80 Hz, 3H)

Example 275

Synthesis of (4S)—N-(4-methylpyridin-2-yl)-7-(2-methylpyridin-4-yl)-3,4-dihydro-1,4-methanopyrido[2,3-b][1,4]diazepine-5(2H)-carboxamide

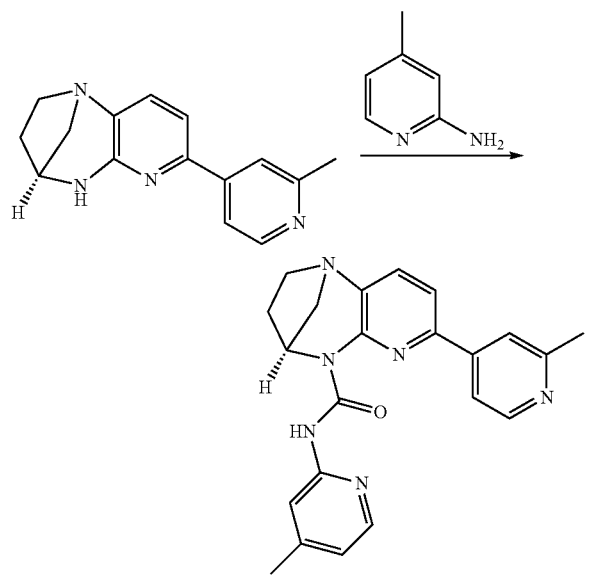

To a stirred solution of (4S)-7-(2-methylpyridin-4-yl)-2,3,4,5-tetrahydro-1,4-methanopyrido[2,3-b][1,4]diazepine (400 mg, 1.585 mmol) in THF (15 mL, in sealed tube) was added triphosgene (282 mg, 0.951 mmol) at RT, and stirred for 30 min, then triethylamine (1.105 mL, 7.93 mmol) and 4-methylpyridin-2-amine (257 mg, 2.378 mmol) were added and heated at 65° C. for 15 h. The reaction mixture was cooled to room temperature. THF was distilled off and was partitioned between water (25 mL) and EtOAc (40 mL). The organic layer was separated and dried over anhydrous $Na_2SO_4$, filtered and filtrate was evaporated to obtain the crude compound. The crude compound was purified by flash column chromatography (silica gel: 100-200 mesh, eluent: 2% methanol in DCM) to obtain 600 mg with 60% LCMS purity. The crude compound was purified by Prep HPLC (Conditions: MP-A: 10 mM Ammonium Bicarbonate (Aq) MP-B: Acetonitrile Column: X-Bridge (250×30) mm 10μ Method: 0/30, 10/50, 10.1/30, 15/30 Flow: 30 ml/min Solubility: THF+ACN+MeOH) to afford (4S)—N-(4-methylpyridin-2-yl)-7-(2-methylpyridin-4-yl)-3,4-dihydro-1,4-methano pyrido[2,3-b][1,4]diazepine-5(2H)-carboxamide (210 mg, 0.541 mmol, 34.1% yield) as an off-white solid (TLC eluent: 10% MeOH in EtOAc, $R_f$: 0.4), LCMS (m/z): 387.27 [M+H]$^+$.

$^1$H NMR (400 MHz, $CDCl_3$): δ ppm: 13.48 (s, 1H), 8.61 (d, J=5.26 Hz, 1H), 8.25-8.17 (m, 2H), 8.07 (s, 1H), 7.71 (d, J=3.95 Hz, 1H), 7.61 (d, J=7.89 Hz, 1H), 7.48 (d, J=8.11 Hz, 1H), 6.85 (d, J=4.82 Hz, 1H), 5.70 (dd, J=5.70, 3.51 Hz, 1H), 3.33-3.14 (m, 3H), 3.14-2.89 (m, 1H), 2.74 (s, 3H), 2.41-2.32 (m, 4H), 2.13-2.00 (m, 1H).

Example 276

Synthesis of (4S)—N-(6-isopropylpyrazin-2-yl)-7-(2-methylpyridin-4-yl)-3,4-dihydro-1,4-methanopyrido[2,3-b][1,4]diazepine-5(2H)-carboxamide

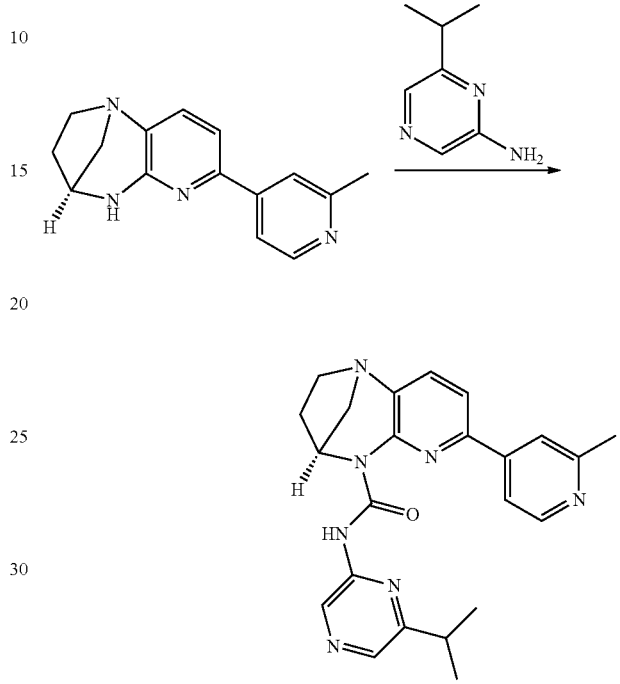

To a stirred solution of 6-isopropylpyrazin-2-amine (141 mg, 1.030 mmol) in THF (5 mL) triethylamine (0.663 mL, 4.76 mmol) and triphosgene (235 mg, 0.793 mmol) were added at RT and stirred for 30 min. Then (4S)-7-(2-methylpyridin-4-yl)-2,3,4,5-tetrahydro-1,4-methanopyrido[2,3-b][1,4]diazepine (200 mg, 0.793 mmol) was added and heated at 80° C. for 16 h. The reaction mixture was cooled to room temperature and was partitioned between water (25 mL) and EtOAc (40 mL). The organic layer was separated and dried over anhydrous $Na_2SO_4$, filtered and filtrate was evaporated to obtain crude compound. The crude mixture was purified by flash column chromatography (silica gel: 100-200 mesh, eluent: 2% methanol in DCM) to obtain the (4S)—N-(6-isopropylpyrazin-2-yl)-7-(2-methylpyridin-4-yl)-3,4-dihydro-1,4-methanopyrido[2,3-b][1,4]diazepine-5(2H)-carboxamide (60 mg, 0.144 mmol, 18.15% yield) as an off white solid (TLC: Eluent: 5% methanol in DCM, $R_f$: 0.4), LCMS (m/z): 416.3 [M+H]$^+$.

$^1$H NMR (400 MHz, $CDCl_3$): δ ppm 13.34 (s, 1H), 9.37 (s, 1H), 8.70 (d, J=5.26 Hz, 1H), 8.21 (s, 1H), 8.00 (br d, J=3.73 Hz, 1H), 7.60-7.69 (m, 2H), 7.47 (d, J=8.11 Hz, 1H), 5.73 (dd, J=5.81, 3.18 Hz, 1H), 3.14-3.37 (m, 3H), 2.98-3.09 (m, 2H), 2.66 (s, 3H), 2.27-2.46 (m, 1H), 2.09 (dt, J=14.03, 7.23 Hz, 1H), 1.33 (dd, J=7.02, 1.10 Hz, 6H).

Example 277

Synthesis of (4S)—N-(pyridin-2-yl)-7-(3-(trifluoromethyl)pyrrolidin-1-yl)-3,4-dihydro-1,4-methanopyrido[2,3-b][1,4]diazepine-5(2H)-carboxamide

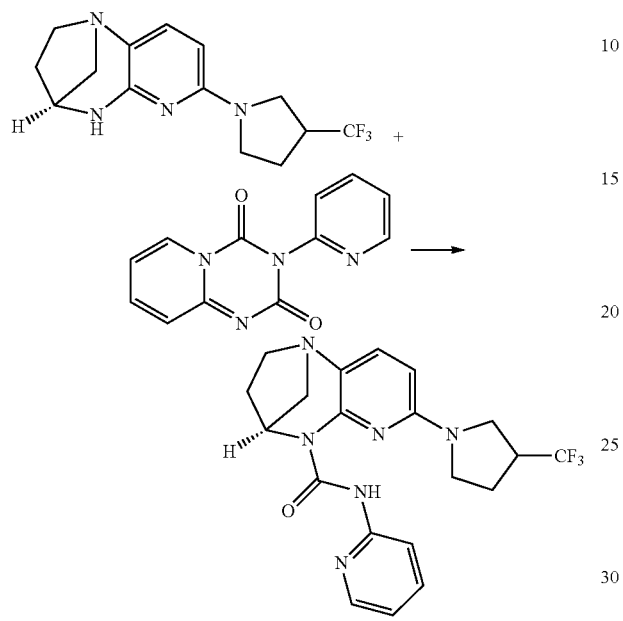

To a solution of (4S)-7-(3-(trifluoromethyl)pyrrolidin-1-yl)-2,3,4,5-tetrahydro-1,4-methanopyrido[2,3-b][1,4]diazepine (Peak 1 from intermediate SFC separation) (440 mg, 1.475 mmol) in tetrahydrofuran (THF) (10 mL) was added NaH (295 mg, 7.37 mmol) at 0° C. After 30 min 3-(pyridin-2-yl)-2H-pyrido[1,2-a][1,3,5]triazine-2,4(3H)-dione (531 mg, 2.212 mmol) was added and the reaction mixture was stirred at 70° C. for 16 h. The reaction mixture was poured on cold water (50 mL) and extracted with ethyl acetate (2×30 mL). The organic layer was dried over anhydrous sodium sulfate and concentrated under reduced pressure to yield crude product. The crude product was purified by flash column chromatography (silica-gel: 100-200 mesh, eluent: 90% Hex/EtOAc) to obtained (4S)—N-(pyridin-2-yl)-7-(3-(trifluoromethyl)pyrrolidin-1-yl)-3,4-dihydro-1,4-methanopyrido[2,3-b][1,4]diazepine-5(2H)-carboxamide (266.8 mg, 0.631 mmol, 42.8% yield) as an off white solid. (TLC system: $R_f$: 04, :EtOAc), LCMS (m/z): 419.2 [M+H]$^+$.

$^1$H NMR (400 MHz, CDCl$_3$): δ ppm 13.33 (s, 1H), 8.19 (d, J=3.73 Hz, 1H), 8.15 (d, J=8.33 Hz, 1H), 7.66-7.60 (m, 1H), 7.32 (d, J=8.55 Hz, 1H), 6.91 (dd, J=6.58, 5.04 Hz, 1H), 5.96 (d, J=8.33 Hz, 1H), 5.58 (dd, J=6.03, 3.18 Hz, 1H), 4.01-3.95 (m, 1H), 3.86 (dd, J=11.29, 7.34 Hz, 1H), 3.66 (td, J=8.99, 4.60 Hz, 1H), 3.60-3.53 (m, 1H), 3.23-3.05 (m, 4H), 2.89 (dd, J=11.84, 3.51 Hz, 1H), 2.37-2.18 (m, 3H), 1.98 (dt, J=13.81, 6.91 Hz, 1H).

Example 278

Synthesis of (4S)-7-(1-methyl-3-(trifluoromethyl)-1H-pyrazol-5-yl)-N-(pyrazin-2-yl)-3,4-dihydro-1,4-methanopyrido[2,3-b][1,4]diazepine-5(2H)-carboxamide

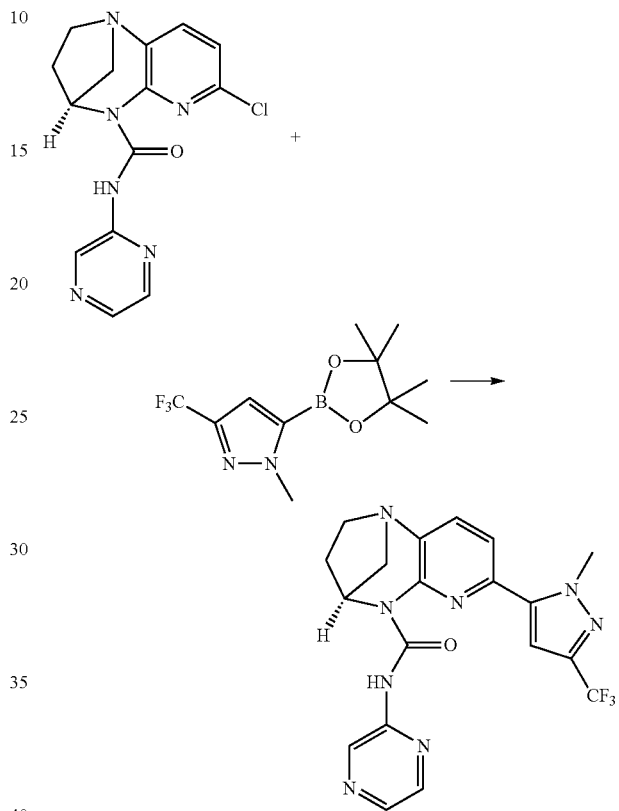

A suspension of (4S)-7-chloro-N-(pyrazin-2-yl)-3,4-dihydro-1,4-methanopyrido[2,3-b][1,4]diazepine-5(2H)-carboxamide (0.400 g, 1.263 mmol), 1-methyl-5-(4,4,5,5-tetramethyl-1,3,2-dioxaborolan-2-yl)-3-(trifluoromethyl)-1H-pyrazole (0.697 g, 2.53 mmol) and potassium phosphate tribasic (0.803 g, 3.79 mmol) in 1,4-dioxane (25 mL) and water (4 mL) was degassed with argon at room temp for 15 mins, then added X-phos (0.0601 g, 0.126 mmol) and Pd(dba)$_2$ (0.046 g, 0.051 mmol). The reaction mixture was further degassed for 15 min and was stirred 16 hours at 100° C. After completion of the reaction as indicated by TLC, the reaction mixture was cooled to 28° C. and was diluted with water (15 mL) and extracted with EtOAc (2×25 mL). The organic layer was washed with water followed by brine solution and dried over anhydrous sodium sulfate, filtered and filtrate was evaporated to get the crude (TLC eluent: 100% Ethyl Acetate in Hexane, $R_f$ value: 0.3, UV active). The crude was purified by column chromatography using neutral alumina, and the product was eluted 40% ethyl acetate in pet ether to afford (4S)-7-(1-methyl-3-(trifluoromethyl)-1H-pyrazol-5-yl)-N-(pyrazin-2-yl)-3,4-dihydro-1,4-methanopyrido[2,3-b][1,4]diazepine-5(2H)-carboxamide (0.208 g, 0.482 mmol, 38.2% yield) as a white solid, LCMS (m/z): 431.23 [M+H]$^+$.

$^1$H NMR (400 MHz, CDCl$_3$): δ 13.08 (s, 1H), 9.51 (d, J=1.5 Hz, 1H), 8.29 (d, J=2.6 Hz, 1H), 8.25-8.22 (m, 1H), 7.65 (d, J=7.9 Hz, 1H), 7.21 (d, J=7.9 Hz, 1H), 7.05 (s, 1H), 5.71 (dd, J=5.8, 3.2 Hz, 1H), 4.24 (s, 3H), 3.33-3.15 (m, 3H), 3.04 (dd, J=12.2, 3.2 Hz, 1H), 2.42-2.30 (m, 1H), 2.10 (dt, J=14.1, 6.9 Hz, 1H).

Example 279

Synthesis of (4S)-7-cyano-N-(pyrazin-2-yl)-3,4-dihydro-1,4-methanopyrido[2,3-b][1,4]diazepine-5(2H)-carboxamide

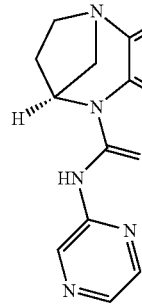

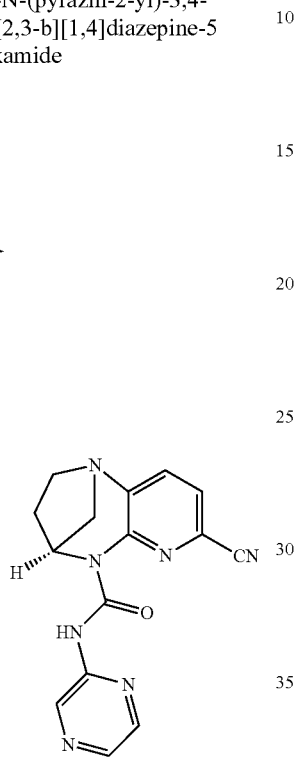

X-phos (0.018 g, 0.047 mmol) and (1,3-Bis(2,6-di-isopropylphenyl)-4,5-dihydroimidazol-2-ylidene)chloro)(3-phenylallyl)palladium(2) (0.031 g, 0.047 mmol) were added to a degassed solution of (4S)-7-chloro-N-(pyrazin-2-yl)-3,4-dihydro-1,4-methanopyrido[2,3 b][1,4]diazepine-5(2H)-carboxamide (0.3 g, 0.947 mmol) and potassium ferro cyanide (0.174 g, 0.474 mmol) in 1,4-dioxane (5 mL): water (1 mL) and heated to 100° C. for 15h.

Cooled to room temperature and filtered through celite bed. The filtrate was diluted with water (25 mL) and ethyl acetate (100 mL). The separated organic layer was dried over anhydrous sodium sulfate, filtered and evaporated to obtain crude compound (TLC eluent: 100% ethyl acetate; UV active; $R_f$-0.3). The crude mixture was purified by column chromatography using neutral alumina and eluted in 50% ethyl acetate in hexane to afford (4S)-7-cyano-N-(pyrazin-2-yl)-3,4-dihydro-1,4-methanopyrido[2,3-b][1,4]diazepine-5(2H)-carboxamide (0.13 g, 0.415 mmol, 43.8% yield) as white solid, LCMS (m/z): 308.19 [M+H]$^+$.

$^1$H NMR (400 MHz, CDCl$_3$): δ ppm 12.48 (br s, 1H), 9.45 (s, 1H), 8.32 (s, 2H), 7.62 (d, J=7.89 Hz, 1H), 7.37 (d, J=7.89 Hz, 1H), 5.68 (dd, J=5.81, 3.18 Hz, 1H), 3.24 (t, J=7.56 Hz, 2H), 2.99-3.14 (m, 2H), 2.36 (td, J=14.09, 6.03 Hz, 1H), 2.01-2.16 (m, 1H).

Example 280

Synthesis of (4S)-7-(1-isopropyl-1H-pyrazol-4-yl)-N-(pyrazin-2-yl)-3,4-dihydro-1,4-methanopyrido[2,3-b][1,4]diazepine-5(2H)-carboxamide

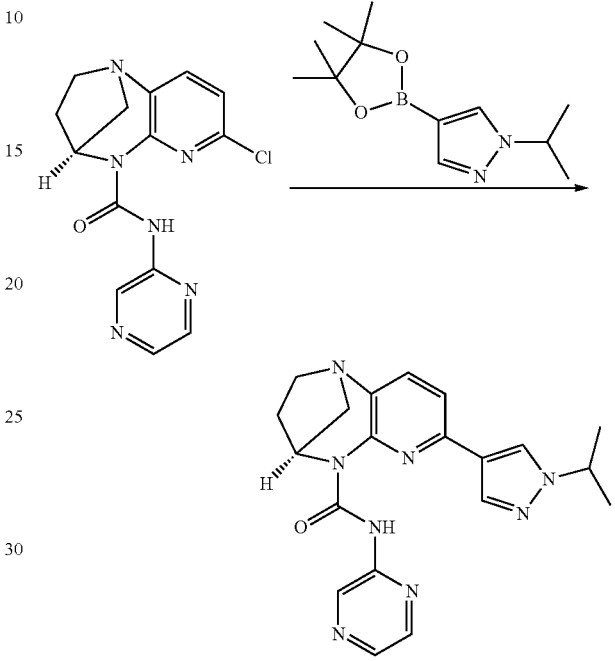

To a solution of (4S)-7-chloro-N-(pyrazin-2-yl)-3,4-dihydro-1,4-methanopyrido[2,3-b][1,4]diazepine-5(2H)-carboxamide (500 mg, 1.579 mmol), 1-isopropyl-4-(4,4,5,5-tetramethyl-1,3,2-dioxaborolan-2-yl)-1H-pyrazole (447 mg, 1.894 mmol) and K$_3$PO$_4$ (670 mg, 3.16 mmol) in 1,4-dioxane (15 mL), water (3 mL) degassed with argon for 20 min was added X-phos (75 mg, 0.158 mmol), tris(dibenzylideneacetone)dipalladium(0) (72.3 mg, 0.079 mmol) and again degassed with argon for 5 min. The reaction mixture was stirred at 100° C. for 16 hours and cooled to room temperature. The reaction mixture was filtered through celite then the filtrate was diluted with water and extracted with EtOAc (3×20 mL). The combined organic layers was washed with water, brine solution, dried over sodium sulfate and evaporated to give crude compound (TLC eluent: 5% MeOH in DCM: $R_f$-0.2; UV active). The crude compound was purified by column chromatography using neutral alumina and eluted with 30-40% EtOAc/hexane to afford pure (4S)-7-(1-isopropyl-1H-pyrazol-4-yl)-N-(pyrazin-2-yl)-3,4-dihydro-1,4-methanopyrido[2,3-b][1,4]diazepine-5 (2H)-carboxamide (418 mg, 1.070 mmol, 67.8% yield) as off white solid, LCMS (m/z): 391.2 [M+H]$^+$.

$^1$H NMR (400 MHz, CDCl$_3$): δ 14.14 (s, 1H), 9.62 (d, J=1.5 Hz, 1H), 8.64 (s, 1H), 8.26-8.32 (m, 2H), 8.02 (s, 1H), 7.50 (d, J=7.9 Hz, 1H), 7.16 (d, J=8.1 Hz, 1H), 5.67 (dd, J=5.8, 3.2 Hz, 1H), 4.61 (m, 1H), 3.12-3.31 (m, 3H), 2.99 (dd, J=11.9, 3.2 Hz, 1H), 2.32 (m, 1H), 2.06 (m, 1H), 1.63 (d, J=6.8 Hz, 6H).

Example 281

Synthesis of (4S)-7-(6-methylpyridin-3-yl)-N-(tetrahydrofuran-3-yl)-3,4-dihydro-1,4-methanopyrido[2,3-b][1,4]diazepine-5(2H)-carboxamide

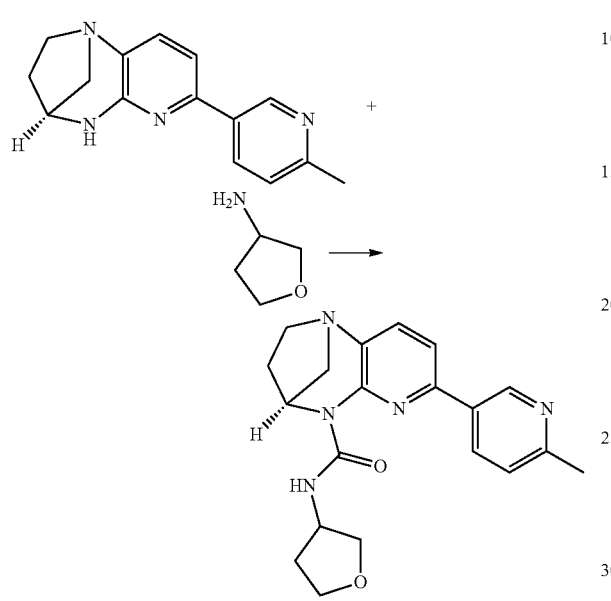

To a solution of (4S)-7-(6-methylpyridin-3-yl)-2,3,4,5-tetrahydro-1,4-methanopyrido[2,3-b][1,4]diazepine (300 mg, 1.189 mmol) in tetrahydrofuran (THF) (10 mL) triphosgene (176 mg, 0.594 mmol) was added at 0° C. After 30 min DIPEA (1.038 mL, 5.94 mmol), tetrahydrofuran-3-amine (155 mg, 1.783 mmol) was added and the reaction mixture was stirred at 70° C. for 16 h. The reaction was allowed to reach RT and then poured on cold water (50 mL) and extracted with ethyl acetate (2×30 mL). The organic layer was dried over anhydrous sodium sulfate, concentrated under reduced pressure to yield the crude product. The crude product was purified by flash column chromatography (silica-gel: 100-200 mesh, eluent: 3% MeOH in DCM) to obtained (4S)-7-(6-methylpyridin-3-yl)-N-(tetrahydrofuran-3-yl)-3,4-dihydro-1,4-methano pyrido[2,3-b][1,4]diazepine-5(2H)-carboxamide (137.1 mg, 0.371 mmol, 31.2% yield) as an off white solid. (TLC system: $R_f$: 0.2, 5% MeOH-DCM), LCMS (m/z): 366.2 [M+H]$^+$.

$^1$H NMR (400 MHz, CDCl$_3$): δ ppm 10.76 (br t, J=6.80 Hz, 1H), 8.89 (s, 1H), 7.99 (dd, J=8.22, 2.08 Hz, 1H), 7.54 (d, J=7.89 Hz, 1H), 7.30-7.21 (m, 2H), 5.62 (dd, J=5.81, 2.96 Hz, 1H), 4.56 (br dd, J=4.82, 1.97 Hz, 1H), 4.01-3.75 (m, 4H), 3.30-3.06 (m, 3H), 2.99-2.91 (m, 1H), 2.62 (s, 3H), 2.39-2.21 (m, 2H), 2.07-1.85 (m, 2H).

Example 282

Synthesis of (4S)-7-(5-fluoro-6-methylpyridin-3-yl)-N-(pyridin-3-yl)-3,4-dihydro-1,4-methanopyrido [2,3-b] [1, 4] diazepine-5(2H)-carboxamide

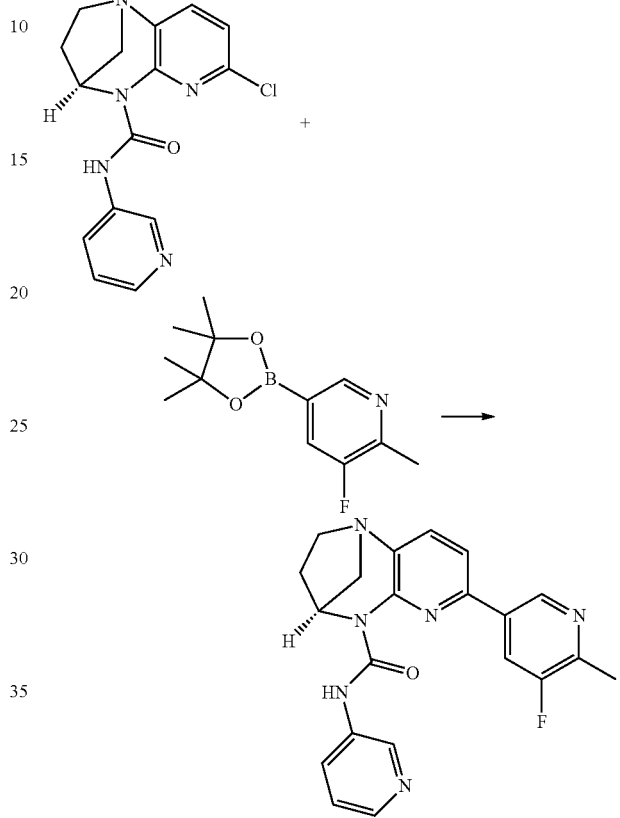

Tripotasium phosphate (323 mg, 1.520 mmol) was added to a solution of (4S)-7-chloro-N-(pyridin-3-yl)-3,4-dihydro-1,4-methanopyrido[2,3-b][1,4]diazepine-5(2H)-carboxamide (240.0 mg, 0.760 mmol) and 3-fluoro-2-methyl-5-(4,4,5,5-tetramethyl-1,3,2-dioxaborolan-2-yl)pyridine (234 mg, 0.988 mmol) in 1,4-dioxane (5.0 mL) and water (1.0 mL) at 25° C. The reaction mixture was degassed for 10 min. X-Phos (36.2 mg, 0.076 mmol) and Pd$_2$(dba)$_3$ (34.8 mg, 0.038 mmol) were added to reaction mixture and was further degassed for 10 min. The reaction was stirred for 1 hour at 100° C. in microwave. The reaction mixture was filtered through a pad of celite and was washed with the ethyl acetate. The filtrate was washed with the water and brine solution. The separated organic phase was dried over anhydrous sodium sulfate, filtered and evaporated to get crude (TLC eluent: 5% MeOH in DCM; UV active; $R_f$-0.3). The crude product was purified on grace column eluted with the 3-5% MeOH in DCM to afford pure (4S)-7-(5-fluoro-6-methylpyridin-3-yl)-N-(pyridin-3-yl)-3,4-dihydro-1,4-methanopyrido[2,3-b][1,4] diaze-pine-5 (2H)-carboxamide (122.0 mg, 0.312 mmol, 41.0% yield) as off white solid, LCMS (m/z): 391.30 [M+H]$^+$.

$^1$H NMR (400 MHz, CDCl$_3$): δ 12.91 (s, 1H), 8.77 (t, J=1.42 Hz, 1H), 8.62 (d, J=2.41 Hz, 1H), 8.32 (dd, J=4.71, 1.43 Hz, 1H), 8.12 (ddd, J=8.33, 2.63, 1.53 Hz, 1H), 7.73 (dd, J=9.87, 1.75 Hz, 1H), 7.64 (d, J=7.89 Hz, 1H), 7.27-

7.32 (m, 2H), 5.70 (dd, J=5.92, 3.29 Hz, 1H), 3.14-3.34 (m, 3H), 3.03 (dd, J=12.06, 3.29 Hz, 1H), 2.62 (d, J=3.07 Hz, 3H), 2.28-2.38 (m, 1H), 2.05-2.14 (m, 1H)

Example 283

Synthesis of (4S)-7-(5-fluoro-6-methylpyridin-3-yl)-N-(pyrazin-2-yl)-3, 4-dihydro-1,4-methanopyrido [2, 3-b] [1, 4] diazepine-5(2H)-carboxamide

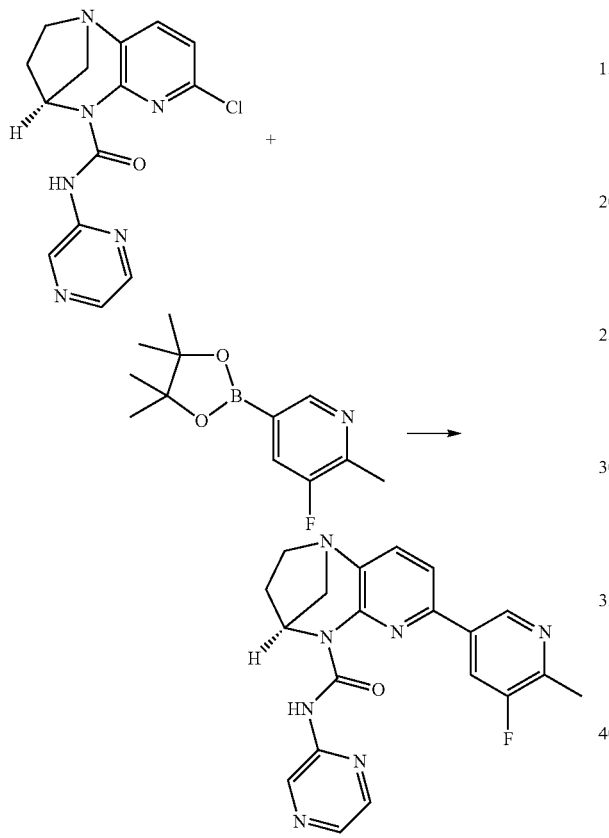

Tripotasium phosphate (402 mg, 1.894 mmol) was added to a solution of (4S)-7-chloro-N-(pyrazin-2-yl)-3,4-dihydro-1,4-methanopyrido[2,3-b][1,4]diazepine-5(2H)-carboxamide (300.0 mg, 0.947 mmol), 3-fluoro-2-methyl-5-(4,4,5,5-tetramethyl-1,3,2-dioxaborolan-2-yl)pyridine (292 mg, 1.231 mmol) in 1,4-dioxane (5.0 mL) and water (1.0 mL) at 25° C. The reaction mixture was degassed for 10 min. X-Phos (45.2 mg, 0.095 mmol) and Pd$_2$(dba)$_3$ (43.4 mg, 0.047 mmol) were added to reaction mixture and was further degassed for 10 min. The reaction was stirred for 1 hour at 100° C. in microwave. The reaction mixture was filtered through a pad of celite and was washed with the ethyl acetate. The filtrate was washed with the water and brine solution. The separated organic phase was dried over anhydrous sodium sulfate, filtered and evaporated to get crude (TLC eluent: 5% MeOH in DCM; UV active; R$_f$~0.3). The crude product was purified on grace column eluted with the 3-5% MeOH in dichloromethane to afford pure (4S)-7-(5-fluoro-6-methylpyridin-3-yl)-N-(pyrazin-2-yl)-3,4-dihydro-1,4-methanopyrido [2,3-b][1,4]diazepine-5(2H)-carboxamide (150.0 mg, 0.365 mmol, 38.5% yield) as off white solid, LCMS (m/z): 392.3 [M+H]$^+$.

$^1$H NMR (400 MHz, CDCl$_3$): δ 13.79 (s, 1H), 9.53 (d, J=1.5 Hz, 1H), 8.88 (t, J=1.5 Hz, 1H), 8.38 (dd, J=10.7, 1.97 Hz, 1H), 8.30-8.34 (m, 2H), 7.64 (d, J=7.9 Hz, 1H), 7.44 (d, J=8.1 Hz, 1H), 5.70 (dd, J=6.03, 3.2 Hz, 1H), 3.1-3.3 (m, 3H), 3.03 (dd, J=12.1, 3.3 Hz, 1H), 2.62 (s, 3H), 2.36 (dddd, J=14.1, 9. 9, 5.9, 4.1 Hz, 1H), 2.04-2.15 (m, 1H)

Example 284

Synthesis of (4S)-7-(1-cyclopropyl-1H-pyrazol-4-yl)-N-(pyrazin-2-yl)-3,4-dihydro-1,4-methanopyrido [2,3-b][1,4]diazepine-5(2H)-carboxamide

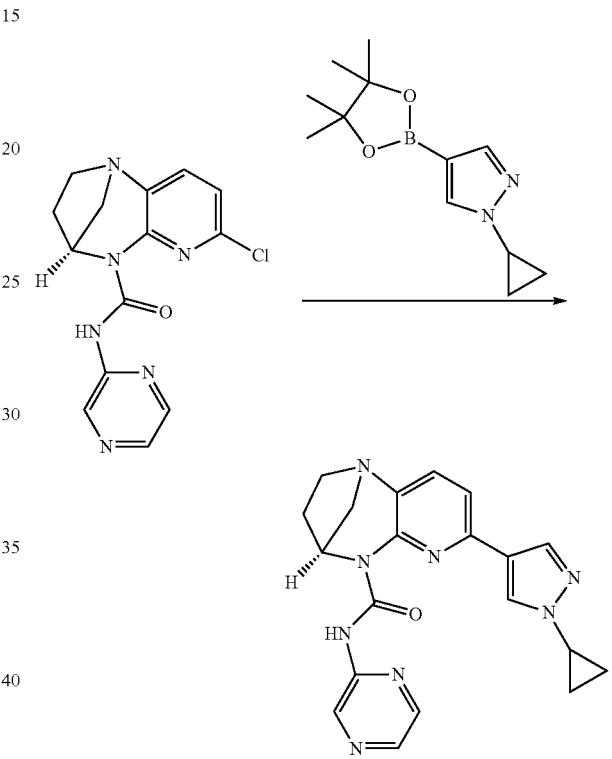

Pd$_2$(dba)$_3$ (0.087 g, 0.095 mmol) and X-phos (0.018 g, 0.047 mmol) was added to degassed solution of (4S)-7-chloro-N-(pyrazin-2-yl)-3,4-dihydro-1,4-methanopyrido[2, 3-b][1,4]diazepine-5(2H)-carboxamide (0.3 g, 0.947 mmol), 1-cyclopropyl-4-(4,4,5,5-tetramethyl-1,3,2-dioxaborolan-2-yl)-1H-pyrazole (0.333 g, 1.421 mmol) and potassium dihydrogen phosphate (0.258 g, 1.894 mmol) in 1,4-dioxane (5 mL): water (1 mL) and heated to 90° C. for 15 hours. Cooled to room temperature and filtered through pad of celite. The filtrate was diluted with water (25 mL) and ethyl acetate (50 mL). The separated organic layer was dried over anhydrous sodium sulfate, filtered and evaporated to get crude (TLC eluent: 10% MeOH in ethyl acetate; UV active; R$_f$~0.30). The crude compound was purified by column chromatography using neutral alumina and eluted in 75% ethyl acetate in hexane to afford (4S)-7-(1-cyclopropyl-1H-pyrazol-4-yl)-N-(pyrazin-2-yl)-3,4-dihydro-1,4-methanopyrido [2,3b][1, 4]diazepine-5(2H)-carboxamide (0.13 g, 0.332 mmol, 35.0% yield) off-white solid, LCMS (m/z): 389.32 [M+H]$^+$.

$^1$H NMR (400 MHz, CDCl$_3$): δ ppm 14.14 (s, 1H), 9.60 (d, J=1.10 Hz, 1H), 8.61 (s, 1H), 8.29-8.33 (m, 2H), 8.03 (s, 1H), 7.47-7.58 (m, 1H), 7.13 (d, J=8.11 Hz, 1H), 5.66 (dd, J=6.03, 3.18 Hz, 1H), 3.73 (tt, J=7.43, 3.75 Hz, 1H), 3.08-3.34 (m, 3H), 2.99 (dd, J=11.95, 3.18 Hz, 1H), 2.32 (dddd, J=14.11, 10.00, 6.03, 4.06 Hz, 1H), 2.02-2.11 (m, 1H), 1.22-1.32 (m, 2H), 1.07-1.18 (m, 2H).

Example 285

Synthesis of (4S)-7-((2S,6R)-2,6-dimethylmorpholino)-N-(pyrazin-2-yl)-3,4-dihydro-1,4-methanopyrido[2,3-b][1,4]diazepine-5(2H)-carboxamide

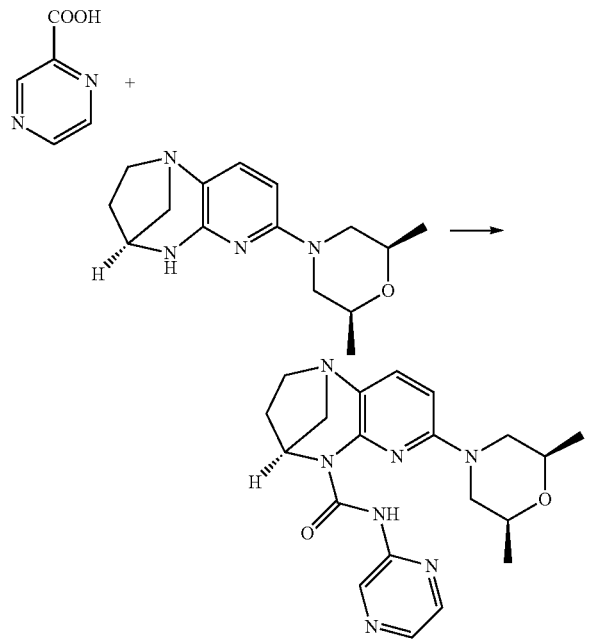

Diisopropylethylamine (3.34 mL, 19.14 mmol) was added to a stirred solution of pyrazine-2-carboxylic acid (0.475 g, 3.83 mmol) in tetrahydrofuran (30 mL) stirred under argon at room temperature. Diphenyl phosphorazidate (1.053 g, 3.83 mmol) was added to the reaction mixture. The reaction mixture was stirred 2 hr at room temperature then, (2S,6R)-2,6-dimethyl-4-((4S)-2,3,4,5-tetrahydro-1,4-methanopyrido[2,3-b][1,4]diazepin-7-yl)morpho line (0.735 g, 2.68 mmol) was added to the reaction mixture and stirred 16 hours at 65° C. The reaction mixture was cooled to room temp, and was partitioned between water (20 mL) and EtOAc (70 mL). Organic layer was separated and was dried over anhydrous Na$_2$SO$_4$, filtered and filtrate was evaporated to give crude as brown solid (TLC eluent: 100% EtOAc: R$_f$-0.3; UV active). The crude residue was purified by column chromatography using neutral alumina and was eluted with 15% EtOAc in hexane to afford pure (4S)-7-((2S,6R)-2,6-dimethylmorpholino)-N-(pyrazin-2-yl)-3,4-dihydro-1,4-methanopyrido[2,3-b][1,4]diazepine-5(2H)-carboxamide (0.132 g, 0.329 mmol, 8.58% yield) as a off-white solid, LCMS (m/z): 396.3 [M+H]$^+$.

$^1$H NMR (400 MHz, CDCl$_3$): δ ppm 13.39 (s, 1H), 9.56 (d, J=1.10 Hz, 1H), 8.26 (s, 1H), 8.25 (s, 1H), 7.39 (s, 1H), 6.30 (s, 1H), 5.63 (dd, J=5.92, 3.29 Hz, 1H), 4.01 (br d, J=12.50 Hz, 2H), 3.68-3.89 (m, 2H), 3.16-3.28 (m, 1H), 3.05-3.15 (m, 2H), 2.92 (dd, J=11.84, 3.29 Hz, 1H), 2.61 (t, J=11.62 Hz, 2H), 2.27 (dddd, J=13.89, 9.95, 6.08, 3.62 Hz, 1H), 1.93-2.06 (m, 1H), 1.33 (d, J=6.14 Hz, 6H)

Example 286

Synthesis of (4S)—N-(pyrazin-2-yl)-7-(2-(trifluoromethyl)pyrimidin-4-yl)-3,4-dihydro-1,4-methanopyrido[2,3-b][1,4]diazepine-5(2H)-carboxamide

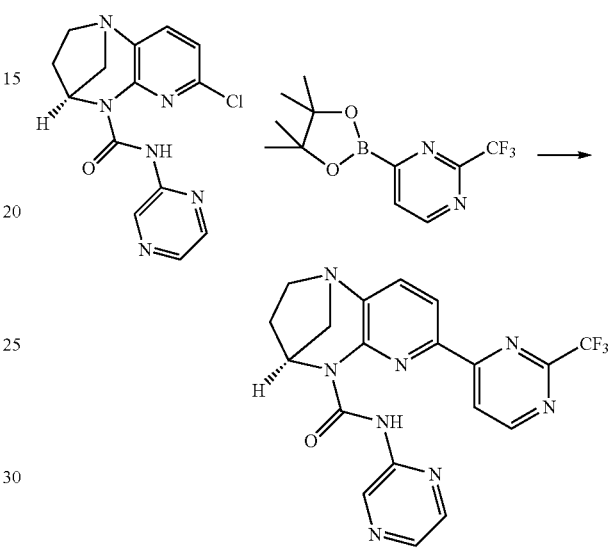

To a solution of (4S)-7-chloro-N-(pyrazin-2-yl)-3,4-dihydro-1,4-methanopyrido[2,3-b][1,4]diazepine-5(2H)-carboxamide (300 mg, 0.947 mmol), 4-(4,4,5,5-tetramethyl-1,3,2-dioxaborolan-2-yl)-2-(trifluoromethyl)pyrimidine (260 mg, 0.947 mmol) and K$_3$PO$_4$ (603 mg, 2.84 mmol) in 1,4-Dioxane (20 mL) was added Water (3 mL). The reaction mixture was degassed with argon at room temp for 15 min. Then to this X-Phos (45.2 mg, 0.095 mmol) and Pd$_2$(dba)$_3$ (43.4 mg, 0.047 mmol) was added. The reaction mixture was stirred at 90° C. for 16 hr. Reaction progress was monitored by TLC. The reaction mass filtered through celite and concentrated under reduced pressure. The residue was diluted with water and extracted with ethyl acetate (2×50 mL). The combined organic layers were washed with water followed by brine solution and dried out with sodium sulfate, filtered and concentrated. The Crude compound was purified by column chromatography (Neutral alumina) product was eluted with 30% ethyl acetate in Hexane. Collected fractions evaporated under reduced pressure and dried under high vacuum to afford (4S)—N-(pyrazin-2-yl)-7-(2-(trifluoromethyl)pyrimidin-4-yl)-3,4-dihydro-1,4-methanopyrido[2,3-b][1,4]diazepine-5(2H)-carboxamide (230 mg, 0.534 mmol, 56.4% yield) as a Off-White solid, LCMS (m/z): 429.3 [M+H]$^+$.

$^1$H NMR (400 MHz, CDCl$_3$): δ ppm 13.60 (s, 1H), 9.59 (d, J=1.32 Hz, 1H), 9.08 (d, J=5.26 Hz, 1H), 8.83 (d, J=5.26 Hz, 1H), 8.22-8.47 (m, 3H), 7.75 (d, J=7.89 Hz, 1H), 5.72 (dd, J=5.92, 3.29 Hz, 1H), 3.15-3.37 (m, 3H), 3.00-3.10 (m, 1H), 2.28-2.46 (m, 1H), 2.03-2.18 (m, 1H)

Example 287

Synthesis of (4S)-7-(1-methyl-1H-pyrazol-3-yl)-N-(pyrazin-2-yl)-3,4-dihydro-1,4-methanopyrido[2,3-b][1,4]diazepine-5(2H)-carboxamide

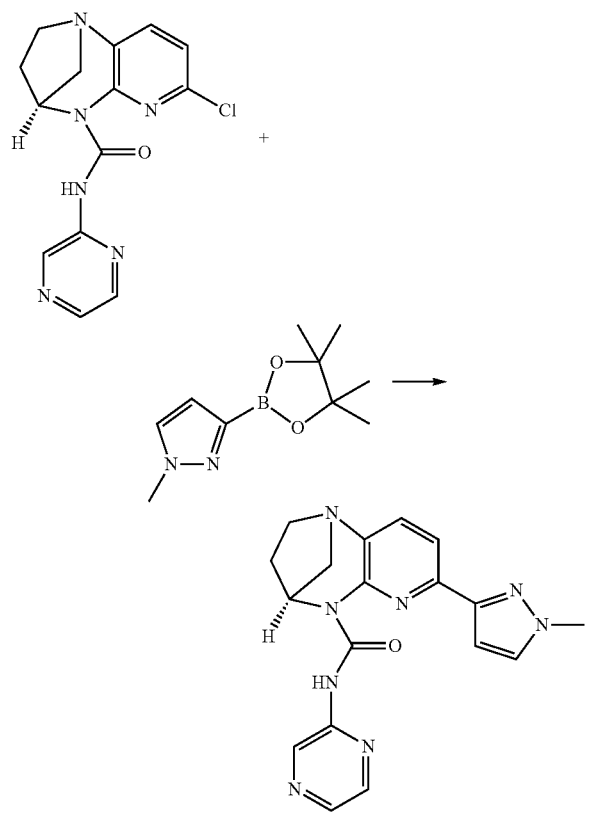

A suspension of (4S)-7-chloro-N-(pyrazin-2-yl)-3,4-dihydro-1,4-methanopyrido[2,3-b][1,4]diazepine-5(2H)-carboxamide (0.350 g, 1.105 mmol), 1-methyl-3-(4,4,5,5-tetramethyl-1,3,2-dioxaborolan-2-yl)-1H-pyrazole (0.690 g, 3.31 mmol) and potassium phosphate tribasic (0.703 g, 3.31 mmol) in 1,4-dioxane (25 mL) and water (4 mL) degassed with argon at room temp for 15 minutes. Then, to above mixture was added X-phos (53 mg, 0.110 mmol) and Pd(dba)$_2$ (0.032 g, 0.055 mmol) and was further degassed for 15 minutes. The reaction mixture was stirred 16 hours at 100° C. After completion of the reaction as indicated by TLC, cooled to 28° C. and was diluted with water (15 mL) and extracted with EtOAc (2×25 mL). The organic layer was washed with water followed by brine solution and dried over anhydrous sodium sulfate, filtered and filtrate was evaporated to get the crude residue (TLC eluent: 5% MeOH in DCM, R$_f$ value: 0.3, UV active). The crude residue was purified by column chromatography using neutral alumina, and the product was eluted 50% ethyl acetate in pet ether to afford (4S)-7-(1-methyl-1H-pyrazol-3-yl)-N-(pyrazin-2-yl)-3,4-dihydro-1,4-methanopyrido[2,3-b][1,4]diazepine-5 (2H)-carboxamide (0.192 g, 0.527 mmol, 47.7% yield) as off white solid, LCMS (m/z): 363.30 [M+H]⁺.

¹H NMR (400 MHz, CDCl$_3$): δ ppm 13.98 (s, 1H), 9.56 (d, J=1.32 Hz, 1H), 8.33-8.27 (m, 2H), 7.66 (d, J=8.11 Hz, 1H), 7.56-7.52 (m, 1H), 7.46 (d, J=2.19 Hz, 1H), 7.42 (d, J=2.41 Hz, 1H), 5.68 (dd, J=5.92, 3.29 Hz, 1H), 3.99 (s, 3H), 3.33-3.12 (m, 3H), 2.99 (dd, J=12.06, 3.29 Hz, 1H), 2.36-2.26 (m, 1H), 2.11-1.98 (m, 1H)

Example 288

Synthesis of (4S)—N-(5-ethoxypyrazin-2-yl)-7-(2-methylpyridin-4-yl)-3,4-dihydro-1,4-methanopyrido[2,3-b][1,4]diazepine-5(2H)-carboxamide

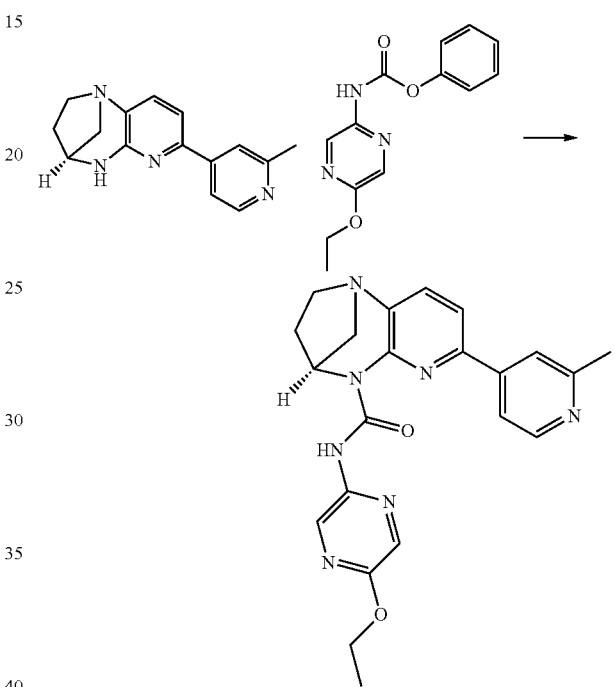

To a stirred solution of (4S)-7-(2-methylpyridin-4-yl)-2,3,4,5-tetrahydro-1,4-methanopyrido[2,3-b][1,4]diazepine (100 mg, 0.396 mmol) in THF (10 mL, in sealed tube) were added DMAP (145 mg, 1.189 mmol) and phenyl (5-ethoxypyrazin-2-yl)carbamate (308 mg, 1.189 mmol) at RT and heated at 90° C. for 16 h. The reaction mixture was cooled to room temperature and was partitioned between water (25 mL) and EtOAc (40 mL). The organic layer was separated and dried over anhydrous Na$_2$SO$_4$, filtered and filtrate was evaporated to obtain the crude compound. The crude residue was purified by flash column chromatography (silica gel: 100-200 mesh, eluent: 2% methanol in DCM) to afford (4S)—N-(5-ethoxypyrazin-2-yl)-7-(2-methylpyridin-4-yl)-3,4-dihydro-1,4-methanopyrido[2,3-b][1,4]diazepine-5 (2H)-carboxamide (38 mg, 0.090 mmol, 22.79% yield) as an off white solid (TLC eluent: 5% methanol in DCM R$_f$: 0.4), LCMS (m/z): 418.36 [M+H]⁺.

¹H NMR (400 MHz, CDCl$_3$): δ ppm 13.50 (s, 1H), 9.01 (d, J=1.32 Hz, 1H), 8.61 (d, J=5.26 Hz, 1H), 8.06 (s, 1H), 7.98 (m, 1H), 7.63 (m, 2H), 7.47 (d, J=7.89 Hz, 1H), 5.71 (dd, J=5.92, 3.07 Hz, 1H), 4.40 (q, J=7.02 Hz, 2H), 3.34-3.10 (m, 3H), 3.01 (dd, J=5.94, 2.96 Hz, 1H), 2.67 (s, 3H), 2.36-2.10 (m, 2H), 1.42 (t, J=7.13 Hz, 3H).

Example 289

Synthesis of (4S)-7-((2S,6S)-2,6-dimethylmorpholino)-N-(pyrazin-2-yl)-3,4-dihydro-1,4-methanopyrido[2,3-b][1,4]diazepine-5(2H)-carboxamide

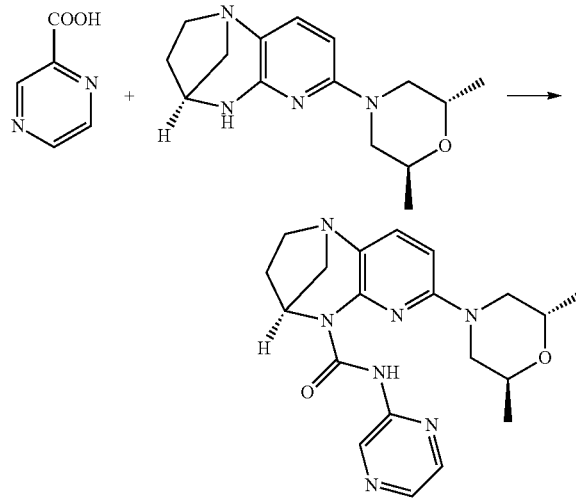

Diisopropylethylamine (3.52 mL, 20.15 mmol) was added to a stirred solution of pyrazine-2-carboxylic acid (0.500 g, 4.03 mmol) in tetrahydrofuran (30 mL) and stirred under argon at room temperature. Diphenyl phosphorazidate (1.109 g, 4.03 mmol) was added to the reaction mixture and was stirred 2 hour at room temperature. Next, (2S, 6S)-2,6-Dimethyl-4-((4S)-2,3,4,5-tetrahydro-1,4-methanopyrido[2,3-b][1,4]diazepin-7-yl) morpholine (0.774 g, 2.82 mmol) was added to the reaction and was stirred 16 hour at 65° C. The reaction mixture was cooled to room temperature, and was partitioned between water (20 mL) and EtOAc (70 mL). Organic layer was separated and was dried over anhydrous $Na_2SO_4$, filtered and filtrate was evaporated to give crude residue as brown solid (TLC eluent: 100% EtOAc: $R_f$-0.3; UV active). The crude was purified by column chromatography using neutral alumina and was eluted with 20% EtOAc in hexane to afford pure (4S)-7-((2S,6S)-2,6-dimethylmorpholino)-N-(pyrazin-2-yl)-3,4-dihydro-1,4-methanopyrido[2,3-b][1,4]diazepine-5(2H)-carboxamide (0.321 g, 0.799 mmol, 19.82% yield) as a white solid, LCMS (m/z): 396.3 [M+H]⁺.

¹H NMR (400 MHz, $CDCl_3$): δ ppm 13.41 (s, 1H), 9.56 (d, J=1.53 Hz, 1H), 8.25 (d, J=2.41 Hz, 1H), 8.16 (dd, J=2.41, 1.53 Hz, 1H), 7.37 (d, J=8.55 Hz, 1H), 6.25 (d, J=8.55 Hz, 1H), 5.63 (dd, J=6.03, 3.18 Hz, 1H), 4.11-4.31 (m, 2H), 3.67 (dd, J=12.50, 3.29 Hz, 2H), 3.19-3.34 (m, 3H), 3.06-3.18 (m, 2H), 2.92 (dd, J=11.84, 3.29 Hz, 1H), 2.27 (dddd, J=13.95, 9.95, 6.03, 3.84 Hz, 1H), 1.92-2.07 (m, 1H), 1.34 (d, J=6.36 Hz, 6H)

Example 290

Synthesis of (4S)-7-(2-methylpyridin-4-yl)-N-(pyridazin-4-yl)-3,4-dihydro-1,4-methano pyrido[2,3-b][1,4]diazepine-5(2H)-carboxamide

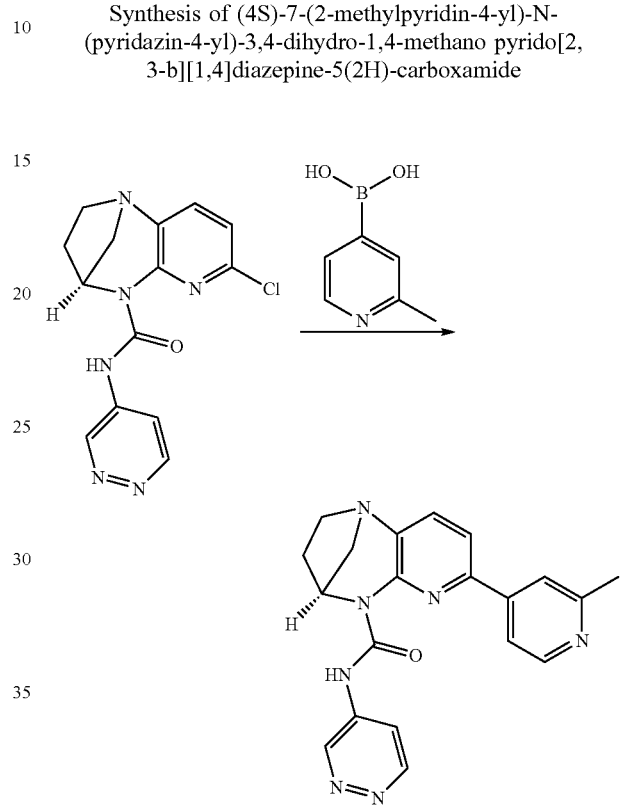

To a degassed solution of (4S)-7-chloro-N-(pyridazin-4-yl)-3,4-dihydro-1,4-methanopyrido[2,3-b][1,4]diazepine-5(2H)-carboxamide (0.3 g, 0.947 mmol) in 1,4-dioxane (10 ml)/water (2 ml), (2-methylpyridin-4-yl)boronic acid (0.195 g, 1.421 mmol) and $K_3PO_4$ (0.402 g, 1.894 mmol) were added tris(dibenzylideneacetone)dipalladium(0) (0.087 g, 0.095 mmol) and x-phos (0.090 g, 0.189 mmol) at RT and heated at 100° C. for 16 h. The reaction mixture was cooled to room temperature and extracted with ethyl acetate (2×50 mL). The combined organic layer was dried over anhydrous $Na_2SO_4$, filtered and filtrate was evaporated to obtain the crude compound. The crude compound was purified by flash column chromatography (silica gel: 100-200 mesh, eluent: 3% methanol in EtOAc) to afford (4S)-7-(2-methylpyridin-4-yl)-N-(pyridazin-4-yl)-3,4-dihydro-1,4-methanopyrido[2,3-b][1,4] diazepine-5(2H)-carboxamide (125 mg, 0.333 mmol, 35.1% yield) as an off white solid (TLC eluent: 10% methanol in EtOAc, $R_f$: 0.4), LCMS (m/z): 374.21 [M+H]⁺.

¹H NMR (400 MHz, $CDCl_3$): δ ppm: 13.50 (s, 1H), 9.10 (d, J=1.97 Hz, 1H), 8.93-9.05 (m, 1H), 8.72 (d, J=5.04 Hz, 1H), 8.00 (dd, J=5.92, 2.85 Hz, 1H), 7.69 (d, J=8.11 Hz, 1H), 7.61-7.53 (m, 1H), 7.48 (dd, J=5.26, 1.32 Hz, 1H), 7.41 (d, J=7.58 Hz, 1H), 5.67 (dd, J=5.92, 3.07 Hz, 1H), 3.35-3.13 (m, 3H), 3.05 (dd, J=12.17, 3.18 Hz, 1H), 2.37 (dddd, J=14.17, 9.84, 5.81, 4.17 Hz, 3H), 2.39 (m, 1H), 2.15 (m, 1H).

Example 291

Synthesis of (4S)-7-(2-methylpyridin-4-yl)-N-(4-methylpyrimidin-2-yl)-3,4-dihydro-1,4-methanopyrido[2,3-b][1,4]diazepine-5(2H)-carboxamide

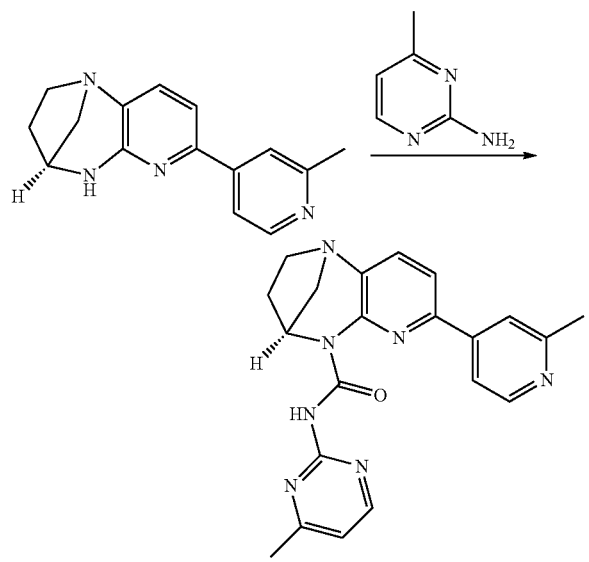

To a stirred solution of (4S)-7-(2-methylpyridin-4-yl)-2,3,4,5-tetrahydro-1,4-methanopyrido[2,3-b][1,4]diazepine (400 mg, 1.585 mmol) in THF (15 mL, sealed tube) was added triphosgene (282 mg, 0.951 mmol) at RT and stirred for 30 min. Then TEA (1.105 mL, 7.93 mmol) and 4-methylpyrimidin-2-amine (260 mg, 2.378 mmol) were added and heated at 65° C. for 15 h. The reaction mixture was cooled to room temperature; THF was distilled off and was partitioned between water (25 mL) and DCM (40 mL). The organic layer was separated and dried over anhydrous $Na_2SO_4$, filtered and filtrate was evaporated to obtain the crude compound. The crude compound was purified by flash column chromatography (silica gel: 100-200 mesh, eluent: 2% methanol in DCM) to obtain 500 mg with 60% LCMS purity, which was purified by prep HPLC (MP-A: 10 mM Ammonium Acetate (Aq) MP-B: Acetonitrile Column: x bridge C18 (100×19) mm 5μ Method—T/% B: 0/25/30,10/55, Flow: 19 ml/min Solubility: THF+ACN) to afford (4S)-7-(2-methylpyridin-4-yl)-N-(4-methylpyrimidin-2-yl)-3,4-dihydro-1,4-methanopyrido[2,3-b][1,4]diazepine-5(2H)-carboxamide (226 mg, 0.582 mmol, 36.7% yield) as an off-white solid (TLC eluent: 10% MeOH in EtOAc, $R_f$: 0.4), LCMS (m/z): 388.2 [M+H]$^+$.

$^1$H NMR (400 MHz, CDCl$_3$): δ ppm: 13.74 (s, 1H), 8.63 (d, J=5.26 Hz, 1H), 8.52 (d, J=5.04 Hz, 1H), 7.90-7.83 (m, 2H), 7.63 (m, J=8.11 Hz, 1H), 7.47 (d, J=8.11 Hz, 1H), 6.87 (d, J=5.04 Hz, 1H), 5.78 (dd, J=5.92, 3.29 Hz, 1H), 3.32-3.10 (m, 3H), 3.10-2.88 (m, 1H), 2.68 (s, 3H), 2.54 (s, 3H), 2.51-2.23 (m, 1H), 2.23-1.99 (m, 1H).

Example 292

Synthesis of (4S)-7-(1-methyl-2-oxo-1,2-dihydropyridin-4-yl)-N-(pyrazin-2-yl)-3,4-dihydro-1,4-methanopyrido[2,3-b][1,4]diazepine-5(2H)-carboxamide

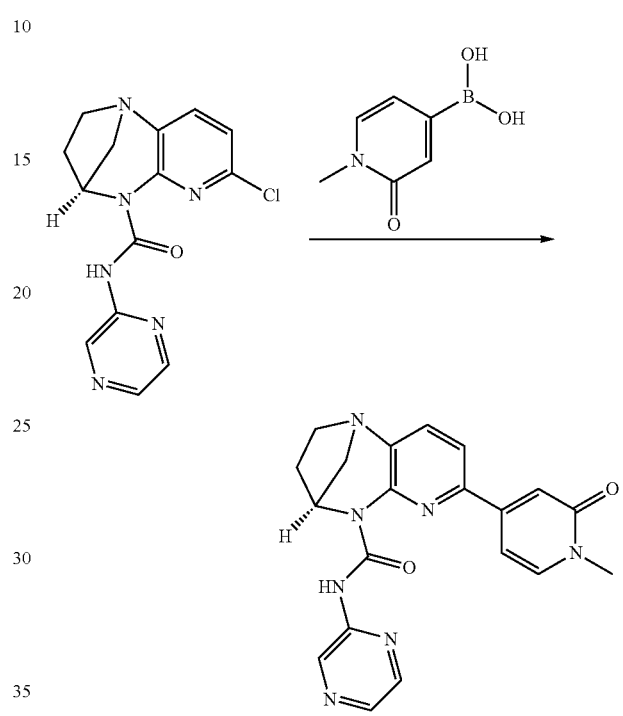

Potassium phosphate (939 mg, 4.43 mmol) and (1-methyl-2-oxo-1,2-dihydropyridin-4-yl)boronic acid (462 mg, 3.322 mmol) were added to a solution of (4S)-7-chloro-N-(pyrazin-2-yl)-3,4-dihydro-1,4-methanopyrido[2,3-b][1,4]diazepine-5(2H)-carboxamide (700 mg, 2.215 mmol) in mixture of 1,4-dioxane: water (10 mL, 8:2) at RT. This mixture was purged with argon for 30 min. PdOAc$_2$ (49.62 mg, 0.221 mmol) and X-Phos (211.2 mg, 0.443 mmol) were added to the reaction mixture and then stirred at 100° C. for 16h. The reaction mixture was cooled to room temperature, concentrated in vacuo, residue was partitioned between water (40 mL) and EtOAc (80 mL). Organic layer was separated and dried over anhydrous $Na_2SO_4$, filtered and filtrate was evaporated to obtain crude compound. The crude compound was purified by column chromatography using silica gel (100-200 mesh) 3% methanol in dichloromethane as a eluent to afford (4S)-7-(1-methyl-2-oxo-1,2-dihydropyridin-4-yl)-N-(pyrazin-2-yl)-3,4-dihydro-1,4-methanopyrido[2,3-b][1,4]diazepine-5(2H)-carboxamide (110 mg, 0.270 mmol, 28.5% yield) as a pale yellow solid. (TLC eluent: 10% MeOH in DCM $R_f$: 0.4; UV active), LCMS (m/z): 390.30 [M+H]$^+$.

$^1$H NMR (400 MHz, CDCl$_3$): δ ppm 13.53 (s, 1H), 9.53 (s, 1H), 8.34-8.28 (m, 2H), 7.63 (d, J=8.11 Hz, 1H), 7.43 (t, J=7.78 Hz, 2H), 7.20 (d, J=1.75 Hz, 1H), 7.04 (dd, J=7.23, 1.97 Hz, 1H), 5.70 (dd, J=5.92, 3.07 Hz, 1H), 3.62 (s, 3H), 3.33-3.14 (m, 3H), 3.03 (dd, J=12.06, 3.29 Hz, 1H), 2.40-2.30 (m, 1H), 2.09 (dt, J=13.92, 6.85 Hz, 1H)

Example 293

Synthesis of (4S)-7-(5-cyano-6-ethoxypyridin-3-yl)-N-(pyrazin-2-yl)-3,4-dihydro-1,4-methanopyrido[2,3-b][1,4]diazepine-5(2H)-carboxamide

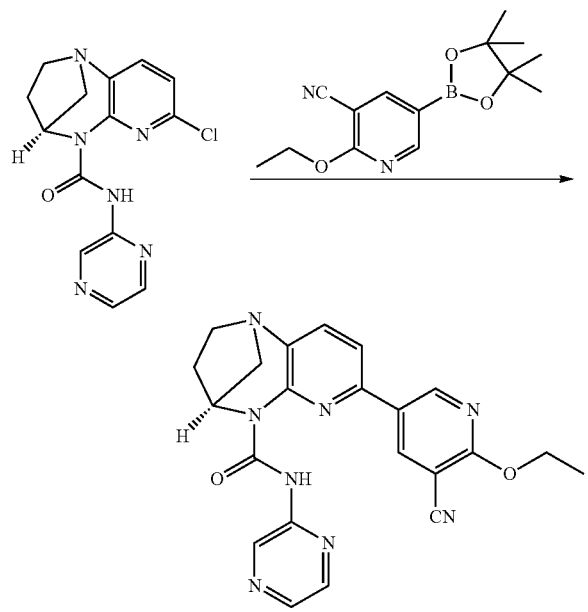

To a solution of (4S)-7-chloro-N-(pyrazin-2-yl)-3,4-dihydro-1,4-methanopyrido[2,3-b][1,4]diazepine-5(2H)-carboxamide (400 mg, 1.263 mmol), 2-ethoxy-5-(4,4,5,5-tetramethyl-1,3,2-dioxaborolan-2-yl)nicotinonitrile (519 mg, 1.894 mmol) and $K_3PO_4$ (536 mg, 2.53 mmol) in 1,4-dioxane (15 mL), water (3 mL) degassed with argon for 20 min was added x-phos (60.2 mg, 0.126 mmol), tris(dibenzylideneacetone)dipalladium(0) (57.8 mg, 0.063 mmol) and again degassed with argon for 5 min. The reaction mixture was stirred at 100° C. for 16 hours and cooled to room temperature. The reaction mixture was filtered through celite then the filtrate was diluted with water and extracted with EtOAc (3×20 mL). The combined organic layers were washed with water, brine solution, dried over sodium sulfate and evaporated to give crude compound (TLC eluent: 5% MeOH in DCM: $R_f$-0.3; UV active). The crude compound was purified by column chromatography using neutral alumina and eluted with 30-40% EtOAc/hexane to afford pure (4S)-7-(5-cyano-6-ethoxypyridin-3-yl)-N-(pyrazin-2-yl)-3,4-dihydro-1,4-methanopyrido[2,3-b][1,4]diazepine-5 (2H)-carboxamide (173 mg, 0.398 mmol, 31.5% yield) as off white solid, LCMS (m/z): 429.2 [M+H]+.

$^1$H NMR (400 MHz, CDCl$_3$): δ 13.83 (s, 1H), 9.51 (d, J=1.5 Hz, 1H), 9.16 (d, J=2.4 Hz, 1H), 8.82 (d, J=2.6 Hz, 1H), 8.55 (dd, J=2.6, 1.5 Hz, 1H), 8.31 (d, J=2.4 Hz, 1H), 7.62 (d, J=7.9 Hz, 1H), 7.38 (d, J=7.9 Hz, 1H), 5.67 (dd, J=6.0, 3.2 Hz, 1H), 4.57 (q, J=7.1 Hz, 2H), 3.12-3.32 (m, 3H), 3.01 (dd, J=12.0, 3.3 Hz, 1H), 2.34 (m, 1H), 2.07 (m, 1H), 1.48 (t, J=7.1 Hz, 3H).

Example 294

Synthesis of (4S)-7-(6-methylpyridin-3-yl)-N-(tetrahydro-2H-pyran-4-yl)-3,4-dihydro-1,4-methanopyrido[2,3-b][1,4]diazepine-5(2H)-carboxamide

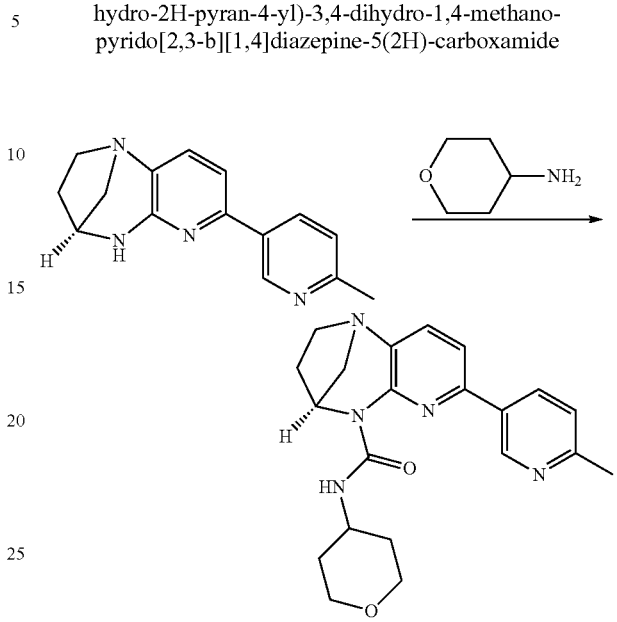

Triphosgene (212 mg, 0.714 mmol) was added slowly in portions to a stirred solution of (4S)-7-(6-methylpyridin-3-yl)-2,3,4,5-tetrahydro-1,4-methanopyrido[2,3-b][1,4]diazepine (300 mg, 1.190 mmol) in Tetrahydrofuran (THF) (15 mL) at RT and stirred for 30 min.

DIPEA (0.622 mL, 3.57 mmol) and tetrahydro-2H-pyran-4-amine (180 mg, 1.785 mmol) were added to above reaction mixture, stirred at 70° C. for 16 h. The reaction mixture was cooled to room temperature, concentrated in vacuo and the residue was partitioned between water (40 mL) and EtOAc (80 mL). Organic layer was separated and dried over anhydrous Na$_2$SO$_4$, filtered and filtrate was evaporated to get crude compound. The crude compound was purified by column chromatography using silica gel (100-200 mesh) 2% methanol in dichloromethane as a eluent to afford (4S)-7-(6-methylpyridin-3-yl)-N-(tetrahydro-2H-pyran-4-yl)-3,4-dihydro-1,4-methanopyrido[2,3-b][1,4]diazepine-5(2H)-carboxamide (110 mg, 0.290 mmol, 29.2% yield) as a Pale yellow solid. (TLC eluent: 10% MeOH in DCM R$_f$: 0.4; UV active), LCMS (m/z): 380.36 [M+H]+.

$^1$H NMR (400 MHz, CDCl$_3$): δ ppm 10.52 (br d, J=7.23 Hz, 1H), 8.88 (d, J=1.97 Hz, 1H), 7.92 (dd, J=8.11, 2.41 Hz, 1H), 7.54 (d, J=7.89 Hz, 1H), 7.28 (s, 1H), 7.22 (d, J=7.89 Hz, 1H), 5.62 (dd, J=5.92, 3.29 Hz, 1H), 4.04-3.94 (m, 3H), 3.51 (tt, J=11.59, 2.33 Hz, 2H), 3.27-3.15 (m, 2H), 3.13-3.06 (m, 1H), 2.95 (dd, J=11.84, 3.29 Hz, 1H) 2.63 (s, 3H), 2.26 (dddd, J=14.00, 9.95, 5.97, 4.06 Hz, 1H), 2.08-1.98 (m, 3H), 1.62-1.55 (m, 2H)

Example 295

Synthesis of (4S)—N-(cyclopropylmethyl)-7-(6-methylpyridin-3-yl)-3,4-dihydro-1,4-methanopyrido[2,3-b][1,4]diazepine-5(2H)-carboxamide

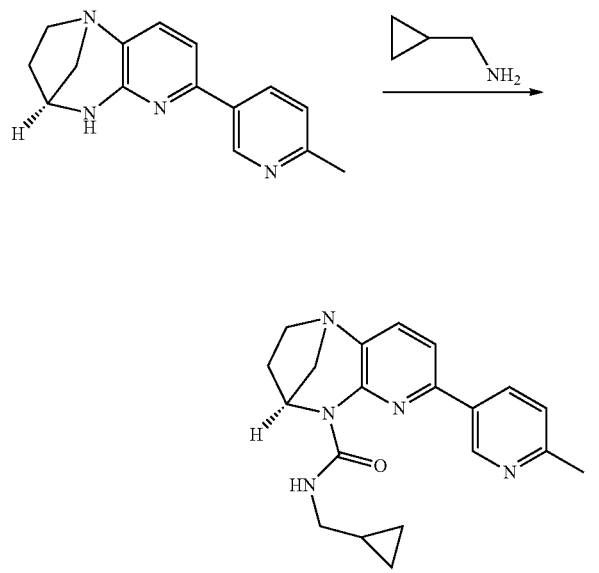 [SMILES: Cc1ccc(-c2ccc3c(n2)N[C@H]2CCN3C2)cn1 ; NCC1CC1 ; Cc1ccc(-c2ccc3c(n2)N(C(=O)NCC2CC2)[C@H]2CCN3C2)cn1]

To a solution of (4S)-7-(6-methylpyridin-3-yl)-2,3,4,5-tetrahydro-1,4-methanopyrido[2,3-b][1,4]diazepine (200 mg, 0.793 mmol) in Tetrahydrofuran (THF) (10 mL) were added TEA (0.331 mL, 2.378 mmol) and tri phosgène (141 mg, 0.476 mmol) at 0° C. and stirred to room temperature for 30 minutes. Then cyclopropylmethanamine (85 mg, 1.189 mmol) was added. The reaction mixture was stirred at 60° C. for 16 h. The reaction mixture allowed to RT and solvent was evaporated and diluted with $CH_2Cl_2$ (25 mL). The solution was washed with water and brine, dried over anhydrous $Na_2SO_4$, filtered and concentrated. The crude product was purified by flash column chromatography (silica-gel: 100-200 mesh, eluted with 5% MeOH/$CH_2Cl_2$) to obtained (4S)—N-(cyclopropylmethyl)-7-(6-methylpyridin-3-yl)-3,4-dihydro-1,4-methanopyrido[2,3-b][1,4]diazepine-5(2H)-carboxamide (140 mg, 0.381 mmol, 48.0% yield) as a pale yellow solid (TLC: $R_f$=0.3, Neat EtOAc), LCMS (m/z): 350.30 [M+H]$^+$.

$^1$H NMR (400 MHz, CDCl$_3$): δ ppm 10.52 (br s, 1H), 8.96 (d, J=1.97 Hz, 1H), 8.02 (dd, J=8.00, 2.30 Hz, 1H), 7.53 (d, J=7.89 Hz, 1H), 7.26-7.20 (m, 2H), 5.64 (dd, J=5.81, 3.18 Hz, 1H), 3.32-3.05 (m, 5H), 2.95 (dd, J=11.84, 3.29 Hz, 1H), 2.62 (s, 3H), 2.26 (dddd, J=14.00, 9.95, 5.97, 4.06 Hz, 1H), 2.10-1.98 (m, 1H), 1.08 (dddt, J=12.78, 7.66, 5.04, 2.38, 2.38 Hz, 1H), 0.65-0.52 (m, 2H), 0.26 (q, J=4.97 Hz, 2H).

Example 296

Synthesis of (4S)—N-(3H-[1,2,3]triazolo[4,5-d]pyrimidin-7-yl)-7-(2-methylpyridin-4-yl)-3,4-dihydro-1,4-methanopyrido[2,3-b][1,4]diazepine-5(2H)-carboxamide

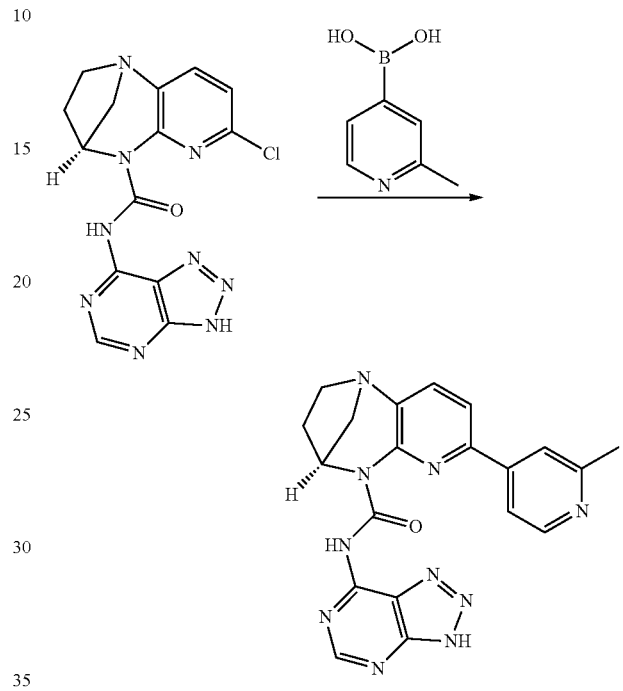

A solution of (4S)—N-(3H-[1,2,3]triazolo[4,5-d]pyrimidin-7-yl)-7-chloro-3,4-dihydro-1,4-methanopyrido[2,3-b][1,4]diazepine-5(2H)-carboxamide (250 mg, 0.699 mmol) and (2-methylpyridin-4-yl) boronic acid (124 mg, 0.908 mmol) in 1,4-Dioxane (9 mL) and water (1 mL) at 25° C. was degassed for 15 min. To this reaction mixture $Cs_2CO_3$ (455 mg, 1.398 mmol) was added and degassed again for 15 min. Finally PdCl$_2$(dppf) (51.1 mg, 0.070 mmol) was added and the reaction mixture was stirred for 2 h at 100° C. The reaction mixture was diluted with water (10 ml) and extracted with ethyl acetate (2×10 ml). The combined organic layer was washed with water (10 ml), brine (10 ml), dried over anhydrous sodium sulfate and concentrated under reduced pressure to afford the crude compound. The crude product was purified by flash column chromatography (2 times) ((100-200 silica gel eluted with 3% of $CH_2Cl_2$/MeOH) to afford compound. This was re-purified by prep HPLC eluting with 3% methanol in dichloromethane to afford pure (4S)—N-(3H-[1,2,3]triazolo[4,5-d]pyrimidin-7-yl)-7-(2-methylpyridin-4-yl)-3,4-dihydro-1,4-methanopyrido[2,3-b][1,4]diazepine-5(2H)-carboxamide (15 mg, 0.036 mmol, 5.15% yield) as off white solid. (TLC system: 5% Methanol in DCM. $R_f$ value: 0.3), LCMS (m/z): 414.9 [M+H]$^+$.

$^1$H NMR (400 MHz, DMSO-d$_6$): δ ppm 13.23 (br s, 1H), 8.47 (br d, J=19.95 Hz, 2H), 8.08 (br s, 1H), 7.92-8.04 (m, 1H), 7.67-7.81 (m, 2H), 5.48-5.64 (m, 1H), 3.20-3.26 (m, 1H), 3.15 (br d, J=11.40 Hz, 2H), 2.90-3.05 (m, 1H), 2.46 (br s, 3H), 2.20-2.38 (m, 1H), 1.92-2.09 (m, 1H).

Example 297

Synthesis of (4S)—N-(3-fluoropyrazin-2-yl)-7-(2-methylpyridin-4-yl)-3,4-dihydro-1,4-methanopyrido[2,3-b][1,4]diazepine-5(2H)-carboxamide

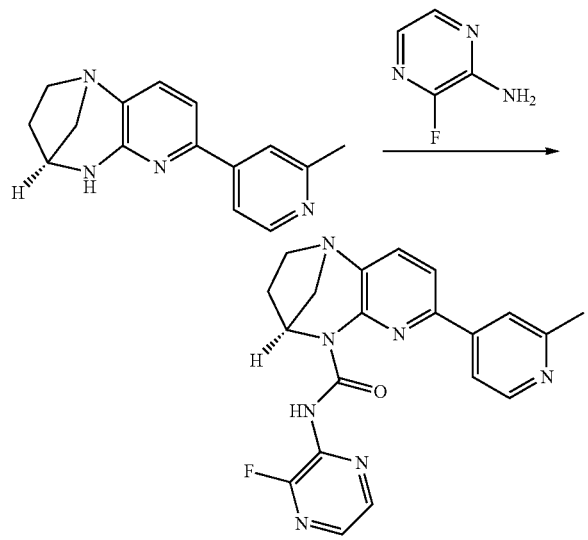

To a stirred solution of (4S)-7-(2-methylpyridin-4-yl)-2,3,4,5-tetrahydro-1,4-methanopyrido[2,3-b][1,4]diazepine (500 mg, 1.982 mmol) in THF (10 mL, sealed tube) triethylamine (1.657 mL, 11.89 mmol) and triphosgene (588 mg, 1.982 mmol) were added at RT and stirred for 30 min then 3-fluoropyrazin-2-amine (336 mg, 2.97 mmol) was added and heated at 80° C. for 15 h. The reaction mixture was cooled to room temperature and was partitioned between water (25 mL) and EtOAc (40 mL). The organic layer was separated and dried over anhydrous $Na_2SO_4$, filtered and filtrate was evaporated to obtain the crude compound. The crude compound was purified by flash column chromatography (silica gel: 100-200 mesh, eluent: 2% methanol in DCM) to obtain the (4S)—N-(3-fluoropyrazin-2-yl)-7-(2-methylpyridin-4-yl)-3,4-dihydro-1,4-methanopyrido[2,3-b][1,4]diazepine-5(2H)-carboxamide (27 mg, 0.068 mmol, 3.44% yield) as an off white solid (TLC eluent: 5% methanol in DCM, $R_f$: 0.4), LCMS (m/z): 392.3 $[M+H]^+$.

$^1$H NMR (400 MHz, $CDCl_3$): δ ppm 13.43 (s, 1H), 8.59 (d, J=5.26 Hz, 1H), 8.32 (d, J=2.63 Hz, 1H), 7.90 (d, J=2.41 Hz, 1H), 7.72-7.55 (m, 3H), 7.37 (br d, J=4.38 Hz, 1H), 5.73 (br dd, J=5.70, 3.07 Hz, 1H), 3.36-3.02 (m, 4H), 2.61 (m, 3H), 2.33 (br dd, J=9.87, 4.17 Hz, 1H), 2.12 (br dd, J=9.72, 3.86 Hz, 1H).

Example 298

Synthesis of (4S)—N-(pyridin-2-yl)-7-(3-(trifluoromethyl)pyrrolidin-1-yl)-3,4-dihydro-1,4-methanopyrido[2,3-b][1,4]diazepine-5(2H)-carboxamide

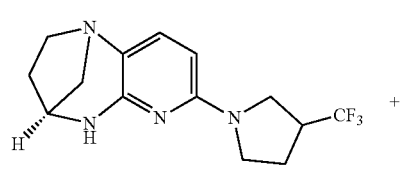

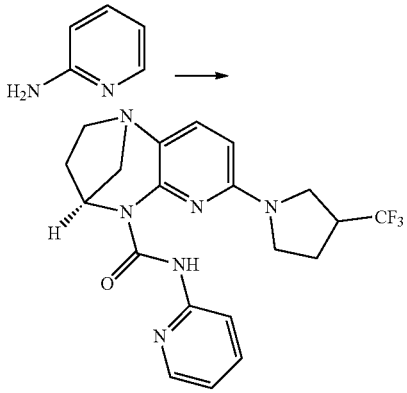

To a solution of (4S)-7-(3-(trifluoromethyl)pyrrolidin-1-yl)-2,3,4,5-tetrahydro-1,4-methanopyrido[2,3-b][1,4]diazepine (Peak 2 from intermediate SFC separation) (350 mg, 1.173 mmol) in tetrahydrofuran (THF) (10 mL) was added triphosgene (209 mg, 0.704 mmol) at 0° C. After 30 min DIPEA (1.025 mL, 5.87 mmol) and pyridin-2-amine (221 mg, 2.347 mmol) were added and the reaction mixture was stirred at 70° C. for 16 h. The reaction mixture was poured onto cold water (50 mL) and extracted with ethyl acetate (2×50 mL). The organic layer was dried over anhydrous sodium sulfate, concentrated under reduced pressure to give crude compound. The crude product was purified by flash column chromatography (silica-gel: 100-200 mesh, eluent: 2% MeOH in DCM) to obtain (4S)—N-(pyridin-2-yl)-7-(3-(trifluoromethyl)pyrrolidin-1-yl)-3,4-dihydro-1,4-methanopyrido[2,3-b][1,4]diazepine-5(2H)-carboxamide (50.8 mg, 0.115 mmol, 9.83% yield) as a pale yellow solid. (TLC system: $R_f$: 02, :EtOAc), LCMS (m/z): 419.2 $[M+H]^+$.

$^1$H NMR (400 MHz, $CDCl_3$): δ ppm 13.34 (s, 1H), 8.25-8.11 (m, 2H), 7.69-7.61 (m, 1H), 7.34 (d, J=8.33 Hz, 1H), 6.98-6.90 (m, 1H), 5.98 (d, J=8.55 Hz, 1H), 5.61 (dd, J=6.14, 3.29 Hz, 1H), 4.02 (dd, J=11.18, 8.55 Hz, 1H), 3.82 (dd, J=11.29, 7.34 Hz, 1H), 3.70 (td, J=8.93, 4.28 Hz, 1H), 3.63-3.51 (m, 1H), 3.29-3.06 (m, 4H), 2.90 (dd, J=11.84, 3.29 Hz, 1H), 2.39-2.19 (m, 3H), 2.05-1.91 (m, 1H).

Example 299

Synthesis of (4S)-7-(2-methylpyridin-4-yl)-N-(9H-purin-6-yl)-3,4-dihydro-1,4-methano pyrido[2,3-b][1,4] diazepine-5(2H)-carboxamide

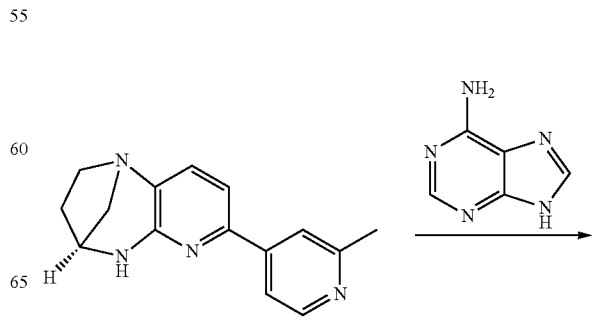

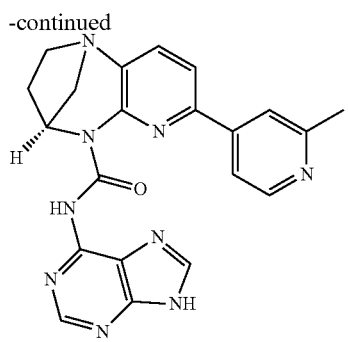

To a solution of (4S)-7-(2-methylpyridin-4-yl)-2,3,4,5-tetrahydro-1,4-methanopyrido[2,3-b][1,4]diazepine (1 g, 3.96 mmol) in Tetrahydrofuran (THF) (20 mL) triphosgene (0.588 g, 1.982 mmol) was added and stirred for 1 h. Triethylamine (2.76 mL, 19.82 mmol) was added followed by the addition of 9H-purin-6-amine (0.696 g, 5.15 mmol). The reaction mixture was stirred at 70° C. for 16 h. The reaction mixture was diluted with water and extracted with 2×25 ml of ethyl acetate. The combined organic layer was washed with brine solution, dried over anhydrous sodium sulfate and concentrated under reduced pressure to afford crude compound. The crude product was purified by flash column chromatography (100-200 silica gel eluted with 3% of CH$_2$Cl$_2$/MeOH) to afford the desired compound which was purified by prep HPLC to give (4S)-7-(2-methylpyridin-4-yl)-N-(9H-purin-6-yl)-3,4-dihydro-1,4-methanopyrido[2,3-b][1,4]diazepine-5(2H)-carboxamide (25 mg, 0.057 mmol, 1.449% yield) as a white solid. (TLC system: 5% Methanol in DCM. R$_f$ value: 0.3), LCMS (m/z): 411.9 [M+H]$^+$.

$^1$H NMR (400 MHz, DMSO-d$_6$): δ ppm 14.08 (br s, 1H), 12.32 (br s, 1H), 8.72 (s, 1H), 8.63 (d, J=5.04 Hz, 1H), 8.45 (s, 1H), 8.20 (br s, 1H), 7.99 (dd, J=5.48, 1.53 Hz, 1H), 7.90-7.81 (m, 1H), 7.81-7.74 (m, 1H), 5.57 (dd, J=5.70, 3.07 Hz, 1H), 3.27-3.07 (m, 3H), 3.02 (br dd, J=11.95, 3.18 Hz, 1H), 2.65 (s, 3H), 2.37-2.18 (m, 1H), 2.08 (br d, J=6.58 Hz, 1H).

Example 300

Synthesis of (4S)-7-(6-methylpyridin-3-yl)-N-(2,2,2-trifluoroethyl)-3,4-dihydro-1,4-methanopyrido[2,3-b][1,4]diazepine-5(2H)-carboxamide

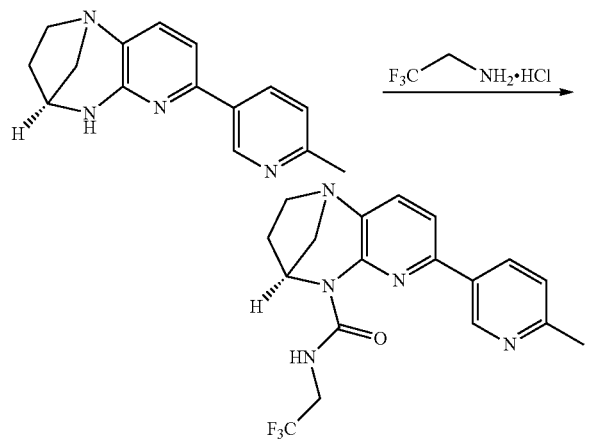

Triphosgene (212 mg, 0.74 mmol) was added slowly in portions to a stirred solution of (4S)-7-(6-methylpyridin-3-yl)-2,3,4,5-tetrahydro-1,4-methanopyrido[2,3-b][1,4]diazepine (300 mg, 1.190 mmol) in Tetrahydrofuran (THF) (15 mL) at RT and stirred for 30 min. DIPEA (0.622 mL, 3.571 mmol) and 2,2,2-trifluoroethanamine hydrochloride (242 mg, 1.785 mmol) were added to above reaction mixture, stirred at 70° C. for 16 h. The reaction mixture was cooled to room temperature, concentrated in vacuo and residue was partitioned between water (40 mL) and EtOAc (80 mL). Organic layer was separated and dried over anhydrous Na$_2$SO$_4$, filtered and filtrate was evaporated to get crude compound. The crude compound was purified by column chromatography using silica gel (100-200 mesh) 2% methanol in dichloromethane as a eluent to afford (4S)-7-(6-methylpyridin-3-yl)-N-(2,2,2-trifluoroethyl)-3,4-dihydro-1,4-methanopyrido[2,3-b][1,4]diazepine-5(2H)-carboxamide (235 mg, 0.615 mmol, 103% yield) as a pale yellow solid. (TLC eluent: 10% MeOH in DCM R$_f$: 0.5; UV active), LCMS (m/z) 378.31 [M+H]$^+$. $^1$H NMR (400 MHz, CDCl$_3$): δ ppm 11.12 (br t, J=6.03 Hz, 1H), 8.88 (d, J=1.97 Hz, 1H), 7.94 (dd, J=8.11, 2.41 Hz, 1H), 7.57 (d, J=7.89 Hz, 1H), 7.31-7.22 (m, 2H), 5.62 (dd, J=6.03, 3.18 Hz, 1H), 4.16-4.02 (m, 2H), 3.32-3.08 (m, 3H), 2.96 (dd, J=12.06, 3.29 Hz, 1H), 2.62 (s, 3H), 2.28 (dddd, J=14.06, 10.00, 6.08, 4.06 Hz, 1H), 2.09-1.97 (m, 1H)

Example 301

Synthesis of (4S)-7-(6-methylpyridin-3-yl)-N-(tetrahydro-2H-pyran-3-yl)-3,4-dihydro1,4-methanopyrido[2,3-b][1,4]diazepine-5(2H)-carboxamide

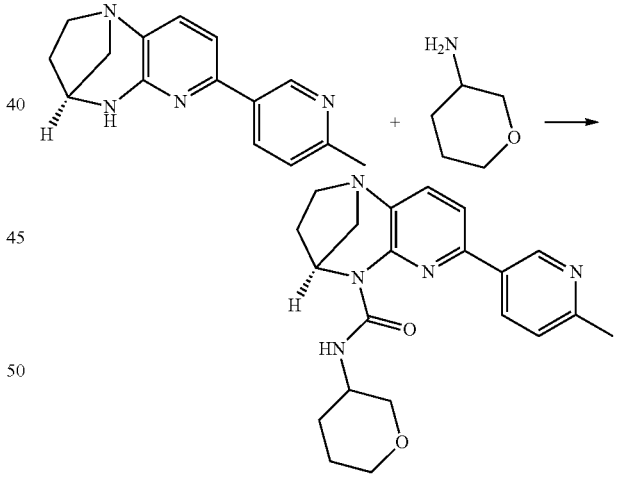

To a solution of (4S)-7-(6-methylpyridin-3-yl)-2,3,4,5-tetrahydro-1,4-methanopyrido[2,3-b][1,4]diazepine (300 mg, 1.189 mmol) in Tetrahydrofuran (THF) (10 mL) was added triphosgene (176 mg, 0.594 mmol) at 0° C. After 30 min DIPEA (1.038 mL, 5.94 mmol), tetrahydro-2H-pyran-3-amine (180 mg, 1.783 mmol) was added and the reaction mixture was stirred at 70° C. for 16 h. The reaction mixture was poured onto cold water (50 mL) and extracted with ethyl acetate (150 mL). The organic layer was dried over anhydrous sodium sulfate, concentrated under reduced pressure to yield crude compound. The crude product was purified by flash column chromatography (silica-gel: 100-200 mesh, eluent: 3% MeOH in DCM) to obtained (4S)-7-(6-methyl-pyridin-3-yl)-N-(tetrahydro-2H-pyran-3-yl)-3,4-dihydro-1,4-methanopyrido[2,3-b][1,4]diazepine-5(2H)-carboxamide (114.5 mg, 0.299 mmol, 25.1% yield) as an off white solid. (TLC system: $R_f$: 0.2, 5% MeOH-DCM), LCMS (m/z): 380.0 [M+H]$^+$.

$^1$H NMR (400 MHz, CDCl$_3$): δ ppm 10.59 (t, J=7.78 Hz, 1H), 8.92 (s, 1H), 8.07 (dt, J=8.11, 2.96 Hz, 1H), 7.52 (d, J=7.89 Hz, 1H), 7.27-7.17 (m, 2H), 5.66-5.59 (m, 1H), 4.10-4.00 (m, 1H), 3.86 (dt, J=11.24, 3.70 Hz, 1H), 3.71-3.62 (m, 2H), 3.53 (dd, J=11.18, 5.70 Hz, 1H), 3.28-3.06 (m, 3H), 2.97-2.89 (m, 1H), 2.60 (s, 3H), 2.24 (dddd, J=16.66, 9.98, 6.25, 3.51 Hz, 1H), 2.07-1.91 (m, 2H), 1.74-1.66 (m, 2H), 1.56-1.50 (m, 1H).

Example 302

Synthesis of (4S)-7-((R)-2-ethylmorpholino)-N-(pyrazin-2-yl)-3,4-dihydro-1,4-methanopyrido[2,3-b][1,4]diazepine-5(2H)-carboxamide

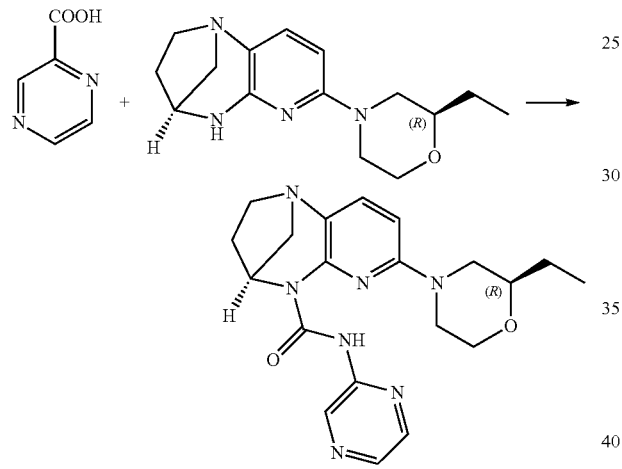

Diisopropylethylamine (2.81 mL, 16.12 mmol) was added to a stirred solution of pyrazine-2-carboxylic acid (400 mg, 3.22 mmol) in tetrahydrofuran (15 mL) stirred under argon at 30° C. Diphenylphosphorazidate (887 mg, 3.22 mmol) was added to the reaction mixture and was stirred for 2 h at 30° C. Then (2R)-2-ethyl-4-((4S)-2,3,4,5-tetrahydro-1,4-methanopyrido[2,3-b][1,4]diazepin-7-yl)morpholine (619 mg, 2.256 mmol) was added to the reaction mixture and stirred for 16 h at 65° C. The reaction mixture was cooled to room temp and was partitioned between water (20 mL) and ethyl acetate (2×30 mL). The organic layer was separated and was dried over anhydrous sodium sulfate, filtered and filtrate was evaporated to give crude. (TLC eluent: 90% Ethyl acetate in hexane, $R_f$=0.3; UV active). The crude was purified by column chromatography using neutral alumina and product was eluted with 10-15% ethyl acetate in hexane to afford pure (4S)-7-((R)-2-ethylmorpholino)-N-(pyrazin-2-yl)-3,4-dihydro-1,4-methanopyrido[2,3-b][1,4]diazepine-5(2H)-carboxamide (35 mg, 0.088 mmol, 2.75% yield) as an off-white solid, LCMS (m/z): 396.31 [M+H]$^+$.

$^1$H NMR (400 MHz, CDCl$_3$): δ ppm 13.37 (s, 1H), 9.55 (d, J=1.53 Hz, 1H), 8.25 (d, J=2.63 Hz, 1H), 8.09-8.18 (m, 1H), 7.38 (d, J=8.55 Hz, 1H), 6.30 (d, J=8.55 Hz, 1H), 5.63 (dd, J=6.03, 3.18 Hz, 1H), 4.00-4.13 (m, 2H), 3.86 (br d, J=12.93 Hz, 1H), 3.75 (td, J=11.62, 2.85 Hz, 1H), 3.45-3.56 (m, 1H), 3.13-3.30 (m, 1H), 3.00-3.17 (m, 3H), 2.92 (dd, J=11.84, 3.29 Hz, 1H), 2.69-2.81 (m, 1H), 2.27 (dddd, J=13.89, 9.95, 6.08, 3.62 Hz, 1H), 2.00 (dt, J=14.09, 6.88 Hz, 1H), 1.59-1.78 (m, 2H), 1.05 (t, J=7.45 Hz, 3H).

Example 303

Synthesis of (4S)-9-methyl-7-(6-methylpyridin-3-yl)-N-(pyridin-3-yl)-3,4-dihydro-1,4-methanopyrido[2,3-b][1,4]diazepine-5(2H)-carboxamide

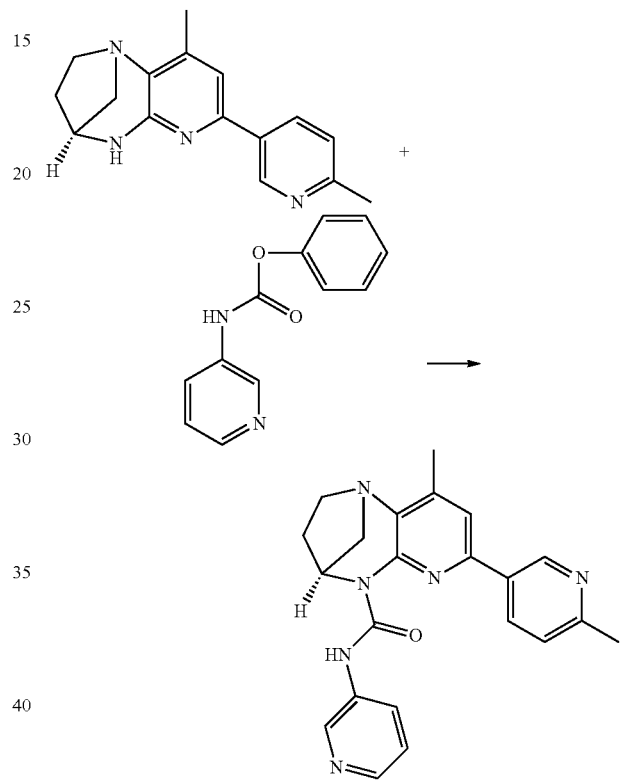

N,N-Dimethylaminopyridine (0.482 g, 3.94 mmol) was added to a stirred solution of of (4S)-9-methyl-7-(6-methylpyridin-3-yl)-2,3,4,5-tetrahydro-1,4-methanopyrido[2,3-b][1,4]diazep-ine (0.350 g, 1.314 mmol) and phenyl pyridin-3-ylcarbamate (0.845 g, 3.94 mmol) in tetrahydrofuran (20 mL) under nitrogen atmosphere at room temperature. The reaction was stirred at 65° C. for 48 hours. Reaction was cooled to room temperature and the solvent was removed under reduced pressure, and was partitioned between water (20 mL) and EtOAc (70 mL). Organic layer was separated and was dried over anhydrous Na$_2$SO$_4$, filtered and filtrate was evaporated to give crude as brown solid (TLC eluent: 100% EtOAc: $R_f$-0.3; UV active). Added ethyl acetate to reaction mass and stirred for 10 minutes. Filtered the reaction mass and washed with EtOAc. Filtrate was concentrated to get brown solid (TLC eluent: 100% EtOAc: $R_f$-0.2; UV active). The crude was purified by column chromatography using neutral alumina and was eluted with 60% EtOAc in hexane to afford pure (4S)-9-methyl-7-(6-methylpyridin-3-yl)-N-(pyridin-3-yl)-3,4-dihydro-1,4-methanopyrido[2,3-b][1,4] diazepine-5(2H)-carboxamide (0.115 g, 0.296 mmol, 22.56% yield) as a white solid, LCMS (m/z) 387.3 [M+H]$^+$.

¹H NMR (400 MHz, CDCl₃): δ ppm 13.29 (s, 1H), 8.92 (d, J=1.97 Hz, 1H), 8.53 (d, J=2.19 Hz, 1H), 8.28 (br d, J=3.51 Hz, 1H), 8.19 (br d, J=8.33 Hz, 1H), 7.99 (dd, J=8.00, 2.30 Hz, 1H), 7.32 (d, J=7.89 Hz, 1H), 7.22-7.29 (m, 1H), 7.19 (s, 1H), 5.68 (dd, J=5.92, 3.07 Hz, 1H), 3.17 (t, J=7.34 Hz, 2H), 3.07-3.13 (m, 1H), 2.97-3.05 (m, 1H), 2.64 (s, 3H), 2.50 (s, 3H), 2.32 (td, J=13.76, 6.47 Hz, 1H), 1.99-2.14 (m, 1H)

Example 304

Synthesis of (4S)-7-(3-methyl-1H-pyrazol-5-yl)-N-(pyrazin-2-yl)-3,4-dihydro-1,4-methanopyrido[2,3-b][1,4]diazepine-5(2H)-carboxamide

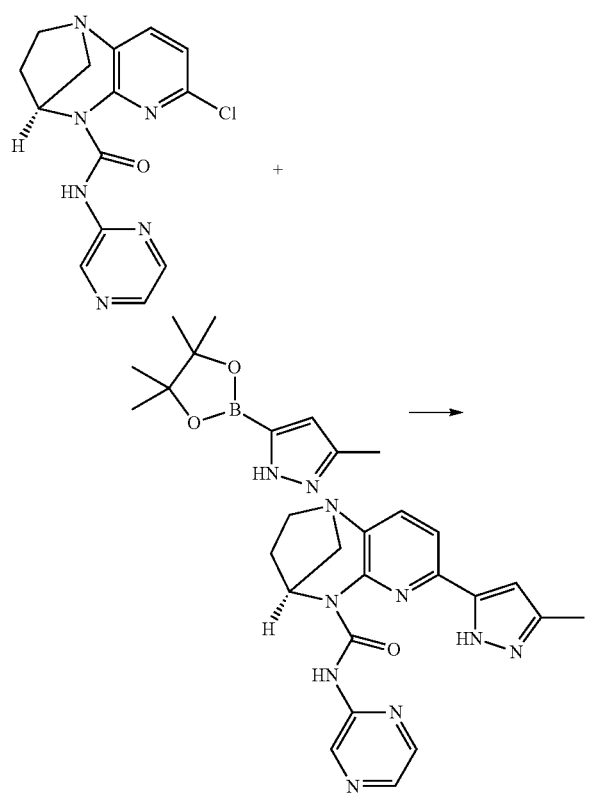

Tripotassium phosphate (469 mg, 2.210 mmol) was added to a stirred solution of (4S)-7-chloro-N-(pyrazin-2-yl)-3,4-dihydro-1,4-methanopyrido[2,3-b][1,4]diazepine-5(2H)-carboxamide (350.0 mg, 1.105 mmol), 3-methyl-5-(4,4,5,5-tetramethyl-1,3,2-dioxaborolan-2-yl)-1H-pyrazole (276 mg, 1.326 mmol) in 1,4-dioxane (10.0 ml) and water (2.0 ml) at 28° C. The reaction mixture was degassed for 15 min, to this was added X-phos (52.7 mg, 0.110 mmol) and Pd₂(dba)₃ (50.6 mg, 0.055 mmol). The reaction mixture was further degassed for 15 min and the was stirred for 16 hours at 100° C. Then the mixture was cooled to 28° C. and was filtered through a pad of celite and was washed with ethyl acetate (40 ml). The filtrate was washed with the water (10 ml). Organic layer was separated and was dried over anhydrous Na₂SO₄, filtered and filtrate was evaporated to give crude as brown solid (TLC eluent: 10% MeOH in DCM; R_f-0.3; UV active). This crude was purified by grace column and was eluted with 2-5% MeOH in dichloromethane to afford pure (4S)-7-(3-methyl-1H-pyrazol-5-yl)-N-(pyrazin-2-yl)-3,4-dihydro-1,4-methanopyrido[2,3-b][1,4]diazepine-5(2H)-carboxamide (181.5 mg, 0.492 mmol, 44.5% yield) as white solid, LCMS (m/z): 363.27 [M+H]⁺.

¹H NMR (400 MHz, CDCl₃): δ 13.80 (s, 1H), 9.55 (d, J=1.10 Hz, 1H), 8.52 (s, 1H), 8.20-8.35 (m, 2H), 7.55 (d, J=8.11 Hz, 1H), 7.12 (d, J=7.89 Hz, 1H), 5.68 (dd, J=5.92, 3.29 Hz, 1H), 3.11-3.34 (m, 3H), 2.89-3.11 (m, 1H), 2.60 (s, 3H), 2.33 (dddd, J=14.06, 9.95, 5.92, 4.06 Hz, 1H), 1.97-2.17 (m, 1H)

Example 305

Synthesis of (4S)—N-isopropyl-7-(6-methylpyridin-3-yl)-3,4-dihydro-1,4-methanopyrido[2,3-b][1,4]diazepine-5(2H)-carboxamide

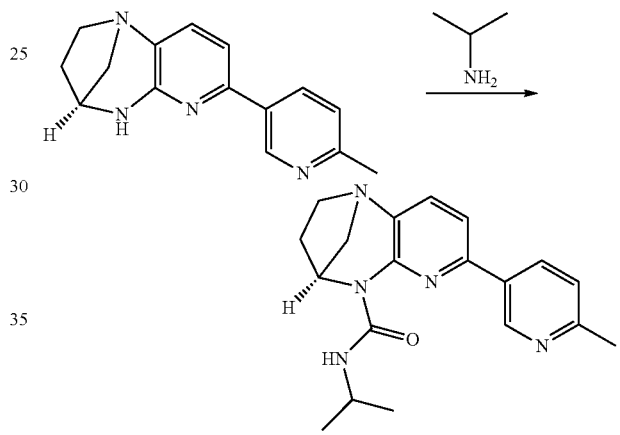

DIPEA (1.038 mL, 5.94 mmol) and followed by triphosgene (353 mg, 1.189 mmol) were added to a stirred solution of (4S)-7-(6-methylpyridin-3-yl)-2,3,4,5-tetrahydro-1,4-methanopyrido[2,3-b][1,4]diazepine (500 mg, 1.982 mmol) in THF (15 mL, in sealed tube) at 0° C. and then stirred at RT for 30 min. Then propan-2-amine (176 mg, 2.97 mmol) was added and heated to 75° C. for 16 h. The reaction mixture was cooled to RT and was partitioned between water (25 mL) and EtOAc (60 mL). Organic layer was separated and was dried over anhydrous Na₂SO₄, filtered and filtrate was evaporated to obtain the crude compound. The crude mixture was purified by flash column chromatography (silica-gel: 100-200 mesh, eluent: 2% MeOH in DCM) to afford the (4S)—N-isopropyl-7-(6-methylpyridin-3-yl)-3,4-dihydro-1,4-methanopyrido[2,3-b][1,4]diazepine-5(2H)-carboxamide (130 mg, 0.384 mmol, 19.39% yield) as an off white solid (TLC eluent: 5% MeOH in DCM, R_f: 0.3), LCMS (m/z): 338.32 [M+H]⁺.

¹H NMR (400 MHz, CDCl₃): δ ppm 10.38 (d, J=6.4 Hz, 1H), 8.91 (d, J=2 Hz, 1H), 7.94 (dd, J=2.4, 8 Hz, 1H), 7.52 (d, J=5.6 Hz, 1H), 7.25-7.20 (m, 2H), 5.66-5.62 (m, 1H), 4.14-4.06 (m, 1H), 3.26-3.06 (m, 3H), 2.97-2.92 (m, 1H), 2.62 (s, 3H), 2.30-2.21 (m, 1H), 2.26-1.98 (m, 1H), 1.27 (d, J=6.8 Hz, 6H)

Example 306

Synthesis of (4S)—N-(1-methylpiperidin-4-yl)-7-(6-methylpyridin-3-yl)-3,4-dihydro-1,4-methanopyrido[2,3-b][1,4]diazepine-5(2H)-carboxamide

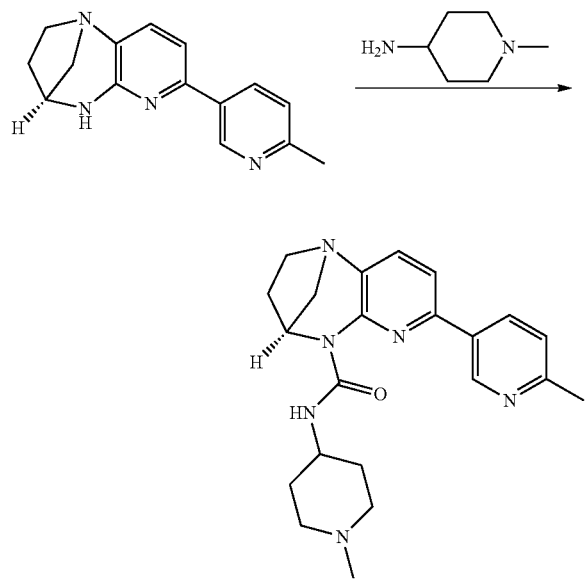

Triphosgene (423.8 mg, 1.428 mmol) was added slowly in portions to a stirred solution of (4S)-7-(6-methylpyridin-3-yl)-2,3,4,5-tetrahydro-1,4-methanopyrido[2,3-b][1,4]diazepine (600 mg, 2.380 mmol) in Tetrahydrofuran (THF) (25 mL) at RT and stirred for 30 min.

DIPEA (1.24 mL, 7.14 mmol) and 1-methylpiperidin-4-amine (408 mg, 3.571 mmol) were added to the reaction mixture, stirred at 70° C. for 16 h. The reaction mixture was cooled to room temperature, concentrated in vacuo and residue was partitioned between water (40 mL) and EtOAc (80 mL). Organic layer was separated and dried over anhydrous $Na_2SO_4$, filtered and filtrate was evaporated to get crude compound. The crude compound was purified by column chromatography using silica gel (100-200 mesh) 2% methanol in dichloromethane as a eluent to afford (4S)—N-(1-methylpiperidin-4-yl)-7-(6-methylpyridin-3-yl)-3,4-dihydro-1,4-methanopyrido[2,3-b][1,4]diazepine-5(2H)-carboxamide (100 mg, 0.252 mmol, 21.21% yield) as a off white solid as a pale yellow solid. (TLC eluent: 10% MeOH in DCM $R_f$: 0.4; UV active), LCMS (m/z): 393.33 [M+H]$^+$. $^1$H NMR (400 MHz, CDCl$_3$): δ ppm 10.46 (br d, J=7.45 Hz, 1H), 8.88 (d, J=2.19 Hz, 1H), 7.92 (dd, J=8.11, 2.41 Hz, 1H), 7.53 (d, J=7.89 Hz, 1H), 7.29-7.24 (m, 1H), 7.20 (d, J=7.89 Hz, 1H), 5.62 (dd, J=5.92, 3.29 Hz, 1H), 3.82-3.73 (m, 1H), 3.12-3.26 (m, 2H), 3.12-3.06 (m, 1H), 2.94 (dd, J=11.84, 3.29 Hz, 1H), 2.85-2.78 (m, 1H), 2.86-2.77 (m, 1H), 2.62 (s, 3H), 2.30-2.22 (m, 4H), 2.15-1.98 (m, 5H), 1.65-1.53 (m, 2H)

Example 307

Synthesis of (4S)-7-((2R,6R)-2,6-dimethylmorpholino)-N-(pyrazin-2-yl)-3,4-dihydro-1,4-methanopyrido[2,3-b][1,4]diazepine-5(2H)-carboxamide

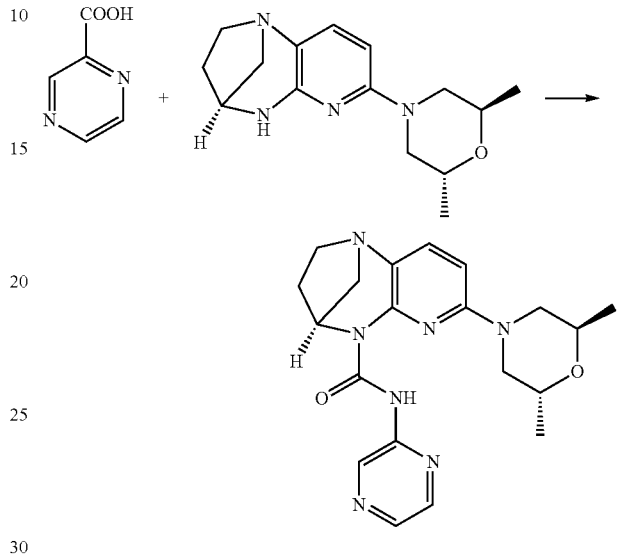

Diphenyl phosphorazidate (0.432 g, 1.571 mmol) was added to a stirred solution of pyrazine-2-carboxylic acid (0.195 g, 1.571 mmol) and DIPEA (1.372 mL, 7.86 mmol) in tetrahydrofuran (30 mL) under argon atmosphere at room temp. The reaction mixture was stirred for 2 h at room temp and subsequently (2R,6R)-2,6-dimethyl-4-((4S)-2,3,4,5-tetrahydro-1,4-methanopyrido[2,3-b][1,4]diazepin-7-yl)morpholine (0.302 g, 1.100 mmol) was added and the reaction mixture was stirred 16 h at 65° C. The reaction mixture was cooled to room temp and the solvent was evaporated under reduced pressure completely, and was partitioned between water (20 mL) and EtOAc (60 mL). Organic layer was separated, dried over anhydrous $Na_2SO_4$, filtered and filtrate was evaporated to give crude as brown solid (TLC eluent: 100% EtOAc: $R_f$-0.3; UV active). The crude was purified by column chromatography using neutral aluminia and was eluted with 20% EtOAc in Hexane to afford pure afford (4S)-7-((2R,6R)-2,6-dimethylmorpholino)-N-(pyrazin-2-yl)-3,4-dihydro-1,4-methanopyrido[2,3-b][1,4]diazepine-5(2H)-carboxamide (0.081 g, 0.203 mmol, 12.93% yield) as a white solid, LCMS (m/z): 396.38 [M+H]$^+$.

$^1$H NMR (400 MHz, cdcl3-d) δ ppm 13.42 (s, 1H), 9.56 (d, J=1.32 Hz, 1H), 8.25 (d, J=2.63 Hz, 1H), 8.09-8.19 (m, 1H), 7.37 (d, J=8.55 Hz, 1H), 6.24 (d, J=8.55 Hz, 1H), 5.63 (dd, J=6.03, 3.18 Hz, 1H), 4.28-4.15 (m, 2H), 3.67 (dd, J=12.39, 3.40 Hz, 2H), 3.32-3.19 (m, 3H), 3.17-3.06 (m, 2H), 2.92 (dd, J=11.84, 3.29 Hz, 1H), 2.27 (dddd, J=13.95, 10.00, 6.19, 3.84 Hz, 1H), 2.00 (dt, J=14.09, 7.10 Hz, 1H), 1.34 (d, J=6.36 Hz, 6H)

Example 308

Synthesis of (4S)-7-(1-(difluoromethyl)-1H-pyrazol-4-yl)-N-(pyrazin-2-yl)-3,4-dihydro-1,4-methanopyrido[2,3-b][1,4]diazepine-5(2H)-carboxamide

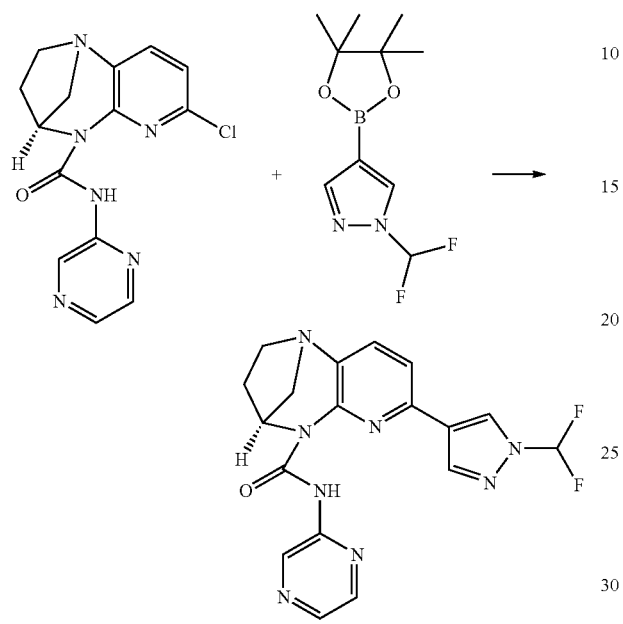

Tripotassium phosphate (469 mg, 2.210 mmol) was added to a stirred solution of (4S)-7-chloro-N-(pyrazin-2-yl)-3,4-dihydro-1,4-methanopyrido[2,3-b][1,4]diazepine-5(2H)-carboxamide (350 mg, 1.105 mmol), 1-(difluoromethyl)-4-(4,4,5,5-tetramethyl-1,3,2-dioxaborolan-2-yl)-1H-pyrazole (324 mg, 1.326 mmol) in 1,4-dioxane (10.0 ml) and water (2.0 ml). The reaction mixture was degassed for 10 min. $Pd_2(dba)_3$ (50.6 mg, 0.055 mmol) and X-phos (52.7 mg, 0.110 mmol) were added to the reaction mixture and was further degassed for 15 min. The reaction mixture was stirred for 16 hours at 100° C. The reaction mixture was cooled to 28° C. and was filtered through a pad of celite and was washed with ethyl acetate (40 ml). The filtrate was washed with the water (10 ml). Organic layer was separated and was dried over anhydrous $Na_2SO_4$, filtered and filtrate was evaporated to give crude as brown solid (TLC eluent: 10% MeOH in DCM: $R_f$-0.4; UV active). The crude was purified by grace column and was eluted with 1-2% MeOH in dichloromethane to afford pure (4S)-7-(1-(difluoromethyl)-1H-pyrazol-4-yl)-N-(pyrazin-2-yl)-3,4-dihydro-1,4-methanopyrido[2,3-b][1,4]diazepine-5(2H)-carboxamide (280.0 mg, 0.702 mmol, 63.6% yield) as white solid, LCMS (m/z): 399.30 $[M+H]^+$.

$^1H$ NMR (400 MHz, $CDCl_3$): δ 14.18 (s, 1H), 9.55 (d, J=1.3 Hz, 1H), 9.17 (s, 1H), 8.36-8.27 (m, 2H), 8.22 (s, 1H), 7.56 (d, J=7.9 Hz, 1H), 7.26-7.06 (m, 2H), 5.66 (dd, J=5.9, 3.3 Hz, 1H), 3.35-3.11 (m, 3H), 3.01 (dd, J=12.3, 3.3 Hz, 1H), 2.34 (dddd, J=14.1, 9.8, 6.0, 4.06 Hz, 1H), 1.93-2.17 (m, 1H).

Example 309

Synthesis of (4S)-7-(6-(dimethylamino)-4-methylpyridin-3-yl)-N-(pyridin-2-yl)-3,4-dihydro-1,4-methanopyrido[2,3-b][1,4]diazepine-5(2H)-carboxamide

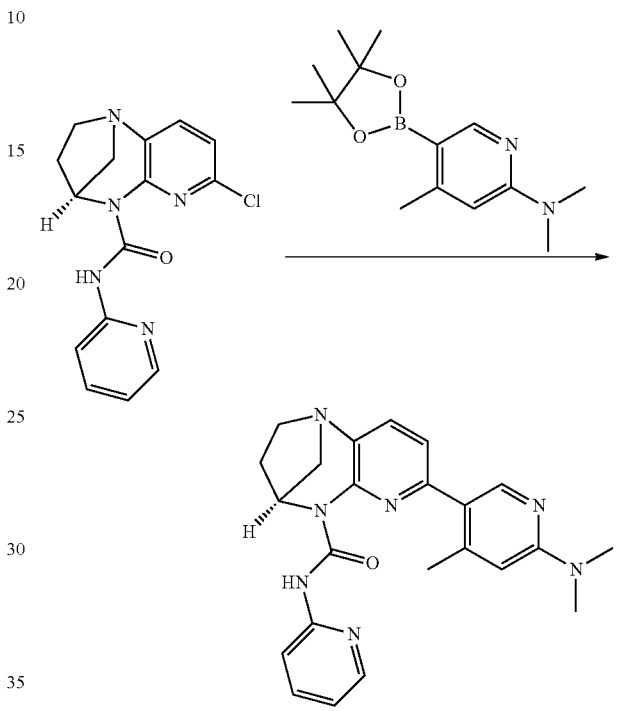

N,N,4-trimethyl-5-(4,4,5,5-tetramethyl-1,3,2-dioxaborolan-2-yl)pyridin-2-amine (274 mg, 1.045 mmol) followed by $K_3PO_4$ (605 mg, 2.85 mmol) were added to a stirred solution of (4S)-7-chloro-N-(pyridin-2-yl)-3,4-dihydro-1,4-methanopyrido[2,3-b][1,4]diazepine-5(2H)-carboxamide (300 mg, 0.950 mmol) in 1-Butanol (10 mL) at RT and degassed for 20 min. Then $Pd_2(dba)_3$ (43.5 mg, 0.048 mmol) and X-phos (45.3 mg, 0.095 mmol) were added to the reaction mixture and the reaction mixture was stirred at 80° C. for 16 h. The reaction mixture was cooled to room temperature and was partitioned between water (25 mL) and EtOAc (40 mL). Organic layer was separated and dried over anhydrous $Na_2SO_4$, filtered and filtrate was evaporated to get crude compound. The crude compound was purified by column chromatography (silica gel: 100-200 mesh), compound was collected at 70% EtOAc in pet ether to obtained (4S)-7-(6-(dimethylamino)-4-methylpyridin-3-yl)-N-(pyridin-2-yl)-3,4-dihydro-1,4-methanopyrido[2,3-b][1,4]diazepine-5(2H)-carboxamide (100 mg, 0.236 mmol, 24.80% yield) as an off-white solid. (TLC eluent: 100% EtOAc in pet ether $R_f$: 0.4, UV active), LCMS (m/z): 416.3 $[M+H]^+$.

$^1H$ NMR (400 MHz, $CDCl_3$) δ ppm 13.31 (s, 1H), 8.36-8.17 (m, 3H), 8.17-7.96 (m, 1H), 7.86-7.57 (m, 1H), 6.99 (d, J=7.89 Hz, 1H), 6.95-6.68 (m, 1H), 6.43 (s, 1H), 5.69 (brdd, J=5.59, 3.18 Hz, 1H), 3.31 (br d, J=8.77 Hz, 1H), 3.24-3.10 (m, 8H), 3.10-2.87 (m, 1H), 2.47 (s, 3H), 2.40-2.20 (m, 1H), 2.19-1.92 (m, 1H)

Example 310

Synthesis of (4S)-7-(6-(piperidin-1-yl)pyridin-3-yl)-N-(pyridin-2-yl)-3,4-dihydro-1,4-methanopyrido[2,3-b][1,4]diazepine-5(2H)-carboxamide

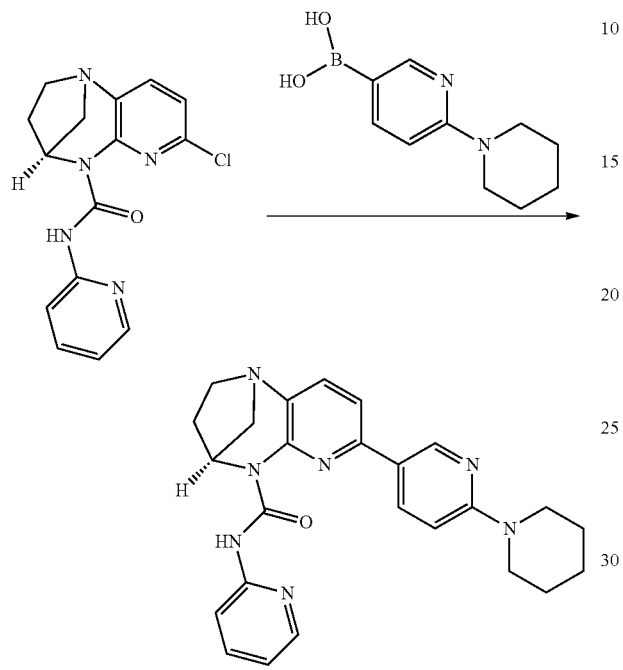

(6-(piperidin-1-yl)pyridin-3-yl)boronic acid (215 mg, 1.045 mmol) followed by $K_3PO_4$ (605 mg, 2.85 mmol) were added to a stirred solution of (4S)-7-chloro-N-(pyridin-2-yl)-3,4-dihydro-1,4-methanopyrido[2,3-b][1,4]diazepine-5(2H)-carboxamide (300 mg, 0.950 mmol) in 1-Butanol (10 mL) at RT and degassed for 20 min. Then $Pd_2(dba)_3$ (43.5 mg, 0.048 mmol) and X-phos (45.3 mg, 0.095 mmol) were added to the reaction mixture and the reaction mixture was stirred at 80° C. for 16 h. The reaction mixture was cooled to room temperature and was partitioned between water (25 mL) and EtOAc (40 mL). Organic layer was separated and dried over anhydrous $Na_2SO_4$, filtered and filtrate was evaporated to get crude compound. The crude compound was purified by column chromatography (silica gel: 100-200 mesh), compound was collected at 70% EtOAc in pet ether to obtain (4S)-7-(6-(piperidin-1-yl)pyridin-3-yl)-N-(pyridin-2-yl)-3,4-dihydro-1,4-methanopyrido[2,3-b][1,4]diazepine-5(2H)-carboxamide (150 mg, 0.336 mmol, 35.3% yield) as a pale yellow solid. (TLC eluent: 100% EtOAc in pet ether, $R_f$: 0.4, UV active), LCMS (m/z): 442.3 $[M+H]^+$.

$^1$H NMR (400 MHz, $CDCl_3$) δ ppm 13.71 (s, 1H), 8.80 (d, J=2.63 Hz, 1H), 8.54 (dd, J=8.99, 2.63 Hz, 1H), 8.37 (dt, J=4.93, 0.82 Hz, 1H), 8.18 (d, J=8.33 Hz, 1H), 7.78-7.59 (m, 1H), 7.51 (d, J=8.11 Hz, 1H), 7.30-7.25 (m, 1H), 6.97 (ddd, J=7.23, 4.82, 0.88 Hz, 1H), 6.79 (d, J=8.99 Hz, 1H), 5.68 (dd, J=5.92, 3.29 Hz, 1H), 3.70-3.59 (m, 4H), 3.09-3.32 (m, 3H), 3.09-2.84 (m, 1H), 2.31 (d, J=1.97 Hz, 1H), 2.17-1.95 (m, 1H), 1.68 (br s, 6H).

Example 311

Synthesis of (4S)—N-(tert-butyl)-7-(6-methylpyridin-3-yl)-3,4-dihydro-1,4-methanopyrido[2,3-b][1,4]diazepine-5(2H)-carboxamide

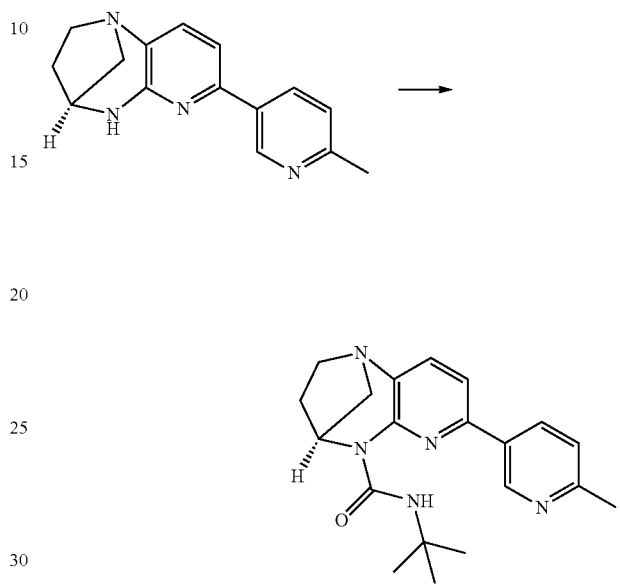

DIPEA (1.038 mL, 5.94 mmol) followed by triphosgene (353 mg, 1.189 mmol) were added to a solution of (4S)-7-(6-methylpyridin-3-yl)-2,3,4,5-tetrahydro-1,4-methanopyrido[2,3-b][1,4] diazepine (500 mg, 1.982 mmol) in Tetrahydrofuran (15 mL) at RT and stirred it for 30 min. Then 2-methylpropan-2-amine (217 mg, 2.97 mmol) was added and heated to 75° C. for 16 h. The reaction mixture was cooled to 28° C. and was partitioned between water (25 mL) and EtOAc (60 mL). The separated organic layer was dried over anhydrous $Na_2SO_4$, filtered and filtrate was evaporated to obtain the crude compound. The crude mixture was purified by flash column chromatography (silica-gel: 100-200 mesh, eluent: 2% MeOH in DCM) to afford the (4S)—N-(tert-butyl)-7-(6-methylpyridin-3-yl)-3,4-dihydro-1,4-methanopyrido[2,3-b] [1,4] diazepine-5(2H)-carboxamide (185 mg, 0.525 mmol, 26.5% yield) as an off white solid (TLC eluent: 5% MeOH in DCM, $R_f$: 0.3; UV active), LCMS (m/z): 352.34 $[M+H]^+$.

$^1$H NMR (400 MHz, $CDCl_3$-d): δ ppm 10.4 (s, 1H), 8.90 (d, J=2 Hz, 1H), 7.95 (dd, J=2.4 Hz, 8 Hz, 1H), 7.51 (d, J=7.6 Hz, 1H), 7.22 (d, J=8 Hz, 1H), 7.17 (d, J=8 Hz, 1H), 5.64-5.61 (m, 1H), 3.28-3.12 (m, 2H), 3.10-3.05 (m, 1H), 2.96-2.91 (m, 1H), 2.61 (s, 3H), 2.30-2.21 (m, 1H), 2.06-1.97 (m, 1H,), 1.43 (s, 9H).

Example 312

Synthesis of (4S)—N-(pyridin-2-yl)-7-(2-(pyrrolidin-1-yl)pyrimidin-5-yl)-3,4-dihydro-1,4-methanopyrido[2,3-b][1,4]diazepine-5(2H)-carboxamide

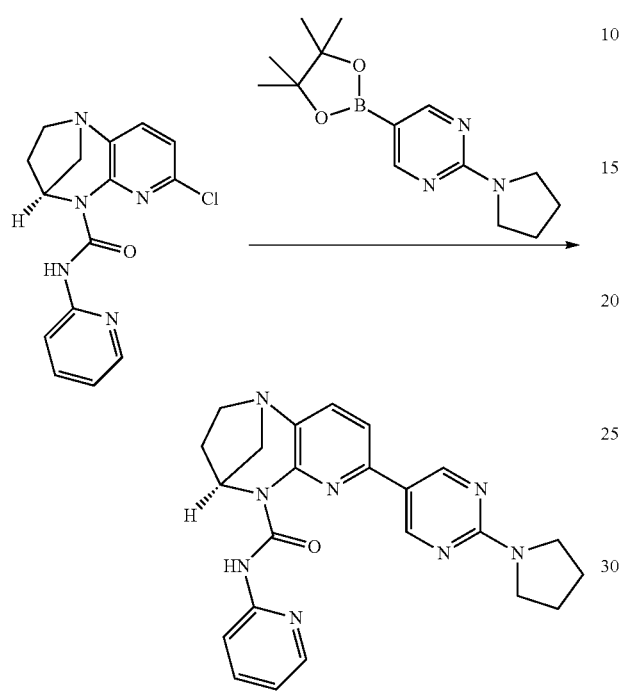

2-(pyrrolidin-1-yl)-5-(4,4,5,5-tetramethyl-1,3,2-dioxaborolan-2-yl)pyrimidine (288 mg, 1.045 mmol) followed by $K_3PO_4$ (605 mg, 2.85 mmol) were added to a stirred solution of (4S)-7-chloro-N-(pyridin-2-yl)-3,4-dihydro-1,4-methanopyrido[2,3-b][1,4]diazepine-5(2H)-carboxamide (300 mg, 0.950 mmol) in 1-Butanol (10 mL) at RT and degassed for 20 min. Then $Pd_2(dba)_3$ (43.5 mg, 0.048 mmol) and X-phos (45.3 mg, 0.095 mmol) were added to the reaction mixture and the reaction mixture was stirred at 80° C. for 16 h. The reaction mixture was cooled to room temperature and was partitioned between water (25 mL) and EtOAc (40 mL). Organic layer was separated and dried over anhydrous $Na_2SO_4$, filtered and filtrate was evaporated to get crude compound. The crude compound was purified by column chromatography (silica gel: 100-200 mesh), compound was collected at 70% EtOAc in pet ether to obtain (4S)—N-(pyridin-2-yl)-7-(2-(pyrrolidin-1-yl)pyrimidin-5-yl)-3,4-dihydro-1,4-methanopyrido[2,3-b][1,4]diazepine-5(2H)-carboxamide (170 mg, 0.377 mmol, 39.7% yield) as a yellow solid. (TLC eluent: 100% EtOAc in pet ether, $R_f$: 0.4, UV active), LCMS (m/z): 429.6 [M+H]$^+$.

$^1$H NMR (400 MHz, CDCl$_3$) δ ppm 13.57 (s, 1H), 9.09 (s, 2H), 8.51-8.26 (m, 1H), 8.14 (d, J=8.33 Hz, 1H), 7.67 (td, J=7.84, 1.86 Hz, 1H), 7.54 (m, J=8.11 Hz, 1H), 7.26 (s, 1H), 6.97 (ddd, J=7.29, 4.88, 0.99 Hz, 1H), 5.68 (dd, J=5.81, 3.18 Hz, 1H), 3.75-3.60 (m, 4H), 3.35-3.09 (m, 3H), 2.99 (dd, J=12.06, 3.29 Hz, 1H), 2.32 (m, 1H), 1.98-2.13 (m, 5H)

Example 313

Synthesis of (4S)-7-(6-(diethylamino)pyridin-3-yl)-N-(pyridin-2-yl)-3,4-dihydro-1,4-methanopyrido[2,3-b][1,4]diazepine-5(2H)-carboxamide

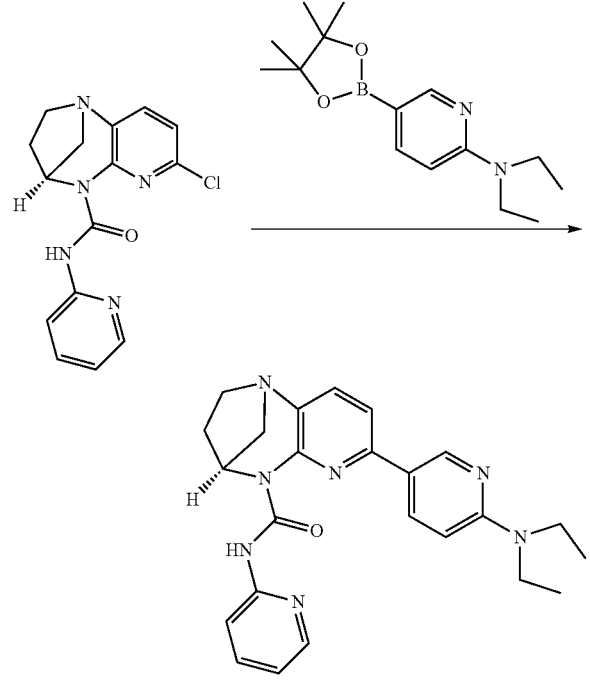

N,N-diethyl-5-(4,4,5,5-tetramethyl-1,3,2-dioxaborolan-2-yl)pyridin-2-amine (289 mg, 1.045 mmol) followed by $K_3PO_4$ (605 mg, 2.85 mmol) were added to a stirred solution of (4S)-7-chloro-N-(pyridin-2-yl)-3,4-dihydro-1,4-methanopyrido[2,3-b][1,4]diazepine-5(2H)-carboxamide (300 mg, 0.950 mmol) in 1-Butanol (10 mL) at RT and degassed for 20 min. Then $Pd_2(dba)_3$ (43.5 mg, 0.048 mmol) and X-phos (45.3 mg, 0.095 mmol) were added to the reaction mixture and the reaction mixture was stirred at 80° C. for 16 h. The reaction mixture was cooled to room temperature and was partitioned between water (25 mL) and EtOAc (40 mL). Organic layer was separated and dried over anhydrous $Na_2SO_4$, filtered and filtrate was evaporated to get crude compound. The crude compound was purified by column chromatography (silica gel: 100-200 mesh), compound was collected at 70% EtOAc in pet ether to obtain (4S)-7-(6-(diethylamino)pyridin-3-yl)-N-(pyridin-2-yl)-3,4-dihydro-1,4-methanopyrido[2,3-b][1,4]diazepine-5(2H)-carboxamide (120 mg, 0.271 mmol, 28.5% yield) as an off-white solid. (TLC eluent: 100% EtOAc in pet ether, $R_f$: 0.4, UV active), LCMS (m/z): 430.3 [M+H]$^+$. $^1$H NMR (400 MHz, CDCl$_3$) δ ppm 13.77 (s, 1H), 8.78 (d, J=2.41 Hz, 1H), 8.64-8.43 (m, 1H), 8.43-8.28 (m, 1H), 8.18 (d, J=8.55 Hz, 1H), 7.75-7.59 (m, 1H), 7.51 (d, J=8.11 Hz, 1H), 7.39-7.15 (m, 1H), 6.97 (ddd, J=7.34, 4.93, 0.88 Hz, 1H), 6.62 (d, J=8.99 Hz, 1H), 5.68 (dd, J=5.92, 3.07 Hz, 1H), 3.69-3.50 (m, 4H), 3.34-3.08 (m, 3H), 3.08-2.89 (m, 1H), 2.39-2.19 (m, 1H), 2.08 (dt, J=13.87, 6.77 Hz, 1H), 1.24 (t, J=7.02 Hz, 6H)

Example 314

Synthesis of (4S)-7-(6-morpholinopyridin-3-yl)-N-(pyridin-2-yl)-3,4-dihydro-1,4-methanopyrido[2,3-b][1,4]diazepine-5(2H)-carboxamide

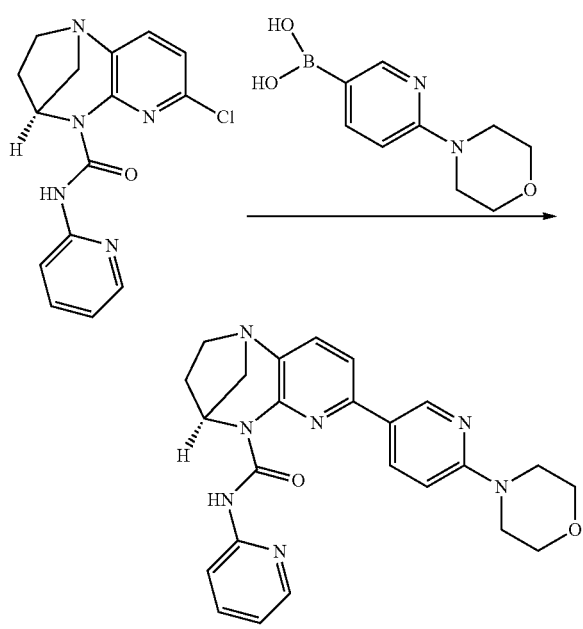

(6-morpholinopyridin-3-yl)boronic acid (296 mg, 1.425 mmol) followed by K₃PO₄ (605 mg, 2.85 mmol) were added to a stirred solution of (4S)-7-chloro-N-(pyridin-2-yl)-3,4-dihydro-1,4-methanopyrido[2,3-b][1,4]diazepine-5(2H)-carboxamide (300 mg, 0.950 mmol) in 1-Butanol (10 mL) at RT and degassed for 20 min. Then Pd$_2$(dba)$_3$ (43.5 mg, 0.048 mmol) and X-phos (45.3 mg, 0.095 mmol) were added to the reaction mixture and the reaction mixture was stirred at 80° C. for 16 h. The reaction mixture was cooled to room temperature and was partitioned between water (25 mL) and EtOAc (40 mL). Organic layer was separated and dried over anhydrous Na$_2$SO$_4$, filtered and filtrate was evaporated to get crude compound. The crude compound was purified by column chromatography (silica gel: 100-200 mesh), compound was collected at 70% EtOAc in pet ether to obtain (4S)-7-(6-morpholinopyridin-3-yl)-N-(pyridin-2-yl)-3,4-dihydro-1,4-methanopyrido[2,3-b][1,4]diazepine-5(2H)-carboxamide (110 mg, 0.245 mmol, 25.8% yield) as an off-white solid. (TLC eluent: 100% EtOAc in pet ether, R$_f$: 0.4, UV active), LCMS (m/z): 444.3 [M+H]⁺.

¹H NMR (400 MHz, CDCl$_3$-d) δ ppm 13.68 (s, 1H), 8.85 (s, 1H), 8.56-8.64 (m, 1H), 8.36 (d, J=3.73 Hz, 1H), 8.19 (d, J=8.33 Hz, 1H), 7.68 (t, J=7.13 Hz, 1H), 7.54 (d, J=8.11 Hz, 1H), 7.32 (s, 1H), 7.02-6.95 (m, 1H), 6.78 (d, J=8.99 Hz, 1H), 5.68 (dd, J=5.70, 3.07 Hz, 1H), 3.91-3.83 (m, 4H), 3.70-3.60 (m, 4H), 3.34-3.14 (m, 3H), 2.99 (dd, J=11.95, 3.18 Hz, 1H), 2.42-2.26 (m, 1H), 2.08 (dt, J=13.87, 7.21 Hz, 1H).

Example 315

Synthesis of (4S)—N-(pyrazin-2-yl)-7-(2H-tetrazol-5-yl)-3,4-dihydro-1,4-methanopyrido[2,3-b][1,4]diazepine-5(2H)-carboxamide

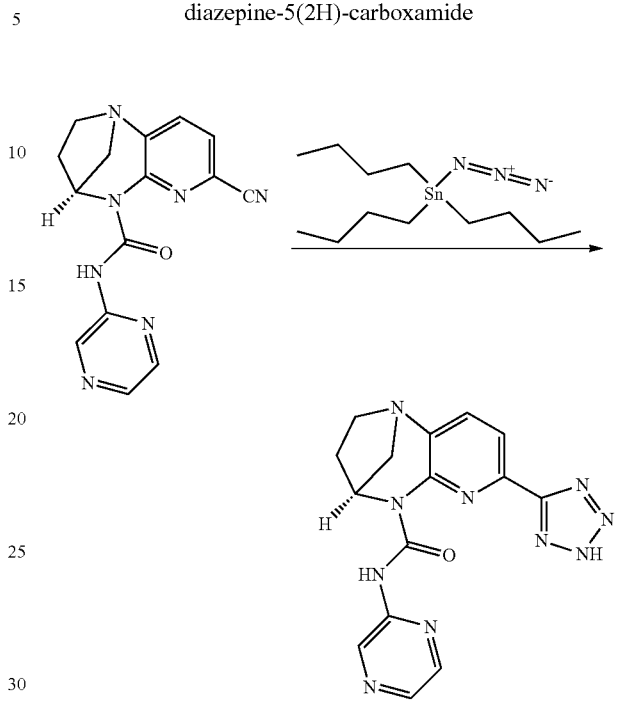

Azidotributylstannane (1.297 g, 3.90 mmol) was added to a stirred solution of (4S)-7-cyano-N-(pyrazin-2-yl)-3,4-dihydro-1,4-methanopyrido[2,3-b][1,4]diazepine-5(2H)-carboxamide (0.4 g, 1.302 mmol) in tetrahydrofuran (25 mL) and heated to 80-90° C. for 48 h in sealed tube. The reaction mixture was cooled to room temperature. Tetrahydrofuran was concentrated under reduced pressure to obtain residue. The residue was diluted with dichloromethane (100 mL). The organic layer was washed with 50 mL of 0.5M HCl, water (50 mL) and brine (50 mL). The organic layer was dried over anhydrous sodium sulfate, filtered and evaporated to obtain crude (TLC eluent: 10% MeOH in DCM; UV active; R$_f$-0.3). The crude compound was triturated with diethyl ether and filtered to afford (4S)—N-(pyrazin-2-yl)-7-(2H-tetrazol-5-yl)-3,4-dihydro-1,4-methanopyrido[2,3-b][1,4]diazepine-5(2H)-carboxamide (0.13 g, 0.369 mmol, 28.4% yield) as white solid, LCMS (m/z): 351.24 [M+H]⁺.

¹H NMR (400 MHz, CDCl$_3$-d) δ ppm 14.75 (br s, 1H), 9.47 (d, J=1.32 Hz, 1H), 8.48-8.40 (m, 2H), 8.02 (d, J=7.89 Hz, 1H), 7.77 (d, J=7.89 Hz, 1H), 5.57 (dd, J=5.92, 3.07 Hz, 1H), 3.37-3.27 (m, 2H), 3.22-3.17 (m, 1H), 3.24-3.04 (m, 1H), 2.39 (ddt, J=14.36, 8.88, 5.48, 5.48 Hz, 1H), 2.18-2.05 (m, 1H)

Example 316

The present invention relates to Sirtuin Modulators, which are known in the scientific literature for being useful for increasing lifespan of a cell, and in treating and/or preventing a wide variety of diseases and disorders, which include, but are not limited to, for example, diseases or disorders related to aging or stress, diabetes, obesity, neurodegenerative diseases, cardiovascular disease, blood clotting disorders, inflammation, cancer, and/or flushing as well as diseases or disorders that would benefit from increased mitochondrial activity.

In addition to therapeutic potential, structural and biophysical studies of SIRT1 activity and activation by small molecule sirtuin modualtors would be useful in advancing understanding of the biological function of sirtuins, mechanism of action of sirtuin activation and to aid in development of assays that identify novel sirtuin modulators.

Based on the foregong, the following literature references, respectively. are hereby incorporated by reference in their entirety, are cited to demonstrate the utility of compounds of the present invention as Sirtuin Modulators and its interconnection with various diseases as exemplified in the following references:

1. Marcia C. Haigis and David A. Sinclair, Mammalian Sirtuins: Biological Insights and Disease Relevance, *Annu Rev Pathol.* 2010; 5: 253-295, which is hereby incorporated by reference in its entirety.

Haigis and Sinclair teach:

"Aging is accompanied by a decline in the healthy function of multiple organ systems, leading to increased incidence and mortality from diseases such as type II diabetes mellitus, neurodegenerative diseases, cancer, and cardiovascular disease. Historically, researchers have focused on investigating individual pathways in isolated organs as a strategy to identify the root cause of a disease, with hopes of designing better drugs. Studies of aging in yeast led to the of a family of conserved enzymes known as the sirtuins, which affect multiple pathways that increase the life span and the overall health of organisms. Since the discovery of the first known mammalian sirtuin, SIRT1, 10 years ago, there have been major advances in our understanding of the enzymology of sirtuins, their regulation, and their ability to broadly improve mammalian physiology and health span. This review summarizes and discusses the discovery advances of the past decade and the challenges that will confront the field in the coming years (see, ABSTRACT, therein and reference)."

2. Gizem Donmezl et. al., SIRT1 and SIRT2: emerging targets in neurodegeneration, EMBO Mol Med (2013) 5, 344-352, which is hereby incorporated by reference in its entirety.

Gizem Donmezl et. al., teaches:

"Sirtuins are NAD-dependent protein deacetylases known to have protective effects against age-related diseases such as cancer, diabetes, cardiovascular and neurodegenerative diseases. In mammals, there are seven sirtuins (SIRT1-7), which display diversity in subcellular localization and function. While SIRT1 has been extensively investigated due to its initial connection with lifespan extension and involvement in calorie restriction, important biological and therapeutic roles of other sirtuins have only recently been recognized. Here, we review the potential roles and effects of SIRT1 and SIRT2 in neurodegenerative diseases. We discuss different functions and targets of SIRT1 and SIRT2 in a variety of neurodegenerative diseases including Alzheimer's disease (AD), Parkinson's disease (PD) and Huntington's Disease (HD). We also cover the role of SIRT1 in neuronal differentiation due to the possible implications in neurodegenerative conditions, and conclude with an outlook on the potential therapeutic value of SIRT1 and SIRT2 in these disorders (see, ABSTRACT, therein and reference)."

3. Bracke et al., Targeted silencing of DEFB4 in a bioengineered skin-humanized mouse model for psoriasis: development of siRNA SECosome-based novel therapies; Exp Dermatol. 2014 March; 23(3):199-201. doi: 10.1111/ exd.12321, which is hereby incorporated by reference in its entirety.

In particular, Bracke et al. teaches

"Psoriasis is a complex inflammatory skin disease that presents a wide variety of clinical manifestations. Human β defensin-2 (hBD-2) is highly up-regulated in psoriatic lesions and has been defined as a biomarker for disease activity. We explored the potential benefits of targeting hBD-2 by topical application of DEFB4-siRNA-containing SECosomes in a bioengineered skin-humanized mouse model for psoriasis. A significant improvement in the psoriatic phenotype was observed by histological examination, with a normalization of the skin architecture and a reduction in the number and size of blood vessels in the dermal compartment. Treatment leads to the recovery of transglutaminase activity, filaggrin expression and stratum corneum appearance to the levels similar to those found in normal regenerated human skin. The availability of a reliable skin-humanized mouse model for psoriasis in conjunction with the use of the SECosome technology may provide a valuable preclinical tool for identifying potential therapeutic targets for this disease."

4. Karline Guilloteau et al., Skin Inflammation Induced by the Synergistic Action of IL-17A, IL-22 Recapitulates Some Features of Psoriasis Oncostatin M, IL-1a, and TNF-A, *J Immunol* 2010; 184:5263-5270; which is hereby incorporated by reference in its entirety.

Guilloteau et al. teaches:

"Keratinocytes play a crucial role in the regulation of skin inflammation, responding to environmental and immune cells stimuli. They produce soluble factors that can act in an autocrine or paracrine manner on immune cells or directly on aggressors. A screening of the activities of 36 cytokines on keratinocyte gene expression identified IL-17A, IL-22, oncostatin M, TNF-A, and IL-1a as potent cytokines in inducing cutaneous inflammation. These five proinflammatory cytokines synergistically increased production of CXCL8 and b-defensin 2 (BD2). In addition, ex vivo studies on human skin explants demonstrated upregulation of BD2, S100A7, and CXCL8 expression in response to the same combination of cytokines. In vivo intradermal injection of these five cytokines in mouse increased CXCL1, CXCL2, CXCL3, S100A9, and BD3 expression, associated with neutrophil infiltration. We confirmed and extended this synergistic effect using quantitative real-time PCR analysis and observed increased expression of nine chemokines and 12 antimicrobial peptides. Production of CXCL, CXCL5, and CXCL8 by keratinocytes stimulated in the presence of this cytokine combination was associated with increased neutrophil chemotactic activity. Similarly, high production of BD2, BD3, and S100A7 was associated with an increased antimicrobial activity. Finally, the transcriptional profile observed in this in vitro model of inflammatory keratinocytes correlated with the one of lesional psoriatic skin. Our results demonstrate the important potentiating activities of IL-17A, IL-22, oncostatin M, TNF-a, and IL-1a on keratinocytes. This is particularly interesting in the context of psoriasis where these cytokines are overexpressed and could synergize to play an important role in upregulation of chemokines and antimicrobial peptides production. The Journal of Immunology, 2010, 184: 5263-5270 (see, ABSTRACT, therein and reference)".

Example 317

Psoriasis Assay

Example 222 from table-1 when tested in a PBMC TNFα assay showed an $IC_{50}$ <5 uM. Additionally, example 222 from table-1 was tested in a Beta-defensin 2 (bD2) assay showing >90% reduction at 10 uM. Example 222 from table-1 was tested in a Psoriasis IL-17 assay resulting in >75% inhibition of IL-17a of mRNA levels, >75% inhibition of IL-17f and >50% inhibition of IL-22 when tested at 10 uM in human skin.

TABLE 1

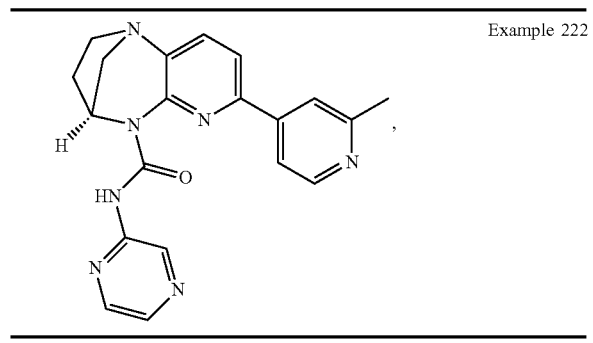

Example 222

Description of Assays:
PBMC Assay

Sirtuin 1 (Sirt1) is a homolog of silent information regulator 2 (Sir2) and a member of the NAD dependent class III histone deacetylase. Sirt1 deacetylates lysine residues on histones, trasncription factors and nonhistone proteins. Sirt1 has been shown to be involved in aging, cell cycle regulation, apoptosis, metabolic modulation and inflammation. The activation of Sirt1 causes deacetylation at lysine 310 of RelA/p65 subunit of nuclear factor kB (NF-kB) transcriptional factor which inhibits NF-kB transcription and down-regulates levels of TNFalpha. TNFalpha is a pleitotropic cytokine that is mainly produced by macrophages and monocytes. TNFalpha is closely involved in immune defense and chronic inflammation including Psoriasis. The expression of type-1 cytokines such as TNFa was known to be increased in psoriatic skin and it plays important role in the etiology of psoriasis (Uyemura K et al, 1993, J. Invest Dermatol, 101, p701). Importantly, anti-TNF agent has been in clinical use for psoriasis. Therefore, Sirt1 activators that induce a reduction in TNFa expression in inflammatory cells should have therapeutic effect in moderate to severe psoriatic patients.

A PBMC/TNFalpha cell based assay was developed to identify activators of Sirt1 that inhibit the release of TNFalpha in response to lipopolysaccharide (LPS) stimulation of peripheral blood mononuclear cells (PBMC's). Briefly, PBMC's were stimulated by LPS, leading to an increase in the production of TNFalpha secretion. TNFalpha protein level was measured by TNFalpha HTRF (homogeneous time resolved fluorescence) kit (CisBio, Inc). Cell lysis and TNFalpha detection were performed according to manufacturer's instructions. Sirt1 activators were tested in the presence of LPS to evaluate their inhibitory effect on TNFa release and IC50 were determined in a dose-response experiment.

Beta-Defensin 2 (bD2) Assay

Sirtuin is a family of NAD-dependent deacetylases which have broad physiological functions and have been implicated in a number of autoimmune and metabolic disorders including rheumatoid arthritis and type I diabetes. Substrates of SIRT1 are diverse and include inflammatory components with well established roles in innate and adaptive immune response such as NF☐B, AP-1, FOXO, and p53.

Psoriasis is a chronic inflammatory skin disorder induced by genetic, autoimmune, and environmental factors. Lesions are characterized by hyperproliferation of keratinocytes in the epidermis and infiltration of inflammatory cells resulting in chronic erythmatous plaques covered by white scales. Previous studies have shown that SIRT1 can impede the effects of IL-22, a key cytokine in psoriasis, through direct inhibition of STAT3 acetylation (Sestito et al, 2011). In addition, both SIRT1 overexpression and resveratrol treatment (SIRT1 activation) can induce keratinocyte differentiation (Blander et al, 2009).

Beta-defensin 2 (bD2) is an antimicrobial peptide that can be secreted from the epithelia where it acts as a chemoattractant for memory T-cells, immature dendritic cells, and neutrophils. As such, bD2 is a major part of the inflammatory response in the skin. Not only is bD2 induced in lesional epidermal cells of psoriasis patients compared to normal skin, but it is also a serum biomarker for disease severity in psoriasis patients (Jansen et al, 2009; Kamsteeg et al 2009). In addition, bD2 may be genetically linked to psoriasis as a recent study uncovered a significant association between increased beta-defensin gene copy number and psoriasis risk (Hollox et al, 2008). Of note, topical delivery of bD2 siRNA resulted in recovery of normal skin architecture and protein expression in a bioengineered skin-humanized mouse model for psoriasis (Bracke et al, 2014).

An in vitro keratinocyte inflammation assay generated to mimic psoriatic inflammation was previously described (Guilloteau et al, 2010; Teng et al 2014). In these studies, a cytokine cocktail of IL-1alpha, IL-17A, IL-22, OSM, and TNFalpha (referred to as "M5") was found to synergize to produce a "psoriasiform" transcriptional profile in primary human keratinocytes in vitro. In these studies, bD2 was one of the strongest responders to the induction of keratinocyte inflammation.

Therefore, this assay was further developed in order to assess the efficacy of SIRT1 activator compounds for the topical psoriasis program. Specifically, conditions were optimized for an immortalized human keratinocyte cell line (HaCaT) treated in vitro with the M5 cytokine combination to induce psoriatic inflammation (as in reference above). In a 48 hour time frame, bD2 secretion, as measured by a bD2 ELISA assay (Alpha Diagnostics), is significantly increased compared to unstimulated keratinocytes. This bD2 induction can be suppressed with treatment of compounds known to suppress psoriatic inflammation or, importantly, with a subset of SIRT1 activators. In parallel, cytotoxicity over the length of the 48 hour assay is ascertained by a CellTiter-Glo Luminescent Cell Viability Assay (Promega) to determine whether toxicity might play a role in bD2 response.

REFERENCES

Blander G, Bhimavarapu A, Mammone T, Maes D, Elliston K, Reich C, Matsui M S, Guarente L, Loureiro J J. SIRT1 promotes differentiation of normal human keratinocytes. *J Invest Dermatol.* 2009 January; 129(1):41-9.

Bracke S, Carretero M, Guerrero-Aspizua S, Desmet E, Illera N, Navarro M, Lambert J, Del Rio M. Targeted silencing of DEFB4 in a bioengineered skin-humanized mouse model for psoriasis: development of siRNA SECosome-based novel therapies. *Exp Dermatol.* 2014 March; 23(3):199-201.

Guilloteau K, Paris I, Pedretti N, Boniface K, Juchaux F, Huguier V, Guillet G, Bernard F X, Lecron J C, Morel F. Skin Inflammation Induced by the Synergistic Action of IL-17A, IL-22, Oncostatin M, IL-1alpha, and TNFalpha Recapitulates Some Features of Psoriasis. *J Immunol.* 2010 Mar. 24.

Jansen P A, Rodijk-Olthuis D, Hollox E J, Kamsteeg M, Tjabringa G S, de Jongh G J, van Vlijmen-Willems I M, Bergboer J G, van Rossum M M, de Jong E M, den Heijer M, Evers A W, Bergers M, Armour J A, Zeeuwen P L, Schalkwijk J. Beta-defensin-2 protein is a serum biomarker for disease activity in psoriasis and reaches biologically relevant concentrations in lesional skin. *PLoS One.* 2009; 4(3):e4725.

Kamsteeg M, Jansen P A, van Vlijmen-Willems I M, van Erp P E, Rodijk-Olthuis D, van der Valk P G, Feuth T, Zeeuwen P L, Schalkwijk J. Molecular diagnostics of psoriasis, atopic dermatitis, allergic contact dermatitis and irritant contact dermatitis. *Br J Dermatol.* 2010 March; 162(3):568-78.

Sestito R, Madonna S, Scarponi C, Cianfarani F, Failla C M, Cavani A, Girolomoni G, Albanesi C. STAT3-dependent effects of IL-22 in human keratinocytes are counterregulated by sirtuin 1 through a direct inhibition of STAT3 acetylation. *FASEB J.* 2011 March; 25(3):916-27.

Teng X, Hu Z, Wei X, Wang Z, Guan T, Liu N, Liu X, Ye N, Deng G, Luo C, Huang N, Sun C, Xu M, Zhou X, Deng H, Edwards C K 3rd, Chen X, Wang X, Cui K, Wei Y, Li J. IL-37 ameliorates the inflammatory process in psoriasis by suppressing proinflammatory cytokine production. *J Immunol.* 2014 Feb. 15; 192(4):1815-23.

Psoriasis & IL-17

Psoriasis is a chronic, relapsing, inflammatory autoimmune skin disorder with a multi-factorial pathogenesis influenced by genetic, environmental, and immunopathologic factors (Griffiths C E et al., Lancet 2007; 370:263-71). Psoriasis is characterized by recurrent episodes of raised, well-demarcated erythematous oval plaques with adherent silvery scales. Histologically, the hallmark of psoriasis is the presence of a thickened nucleated keratinocyte layer, with exaggeration of the rete pegs, caused by hyperproliferation of keratinocytes and dermal infiltration by activated T cells, neutrophils, and dendritic cells (Schon M P N. Engl. J. Med. 352: 1899-1912).

An accumulating body of evidence suggests psoriasis as a Th17-mediated disease, driven by its signature cytokines IL-17 A, IL-17 F and IL-22. IL-22 induces proliferation of keratinocytes, whereas IL-17A stimulates keratinocytes to secrete chemokines and other proinflammatory mediators that recruit additional inflammatory cells, including neutrophils, dendritic cells, and innate lymphoid cells (Martin D A et al, J Invest Dermatol 2013; 133:17-26).

The clinical validation of the IL-17 pathway in mediating psoriasis is demonstrated by successful Ph3 studies that show significant improvement of disease using monoclonal antibody therapy targeting IL-17 (Langley et al., NEJM 2014). In addition, global transcription profiling in psoriasis lesions following IL-17 inhibition suppressed multiple inflammatory factors from keratinocytes and leukocyte subsets to similar levels as observed in non-lesional skin (Russell et al., J Immunol 2014, 192: 3828-3836). Taken together, these findings support the role of IL-17 in mediating psoriasis pathogenesis.

Method (Ex Vivo Skin Assay)

Stimulation of skin-resident immune cells in ex vivo human skin explants using a Th17 cytokine cocktail results in a dramatic upregulation of Th17 related cytokines (IL-17A, IL-17F and IL-22), which establishes this system as a human tissue-based model for psoriasis. The ability of test compounds to modulate the expression of IL-17A, IL-17 F and IL-22 was assessed using the ex vivo skin culture method post stimulation with Th17 cytokine cocktail. Briefly, ex vivo human skin obtained from abdominoplasty surgery was processed to remove fat and the tissue was dermatomed to ~750 microns. Dermatomed skin was then cleaned in two serial rinses of 5-10 minutes each in room temperature PBS containing an antibiotic/antimycotic solution. The skin section was cut with disposable single-use biopsy punches to 10 mm diameter round sections, which were then placed in the upper chamber of a 0.4 □m PCF membrane transwell (Millicell # PIHP01250) containing 30 µl of a 64% bovine collagen solution (Organogenesis, #200-055) prepared with Cornification media. The skin samples were allowed to set on the collagen solution for 30 min at 37° C. in a humidified chamber. The skin samples on transwells were transferred to 6-well plates (1 sample per well) and the lower chamber was filled with 1 ml complete media (Cornification Media).

On the first day following abdominoplasty surgery, skin explants were cultured in Cornification media and allowed to incubate overnight at 37° C. Specifically, human skin explants (N=3 per condition) were stimulated with the Th17 cocktail (CD3, 1 µg/ml, CD28, 2 µg/ml, IL-1b, 10 ng/ml, IL-6, 5 ng/ml, TGFb, 1 ng/ml, IL-21, 10 ng/ml, anti-IL-4, 1 µg/ml and anti-INFg, 1 µg/ml). Test compound at 1,3 and 10 uM was added at the same time as Th17 cocktail. Tissue was harvested 24 hrs after Th17 activation and RNA was isolated for transcript quantification (IL-17A, IL-17F, IL-22) using qPCR.

Total RNA was isolated from ~40 mg of tissue using Qiagen's Mini RNA Isolation kit (Cat #74106). Briefly, tissue was minced and homogenized in the Precellys-24 machine using 300 µl of RLT buffer supplemented with 1% 2-Beta-Mercapto-Ethanol at 6300 rpm for 30 seconds for 10 cycles with a 2-minute ice break. 490 µl of water containing 10 µl Proteinase K was added to the homogenate and digested at 55° C. for 15 minutes. Digested tissue was spun down for 3 minutes at 10,000 G to pellet cell debri and the supernatant was used for RNA isolation using Qiagen's RNeasy mini columns according to manufacturer's protocol. Total RNA was quantified using Nanodrop 2000 and analyzed on Agilent bioanalyser (files attached). 1.4 µg of RNA was used as template in a 20 µl PCR volume using Invitrogen SuperScript VILO cDNA Synthesis kit (#11754-050) to create a cDNA template. Then cDNA was diluted 1:25 for the subsequent qPCR with the specific TaqMan probe for each gene to be quantified. RNA levels of gene of interest's relative expression were calculated using the Delta Delta CT formula.

EQUIVALENTS

The present invention provides among other things sirtuin-modulating compounds and methods of use thereof. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) (www.tigr.org) and/or the National Center for Biotechnology Information (NCBI) (www.ncbi.nlm.nih.gov).

What is claimed is:

1. A compound of Formula (I):

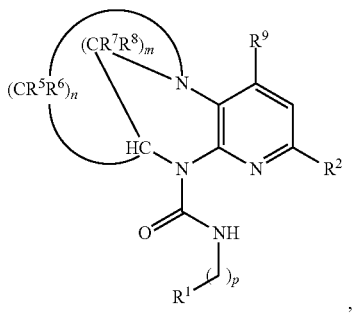

(I)

or a salt thereof
wherein:
m is 1 or 2;
n is 2 or 3;
p is 0 to 4;
$R^1$ is selected from the group consisting of a carbocycle and heterocycle, wherein $R^1$ is optionally substituted with one or more substituents independently selected from the group consisting of halo, $C_1$-$C_4$ alkyl, fluoro-substituted $C_1$-$C_4$ alkyl, —C≡N, —Y, —X—C(=O)—Y, —X—O—Y, —X—OR$^4$, —X—C(=O)—NR$^3$R$^3$, —X—NH—C(=O)—Y—NR$^3$R$^3$, —X—NH—C(=O)—O—Y, —X—NR$^3$R$^3$, =O, —NH—S(=O)$_2$—R$_3$, —S(=O)$_2$—R$^3$, —S—R$^3$, —(C$_3$-C$_7$) cycloalkyl, —C(=N)—NR$^3$R$^3$, —C(=N)—NH—X—NR$^3$R$^3$, —X—NH—C(=O)—Y, —C(=O)—NH—X, —NH—X, phenyl, —O-phenyl, 3- to 6-membered saturated or unsaturated heterocycle and —O-(5- to 6-membered saturated heterocycle), wherein any phenyl, 3- to 6-membered saturated or unsaturated heterocycle or —O-5- to 6-membered saturated heterocycle substituent of $R^1$ is optionally substituted at any substitutable carbon atom with one or more substituents selected from the group consisting of halo, —OR$^4$, —X—O—Y, —CF$_3$, —Y, —X—R$^3$R$^3$, —X—NH—C(=O)—Y—NR$^3$R$^3$, —X—NH—C(=O)—O—Y-(5- to 6-membered saturated heterocycle or carbocycle), —X—C(=N)—NR$^3$R$^3$ and —S—Y and optionally substituted at any substitutable nitrogen atom with —Y, —C(=O)—Y, —C(=O)—O—Y, —C(=O)—OR$^4$, —Y—C(=O)—Y—NR$^3$R$^3$, —Y—NH—C(=O)—O—Y, —Y—NH—C(=O)—OR$^4$, —Y—NH$_2$, —C(=O)—NH—Y or —C(=O)-3- to 5-membered saturated carbocycle;

$R^2$ is selected from the group consisting of a carbocycle and a heterocycle, wherein $R^2$ is optionally substituted with one or more substituents independently selected from the group consisting of halo, $C_1$-$C_4$ alkyl, fluoro-substituted $C_1$-$C_4$ alkyl, —C≡N, —Y, —X—OR$^4$, —X—O—Y, —SO$_2$—R$^3$, —X—NR$^3$R$^3$, —NH—S(=O)$_2$R$^3$, —C(=O)—NR$^3$R$^3$, —C(=O)—Y, —C(=O)—O—Y, —SO$_2$—R$_y$, —SO$_2$—NH—R$_y$, —SO$_2$—NR$^3$R$^3$, 3- to 6-membered saturated carbocycle or heterocycle and phenyl, wherein any 3- to 6-membered saturated heterocycle substituent of $R^2$ is optionally substituted at any carbon atom with one or more substituents selected from the group consisting of halo, —CF$_3$, —Y, —X—O—Y, —NH—Y and —N(Y)$_2$, and is optionally substituted at any nitrogen atom with one or more substituents selected from the group consisting of —C(=O)—O—Y, —Y and —C(=O)—Y, and when $R^2$ is an N-linked 5- to 7-membered saturated or unsaturated heterocycle it is further substituted at any nitrogen atom with one or more substituents selected from the group consisting of —C(=O)—O—Y, —Y and —C(=O)—Y;

each $R^3$ is independently selected from the group consisting of hydrogen, —C(=N)—NH$_2$, —C(=O)—Y, —Y, —Y—NH—C(=O)—O—Y, —Y—NH—C(=O)—OH, —Y—NH—C(=O)—CF$_3$, —C(=O)—Y-3- to 5-membered saturated heterocycle, —C(=O)—O—Y-(3- to 5-membered saturated heterocycle), —C(=O)—CF$_3$, —C(=O)—O—Y, —C(=O)—OH, —C(=O)—O—CF$_3$, —S(=O)$_2$—Y, —S(=O)$_2$—OH;

two $R^3$ are taken together with the nitrogen or carbon atom to which they are bound to form a 4- to 8-membered saturated heterocycle optionally comprising one additional heteroatom selected independently from the group consisting of N, S, S(=O), S(=O)$_2$, and O, wherein the heterocycle formed by two $R^3$ is optionally substituted at any carbon atom with one or more of OH, halo, Y, NH$_2$, NH—Y, N(Y)$_2$, O—Y, and optionally substituted at any substitutable nitrogen atom with C(=O)—O—Y, Y or C(=O)—Y;

each $R^4$ is independently selected from hydrogen, Y, —CF$_3$, —C(=O)—Y, —C(=O)—O—Y, —Y—C(=O)—Y or —Y—C(=O)—O—Y;

$R^5$ and $R^6$ are independently selected from the group consisting of hydrogen, —OH, —OCF$_3$, —O—Y, —O—C(=O)—Y, —O—C(=O)—O—Y, —O—C(=O)—NH—Y, —O—C(=O)—N(Y)$_2$, —O—C(=O)-5- to 6-membered saturated or unsaturated heterocycle or carbocycle, wherein only one of $R^5$ and $R^6$ is O—C(=O)-5- to 6-membered saturated or unsaturated heterocycle or carbocycle, and when $R^5$ or $R^6$ is O—C(=O)-5- to 6-membered saturated or unsaturated heterocycle or carbocycle it is further substituted with halo, —OH, Y, —O—Y, —OCF$_3$ or —O—C(=O)—Y; or $R^5$ and $R^6$ can be taken together to the carbon atom to which they are bound to form =O;

$R^7$ and $R^8$ are independently selected from the group consisting of hydrogen, halo, —OH, —O—Y and Y;

$R^9$ is selected from the group consisting of hydrogen, halo, —OH, —OCF$_3$, —O—Y, Y, —O—C(=O)—Y, —NH—Y and —N(Y)$_2$;

each X is $C_0$-$C_5$ straight chain or branched alkyl, alkenyl or alkynyl; and each Y is $C_1$-$C_5$ straight chain or branched alkyl, alkenyl or alkynyl;

wherein any Y or X is optionally substituted with one or more of —OH, —$C_1$-$C_4$ straight chain or branched alkyl, —$C_1$-$C_4$ alkene, —$C_1$-$C_4$ alkynyl, —O—($C_1$-$C_4$ alkyl), —O—($C_1$-$C_4$ alkene), —O—($C_1$-$C_4$ alkynyl), —C(=O)—$C_1$-$C_4$ straight chain or branched alkyl, —C(=O)—$C_1$-$C_4$ alkene, —C(=O)—$C_1$-$C_4$ alkynyl, —C(=O)—O—$C_1$-$C_4$ straight chain or branched alkyl, —C(=O)—O—$C_1$-$C_4$ alkene, —C(=O)—O—$C_1$-$C_4$ alkynyl, halo, —NH$_2$, —NH($C_1$-$C_4$ alkyl), —N($C_1$-$C_4$ alkyl)$_2$, —($C_1$-$C_3$ straight chain or branched alkyl)-NH—(=NH)—NH$_2$, —NH(alkoxy-substituted $C_1$-$C_4$ alkyl), —NH(hydroxy-substituted $C_1$-$C_4$ alkyl), —N(alkoxy-substituted $C_1$-$C_4$ alkyl)(hydroxy-substituted $C_1$-$C_4$ alkyl), —N(hydroxy-substituted $C_1$-$C_4$ alkyl)$_2$ or —N(alkoxy-substituted $C_1$-$C_4$ alkyl)$_2$; or a pharmaceutically acceptable salt thereof.

2. The compound according to claim 1, wherein the compounds or pharmaceutically acceptable salts are represented by Structural Formula (IIa):

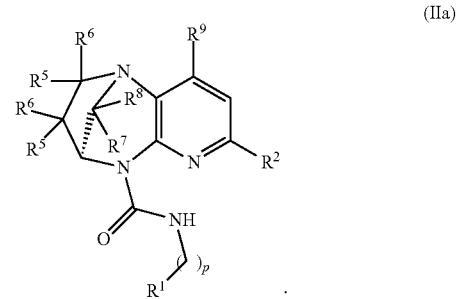

(IIa)

3. A method for treating acne, rosacea or Inflammatory Bowel Disease, which comprises administering a compound or a pharmaceutically acceptable salt thereof according to Formula (I), to a subject in need thereof; wherein Formula (I) is

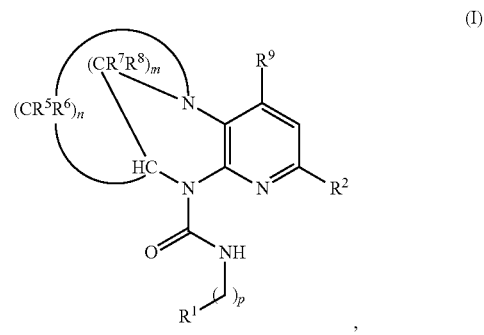

(I)

wherein:
m is 1 or 2;
n is 2 or 3;
p is 0 to 4;
$R^1$ is selected from the group consisting of a carbocycle and heterocycle, wherein $R^1$ is optionally substituted with one or more substituents independently selected from the group consisting of halo, $C_1$-$C_4$ alkyl, fluoro-substituted $C_1$-$C_4$ alkyl, —C≡N, —Y, —X—C(=O)—Y, —X—O—Y, —X—OR$^4$, —X—C(=O)—NR$^3$R$^3$, —X—NH—C(=O)—Y—NR$^3$R$^3$, —X—NH—C(=O)—O—Y, —X—NR$^3$R$^3$, =O, —NH—S(=O)$_2$—R$_3$, —S(=O)$_2$—R$^3$, —S—R$^3$, —(C$_3$-C$_7$) cycloalkyl, —C(=N)—NR$^3$R$^3$, —C(=N)—NH—X—NR$^3$R$^3$, —X—NH—C(=O)—Y, —C(=O)—NH—X, —NH—X, phenyl, —O-phenyl, 3- to 6-membered saturated or unsaturated heterocycle and —O-(5- to 6-membered saturated heterocycle), wherein any phenyl, 3- to 6-membered saturated or unsaturated heterocycle or —O-5- to 6-membered saturated heterocycle substituent of $R^1$ is optionally substituted at any substitutable carbon atom with one or more substituents selected from the group consisting of halo, —OR$^4$, —X—O—Y, —CF$_3$, —Y, —X—R$^3$R$^3$, —X—NH—C(=O)—Y—NR$^3$R$^3$, —X—NH—C(=O)—O—Y-(5- to 6-membered saturated heterocycle or carbocycle), —X—C(=N)—NR$^3$R$^3$ and —S—Y and optionally substituted at any substitutable nitrogen atom with —Y, —C(=O)—Y, —C(=O)—O—Y, —C(=O)—OR⁴, —Y—C(=O)—Y—NR³R³, —Y—NH—C(=O)—O—Y, —Y—NH—C(=O)—OR⁴, —Y—NH₂, —C(=O)—NH—Y or —C(=O)-3- to 5-membered saturated carbocycle;

R² is selected from the group consisting of a carbocycle and a heterocycle, wherein R² is optionally substituted with one or more substituents independently selected from the group consisting of halo, C₁-C₄ alkyl, fluoro-substituted C₁-C₄ alkyl, —C≡N, —Y, —X—OR⁴, —X—O—Y, —SO₂—R³, —X—NR³R³, —NH—S(=O)₂R³, —C(=O)—NR³R³, —C(=O)—Y, —C(=O)—O—Y, —SO₂—R_y, —SO₂—NH—R_y, —SO₂—NR³R³, 3- to 6-membered saturated carbocycle or heterocycle and phenyl, wherein any 3- to 6-membered saturated heterocycle substituent of R² is optionally substituted at any carbon atom with one or more substituents selected from the group consisting of halo, —CF₃, —Y, —X—O—Y, —NH—Y and —N(Y)₂, and is optionally substituted at any nitrogen atom with one or more substituents selected from the group consisting of —C(=O)—O—Y, —Y and —C(=O)—Y, and when R² is an N-linked 5- to 7-membered saturated or unsaturated heterocycle it is further substituted at any nitrogen atom with one or more substituents selected from the group consisting of —C(=O)—O—Y, —Y and —C(=O)—Y;

each R³ is independently selected from the group consisting of hydrogen, —C(=N)—NH₂, —C(=O)—Y, —Y, —Y—NH—C(=O)—O—Y, —Y—NH—C(=O)—OH, —Y—NH—C(=O)—CF₃, —C(=O)—Y-3- to 5-membered saturated heterocycle, —C(=O)—O—Y-(3- to 5-membered saturated heterocycle), —C(=O)—CF₃, —C(=O)—O—Y, —C(=O)—OH, —C(=O)—O—CF₃, —S(=O)₂—Y, —S(=O)₂—OH;

two R³ are taken together with the nitrogen or carbon atom to which they are bound to form a 4- to 8-membered saturated heterocycle optionally comprising one additional heteroatom selected independently from the group consisting of N, S, S(=O), S(=O)₂, and O, wherein the heterocycle formed by two R³ is optionally substituted at any carbon atom with one or more of OH, halo, Y, NH₂, NH—Y, N(Y)₂, O—Y, and optionally substituted at any substitutable nitrogen atom with C(=O)—O—Y, Y or C(=O)—Y;

each R⁴ is independently selected from hydrogen, Y, —CF₃, —C(=O)—Y, —C(=O)—O—Y, —Y—C(=O)—Y or —Y—C(=O)—O—Y;

R⁵ and R⁶ are independently selected from hydrogen, —OH, —OCF₃, —O—Y, —O—C(=O)—Y, —O—C(=O)—O—Y, —O—C(=O)—NH—Y, —O—C(=O)—N(Y)₂, —O—C(=O)-5- to 6-membered saturated or unsaturated heterocycle or carbocycle, wherein only one of R⁵ and R⁶ is O—C(=O)-5- to 6-membered saturated heterocycle or carbocycle, and when R⁵ or R⁶ is O—C(=O)-5- to 6-membered saturated or unsaturated heterocycle or carbocycle it is further substituted with halo, —OH, Y, —O—Y, —OCF₃ or —O—C(=O)—Y; or R⁵ and R⁶ can be taken together to the carbon atom to which they are bound to form =O;

R⁷ and R⁸ are independently selected from the group consisting of hydrogen, halo, —OH, —O—Y and Y;

R⁹ is selected from hydrogen, the group consisting of halo, —OH, —OCF₃, —O—Y, Y, —O—C(=O)—Y, —NH—Y and —N(Y)₂; each X is C₀-C₅ straight chain or branched alkyl, alkenyl or alkynyl; and each Y is C₁-C₅ straight chain or branched alkyl, alkenyl or alkynyl;

wherein any Y or X is optionally substituted with one or more of —OH, —C₁-C₄ straight chain or branched alkyl, —C₁-C₄ alkene, —C₁-C₄ alkynyl, —O—(C₁-C₄ alkyl), —O—(C₁-C₄ alkene), —O—(C₁-C₄ alkynyl), —C(=O)—C₁-C₄ straight chain or branched alkyl, —C(=O)—C₁-C₄ alkene, —C(=O)—C₁-C₄ alkynyl, —C(=O)—O—C₁-C₄ straight chain or branched alkyl, —C(=O)—O—C₁-C₄ alkene, —C(=O)—O—C₁-C₄ alkynyl, halo, —NH₂, —NH(C₁-C₄ alkyl), —N(C₁-C₄ alkyl)₂, —(C₁-C₃ straight chain or branched alkyl)-NH—(=NH)—NH₂, —NH(alkoxy-substituted C₁-C₄ alkyl), —NH(hydroxy-substituted C₁-C₄ alkyl), —N(alkoxy-substituted C₁-C₄ alkyl)(hydroxy-substituted C₁-C₄ alkyl), —N(hydroxy-substituted C₁-C₄ alkyl)₂ or —N(alkoxy-substituted C₁-C₄ alkyl)₂; or a pharmaceutically acceptable salt thereof.

4. A method according to claim 3, wherein the compound or pharmaceutically acceptable salts are represented by Structural Formula (IIa):

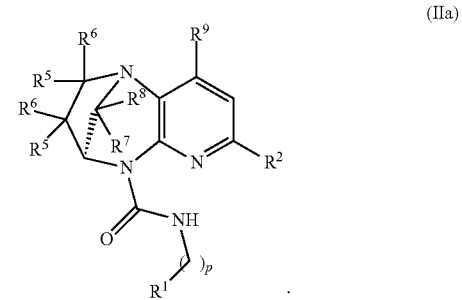

(IIa)

5. A method according to claim 4 wherein the compound or pharmaceutically acceptable salt of Formula (I) is

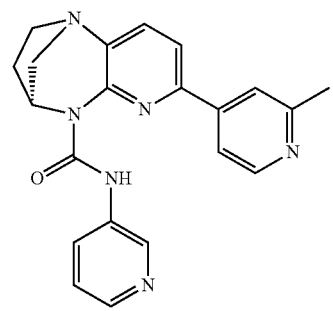

or

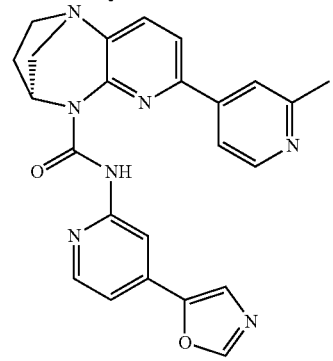

or a pharmaceutically acceptable salt thereof.

6. A compound which is:

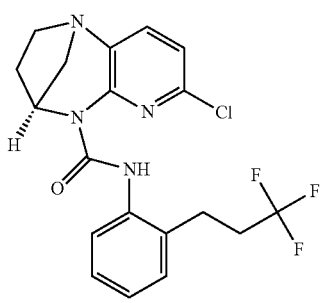

(9S)-5-chloro-N-[2-(3,3,3-trifluoropropyl)phenyl]-1,6,8-triazatricyclo[7.2.1.0²,⁷]dodeca-2(7),3,5-triene-8-carboxamide

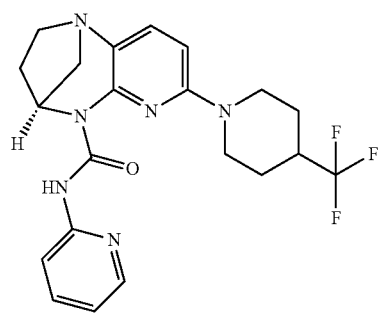

(9S)-N-(pyridin-2-yl)-5-[4-(trifluoromethyl)piperidin-1-yl]-1,6,8-triazatricyclo[7.2.1.0²,⁷]dodeca-2,4,6-triene-8-carboxamide

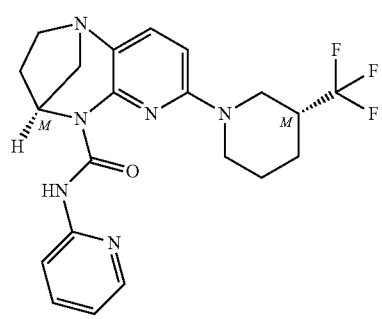

(9S)-N-(pyridin-2-yl)-5-[(3R)-3-(trifluoromethyl)piperidin-1-yl]-1,6,8-triazatricyclo[7.2.1.0²,⁷]dodeca-2,4,6-triene-8-carboxamide -continued

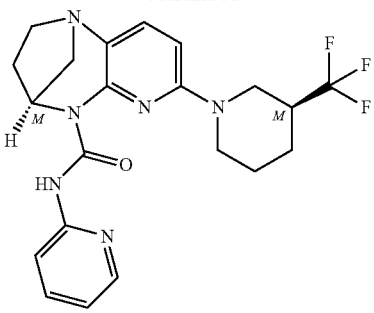

(9S)-N-(pyridin-2-yl)-5-[(3S)-3-(trifluoromethyl)piperidin-1-yl]-1,6,8-triazatricyclo[7.2.1.0²,⁷]dodeca-2,4,6-triene-8-carboxamide

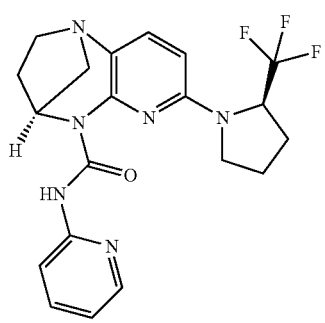

(9S)-N-(pyridin-2-yl)-5-[(2R)-2-(trifluoromethyl)pyrrolidin-1-yl]-1,6,8-triazatricyclo[7.2.1.0²,⁷]dodeca-2(7),3,5-triene-8-carboxamide

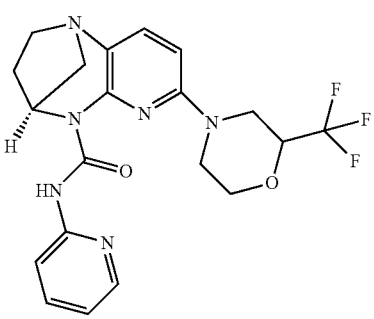

(9S)-N-(pyridin-2-yl)-5-[2-(trifluoromethyl)morpholin-4-yl]-1,6,8-triazatricyclo[7.2.1.0²,⁷]dodeca-2(7),3,5-triene-8-carboxamide

989
-continued

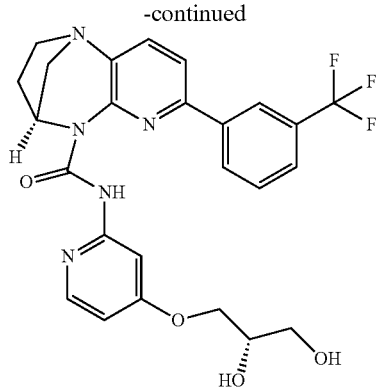

(9S)-N-{4-[(2S)-2,3-
dihydroxypropxy]pyridin-2-
yl}-5-[3-
(trifluoromethyl)phenyl]-1,6,8-
triazatricyclo[7.2.1.0²,⁷]dodeca-
2(7),3,5-triene-8-carboxamide

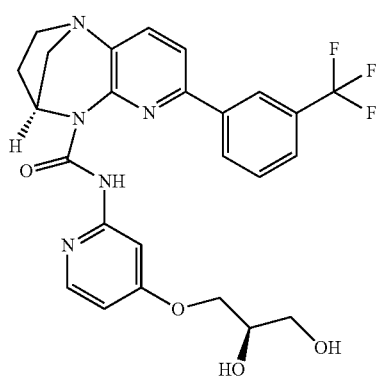

(9S)-N-{4-[(2R)-2,3-
dihydroxypropoxy]pyridin-2-
yl}-5-[3-
(trifluoromethyl)phenyl]-1,6,8-
triazatricyclo[7.2.1.0²,⁷]dodeca-
2(7),3,5-triene-8-carboxamide

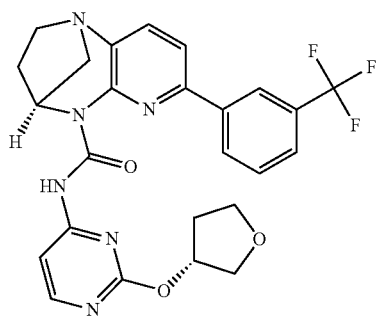

(9S)-N-{2-[(3R)-oxolan-3-
yloxy]pyrimidin-4-yl}-5-[3-
(trifluoromethyl)phenyl]-1,6,8-
triazatricyclo[7.2.1.0²,⁷]dodeca-
2(7),3,5-triene-8-carboxamide

990
-continued

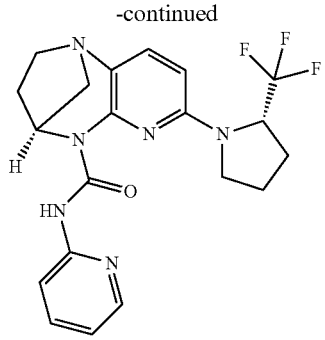

(9S)-N-(pyridin-2-yl)-5-[(2S)-
2-(trifluoromethyl)pyrrolidin-1-
yl]-1,6,8-
triazatricyclo[7.2.1.0²,⁷]dodeca-
2(7),3,5-triene-8-carboxamide

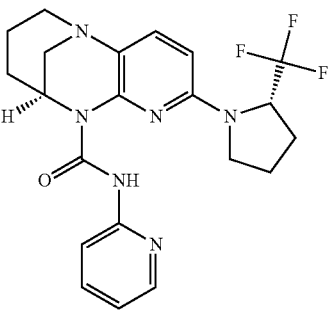

(9S)-N-(pyridin-2-yl)-5-[(2S)-
2-(trifluoromethyl)pyrrolidin-1-
yl]-1,6,8-
triazatricyclo[7.3.1.0²,⁷]trideca-
2(7),3,5-triene-8-carboxamide

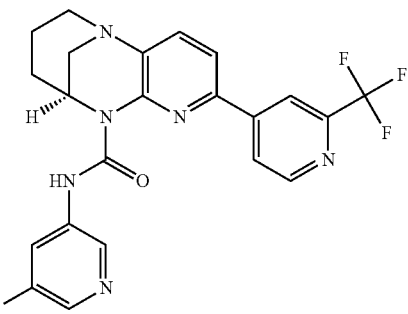

(9S)-N-(5-fluoropyridin-3-yl)-
5-[2-(trifluoromethyl)pyridin-
4-yl]-1,6,8-
triazatricyclo[7.3.1.0²,⁷]trideca-
2(7),3,5-triene-8-carboxamide 991
-continued

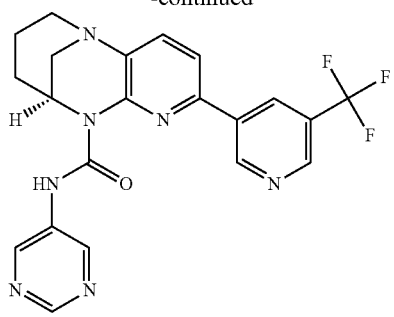

(9S)-N-(pyrimidin-5-yl)-5-[5-
(trifluoromethyl)pyridin-3-yl]-
1,6,8-
triazatricyclo[7.3.1.0²,⁷]trideca-
2(7),3,5-triene-8-carboxamide

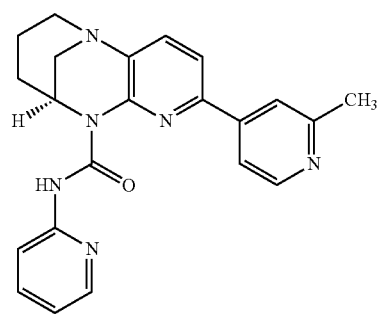

(9S)-5-(2-methylpyridin-4-yl)-
N-(pyridin-2-yl)-1,6,8-
triazatricyclo[7.3.1.0²,⁷]trideca-
2(7),3,5-triene-8-carboxamide

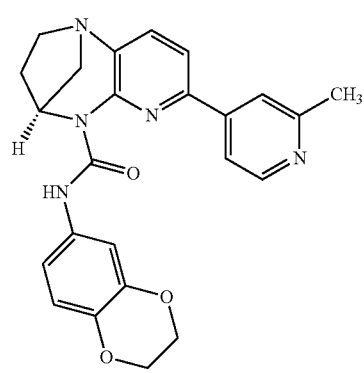

(9S)-N-(2,3-dihydro-1,4-
benzodioxin-6-yl)-5-(2-
methylpyridin-4-yl)-1,6,8-
triazatricyclo[7.2.1.0²,⁷]dodeca-
2(7),3,5-triene-8-carboxamide 992
-continued

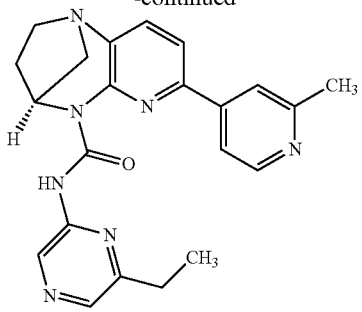

(9S)-N-(6-ethylpyrazin-2-yl)-5-
(2-methylpyridin-4-yl)-1,6,8-
triazatricyclo[7.2.1.0²,⁷]dodeca-
2(7),3,5-triene-8-carboxamide

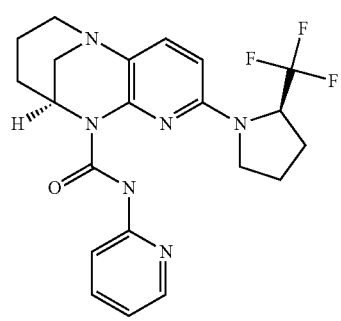

(9S)-N-(pyridin-2-yl)-5-[(2R)-
2-(trifluoromethyl)pyrrolidin-1-
yl]-1,6,8-
triazatricyclo[7.3.1.0²,⁷]trideca-
2(7),3,5-triene-8-carboxamide

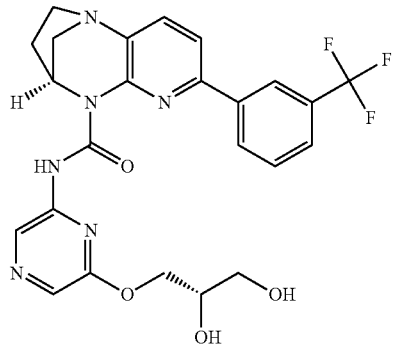

(9S)-N-{6-[(2S)-2,3-
dihydroxypropoxy]pyrazin-2-
yl}-5-[3-
(trifluoromethyl)phenyl]-1,6,8-
triazatricyclo[7.2.1.0²,⁷]dodeca-
2(7),3,5-triene-8-carboxamide 993
-continued

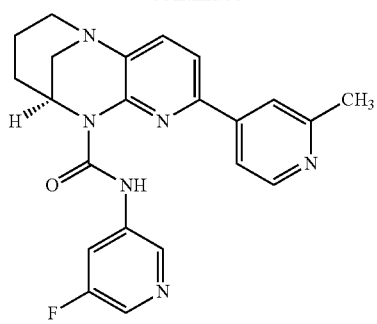

(9S)-N-(5-fluoropyridin-3-yl)-
5-(2-methylpyridin-4-yl)-1,6,8-
triazatricyclo[7.3.1.0$^{2,7}$]trideca-
2(7),3,5-triene-8-carboxamide

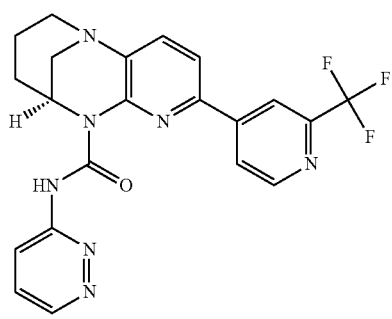

(9S)-N-(pyridazin-3-yl)-5-[2-
(trifluoromethyl)pyridin-4-yl)-
1,6,8-
triazatricyclo[7.3.1.0$^{2,7}$]trideca-
2(7),3,5-triene-8-carboxamide

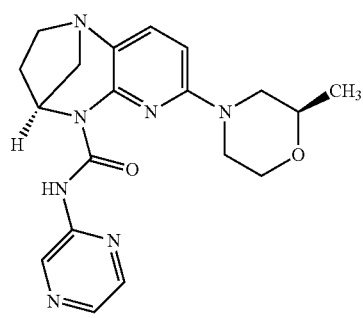

(9S)-5-[(2R)-2-
methylmorpholin-4-yl]-N-
(pyrazin-2-yl)-1,6,8-
triazatricyclo[7.2.1.0$^{2,7}$]dodeca-
2,4,6-triene-8-carboxamide 994
-continued

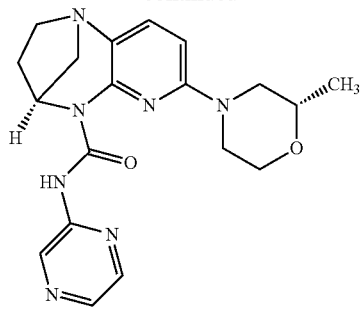

(9S)-5-[(2S)-2-
methylmorpholin-4-yl]-N-
(pyrazin-2-yl)-1,6,8-
triazatricyclo[7.2.1.0$^{2,7}$]dodeca-
2,4,6-triene-8-carboxamide

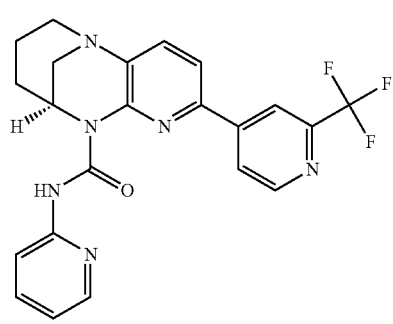

(9S)-N-(pyridin-2-yl)-5-[2-
(trifluoromethyl)pyridin-4-yl)-
1,6,8-
triazatricyclo[7.3.1.0$^{2,7}$]trideca-
2(7),3,5-triene-8-carboxamide

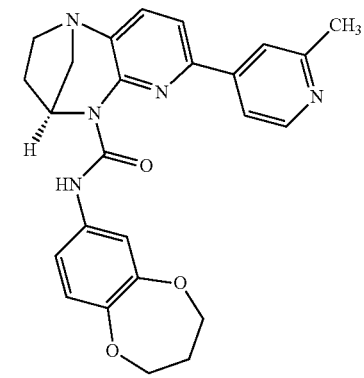

(9S)-N-(3,4-dihydro-2H-1,5-
benzodioxepin-7-yl)-5-(2-
methylpyridin-4-yl)-1,6,8-
triazatricyclo[7.2.1.0$^{2,7}$]dodeca-
2,4,6-triene-8-carboxamide

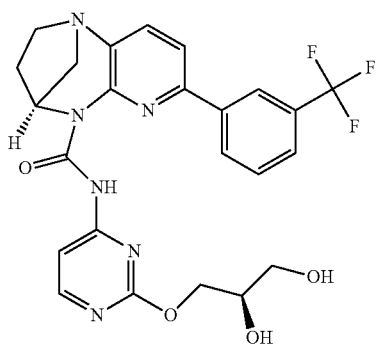

(9S)-N-{(2R)-2,3-dihydroxypropoxy]pyrimidin-4-yl}-5-[3-(trifluoromethyl)phenyl]-1,6,8-triazatricyclo[7.2.1.0²,⁷]dodeca-2(7),3,5-triene-8-carboxamide

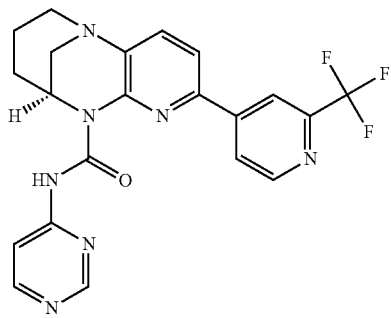

(9S)-N-(pyrimidin-4-yl)-5-[2-(trifluoromethyl)pyridin-4-yl]-1,6,8-triazatricyclo[7.3.1.0²,⁷]trideca-2(7),3,5-triene-8-carboxamide

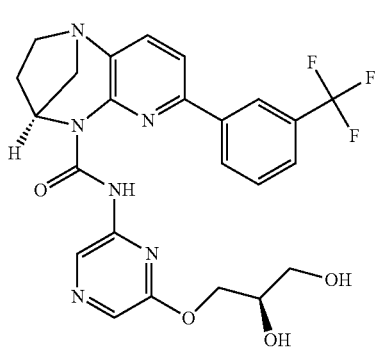

(9S)-N-{6-(2R)-2,3-dihydroxypropoxy]pyrazin-2-yl}-5-[3-(trifluoromethyl)phenyl]-1,6,8-triazatricyclo[7.2.1.0²,⁷]dodeca-2(7),3,5-triene-8-carboxamide

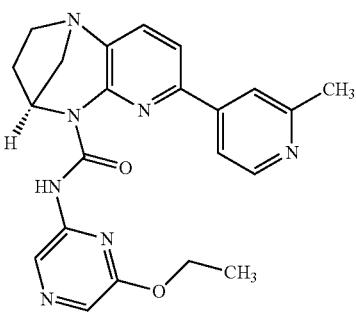

(9S)-N-(6-ethoxypyrazin-2-yl)-5-(2-methylpyridin-4-yl)-1,6,8-triazatricyclo[7.2.1.0²,⁷]dodeca-2(7),3,5-triene-8-carboxamide

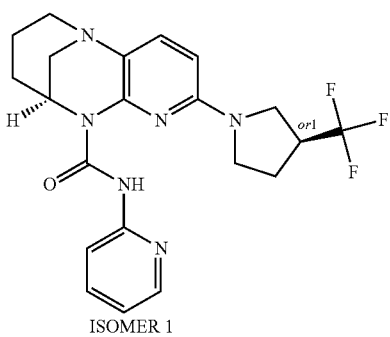

ISOMER 1

(9S)-N-(pyridin-2-yl)-5-[(3S)-3-(trifluoromethyl)pyrrolidin-1-yl]-1,6,8-triazatricyclo[7.3.1.0²,⁷]trideca-2(7),3,5-triene-8-carboxamide

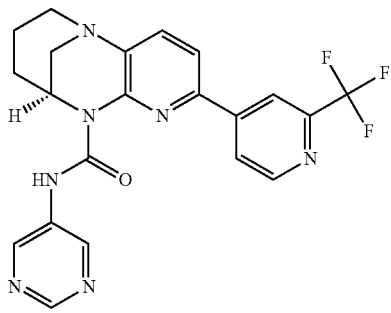

(9S)-N-(pyrimidin-5-yl)-5-[2-(trifluoromethyl)pyridin-4-yl]-1,6,8-triazatricyclo[7.3.1.0²,⁷]trideca-2(7),3,5-triene-8-carboxamide

997

-continued

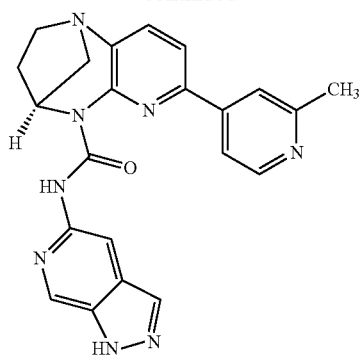

(9S)-5-(2-methylpyridin-4-yl)-
N-{1H-pyrazolo[3,4-c]pyridin-
5-yl}-1,6,8-
triazatricyclo[7.2.1.0²,⁷]dodeca-
2(7),3,5-triene-8-carboxamide

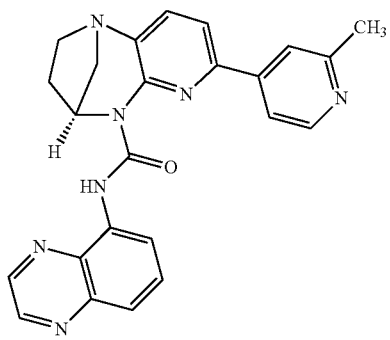

(9S)-5-(3,4-dihydro-2H-1,5-
benzodioxepin-7-yl)-5-(2-
methylpyridin-4-yl)-1,6,8-
triazatricyclo[7.2.1.0²,⁷]dodeca-
2,4,6-triene-8-carboxamide

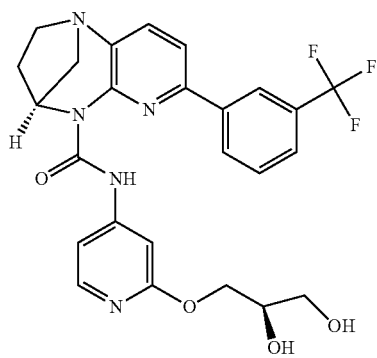

(9S)-N-{2-[(2R)-2,3-
dihydroxypropoxy]pyridin-4-
yl}-5-[3-
(trifluoromethyl)phenyl]-1,6,8-
triazatricyclo[7.2.1.0²,⁷]dodeca-
2(7),3,5-triene-8-carboxamide

998

-continued

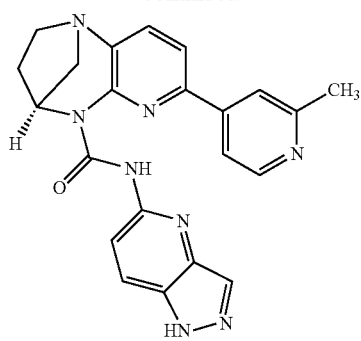

(9S)-5-(2-methylpyridin-4-yl)-
N-{1H-pyrazolo[4,3-b]pyridin-
5-yl}-1,6,8-
triazatricyclo[7.2.1.0²,⁷]dodeca-
2(7),3,5-triene-8-carboxamide

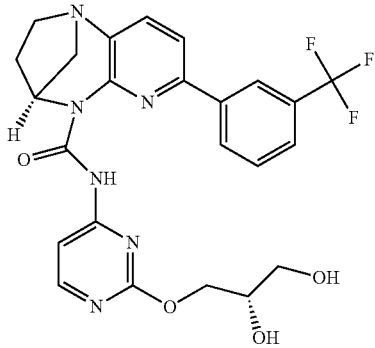

(9S)-N-{2-[(2S)-2,3-
dihydroxypropoxy]pyrimidin-
4-yl}-5-[3-
(trifluoromethyl)phenyl]-1,6,8-
triazatricyclo[7.2.1.0²,⁷]dodeca-
2(7),3,5-triene-8-carboxamide

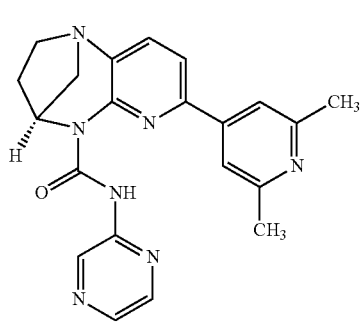

(9S)-5-(2,6-dimethylpyridin-4-
yl)-N-(pyrazin-2-yl)-1,6,8-
triazatricyclo[7.2.1.0²,⁷]dodeca-
2,4,6-triene-8-carboxamide

999
-continued

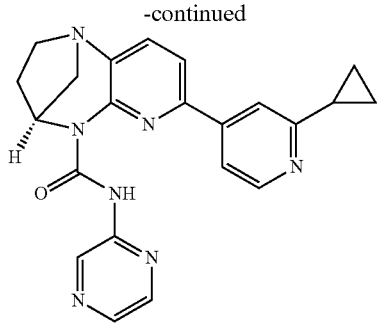

(9S)-5-(2-cyclopropylpyridin-
4-yl)-N-(pyrazin-2-yl)-1,6,8-
triazatricyclo[7.2.1.0$^{2,7}$]dodeca-
2,4,6-triene-8-carboxamide

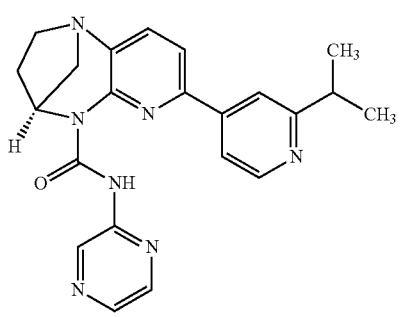

(9S)-5-[2-(propan-2-yl)pyridin-
4-yl]-N-(pyrazin-2-yl)-1,6,8-
triazatricyclo[7.2.1.0$^{2,7}$]dodeca-
2,4,6-triene-8-carboxamide

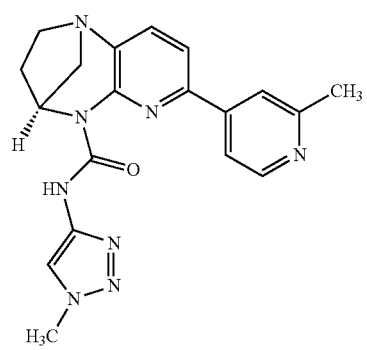

(9S)-N-(1-methyl-1H-1,2,3-
triazol-4-yl)-5-(2-
methylpyridin-4-yl)-1,6,8-
triazatricyclo[7.2.1.0$^{2,7}$]dodeca-
2(7),3,5-triene-8-carboxamide

1000
-continued

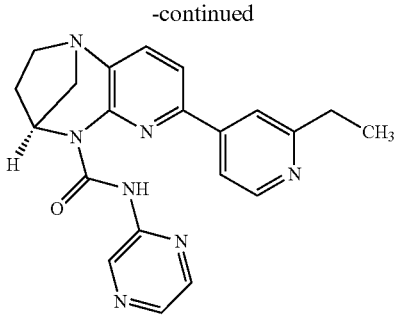

(9S)-5-(2-ethylpyridin-4-yl)-N-
(pyrazin-2-yl)-1,6,8-
triazatricyclo[7.2.1.0$^{2,7}$]dodeca-
2(7),3,5-triene-8-carboxamide

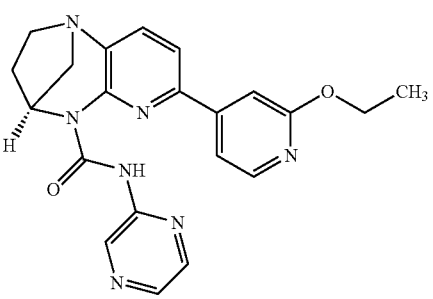

(9S)-5-(2-ethoxypyridin-4-yl)-
N-(pyrazin-2-yl)-1,6,8-
triazatricyclo[7.2.1.0$^{2,7}$]dodeca-
2(7),3,5-triene-8-carboxamide

1001
-continued

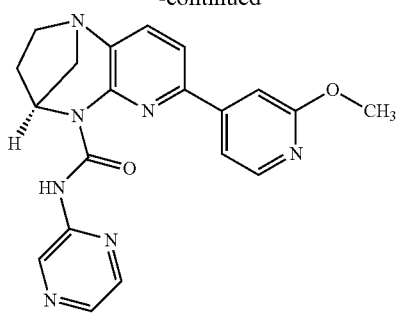

(9S)-5-(2-methoxypyridin-4-
yl)-N-(pyrazin-2-yl)-1,6,8-
triazatricyclo[7.2.1.0$^{2,7}$]dodeca-
2(7),3,5-triene-8-carboxamide

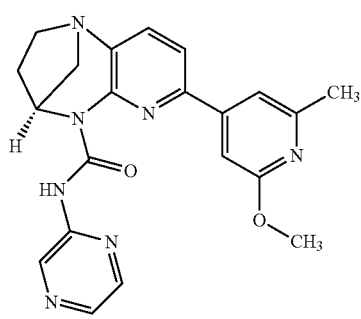

(9S)-5-(2-methoxy-6-
methylpyridin-4-yl)-N-
(pyrazin-2-yl)-1,6,8-
triazatricyclo[7.2.1.0$^{2,7}$]dodeca-
2(7),3,5-triene-8-carboxamide

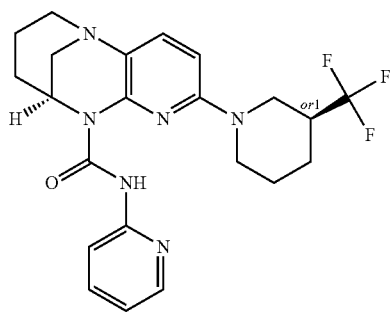

ISOMER 1

(9S)-N-(pyridin-2-yl)-5-[(3S)-
3-(trifluoromethyl)piperidin-1-
yl]-1,6,8-
triazatricyclo[7.3.1.0$^{2,7}$]trideca-
2(7),3,5-triene-8-carboxamide

1002
-continued

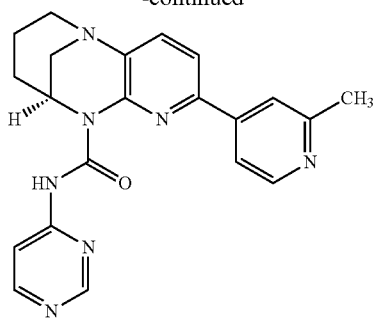

(9S)-5-(2-methylpyridin-4-yl)-
N-(pyrimidin-4-yl)-1,6,8-
triazatricyclo[7.3.1.0$^{2,7}$]trideca-
2(7),3,5-triene-8-carboxamide

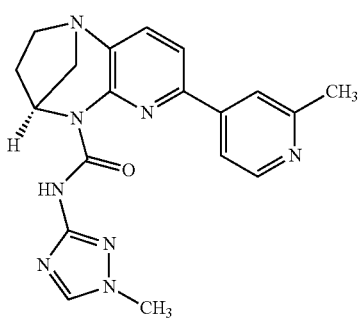

(9S)-N-(1-methy-1H-1,2,4-
triazol-3-yl)-5-(2-
methylpyridin-4-yl)-1,6,8-
triazatricyclo[7.2.1.0$^{2,7}$]dodeca-
2(7),3,5-triene-8-carboxamide

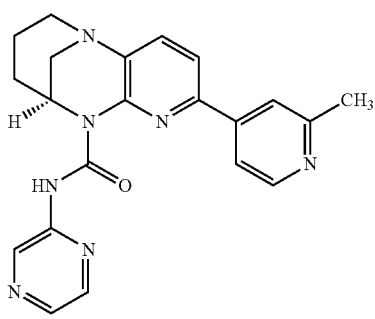

(9S)-5-(2-methylpyridin-4-yl)-
N-(pyrazin-2-yl)-1,6,8-
triazatricyclo[7.3.1.0$^{2,7}$]trideca-
2(7),3,5-triene-8-carboxamide

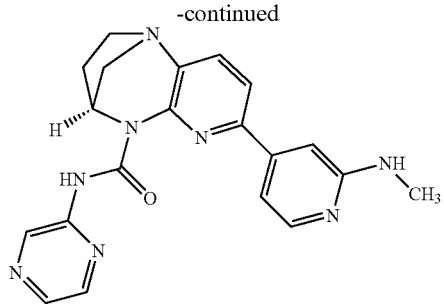

(9S)-5-[2-(methylamino)pyridin-4-yl]-N-(pyrazin-2-yl)-1,6,8-triazatricyclo[7.2.1.0²,⁷]dodeca-2(7),3,5-triene-8-carboxamide

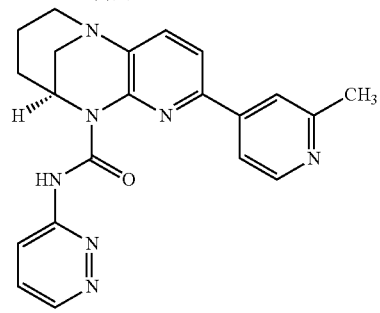

(9S)-5-(2-methylpyridin-4-yl)-N-(pyridazin-3-yl)-1,6,8-triazatricyclo[7.3.1.0²,⁷]trideca-2(7),3,5-triene-8-carboxamide

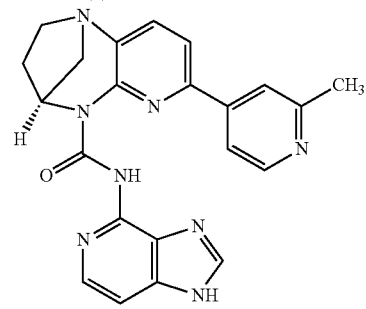

(9S)-N-{1H-imidazo[4,5-c]pyridin-4-yl}-5-(2-methylpyridin-4-yl)-1,6,8-triazatricyclo[7.2.1.0²,⁷]dodeca-2,4,6-triene-8-carboxamide

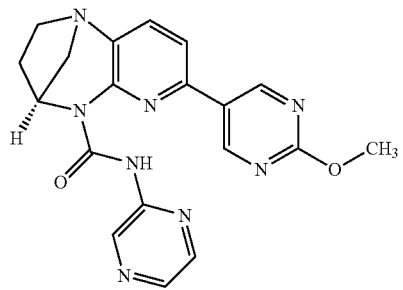

(9S)-5-(2-methoxypyrimidin-5-yl)-N-(pyrazin-2-yl)-1,6,8-triazatricyclo[7.2.1.0²,⁷]dodeca-2(7),3,5-triene-8-carboxamide

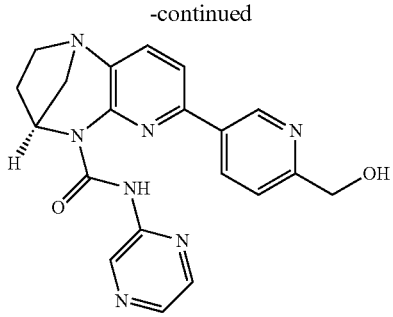

(9S)-5-[6-(hydroxymethyl)pyridin-3-yl]-N-(pyrazin-2-yl)-1,6,8-triazatricyclo[7.2.1.0²,⁷]dodeca-2(7),3,5-triene-8-carboxamide

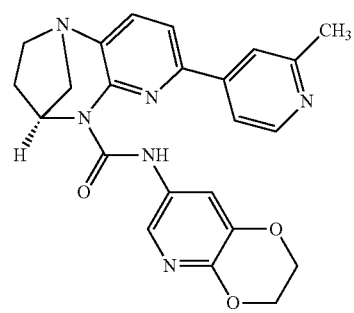

(9S)-N-{2H,3H-[1,4]dioxino[2,3-b]pyridin-7-yl}-5-(2-methylpyridin-4-yl)-1,6,8-triazatricyclo[7.2.1.0²,⁷]dodeca-2,4,6-triene-8-carboxamide

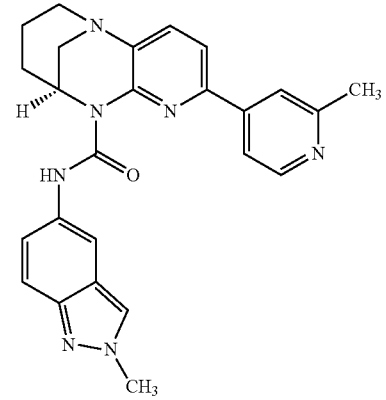

(9S)-N-(2-methyl-2H-indazol-5-yl)-5-(2-methylpyridin-4-yl)-1,6,8-triazatricyclo[7.3.1.0²,⁷]trideca-2,4,6-triene-8-carboxamide

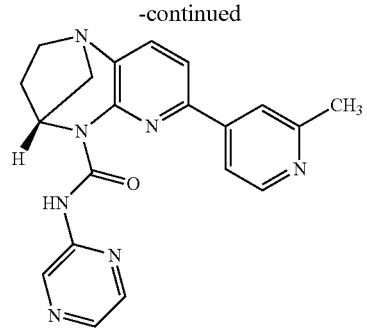

(9R)-5-(2-methylpyridin-4-yl)-
N-(pyrazin-2-yl)-1,6,8-
triazatricyclo[7.2.1.0²,⁷]dodeca-
2(7),3,5-triene-8-carboxamide

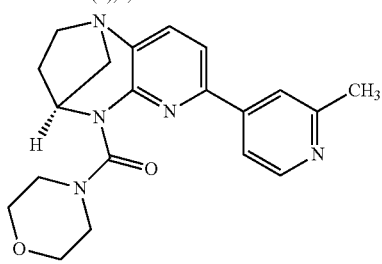

(9S)-5-(2-methylpyridin-4-yl)-
8-(morpholine-4-carbonyl)-
1,6,8-
triazatricyclo[7.2.1.0²,⁷]dodeca-
2,6,8-triene

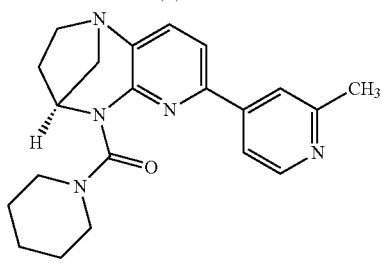

(9S)-5-(2-methylpyridin-4-yl)-
8-(piperidine-1-carbonyl)-
1,6,8-
triazatricyclo[7.2.1.0²,⁷]dodeca-
2,4,6-triene

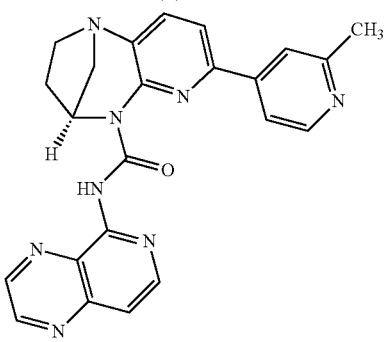

(9S)-5-(2-methylpyridin-4-yl)-
N-{pyrido[3,4-b]pyrazin-5-yl}-
1,6,8-
triazatricyclo[7.2.1.0²,⁷]dodeca-
2,4,6-triene-8-carboxamide

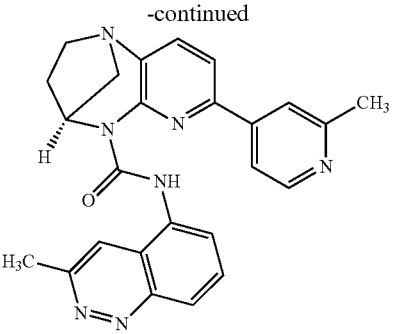

(9S)-N-(3-methylcinnolin-5-
yl)-5-(2-methylpyridin-4-yl)-
1,6,8-
triazatricyclo[7.2.1.0²,⁷]dodeca-
2(7),3,5-triene-8-carboxamide

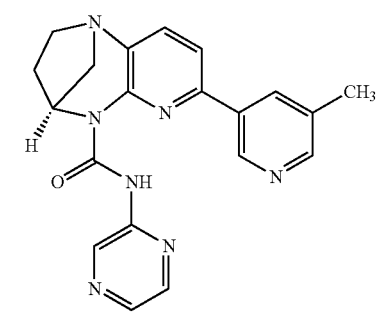

(9S)-5-(5-methylpyridin-3-yl)-
N-(pyrazin-2-yl)-1,6,8-
triazatricyclo[7.2.1.0²,⁷]dodeca-
2(7),3,5-triene-8-carboxamide

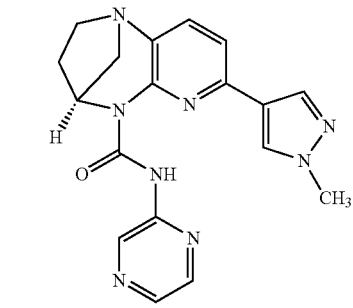

(9S)-5-(1-methyl-pyrazol-
4-yl)-N-(pyrazin-2-yl)-1,6,8-
triazatricyclo[7.2.1.0²,⁷]dodeca-
2(7),3,5-triene-8-carboxamide

1007

-continued

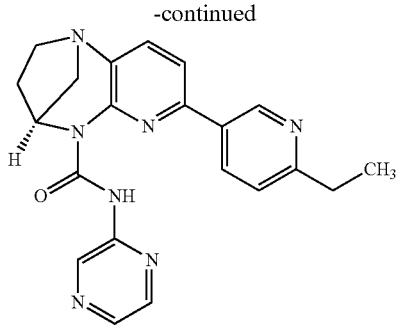

(9S)-5-(5-ethylpyridin-3-yl)-N-
(pyrazin-2-yl)-1,6,8-
triazatricyclo[7.2.1.0²,⁷]dodeca-
2(7),3,5-triene-8-carboxamide

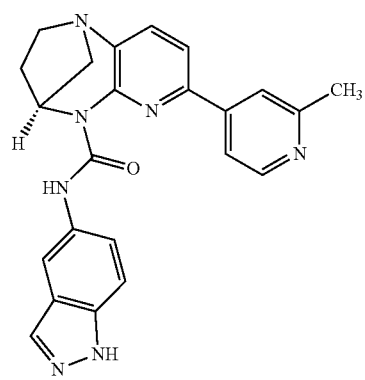

(9S)-N-(1H-indazol-5-yl)-5-(2-
methylpyridin-4-yl)-1,6,8-
triazatricyclo[7.2.1.0²,⁷]dodeca-
2(7),3,5-triene-8-carboxamide

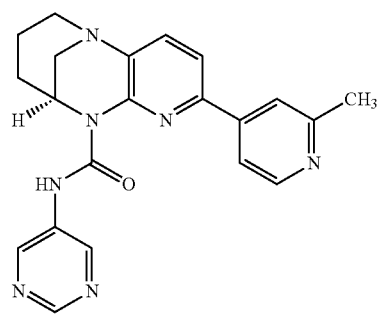

(9S)-5-(2-methylpyridin-4-yl)-
N-(pyrimidin-5-yl)-1,6,8-
triazatricyclo[7.3.1.0²,⁷]trideca-
2(7),3,5-triene-8-carboxamide

1008

-continued

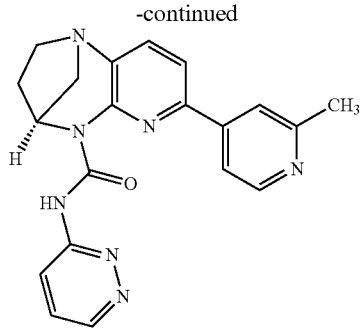

(9S)-5-(2-methylpyridin-4-yl)-
(pyridazin-3-yl)-1,6,8-
triazatricyclo[7.2.1.0²,⁷]dodeca-
2(7),3,5-triene-8-carboxamide

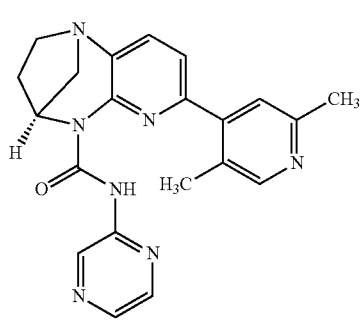

(9S)-5-(2,5-dimethylpyridin-4-
yl)-N-(pyrazin-2-yl)-1,6,8-
triazatricyclo[7.2.1.0²,⁷]dodeca-
2,4,6-triene-8-carboxamide

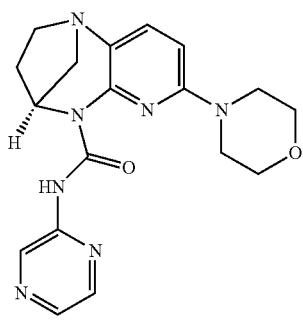

(9S)-5-(morpholin-4-yl)-N-
(pyrazin-2-yl)-1,6,8-
triazatricyclo[7.2.1.0²,⁷]dodeca-
2,4,6-triene-8-carboxamide

1009

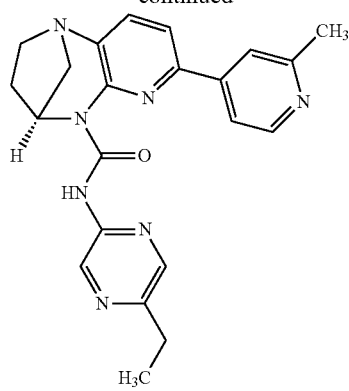

(9S)-N-(5-ethylpyrazin-2-yl)-5-
(2-methylpyridin-4-yl)-1,6,8-
triazatricyclo[7.2.1.0$^{2,7}$]dodeca-
2(7),3,5-triene-8-carboxamide

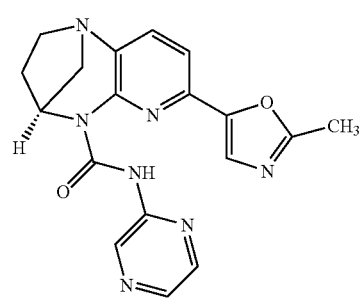

(9S)-5-(2-methyl-1,3-oxazol-5-
yl)-N-(pyrazin-2-yl)-1,6,8-
triazatricyclo[7.2.1.0$^{2,7}$]dodeca-
2(7),3,5-triene-8-carboxamide

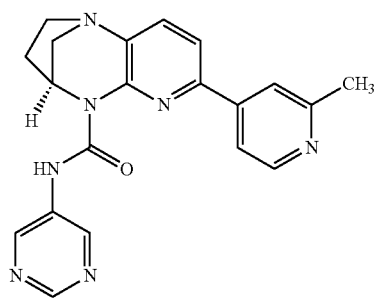

(9S)-5-(2-methylpyridin-4-yl)-
N-(pyrimidin-5-yl)-1,6,8-
triazatricyclo[7.2.1.0$^{2,7}$]dodeca-
2(7),3,5-triene-8-carboxamide

1010

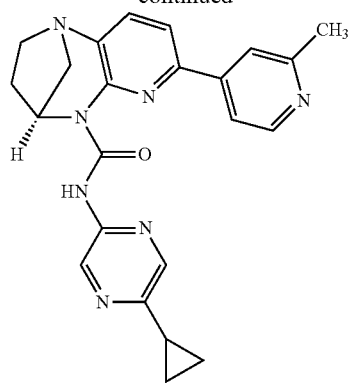

(9S)-N-(5-cyclopropylpyrazin-
2-yl)-5-(2-methylpyridin-4-yl)-
1,6,8-
triazatricyclo[7.2.1.0$^{2,7}$]dodeca-
2(7),3,5-triene-8-carboxamide

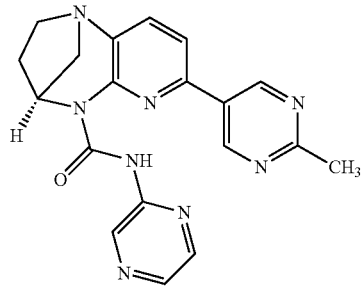

(9S)-5-(2-methylpyrimidin-5-
yl)-N-(pyrazin-2-yl)-1,6,8-
triazatricyclo[7.2.1.0$^{2,7}$]dodeca-
2(7),3,5-triene-8-carboxamide

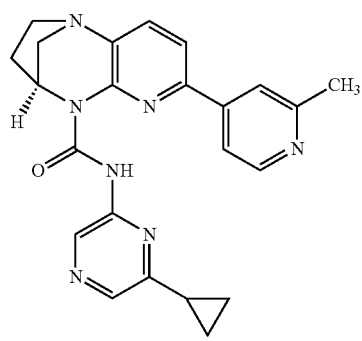

(9S)-N-(6-cyclopropylpyrazin-
2-yl)-5-(2-methylpyridin-4-yl)-
1,6,8-
triazatricyclo[7.2.1.0$^{2,7}$]dodeca-
2(7),3,5-triene-8-carboxamide

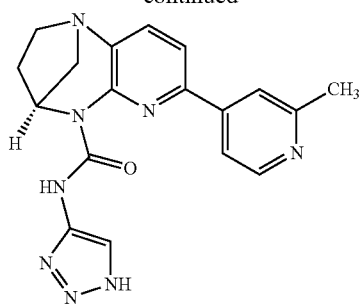

(9S)-5-(2-methylpyrimidin-4-yl)-
N-(1H-1,2,3-triazol-4-yl)-1,6,8-
triazatricyclo[7.2.1.0²,⁷]dodeca-
2(7),3,5-triene-8-carboxamide

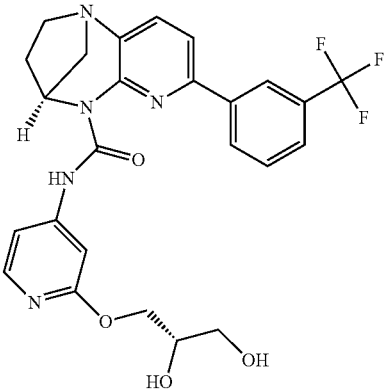

(9S)-N-{2-[(2S)-2,3-
dihydroxypropoxy]pyridin-4-
yl}-5-[3-
(trifluoromethyl)phenyl]-1,6,8-
triazatricyclo[7.2.1.0²,⁷]dodeca-
2,4,6-triene-8-carboxamide

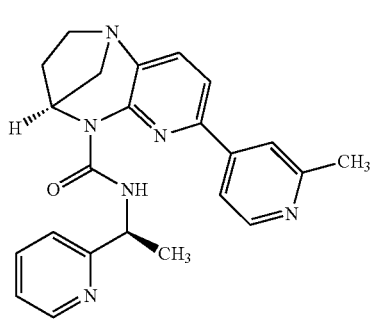

(9S)-5-(2-methylpyridin-4-yl)-
N-[(1S)-1-(pyridin-2-yl)ethyl]-
1,6,8-
triazatricyclo[7.2.1.0²,⁷]dodeca-
2,4,6-triene-8-carboxamide

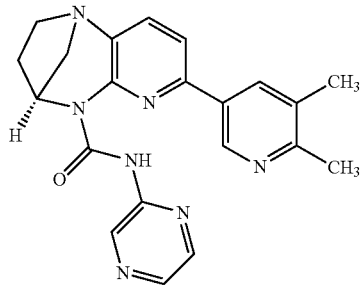

(9S)-5-(5,6-dimethylpyridin-3-
yl)-N-(pyrazin-2-yl)-1,6,8-
triazatricyclo[7.2.1.0²,⁷]dodeca-
2(7),3,5-triene-8-carboxamide

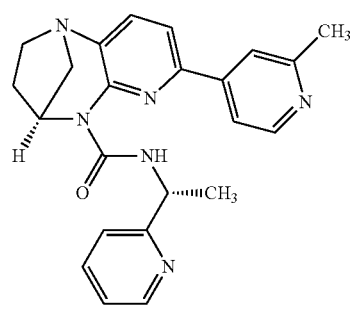

(9S)-5-(2-methylpyridin-4-yl)-
N-[(1R)-1-(pyridin-2-yl)ethyl]-
1,6,8-
triazatricyclo[7.2.1.0²,⁷]dodeca-
2,4,6-triene-8-carboxamide

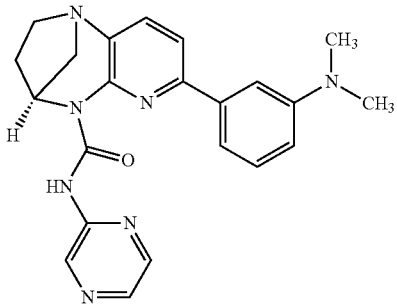

(9S)-5-[3-
(dimethylamino)phenyl]-N-
(pyrazin-2-yl)-1,6,8-
triazatricyclo[7.2.1.0²,⁷]dodeca-
2(7),3,5-triene-8-carboxamide -continued

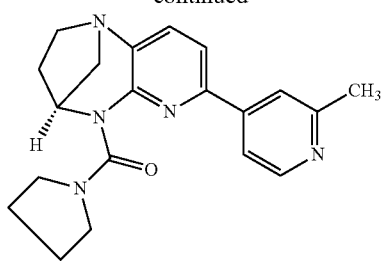

(9S)-5-(2-methylpyridin-4-yl)-
8-(pyrrolidine-1-carbonyl)-
1,6,8-
triazatricyclo[7.2.1.0²,⁷]dodeca-
2,4,6-triene-8-carboxamide

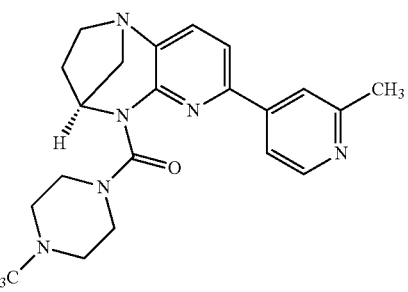

(9S)-8-(4-methylpiperazine-1-
carbonyl)-5-(2-methylpyridin-
4-yl)-1,6,8-
triazatricyclo[7.2.1.0²,⁷]dodeca-
2,4,6-triene

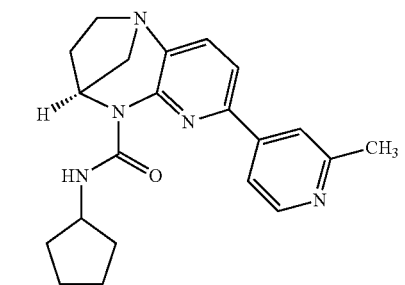

(9S)-N-cyclopentyl-5-(2-
methylpyridin-4-yl)-1,6,8-
triazatricyclo[7.2.1.0²,⁷]dodeca-
2,4,6-triene-8-carboxamide

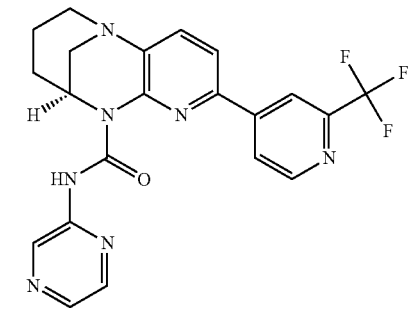

(9S)-N-(pyrazin-2-yl)-5-[2-
(trifluoromethyl)pyridin-4-yl]-
1,6,8-
triazatricyclo[7.3.1.0²,⁷]trideca-
2(7),3,5-triene-8-carboxamide -continued

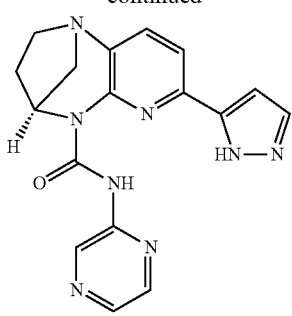

(9S)-N-(pyrazin-2-yl)-5-(1H-
pyrazol-5-yl)-1,6,8-
triazatricyclo[7.2.1.0²,⁷]dodeca-
2(7),3,5-triene-8-carboxamide

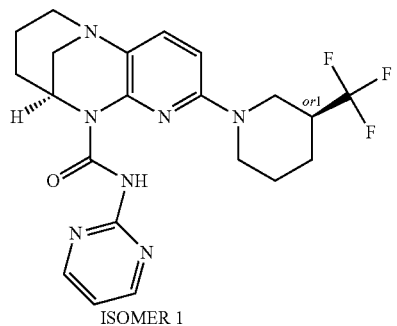

ISOMER 1

(9S)-N-(pyrimidin-2-yl)-5-
[(3S)-3-
(trifluoromethyl)piperidin-1-
yl]-1,6,8-
triazatricyclo[7.3.1.0²,⁷]trideca-
2(7),3,5-triene-8-carboxamide

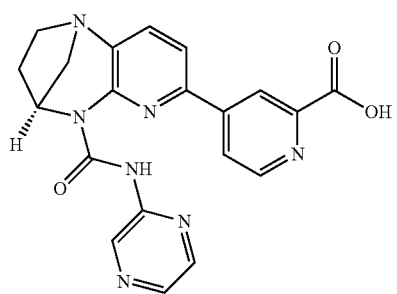

4-[(9S)-8-[(pyrazin-2-
yl)carbamoyl]-1,6,8-
triazatricyclo[7.2.1.0²,⁷]dodeca-
2(7),3,5-trien-5-yl]pyridine-2-
carboxylic acid

1015

-continued

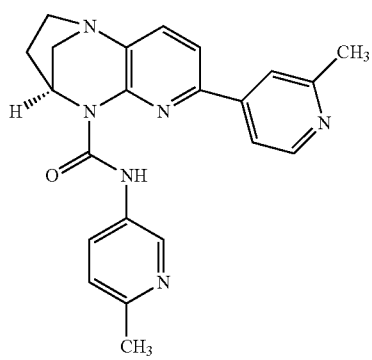

(9S)-N-(6-methylpyridin-3-yl)-
5-(2-methylpyridin-4-yl)-1,6,8-
triazatricyclo[7.2.1.0²,⁷]dodeca-
2(7),3,5-triene-8-carboxamide

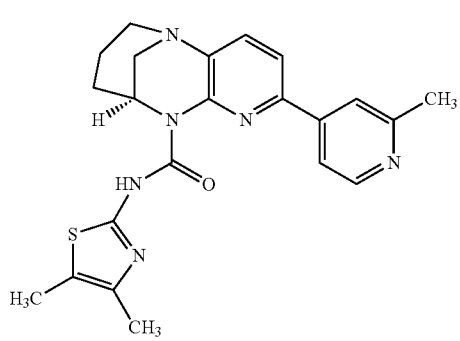

(9S)-N-(dimethyl-1,3-thiazol-2-
yl)-5-(2-methylpyridin-4-yl)-
1,6,8-
triazatricyclo[7.3.1.02,7]trideca-
2(7),3,5-triene-8-carboxamide

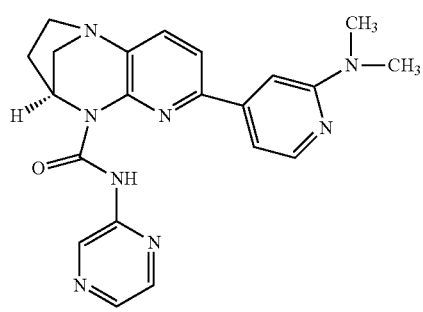

(9S)-5-[(2-
(dimethylamino)pyridin-4-yl]-
N-(pyrazin-2-yl)-1,6,8-
triazatricyclo[7.2.1.0²,⁷]dodeca-
2(7),3,5-triene-8-carboxamide

1016

-continued

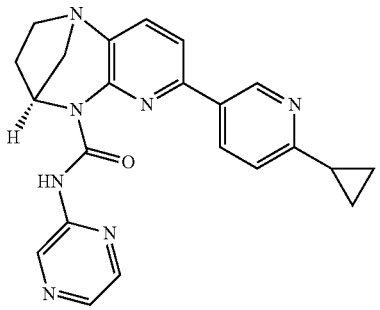

(9S)-5-(6-cyclopropylpyridin-
3-yl)-N-(pyrazin-2-yl)-1,6,8-
triazatricyclo[7.2.1.0²,⁷]dodeca-
2(7),3,5-triene-8-carboxamide

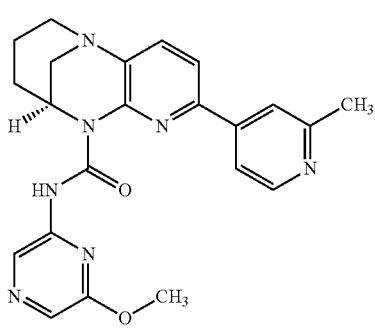

(9S)-N-(6-methoxypyrazin-2-
yl)-5-(2-methylpyridin-4-yl)-
1,6,8-
triazatricyclo[7.3.1.0²,⁷]trideca-
2(7),3,5-triene-8-carboxamide

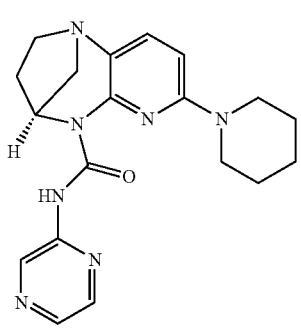

(9S)-5-(piperidin-1-yl)-N-
(pyrazin-2-yl)-1,6,8-
triazatricyclo[7.2.1.0²,⁷]dodeca-
2,4,6-triene-8-carboxamide 1017 -continued

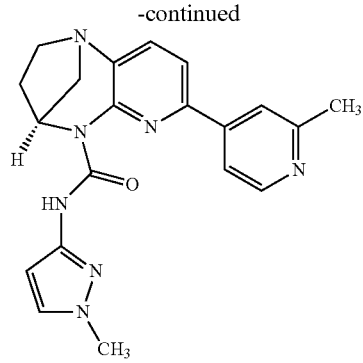

(9S)-N-(1-methyl-1H-pyrazol-
3-yl)-5-(2-methylpyridin-4-yl)-
1,6,8-
triazatricyclo[7.2.1.0$^{2,7}$]dodeca-
2,4,6-triene-8-carboxamide

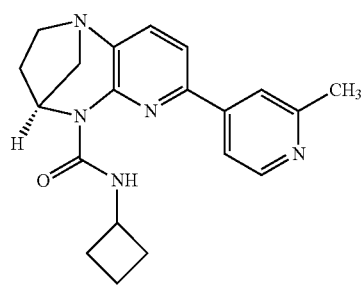

(9S)-N-cyclobutyl-5-(2-
methylpyridin-4-yl)-1,6,8-
triazatricyclo[7.2.1.0$^{2,7}$]dodeca-
2(7),3,5-triene-8-carboxamide

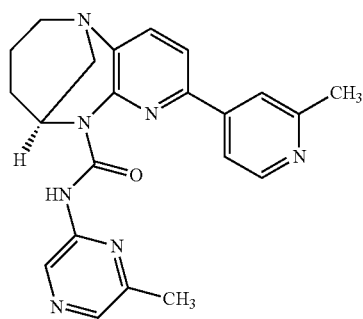

(9S)-N-(6-methylpyrazin-2-yl)-
5-(2-methylpyridin-4-yl)-1,6,8-
triazatricyclo[7.3.1.0$^{2,7}$]trideca-
2(7),3,5-triene-8-carboxamide

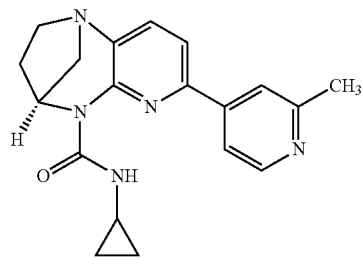

(9S)-N-cyclopropyl-5-(2-
methylpyridin-4-yl)-1,6,8-
triazatricyclo[7.2.1.0$^{2,7}$]dodeca-
2,4,6-triene-8-carboxamide 1018 -continued

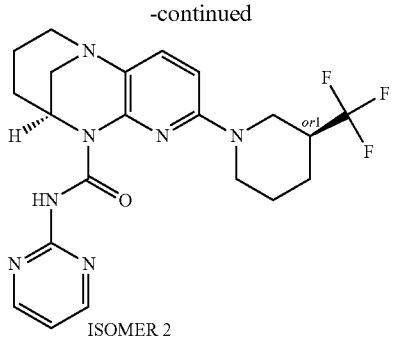

ISOMER 2

(9S)-N-(pyrimidin-2-yl)-5-
[(3S)-3-
(trifluoromethyl)piperidin-1-
yl]-1,6,8-
triazatricyclo[7.3.1.0$^{2,7}$]trideca-
2(7),3,5-triene-8-carboxamide

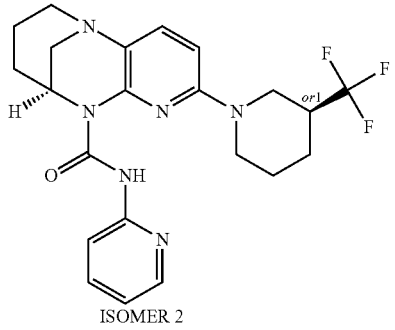

ISOMER 2

(9S)-N-(pyridin-2-yl)-5-[(3S)-
3-(trifluoromethyl)piperidin-1-
yl]-1,6,8-
triazatricyclo[7.3.1.0$^{2,7}$]trideca-
2(7),3,5-triene-8-carboxamide

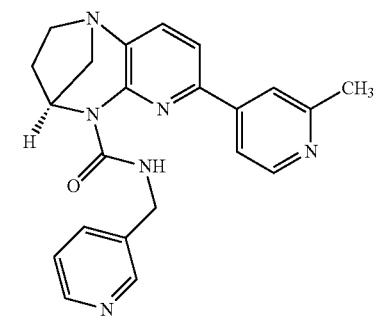

(9S)-5-(2-methylpyridin-4-yl)-
N-(pyridin-3-ylmethyl)-1,6,8-
triazatricyclo[7.2.1.0$^{2,7}$]dodeca-
2(7),3,5-triene-8-carboxamide

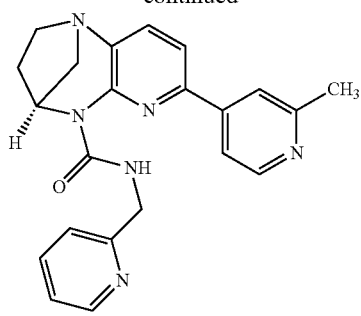

(9S)-5-(2-methylpyridin-4-yl)-
N-(pyridin-2-ylmethyl)-1,6,8-
triazatricyclo[7.2.1.0²,⁷]dodeca-
2(7),3,5-triene-8-carboxamide

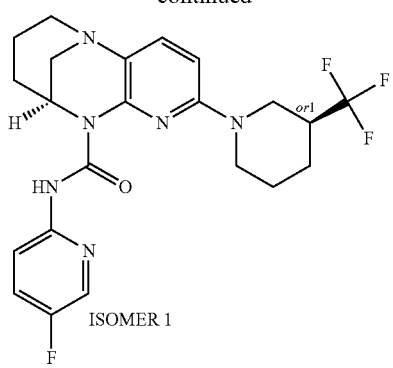

ISOMER 1

(9S)-N-(5-fluoropyridin-2-yl)-
5-[(3S)-3-
(trifluoromethyl)piperidin-1-
yl]-1,6,8-
triazatricyclo[7.3.1.0²,⁷]trideca-
2(7),3,5-triene-8-carboxamide

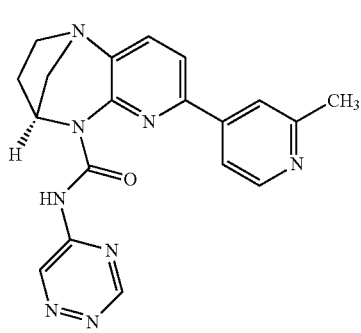

(9S)-5-(2-methylpyridin-4-yl)-
N-(1,2,4-triazin-5-yl)-1,6,8-
triazatricyclo[7.2.1.0²,⁷]dodeca-
2,4,6-triene-8-carboxamide

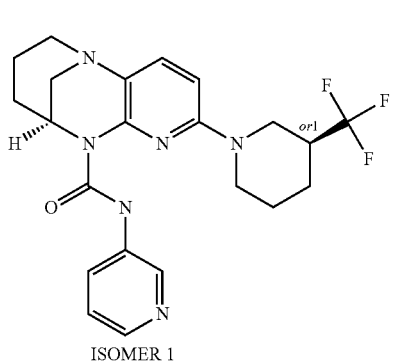

ISOMER 1

(9S)-N-(pyridin-3-yl)-5-[(3S)-
3-(trifluoromethyl)piperidin-1-
yl]-1,6,8-
triazatricyclo[7.3.1.0²,⁷]trideca-
2(7),3,5-triene-8-carboxamide

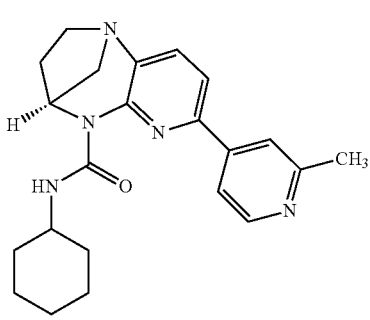

(9S)-N-cyclohexyl-5-(2-
methylpyridin-4-yl)-1,6,8-
triazatricyclo[7.2.1.0²,⁷]dodeca-
2,4,6-triene-8-carboxamide

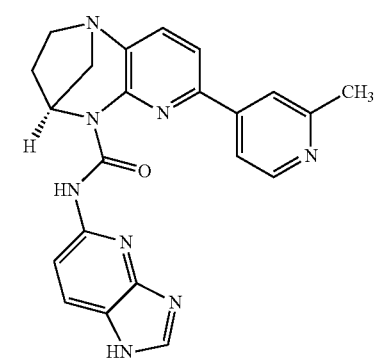

(9S)-N-{1H-imidazo[4,5-
b]pyridin-5-yl}-5-(2-
methylpyridin-4-yl)-1,6,8-
triazatricyclo[7.2.1.0²,⁷]dodeca-
2(7),3,5-triene-8-carboxamide 1021
-continued

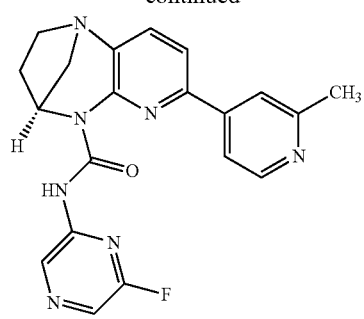

(9S)-N-(6-flouropyridin-2-yl)-
5-(2-methylpyridin-4-yl)-1,6,8-
triazatricyclo[7.2.1.0$^{2,7}$]dodeca-
2(7),3,5-triene-8-carboxamide

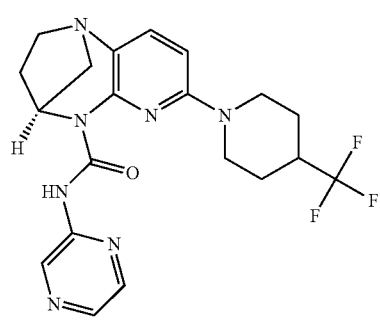

(9S)-N-(pyrazin-2-yl)-5-[4-
(trifluoromethyl)piperidin-1-
yl]-1,6,8-
triazatricyclo[7.2.1.0$^{2,7}$]dodeca-
2(7),3,5-triene-8-carboxamide

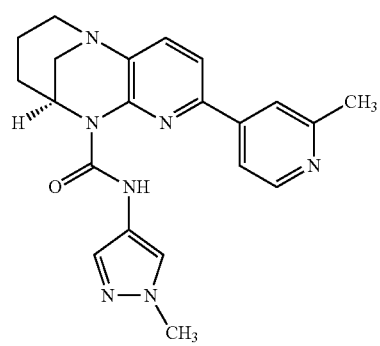

(9S)-N-(1-methyl-1H-pyrazol-
4-yl)-5-(2-methylpyridin-4-yl)-
1,6,8-
triazatricyclo[7.3.1.0$^{2,7}$]trideca-
2(7),3,5-triene-8-carboxamide 1022
-continued

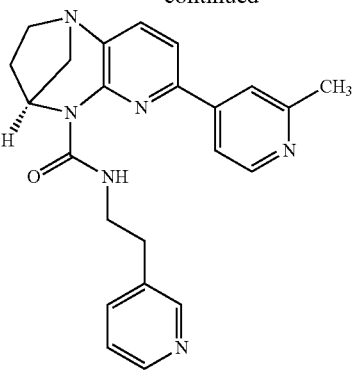

HCl (9S)-5-(2-methylpyridin-4-yl)-
N-[2-(pyridin-3-yl)ethyl]-1,6,8-
triazatricyclo[7.2.1.0$^{2,7}$]dodeca-
2(7),3,5-triene-8-carboxamide
hydrochloride

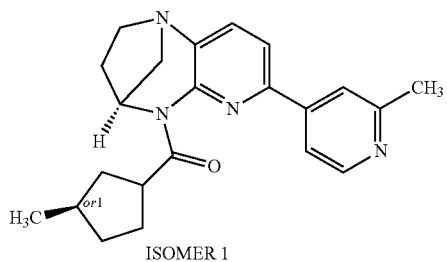

ISOMER 1

(9S)-5-(2-methylpyridin-4-yl)-
8-[(3R)-3-methylpyrrrolidine-1-
carbonyl]-1,6,8-
triazatricyclo[7.2.1.0$^{2,7}$]dodeca-
2,4,6-triene

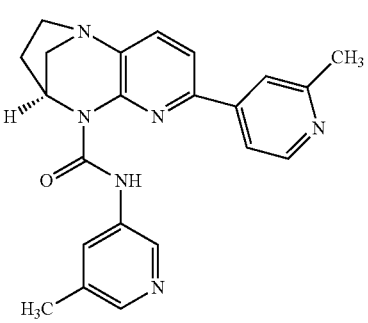

(9S)-N-(5-methylpyridin-3-yl)-
5-(2-methylpyridin-4-yl)-1,6,8-
triazatricyclo[7.2.1.0$^{2,7}$]dodeca-
2(7),3,5-triene-8-carboxamide

1023
-continued

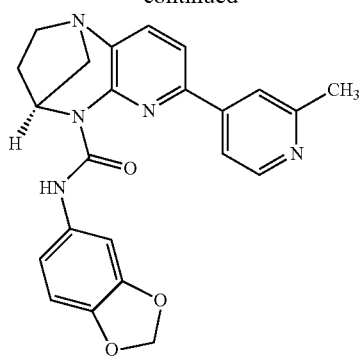

(9S)-5-(2-methylpyridin-4-yl)-
8-[(3R)-3-methylpyrrrolidine-1-
carbonyl]-1,6,8-
triazatricyclo[7.2.1.0²,⁷]dodeca-
2(7),3,5-triene-8-carboxamide

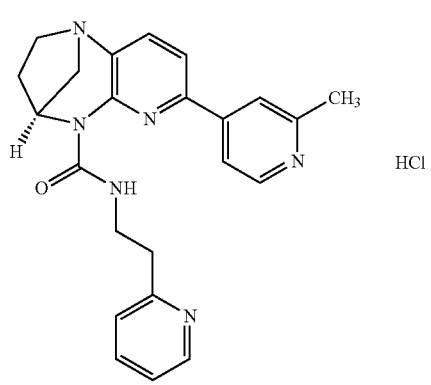

HCl (9S)-5-(2-methylpyridin-4-yl)-
N-[2-(pyridin-2-yl)ethyl]-1,6,8-
triazatricyclo[7.2.1.0²,⁷]dodeca-
2(7),3,5-triene-8-carboxamide
hydrochloride

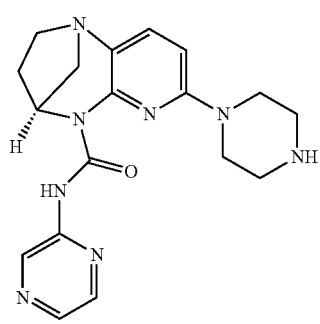

(9S)-5-(piperazin-1-yl)-N-
(pyrazin-2-yl)-1,6,8-
triazatricyclo[7.2.1.0²,⁷]dodeca-
2,4,6-triene-8-carboxamide

1024
-continued

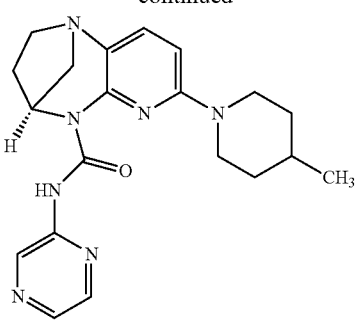

(9S)-5-(4-methylpiperidin-1-
yl)-N-(pyrazin-2-yl)-1-6,8-
triazatricyclo[7.2.1.0²,⁷]dodeca-
2,4,6-triene-8-carboxamide

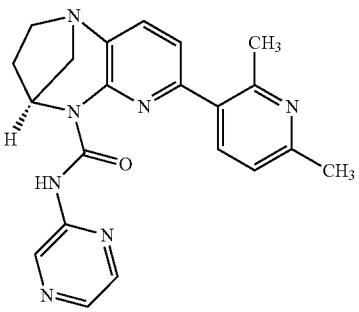

(9S)-5-(2,6-dimethylpyridin-3-
yl)-N-(pyrazin-2-yl)-1,6,8-
triazatricyclo[7.2.1.0²,⁷]dodeca-
2(7),3,5-triene-8-carboxamide

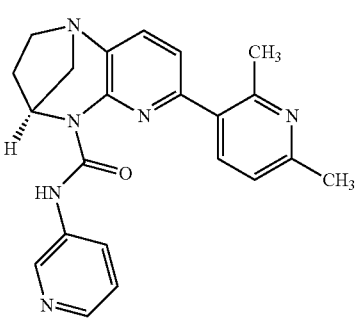

(9S)-5-(2,6-dimethylpyridin-3-
yl)-N-(pyridin-3-yl)-1,6,8-
triazatricyclo[7.2.1.0²,⁷]dodeca-
2(7),3,5-triene-8-carboxamide

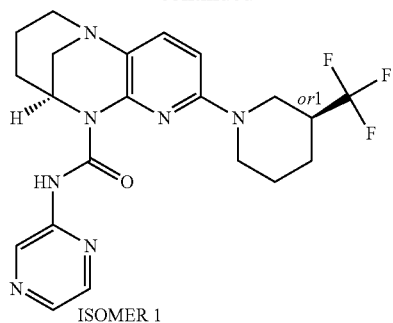

ISOMER 1

(9S)-N-(pyrazin-2-yl)-5-[(3S)-
3-(trifluoromethyl)piperidin-1-
yl]-1-6,8-
triazatricyclo[7.3.1.0$^{2,7}$]trideca-
2(7),3,5-triene-8-carboxamide

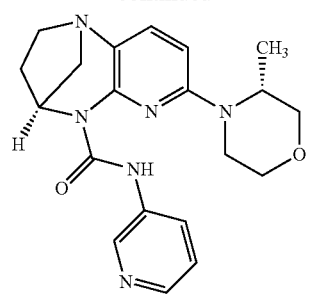

(9S)-5-[(3S)-3-
methylmorpholin-4-yl]-N-
(pyridin-3-yl)-1,6,8-
triazatricyclo[7.2.1.0$^{2,7}$]dodeca-
2(7),3,5-triene-8-carboxamide

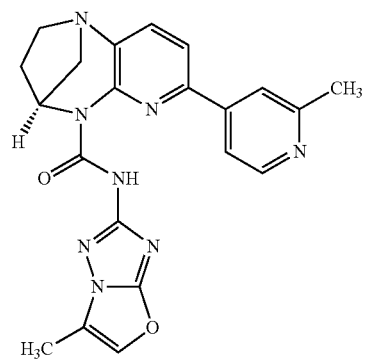

(9S)-N-{6-methyl-
[1,2,4]triazolo[3,2-
b][1,3]thiazol-2-yl}-5-(2-
methylpiperidin-4-yl)-1-6,8-
triazatricyclo[7.2.1.0$^{2,7}$]dodeca-
2(7),3,5-triene-8-carboxamide

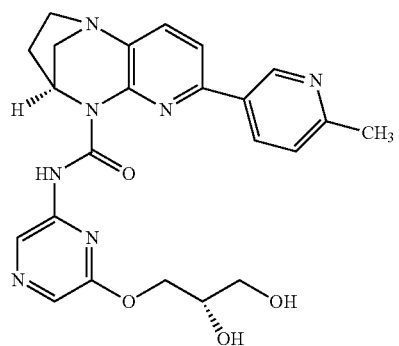

(9S)-N-{6-[(2S)-2,3-
dihydroxypropoxy]pyrazin-2-
yl}-5-(6-methylpyridin-3-yl)-
1,6,8-
triazatricyclo[7.2.1.0$^{2,7}$]dodeca-
2(7),3,5-triene-8-carboxamide

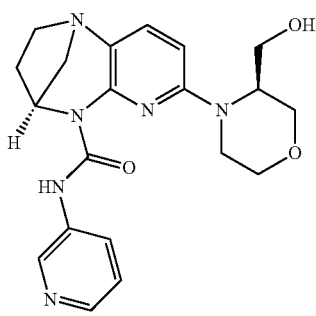

(9S)-5-[(3S)-3-
(hydroxymethyl)morpholin-4-
yl]-N-(pyridin-3-yl)-1,6,8-
triazatricyclo[7.2.1.0$^{2,7}$]dodeca-
2(7),3,5-triene-8-carboxamide

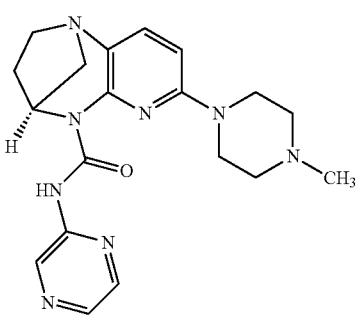

(9S)-5-(4-methylpiperazin-1-
yl)-N-(pyrazin-2-yl)-1,6,8-
triazatricyclo[7.2.1.0$^{2,7}$]dodeca-
2(7),3,5-triene-8-carboxamide

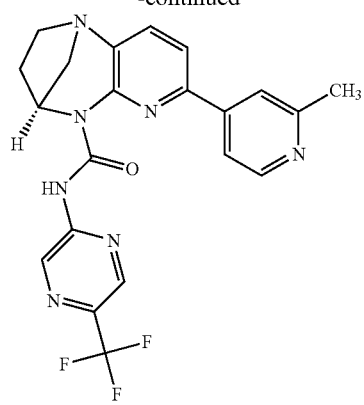

(9S)-5-(2-methylpyridin-4-yl)-
N-[5-(trifluoromethyl)pyrazin-
2-yl]-1,6,8-
triazatricyclo[7.2.1.0²,⁷]dodeca-
2(7),3,5-triene-8-carboxamide

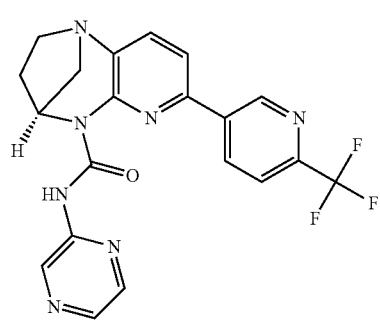

(9S)-N-(pyrazin-2-yl)-5-[6-
(trifluoromethyl)pyridin-3-yl]-
1,6,8-
triazatricyclo[7.2.1.0²,⁷]dodeca-
2(7),3,5-triene-8-carboxamide

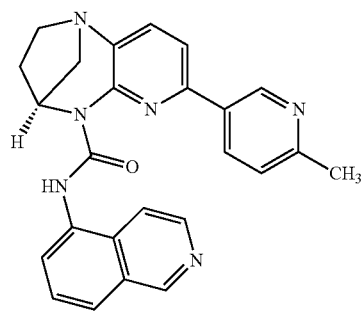

(9S)-N-(isoquinolin-5-yl)-5-(6-
methylpyridin-3-yl)-1,6,8-
triazatricyclo[7.2.1.0²,⁷]dodeca-
2,4,6-triene-8-carboxamide

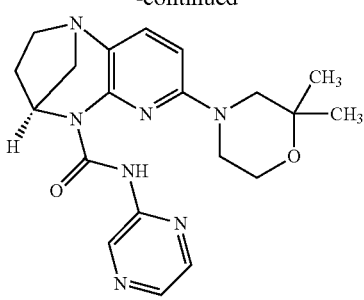

(9S)-5-(2,2-
dimethylmorpholin-4-yl)-N-
(pyrazin-2-yl)-1,6,8-
triazatricyclo[7.2.1.0²,⁷]dodeca-
2(7),3,5-triene-8-carboxamide

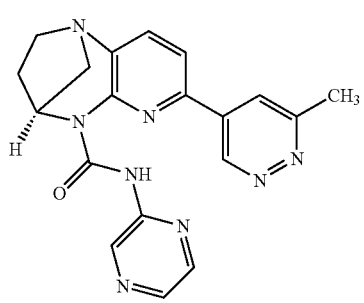

(9S)-5-(6-methylpyridazin-4-
yl)-N-(pyrazin-2-yl)-1,6,8-
triazatricyclo[7.2.1.0²,⁷]dodeca-
2(7),3,5-triene-8-carboxamide

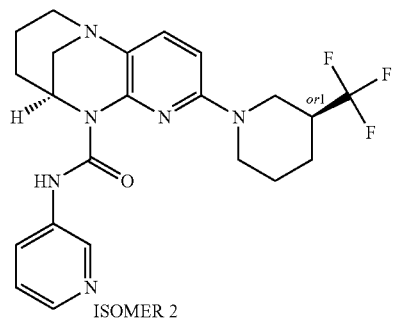

ISOMER 2

(9S)-N-(pyridin-3-yl)-5-[(3S)-
3-(trifluoromethyl)piperidin-1-
yl]-1,6,8-
triazatricyclo[7.3.1.0²,⁷]trideca-
2(7),3,5-triene-8-carboxamide

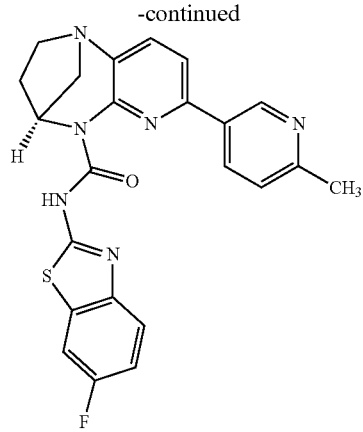

(9S)-N-(6-fluoro-1,3-benzothiazol-2-yl)-5-(6-methylpyridin-3-yl)-1,6,8-triazatricyclo[7.2.1.0²,⁷]dodeca-2,4,6-triene-8-carboxamide

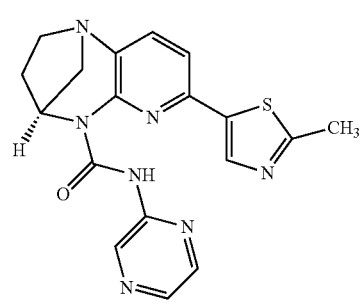

(9S)-5-(2-methyl-1,-thiazol-5-yl)-N-(pyrazin-2-yl)-1,6,8-triazatricyclo[7.2.1.0²,⁷]dodeca-2(7),3,5-triene-8-carboxamide

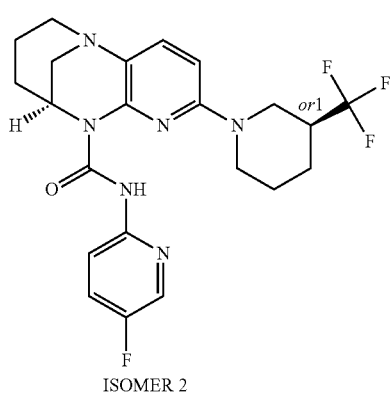

ISOMER 2

(9S)-N-(5-fluoropyridin-2-yl)-5-[(3S)-3-(trifluoromethyl)piperidin-1-yl]-1,6,8-triazatricyclo[7.3.1.0²,⁷]trideca-2(7),3,5-triene-8-carboxamide

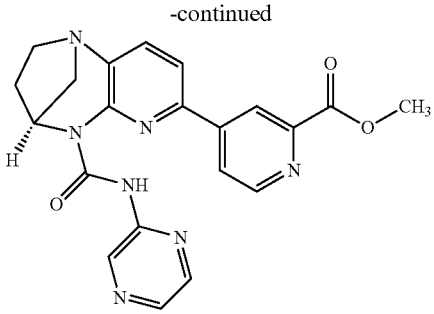

methyl4-[(9S)-8-[(pyrazin-2-yl)carbamoyl-1,6,8-triazatricyclo[7.2.1.0²,⁷]dodeca-2,4,6-triene-5-yl]pyridine-2-carboxylate

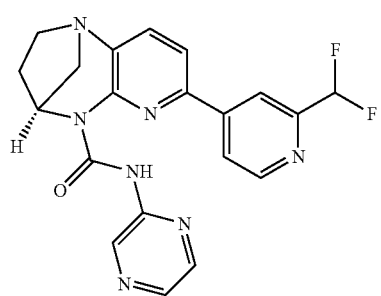

(9S)-5-[2-(difluoromethyl)pyridin-4-yl]-N-(pyrazin-2-yl)-1,6,8-triazatricyclo[7.2.1.0²,⁷]dodeca-2(7),3,5-triene-8-carboxamide

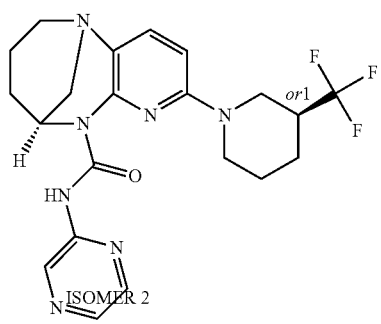

ISOMER 2

(9S)-N-(pyrazin-2-yl)-5-[(3S)-3-(trifluoromethyl)piperidin-1-yl]-1,6,8-triazatricyclo[7.3.1.0²,⁷]trideca-2(7),3,5-triene-8-carboxamide

1031
-continued

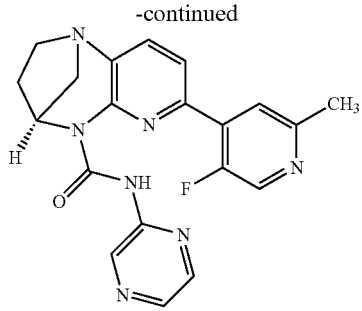

(9S)-5-(5-fluoro-2-
methylpyridin-4-yl)-N-
(pyrazin-2-yl)-1,6,8-
triazatricyclo[7.2.1.0$^{2,7}$]dodeca-
2(7),3,5-triene-8-carboxamide

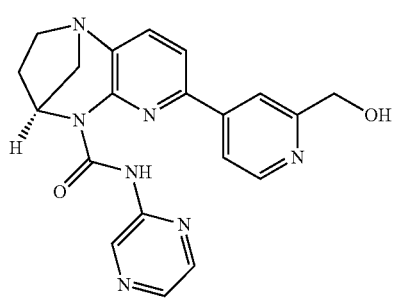

(9S)-5-[2-
(hydroxymethyl)pyridin-4-yl]-
N-(pyrazin-2-yl)-1,6,8-
triazatricyclo[7.2.1.0$^{2,7}$]dodeca-
2(7),3,5-triene-8-carboxamide

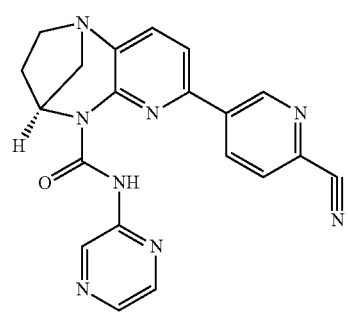

(9S)-5-(6-cyanopyridin-3-yl)-
N-(pyrazin-2-yl)-1,6,8-
triazatricyclo[7.2.1.0$^{2,7}$]dodeca-
2,4,6-triene-8-carboxamide

1032
-continued

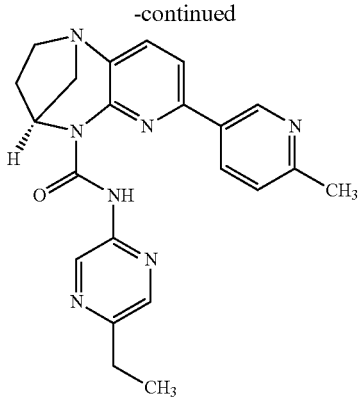

(9S)-N-(5-ethylpyrazin-2-yl)-5-
(6-methylpyridin-3-yl)-1,6,8-
triazatricyclo[7.2.1.0$^{2,7}$]dodeca-
2,4,6-triene-8-carboxamide

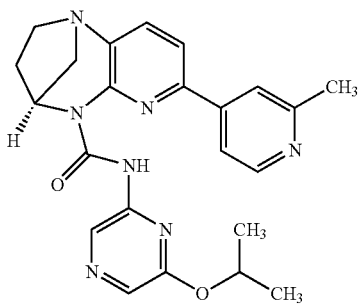

(9S)-5-(2-methylpyridin-4-yl)-
N-[6-(propan-2-yloxy)pyrazin-
2-yl]-1,6,8-
triazatricyclo[7.2.1.0$^{2,7}$]dodeca-
2(7),3,5-triene-8-carboxamide

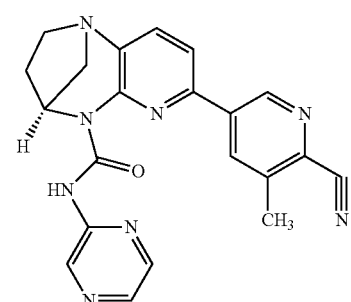

(9S)-5-(6-cyano-5-
methylpyridin-3-yl)-N-
(pyrazin-2-yl)-1,6,8-
triazatricyclo[7.2.1.0$^{2,7}$]dodeca-
2(7),3,5-triene-8-carboxamide 1033
-continued

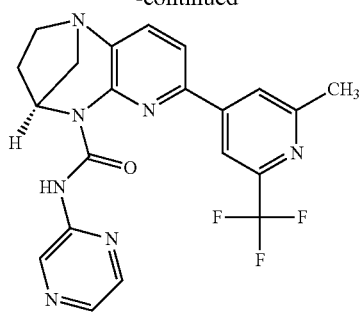

(9S)-5-[2-methyl-6-
(trifluoromethyl)pyridin-4-yl]-
N-(pyrazin-2-yl)-1,6,8-
triazatricyclo[7.2.1.0$^{2,7}$]dodeca-
2(7),3,5-triene-8-carboxamide

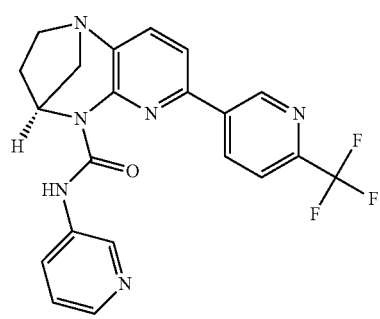

(9S)-N-(pyridin-3-yl)-5-[6-
(trifluoromethyl)pyridin-3-yl]-
1,6,8-
triazatricyclo[7.2.1.0$^{2,7}$]dodeca-
2(7),3,5-triene-8-carboxamide

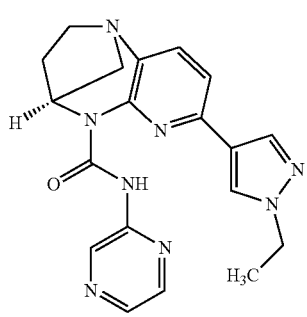

(9S)-5-(1-ethyl-1H-pyrazol-4-
yl)-N-(pyrazin-2-yl)-1,6,8-
triazatricyclo[7.2.1.0$^{2,7}$]dodeca-
2(7),3,5-triene-8-carboxamide 1034
-continued

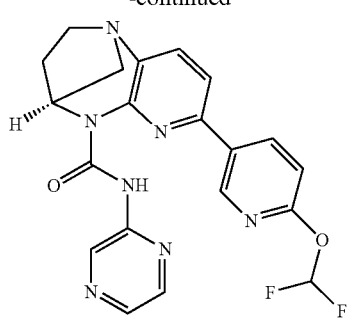

(9S)-5-[6-
(difluoromethoxy)pyridin-3-
yl]-N-(pyrazin-2-yl)-1,6,8-
triazatricyclo[7.2.1.0$^{2,7}$]dodeca-
2(7),3,5-triene-8-carboxamide

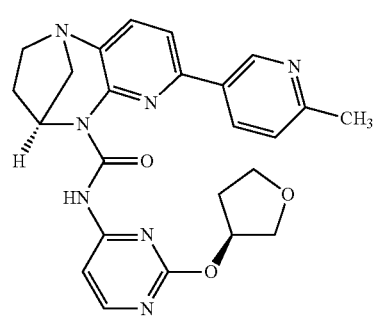

(9S)-5-(6-methylpyridin-3-yl)-
N-{2-[(3S)-oxolan-3-
yloxy]pyrimidin-4-yl}-1,6,8-
triazatricyclo[7.2.1.0$^{2,7}$]dodeca-
2,4,6-triene-8-carboxamide

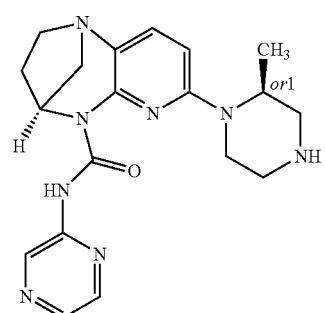

ISOMER 1

(9S)-5-[(2S)-2-
methylpiperazin-1-yl]-N-
(pyrazin-2-yl)-1,6,8-
triazatricyclo[7.2.1.0$^{2,7}$]dodeca-
2,4,6-triene-8-carboxamide

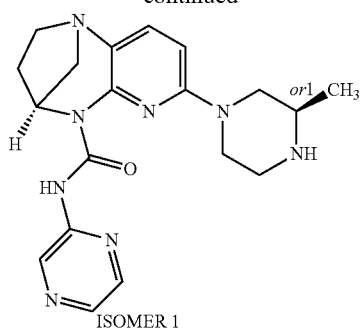

ISOMER 1

(9S)-5-[(3R)-3-methylpiperazin-1-yl]-N-(pyrazin-2-yl)-1,6,8-triazatricyclo[7.2.1.0²,⁷]dodeca-2,4,6-triene-8-carboxamide

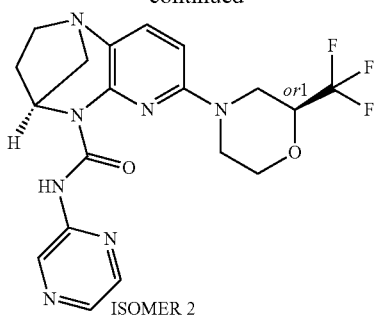

ISOMER 2

(9S)-N-(pyrazin-2-yl)-5-[(2S)-2-(trifluoromethyl)morpholin-4-yl]-1,6,8-triazatricyclo[7.2.1.0²,⁷]dodeca-2(7),3,5-triene-8-carboxamide

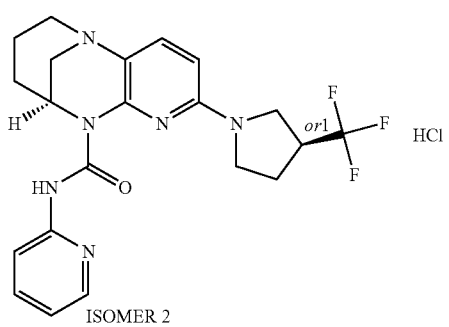

ISOMER 2

(9S)-N-(pyridin-2-yl)-5-[(3S)-3-(trifluoromethyl)pyrrolidin-1-yl]-1,6,8-triazatricyclo[7.3.1.0²,⁷]trideca-2(7),3,5-triene-8-carboxamide hydrochloride

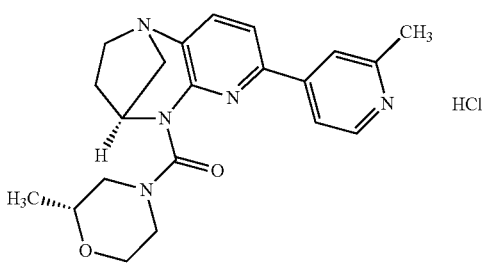

(9S)-8-[(2R)-2-methylmorpholine-4-carbonyl]-5-(2-methylpyridin-4-yl)-1,6,8-triazatricyclo[7.2.1.0²,⁷]dodeca-2(7),3,5-triene hydrochloride

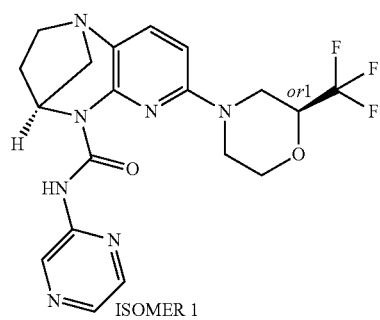

ISOMER 1

(9S)-N-(pyrazin-2-yl)-5-[(2S)-2-(trifluoromethyl)morpholin-4-yl]-1,6,8-triazatricyclo[7.2.1.0²,⁷]dodeca-2(7),3,5-triene-8-carboxamide

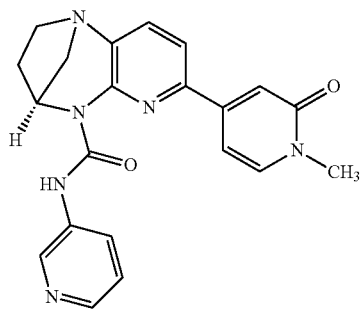

(9S)-5-(1-methyl-2-oxo-1,2-dihydropyridin-4-yl)-N-(pyridin-3-yl)-1,6,8-triazatricyclo[7.2.1.0²,⁷]dodeca-2(7),3,5-triene-8-carboxamide -continued

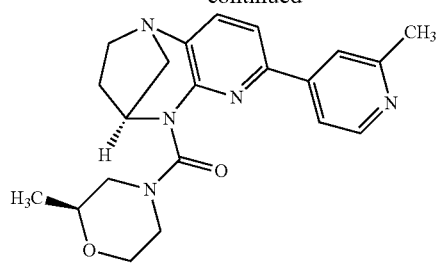

(9S)-8-[(2S)-2-methylmorpholine-4-carbonyl]-5-(2-methylpyridin-4-yl)-1,6,8-triazatricyclo[7.2.1.0²,⁷]dodeca-2(7),3,5-triene hydrochloride

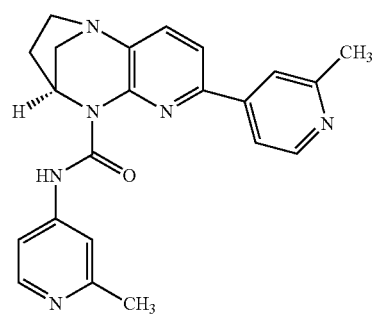

(9S)-N,5-bis(2-methylpyridin-4-yl)-1,6,8-triazatricyclo[7.2.1.0²,⁷]dodeca-2(7),3,5-triene-8-carboxamide

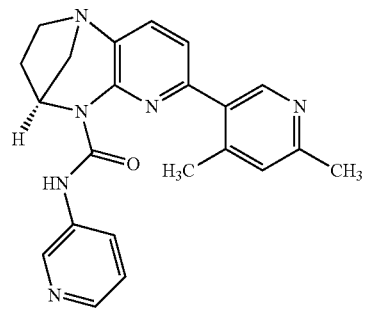

(9S)-5-(4,6-dimethylpyridin-3-yl)-N-(pyridin-3-yl)-1,6,8-triazatricyclo[7.2.1.0²,⁷]dodeca-2(7),3,5-triene-8-carboxamide

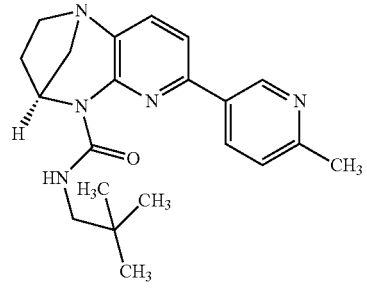

(9S)-N-(2,2-dimethylpropyl)-5-6-methylpyridin-3-yl)-1,6,8-triazatricyclo[7.2.1.0²,⁷]dodeca-2(7),3,5-triene-8-carboxamide -continued

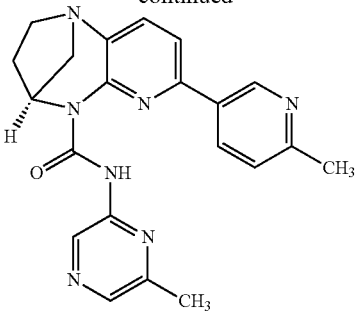

(9S)-N-(6-methylpyrazin-2-yl)-5-(6-methylpyridin-3-yl)-1,6,8-triazatricyclo[7.2.1.0²,⁷]dodeca-2,4,6-triene-8-carboxamide

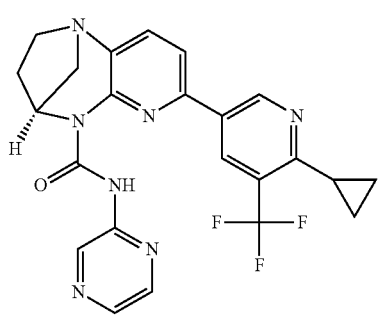

(9S)-5-[6-cyclopropyl-5-(trifluoromethyl)pyridin-3-yl]-N-(pyrazin-2-yl)-1,6,8-triazatricyclo[7.2.1.0²,⁷]dodeca-2,4,6-triene-8-carboxamide

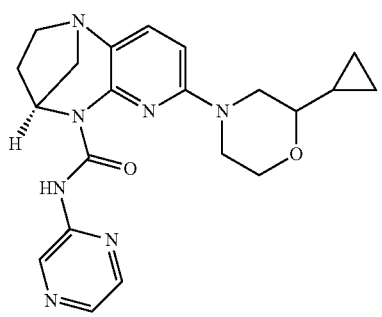

(9S)-5-(2-cyclopropylmorpholin-4-yl)-N-(pyrazin-2-yl)-1,6,8-triazatricyclo[7.2.1.0²,⁷]dodeca-2,4,6-triene-8-carboxamide

1039

-continued

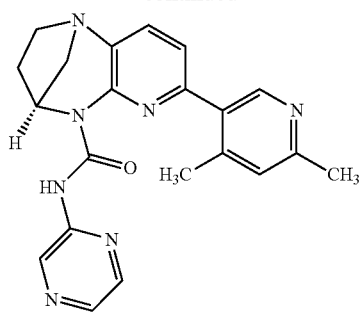

(9S)-5-(4,6-dimethylpyridin-3-
yl)-N-(pyrazin-2-yl)-1,6,8-
triazatricyclo[7.2.1.0²,⁷]dodeca-
2(7),3,5-triene-8-carboxamide

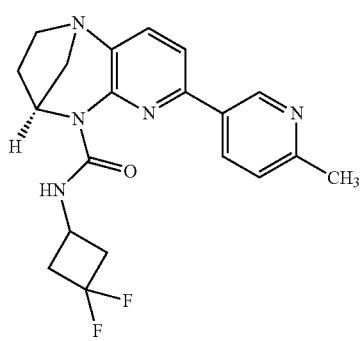

(9S)-N-(3,3-
difluorocyclobutyl)-5-(6-
methylpyrazin-3-yl)-1,6,8-
triazatricyclo[7.2.1.0²,⁷]dodeca-
2(7),3,5-triene-8-carboxamide

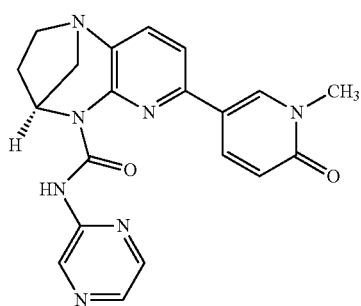

(9S)-5-(1-methyl-6-oxo-1,6-
dihydropyridin-3-yl)-N-
(pyrazin-2-yl)-1,6,8-
triazatricyclo[7.2.1.0²,⁷]dodeca-
2(7),3,5-triene-8-carboxamide

1040

-continued

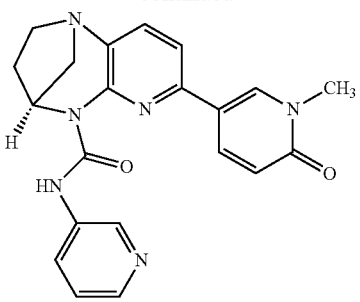

(9S)-5-(1-methyl-6-oxo-1,6-
dihydropyridin-3-yl)-N-
(pyrazin-3-yl)-1,6,8-
triazatricyclo[7.2.1.0²,⁷]dodeca-
2(7),3,5-triene-8-carboxamide

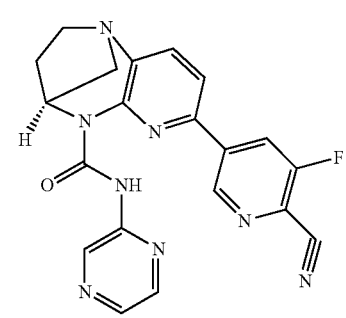

(9S)-5-(6-cyano-5-
fluoropyridin-3-yl)-N-(pyrazin-2-
yl)-1,6,8-
triazatricyclo[7.2.1.0²,⁷]dodeca-
2(7),3,5-triene-8-carboxamide

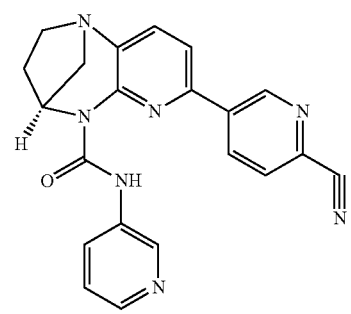

(9S)-5-(6-cyanopyridin-3-yl)-
N-(pyridin-3-yl)-1,6,8-
triazatricyclo[7.2.1.0²,⁷]dodeca-
2,4,6-triene-8-carboxamide

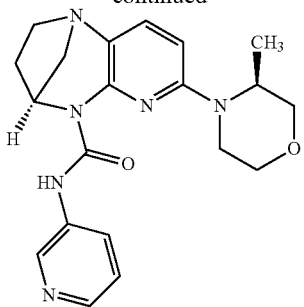

(9S)-5-[(3S)-3-
methylmorpholin-4-yl]-N-
(pyridin-3-yl)-1,6,8-
triazatricyclo[7.2.1.0²,⁷]dodeca-
2(7),3,5-triene-8-carboxamide

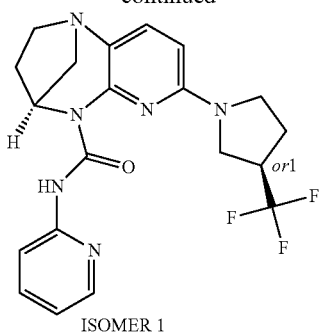

ISOMER 1

(9S)-N-(pyridin-2-yl)-5-[(3R)-
3-(trifluoromethyl)pyrrolidin-1-
yl]-1,6,8-
triazatricyclo[7.2.1.0²,⁷]dodeca-
2,4,6-triene-8-carboxamide

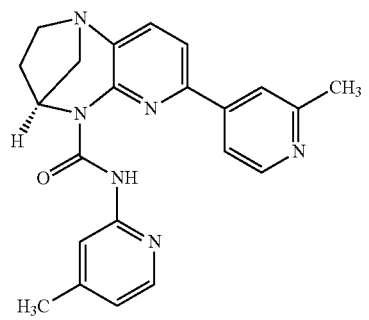

(9S)-N-(4-methylpyridin-2-yl)-
5-(2-methylpyridin-4-yl)-1,6,8-
triazatricyclo[7.2.1.0²,⁷]dodeca-
2,4,6-triene-8-carboxamide

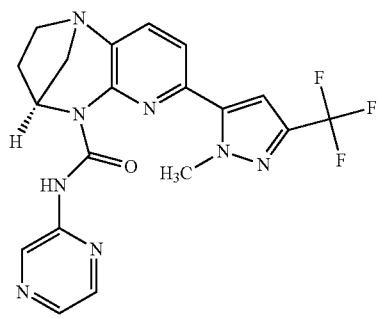

(9S)-5-[1-methyl-3-
(trifluoromethyl)-1H-pyrazol-
5-yl]-N-(pyrazin-2-yl)-1,6,8-
triazatricyclo[7.2.1.0²,⁷]dodeca-
2(7),3,5-triene-8-carboxamide

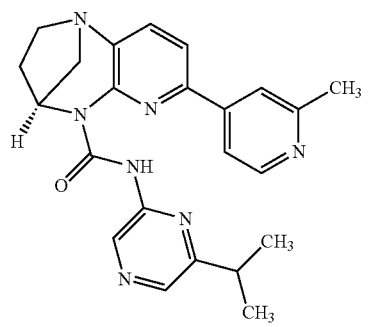

(9S)-5-(2-methylpyridin-4-yl)-
N-[6-(propan-2-yl)pyrazin-2-
yl]-1,6,8-
triazatricyclo[7.2.1.0²,⁷]dodeca-
2(7),3,5-triene-8-carboxamide

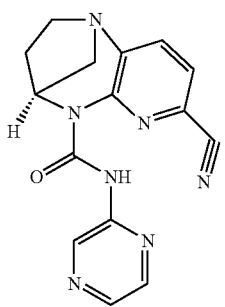

(9S)-5-cyano-N-(pyrazin-2-yl)-
1,6,8-
triazatricyclo[7.2.1.0²,⁷]dodeca-
2(7),3,5-triene-8-carboxamide

| 1043 | 1044 |
|---|---|
| 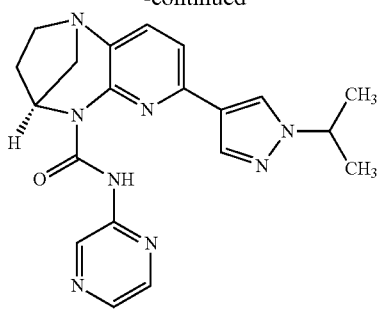 (9S)-5-[1-(propan-2-yl)-1H-pyrazol-4-yl]-N-(pyrazin-2-yl)-1,6,8-triazatricyclo[7.2.1.0²,⁷]dodeca-2,4,6-triene-8-carboxamide | 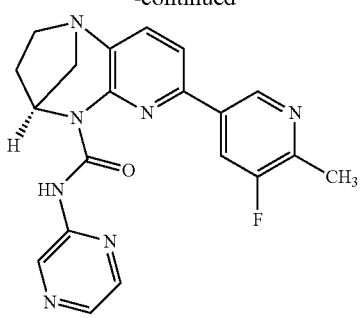 (9S)-5-(5-fluoro-6-methylpyridin-3-yl)-N-(pyridin-2-yl)-1,6,8-triazatricyclo[7.2.1.0²,⁷]dodeca-2(7),3,5-triene-8-carboxamide |
| 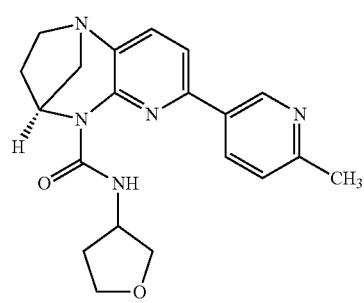 (9S)-5-(6-methylpyridin-3-yl)-N-(oxolan-3-yl)-1,6,8-triazatricyclo[7.2.1.0²,⁷]dodeca-2,4,6-triene-8-carboxamide | 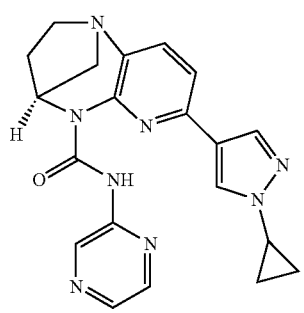 (9S)-5-(1-cyclopropyl-1H-pyrazol-4-yl)-N-(pyrazin-2-yl)-1,6,8-triazatricyclo[7.2.1.0²,⁷]dodeca-2(7),3,5-triene-8-carboxamide |
| 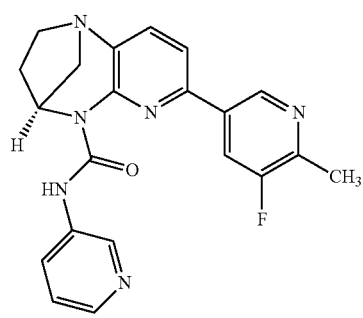 (9S)-5-(5-fluoro-6-methylpyridin-3-yl)-N-(pyridin-3-yl)-1,6,8-triazatricyclo[7.2.1.0²,⁷]dodeca-2(7),3,5-triene-8-carboxamide | 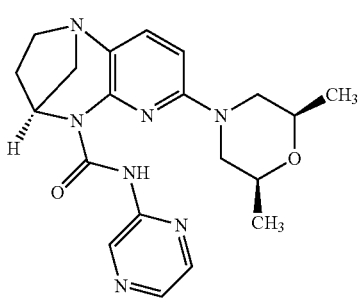 (9S)-5-[(2R,6S)-2,6-dimethylmorpholin-4-yl]-N-(pyrazin-2-yl)-1,6,8-triazatricyclo[7.2.1.0²,⁷]dodeca-2(7),3,5-triene-8-carboxamide |

-continued

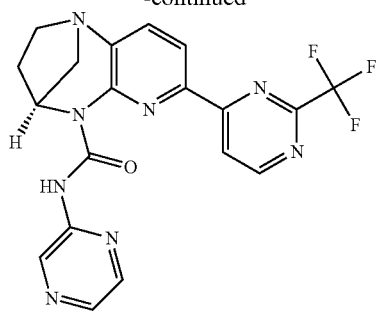

(9S)-N-(pyrazin-2-yl)-5-[2-(trifluoromethyl)pyrimidin-4-yl]-1,6,8-triazatricyclo[7.2.1.0$^{2,7}$]dodeca-2(7),3,5-triene-8-carboxamide

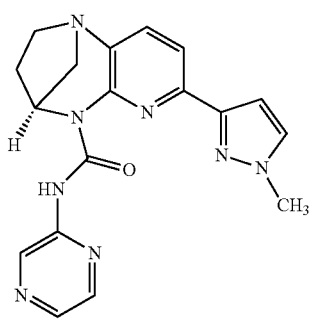

(9S)-5-(1-methyl-1H-pyrazol-3-yl)-N-(pyrazin-2-yl)-1,6,8-triazatricyclo[7.2.1.0$^{2,7}$]dodeca-2(7),3,5-triene-8-carboxamide

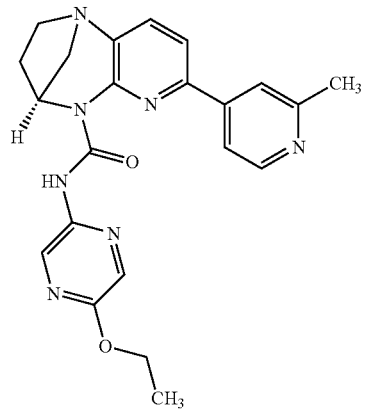

(9S)-N-(5-ethoxypyrazin-2-yl)-5-(2-methylpyridin-4-yl)-1,6,8-triazatricyclo[7.2.1.0$^{2,7}$]dodeca-2(7),3,5-triene-8-carboxamide -continued

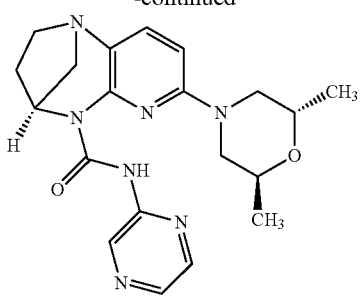

(9S)-5-[(2S,6S)-2,6-dimethylmorpholin-4-yl]-N-(pyrazin-2-yl)-1,6,8-triazatricyclo[7.2.1.0$^{2,7}$]dodeca-2(7),3,5-triene-8-carboxamide

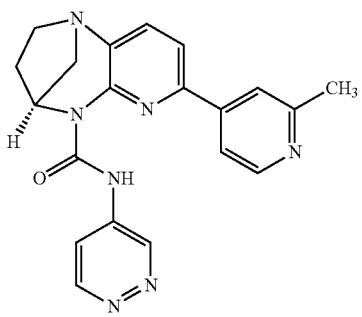

(9S)-5-(2-methylpyridin-4-yl)-N-(pyridazin-4-yl)-1,6,8-triazatricyclo[7.2.1.0$^{2,7}$]dodeca-2,4,6-triene-8-carboxamide

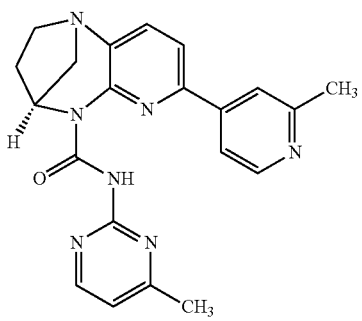

(9S)-5-(2-methylpyridin-4-yl)-N-(4-methylpyrimidin-2-yl)-1,6,8-triazatricyclo[7.2.1.0$^{2,7}$]dodeca-2,4,6-triene-8-carboxamide

1047

-continued

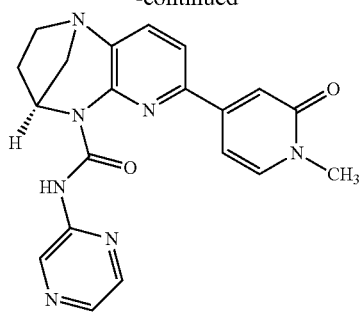

(9S)-5-(1-methyl-2-oxo-1,2-
dihydropyridin-4-yl)-N-
(pyrazin-2-yl)-1,6,8-
triazatricyclo[7.2.1.0$^{2,7}$]dodeca-
2(7),3,5-triene-8-carboxamide

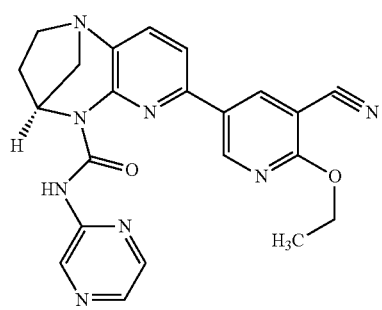

(9S)-5-(5-cyano-6-
ethoxypyridin-3-yl)-N-
(pyrazin-2-yl)-1,6,8-
triazatricyclo[7.2.1.0$^{2,7}$]dodeca-
2(7),3,5-triene-8-carboxamide

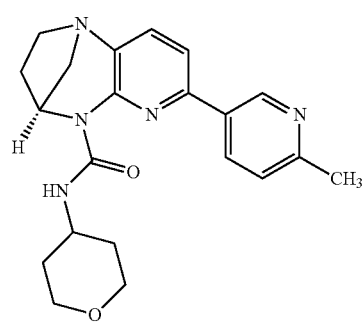

(9S)-5-(6-methylpyridin-3-yl)-
N-(oxan-4-yl)-1,6,8-
triazatricyclo[7.2.1.0$^{2,7}$]dodeca-
2(7),3,5-triene-8-carboxamide

1048

-continued

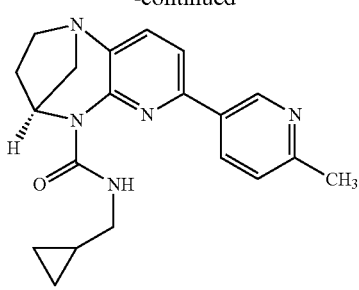

(9S)-N-(cyclopropylmethyl)-5-
(6-methylpyrimidin-3-yl)-1,6,8-
triazatricyclo[7.2.1.0$^{2,7}$]dodeca-
2,4,6-triene-8-carboxamide

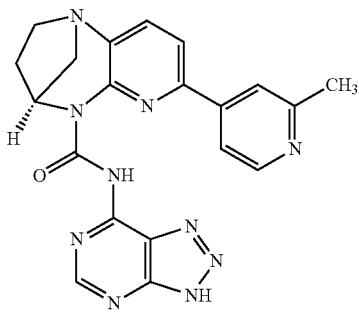

(9S)-5-(2-methylpyridin-4-yl)-
N-{3H-[1,2,3]triazolo[4,5-
d]pyrimidin-7-yl}-1,6,8-
triazatricyclo[7.2.1.0$^{2,7}$]dodeca-
2,4,6-triene-8-carboxamide

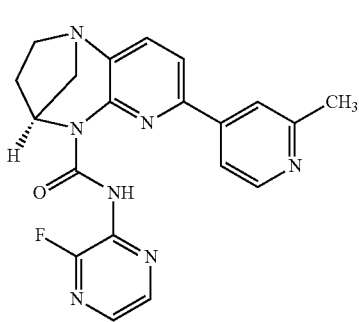

(9S)-N-(3-fluoropyrazin-2-yl)-
5-(2-methylpyridin-4-yl)-1,6,8-
triazatricyclo[7.2.1.0$^{2,7}$]dodeca-
2,4,6-triene-8-carboxamide

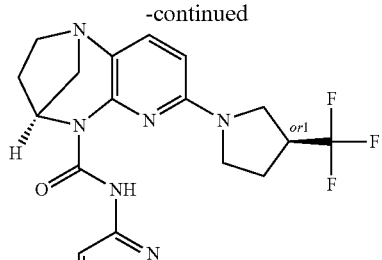

ISOMER 2

(9S)-N-(pyridin-2-yl)-5-[(3S)-3-(trifluoromethyl)pyrrolidin-1-yl]-1,6,8-triazatricyclo[7.2.1.0²,⁷]dodeca-2(7),3,5-triene-8-carboxamide

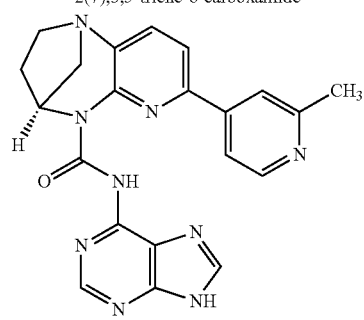

(9S)-5-(2-methylpyridin-4-yl)-N-(9H-purin-6-yl)-1,6,8-triazatricyclo[7.2.1.0²,⁷]dodeca-2,4,6-triene-8-carboxamide

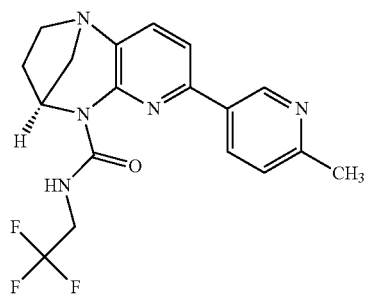

(9S)-5-(6-methylpyridin-3-yl)-N-(2,2,2-trifluoroethyl)-1,6,8-triazatricyclo[7.2.1.0²,⁷]dodeca-2(7),3,5-triene-8-carboxamide

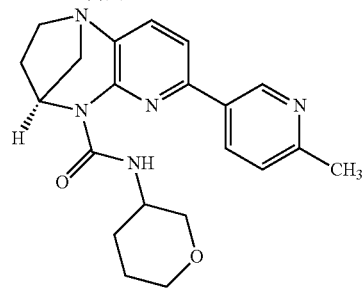

(9S)-5-(6-methylpyridin-3-yl)-N-(oxan-3-yl)-1,6,8-triazatricyclo[7.2.1.0²,⁷]dodeca-2(7),3,5-triene-8-carboxamide

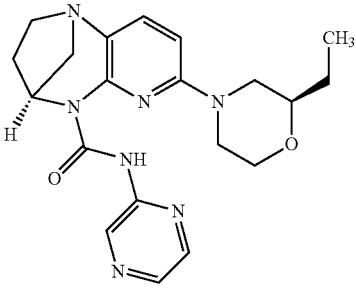

(9S)-5-[(2R)-2-ethylmorpholin-4-yl]-N-(pyrazin-2-yl)-1,6,8-triazatricyclo[7.2.1.0²,⁷]dodeca-2(7),3,5-triene-8-carboxamide

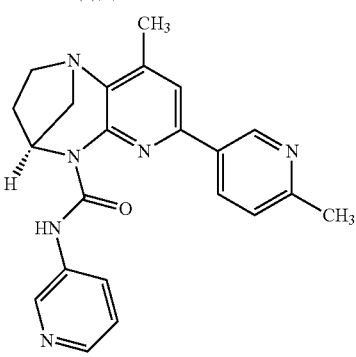

(9S)-3-methyl-5-(6-methylpyridin-3-yl)-N-(pyridin-3-yl)-1,6,8-triazatricyclo[7.2.1.0²,⁷]dodeca-2,4,6-triene-8-carboxamide

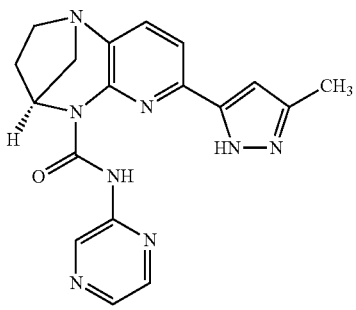

(9S)-5-(3-methyl-1H-pyrazol)-5-yl)-N-(pyrazin-2-yl)-1,6,8-triazatricyclo[7.2.1.0²,⁷]dodeca-2(7),3,5-triene-8-carboxamide

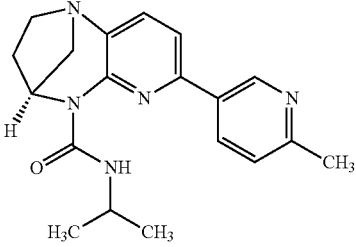

(9S)-5-(6-methylpyridin-3-yl)-N-(propan-2-yl)-1,6,8-triazatricyclo[7.2.1.0²,⁷]dodeca-2,6,8-triene-8-carboxamide

1051

-continued

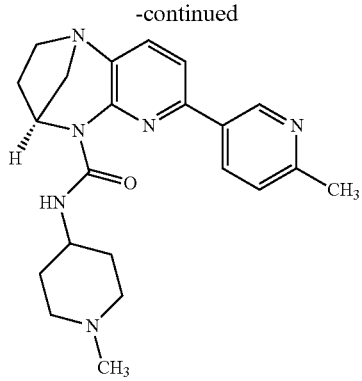

(9S)-N-(1-methylpiperidin-4-yl)-5-(6-methylpyridin-3-yl)-1,6,8-triazatricyclo[7.2.1.0$^{2,7}$]dodeca-2(7),3,5-triene-8-carboxamide

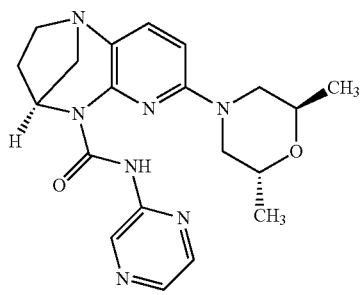

(9S)-5-[(2R,6R)-2,6-dimethylmorpholin-4-yl]-N-(pyrazin-2-yl)-1,6,8-triazatricyclo[7.2.1.0$^{2,7}$]dodeca-2(7),3,5-triene-8-carboxamide

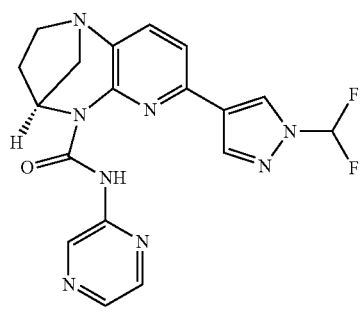

(9S)-5-[1-(difluoromethyl)-1H-pyrazol-4-yl]-N-(pyrazin-2-yl)-1,6,8-triazatricyclo[7.2.1.0$^{2,7}$]dodeca-2(7),3,5-triene-8-carboxamide

1052

-continued

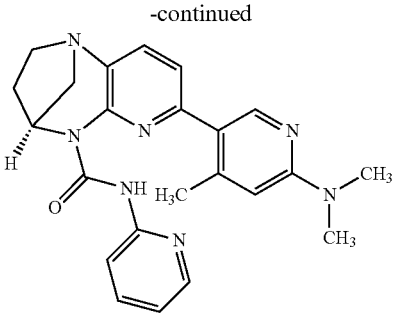

(9S)-5-[6-(dimethylamino)-4-methylpyridin-3-yl]-N-(pyridin-2-yl)-1,6,8-triazatricyclo[7.2.1.0$^{2,7}$]dodeca-2(7),3,5-triene-8-carboxamide

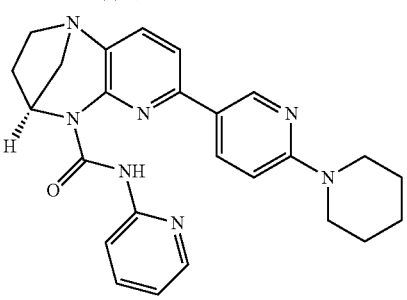

(9S)-5-[6-(piperidin-1-yl)pyridin-3-yl]-N-(pyridin-2-yl)-1,6,8-triazatricyclo[7.2.1.0$^{2,7}$]dodeca-2(7),3,5-triene-8-carboxamide

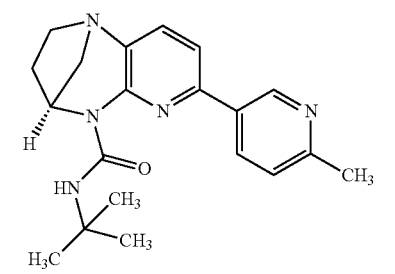

(9S)-N-tert-butyl-5-(6-methylpyridin-3-yl)-1,6,8-triazatricyclo[7.2.1.0$^{2,7}$]dodeca-2(7),3,5-triene-8-carboxamide

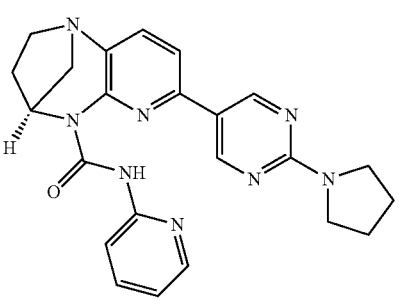

(9S)-N-(pyridin-2-yl)-5-[2-(pyrrolidin-1-yl)pyrimidin-5-yl]-1,6,8-triazatricyclo[7.2.1.0$^{2,7}$]dodeca-2(7),3,5-triene-8-carboxamide

1053

-continued

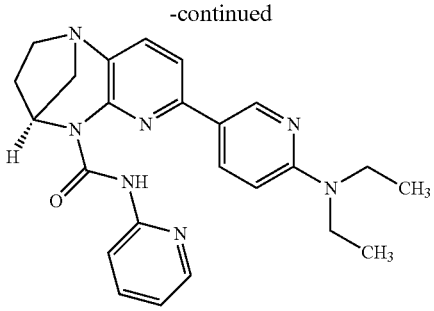

(9S)-5-[6-(diethylamino)pyridin-3-yl]-N-(pyridin-2-yl)-1,6,8-triazatricyclo[7.2.1.0$^{2,7}$]dodeca-2(7),3,5-triene-8-carboxamide

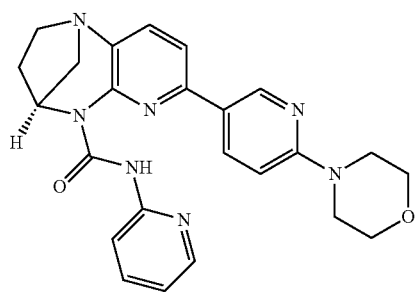

(9S)-5-[6-(morpholin-4-yl)pyridin-3-yl]-N-(pyridin-2-yl)-1,6,8-triazatricyclo[7.2.1.0$^{2,7}$]dodeca-2(7),3,5-triene-8-carboxamide

1054

-continued

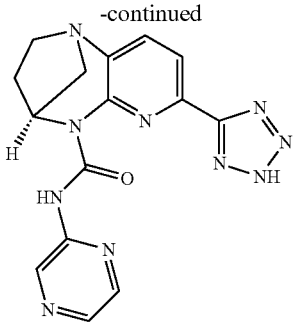

(9S)-N-(pyrazin-2-yl)-5-(2H-1,2,3,4-tetrazol-5-yl)-1,6,8-triazatricyclo[7.2.1.0$^{2,7}$]dodeca-2,4,6-triene-8-carboxamide or a pharmaceutically sat thereof.

7. A pharmaceutical composition comprising a compound according to claim 6 and at least one pharmaceutically acceptable carrier.

8. A method for treating aging, stress, diabetes, metabolic dysfunctions, neurodegenerative diseases, cardiovascular disease, cancer or inflammatory disease, which comprises administering a compound or a pharmaceutically acceptable salt thereof according to claim 6 to a subject in need thereof.

9. A method of treating psoriasis, atopic dermatitis, acne, rosacea, inflammatory bowel disease, osteoporosis, sepsis, arthritis, COPD, systemic lupus erythematosus or ophthalmic inflammation, which comprises administering a compound or a pharmaceutically acceptable salt thereof according to claim 6 to a subject in need thereof.

10. A method for treating aging, stress, diabetes, metabolic dysfunctions, neurodegenerative diseases, cardiovascular disease, cancer or inflammatory disease which comprises administering a pharmaceutical composition according to claim 7 to a subject in need thereof.

11. A method of treating psoriasis, atopic dermatitis, acne, rosacea, inflammatory bowel disease, osteoporosis, sepsis, arthritis, COPD, systemic lupus erythematosus or ophthalmic inflammation, which comprises administering a pharmaceutical composition according to claim 7 to a subject in need thereof.

* * * * *